(12) United States Patent
Leit De Moradei et al.

(10) Patent No.: US 12,325,697 B2
(45) Date of Patent: Jun. 10, 2025

(54) CBL-B MODULATORS AND USES THEREOF

(71) Applicant: Nimbus Clio, Inc., Cambridge, MA (US)

(72) Inventors: Silvana Marcel Leit De Moradei, Burlington, MA (US); Angela V. West, Franklin, MA (US); Thomas Baker, Nottingham (GB); Jokin Carrillo Arregui, Nottingham (GB); Diana Castagna, Nottingham (GB); Jeremy Robert Greenwood, Brooklyn, NY (US); Salma Rafi, Lexington, MA (US); Fiona McRobb, New York, NY (US); Yan Zhang, Jersey City, NJ (US)

(73) Assignee: Nimbus Clio, Inc., Boston, MA (US)

( * ) Notice: Subject to any disclaimer, the term of this patent is extended or adjusted under 35 U.S.C. 154(b) by 0 days.

(21) Appl. No.: 17/658,587

(22) Filed: Apr. 8, 2022

(65) Prior Publication Data
US 2023/0086064 A1 Mar. 23, 2023

Related U.S. Application Data

(60) Provisional application No. 63/264,940, filed on Dec. 3, 2021, provisional application No. 63/173,121, filed on Apr. 9, 2021.

(51) Int. Cl.
| | |
|---|---|
| *C07D 403/10* | (2006.01) |
| *A61P 35/02* | (2006.01) |
| *C07D 209/44* | (2006.01) |
| *C07D 249/08* | (2006.01) |
| *C07D 401/14* | (2006.01) |
| *C07D 403/12* | (2006.01) |
| *C07D 405/14* | (2006.01) |
| *C07D 413/10* | (2006.01) |
| *C07D 413/14* | (2006.01) |
| *C07D 471/04* | (2006.01) |
| *C07D 491/048* | (2006.01) |
| *C07D 491/107* | (2006.01) |
| *C07D 498/08* | (2006.01) |
| *C07D 498/10* | (2006.01) |
| *C07F 5/02* | (2006.01) |

(52) U.S. Cl.
CPC ............ *C07D 403/10* (2013.01); *A61P 35/02* (2018.01); *C07D 209/44* (2013.01); *C07D 249/08* (2013.01); *C07D 401/14* (2013.01); *C07D 403/12* (2013.01); *C07D 405/14* (2013.01); *C07D 413/10* (2013.01); *C07D 413/14* (2013.01); *C07D 471/04* (2013.01); *C07D 491/048* (2013.01); *C07D 491/107* (2013.01); *C07D 498/08* (2013.01); *C07D 498/10* (2013.01); *C07F 5/022* (2013.01)

(58) Field of Classification Search
CPC .. C07D 403/10; C07D 209/44; C07D 249/08; C07D 401/14; C07D 403/12; C07D 405/14; C07D 413/10; C07D 413/14; C07D 471/04; C07D 491/048; C07D 491/107; C07D 498/08; C07D 498/10; C07D 491/08; A61P 35/02; C07F 5/022
USPC ........................................................ 514/64
See application file for complete search history.

(56) References Cited

U.S. PATENT DOCUMENTS

| | | | |
|---|---|---|---|
| 4,650,750 A | 3/1987 | Giese | |
| 4,709,016 A | 11/1987 | Giese | |
| 5,360,819 A | 11/1994 | Giese | |
| 5,516,931 A | 5/1996 | Giese et al. | |
| 5,602,273 A | 2/1997 | Giese et al. | |
| 5,604,104 A | 2/1997 | Giese et al. | |
| 5,610,020 A | 3/1997 | Giese et al. | |
| 5,650,270 A | 7/1997 | Giese et al. | |
| 6,552,065 B2 | 4/2003 | Remiszewski et al. | |
| 7,390,799 B2 | 6/2008 | Bruncko et al. | |
| 8,138,347 B2 | 3/2012 | Knight et al. | |
| 8,906,682 B2 | 12/2014 | June et al. | |
| 11,401,267 B2 * | 8/2022 | Sands | A61P 37/00 |
| 11,464,802 B2 * | 10/2022 | Sands | A61K 31/4545 |
| 2003/0134859 A1 | 7/2003 | Amemiya et al. | |
| 2010/0324338 A1 | 12/2010 | Maeda et al. | |
| 2017/0174671 A1 | 6/2017 | Wu et al. | |

FOREIGN PATENT DOCUMENTS

| | | |
|---|---|---|
| JP | 2013166750 A | 8/2013 |
| WO | WO-2002088112 A1 | 11/2002 |
| WO | WO-2003063794 A2 | 8/2003 |
| WO | WO-2004019973 A1 | 3/2004 |
| WO | WO-2004089925 A1 | 10/2004 |
| WO | WO-2004106328 A1 | 12/2004 |
| WO | WO-2005007623 A2 | 1/2005 |
| WO | WO-2005113554 A2 | 12/2005 |
| WO | WO-2006029879 A2 | 3/2006 |
| WO | WO-2006078846 A1 | 7/2006 |

(Continued)

OTHER PUBLICATIONS

Keinan et al., Isr. J. Chem. 2018, 58, 7-10, "Organic Synthesis: From Glorious Past to Brilliant Future" (Year: 2018).*

(Continued)

*Primary Examiner* — Jared Barsky
*Assistant Examiner* — Liyuan Mou
(74) *Attorney, Agent, or Firm* — Dechert LLP; Andrea L. C. Reid; Todd K. Macklin

(57) ABSTRACT

The present invention provides compounds, compositions thereof, and methods of using the same for the inhibition of Cbl-b, and the treatment of Cbl-b-mediated disorders.

8 Claims, No Drawings

(56) References Cited

FOREIGN PATENT DOCUMENTS

| | | | |
|---|---|---|---|
| WO | WO-2006105021 A2 | 10/2006 | |
| WO | WO-2006122806 A2 | 11/2006 | |
| WO | WO-2007005874 A2 | 1/2007 | |
| WO | WO-2007016176 A2 | 2/2007 | |
| WO | WO-2007044729 A2 | 4/2007 | |
| WO | WO-2007053452 A1 | 5/2007 | |
| WO | WO-2007070514 A1 | 6/2007 | |
| WO | WO-2007084786 A1 | 7/2007 | |
| WO | WO-2007129161 A2 | 11/2007 | |
| WO | WO-2008039218 A2 | 4/2008 | |
| WO | WO-2008109943 A1 | 9/2008 | |
| WO | WO-2008118802 A1 | 10/2008 | |
| WO | WO-2008132601 A1 | 11/2008 | |
| WO | WO-2009009116 A2 | 1/2009 | |
| WO | WO-2009044273 A2 | 4/2009 | |
| WO | WO-2009073620 A2 | 6/2009 | |
| WO | WO-2009076140 A1 * | 6/2009 | ........... C07D 413/14 |
| WO | WO-2009114512 A1 | 9/2009 | |
| WO | WO-2009115665 A1 | 9/2009 | |
| WO | WO-2010019570 A2 | 2/2010 | |
| WO | WO-2010077634 A1 | 7/2010 | |
| WO | WO-2011028683 A1 | 3/2011 | |
| WO | WO-2011056652 A1 | 5/2011 | |
| WO | WO-2011070024 A1 | 6/2011 | |
| WO | WO-2011090760 A1 | 7/2011 | |
| WO | WO-2011107553 A1 | 9/2011 | |
| WO | WO-2011109400 A2 | 9/2011 | |
| WO | WO-2011131407 A1 | 10/2011 | |
| WO | WO-2011140249 A2 | 11/2011 | |
| WO | WO-2012032433 A1 | 3/2012 | |
| WO | WO-2012142237 A1 | 10/2012 | |
| WO | WO-2012145493 A1 | 10/2012 | |
| WO | WO-2013079174 A1 | 6/2013 | |
| WO | WO-2013087699 A1 | 6/2013 | |
| WO | WO-2013119716 A1 | 8/2013 | |
| WO | WO-2013132044 A1 | 9/2013 | |
| WO | WO-2013169264 A1 | 11/2013 | |
| WO | WO-2014008218 A1 | 1/2014 | |
| WO | WO-2014036357 A1 | 3/2014 | |
| WO | WO-2014074660 A1 | 5/2014 | |
| WO | WO-2014074661 A1 | 5/2014 | |
| WO | WO-2015089143 A1 | 6/2015 | |
| WO | WO-2015131080 A1 | 9/2015 | |
| WO | 2017195149 A1 | 11/2017 | |
| WO | WO-2019148005 A1 * | 8/2019 | ......... A61K 31/4155 |
| WO | 2020023355 A1 | 1/2020 | |
| WO | 2020080979 A1 | 4/2020 | |
| WO | WO-2020210508 A1 * | 10/2020 | ........... A61K 31/438 |
| WO | WO-2020264398 A1 * | 12/2020 | ............... A61P 35/00 |

OTHER PUBLICATIONS

"Chimeric Antigen Receptors," ClinicalTrials.gov Search Results. Jul. 13, 2022: https://clinicaltrials.gov/ct2/results?term=chimeric+antigen+receptors&pg=1.

Adams et al., "Big opportunities for small molecules in immuno-oncology," Nat Rev Drug Discov. Sep. 2015;14(9):603-22.

Bachmaier et al., "Negative regulation of lymphocyte activation and autoimmunity by the molecular adaptor Cbl-b," Nature. Jan. 13, 2000;403(6766):211-6.

Berge et al., "Pharmaceutical salts," J Pharm Sci. Jan. 1977;66(1):1-19.

Dou et al., "Essentiality of a non-RING element in priming donor ubiquitin for catalysis by a monomeric E3," Nat Struct Mol Biol. Aug. 2013;20(8):982-986.

Eisenhauer et al., "New response evaluation criteria in solid tumours: revised RECIST guideline (version 1.1)," Eur J Cancer. Jan. 2009;45(2):228-47.

Jeon et al., "Essential role of the E3 ubiquitin ligase Cbl-b in T cell anergy induction," Immunity. Aug. 2004;21(2):167-77.

Loeser et al., "Spontaneous tumor rejection by cbl-b-deficient CD8+ T cells," J Exp Med. 2007;204(4): 879-91.

Martínez-Losato et al., "How Do Cytotoxic Lymphocytes Kill Cancer Cells?" Clin Cancer Res. Nov. 15, 2015;21(22):5047-56.

Nishino et al., "Revised RECIST guideline version 1.1: What oncologists want to know and what radiologists need to know," AJR Am J Roentgenol. Aug. 2010;195(2):281-9.

Okazaki et al., "A rheostat for immune responses: the unique properties of PD-1 and their advantages for clinical application," Nat Immunol. Dec. 2013;14(12):1212-8.

Paolino et al., "The E3 ligase Cbl-b and TAM receptors regulate cancer metastasis via natural killer cells," Nature. Mar. 27, 2014;507(7493):508-12.

Ramirez et al., "Defining causative factors contributing in the activation of hedgehog signaling in diffuse large B-cell lymphoma," Leuk Res. Oct. 2012;36(10):1267-73.

Ross et al., "Bispecific T cell engager (BiTE®) antibody constructs can mediate bystander tumor cell killing," PLoS One. Aug. 24, 2017;12(8):e0183390.

Rostovtsev et al., "A stepwise huisgen cycloaddition process: copper(I)-catalyzed regioselective 'ligation' of azides and terminal alkynes," Angew Chem Int Ed Engl. Jul. 15, 2002;41(14):2596-9.

Saravaria et al., "B cell regulation in cancer and anti-tumor immunity," Cell Mol Immunol. Aug. 2017;14(8):662-674.

Schietinger et al., "Tolerance and exhaustion: defining mechanisms of T cell dysfunction," Trends Immunol. Feb. 2014;35(2):51-60.

Schwartz, "T cell anergy," Annu Rev Immunol. 2003;21:305-34.

Sun et al., "Carbohydrate and protein immobilization onto solid surfaces by sequential Diels-Alder and azide-alkyne cycloadditions," Bioconjug Chem. Jan.-Feb. 2006;17(1):52-7.

Toogood, "Small molecule immuno-oncology therapeutic agents," Bioorg Med Chem Lett. Feb. 1, 2018;28(3):319-329.

Zou et al., "PD-L1 (B7-H1) and PD-1 pathway blockade for cancer therapy: Mechanisms, response biomarkers, and combinations," Sci Transl Med. Mar. 2, 2016;8(328):328rv4.

International Search Report for PCT Application No. PCT/US22/71633 mailed Aug. 9, 2022 (5 pages).

Mukherjee et al., "Kinase Crystal Miner: A Powerful Approach to Repurposing 3D Hinge Binding Fragments and Its Application to Finding Novel Bruton Tyrosine Kinase Inhibitors," J Chem Inf Model. 2017;57(9):2152-2160.

* cited by examiner

CBL-B MODULATORS AND USES THEREOF

CROSS-REFERENCE TO RELATED APPLICATION

This application claims the benefit of priority to U.S. Provisional Appl. No. 63/264,940, filed Dec. 3, 2021, and U.S. Provisional Appl. No. 63/173,121, filed Apr. 9, 2021, the entirety of each of which is herein incorporated by reference.

TECHNICAL FIELD OF THE INVENTION

The present invention relates to compounds and methods useful for inhibiting E3 ligase Casitas B-lineage lymphoma b (Cbl-b). The invention also provides pharmaceutically acceptable compositions comprising compounds of the present invention and methods of using said compositions in the treatment of various disorders.

BACKGROUND OF THE INVENTION

Ubiquitination is a post-translational modification that regulates the function and fate of proteins involved with physiological processes. The addition of ubiquitin to target proteins occurs via a three-step enzymatic process that involves three enzymes. The first enzyme, E1, catalyzes ubiquitin activation. Activated ubiquitin is then transferred from E1 to the ubiquitin-conjugating enzyme, E2. The third enzyme, or E3 ligase, confers substrate specificity and directly catalyzes the transfer of ubiquitin from the E2 into the protein substrate. The addition of poly-ubiquitin chains to proteins serves as a signal leading to degradation into peptides of the ubiquitin-conjugated protein by the proteasome. Additionally, poly- and mono-ubiquitination can also alter cellular localization, function, and interactions of the protein substrate with proteins required for downstream activity and signaling events.

Ubiquitination controls multiple biological processes that are often dysregulated in disease, including cell cycle, DNA repair, differentiation, and innate and adaptive immunity. Therefore, the discovery of molecules that modulate components of the ubiquitin proteasome system represents an attractive therapeutic opportunity for a wide range of conditions, including cancer and auto-immune disease.

The compounds and compositions described herein are generally useful for the inhibition of the E3 ligase Casitas B-lineage lymphoma b (Cbl-b).

Cbl-b is a RING finger E3 ligase and a member of a highly conserved family of Cbl proteins, which in mammals consists of three Cbl genes: Cbl, Cbl-b, and Cbl-c. Cbl proteins interact with target proteins via their protein-protein interaction domains, allowing regulation of multiple signaling pathways, including tyrosine kinase (TK) signaling in multiple cell types. The structure of Cbl proteins consists of an amino-terminal tyrosine kinase binding domain (TKBD), a linker helix region (LHR) and a really interesting new gene (RING) domain, followed by a carboxy-terminal region containing binding sites for Src homology 2 (SH2) and Src homology 3 (SH3) domains. Cbl TKBD is composed of a four-helix bundle (4H), an EF-hand, and a variant SH2 domain, which binds substrates, such as activated TKs, in a phospho-tyrosine dependent manner.

Ubiquitination of activated receptor TKs by Cbl-b regulates the assembly of endocytic proteins both at the membrane and at sorting endosomes to promote lysosome targeting, degradation and signal termination. Cbl-b is also important for down regulation of signaling from antigen and cytokine receptors through ubiquitination of receptor chains and associated cytosolic TKs, leading to inactivation and/or proteasomal degradation.

Cbl-b is expressed in immune cell lineages and acts as a major regulator of immune cell activation and maintenance of peripheral tolerance. Cbl-b negatively regulates adaptive immune system signaling by establishing the threshold for the activation of antigen receptors. In T cells, Cbl-b imposes a requirement for a co-stimulatory signal to mount a productive immune response upon T cell receptor (TCR) engagement. Mice deficient in Cbl-b, and more specifically in the RING Zn-finger ligase domain of Cbl-b, showed tumor rejection that is mediated by CD8+ T cells.

Additionally, Cbl-b regulates the activity of multiple cell lineages involved in innate immunity, including NK cells, antigen-presenting dendritic cells (DC) and monocytes. Therefore, due to the complexity and diversity of the protein targets of Cbl-b in a variety of immune cells, it is possible that the functions of Cbl-b are cell-type dependent.

Novel therapeutic approaches aimed at removing inhibitory signals in immune cells to boost a productive immune system have gained recent attention. Given the central role that Cbl-b plays in regulating multiples signaling mechanisms in both innate and adaptive immunity, inhibition of Cbl-b provides therapeutic opportunities, including cancer immunotherapies.

Cbl-b inhibitors may strengthen the activity of cancer vaccines. For example, it was reported that the adoptive transfer of Cbl-b–/– CD8+ T cells combined with DC vaccines delays tumor growth. Additionally, Cbl-b–/– T cells are resistant to inhibition by PDL-1/PD-1 in vitro and in vivo, which supports the rationale combination of Cbl-b inhibitors with anti-PD-1/PD-L1 checkpoint blockade.

Enhanced expression of Cbl-b associates with better prognosis in lung adenocarcinoma. Moreover, mutations in the RING finger domain of Cbl proteins and Cbl-b linker sequence are found in a variety of disorders and cancers, including Juvenile myelomonocytic leukemia (JMML), preleukemic chronic myelomonocytic leukemia (CMML), Myeloproliferative Neoplasms (MPN), and Acute myeloid leukemia (AML). These observations suggest that that degradation impairment of activated TKs represents an important cancer mechanism that involves Cbl proteins. In agreement, multiple reports have demonstrated the ubiquitination of the epidermal growth factor receptor (EGFR) and the platelet derived growth factor receptor alpha (PDGFRa) by Cbl-b. The ubiquitination of these receptors promotes their proteasomal-dependent degradation in a variety of cancer lineages. The degradation of EGFR by Cbl-b leads to lung and gastric cancer cell proliferation and mediates epithelial to mesenchymal transition (EMT) in metastatic breast and gastric cancers. Additionally, amplifications and mutations of both EGFR and PDGFR are major drivers of oncogenic transformation and are commonly found in multiple types of cancer. Thus, Cbl-b inhibition represents an opportunity for both tumor intrinsic and tumor extrinsic therapies.

SUMMARY OF THE INVENTION

It has now been found that compounds of this invention, and pharmaceutically acceptable compositions thereof, are effective as inhibitors of Cbl-b. In certain embodiments, the invention provides for compounds of the formulae presented herein.

Compounds of the present invention, and pharmaceutically acceptable compositions thereof, are useful for treating a variety of diseases, disorders or conditions, associated with modulating the immune system implicating Cbl-b. Such diseases, disorders, or conditions include those described herein.

Compounds provided by this invention are also useful for the study of Cbl-b enzymes in biological and pathological phenomena; the study of ubiquitination occurring in bodily tissues; and the comparative evaluation of new Cbl-b inhibitors or other regulators of cell cycle, DNA repair, differentiation, and innate and adaptive immunity in vitro or in vivo.

DETAILED DESCRIPTION OF CERTAIN EMBODIMENTS

1. General Description of Certain Embodiments of the Invention

In certain aspects, the present invention provides a compound of formula I.

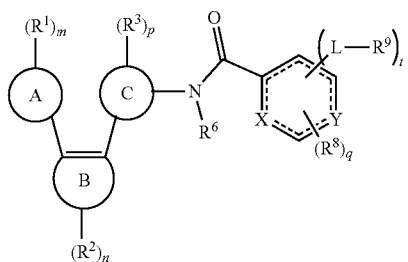

or a pharmaceutically acceptable salt thereof, wherein each of L, X, Y, $R^1$, $R^2$, $R^3$, $R^6$, $R^8$, $R^9$, m, n, p, q, and t is as defined below and described in embodiments herein, both singly and in combination.

In some embodiments, the present invention provides a pharmaceutical composition comprising a compound of formula I and a pharmaceutically acceptable carrier, adjuvant, or diluent.

In some embodiments, the present invention provides a method of treating a Cbl-b-mediated disease, disorder, or condition comprising administering to a patient in need thereof, a compound of formula I, or a pharmaceutically acceptable salt thereof.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

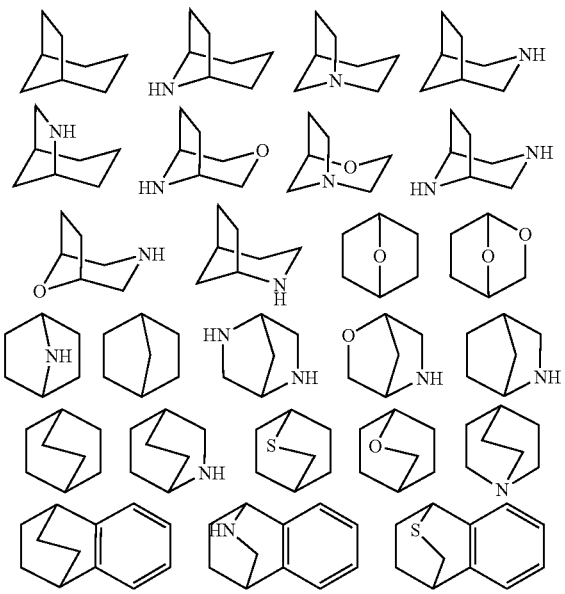

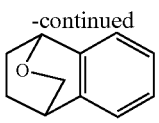

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where unless otherwise specified, the radical or point of attachment is on the heteroaromatic ring or on one of the rings to which the heteroaromatic ring is fused. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent.

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$N(R°)C(NR°)N(R°)_2$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$(CH_2)_{0-4}P(O)_2R°$; —$(CH_2)_{0-4}P(O)R°_2$; —$(CH_2)_{0-4}OP(O)R°_2$; —$(CH_2)_{0-4}OP(O)(OR°)_2$; —$SiR°_3$; —$(C_{1-4}$ straight or branched alkylene)O—$N(R°)_2$; or —$(C_{1-4}$ straight or branched alkylene)C(O)O—$N(R°)_2$, wherein each R° may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^•$, -(haloR$^•$), —$(CH_2)_{0-2}OH$, —$(CH_2)_{0-2}OR^•$, —$(CH_2)_{0-2}CH(OR^•)_2$; —$O(haloR^•)$, —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)C(O)OR$^•$, or —SSR$^•$ wherein each R$^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —$O(C(R*_2)_{2-3}O$—, or —$S(C(R*_2))_{2-3}S$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR*_2)_{2-3}O$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —$NH_2$, —NHR$^•$, —NR$^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —$NH_2$, —NHR$^•$, —NR$^•_2$, or —$NO_2$, wherein each R$^•$ is unsubstituted or where preceded by "halo" is substituted only with one or more halogens, and is independently $C_{1-6}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms. In certain embodiments, Ring B of a provided compound may be substituted with one or more deuterium atoms.

The structures as drawn represent relative configurations, unless labeled as absolute configurations. The invention contemplates individual enantiomers and racemic mixtures.

As used herein, a "Cbl-b inhibitor" is a molecule that reduces, inhibits, or otherwise diminishes one or more of the biological activities of Cbl-b (e.g., ubiquitination, regulation of tyrosine kinase signaling, or regulation of immune cell activation and maintenance of peripheral tolerance). Inhibition using the Cbl-b inhibitor does not necessarily indicate a total elimination of the Cbl-b activity. Instead, the activity could decrease by a statistically significant amount including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the activity of Cbl-b compared to an appropriate control. In some embodiments, the Cbl-b inhibitor reduces, inhibits, or otherwise diminishes the ubiquitination activity of Cbl-b. In some of these embodiments, the Cbl-b inhibitor reduces, inhibits, or otherwise diminishes the Cbl-b-mediated ubiquitination of tyrosine kinases. The presently disclosed compounds bind directly to CBl-b and inhibit its ubiquitinating activity.

By "specific inhibitor" is intended an agent that reduces, inhibits, or otherwise diminishes the activity of a defined target greater than that of an unrelated target. For example, a Cbl-b specific inhibitor reduces at least one biological activity of Cbl-b by an amount that is statistically greater than the inhibitory effect of the antagonist on any other protein (e.g., other E3 ligases). In some embodiments, the $IC_{50}$ of the inhibitor for the target is about 90%, 80%, 70%, 60%, 50%, 40%, 30%, 20%, 10%, 5%, 1%, 0.1%, 0.01%, 0.001% or less of the $IC_{50}$ of the antagonist for a non-target. The presently disclosed compounds may or may not be a specific Cbl-b inhibitor. A specific Cbl-b inhibitor reduces the biological activity of Cbl-b by an amount that is statistically greater than the inhibitory effect of the antagonist on any other protein (e.g., other E3 ligases). In certain embodiments, the Cbl-b inhibitor specifically inhibits the ubiquitinating activity of Cbl-b. In some of these embodiments, the $IC_{50}$ of the Cbl-b inhibitor for Cbl-b is about 90%, 80%, 70%, 60%, 50%, 40%, 30%, 20%, 10%, 0.1%, 0.01%, 0.001%, or less of the $IC_{50}$ of the Cbl-b inhibitor for another RING finger E3 ligase or other type of E3 ligase (e.g., Cullin-RING ligase).

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}P$, $^{33}P$, $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a Cbl-b ubquitination activity between a sample comprising a compound of the present invention, or composition thereof, and a Cbl-b E3 ligase, and an equivalent sample comprising an Cbl-b E3 ligase, in the absence of said compound, or composition thereof.

3. Description of Exemplary Embodiments

As described above, in certain embodiments, the present invention provides a compound of formula I:

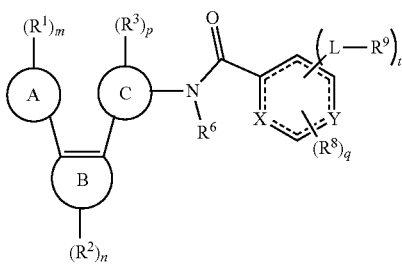

or a pharmaceutically acceptable salt thereof, wherein:

Ring A is a 5-6-membered heteroaryl ring having 1-4 heteroatoms independently selected from nitrogen, oxygen, and sulfur; or a 5-6-membered saturated or partially unsaturated heterocyclic ring having 1-4 heteroatoms independently selected from nitrogen, oxygen, and sulfur;

each $R^1$ is independently hydrogen, oxo, halogen, —CN, —$NO_2$, —$CHF_2$, —$CF_3$, —OR, —SR, —$N(R)_2$, —$S(O)_2R$, —$S(O)_2N(R)_2$, —S(O)R, —$S(O)N(R)_2$, —C(O)R, —C(O)OR, —$C(O)N(R)_2$, —C(O)N(R)OR, —OC(O)R, —$OC(O)N(R)_2$, —N(R)C(O)OR, —N(R)C(O)R, —$N(R)C(O)N(R)_2$, —$N(R)C(NR)N(R)_2$, —$N(R)N(R)_2$, —$N(R)S(O)_2N(R)_2$, —$N(R)S(O)_2R$, —N=$S(O)(R)_2$, —S(NR)(O)R, —N(R)S(O)R, —N(R)CN, —$P(O)(R)N(R)_2$, —P(O)(R)OR, or —$P(O)(R)_2$; or an optionally substituted $C_{1-6}$ aliphatic;

Ring B is a divalent phenyl or a divalent 5-6 membered heteroaryl ring having 1-4 heteroatoms independently selected from nitrogen, oxygen, and sulfur;

each $R^2$ is independently hydrogen, oxo, halogen, —CN, —$NO_2$, —$CH_2OR$, —$CHF_2$, —$CF_3$, —OR, —SR, —$N(R)_2$, —$S(O)_2R$, —$S(O)_2N(R)_2$, —S(O)R, —$S(O)N(R)_2$, —C(O)R, —C(O)OR, —$C(O)N(R)_2$, —C(O)N(R)OR, —OC(O)R, —$OC(O)N(R)_2$, —N(R)C(O)OR, —N(R)C(O)R, —$N(R)C(O)N(R)_2$, —$N(R)C(NR)N(R)_2$, —$N(R)N(R)_2$, —$N(R)S(O)_2N(R)_2$, —$N(R)S(O)_2R$, —N=$S(O)(R)_2$, —S(NR)(O)R, —N(R)S(O)R, —N(R)CN, —$P(O)(R)N(R)_2$, —P(O)(R)OR, or —$P(O)(R)_2$; or an optionally substituted $C_{1-6}$ aliphatic;

Ring C is a divalent phenyl or a divalent 5-6 membered heteroaryl ring having 1-4 heteroatoms independently selected from nitrogen, oxygen, and sulfur;

each $R^3$ is independently hydrogen, oxo, halogen, —CN, —$NO_2$, —$CHF_2$, —$CF_3$, —OR, —SR, —$N(R)_2$, —$S(O)_2R$, —$S(O)_2N(R)_2$, —S(O)R, —$S(O)N(R)_2$, —C(O)R, —C(O)OR, —$C(O)N(R)_2$, —C(O)N(R)OR, —OC(O)R, —$OC(O)N(R)_2$, —N(R)C(O)OR, —N(R)C(O)R, —$N(R)C(O)N(R)_2$, —$N(R)C(NR)N(R)_2$, —$N(R)N(R)_2$, —$N(R)S(O)_2N(R)_2$, —$N(R)S(O)_2R$, —N=$S(O)(R)_2$, —S(NR)(O)R, —N(R)S(O)R, —N(R)CN, —$P(O)(R)N(R)_2$, —P(O)(R)OR, or —$P(O)(R)_2$; or an optionally substituted group selected from $C_{1-6}$ aliphatic; a phenyl ring; a 3-7 membered saturated or partially unsaturated monocyclic carbocyclic ring; a 5-6 membered monocyclic heteroaryl ring having 1-4 heteroatoms independently selected from nitrogen, oxygen, and sulfur; and a 4-8 membered saturated or partially unsaturated monocyclic heterocyclic ring having 1-2 heteroatoms independently selected from nitrogen, oxygen, and sulfur;

or two $R^3$ groups, and the atoms to which each $R^3$ group is attached, are optionally taken together to form a fused 3-7 membered saturated or partially unsaturated monocyclic carbocyclic ring; a fused 5-6 membered monocyclic aryl ring; a fused 3-7 membered saturated or partially unsaturated monocyclic heterocyclic ring having 1-2 heteroatoms independently selected from nitrogen, oxygen, phosphorous, silicon and sulfur; or a fused 5-6 membered monocyclic heteroaryl ring having 1-4 heteroatoms independently selected from nitrogen, oxygen, and sulfur;

X is N, $N^+$—$O^-$, $NR^4$, $CR^4$, or C-L-$R^9$;

$R^4$ is hydrogen, oxo, halogen, —CN, —$NO_2$, —$CHF_2$, —$CF_3$, —OR, —SR, —N(R)$_2$, —S(O)$_2$R, —S(O)$_2$N(R)$_2$, —S(O)R, —S(O)N(R)$_2$, —C(O)R, —C(O)OR, —C(O)N(R)$_2$, —C(O)N(R)OR, —OC(O)R, —OC(O)N(R)$_2$, —N(R)C(O)OR, —N(R)C(O)R, —N(R)C(O)N(R)$_2$, —N(R)C(NR)N(R)$_2$, —N(R)N(R)$_2$, —N(R)S(O)$_2$N(R)$_2$, —N(R)S(O)$_2$R, —N=S(O)(R)$_2$, —S(NR)(O)R, —N(R)S(O)R, —N(R)CN, —P(O)(R)N(R)$_2$, —P(O)(R)OR, or —P(O)(R)$_2$; or an optionally substituted $C_{1-6}$ aliphatic;

Y is N, $N^+$—$O^-$, $NR^5$, $CR^5$, or C-L-$R^9$;

$R^5$ is hydrogen, oxo, halogen, —CN, —$NO_2$, —$CHF_2$, —$CF_3$, —OR, —SR, —N(R)$_2$, —S(O)$_2$R, —S(O)$_2$N(R)$_2$, —S(O)R, —S(O)N(R)$_2$, —C(O)R, —C(O)OR, —C(O)N(R)$_2$, —C(O)N(R)OR, —OC(O)R, —OC(O)N(R)$_2$, —N(R)C(O)OR, —N(R)C(O)R, —N(R)C(O)N(R)$_2$, —N(R)C(NR)N(R)$_2$, —N(R)N(R)$_2$, —N(R)S(O)$_2$N(R)$_2$, —N(R)S(O)$_2$R, —N=S(O)(R)$_2$, —S(NR)(O)R, —N(R)S(O)R, —N(R)CN, —P(O)(R)N(R)$_2$, —P(O)(R)OR, or —P(O)(R)$_2$; or an optionally substituted $C_{1-6}$ aliphatic;

$R^6$ is hydrogen or $C_{1-3}$ aliphatic; or $R^4$ and $R^6$ are optionally taken together with their intervening atoms to form a 5-6 membered partially unsaturated fused ring having, in addition to the nitrogen, 0-2 heteroatoms independently selected from nitrogen, oxygen and sulfur, wherein the fused ring is optionally substituted with u instances of $R^7$;

each $R^7$ is independently hydrogen, oxo, halogen, —CN, —$NO_2$, —$CHF_2$, —$CF_3$, —OR, —SR, —N(R)$_2$, —S(O)$_2$R, —S(O)$_2$N(R)$_2$, —S(O)R, —S(O)N(R)$_2$, —C(O)R, —C(O)OR, —C(O)N(R)$_2$, —C(O)N(R)OR, —OC(O)R, —OC(O)N(R)$_2$, —N(R)C(O)OR, —N(R)C(O)R, —N(R)C(O)N(R)$_2$, —N(R)C(NR)N(R)$_2$, —N(R)N(R)$_2$, —N(R)S(O)$_2$N(R)$_2$, —N(R)S(O)$_2$R, —N=S(O)(R)$_2$, —S(NR)(O)R, —N(R)S(O)R, —N(R)CN, —P(O)(R)N(R)$_2$, —P(O)(R)OR, or —P(O)(R)$_2$; or an optionally substituted $C_{1-6}$ aliphatic;

each $R^8$ is independently hydrogen, oxo, halogen, —CN, —$NO_2$, —$CHF_2$, —$CF_3$, —OR, —SR, —N(R)$_2$, —S(O)$_2$R, —S(O)$_2$N(R)$_2$, —S(O)R, —S(O)N(R)$_2$, —C(O)R, —C(O)OR, —C(O)N(R)$_2$, —C(O)N(R)OR, —OC(O)R, —OC(O)N(R)$_2$, —N(R)C(O)OR, —N(R)C(O)R, —N(R)C(O)N(R)$_2$, —N(R)C(NR)N(R)$_2$, —N(R)N(R)$_2$, —N(R)S(O)$_2$N(R)$_2$, —N(R)S(O)$_2$R, —N=S(O)(R)$_2$, —S(NR)(O)R, —N(R)S(O)R, —N(R)CN, —P(O)(R)N(R)$_2$, —P(O)(R)OR, or —P(O)(R)$_2$; or an optionally substituted $C_{1-6}$ aliphatic;

L is a covalent bond; or L is a $C_{1-4}$ bivalent saturated or unsaturated, straight or branched hydrocarbon chain wherein one or two methylene units of the chain are optionally and independently replaced by —C(R)$_2$—, —C(OR)(R)—, —N(R)—, —O—, —S—, —S(O)—, —S(O)$_2$—, —S(O)N(R)—, —N(R)S(O)—, —S(O)$_2$N(R)—, —N(R)S(O)$_2$—, —C(O)—, —C(O)O—, —OC(O)—, —C(O)N(R)—, —N(R)C(O)—, —C(O)N(R)O—, —ON(R)C(O)—, —OC(O)N(R)—, —N(R)C(O)O—, or —N(R)C(O)N(R)—;

$R^9$ is halogen, —CN, —$NO_2$, —OR, —SR, —N(R)$_2$, —S(O)$_2$R, —S(O)$_2$N(R)$_2$, —S(O)R, —S(O)N(R)$_2$, —$CF_2$R, —$CF_3$, —C(R)$_2$OR, —C(R)$_2$N(R)$_2$, —C(O)R, —C(O)OR, —C(O)N(R)$_2$, —C(O)N(R)OR, —OC(O)R, —OC(O)N(R)$_2$, —C(S)N(R)$_2$, —N(R)C(O)OR, —N(R)C(O)R, —N(R)C(O)N(R)$_2$, —N(R)C(NR)N(R)$_2$, —N(R)N(R)$_2$, —N(R)S(O)$_2$N(R)$_2$, —N(R)S(O)$_2$R, —N=S(O)(R)$_2$, —S(NR)(O)R, —N(R)S(O)R, —N(R)CN, —Si(OR)(R)$_2$, —Si(R)$_3$, —P(O)(R)N(R)$_2$, —P(O)(R)OR, or —P(O)(R)$_2$; or $R^9$ is an optionally substituted group selected from $C_{1-6}$ aliphatic; phenyl; a 3-7 membered saturated or partially unsaturated monocyclic carbocyclic ring; a 4-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; a 5-8 membered saturated or partially unsaturated bridged bicyclic ring having 0-3 heteroatoms selected from nitrogen, oxygen, and sulfur; a 6-10 membered saturated or partially unsaturated spiro bicyclic ring having 0-3 heteroatoms independently selected from nitrogen, oxygen, and sulfur; and an 8-10 membered partially aromatic or heteroaromatic bicyclic heterocyclic ring having 1-4 heteroatoms independently selected from nitrogen, oxygen, and sulfur;

each instance of $R^1$, $R^2$, $R^3$, $R^4$, $R^5$, $R^6$, $R^7$, $R^8$, and $R^9$ is independently and optionally substituted with v instances of $R^A$, wherein each $R^A$ is independently oxo, halogen, —CN, —$NO_2$, —OR, —SR, —N(R)$_2$, —S(O)$_2$R, —S(O)$_2$N(R)$_2$, —S(O)R, —S(O)N(R)$_2$, —C(R)$_2$OR, —C(O)R, —C(O)OR, —C(O)N(R)$_2$, —C(O)N(R)OR, —OC(O)R, —OC(O)N(R)$_2$, —N(R)C(O)OR, —N(R)C(O)R, —N(R)C(O)N(R)$_2$, —N(R)C(NR)N(R)$_2$, —N(R)N(R)$_2$, —N(R)S(O)$_2$N(R)$_2$, —N(R)S(O)$_2$R, —N=S(O)(R)$_2$, —S(NR)(O)R, —N(R)S(O)R, —N(R)CN, —P(O)(R)N(R)$_2$, —P(O)(R)OR, —P(O)(R)$_2$, or an optionally substituted group selected from $C_{1-6}$ aliphatic; phenyl; naphthyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; and a 6-11 membered saturated or partially unsaturated bicyclic heterocyclic ring having 1-2 heteroatoms independently selected from nitrogen, oxygen, and sulfur;

each R is independently hydrogen, —CN, halogen, or an optionally substituted group selected from $C_{1-6}$ aliphatic; phenyl; naphthyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic carbocyclic ring having 1-2 heteroatoms independently selected from nitrogen, oxygen, and sulfur; or:

two R groups on the same atom are optionally taken together with the atom to form an optionally substituted 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur;

m is 0, 1, 2, 3, 4, or 5;
n is 0, 1, 2, 3, or 4;
p is 0, 1, 2, 3, or 4;
q is 0, 1, 2, or 3;
t is 0 or 1;
u is 0, 1, 2, 3, or 4; and
each instance of v is independently 0, 1, 2, 3, 4, or 5; and wherein === denotes a single or double bond.

As defined generally above, Ring A is a 5-6-membered heteroaryl ring having 1-4 heteroatoms independently selected from nitrogen, oxygen, and sulfur; or a 5-6-membered saturated or partially unsaturated heterocyclic ring having 1-4 heteroatoms independently selected from nitrogen, oxygen, and sulfur.

In certain embodiments, Ring A is a 5-6-membered heteroaryl ring having 1-4 heteroatoms independently selected from nitrogen, oxygen, and sulfur.

In certain embodiments. Ring A is 5-6-membered saturated or partially unsaturated heterocyclic ring having 1-4 heteroatoms independently selected from nitrogen, oxygen, and sulfur.

In certain embodiments, Ring A is a 5 membered heteroaryl ring having 1-4 heteroatoms independently selected from nitrogen, oxygen, and sulfur.

In some embodiments, Ring A is a furanyl, imidazolyl, isothiazolyl, isoxazolyl, oxadiazolyl, oxazolyl, pyrazolyl, pyrrolyl, thiazolyl, thienyl, triazinyl, or triazolyl.

In certain embodiments, Ring A is selected from

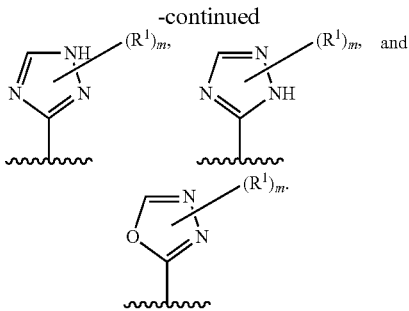

-continued

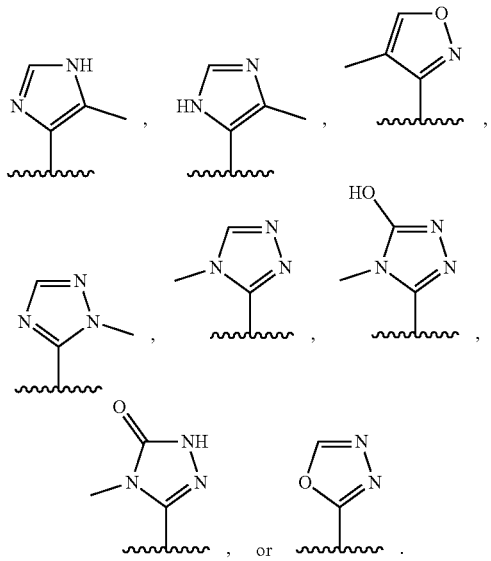

In certain embodiments, Ring A together with its $R^1$ substituents is

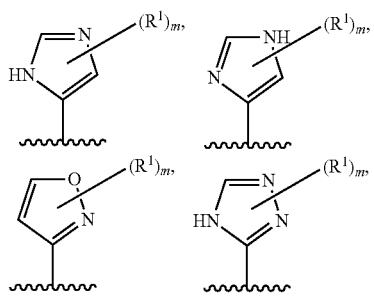

In certain embodiments, Ring A together with its $R^1$ substituents is

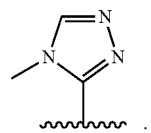 [SMILES: *c1nncn1C]

In some embodiments, Ring A is selected from those depicted in Table 1, below.

In some embodiments, Ring A together with its $R^1$ substituents is selected from those depicted in Table 1, below.

As defined generally above, each $R^1$ is independently hydrogen, oxo, halogen, —CN, —NO$_2$, —CHF$_2$, —CF$_3$, —OR, —SR, —N(R)$_2$, —S(O)$_2$R, —S(O)$_2$N(R)$_2$, —S(O)R, —S(O)N(R)$_2$, —C(O)R, —C(O)OR, —C(O)N(R)$_2$, —C(O)N(R)OR, —OC(O)R, —OC(O)N(R)$_2$, —N(R)C(O)OR, —N(R)C(O)R, —N(R)C(O)N(R)$_2$, —N(R)C(NR)N(R)$_2$, —N(R)N(R)$_2$, —N(R)S(O)$_2$N(R)$_2$, —N(R)S(O)$_2$R, —N=S(O)(R)$_2$, —S(NR)(O)R, —N(R)S(O)R, —N(R)CN, —P(O)(R)N(R)$_2$, —P(O)(R)OR, or —P(O)(R)$_2$; or an optionally substituted $C_{1-6}$ aliphatic.

In certain embodiments, $R^1$ is halogen, —CN, —NO$_2$, —CHF$_2$, —CF$_3$, —OR, —SR, —N(R)$_2$, —S(O)$_2$R, —S(O)₂N(R)₂, —S(O)R, —S(O)N(R)₂, —C(O)R, —C(O)OR, —C(O)N(R)₂, —C(O)N(R)OR, —OC(O)R, —OC(O)N(R)₂, —N(R)C(O)OR, —N(R)C(O)R, —N(R)C(O)N(R)₂, —N(R)C(NR)N(R)₂, —N(R)N(R)₂, —N(R)S(O)₂N(R)₂, —N(R)S(O)₂R, —N=S(O)(R)₂, —S(NR)(O)R, —N(R)S(O)R, —N(R)CN, —P(O)(R)N(R)₂, —P(O)(R)OR, or —P(O)(R)₂; or an optionally substituted C₁₋₆ aliphatic.

In certain embodiments, R¹ is halogen, —CN, —NO₂, —CHF₂, —CF₃, —OR, —N(R)₂, —C(O)R, —C(O)OR, —C(O)N(R)₂, —OC(O)R, —OC(O)N(R)₂, —N(R)C(O)OR, —N(R)C(O)R, —N(R)C(O)N(R)₂, —N(R)S(O)₂R, or —N(R)S(O)R; or an optionally substituted -Me, -Et, -Pr, -i-Pr, -n-Bu, -s-Bu, -t-Bu, straight chain or branched pentyl, or straight chain or branched hexyl.

In certain embodiments, R¹ is hydrogen, -Me, or —OH.

In certain embodiments, R¹ is oxo.

In some embodiments, R¹ is selected from those depicted in Table 1, below.

As defined generally above, Ring B is a divalent phenyl or a divalent 5-6 membered heteroaryl ring having 1-4 heteroatoms independently selected from nitrogen, oxygen, and sulfur.

In some embodiments, Ring B is a divalent phenyl, furanyl, imidazolyl, isothiazolyl, isoxazolyl, oxadiazolyl, oxazolyl, pyrimidinyl, pyrazinyl, pyrazolyl, pyridazinyl, pyridinyl, pyrimidinyl, pyrrolyl, thiazolyl, thienyl, triazinyl, or triazolyl.

In some embodiments, Ring B is a divalent phenyl, pyrazolyl, imidazolyl, or pyridinyl.

In some embodiments, Ring B is a divalent group selected from

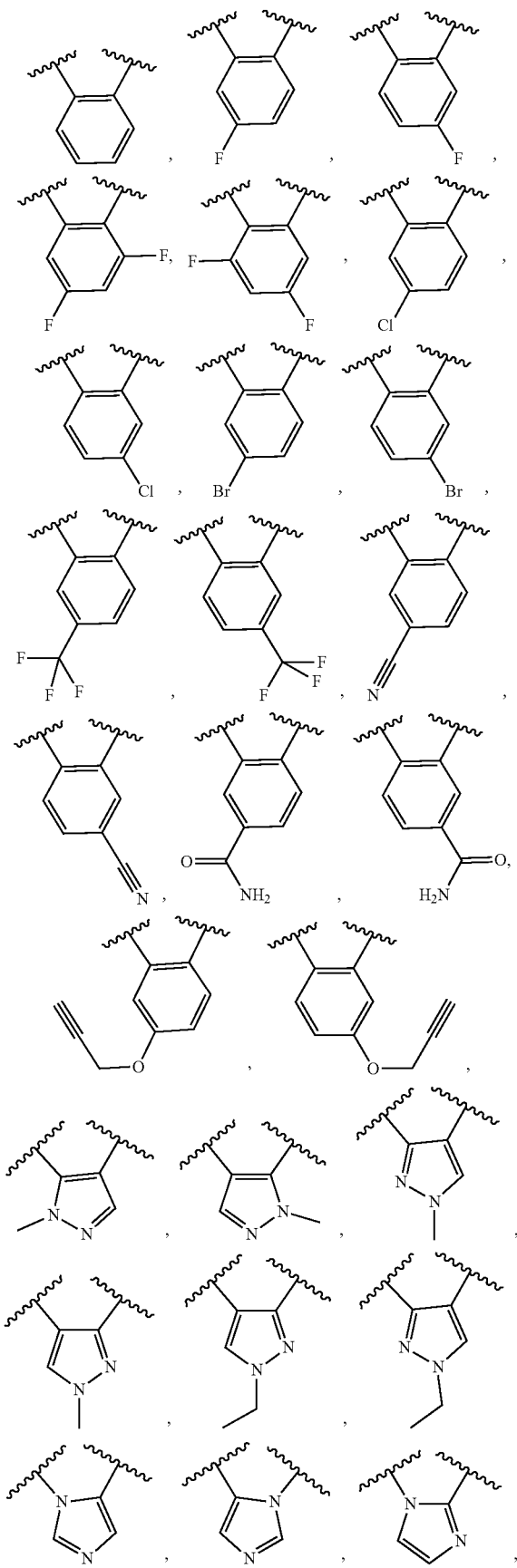

In certain embodiments, Ring B together with its R² substituents is

-continued

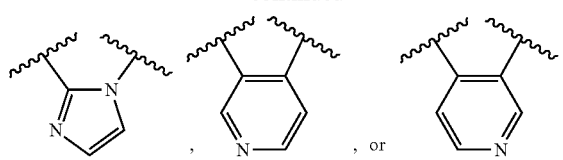, or

In certain embodiments, Ring B together with its R² substituents is selected from

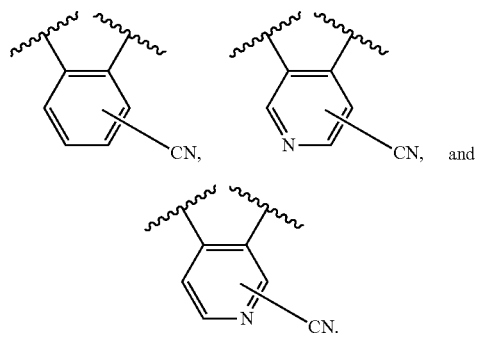

In certain embodiments, Ring B together with its R² substituents is

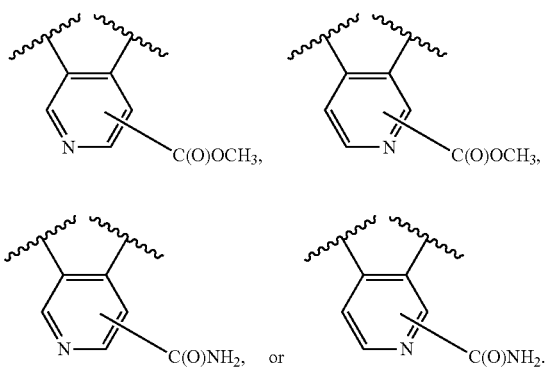

In certain embodiments, Ring B together with its R² substituents is

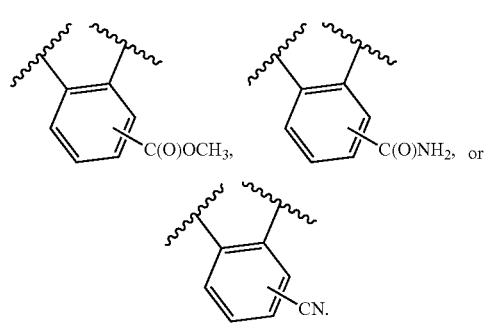

In certain embodiments, Ring B together with its R² substituents is

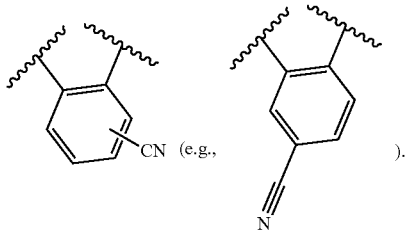

In certain embodiments, Ring B together with its R² substituents is

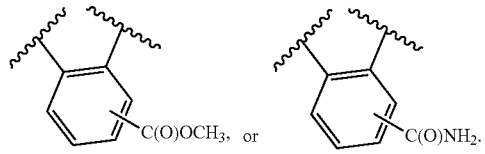

In certain embodiments, Ring B is selected from

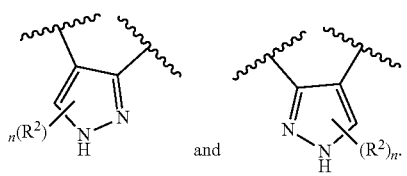

In certain embodiments, Ring B together with its R² substituents is selected from

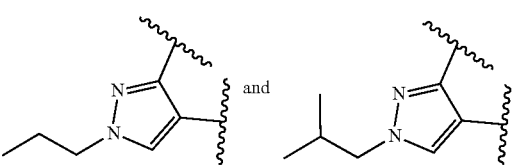

In some embodiments, Ring B is selected from those depicted in Table 1, below.

In some embodiments, Ring B together with its R² substituents is selected from those depicted in Table 1, below.

As defined generally above, each R² is independently hydrogen, oxo, halogen, —CN, —NO$_2$, —CHF$_2$, —CF$_3$, —OR, —SR, —N(R)$_2$, —S(O)$_2$R, —S(O)$_2$N(R)$_2$, —S(O)R, —S(O)N(R)$_2$, —C(O)R, —C(O)OR, —C(O)N(R)$_2$, —C(O)N(R)OR, —OC(O)R, —OC(O)N(R)$_2$, —N(R)C(O)OR, —N(R)C(O)R, —N(R)C(O)N(R)$_2$, —N(R)C(NR)N(R)$_2$, —N(R)N(R)$_2$, —N(R)S(O)$_2$N(R)$_2$, —N(R)S(O)$_2$R, —N=S(O)(R)$_2$, —S(NR)(O)R, —N(R)S(O)R, —N(R)CN, —P(O)(R)N(R)$_2$, —P(O)(R)OR, or —P(O)(R)$_2$; or an optionally substituted C$_{1-6}$ aliphatic.

In certain embodiments, R² is hydrogen, oxo, halogen, —CN, —NO$_2$, —CHF$_2$, —CF$_3$, —OR, —SR, —N(R)$_2$, —S(O)$_2$R, —S(O)$_2$N(R)$_2$, —S(O)R, —S(O)N(R)$_2$, —C(O) R, —C(O)OR, —C(O)N(R)$_2$, —C(O)N(R)OR, —OC(O)R, —OC(O)N(R)$_2$, —N(R)C(O)OR, —N(R)C(O)R, —N(R)C (O)N(R)$_2$, —N(R)C(NR)N(R)$_2$, —N(R)N(R)$_2$, —N(R)S (O)$_2$ N(R)$_2$, —N(R)S(O)$_2$R, —N=S(O)(R)$_2$, —S(NR)(O)

R, —N(R)S(O)R, —N(R)CN, —P(O)(R)N(R)$_2$, —P(O)(R) OR, or —P(O)(R)$_2$; or an optionally substituted C$_{1-6}$ aliphatic.

In certain embodiments, R$^2$ is halogen, —CN, —NO$_2$, —CHF$_2$, —CF$_3$, —OR, —SR, —N(R)$_2$, —S(O)$_2$R, —S(O)$_2$ N(R)$_2$, —S(O)R, —S(O)N(R)$_2$, —C(O)R, —C(O) OR, —C(O)N(R)$_2$, —OC(O)R, —OC(O)N(R)$_2$, —N(R)C (O)OR, —N(R)C(O)R, —N(R)C(O)N(R)$_2$, —N(R)S(O)$_2$R, —N(R)S(O)R, or an optionally substituted C$_{1-6}$ aliphatic.

In certain embodiments, R$^2$ is an optionally substituted -Me, -Et, -Pr, -i-Pr, -n-Bu, -s-Bu, -t-Bu, straight chain or branched pentyl, or straight chain or branched hexyl.

In certain embodiments, R$^2$ is hydrogen, -Me, -Et, —CF$_3$, —F, —Cl, —Br, —CN, or —C(O)NH$_2$.

In certain embodiments, when Ring B together with its R$^2$ substituents is

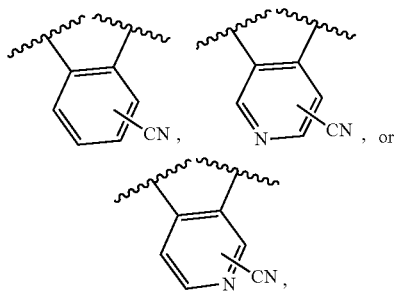

where t is 1.

In certain embodiments, Ring B together with its R$^2$ substituents is

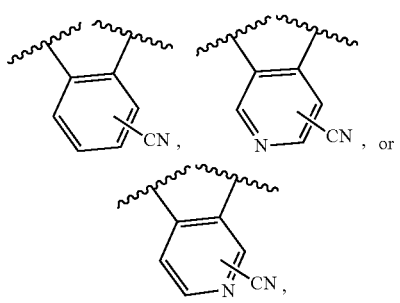

where t is 1.

In certain embodiments, when Ring B together with its R$^2$ substituents is

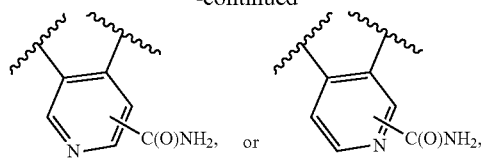

where t is 1.

In certain embodiments, Ring B together with its R$^2$ substituents is

where t is 1.

In some embodiments, R$^2$ is selected from those depicted in Table 1, below.

As defined generally above, Ring C is a divalent phenyl or a divalent 5-6 membered heteroaryl ring having 1-4 heteroatoms independently selected from nitrogen, oxygen, and sulfur.

In some embodiments, Ring C is a divalent phenyl or a divalent 5-6 membered heteroaryl ring having 1-4 heteroatoms independently selected from nitrogen, oxygen, and sulfur.

In some embodiments, Ring C is a divalent phenyl, pyrimidinyl, pyrazinyl, pyridazinyl, pyridinyl, or pyrimidinyl.

In certain embodiments, Ring C is

-continued
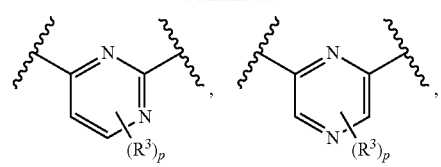
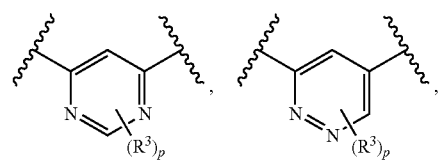
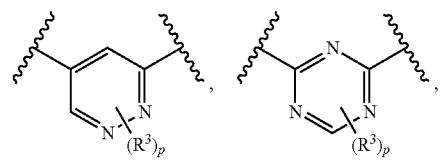
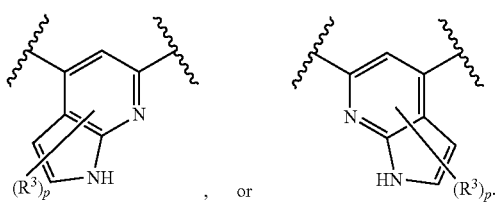
In certain embodiments, Ring C is
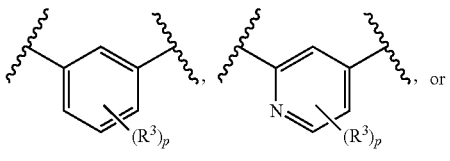
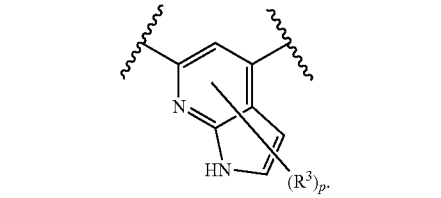
In some embodiments, Ring C is selected from those depicted in Table 1, below.
In certain embodiments, Ring C together with its R³ substituents is
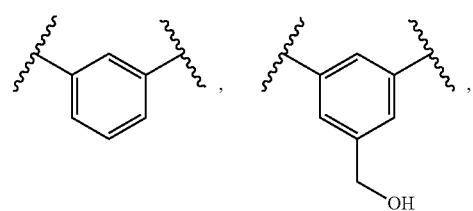
-continued
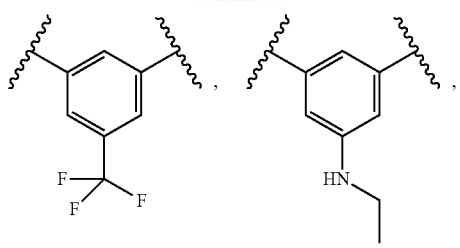
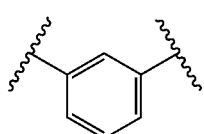
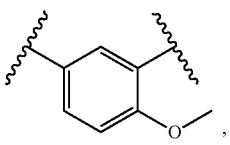
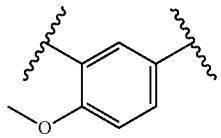
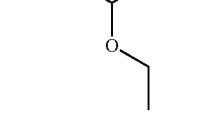
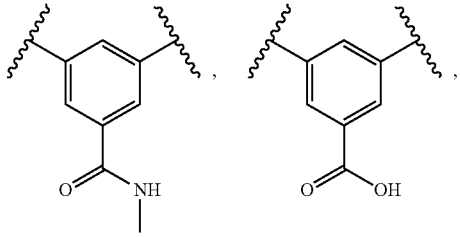
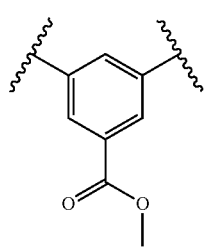
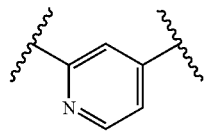, 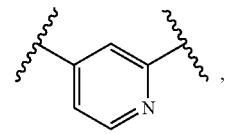,
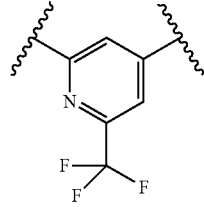 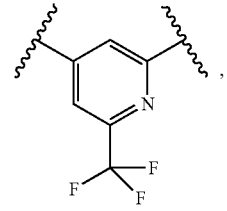

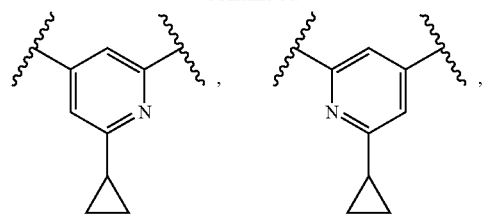
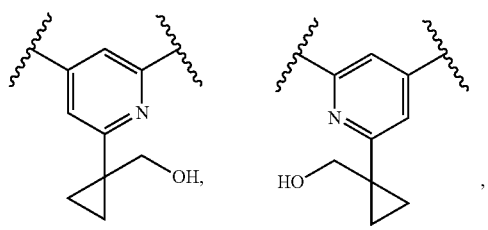
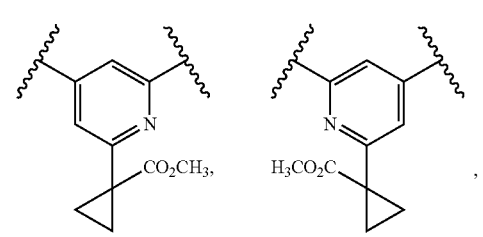
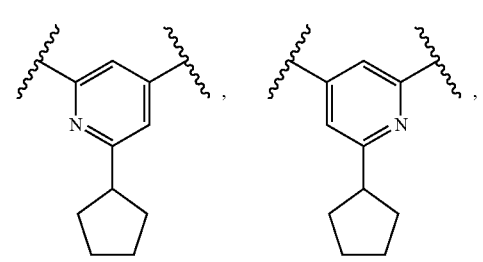
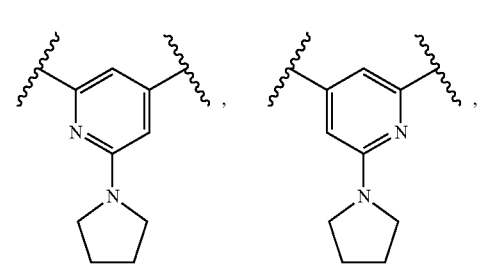
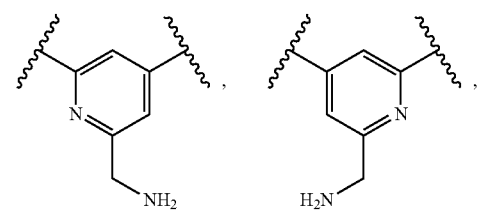
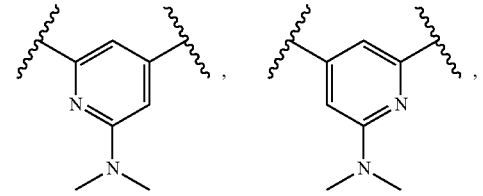
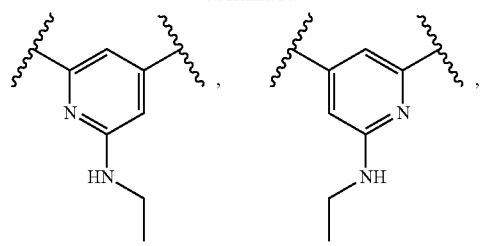
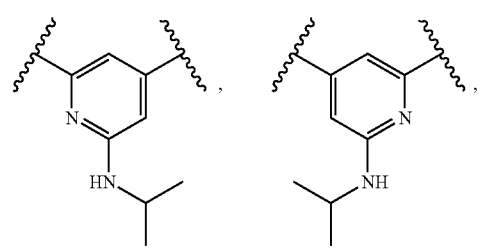
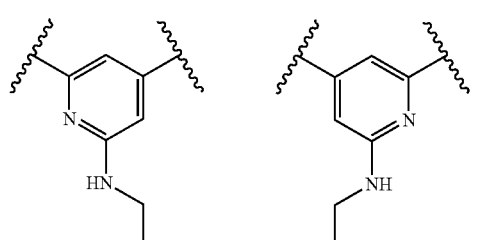
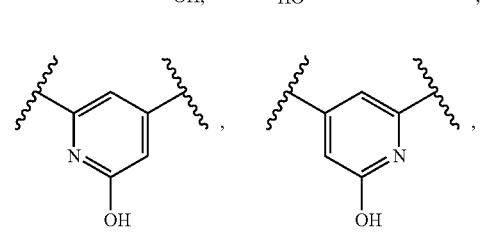
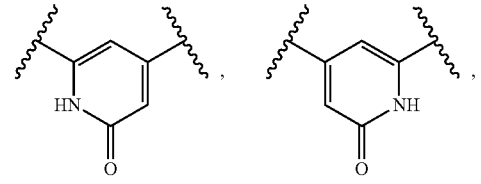
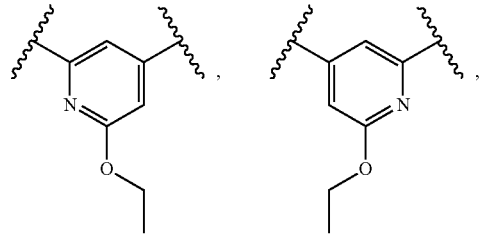
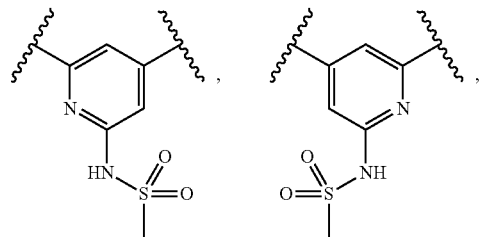

-continued

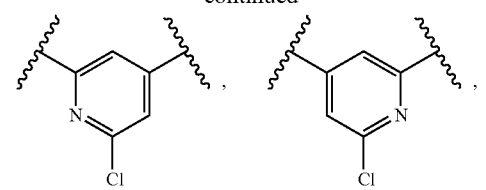

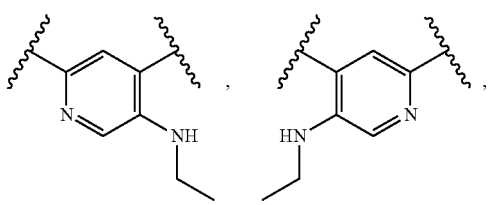

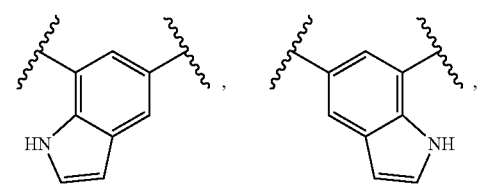

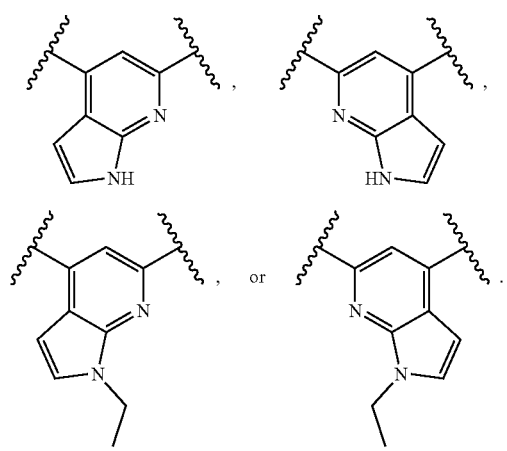

In certain embodiments, Ring C together with its R³ substituents is

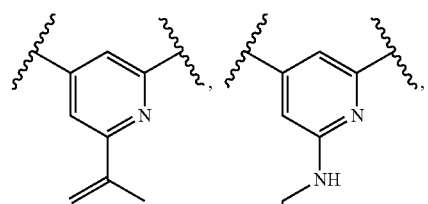

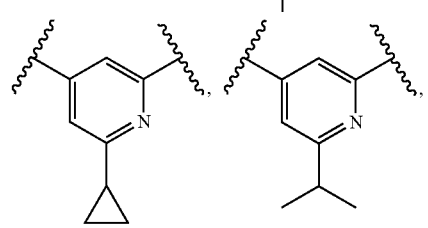

-continued

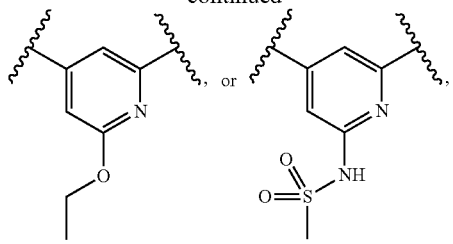

In certain embodiments, Ring C together with its R³ substituents is

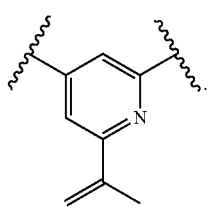 [SMILES: *c1cc(*)nc(C(=C)C)c1]

In certain embodiments, Ring C together with its R³ substituents is

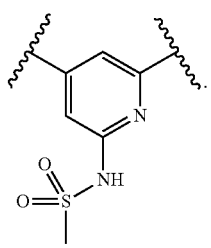 [SMILES: *c1cc(*)nc(NS(C)(=O)=O)c1]

In certain embodiments, Ring C together with its R³ substituents is

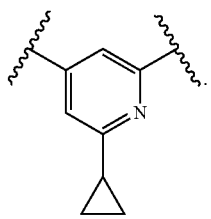 [SMILES: *c1cc(*)nc(C2CC2)c1]

In certain embodiments, Ring C together with its R³ substituents is

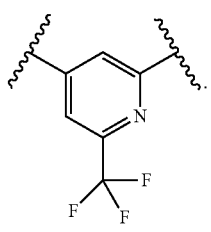 [SMILES: *c1cc(*)nc(C(F)(F)F)c1]

In certain embodiments, Ring C together with its R³ substituents is

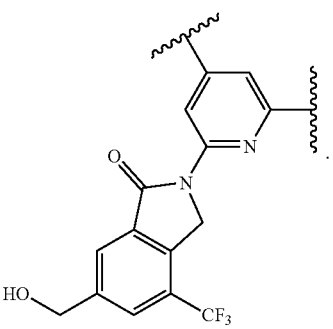 [SMILES: *c1cc(*)nc(N2Cc3c(cc(CO)cc3C(F)(F)F)C2=O)c1]

In some embodiments, Ring C together with its $R^3$ substituents is selected from those depicted in Table 1, below.

As defined generally above, each $R^3$ is independently hydrogen, oxo, halogen, —CN, —NO$_2$, —CHF$_2$, —CF$_3$, —OR, —SR, —N(R)$_2$, —S(O)$_2$R, —S(O)$_2$N(R)$_2$, —S(O)R, —S(O)N(R)$_2$, —C(O)R, —C(O)OR, —C(O)N(R)$_2$, —C(O)N(R)OR, —OC(O)R, —OC(O)N(R)$_2$, —N(R)C(O)OR, —N(R)C(O)R, —N(R)C(O)N(R)$_2$, —N(R)C(NR)N(R)$_2$, —N(R)N(R)$_2$, —N(R)S(O)$_2$N(R)$_2$, —N(R)S(O)$_2$R, —N=S(O)(R)$_2$, —S(NR)(O)R, —N(R)S(O)R, —N(R)CN, —P(O)(R)N(R)$_2$, —P(O)(R)OR, or —P(O)(R)$_2$; or an optionally substituted group selected from C$_{1-6}$ aliphatic; a phenyl ring; a 3-7 membered saturated or partially unsaturated monocyclic carbocyclic ring; a 5-6 membered monocyclic heteroaryl ring having 1-4 heteroatoms independently selected from nitrogen, oxygen, and sulfur; and a 4-8 membered saturated or partially unsaturated monocyclic heterocyclic ring having 1-2 heteroatoms independently selected from nitrogen, oxygen, and sulfur, or two $R^3$ groups, and the atoms to which each $R^3$ group is attached, are optionally taken together to form a fused 3-7 membered saturated or partially unsaturated monocyclic carbocyclic ring; a fused 5-6 membered monocyclic aryl ring; a fused 3-7 membered saturated or partially unsaturated monocyclic heterocyclic ring having 1-2 heteroatoms independently selected from nitrogen, oxygen, phosphorous, silicon and sulfur; or a fused 5-6 membered monocyclic heteroaryl ring having 1-4 heteroatoms independently selected from nitrogen, oxygen, and sulfur.

In certain embodiments, $R^3$ is hydrogen, oxo, halogen, —CN, —NO$_2$, —CHF$_2$, —CF$_3$, —OR, —SR, —N(R)$_2$, —S(O)$_2$R, —S(O)$_2$N(R)$_2$, —S(O)R, —S(O)N(R)$_2$, —C(O)R, —C(O)OR, —C(O)N(R)$_2$, —C(O)N(R)OR, —OC(O)R, —OC(O)N(R)$_2$, —N(R)C(O)OR, —N(R)C(O)R, —N(R)C(O)N(R)$_2$, —N(R)C(NR)N(R)$_2$, —N(R)N(R)$_2$, —N(R)S(O)$_2$ N(R)$_2$, —N(R)S(O)$_2$R, —N=S(O)(R)$_2$, —S(NR)(O)R, —N(R)S(O)R, —N(R)CN, —P(O)(R)N(R)$_2$, —P(O)(R)OR, or —P(O)(R)$_2$; or an optionally substituted group selected from C$_{1-6}$ aliphatic; a phenyl ring; a 3-7 membered saturated or partially unsaturated monocyclic carbocyclic ring; a 5-6 membered monocyclic heteroaryl ring having 1-4 heteroatoms independently selected from nitrogen, oxygen, and sulfur; and a 4-8 membered saturated or partially unsaturated monocyclic heterocyclic ring having 1-2 heteroatoms independently selected from nitrogen, oxygen, and sulfur.

In certain embodiments, $R^3$ is an optionally substituted 8-10 membered partially unsaturated or heteroaromatic bicyclic ring having 1-4 heteroatoms independently selected from nitrogen, oxygen, and sulfur.

In certain embodiments, two $R^3$ groups, and the atoms to which each $R^3$ group is attached, are taken together to form a fused 3-7 membered saturated or partially unsaturated monocyclic carbocyclic ring; a fused 5-6 membered monocyclic aryl ring; a fused 3-7 membered saturated or partially unsaturated monocyclic heterocyclic ring having 1-2 heteroatoms independently selected from nitrogen, oxygen, phosphorous, silicon and sulfur; or a fused 5-6 membered monocyclic heteroaryl ring having 1-4 heteroatoms independently selected from nitrogen, oxygen, and sulfur.

In certain embodiments, $R^3$ is hydrogen, oxo, halogen, —CN, —NO$_2$, —OR, —SR, —N(R)$_2$, —S(O)$_2$R, —S(O)$_2$ N(R)$_2$, —S(O)R, —S(O)N(R)$_2$, —C(O)R, —C(O)OR, —C(O)N(R)$_2$, —C(O)N(R)OR, —OC(O)R, —OC(O) N(R)$_2$, —N(R)C(O)OR, —N(R)C(O)R, —N(R)C(O)N(R)$_2$, —N(R)C(NR)N(R)$_2$, —N(R)N(R)$_2$, —N(R)S(O)$_2$N(R)$_2$, —N(R)S(O)$_2$R, —N=S(O)(R)$_2$, —S(NR)(O)R, —N(R)S (O)R, —N(R)CN; or an optionally substituted C$_{1-6}$ aliphatic; or an optionally substituted 3-7 membered saturated or partially unsaturated monocyclic carbocyclic ring.

In certain embodiments, each $R^3$ is independently —H, halogen, —OR, —NR$_2$, —C(O)R, —C(O)OR, —C(O)NR$_2$, —C(O)N(R)OR, —N(R)C(O)OR, —N(R)C(O)R, —N(R)C (O)NR$_2$, —N(R)S(O)$_2$R, or —N(R)S(O)R; or each instance of $R^3$ is independently an optionally substituted C$_{1-6}$ aliphatic; or a 3-7 membered saturated or partially unsaturated monocyclic carbocyclic ring.

In certain embodiments, $R^3$ is hydrogen, oxo, -Me, -Et, —Pr, -i-Pr, straight chain or branched butyl, straight chain or branched pentyl, straight chain or branched hexyl, —CF$_3$, —F, —Cl, —Br, —OH, —OMe,

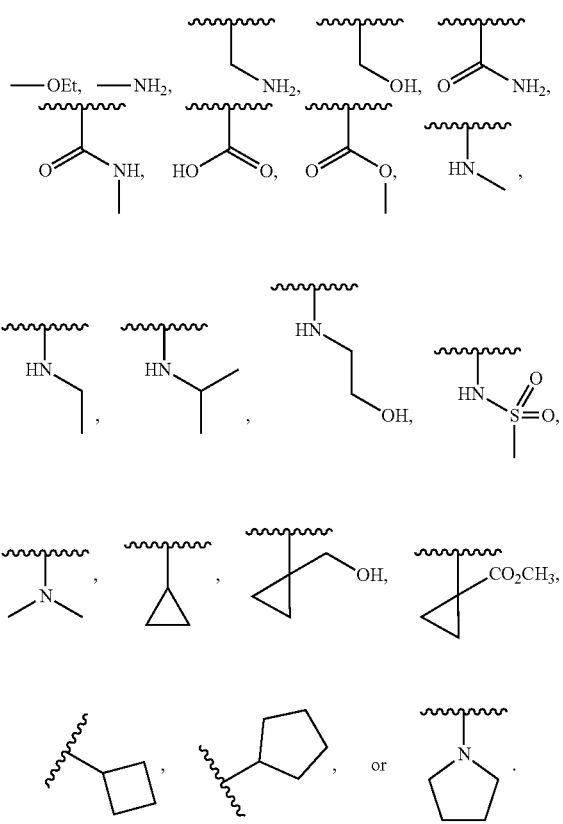

In certain embodiments, R³ is

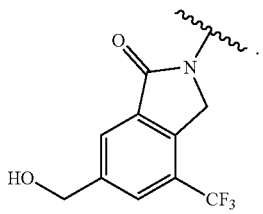 [SMILES: *N1Cc2c(cc(CO)cc2C(F)(F)F)C1=O]

In certain embodiments, R³ is hydrogen, -Me, -Et, —CF₃, —Cl, —OH, —OMe, —OEt,

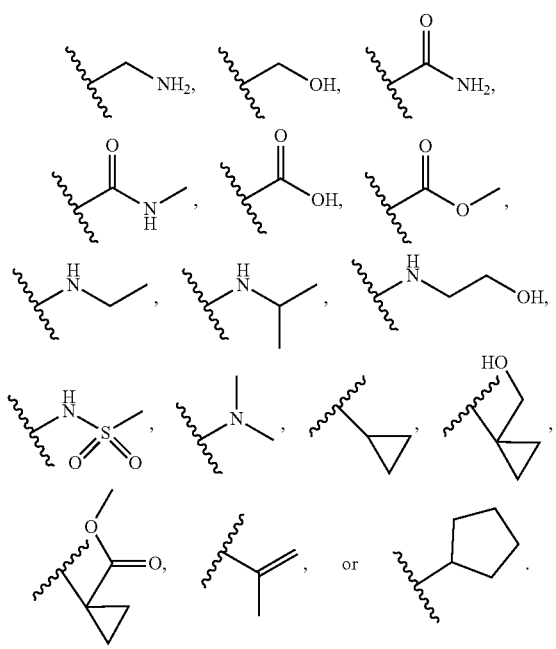

In certain embodiments, R³ is

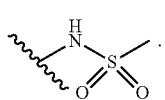

In certain embodiments, R³ is

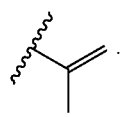

In certain embodiments, R³ is

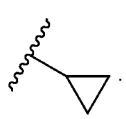

In certain embodiments, R³ is —CF₃.

In some embodiments, R³ is selected from those depicted in Table 1, below.

As defined generally above, X is N, N⁺—O⁻, NR⁴, CR⁴, or C-L-R⁹.

In certain embodiments, X is N. In certain embodiments, X is N⁺—O⁻. In certain embodiments, X is NR⁴. In certain embodiments, X is NMe. In certain embodiments, X is CR⁴. In certain embodiments, X is CH. In certain embodiments, X is C-L-R⁹.

In some embodiments, X is selected from those depicted in Table 1, below.

As defined generally above, R⁴ is hydrogen, oxo, halogen, —CN, —NO₂, —CHF₂, —CF₃, —OR, —SR, —N(R)₂, —S(O)₂R, —S(O)₂N(R)₂, —S(O)R, —S(O)N(R)₂, —C(O)R, —C(O)OR, —C(O)N(R)₂, —C(O)N(R)OR, —OC(O)R, —OC(O)N(R)₂, —N(R)C(O)OR, —N(R)C(O)R, —N(R)C(O)N(R)₂, —N(R)C(NR)N(R)₂, —N(R)N(R)₂, —N(R)S(O)₂N(R)₂, —N(R)S(O)₂R, —N=S(O)(R)₂, —S(NR)(O)R, —N(R)S(O)R, —N(R)CN, —P(O)(R)N(R)₂, —P(O)(R)OR, or —P(O)(R)₂; or an optionally substituted C₁₋₆ aliphatic.

In certain embodiments, R⁴ is hydrogen, oxo, halogen, —CN, —NO₂, —CHF₂, —CF₃, —OR, —SR, —N(R)₂, —S(O)₂R, —S(O)₂N(R)₂, —S(O)R, —S(O)N(R)₂, —C(O)R, —C(O)OR, —C(O)N(R)₂, —C(O)N(R)OR, —OC(O)R, —OC(O)N(R)₂, —N(R)C(O)OR, —N(R)C(O)R, —N(R)C(O)N(R)₂, —N(R)C(NR)N(R)₂, —N(R)N(R)₂, —N(R)S(O)₂N(R)₂, —N(R)S(O)₂R, —N=S(O)(R)₂, —S(NR)(O)R, —N(R)S(O)R, —N(R)CN, —P(O)(R)N(R)₂, —P(O)(R)OR, or —P(O)(R)₂; or an optionally substituted C₁₋₆ aliphatic.

In certain embodiments, R⁴ is hydrogen.

In some embodiments, R⁴ is —OH, —CF₃, —CH₂OH, —CH₂NH₂, or methyl.

In some embodiments, R⁴ is oxo.

In some embodiments, R⁴ is selected from those depicted in Table 1, below.

As defined generally above, Y is N, N⁺—O⁻, NR⁵, CR⁵ or C-L-R⁹.

In certain embodiments, Y is N. In certain embodiments, Y is N⁺—O⁻. In certain embodiments, Y is NR⁵. In certain embodiments, Y is NH. In certain embodiments, Y is NMe. In certain embodiments, Y is

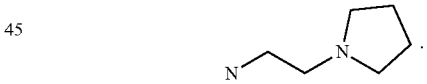

In certain embodiments, Y is CR⁵. In certain embodiments, Y is CH. In certain embodiments Y is C-L-R⁹.

In some embodiments, Y is selected from those depicted in Table 1, below.

As defined generally above, R⁵ is hydrogen, oxo, halogen, —CN, —NO₂, —CHF₂, —CF₃, —OR, —SR, —N(R)₂, —S(O)₂R, —S(O)₂N(R)₂, —S(O)R, —S(O)N(R)₂, —C(O)R, —C(O)OR, —C(O)N(R)₂, —C(O)N(R)OR, —OC(O)R, —OC(O)N(R)₂, —N(R)C(O)OR, —N(R)C(O)R, —N(R)C(O)N(R)₂, —N(R)C(NR)N(R)₂, —N(R)N(R)₂, —N(R)S(O)₂N(R)₂, —N(R)S(O)₂R, —N=S(O)(R)₂, —S(NR)(O)R, —N(R)S(O)R, —N(R)CN, —P(O)(R)N(R)₂, —P(O)(R)OR, or —P(O)(R)₂; or an optionally substituted C₁₋₆ aliphatic.

In certain embodiments, R⁵ is hydrogen, oxo, halogen, —CN, —NO₂, —CHF₂, —CF₃, —OR, —SR, —N(R)₂, —S(O)₂R, —S(O)₂N(R)₂, —S(O)R, —S(O)N(R)₂, —C(O)R, —C(O)OR, —C(O)N(R)₂, —C(O)N(R)OR, —OC(O)R, —OC(O)N(R)₂, —N(R)C(O)OR, —N(R)C(O)R, —N(R)C (O)N(R)₂, —N(R)C(NR)N(R)₂, —N(R)N(R)₂, —N(R)S(O)₂N(R)₂, —N(R)S(O)₂R, —N=S(O)(R)₂, —S(NR)(O)R, —N(R)S(O)R, —N(R)CN, —P(O)(R)N(R)₂, —P(O)(R)OR, or —P(O)(R)₂; or an optionally substituted C₁₋₆ aliphatic.

In certain embodiments, R⁵ is hydrogen.

In some embodiments, R⁵ is —OH, —CF₃, —CH₂OH, —CH₂NH₂, or methyl.

In some embodiments, R⁵ is oxo.

In certain embodiments, R⁵ is

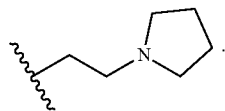 [SMILES: *CCN1CCCC1]

In some embodiments, R⁵ is selected from those depicted in Table 1, below.

As defined generally above, R⁶ is hydrogen or C₁₋₃ aliphatic; or R⁴ and R⁶ are optionally taken together with their intervening atoms to form a 5-6 membered partially unsaturated fused ring having, in addition to the nitrogen, 0-2 heteroatoms independently selected from nitrogen, oxygen and sulfur, wherein the fused ring is optionally substituted with u instances of R⁷.

In certain embodiments, R⁶ is hydrogen or C₁₋₃ aliphatic; or R⁴ and R⁶ are optionally taken together with their intervening atoms to form a 5-6 membered partially unsaturated fused ring having, in addition to the nitrogen, 0-2 heteroatoms independently selected from nitrogen, oxygen and sulfur, wherein the fused ring is optionally substituted with u instances of R⁷.

In certain embodiments, R⁶ is hydrogen. In certain embodiments, R is methyl. In certain embodiments, R⁶ is ethyl.

In certain embodiments, R⁴ and R⁶ are taken together with their intervening atoms to form a 5-6 membered partially unsaturated fused ring having, in addition to the nitrogen, 0-2 heteroatoms independently selected from nitrogen, oxygen and sulfur, wherein the fused ring is optionally substituted with u instances of R⁷.

In certain embodiments, R⁴ and R⁶ are taken together with their intervening atoms to form a 5 membered partially unsaturated fused ring having, in addition to the nitrogen, 0 heteroatoms.

In certain embodiments, R⁴ and R⁶ are taken together with their intervening atoms to form

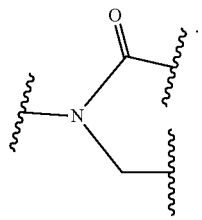 [SMILES: *CN(*)C(*)=O]

In some embodiments, R⁶ is selected from those depicted in Table 1, below.

In some embodiments, the combination of R⁴ and R⁶ together with their intervening atoms is selected from those depicted in Table 1, below.

As defined generally above, each R⁷ is independently hydrogen, oxo, halogen, —CN, —NO₂, —CHF₂, —CF₃, —OR, —SR, —N(R)₂, —S(O)₂R, —S(O)₂N(R)₂, —S(O)R, —S(O)N(R)₂, —C(O)R, —C(O)OR, —C(O)N(R)₂, —C(O)N(R)OR, —OC(O)R, —OC(O)N(R)₂, —N(R)C(O)OR, —N(R)C(O)R, —N(R)C(O)N(R)₂, —N(R)C(NR)N(R)₂, —N(R)N(R)₂, —N(R)S(O)₂N(R)₂, —N(R)S(O)₂R, —N=S(O)(R)₂, —S(NR)(O)R, —N(R)S(O)R, —N(R)CN, —P(O)(R)N(R)₂, —P(O)(R)OR, or —P(O)(R)₂; or an optionally substituted C₁₋₆ aliphatic.

In some embodiments, R⁷ is hydrogen, oxo, halogen, —CN, —NO₂, —CHF₂, —CF₃, —OR, —SR, —N(R)₂, —S(O)₂R, —S(O)₂N(R)₂, —S(O)R, —S(O)N(R)₂, —C(O)R, —C(O)OR, —C(O)N(R)₂, —C(O)N(R)OR, —OC(O)R, —OC(O)N(R)₂, —N(R)C(O)OR, —N(R)C(O)R, —N(R)C(O)N(R)₂, —N(R)C(NR)N(R)₂, —N(R)N(R)₂, —N(R)S(O)₂N(R)₂, —N(R)S(O)₂R, —N=S(O)(R)₂, —S(NR)(O)R, —N(R)S(O)R, —N(R)CN, —P(O)(R)N(R)₂, —P(O)(R)OR, or —P(O)(R)₂; or an optionally substituted C₁₋₆ aliphatic.

In some embodiments, R⁷ is hydrogen. In some embodiments, R⁷ is methyl.

In some embodiments, R⁷ is selected from those depicted in Table 1, below.

As defined generally above, each R⁷ is independently hydrogen, oxo, halogen, —CN, —NO₂, —CHF₂, —CF₃, —OR, —SR, —N(R)₂, —S(O)₂R, —S(O)₂N(R)₂, —S(O)R, —S(O)N(R)₂, —C(O)R, —C(O)OR, —C(O)N(R)₂, —C(O)N(R)OR, —OC(O)R, —OC(O)N(R)₂, —N(R)C(O)OR, —N(R)C(O)R, —N(R)C(O)N(R)₂, —N(R)C(NR)N(R)₂, —N(R)N(R)₂, —N(R)S(O)₂N(R)₂, —N(R)S(O)₂R, —N=S(O)(R)₂, —S(NR)(O)R, —N(R)S(O)R, —N(R)CN, —P(O)(R)N(R)₂, —P(O)(R)OR, or —P(O)(R)₂; or an optionally substituted C₁₋₆ aliphatic.

In some embodiments, R⁸ is hydrogen, oxo, halogen, —CN, —NO₂, —CHF₂, —CF₃, —OR, —SR, —N(R)₂, —S(O)₂R, —S(O)₂N(R)₂, —S(O)R, —S(O)N(R)₂, —C(O)R, —C(O)OR, —C(O)N(R)₂, —C(O)N(R)OR, —OC(O)R, —OC(O)N(R)₂, —N(R)C(O)OR, —N(R)C(O)R, —N(R)C(O)N(R)₂, —N(R)C(NR)N(R)₂, —N(R)N(R)₂, —N(R)S(O)₂N(R)₂, —N(R)S(O)₂R, —N=S(O)(R)₂, —S(NR)(O)R, —N(R)S(O)R, —N(R)CN, —P(O)(R)N(R)₂, —P(O)(R)OR, or —P(O)(R)₂; or an optionally substituted C₁₋₆ aliphatic.

In some embodiments, R⁸ is hydrogen.

In some embodiments, R⁸ is halogen, —OH, —OCH₃, —NHCH₃, —CF₃, —CH₂OH, —CH₂NH₂, or methyl.

In some embodiments, R⁸ is halogen, —OCH₃, —NHCH₃, or —CH₂NH₂.

In some embodiments, R⁸ is halogen. In some embodiments, R⁸ is —OH. In some embodiments, R⁸ is —OCH₃. In some embodiments, R⁸ is —NHCH₃. In some embodiments, R⁸ is —CF₃. In some embodiments, R⁸ is —CH₂OH. In some embodiments, R⁸ is —CH₂NH₂. In some embodiments, R⁸ is methyl.

In some embodiments, R⁸ is —C(O)R. In some embodiments, R⁸ is C(O)CH₃.

In some embodiments, R⁸ is oxo.

In some embodiments, R⁸ is fluoro. In some embodiments, R⁸ is chloro. In some embodiments, R⁸ is bromo. In some embodiments, R⁸ is —CF₃.

In some embodiments, R⁸ is selected from those depicted in Table 1, below.

As defined generally above, L is a covalent bond; or L is a C₁₋₄ bivalent saturated or unsaturated, straight or branched hydrocarbon chain wherein one or two methylene units of the chain are optionally and independently replaced by —C(R)₂—, —N(R)—, —O—, —S—, —S(O)—, —S(O)₂—, —S(O)N(R)—, —N(R)S(O)—, —S(O)₂N(R)—, —N(R)S(O)₂—, —C(O)—, —C(O)O—, —OC(O)—, —C(O)N(R)—, —N(R)C(O)—, —C(O)N(R)O—, —ON(R)C(O)—, —OC(O)N(R)—, —N(R)C(O)O—, or —N(R)C(O)N(R)—.

In certain embodiments, L is a covalent bond. In certain embodiments, L is a $C_{1-4}$ bivalent saturated or unsaturated, straight or branched hydrocarbon chain wherein one or two methylene units of the chain are optionally and independently replaced by —C(R)₂—, —N(R)—, —O—, —S—, —S(O)—, —S(O)₂—, —S(O)N(R)—, —N(R)S(O)—, —S(O)₂N(R)—, —N(R)S(O)₂—, —C(O)—, —C(O)O—, —OC(O)—, —C(O)N(R)—, —N(R)C(O)—, —C(O)N(R)O—, —ON(R)C(O)—, —OC(O)N(R)—, —N(R)C(O)O—, or —N(R)C(O)N(R)—.

In certain embodiments, L is —CH₂—, —CHMe—, —CMe₂-, —CH₂CH₂—. —O—, —CH₂O—, —OCH₂—, —CH₂OCH₂—, —CH₂CH₂OCH₂—, —CH₂OCH₂CH₂—, —OCH₂CH₂—, —CH₂CH₂O—, —CH₂NH—, —CH₂NHCH₂—, —CH₂NHCH₂CH₂—, —NHCH₂—, or —C(O)—.

In certain embodiments, L is —CH₂—.

In some embodiments, L is selected from those depicted in Table 1, below.

As defined generally above, $R^9$ is halogen, —CN, —NO₂, —OR, —SR, —N(R)₂, —S(O)₂R, —S(O)₂N(R)₂, —S(O)R, —S(O)N(R)₂, —CF₂R, —CF₃, —C(R)₂OR, —C(R)₂N(R)₂, —C(O)R, —C(O)OR, —C(O)N(R)₂, —C(O)N(R)OR, —OC(O)R, —OC(O)N(R)₂, —C(S)N(R)₂, —N(R)C(O)OR, —N(R)C(O)R, —N(R)C(O)N(R)₂, —N(R)C(NR)N(R)₂, —N(R)N(R)₂, —N(R)S(O)₂N(R)₂, —N(R)S(O)₂R, —N=S(O)(R)₂, —S(NR)(O)R, —N(R)S(O)R, —N(R)CN, —Si(OR)(R)₂, —Si(R)₃, —P(O)(R)N(R)₂, —P(O)(R)OR, or —P(O)(R)₂; or $R^9$ is an optionally substituted group selected from $C_{1-6}$ aliphatic; phenyl; a 3-7 membered saturated or partially unsaturated monocyclic carbocyclic ring; a 4-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; a 5-8 membered saturated or partially unsaturated bridged bicyclic ring having 0-3 heteroatoms selected from nitrogen, oxygen, and sulfur; a 6-10 membered saturated or partially unsaturated spiro bicyclic ring having 0-3 heteroatoms independently selected from nitrogen, oxygen, and sulfur; and an 8-10 membered partially aromatic or heteroaromatic bicyclic heterocyclic ring having 1-4 heteroatoms independently selected from nitrogen, oxygen, and sulfur.

In certain embodiments, $R^9$ is halogen, —CN, —NO₂, —OR, —SR, —N(R)₂, —S(O)₂R, —S(O)₂N(R)₂, —S(O)R, —S(O)N(R)₂, —CF₂R, —CF₃, —C(R)₂OR, —C(R)₂N(R)₂, —C(O)R, —C(O)OR, —C(O)N(R)₂, —C(O)N(R)OR, —OC(O)R, —OC(O)N(R)₂, —C(S)N(R)₂, —N(R)C(O)OR, —N(R)C(O)R, —N(R)C(O)N(R)₂, —N(R)C(NR)N(R)₂, —N(R)N(R)₂, —N(R)S(O)₂N(R)₂, —N(R)S(O)₂R, —N=S(O)(R)₂, —S(NR)(O)R, —N(R)S(O)R, —N(R)CN, —Si(OR)(R)₂, —Si(R)₃, —P(O)(R)N(R)₂, —P(O)(R)OR, or —P(O)(R)₂.

In certain embodiments, $R^9$ is methyl, i-Pr, OCH₃, or —OH.

In certain embodiments, $R^9$ is

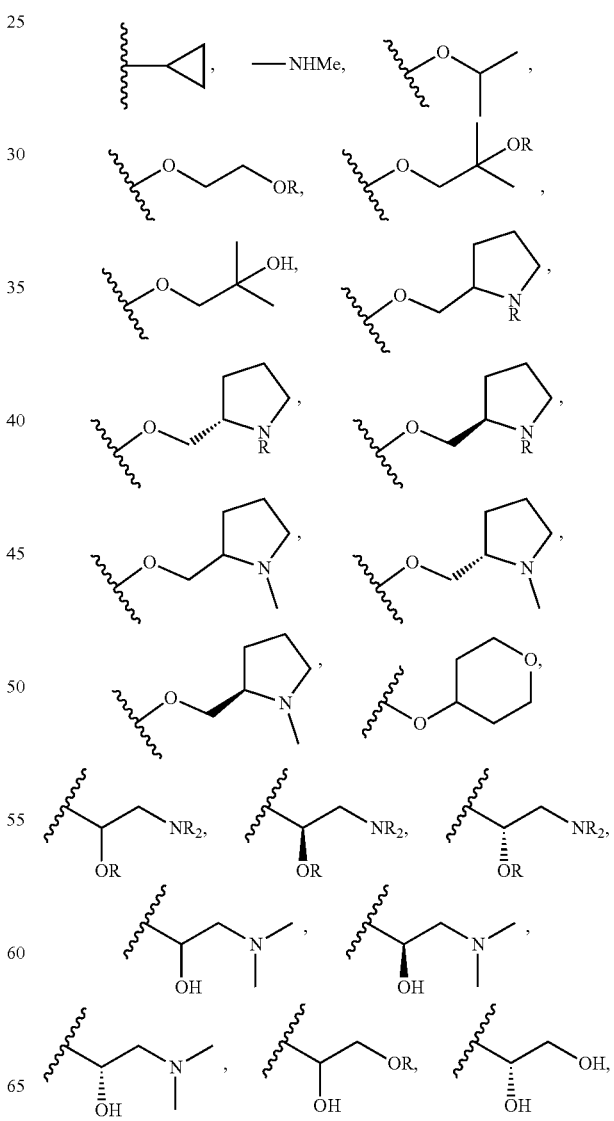

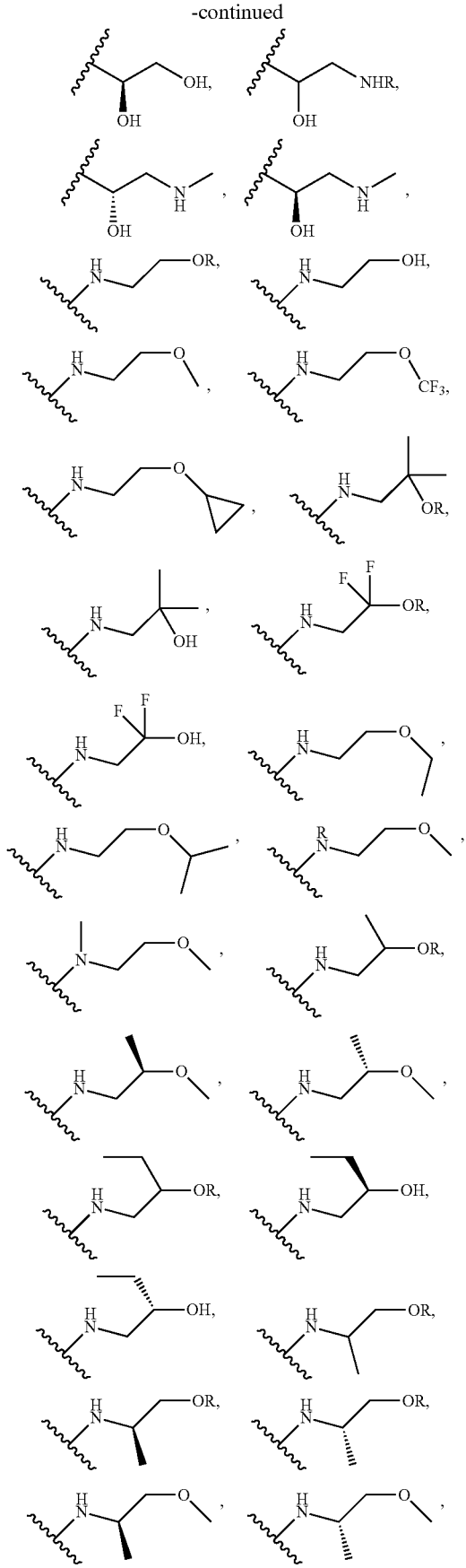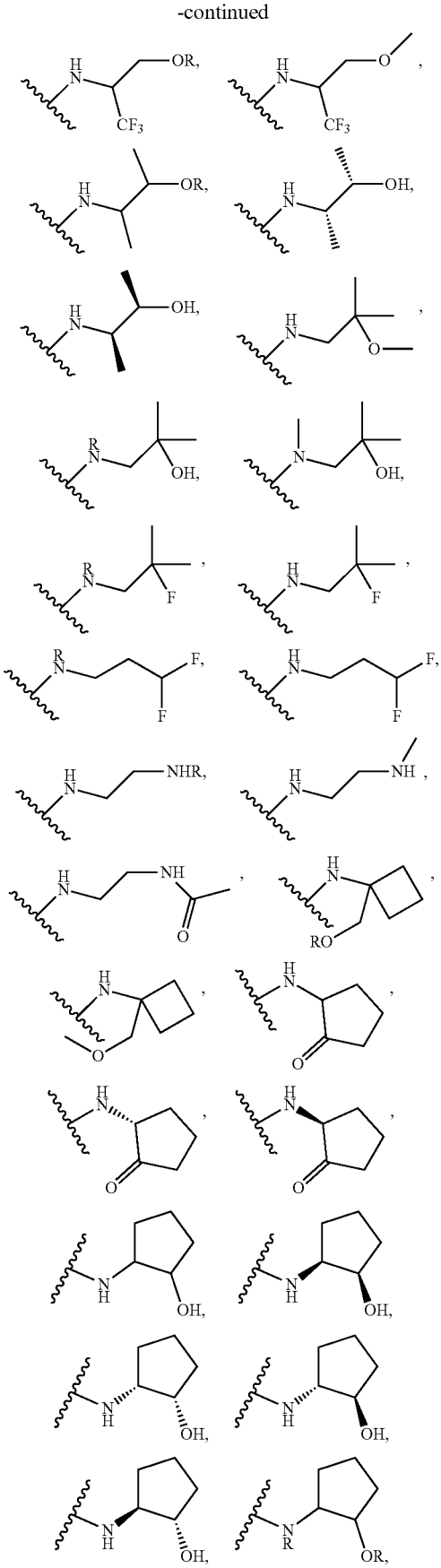

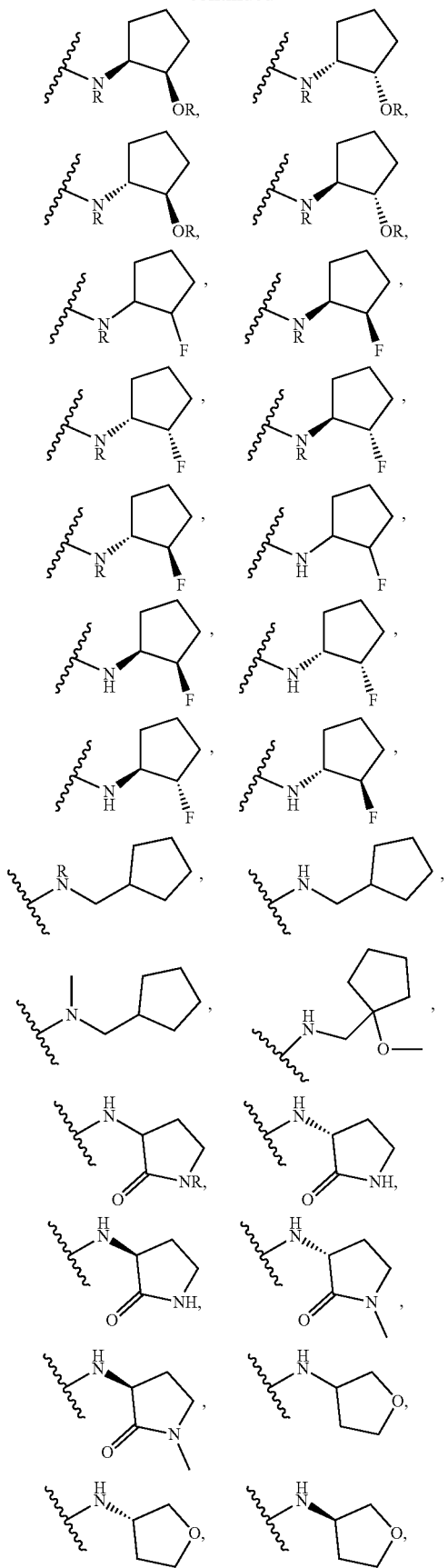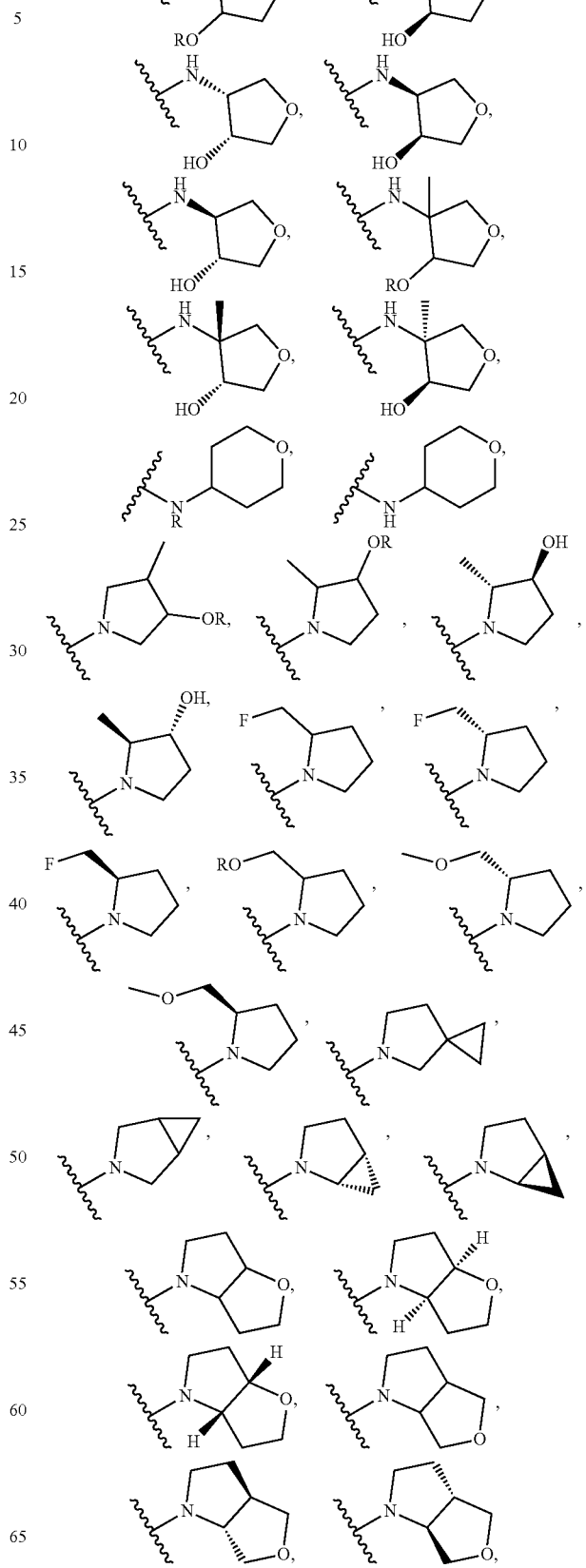

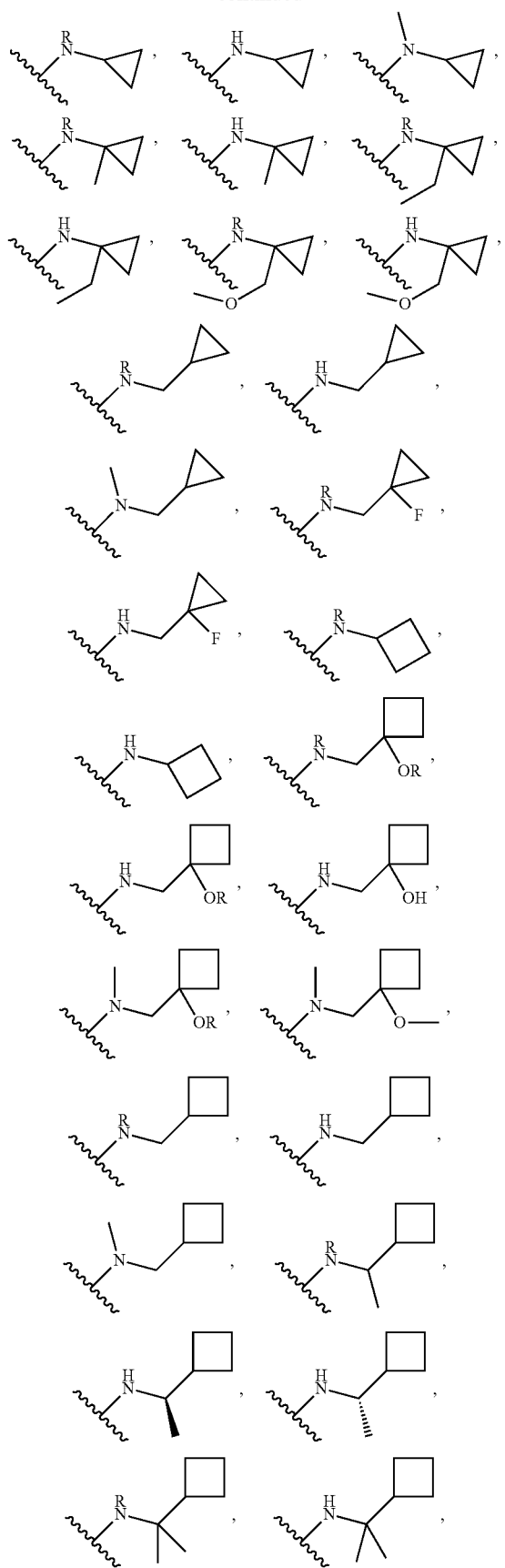
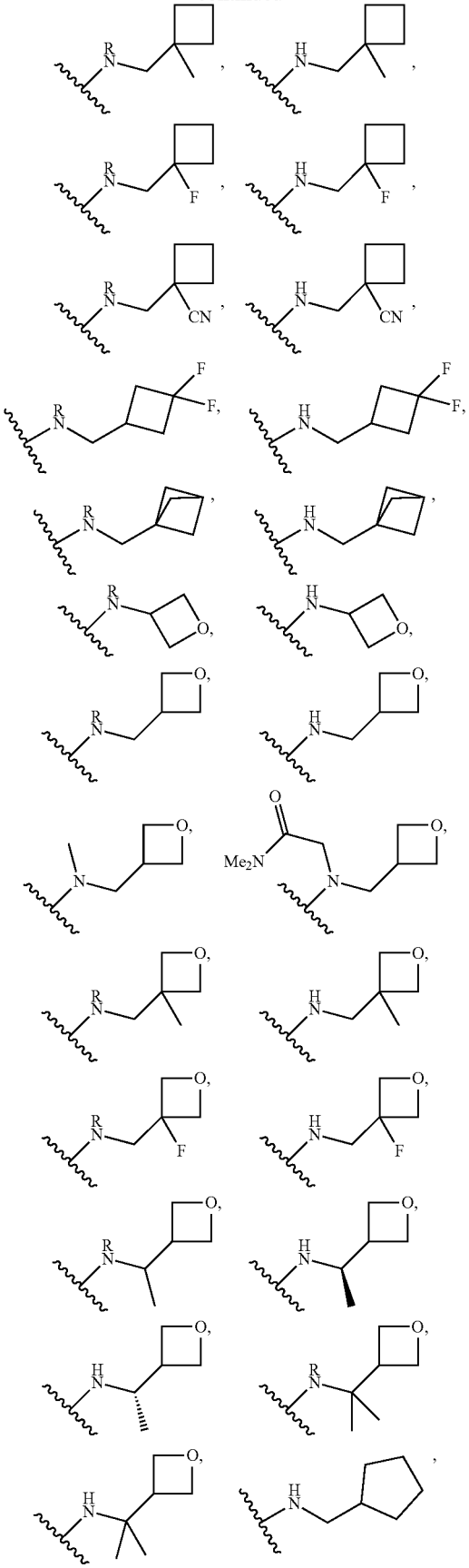

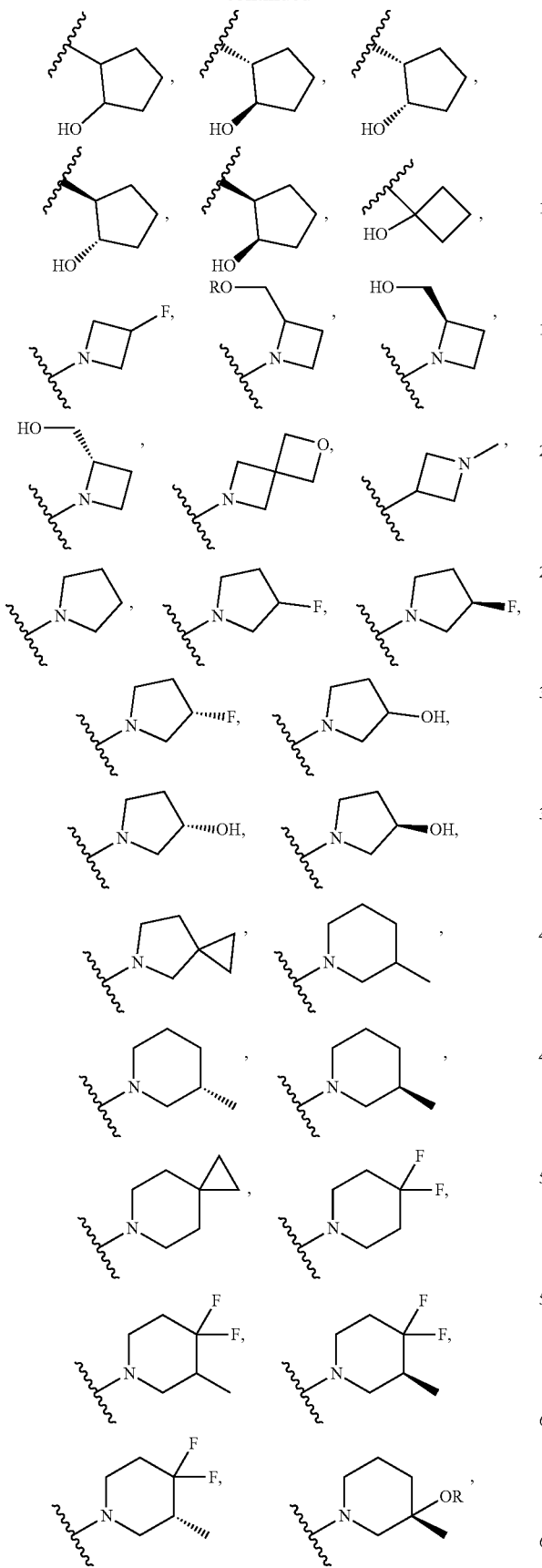
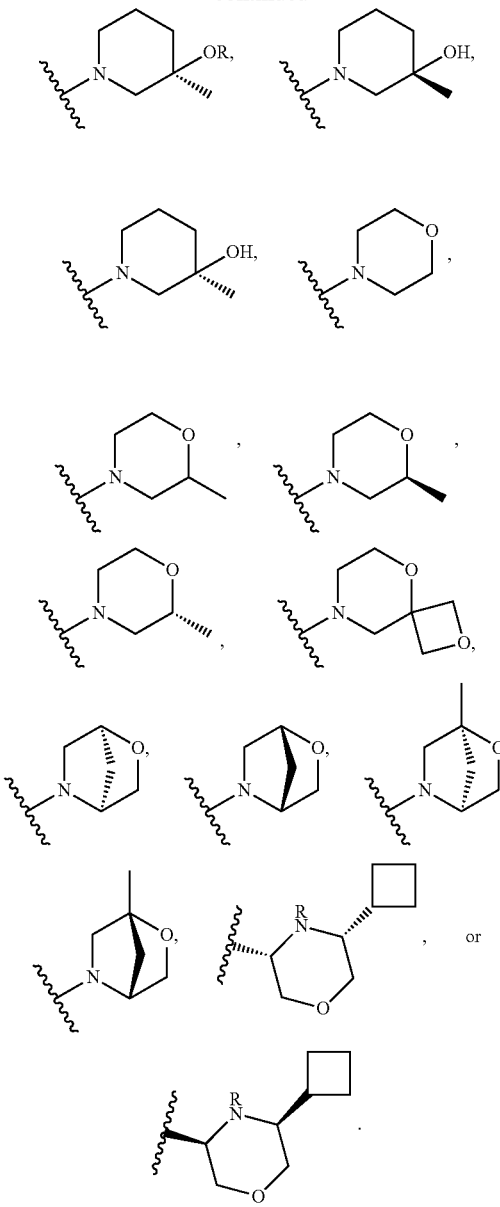
In certain embodiments, $R^9$ is a $C_{1-6}$ aliphatic substituted with a fluorophore, such as
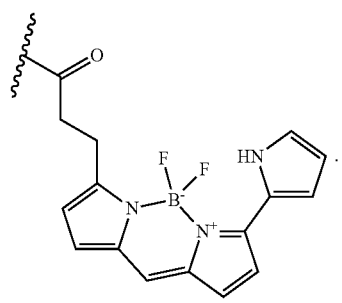 [SMILES: *C(=O)CCc1ccc2n1[B-](F)(F)[N+]1=C(c3ccc[nH]3)C=CC1=C2]
In certain embodiments, $R^9$ is a $C_{1-6}$ aliphatic substituted with a fluorophore, such as

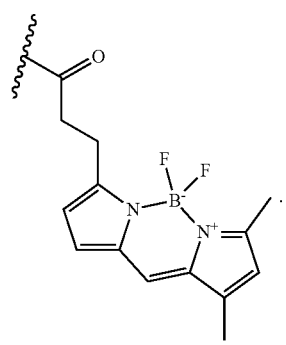 [SMILES: *C(=O)CCc1ccc2n1[B-](F)(F)[N+]1=C(C)C=C(C)C1=C2]

In certain embodiments, R⁹ is a 2,2'-((oxybis(ethane-2,1-diyl))bis(oxy))bis(ethan-1-amine) substituted with fluorophore

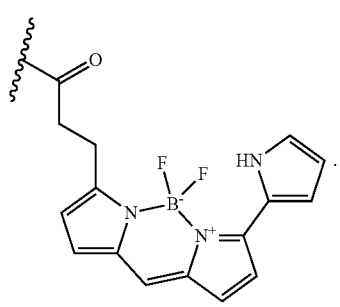 [SMILES: *C(=O)CCc1ccc2n1[B-](F)(F)[N+]1=C(c3ccc[nH]3)C=CC1=C2]

In certain embodiments, R⁹ is a 2,2'-((oxybis(ethane-2,1-diyl))bis(oxy))bis(ethan-1-amine) substituted with fluorophore

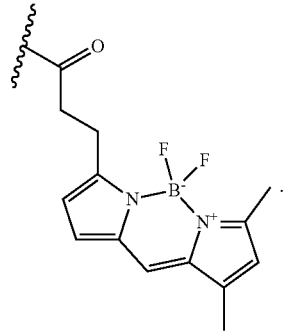 [SMILES: *C(=O)CCc1ccc2n1[B-](F)(F)[N+]1=C(C)C=C(C)C1=C2]

In certain embodiments, R⁹ is

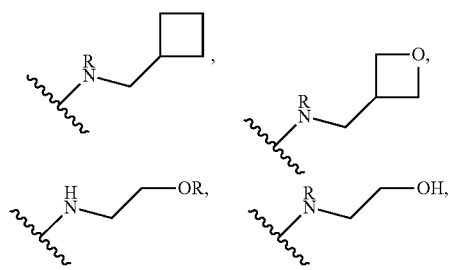

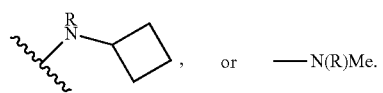

In certain embodiments, R⁹ is

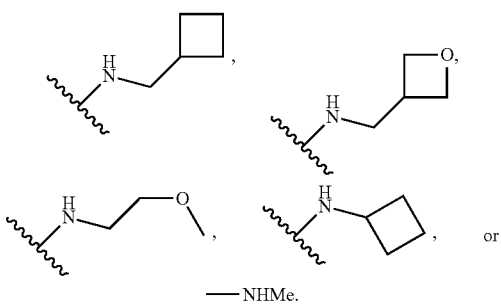

In some embodiments, R⁹ is selected from those depicted in Table 1, below.

In some embodiments, -L-R⁹ is

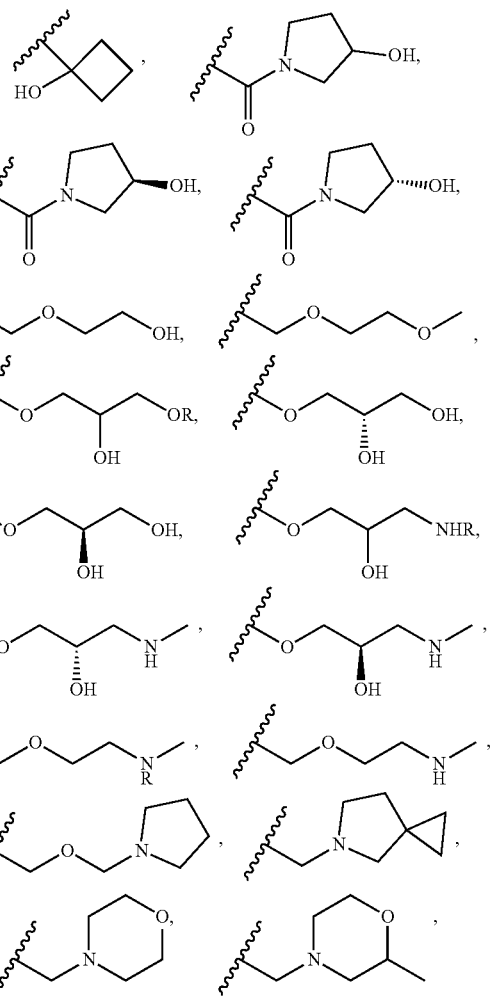

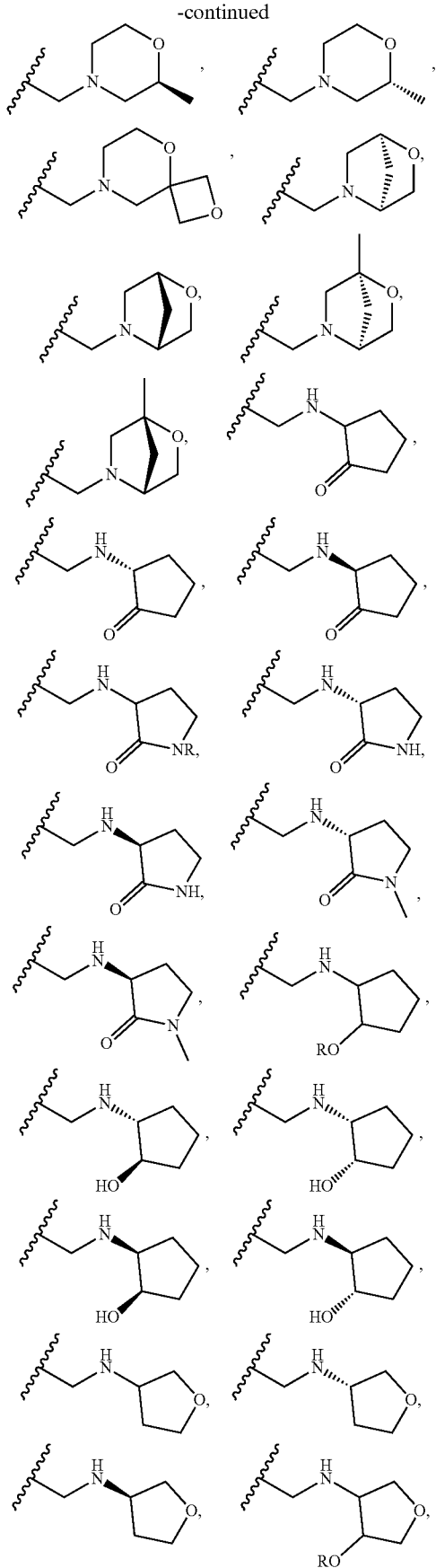
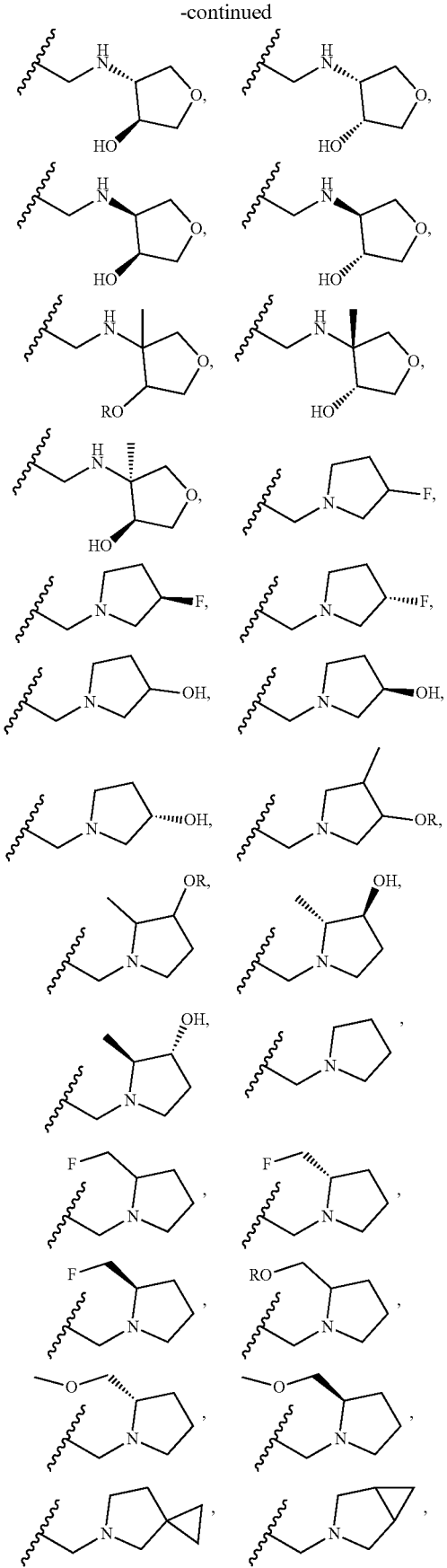

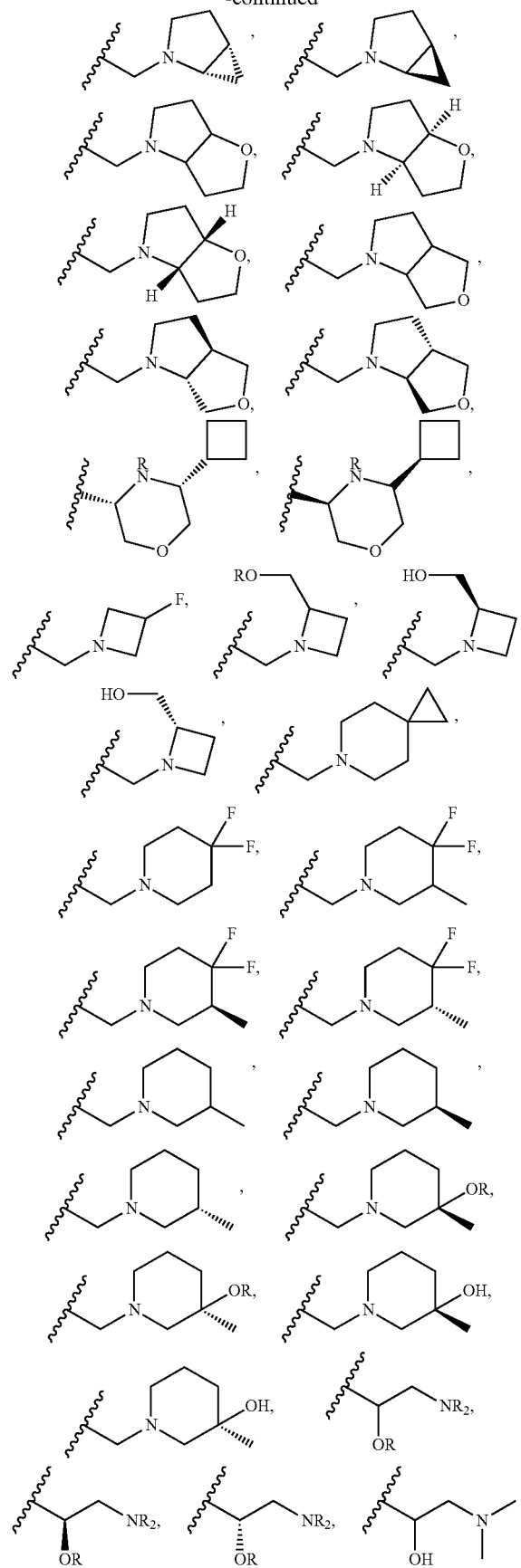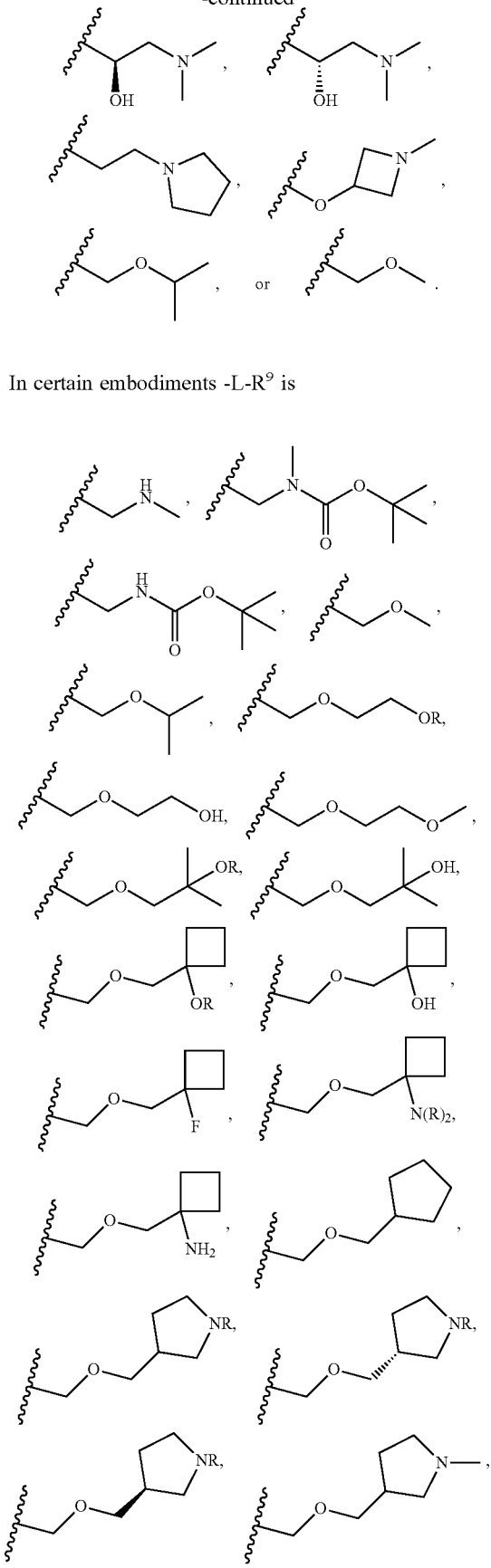
In certain embodiments -L-R⁹ is

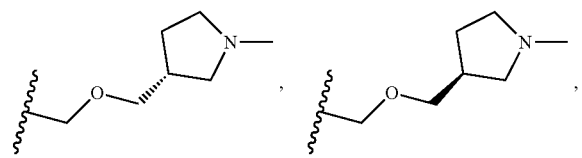
In certain embodiments -L-R$^9$ is
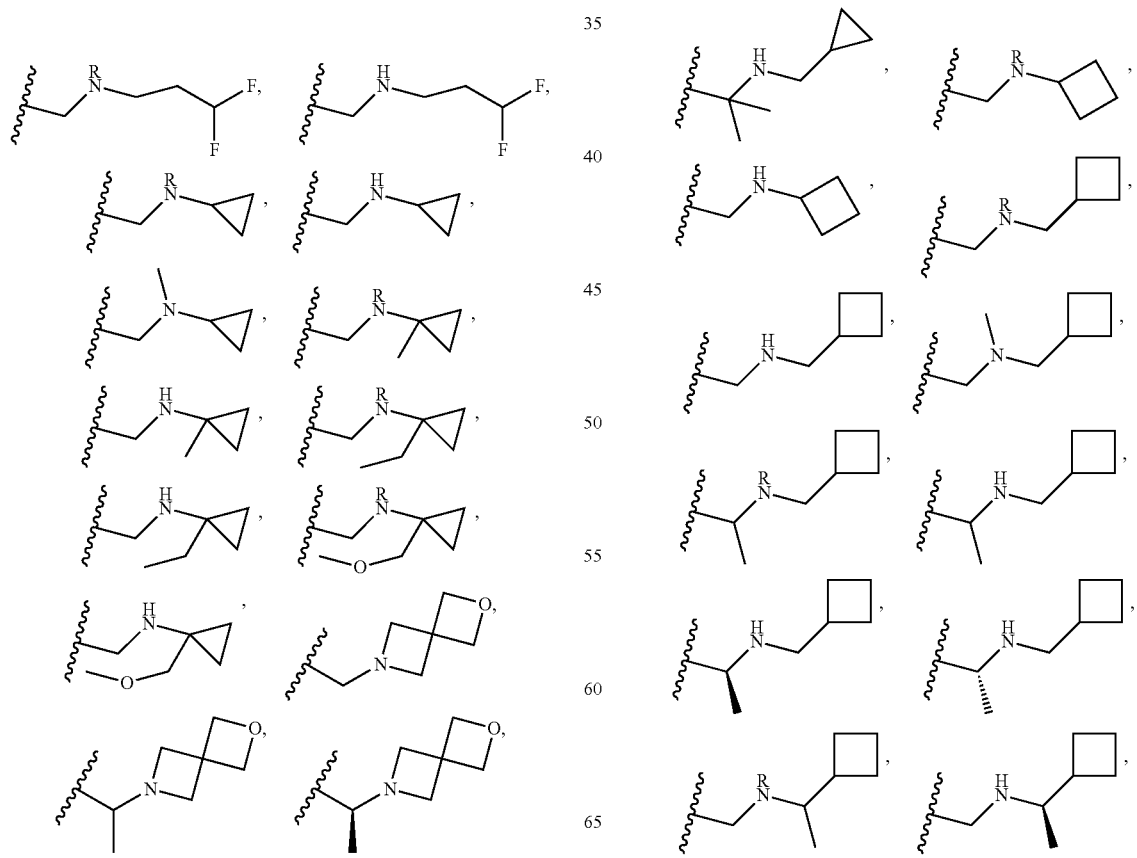
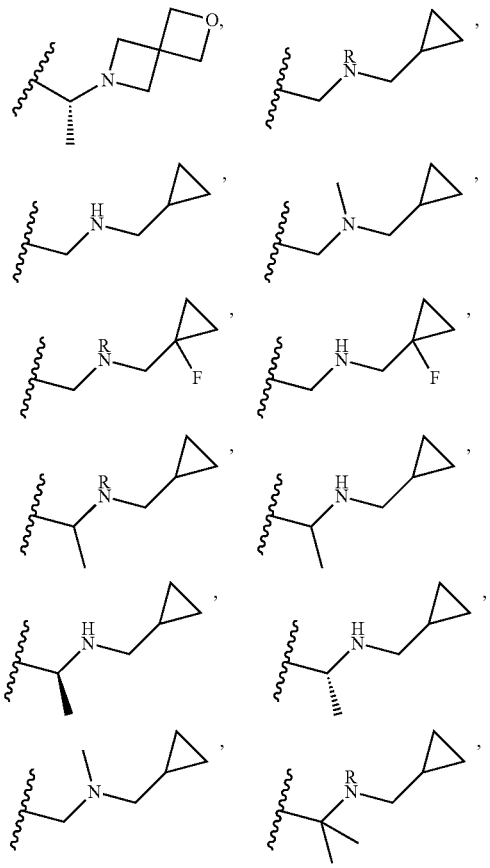

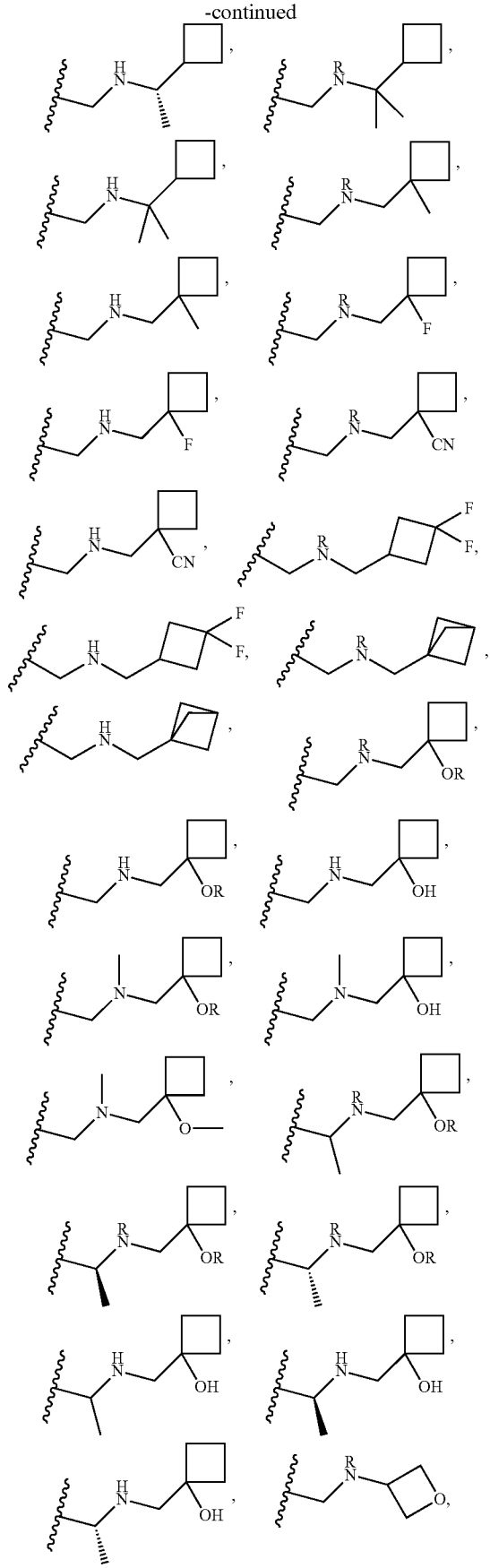
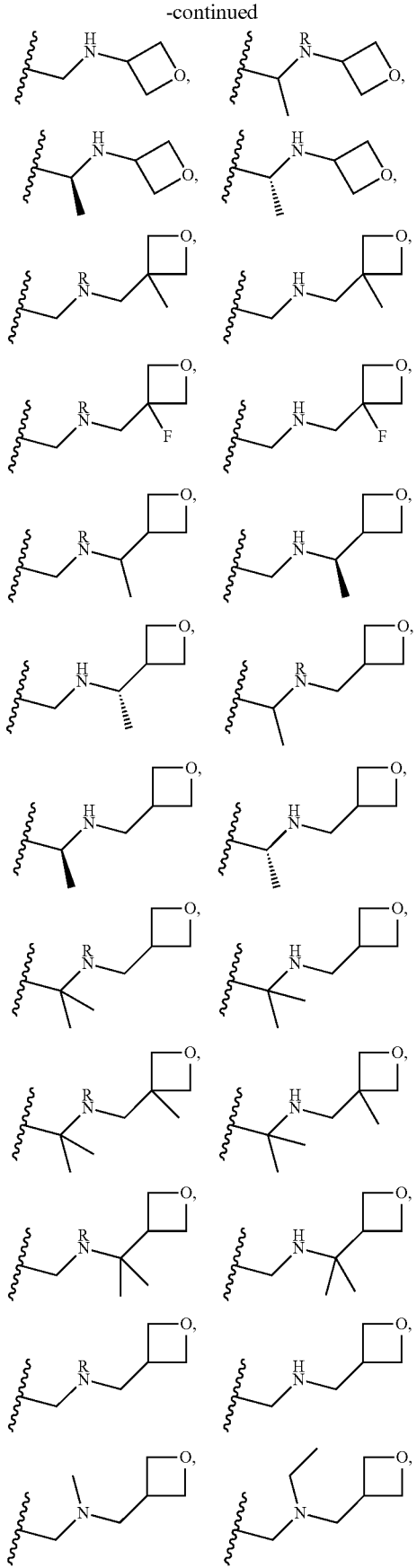

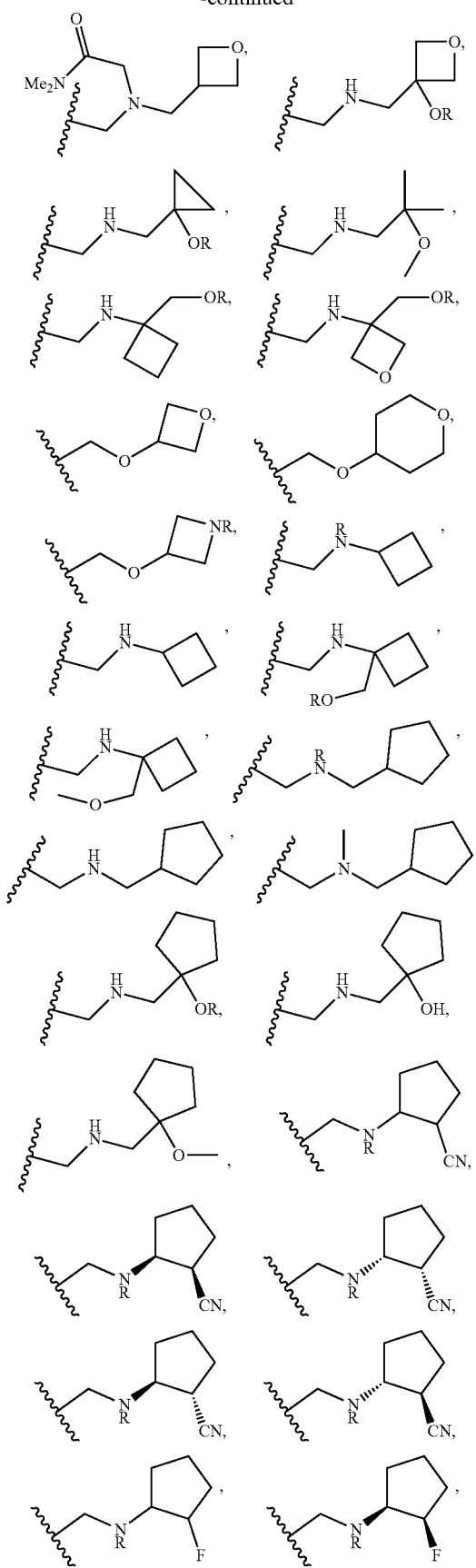
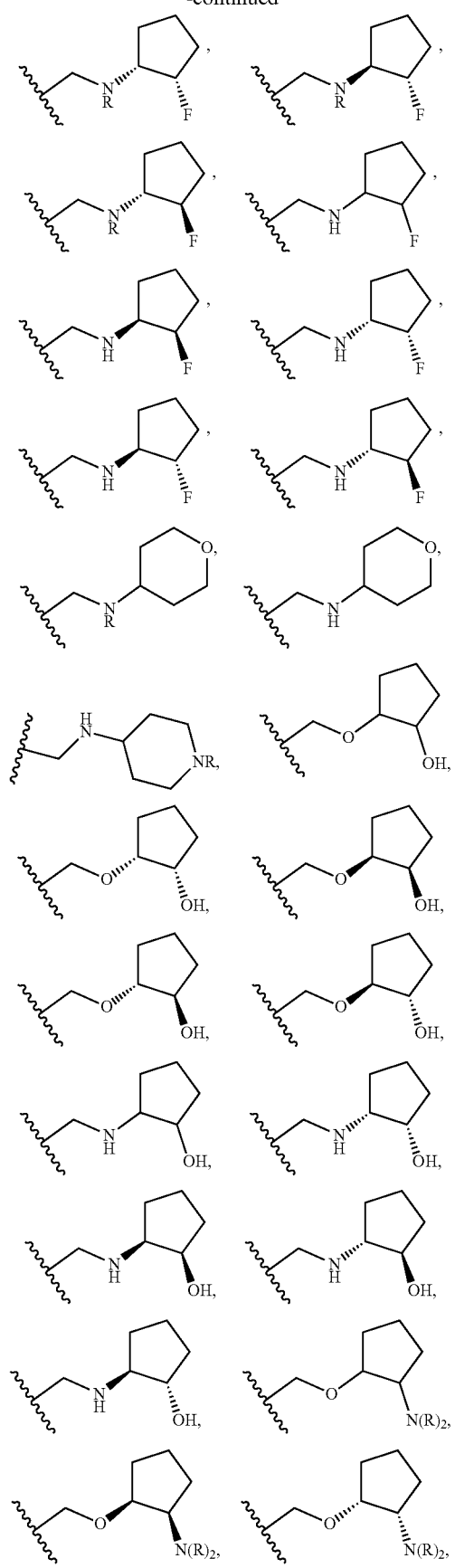

-continued

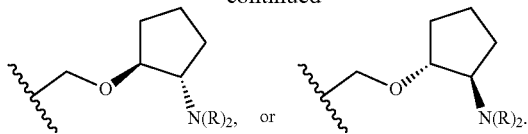

In certain embodiments -L-R⁹ is

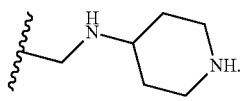 [SMILES: *CNC1CCNCC1]

In certain embodiments -L-R⁹ is

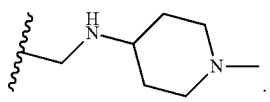 [SMILES: *CNC1CCN(C)CC1]

In certain embodiments -L-R⁹ is

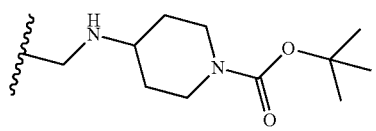

In certain embodiments -L-R⁹ is

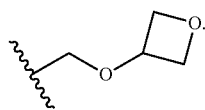

In certain embodiments -L-R⁹ is

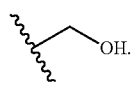

In certain embodiments -L-R⁹ is

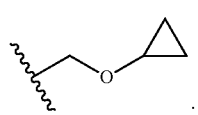 [SMILES: *COC1CC1]

In certain embodiments -L-R⁹ is

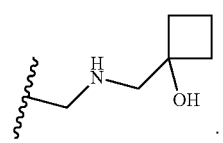 [SMILES: *CNCC1(O)CCC1]

In certain embodiments -L-R⁹ is

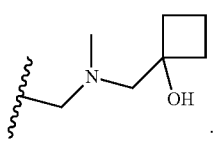 [SMILES: *CN(C)CC1(O)CCC1]

In certain embodiments -L-R⁹ is

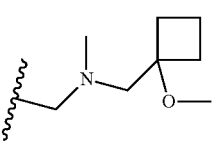

In certain embodiments -L-R⁹ is

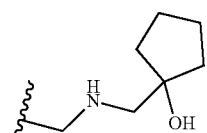

In certain embodiments -L-R⁹ is

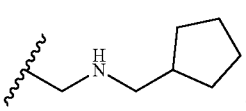

In certain embodiments -L-R⁹ is

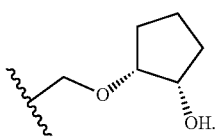

In certain embodiments -L-R⁹ is

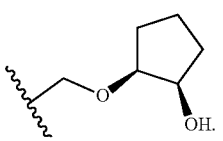 [SMILES: *CO[C@H]1CCC[C@H]1O]

In certain embodiments -L-R⁹ is

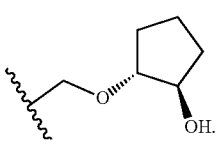 [SMILES: *CO[C@@H]1CCC[C@H]1O]

In certain embodiments -L-R⁹ is
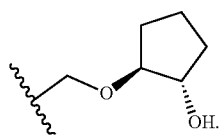 [SMILES: *CO[C@H]1CCC[C@@H]1O]
In certain embodiments -L-R⁹ is
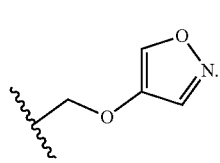 [SMILES: *COc1cnoc1]
In certain embodiments -L-R⁹ is
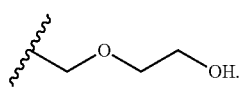
In further embodiments the R group of -L-R⁹ is not hydrogen, —CN, or halogen.
In certain embodiments -L-R⁹ is
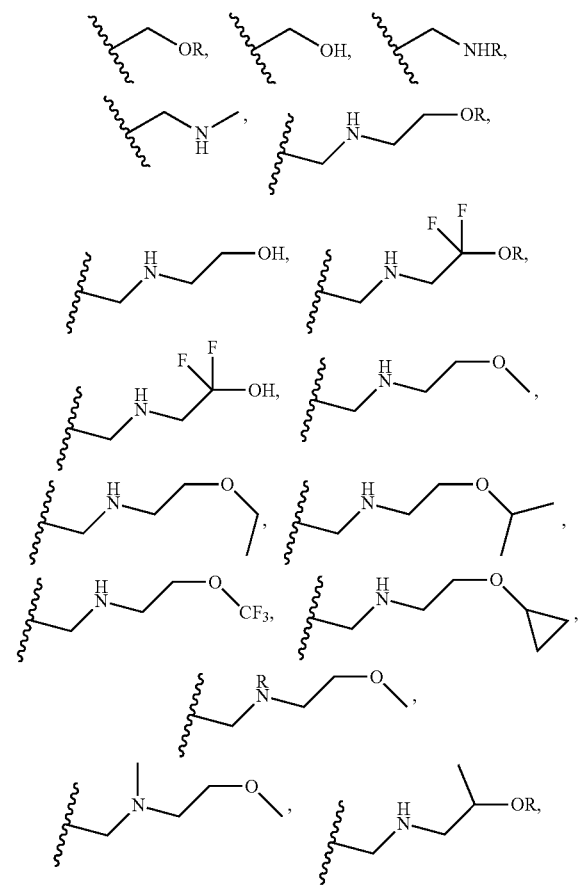
-continued
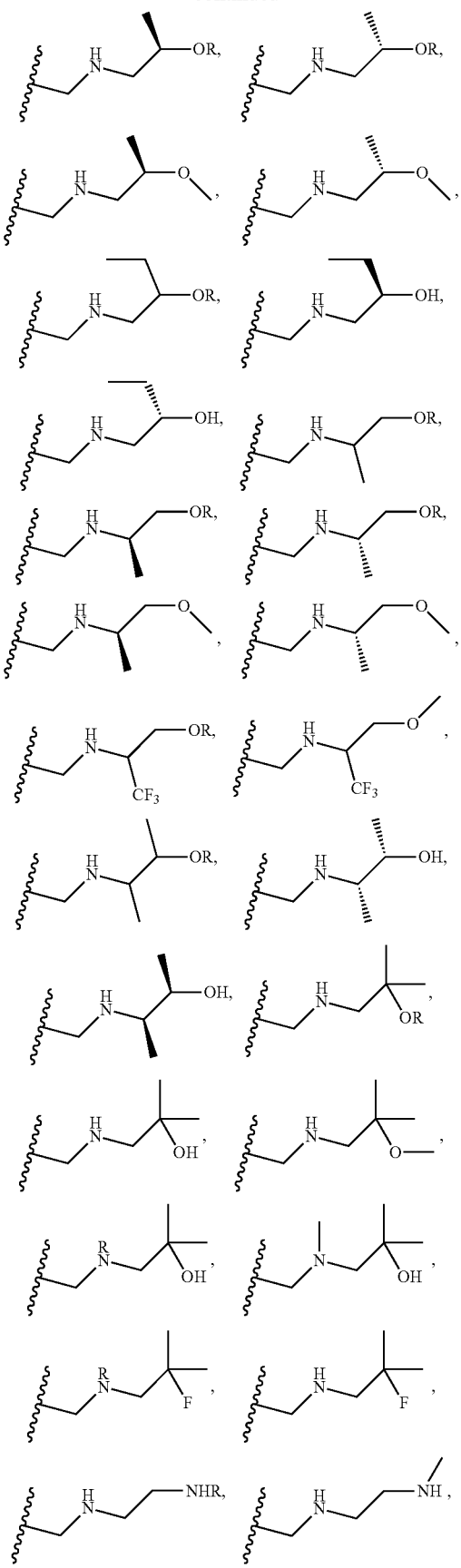

-continued

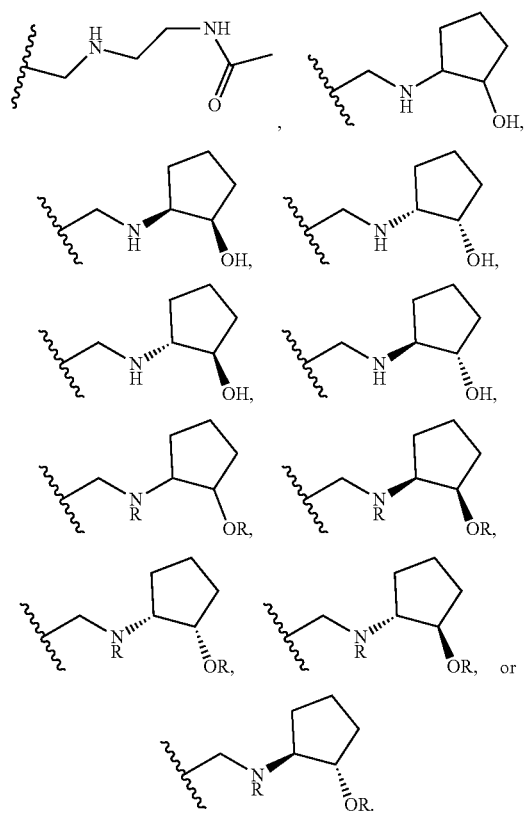

In certain embodiments -L-R⁹ is

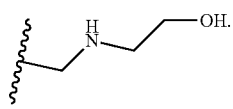 [SMILES: *CNCCO]

In certain embodiments -L-R⁹ is

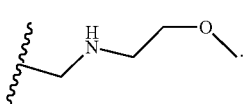 [SMILES: *CNCCOC]

In certain embodiments -L-R⁹ is

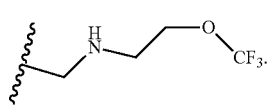 [SMILES: *CNCCOC(F)(F)F]

In certain embodiments -L-R⁹ is

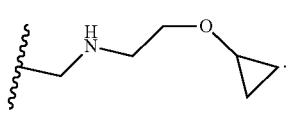 [SMILES: *CNCCOC1CC1]

In certain embodiments -L-R⁹ is

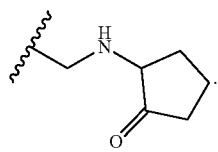 [SMILES: *CNC1CCCC1=O]

In certain embodiments -L-R⁹ is

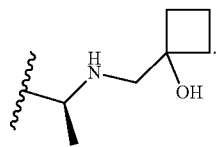 [SMILES: *[C@H](C)NCC1(O)CCC1]

In certain embodiments -L-R⁹ is

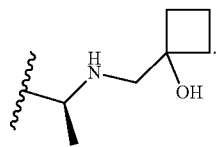 [SMILES: *[C@H](C)NCC1(O)CCC1]

In certain embodiments -L-R⁹ is

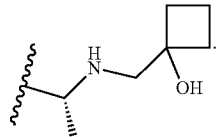

In certain embodiments -L-R⁹ is

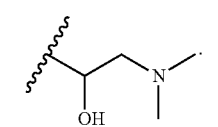

In certain embodiments -L-R⁹ is

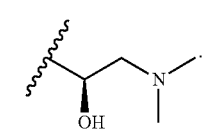 [SMILES: *[C@H](O)CN(C)C]

In certain embodiments -L-R⁹ is

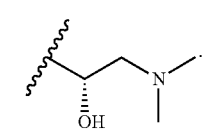

In certain embodiments -L-R⁹ is

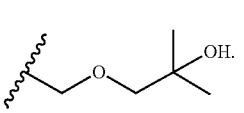 [SMILES: *COCC(C)(C)O]

In certain embodiments -L-R⁹ is

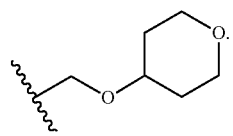

In certain embodiments -L-R⁹ is

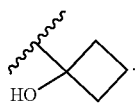

In some embodiments -L-R⁹ is

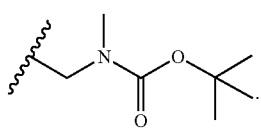 [SMILES: *CN(C)C(=O)OC(C)(C)C]

In certain embodiments -L-R⁹ is

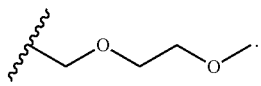 [SMILES: *COCCOC]

In certain embodiments -L-R⁹ is

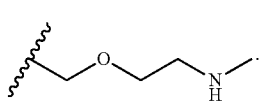 [SMILES: *COCCNC]

In certain embodiments -L-R⁹ is

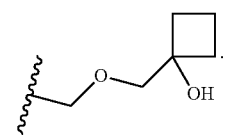 [SMILES: *COCC1(O)CCC1]

In certain embodiments -L-R⁹ is

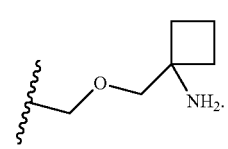 [SMILES: *COCC1(N)CCC1]

In certain embodiments -L-R⁹ is

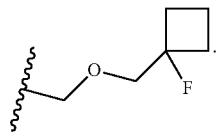 [SMILES: *COCC1(F)CCC1]

In certain embodiments -L-R⁹ is

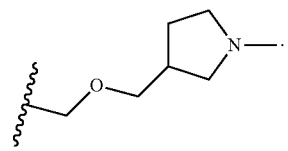 [SMILES: *COCC1CCN(C)C1]

In certain embodiments -L-R⁹ is

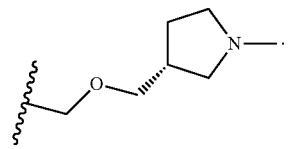 [SMILES: *COC[C@@H]1CCN(C)C1]

In certain embodiments -L-R⁹ is

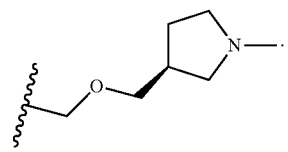 [SMILES: *COC[C@H]1CCN(C)C1]

In certain embodiments -L-R⁹ is

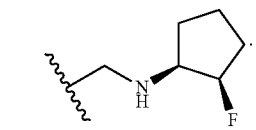 [SMILES: *CN[C@H]1CCC[C@H]1F]

In certain embodiments -L-R⁹ is

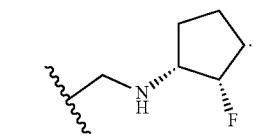 [SMILES: *CN[C@@H]1CCC[C@@H]1F]

In certain embodiments -L-R⁹ is

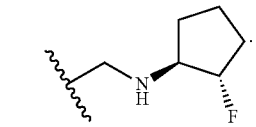 [SMILES: *CN[C@H]1CCC[C@@H]1F]

In certain embodiments -L-R⁹ is


In certain embodiments -L-R⁹ is

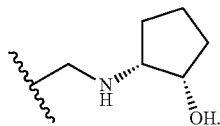

In certain embodiments -L-R⁹ is

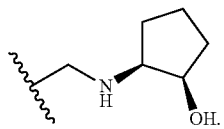

In certain embodiments -L-R⁹ is

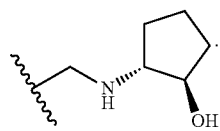 [SMILES: *CN[C@@H]1CCC[C@H]1O]

In certain embodiments -L-R⁹ is

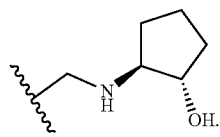 [SMILES: *CN[C@H]1CCC[C@@H]1O]

In certain embodiments -L-R⁹ is

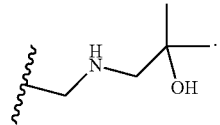 [SMILES: *CNCC(C)(C)O]

In certain embodiments -L-R⁹ is

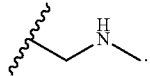

In certain embodiments -L-R⁹ is

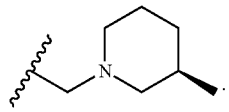

In certain embodiments -L-R⁹ is

In certain embodiments -L-R⁹ is

In certain embodiments -L-R⁹ is

In certain embodiments -L-R⁹ is

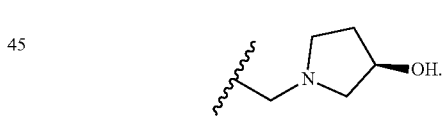

In certain embodiments -L-R⁹ is

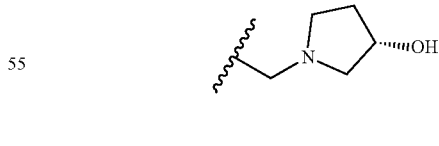

In certain embodiments -L-R⁹ is

In certain embodiments -L-R⁹ is

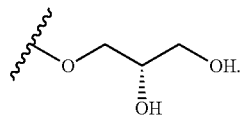 [SMILES: *OC[C@@H](O)CO]

In certain embodiments -L-R⁹ is

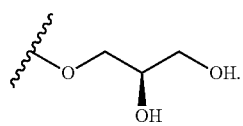 [SMILES: *OC[C@H](O)CO]

In certain embodiments -L-R⁹ is


In certain embodiments -L-R⁹ is


In certain embodiments -L-R⁹ is

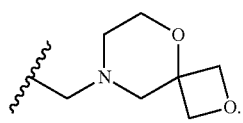 [SMILES: *CN1CCOC2(COC2)C1]

In certain embodiments -L-R⁹ is

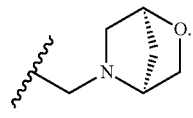

In certain embodiments -L-R⁹ is

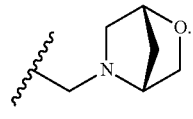

In certain embodiments -L-R⁹ is

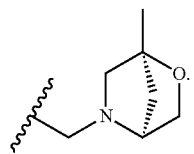

In certain embodiments -L-R⁹ is

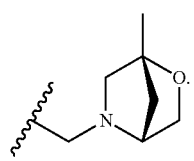 [SMILES: *CN1C[C@@]2(C)C[C@@H]1CO2]

In certain embodiments -L-R⁹ is

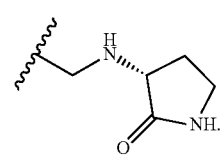

In certain embodiments -L-R⁹ is

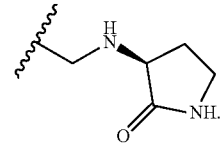 [SMILES: *CN[C@H]1CCNC1=O]

In certain embodiments -L-R⁹ is

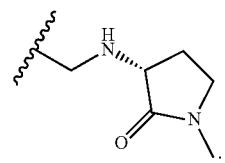 [SMILES: *CN[C@@H]1CCN(C)C1=O]

In certain embodiments -L-R⁹ is

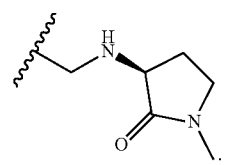 [SMILES: *CN[C@H]1CCN(C)C1=O]

In certain embodiments -L-R⁹ is

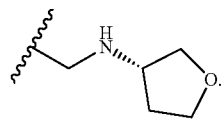

In certain embodiments -L-R⁹ is

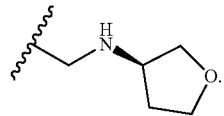 [SMILES: *CN[C@@H]1CCOC1]

In certain embodiments -L-R⁹ is

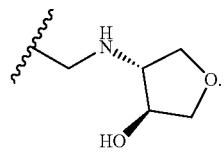 [SMILES: *CN[C@@H]1COC[C@H]1O]

In certain embodiments -L-R⁹ is

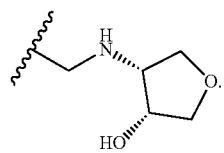 [SMILES: *CN[C@@H]1COC[C@@H]1O]

In certain embodiments -L-R⁹ is


In certain embodiments -L-R⁹ is

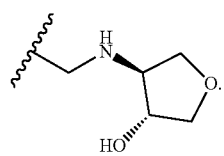 [SMILES: *CN[C@H]1COC[C@@H]1O]

In certain embodiments -L-R⁹ is

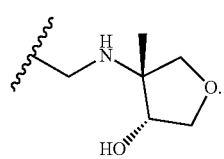 [SMILES: *CN[C@]1(C)COC[C@@H]1O]

In certain embodiments -L-R⁹ is

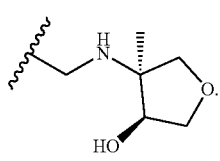 [SMILES: *CN[C@@]1(C)COC[C@H]1O]

In certain embodiments -L-R⁹ is

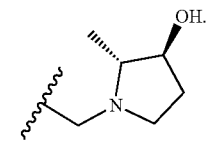

In certain embodiments -L-R⁹ is

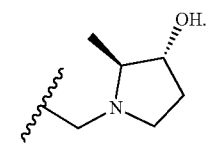

In certain embodiments -L-R⁹ is

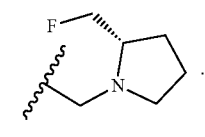

In certain embodiments -L-R⁹ is

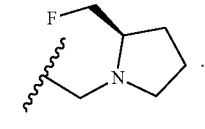

In certain embodiments -L-R⁹ is

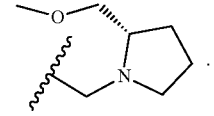 [SMILES: *CN1CCC[C@H]1COC]

In certain embodiments -L-R⁹ is

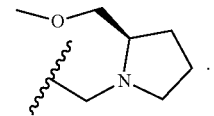 [SMILES: *CN1CCC[C@@H]1COC]

In certain embodiments -L-R⁹ is

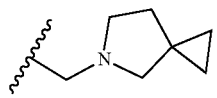

In certain embodiments -L-R⁹ is

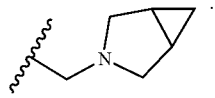

In certain embodiments -L-R⁹ is

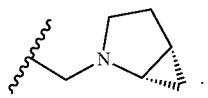

In certain embodiments -L-R⁹ is

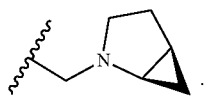 [SMILES: *CN1CC[C@H]2C[C@H]21]

In certain embodiments -L-R⁹ is

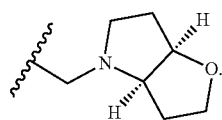

In certain embodiments -L-R⁹ is

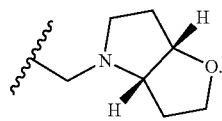

In certain embodiments -L-R⁹ is

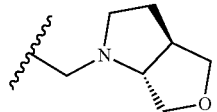

In certain embodiments -L-R⁹ is

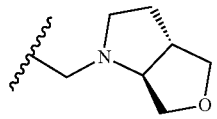

In certain embodiments -L-R⁹ is

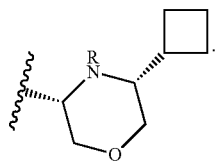

In certain embodiments -L-R⁹ is

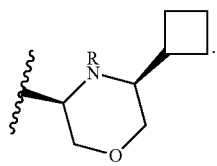

In certain embodiments -L-R⁹ is

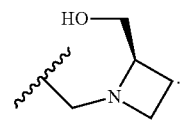

In certain embodiments -L-R⁹ is

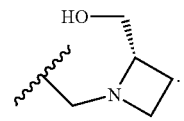

In certain embodiments -L-R⁹ is

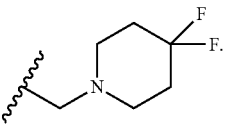 [SMILES: *CN1CCC(F)(F)CC1]

In certain embodiments -L-R⁹ is

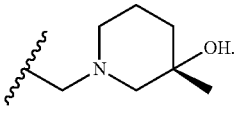 [SMILES: *CN1CCC[C@](C)(O)C1]

In certain embodiments -L-R⁹ is

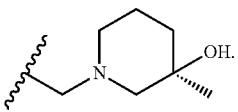 [SMILES: *CN1CCC[C@@](C)(O)C1]

In certain embodiments -L-R⁹ is

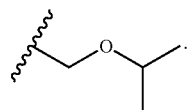 [SMILES: *COC(C)C]

In certain embodiments -L-R⁹ is

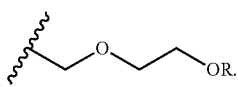

In certain embodiments -L-R⁹ is

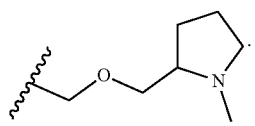 [SMILES: *COCC1CCCN1C]

In certain embodiments -L-R⁹ is

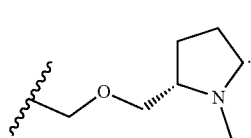 [SMILES: *COC[C@@H]1CCCN1C]

In certain embodiments -L-R⁹ is

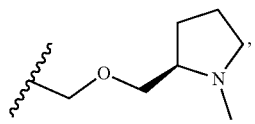 [SMILES: *COC[C@H]1CCCN1C]

In certain embodiments -L-R⁹ is

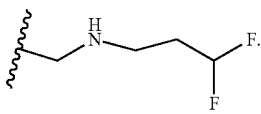 [SMILES: *CNCCC(F)F]

In certain embodiments -L-R⁹ is

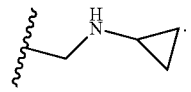 [SMILES: *CNC1CC1]

In certain embodiments -L-R⁹ is

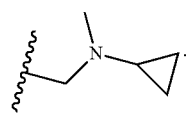

In certain embodiments -L-R⁹ is

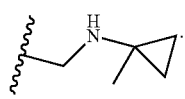

In certain embodiments -L-R⁹ is

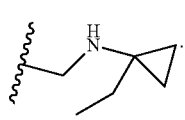

In certain embodiments -L-R⁹ is

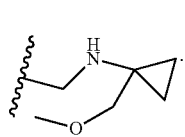

In certain embodiments -L-R⁹ is

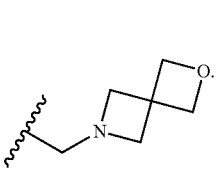 [SMILES: *CN1CC2(COC2)C1]

In certain embodiments -L-R⁹ is

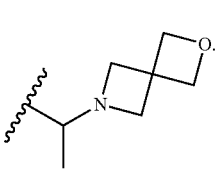 [SMILES: *C(C)N1CC2(COC2)C1]

In certain embodiments -L-R⁹ is

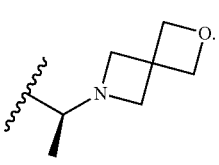 [SMILES: *[C@H](C)N1CC2(COC2)C1]

In certain embodiments -L-R⁹ is

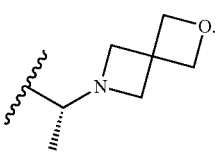 [SMILES: *[C@@H](C)N1CC2(COC2)C1]

In certain embodiments -L-R⁹ is

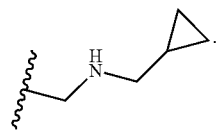 [SMILES: *CNCC1CC1]

In certain embodiments -L-R⁹ is

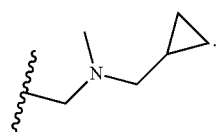 [SMILES: *CN(C)CC1CC1]

In certain embodiments -L-R⁹ is

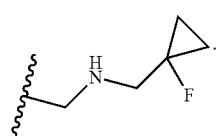 [SMILES: *CNCC1(F)CC1]

In certain embodiments -L-R⁹ is

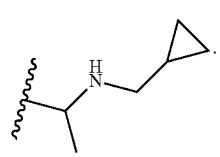 [SMILES: *C(C)NCC1CC1]

In certain embodiments -L-R⁹ is

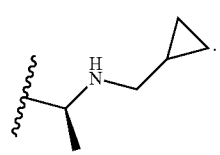 [SMILES: *[C@H](C)NCC1CC1]

In certain embodiments -L-R⁹ is

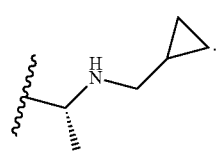 [SMILES: *[C@@H](C)NCC1CC1]

In certain embodiments -L-R⁹ is

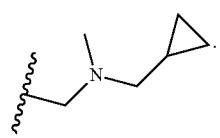 [SMILES: *CN(C)CC1CC1]

In certain embodiments -L-R⁹ is

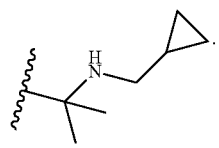 [SMILES: *C(C)(C)NCC1CC1]

In certain embodiments -L-R⁹ is

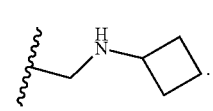

In certain embodiments -L-R⁹ is

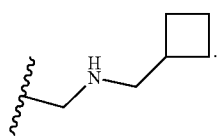 [SMILES: *CNCC1CCC1]

In certain embodiments -L-R⁹ is

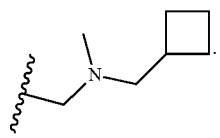

In certain embodiments -L-R⁹ is

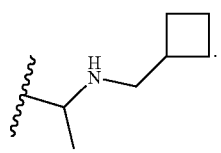 [SMILES: *C(C)NCC1CCC1]

In certain embodiments -L-R⁹ is

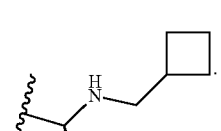

In certain embodiments -L-R⁹ is

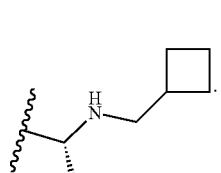

In certain embodiments -L-R⁹ is

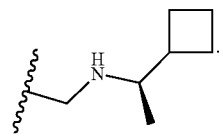 [SMILES: *CN[C@H](C)C1CCC1]

In certain embodiments -L-R⁹ is


In certain embodiments -L-R⁹ is


In certain embodiments -L-R⁹ is


In certain embodiments -L-R⁹ is

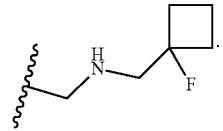 [SMILES: *CNCC1(C)CCC1]

In certain embodiments -L-R⁹ is


In certain embodiments -L-R⁹ is

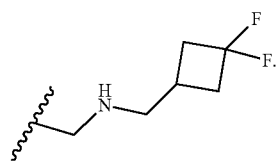 [SMILES: *CNCC1CC(F)(F)C1]

In certain embodiments -L-R⁹ is

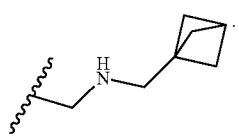 [SMILES: *CNCC12CC(C1)C2]

In certain embodiments -L-R⁹ is

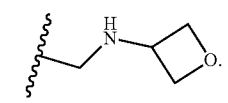 [SMILES: *CNC1COC1]

In certain embodiments -L-R⁹ is

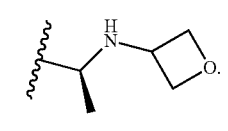

In certain embodiments -L-R⁹ is

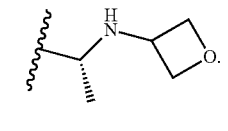 [SMILES: *[C@@H](C)NC1COC1]

In certain embodiments -L-R⁹ is

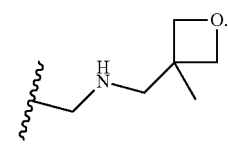 [SMILES: *CNCC1(C)COC1]

In certain embodiments -L-R⁹ is

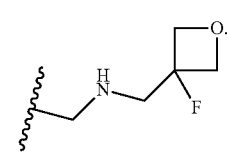 [SMILES: *CNCC1(F)COC1]

In certain embodiments -L-R⁹ is

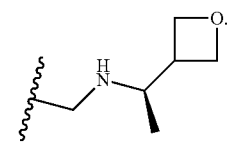 [SMILES: *CN[C@H](C)C1COC1]

In certain embodiments -L-R⁹ is

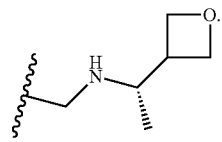 [SMILES: *CN[C@@H](C)C1COC1]

In certain embodiments -L-R⁹ is

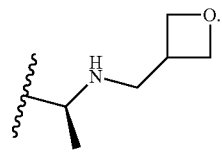 [SMILES: *[C@H](C)NCC1COC1]

In certain embodiments -L-R⁹ is

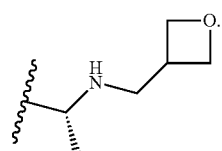

In certain embodiments -L-R⁹ is


In certain embodiments -L-R⁹ is

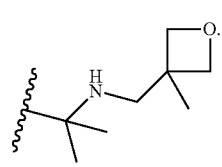 [SMILES: *C(C)(C)NCC1(C)COC1]

In certain embodiments -L-R⁹ is

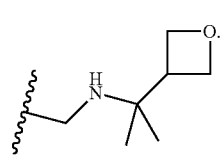 [SMILES: *CNC(C)(C)C1COC1]

In certain embodiments -L-R⁹ is

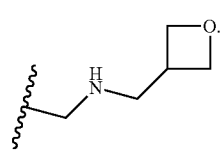 [SMILES: *CNCC1COC1]

In certain embodiments -L-R⁹ is

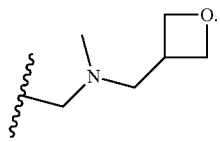 [SMILES: *CN(C)CC1COC1]

In certain embodiments -L-R⁹ is

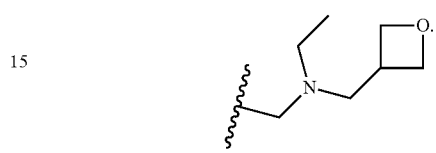

In certain embodiments -L-R⁹ is

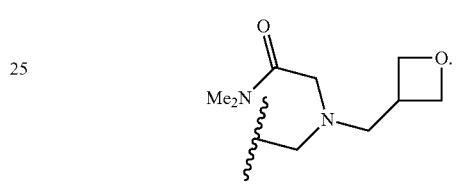

In certain embodiments -L-R⁹ is

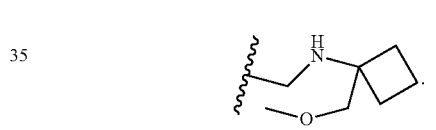

In certain embodiments -L-R⁹ is

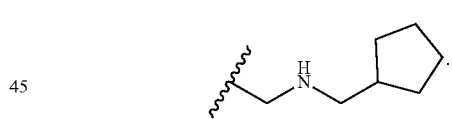

In certain embodiments -L-R⁹ is

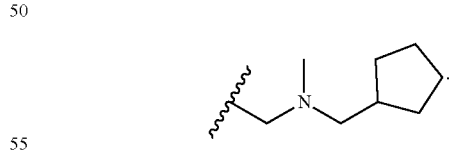

In certain embodiments -L-R⁹ is

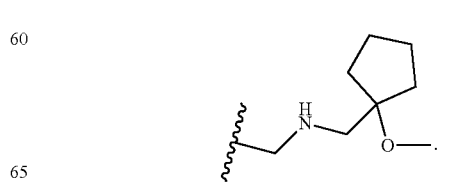

In certain embodiments -L-R⁹ is

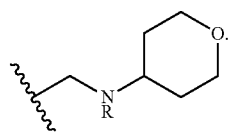

In certain embodiments -L-R⁹ is

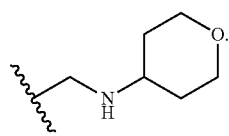 [SMILES: *CNC1CCOCC1]

In certain embodiments -L-R⁹ is

In certain embodiments -L-R⁹ is

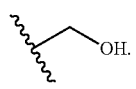

In certain embodiments -L-R⁹ is

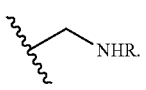

In certain embodiments -L-R⁹ is H

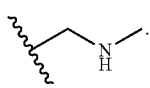 [SMILES: *CNC]

In certain embodiments -L-R⁹ is

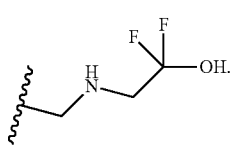 [SMILES: *CNCC(O)(F)F]

In certain embodiments -L-R⁹ is

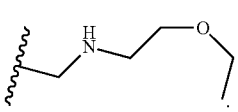 [SMILES: *CNCCOCC]

In certain embodiments -L-R⁹ is

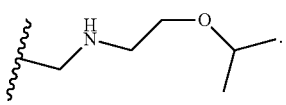

In certain embodiments -L-R⁹ is

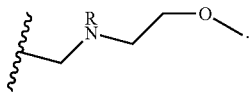

In certain embodiments -L-R⁹ is

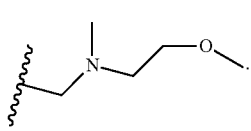 [SMILES: *CN(C)CCOC]

In certain embodiments -L-R⁹ is

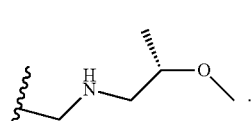

In certain embodiments -L-R⁹ is

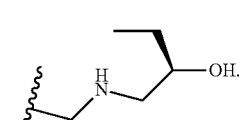

In certain embodiments -L-R⁹ is

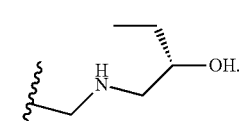

In certain embodiments -L-R$^9$ is

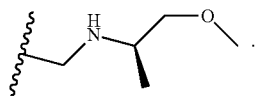 [SMILES: *CN[C@H](C)COC]

In certain embodiments -L-R$^9$ is

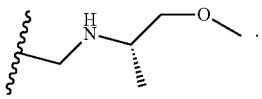 [SMILES: *CN[C@@H](C)COC]

In certain embodiments -L-R$^9$ is

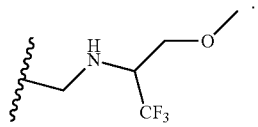

In certain embodiments -L-R$^9$ is

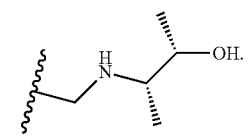 [SMILES: *CN[C@@H](C)[C@H](C)O]

In certain embodiments -L-R$^9$ is

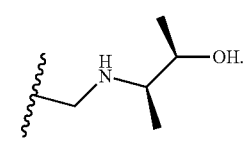 [SMILES: *CN[C@H](C)[C@@H](C)O]

In certain embodiments -L-R$^9$ is

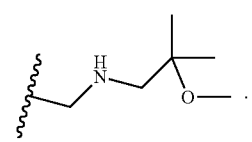 [SMILES: *CNCC(C)(C)OC]

In certain embodiments -L-R$^9$ is

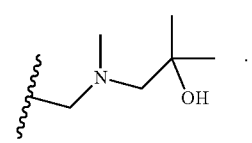 [SMILES: *CN(C)CC(C)(C)O]

In certain embodiments -L-R$^9$ is

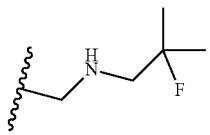

In certain embodiments -L-R$^9$ is

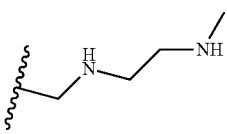

In certain embodiments, -L-R$^9$ is

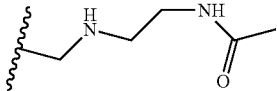

In certain embodiments, -L-R$^9$ is

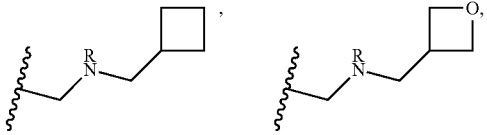
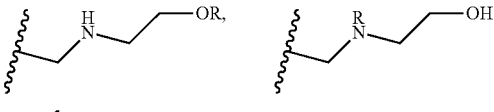
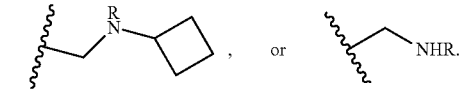

In certain embodiments, -L-R$^9$ is

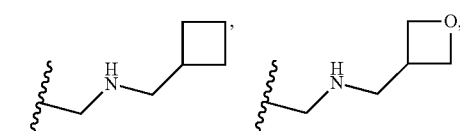
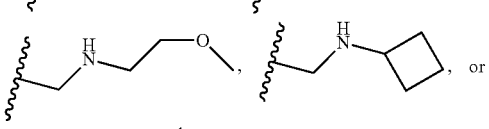
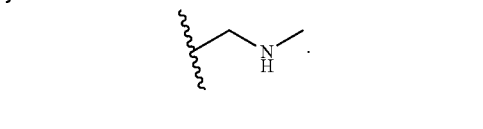

In a further embodiment, the R group of -L-R$^9$ is not hydrogen, —CN, or halogen.

In certain embodiments, -L-R$^9$ is
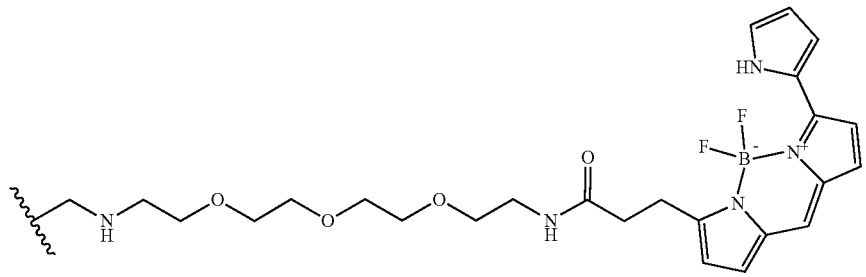
In certain embodiments, -L-R$^9$ is
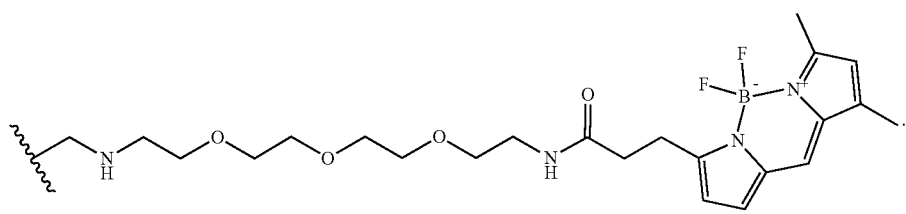
In some embodiments, -L-R$^9$ is selected from those depicted in Table 1, below.
In certain embodiments, when Ring B is unsubstituted phenyl, -L-R$^9$ is selected from
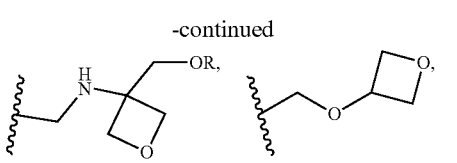
-continued
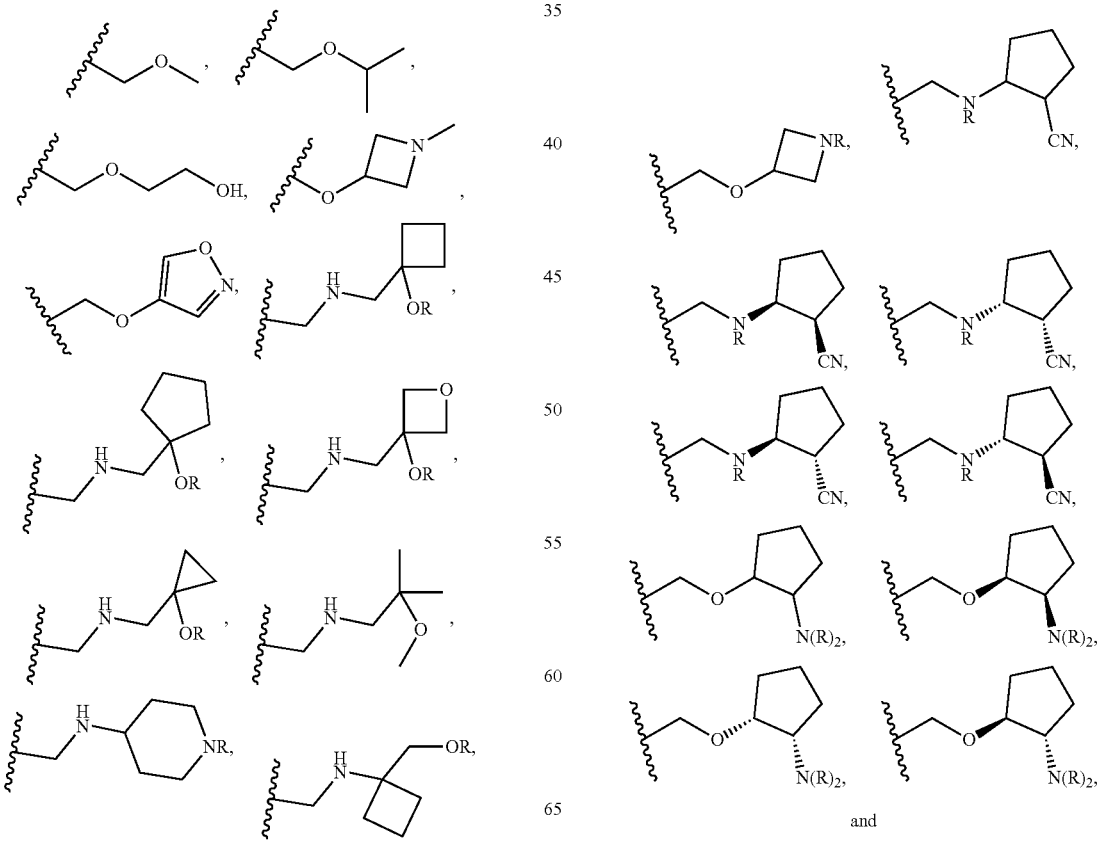
and

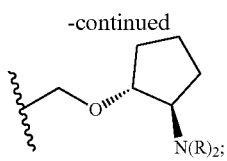

or -L-R⁹ is selected from

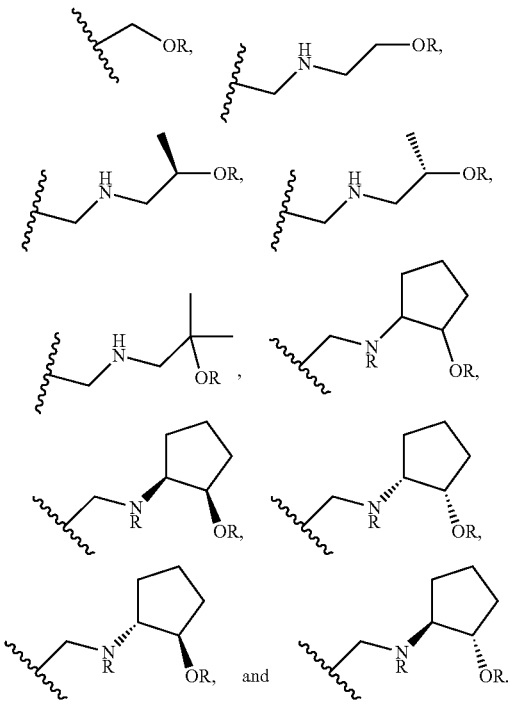

In further embodiments, the R group of -L-R⁹ is not hydrogen, —CN, or halogen.

As defined generally above, each instance of $R^1$, $R^2$, $R^3$, $R^4$, $R^5$, $R^6$, $R^7$, $R^8$, and $R^9$ is independently and optionally substituted with v instances of $R^A$, wherein each $R^A$ is independently oxo, halogen, —CN, —NO₂, —OR, —SR, —N(R)₂, —S(O)₂R, —S(O)₂N(R)₂, —S(O)R, —S(O)N(R)₂, —C(R)₂OR, —C(O)R, —C(O)OR, —C(O)N(R)₂, —C(O)N(R)OR, —OC(O)R, —OC(O)N(R)₂, —N(R)C(O)OR, —N(R)C(O)R, —N(R)C(O)N(R)₂, —N(R)C(NR)N(R)₂, —N(R)N(R)₂, —N(R)S(O)₂N(R)₂, —N(R)S(O)₂R, —N=S(O)(R)₂, —S(NR)(O)R, —N(R)S(O)R, —N(R)CN, —P(O)(R)N(R)₂, —P(O)(R)OR, —P(O)(R)₂, or an optionally substituted group selected from $C_{1-6}$ aliphatic; phenyl; naphthyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; and a 6-11 membered saturated or partially unsaturated bicyclic heterocyclic ring having 1-2 heteroatoms independently selected from nitrogen, oxygen, and sulfur.

In certain embodiments, $R^1$, $R^2$, $R^3$, $R^4$, $R^5$, $R^6$, $R^7$, $R^8$, or $R^9$ is independently and optionally substituted with v instances of $R^A$, wherein each $R^A$ is independently oxo, halogen, —CN, —NO₂, —OR, —SR, —N(R)₂, —S(O)₂R, —S(O)₂N(R)₂, —S(O)R, —S(O)N(R)₂, —C(R)₂OR, —C(O)R, —C(O)OR, —C(O)N(R)₂, —C(O)N(R)OR, —OC(O)R, —OC(O)N(R)₂, —N(R)C(O)OR, —N(R)C(O)R, —N(R)C(O)N(R)₂, —N(R)C(NR)N(R)₂, —N(R)N(R)₂, —N(R)S(O)₂N(R)₂, —N(R)S(O)₂R, —N=S(O)(R)₂, —S(NR)(O)R, —N(R)S(O)R, —N(R)CN, —P(O)(R) N(R)₂, —P(O)(R)OR, —P(O)(R)₂, or an optionally substituted group selected from $C_{1-6}$ aliphatic; phenyl; naphthyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; and a 6-11 membered saturated or partially unsaturated bicyclic heterocyclic ring having 1-2 heteroatoms independently selected from nitrogen, oxygen, and sulfur.

In some embodiments, $R^A$ is oxo, halogen, —CN, —NO₂, —OR, —SR, —N(R)₂, —S(O)₂R, —S(O)₂N(R)₂, —S(O)R, —S(O)N(R)₂, —C(R)₂OR, —C(O)R, —C(O)OR, —C(O) N(R)₂, —C(O)N(R)OR, —OC(O)R, —OC(O)N(R)₂, —N(R)C(O)OR, —N(R)C(O)R, —N(R)C(O)N(R)₂, —N(R)C(NR)N(R)₂, —N(R)N(R)₂, —N(R)S(O)₂N(R)₂, —N(R)S(O)₂R, —N=S(O)(R)₂, —S(NR)(O)R, —N(R)S (O)R, —N(R)CN, —P(O)(R)N(R)₂, —P(O)(R)OR, —P(O) (R)₂, or an optionally substituted group selected from $C_{1-6}$ aliphatic; phenyl; naphthyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; and a 6-11 membered saturated or partially unsaturated bicyclic heterocyclic ring having 1-2 heteroatoms independently selected from nitrogen, oxygen, and sulfur.

In some embodiments, $R^A$ is methyl, —OH, fluoro, —CO₂Me, or —NH₂.

In some embodiments, $R^A$ is selected from those depicted in Table 1, below.

As defined generally above, each R is independently hydrogen, —CN, halogen, or an optionally substituted group selected from $C_{1-6}$ aliphatic; phenyl; naphthyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic carbocyclic ring having 1-2 heteroatoms independently selected from nitrogen, oxygen, and sulfur; or two R groups on the same atom are optionally taken together with the atom to form an optionally substituted 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur.

In some embodiments, R is hydrogen, —CN, halogen, or an optionally substituted group selected from $C_{1-6}$ aliphatic; phenyl; naphthyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic carbocyclic ring having 1-2 heteroatoms independently selected from nitrogen, oxygen, and sulfur; or two R groups on the same atom are optionally taken together with the atom to form an optionally substituted 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur.

In some embodiments, R is hydrogen.

In some embodiments, R is —CN or halogen.

In some embodiments, R is an optionally substituted group selected from $C_{1-6}$ aliphatic; phenyl; naphthyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic carbocyclic ring having 1-2 heteroatoms independently selected from nitrogen, oxygen, and sulfur.

In some embodiments, R is hydrogen. In some embodiments, R is $CF_3$. In some embodiments, R is $C(O)OC(CH_3)$. In some embodiments, R is an optionally substituted $C_{1-6}$ aliphatic.

In some embodiments, two R groups on the same atom are taken together with the atom to form an optionally substituted 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur.

In some embodiments, R is selected from those depicted in Table 1, below.

As defined generally above, m is 0, 1, 2, 3, 4, or 5.

In certain embodiments, m is 0, 1, 2, 3, 4, or 5.

In some embodiments, m is 0. In some embodiments, m is 1. In some embodiments, m is 2. In some embodiments, m is 3. In some embodiments, m is 4. In some embodiments, m is 5.

In some embodiments, m is 0 or 1. In some embodiments, m is 0, 1, or 2. In some embodiments, m is 0, 1, 2, or 3. In some embodiments, m is 1 or 2. In some embodiments, m is 1, 2, or 3. In some embodiments, m is 1, 2, 3, or 4. In some embodiments, m is 2 or 3. In some embodiments, m is 2, 3, or 4. In some embodiments, m is 3 or 4. In some embodiments, m is 3, 4, or 5.

In some embodiments, m is selected from the values represented in the compounds depicted in Table 1, below.

As defined generally above, n is 0, 1, 2, 3, or 4.

In certain embodiments, n is 0, 1, 2, 3, or 4.

In certain embodiments, n is 0. In certain embodiments, n is 1. In certain embodiments, n is 2. In certain embodiments, n is 3. In certain embodiments, n is 4.

In some embodiments, n is 0 or 1. In some embodiments, n is 0, 1, or 2. In some embodiments, n is 0, 1, 2, or 3. In some embodiments, n is 1 or 2. In some embodiments, n is 1, 2, or 3. In some embodiments, n is 1, 2, 3, or 4. In some embodiments, n is 2 or 3. In some embodiments, n is 2, 3, or 4. In some embodiments, n is 3 or 4.

In some embodiments, n is selected from the values represented in the compounds depicted in Table 1, below.

As defined generally above, p is 0, 1, 2, 3, or 4.

In certain embodiments, p is 0, 1, 2, 3, or 4.

In certain embodiments, p is 0. In certain embodiments, p is 1. In certain embodiments, p is 2. In certain embodiments, p is 3. In certain embodiments, p is 4.

In some embodiments, p is 0 or 1. In some embodiments, p is 0, 1, or 2. In some embodiments, p is 0, 1, 2, or 3. In some embodiments, p is 0, 1, 2, 3, or 4. In some embodiments, p is 1 or 2. In some embodiments, p is 1, 2, or 3. In some embodiments, p is 1, 2, 3, or 4. In some embodiments, p is 2 or 3. In some embodiments, p is 2, 3, or 4. In some embodiments, p is 3 or 4.

In some embodiments, p is selected from the values represented in the compounds depicted in Table 1, below.

As defined generally above, q is 0, 1, 2, or 3.

In certain embodiments, q is 0, 1, 2, or 3.

In certain embodiments, q is 0. In certain embodiments, q is 1. In certain embodiments, q is 2. In certain embodiments, q is 3.

In certain embodiments, q is 0, 1, or 2. In certain embodiments, q is 1, 2, or 3. In certain embodiments, q is 1 or 2. In certain embodiments, q is 2 or 3.

In some embodiments, q is selected from the values represented in the compounds depicted in Table 1, below.

As defined generally above, t is 0 or 1.

In certain embodiments, t is 0 or 1.

In certain embodiments, t is 0. In certain embodiments, t is 1.

In some embodiments, t is selected from those depicted in Table 1, below.

As defined generally above, u is 0, 1, 2, 3, or 4.

In some embodiments, u is 0, 1, 2, 3, or 4.

In some embodiments, u is 0. In some embodiments, u is 1. In some embodiments, u is 2. In some embodiments, u is 3. In some embodiments, u is 4.

In some embodiments, u is selected from those depicted in Table 1, below.

As defined generally above, each instance of v is independently 0, 1, 2, 3, 4, or 5.

In some embodiments, v is 0, 1, 2, 3, 4, or 5.

In some embodiments, v is 0. In some embodiments, v is 1. In some embodiments, v is 2. In some embodiments, v is 3. In some embodiments, v is 4. In some embodiments, v is 5.

In some embodiments, v is 0 or 1. In some embodiments, v is 0, 1, or 2. In some embodiments, v is 0, 1, 2, or 3. In some embodiments, v is 1 or 2. In some embodiments, v is 1, 2, or 3. In some embodiments, v is 1, 2, 3, or 4. In some embodiments, v is 2 or 3. In some embodiments, v is 2, 3, or 4. In some embodiments, v is 3 or 4. In some embodiments, v is 3, 4, or 5.

In some embodiments, v is selected from those depicted in Table 1, below.

As defined generally above, === denotes a single or double bond.

In some embodiments, === denotes a single bond. In some embodiments, === denotes a double bond.

In some embodiments, === is selected from those depicted in Table 1, below.

In some embodiments, the present invention provides compounds of formula II-a to II-zz:

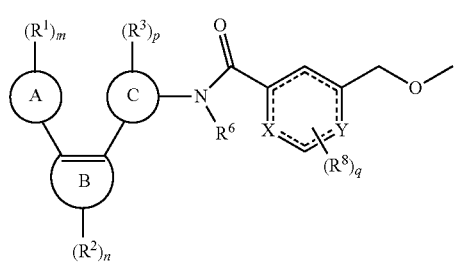

II-a

-continued

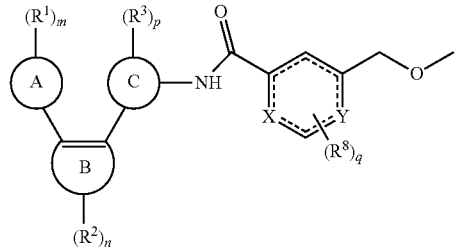

II-b

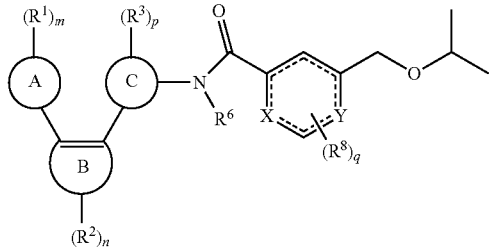

II-c

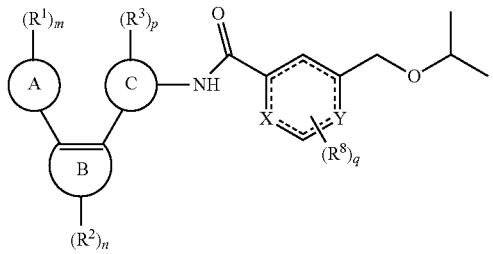

II-d

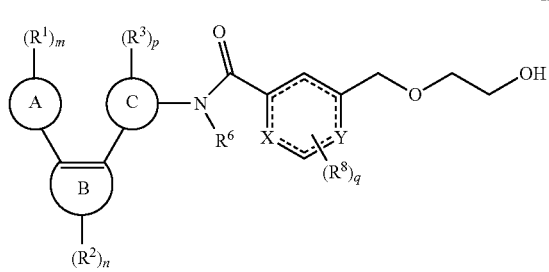

II-e

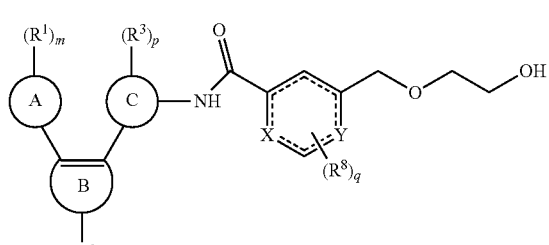

II-f

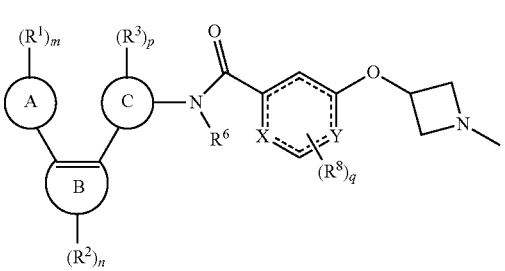

II-g

II-h
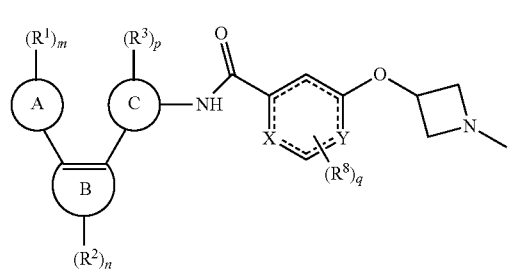
II-m
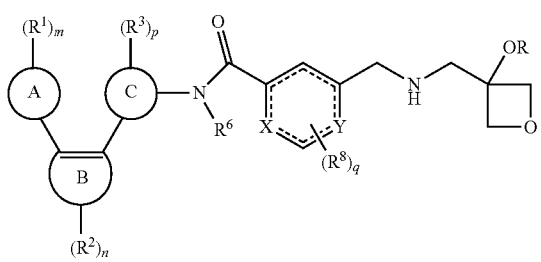
II-i
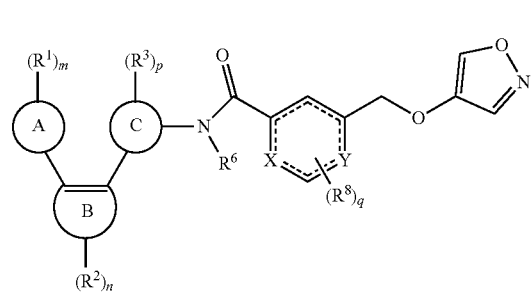
II-n
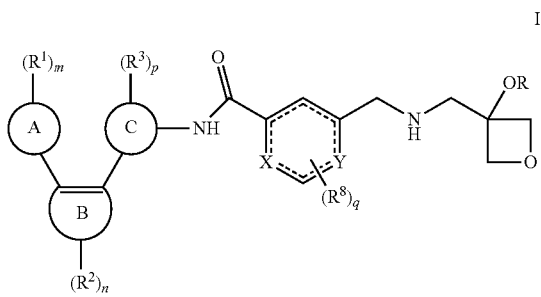
II-j
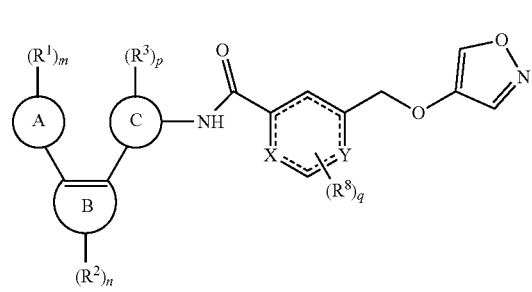
II-o
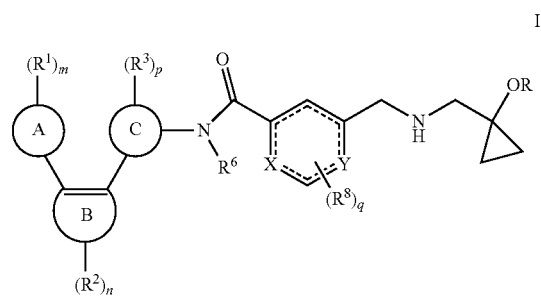
II-k
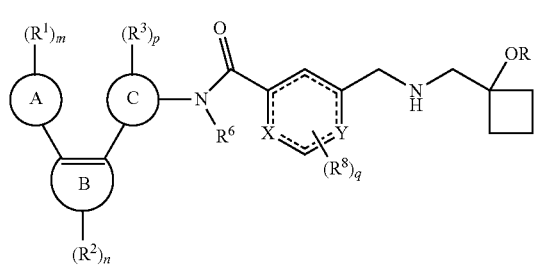
II-p
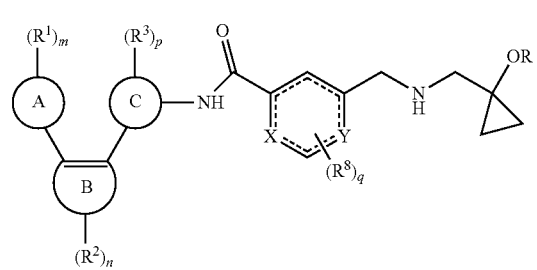
II-l
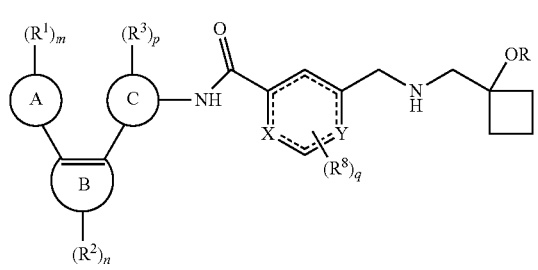
II-q
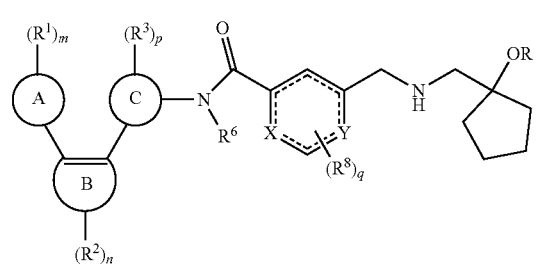

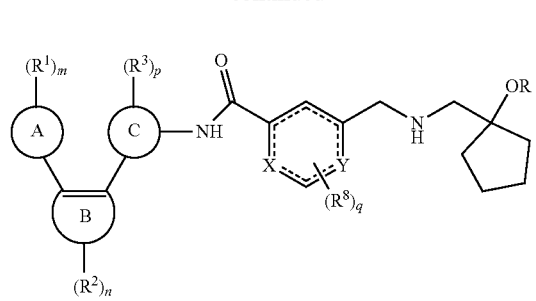
II-r
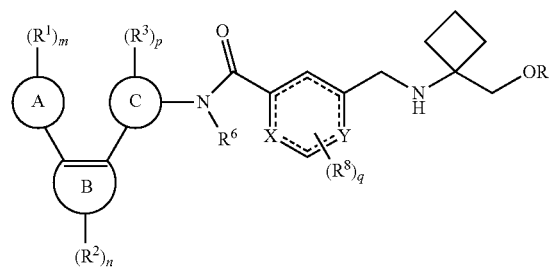
II-s
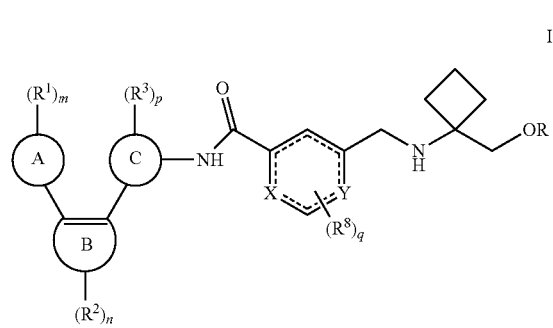
II-t
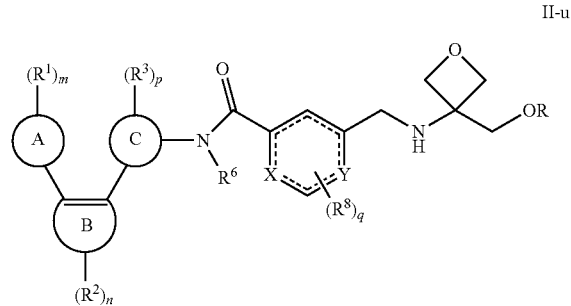
II-u
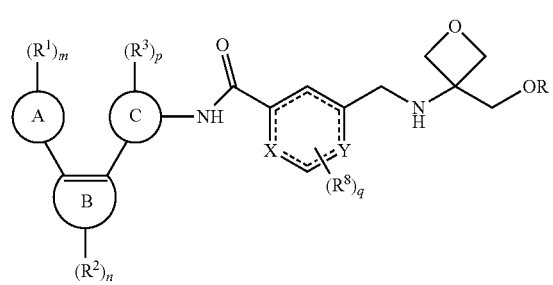
II-v
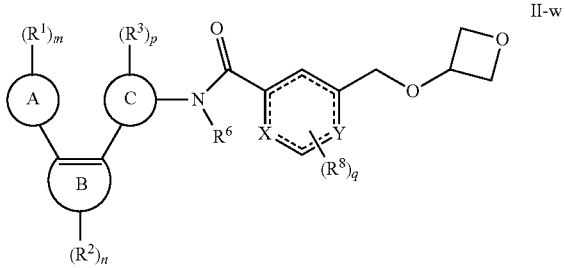
II-w
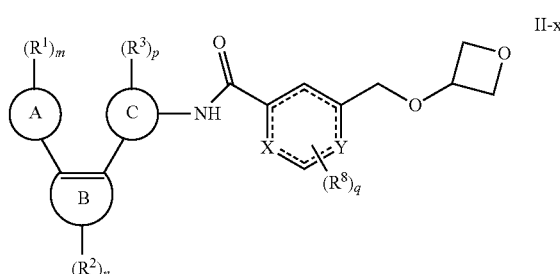
II-x
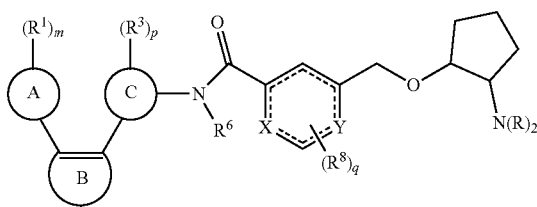
II-y
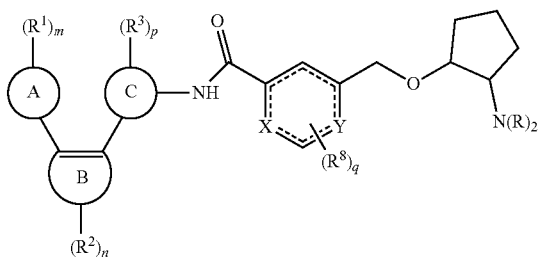
II-z
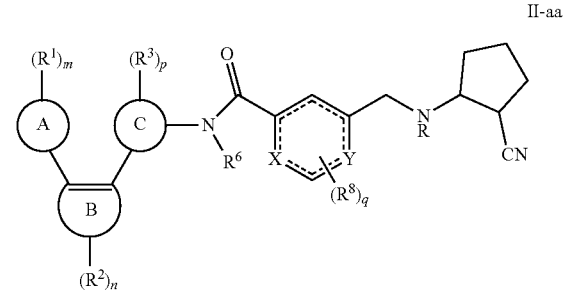
II-aa

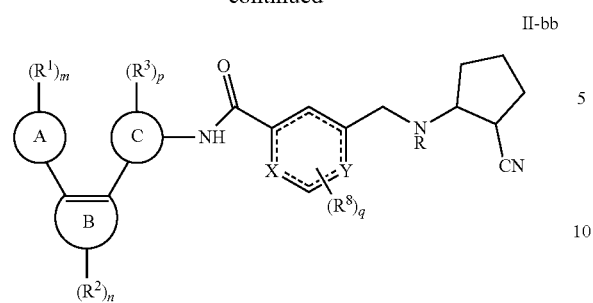
II-bb
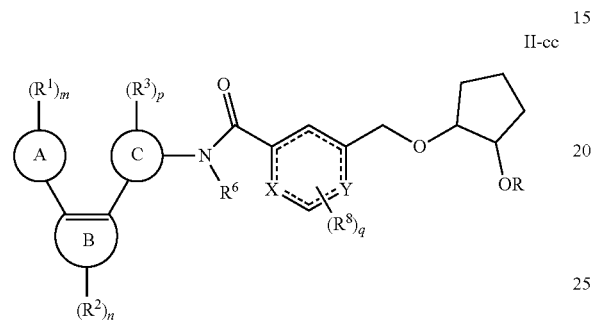
II-cc
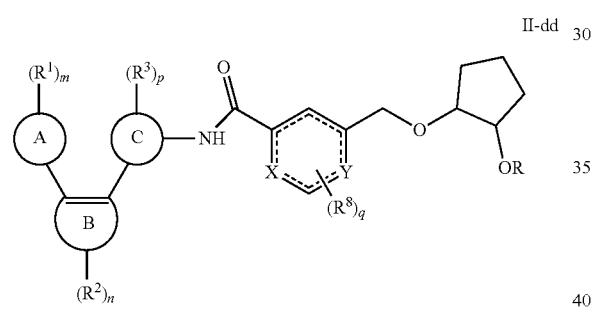
II-dd
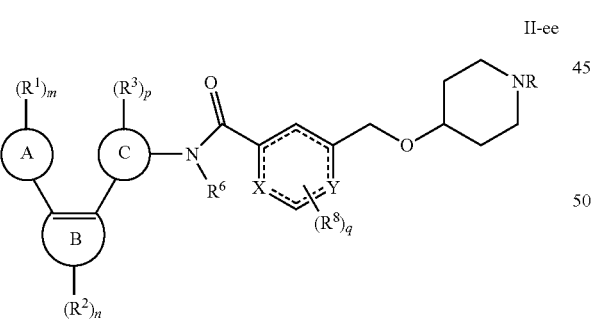
II-ee
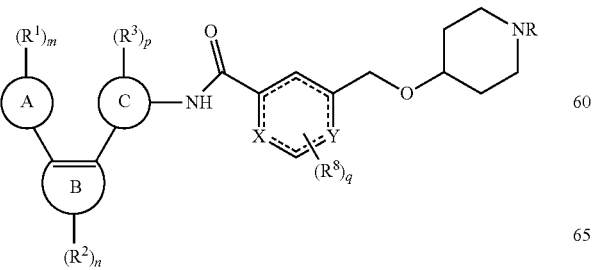
II-ff
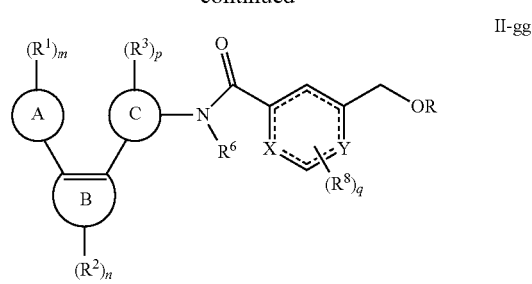
II-gg
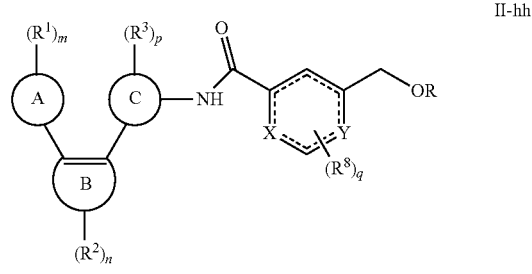
II-hh
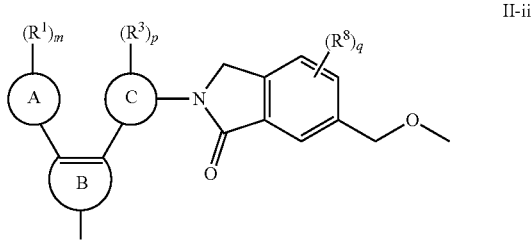
II-ii
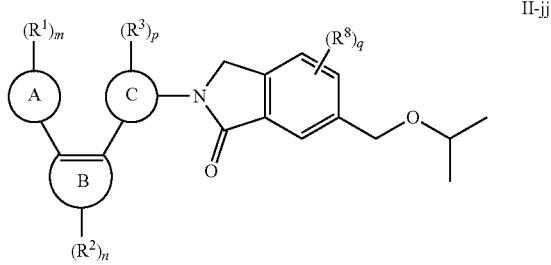
II-jj
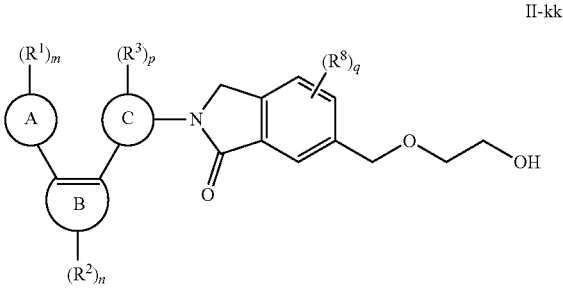
II-kk
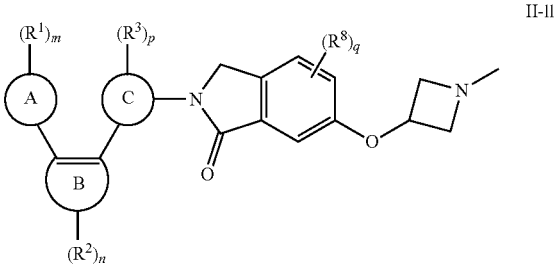
II-ll II-mm
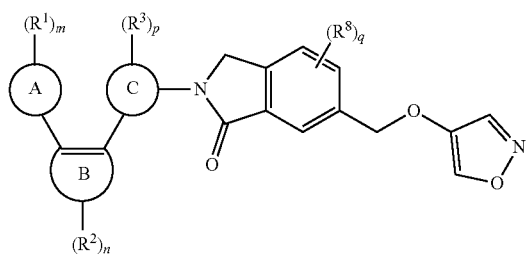
II-rr
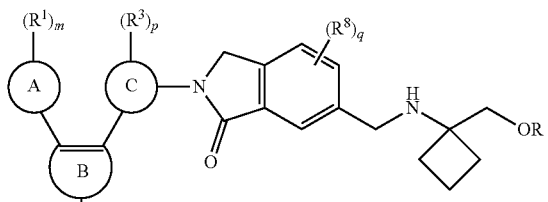
II-nn
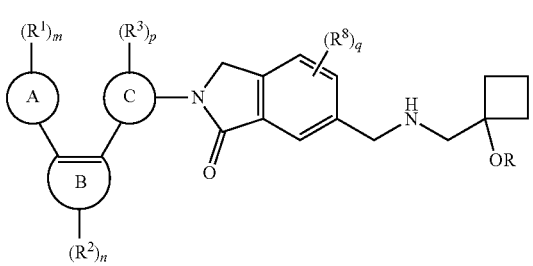
II-ss
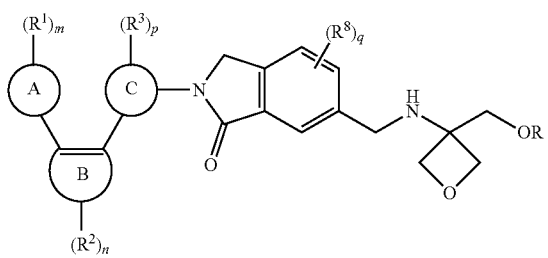
II-oo
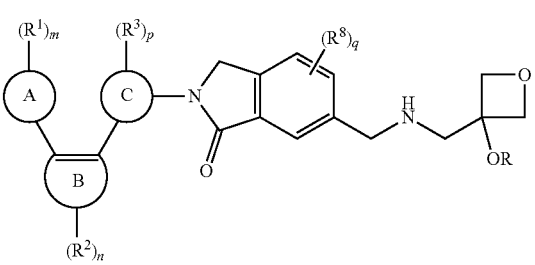
II-tt
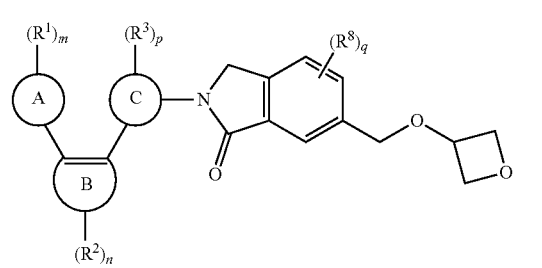
II-pp
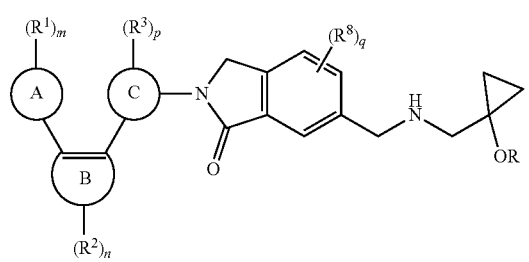
II-uu
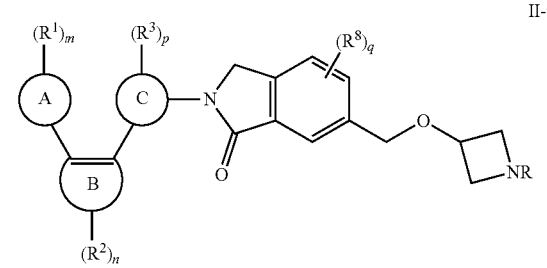
II-qq
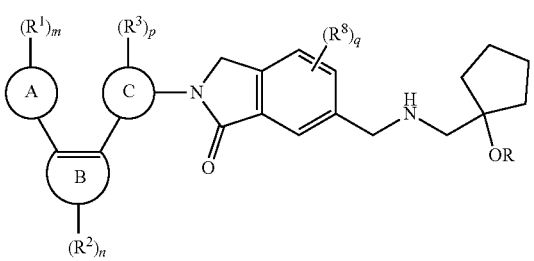
II-vv
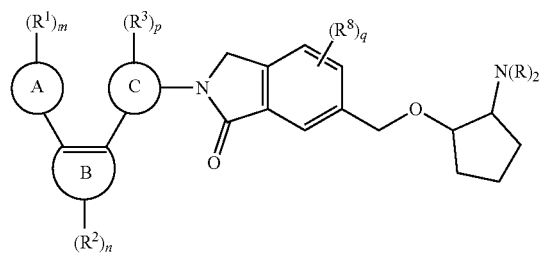
II-ww
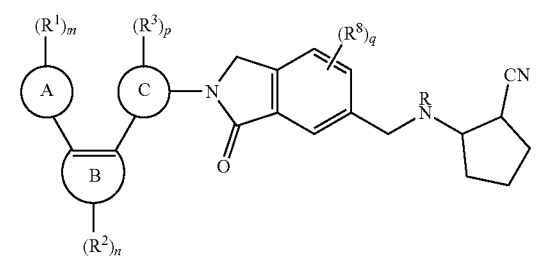

II-xx
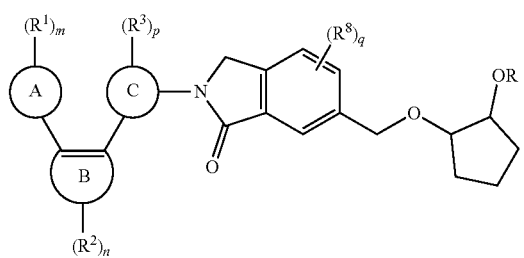

II-yy
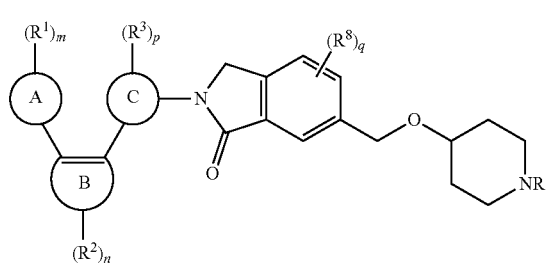

II-zz
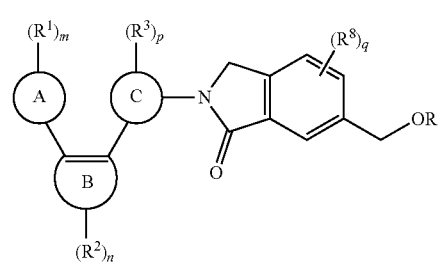

II-aaa
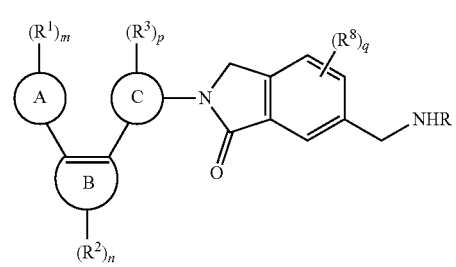

or a pharmaceutically acceptable salt thereof, wherein the R group of —OR, —NHR, —NR—, or —N(R)$_2$ is not hydrogen, —CN, or halogen and wherein each of X, Y, Ring A, Ring B, Ring C, R$^1$, R$^2$, R$^3$, R$^6$, R$^8$, m, n, p, and q is as defined above and described in embodiments herein, both singly and in combination.

In some embodiments, the present invention provides compounds of formula II-a to II-zz:

II-a
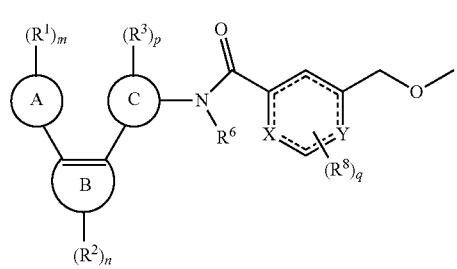

II-b
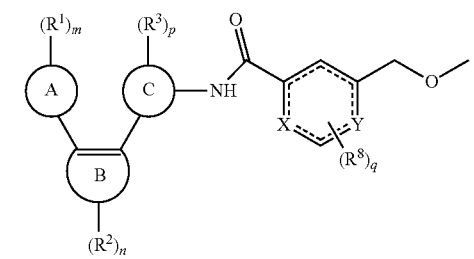

II-c
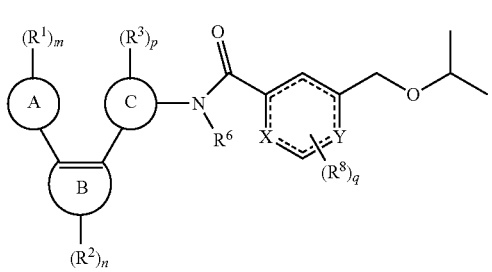

II-d
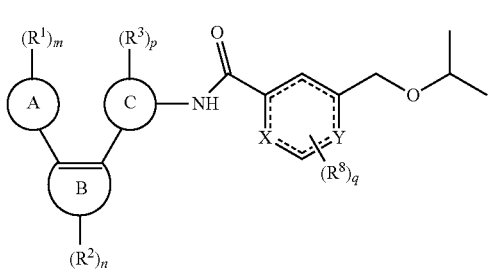

II-e
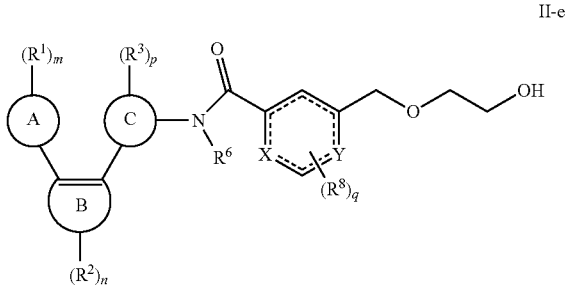

II-f
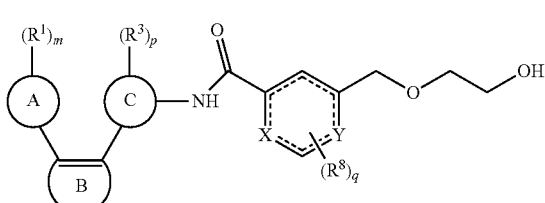

II-g
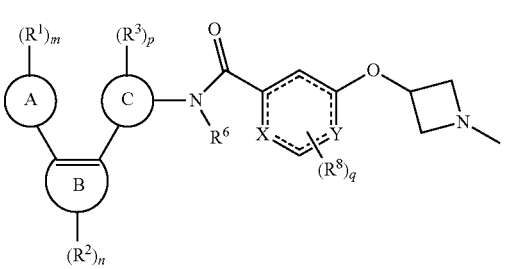

II-h
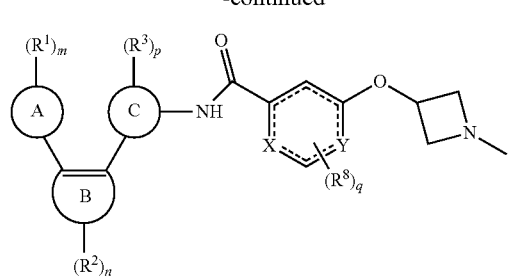
II-m
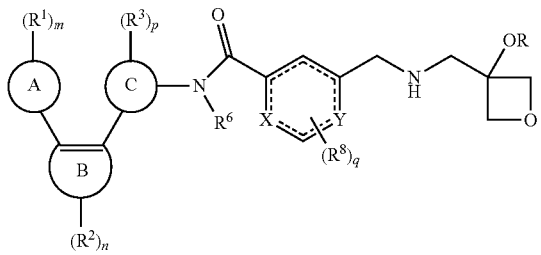
II-i
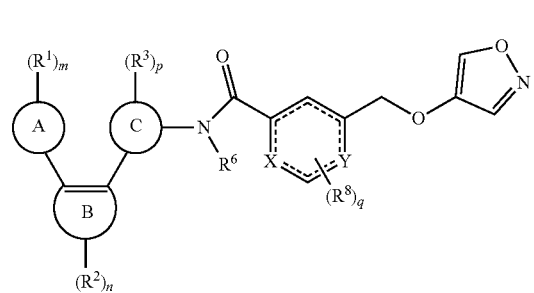
II-n
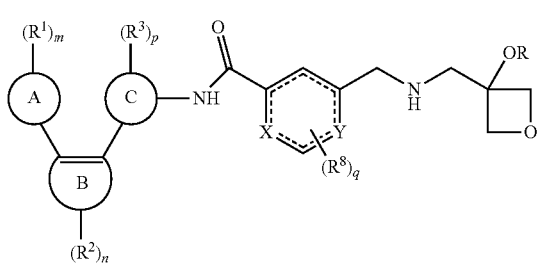
II-j
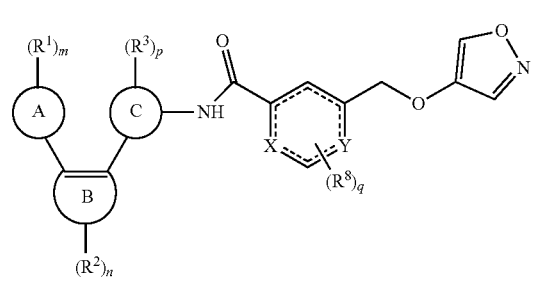
II-o
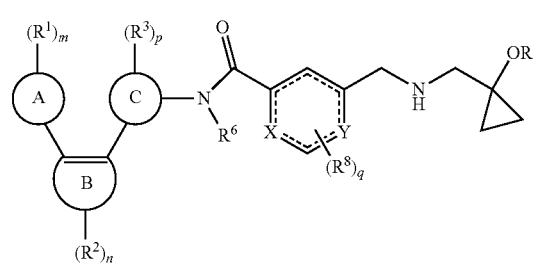
II-k
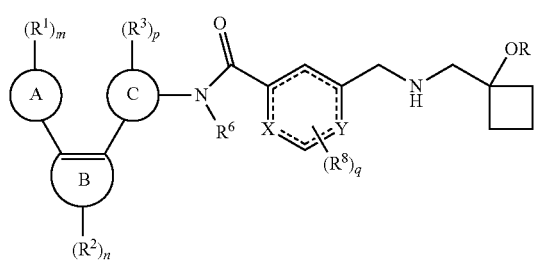
II-p
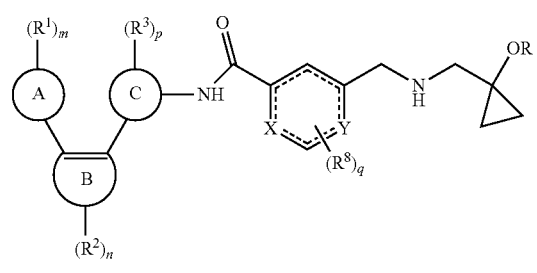
II-l
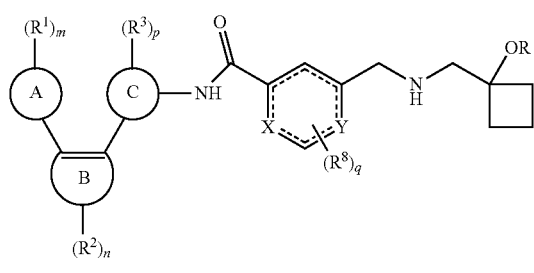
II-q
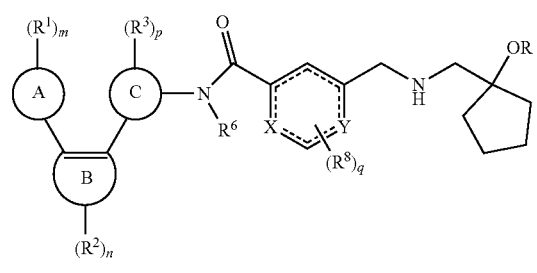

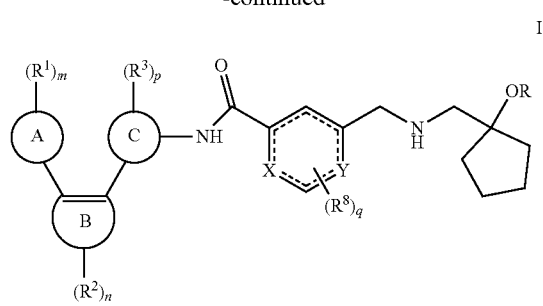
II-r
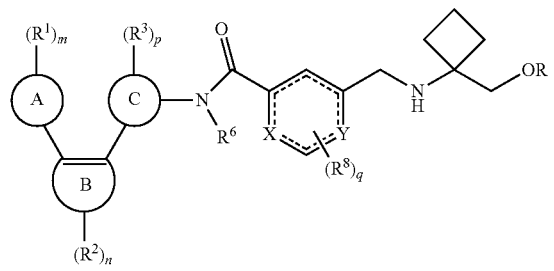
II-s
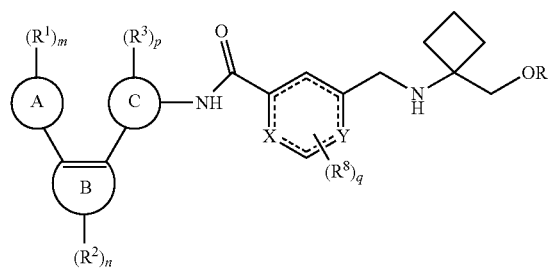
II-t
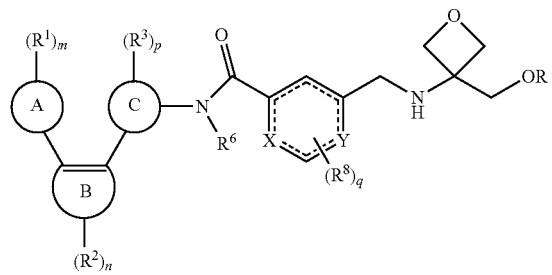
II-u
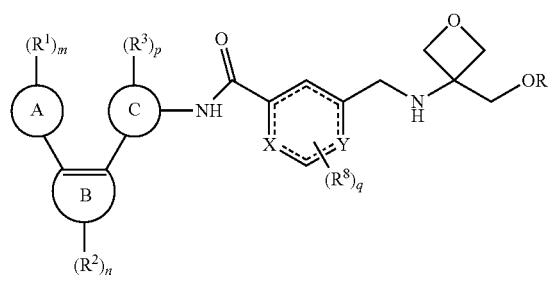
II-v
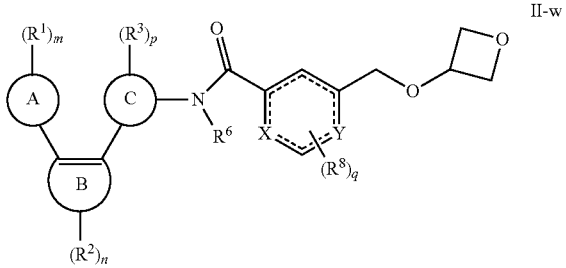
II-w
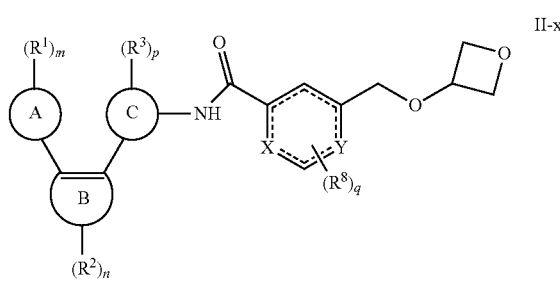
II-x
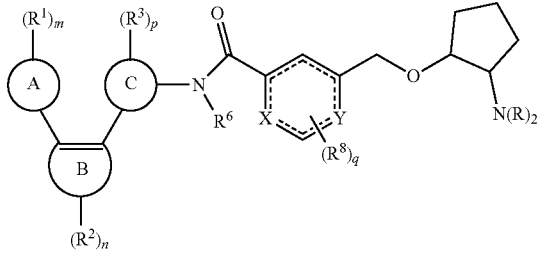
II-y
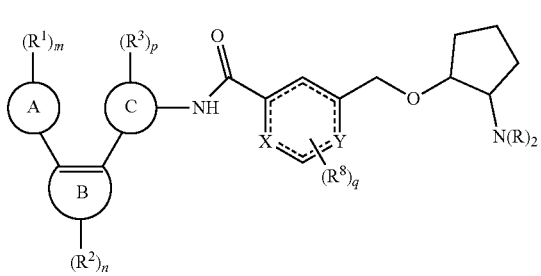
II-z
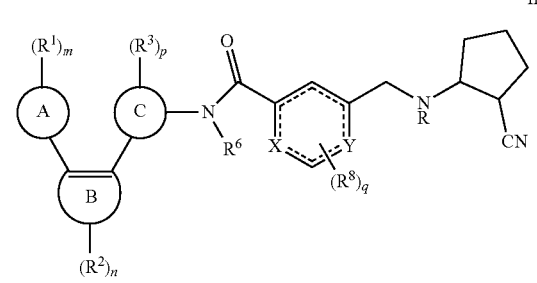
II-aa

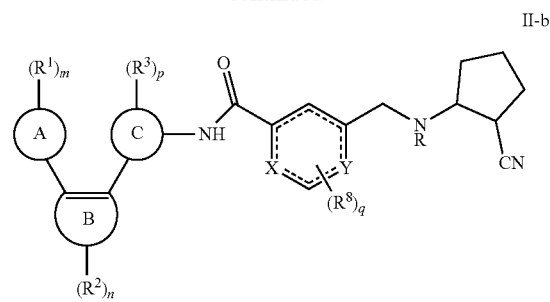 II-bb
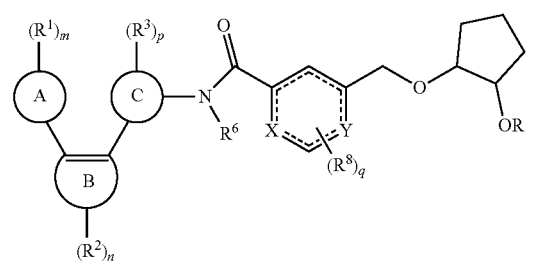 II-cc
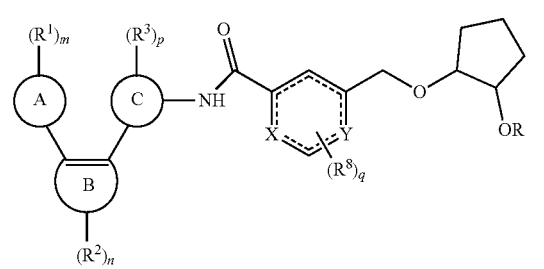 II-dd
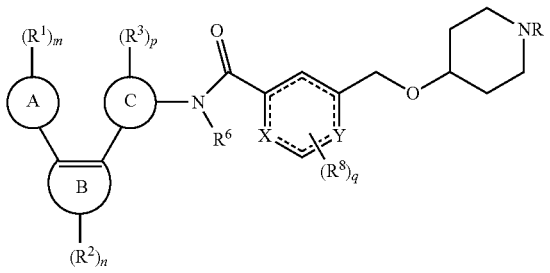 II-ee
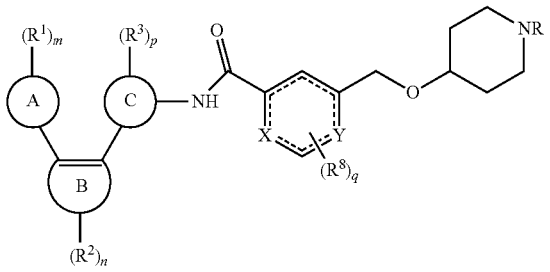 II-ff
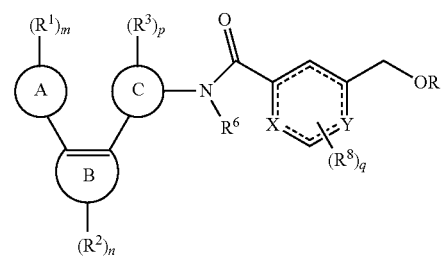 II-gg
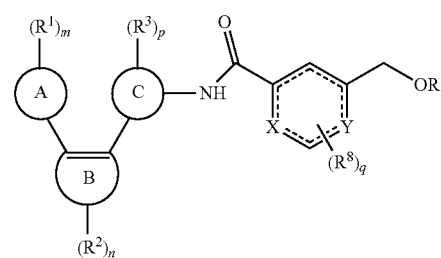 II-hh
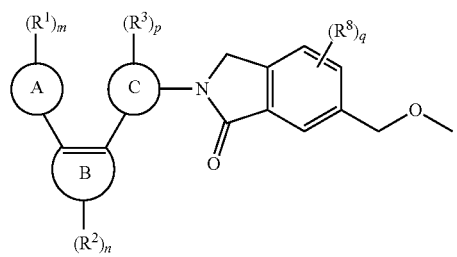 II-ii
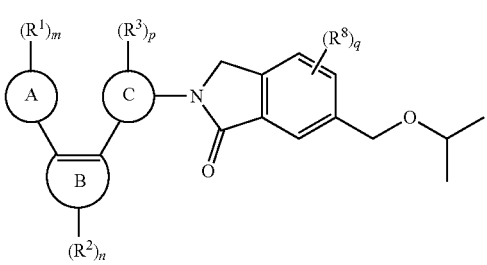 II-jj
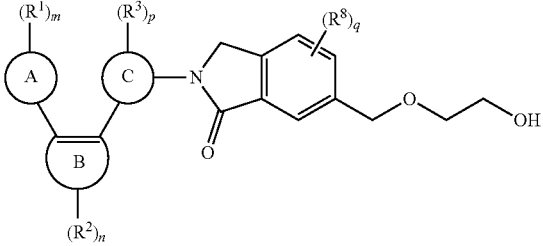 II-kk
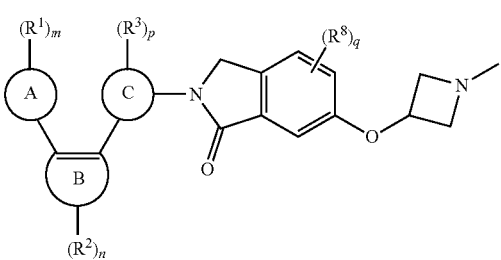 II-ll II-mm
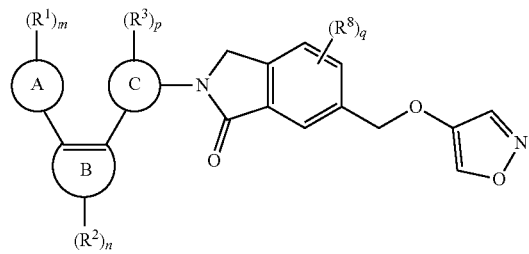
II-rr
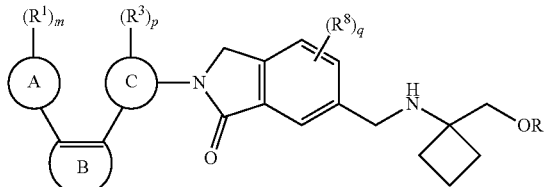
II-nn
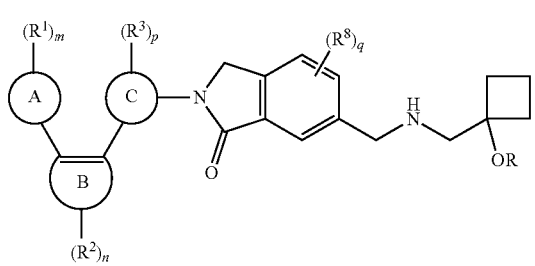
II-ss
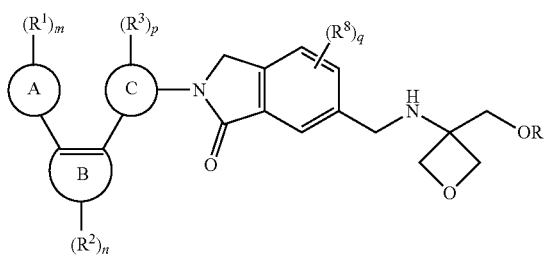
II-oo
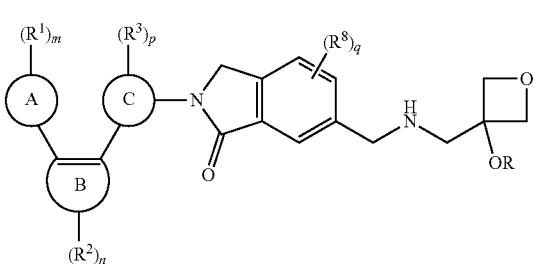
II-tt
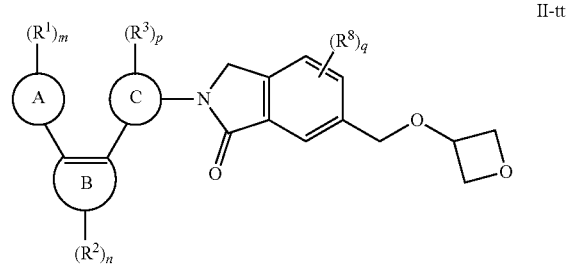
II-uu
II-pp
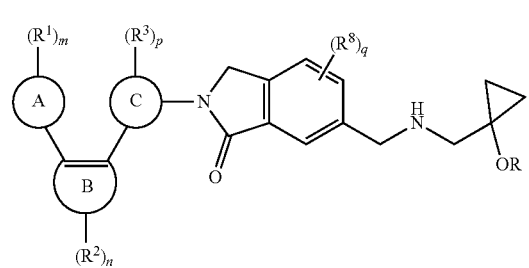
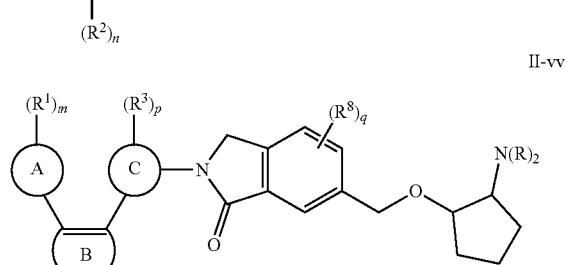
II-vv
II-qq
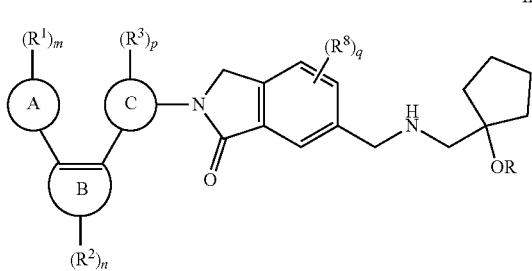
II-ww
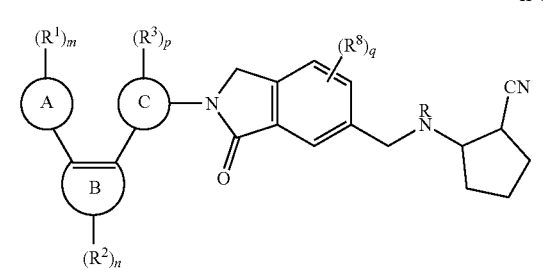

II-xx

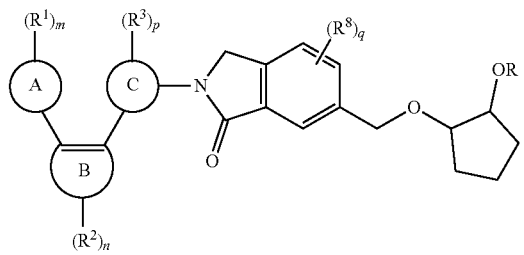

II-yy

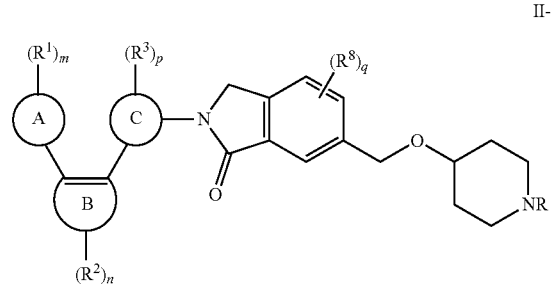

II-zz

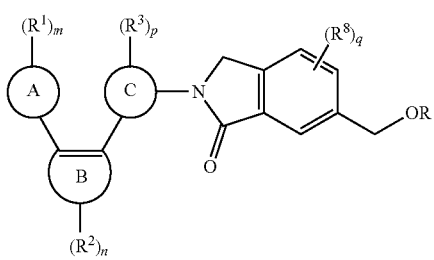

II-aaa

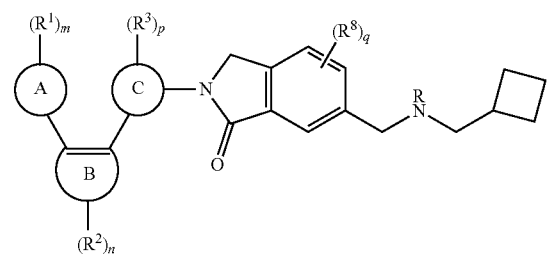

II-bbb

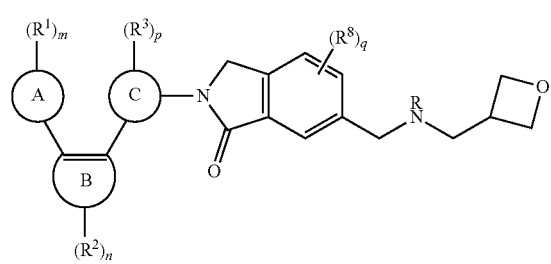

II-ccc

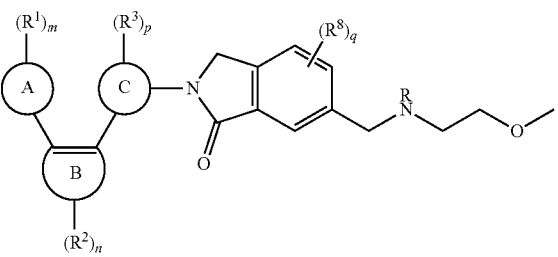

II-ddd

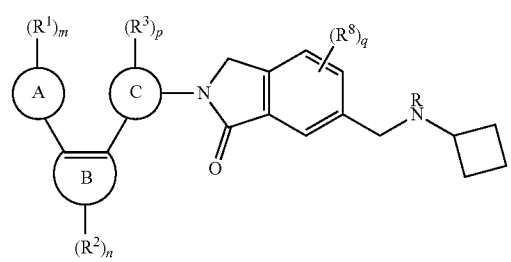

II-eee

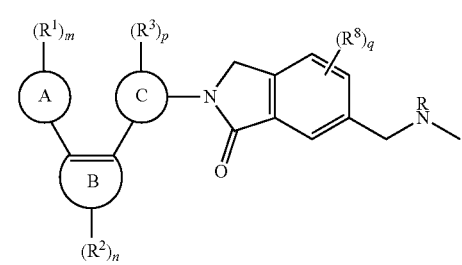

or a pharmaceutically acceptable salt thereof, wherein each of X, Y, Ring A, Ring B, Ring C, $R^1$, $R^2$, $R^3$, $R^6$, $R^8$, m, n, p, and q is as defined above and described in embodiments herein, both singly and in combination.

In some embodiments, the present invention provides a compound of formula II-k, II-l, II-m, II-n, II-o, II-p, II-q, II-r, II-s, II-t, II-u, II-v, II-y, II-z, II-cc, II-dd, II-ee, II-ff, II-gg, II-hh, II-nn, II-oo, II-pp, II-qq, II-rr, II-ss, II-uu, II-vv, II-xx, II-yy, II-zz, II-aaa, II-bbb, II-ccc, II-ddd, or II-eee, wherein R is hydrogen, thereby forming a compound of formula II-k-a, II-l-a, II-m-a, II-n-a, II-o-a, II-p-a, II-q-a, II-r-a, II-s-a, II-t-a, II-u-a, II-v-a, II-y-a, II-z-a, II-cc-a, II-dd-a, II-ee-a, II-ff-a, II-gg-a, II-hh-a, II-nn-a, II-oo-a, II-pp-a, II-qq-a, II-rr-a, II-ss-a, II-uu-a, II-vv-a, II-xx-a, II-yy-a, II-zz-a, II-aaa-a, II-bbb-a, II-ccc-a, II-ddd-a, or II-eee-a, respectively:

II-k-a

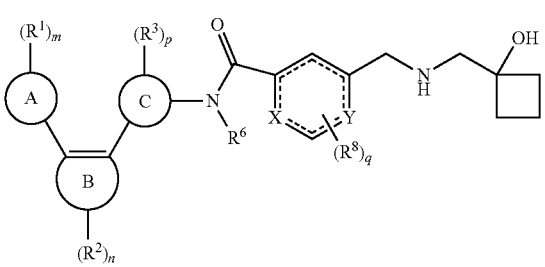

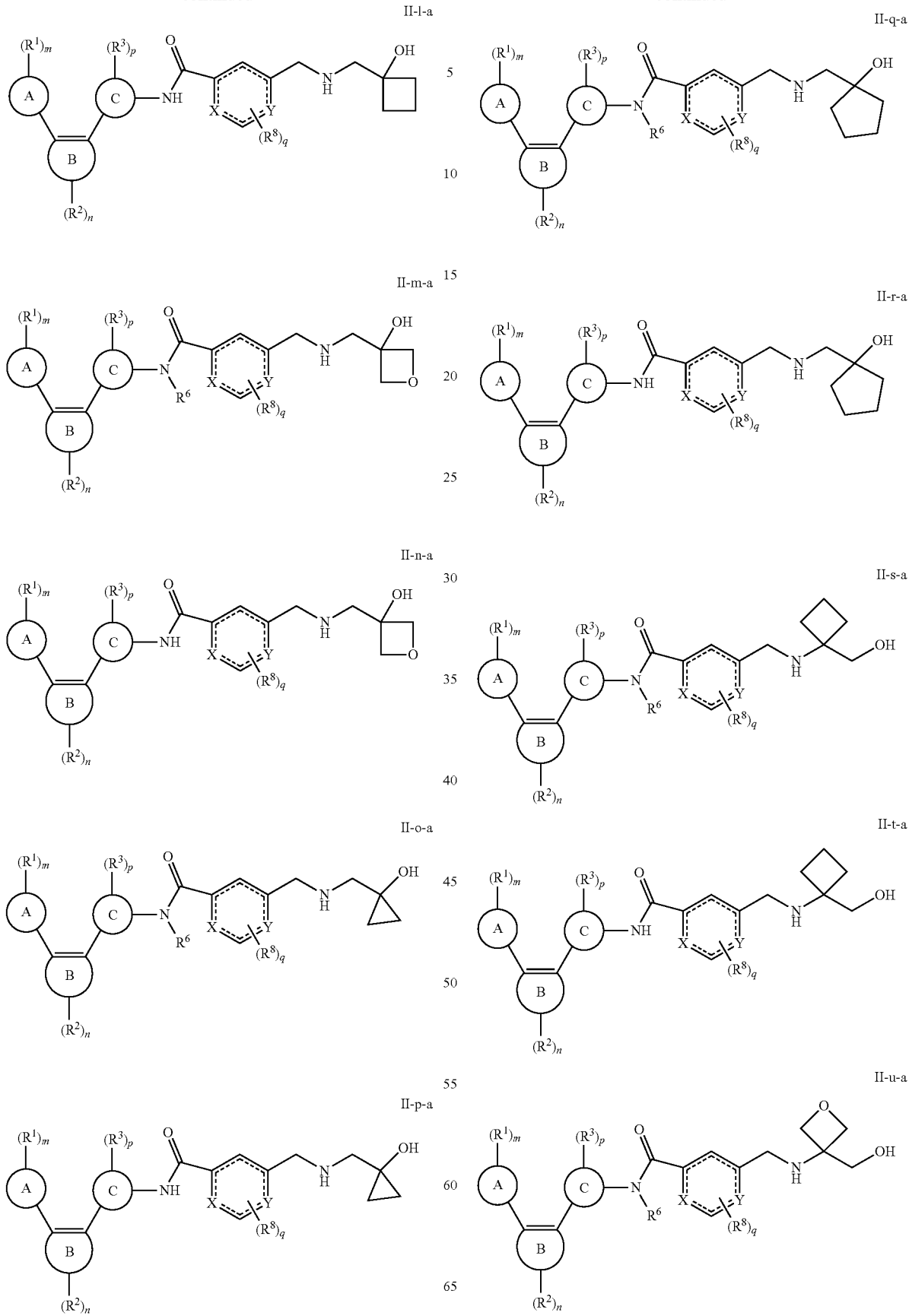

II-v-a
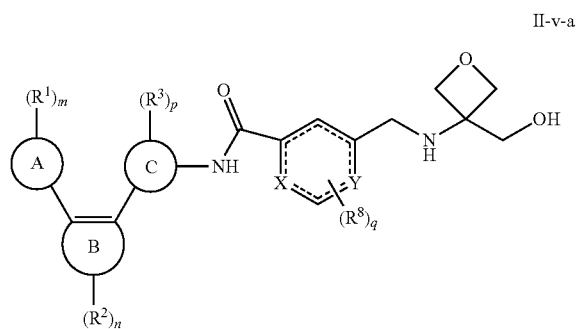
II-ee-a
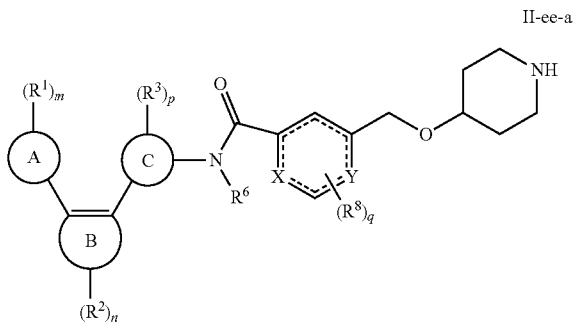
II-y-a
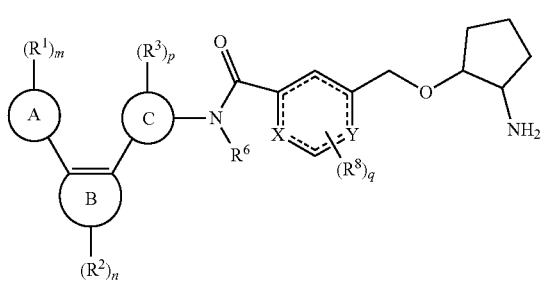
II-ff-a
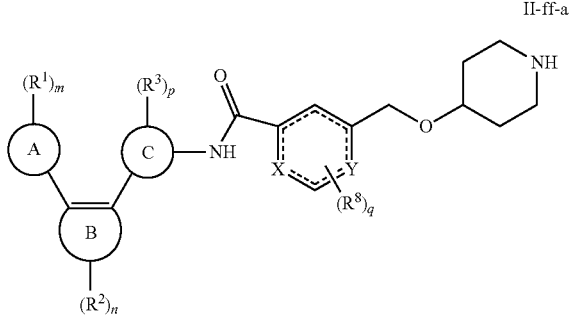
II-z-a
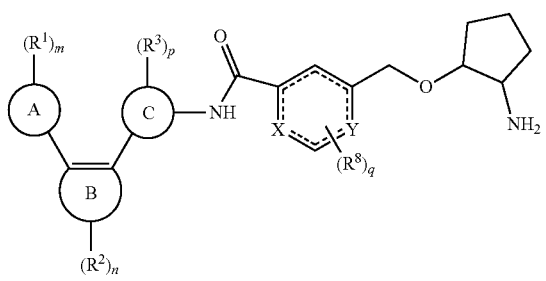
II-gg-a
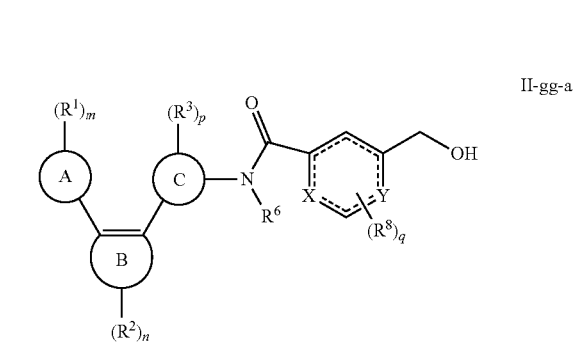
II-cc-a
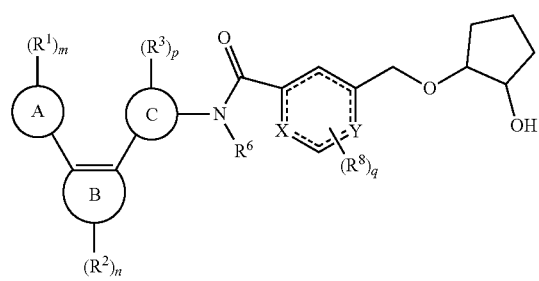
II-hh-a
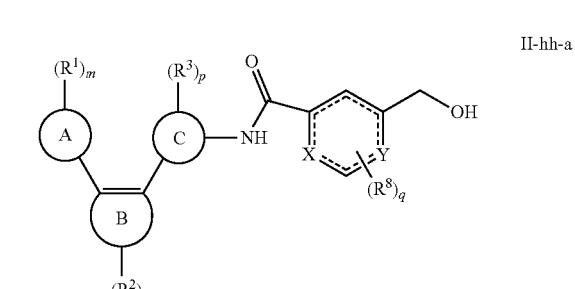
II-dd-a
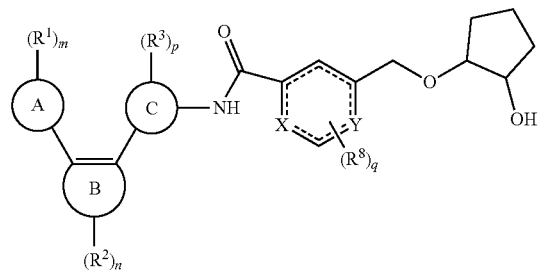
II-nn-a
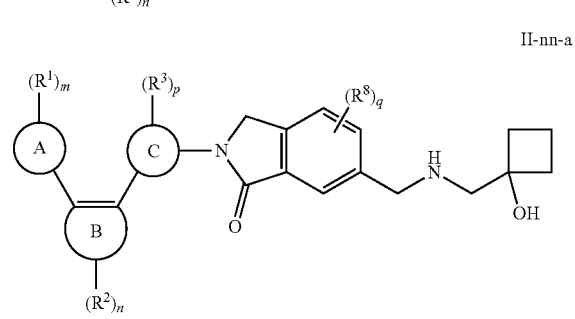

II-oo-a
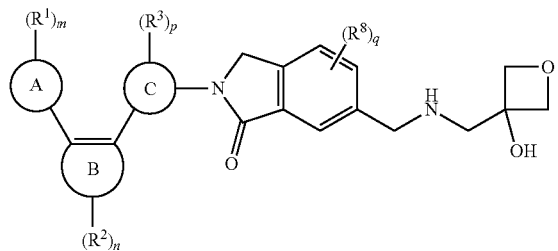
II-uu-a
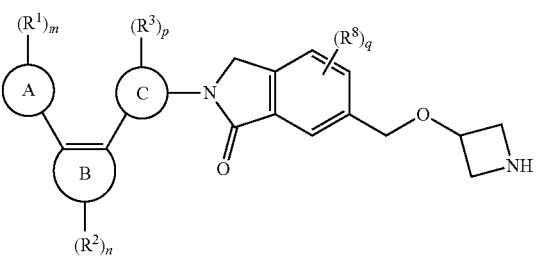
II-pp-a
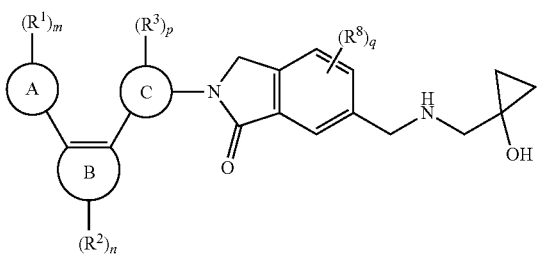
II-vv-a
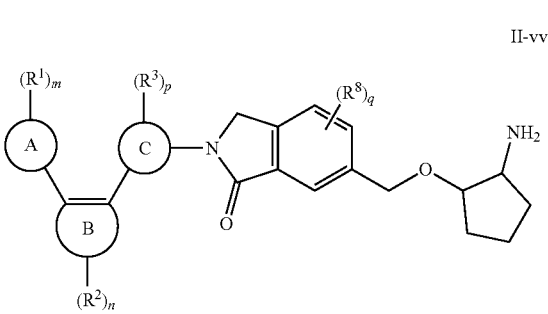
II-qq-a
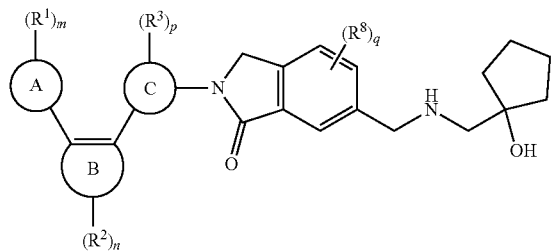
II-xx-a
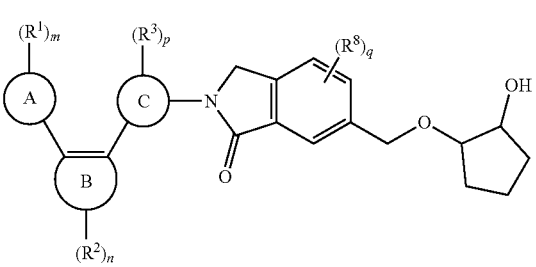
II-rr-a
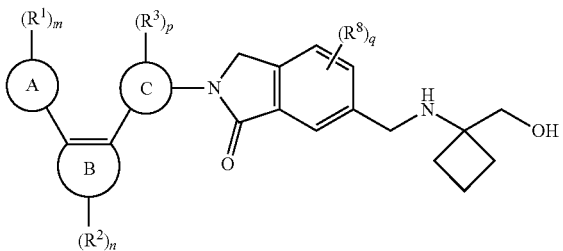
II-yy-a
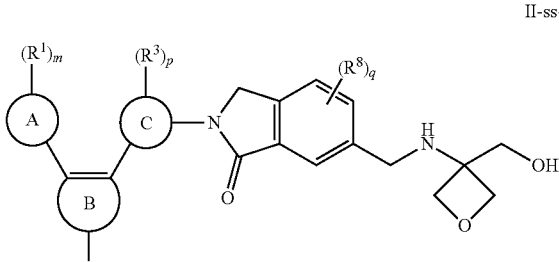
II-ss-a
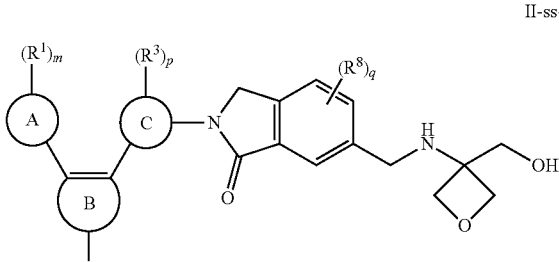
II-zz-a
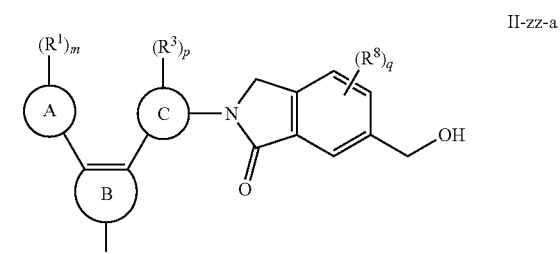

II-aaa-a

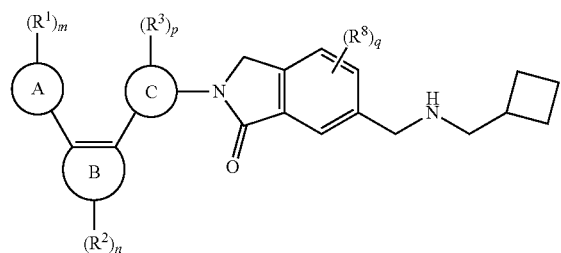

II-nn-a

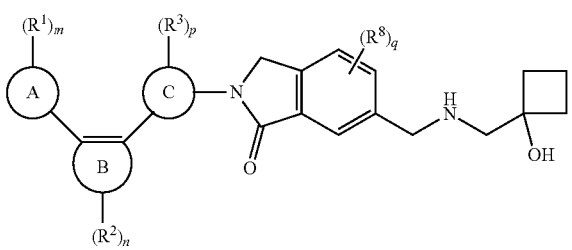

II-bbb-a

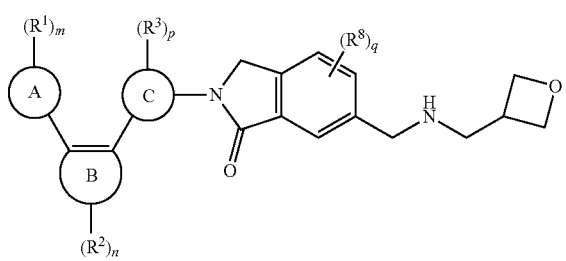

II-qq-a

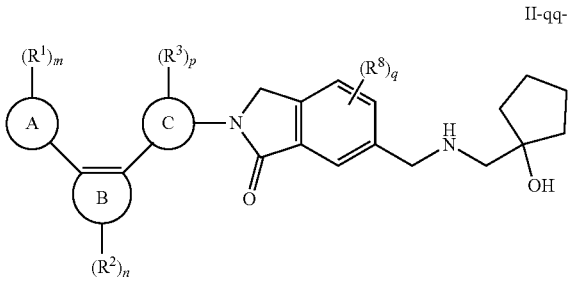

II-ccc-a

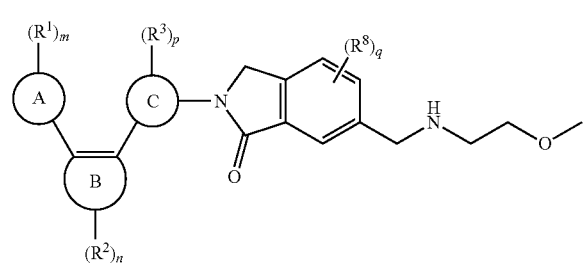

II-xx-a

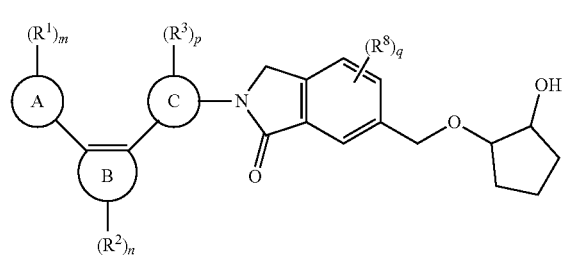

II-ddd-a

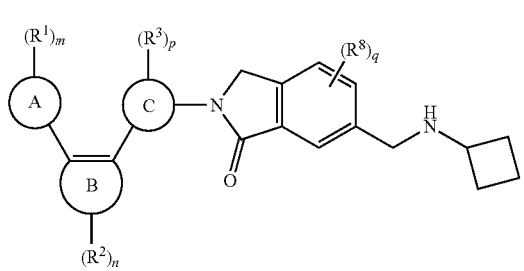

II-eee-a

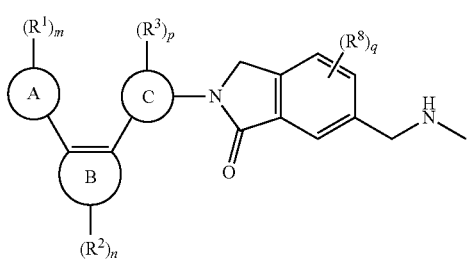

In some embodiments, the present invention provides a compound of formula II-nn, II-qq, or II-xx, wherein R is hydrogen, thereby forming a compound of formula II-nn-a, II-qq-a, or II-xx-a, respectively:

or a pharmaceutically acceptable salt thereof, and wherein each of Ring A, Ring B, Ring C, $R^1$, $R^2$, $R^3$, $R^8$, m, n, p, and q is as defined above and described in embodiments herein, both singly and in combination.

In some embodiments, the present invention provides a compound of formula II-ee, II-ff, or II-yy, wherein R is $CH_3$, thereby forming a compound of formula II-ee-b, II-ff-b, or II-yy-b, respectively:

II-ee-b

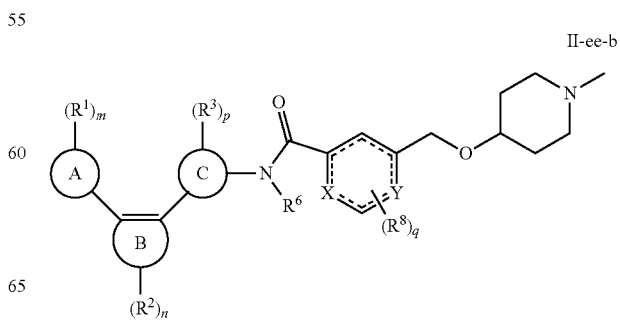

121
-continued

II-ff-b

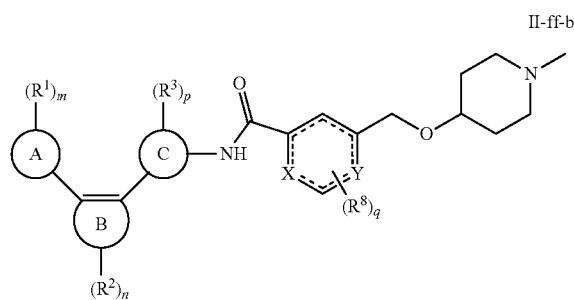

II-yy-b

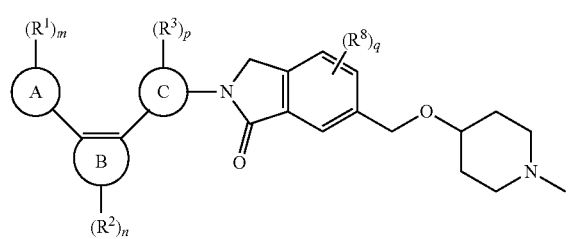

or a pharmaceutically acceptable salt thereof, and wherein each of Ring A, Ring B, Ring C, $R^1$, $R^2$, $R^3$, $R^8$, m, n, p, and q is as defined above and described in embodiments herein, both singly and in combination.

In some embodiments, the present invention provides a compound of formula II-ee, II-ff, or II-yy, wherein R is $C(O)OC(CH_3)$, thereby forming a compound of formula II-ee-c, II-ff-c, or II-yy-c, respectively:

II-ee-c

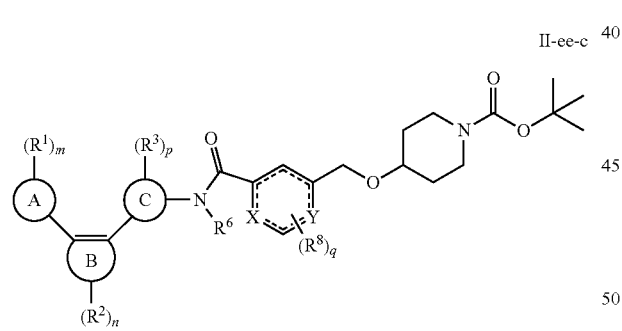

II-ff-c

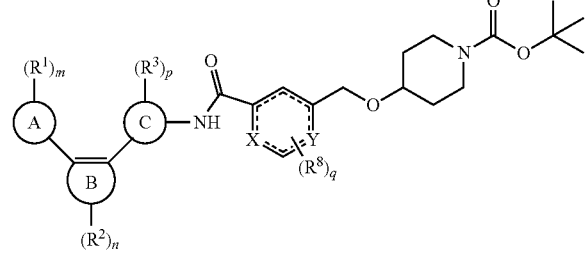

122
-continued

II-yy-c

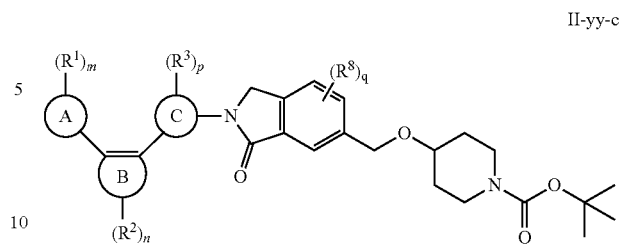

or a pharmaceutically acceptable salt thereof, and wherein each of Ring A, Ring B, Ring C, $R^1$, $R^2$, $R^3$, $R^8$, m, n, p, and q, is as defined above and described in embodiments herein, both singly and in combination.

In some embodiments, the present invention provides a compound of formula II-gg, II-hh, or II-zz, wherein R is cyclopropyl, thereby forming a compound of formula II-gg-b, II-hh-b, or II-zz-b, respectively:

II-gg-b

II-hh-b

II-zz-b

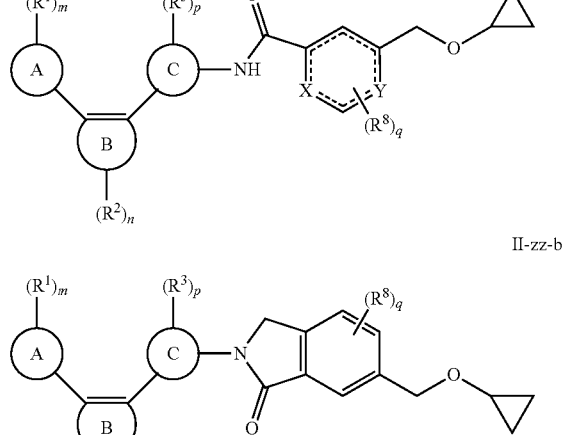

or a pharmaceutically acceptable salt thereof, wherein R is cyclopropyl and wherein each of Ring A, Ring B, Ring C, $R^1$, $R^2$, $R^3$, $R^8$, m, n, p, and q is as defined above and described in embodiments herein, both singly and in combination.

In some embodiments, the present invention provides a compound of formula II'-a to II'-ww:

II'-a
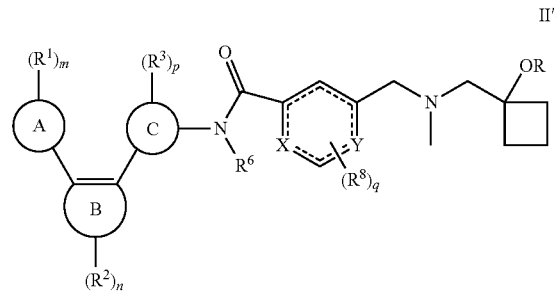
II'-f
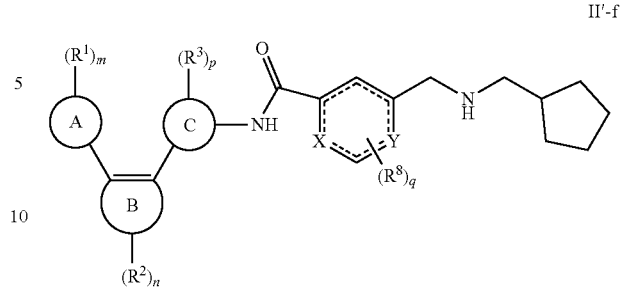
II'-b
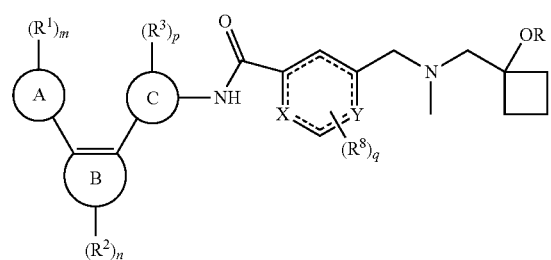
II'-g
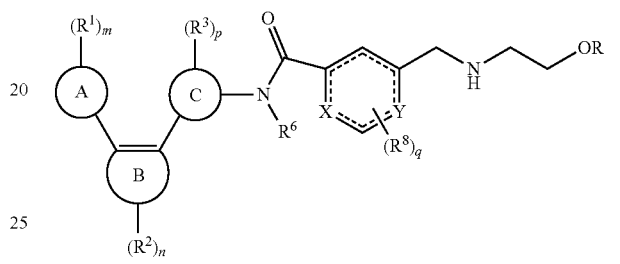
II'-c
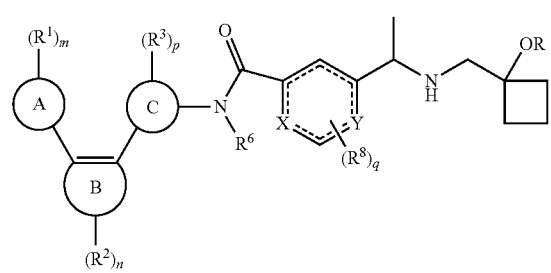
II'-h
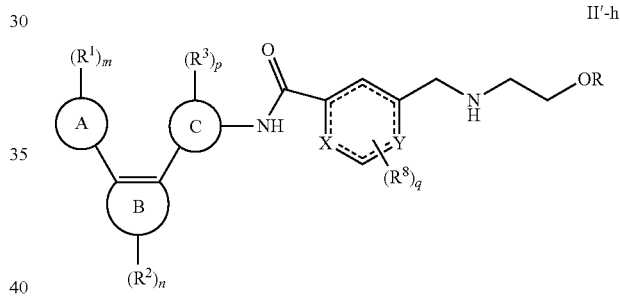
II'-d
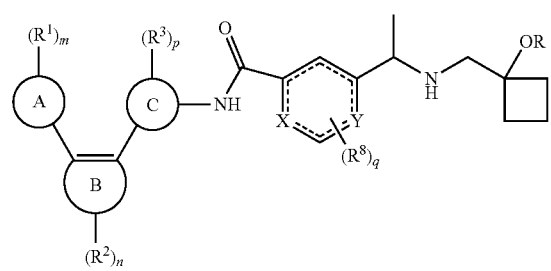
II'-i
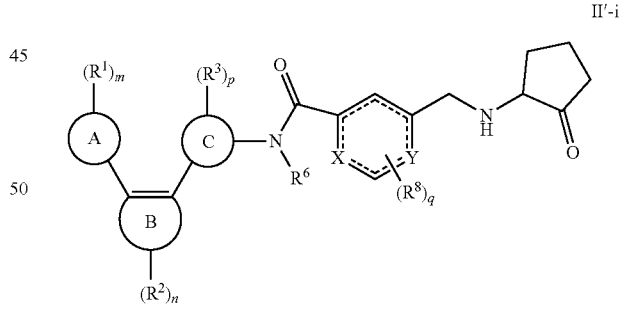
II'-e
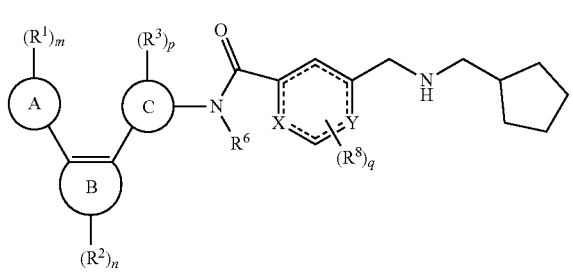
II'-j
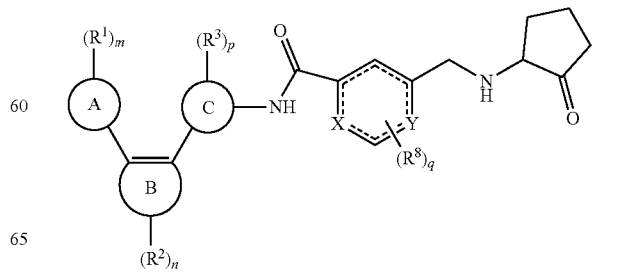

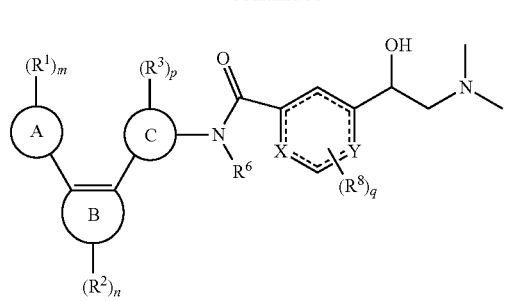
II'-k
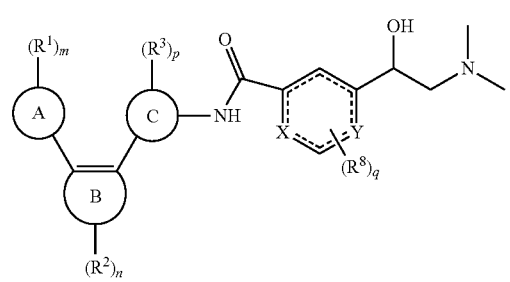
II'-l
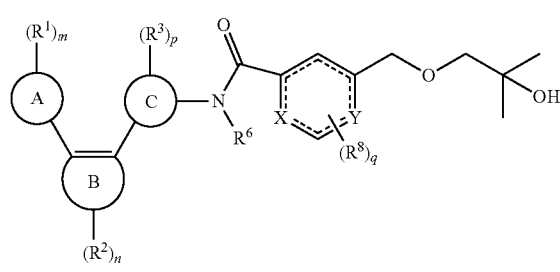
II'-m
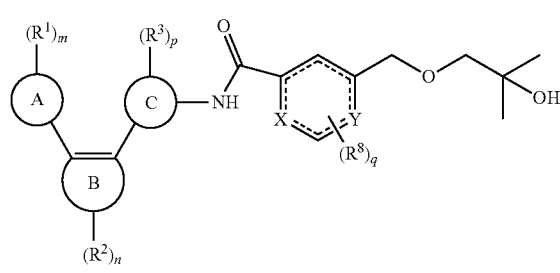
II'-n
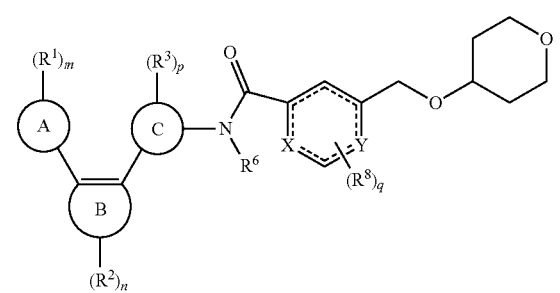
II'-o
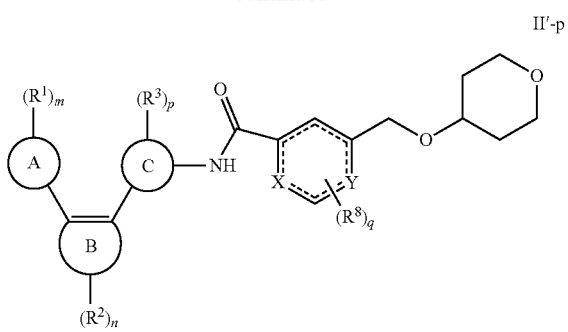
II'-p
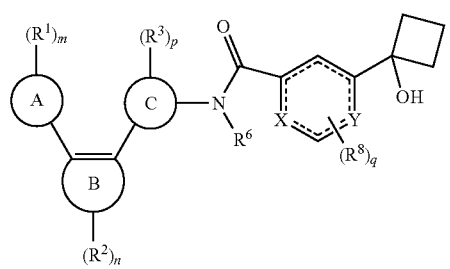
II'-q
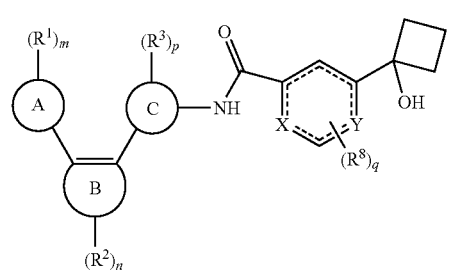
II'-r
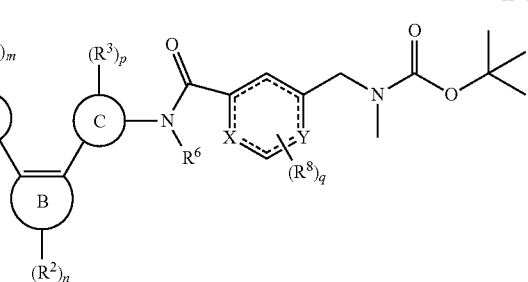
II'-s
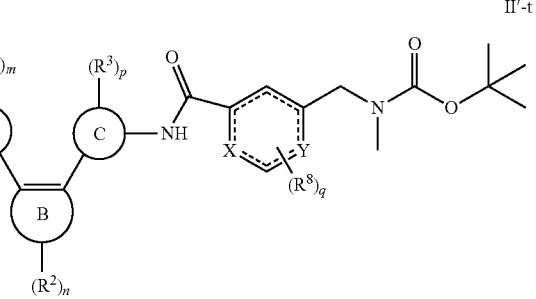
II'-t

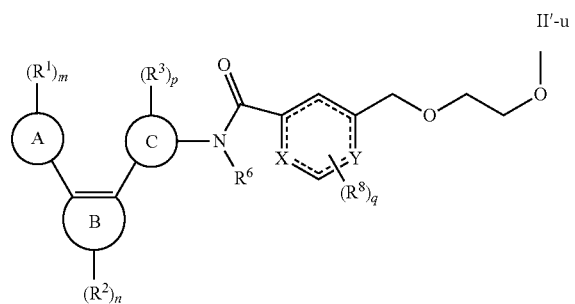
II'-u
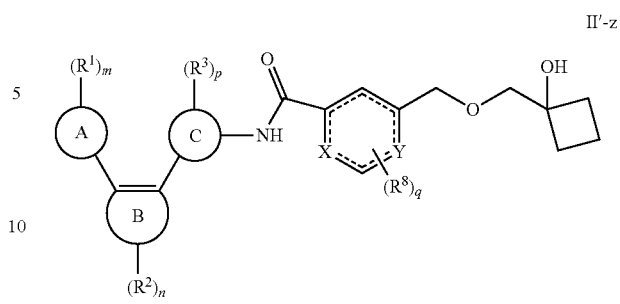
II'-z
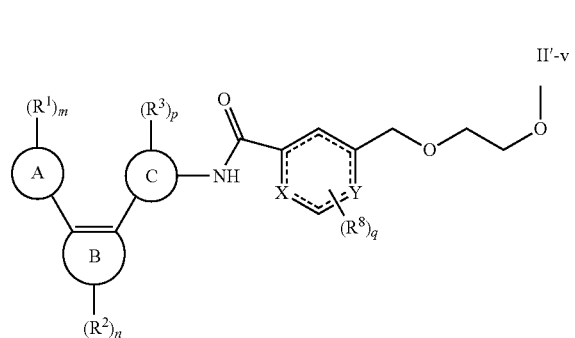
II'-v
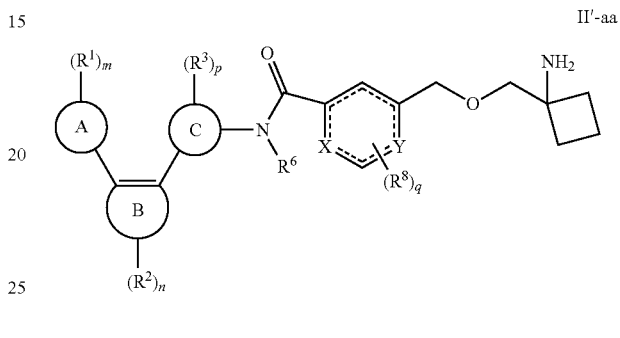
II'-aa
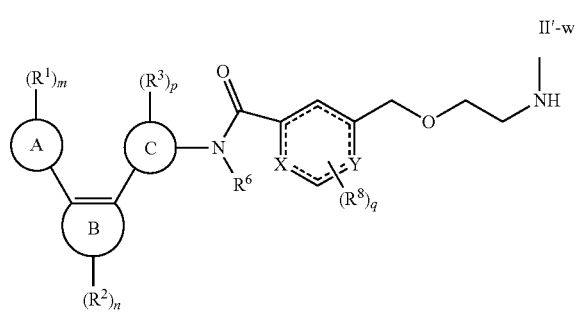
II'-w
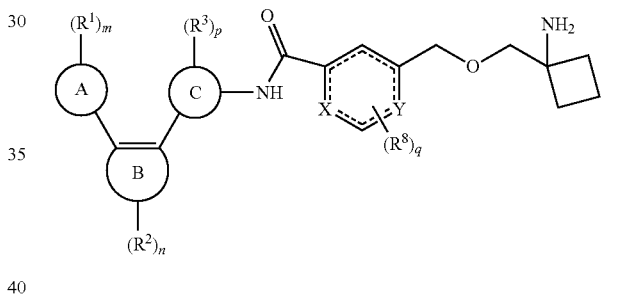
II'-bb
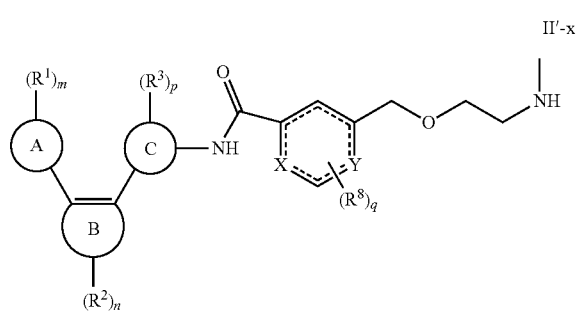
II'-x
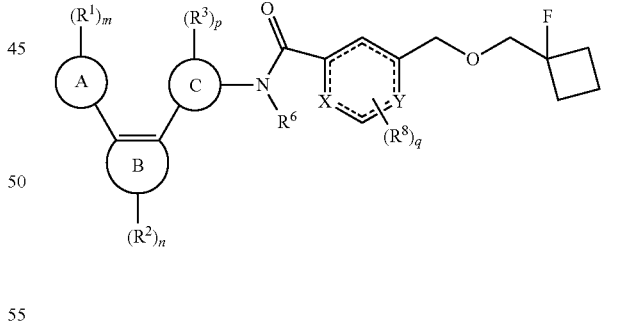
II'-cc
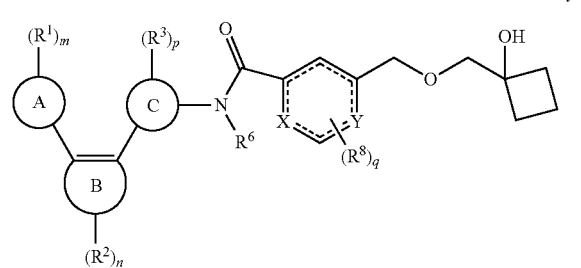
II'-y
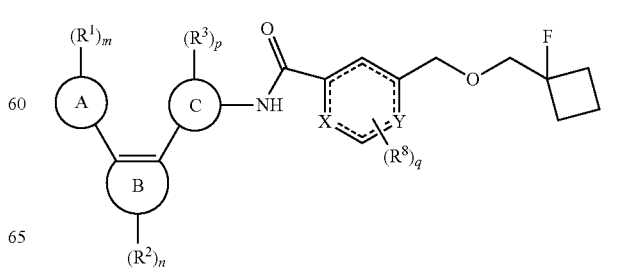
II'-dd II′-ee
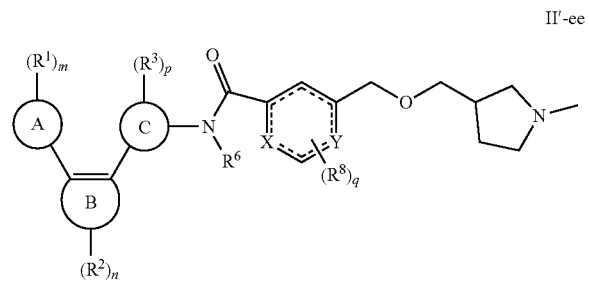
II′-jj
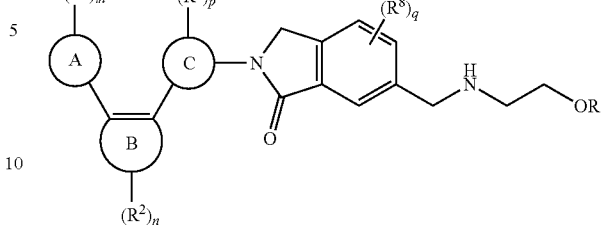
II′-ff
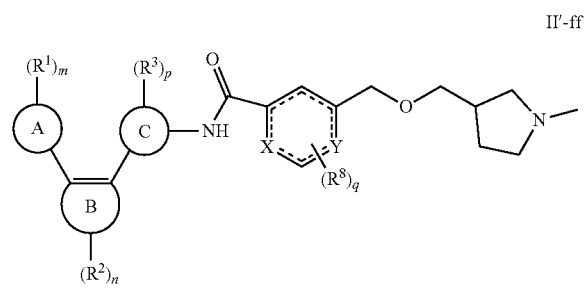
II′-kk
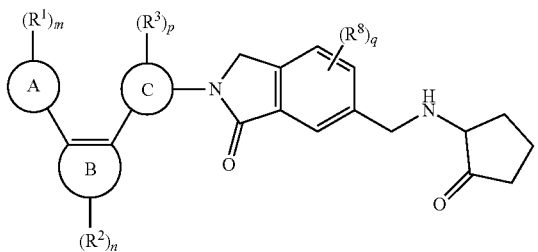
II′-gg
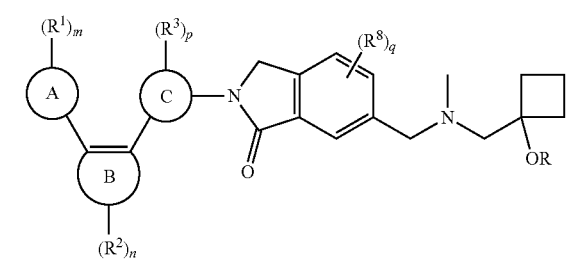
II′-ll
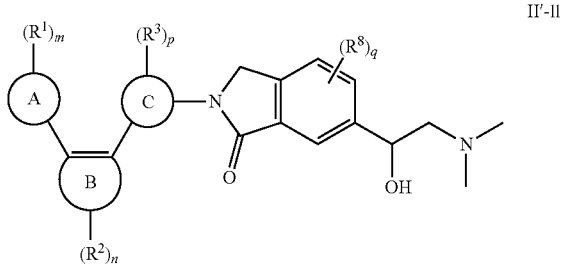
II′-mm
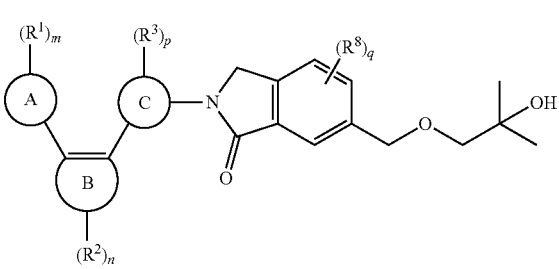
II′-hh
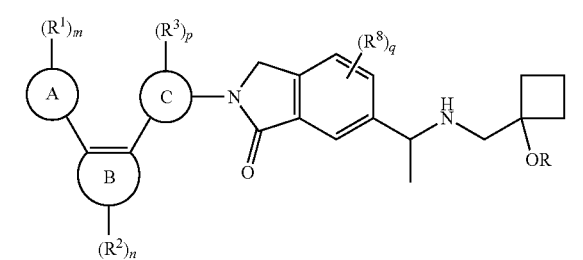
II′-nn
II′-ii
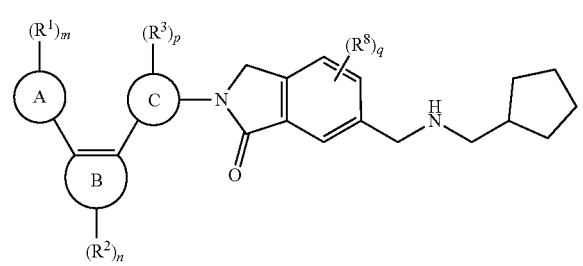
II′-oo
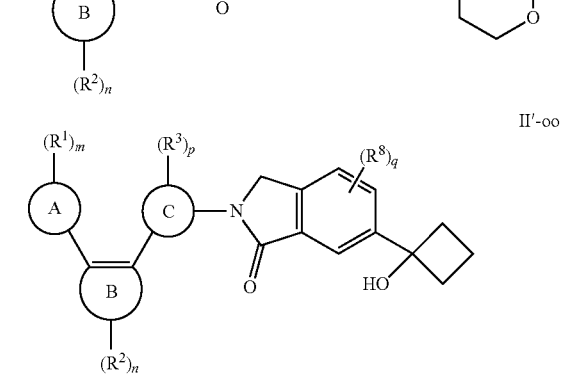

II'-pp
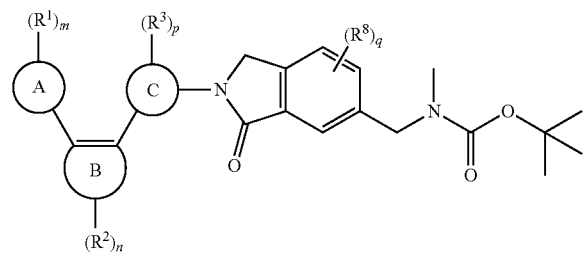

II'-qq
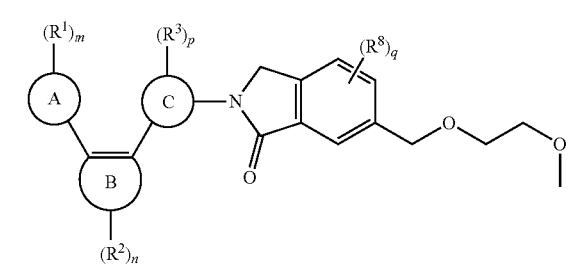

II'-rr
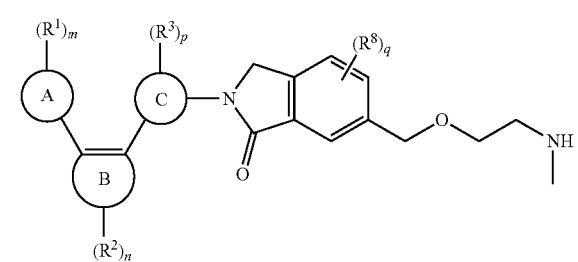

II'-ss
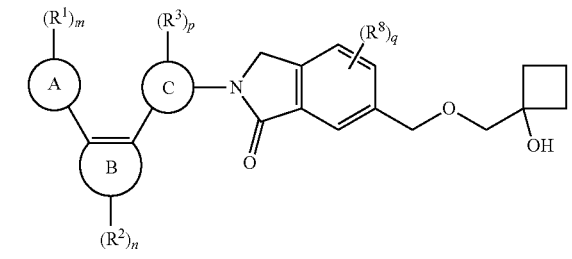

II'-tt
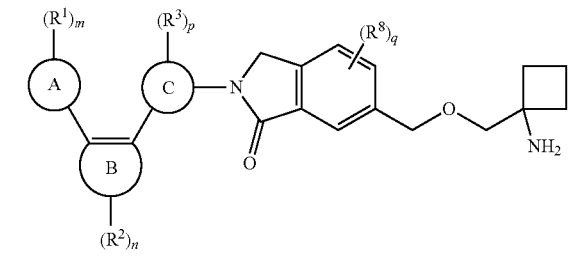

II'-uu
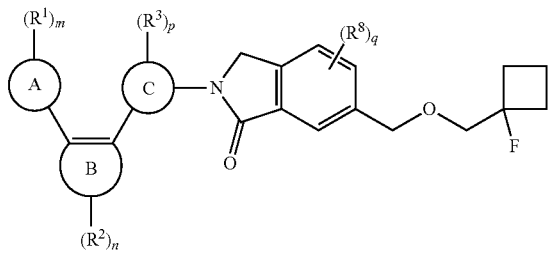

II'-vv
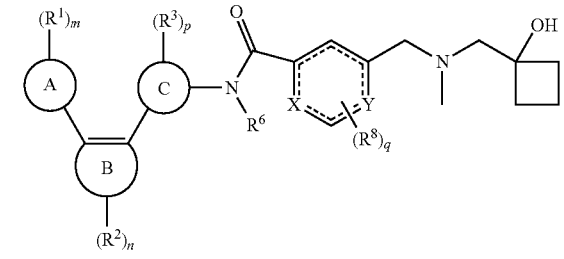

or a pharmaceutically acceptable salt thereof, wherein each of X, Y, Ring A, Ring B, Ring C, $R^1$, $R^2$, $R^3$, $R^6$, $R^8$, m, n, p, and q is as defined above and described in embodiments herein, both singly and in combination. In some of the embodiments, the R in OR is not hydrogen. In some of the embodiments, the R in OR is not —CN or halogen.

In some embodiments, the present invention provides a compound of formula II'-a, II'-b, II'-c, II'-d, II'-gg, or II'-hh, wherein R is hydrogen, thereby forming a compound of formula II"-a, II"-b, II"-c, II"-d, II"-gg, or II"-hh, respectively:

II"-a
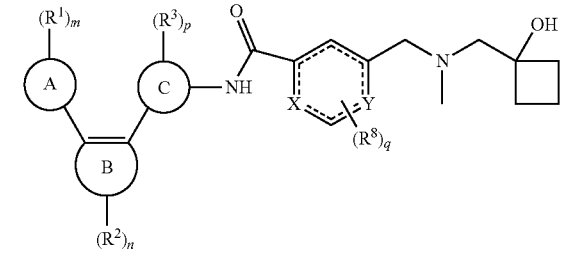

II"-b
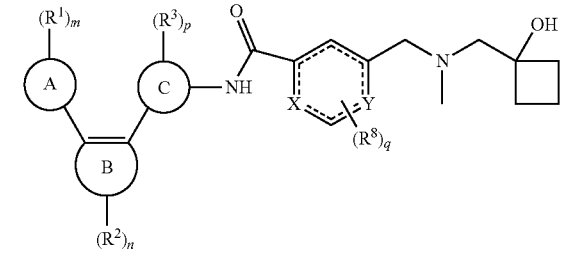

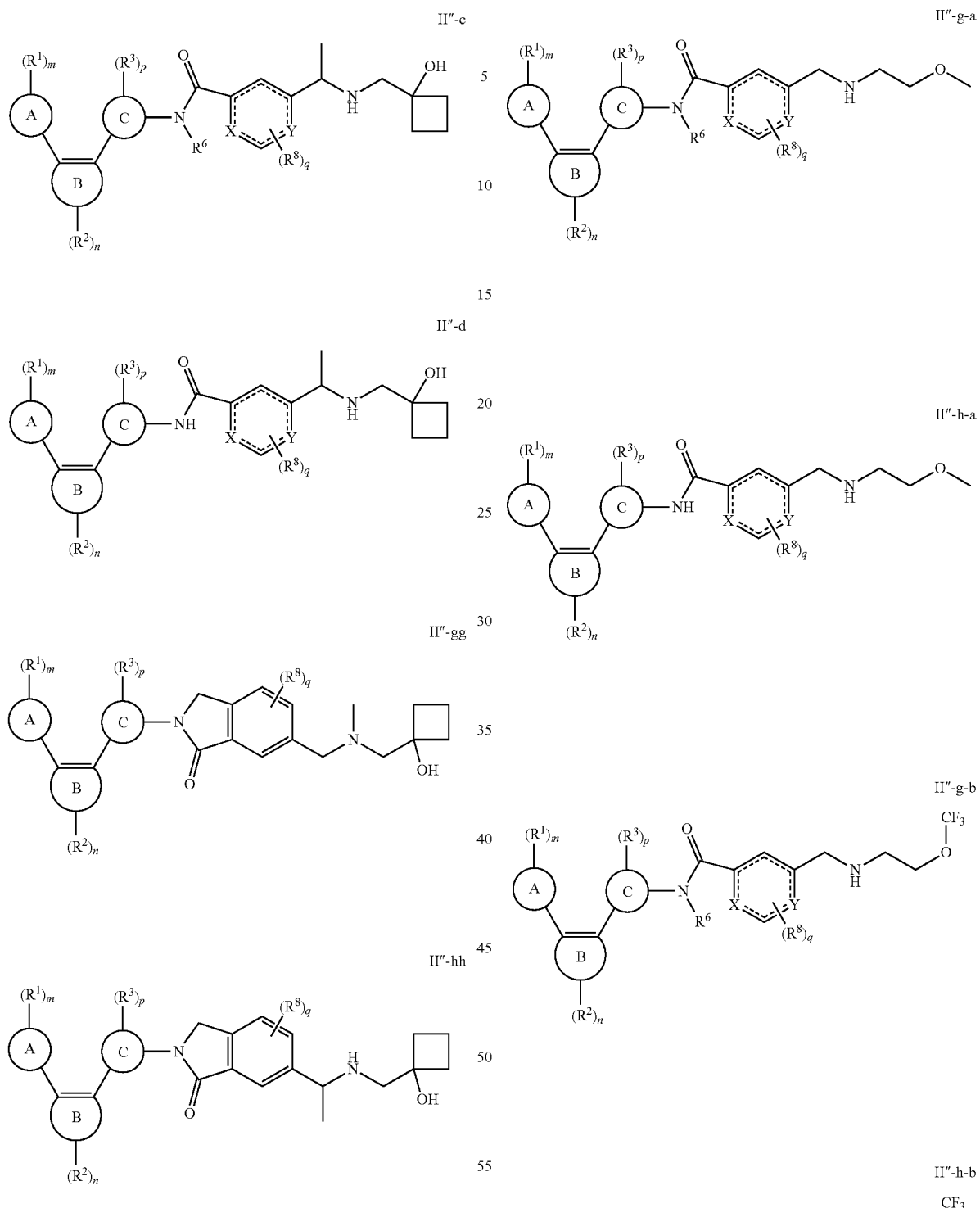

or a pharmaceutically acceptable salt thereof, wherein each of X, Y, Ring A, Ring B, Ring C, $R^1$, $R^2$, $R^3$, $R^6$, $R^8$, m, n, p, and q is as defined above and described in embodiments herein, both singly and in combination.

In some embodiments, the present invention provides a compound of formula II'-g, II'-h, or II'-jj, wherein R is methyl, trifluoromethyl, or cyclopropyl, thereby forming a compound of formula II"-g-a, II"-h-a, II"-g-b, II"-h-b, II"-g-c, II"-h-c, II"-jj-a, II"-jj-b, or II"-jj-c, respectively:

-continued

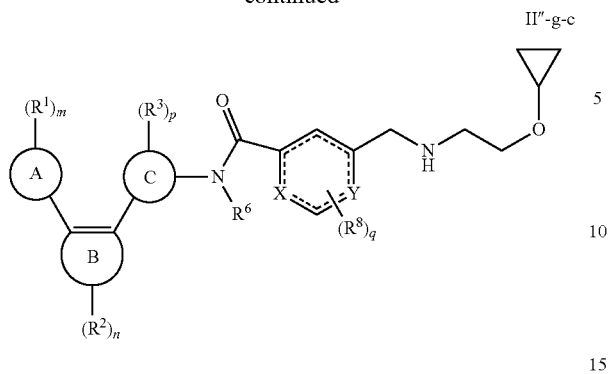

II''-g-c

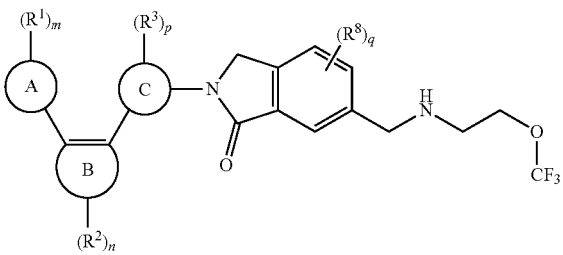

II''-jj-b

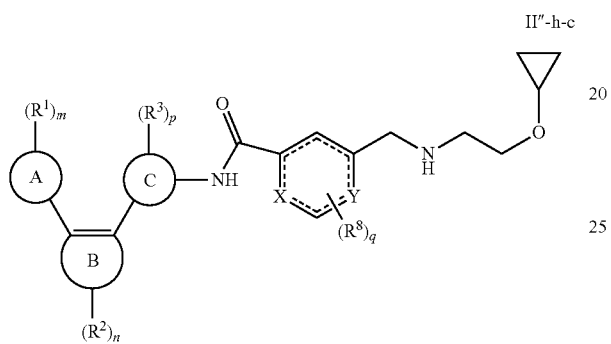

II''-h-c

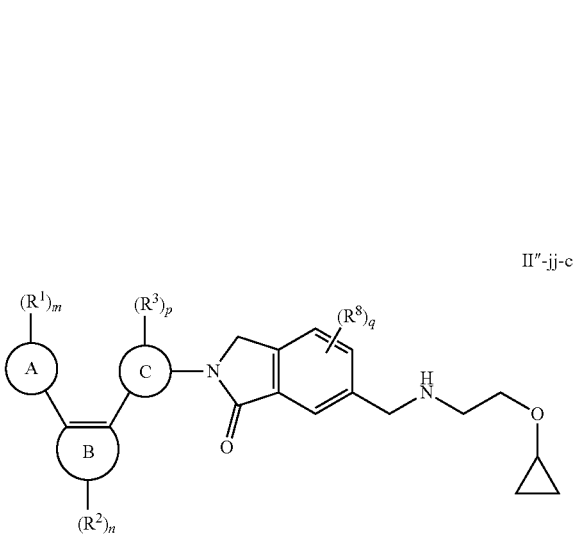

II''-jj-c

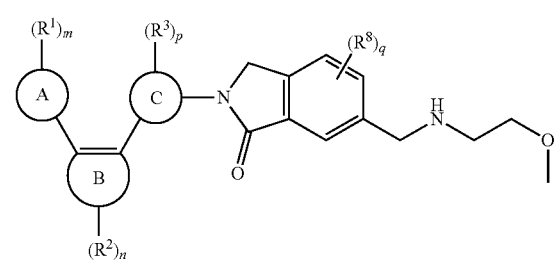

II''-jj-a

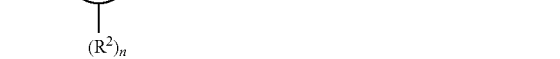

or a pharmaceutically acceptable salt thereof, wherein each of X, Y, Ring A, Ring B, Ring C, $R^1$, $R^2$, $R^3$, $R^6$, $R^8$, m, n, p, and q is as defined above and described in embodiments herein, both singly and in combination.

In some embodiments, the present invention provides compounds of formula II'-ww to II'-zz, II'-aaa, and II'-bbb:

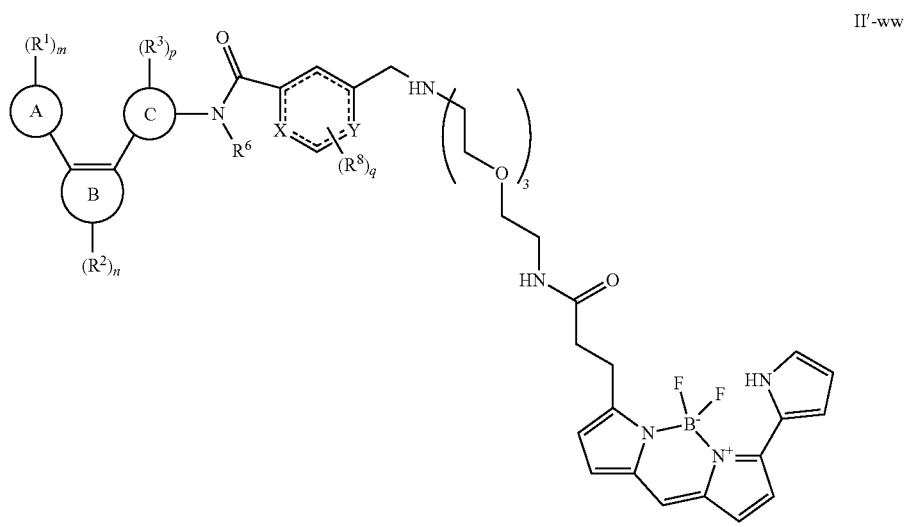

II'-ww

-continued
II'-xx
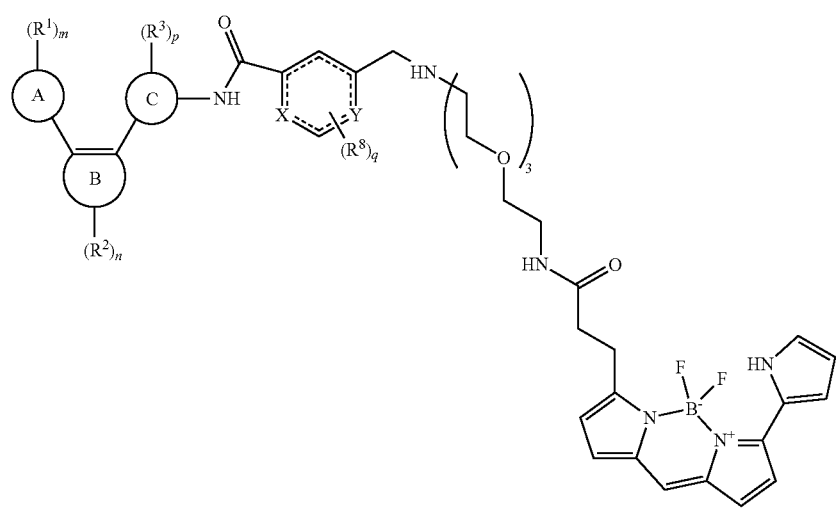
II'-yy
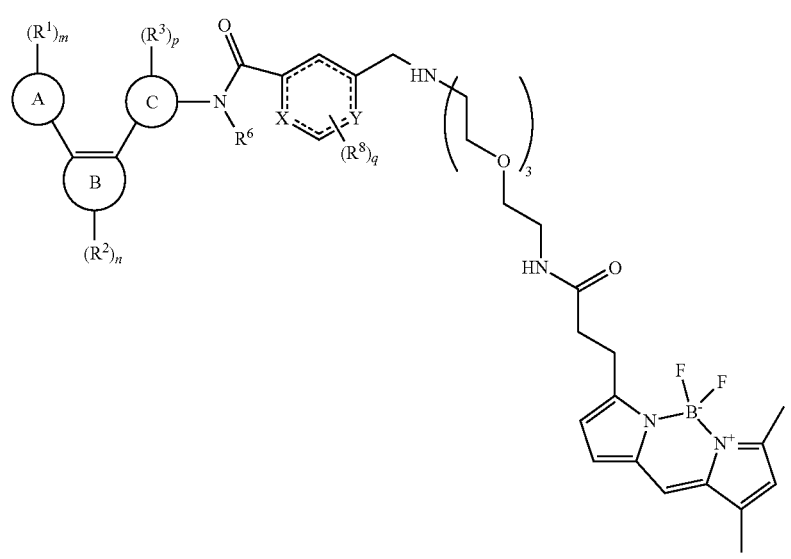
II'-zz
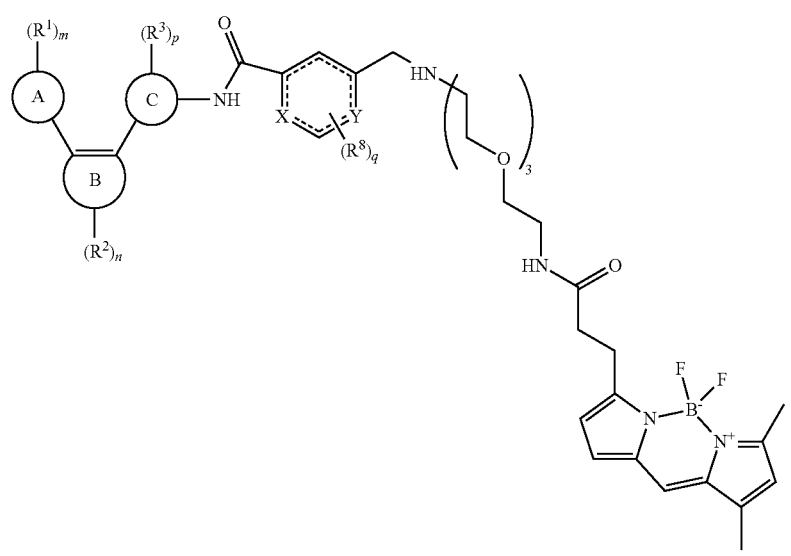

-continued
II'-aaa
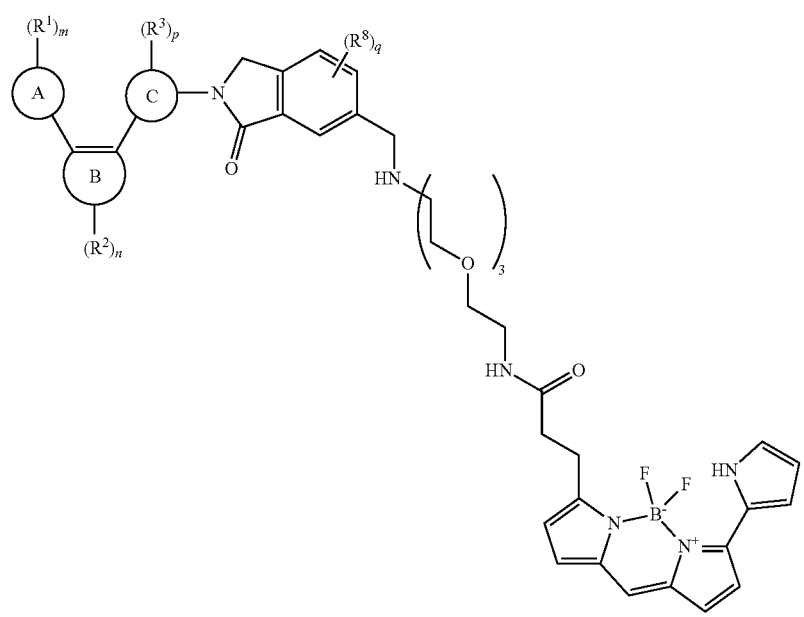
II'-bbb
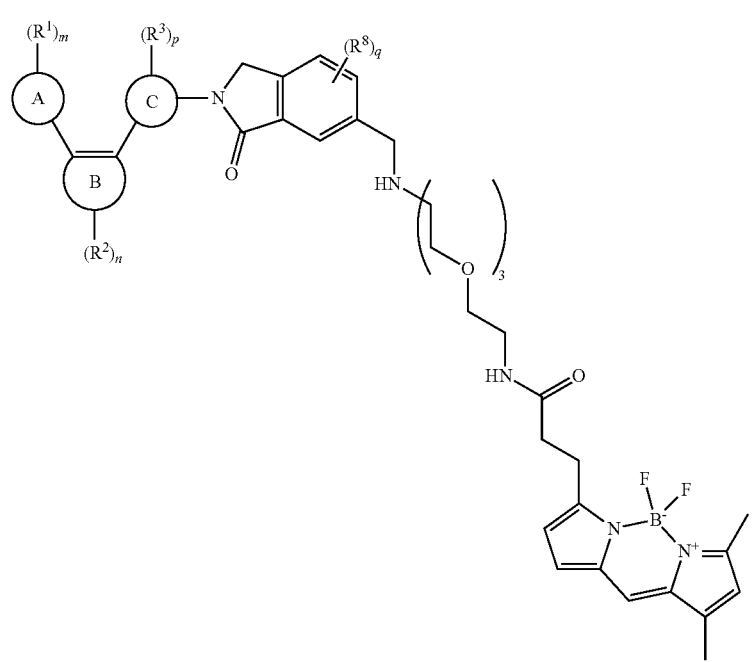

or a pharmaceutically acceptable salt thereof, wherein each of X, Y, Ring A, Ring B, Ring C, $R^1$, $R^2$, $R^3$, $R^6$, $R^8$, m, n, p, and q is as defined above and described in embodiments herein, both singly and in combination.

In some embodiments the present invention provides a compound of formula III-a, III-b, or III-c:

III-a
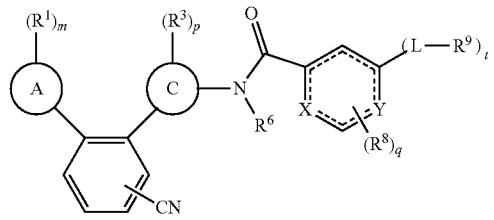

III-b
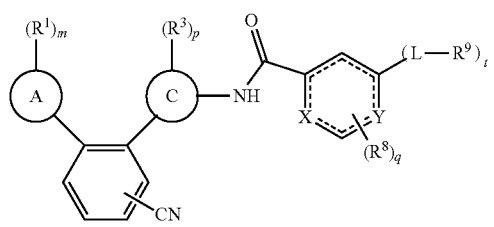

III-c
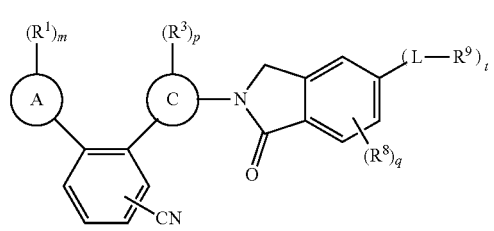

or a pharmaceutically acceptable salt thereof, wherein each of X, Y, Ring A, Ring C, L, $R^1$, $R^3$, $R^6$, $R^8$, $R^9$, m, p, q, and t, is as defined above and described in embodiments herein, both singly and in combination.

In some embodiments the present invention provides a compound of formula III-d, III-e, III-f, III-g, III-h, or III-i III-d
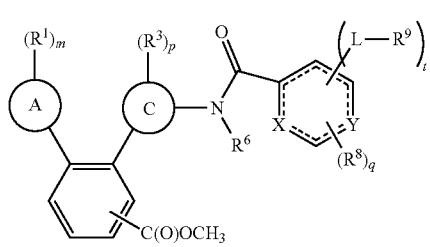

III-e
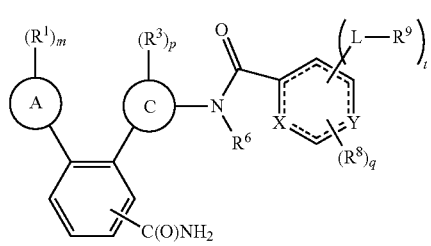

III-f
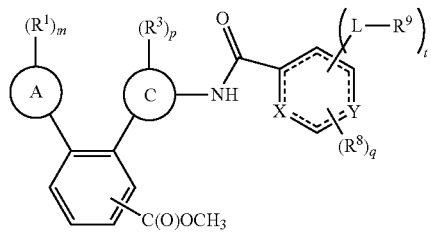

III-g
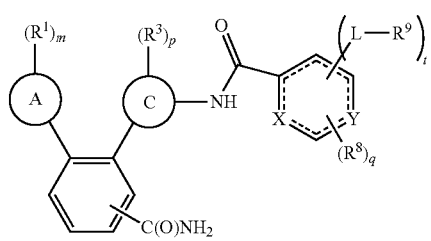

III-h
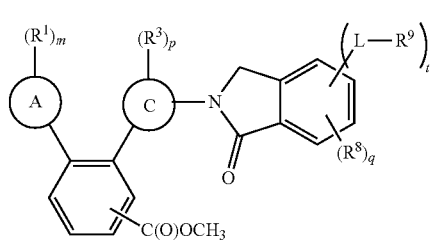

III-i
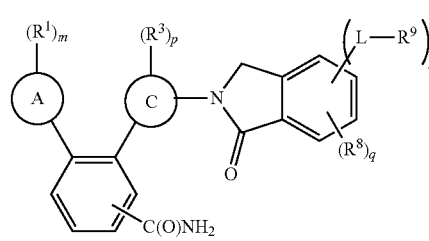

or a pharmaceutically acceptable salt thereof, wherein each of X, Y, Ring A, Ring C, L, $R^1$, $R^3$, $R^6$, $R^8$, $R^9$, m, p, q, and t is as defined above and described in embodiments herein, both singly and in combination.

In some embodiments the present invention provides a compound of formula III-j, III-k, III-l, III-m, or III-n.

III-j
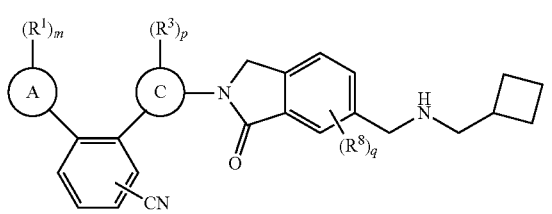

III-k
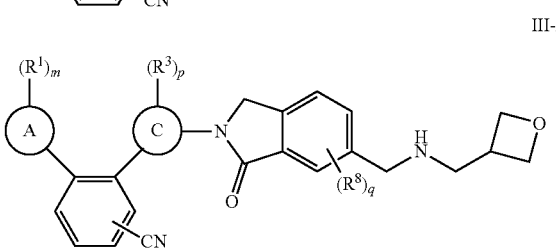

III-1

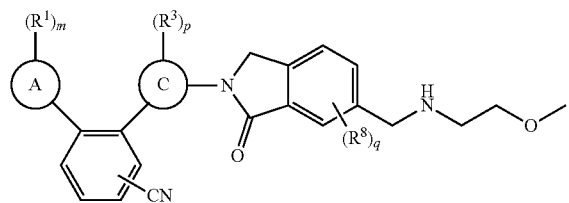

III-m

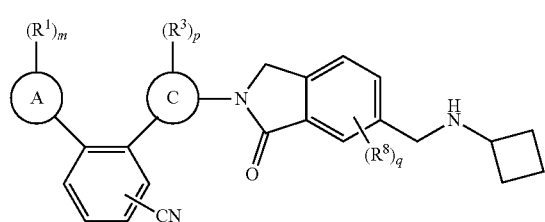

III-n

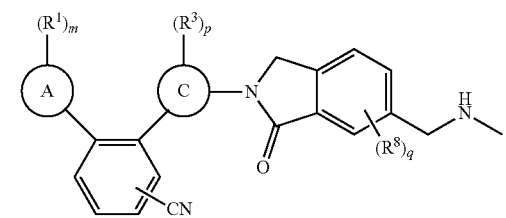

or a pharmaceutically acceptable salt thereof, wherein each of X, Y, Ring A, Ring C, $R^1$, $R^3$, $R^6$, $R^8$, m, p, and q, and t is as defined above and described in embodiments herein, both singly and in combination.

In some embodiments, the present invention provides a compound of formula IV-a, IV-b, IV-c, IV-d, IV-e, or IV-f:

IV-a

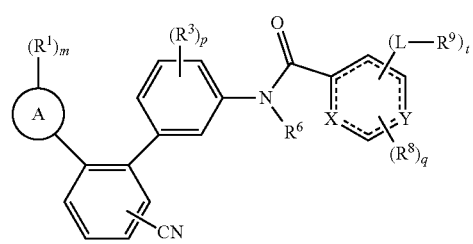

IV-b

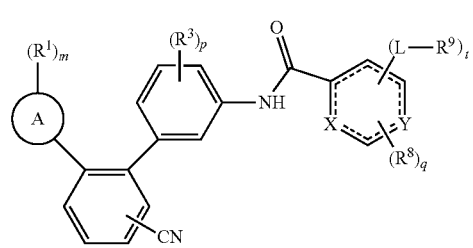

IV-c

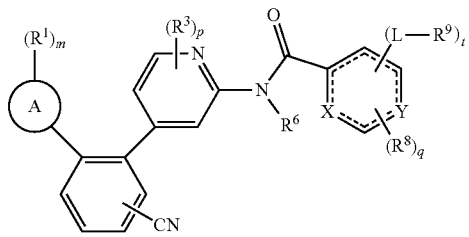

IV-d

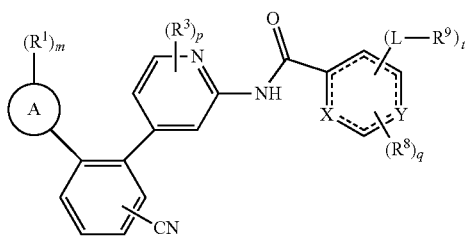

IV-e

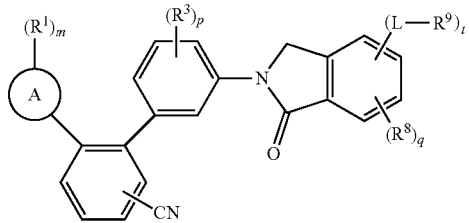

IV-f

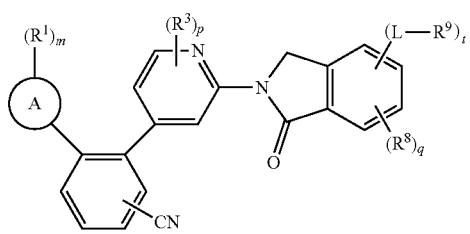

or a pharmaceutically acceptable salt thereof, wherein each of X, Y, Ring A, L, $R^1$, $R^3$, $R^6$, $R^8$, $R^9$, m, p, q, and t is as defined above and described in embodiments herein, both singly and in combination.

In some embodiments, the present invention provides a compound of formula IV-g to IV-r:

IV-g

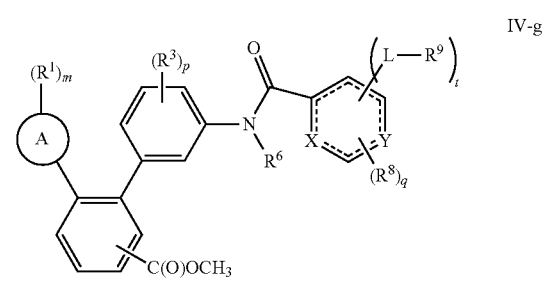

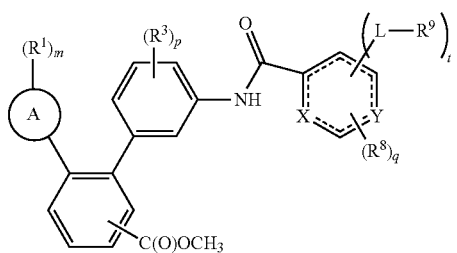
IV-h
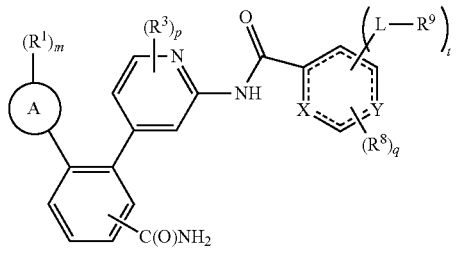
IV-n
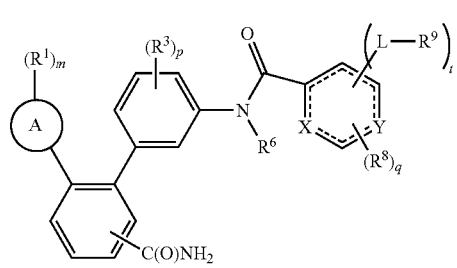
IV-i
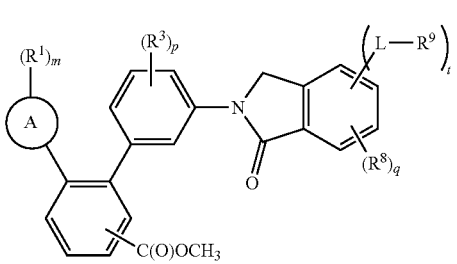
IV-o
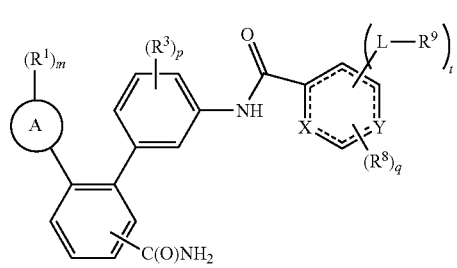
IV-j
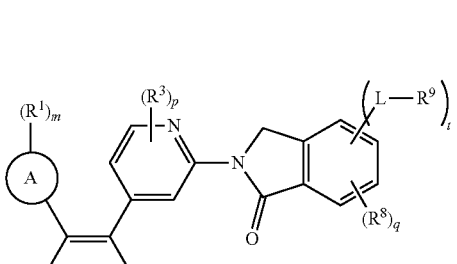
IV-p
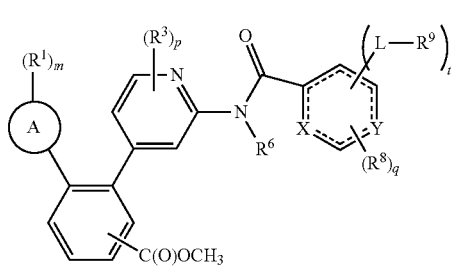
IV-k
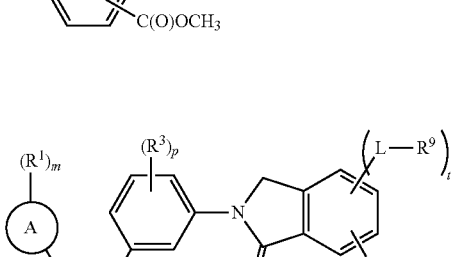
IV-q
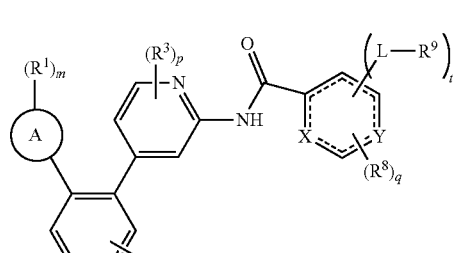
IV-l
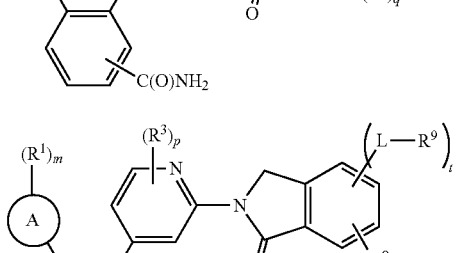
IV-r
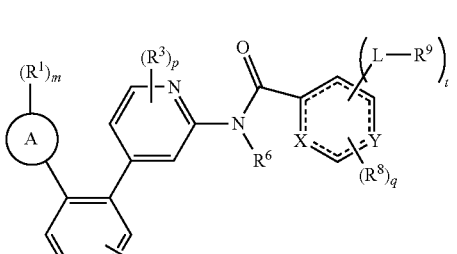
IV-m
or a pharmaceutically acceptable salt thereof, wherein each of Ring A, L, $R^1$, $R^3$, $R^6$, $R^8$, $R^9$, m, p, q, and t is as defined above and described in embodiments herein, both singly and in combination.
In some embodiments the present invention provides a compound of formula IV-s, IV-t, IV-u, IV-v, or IV-w.

IV-s

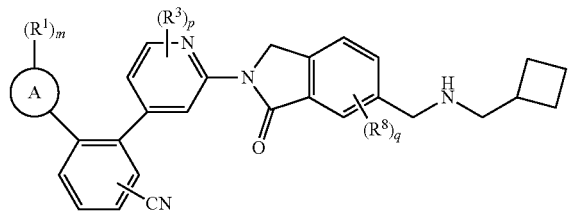

IV-t

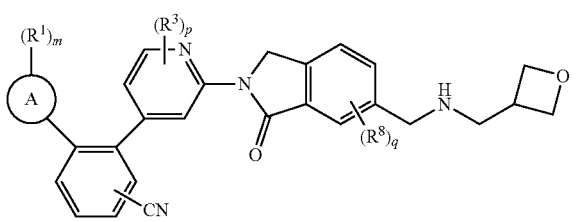

IV-u

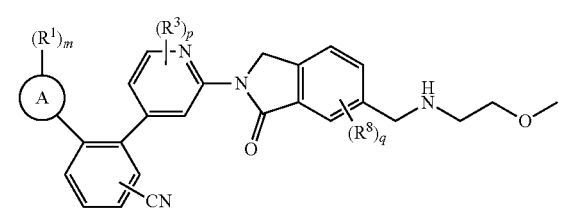

IV-v

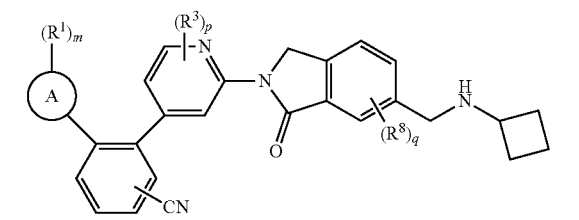

IV-w

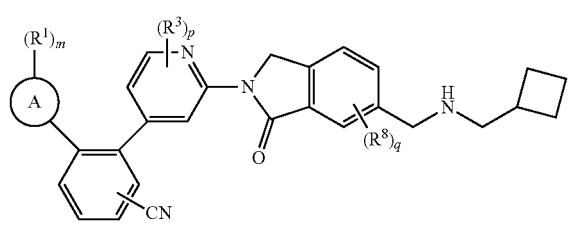

or a pharmaceutically acceptable salt thereof, wherein each of X, Y, Ring A, $R^1$, $R^3$, $R^6$, $R^8$, m, p, and q, and t is as defined above and described in embodiments herein, both singly and in combination.

In certain aspects, the invention provides a compound of formula V:

V

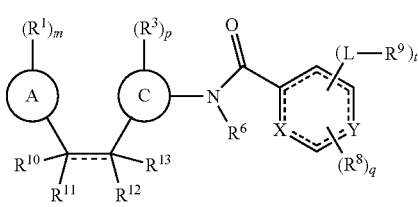

or a pharmaceutically acceptable salt thereof, wherein:

Ring A is a 5-6-membered heteroaryl ring having 1-4 heteroatoms independently selected from nitrogen, oxygen, and sulfur; or a 5-6-membered saturated or partially unsaturated heterocyclic ring having 1-4 heteroatoms independently selected from nitrogen, oxygen, and sulfur;

each $R^1$ is independently hydrogen, oxo, halogen, —CN, —$NO_2$, —$CHF_2$, —$CF_3$, —OR, —SR, —N(R)$_2$, —S(O)$_2$R, —S(O)$_2$N(R)$_2$, —S(O)R, —S(O)N(R)$_2$, —C(O)R, —C(O)OR, —C(O)N(R)$_2$, —C(O)N(R)OR, —OC(O)R, —OC(O)N(R)$_2$, —N(R)C(O)OR, —N(R)C(O)R, —N(R)C(O)N(R)$_2$, —N(R)C(NR)N(R)$_2$, —N(R)N(R)$_2$, —N(R)S(O)$_2$N(R)$_2$, —N(R)S(O)$_2$R, —N=S(O)(R)$_2$, —S(NR)(O)R, —N(R)S(O)R, —N(R)CN, —P(O)(R)N(R)$_2$, —P(O)(R)OR, or —P(O)(R)$_2$; or an optionally substituted $C_{1-6}$ aliphatic;

$R^{10}$, $R^{11}$, $R^{12}$, and $R^{13}$, are each independently $R^3$; or two of $R^{10}$, $R^{11}$, $R^{12}$, and $R^{13}$, along with the atoms to which each is attached, together form a phenyl ring; a 3-7 membered saturated or partially unsaturated monocyclic carbocyclic ring; a 5-6 membered monocyclic heteroaryl ring having 1-4 heteroatoms independently selected from nitrogen, oxygen, and sulfur; or a 4-8 membered saturated or partially unsaturated monocyclic heterocyclic ring having 1-2 heteroatoms independently selected from nitrogen, oxygen, and sulfur; or $R^{11}$ and $R^{13}$ are absent as required by valence;

Ring C is a divalent phenyl or a divalent 5-6 membered heteroaryl ring having 1-4 heteroatoms independently selected from nitrogen, oxygen, and sulfur;

each $R^3$ is independently hydrogen, oxo, halogen, —CN, —$NO_2$, —$CHF_2$, —$CF_3$, —OR, —SR, —N(R)$_2$, —S(O)$_2$R, —S(O)$_2$N(R)$_2$, —S(O)R, —S(O)N(R)$_2$, —C(O)R, —C(O)OR, —C(O)N(R)$_2$, —C(O)N(R)OR, —OC(O)R, —OC(O)N(R)$_2$, —N(R)C(O)OR, —N(R)C(O)R, —N(R)C(O)N(R)$_2$, —N(R)C(NR)N(R)$_2$, —N(R)N(R)$_2$, —N(R)S(O)$_2$N(R)$_2$, —N(R)S(O)$_2$R, —N=S(O)(R)$_2$, —S(NR)(O)R, —N(R)S(O)R, —N(R)CN, —P(O)(R)N(R)$_2$, —P(O)(R)OR, or —P(O)(R)$_2$; or an optionally substituted group selected from $C_{1-6}$ aliphatic; a phenyl ring; a 3-7 membered saturated or partially unsaturated monocyclic carbocyclic ring; a 5-6 membered monocyclic heteroaryl ring having 1-4 heteroatoms independently selected from nitrogen, oxygen, and sulfur; and a 4-8 membered saturated or partially unsaturated monocyclic heterocyclic ring having 1-2 heteroatoms independently selected from nitrogen, oxygen, and sulfur;

or two $R^3$ groups, and the atoms to which each $R^3$ group is attached, are optionally taken together to form a fused 3-7 membered saturated or partially unsaturated monocyclic carbocyclic ring; a fused 5-6 membered monocyclic aryl ring; a fused 3-7 membered saturated or partially unsaturated monocyclic heterocyclic ring having 1-2 heteroatoms independently selected from nitrogen, oxygen, phosphorous, silicon and sulfur; or a fused 5-6 membered monocyclic heteroaryl ring having 1-4 heteroatoms independently selected from nitrogen, oxygen, and sulfur;

X is N, $N^+$—$O^-$, $NR^4$, $CR^4$, or C-L-$R^9$;

$R^4$ is hydrogen, oxo, halogen, —CN, —$NO_2$, —$CHF_2$, —$CF_3$, —OR, —SR, —N(R)$_2$, —S(O)$_2$R, —S(O)$_2$N(R)$_2$, —S(O)R, —S(O)N(R)$_2$, —C(O)R, —C(O)OR, —C(O)N(R)OR, —OC(O)R, —OC(O)N(R)$_2$, —N(R)C(O)OR, —N(R)C(O)R, —N(R)C(O)N(R)$_2$, —N(R)C(NR)N(R)$_2$, —N(R)N(R)$_2$, —N(R)

$S(O)_2N(R)_2$, $-N(R)S(O)_2R$, $-N=S(O)(R)_2$, $-S(NR)(O)R$, $-N(R)S(O)R$, $-N(R)CN$, $-P(O)(R)N(R)_2$, $-P(O)(R)OR$, or $-P(O)(R)_2$; or an optionally substituted $C_{1-6}$ aliphatic;

Y is N, $N^+-O^-$, NR, $CR^5$, or $C-L-R^9$;

$R^5$ is hydrogen, oxo, halogen, $-CN$, $-NO_2$, $-CHF_2$, $-CF_3$, $-OR$, $-SR$, $-N(R)_2$, $-S(O)_2R$, $-S(O)_2N(R)_2$, $-S(O)R$, $-S(O)N(R)_2$, $-C(O)R$, $-C(O)OR$, $-C(O)N(R)_2$, $-C(O)N(R)OR$, $-OC(O)R$, $-OC(O)N(R)_2$, $-N(R)C(O)OR$, $-N(R)C(O)R$, $-N(R)C(O)N(R)_2$, $-N(R)C(NR)N(R)_2$, $-N(R)N(R)_2$, $-N(R)S(O)_2N(R)_2$, $-N(R)S(O)_2R$, $-N=S(O)(R)_2$, $-S(NR)(O)R$, $-N(R)S(O)R$, $-N(R)CN$, $-P(O)(R)N(R)_2$, $-P(O)(R)OR$, or $-P(O)(R)_2$; or an optionally substituted $C_{1-6}$ aliphatic;

$R^6$ is hydrogen or $C_{1-3}$ aliphatic; or $R^4$ and $R^6$ are optionally taken together with their intervening atoms to form a 5-6 membered partially unsaturated fused ring having, in addition to the nitrogen, 0-2 heteroatoms independently selected from nitrogen, oxygen and sulfur, wherein the fused ring is optionally substituted with u instances of $R^7$;

each $R^7$ is independently hydrogen, oxo, halogen, $-CN$, $-NO_2$, $-CHF_2$, $-CF_3$, $-OR$, $-SR$, $-N(R)_2$, $-S(O)_2R$, $-S(O)_2N(R)_2$, $-S(O)R$, $-S(O)N(R)_2$, $-C(O)R$, $-C(O)OR$, $-C(O)N(R)_2$, $-C(O)N(R)OR$, $-OC(O)R$, $-OC(O)N(R)_2$, $-N(R)C(O)OR$, $-N(R)C(O)R$, $-N(R)C(O)N(R)_2$, $-N(R)C(NR)N(R)_2$, $-N(R)N(R)_2$, $-N(R)S(O)_2N(R)_2$, $-N(R)S(O)_2R$, $-N=S(O)(R)_2$, $-S(NR)(O)R$, $-N(R)S(O)R$, $-N(R)CN$, $-P(O)(R)N(R)_2$, $-P(O)(R)OR$, or $-P(O)(R)_2$; or an optionally substituted $C_{1-6}$ aliphatic;

each $R^7$ is independently hydrogen, oxo, halogen, $-CN$, $-NO_2$, $-CHF_2$, $-CF_3$, $-OR$, $-SR$, $-N(R)_2$, $-S(O)_2R$, $-S(O)_2N(R)_2$, $-S(O)R$, $-S(O)N(R)_2$, $-C(O)R$, $-C(O)OR$, $-C(O)N(R)_2$, $-C(O)N(R)OR$, $-OC(O)R$, $-OC(O)N(R)_2$, $-N(R)C(O)OR$, $-N(R)C(O)R$, $-N(R)C(O)N(R)_2$, $-N(R)C(NR)N(R)_2$, $-N(R)N(R)_2$, $-N(R)S(O)_2N(R)_2$, $-N(R)S(O)_2R$, $-N=S(O)(R)_2$, $-S(NR)(O)R$, $-N(R)S(O)R$, $-N(R)CN$, $-P(O)(R)N(R)_2$, $-P(O)(R)OR$, or $-P(O)(R)_2$; or an optionally substituted $C_{1-6}$ aliphatic;

L is a covalent bond; or L is a $C_{1-4}$ bivalent saturated or unsaturated, straight or branched hydrocarbon chain wherein one or two methylene units of the chain are optionally and independently replaced by $-C(R)_2-$, $-C(OR)(R)-$, $-N(R)-$, $-O-$, $-S-$, $-S(O)-$, $-S(O)_2-$, $-S(O)N(R)-$, $-N(R)S(O)-$, $-S(O)_2N(R)-$, $-N(R)S(O)_2-$, $-C(O)-$, $-C(O)O-$, $-OC(O)-$, $-C(O)N(R)-$, $-N(R)C(O)-$, $-C(O)N(R)O-$, $-ON(R)C(O)-$, $-OC(O)N(R)-$, $-N(R)C(O)O-$, or $-N(R)C(O)N(R)-$;

$R^9$ is halogen, $-CN$, $-NO_2$, $-OR$, $-SR$, $-N(R)_2$, $-S(O)_2R$, $-S(O)_2N(R)_2$, $-S(O)R$, $-S(O)N(R)_2$, $-CF_2R$, $-CF_3$, $-C(R)_2OR$, $-C(R)_2N(R)_2$, $-C(O)R$, $-C(O)OR$, $-C(O)N(R)_2$, $-C(O)N(R)OR$, $-OC(O)R$, $-OC(O)N(R)_2$, $-C(S)N(R)_2$, $-N(R)C(O)OR$, $-N(R)C(O)R$, $-N(R)C(O)N(R)_2$, $-N(R)C(NR)N(R)_2$, $-N(R)N(R)_2$, $-N(R)S(O)_2N(R)_2$, $-N(R)S(O)_2R$, $-N=S(O)(R)_2$, $-S(NR)(O)R$, $-N(R)S(O)R$, $-N(R)CN$, $-Si(OR)(R)_2$, $-Si(R)_3$, $-P(O)(R)N(R)_2$, $-P(O)(R)OR$, or $-P(O)(R)_2$; or $R^9$ is an optionally substituted group selected from $C_{1-6}$ aliphatic; phenyl; a 3-7 membered saturated or partially unsaturated monocyclic carbocyclic ring; a 4-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; a 5-8 membered saturated or partially unsaturated bridged bicyclic ring having 0-3 heteroatoms selected from nitrogen, oxygen, and sulfur; a 6-10 membered saturated or partially unsaturated spiro bicyclic ring having 0-3 heteroatoms independently selected from nitrogen, oxygen, and sulfur; and an 8-10 membered partially aromatic or heteroaromatic bicyclic heterocyclic ring having 1-4 heteroatoms independently selected from nitrogen, oxygen, and sulfur;

each instance of $R^1$, $R^2$, $R^3$, $R^4$, $R^5$, $R^6$, $R^7$, $R^8$, and $R^9$ is independently and optionally substituted with v instances of $R^A$, wherein each $R^A$ is independently oxo, halogen, $-CN$, $-NO_2$, $-OR$, $-SR$, $-N(R)_2$, $-S(O)_2R$, $-S(O)_2N(R)_2$, $-S(O)R$, $-S(O)N(R)_2$, $-C(R)_2OR$, $-C(O)R$, $-C(O)OR$, $-C(O)N(R)_2$, $-C(O)N(R)OR$, $-OC(O)R$, $-OC(O)N(R)_2$, $-N(R)C(O)OR$, $-N(R)C(O)R$, $-N(R)C(O)N(R)_2$, $-N(R)C(NR)N(R)_2$, $-N(R)N(R)_2$, $-N(R)S(O)_2N(R)_2$, $-N(R)S(O)_2R$, $-N=S(O)(R)_2$, $-S(NR)(O)R$, $-N(R)S(O)R$, $-N(R)CN$, $-P(O)(R)N(R)_2$, $-P(O)(R)OR$, or $-P(O)(R)_2$, or an optionally substituted group selected from $C_{1-6}$ aliphatic; phenyl; naphthyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; and a 6-11 membered saturated or partially unsaturated bicyclic heterocyclic ring having 1-2 heteroatoms independently selected from nitrogen, oxygen, and sulfur;

each R is independently hydrogen, $-CN$, halogen, or an optionally substituted group selected from $C_{1-6}$ aliphatic; phenyl; naphthyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic carbocyclic ring having 1-2 heteroatoms independently selected from nitrogen, oxygen, and sulfur; or:

two R groups on the same atom are optionally taken together with the atom to form an optionally substituted 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur;

m is 0, 1, 2, 3, 4, or 5;
p is 0, 1, 2, 3, or 4;
q is 0, 1, 2, or 3;
t is 0 or 1;
u is 0, 1, 2, 3, or 4;
each instance of v is independently 0, 1, 2, 3, 4, or 5; and
wherein $=\!=\!=$ denotes a single or double bond.

Exemplary compounds of the invention are set forth in Table 1, below.

TABLE 1

Selected Compounds

| Compound # | Compound ID | Structure |
|---|---|---|
| 1 | ACU-2 | 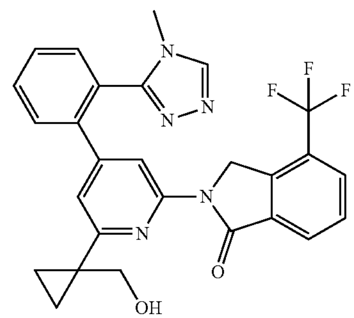 [SMILES: Cn1cnnc1-c1ccccc1-c1cc(N2Cc3c(cccc3C(F)(F)F)C2=O)nc(C2(CO)CC2)c1] |
| 2 | ACS-4 | 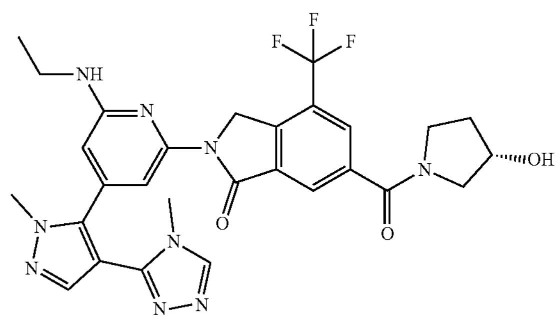 [SMILES: CCNc1cc(-c2c(-c3nncn3C)cnn2C)cc(N2Cc3c(cc(C(=O)N4CC[C@H](O)C4)cc3C(F)(F)F)C2=O)n1] |
| 3 | ACT-2 | 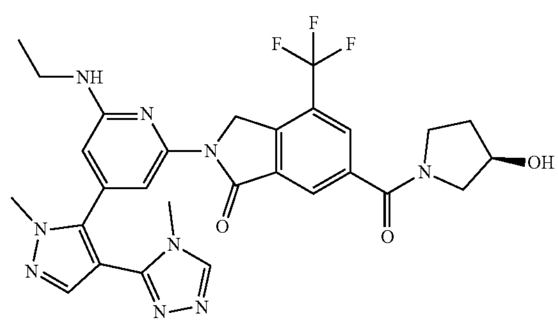 [SMILES: CCNc1cc(-c2c(-c3nncn3C)cnn2C)cc(N2Cc3c(cc(C(=O)N4CC[C@@H](O)C4)cc3C(F)(F)F)C2=O)n1] |
| 4 | ACR-7 | 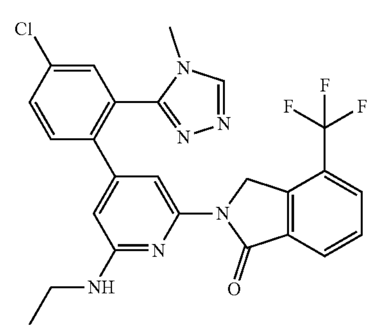 [SMILES: CCNc1cc(-c2ccc(Cl)cc2-c2nncn2C)cc(N2Cc3c(cccc3C(F)(F)F)C2=O)n1] |

TABLE 1-continued
Selected Compounds
| Compound # | Compound ID | Structure |
|---|---|---|
| 5 | ACQ-7 | 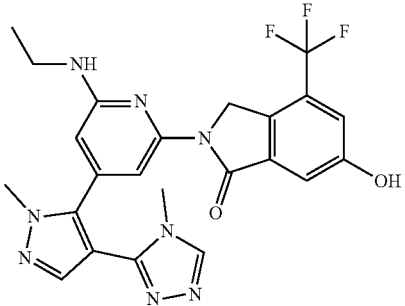 [SMILES: CCNc1cc(-c2c(-c3nncn3C)cnn2C)cc(N2Cc3c(cc(O)cc3C(F)(F)F)C2=O)n1] |
| 6 | ACP-3 | 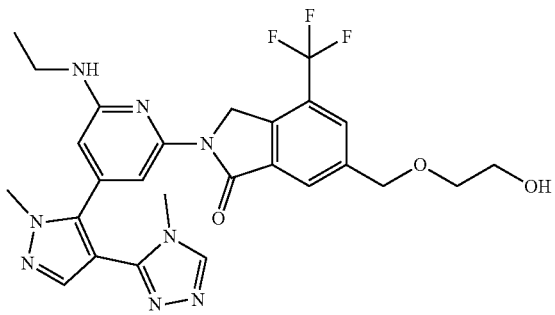 [SMILES: CCNc1cc(-c2c(-c3nncn3C)cnn2C)cc(N2Cc3c(cc(COCCO)cc3C(F)(F)F)C2=O)n1] |
| 7 | ACO-1 | 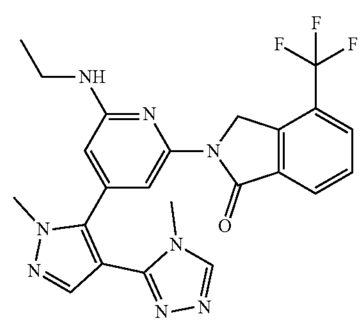 [SMILES: CCNc1cc(-c2c(-c3nncn3C)cnn2C)cc(N2Cc3c(cccc3C(F)(F)F)C2=O)n1] |
| 8 | AAU-1 | 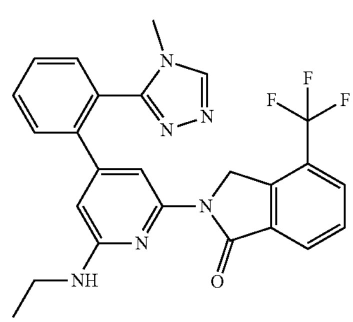 [SMILES: CCNc1cc(-c2ccccc2-c2nncn2C)cc(N2Cc3c(cccc3C(F)(F)F)C2=O)n1] |

TABLE 1-continued

Selected Compounds

| Compound # | Compound ID | Structure |
|---|---|---|
| 9 | ACN-5 | 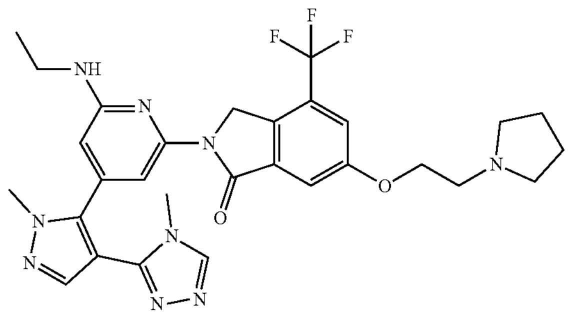 [SMILES: CCNc1cc(-c2c(-c3nncn3C)cnn2C)cc(N2Cc3c(cc(OCCN4CCCC4)cc3C(F)(F)F)C2=O)n1] |
| 10 | ACM-8 | 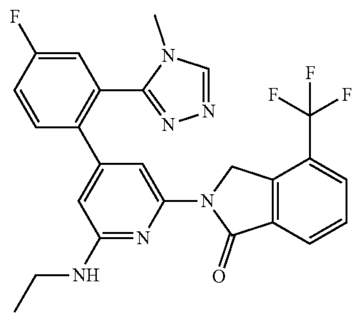 [SMILES: CCNc1cc(-c2ccc(F)cc2-c2nncn2C)cc(N2Cc3c(cccc3C(F)(F)F)C2=O)n1] |
| 11 | ACK-3 | 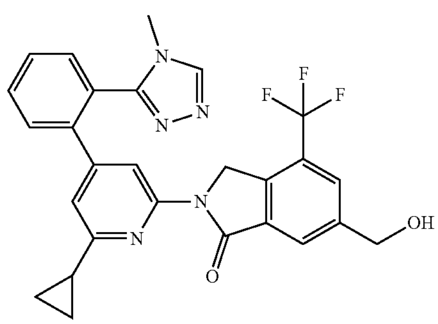 [SMILES: Cn1cnnc1-c1ccccc1-c1cc(C2CC2)nc(N2Cc3c(cc(CO)cc3C(F)(F)F)C2=O)c1] |
| 12 | ACL-1 | 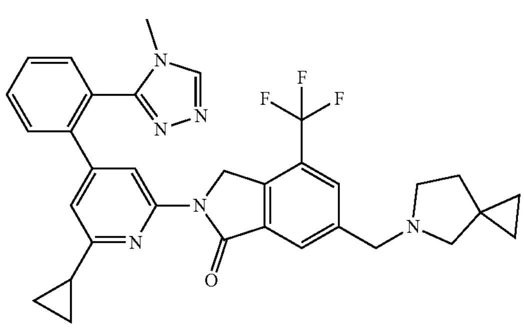 [SMILES: Cn1cnnc1-c1ccccc1-c1cc(C2CC2)nc(N2Cc3c(cc(CN4CCC5(CC5)C4)cc3C(F)(F)F)C2=O)c1] |

TABLE 1-continued

Selected Compounds

| Compound # | Compound ID | Structure |
|---|---|---|
| 13 | ACJ-6 | 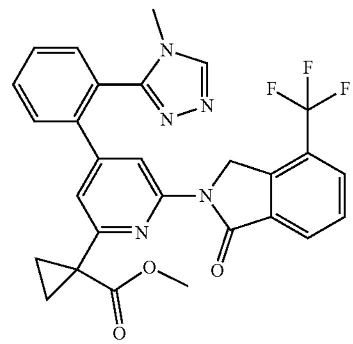 [SMILES: COC(=O)C1(c2cc(-c3ccccc3-c3nncn3C)cc(N3Cc4c(cccc4C(F)(F)F)C3=O)n2)CC1] |
| 14 | ACI-1 | 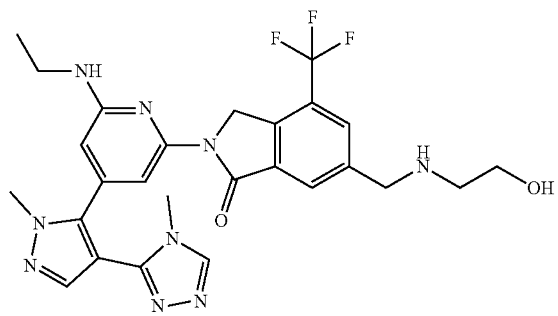 [SMILES: CCNc1cc(-c2c(-c3nncn3C)cnn2C)cc(N2Cc3c(cc(CNCCO)cc3C(F)(F)F)C2=O)n1] |
| 15 | ACC-8 | 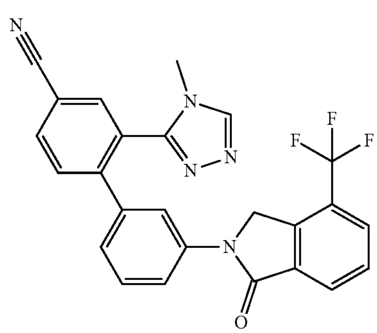 [SMILES: Cn1cnnc1-c1cc(C#N)ccc1-c1cccc(N2Cc3c(cccc3C(F)(F)F)C2=O)c1] |
| 16 | AN-1 | 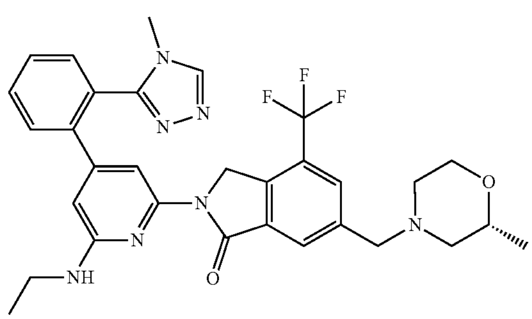 |

TABLE 1-continued
| Compound # | Compound ID | Structure |
|---|---|---|
| 17 | AO-1 | 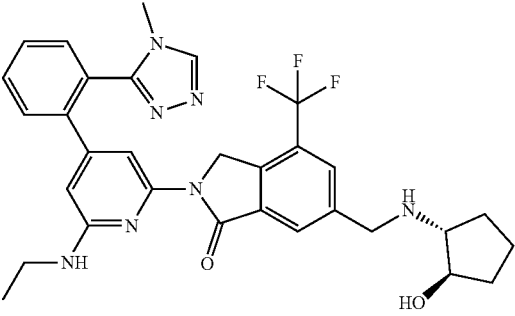 |
| 18 | AP-1 | 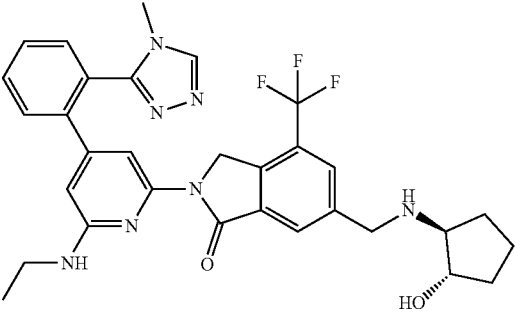 [SMILES: CCNc1cc(-c2ccccc2-c2nncn2C)cc(N2Cc3c(cc(CN[C@H]4CCC[C@@H]4O)cc3C(F)(F)F)C2=O)n1] |
| 19 | ACH-1 | 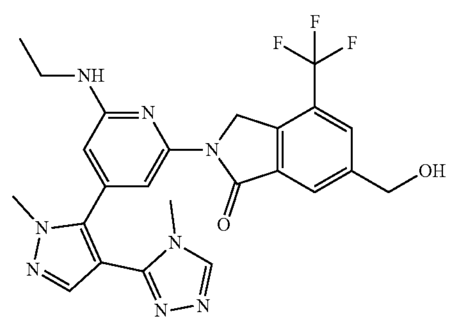 [SMILES: CCNc1cc(-c2c(-c3nncn3C)cnn2C)cc(N2Cc3c(cc(CO)cc3C(F)(F)F)C2=O)n1] |
| 20 | ACG-3 | 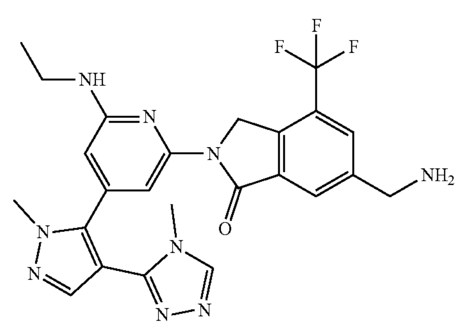 [SMILES: CCNc1cc(-c2c(-c3nncn3C)cnn2C)cc(N2Cc3c(cc(CN)cc3C(F)(F)F)C2=O)n1] |

TABLE 1-continued

Selected Compounds

| Compound # | Compound ID | Structure |
|---|---|---|
| 21 | X-2 | 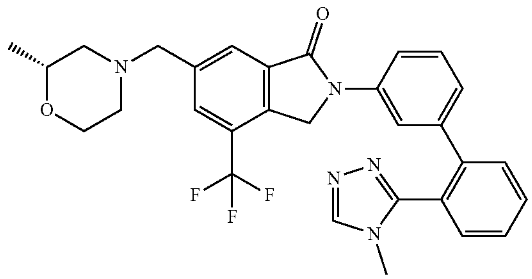 [SMILES: C[C@@H]1CN(Cc2cc3c(c(C(F)(F)F)c2)CN(c2cccc(-c4ccccc4-c4nncn4C)c2)C3=O)CCO1] |
| 22 | AL-1 | 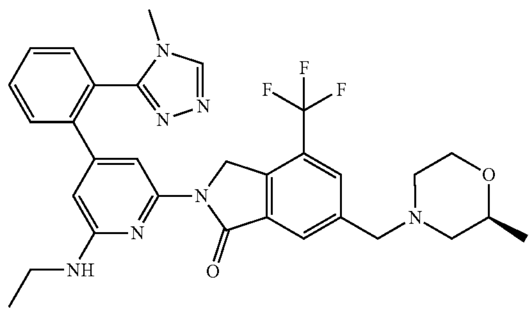 |
| 23 | AM-2 | 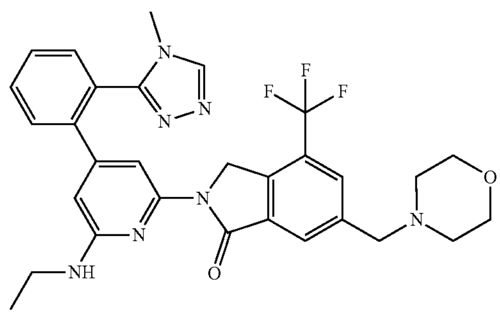 [SMILES: CCNc1cc(-c2ccccc2-c2nncn2C)cc(N2Cc3c(cc(CN4CCOCC4)cc3C(F)(F)F)C2=O)n1] |
| 24 | ABX-6 | 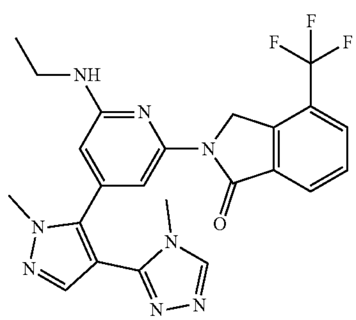 [SMILES: CCNc1cc(-c2c(-c3nncn3C)cnn2C)cc(N2Cc3c(cccc3C(F)(F)F)C2=O)n1] |
| 25 | ACF-1 | 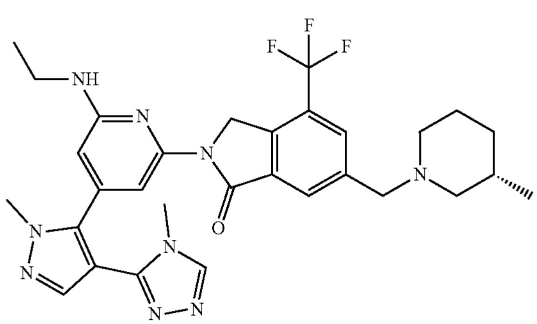 |

TABLE 1-continued

Selected Compounds

| Compound # | Compound ID | Structure |
|---|---|---|
| 26 | ACE-1 | 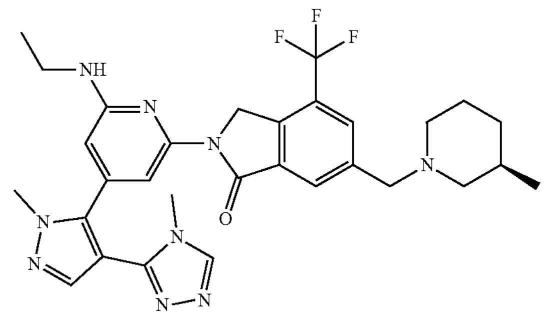 |
| 27 | ACD-1 | 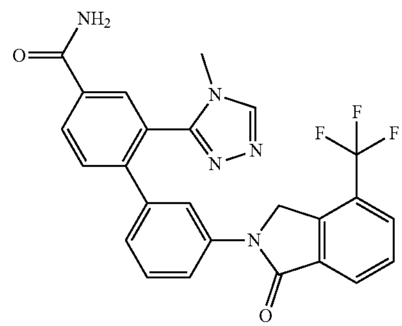 [SMILES: Cn1cnnc1-c1cc(C(N)=O)ccc1-c1cccc(N2Cc3c(cccc3C(F)(F)F)C2=O)c1] |
| 28 | ACB-1 | 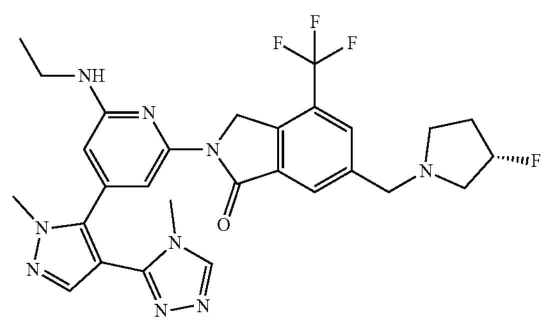 [SMILES: CCNc1cc(-c2c(-c3nncn3C)cnn2C)cc(N2Cc3c(cc(CN4CC[C@H](F)C4)cc3C(F)(F)F)C2=O)n1] |
| 29 | ACA-1 | 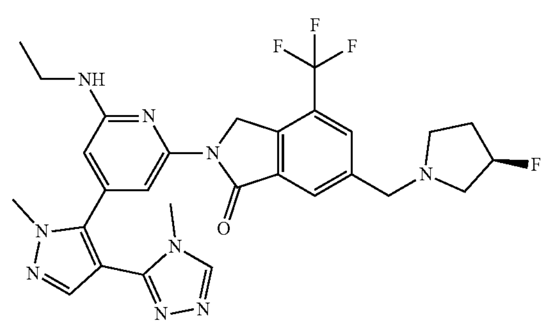 [SMILES: CCNc1cc(-c2c(-c3nncn3C)cnn2C)cc(N2Cc3c(cc(CN4CC[C@@H](F)C4)cc3C(F)(F)F)C2=O)n1] |

TABLE 1-continued
Selected Compounds
| Compound # | Compound ID | Structure |
|---|---|---|
| 30 | ABZ-7 | 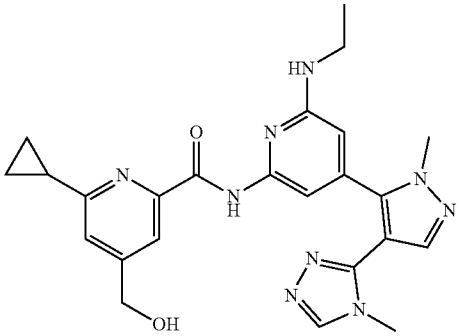 [SMILES: CCNc1cc(-c2c(-c3nncn3C)cnn2C)cc(NC(=O)c2cc(CO)cc(C3CC3)n2)n1] |
| 31 | ABY-1 | 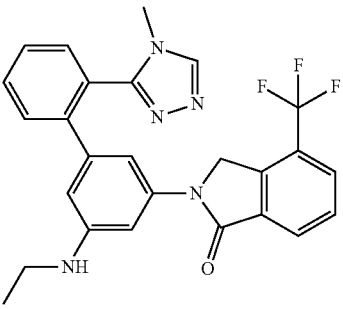 [SMILES: CCNc1cc(-c2ccccc2-c2nncn2C)cc(N2Cc3c(cccc3C(F)(F)F)C2=O)c1] |
| 32 | ABW-3 | 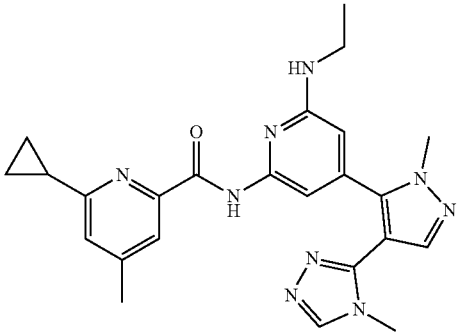 [SMILES: CCNc1cc(-c2c(-c3nncn3C)cnn2C)cc(NC(=O)c2cc(C)cc(C3CC3)n2)n1] |
| 33 | R-2 | 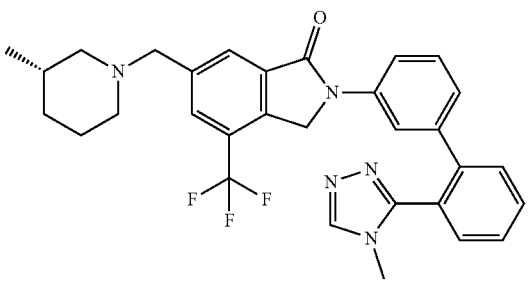 [SMILES: C[C@H]1CCCN(Cc2cc3c(c(C(F)(F)F)c2)CN(c2cccc(-c4ccccc4-c4nncn4C)c2)C3=O)C1] |

TABLE 1-continued

Selected Compounds

| Compound # | Compound ID | Structure |
|---|---|---|
| 34 | V-2 | 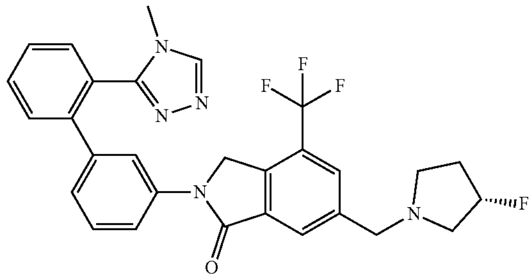 [SMILES: Cn1cnnc1-c1ccccc1-c1cccc(N2Cc3c(cc(CN4CC[C@H](F)C4)cc3C(F)(F)F)C2=O)c1] |
| 35 | AE-2 | 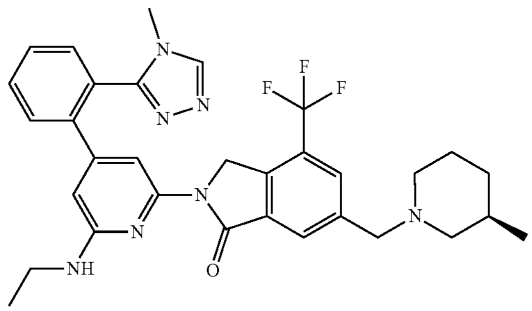 [SMILES: CCNc1cc(-c2ccccc2-c2nncn2C)cc(N2Cc3c(cc(CN4CCC[C@@H](C)C4)cc3C(F)(F)F)C2=O)n1] |
| 36 | AF-1 | 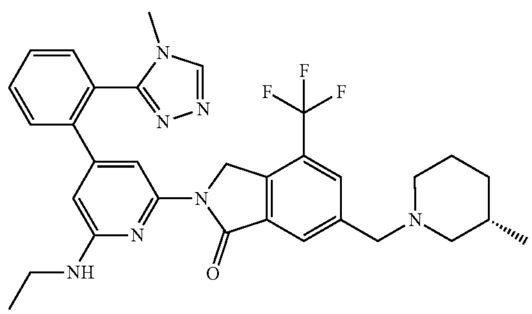 [SMILES: CCNc1cc(-c2ccccc2-c2nncn2C)cc(N2Cc3c(cc(CN4CCC[C@H](C)C4)cc3C(F)(F)F)C2=O)n1] |
| 37 | AG-1 | 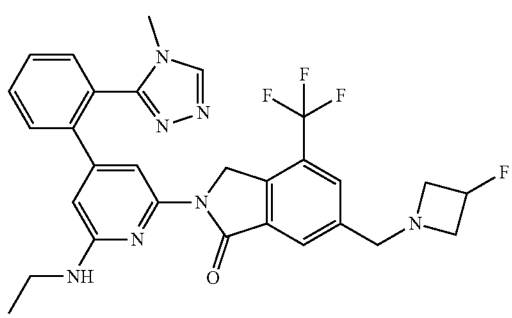 [SMILES: CCNc1cc(-c2ccccc2-c2nncn2C)cc(N2Cc3c(cc(CN4CC(F)C4)cc3C(F)(F)F)C2=O)n1] |
| 38 | AH-2 | 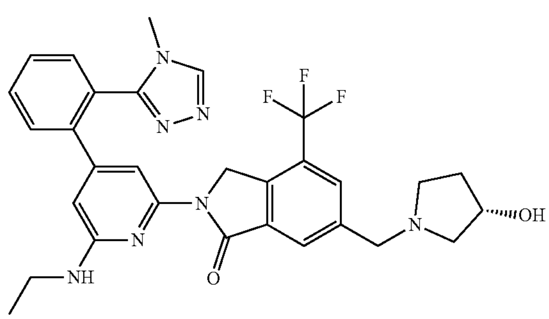 [SMILES: CCNc1cc(-c2ccccc2-c2nncn2C)cc(N2Cc3c(cc(CN4CC[C@H](O)C4)cc3C(F)(F)F)C2=O)n1] |

TABLE 1-continued

Selected Compounds

| Compound # | Compound ID | Structure |
|---|---|---|
| 39 | AI-2 | 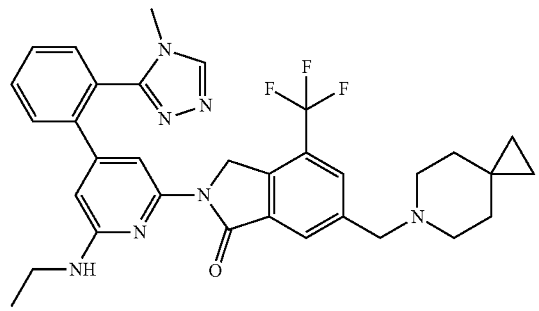 [SMILES: CCNc1cc(-c2ccccc2-c2nncn2C)cc(N2Cc3c(cc(CN4CCC5(CC4)CC5)cc3C(F)(F)F)C2=O)n1] |
| 40 | AJ-1 | 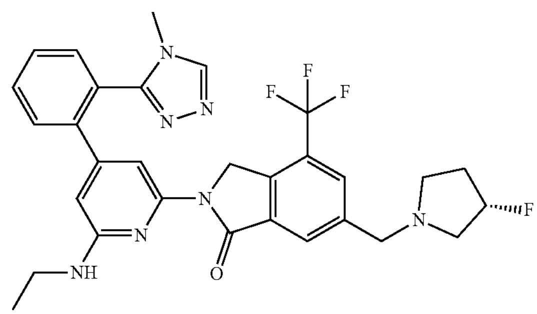 [SMILES: CCNc1cc(-c2ccccc2-c2nncn2C)cc(N2Cc3c(cc(CN4CC[C@H](F)C4)cc3C(F)(F)F)C2=O)n1] |
| 41 | W-2 | 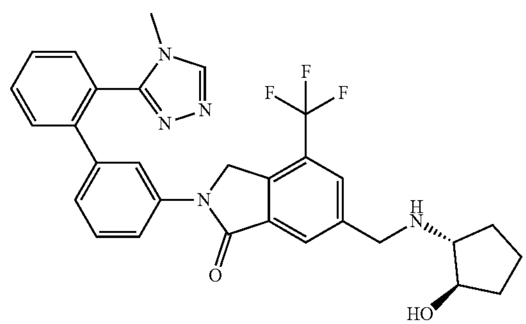 [SMILES: Cn1cnnc1-c1ccccc1-c1cccc(N2Cc3c(cc(CN[C@@H]4CCC[C@H]4O)cc3C(F)(F)F)C2=O)c1] |
| 42 | AK-2 | 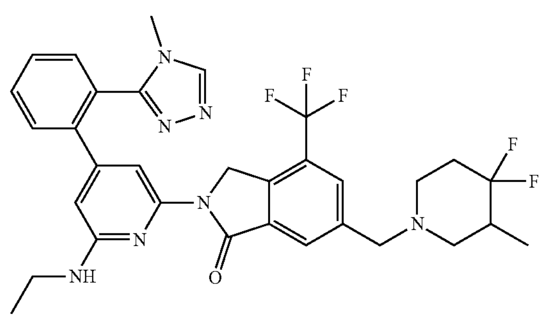 [SMILES: CCNc1cc(-c2ccccc2-c2nncn2C)cc(N2Cc3c(cc(CN4CCC(F)(F)C(C)C4)cc3C(F)(F)F)C2=O)n1] |
| 43 | ABK-7 | 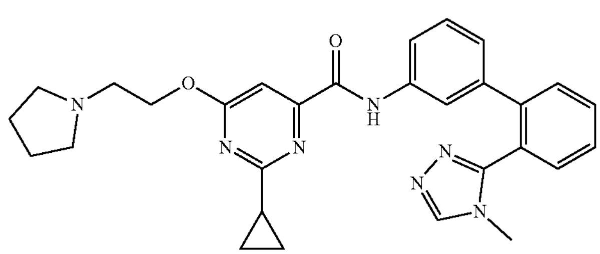 [SMILES: Cn1cnnc1-c1ccccc1-c1cccc(NC(=O)c2cc(OCCN3CCCC3)nc(C3CC3)n2)c1] |

TABLE 1-continued
Selected Compounds
| Compound # | Compound ID | Structure |
|---|---|---|
| 44 | ABU-2 | 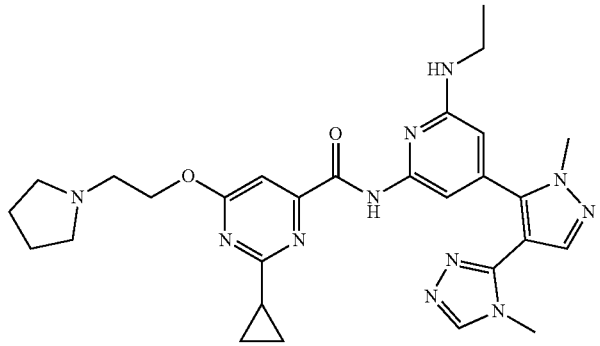 [SMILES: CCNc1cc(-c2c(-c3nncn3C)cnn2C)cc(NC(=O)c2cc(OCCN3CCCC3)nc(C3CC3)n2)n1] |
| 45 | ABT-2 | 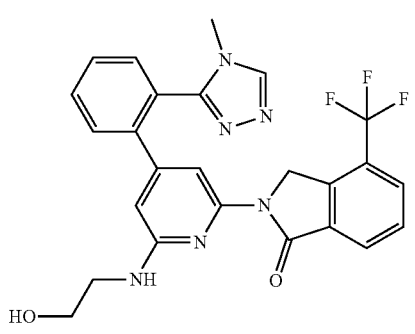 [SMILES: Cn1cnnc1-c1ccccc1-c1cc(NCCO)nc(N2Cc3c(cccc3C(F)(F)F)C2=O)c1] |
| 46 | AC-3 | 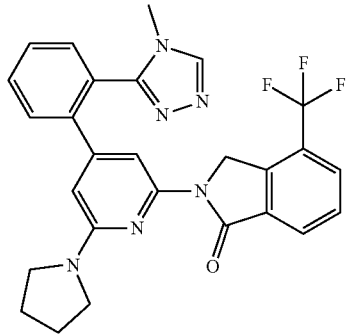 [SMILES: Cn1cnnc1-c1ccccc1-c1cc(N2CCCC2)nc(N2Cc3c(cccc3C(F)(F)F)C2=O)c1] |
| 47 | T-2 | 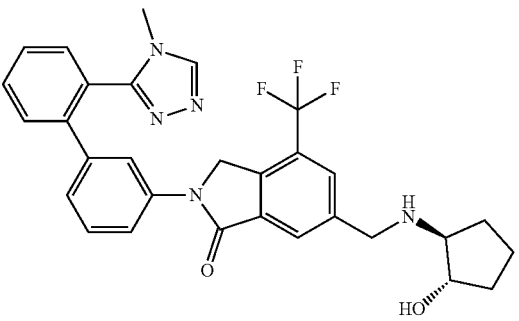 [SMILES: Cn1cnnc1-c1ccccc1-c1cccc(N2Cc3c(cc(CN[C@H]4CCC[C@@H]4O)cc3C(F)(F)F)C2=O)c1] |

TABLE 1-continued
Selected Compounds
| Compound # | Compound ID | Structure |
|---|---|---|
| 48 | U-2 | 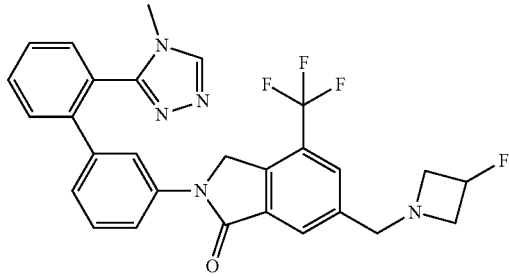 [SMILES: Cn1cnnc1-c1ccccc1-c1cccc(N2Cc3c(cc(CN4CC(F)C4)cc3C(F)(F)F)C2=O)c1] |
| 49 | ABS-1 | 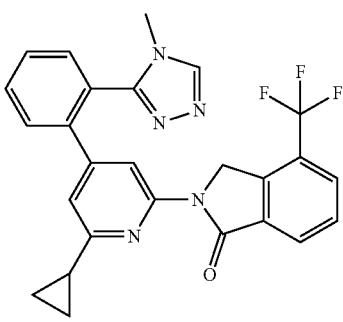 [SMILES: Cn1cnnc1-c1ccccc1-c1cc(C2CC2)nc(N2Cc3c(cccc3C(F)(F)F)C2=O)c1] |
| 50 | ABR-1 | 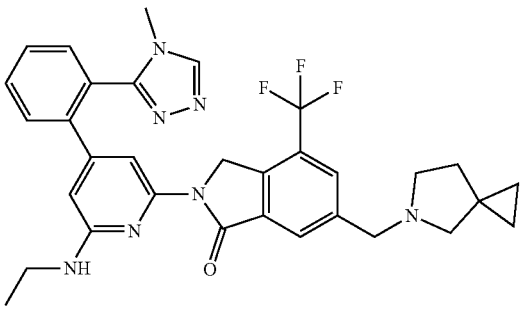 [SMILES: CCNc1cc(-c2ccccc2-c2nncn2C)cc(N2Cc3c(cc(CN4CCC5(CC5)C4)cc3C(F)(F)F)C2=O)n1] |
| 51 | ABP-3 | 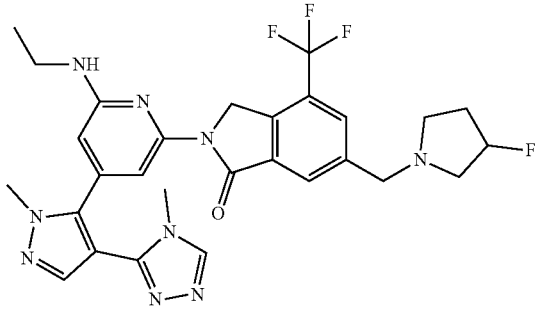 |
| 52 | AD-3 | 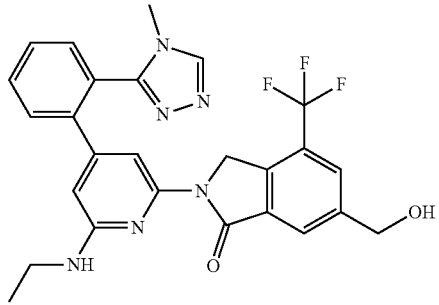 [SMILES: CCNc1cc(-c2ccccc2-c2nncn2C)cc(N2Cc3c(cc(CO)cc3C(F)(F)F)C2=O)n1] |

TABLE 1-continued
Selected Compounds
| Compound # | Compound ID | Structure |
|---|---|---|
| 53 | AD-4 | 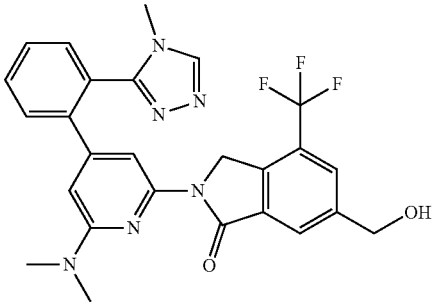 [SMILES: CN(C)c1cc(-c2ccccc2-c2nncn2C)cc(N2Cc3c(cc(CO)cc3C(F)(F)F)C2=O)n1] |
| 54 | ABO-5 | 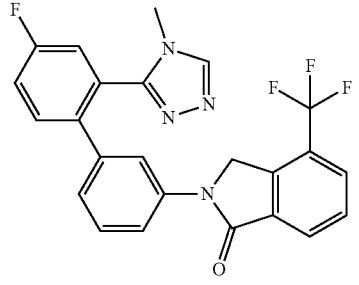 [SMILES: Cn1cnnc1-c1cc(F)ccc1-c1cccc(N2Cc3c(cccc3C(F)(F)F)C2=O)c1] |
| 55 | ABN-2 | 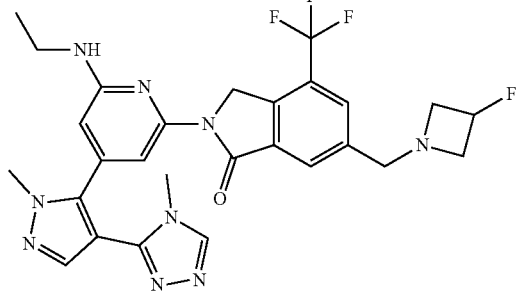 |
| 56 | ABM-1 | 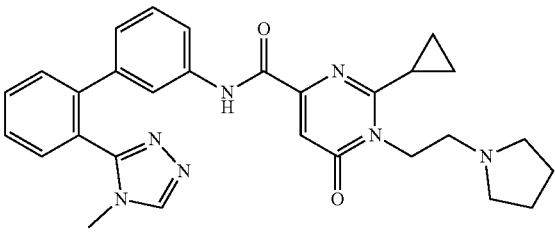 |
| 57 | ABL-4 | 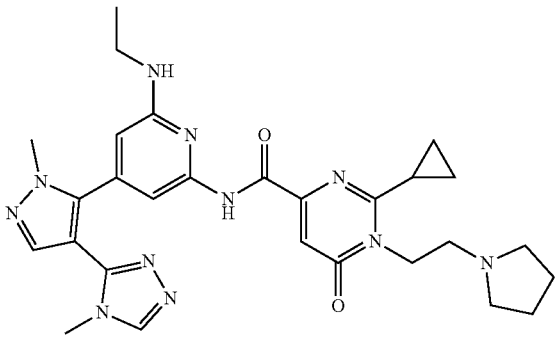 |

TABLE 1-continued
Selected Compounds
| Compound # | Compound ID | Structure |
|---|---|---|
| 58 | M-2 | 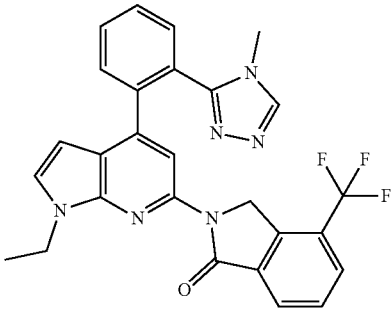 [SMILES: CCn1ccc2c(-c3ccccc3-c3nncn3C)cc(N3Cc4c(cccc4C(F)(F)F)C3=O)nc21] |
| 59 | P-2 | 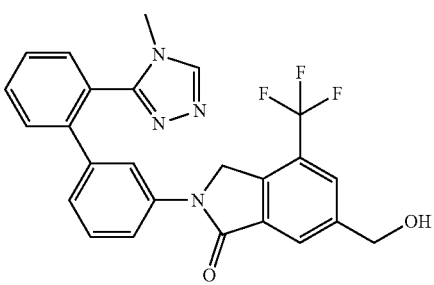 [SMILES: Cn1cnnc1-c1ccccc1-c1cccc(N2Cc3c(cc(CO)cc3C(F)(F)F)C2=O)c1] |
| 60 | S-2 | 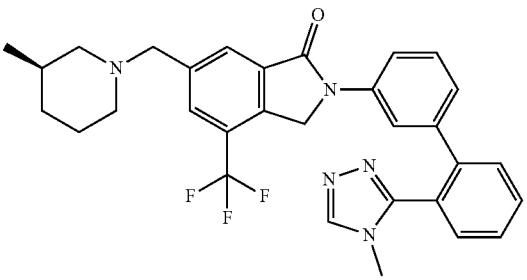 [SMILES: C[C@@H]1CCCN(Cc2cc3c(c(C(F)(F)F)c2)CN(c2cccc(-c4ccccc4-c4nncn4C)c2)C3=O)C1] |
| 61 | ABJ-4 | 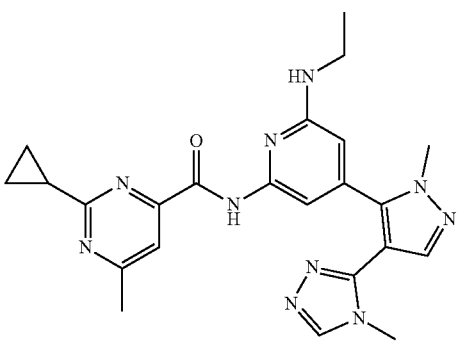 [SMILES: CCNc1cc(-c2c(-c3nncn3C)cnn2C)cc(NC(=O)c2cc(C)nc(C3CC3)n2)n1] |
| 62 | ABI-1 | 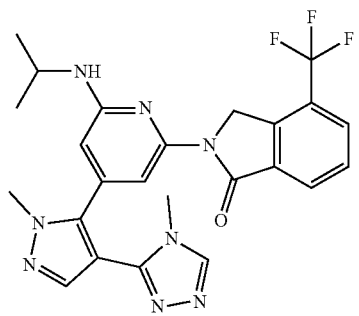 [SMILES: CC(C)Nc1cc(-c2c(-c3nncn3C)cnn2C)cc(N2Cc3c(cccc3C(F)(F)F)C2=O)n1] |

TABLE 1-continued
Selected Compounds
| Compound # | Compound ID | Structure |
|---|---|---|
| 63 | ABH-2 | 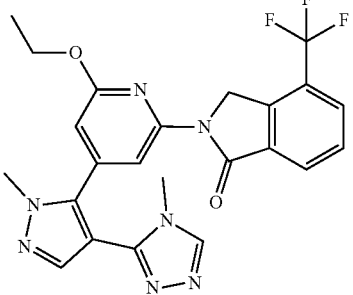 |
| 64 | ABG-3 | 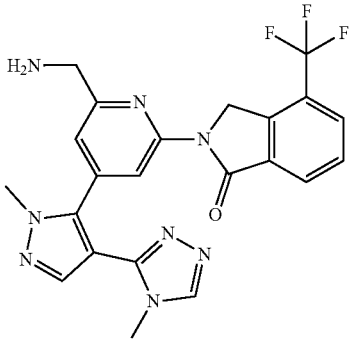 [SMILES: Cn1cnnc1-c1cnn(C)c1-c1cc(CN)nc(N2Cc3c(cccc3C(F)(F)F)C2=O)c1] |
| 65 | ABC-7 | 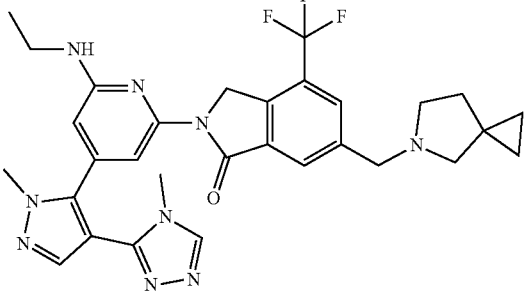 |
| 66 | ABF-8 | 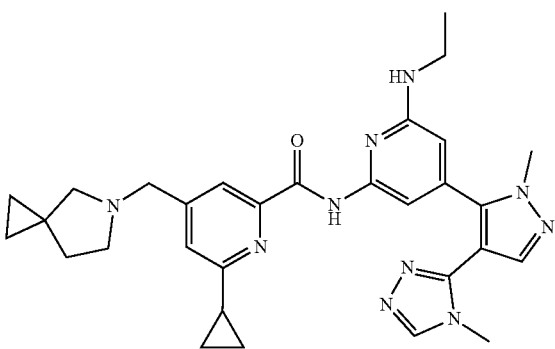 [SMILES: CCNc1cc(-c2c(-c3nncn3C)cnn2C)cc(NC(=O)c2cc(CN3CCC4(CC4)C3)cc(C3CC3)n2)n1] |

TABLE 1-continued
Selected Compounds
| Compound # | Compound ID | Structure |
|---|---|---|
| 67 | ABE-1 | 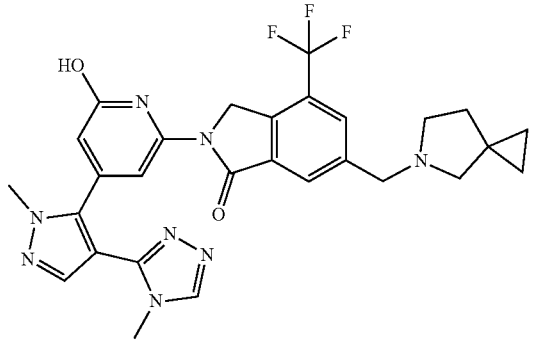 |
| 68 | ABD-1 | 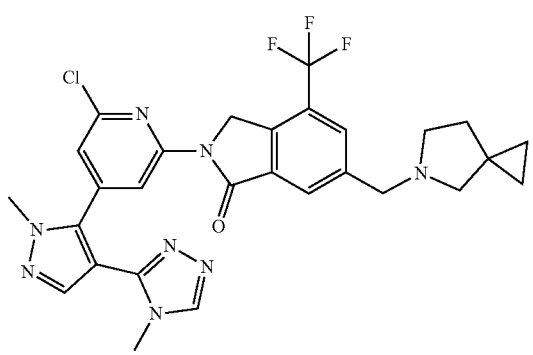 [SMILES: Cn1cnnc1-c1cnn(C)c1-c1cc(Cl)nc(N2Cc3c(cc(CN4CCC5(CC5)C4)cc3C(F)(F)F)C2=O)c1] |
| 69 | N-5 | 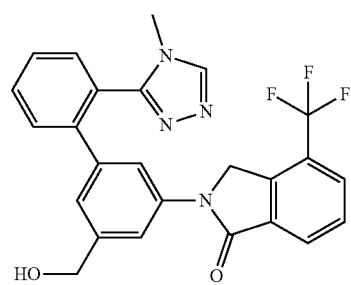 [SMILES: Cn1cnnc1-c1ccccc1-c1cc(CO)cc(N2Cc3c(cccc3C(F)(F)F)C2=O)c1] |
| 70 | O-3 | 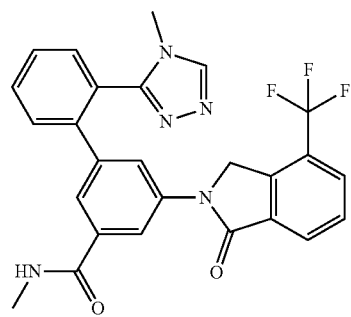 [SMILES: CNC(=O)c1cc(-c2ccccc2-c2nncn2C)cc(N2Cc3c(cccc3C(F)(F)F)C2=O)c1] |

TABLE 1-continued

| Compound # | Compound ID | Structure |
|---|---|---|
| 71 | ABB-5 | 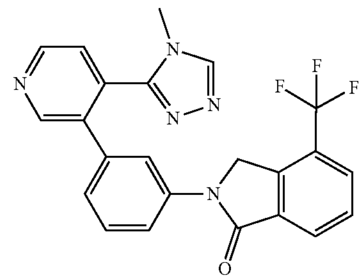 [SMILES: Cn1cnnc1-c1ccncc1-c1cccc(N2Cc3c(cccc3C(F)(F)F)C2=O)c1] |
| 72 | ABA-4 | 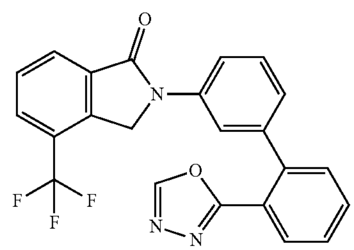 [SMILES: O=C1c2cccc(C(F)(F)F)c2CN1c1cccc(-c2ccccc2-c2nnco2)c1] |
| 73 | L-5 | 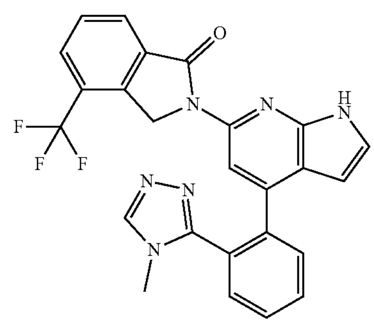 [SMILES: Cn1cnnc1-c1ccccc1-c1cc(N2Cc3c(cccc3C(F)(F)F)C2=O)nc2[nH]ccc12] |
| 74 | AAZ-7 | 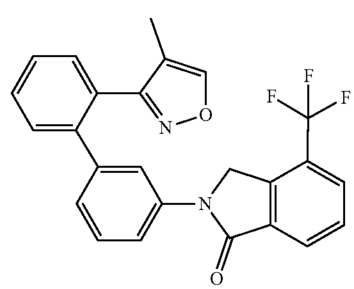 [SMILES: Cc1conc1-c1ccccc1-c1cccc(N2Cc3c(cccc3C(F)(F)F)C2=O)c1] |
| 75 | AAY-6 | 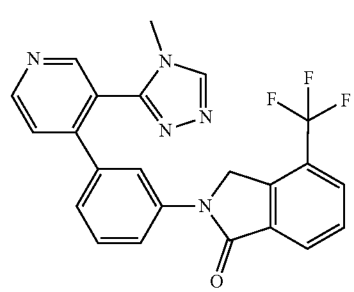 [SMILES: Cn1cnnc1-c1cnccc1-c1cccc(N2Cc3c(cccc3C(F)(F)F)C2=O)c1] |

TABLE 1-continued
Selected Compounds
| Compound # | Compound ID | Structure |
|---|---|---|
| 76 | AAX-2 | 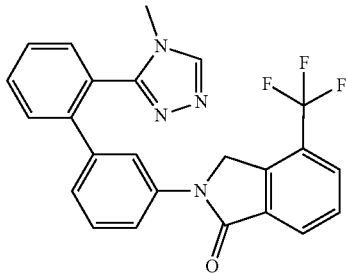 [SMILES: Cn1cnnc1-c1ccccc1-c1cccc(N2Cc3c(cccc3C(F)(F)F)C2=O)c1] |
| 77 | K-3 | 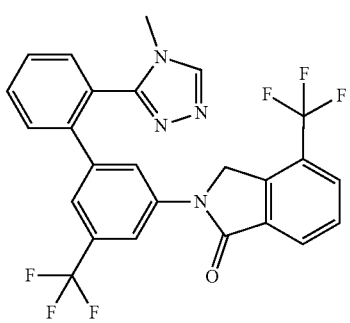 [SMILES: Cn1cnnc1-c1ccccc1-c1cc(N2Cc3c(cccc3C(F)(F)F)C2=O)cc(C(F)(F)F)c1] |
| 78 | AAW-2 | 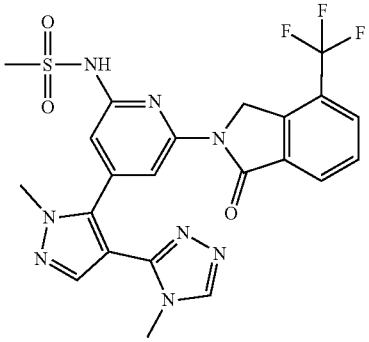 [SMILES: Cn1cnnc1-c1cnn(C)c1-c1cc(NS(C)(=O)=O)nc(N2Cc3c(cccc3C(F)(F)F)C2=O)c1] |
| 79 | I-1 | 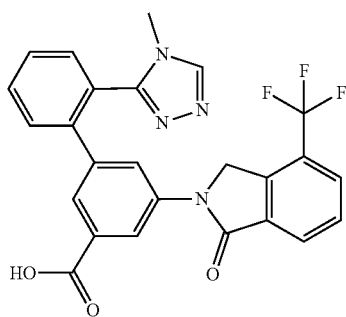 [SMILES: Cn1cnnc1-c1ccccc1-c1cc(C(=O)O)cc(N2Cc3c(cccc3C(F)(F)F)C2=O)c1] |

TABLE 1-continued

Selected Compounds

| Compound # | Compound ID | Structure |
|---|---|---|
| 80 | J-4 | 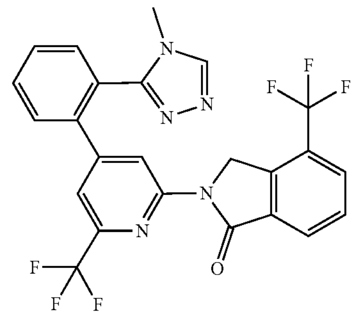 [SMILES: Cn1cnnc1-c1ccccc1-c1cc(N2Cc3c(cccc3C(F)(F)F)C2=O)nc(C(F)(F)F)c1] |
| 81 | H-5 | 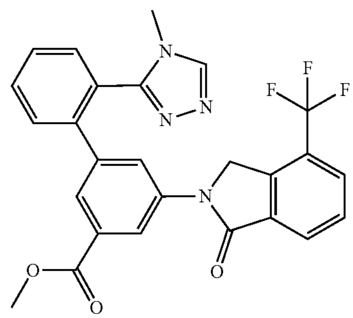 [SMILES: COC(=O)c1cc(-c2ccccc2-c2nncn2C)cc(N2Cc3c(cccc3C(F)(F)F)C2=O)c1] |
| 82 | G-4 | 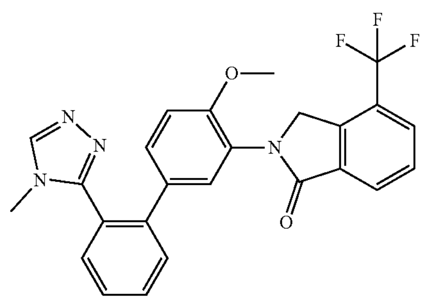 [SMILES: COc1ccc(-c2ccccc2-c2nncn2C)cc1N1Cc2c(cccc2C(F)(F)F)C1=O] |
| 83 | AAV-6 | 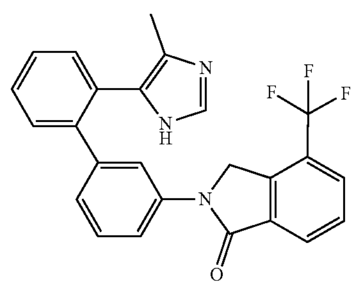 [SMILES: Cc1nc[nH]c1-c1ccccc1-c1cccc(N2Cc3c(cccc3C(F)(F)F)C2=O)c1] |
| 84 | AAT-1 | 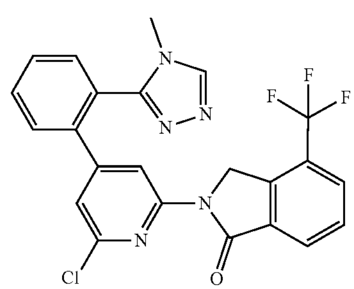 [SMILES: Cn1cnnc1-c1ccccc1-c1cc(Cl)nc(N2Cc3c(cccc3C(F)(F)F)C2=O)c1] |

TABLE 1-continued

Selected Compounds

| Compound # | Compound ID | Structure |
|---|---|---|
| 85 | AAR-5 | 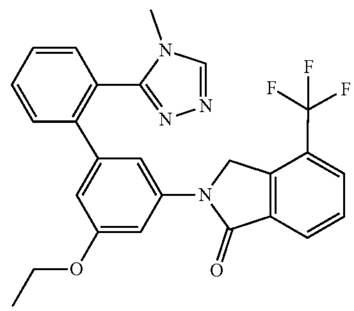 [SMILES: CCOc1cc(-c2ccccc2-c2nncn2C)cc(N2Cc3c(cccc3C(F)(F)F)C2=O)c1] |
| 86 | AAQ-1 | 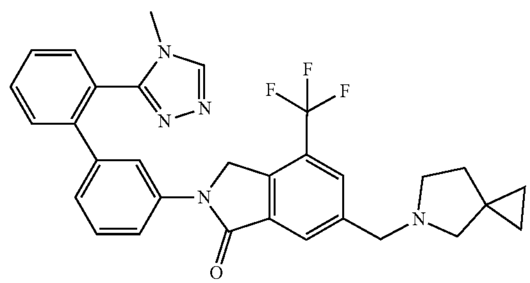 [SMILES: Cn1cnnc1-c1ccccc1-c1cccc(N2Cc3c(cc(CN4CCC5(CC5)C4)cc3C(F)(F)F)C2=O)c1] |
| 87 | AAP-1 | 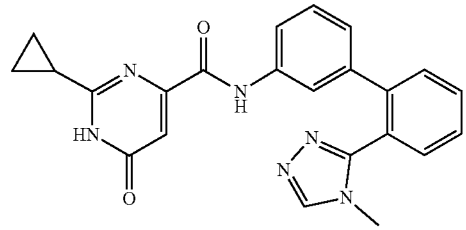 [SMILES: Cn1cnnc1-c1ccccc1-c1cccc(NC(=O)c2cc(=O)[nH]c(C3CC3)n2)c1] |
| 88 | AAO-1 | 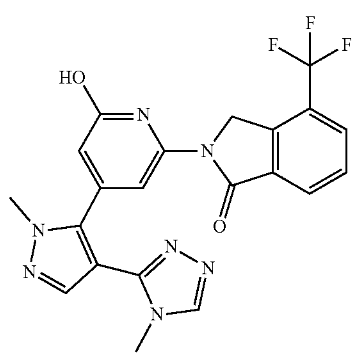 [SMILES: Cn1cnnc1-c1cnn(C)c1-c1cc(O)nc(N2Cc3c(cccc3C(F)(F)F)C2=O)c1] |
| 89 | AAN-7 | 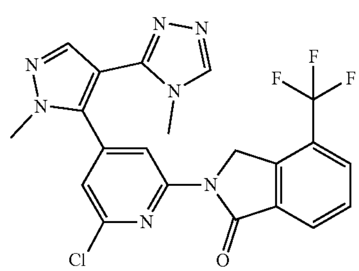 [SMILES: Cn1cnnc1-c1cnn(C)c1-c1cc(Cl)nc(N2Cc3c(cccc3C(F)(F)F)C2=O)c1] |

TABLE 1-continued

Selected Compounds

| Compound # | Compound ID | Structure |
|---|---|---|
| 90 | AAM-3 | 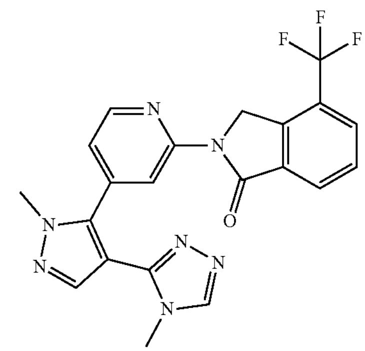 [SMILES: Cn1cnnc1-c1cnn(C)c1-c1ccnc(N2Cc3c(cccc3C(F)(F)F)C2=O)c1] |
| 91 | AAL-8 | 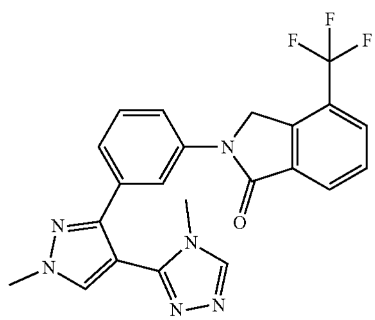 [SMILES: Cn1cc(-c2nncn2C)c(-c2cccc(N3Cc4c(cccc4C(F)(F)F)C3=O)c2)n1] |
| 92 | AAK-2 | 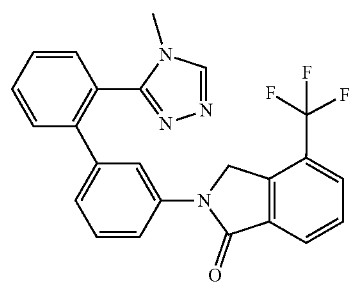 [SMILES: Cn1cnnc1-c1ccccc1-c1cccc(N2Cc3c(cccc3C(F)(F)F)C2=O)c1] |
| 93 | AAJ-9 | 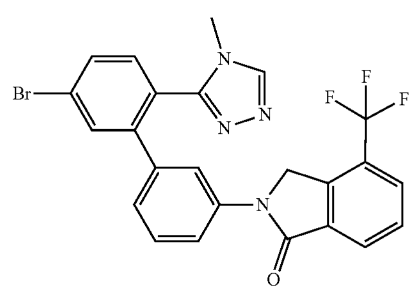 [SMILES: Cn1cnnc1-c1ccc(Br)cc1-c1cccc(N2Cc3c(cccc3C(F)(F)F)C2=O)c1] |
| 94 | AAI-7 | 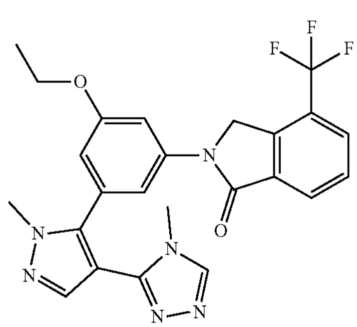 [SMILES: CCOc1cc(-c2c(-c3nncn3C)cnn2C)cc(N2Cc3c(cccc3C(F)(F)F)C2=O)c1] |

TABLE 1-continued

Selected Compounds

| Compound # | Compound ID | Structure |
|---|---|---|
| 95 | AAG-8 | 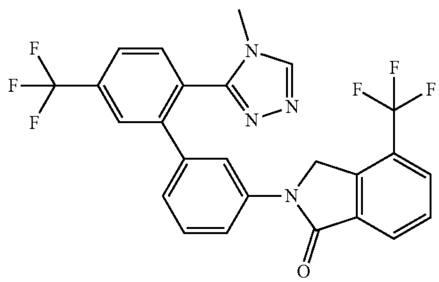 [SMILES: Cn1cnnc1-c1ccc(C(F)(F)F)cc1-c1cccc(N2Cc3c(cccc3C(F)(F)F)C2=O)c1] |
| 96 | AAF-9 | 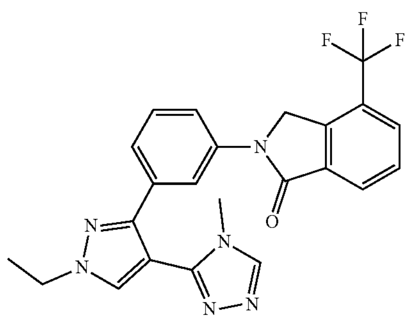 [SMILES: CCn1cc(-c2nncn2C)c(-c2cccc(N3Cc4c(cccc4C(F)(F)F)C3=O)c2)n1] |
| 97 | AAE-6 | 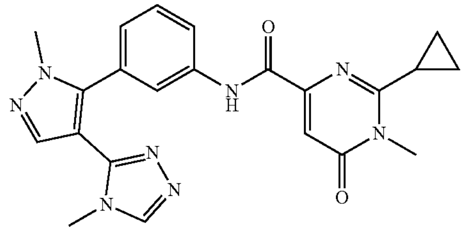 [SMILES: Cn1cnnc1-c1cnn(C)c1-c1cccc(NC(=O)c2cc(=O)n(C)c(C3CC3)n2)c1] |
| 98 | AAD-1 | 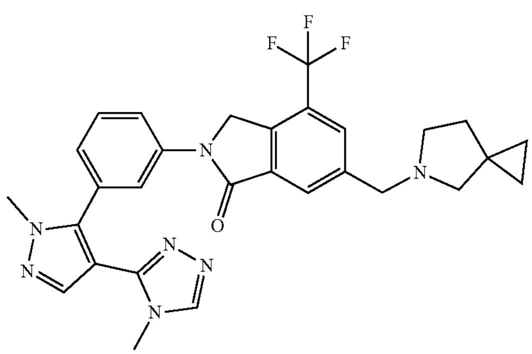 [SMILES: Cn1cnnc1-c1cnn(C)c1-c1cccc(N2Cc3c(cc(CN4CCC5(CC5)C4)cc3C(F)(F)F)C2=O)c1] |
| 99 | AAA-8 | 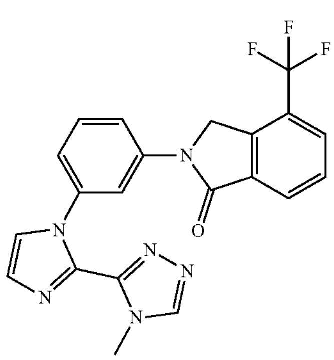 [SMILES: Cn1cnnc1-c1nccn1-c1cccc(N2Cc3c(cccc3C(F)(F)F)C2=O)c1] |

TABLE 1-continued
Selected Compounds
| Compound # | Compound ID | Structure |
|---|---|---|
| 100 | ACV-2 | 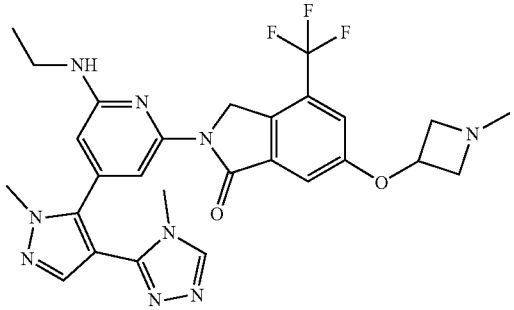 |
| 101 | Y-2 | 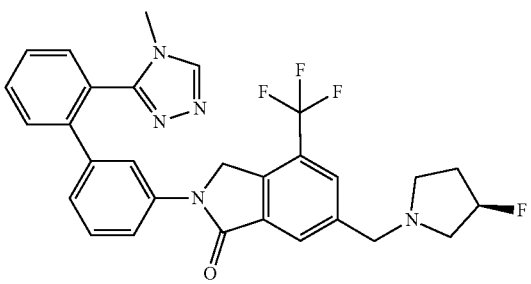 [SMILES: Cn1cnnc1-c1ccccc1-c1cccc(N2Cc3c(cc(CN4CC[C@@H](F)C4)cc3C(F)(F)F)C2=O)c1] |
| 102 | Z-2 | 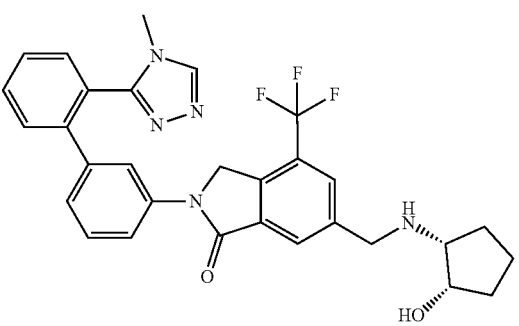 [SMILES: Cn1cnnc1-c1ccccc1-c1cccc(N2Cc3c(cc(CN[C@@H]4CCC[C@@H]4O)cc3C(F)(F)F)C2=O)c1] |
| 103 | AA-2 | 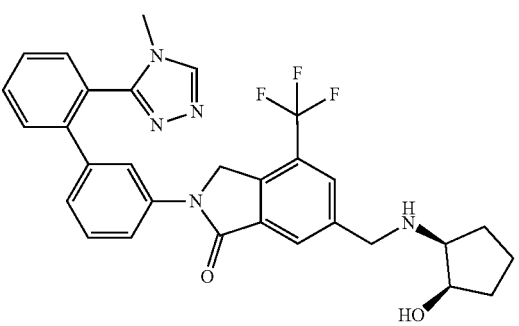 [SMILES: Cn1cnnc1-c1ccccc1-c1cccc(N2Cc3c(cc(CN[C@H]4CCC[C@H]4O)cc3C(F)(F)F)C2=O)c1] |
| 104 | AB-2 | 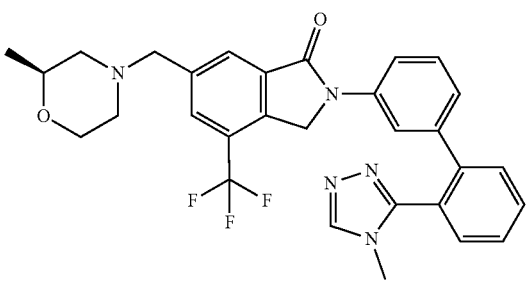 |

TABLE 1-continued
Selected Compounds
| Compound # | Compound ID | Structure |
|---|---|---|
| 105 | ACW-1 | 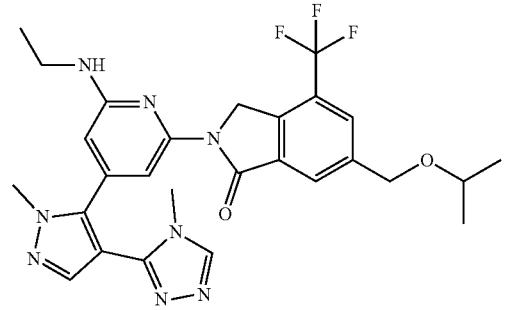 [SMILES: CCNc1cc(-c2c(-c3nncn3C)cnn2C)cc(N2Cc3c(cc(COC(C)C)cc3C(F)(F)F)C2=O)n1] |
| 106 | AQ-1 | 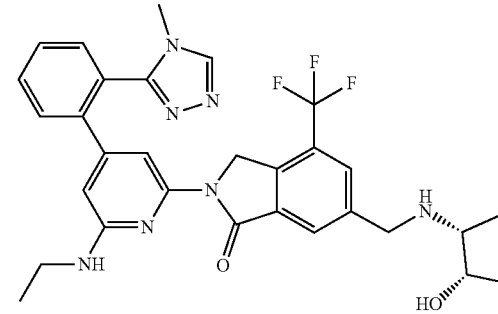 |
| 107 | AS-2 | 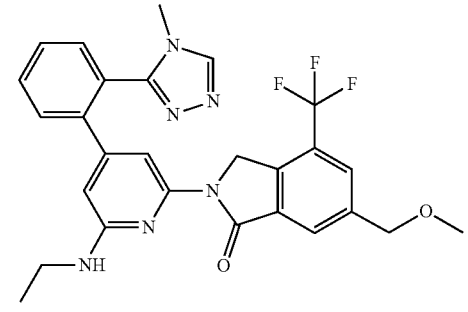 [SMILES: CCNc1cc(-c2ccccc2-c2nncn2C)cc(N2Cc3c(cc(COC)cc3C(F)(F)F)C2=O)n1] |
| 108 | AR-1 | 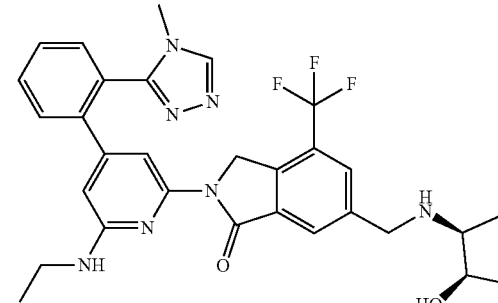 |

TABLE 1-continued

Selected Compounds

| Compound # | Compound ID | Structure |
|---|---|---|
| 109 | AT-1 | 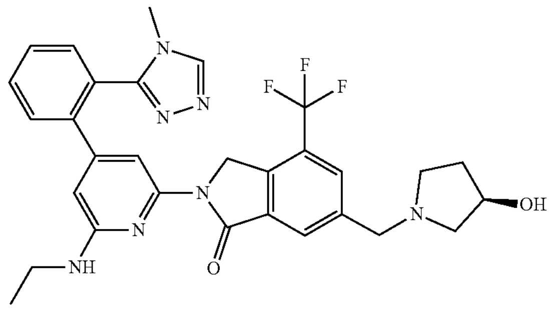 [SMILES: CCNc1cc(-c2ccccc2-c2nncn2C)cc(N2Cc3c(cc(CN4CC[C@@H](O)C4)cc3C(F)(F)F)C2=O)n1] |
| 110 | AU-2 | 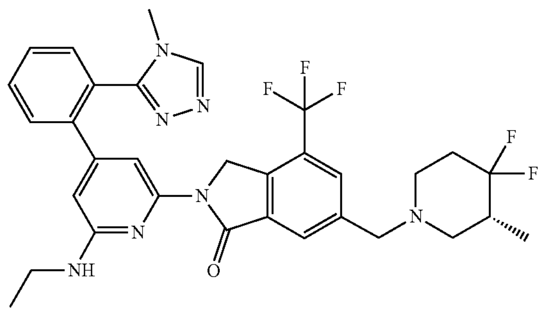 [SMILES: CCNc1cc(-c2ccccc2-c2nncn2C)cc(N2Cc3c(cc(CN4CCC(F)(F)[C@H](C)C4)cc3C(F)(F)F)C2=O)n1] |
| 111 | AV-3 | 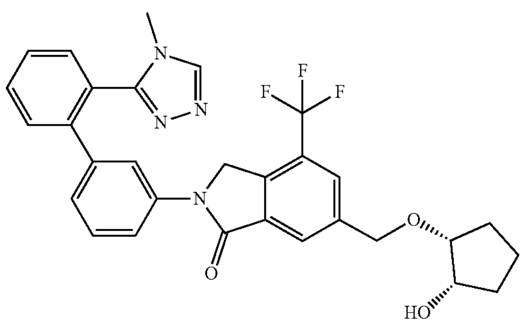 [SMILES: Cn1cnnc1-c1ccccc1-c1cccc(N2Cc3c(cc(CO[C@@H]4CCC[C@@H]4O)cc3C(F)(F)F)C2=O)c1] |
| 112 | AW-2 | 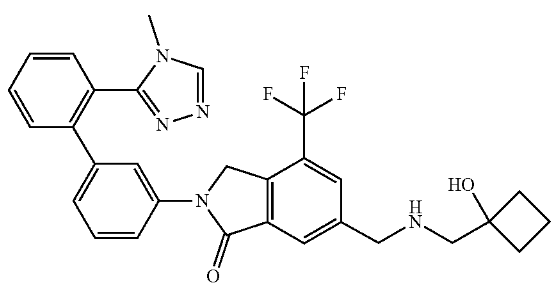 [SMILES: Cn1cnnc1-c1ccccc1-c1cccc(N2Cc3c(cc(CNCC4(O)CCC4)cc3C(F)(F)F)C2=O)c1] |
| 113 | AY-1 | 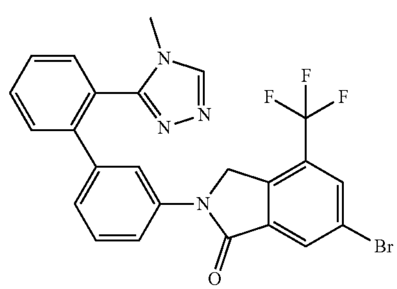 [SMILES: Cn1cnnc1-c1ccccc1-c1cccc(N2Cc3c(cc(Br)cc3C(F)(F)F)C2=O)c1] |

TABLE 1-continued
Selected Compounds
| Compound # | Compound ID | Structure |
|---|---|---|
| 114 | AZ-2 | 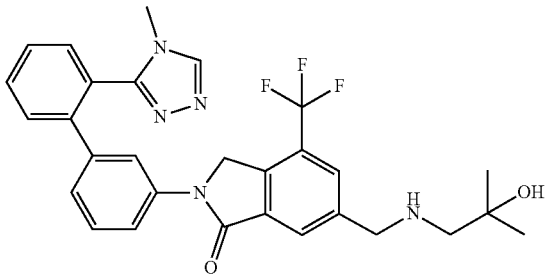 [SMILES: Cn1cnnc1-c1ccccc1-c1cccc(N2Cc3c(cc(CNCC(C)(C)O)cc3C(F)(F)F)C2=O)c1] |
| 115 | BA-4 | 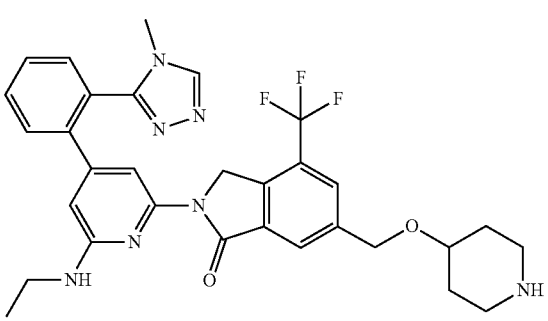 [SMILES: CCNc1cc(-c2ccccc2-c2nncn2C)cc(N2Cc3c(cc(COC4CCNCC4)cc3C(F)(F)F)C2=O)n1] |
| 116 | BB-1 | 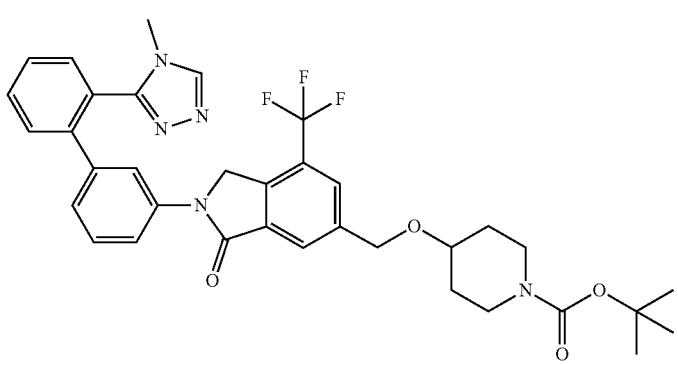 [SMILES: Cn1cnnc1-c1ccccc1-c1cccc(N2Cc3c(cc(COC4CCN(C(=O)OC(C)(C)C)CC4)cc3C(F)(F)F)C2=O)c1] |
| 117 | BC-4 | 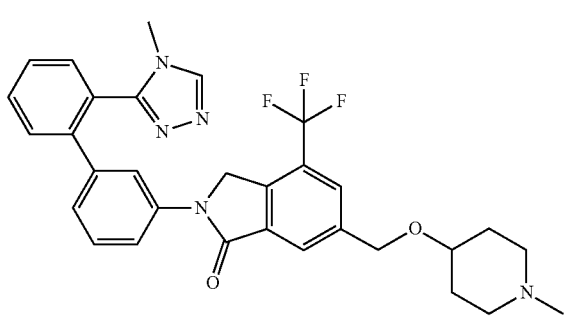 [SMILES: CN1CCC(OCc2cc3c(c(C(F)(F)F)c2)CN(c2cccc(-c4ccccc4-c4nncn4C)c2)C3=O)CC1] |

TABLE 1-continued

Selected Compounds

| Compound # | Compound ID | Structure |
|---|---|---|
| 118 | BD-3 | 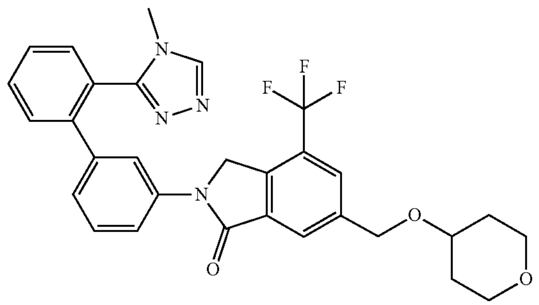 [SMILES: Cn1cnnc1-c1ccccc1-c1cccc(N2Cc3c(cc(COC4CCOCC4)cc3C(F)(F)F)C2=O)c1] |
| 119 | BE-3 | 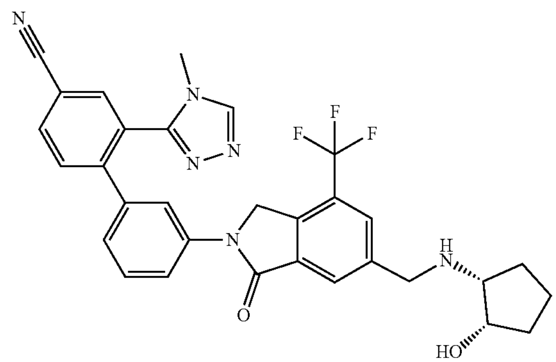 [SMILES: Cn1cnnc1-c1cc(C#N)ccc1-c1cccc(N2Cc3c(cc(CN[C@@H]4CCC[C@@H]4O)cc3C(F)(F)F)C2=O)c1] |
| 120 | ACX-2 | 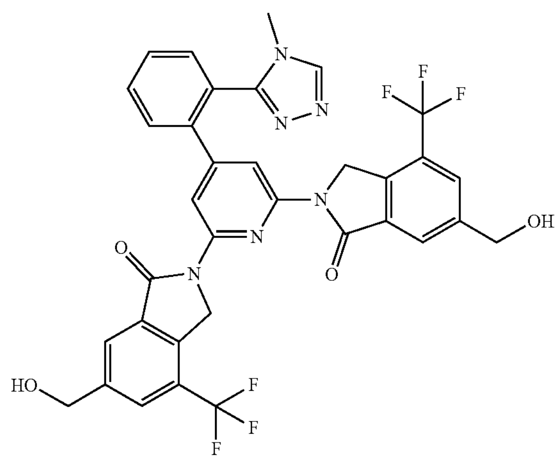 [SMILES: Cn1cnnc1-c1ccccc1-c1cc(N2Cc3c(cc(CO)cc3C(F)(F)F)C2=O)nc(N2Cc3c(cc(CO)cc3C(F)(F)F)C2=O)c1] |
| 121 | ACY-4 | 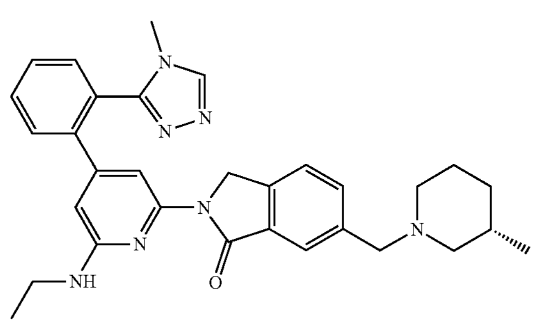 [SMILES: CCNc1cc(-c2ccccc2-c2nncn2C)cc(N2Cc3ccc(CN4CCC[C@H](C)C4)cc3C2=O)n1] |

TABLE 1-continued

| Selected Compounds | | |
|---|---|---|
| Compound # | Compound ID | Structure |
| 122 | ACZ-5 | |
| 123 | ADA-2 | |
| 124 | ADB-1 | |

TABLE 1-continued
| Selected Compounds | | |
|---|---|---|
| Compound # | Compound ID | Structure |
| 125 | ADC-2 | 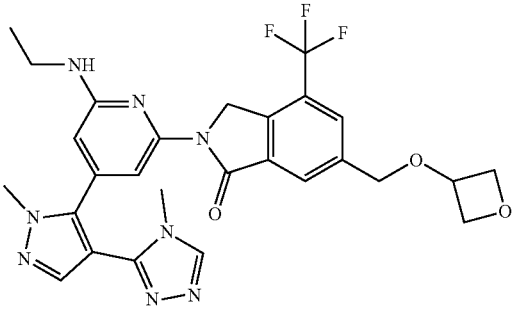 [SMILES: CCNc1cc(-c2c(-c3nncn3C)cnn2C)cc(N2Cc3c(cc(COC4COC4)cc3C(F)(F)F)C2=O)n1] |
| 126 | ADD-2 | 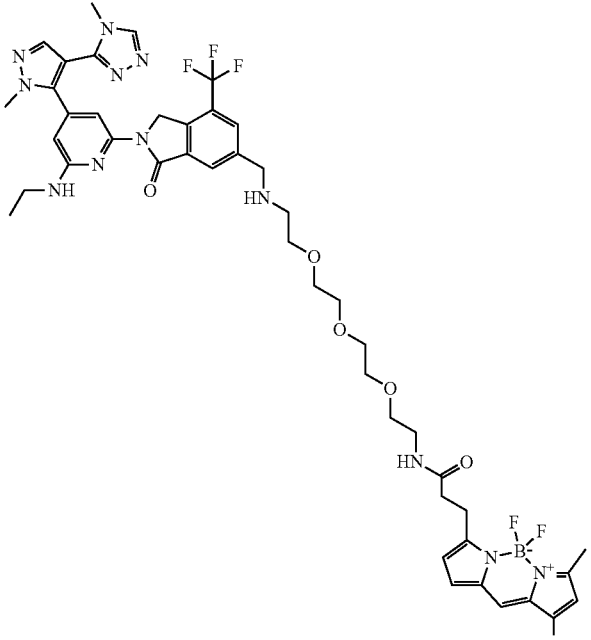 |
| 127 | ADE-2 | 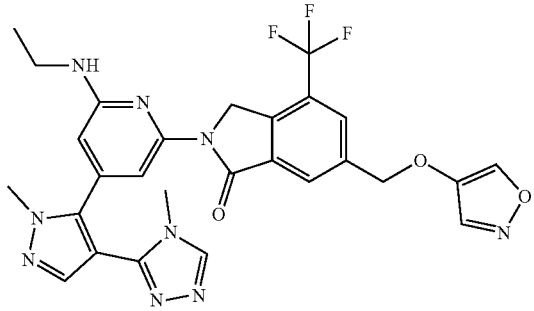 [SMILES: CCNc1cc(-c2c(-c3nncn3C)cnn2C)cc(N2Cc3c(cc(COc4cnoc4)cc3C(F)(F)F)C2=O)n1] |

TABLE 1-continued

Selected Compounds

| Compound # | Compound ID | Structure |
|---|---|---|
| 128 | ADF-2 | 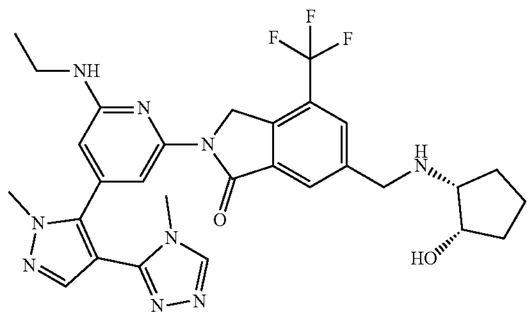 [SMILES: CCNc1cc(-c2c(-c3nncn3C)cnn2C)cc(N2Cc3c(cc(CN[C@@H]4CCC[C@@H]4O)cc3C(F)(F)F)C2=O)n1] |
| 129 | ADG-3 | 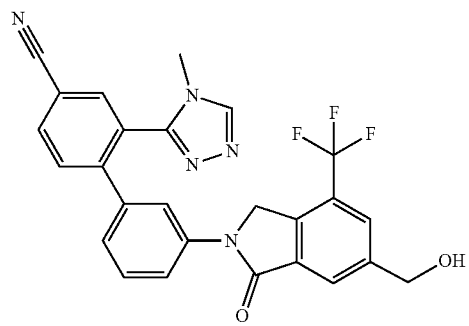 [SMILES: Cn1cnnc1-c1cc(C#N)ccc1-c1cccc(N2Cc3c(cc(CO)cc3C(F)(F)F)C2=O)c1] |
| 130 | ADH-1 | 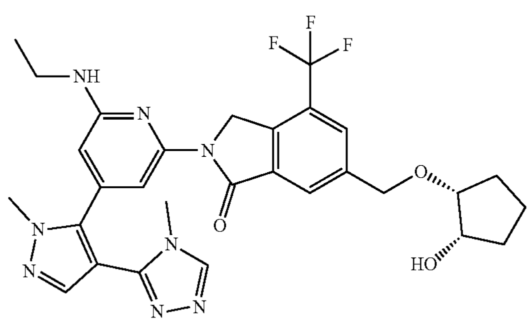 [SMILES: CCNc1cc(-c2c(-c3nncn3C)cnn2C)cc(N2Cc3c(cc(CO[C@@H]4CCC[C@@H]4O)cc3C(F)(F)F)C2=O)n1] |
| 131 | ADI-1 | 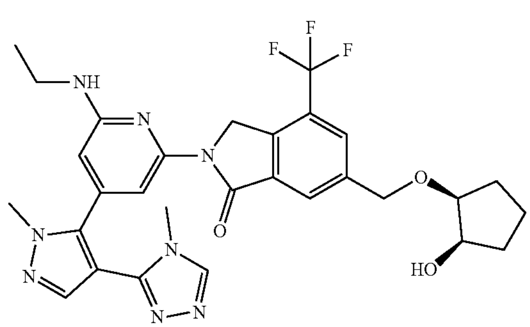 [SMILES: CCNc1cc(-c2c(-c3nncn3C)cnn2C)cc(N2Cc3c(cc(CO[C@H]4CCC[C@H]4O)cc3C(F)(F)F)C2=O)n1] |

TABLE 1-continued

Selected Compounds

| Compound # | Compound ID | Structure |
|---|---|---|
| 132 | ADJ-1 | 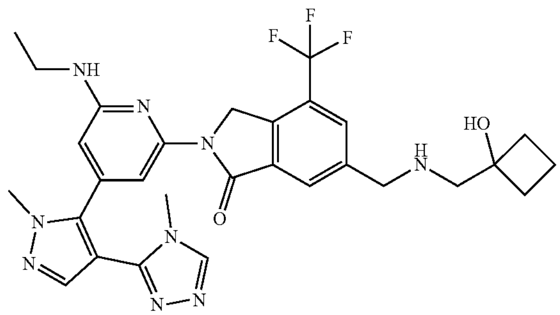 [SMILES: CCNc1cc(-c2c(-c3nncn3C)cnn2C)cc(N2Cc3c(cc(CNCC4(O)CCC4)cc3C(F)(F)F)C2=O)n1] |
| 133 | ADK-1 | 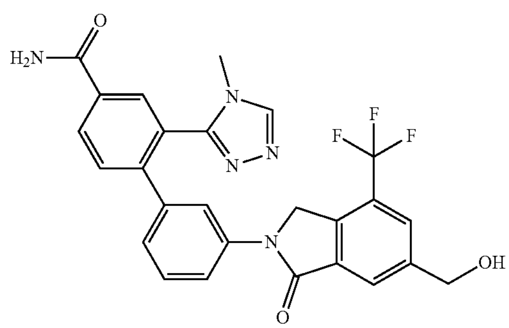 [SMILES: Cn1cnnc1-c1cc(C(N)=O)ccc1-c1cccc(N2Cc3c(cc(CO)cc3C(F)(F)F)C2=O)c1] |
| 134 | ADL-4 | 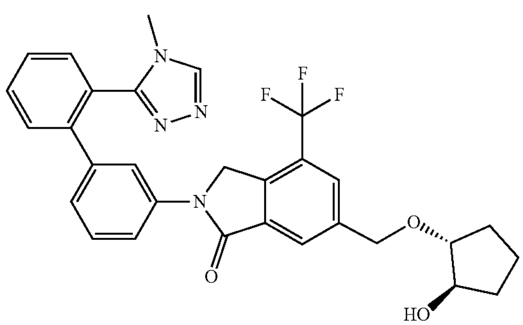 [SMILES: Cn1cnnc1-c1ccccc1-c1cccc(N2Cc3c(cc(CO[C@@H]4CCC[C@H]4O)cc3C(F)(F)F)C2=O)c1] |
| 135 | ADM-6 | 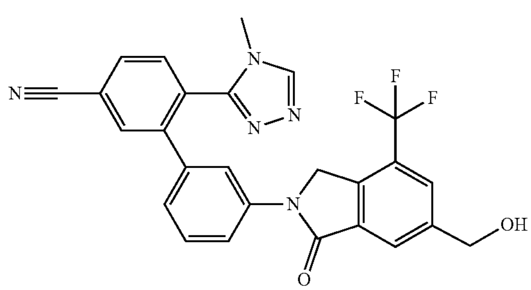 [SMILES: Cn1cnnc1-c1ccc(C#N)cc1-c1cccc(N2Cc3c(cc(CO)cc3C(F)(F)F)C2=O)c1] |

TABLE 1-continued
Selected Compounds
| Compound # | Compound ID | Structure |
|---|---|---|
| 136 | ADN-2 | 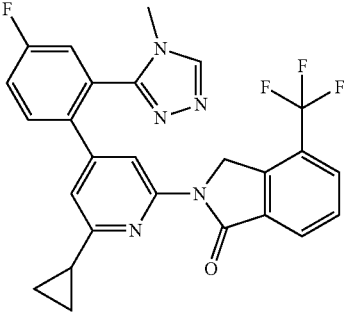 [SMILES: Cn1cnnc1-c1cc(F)ccc1-c1cc(C2CC2)nc(N2Cc3c(cccc3C(F)(F)F)C2=O)c1] |
| 137 | ADO-2 | 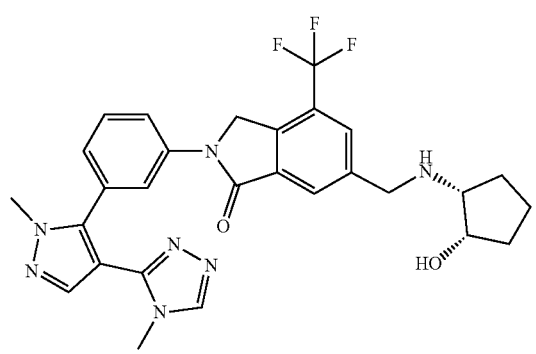 [SMILES: Cn1cnnc1-c1cnn(C)c1-c1cccc(N2Cc3c(cc(CN[C@@H]4CCC[C@@H]4O)cc3C(F)(F)F)C2=O)c1] |
| 138 | ADP-8 | 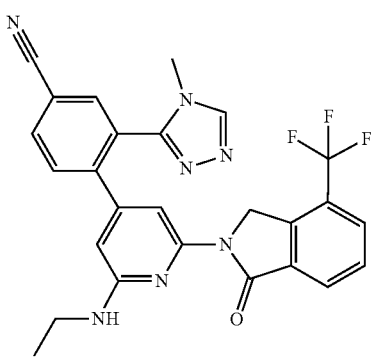 [SMILES: CCNc1cc(-c2ccc(C#N)cc2-c2nncn2C)cc(N2Cc3c(cccc3C(F)(F)F)C2=O)n1] |
| 139 | ADQ-2 | 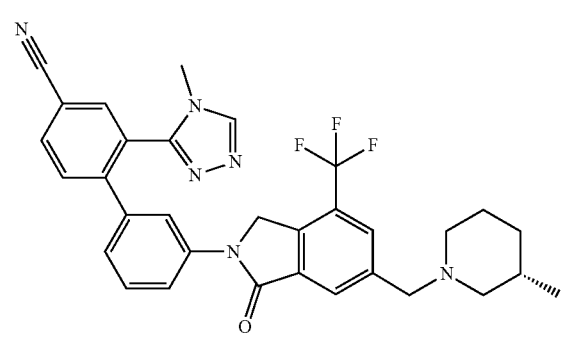 [SMILES: C[C@H]1CCCN(Cc2cc3c(c(C(F)(F)F)c2)CN(c2cccc(-c4ccc(C#N)cc4-c4nncn4C)c2)C3=O)C1] |

TABLE 1-continued

Selected Compounds

| Compound # | Compound ID | Structure |
|---|---|---|
| 140 | ADR-3 | 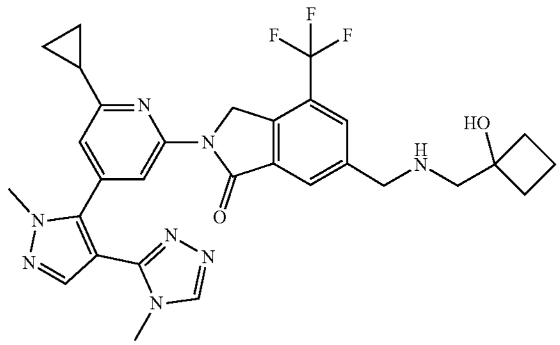 [SMILES: Cn1cnnc1-c1cnn(C)c1-c1cc(C2CC2)nc(N2Cc3c(cc(CNCC4(O)CCC4)cc3C(F)(F)F)C2=O)c1] |
| 141 | ADS-6 | 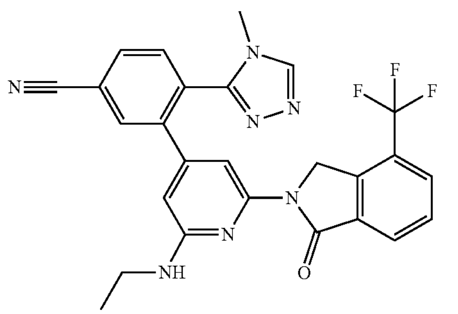 [SMILES: CCNc1cc(-c2cc(C#N)ccc2-c2nncn2C)cc(N2Cc3c(cccc3C(F)(F)F)C2=O)n1] |
| 142 | ADT-2 | 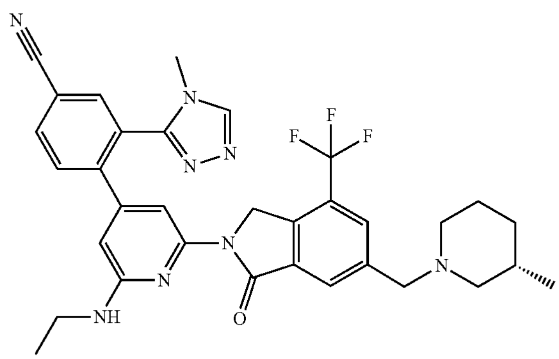 [SMILES: CCNc1cc(-c2ccc(C#N)cc2-c2nncn2C)cc(N2Cc3c(cc(CN4CCC[C@H](C)C4)cc3C(F)(F)F)C2=O)n1] |
| 143 | ADU-2 | 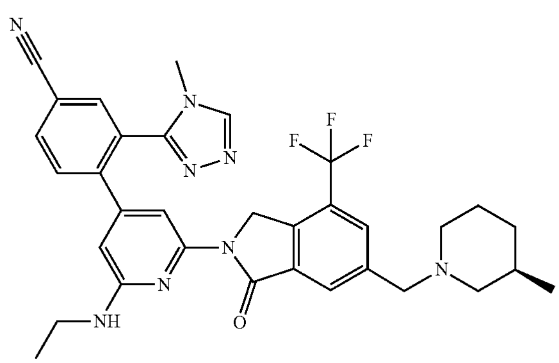 [SMILES: CCNc1cc(-c2ccc(C#N)cc2-c2nncn2C)cc(N2Cc3c(cc(CN4CCC[C@@H](C)C4)cc3C(F)(F)F)C2=O)n1] |

TABLE 1-continued
Selected Compounds
| Compound # | Compound ID | Structure |
|---|---|---|
| 144 | ADV-1 | 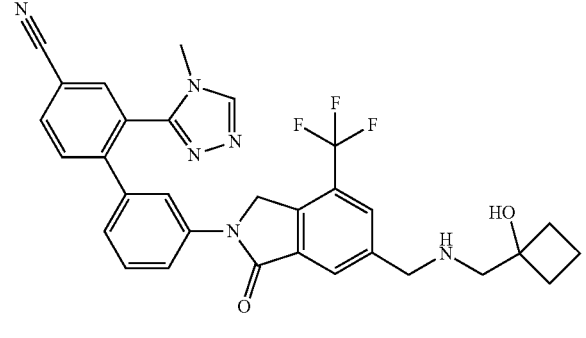 [SMILES: Cn1cnnc1-c1cc(C#N)ccc1-c1cccc(N2Cc3c(cc(CNCC4(O)CCC4)cc3C(F)(F)F)C2=O)c1] |
| 145 | ADW-5 | 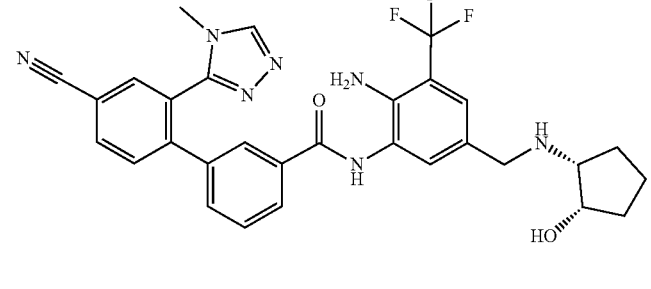 |
| 146 | ADX-2 | 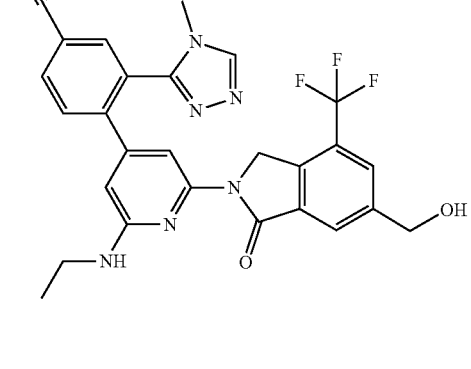 |
| 147 | ADY-2 | 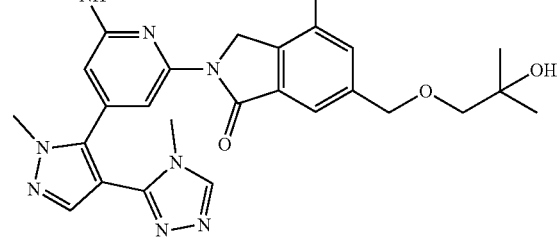 |

TABLE 1-continued
Selected Compounds
| Compound # | Compound ID | Structure |
|---|---|---|
| 148 | ADZ-2 | 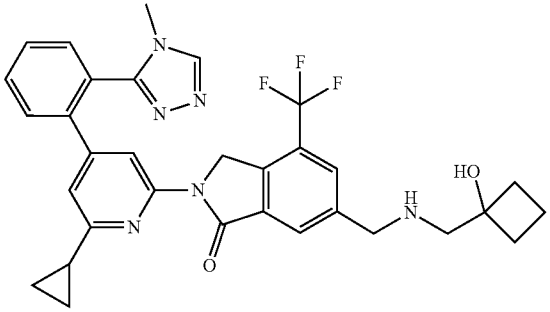 [SMILES: Cn1cnnc1-c1ccccc1-c1cc(C2CC2)nc(N2Cc3c(cc(CNCC4(O)CCC4)cc3C(F)(F)F)C2=O)c1] |
| 149 | AEA-2 | 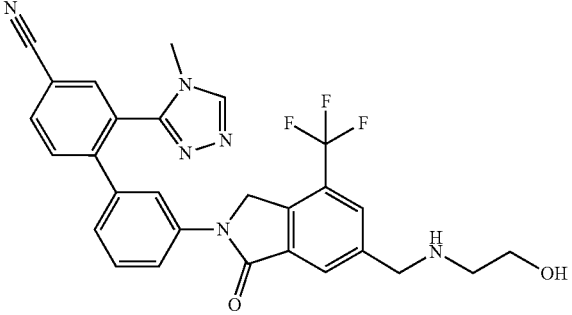 [SMILES: Cn1cnnc1-c1cc(C#N)ccc1-c1cccc(N2Cc3c(cc(CNCCO)cc3C(F)(F)F)C2=O)c1] |
| 150 | AEB-2 | 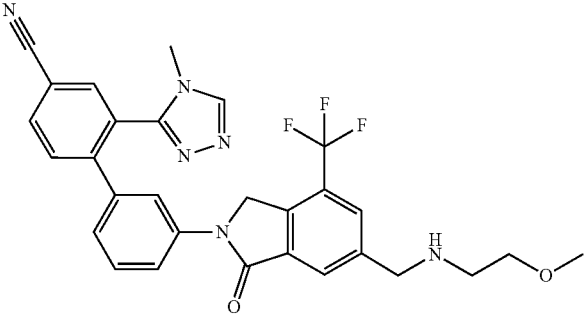 [SMILES: COCCNCc1cc2c(c(C(F)(F)F)c1)CN(c1cccc(-c3ccc(C#N)cc3-c3nncn3C)c1)C2=O] |
| 151 | AEC-2 | 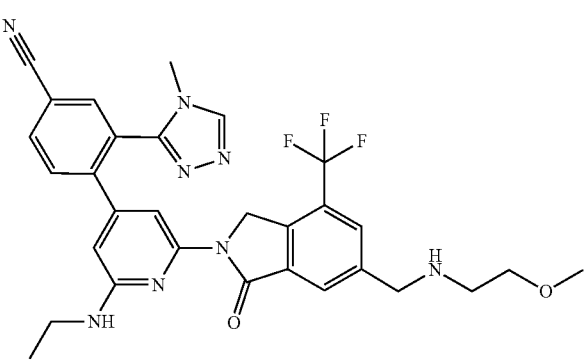 [SMILES: CCNc1cc(-c2ccc(C#N)cc2-c2nncn2C)cc(N2Cc3c(cc(CNCCOC)cc3C(F)(F)F)C2=O)n1] |

TABLE 1-continued
Selected Compounds
| Compound # | Compound ID | Structure |
|---|---|---|
| 152 | AED-2 | 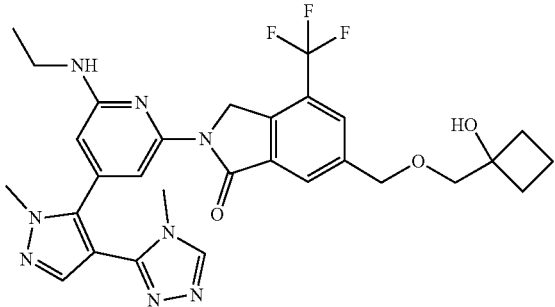 [SMILES: CCNc1cc(-c2c(-c3nncn3C)cnn2C)cc(N2Cc3c(cc(COCC4(O)CCC4)cc3C(F)(F)F)C2=O)n1] |
| 153 | AEE-2 | 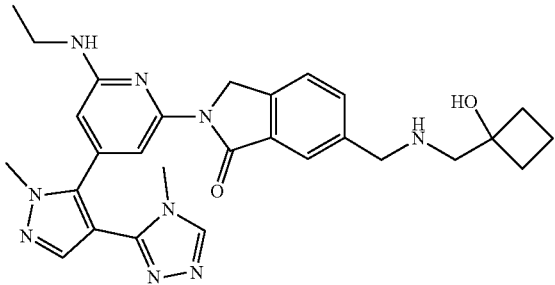 [SMILES: CCNc1cc(-c2c(-c3nncn3C)cnn2C)cc(N2Cc3ccc(CNCC4(O)CCC4)cc3C2=O)n1] |
| 154 | AEF-1 | 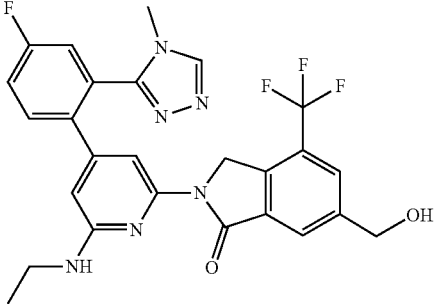 [SMILES: CCNc1cc(-c2ccc(F)cc2-c2nncn2C)cc(N2Cc3c(cc(CO)cc3C(F)(F)F)C2=O)n1] |
| 155 | AEG-3 | 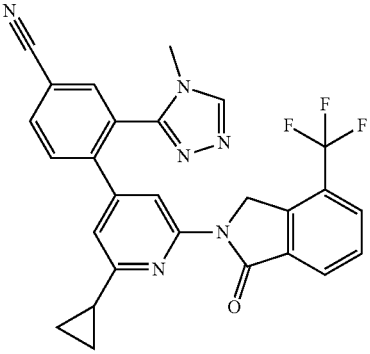 [SMILES: Cn1cnnc1-c1cc(C#N)ccc1-c1cc(C2CC2)nc(N2Cc3c(cccc3C(F)(F)F)C2=O)c1] |

TABLE 1-continued
Selected Compounds
| Compound # | Compound ID | Structure |
|---|---|---|
| 156 | AEH-1 | 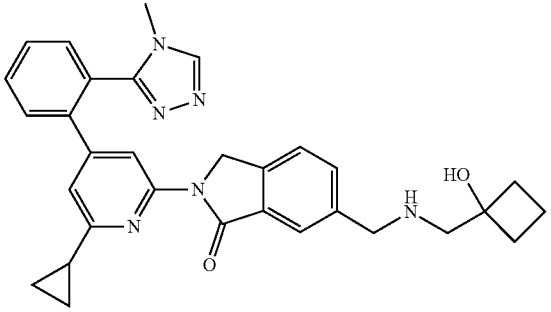 [SMILES: Cn1cnnc1-c1ccccc1-c1cc(C2CC2)nc(N2Cc3ccc(CNCC4(O)CCC4)cc3C2=O)c1] |
| 157 | AEI-5 | 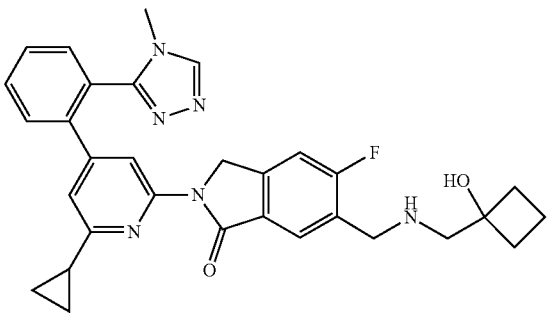 [SMILES: Cn1cnnc1-c1ccccc1-c1cc(C2CC2)nc(N2Cc3cc(F)c(CNCC4(O)CCC4)cc3C2=O)c1] |
| 158 | AEJ-3 | 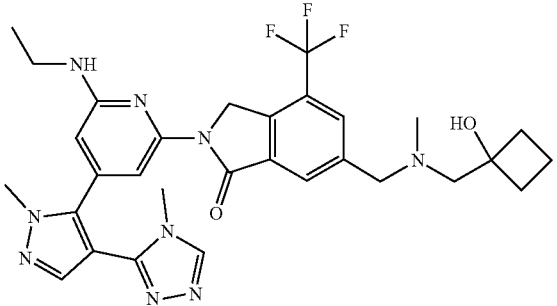 [SMILES: CCNc1cc(-c2c(-c3nncn3C)cnn2C)cc(N2Cc3c(cc(CN(C)CC4(O)CCC4)cc3C(F)(F)F)C2=O)n1] |
| 159 | AEK-3 | 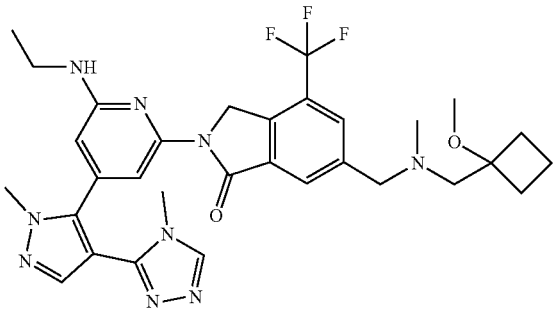 [SMILES: CCNc1cc(-c2c(-c3nncn3C)cnn2C)cc(N2Cc3c(cc(CN(C)CC4(OC)CCC4)cc3C(F)(F)F)C2=O)n1] |

TABLE 1-continued

Selected Compounds

| Compound # | Compound ID | Structure |
|---|---|---|
| 160 | AEL-2 | 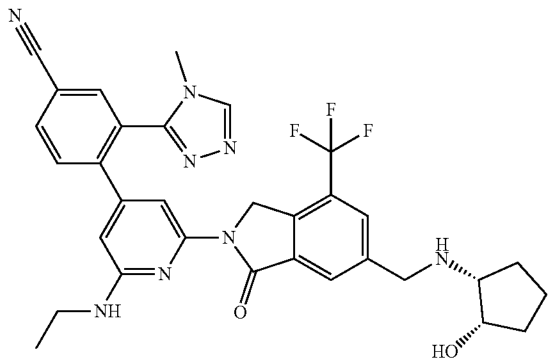 [SMILES: CCNc1cc(-c2ccc(C#N)cc2-c2nncn2C)cc(N2Cc3c(cc(CN[C@@H]4CCC[C@@H]4O)cc3C(F)(F)F)C2=O)n1] |
| 161 | AEM-9 | 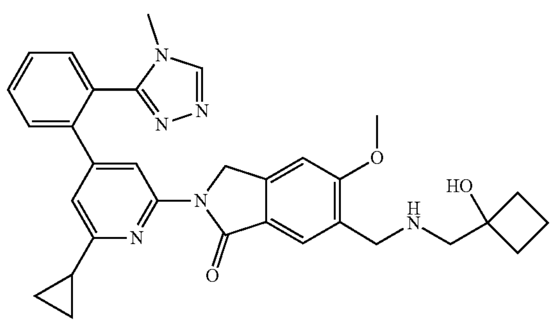 [SMILES: COc1cc2c(cc1CNCC1(O)CCC1)C(=O)N(c1cc(-c3ccccc3-c3nncn3C)cc(C3CC3)n1)C2] |
| 162 | AEN-1 | 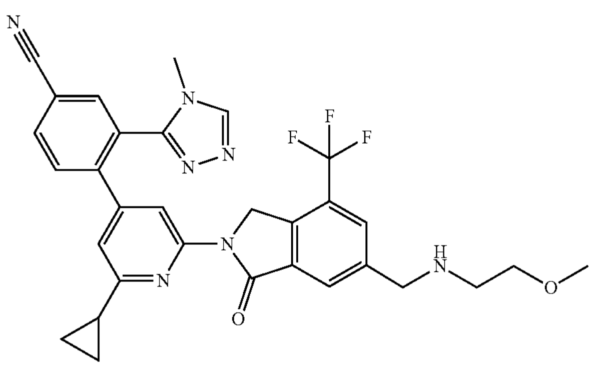 [SMILES: COCCNCc1cc2c(c(C(F)(F)F)c1)CN(c1cc(-c3ccc(C#N)cc3-c3nncn3C)cc(C3CC3)n1)C2=O] |
| 163 | AEO-2 | 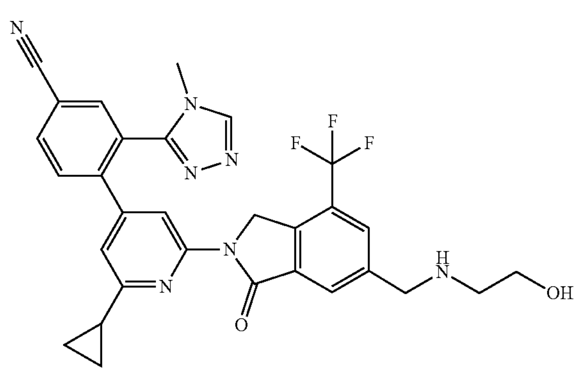 [SMILES: Cn1cnnc1-c1cc(C#N)ccc1-c1cc(C2CC2)nc(N2Cc3c(cc(CNCCO)cc3C(F)(F)F)C2=O)c1] |

TABLE 1-continued

Selected Compounds

| Compound # | Compound ID | Structure |
|---|---|---|
| 164 | AEP-2 | 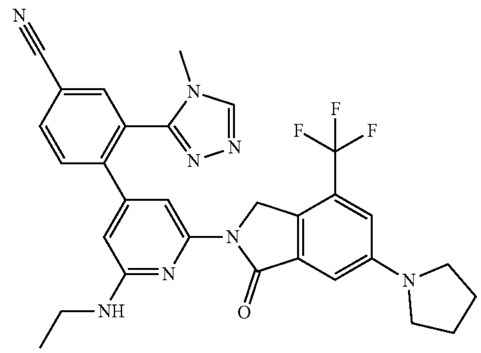 [SMILES: CCNc1cc(-c2ccc(C#N)cc2-c2nncn2C)cc(N2Cc3c(cc(N4CCCC4)cc3C(F)(F)F)C2=O)n1] |
| 165 | AEQ-3 | 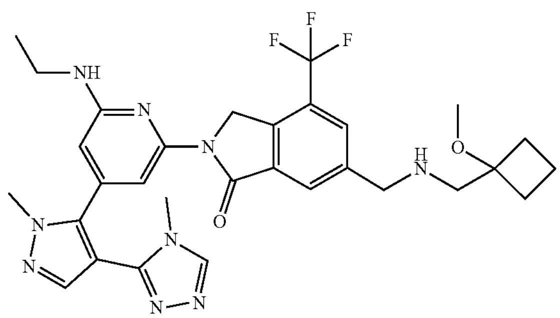 [SMILES: CCNc1cc(-c2c(-c3nncn3C)cnn2C)cc(N2Cc3c(cc(CNCC4(OC)CCC4)cc3C(F)(F)F)C2=O)n1] |
| 166 | AER-1 | 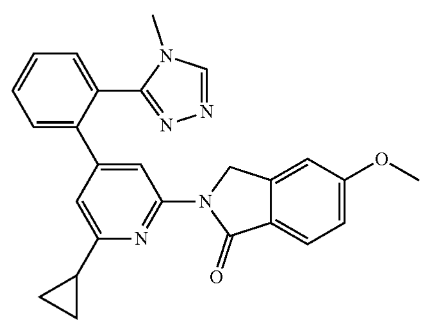 [SMILES: COc1ccc2c(c1)CN(c1cc(-c3ccccc3-c3nncn3C)cc(C3CC3)n1)C2=O] |
| 167 | AES-1 | 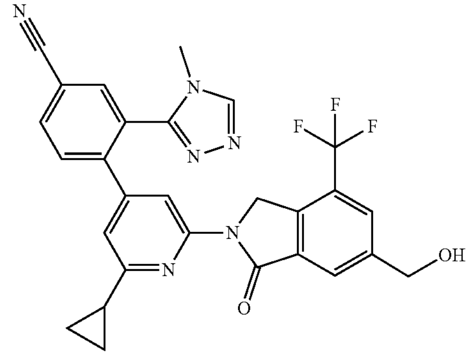 [SMILES: Cn1cnnc1-c1cc(C#N)ccc1-c1cc(C2CC2)nc(N2Cc3c(cc(CO)cc3C(F)(F)F)C2=O)c1] |

TABLE 1-continued

| Selected Compounds | | |
|---|---|---|
| Compound # | Compound ID | Structure |
| 168 | AET-6 | |
| 169 | AEU-8 | |
| 170 | AEV-3 | |
| 171 | AEW-2 | |

TABLE 1-continued

Selected Compounds

| Compound # | Compound ID | Structure |
|---|---|---|
| 172 | AEX-2 | 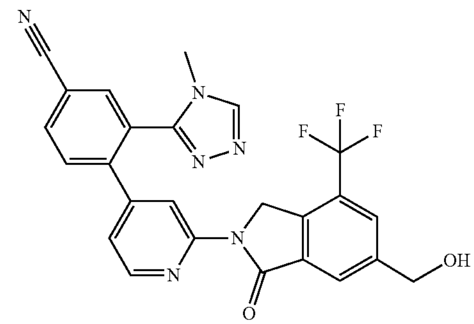 [SMILES: Cn1cnnc1-c1cc(C#N)ccc1-c1ccnc(N2Cc3c(cc(CO)cc3C(F)(F)F)C2=O)c1] |
| 173 | AEY-1 | 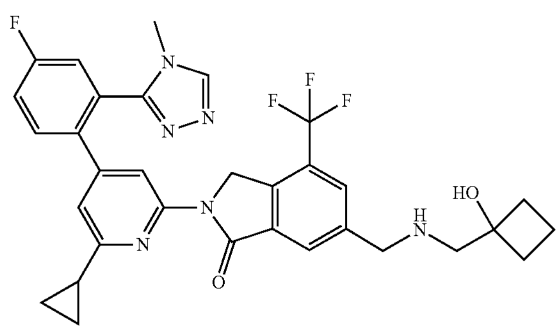 [SMILES: Cn1cnnc1-c1cc(F)ccc1-c1cc(C2CC2)nc(N2Cc3c(cc(CNCC4(O)CCC4)cc3C(F)(F)F)C2=O)c1] |
| 174 | AEZ-1 | 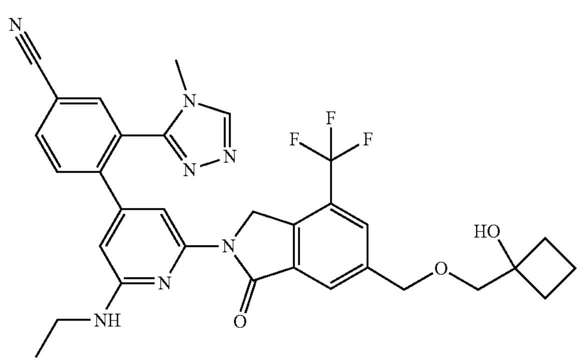 [SMILES: CCNc1cc(-c2ccc(C#N)cc2-c2nncn2C)cc(N2Cc3c(cc(COCC4(O)CCC4)cc3C(F)(F)F)C2=O)n1] |
| 175 | AFA-2 | 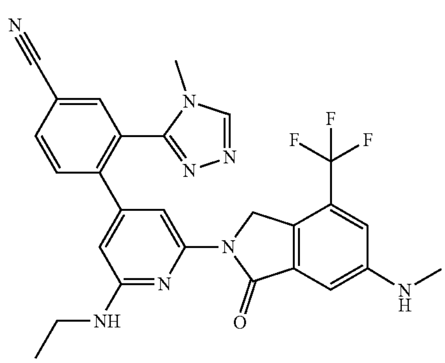 [SMILES: CCNc1cc(-c2ccc(C#N)cc2-c2nncn2C)cc(N2Cc3c(cc(NC)cc3C(F)(F)F)C2=O)n1] |

TABLE 1-continued

Selected Compounds

| Compound # | Compound ID | Structure |
|---|---|---|
| 176 | AFB-8 | 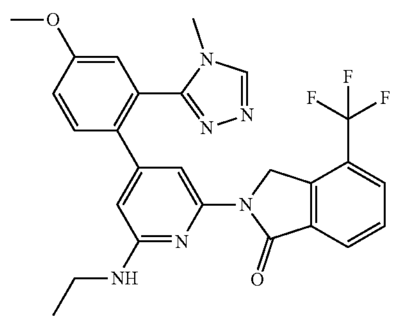 [SMILES: CCNc1cc(-c2ccc(OC)cc2-c2nncn2C)cc(N2Cc3c(cccc3C(F)(F)F)C2=O)n1] |
| 177 | AFD-1 | 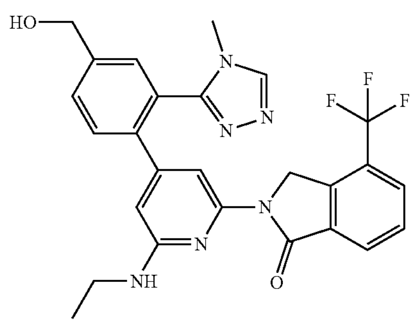 [SMILES: CCNc1cc(-c2ccc(CO)cc2-c2nncn2C)cc(N2Cc3c(cccc3C(F)(F)F)C2=O)n1] |
| 178 | AFE-1 | 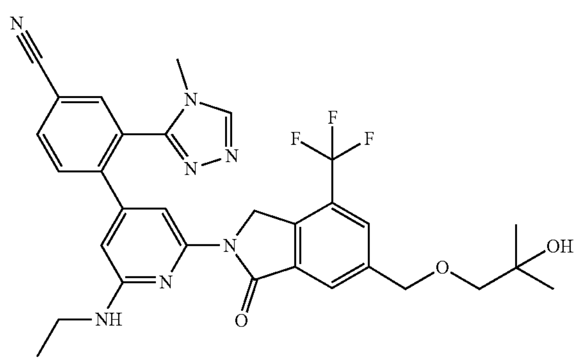 [SMILES: CCNc1cc(-c2ccc(C#N)cc2-c2nncn2C)cc(N2Cc3c(cc(COCC(C)(C)O)cc3C(F)(F)F)C2=O)n1] |
| 179 | AFF-2 | 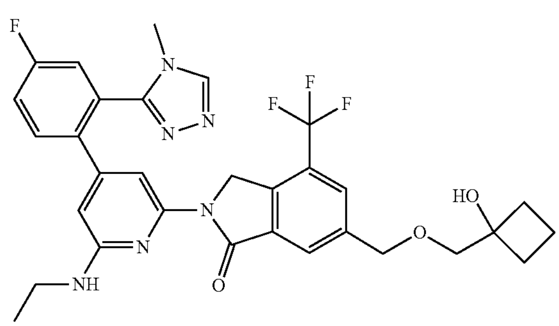 |

TABLE 1-continued
Selected Compounds
| Compound # | Compound ID | Structure |
|---|---|---|
| 180 | AFC-1 | 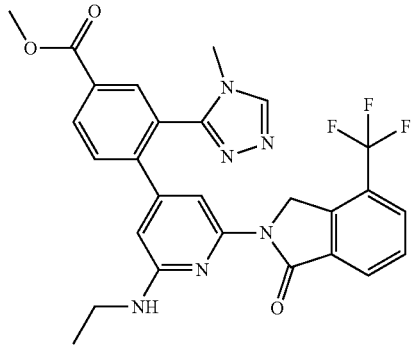 [SMILES: CCNc1cc(-c2ccc(C(=O)OC)cc2-c2nncn2C)cc(N2Cc3c(cccc3C(F)(F)F)C2=O)n1] |
| 181 | AFG-1 | 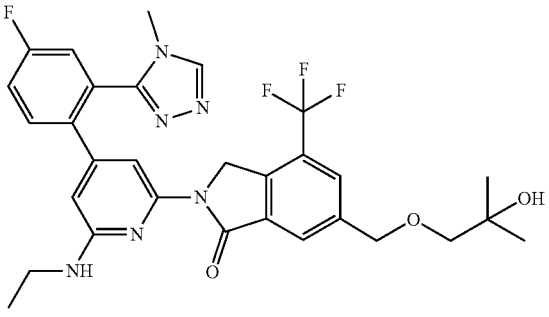 [SMILES: CCNc1cc(-c2ccc(F)cc2-c2nncn2C)cc(N2Cc3c(cc(COCC(C)(C)O)cc3C(F)(F)F)C2=O)n1] |
| 182 | AFH-1 | 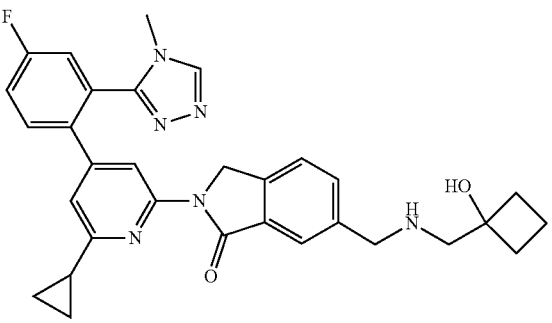 [SMILES: Cn1cnnc1-c1cc(F)ccc1-c1cc(C2CC2)nc(N2Cc3ccc(CNCC4(O)CCC4)cc3C2=O)c1] |
| 183 | AFI-1 | 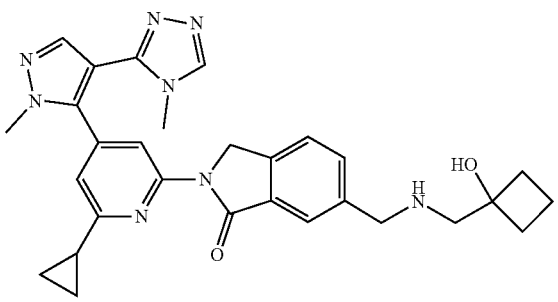 [SMILES: Cn1cnnc1-c1cnn(C)c1-c1cc(C2CC2)nc(N2Cc3ccc(CNCC4(O)CCC4)cc3C2=O)c1] |

TABLE 1-continued

Selected Compounds

| Compound # | Compound ID | Structure |
|---|---|---|
| 184 | AFJ-1 | 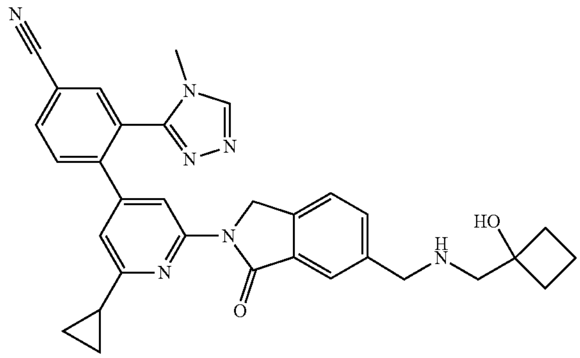 [SMILES: Cn1cnnc1-c1cc(C#N)ccc1-c1cc(C2CC2)nc(N2Cc3ccc(CNCC4(O)CCC4)cc3C2=O)c1] |
| 185 | AFK-1 | 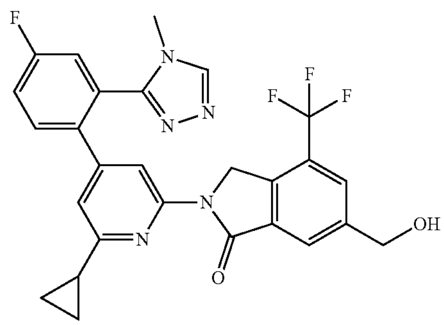 [SMILES: Cn1cnnc1-c1cc(F)ccc1-c1cc(C2CC2)nc(N2Cc3c(cc(CO)cc3C(F)(F)F)C2=O)c1] |
| 186 | AFL-2 | 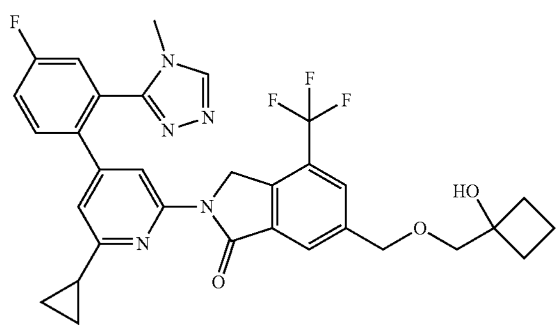 [SMILES: Cn1cnnc1-c1cc(F)ccc1-c1cc(C2CC2)nc(N2Cc3c(cc(COCC4(O)CCC4)cc3C(F)(F)F)C2=O)c1] |
| 187 | AFM-2 | 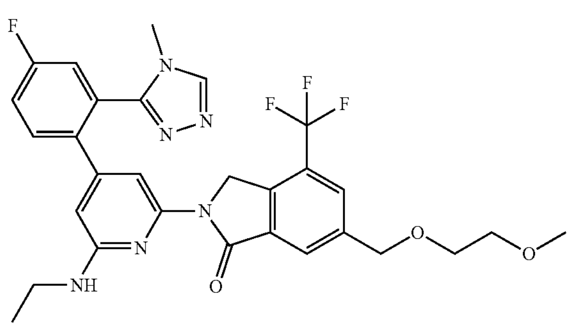 [SMILES: CCNc1cc(-c2ccc(F)cc2-c2nncn2C)cc(N2Cc3c(cc(COCCOC)cc3C(F)(F)F)C2=O)n1] |

TABLE 1-continued
Selected Compounds
| Compound # | Compound ID | Structure |
|---|---|---|
| 188 | AFN-3 | 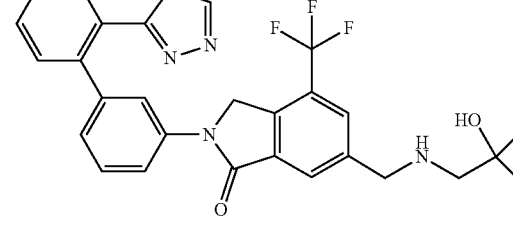 |
| 189 | AFO-2 | 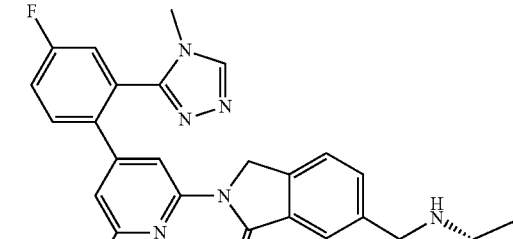 |
| 190 | AFP-2 | 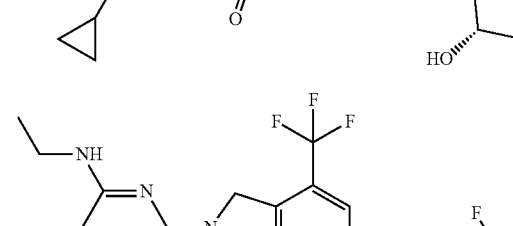 |
| 191 | AFQ-3 | 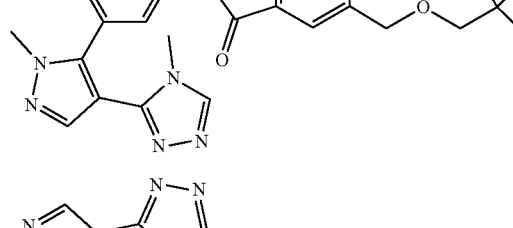 |
| 192 | AFT-2 | 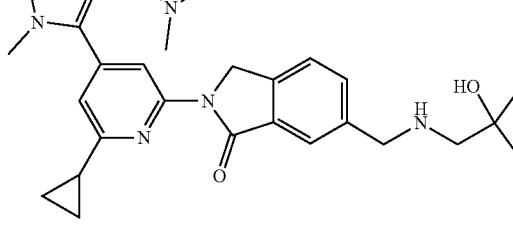 |

TABLE 1-continued

Selected Compounds

| Compound # | Compound ID | Structure |
|---|---|---|
| 193 | AFU-1 | 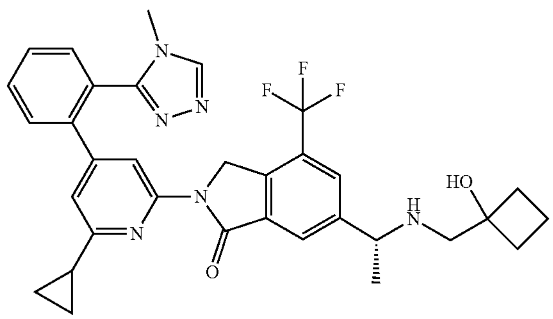 [SMILES: C[C@@H](NCC1(O)CCC1)c1cc2c(c(C(F)(F)F)c1)CN(c1cc(-c3ccccc3-c3nncn3C)cc(C3CC3)n1)C2=O] |
| 194 | AFV-3 | 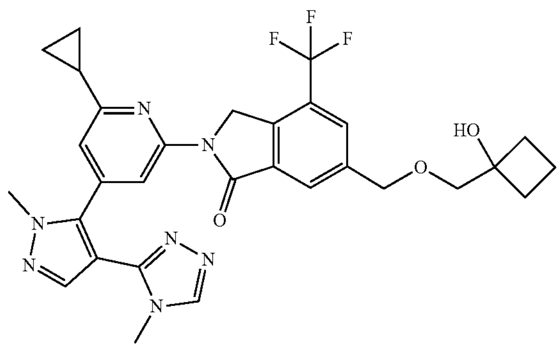 [SMILES: Cn1cnnc1-c1cnn(C)c1-c1cc(C2CC2)nc(N2Cc3c(cc(COCC4(O)CCC4)cc3C(F)(F)F)C2=O)c1] |
| 195 | AFX-1 | 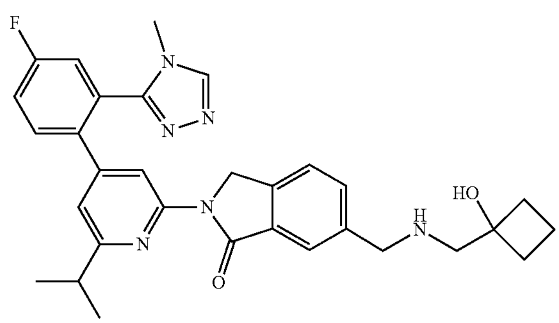 [SMILES: CC(C)c1cc(-c2ccc(F)cc2-c2nncn2C)cc(N2Cc3ccc(CNCC4(O)CCC4)cc3C2=O)n1] |
| 196 | AFZ-1 | 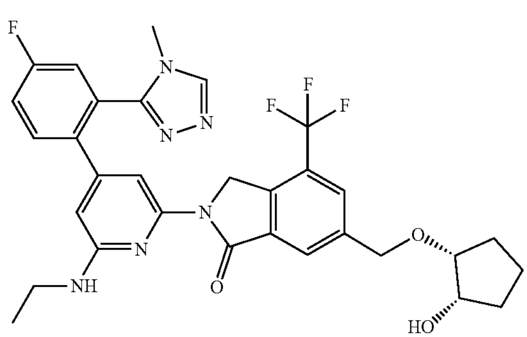 [SMILES: CCNc1cc(-c2ccc(F)cc2-c2nncn2C)cc(N2Cc3c(cc(CO[C@@H]4CCC[C@@H]4O)cc3C(F)(F)F)C2=O)n1] |

TABLE 1-continued

Selected Compounds

| Compound # | Compound ID | Structure |
|---|---|---|
| 197 | AGA-1 | 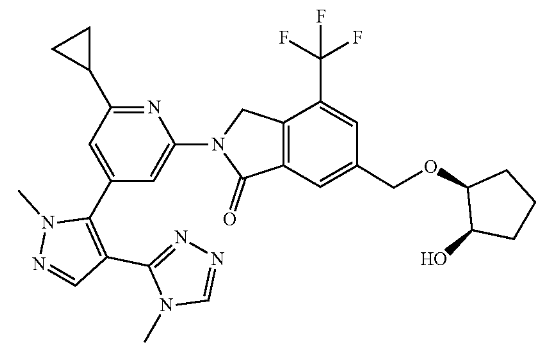 [SMILES: Cn1cnnc1-c1cnn(C)c1-c1cc(C2CC2)nc(N2Cc3c(cc(CO[C@H]4CCC[C@H]4O)cc3C(F)(F)F)C2=O)c1] |
| 198 | AGB-1 | 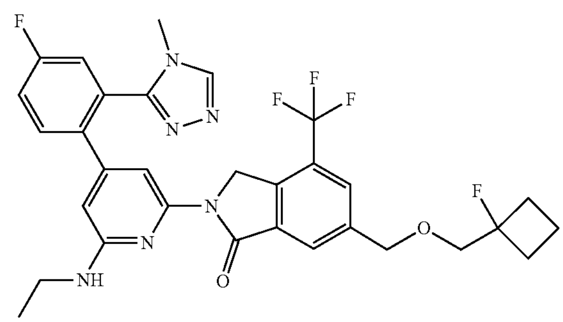 [SMILES: CCNc1cc(-c2ccc(F)cc2-c2nncn2C)cc(N2Cc3c(cc(COCC4(F)CCC4)cc3C(F)(F)F)C2=O)n1] |
| 199 | AFW-3 | 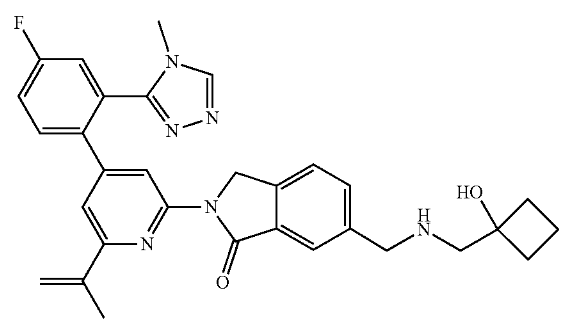 [SMILES: C=C(C)c1cc(-c2ccc(F)cc2-c2nncn2C)cc(N2Cc3ccc(CNCC4(O)CCC4)cc3C2=O)n1] |
| 200 | AGC-5 | 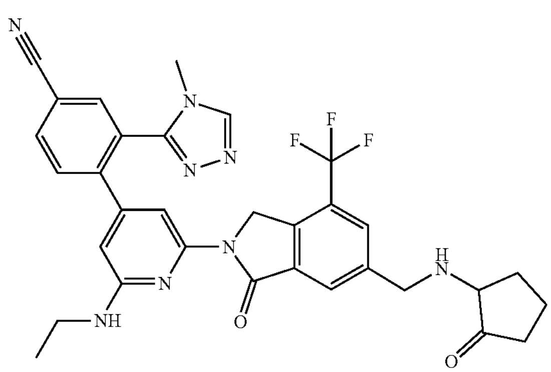 [SMILES: CCNc1cc(-c2ccc(C#N)cc2-c2nncn2C)cc(N2Cc3c(cc(CNC4CCCC4=O)cc3C(F)(F)F)C2=O)n1] |

TABLE 1-continued

Selected Compounds

| Compound # | Compound ID | Structure |
|---|---|---|
| 201 | AFS-1 | 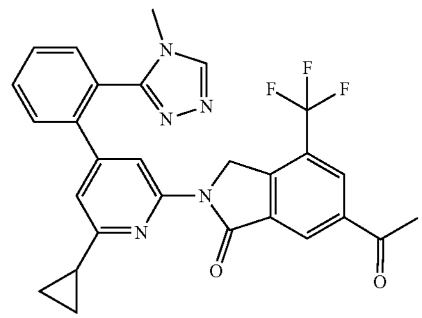 [SMILES: CC(=O)c1cc2c(c(C(F)(F)F)c1)CN(c1cc(-c3ccccc3-c3nncn3C)cc(C3CC3)n1)C2=O] |
| 202 | AFY-1 | 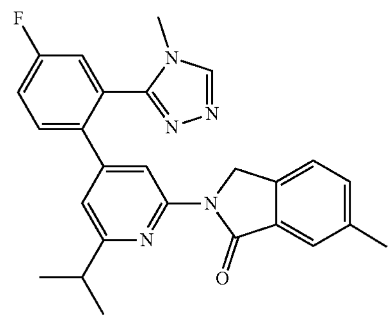 [SMILES: Cc1ccc2c(c1)C(=O)N(c1cc(-c3ccc(F)cc3-c3nncn3C)cc(C(C)C)n1)C2] |
| 203 | AGD-2 | 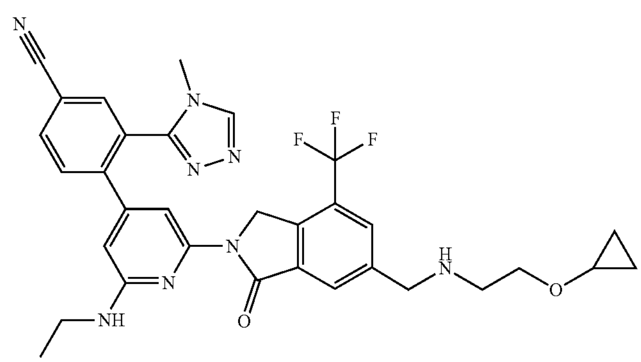 [SMILES: CCNc1cc(-c2ccc(C#N)cc2-c2nncn2C)cc(N2Cc3c(cc(CNCCOC4CC4)cc3C(F)(F)F)C2=O)n1] |
| 204 | AGE-3 | 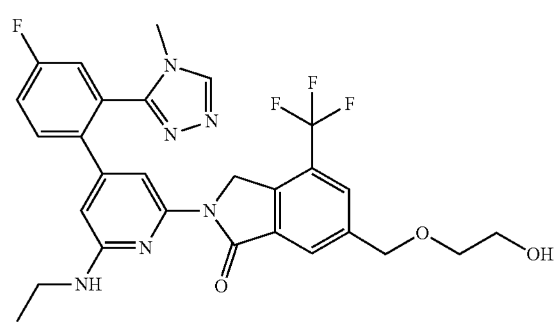 [SMILES: CCNc1cc(-c2ccc(F)cc2-c2nncn2C)cc(N2Cc3c(cc(COCCO)cc3C(F)(F)F)C2=O)n1] |

TABLE 1-continued
Selected Compounds
| Compound # | Compound ID | Structure |
|---|---|---|
| 205 | AGF-3 | 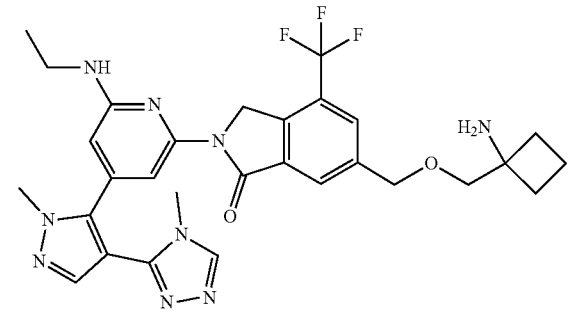 [SMILES: CCNc1cc(-c2c(-c3nncn3C)cnn2C)cc(N2Cc3c(cc(COCC4(N)CCC4)cc3C(F)(F)F)C2=O)n1] |
| 206 | AGG-2 | 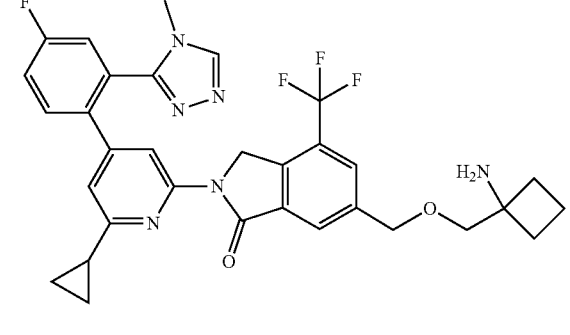 |
| 207 | AGI-3 | 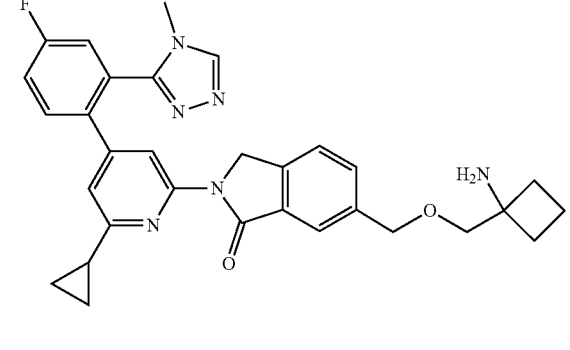 |
| 208 | AGH-2 | 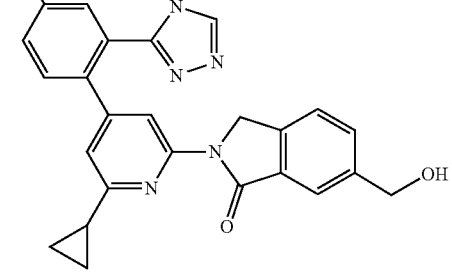 |

TABLE 1-continued

Selected Compounds

| Compound # | Compound ID | Structure |
|---|---|---|
| 209 | AFR-7 | 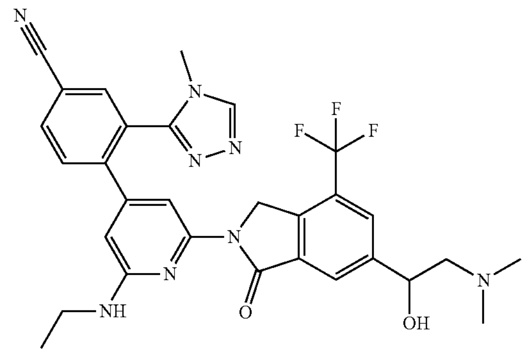 [SMILES: CCNc1cc(-c2ccc(C#N)cc2-c2nncn2C)cc(N2Cc3c(cc(C(O)CN(C)C)cc3C(F)(F)F)C2=O)n1] |
| 210 | AGJ-2 | 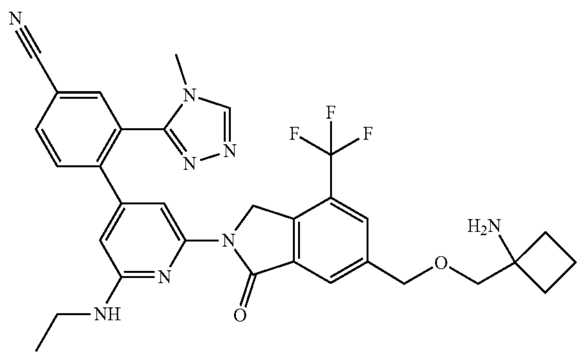 [SMILES: CCNc1cc(-c2ccc(C#N)cc2-c2nncn2C)cc(N2Cc3c(cc(COCC4(N)CCC4)cc3C(F)(F)F)C2=O)n1] |
| 211 | AGK-1 | 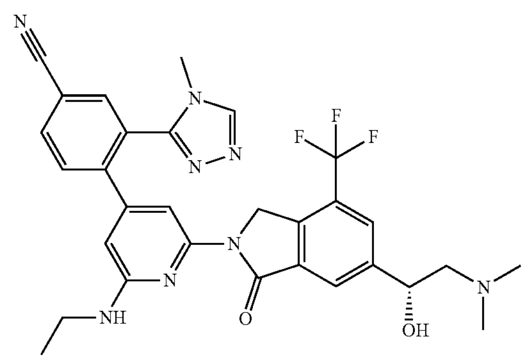 [SMILES: CCNc1cc(-c2ccc(C#N)cc2-c2nncn2C)cc(N2Cc3c(cc([C@@H](O)CN(C)C)cc3C(F)(F)F)C2=O)n1] |
| 212 | AGL-1 | 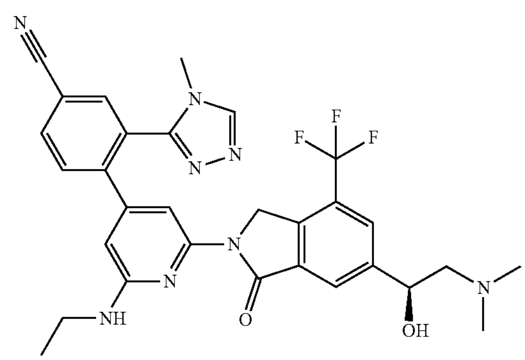 [SMILES: CCNc1cc(-c2ccc(C#N)cc2-c2nncn2C)cc(N2Cc3c(cc([C@H](O)CN(C)C)cc3C(F)(F)F)C2=O)n1] |

TABLE 1-continued
Selected Compounds
| Compound # | Compound ID | Structure |
|---|---|---|
| 213 | AGM-5 | 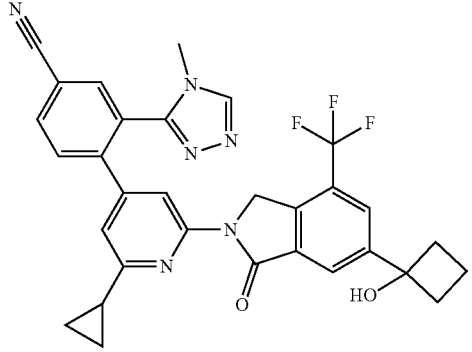 [SMILES: Cn1cnnc1-c1cc(C#N)ccc1-c1cc(C2CC2)nc(N2Cc3c(cc(C4(O)CCC4)cc3C(F)(F)F)C2=O)c1] |
| 214 | AGN-3 | 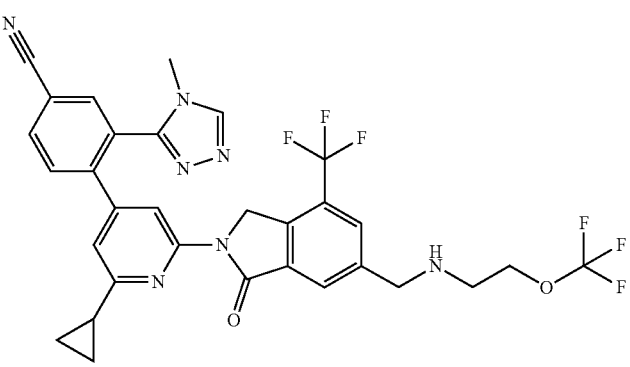 [SMILES: Cn1cnnc1-c1cc(C#N)ccc1-c1cc(C2CC2)nc(N2Cc3c(cc(CNCCOC(F)(F)F)cc3C(F)(F)F)C2=O)c1] |
| 215 | AGO-2 | 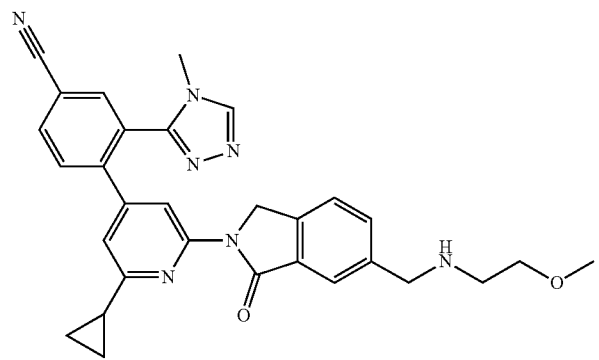 [SMILES: COCCNCc1ccc2c(c1)C(=O)N(c1cc(-c3ccc(C#N)cc3-c3nncn3C)cc(C3CC3)n1)C2] |
| 216 | AGP-1 | 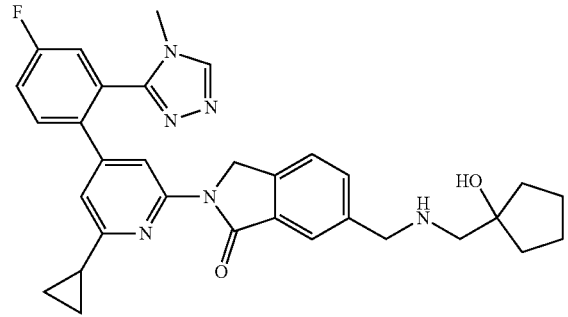 [SMILES: Cn1cnnc1-c1cc(F)ccc1-c1cc(C2CC2)nc(N2Cc3ccc(CNCC4(O)CCCC4)cc3C2=O)c1] |

TABLE 1-continued
Selected Compounds
| Compound # | Compound ID | Structure |
|---|---|---|
| 217 | AGQ-2 | 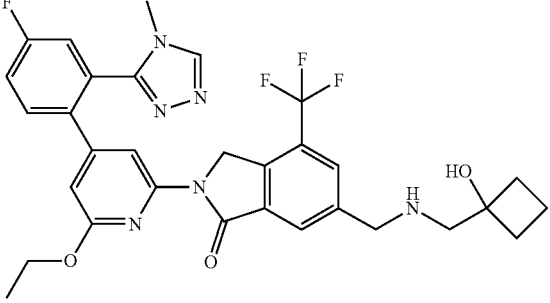 |
| 218 | AGR-1 | 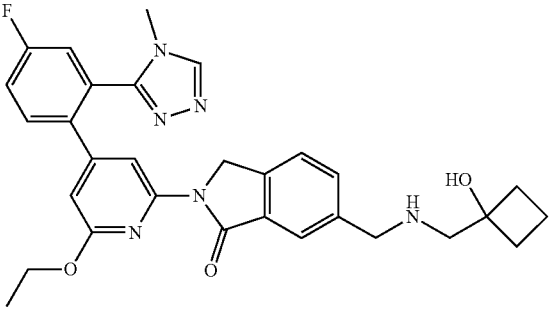 [SMILES: CCOc1cc(-c2ccc(F)cc2-c2nncn2C)cc(N2Cc3ccc(CNCC4(O)CCC4)cc3C2=O)n1] |
| 219 | AGS-2 | 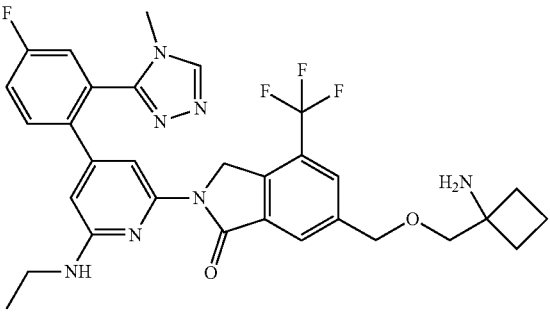 [SMILES: CCNc1cc(-c2ccc(F)cc2-c2nncn2C)cc(N2Cc3c(cc(COCC4(N)CCC4)cc3C(F)(F)F)C2=O)n1] |
| 220 | AGT-3 | 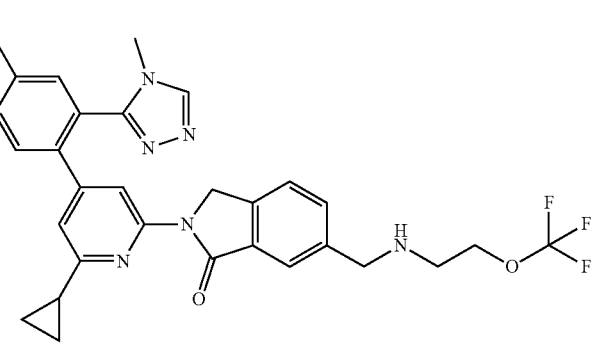 |

TABLE 1-continued
| Selected Compounds | | |
|---|---|---|
| Compound # | Compound ID | Structure |
| 221 | AGU-10 | 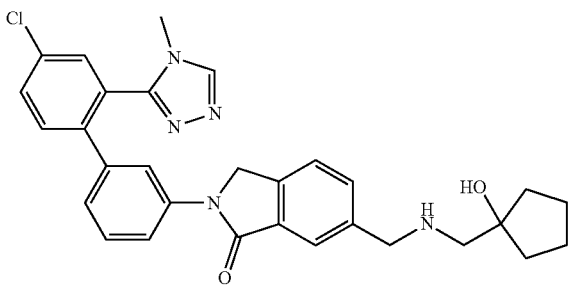 [SMILES: Cn1cnnc1-c1cc(Cl)ccc1-c1cccc(N2Cc3ccc(CNCC4(O)CCCC4)cc3C2=O)c1] |
| 222 | AGV-1 | 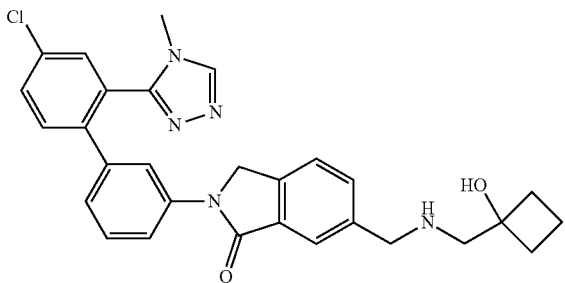 [SMILES: Cn1cnnc1-c1cc(Cl)ccc1-c1cccc(N2Cc3ccc(CNCC4(O)CCC4)cc3C2=O)c1] |
| 223 | AGW-6 | 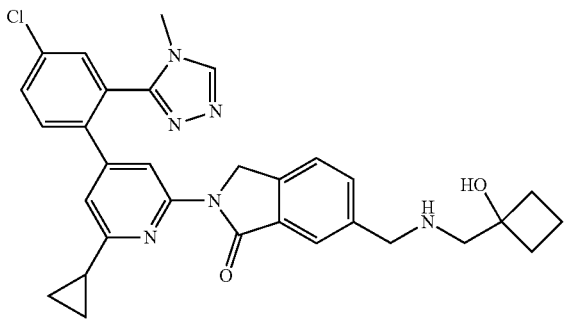 [SMILES: Cn1cnnc1-c1cc(Cl)ccc1-c1cc(C2CC2)nc(N2Cc3ccc(CNCC4(O)CCC4)cc3C2=O)c1] |
| 224 | AGX-8 | 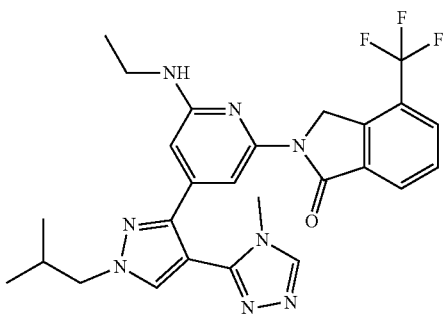 [SMILES: CCNc1cc(-c2nn(CC(C)C)cc2-c2nncn2C)cc(N2Cc3c(cccc3C(F)(F)F)C2=O)n1] |

TABLE 1-continued

Selected Compounds

| Compound # | Compound ID | Structure |
|---|---|---|
| 225 | AGZ-1 | 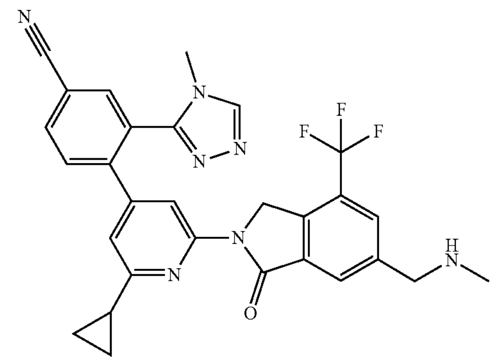 [SMILES: CNCc1cc2c(c(C(F)(F)F)c1)CN(c1cc(-c3ccc(C#N)cc3-c3nncn3C)cc(C3CC3)n1)C2=O] |
| 226 | AHA-2 | 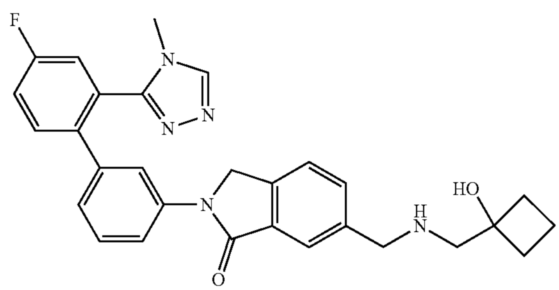 [SMILES: Cn1cnnc1-c1cc(F)ccc1-c1cccc(N2Cc3ccc(CNCC4(O)CCC4)cc3C2=O)c1] |
| 227 | AHB-1 | 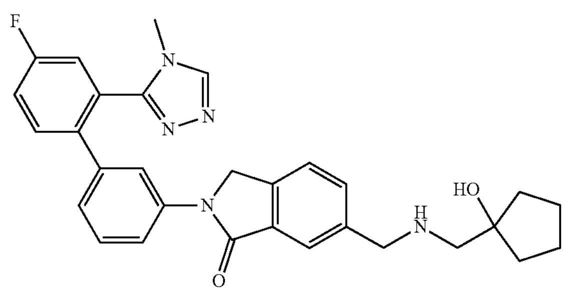 [SMILES: Cn1cnnc1-c1cc(F)ccc1-c1cccc(N2Cc3ccc(CNCC4(O)CCCC4)cc3C2=O)c1] |
| 228 | AHC-1 | 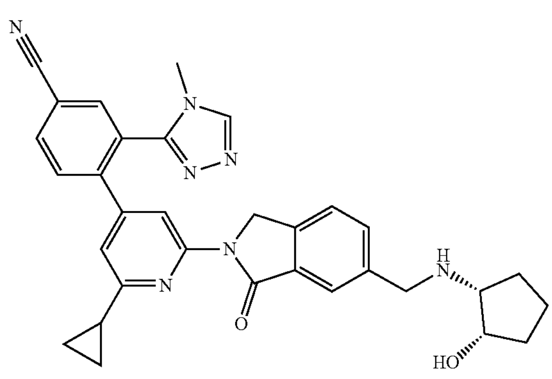 [SMILES: Cn1cnnc1-c1cc(C#N)ccc1-c1cc(C2CC2)nc(N2Cc3ccc(CN[C@@H]4CCC[C@@H]4O)cc3C2=O)c1] |

TABLE 1-continued

| Selected Compounds | | |
|---|---|---|
| Compound # | Compound ID | Structure |
| 229 | AGY-3 | |
| 230 | AHD-9 | |
| 231 | AHE-4 | |
| 232 | AHF-4 | |

TABLE 1-continued

Selected Compounds

| Compound # | Compound ID | Structure |
|---|---|---|
| 233 | AHG-2 | 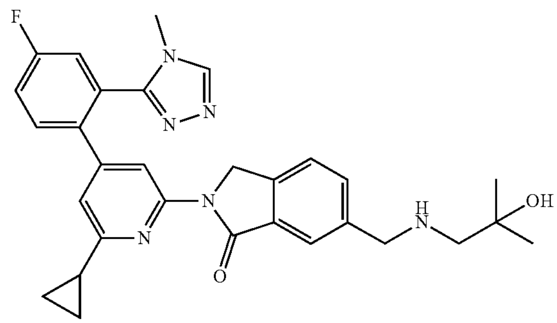 [SMILES: Cn1cnnc1-c1cc(F)ccc1-c1cc(C2CC2)nc(N2Cc3ccc(CNCC(C)(C)O)cc3C2=O)c1] |
| 234 | AHH-3 | 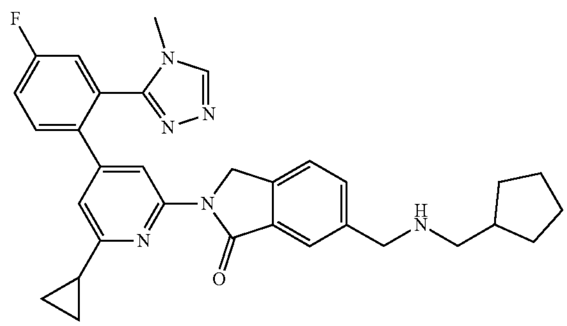 [SMILES: Cn1cnnc1-c1cc(F)ccc1-c1cc(C2CC2)nc(N2Cc3ccc(CNCC4CCCC4)cc3C2=O)c1] |
| 235 | AHI-4 | 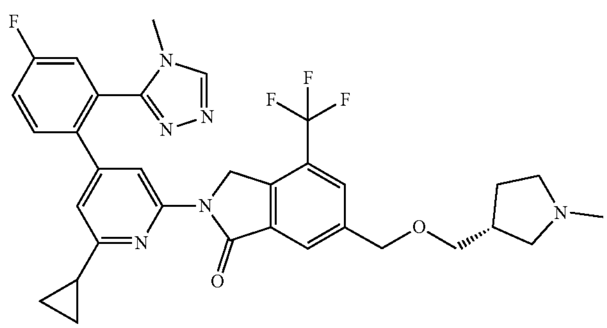 [SMILES: CN1CC[C@@H](COCc2cc3c(c(C(F)(F)F)c2)CN(c2cc(-c4ccc(F)cc4-c4nncn4C)cc(C4CC4)n2)C3=O)C1] |
| 236 | AHN-9 | 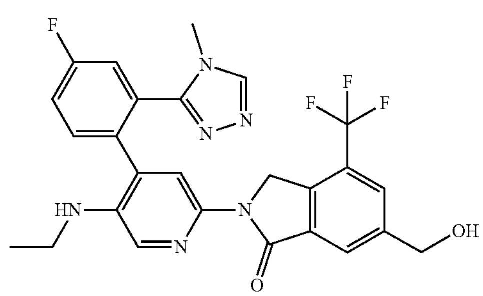 [SMILES: CCNc1cnc(N2Cc3c(cc(CO)cc3C(F)(F)F)C2=O)cc1-c1ccc(F)cc1-c1nncn1C] |

TABLE 1-continued

Selected Compounds

| Compound # | Compound ID | Structure |
|---|---|---|
| 237 | AHO-4 | 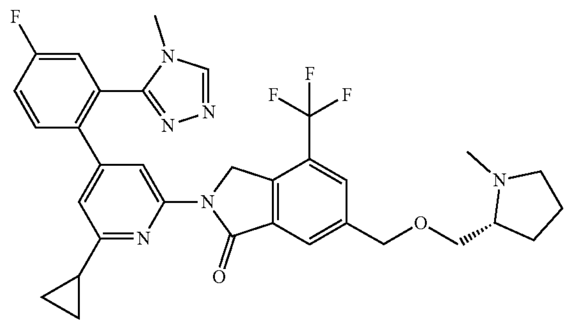 [SMILES: CN1CCC[C@@H]1COCc1cc2c(c(C(F)(F)F)c1)CN(c1cc(-c3ccc(F)cc3-c3nncn3C)cc(C3CC3)n1)C2=O] |
| 238 | AHP-1 | 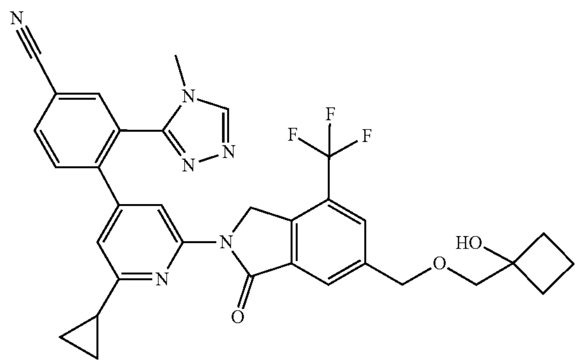 [SMILES: Cn1cnnc1-c1cc(C#N)ccc1-c1cc(C2CC2)nc(N2Cc3c(cc(COCC4(O)CCC4)cc3C(F)(F)F)C2=O)c1] |
| 239 | AHV-1 | 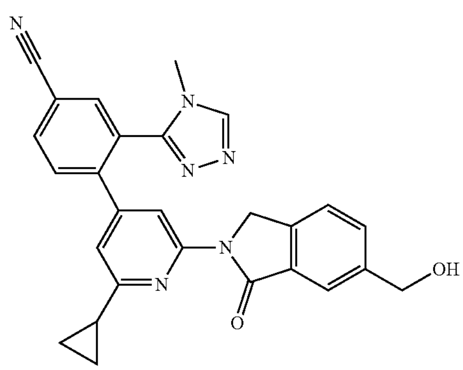 [SMILES: Cn1cnnc1-c1cc(C#N)ccc1-c1cc(C2CC2)nc(N2Cc3ccc(CO)cc3C2=O)c1] |
| 240 | AHW-1 | 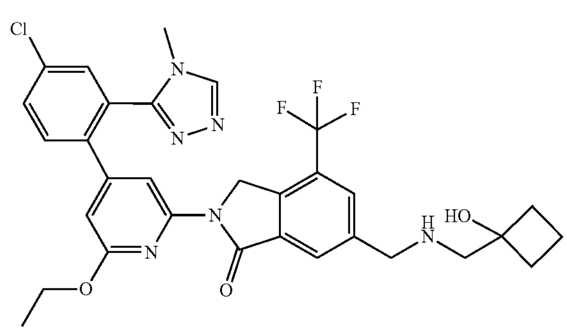 [SMILES: CCOc1cc(-c2ccc(Cl)cc2-c2nncn2C)cc(N2Cc3c(cc(CNCC4(O)CCC4)cc3C(F)(F)F)C2=O)n1] |

TABLE 1-continued
Selected Compounds
| Compound # | Compound ID | Structure |
|---|---|---|
| 241 | AHX-2 | 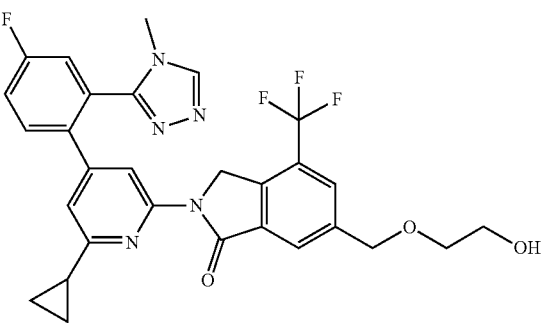 [SMILES: Cn1cnnc1-c1cc(F)ccc1-c1cc(C2CC2)nc(N2Cc3c(cc(COCCO)cc3C(F)(F)F)C2=O)c1] |
| 242 | AHQ-4 | 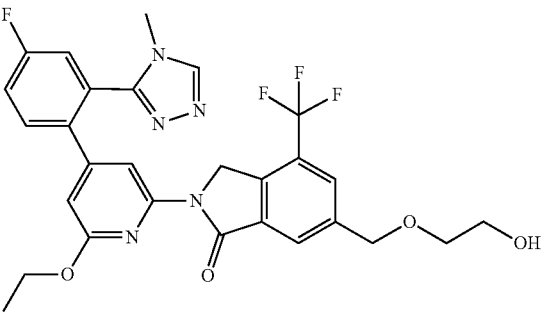 [SMILES: CCOc1cc(-c2ccc(F)cc2-c2nncn2C)cc(N2Cc3c(cc(COCCO)cc3C(F)(F)F)C2=O)n1] |
| 243 | AHR-4 | 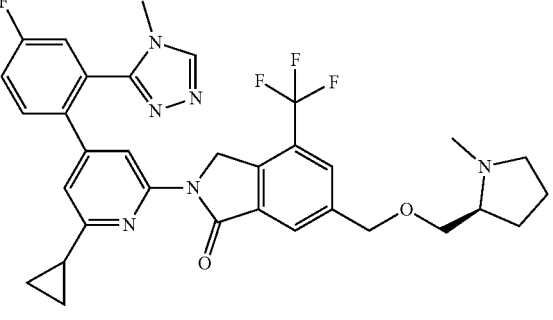 |
| 244 | AHY-5 | 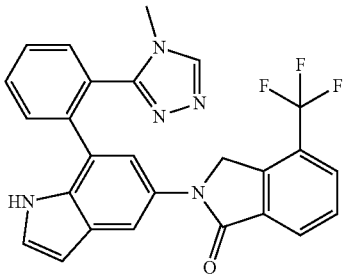 [SMILES: Cn1cnnc1-c1ccccc1-c1cc(N2Cc3c(cccc3C(F)(F)F)C2=O)cc2cc[nH]c12] |

TABLE 1-continued

Selected Compounds

| Compound # | Compound ID | Structure |
|---|---|---|
| 245 | AII-9 | 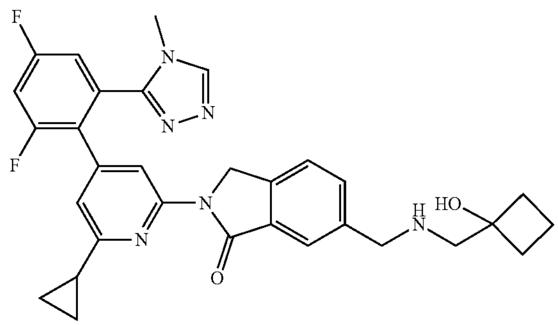 [SMILES: Cn1cnnc1-c1cc(F)cc(F)c1-c1cc(C2CC2)nc(N2Cc3ccc(CNCC4(O)CCC4)cc3C2=O)c1] |
| 246 | AIL-3 | 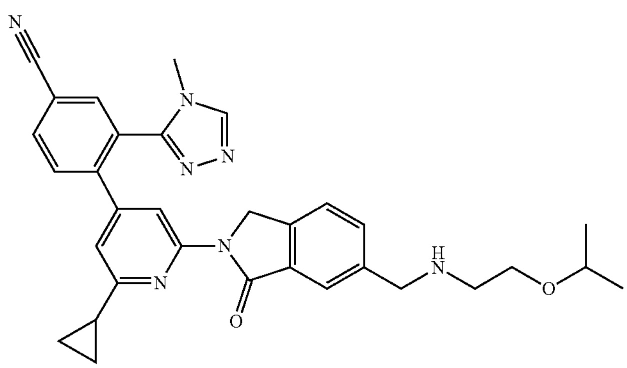 [SMILES: CC(C)OCCNCc1ccc2c(c1)C(=O)N(c1cc(-c3ccc(C#N)cc3-c3nncn3C)cc(C3CC3)n1)C2] |
| 247 | AHS-2 | 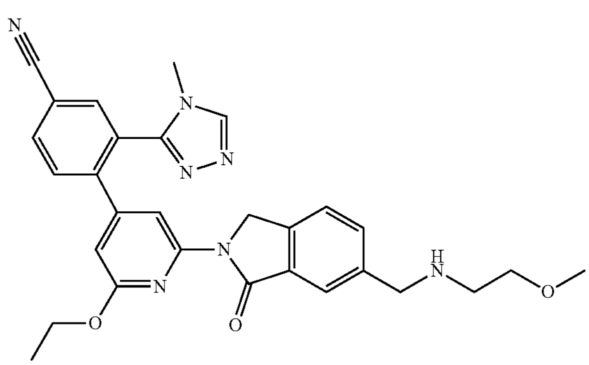 [SMILES: CCOc1cc(-c2ccc(C#N)cc2-c2nncn2C)cc(N2Cc3ccc(CNCCOC)cc3C2=O)n1] |
| 248 | AHT-2 | 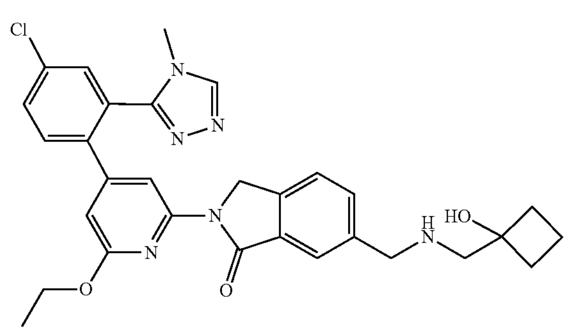 [SMILES: CCOc1cc(-c2ccc(Cl)cc2-c2nncn2C)cc(N2Cc3ccc(CNCC4(O)CCC4)cc3C2=O)n1] |

TABLE 1-continued

Selected Compounds

| Compound # | Compound ID | Structure |
|---|---|---|
| 249 | AHU-12 | 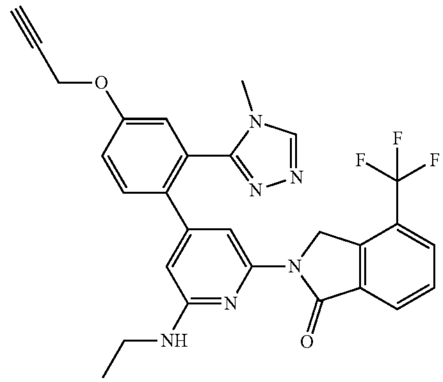 [SMILES: C#CCOc1ccc(-c2cc(NCC)nc(N3Cc4c(cccc4C(F)(F)F)C3=O)c2)c(-c2nncn2C)c1] |
| 250 | AIJ-2 | 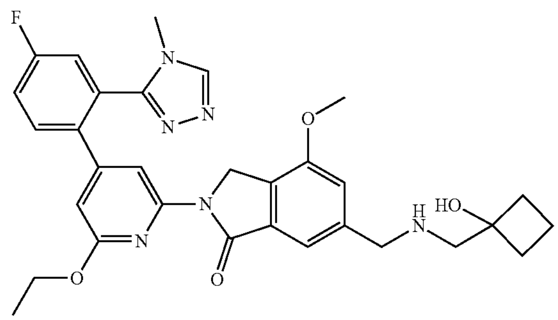 [SMILES: CCOc1cc(-c2ccc(F)cc2-c2nncn2C)cc(N2Cc3c(OC)cc(CNCC4(O)CCC4)cc3C2=O)n1] |
| 251 | AHZ-2 | 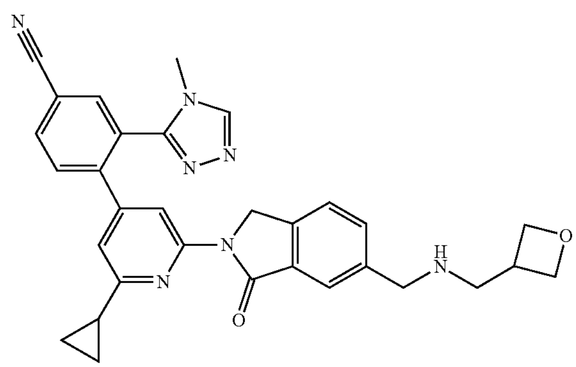 [SMILES: Cn1cnnc1-c1cc(C#N)ccc1-c1cc(C2CC2)nc(N2Cc3ccc(CNCC4COC4)cc3C2=O)c1] |
| 252 | AIA-2 | 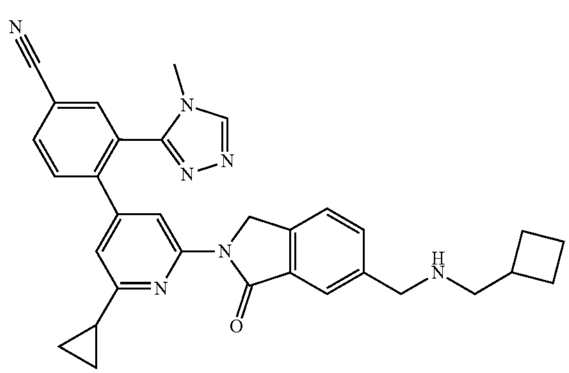 [SMILES: Cn1cnnc1-c1cc(C#N)ccc1-c1cc(C2CC2)nc(N2Cc3ccc(CNCC4CCC4)cc3C2=O)c1] |

TABLE 1-continued

Selected Compounds

| Compound # | Compound ID | Structure |
|---|---|---|
| 253 | AIB-2 | 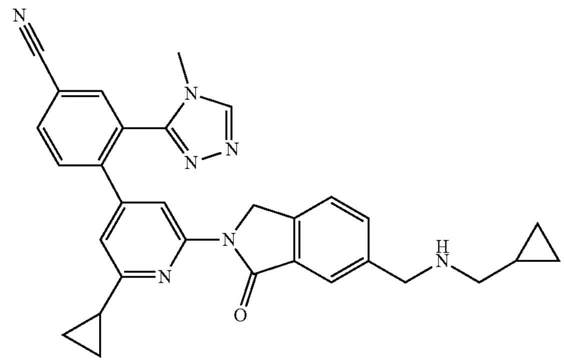 [SMILES: Cn1cnnc1-c1cc(C#N)ccc1-c1cc(C2CC2)nc(N2Cc3ccc(CNCC4CC4)cc3C2=O)c1] |
| 254 | AIC-11 | 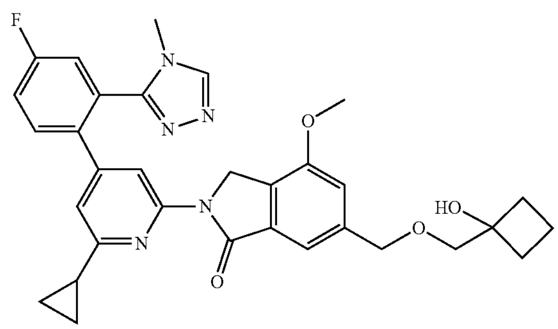 [SMILES: COc1cc(COCC2(O)CCC2)cc2c1CN(c1cc(-c3ccc(F)cc3-c3nncn3C)cc(C3CC3)n1)C2=O] |
| 255 | ANR-2 | 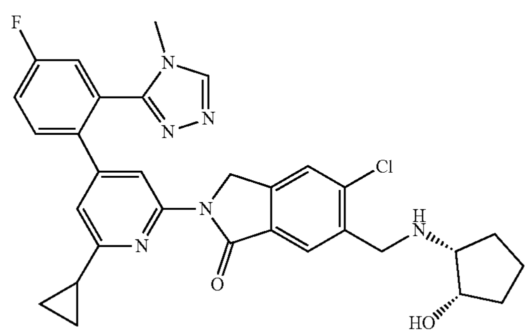 [SMILES: Cn1cnnc1-c1cc(F)ccc1-c1cc(C2CC2)nc(N2Cc3cc(Cl)c(CN[C@@H]4CCC[C@@H]4O)cc3C2=O)c1] |
| 256 | AID-2 | 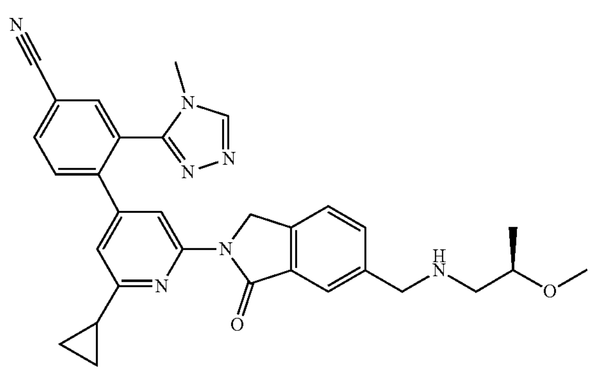 [SMILES: CO[C@H](C)CNCc1ccc2c(c1)C(=O)N(c1cc(-c3ccc(C#N)cc3-c3nncn3C)cc(C3CC3)n1)C2] |

TABLE 1-continued
Selected Compounds
| Compound # | Compound ID | Structure |
|---|---|---|
| 257 | AIE-1 | 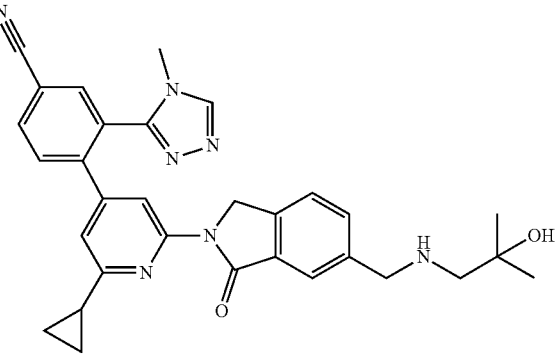 |
| 258 | AIF-1 | 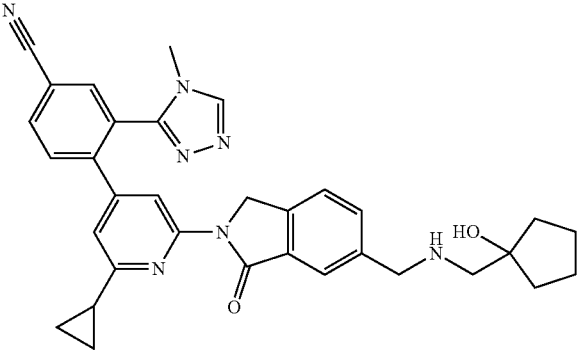 [SMILES: Cn1cnnc1-c1cc(C#N)ccc1-c1cc(C2CC2)nc(N2Cc3ccc(CNCC4(O)CCCC4)cc3C2=O)c1] |
| 259 | AIK-2 | 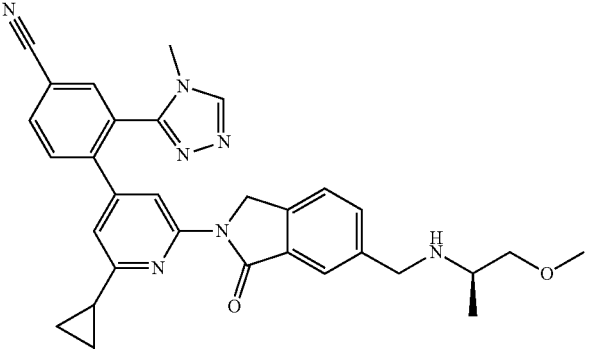 [SMILES: COC[C@@H](C)NCc1ccc2c(c1)C(=O)N(c1cc(-c3ccc(C#N)cc3-c3nncn3C)cc(C3CC3)n1)C2] |
| 260 | AIG-1 | 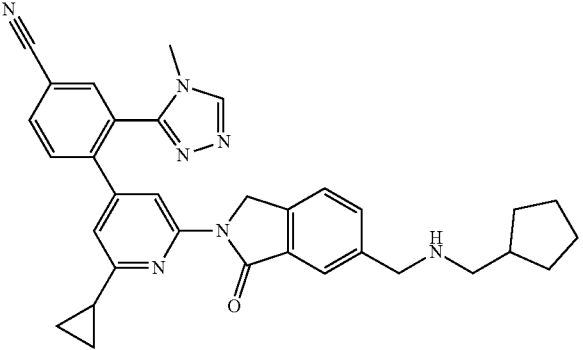 [SMILES: Cn1cnnc1-c1cc(C#N)ccc1-c1cc(C2CC2)nc(N2Cc3ccc(CNCC4CCCC4)cc3C2=O)c1] |

TABLE 1-continued

Selected Compounds

| Compound # | Compound ID | Structure |
|---|---|---|
| 261 | AIH-2 | 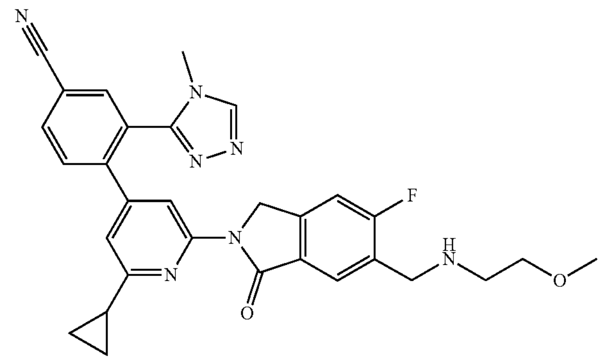 [SMILES: COCCNCc1cc2c(cc1F)CN(c1cc(-c3ccc(C#N)cc3-c3nncn3C)cc(C3CC3)n1)C2=O] |
| 262 | AIM-2 | 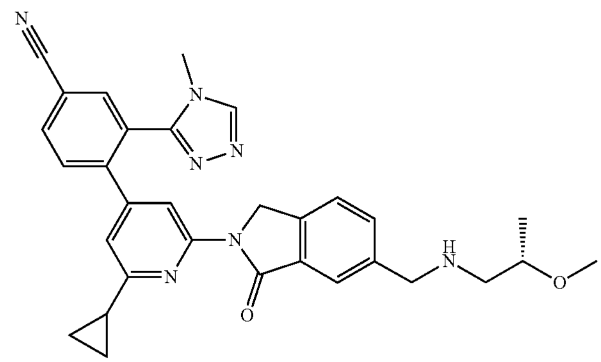 [SMILES: CO[C@@H](C)CNCc1ccc2c(c1)C(=O)N(c1cc(-c3ccc(C#N)cc3-c3nncn3C)cc(C3CC3)n1)C2] |
| 263 | AIN-2 | 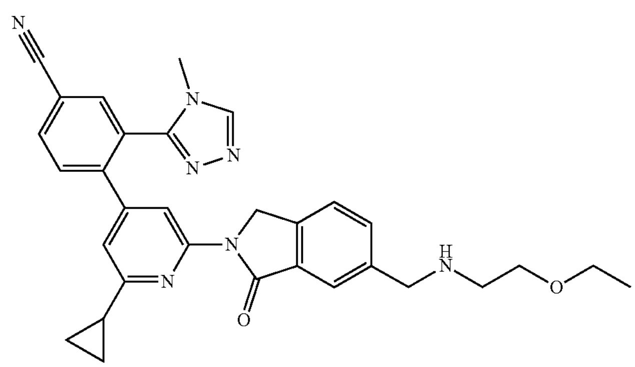 [SMILES: CCOCCNCc1ccc2c(c1)C(=O)N(c1cc(-c3ccc(C#N)cc3-c3nncn3C)cc(C3CC3)n1)C2] |
| 264 | AIO-9 | 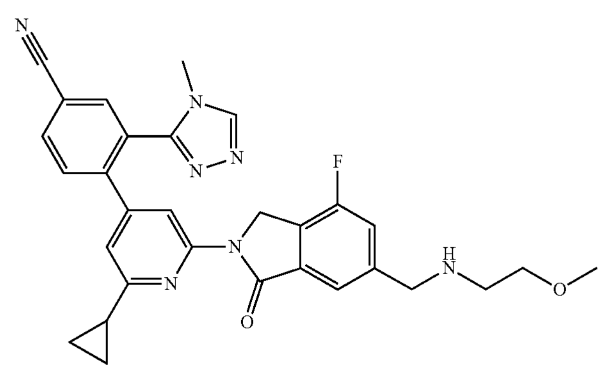 [SMILES: COCCNCc1cc(F)c2c(c1)C(=O)N(c1cc(-c3ccc(C#N)cc3-c3nncn3C)cc(C3CC3)n1)C2] |

TABLE 1-continued
Selected Compounds
| Compound # | Compound ID | Structure |
|---|---|---|
| 265 | AIP-2 | 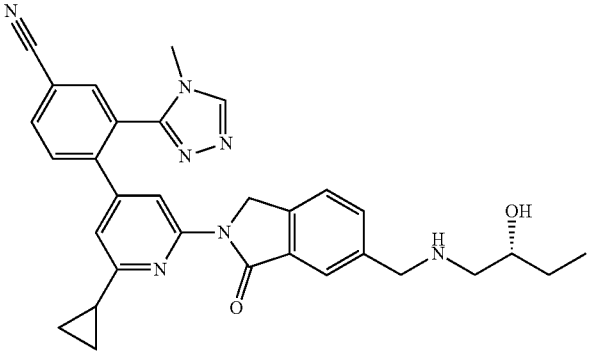 [SMILES: CC[C@@H](O)CNCc1ccc2c(c1)C(=O)N(c1cc(-c3ccc(C#N)cc3-c3nncn3C)cc(C3CC3)n1)C2] |
| 266 | AIQ-2 | 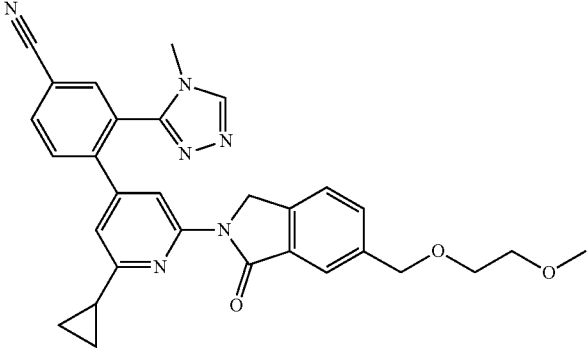 [SMILES: COCCOCc1ccc2c(c1)C(=O)N(c1cc(-c3ccc(C#N)cc3-c3nncn3C)cc(C3CC3)n1)C2] |
| 267 | AIR-2 | 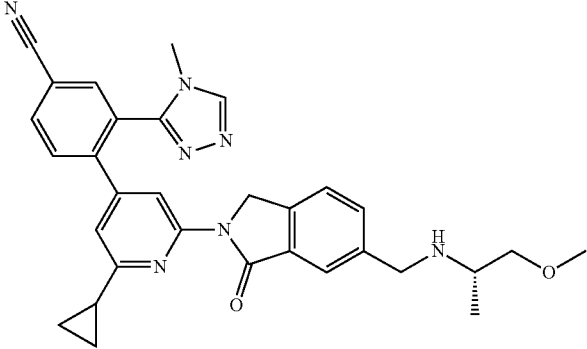 [SMILES: COC[C@H](C)NCc1ccc2c(c1)C(=O)N(c1cc(-c3ccc(C#N)cc3-c3nncn3C)cc(C3CC3)n1)C2] |
| 268 | AIS-2 | 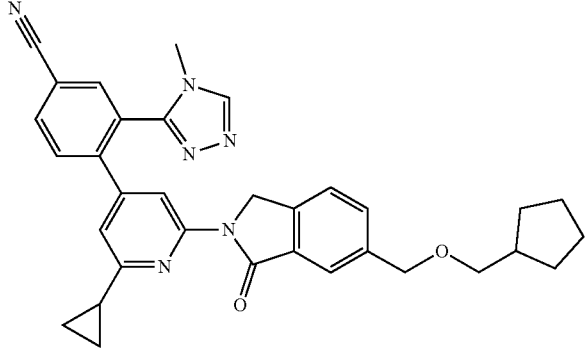 [SMILES: Cn1cnnc1-c1cc(C#N)ccc1-c1cc(C2CC2)nc(N2Cc3ccc(COCC4CCCC4)cc3C2=O)c1] |

TABLE 1-continued
| Compound # | Compound ID | Structure |
|---|---|---|
| 269 | AIT-1 | 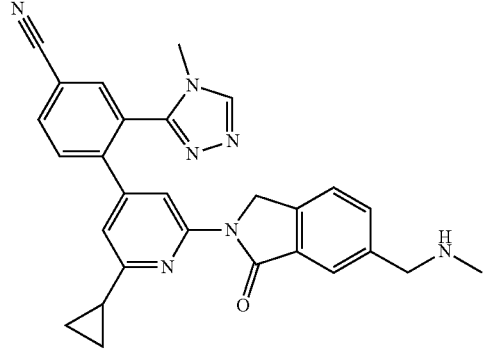 [SMILES: CNCc1ccc2c(c1)C(=O)N(c1cc(-c3ccc(C#N)cc3-c3nncn3C)cc(C3CC3)n1)C2] |
| 270 | ALZ-3 | 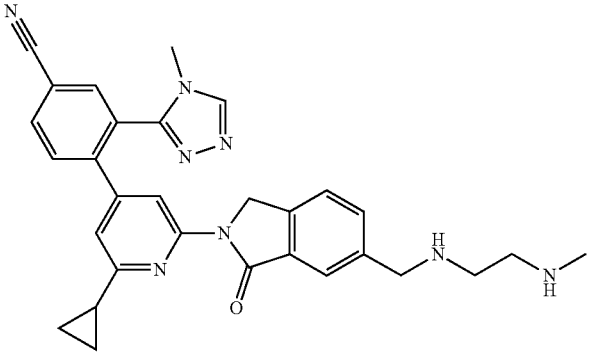 [SMILES: CNCCNCc1ccc2c(c1)C(=O)N(c1cc(-c3ccc(C#N)cc3-c3nncn3C)cc(C3CC3)n1)C2] |
| 271 | AMB-1 | 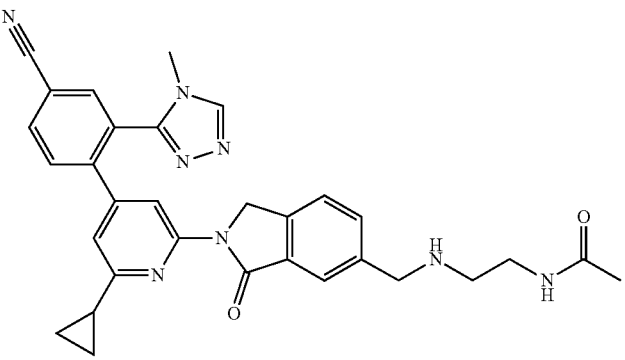 [SMILES: CC(=O)NCCNCc1ccc2c(c1)C(=O)N(c1cc(-c3ccc(C#N)cc3-c3nncn3C)cc(C3CC3)n1)C2] |
| 272 | AIV-2 | 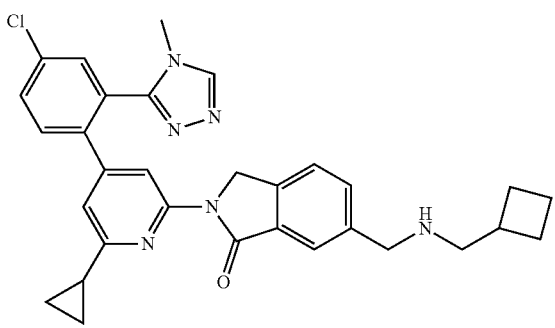 [SMILES: Cn1cnnc1-c1cc(Cl)ccc1-c1cc(C2CC2)nc(N2Cc3ccc(CNCC4CCC4)cc3C2=O)c1] |

TABLE 1-continued
Selected Compounds
| Compound # | Compound ID | Structure |
|---|---|---|
| 273 | AIW-2 | 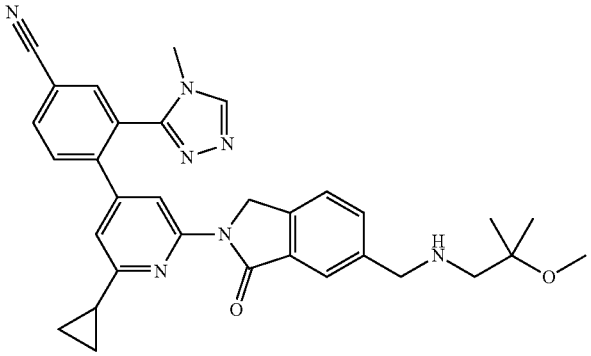 [SMILES: COC(C)(C)CNCc1ccc2c(c1)C(=O)N(c1cc(-c3ccc(C#N)cc3-c3nncn3C)cc(C3CC3)n1)C2] |
| 274 | AIX-2 | 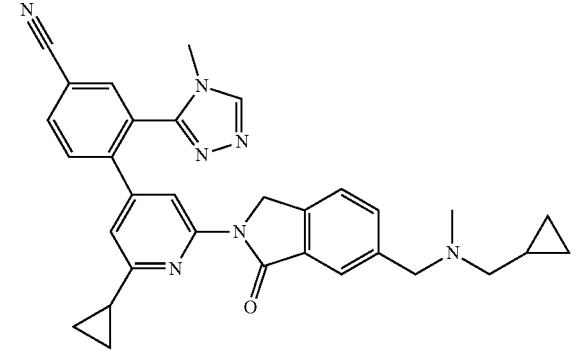 [SMILES: CN(Cc1ccc2c(c1)C(=O)N(c1cc(-c3ccc(C#N)cc3-c3nncn3C)cc(C3CC3)n1)C2)CC1CC1] |
| 275 | AIY-2 | 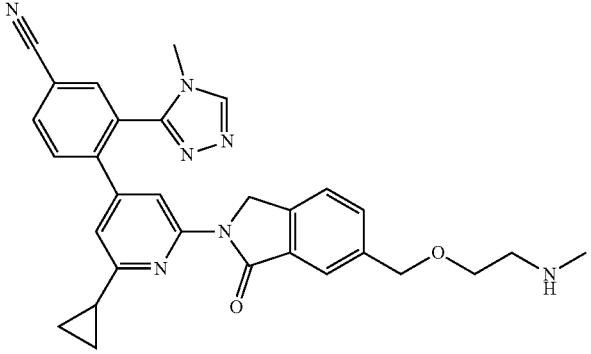 [SMILES: CNCCOCc1ccc2c(c1)C(=O)N(c1cc(-c3ccc(C#N)cc3-c3nncn3C)cc(C3CC3)n1)C2] |
| 276 | AIZ-2 | 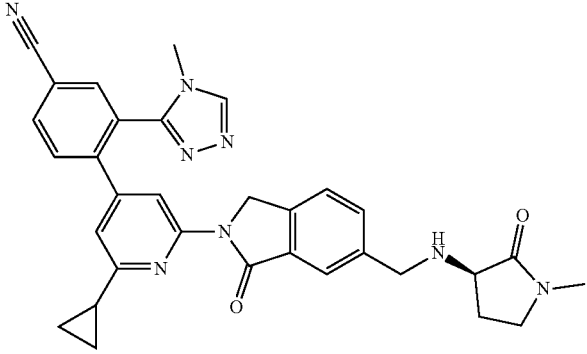 [SMILES: CN1CC[C@@H](NCc2ccc3c(c2)C(=O)N(c2cc(-c4ccc(C#N)cc4-c4nncn4C)cc(C4CC4)n2)C3)C1=O] |

TABLE 1-continued

Selected Compounds

| Compound # | Compound ID | Structure |
|---|---|---|
| 277 | AMC-2 | 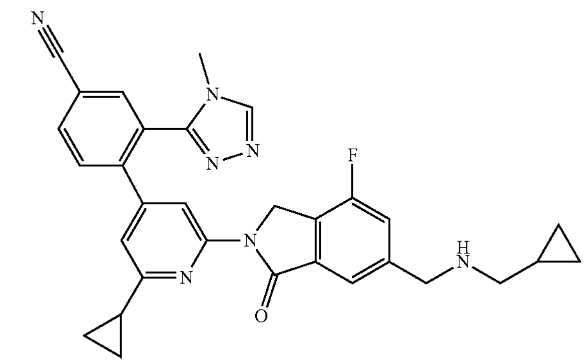 |
| 278 | AJA-2 | 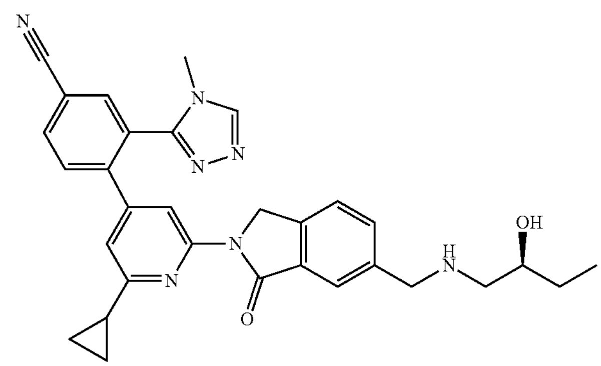 [SMILES: CC[C@H](O)CNCc1ccc2c(c1)C(=O)N(c1cc(-c3ccc(C#N)cc3-c3nncn3C)cc(C3CC3)n1)C2] |
| 279 | AJB-2 | 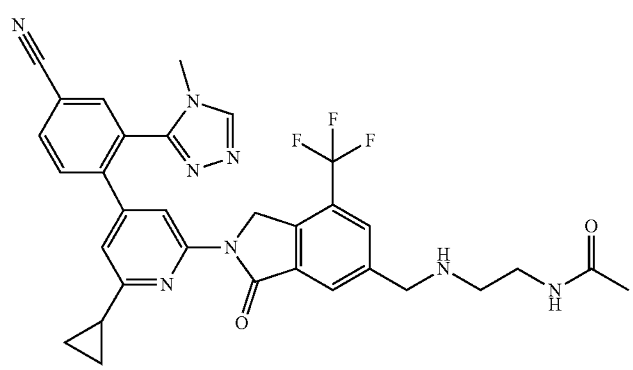 [SMILES: CC(=O)NCCNCc1cc2c(c(C(F)(F)F)c1)CN(c1cc(-c3ccc(C#N)cc3-c3nncn3C)cc(C3CC3)n1)C2=O] |
| 280 | AJC-1 | 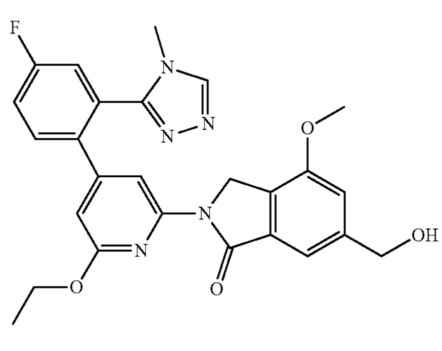 [SMILES: CCOc1cc(-c2ccc(F)cc2-c2nncn2C)cc(N2Cc3c(OC)cc(CO)cc3C2=O)n1] |

TABLE 1-continued
Selected Compounds
| Compound # | Compound ID | Structure |
|---|---|---|
| 281 | ANS-1 | 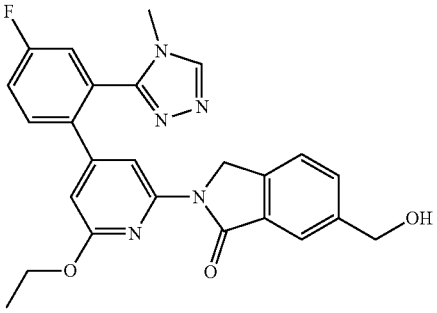 [SMILES: CCOc1cc(-c2ccc(F)cc2-c2nncn2C)cc(N2Cc3ccc(CO)cc3C2=O)n1] |
| 282 | AJD-2 | 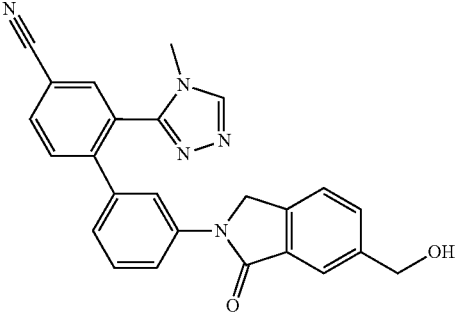 [SMILES: Cn1cnnc1-c1cc(C#N)ccc1-c1cccc(N2Cc3ccc(CO)cc3C2=O)c1] |
| 283 | AMK-3 | 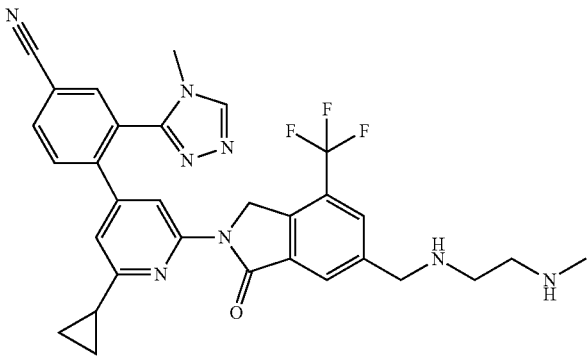 [SMILES: CNCCNCc1cc2c(c(C(F)(F)F)c1)CN(c1cc(-c3ccc(C#N)cc3-c3nncn3C)cc(C3CC3)n1)C2=O] |
| 284 | AJE-2 | 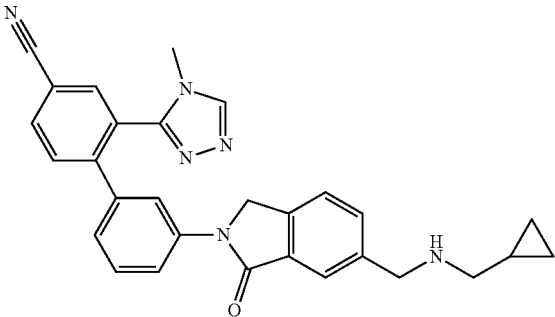 [SMILES: Cn1cnnc1-c1cc(C#N)ccc1-c1cccc(N2Cc3ccc(CNCC4CC4)cc3C2=O)c1] |

TABLE 1-continued

Selected Compounds

| Compound # | Compound ID | Structure |
|---|---|---|
| 285 | AJF-1 | 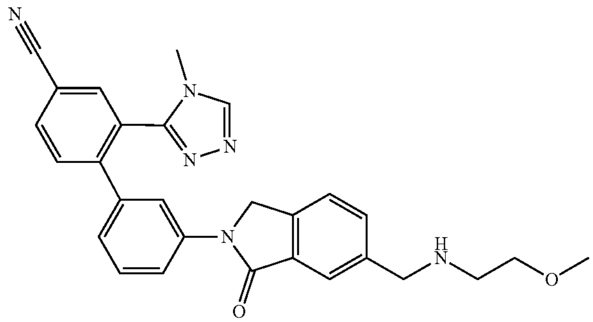 [SMILES: COCCNCc1ccc2c(c1)C(=O)N(c1cccc(-c3ccc(C#N)cc3-c3nncn3C)c1)C2] |
| 286 | AJG-2 | 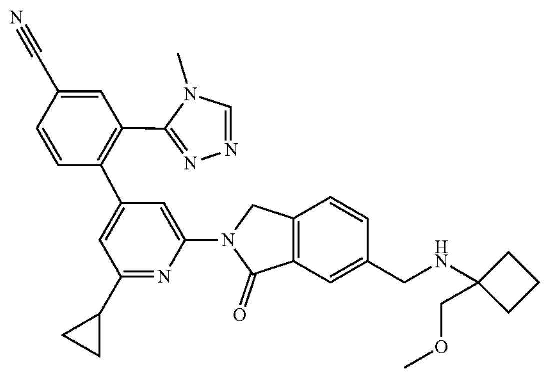 [SMILES: COCC1(NCc2ccc3c(c2)C(=O)N(c2cc(-c4ccc(C#N)cc4-c4nncn4C)cc(C4CC4)n2)C3)CCC1] |
| 287 | AJJ-1 | 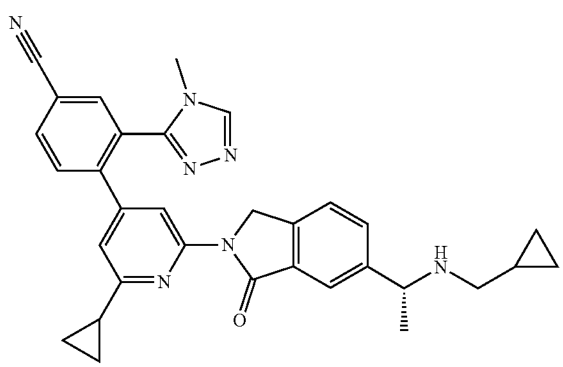 [SMILES: C[C@@H](NCC1CC1)c1ccc2c(c1)C(=O)N(c1cc(-c3ccc(C#N)cc3-c3nncn3C)cc(C3CC3)n1)C2] |
| 288 | AJK-1 | 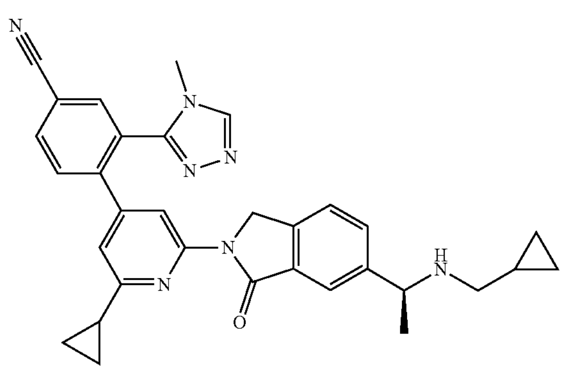 [SMILES: C[C@H](NCC1CC1)c1ccc2c(c1)C(=O)N(c1cc(-c3ccc(C#N)cc3-c3nncn3C)cc(C3CC3)n1)C2] |

TABLE 1-continued

| Selected Compounds | | |
|---|---|---|
| Compound # | Compound ID | Structure |
| 289 | AJM-3 | |
| 290 | AJN-3 | |
| 291 | AJO-2 | |
| 292 | AJL-2 | |

TABLE 1-continued

Selected Compounds

| Compound # | Compound ID | Structure |
|---|---|---|
| 293 | AJI-1 | 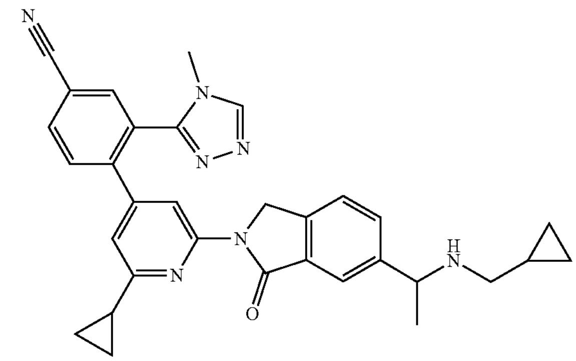 |
| 294 | AJH-3 | 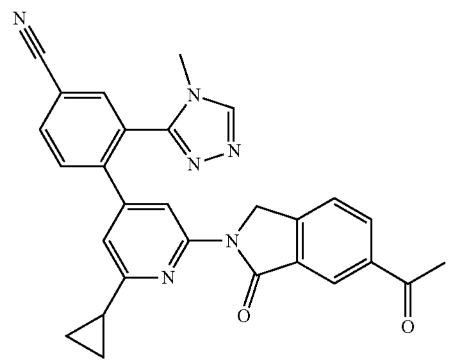 [SMILES: CC(=O)c1ccc2c(c1)C(=O)N(c1cc(-c3ccc(C#N)cc3-c3nncn3C)cc(C3CC3)n1)C2] |
| 295 | AJR-1 | 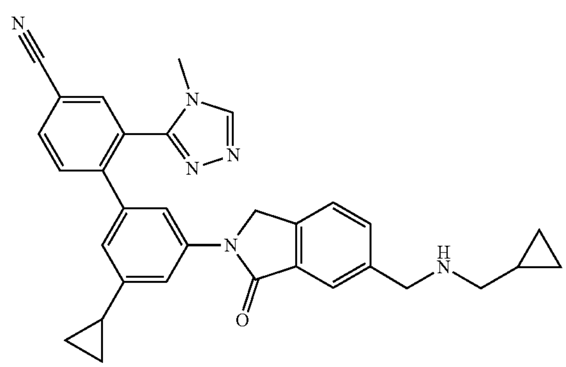 [SMILES: Cn1cnnc1-c1cc(C#N)ccc1-c1cc(C2CC2)cc(N2Cc3ccc(CNCC4CC4)cc3C2=O)c1] |
| 296 | AJQ-2 | 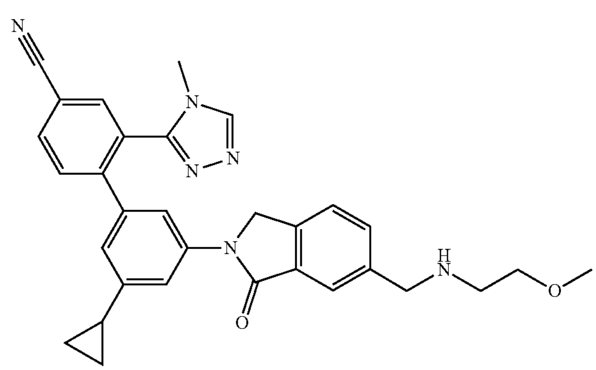 [SMILES: COCCNCc1ccc2c(c1)C(=O)N(c1cc(-c3ccc(C#N)cc3-c3nncn3C)cc(C3CC3)c1)C2] |

TABLE 1-continued
Selected Compounds
| Compound # | Compound ID | Structure |
|---|---|---|
| 297 | AJS-1 | 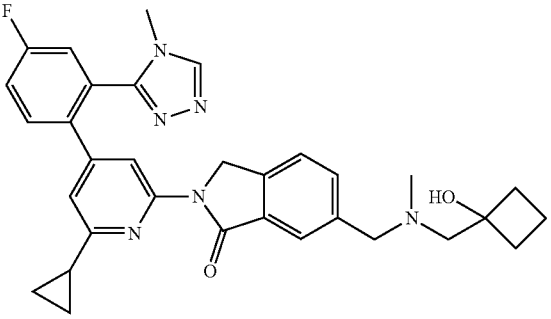 |
| 298 | AJT-1 | 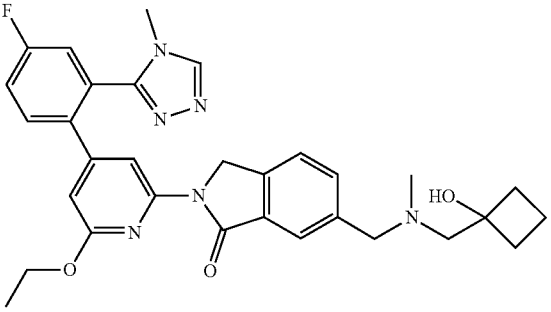 [SMILES: CCOc1cc(-c2ccc(F)cc2-c2nncn2C)cc(N2Cc3ccc(CN(C)CC4(O)CCC4)cc3C2=O)n1] |
| 299 | AJU-3 | 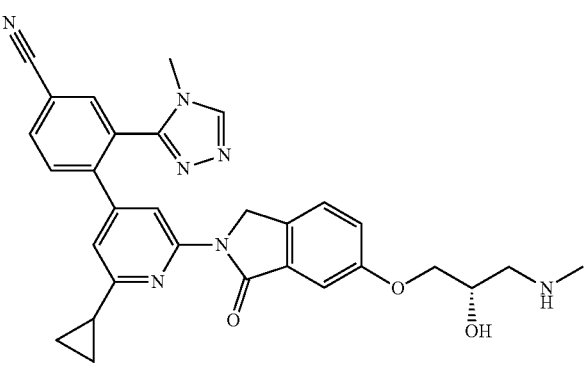 [SMILES: CNC[C@H](O)COc1ccc2c(c1)C(=O)N(c1cc(-c3ccc(C#N)cc3-c3nncn3C)cc(C3CC3)n1)C2] |
| 300 | AJV-3 | 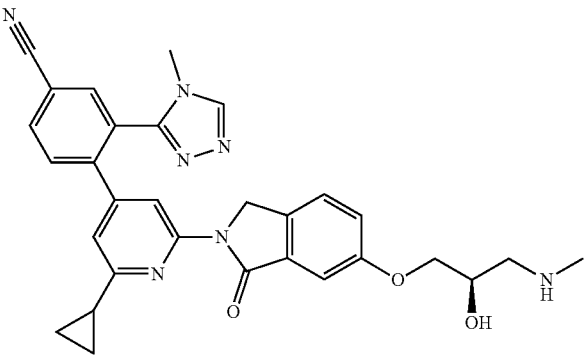 [SMILES: CNC[C@@H](O)COc1ccc2c(c1)C(=O)N(c1cc(-c3ccc(C#N)cc3-c3nncn3C)cc(C3CC3)n1)C2] |

TABLE 1-continued

| Selected Compounds | | |
|---|---|---|
| Compound # | Compound ID | Structure |
| 301 | AJW-1 | |
| 302 | AJX-1 | |
| 303 | AMA-2 | |
| 304 | AJP-7 | |

TABLE 1-continued

Selected Compounds

| Compound # | Compound ID | Structure |
|---|---|---|
| 305 | AJY-1 | 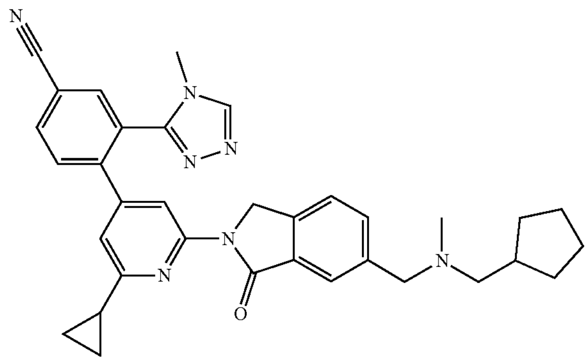 [SMILES: CN(Cc1ccc2c(c1)C(=O)N(c1cc(-c3ccc(C#N)cc3-c3nncn3C)cc(C3CC3)n1)C2)CC1CCCC1] |
| 306 | AKA-1 | 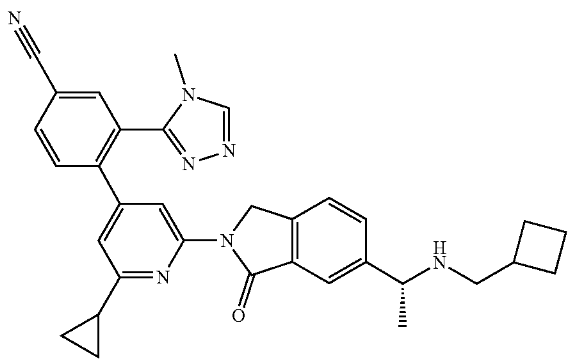 [SMILES: C[C@@H](NCC1CCC1)c1ccc2c(c1)C(=O)N(c1cc(-c3ccc(C#N)cc3-c3nncn3C)cc(C3CC3)n1)C2] |
| 307 | AKB-1 | 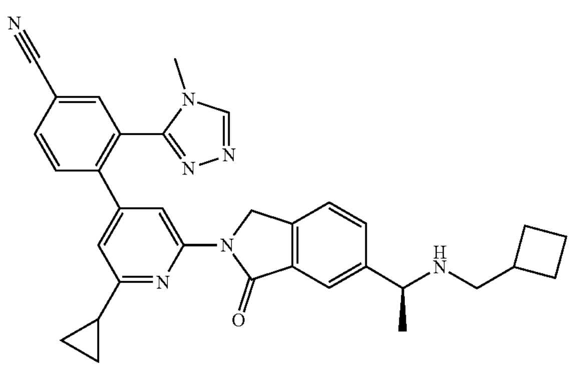 [SMILES: C[C@H](NCC1CCC1)c1ccc2c(c1)C(=O)N(c1cc(-c3ccc(C#N)cc3-c3nncn3C)cc(C3CC3)n1)C2] |
| 308 | AKC-2 | 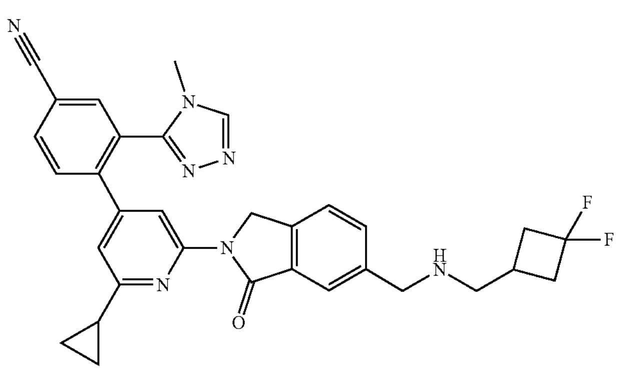 [SMILES: Cn1cnnc1-c1cc(C#N)ccc1-c1cc(C2CC2)nc(N2Cc3ccc(CNCC4CC(F)(F)C4)cc3C2=O)c1] |

TABLE 1-continued
Selected Compounds
| Compound # | Compound ID | Structure |
|---|---|---|
| 309 | AKD-2 | 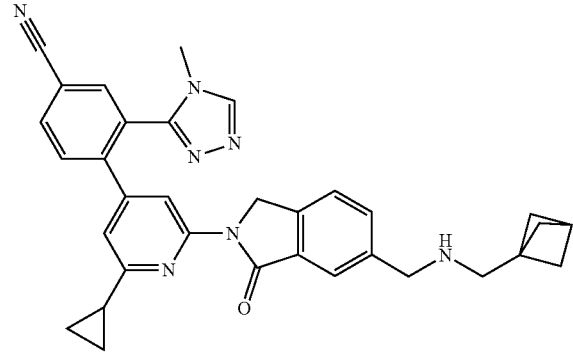 [SMILES: Cn1cnnc1-c1cc(C#N)ccc1-c1cc(C2CC2)nc(N2Cc3ccc(CNCC45CC(C4)C5)cc3C2=O)c1] |
| 310 | AJZ-1 | 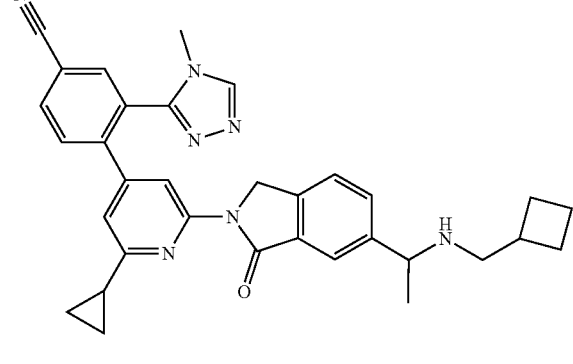 |
| 311 | AKE-2 | 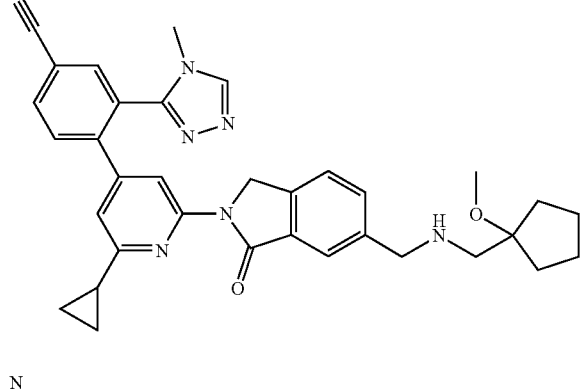 |
| 312 | AKF-2 | 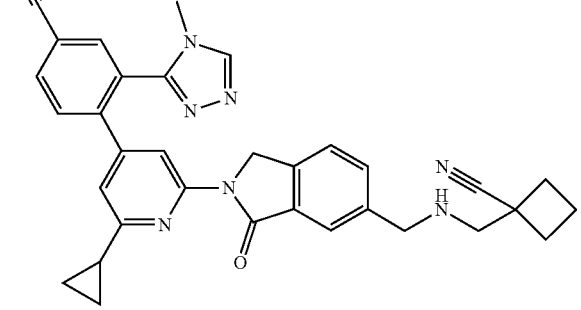 |

TABLE 1-continued
| Selected Compounds | | |
|---|---|---|
| Compound # | Compound ID | Structure |
| 313 | AKG-1 | 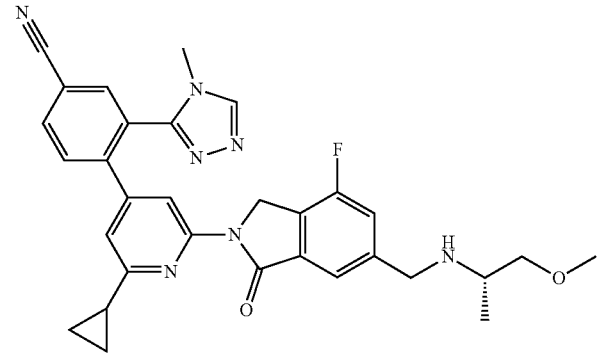 [SMILES: COC[C@H](C)NCc1cc(F)c2c(c1)C(=O)N(c1cc(-c3ccc(C#N)cc3-c3nncn3C)cc(C3CC3)n1)C2] |
| 314 | ANT-1 | 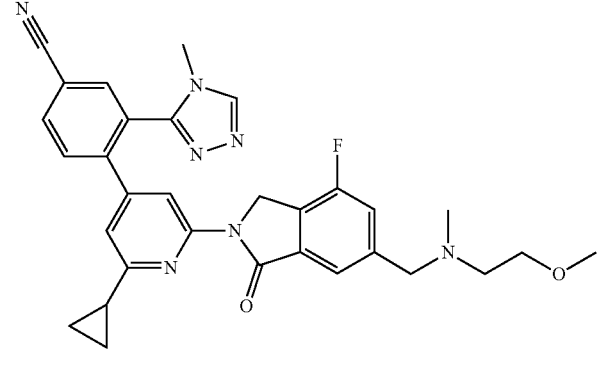 [SMILES: COCCN(C)Cc1cc(F)c2c(c1)C(=O)N(c1cc(-c3ccc(C#N)cc3-c3nncn3C)cc(C3CC3)n1)C2] |
| 315 | AKH-1 | 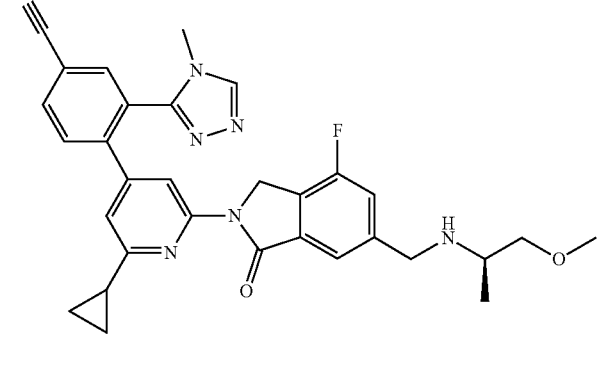 |
| 316 | AKI-1 | 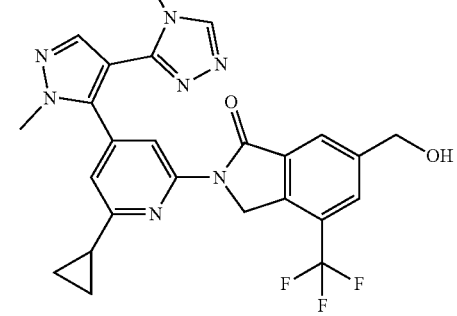 |

TABLE 1-continued
Selected Compounds
| Compound # | Compound ID | Structure |
|---|---|---|
| 317 | AKJ-1 | 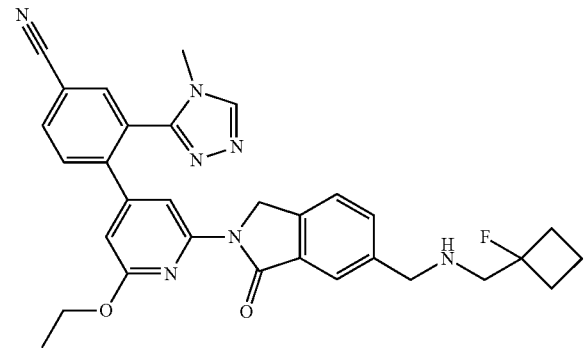 [SMILES: CCOc1cc(-c2ccc(C#N)cc2-c2nncn2C)cc(N2Cc3ccc(CNCC4(F)CCC4)cc3C2=O)n1] |
| 318 | AKK-1 | 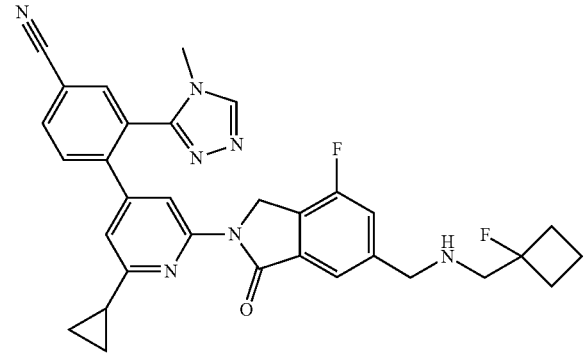 [SMILES: Cn1cnnc1-c1cc(C#N)ccc1-c1cc(C2CC2)nc(N2Cc3c(F)cc(CNCC4(F)CCC4)cc3C2=O)c1] |
| 319 | AKM-2 | 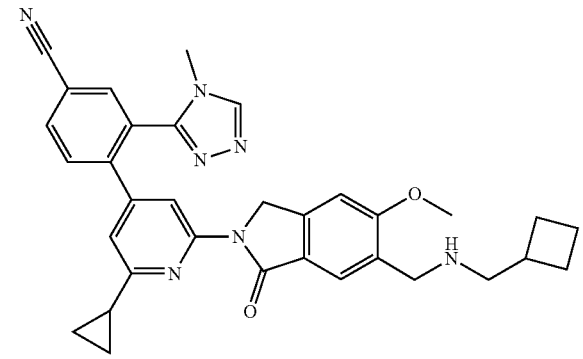 [SMILES: COc1cc2c(cc1CNCC1CCC1)C(=O)N(c1cc(-c3ccc(C#N)cc3-c3nncn3C)cc(C3CC3)n1)C2] |
| 320 | AKO-2 | 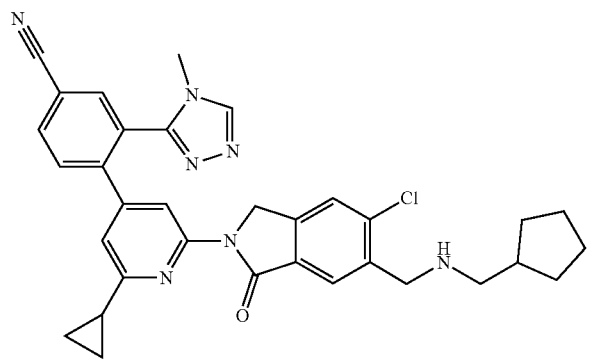 [SMILES: Cn1cnnc1-c1cc(C#N)ccc1-c1cc(C2CC2)nc(N2Cc3cc(Cl)c(CNCC4CCCC4)cc3C2=O)c1] |

TABLE 1-continued
Selected Compounds
| Compound # | Compound ID | Structure |
|---|---|---|
| 321 | AKP-1 | 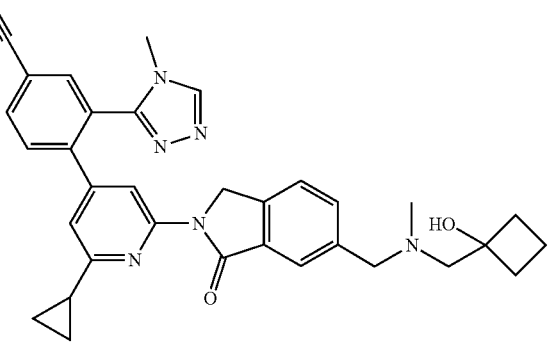 |
| 322 | AKQ-2 | 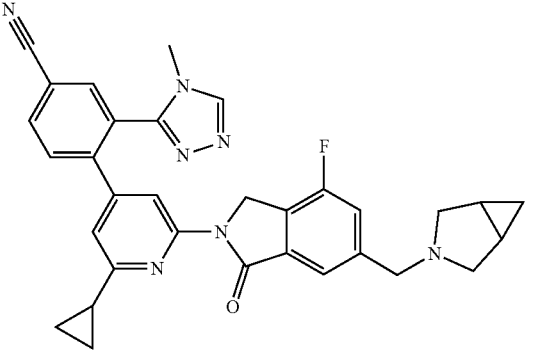 [SMILES: Cn1cnnc1-c1cc(C#N)ccc1-c1cc(C2CC2)nc(N2Cc3c(F)cc(CN4CC5CC5C4)cc3C2=O)c1] |
| 323 | AKR-3 | 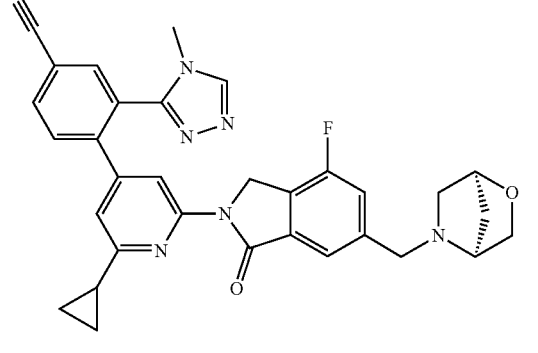 |
| 324 | AKS-1 | 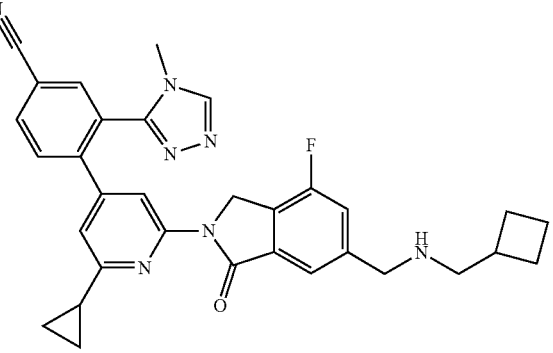 |

TABLE 1-continued
Selected Compounds
| Compound # | Compound ID | Structure |
|---|---|---|
| 325 | AKT-1 | 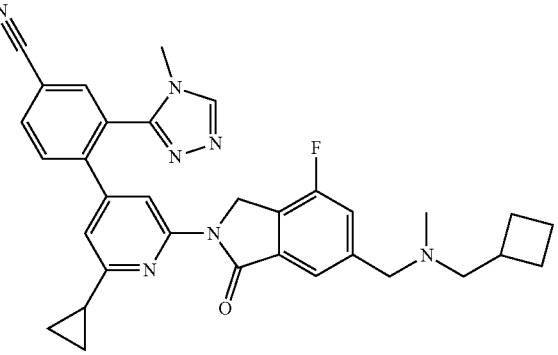 |
| 326 | AKN-12 | 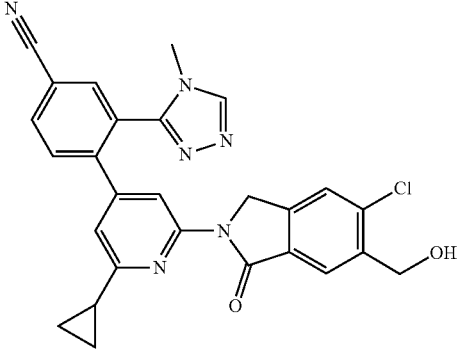 [SMILES: Cn1cnnc1-c1cc(C#N)ccc1-c1cc(C2CC2)nc(N2Cc3cc(Cl)c(CO)cc3C2=O)c1] |
| 327 | AKU-2 | 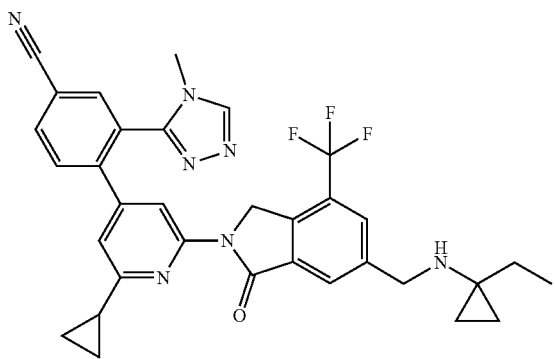 [SMILES: CCC1(NCc2cc3c(c(C(F)(F)F)c2)CN(c2cc(-c4ccc(C#N)cc4-c4nncn4C)cc(C4CC4)n2)C3=O)CC1] |
| 328 | AKV-1 | 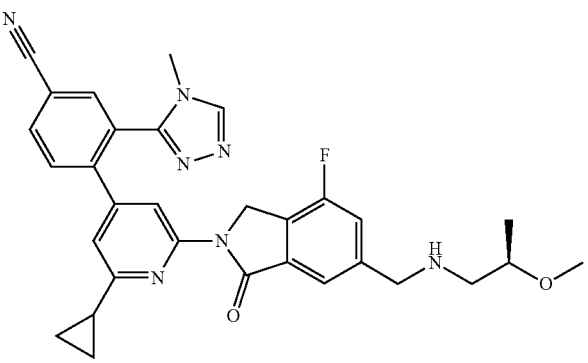 [SMILES: CO[C@H](C)CNCc1cc(F)c2c(c1)C(=O)N(c1cc(-c3ccc(C#N)cc3-c3nncn3C)cc(C3CC3)n1)C2] |

TABLE 1-continued

Selected Compounds

| Compound # | Compound ID | Structure |
|---|---|---|
| 329 | AKW-1 | 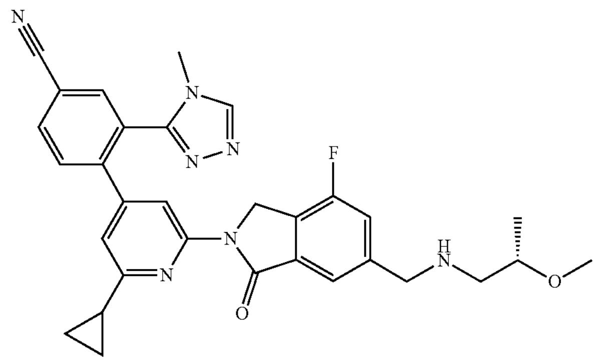 |
| 330 | AKX-1 | 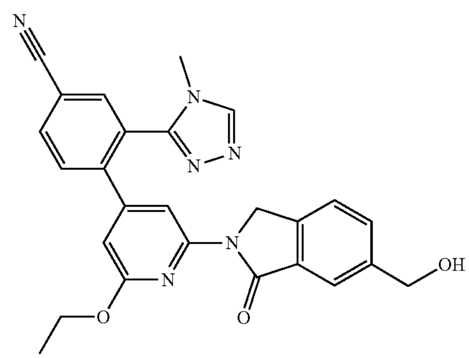 [SMILES: CCOc1cc(-c2ccc(C#N)cc2-c2nncn2C)cc(N2Cc3ccc(CO)cc3C2=O)n1] |
| 331 | AKL-2 | 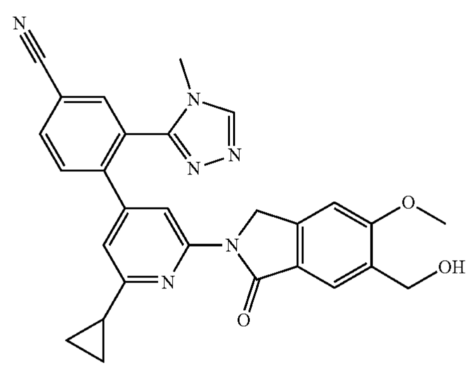 [SMILES: COc1cc2c(cc1CO)C(=O)N(c1cc(-c3ccc(C#N)cc3-c3nncn3C)cc(C3CC3)n1)C2] |
| 332 | AKY-1 | 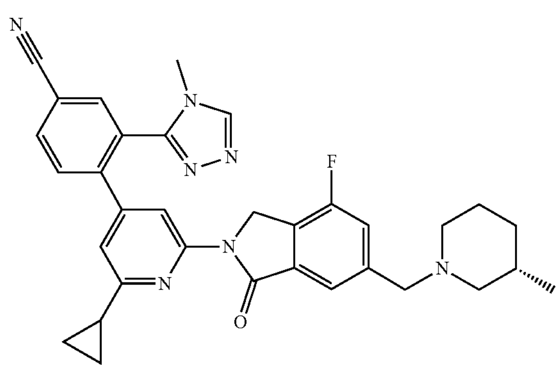 [SMILES: C[C@H]1CCCN(Cc2cc(F)c3c(c2)C(=O)N(c2cc(-c4ccc(C#N)cc4-c4nncn4C)cc(C4CC4)n2)C3)C1] |

TABLE 1-continued
Selected Compounds
| Compound # | Compound ID | Structure |
|---|---|---|
| 333 | AKZ-2 | 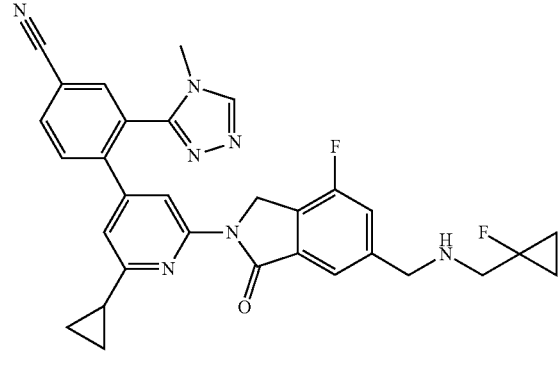 [SMILES: Cn1cnnc1-c1cc(C#N)ccc1-c1cc(C2CC2)nc(N2Cc3c(F)cc(CNCC4(F)CC4)cc3C2=O)c1] |
| 334 | ALA-5 | 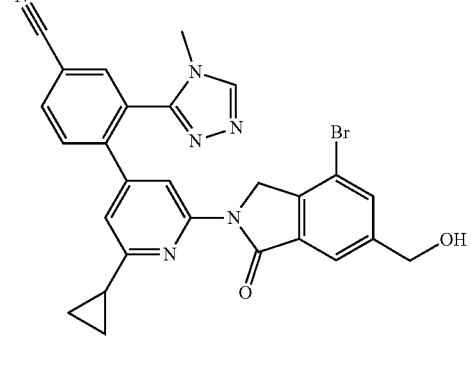 |
| 335 | ALB-2 | 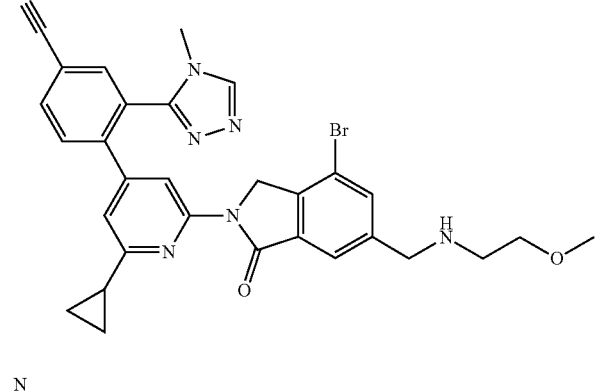 |
| 336 | AMD-2 | 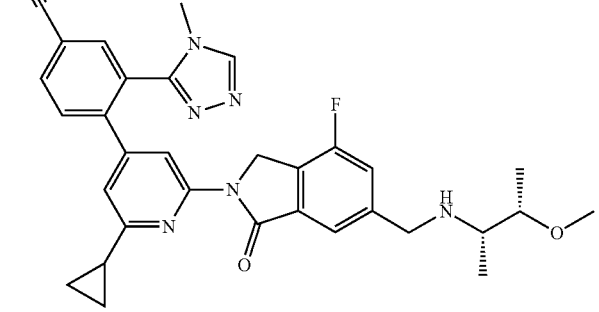 |

TABLE 1-continued
Selected Compounds
| Compound # | Compound ID | Structure |
|---|---|---|
| 337 | ALC-2 | 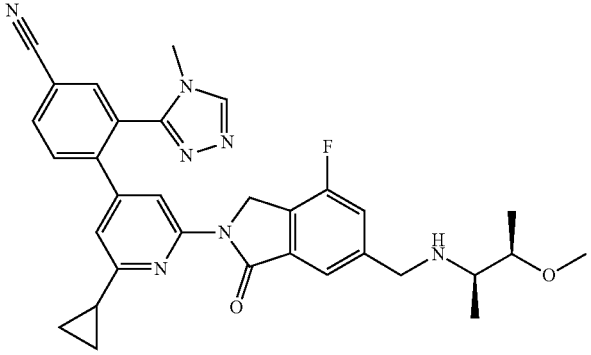 [SMILES: CO[C@H](C)[C@@H](C)NCc1cc(F)c2c(c1)C(=O)N(c1cc(-c3ccc(C#N)cc3-c3nncn3C)cc(C3CC3)n1)C2] |
| 338 | ALD-2 | 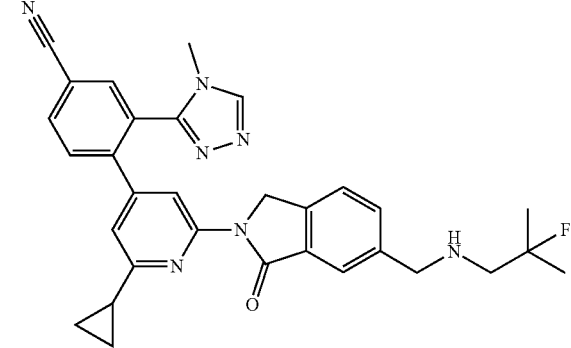 [SMILES: Cn1cnnc1-c1cc(C#N)ccc1-c1cc(C2CC2)nc(N2Cc3ccc(CNCC(C)(C)F)cc3C2=O)c1] |
| 339 | ALF-2 | 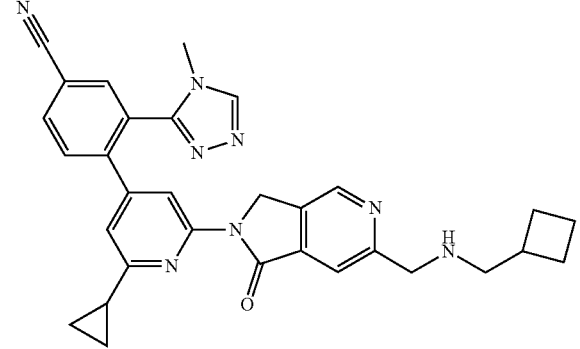 |
| 340 | ALG-3 | 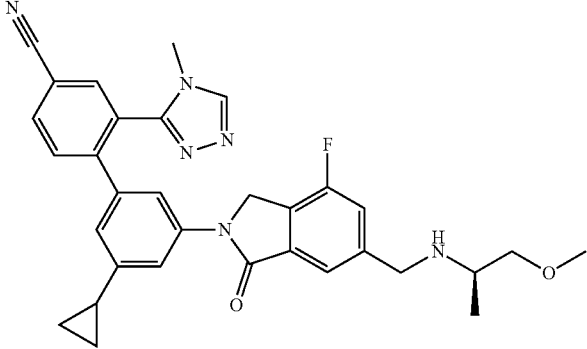 |

TABLE 1-continued

Selected Compounds

| Compound # | Compound ID | Structure |
|---|---|---|
| 341 | ALH-1 | 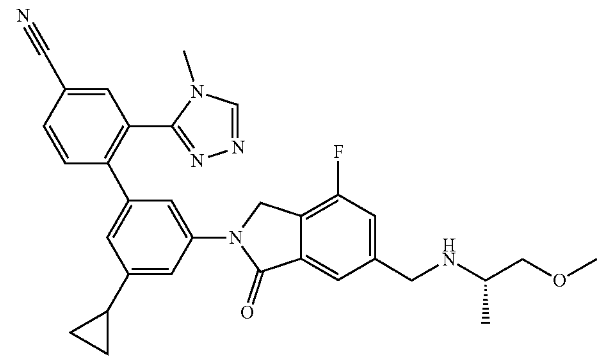 [SMILES: COC[C@H](C)NCc1cc(F)c2c(c1)C(=O)N(c1cc(-c3ccc(C#N)cc3-c3nncn3C)cc(C3CC3)c1)C2] |
| 342 | ALI-2 | 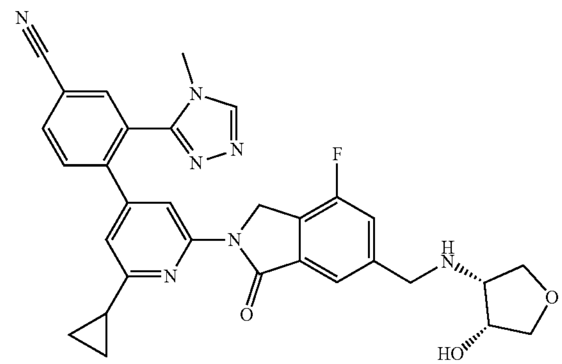 [SMILES: Cn1cnnc1-c1cc(C#N)ccc1-c1cc(C2CC2)nc(N2Cc3c(F)cc(CN[C@@H]4COC[C@@H]4O)cc3C2=O)c1] |
| 343 | AME-2 | 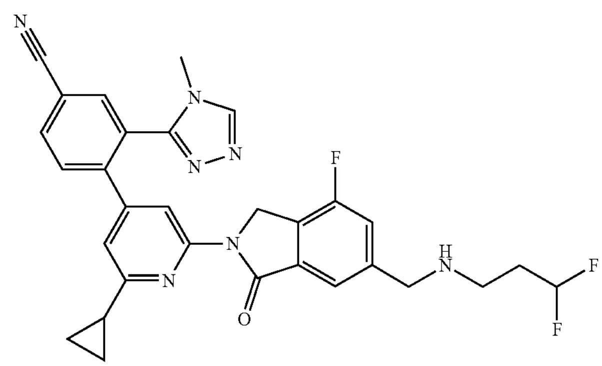 [SMILES: Cn1cnnc1-c1cc(C#N)ccc1-c1cc(C2CC2)nc(N2Cc3c(F)cc(CNCCC(F)F)cc3C2=O)c1] |
| 344 | ALJ-1 | 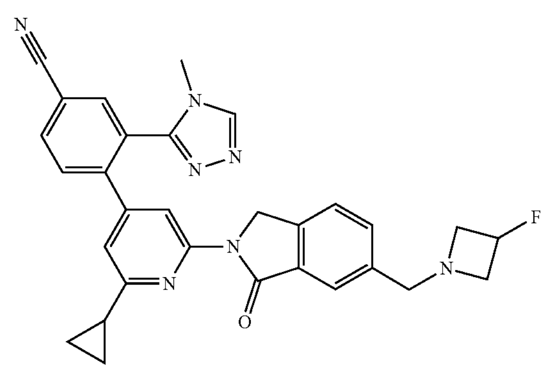 [SMILES: Cn1cnnc1-c1cc(C#N)ccc1-c1cc(C2CC2)nc(N2Cc3ccc(CN4CC(F)C4)cc3C2=O)c1] |

TABLE 1-continued
Selected Compounds
| Compound # | Compound ID | Structure |
|---|---|---|
| 345 | ALE-7 | 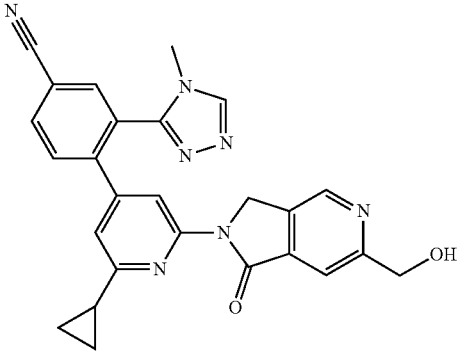 |
| 346 | ALL-2 | 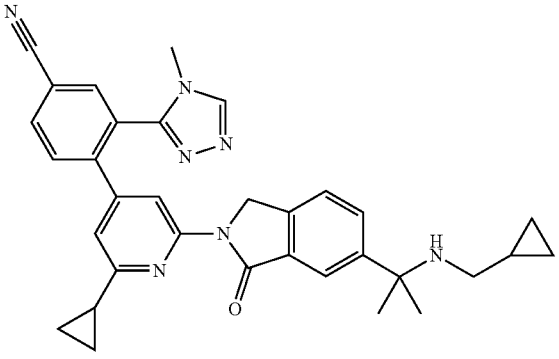 [SMILES: Cn1cnnc1-c1cc(C#N)ccc1-c1cc(C2CC2)nc(N2Cc3ccc(C(C)(C)NCC4CC4)cc3C2=O)c1] |
| 347 | ALN-2 | 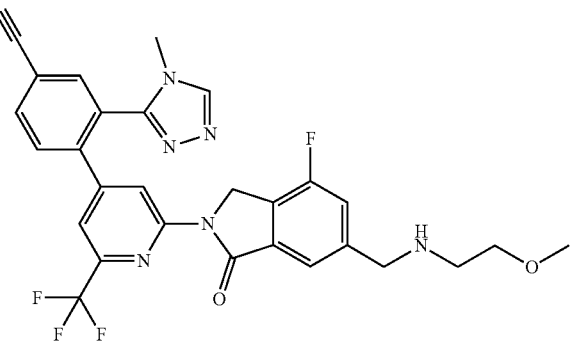 |
| 348 | ALM-3 | 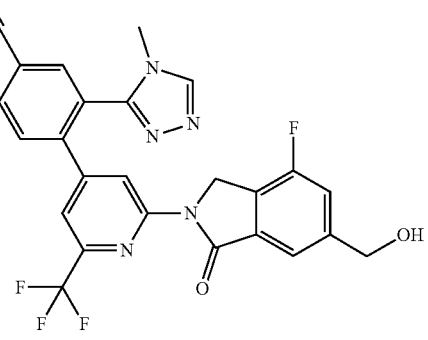 |

TABLE 1-continued

Selected Compounds

| Compound # | Compound ID | Structure |
|---|---|---|
| 349 | ALO-2 | 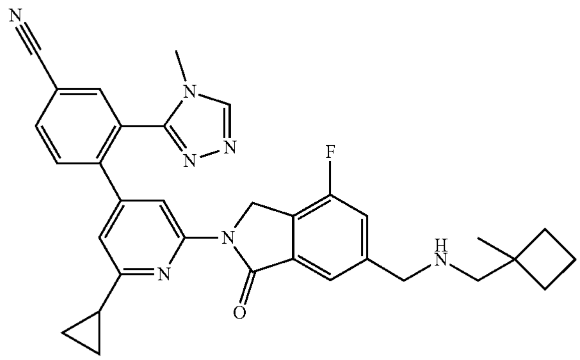 [SMILES: Cn1cnnc1-c1cc(C#N)ccc1-c1cc(C2CC2)nc(N2Cc3c(F)cc(CNCC4(C)CCC4)cc3C2=O)c1] |
| 350 | ALP-1 | 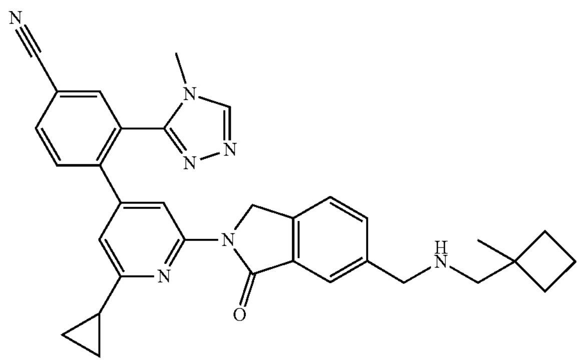 [SMILES: Cn1cnnc1-c1cc(C#N)ccc1-c1cc(C2CC2)nc(N2Cc3ccc(CNCC4(C)CCC4)cc3C2=O)c1] |
| 351 | ALK-9 | 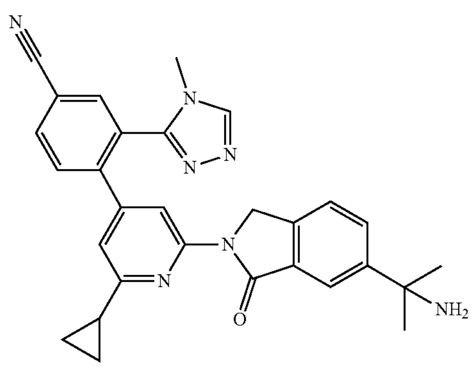 [SMILES: Cn1cnnc1-c1cc(C#N)ccc1-c1cc(C2CC2)nc(N2Cc3ccc(C(C)(C)N)cc3C2=O)c1] |
| 352 | ALQ-2 | 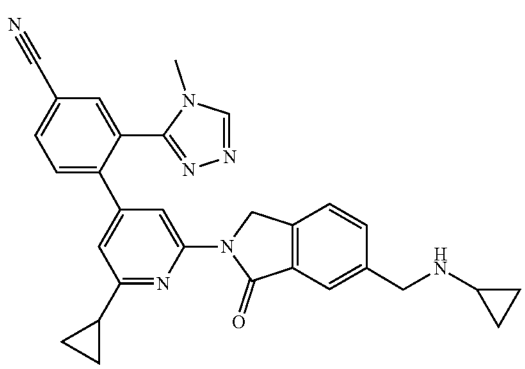 [SMILES: Cn1cnnc1-c1cc(C#N)ccc1-c1cc(C2CC2)nc(N2Cc3ccc(CNC4CC4)cc3C2=O)c1] |

TABLE 1-continued

Selected Compounds

| Compound # | Compound ID | Structure |
|---|---|---|
| 353 | ALR-1 | 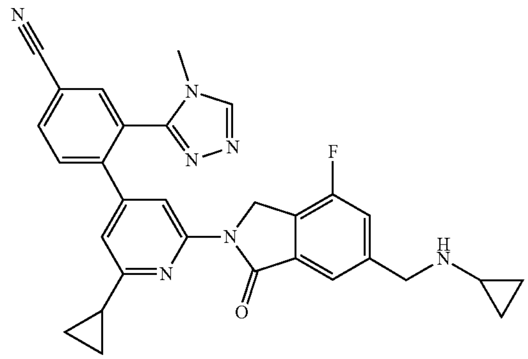 [SMILES: Cn1cnnc1-c1cc(C#N)ccc1-c1cc(C2CC2)nc(N2Cc3c(F)cc(CNC4CC4)cc3C2=O)c1] |
| 354 | AMF-1 | 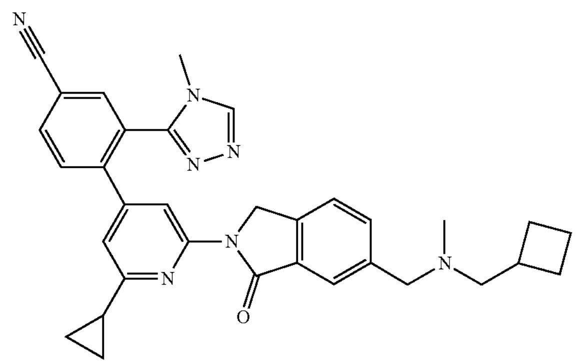 |
| 355 | AMG-1 | 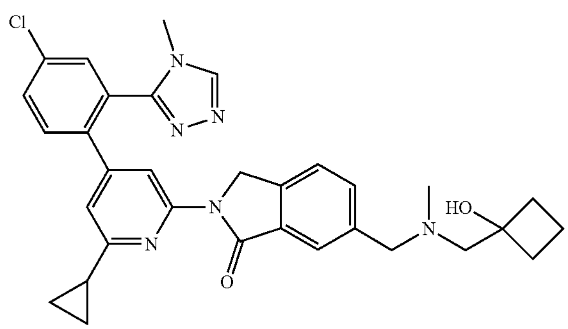 [SMILES: CN(Cc1ccc2c(c1)C(=O)N(c1cc(-c3ccc(Cl)cc3-c3nncn3C)cc(C3CC3)n1)C2)CC1(O)CCC1] |
| 356 | AIU-1 | 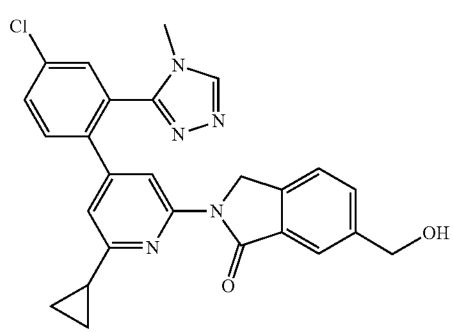 [SMILES: Cn1cnnc1-c1cc(Cl)ccc1-c1cc(C2CC2)nc(N2Cc3ccc(CO)cc3C2=O)c1] |

TABLE 1-continued

Selected Compounds

| Compound # | Compound ID | Structure |
|---|---|---|
| 357 | ALS-1 | 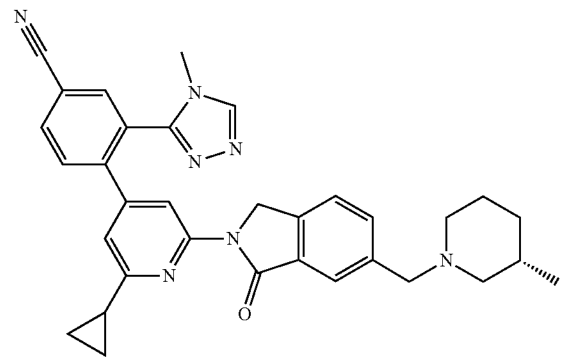 [SMILES: C[C@H]1CCCN(Cc2ccc3c(c2)C(=O)N(c2cc(-c4ccc(C#N)cc4-c4nncn4C)cc(C4CC4)n2)C3)C1] |
| 358 | ALT-2 | 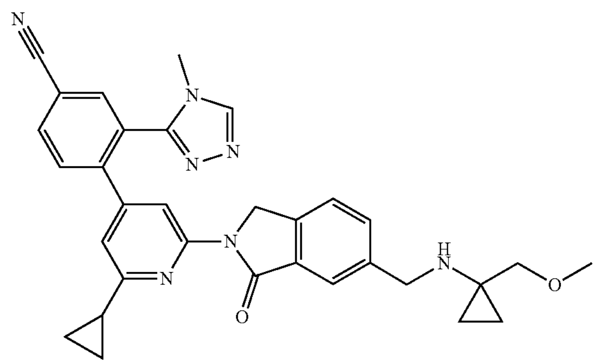 [SMILES: COCC1(NCc2ccc3c(c2)C(=O)N(c2cc(-c4ccc(C#N)cc4-c4nncn4C)cc(C4CC4)n2)C3)CC1] |
| 359 | ALU-2 | 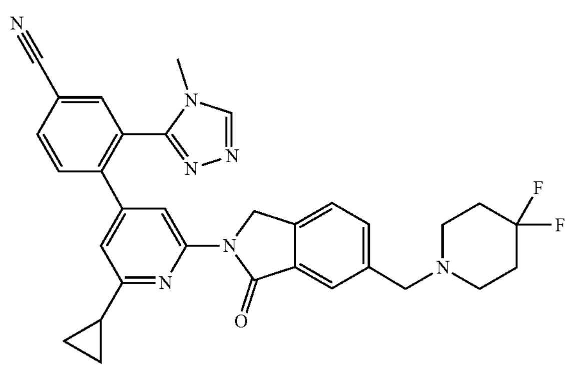 [SMILES: Cn1cnnc1-c1cc(C#N)ccc1-c1cc(C2CC2)nc(N2Cc3ccc(CN4CCC(F)(F)CC4)cc3C2=O)c1] |
| 360 | ALV-4 | 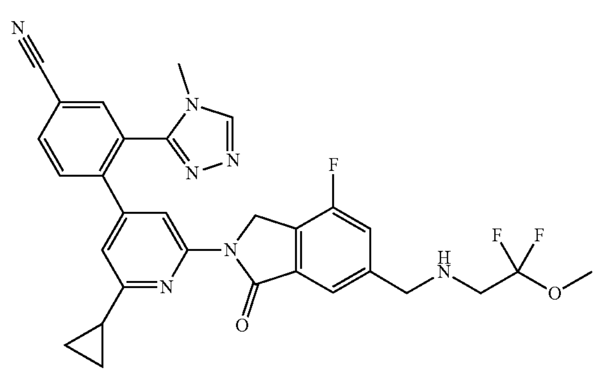 [SMILES: COC(F)(F)CNCc1cc(F)c2c(c1)C(=O)N(c1cc(-c3ccc(C#N)cc3-c3nncn3C)cc(C3CC3)n1)C2] |

TABLE 1-continued

Selected Compounds

| Compound # | Compound ID | Structure |
|---|---|---|
| 361 | ALY-2 | 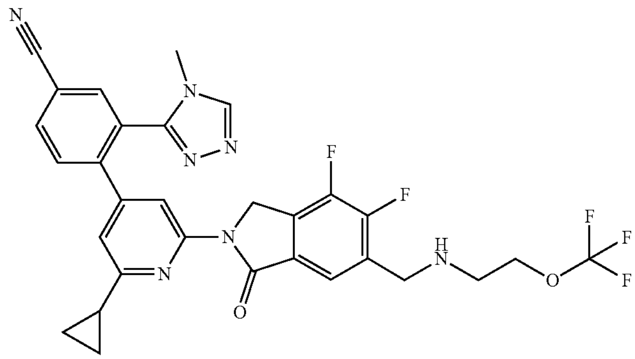 [SMILES: Cn1cnnc1-c1cc(C#N)ccc1-c1cc(C2CC2)nc(N2Cc3c(cc(CNCCOC(F)(F)F)c(F)c3F)C2=O)c1] |
| 362 | AMH-1 | 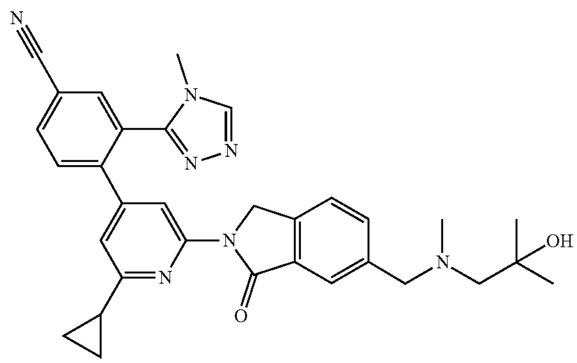 [SMILES: CN(Cc1ccc2c(c1)C(=O)N(c1cc(-c3ccc(C#N)cc3-c3nncn3C)cc(C3CC3)n1)C2)CC(C)(C)O] |
| 363 | ALW-1 | 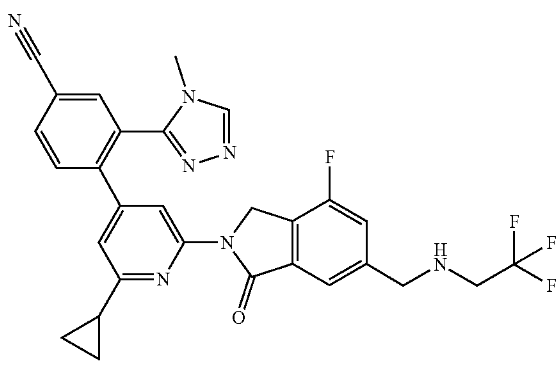 [SMILES: Cn1cnnc1-c1cc(C#N)ccc1-c1cc(C2CC2)nc(N2Cc3c(F)cc(CNCC(F)(F)F)cc3C2=O)c1] |
| 364 | AMJ-1 | 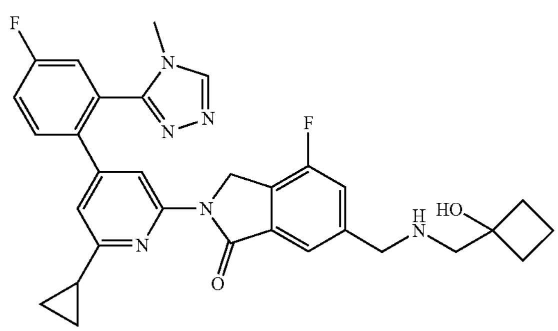 [SMILES: Cn1cnnc1-c1cc(F)ccc1-c1cc(C2CC2)nc(N2Cc3c(F)cc(CNCC4(O)CCC4)cc3C2=O)c1] |

TABLE 1-continued

Selected Compounds

| Compound # | Compound ID | Structure |
|---|---|---|
| 365 | AMI-1 | 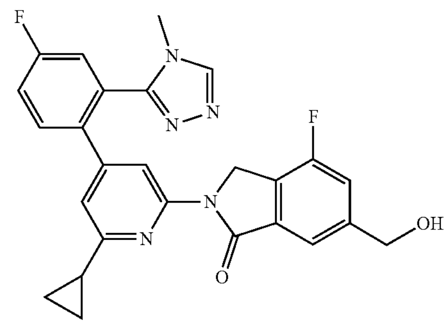 [SMILES: Cn1cnnc1-c1cc(F)ccc1-c1cc(C2CC2)nc(N2Cc3c(F)cc(CO)cc3C2=O)c1] |
| 366 | AML-1 | 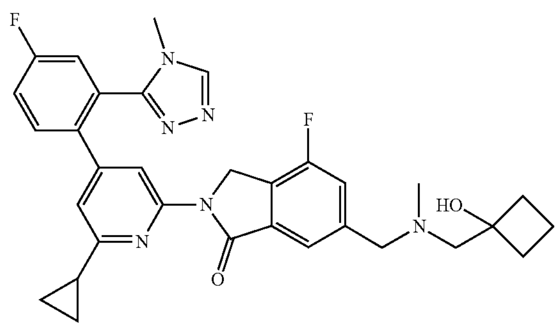 [SMILES: CN(Cc1cc(F)c2c(c1)C(=O)N(c1cc(-c3ccc(F)cc3-c3nncn3C)cc(C3CC3)n1)C2)CC1(O)CCC1] |
| 367 | AMM-1 | 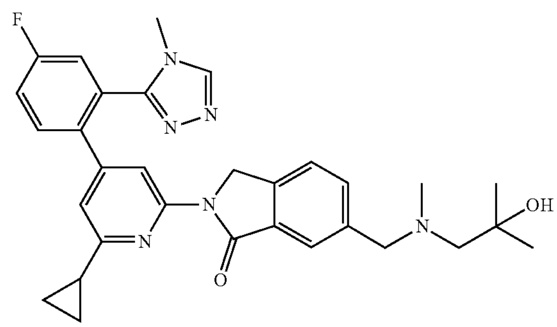 [SMILES: CN(Cc1ccc2c(c1)C(=O)N(c1cc(-c3ccc(F)cc3-c3nncn3C)cc(C3CC3)n1)C2)CC(C)(C)O] |
| 368 | AMN-1 | 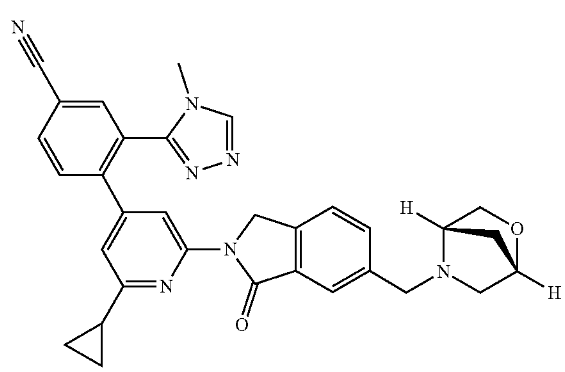 [SMILES: Cn1cnnc1-c1cc(C#N)ccc1-c1cc(C2CC2)nc(N2Cc3ccc(CN4C[C@@H]5C[C@H]4CO5)cc3C2=O)c1] |

TABLE 1-continued

Selected Compounds

| Compound # | Compound ID | Structure |
|---|---|---|
| 369 | AMO-2 | 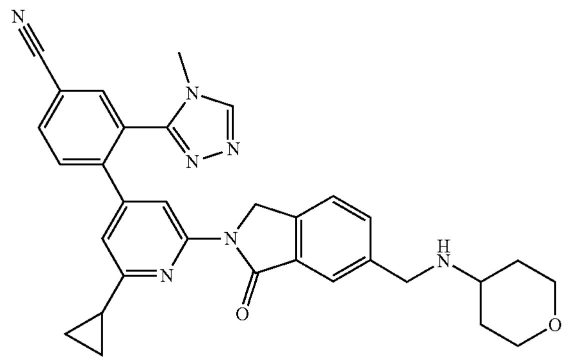 [SMILES: Cn1cnnc1-c1cc(C#N)ccc1-c1cc(C2CC2)nc(N2Cc3ccc(CNC4CCOCC4)cc3C2=O)c1] |
| 370 | ALX-9 | 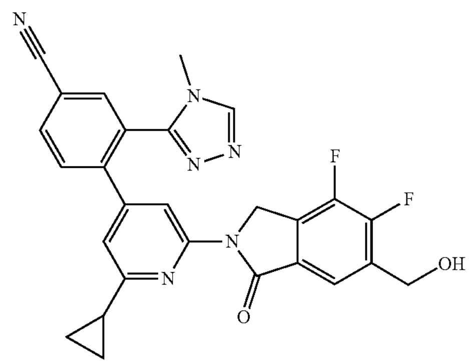 [SMILES: Cn1cnnc1-c1cc(C#N)ccc1-c1cc(C2CC2)nc(N2Cc3c(cc(CO)c(F)c3F)C2=O)c1] |
| 371 | AMP-1 | 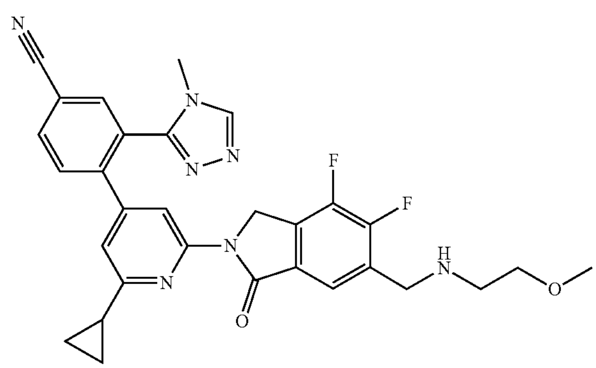 [SMILES: COCCNCc1cc2c(c(F)c1F)CN(c1cc(-c3ccc(C#N)cc3-c3nncn3C)cc(C3CC3)n1)C2=O] |
| 372 | AMQ-2 | 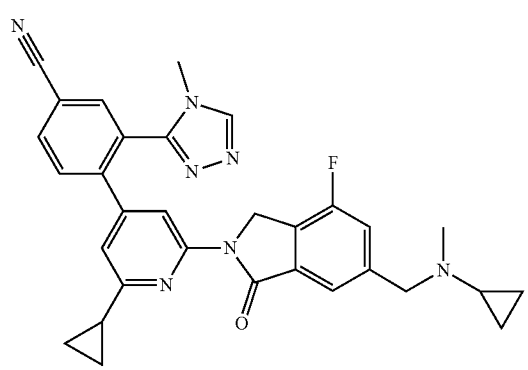 [SMILES: CN(Cc1cc(F)c2c(c1)C(=O)N(c1cc(-c3ccc(C#N)cc3-c3nncn3C)cc(C3CC3)n1)C2)C1CC1] |

TABLE 1-continued
Selected Compounds
| Compound # | Compound ID | Structure |
|---|---|---|
| 373 | AMR-2 | 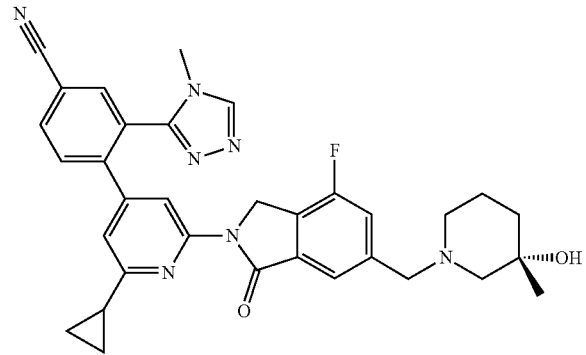 [SMILES: Cn1cnnc1-c1cc(C#N)ccc1-c1cc(C2CC2)nc(N2Cc3c(F)cc(CN4CCC[C@](C)(O)C4)cc3C2=O)c1] |
| 374 | AMS-2 | 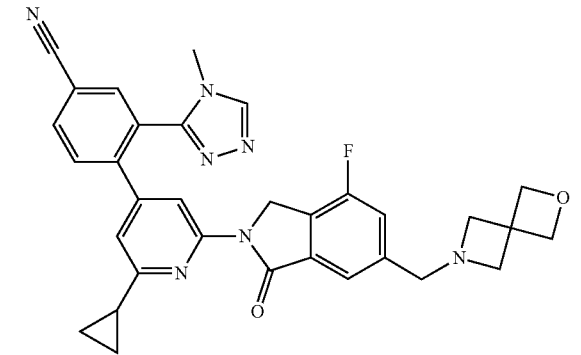 [SMILES: Cn1cnnc1-c1cc(C#N)ccc1-c1cc(C2CC2)nc(N2Cc3c(F)cc(CN4CC5(COC5)C4)cc3C2=O)c1] |
| 375 | AMT-2 | 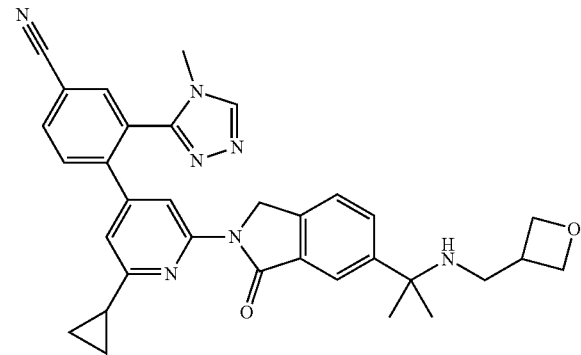 [SMILES: Cn1cnnc1-c1cc(C#N)ccc1-c1cc(C2CC2)nc(N2Cc3ccc(C(C)(C)NCC4COC4)cc3C2=O)c1] |
| 376 | AMU-2 | 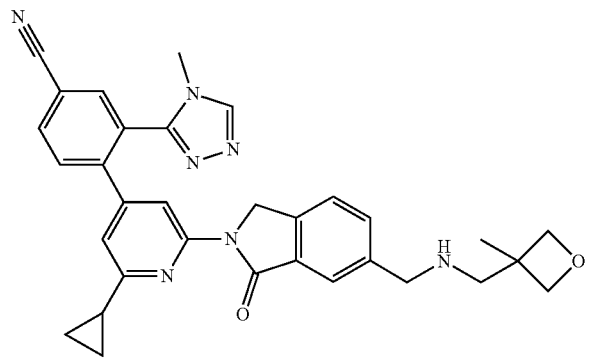 [SMILES: Cn1cnnc1-c1cc(C#N)ccc1-c1cc(C2CC2)nc(N2Cc3ccc(CNCC4(C)COC4)cc3C2=O)c1] |

TABLE 1-continued

| Compound # | Compound ID | Structure |
|---|---|---|
| 377 | AMV-2 | 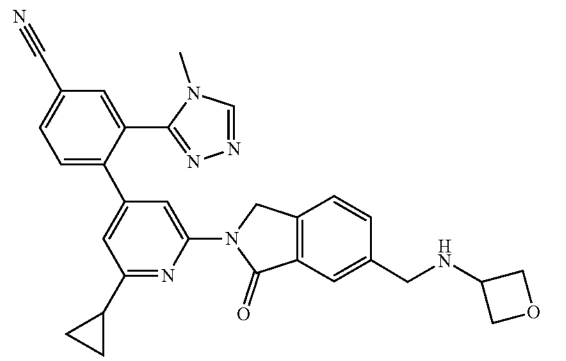 [SMILES: Cn1cnnc1-c1cc(C#N)ccc1-c1cc(C2CC2)nc(N2Cc3ccc(CNC4COC4)cc3C2=O)c1] |
| 378 | AMW-2 | 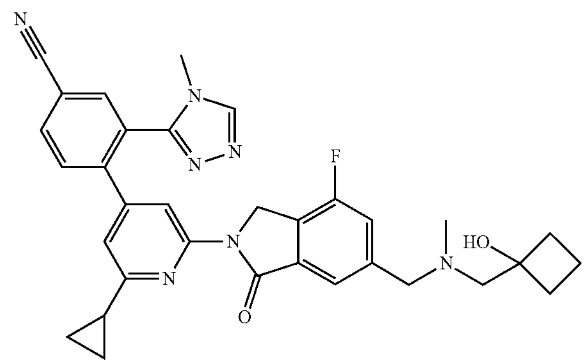 [SMILES: CN(Cc1cc(F)c2c(c1)C(=O)N(c1cc(-c3ccc(C#N)cc3-c3nncn3C)cc(C3CC3)n1)C2)CC1(O)CCC1] |
| 379 | AMZ-3 | 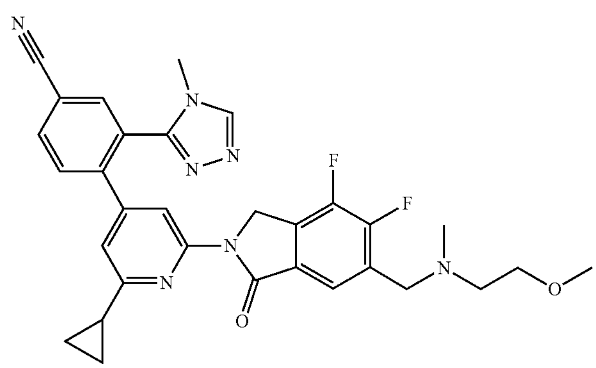 [SMILES: COCCN(C)Cc1cc2c(c(F)c1F)CN(c1cc(-c3ccc(C#N)cc3-c3nncn3C)cc(C3CC3)n1)C2=O] |
| 380 | AMX-3 | 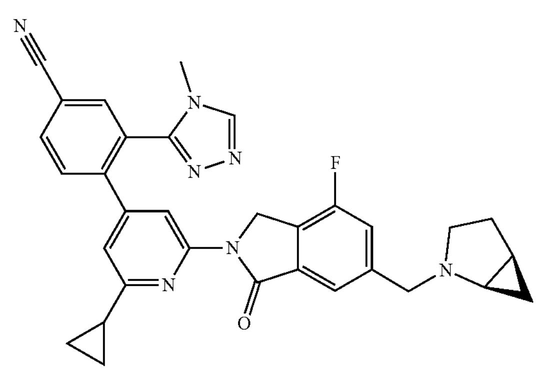 [SMILES: Cn1cnnc1-c1cc(C#N)ccc1-c1cc(C2CC2)nc(N2Cc3c(F)cc(CN4CC[C@H]5C[C@H]54)cc3C2=O)c1] |

TABLE 1-continued

Selected Compounds

| Compound # | Compound ID | Structure |
|---|---|---|
| 381 | AMY-1 | 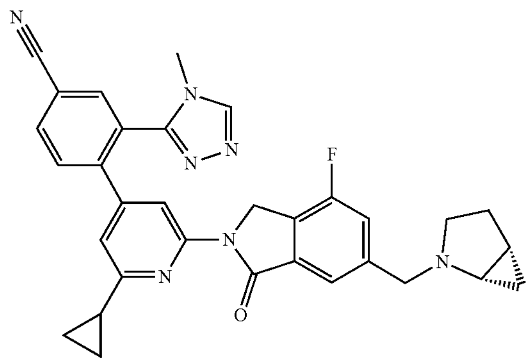 [SMILES: Cn1cnnc1-c1cc(C#N)ccc1-c1cc(C2CC2)nc(N2Cc3c(F)cc(CN4CC[C@@H]5C[C@@H]54)cc3C2=O)c1] |
| 382 | ANA-1 | 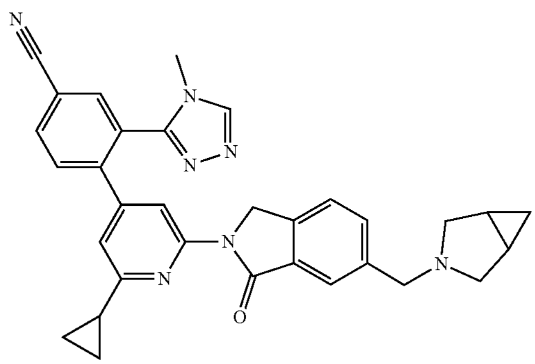 [SMILES: Cn1cnnc1-c1cc(C#N)ccc1-c1cc(C2CC2)nc(N2Cc3ccc(CN4CC5CC5C4)cc3C2=O)c1] |
| 383 | ANB-1 | 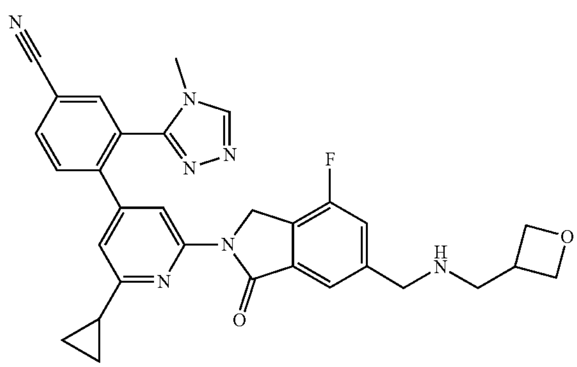 [SMILES: Cn1cnnc1-c1cc(C#N)ccc1-c1cc(C2CC2)nc(N2Cc3c(F)cc(CNCC4COC4)cc3C2=O)c1] |
| 384 | ANC-2 | 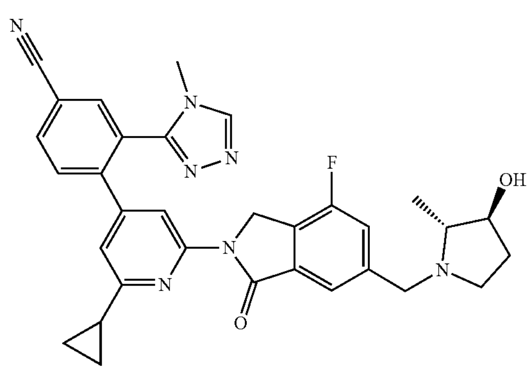 [SMILES: C[C@@H]1[C@@H](O)CCN1Cc1cc(F)c2c(c1)C(=O)N(c1cc(-c3ccc(C#N)cc3-c3nncn3C)cc(C3CC3)n1)C2] |

TABLE 1-continued
Selected Compounds
| Compound # | Compound ID | Structure |
|---|---|---|
| 385 | AND-1 | 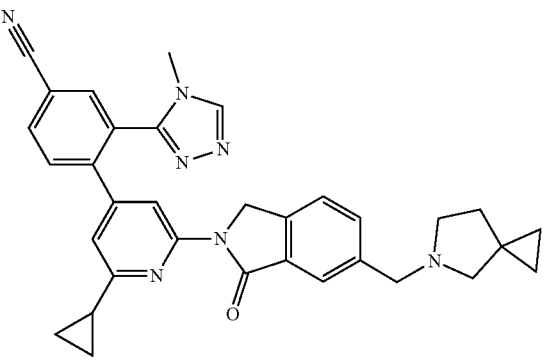 [SMILES: Cn1cnnc1-c1cc(C#N)ccc1-c1cc(C2CC2)nc(N2Cc3ccc(CN4CCC5(CC5)C4)cc3C2=O)c1] |
| 386 | ANE-1 | 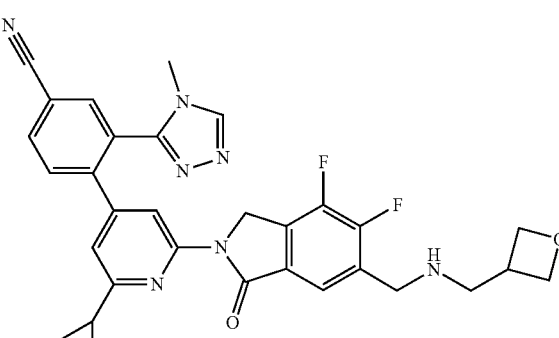 |
| 387 | ANF-11 | 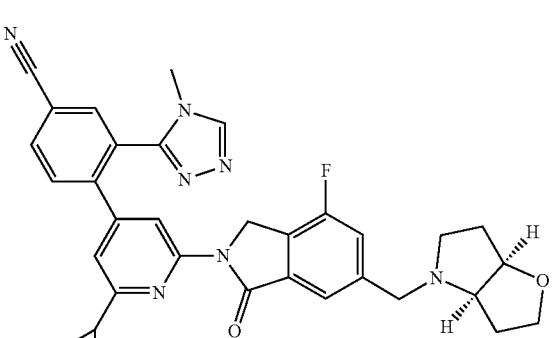 |
| 388 | ANG-1 | 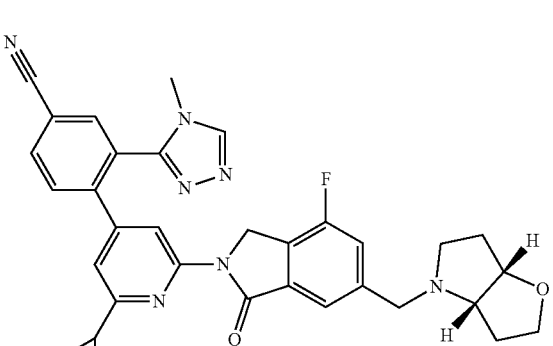 |

TABLE 1-continued

Selected Compounds

| Compound # | Compound ID | Structure |
|---|---|---|
| 389 | ANH-1 | 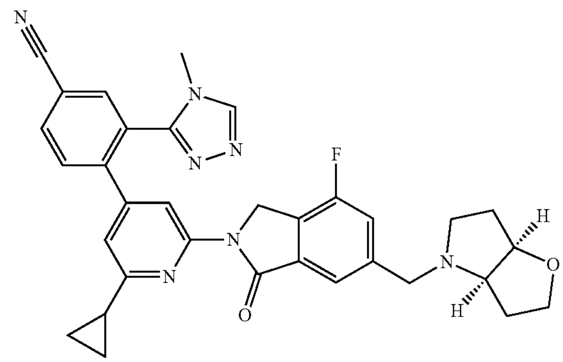 [SMILES: Cn1cnnc1-c1cc(C#N)ccc1-c1cc(C2CC2)nc(N2Cc3c(F)cc(CN4CC[C@H]5OCC[C@H]54)cc3C2=O)c1] |
| 390 | ANI-2 | 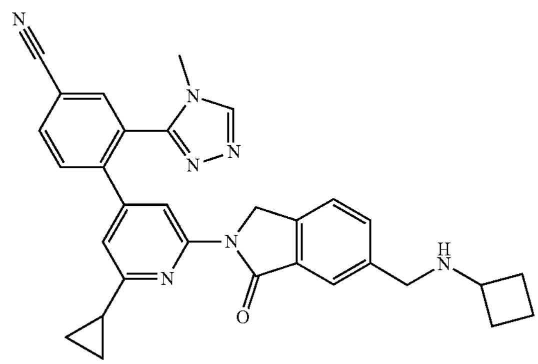 [SMILES: Cn1cnnc1-c1cc(C#N)ccc1-c1cc(C2CC2)nc(N2Cc3ccc(CNC4CCC4)cc3C2=O)c1] |
| 391 | ANJ-2 | 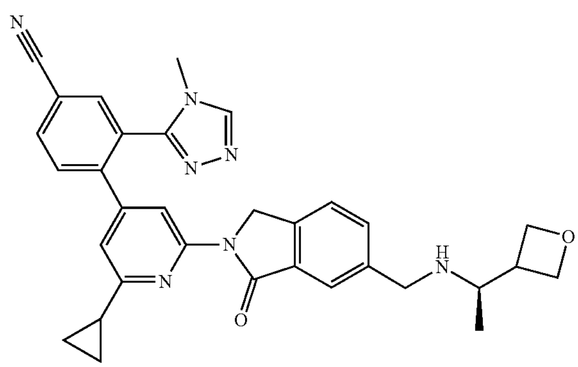 [SMILES: C[C@@H](NCc1ccc2c(c1)C(=O)N(c1cc(-c3ccc(C#N)cc3-c3nncn3C)cc(C3CC3)n1)C2)C1COC1] |
| 392 | ANK-2 | 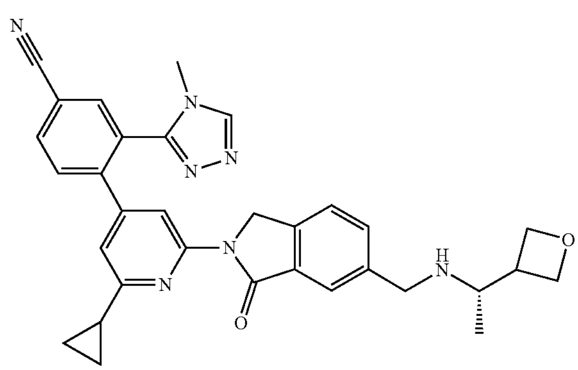 [SMILES: C[C@H](NCc1ccc2c(c1)C(=O)N(c1cc(-c3ccc(C#N)cc3-c3nncn3C)cc(C3CC3)n1)C2)C1COC1] |

TABLE 1-continued
Selected Compounds
| Compound # | Compound ID | Structure |
|---|---|---|
| 393 | ANL-2 | 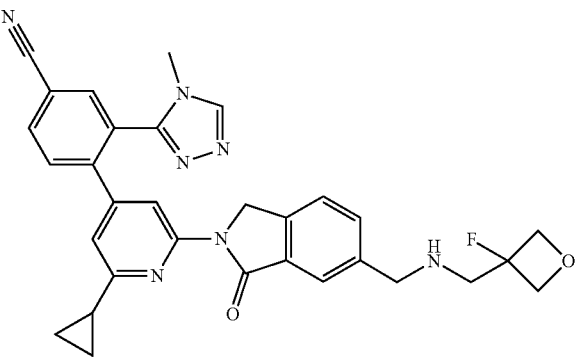 [SMILES: Cn1cnnc1-c1cc(C#N)ccc1-c1cc(C2CC2)nc(N2Cc3ccc(CNCC4(F)COC4)cc3C2=O)c1] |
| 394 | ANM-2 | 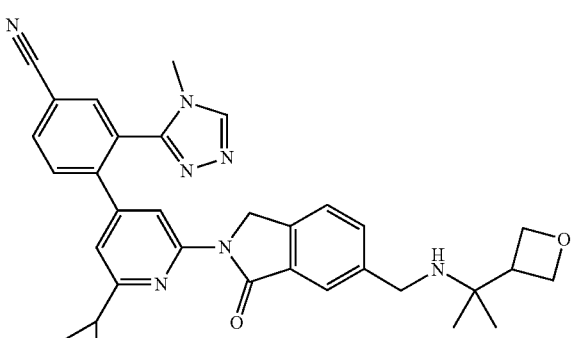 |
| 395 | ANN-2 | 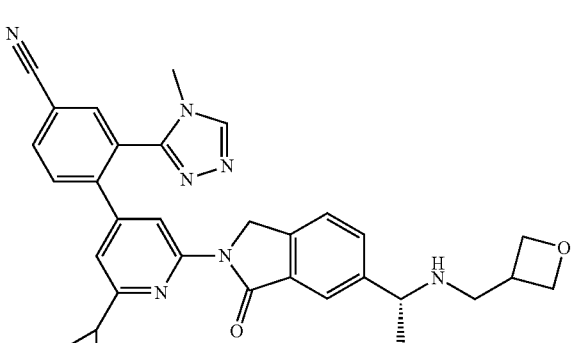 |
| 396 | ANO-1 | 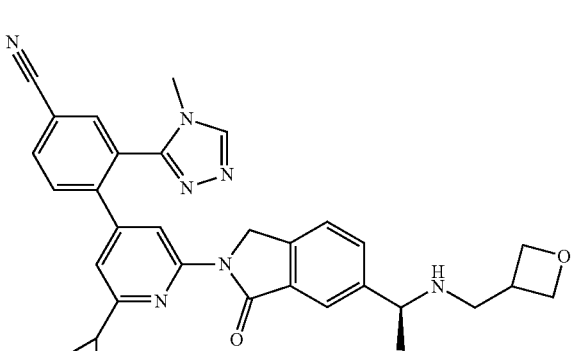 |

TABLE 1-continued

Selected Compounds

| Compound # | Compound ID | Structure |
|---|---|---|
| 397 | ANP-2 | 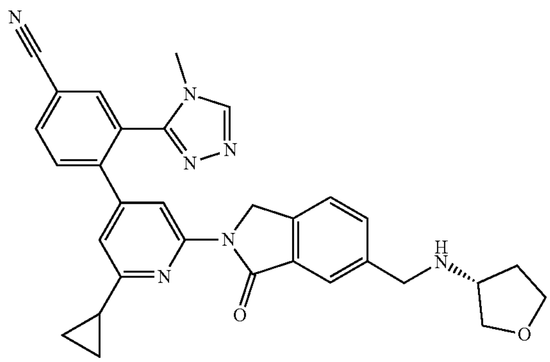 [SMILES: Cn1cnnc1-c1cc(C#N)ccc1-c1cc(C2CC2)nc(N2Cc3ccc(CN[C@@H]4CCOC4)cc3C2=O)c1] |
| 398 | ANQ-2 | 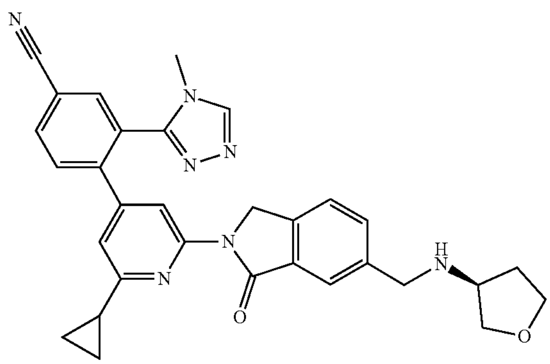 [SMILES: Cn1cnnc1-c1cc(C#N)ccc1-c1cc(C2CC2)nc(N2Cc3ccc(CN[C@H]4CCOC4)cc3C2=O)c1] |
| 399 | ANU-3 | 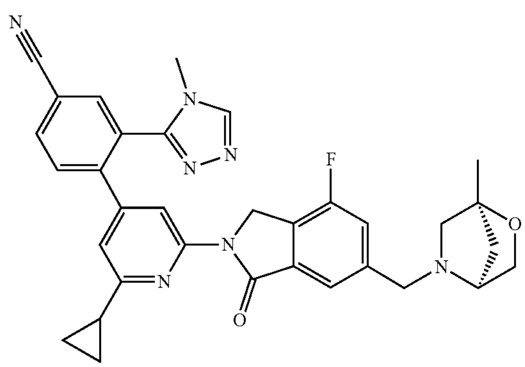 [SMILES: Cn1cnnc1-c1cc(C#N)ccc1-c1cc(C2CC2)nc(N2Cc3c(F)cc(CN4C[C@]5(C)C[C@H]4CO5)cc3C2=O)c1] |
| 400 | ANV-1 | 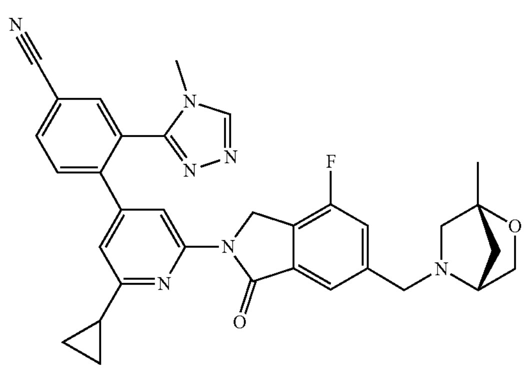 [SMILES: Cn1cnnc1-c1cc(C#N)ccc1-c1cc(C2CC2)nc(N2Cc3c(F)cc(CN4C[C@@]5(C)C[C@@H]4CO5)cc3C2=O)c1] |

TABLE 1-continued

Selected Compounds

| Compound # | Compound ID | Structure |
|---|---|---|
| 401 | ANW-3 | 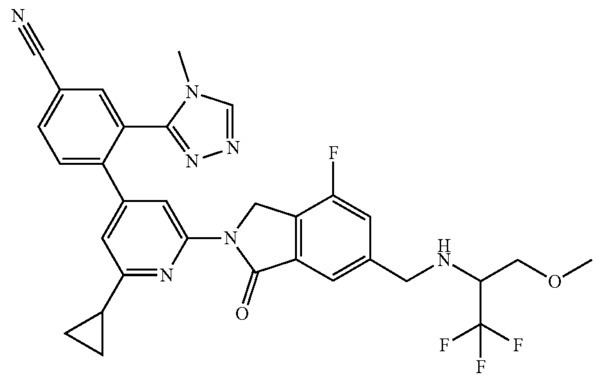 [SMILES: COCC(NCc1cc(F)c2c(c1)C(=O)N(c1cc(-c3ccc(C#N)cc3-c3nncn3C)cc(C3CC3)n1)C2)C(F)(F)F] |
| 402 | ANX-2 | 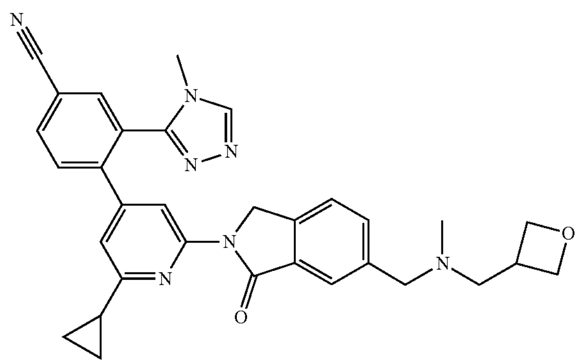 [SMILES: CN(Cc1ccc2c(c1)C(=O)N(c1cc(-c3ccc(C#N)cc3-c3nncn3C)cc(C3CC3)n1)C2)CC1COC1] |
| 403 | ANY-2 | 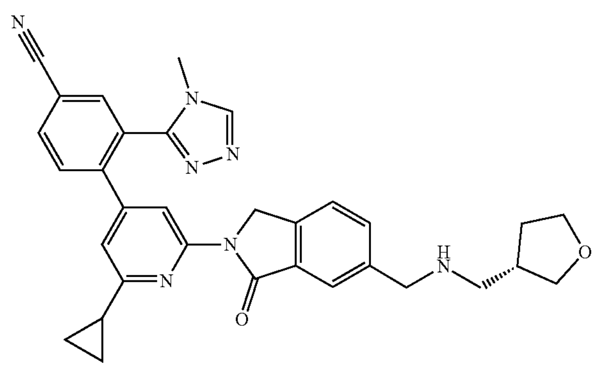 [SMILES: Cn1cnnc1-c1cc(C#N)ccc1-c1cc(C2CC2)nc(N2Cc3ccc(CNC[C@@H]4CCOC4)cc3C2=O)c1] |
| 404 | ANZ-2 | 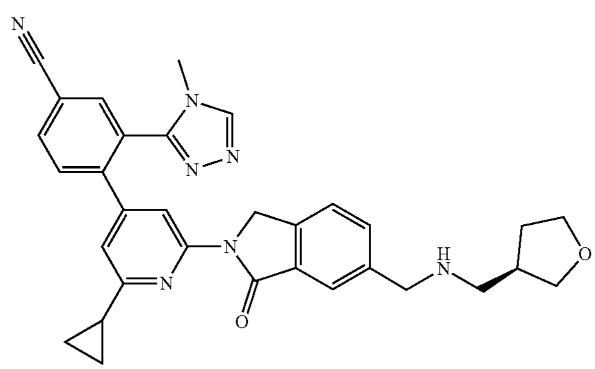 [SMILES: Cn1cnnc1-c1cc(C#N)ccc1-c1cc(C2CC2)nc(N2Cc3ccc(CNC[C@H]4CCOC4)cc3C2=O)c1] |

TABLE 1-continued

Selected Compounds

| Compound # | Compound ID | Structure |
|---|---|---|
| 405 | AOA-1 | 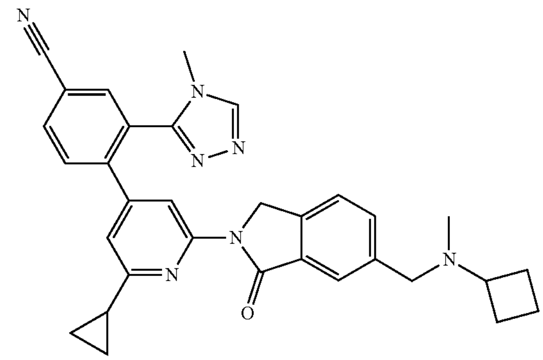 [SMILES: CN(Cc1ccc2c(c1)C(=O)N(c1cc(-c3ccc(C#N)cc3-c3nncn3C)cc(C3CC3)n1)C2)C1CCC1] |
| 406 | AOB-2 | 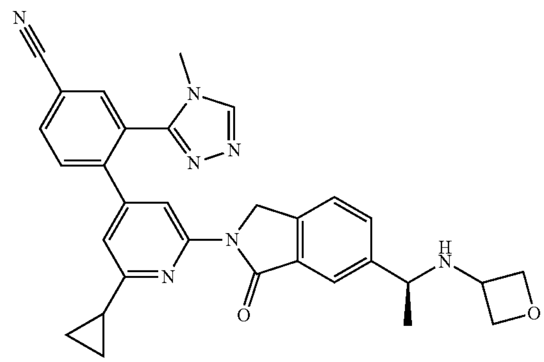 [SMILES: C[C@H](NC1COC1)c1ccc2c(c1)C(=O)N(c1cc(-c3ccc(C#N)cc3-c3nncn3C)cc(C3CC3)n1)C2] |
| 407 | AOC-2 | 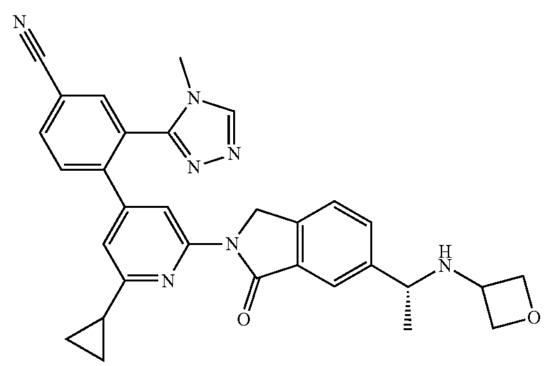 [SMILES: C[C@@H](NC1COC1)c1ccc2c(c1)C(=O)N(c1cc(-c3ccc(C#N)cc3-c3nncn3C)cc(C3CC3)n1)C2] |
| 408 | AOF-9 | 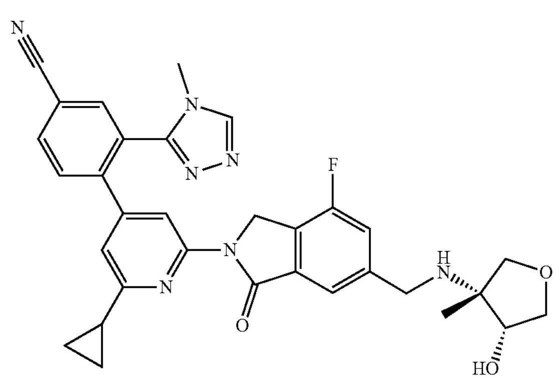 [SMILES: Cn1cnnc1-c1cc(C#N)ccc1-c1cc(C2CC2)nc(N2Cc3c(F)cc(CN[C@]4(C)COC[C@@H]4O)cc3C2=O)c1] |

TABLE 1-continued

Selected Compounds

| Compound # | Compound ID | Structure |
|---|---|---|
| 409 | AOO-2 | 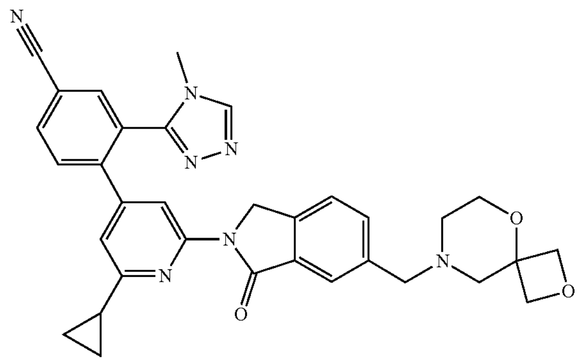 [SMILES: Cn1cnnc1-c1cc(C#N)ccc1-c1cc(C2CC2)nc(N2Cc3ccc(CN4CCOC5(COC5)C4)cc3C2=O)c1] |
| 410 | AOD-2 | 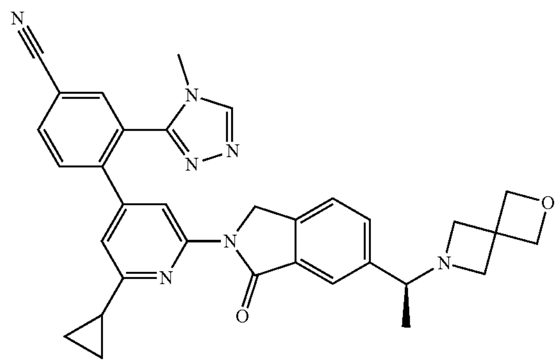 [SMILES: C[C@@H](c1ccc2c(c1)C(=O)N(c1cc(-c3ccc(C#N)cc3-c3nncn3C)cc(C3CC3)n1)C2)N1CC2(COC2)C1] |
| 411 | AOE-1 | 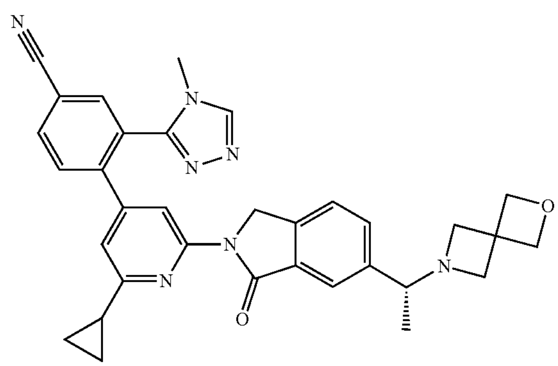 [SMILES: C[C@H](c1ccc2c(c1)C(=O)N(c1cc(-c3ccc(C#N)cc3-c3nncn3C)cc(C3CC3)n1)C2)N1CC2(COC2)C1] |
| 412 | AOG-1 | 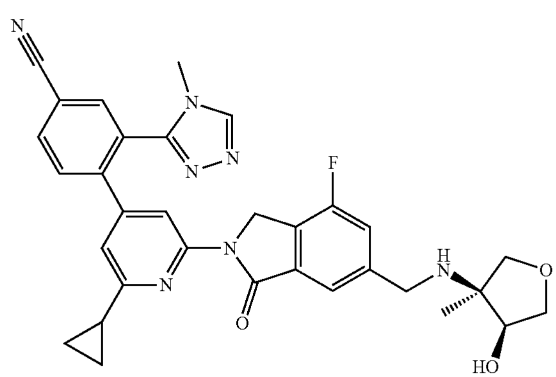 [SMILES: Cn1cnnc1-c1cc(C#N)ccc1-c1cc(C2CC2)nc(N2Cc3c(F)cc(CN[C@@]4(C)COC[C@H]4O)cc3C2=O)c1] |

TABLE 1-continued

Selected Compounds

| Compound # | Compound ID | Structure |
|---|---|---|
| 413 | AOH-1 | 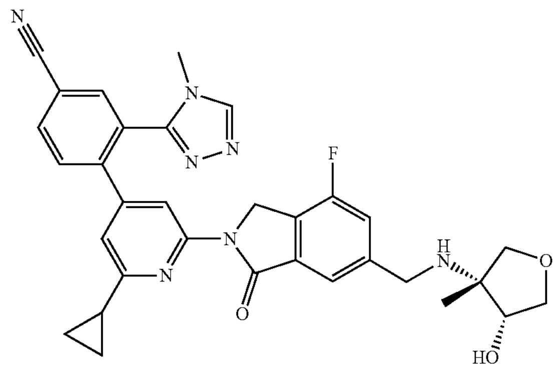 [SMILES: Cn1cnnc1-c1cc(C#N)ccc1-c1cc(C2CC2)nc(N2Cc3c(F)cc(CN[C@]4(C)COC[C@@H]4O)cc3C2=O)c1] |
| 414 | AOI-1 | 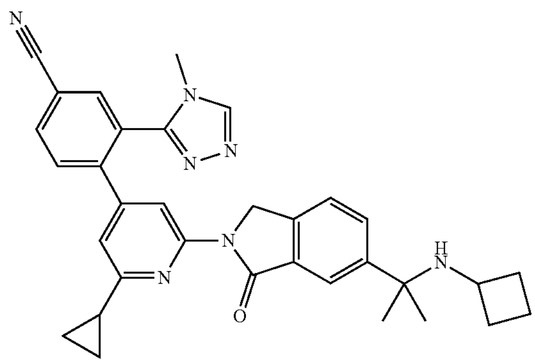 [SMILES: Cn1cnnc1-c1cc(C#N)ccc1-c1cc(C2CC2)nc(N2Cc3ccc(C(C)(C)NC4CCC4)cc3C2=O)c1] |
| 415 | AOL-1 | 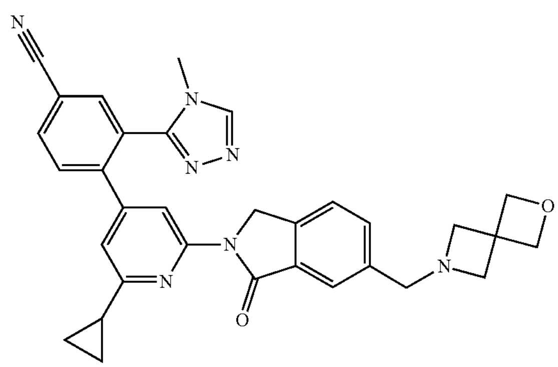 [SMILES: Cn1cnnc1-c1cc(C#N)ccc1-c1cc(C2CC2)nc(N2Cc3ccc(CN4CC5(COC5)C4)cc3C2=O)c1] |
| 416 | AOM-2 | 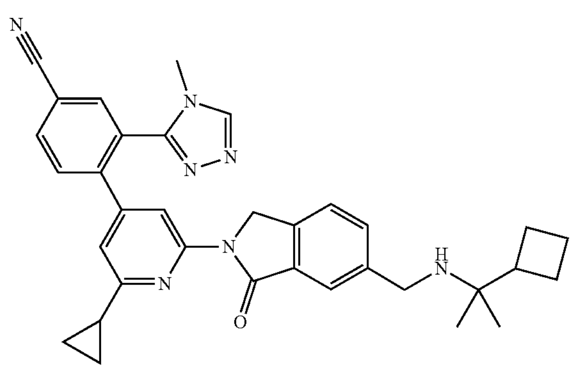 [SMILES: Cn1cnnc1-c1cc(C#N)ccc1-c1cc(C2CC2)nc(N2Cc3ccc(CNC(C)(C)C4CCC4)cc3C2=O)c1] |

TABLE 1-continued
Selected Compounds
| Compound # | Compound ID | Structure |
|---|---|---|
| 417 | AOJ-2 | 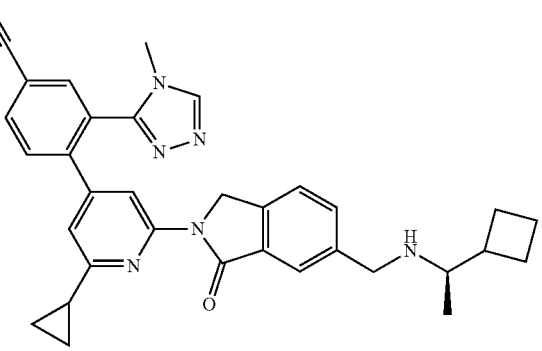 |
| 418 | AOK-2 | 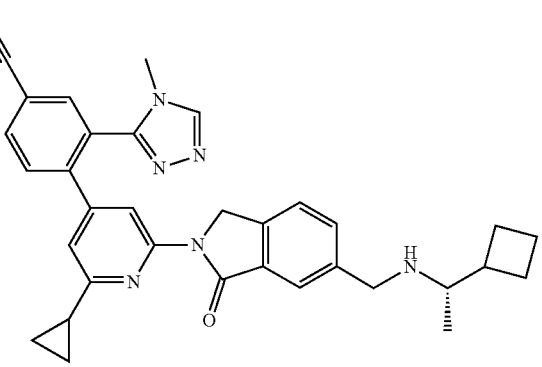 |
| 419 | AON-2 | 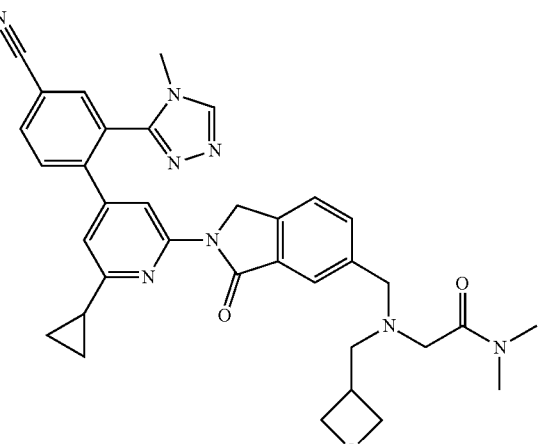 |
| 420 | AOR-1 | 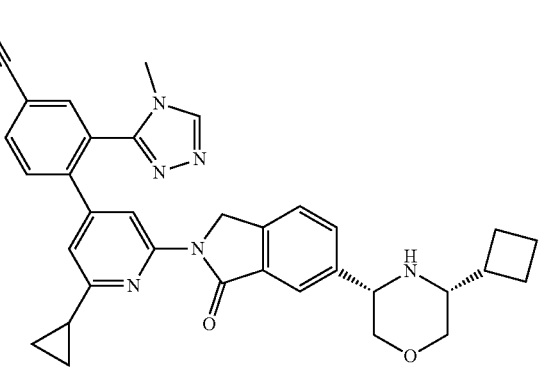 |

TABLE 1-continued

Selected Compounds

| Compound # | Compound ID | Structure |
|---|---|---|
| 421 | AOQ-1 | 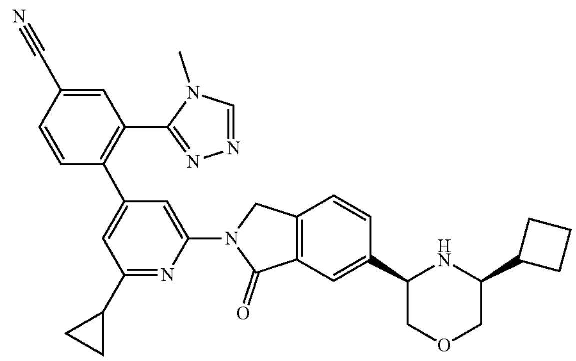 [SMILES: Cn1cnnc1-c1cc(C#N)ccc1-c1cc(C2CC2)nc(N2Cc3ccc([C@@H]4COC[C@H](C5CCC5)N4)cc3C2=O)c1] |
| 422 | AOS-2 | 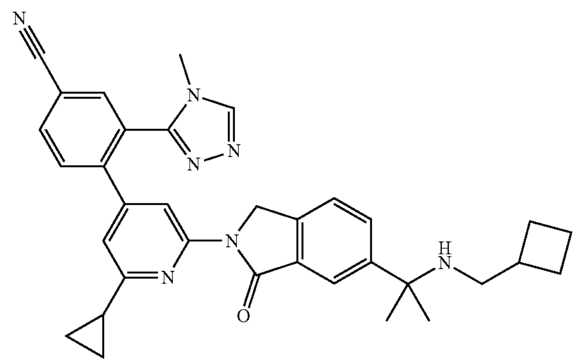 [SMILES: Cn1cnnc1-c1cc(C#N)ccc1-c1cc(C2CC2)nc(N2Cc3ccc(C(C)(C)NCC4CCC4)cc3C2=O)c1] |
| 423 | AOT-2 | 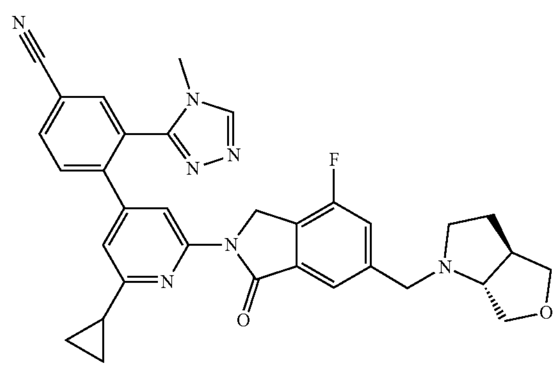 [SMILES: Cn1cnnc1-c1cc(C#N)ccc1-c1cc(C2CC2)nc(N2Cc3c(F)cc(CN4CC[C@H]5COC[C@@H]54)cc3C2=O)c1] |
| 424 | AOU-1 | 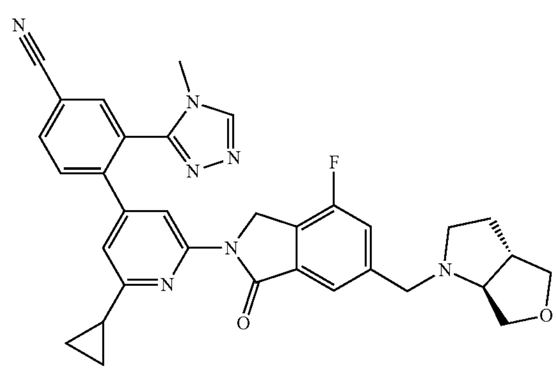 [SMILES: Cn1cnnc1-c1cc(C#N)ccc1-c1cc(C2CC2)nc(N2Cc3c(F)cc(CN4CC[C@@H]5COC[C@H]54)cc3C2=O)c1] |

TABLE 1-continued

Selected Compounds

| Compound # | Compound ID | Structure |
|---|---|---|
| 425 | AOV-1 | 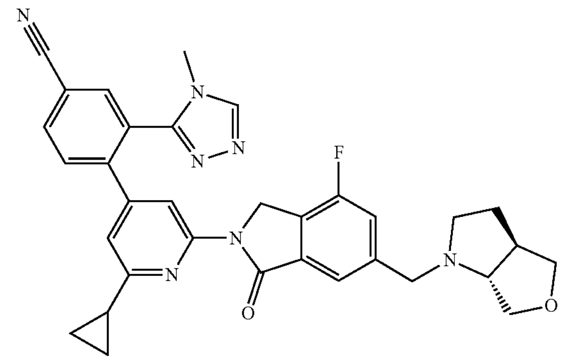 [SMILES: Cn1cnnc1-c1cc(C#N)ccc1-c1cc(C2CC2)nc(N2Cc3c(F)cc(CN4CC[C@H]5COC[C@@H]54)cc3C2=O)c1] |
| 426 | AOP-4 | 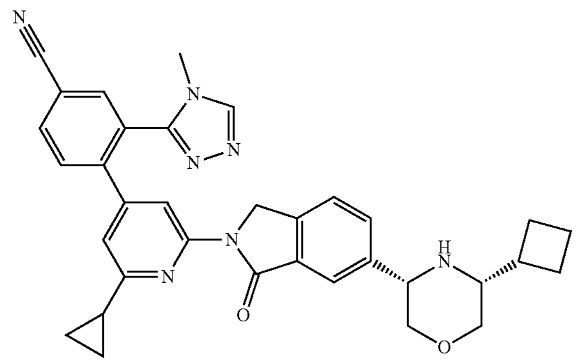 [SMILES: Cn1cnnc1-c1cc(C#N)ccc1-c1cc(C2CC2)nc(N2Cc3ccc([C@H]4COC[C@@H](C5CCC5)N4)cc3C2=O)c1] |
| 427 | AOZ-2 | 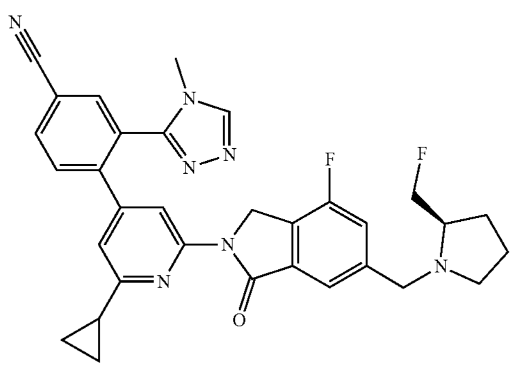 [SMILES: Cn1cnnc1-c1cc(C#N)ccc1-c1cc(C2CC2)nc(N2Cc3c(F)cc(CN4CCC[C@@H]4CF)cc3C2=O)c1] |
| 428 | APA-2 | 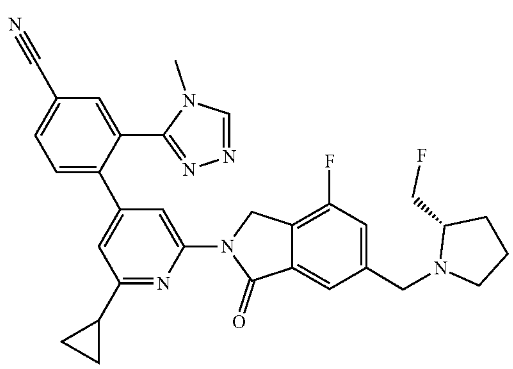 [SMILES: Cn1cnnc1-c1cc(C#N)ccc1-c1cc(C2CC2)nc(N2Cc3c(F)cc(CN4CCC[C@H]4CF)cc3C2=O)c1] |

TABLE 1-continued
Selected Compounds
| Compound # | Compound ID | Structure |
|---|---|---|
| 429 | AOW-2 | 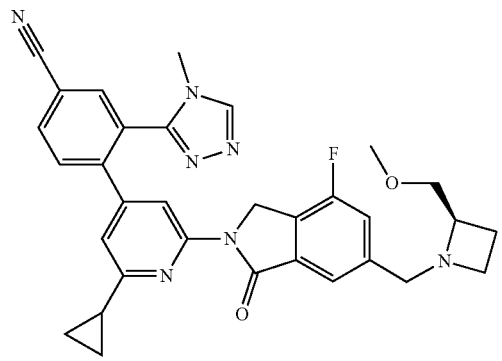 [SMILES: COC[C@H]1CCN1Cc1cc(F)c2c(c1)C(=O)N(c1cc(-c3ccc(C#N)cc3-c3nncn3C)cc(C3CC3)n1)C2] |
| 430 | APB-2 | 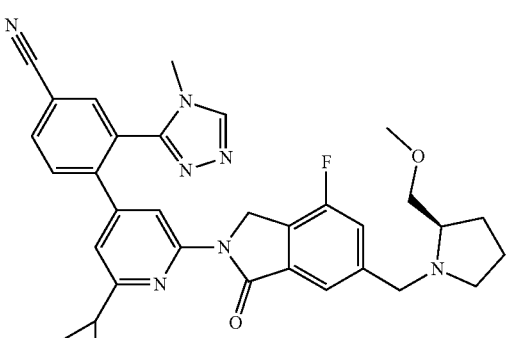 |
| 431 | AOY-2 | 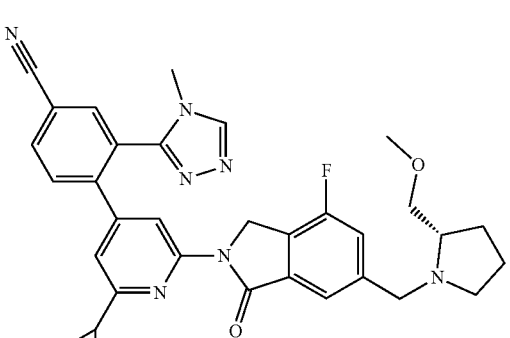 |
| 432 | AOX-1 | 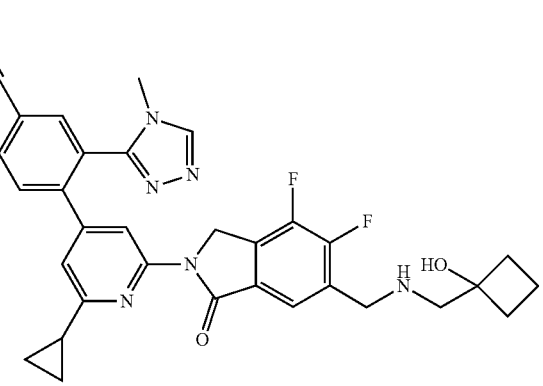 |

TABLE 1-continued

Selected Compounds

| Compound # | Compound ID | Structure |
|---|---|---|
| 433 | AOX-2 | 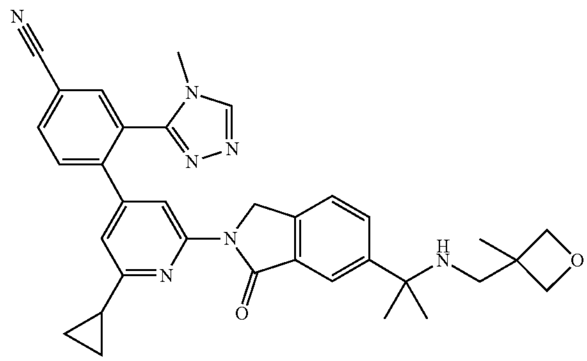 [SMILES: Cn1cnnc1-c1cc(C#N)ccc1-c1cc(C2CC2)nc(N2Cc3ccc(C(C)(C)NCC4(C)COC4)cc3C2=O)c1] |
| 434 | AOX-3 | 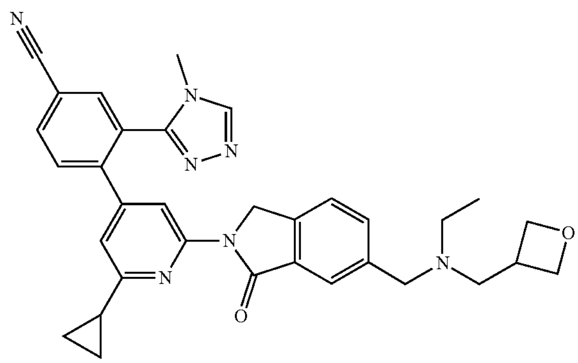 [SMILES: CCN(Cc1ccc2c(c1)C(=O)N(c1cc(-c3ccc(C#N)cc3-c3nncn3C)cc(C3CC3)n1)C2)CC1COC1] |
| 435 | AOX-4 | 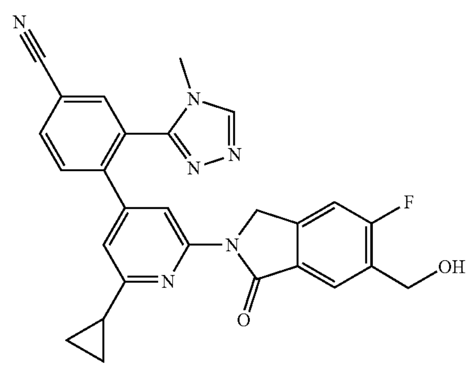 [SMILES: Cn1cnnc1-c1cc(C#N)ccc1-c1cc(C2CC2)nc(N2Cc3cc(F)c(CO)cc3C2=O)c1] |
| 436 | AOX-5 | 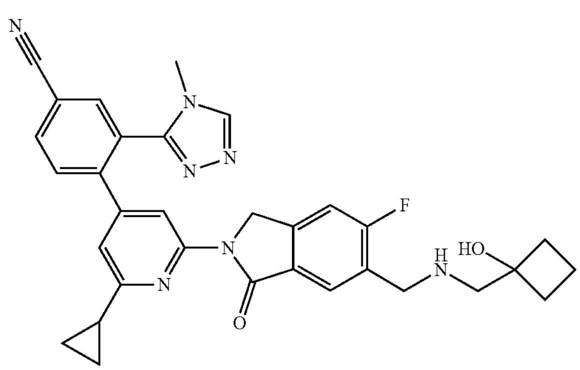 [SMILES: Cn1cnnc1-c1cc(C#N)ccc1-c1cc(C2CC2)nc(N2Cc3cc(F)c(CNCC4(O)CCC4)cc3C2=O)c1] |

In some embodiments, the present invention provides a compound set forth in Table 1, above, or a pharmaceutically acceptable salt thereof. In some embodiments, the present invention provides a compound set forth in Table 1, above.

In some embodiments, the present invention provides a pharmaceutical composition comprising a compound disclosed herein (described in embodiments herein, both singly and in combination), or a pharmaceutically acceptable salt thereof, together with a pharmaceutically acceptable carrier, excipient, or diluent. For example, in some embodiments, the present invention provides a pharmaceutical composition comprising a compound of formula I as defined above, or a pharmaceutically acceptable salt thereof, together with a pharmaceutically acceptable carrier, excipient, or diluent. In some embodiments, the present invention provides a pharmaceutical composition comprising a compound of formula I as defined above, together with a pharmaceutically acceptable carrier, excipient, or diluent. In some embodiments, the present invention provides a pharmaceutical composition comprising a compound set forth in Table 1 above, or a pharmaceutically acceptable salt thereof, together with a pharmaceutically acceptable carrier, excipient, or diluent. In some embodiments, the present invention provides a pharmaceutical composition comprising a compound set forth in Table 1 above, together with a pharmaceutically acceptable carrier, excipient, or diluent.

Exemplary compounds of the invention are set forth in Table 2, below.

TABLE 2

Selected Compounds

| Compound # | Compound ID | Structure |
|---|---|---|
| 437 | ABV-1 | 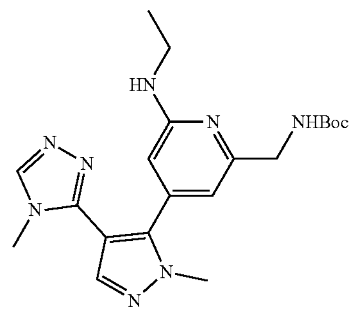 [SMILES: CCNc1cc(-c2c(-c3nncn3C)cnn2C)cc(CNC(=O)OC(C)(C)C)n1] |
| 438 | ABQ-1 | 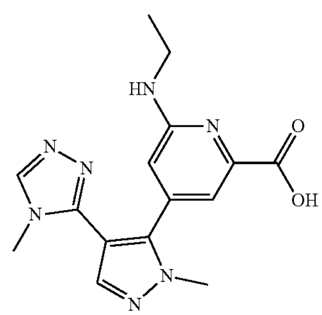 [SMILES: CCNc1cc(-c2c(-c3nncn3C)cnn2C)cc(C(=O)O)n1] |
| 439 | F-9 | 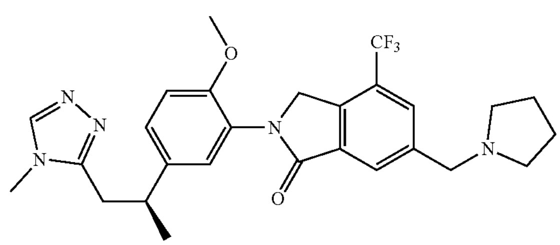 [SMILES: COc1ccc([C@@H](C)Cc2nncn2C)cc1N1Cc2c(cc(CN3CCCC3)cc2C(F)(F)F)C1=O] |
| 440 | AHJ-11 | 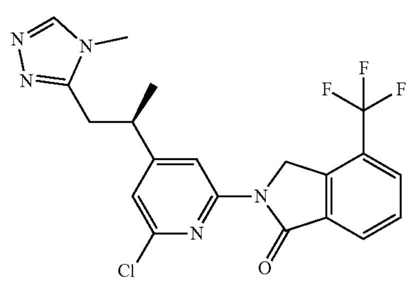 [SMILES: C[C@H](Cc1nncn1C)c1cc(Cl)nc(N2Cc3c(cccc3C(F)(F)F)C2=O)c1] |

TABLE 2-continued

Selected Compounds

| Compound # | Compound ID | Structure |
|---|---|---|
| 441 | AHK-1 | 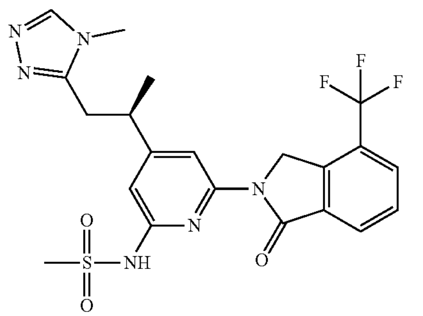 [SMILES: C[C@H](Cc1nncn1C)c1cc(NS(C)(=O)=O)nc(N2Cc3c(cccc3C(F)(F)F)C2=O)c1] |
| 442 | AHL-8 | 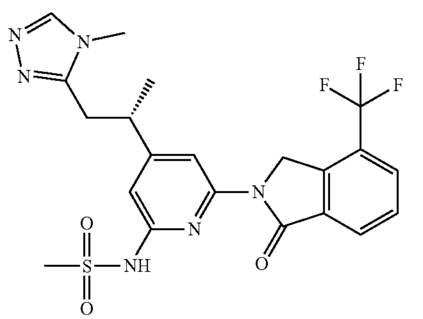 [SMILES: C[C@@H](Cc1nncn1C)c1cc(NS(C)(=O)=O)nc(N2Cc3c(cccc3C(F)(F)F)C2=O)c1] |
| 443 | AHM-12 | 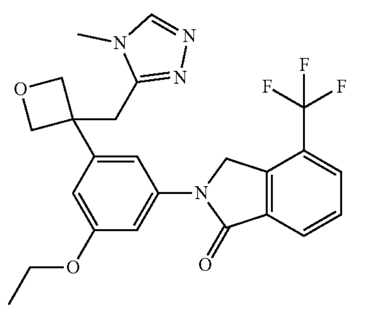 [SMILES: CCOc1cc(N2Cc3c(cccc3C(F)(F)F)C2=O)cc(C2(Cc3nncn3C)COC2)c1] |
| 444 | AX-3 | 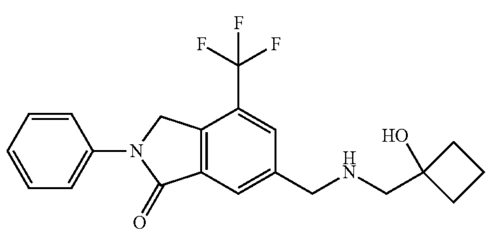 [SMILES: O=C1c2cc(CNCC3(O)CCC3)cc(C(F)(F)F)c2CN1c1ccccc1] |

In some embodiments, the present invention provides a compound of formula I as defined above, or a pharmaceutically acceptable salt thereof, or a pharmaceutical composition comprising a compound of formula I as defined above, or a pharmaceutically acceptable salt thereof, and a pharmaceutically acceptable carrier, adjuvant, or vehicle for use as a medicament.

In some embodiments, the invention also provides a compound described herein (such as a compound of formula I), or pharmaceutical compositions described herein, for use in a method for inhibiting Cbl-b as described herein and/or in a method for treating a Cbl-b-dependent disorder as described herein. In some embodiments, the invention also provides a compound described herein (such as a compound of formula I), or pharmaceutical compositions described herein, for use in a method for inhibiting Cbl-b as described herein. In some embodiments, the invention also provides a compound described herein (such as a compound of formula I), or pharmaceutical compositions described herein, for use in a method for treating a Cbl-b-dependent disorder as described herein.

In some embodiments, the invention also provides a compound described herein (such as a compound of formula I), or pharmaceutical compositions described herein, for use in a method for modulating Cbl-b as described herein and/or in a method for treating a Cbl-b-dependent disorder as described herein. In some embodiments, the invention also provides a compound described herein (such as a compound of formula I), or pharmaceutical compositions described herein, for use in a method for modulating Cbl-b as described herein. In some embodiments, the invention also provides a compound described herein (such as a compound of formula I), or pharmaceutical compositions described herein, for use in a method for treating a Cbl-b-dependent disorder as described herein.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. In certain embodiments, the amount of compound in compositions of this invention is such that is effective to measurably inhibit Cbl-b, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "active metabolite or residue thereof" means that a metabolite or residue thereof is also an inhibitor of Cbl-b, or a mutant thereof.

The subject matter disclosed herein includes prodrugs, metabolites, derivatives, and pharmaceutically acceptable salts of compounds of the invention. Metabolites include compounds produced by a process comprising contacting a compound of the invention with a mammal for a period of time sufficient to yield a metabolic product thereof. If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A compound of the invention can be in the form of a "prodrug," which includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs which are converted to active forms through other mechanisms in vivo are also included. In aspects, the compounds of the invention are prodrugs of any of the formulae herein.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Alternatively, pharmaceutically acceptable compositions of this invention may be administered in the form of suppositories for rectal or vaginal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch.

When aqueous suspensions are required for oral use, the active ingredient is combined with emulsifying and suspending agents. If desired, certain sweetening, flavoring or coloring agents may also be added.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

The amount of compounds of the present invention that may be combined with the carrier materials to produce a composition in a single dosage form will vary depending upon the host treated, the particular mode of administration. Preferably, provided compositions should be formulated so that a dosage of between 0.01 and 100 mg/kg, 0.01 and 50 mg/kg, or 1 and 25 mg/kg, body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment.

Uses of Compounds and Pharmaceutically Acceptable Compositions

The compounds and compositions described herein are generally useful for the inhibition of E3 ligase activity of one or more enzymes. In some embodiments the E3 ligase inhibited by the compounds and methods of the invention is Cbl-b.

The presently disclosed compounds find use in inhibiting the enzyme Cbl-b. In one embodiment, the subject matter disclosed herein is directed to a method of inhibiting Cbl-b, the method comprising contacting Cbl-b with an effective amount of a compound of the invention or a pharmaceutical composition described herein.

The presently disclosed compounds can be used in a method for inhibiting Cbl-b. Such methods comprise contacting Cbl-b with an effective amount of a presently disclosed compound. By "contact" is intended bringing the compound within close enough proximity to an isolated Cbl-b enzyme or a cell expressing Cbl-b such that the compound is able to bind to and inhibit the Cbl-b. The compound can be contacted with Cbl-b in vitro or in vivo via administration of the compound to a subject.

In one aspect, provided herein is a method of inhibiting Cbl-b in a biological sample. The method comprises contacting the sample with a compound disclosed herein (such as a compound of formula I), a pharmaceutically acceptable salt thereof, or a pharmaceutical composition disclosed herein (such as a composition comprising a compound disclosed herein [such as a compound of formula I] and a pharmaceutically acceptable carrier, adjuvant, or vehicle). The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

The present disclosure provides methods of inhibiting Cbl-b in a patient. The method comprises administering to a patient a compound disclosed herein (such as a compound of formula I), a pharmaceutically acceptable salt thereof, or a pharmaceutical composition disclosed herein (such as a composition comprising a compound disclosed herein [such as a compound of formula I] and a pharmaceutically acceptable carrier, adjuvant, or vehicle).

The presently disclosed compounds may or may not be selective Cbl-b inhibitors. A selective Cbl-b inhibitor inhibits the biological activity of Cbl-b by an amount that is statistically greater than the inhibiting effect of the inhibitor on any other protein (e.g., other E3 ligases). In some of these embodiments, the $IC_{50}$ of the Cbl-b inhibitor for Cbl-b is about 90%, 80%, 70%, 60%, 50%, 40%, 30%, 20%, 10%, 0.1%, 0.01%, 0.001%, or less of the $IC_{50}$ of the Cbl-b inhibitor for another E3 ligase.

Any method known in the art to measure the ligase activity of Cbl-b may be used to determine if Cbl-b has been inhibited, including in vitro kinase assays, immunoblots with antibodies specific for ubiquitinated targets of Cbl-b, or the measurement of a downstream biological effect of Cbl-b ligase activity.

The presently disclosed compounds can be used to treat an Cbl-b-dependent disorder. As used herein, a "Cbl-b-dependent disorder" is a pathological condition in which Cbl-b activity is necessary for the genesis or maintenance of the pathological condition.

Accordingly, in one aspect, provided herein is a method of treating a Cbl-b-mediated disorder, disease, or condition in a patient. The method comprises administering to said patient a compound disclosed herein (such as a compound of formula I), a pharmaceutically acceptable salt thereof, or a pharmaceutical composition disclosed herein (such as a composition comprising a compound disclosed herein [such as a compound of formula I] and a pharmaceutically acceptable carrier, adjuvant, or vehicle).

Provided herein are compounds and pharmaceutical compositions that inhibit the Cbl-b enzyme, as well as methods of treatment using such compounds and pharmaceutical compositions. The compounds and compositions can be used in methods of modulating the immune system, for treatment of diseases, and for treatment of cells in vivo, in vitro, or ex vivo.

T-cell activation and T-cell tolerance are tightly controlled processes regulating the immune response to tumors while preventing autoimmunity. Tolerance prevents the immune system from attacking cells expressing "self" antigens. During peripheral tolerance, T-cells that recognize "self" antigens (i.e., self-reactive T-cells) become functionally unresponsive or are deleted after encountering "self" antigens outside of the thymus. Peripheral tolerance processes therefore are important for preventing autoimmune diseases. Normally, cancer cells are removed by activated T-cells that recognize tumor antigens expressed on the surface of the cancer cells. However, in cancer, the tumor microenvironment can support T-cell tolerance to cancer cells, which allows cancer cells to avoid recognition and removal by the immune system. The ability of cancer cells to avoid tumor immunosurveillance can contribute to uncontrolled tumor growth. Therefore, T-cell tolerance can be a form of T-cell dysfunction. General principles of T-cell dysfunction are well known in the art (see Schietinger et al, Trends Immunol., 35: 51-60, 2014). Additional types of T-cell dysfunction that can contribute to uncontrolled tumor growth include T-cell exhaustion, T-cell senescence, and/or T-cell anergy. Therefore, treating T-cell dysfunction, for example, by increasing T-cell activation, increasing T-cell proliferation, decreasing T-cell tolerance, and/or decreasing T-cell exhaustion, is beneficial for preventing or treating cancer. Additional cells of the immune system are important for recognition and removal of cancer cells during immune surveillance. For example, Natural Killer (NK)-cells are lymphocytes of the innate immune system that are able to identify and kill cancer cells (see Martinez-Losato et al, Clin Cancer Res., 21: 5048-5056, 2015). Recent studies have also shown that B-cell subsets with distinct phenotypes and functions exhibit diverse roles in the anti-tumor response (see Saravaria et al, Cell Mol Immunol., 14: 662-674, 2017). Due to their role in tumor surveillance, NK-cells and B-cells may also be amenable as therapeutic targets for the prevention or treatment of cancer.

Cbl-b is a RING-type E3 ligase that plays an important role in the immune system due to its function as a negative regulator of immune activation. Cbl-b has an essential role in decreasing the activation of T-cells, thereby enhancing T-cell tolerance. Studies have found that Cbl-b-deficient T-cells display lower thresholds for activation by antigen recognition receptors and co-stimulatory molecules (e.g., CD28). For example, loss of Cbl-b in T-cells uncouples the requirement for CD28 costimulation during T-cell activation and proliferation (see Bachmaier el al, Nature, 403: 211-216, 2000). Such cbl-b−/− T-cells are largely resistant to T-cell anergy, a tolerance mechanism in which T-cells are functionally inactivated and T-cell proliferation is greatly impaired (see Jeon el al, Immunity, 21: 167-177, 2004; and Schwartz et al, Annu Rev Immunol., 21: 305-34, 2003). In support of this, loss of Cbl-b in cbl-b knockout mice resulted in impaired induction of T-cell tolerance and exacerbated autoimmunity (see Jeon el al, Immunity, 21: 167-177, 2004). Importantly, loss of Cbl-b in mice also resulted in a robust anti-tumor response that depends primarily on cytotoxic T-cells. One study showed that cbl-b−/− CD8+ T-cells are resistant to T regulatory cell-mediated suppression and exhibit enhanced activation and tumor infiltration. Therapeutic transfer of naive cbl-b−/− CD8+ T-cells was sufficient to mediate rejection of established tumors (see Loeser et al, J Exp Med., 204: 879-891, 2007). Recent studies have shown that Cbl-b also plays a role in NK-cell activation. Genetic deletion of Cbl-b or targeted inactivation of its E3 ligase activity allowed NK-cells to spontaneously reject metastatic tumors in a mouse model (see Paolino et al, Nature, 507: 508-512, 2014).

Provided herein are compounds and compositions that are potent inhibitors of Cbl-b and can be used in novel approaches to treat diseases such as cancer. In some embodiments, the compounds and compositions provided herein can be used in methods of modulating the immune system, such as increasing activation of T-cells, NK-cells and B-cells, as well as in the treatment of such cells in vivo, in vitro, or ex vivo.

Provided herein are methods for modulating activity of an immune cell (e.g., a T-cell, a B-cell, or a NK-cell) such as by contacting the immune cell with an effective amount of a Cbl-b inhibitor described herein or a composition thereof. Further provided are in vivo methods of modulating a response in an individual in need thereof (e.g., an individual with cancer), wherein the method comprises administration of an effective amount of a Cbl-b inhibitor described herein or a composition thereof.

Additionally, provided are Cbl-b inhibitors for use as therapeutic active substances. A Cbl-b inhibitor for use in treating or preventing a disease or condition associated with Cbl-b activity is provided. Also, a Cbl-b inhibitor for use in treating cancer is provided. Further provided is the use of a Cbl-b inhibitor in the manufacture of a medicament for treating or preventing a disease or condition associated with Cbl-b activity. Also provided is the use of a Cbl-b inhibitor in the manufacture of a medicament for treating cancer.

Moreover, this disclosure provides treatment methods, medicaments, and uses comprising a Cbl-b inhibitor as part of a combination therapy for treating cancer involving one or more of an immune checkpoint inhibitor, an antineoplastic agent, and radiation therapy.

In some embodiments of the treatment methods, medicaments, and uses of this disclosure, the cancer is a hematologic cancer such as lymphoma, a leukemia, or a myeloma. In other embodiments of the treatment methods, medicaments, and uses of this disclosure, the cancer is a non-hematologic cancer such as a sarcoma, a carcinoma, or a melanoma.

Hematologic cancers include, but are not limited to, one or more leukemias such as B-cell acute lymphoid leukemia ("BALL"), T-cell acute lymphoid leukemia ("TALL"), acute lymphoid leukemia (ALL); one or more chronic leukemias including, but not limited to, chronic myelogenous leukemia (CML) and chronic lymphocytic leukemia (CLL); additional hematologic cancers or hematologic conditions including, but not limited to, B-cell prolymphocytic leukemia, blastic plasmacytoid dendritic cell neoplasm, Burkitf s lymphoma, diffuse large B-cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and"preleukemia," which are a diverse collection of hematological conditions united by ineffective production (or dysplasia) of myeloid blood cells.

Non-hematologic cancers include, but are not limited to, a neuroblastoma, renal cell carcinoma, colon cancer, colorectal cancer, breast cancer, epithelial squamous cell cancer, melanoma, stomach cancer, brain cancer, lung cancer (e.g., NSCLC), pancreatic cancer, cervical cancer, ovarian cancer, liver cancer, bladder cancer, prostate cancer, testicular cancer, thyroid cancer, uterine cancer, adrenal cancer, and head and neck cancer.

In some aspects, the effectiveness of administration of a Cbl-b inhibitor in the treatment of a disease or disorder such as cancer is measured by assessing clinical outcome, such as reduction in tumor size or number of tumors, and/or survival. In certain embodiments, "treating cancer" comprises assessing a patient's response to the treatment regimen according to the Response Evaluation Criteria in Solid Tumors (RECIST version 1.1) as described (see, e.g., Eisenhauer et al, Eur J Cancer, 45:228-247, 2009; and Nishino et al., Am J Roentgenol, 195: 281-289, 2010). Response criteria to determine objective anti-tumor responses per RECIST 1.1 include complete response (CR); partial response (PR); progressive disease (PD); and stable disease (SD).

Accordingly, in some embodiments, the Cbl-b-mediated disorder is a hematologic cancer. In one aspect, provided herein is a method of treating a hematologic cancer in a patient. The method comprises administering to said patient a compound disclosed herein (such as a compound of formula I), a pharmaceutically acceptable salt thereof, or a pharmaceutical composition disclosed herein (such as a composition comprising a compound disclosed herein [such as a compound of formula I] and a pharmaceutically acceptable carrier, adjuvant, or vehicle).

More generally, in some embodiments, the Cbl-b-mediated disorder is a non-hematologic cancer. In one aspect, provided herein is a method of treating a non-hematologic cancer in a patient. The method comprises administering to said patient a compound disclosed herein (such as a compound of formula I), a pharmaceutically acceptable salt thereof, or a pharmaceutical composition disclosed herein (such as a composition comprising a compound disclosed herein [such as a compound of formula I] and a pharmaceutically acceptable carrier, adjuvant, or vehicle). In some embodiments, the non-hematologic cancer is a neuroblastoma, renal cell carcinoma, colon cancer, colorectal cancer, breast cancer, epithelial squamous cell cancer, melanoma, stomach cancer, brain cancer, lung cancer (e.g., NSCLC), pancreatic cancer, cervical cancer, ovarian cancer, liver cancer, bladder cancer, prostate cancer, testicular cancer, thyroid cancer, uterine cancer, adrenal cancer, and head and neck cancer. In some embodiments, the non-hematologic cancer is colon cancer. In some embodiments, the non-hematologic cancer is liver cancer. In some embodiments, the non-hematologic cancer is lung cancer. In some embodiments, the non-hematologic cancer is breast cancer. In some embodiments, the non-hematologic cancer is brain cancer.

It has also been reported that Cbl-b inhibitors may provide benefit to patients suffering from cancer. Accordingly, in some embodiments, the Cbl-b-mediated disorder is a cancer. In one aspect, provided herein is a method of treating a cancer in a patient. The method comprises administering to said patient a compound disclosed herein (such as a compound of formula I), a pharmaceutically acceptable salt thereof, or a pharmaceutical composition disclosed herein (such as a composition comprising a compound disclosed herein [such as a compound of formula I] and a pharmaceutically acceptable carrier, adjuvant, or vehicle).

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In certain embodiments, the cancer is brain cancer, leukemia, skin cancer, prostate cancer, thyroid cancer, colon cancer, lung cancer or sarcoma. In another embodiment the cancer is selected from the group consisting of glioma, glioblastoma multiforme, paraganglioma, suprantentorial primordial neuroectodermal tumors, acute myeloid leukemia, myelodysplastic syndrome, chronic myelogenous leukemia, melanoma, breast, prostate, thyroid, colon, lung, central chondrosarcoma, central and periosteal chondroma tumors, fibrosarcoma, and cholangiocarcinoma.

In certain embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary (cancers in which a metastasized cancer is found but the original cancer site is not known). In particular embodiments, the cancer is present in an adult patient; in additional embodiments, the cancer is present in a pediatric patient. In particular embodiments, the cancer is AIDS-related.

In a further embodiment, the cancer is selected from brain and spinal cancers. In particular embodiments, the cancer is selected from the group consisting of anaplastic astrocytomas, glioblastomas, astrocytomas, and estheosioneuroblastomas (olfactory blastomas). In particular embodiments, the brain cancer is selected from the group consisting of astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma), oligodendroglial tumor (e.g., oligodendroglioma, and anaplastic oligodendroglioma), oligoastrocytic tumor (e.g., oligoastrocytoma, and anaplastic oligoastrocytoma), ependymoma (e.g., myxopapillary ependymoma, and anaplastic ependymoma); medulloblastoma, primitive neuroectodermal tumor, schwannoma, meningioma, atypical meningioma, anaplastic meningioma, pituitary adenoma, brain stem glioma, cerebellar astrocytoma, cerebral astorcytoma/malignant glioma, visual pathway and hypothalmic glioma, and primary central nervous system lymphoma. In specific instances of these embodiments, the brain cancer is selected from the group consisting of glioma, glioblastoma multiforme, paraganglioma, and suprantentorial primordial neuroectodermal tumors (sPNET).

In specific embodiments, the cancer is selected from cancers of the head and neck, including nasopharyngeal cancers, nasal cavity and paranasal sinus cancers, hypopharyngeal cancers, oral cavity cancers (e.g., squamous cell carcinomas, lymphomas, and sarcomas), lip cancers, oropharyngeal cancers, salivary gland tumors, cancers of the larynx (e.g., laryngeal squamous cell carcinomas, rhabdomyosarcomas), and cancers of the eye or ocular cancers. In particular embodiments, the ocular cancer is selected from the group consisting of intraocular melanoma and retinoblastoma.

In specific embodiments, the cancer is selected from leukemia and cancers of the blood. In particular embodiments, the cancer is selected from the group consisting of myeloproliferative neoplasms, myelodysplastic syndromes, myelodysplastic/myeloproliferative neoplasms, acute myeloid leukemia (AML), myelodysplastic syndrome (MDS), chronic myelogenous leukemia (CML), myeloproliferative neoplasm (MPN), post-MPN AML, post-MDS AML, del(5q)-associated high risk MDS or AML, blast-phase chronic myelogenous leukemia, angioimmunoblastic lymphoma, acute lymphoblastic leukemia, Langerans cell histiocytosis, hairy cell leukemia, and plasma cell neoplasms including plasmacytomas and multiple myelomas. Leukemias referenced herein may be acute or chronic.

In specific embodiments, the cancer is selected from skin cancers. In particular embodiments, the skin cancer is selected from the group consisting of melanoma, squamous cell cancers, and basal cell cancers.

In specific embodiments, the cancer is selected from cancers of the reproductive system. In particular embodiments, the cancer is selected from the group consisting of breast cancers, cervical cancers, vaginal cancers, ovarian cancers, prostate cancers, penile cancers, and testicular cancers. In specific instances of these embodiments, the cancer is a breast cancer selected from the group consisting of ductal carcinomas and phyllodes tumors. In specific instances of these embodiments, the breast cancer may be male breast cancer or female breast cancer. In specific instances of these embodiments, the cancer is a cervical cancer selected from the group consisting of squamous cell carcinomas and adenocarcinomas. In specific instances of these embodiments, the cancer is an ovarian cancer selected from the group consisting of epithelial cancers.

In specific embodiments, the cancer is selected from cancers of the gastrointestinal system. In particular embodiments, the cancer is selected from the group consisting of esophageal cancers, gastric cancers (also known as stomach cancers), gastrointestinal carcinoid tumors, pancreatic cancers, gallbladder cancers, colorectal cancers, and anal cancer. In instances of these embodiments, the cancer is selected from the group consisting of esophageal squamous cell carcinomas, esophageal adenocarcinomas, gastric adenocarcinomas, gastrointestinal carcinoid tumors, gastrointestinal stromal tumors, gastric lymphomas, gastrointestinal lymphomas, solid pseudopapillary tumors of the pancreas, pancreatoblastoma, islet cell tumors, pancreatic carcinomas including acinar cell carcinomas and ductal adenocarcinomas, gallbladder adenocarcinomas, colorectal adenocarcinomas, and anal squamous cell carcinomas.

In specific embodiments, the cancer is selected from liver and bile duct cancers. In particular embodiments, the cancer is liver cancer (hepatocellular carcinoma). In particular embodiments, the cancer is bile duct cancer (cholangiocarcinoma); in instances of these embodiments, the bile duct cancer is selected from the group consisting of intrahepatic cholangiocarcinoma and extrahepatic cholangiocarcinoma.

In specific embodiments, the cancer is selected from kidney and bladder cancers. In particular embodiments, the cancer is a kidney cancer selected from the group consisting of renal cell cancer, Wilms tumors, and transitional cell cancers. In particular embodiments, the cancer is a bladder cancer selected from the group consisting of urethelial carcinoma (a transitional cell carcinoma), squamous cell carcinomas, and adenocarcinomas.

In specific embodiments, the cancer is selected from bone cancers. In particular embodiments, the bone cancer is selected from the group consisting of osteosarcoma, malignant fibrous histiocytoma of bone, Ewing sarcoma, and chordoma.

In specific embodiments, the cancer is selected from lung cancers. In particular embodiments, the lung cancer is selected from the group consisting of non-small cell lung cancer, small cell lung cancers, bronchial tumors, and pleuropulmonary blastomas.

In specific embodiments, the cancer is selected from malignant mesothelioma. In particular embodiments, the cancer is selected from the group consisting of epithelial mesothelioma and sarcomatoids.

In specific embodiments, the cancer is selected from sarcomas. In particular embodiments, the sarcoma is selected from the group consisting of central chondrosarcoma, central and periosteal chondroma, fibrosarcoma, clear cell sarcoma of tendon sheaths, and Kaposi's sarcoma.

In specific embodiments, the cancer is selected from lymphomas. In particular embodiments, the cancer is selected from the group consisting of Hodgkin lymphoma (e.g., Reed-Sternberg cells), non-Hodgkin lymphoma (e.g., diffuse large B-cell lymphoma, follicular lymphoma, mycosis fungoides, Sezary syndrome, primary central nervous system lymphoma), cutaneous T-cell lymphomas, and primary central nervous system lymphomas.

In specific embodiments, the cancer is selected from glandular cancers. In particular embodiments, the cancer is selected from the group consisting of adrenocortical cancer, pheochromocytomas, paragangliomas, pituitary tumors, thymoma, and thymic carcinomas.

In specific embodiments, the cancer is selected from thyroid cancers. In particular embodiments, the thyroid cancer is selected from the group consisting of medullary thyroid carcinomas, papillary thyroid carcinomas, and follicular thyroid carcinomas.

In specific embodiments, the cancer is selected from germ cell tumors. In particular embodiments, the cancer is selected from the group consisting of malignant extracranial germ cell tumors and malignant extragonadal germ cell tumors. In specific instances of these embodiments, the malignant extragonadal germ cell tumors are selected from the group consisting of nonseminomas and seminomas.

In specific embodiments, the cancer is selected from heart tumors. In particular embodiments, the heart tumor is selected from the group consisting of malignant teratoma, lymphoma, rhabdomyosacroma, angiosarcoma, chondrosarcoma, infantile fibrosarcoma, and synovial sarcoma.

In some embodiments, cancers treatable with compounds of the present disclosure include melanoma (e.g., metastatic malignant melanoma), renal cancer (e.g. clear cell carcinoma), prostate cancer (e.g. hormone refractory prostate adenocarcinoma), breast cancer, triple-negative breast cancer, colon cancer and lung cancer (e.g. non-small cell lung cancer and small cell lung cancer). Additionally, the disclosure includes refractory or recurrent malignancies whose growth may be inhibited using the compounds of the disclosure.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), T-cell acute lymphoblastic lymphoma (T-ALL), multiple myeloma, cutaneous T-cell lymphoma, Waldenstrom's Macroglubulinemia, hairy cell lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers.

The presently disclosed compounds may be administered in any suitable manner known in the art. In some embodiments, the compound of the invention or a pharmaceutically acceptable salt, prodrug, metabolite, or derivative thereof is administered intravenously, intramuscularly, subcutaneously, topically, orally, transdermally, intraperitoneally, intraorbitally, by implantation, by inhalation, intrathecally, intraventricularly, intratumorally, or intranasally.

In some embodiments, the Cbl-b inhibitor is administered continuously. In other embodiments, the Cbl-b inhibitor is administered intermittently. Moreover, treatment of a subject with an effective amount of a Cbl-b inhibitor can include a single treatment or can include a series of treatments.

It is understood that appropriate doses of the active compound depends upon a number of factors within the knowledge of the ordinarily skilled physician or veterinarian. The dose(s) of the active compound will vary, for example, depending upon the age, body weight, general health, gender, and diet of the subject, the time of administration, the route of administration, the rate of excretion, and any drug combination.

It will also be appreciated that the effective dosage of a compound of the invention or a pharmaceutically acceptable salt, prodrug, metabolite, or derivative thereof used for treatment may increase or decrease over the course of a particular treatment. Changes in dosage may result and become apparent from the results of diagnostic assays.

In some embodiments, the Cbl-b inhibitor is administered to the subject at a dose of between about 0.001 µg/kg and about 1000 mg/kg, including but not limited to about 0.001 µg/kg, 0.01 µg/kg, 0.05 µg/kg, 0.1 µg/kg, 0.5 µg/kg, 1 µg/kg, 10 µg/kg, 25 µg/kg, 50 µg/kg, 100 µg/kg, 250 µg/kg, 500 g/kg, 1 mg/kg, 5 mg/kg, 10 mg/kg, 25 mg/kg, 50 mg/kg, 100 mg/kg, and 200 mg/kg.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "subject" refers to animals such as mammals, including, but not limited to, primates (e.g., humans), cows, sheep, goats, horses, dogs, cats, rabbits, rats, mice and the like. In certain embodiments, the subject is a human.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent. Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anticonvulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In some embodiments, the present invention provides a method of treating a metabolic disorder, disease, or condition described herein, comprising administering a compound of the invention in conjunction with one or more pharmaceutical agents. Suitable pharmaceutical agents that may be used in combination with the compounds of the present invention include anti-diabetic agents, anti-obesity agents (including appetite suppressants), anti-hyperglycemic agents, lipid lowering agents, and anti-hypertensive agents.

Suitable anti-diabetic agents that can be used in conjunction with a provided compound or composition thereof include but are not limited to other acetyl-CoA carboxylase (ACC) inhibitors, DGAT-1 inhibitors, AZD7687, LCQ908, DGAT-2 inhibitors, monoacylglycerol O-acyltransferase inhibitors, PDE-10 inhibitors, AMPK activators, sulfonylureas (e.g. acetohexamide, chlorpropamide, diabinese, glibenclamide, glipizide, glyburide, blimipiride, gliclazide, glipentide, gliquidone, glisolamide, tolazamide, tolbutamide), meglitinides, alpha-amylase inhibitors (e.g. tendamistat, treastatin, AL-3688), alpha-glucoside hydrolase inhibitors (e.g. acarbose), alpha-glucosidase inhibitors (e.g. adiposine, camiglibose, emiglitate, miglitol, voglibose, pradimicin-Q, sarbostatin), PPAR-gamma agonists (e.g. balaglitazone, ciglitazone, darglitazone, englitazone, isaglitazone, pioglitazone, rosiglitazone, troglitazone), PPAR-alpha/gamma agonists (e.g. CLX-0940, GW-1536, GW-1929, GW-2433, KRP-297, L-796449, LR-90, MK-0767, SB-219994), biguanides (e.g. metformin, buformin), GLP-1 modulators (exendin-3, exendin-4), liraglutide, albiglutide, exenatide (Byetta), taspoglutide, lixisenatide, dulaglutide, semaglutide, N,N-9924, TTP-054, PTP-1B inhibitors (trodusquemine, hyrtiosal extract), SIRT-1 inhibitors (e.g. resveratrol, GSK2245840, GSK184072), DPP-IV inhibitors (e.g. sitagliptin, vildagliptin, alogliptin, dutogliptin, linagliptin, saxagliptin), insulin secretagogues, fatty acid oxidation inhibitors, A2 antagonists, JNK inhibitors, glucokinase activators (e.g. TTP-399, TTP-355, TTP-547, AZD1656, ARRY403, MK-0599, TAK-329, AZD5658, GKM-001), insulin, insulin mimetics, glycogen phosphorylase inhibitors (e.g. GSK1362885), VPAC2 receptor agonists, SGLT2 inhibitors (dapagliflozin, canagliflozin, BI-10733, tofogliflozin, ASP-1941, THR1474, TS-071, ISIS388626, LX4211), glucagon receptor modulators, GPR119 modulators (e.g. MBX-2982, GSK1292263, APD597, PSN821), FGF21 derivatives, TGR5 (GPBAR1) receptor agonists (e.g. INT777), GPR40 agonists (e.g. TAK-875), GPR120 agonists, nicotinic acid receptor (HM74A) activators, SGLT1 inhibitors (e.g. GSK1614235), carnitine palmitoyl transferase enzyme inhibitors, fructose 1,6-diphosphatase inhibitors, aldose reductase inhibitors, mineralocorticoid receptor inhibitors, TORC2 inhibitors, CCR2 inhibitors, CCR5 inhibitors, PKC (e.g. PKC-alpha, PKC-beta, PKC-gamma) inhibitors, fatty acid synthetase inhibitors, serine palmitoyl transferase inhibitors, GPR81 modulators, GPR39 modulators, GPR43 modulators, GPR41 modulators, GPR105 modulators, Kv1.3 inhibitors, retinol binding protein 4 inhibitors, glucocorticoid receptor modulators, somatostatin receptor (e.g. SSTR1, SSTR2, SSTR3, SSTR5) inhibitors, PDHK2 inhibitors, PDHK4 inhibitors, MAP4K4 inhibitors, IL1-beta modulators, and RXR-alpha modulators.

Suitable lipid lowering agents that can be used in conjunction with a provided compound or composition thereof include but are not limited to, bile acid sequestrants, HMG-CoA reductase inhibitors, HMG-CoA synthase inhibitors, cholesterol absorption inhibitors, acyl coenzyme A-cholesterol acyl transferase (ACAT) inhibitors, CETP inhibitors, squalene synthetase inhibitors, PPAR-alpha agonists, FXR receptor modulators, LXR receptor modulators, lipoprotein synthesis inhibitors, renin-angiotensin system inhibitors, PPAR-delta partial agonists, bile acid reabsorption inhibitors, PPAR-gamma agonists, triglyceride synthesis inhibitors, microsomal triglyceride transport inhibitors, transcription modulators, squalene epoxidase inhibitors, low density lipoprotein receptor inducers, platelet aggregation inhibitors, 5-LO or FLAP inhibitors, niacin, and niacin-bound chromium.

Suitable anti-obesity agents include but are not limited to, 11-beta-hydroxysteroid dehydrogenase 1 inhibitors, stearoyl-CoA desaturase (SCD-1) inhibitors, MCR-4 agonists, CCK-A agonists, monoamine reuptake inhibitors (e.g. sibutramine), sympathomimetic agents, beta-3-adrenergic receptor agonists, dopamine receptor agonists (e.g. bromocriptine), melanocyte-stimulating hormone and analogs thereof, 5-HT2c agonists (e.g. lorcaserin/Belviq), melanin concentrating hormone antagonists, leptin, leptin analogs, leptin agonists, galanin antagonists, lipase inhibitors (e.g. tetrahydrolipstatin/Orlistat), anorectic agents (e.g. bombesin agonists), NPY antagonists (e.g. velneperit), PYY3-36 (and analogs thereof), BRS3 modulators, opioid receptor mixed antagonists, thyromimetic agents, dehydroepiandrosterone, glucocorticoid agonists or antagonists, orexin antagonists, GLP-1 agonists, ciliary neurotrophic factors (e.g. Axokine), human agouti-related protein (AGRP) inhibitors, H3 antagonists or inverse agonists, neuromedin U agonists, MTP/ApoB inhibitors (e.g. gut-selective MTP inhibitors such as dirlotapide, JTT130, Usistapide, SLX4090), MetAp2 inhibitors (e.g. ZGN-433), agents with mixed modulatory activity at two or more of glucagon, GIP, and GLP1 receptors (e.g. MAR-701, ZP2929), norepinephrine reuptake inhibitors, opioid antagonists (e.g. naltrexone), CB1 receptor antagonists or inverse agonists, ghrelin agonists or antagonists, oxyntomodulin and analogs thereof, monoamine uptake inhibitors (e.g. tesofensine), and combination agents (e.g. buprorion plus zonisamide (Empatic), pramlintide plus metreleptin, buprorion plus naltrexone (Contrave), phentermine plus topiramate (Qsymia).

In some embodiments, the anti-obesity agents used in combination with a provided compound or composition thereof are selected from gut-selective MTP inhibitors (e.g. dirlotapide, mitratapide, implitapide, R56918), CCK-A agonists, 5-HT2C agonists (e.g. lorcaserin/Belviq), MCR4 agonists, lipase inhibitors (e.g. Cetilistat), PYY3-36 (including analogs and PEGylated analogs thereof), opioid antagonists (e.g. naltrexone), oleoyl estrone, obinepitide, pramlintide, tesofensine, leptin, bromocriptine, orlistat, AOD-9604, and sibutramine.

In another embodiment, the present invention provides a method of treating an inflammatory disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating a hematological malignancy comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a compound of formula I and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereof a compound of formula I and a BTK inhibitor, wherein the disease is selected from inflammatory bowel disease, arthritis, cutaneous lupus erythematosus, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, cutaneous lupus erythematosus, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), cutaneous lupus erythematosus, systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treating or lessening the severity of a disease comprising administering to a patient in need thereof a compound of formula I and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, non-small-cell lung cancer, myelodysplastic syndrome, lymphoma, a hematological neoplasm, or solid tumor.

In some embodiments, the disease is an autoimmune disorder, an inflammatory disorder, a proliferative disorder, an endocrine disorder, a neurological disorder, or a disorder associated with transplantation. In some embodiments the JH2 binding compound is a compound of formula I. Other suitable JH2 domain binding compounds include those described in WO2014074660A1, WO2014074661A1, WO2015089143A1, the entirety of each of which is incorporated herein by reference. Suitable JH1 domain binding compounds include those described in WO2015131080A1, the entirety of which is incorporated herein by reference.

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™ Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™ Teniposide is marketed under the trade name VM 26-Bristol Doxorubicin is marketed under the trade name Acriblastin™ or Adriamycin™. Epirubicin is marketed under the trade name Farmorubicin™ Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, ELI, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof, see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™ Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g. midostaurin or lestaurtinib), sorafenib, tandutinib, LY-2401401, LS-104, EB-10, famitinib, NOV-110302, NMS-P948, AST-487, G-749, SB-1317, S-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden),V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonist of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MEDI4736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or IMP-321 (WO08/132601, WO009/44273).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO006/105021, WO009/009116), or MK-4166 (WO11/028683).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Ikena Oncology, formerly known as Kyn Therapeutics); and NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO06/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (OPDIVO®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (POMALYST®, Celgene); lenalidomide (REVLIMID®, Celgene); ingenol mebutate (PICATO®, LEO Pharma).

In some embodiments, an immuno-oncology agent is a cancer vaccine. In some embodiments, the cancer vaccine is selected from sipuleucel-T (PROVENGE®, Dendreon/Valeant Pharmaceuticals), which has been approved for treatment of asymptomatic, or minimally symptomatic metastatic castrate-resistant (hormone-refractory) prostate cancer; and talimogene laherparepvec (IMLYGIC®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (REOLYSIN®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucuronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific $CD8^+$ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June et al.; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+ (Th17) and CD8+ (Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that can be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams et al., "Big opportunities for small molecules in immuno-oncology," Cancer Therapy 2015, Vol. 14, pages 603-622, the content of which is incorporated herein by reference in its entirety. In some embodiment, an immuno-oncology agent is selected from the examples described in Table 1 of Jerry L. Adams et al. In some embodiments, an immuno-oncology agent is a small molecule targeting an immuno-oncology target selected from those listed in Table 2 of Jerry L. Adams et al. In some embodiments, an immuno-oncology agent is a small molecule agent selected from those listed in Table 2 of Jerry L. Adams et al.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BITE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BITE®) antibody construct. In some embodiments, a bispecific T cell engager (BITE®) antibody construct is a CD19/CD3 bispecific antibody construct. In some embodiments, a bispecific T cell engager (BITE®) antibody construct is an EGFR/CD3 bispecific antibody construct. In some embodiments, a bispecific T cell engager (BITE®) antibody construct activates T cells. In some embodiments, a bispecific T cell engager (BITE®) antibody construct activates T cells, which release cytokines inducing upregulation of intercellular adhesion molecule 1 (ICAM-1) and FAS on bystander cells. In some embodiments, a bispecific T cell engager (BITE®) antibody construct activates T cells which result in induced bystander cell lysis. In some embodiments, the bystander cells are in solid tumors. In some embodiments, the bystander cells being lysed are in proximity to the BITE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In some embodiments, the checkpoint inhibitor is a biologic therapeutic or a small molecule. In some embodiments, the checkpoint inhibitor is a monoclonal antibody, a humanized antibody, a fully human antibody, a fusion protein or a combination thereof. In some embodiments, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In some embodiments, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In some embodiments, the checkpoint inhibitor is an immunostimulatory agent, a T cell growth factor, an interleukin, an antibody, a vaccine or a combination thereof. In some embodiments, the interleukin is IL-7 or IL-15. In some embodiments, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors can include small molecule inhibitors or can include antibodies, or antigen binding fragments thereof, that bind to and block or inhibit immune checkpoint receptors or antibodies that bind to and block or inhibit immune checkpoint receptor ligands. Illustrative checkpoint molecules that can be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory $CD8^+$ (αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include, but are not limited to, Tremelimumab (CTLA-4 blocking antibody), anti-OX40, PD-L1 monoclonal Antibody (Anti-B7-Hl; MED14736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (OPDIVO®), ipilimumab (YERVOY®), and pembrolizumab (KEYTRUDA®). In some embodiments, the checkpoint inhibitor is selected from nivolumab (anti-PD-1 antibody, OPDIVO®, Bristol-Myers Squibb); pembrolizumab (anti-PD-1 antibody, KEYTRUDA®, Merck); ipilimumab (anti-CTLA-4 antibody, YERVOY®, Bristol-Myers Squibb); durvalumab (anti-PD-L1 antibody, IMFINZI®, AstraZeneca); and atezolizumab (anti-PD-L1 antibody, TECENTRIQ®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (KEYTRUDA®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (BAVENCIO®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that can be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MED10562 (Medimmune/AstraZeneca), an agonistic anti-OX40 antibody, in advanced solid tumors (NCT02318394 and NCT02705482); MED16469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that can be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981); and CTX-471 (Compass Therapeutics), an agonistic anti-CD137 antibody in metastatic or locally advanced malignancies (NCT03881488).

Checkpoint inhibitors that can be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that can be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that can be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that can be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that can be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that can be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that can be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that can be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that can be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein. Additional compounds of the invention were prepared by methods substantially similar to those described herein in the Examples and methods known to one skilled in the art.

Synthesis of Intermediates

Synthesis of Methyl 2-(bromomethyl)-3-(trifluoromethyl)benzoate (Intermediate A3)

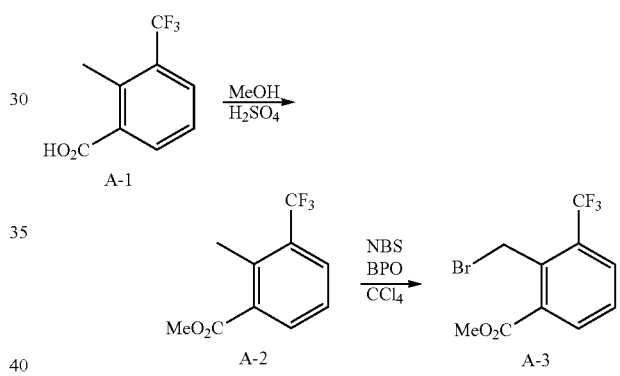

Step 1: Synthesis of Methyl 2-methyl-3-(trifluoromethyl)benzoate (A-2)

To a solution of 2-methyl-3-(trifluoromethyl)benzoic acid, (A-1) (10 g, 1 Eq, 49 mmol) in MeOH (100 mL) was added sulfuric acid (0.24 g, 0.13 mL, 0.05 Eq, 2.4 mmol) and stirred at 75° C. for 3 days. Most of the solvent was removed under vacuum. The reaction mixture was diluted with EtOAc (50 mL) and washed with sat. aq. sol. of NaHCO$_3$ (3×10 mL) and brine (10 mL). The combined organic layers were dried (MgSO$_4$), filtered and concentrated in vacuo to afford the sub-title compound (A-2) (9.2 g, 39 mmol, 80%, 93% Purity) as a pale orange oil. $^1$H NMR (400 MHz, DMSO-d6) δ 7.96 (dd, J=7.8, 1.4 Hz, 1H), 7.90 (dd, J=7.9, 1.4 Hz, 1H), 7.52 (tt, J=7.9, 0.9 Hz, 1H), 3.87 (s, 3H), 2.54 (d, J=1.8 Hz, 3H).

Step 2: Synthesis of Methyl 2-(bromomethyl)-3-(trifluoromethyl)benzoate (A-3)

To a solution of the product from Step 1, above (A-2) (2.00 g, 1 Eq, 9.17 mmol) in CCl$_4$ (45 mL) were successively added NBS (2.45 g, 1.5 Eq, 13.8 mmol) and BPO (888 mg, 75% Wt, 0.3 Eq, 2.75 mmol) and stirred at reflux overnight. The reaction mixture was diluted with DCM (10 mL), washed with sat. aq. sol. of NaHCO$_3$ (2×10 mL), sat. aq. sol. of NH4Cl (2×10 mL) and brine (10 mL). The combined organic layers were dried (MgSO$_4$), filtered and concentrated in vacuo. The crude product was purified by chromatography on silica gel (40 g cartridge, 0-10% EtOAc/isohexane) to afford the title compound (A-3) (2.10 g, 7.0 mmol, 76%, 99% Purity) as a clear colourless oil. $^1$H NMR (400 MHz, Chloroform-d) δ 8.08-8.02 (m, 1H), 7.82 (dd, J=7.9, 1.4 Hz, 1H), 7.49 (td, J=7.9, 0.9 Hz, 1H), 5.11 (s, 2H), 3.99 (s, 3H).

Synthesis of Methyl 2-(bromomethyl)-5-(hydroxymethyl)-3-(trifluoromethyl)benzoate (Intermediate B-5)

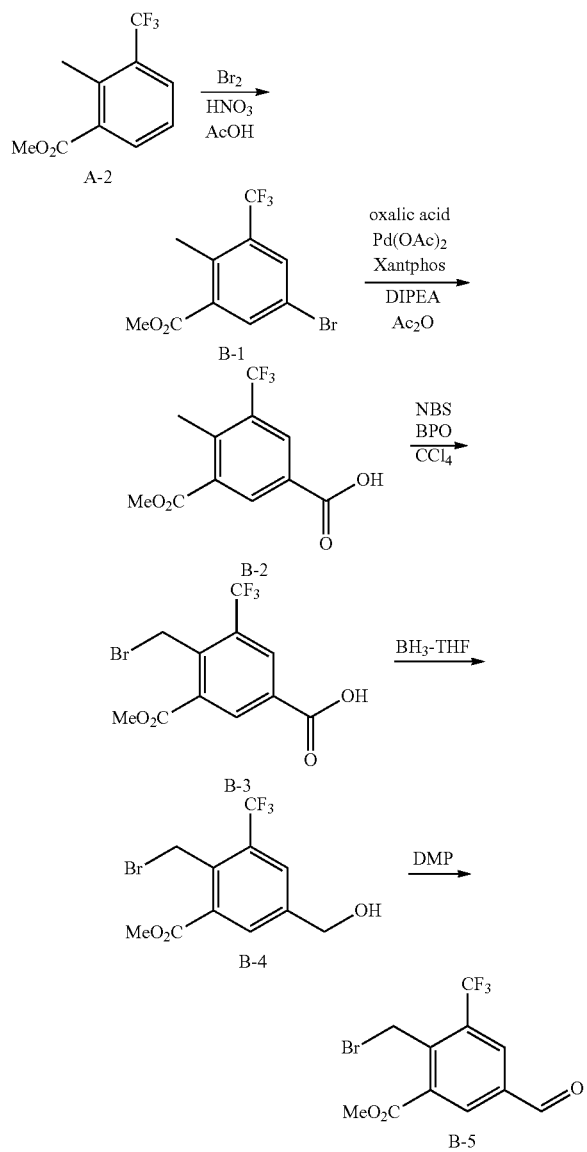

Step 1: Synthesis of Methyl 5-bromo-2-methyl-3-(trifluoromethyl)benzoate (B-1)

To a solution of methyl 2-methyl-3-(trifluoromethyl)benzoate (A-2) (5.00 g, 1 Eq, 22.9 mmol) in AcOH (45 mL) and nitric acid (21.2 g, 15.1 mL, 68% Wt, 10 Eq, 229 mmol) was added Br2 (4.03 g, 1.30 mL, 1.1 Eq, 25.2 mmol) at 0° C. To the solution was added dropwise a solution of silver nitrate (5.06 g, 1.3 Eq, 29.8 mmol) in water (12 mL) at 0° C. The resulting mixture was stirred at 0° C. for 3h. The mixture was diluted with water (50 mL) and extracted with DCM (50 mL). The combined organic layers were washed with brine (20 mL), dried (Na$_2$SO$_4$), filtered and concentrated in vacuo. The crude product was purified by chromatography on silica gel (80 g cartridge, 0-20% EtOAc/isohexane) to afford the sub-title compound (B-1) (5.74 g, 94% Purity) as a colourless oil. $^1$H NMR (400 MHz, DMSO-d6) δ 8.16 (d, J=2.2 Hz, 1H), 8.08 (d, J=2.2 Hz, 1H), 3.90 (s, 3H), 2.50 (q, J=1.7 Hz, 3H).

Step 2: Synthesis of 3-(Methoxycarbonyl)-4-methyl-5-(trifluoromethyl)benzoic acid (B-2)

To a solution of the product from step 1 above (B-1) (5.74 g, 94% Wt, 1 Eq, 18.2 mmol) in DMF (85 mL) was added oxalic acid (2.45 g, 1.5 Eq, 27.2 mmol), DIPEA (2.35 g, 3.16 mL, 1 Eq, 18.2 mmol), Ac$_2$O (2.78 g, 2.57 mL, 1.5 Eq, 27.2 mmol), Pd(OAc)$_2$ (408 mg, 0.1 Eq, 1.82 mmol) and Xantphos (2.10 g, 0.2 Eq, 3.63 mmol) at rt under N$_2$. The resulting mixture was stirred at 100° C. for 16 h. The mixture was cooled to rt diluted with water (50 mL) and extracted with DCM (3×50 mL). The combined organic layer was washed with brine (50 mL), dried (MgSO4), filtered and concentrated in vacuo. The crude product was purified by chromatography on silica gel (220 g cartridge, 10-50% MTBE/isohexanes) to afford the sub-title compound (B-2) (1.57 g, 95% Purity) as a colourless solid. m/z 261.0 (M–H)$^-$ (ES–). $^1$H NMR (400 MHz, DMSO-d6) δ 13.69 (bs, 1H), 8.47 (d, J=1.8 Hz, 1H), 8.29 (d, J=1.9 Hz, 1H), 3.90 (s, 3H), 2.66-2.56 (m, 3H).

Step 3: Synthesis of 4-(Bromomethyl)-3-(methoxycarbonyl)-5-(trifluoromethyl)benzoic acid (B-3)

To a solution of the product from step 2 above (B-2) (1.51 g, 1 Eq, 5.76 mmol) in CCl$_4$ (55 mL) was added NBS (1.54 g, 1.5 Eq, 8.64 mmol) and BPO (558 mg, 75% Wt, 0.3 Eq, 1.73 mmol). The resulting mixture was stirred at reflux for 64 h. The mixture was cooled to rt and concentrated in vacuo. The crude product was purified (dry loaded) by chromatography on silica gel (120 g cartridge, 0-50% MTBE/Isohexane) to afford the sub-title compound (B-3) (1.65 g, 99% Purity) as a colourless solid. m/z 339.1 and 341.1 (M–H)$^-$ (ES–). $^1$H NMR (400 MHz, DMSO-d6) δ 13.9 (s, 1H), 8.57 (d, J=1.8 Hz, 1H), 8.34 (d, J=1.8 Hz, 1H), 5.07 (s, 2H), 3.95 (s, 3H).

Step 4: Synthesis of Methyl 2-(bromomethyl)-5-(hydroxymethyl)-3-(trifluoromethyl)benzoate (B-4)

To a solution of the product from step 3 above (B-3) (1.65 g, 1 Eq, 4.84 mmol) in dry THF (45 mL) was added BH$_3$·THF (1.25 g, 14.5 mL, 1 molar, 3 Eq, 14.5 mmol). The resulting mixture was stirred at rt under N$_2$ atmosphere 48 h. The mixture was slowly quenched with MeOH and concentrated in vacuo. The crude product was purified by chromatography on silica gel (80 g cartridge, 10-60 MTBE/Hexanes) to afford the sub-title compound (B-4) (1.54 g, 97% Purity) as a clear colourless oil. $^1$H NMR (400 MHz, DMSO-d6) δ 8.05 (d, J=1.8 Hz, 1H), 7.90 (s, 1H), 5.03 (s, 2H), 4.63 (s, 2H), 3.92 (s, 3H). Exchangeable proton not observed.

Step 5: Synthesis of Methyl 2-(bromomethyl)-5-formyl-3-(trifluoromethyl)benzoate (B-5)

To a solution of the product from step 4 above (B-4) (500 mg, 1 Eq, 1.53 mmol) and in DCM (25 mL) was added DMP (973 mg, 1.5 Eq, 2.29 mmol). This mixture was stirred at rt 2h. The reaction mixture was diluted with DCM (10 mL) and transferred into a separating funnel. The layer was washed with sat. aq. sol. of $Na_2S_2O_3$ (3×10 mL), then with sat. aq. sol. of $NaHCO_3$ (3×10 mL) and brine. The combined organic extracts were, dried ($Na_2SO_4$), filtered and concentrated in vacuo. The crude product was purified by chromatography on silica gel (24 g cartridge, 5-20% MTBE/Isohexane) to afford the title compound (B-5) (357 mg, 99% Purity) as a colourless oil. m/z 325.00 and 327.00 $(M+H)^+$ (ES+). $^1H$ NMR (400 MHz, Chloroform-d) δ 10.12 (s, 1H), 8.56 (d, J=1.8 Hz, 1H), 8.45 (d, J=1.8 Hz, 1H), 5.08 (s, 2H), 3.86 (s, 3H).

Synthesis of 6-(Hydroxymethyl)-4-(trifluoromethyl) isoindolin-1-one (Intermediate C-1)

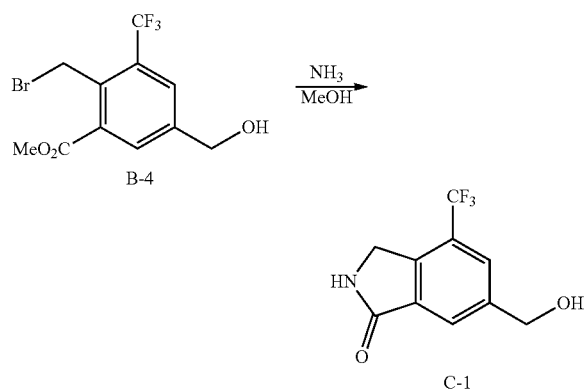

To a solution of intermediate B-4 (200 mg, 1 Eq, 611 μmol) in MeOH (2 mL) was added ammonia (125 mg, 1.05 mL, 7 molar, 12 Eq, 7.34 mmol). The reaction mixture was stirred at rt overnight. The reaction mixture was diluted with MeOH and adsorbed onto Silica gel and concentrated in vacuo. The crude product was purified by chromatography on silica gel (12 g cartridge, 0-10% MeOH/DCM) to afford the title compound (C-1) (100 mg, 0.43 mmol, 70%, 99% Purity) as a clear white solid. m/z 232.2 $(M+H)^+$ (ES+). $^1H$ NMR (400 MHz, DMSO-d6) δ 8.86 (s, 1H), 7.88 (d, J=14.9 Hz, 2H), 5.52 (t, J=5.8 Hz, 1H), 4.67 (d, J=5.8 Hz, 2H), 4.53 (s, 2H).

Synthesis of 3-(2-Bromophenyl)-4-methyl-4H-1,2,4-triazole (Intermediate D-5)

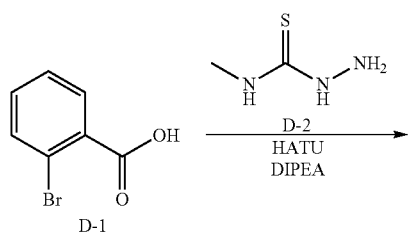

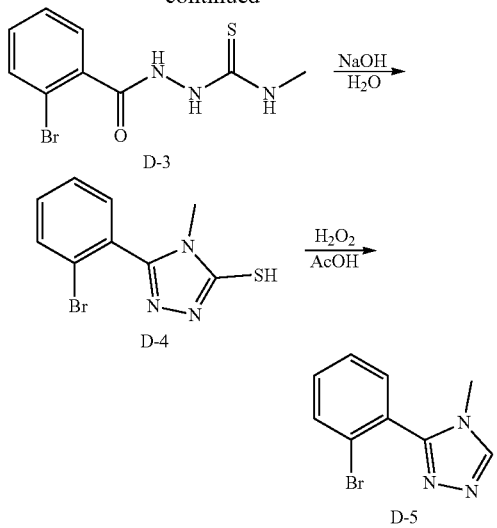

Step 1: Synthesis of 2-(2-Bromobenzoyl)-N-methyl-hydrazine-1-carbothioamide (D-3)

To a stirred solution of 2-bromobenzoic acid (D-1) (10.2 g, 1 Eq, 50.6 mmol) and 1-amino-3-methyl-thiourea (D-2) (5.32 g, 1.0 Eq, 50.6 mmol) in DMF (100 mL) was added HATU (23.1 g, 1.2 Eq, 60.7 mmol)) in portions at 0° C. Then DIPEA (32.7 g, 44.1 mL, 5.0 Eq, 253 mmol) was added at the same temperature under nitrogen. The resulting mixture was stirred for 16 h at rt. Water (200 mL) was added and the aqueous layer was extracted with EtOAc (3×200 mL). The combined organic layers were washed with brine (3×200 mL) and dried ($Na_2SO_4$), then concentrated in vacuo to afford crude sub-title compound (D-3) (15.3 g, 37 mmol, 73%, 70% Purity) as a yellow oil, which was taken forward without purification. m/z 286/288 $(M-H)^-$ (ES-).

Step 2: Synthesis of 5-(2-Bromophenyl)-4-methyl-4H-1,2,4-triazole-3-thiol (D-4)

A solution of the product from step 1, above (D-3) (15.3 g, 70% Wt, 1.0 Eq, 37.2 mmol) in NaOH solution (4.31 g, 108 mL, 1.0 molar, 2.90 Eq, 108 mmol) was stirred overnight at 50° C. Water (300 mL) was added, the mixture was acidified to pH5 with HCl (aq. 1 M) at 0° C. The aqueous layer was extracted with EtOAc (3×200 mL). The organic extracts were combined, dried ($Na_2SO_4$), and concentrated in vacuo to afford the sub-title compound (D-4) (6.55 g, 21 mmol, 55%, 85% Purity) as a yellow oil. m/z 270/272 $(M+H)^+$ (ES+)

Step 3: Synthesis of 3-(2-Bromophenyl)-4-methyl-4H-1,2,4-triazole (D-5)

To a stirred mixture of the product from step 2, above (D-4) (6.55 g, 30% Wt, 1 Eq, 7.27 mmol) in DCM (80 mL) was added AcOH (874 mg, 833 μL, 2 Eq, 14.5 mmol) dropwise at 0° C. To the above mixture was added $H_2O_2$ (30 wt %) (4.95 g, 4.46 mL, 30% Wt, 6 Eq, 43.6 mmol) dropwise at 0° C. The resulting mixture was stirred for 1.5 h at room temperature. The resulting mixture was diluted with water (200 mL). The mixture was basified to pH 8 with saturated $NaHCO_3$ aq. solution. The aqueous layer was extracted with DCM (3×200 mL). The organic phase was dried (Na₂SO₄), then concentrated in vacuo. The crude product was purified by chromatography on silica gel (80 g cartridge, 0-10% MeOH/DCM) to afford impure material which was triturated with DCM (10 mL) and the precipitate filtered. The filtrate was concentrated in vacuo and was purified by chromatography on RP Flash C18 (40 g cartridge, 0-100% MeCN/10 mM Ammonium Bicarbonate) to afford the title compound (D-5) (400 mg, 1.5 mmol, 21%, 90% Purity) as a pale tan solid. m/z 238.1/240.1 (M+H)⁺ (ES+). ¹H NMR (400 MHz, DMSO-d6) δ 8.63 (s, 1H), 7.86-7.81 (m, 1H), 7.59-7.50 (m, 3H), 3.48 (s, 3H).

Synthesis of 2,6-Dichloro-4-(2-(4-methyl-4H-1,2,4-triazol-3-yl)phenyl)pyridine (Intermediate E-7)

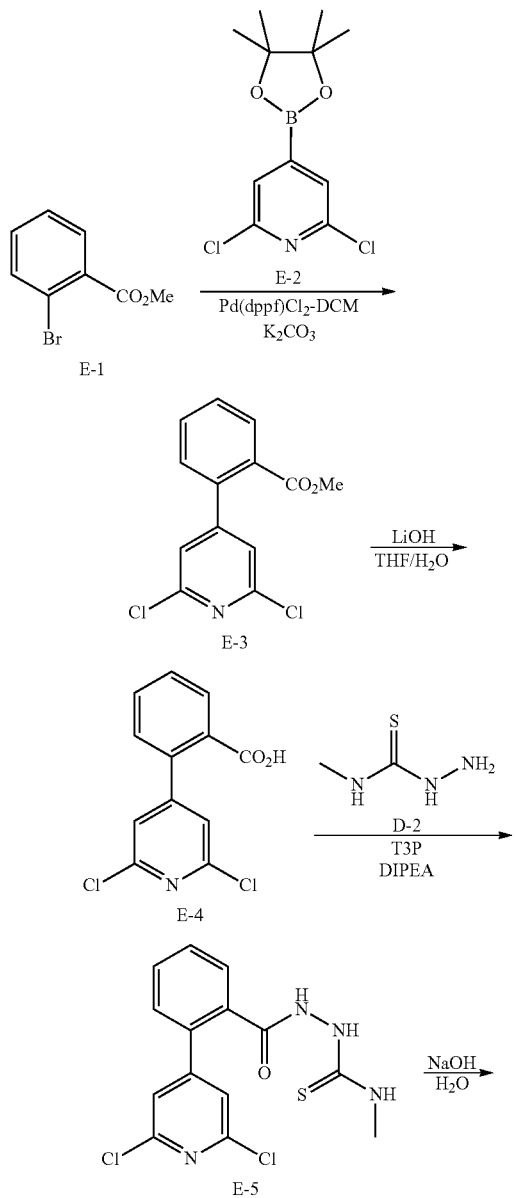

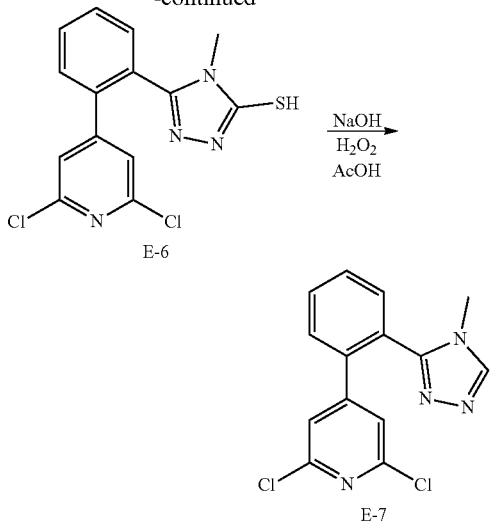

Step 1: Synthesis of Methyl 2-(2,6-dichloropyridin-4-yl)benzoate (E-3)

A solution of methyl 2-bromobenzoate (E-1) (765 mg, 0.500 mL, 1 Eq, 3.56 mmol) and 2,6-dichloro-4-(4,4,5,5-tetramethyl-1,3,2-dioxaborolan-2-yl)pyridine (E-2) (1.34 g, 80% Wt, 1.1 Eq, 3.91 mmol) in 1,4-Dioxane (24 mL)) and water (6 mL) were added Pd(dppf)Cl2.DCM (145 mg, 0.05 Eq, 178 μmol) and potassium carbonate (1.47 g, 3 Eq, 10.7 mmol) was degassed with nitrogen three times and heated overnight at 80° C. The reaction mixture was put through a celite plug, eluting with EtOAc (30 mL). The filtrate was concentrated in vacuo and the crude product was purified by chromatography on silica gel (24 g cartridge, 0-10% MeOH/DCM) to afford the sub-title compound (E-3) (873.6 mg, 2.9 mmol, 83%, 95% Purity) as a pale yellow solid. ¹H NMR (400 MHz, DMSO-d6) δ 8.00-7.95 (m, 1H), 7.77-7.69 (m, 1H), 7.67-7.61 (m, 1H), 7.56 (s, 2H), 7.50-7.46 (m, 1H), 3.68 (s, 3H).

Step 2: Synthesis of 2-(2,6-Dichloropyridin-4-yl)benzoic acid (E-4)

To a solution of the product from step 1, above (E-3) (8.38 g, 93% Wt, 1 Eq, 27.6 mmol) in THF (10 mL) was added a solution of LiOH (662 mg, 10 mL, 1 Eq, 27.6 mmol) in water (10 mL) and the mixture was stirred at 40° C. for 16 h. The reaction mixture was concentrated in vacuo. The residue was dissolved in water (30 mL), acidified with 1M HCl, and extracted with EtOAc (3×50 mL). The organic extracts were combined, dried (MgSO₄) and concentrated in vacuo to afford the sub-title compound (E-4) (7.34 g, 27 mmol, 97%, 98% Purity) as an off-white solid. m/z 268.1/270.2 (M+H)⁺ (ES+). ¹H NMR (400 MHz, DMSO-d6) δ 13.14 (s, 1H), 7.95 (dd, J=7.7, 1.4 Hz, 1H), 7.76-7.64 (m, 1H), 7.64-7.57 (m, 1H), 7.56 (s, 2H), 7.48-7.42 (m, 1H).

Step 3: Synthesis of 2-(2-(2,6-Dichloropyridin-4-yl)benzoyl)-N-methylhydrazine-1-carbothioamide (E-5)

The product from step 2, above (E-4) (6.67 g, 1 Eq, 24.9 mmol) and 1-amino-3-methyl-thiourea (D-2) (2.88 g, 1.1 Eq, 27.4 mmol) were dissolved in EtOAc (10 mL). Then DIPEA (7.33 g, 9.88 mL, 2.28 Eq, 56.7 mmol) was added followed by T3P (23.7 g, 22.2 mL, 50% Wt, 1.5 Eq, 37.3 mmol) dropwise. The resulting mixture was then stirred at 70° C. for 16 h. The mixture was diluted with water (20 mL) and the precipitate filtered to afford the sub-title compound (E-5) (8.84 g, 24.9 mmol, 100%) as a brown solid, which was taken forward without further purification or analysis.

Step 4: Synthesis of 5-(2-(2,6-Dichloropyridin-4-yl)phenyl)-4-methyl-4H-1,2,4-triazole-3-thiol (E-6)

A solution of the product from step 3, above (E-5) (8.85 g, 1 Eq, 24.9 mmol) in NaOH solution (2.99 g, 37.3 mL, 2 molar, 3 Eq, 74.7 mmol) was stirred at 50° C. for 16 h. Water (100 mL) was added, the mixture was acidified to pH5 with HCl (aq. 1M). The precipitate was filtered and concentrated in vacuo to afford the sub-title compound (E-6) (3.53 g, 10 mmol, 41%, 98% Purity) as a pale brown solid. $^1$H NMR (400 MHz, DMSO-d6) δ 13.85 (s, 1H), 7.83-7.68 (m, 4H), 7.44 (s, 2H), 3.26-3.23 (m, 3H).

Step 5: Synthesis of 5-(2-(2,6-Dichloropyridin-4-yl)phenyl)-4-methyl-4H-1,2,4-triazole-3-thiol (E-7)

To a solution of the product from step 4, above (E-6) (3.54 g, 98% Wt, 1 Eq, 10.3 mmol) in DCM (90 mL) and AcOH (18.5 g, 17.7 mL, 30 Eq, 309 mmol) was added H$_2$O$_2$ (30% in water) (11.7 g, 10.5 mL, 30% Wt, 10 Eq, 103 mmol) dropwise with stirring at 0° C. The mixture was stirred at this temperature for 1 h before being concentrated in vacuo. The residue was dissolved in water and basified with NaOH (2M) to pH 10, then organics were separated and aqueous phase extracted with EtOAc (2×100 mL) and organics washed with brine (50 mL). Organics were combined, dried (MgSO$_4$), filtered and concentrated in vacuo to afford the title compound (E-7) (2.94 g, 9.2 mmol, 89%, 95% Purity) as a pale yellow solid. m/z 305.2/307.1 (M+H)$^+$ (ES+). $^1$H NMR (400 MHz, Methanol-d4) δ 8.54 (s, 1H), 7.85-7.67 (m, 4H), 7.26 (s, 2H), 3.42 (s, 3H).

Synthesis of 2-(2'-(4-Methyl-4H-1,2,4-triazol-3-yl)-[1,1'-biphenyl]-3-yl)-3-oxo-7-(trifluoromethyl)isoindoline-5-carbaldehyde (Intermediate Q-1)

Compound P-2 (167 mg, 1 Eq, 360 μmol) and Dess-Martin periodinane (229 mg, 1.5 Eq, 539 μmol) were stirred in DCM (6 mL) at rt for 90 min. The reaction mixture was diluted with DCM (10 mL) and washed with sat. aq. NaHCO$_3$ (10 mL). Organics were separated, dried (MgSO$_4$), filtered and concentrated in vacuo to afford the title compound (Q-1) (0.21 g, 360 μmol, 100%, 80% Purity) as a yellow solid, which was used without further purification in the next step. m/z 463.2 (M+H)$^+$ (ES+).

Synthesis of 3-(1-Methyl-4-(4-methyl-4H-1,2,4-triazol-3-yl)-1H-pyrazol-5-yl)aniline (Intermediate AAB-8)

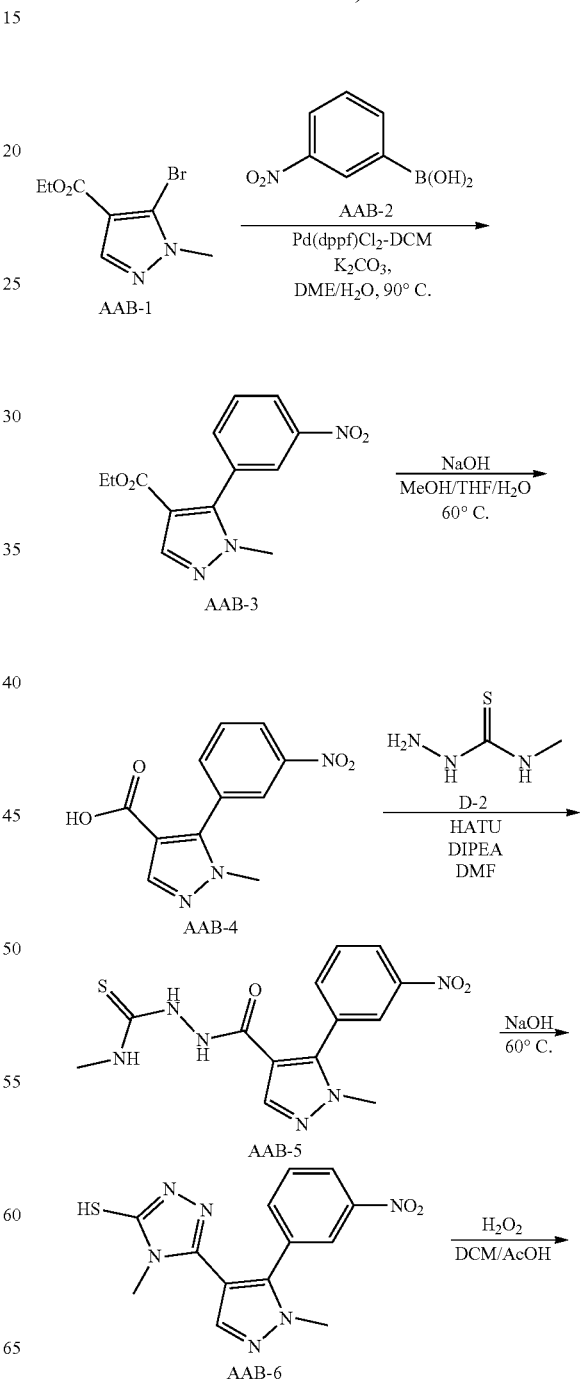

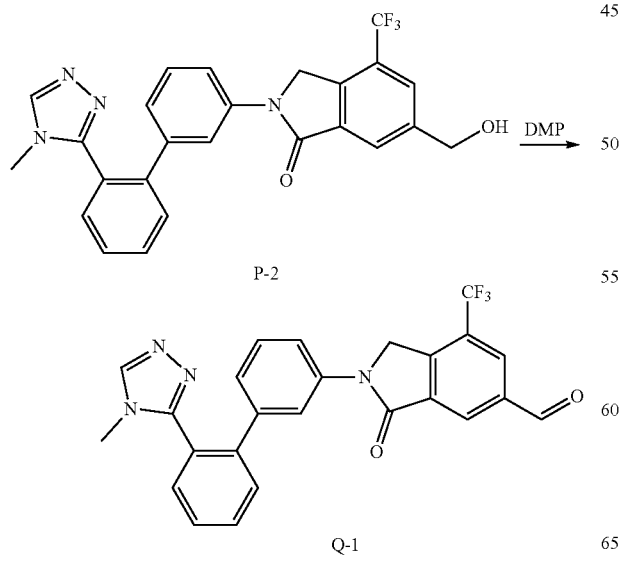

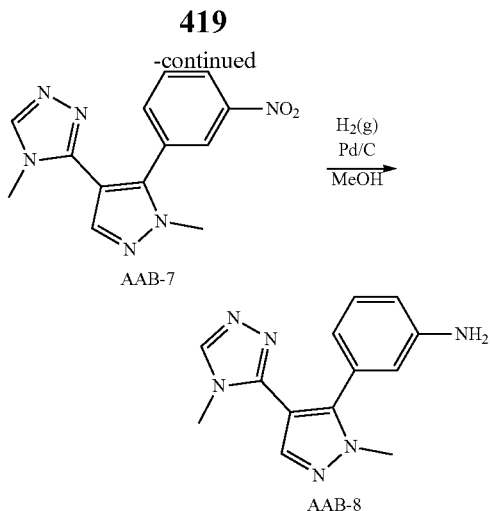

Step 1: Synthesis of Ethyl 1-methyl-5-(3-nitrophenyl)pyrazole-4-carboxylate (AAB-3)

To a stirred mixture of ethyl 5-bromo-1-methylpyrazole-4-carboxylate (AAB-1) (1.00 g, 1 Eq, 4.29 mmol), 3-nitrophenylboronic acid (AAB-2) (1.07 g, 1.5 Eq, 6.44 mmol) and sodium carbonate (1.36 g, 3 Eq, 12.9 mmol) in 1,2-dimethoxy-ethane (15 mL) and water (1.5 mL) was added Pd(dppf)Cl$_2$.DCM (700.7 mg, 0.2 Eq, 858 μmol) at rt under nitrogen atmosphere. The resulting mixture was stirred overnight at 90° C. under nitrogen atmosphere. The mixture was allowed to cool to rt and concentrated in vacuo. The residue was purified by silica gel column chromatography, eluted with petroleum ether/EtOAc (1/1) to afford the sub-title compound (AAB-3) (900 mg, 3.27 mmol, 76%) as a brown solid. m/z 275.3 (M+H)$^+$ (ES+).

Step 2: Synthesis of 1-Methyl-5-(3-nitrophenyl) pyrazole-4-carboxylic acid (AAB-4)

To a stirred mixture of the product from step 1 above (AAB-3) (500 mg, 1 Eq, 1.82 mmol) in MeOH (8 mL) and THF (8 mL) was added a solution of NaOH (363 mg, 5 Eq, 9.08 mmol) in water (4 mL) at rt. The resulting mixture was stirred for 1.5 h at 60° C. The mixture was allowed to cool to rt, diluted with water, acidified to pH 5 with HCl (aq. 1M) at 0° C. The resulting mixture was diluted with water and extracted with EtOAc (3×80 mL). The combined organic layers were washed with brine (2×80 mL), dried (Na$_2$SO$_4$), filtered and concentrated in vacuo to afford the sub-title compound (AAB-4) (440 mg, 1.78 mmol, 98%) as a white solid. m/z 248.2 (M+H)$^+$ (ES+).

Step 3: Synthesis of 1-Methyl-N-[(methylcarbamothioyl) amino]-5-(3-nitrophenyl) pyrazole-4-carboxamide (AAB-5)

To a stirred mixture of the product from step 2 above (AAB-4) (360 mg, 1 Eq, 1.46 mmol) in DMF (5 mL) were added HATU (831 mg, 1.5 Eq, 2.18 mmol) and DIPEA (565 mg, 3 Eq, 4.37 mmol) at 0° C. The resulting mixture was stirred for 0.5 h at rt. To the above mixture was added 4-methyl-3-thiosemicarbazide (D-2) (161 mg, 1.05 Eq, 1.53 mmol) at rt. The resulting mixture was stirred for additional overnight at rt. The reaction was concentrated affording the sub-title compound (AAB-5) which was used directly in the next step. m/z 335.4 (M+H)$^+$ (ES+).

Step 4: Synthesis of 4-Methyl-5-[1-methyl-5-(3-nitrophenyl) pyrazol-4-yl]-1,2,4-triazole-3-thiol (AAB-6)

A solution of the product from step 3 above (AAB-5) (486 mg, 1 Eq, 1.45 mmol) in NaOH (aq., 1M) (10 mL) was stirred for 3 h at 60° C. The mixture was allowed to cool to rt, diluted with water, acidified to pH 5 with HCl (aq., 1M) and extracted with EtOAc (3×50 mL). The combined organic layers were washed with brine (2×50 mL), dried (Na$_2$SO$_4$), filtered and concentrated in vacuo. The crude product was purified by reverse flash column chromatography with the following conditions: Column, C18; mobile phase, Water (0.1% NH$_4$HCO$_3$) and ACN (10% ACN up to 80% in 20 min); Detector, UV 254/220 nm to afford the sub-title compound (AAB-6) (160 mg, 5.6 μmol, 35%) as a brown solid. m/z 317.3 (M+H)$^+$ (ES+).

Step 5: Synthesis of 4-Methyl-3-[1-methyl-5-(3-nitrophenyl)pyrazol-4-yl]-1,2,4-triazole (AAB-7)

To a stirred solution of the product from step 4 above (AAB-6) (160 mg, 1 Eq, 506 μmol) in DCM (20 mL) was added acetic acid (30 mg, 1 Eq, 506 μmol) and hydrogen peroxide (344 mg, 30% Wt, 6 Eq, 3.04 mmol) at 0° C. The resulting mixture was stirred for 3 h at rt then concentrated in vacuo and purified by silica gel column chromatography, eluted with DCM/MeOH (10/1) to afford the sub-title compound (AAB-7) (120 mg, 422 μmol, 83%) as a brown oil. m/z 285.3 (M+H)$^+$ (ES+).

Step 6: Synthesis of 3-[2-Methyl-4-(4-methyl-1,2,4-triazol-3-yl) pyrazol-3-yl] aniline (AAB-8)

To a stirred solution of the product from step 5 above (AAB-7) (120 mg, 1 Eq, 422 μmol) in MeOH (13 mL) was added Pd/C 39 (44.9 mg, 10% Wt, 0.1 Eq, 42.2 μmol) portion-wise at rt under nitrogen atmosphere. The mixture was hydrogenated at rt for 2 h under hydrogen atmosphere using a hydrogen balloon. The mixture was filtered through a Celite pad and concentrated in vacuo. The filtrate was concentrated to afford the sub-title compound (AAB-8) (60 mg, 236 μmol, 56%) as a white solid and used in the next step without further purification. m/z 255.3 (M+H)$^+$ (ES+).

Synthesis of Methyl 5-((5-azaspiro [2.4] heptan-5-yl)methyl)-2-(bromomethyl)-3-(trifluoromethyl) benzoate (Intermediate AAC-2)

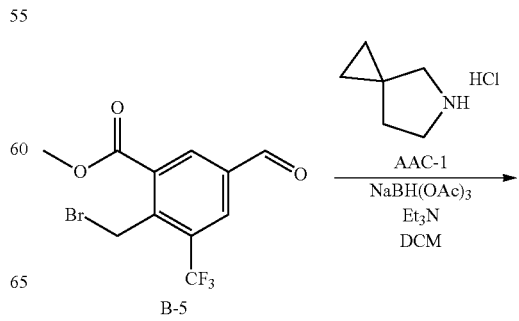

-continued

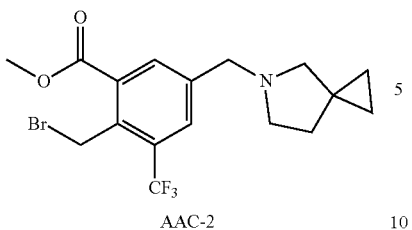

AAC-2

To a stirred solution of intermediate (B-5) (325 mg, 1 Eq, 1.00 mmol) and 5-azaspiro [2.4] heptane, HCl (AAC-1) (134 mg, 1 Eq, 1.00 mmol) in DCM (10 mL) were added Et$_3$N (101 mg, 1 Eq, 1.00 mmol) and NaBH(OAc)$_3$ (424 mg, 2 Eq, 2.00 mmol) at rt. The resulting mixture was stirred for 3 h at rt then concentrated in vacuo. The crude product was purified by reverse flash column chromatography with the following conditions: Column, C18; mobile phase, Water (0.1% NH$_4$HCO$_3$) and ACN (10% ACN up to 50% in 10 min); Detector, UV 254/220 nm. This resulted in the title compound (AAC-2) (65 mg, 160 μmol, 16%) as a yellow oil. m/z 406.2 (M+H)$^+$ (ES+)

Synthesis of 3-(5-Bromo-1-methyl-1H-pyrazol-4-yl)-4-methyl-4H-1,2,4-triazole (Intermediate AAH-4)

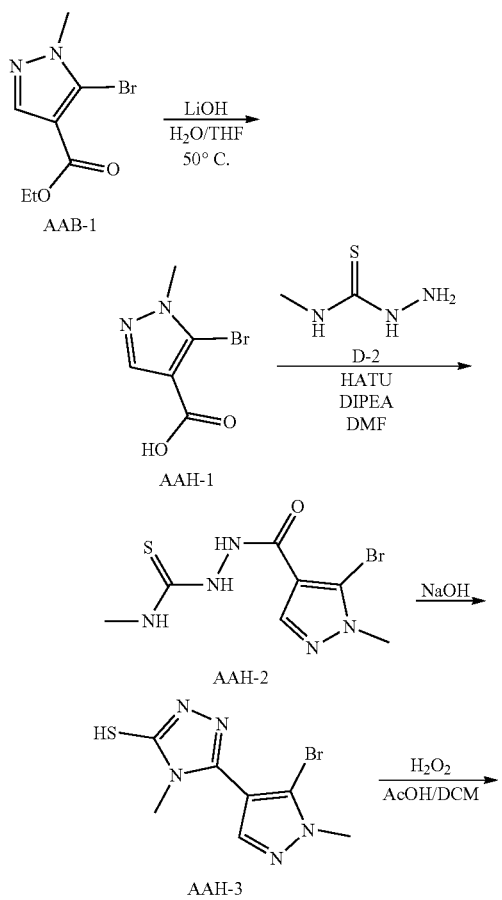

-continued

AAH-4

Step 1: Synthesis of 5-Bromo-1-methyl-1H-pyrazole-4-carboxylic acid (AAH-1)

To a solution of ethyl 5-bromo-1-methyl-1H-pyrazole-4-carboxylate (AAB-1) (1.2 g, 1 Eq, 5.17 mmol) in THF (20 mL) and water (5 mL) was added LiOH (373 mg, 3 Eq, 15.5 mmol) at rt. The resulting solution was stirred for 16 h at 50° C. The mixture was cooled to rt and concentrated in vacuo. The residue was diluted with water and the mixture acidified to pH 3 with HCl (aq., 1 M). The solids were collected by filtration to afford the sub-title compound (AAH-1) (780 mg, 3.82 mmol, 74%) as an off-white solid. m/z 205.0 (M+H)$^+$ (ES+).

Step 2: Synthesis of 2-(5-Bromo-1-methyl-1H-pyrazole-4-carbonyl)-N-methylhydrazine-1-carbothioamide (AAH-2)

To a stirred solution of the product from step 1 above (AAH-1) (780 mg, 1 Eq, 3.82 mmol) and 4-methyl-3-thiosemicarbazide (D-2) (481 mg, 1.2 Eq, 4.58 mmol) in DMF (8 mL) was added DIPEA (1.48 g, 3 Eq, 11.46 mmol) and HATU (1.6 g, 1.1 Eq, 4.2 mmol) at rt. The resulting mixture was stirred for 16 h at rt then concentrated in vacuo. The resulting mixture was diluted with water and extracted with DCM (3×80 mL). The combined organic layers were washed with brine (2×80 mL), dried (Na$_2$SO$_4$), filtered and concentrated in vacuo affording the sub-title compound (AAH-2) (930 mg, 3.19 mmol, 84%) as a yellow oil. m/z 292.2 (M+H)$^+$ (ES+).

Step 3: Synthesis of 5-(5-Bromo-1-methyl-1H-pyrazol-4-yl)-4-methyl-4H-1,2,4-triazole-3-thiol (AAH-3)

A mixture of the product from step 2 above (AAH-2) (930 mg, 1 Eq, 3.19 mmol) in NaOH (aq., 1 M) (10 mL) was stirred overnight at rt. The mixture was diluted with water. The mixture was acidified to pH 3 with HCl (aq.). The resulting mixture was diluted with water and extracted with EtOAc (3×100 mL). The combined organic layers were washed with brine (2×100 mL), dried (Na$_2$SO$_4$), filtered and concentrated in vacuo. The residue was purified by reverse flash chromatography with the following conditions: Column, C18; mobile phase, Water (0.1% FA) and ACN (24% ACN up to 41% in 10 min); Detector, UV 254/220 nm. This resulted in the sub-title compound (AAH-3) (630 mg, 2.30 mmol, 72%) as a yellow solid. m/z 274.1 (M+H)$^+$ (ES+).

Step 4: Synthesis of 3-(5-Bromo-1-methyl-1H-pyrazol-4-yl)-4-methyl-4H-1,2,4-triazole (AAH-4)

To a solution of the product from step 3 above (AAH-3) (630 mg, 1 Eq, 2.3 mmol) in DCM (10 mL) and acetic acid (5 mL) was added hydrogen peroxide (2.63 mL, 30% Wt, 10

Eq, 23 mmol) at 0° C. and the resulting mixture was stirred for 2h. The mixture was diluted with water and basified to pH 8 with saturated NaHCO$_3$ (aq.). The resulting mixture was diluted with water and extracted with EtOAc (3×80 mL). The combined organic layers were washed with brine (2×80 mL), dried (Na$_2$SO$_4$), filtered and concentrated in vacuo. The residue was applied on a silica gel column chromatography with DCM/MeOH (20/1) to obtain the title compound (AAH-4) (400 mg, 1.66 mmol, 72%) as a white solid. m/z 242.1 (M+H)$^+$ (ES+).

Synthesis of 2-(3-(3-(5-Hydroxy-4-methyl-4H-1,2,4-triazol-3-yl)pyridin-4-yl)phenyl)-4-(trifluoromethyl)isoindolin-1-one (Intermediate AAS-6)

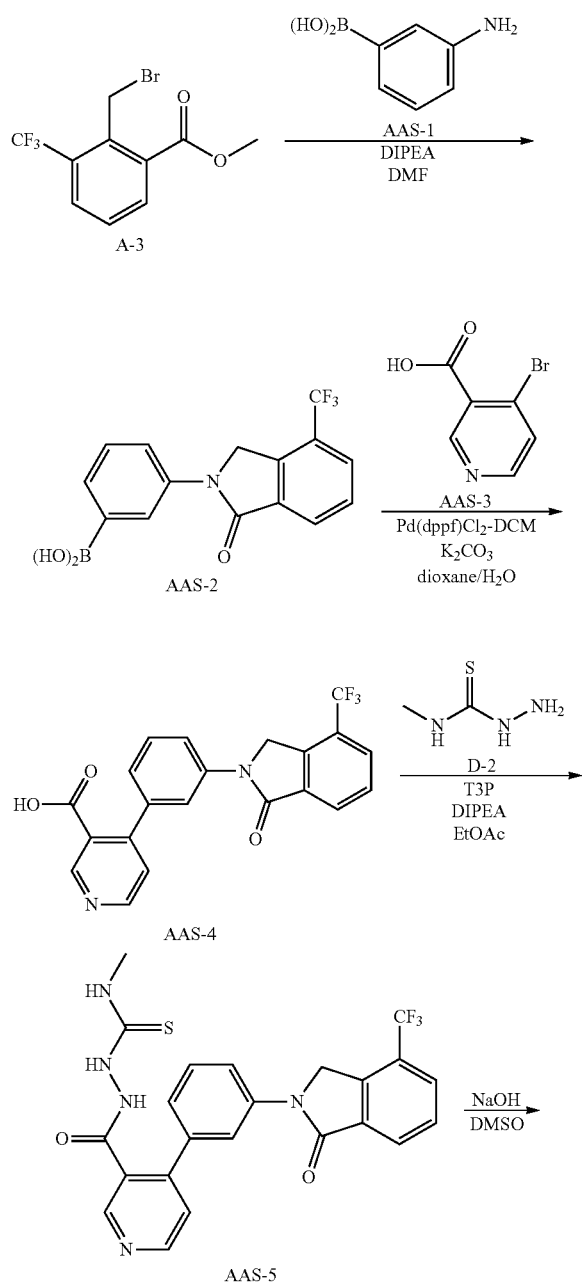

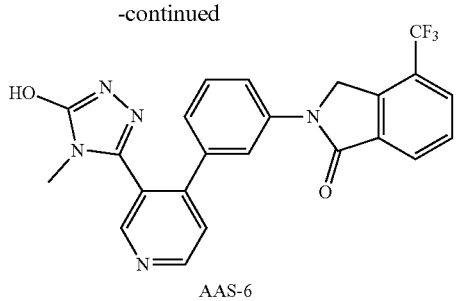

Step 1: Synthesis of (3-(1-Oxo-4-(trifluoromethyl)isoindolin-2-yl)phenyl)boronic acid (AAS-2)

To a stirred mixture of intermediate (A-3) (100 mg, 1 Eq, 330 µmol) and 3-aminophenylboronic acid (AAS-1) (55 mg, 1.2 Eq, 400 µmol) in DMF (3 mL) was added DIPEA (218 mg, 5 Eq, 1.68 mmol) at rt under nitrogen atmosphere. The resulting mixture was stirred for 16 hours at 60° C. under nitrogen atmosphere. The mixture was cooled to rt and concentrated in vacuo. The crude product was purified by reverse flash column chromatography with the following conditions: Column, C18; mobile phase, Water (0.1% FA) and ACN (45% ACN up to 55% in 10 min); Detector, UV 254/220 nm. The product-containing fractions were combined and concentrated in vacuo. This resulted in the sub-title compound (AAS-2) (91 mg, 283 µmol, 84%) as a white solid. m/z 322.1 (M+H)$^+$ (ES+).

Step 2: Synthesis of 4-(3-(1-Oxo-4-(trifluoromethyl)isoindolin-2-yl)phenyl)nicotinic acid (AAS-4)

To a stirred mixture of the product from step 1 above (AAS-2) (60 mg, 1 Eq, 180 µmol) and 4-bromopyridine-3-carboxylic acid (AAS-3) (42 mg, 1.1 Eq, 200 µmol) and potassium phosphate (77 mg, 3 Eq, 560 µmol) in 1,4-dioxane (4 mL) and water (1 mL) was added Pd(dppf)Cl$_2$.DCM (27 mg, 0.2 Eq, 30 mmol) at rt under nitrogen atmosphere. The resulting mixture was stirred for 3 h at 80° C. under nitrogen atmosphere. The mixture was cooled to rt and the residue diluted with water. The mixture was acidified to pH 4 with HCl (aq.) and the resulting mixture extracted with EtOAc (3×10 mL). The combined organic layers were washed with brine (2×10 mL), dried (Na$_2$SO$_4$), filtered and concentrated in vacuo. This resulted in the sub-title compound (AAS-4) (65 mg, 163 µmol, 87%) as a white solid. m/z 399.1 (M+H)$^+$ (ES+).

Step 3: Synthesis of N-Methyl-2-(4-(3-(1-oxo-4-(trifluoromethyl)isoindolin-2-yl)phenyl)nicotinoyl)hydrazine-1-carbothioamide (AAS-5)

To a stirred solution of the product from step 2 above (AAS-4) (60 mg, 1 Eq, 150 µmol) and 4-methyl-3-thiosemicarbazide (D-2) (19 mg, 1.2 Eq, 180 µmol) in EtOAc (5 mL) were added T$_3$P (191 mg, 4 Eq, 600 µmol) and DIPEA (116 mg, 6 Eq, 910 µmol) at rt. The resulting mixture was stirred for 16 h at rt. The resulting mixture was concentrated in vacuo and the crude product used in the next step directly without further purification. m/z 486.1 (M+H)$^+$ (ES+).

Step 4: Synthesis of 2-(3-(3-(5-Hydroxy-4-methyl-4H-1,2,4-triazol-3-yl)pyridin-4-yl)phenyl)-4-(trifluoromethyl)isoindolin-1-one (AAS-6)

The crude product from step 3 above (AAS-5) in DMSO (8 mL) was added NaOH (24.6 mg, 5 Eq, 610 µmol) at rt under nitrogen atmosphere. The resulting mixture was stirred for 48 h at 50° C. under nitrogen atmosphere then cooled to rt. The crude product was purified by reverse flash column chromatography with the following conditions: Column, C18; mobile phase, Water (0.1% NH$_4$HCO$_3$) and ACN (40% ACN up to 60% in 10 min); Detector, UV 254/220 nm. The product-containing fractions were combined and concentrated in vacuo. The crude product was purified by Prep-HPLC with the following conditions: Column: SunFire Prep C18 OBD Column, 20×250 mm 5 um; Mobile Phase A: Water (0.1% NH$_4$HCO$_3$+0.1% NH$_3$·H$_2$O), Mobile Phase B: ACN; Flow rate:60 mL/min; Gradient:25 B to 50 B in 10 min; Detector, UV 254/210 nm; RT: 9.78. The product-containing fractions were combined and evaporated partially in vacuo and lyophilized overnight to afford the title compound (AAS-6) (22.9 mg, 51 μmol, 27%) as a white solid. m/z 452.2 (M+H)$^+$ (ES+). $^1$H NMR (400 MHz, MeOH-d4) δ 9.03 (d, J=0.8 Hz, 1H), 8.77 (d, J=5.2 Hz, 1H), 8.13 (d, J=7.7 Hz, 1H), 8.04-7.93 (m, 3H), 7.80 (t, J=7.7 Hz, 1H), 7.68-7.63 (m, 1H), 7.59 (t, J=8.0 Hz, 1H), 7.30-7.23 (m, 1H), 5.21 (s, 2H), 2.83 (s, 3H).

Example 1: Synthesis of (S)-2-(2-Methoxy-5-(1-(4-methyl-4H-1,2,4-triazol-3-yl)propan-2-yl)phenyl)-6-(pyrrolidin-1-ylmethyl)-4-(trifluoromethyl)isoindolin-1-one (F-9)

Step 1: Synthesis of 1-(4-Methoxy-3-nitrophenyl) ethan-1-ol (F-2)

To a stirring solution of 1-(4-methoxy-3-nitrophenyl) ethan-1-one (F-1) (1.0 g, 1 Eq, 5.1 mmol) in EtOH (20 mL) at rt, NaBH$_4$ (0.29 g, 1.5 Eq, 7.6 mmol) was added portionwise and the reaction stirred for 2 h. The reaction mixture was concentrated in vacuo. The reaction mixture was diluted with EtOAc (25 mL) and transferred into a separating funnel. The layer was washed with sat. aq. sol. of NH$_4$Cl (3×5 mL), sat. aq. sol. of NaHCO$_3$ (3×5 mL) and brine. The combined organic layers was collected, dried (MgSO$_4$), filtered and concentrated in vacuo to afford the sub-title compound (F-2) (930 mg, 4.6 mmol, 91%, 98% Purity) as a pale yellow oil. $^1$H NMR (400 MHz, DMSO-d$_6$) δ 7.81 (dd, J=2.2, 0.7 Hz, 1H), 7.61 (ddd, J=8.7, 2.3, 0.6 Hz, 1H), 7.31 (d, J=8.7 Hz, 1H), 5.33 (d, J=4.4 Hz, 1H), 4.74 (qd, J=6.4, 4.4 Hz, 1H), 3.90 (s, 3H), 1.32 (d, J=6.5 Hz, 3H).

Step 2: Synthesis of 4-(1-Bromoethyl)-1-methoxy-2-nitrobenzene (F-3)

To a solution of the product from step 1 above (F-2) (0.930 g, 98% Wt, 1 Eq, 4.62 mmol) in glacial AcOH (4 mL), was added a solution of HBr (33% in glacial AcOH) (2.27 g, 1.52 mL, 33% Wt, 2 Eq, 9.24 mmol) dropwise. The reaction mixture was stirred at rt 16 h. The mixture was

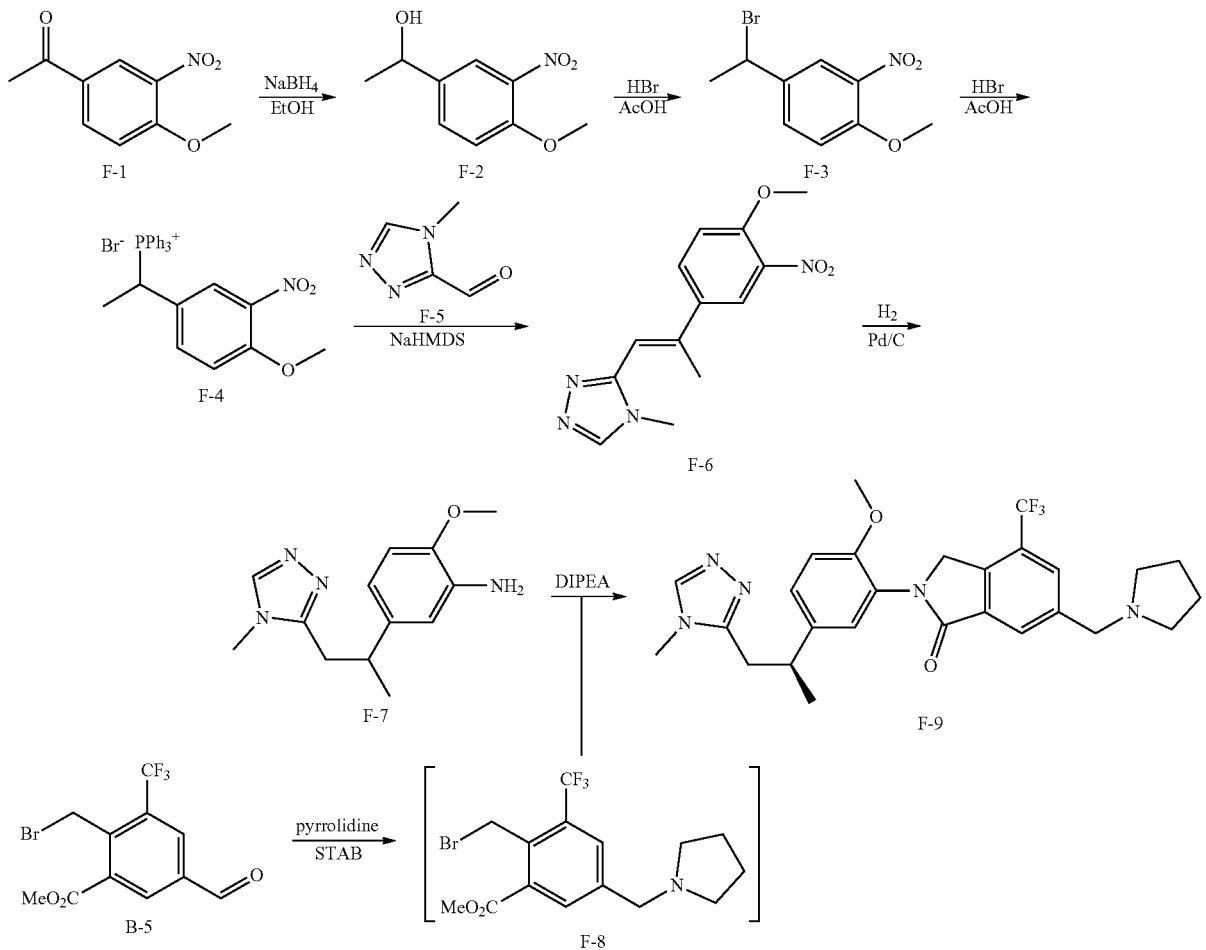

heated to 90° C. and stirred for further 16 h. The mixture was diluted with EtOAc (20 mL), washed with water (3×10 mL), sat. sol. of NaHCO$_3$ (3×10 mL) and brine (10 mL), dried (MgSO$_4$), filtered and concentrated in vacuo. The crude product was purified by chromatography on silica gel (40 g cartridge, 0-50% EtOAc/isohexane) to afford the sub-title compound (F-3) (381 mg, 1.4 mmol, 30%, 94% Purity) as a pale yellow oil. $^1$H NMR (400 MHz, Chloroform-d) δ 7.92 (d, J=2.4 Hz, 1H), 7.63 (dd, J=8.7, 2.4 Hz, 1H), 7.07 (d, J=8.8 Hz, 1H), 5.18 (q, J=7.0 Hz, 1H), 3.97 (s, 3H), 2.04 (d, J=7.0 Hz, 3H).

Step 3: Synthesis of (1-(4-Methoxy-3-nitrophenyl) ethyl)triphenylphosphonium, Bromide (F-4)

Triphenylphosphane (361 mg, 1 Eq, 1.38 mmol) was added to a solution of the product from step 2 above (F-3) (381 mg, 94% Wt, 1 Eq, 1.38 mmol) in toluene (5 mL) and stirred at reflux for 72 h. The mixture was allowed to cool to rt. The precipitate filtered, washed with toluene (2×5 mL) then hexane (2×5 mL) and dried under vacuum to afford the sub-title compound (F-4) (320 mg, 0.55 mmol, 40%, 90% Purity) as a pale brown solid. m/z 442.4 (M+H)$^+$ (ES+). $^1$H NMR (400 MHz, DMSO-d$_6$) δ 7.97-7.89 (m, 3H), 7.81-7.70 (m, 12H), 7.35 (d, J=1.8 Hz, 1H), 7.32 (d, J=1.3 Hz, 2H), 5.77 (dq, J=15.2, 7.5 Hz, 1H), 3.90 (s, 3H), 1.72 (dd, J=18.5, 7.3 Hz, 3H).

Step 4: Synthesis of (E)-3-(2-(4-Methoxy-3-nitrophenyl)prop-1-en-1-yl)-4-methyl-4H-1,2,4-triazole (F-6)

Sodium bis(trimethylsilyl)amide (2M in THF) (132 mg, 360 µL, 2 molar, 2 Eq, 720 µmol) was added to a solution of the product from step 3 above (F-4) (320 mg, 1.7 Eq, 612 µmol) in THF (5 mL) and stirred at rt for 1 h. The reaction was cooled to −40° C. and 4-methyl-4H-1,2,4-triazole-3-carbaldehyde (F-5) (40.0 mg, 1 Eq, 360 µmol) in THF (1 mL) was added. The mixture was stirred 1 h at −40° C., then warmed to rt overnight. Saturated NH$_4$Cl (10 mL) was added and the mixture partitioned between DCM (25 mL) and water (20 mL). The organic layer was washed with sat. aq. sol. of NH$_4$Cl (2×5 mL), sat. aq. sol. of NaHCO$_3$ (2×5 mL) and brine (5 mL). The combined organic layers were collected, dried (MgSO$_4$), filtered and concentrated in vacuo. The crude product was purified by chromatography on silica gel (12 g cartridge, 0-50% EtOAc/isohexane) to afford the sub-title compound (F-6) (40 mg, 0.14 mmol, 40%, 99% Purity) as a pale yellow oil. m/z 275.2 (M+H)$^+$ (ES+). $^1$H NMR (400 MHz, Chloroform-d) δ 9.06 (s, 1H), 7.72 (d, J=2.3 Hz, 1H), 7.41 (dd, J=8.7, 2.4 Hz, 1H), 7.03 (d, J=8.8 Hz, 1H), 6.38 (d, J=1.6 Hz, 1H), 3.97 (s, 3H), 3.59 (s, 3H), 2.38 (d, J=1.5 Hz, 3H).

Step 5: Synthesis of 2-Methoxy-5-(1-(4-methyl-4H-1,2,4-triazol-3-yl)propan-2-yl)aniline (F-7)

To a solution of the product from step 4 above (F-6) (39 mg, 1 Eq, 0.14 mmol) in EtOH (2 mL) was added Pd/C (4 mg, 10% Wt, 0.03 Eq, 4 µmol). The reaction mixture was stirred at rt with 5 atm of H$_2$ for 16 h. The catalyst was filtered and the solvent was removed under vacuum. The process was repeated 3 times filtering and adding fresh catalyst. The crude product was loaded onto a column of SCX (150 mg) in MeOH. The column was washed with MeOH (30 mL) and the product was eluted with 0.7 M ammonia in MeOH (30 mL). The ammonia in MeOH extract was concentrated in vacuo to afford the sub-title compound (F-7) (15 mg, 55 µmol, 39%, 90% Purity) as a dark orange oil. m/z 247.2 (M+H)$^+$ (ES+). $^1$H NMR (400 MHz, Chloroform-d) δ 7.91 (s, 1H), 6.66 (d, J=8.8 Hz, 1H), 6.48-6.43 (m, 2H), 3.80 (s, 3H), 3.20-3.10 (m, 4H), 3.03 (dd, J=14.4, 6.7 Hz, 1H), 2.81 (dd, J=14.4, 7.6 Hz, 1H), 1.35 (d, J=7.0 Hz, 3H). Exchangeable proton not visible.

Step 6: Synthesis of (S)-2-(2-methoxy-5-(1-(4-methyl-4H-1,2,4-triazol-3-yl)propan-2-yl)phenyl)-6-(pyrrolidin-1-ylmethyl)-4-(trifluoromethyl)isoindolin-1-one (F-9)

To a solution of intermediate B-5 (24 mg, 99% Wt, 1.2 Eq, 73 µmol) and pyrrolidine (6.5 mg, 7.6 µL, 1.5 Eq, 91 µmol) was added NaBH(OAc)$_3$ (32 mg, 2.5 Eq, 0.15 mmol) in DCM (2 mL) and stirred at rt for 2 h. The reaction mixture was diluted with DCM (10 mL) and washed with sat. aq. NaHCO$_3$ (10 mL). The organic layer was dried (phase separator) and concentrated in vacuum. The resultant gum was dissolved in EtOH (1 mL) and the product from step 5 (15 mg, 1 Eq, 61 µmol) in EtOH (1 mL) was added, followed by DIPEA (12 mg, 16 µL, 1.5 Eq, 91 µmol) and stirred at 60° C. overnight. The reaction mixture was diluted with EtOAc (10 mL) and washed with sat. aq. sol. of NH$_4$Cl (5 mL), sat. aq. sol. of NaHCO$_3$ (5 mL) and brine (5 mL). The combined organic layers were dried (MgSO$_4$), filtered and concentrated in vacuo. The crude product was purified by chromatography on silica gel (4 g cartridge, 0-10% MeOH/DCM) to afford a racemic mixture of the subtitled compound as a pale-yellow oil (11 mg). The crude was purified by chiral SFC (Waters, Basic (0.1% Ammonia), IH 10×250 mm, 5 um, 25% MeOH (0.1% Ammonia), 75% CO$_2$ to afford the title compound (S) enantiomer (F-9) (3.1 mg, 5.7 µmol, 9%, 95% Purity). m/z 514.2 (M+H)$^+$ (ES+). $^1$H NMR (400 MHz, Methanol-d$_4$) δ 8.29 (s, 1H), 8.10 (s, 1H), 8.01 (s, 1H), 7.28-7.21 (m, 2H), 7.11 (d, J=8.3 Hz, 1H), 4.98 (d, J=10.0 Hz, 2H), 3.89 (s, 2H), 3.85 (s, 3H), 3.44 (s, 3H), 3.30 (d, J=7.6 Hz, 1H), 3.14 (dd, J=14.8, 6.5 Hz, 1H), 3.06 (dd, J=14.8, 8.3 Hz, 1H), 2.63 (d, J=5.3 Hz, 4H), 1.88 (p, J=3.1 Hz, 4H), 1.44 (d, J=7.0 Hz, 3H).

Example 2: Synthesis of 2-(4-Methoxy-2'-(4-methyl-4H-1,2,4-triazol-3-yl)-[1,1'-biphenyl]-3-yl)-4-(trifluoromethyl)isoindolin-1-one (G-4)

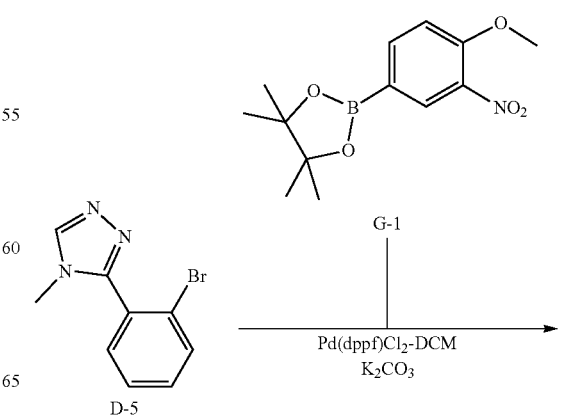

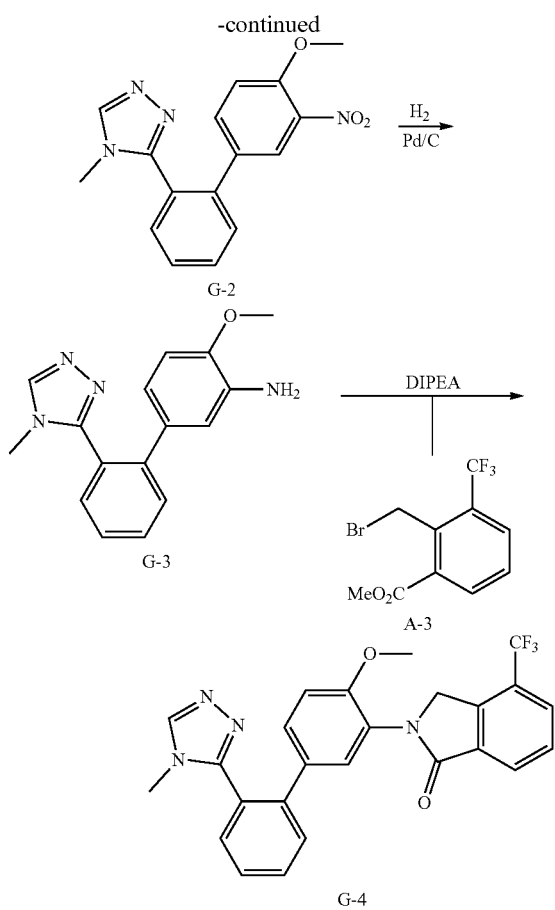

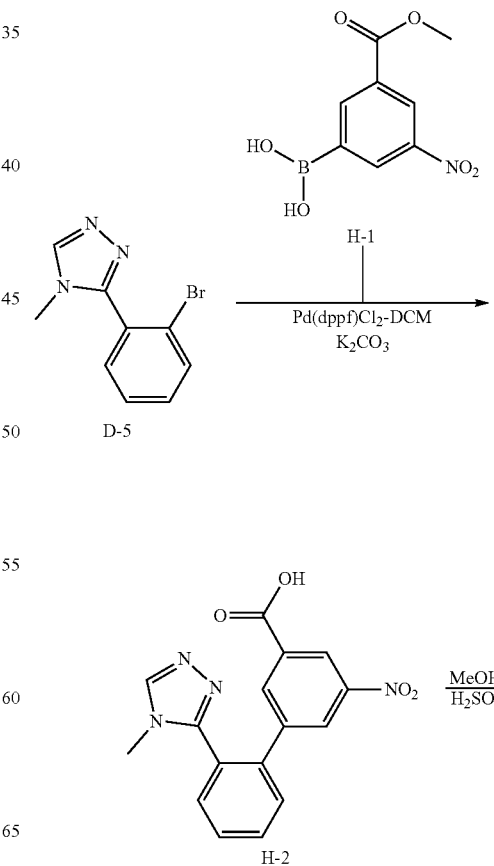

pound (G-3) (59 mg, 0.20 mmol, 95%, 95% Purity) as a pale yellow solid. m/z 280.9 (M+H)⁺ (ES+). 1H NMR (400 MHz, Chloroform-d) δ 8.42 (s, 1H), 7.66-7.35 (m, 5H), 6.74 (d, J=4.3 Hz, 1H), 6.67 (s, 1H), 3.85 (s, 3H), 3.03 (s, 3H). Two exchangeable protons not observed.

Step 3: Synthesis of 2-(4-Methoxy-2'-(4-methyl-4H-1,2,4-triazol-3-yl)-[1,1'-biphenyl]-3-yl)-4-(trifluoromethyl)isoindolin-1-one (G-4)

To a solution of the product from step 2 above (G-3) (31 mg, 1 Eq, 0.11 mmol) and intermediate A-3 (39 mg, 1.2 Eq, 0.13 mmol) in EtOH (1 mL) was added DIPEA (21 mg, 25 µL, 1.5 Eq, 0.17 mmol) and stirred at 60° C. for 3 days. The crude product was purified by preparative HPLC (Waters, Acidic (0.1% Formic acid), Acidic, Waters X-Select Prep-C18, 5 µm, 30×100 mm column, 0-100% MeCN in Water) to afford the title compound (G-4) (13 mg, 28 µmol, 25%, 99% Purity) as a white solid. m/z 465.3 (M+H)⁺ (ES+). ¹H NMR (400 MHz, Methanol-d4) δ 8.43 (s, 1H), 8.12 (d, J=7.6 Hz, 1H), 8.03-7.98 (m, 1H), 7.84-7.77 (m, 1H), 7.76-7.68 (m, 2H), 7.64-7.55 (m, 2H), 7.28 (dq, J=4.5, 2.4 Hz, 2H), 7.18 (d, J=9.2 Hz, 1H), 4.97 (d, J=1.6 Hz, 2H), 3.89 (s, 3H), 3.16 (s, 3H).

Example 3: Synthesis of Methyl 2'-(4-methyl-4H-1, 2,4-triazol-3-yl)-5-(1-oxo-4-(trifluoromethyl)isoindolin-2-yl)-[1,1'-biphenyl]-3-carboxylate (H-5)

Step 1: Synthesis of 3-(4'-Methoxy-3'-nitro-[1,1'-biphenyl]-2-yl)-4-methyl-4H-1,2,4-triazole (G-2)

To a solution of 2-(4-methoxy-3-nitrophenyl)-4,4,5,5-tetramethyl-1,3,2-dioxaborolane (G-1) (141 mg, 1.2 Eq, 504 µmol) and 3-(2-bromophenyl)-4-methyl-4H-1,2,4-triazole (D-5) (100 mg, 1.0 Eq, 420 µmol) in degassed 1,4-Dioxane (2 mL) and water (0.5 mL) were successively added Pd(dppf)Cl₂.DCM (34.3 mg, 0.1 Eq, 42.0 µmol) and K₂CO₃ (174 mg, 3 Eq, 1.26 mmol) and stirred at 90° C. overnight. The reaction mixture was diluted with EtOAc (10 mL) washed with sat. aq. NH₄Cl (1×5 mL), sat. aq. sol. of NaHCO₃ (1×5 mL) and brine (5 mL). The combined organic layers were dried (MgSO₄), filtered, and concentrated in vacuo. The crude product was purified by chromatography on silica gel (12 g cartridge, 0-30% MeOH/DCM) to afford the sub-title compound (G-2) as a pale yellow oil. m/z 310.9 (M+H)⁺ (ES+). ¹H NMR (400 MHz, DMSO-d6) δ 8.45 (s, 1H), 7.74-7.66 (m, 1H), 7.63 (dd, J=8.8, 1.8 Hz, 2H), 7.60-7.56 (m, 2H), 7.36 (dd, J=8.8, 2.3 Hz, 1H), 7.30 (d, J=8.8 Hz, 1H), 3.91 (s, 3H), 3.13 (s, 3H)

Step 2: Synthesis of 4-Methoxy-2'-(4-methyl-4H-1, 2,4-triazol-3-yl)-[1,1'-biphenyl]-3-amine (G-3)

To a solution of the product from step 1 above (G-2) (65 mg, 1 Eq, 0.21 mmol) in EtOH (2 mL) was added Pd/C 39 (6.5 mg, 10% Wt, 0.029 Eq, 6.1 µmol) and stirred at 26° C. with 5 atm of H₂ for 16 h. The catalyst was filtered and the solvent was removed in vacuo to afford the sub-title com-

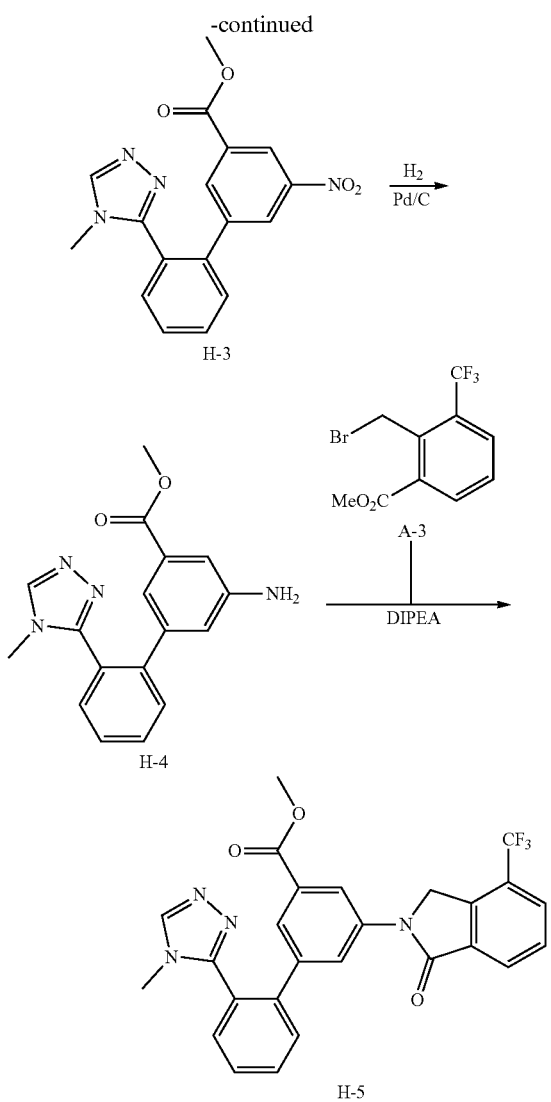

Step 1: Synthesis of 2'-(4-Methyl-4H-1,2,4-triazol-3-yl)-5-nitro-[1,1'-biphenyl]-3-carboxylic acid (H-2)

To a solution of (3-(methoxycarbonyl)-5-nitrophenyl)boronic acid (H-1) (138 mg, 1.2 Eq, 615 μmol) and intermediate D-5 (122 mg, 1.0 Eq, 512 μmol) in degassed 1,4-Dioxane (3 mL) and water (0.75 mL) were successively added Pd(dppf)Cl$_2$.DCM (41.8 mg, 0.1 Eq, 51.2 μmol) and K$_2$CO$_3$ (212 mg, 3 Eq, 1.54 mmol) and stirred at 90° C. overnight. The reaction mixture was diluted with EtOAc (10 mL), washed with sat. aq. sol. of NH$_4$Cl (5 mL), sat. aq. sol. of NaHCO$_3$ (5 mL) and brine (5 mL). The aqueous phase was extracted using CHCl$_3$/IPA (7:3, 5×10 mL), he combined organic extracts were dried (MgSO$_4$), filtered and concentrated in vacuo to afford the sub-title compound (H-2) (106 mg, 0.31 mmol, 61%, 95% Purity) as a pale yellow oil. m/z 325.3 (M+H)$^+$ (ES+); 323.1 (M−H)$^-$ (ES−). $^1$H NMR (400 MHz, Methanol-d$_4$) δ 8.81 (s, 1H), 8.77 (dd, J=2.3, 1.4 Hz, 1H), 8.33 (t, J=2.0 Hz, 1H), 8.20 (t, J=1.6 Hz, 1H), 7.89 (ddd, J=7.8, 5.7, 3.0 Hz, 1H), 7.83 (dt, J=7.8, 1.1 Hz, 1H), 7.78-7.75 (m, 2H), 3.42 (s, 3H). Exchangeable proton not visible.

Step 2: Synthesis of Methyl 2'-(4-methyl-4H-1,2,4-triazol-3-yl)-5-nitro-[1,1'-biphenyl]-3-carboxylate (H-3)

To a solution of the product from step 1 (H-2) (100 mg, 1 Eq, 308 μmol) in MeOH (25 mL) was added H$_2$SO$_4$ (1.51 mg, 0.826 μL, 0.05 Eq, 15.4 μmol) and stirred for 3 days at 80° C. The reaction mixture was concentrated in vacuo and the crude product was purified by chromatography on silica gel (12 g cartridge, 0-10% MeOH/DCM) to afford the sub-title compound (H-3) (90 mg, 0.24 mmol, 78%, 90% Purity) as a dark brown oil. m/z 339.3 (M+H)$^+$ (ES+). $^1$H NMR (400 MHz, Methanol-d$_4$) δ 8.74 (dd, J=2.2, 1.5 Hz, 1H), 8.49 (s, 1H), 8.31 (t, J=2.0 Hz, 1H), 8.19 (t, J=1.6 Hz, 1H), 7.87-7.77 (m, 2H), 7.77-7.68 (m, 2H), 3.98 (s, 3H), 3.34 (s, 3H).

Step 3: Synthesis of Methyl 5-amino-2'-(4-methyl-4H-1,2,4-triazol-3-yl)-[1,1'-biphenyl]-3-carboxylate (H-4)

To a solution of the product from step 2 (H-3) (90 mg, 90% Wt, 1 Eq, 0.24 mmol) in EtOH (3 mL) was added Pd/C 39 (9 mg, 10% Wt, 0.04 Eq, 8 μmol). The reaction mixture was stirred at 26° C. with 5 atm of H$_2$ for 16 h. The catalyst was filtered and the solvent was removed in vacuo to afford the sub-title compound (H-4) (73 mg, 0.22 mmol, 94%, 95% Purity) as a pale yellow solid. m/z 309.0 (M+H)$^+$ (ES+). $^1$H NMR (400 MHz, Methanol-d$_4$) δ 8.42 (s, 1H), 7.77-7.71 (m, 1H), 7.65-7.59 (m, 3H), 7.34-7.27 (m, 1H), 7.12 (t, J=1.6 Hz, 1H), 6.76 (dd, J=2.3, 1.7 Hz, 1H), 3.85 (s, 3H), 3.14 (s, 3H). Exchangeable proton not visible.

Step 4: Synthesis of Methyl 2'-(4-methyl-4H-1,2,4-triazol-3-yl)-5-(1-oxo-4-(trifluoromethyl)isoindolin-2-yl)-[1,1'-biphenyl]-3-carboxylate (H-5)

To a solution of the product from step 3 (H-4) (35 mg, 1 Eq, 0.11 mmol) and intermediate A-3 (40 mg, 1.2 Eq, 0.14 mmol) in MeOH (2.5 mL) was added DIPEA (22 mg, 26 μL, 1.5 Eq, 0.17 mmol). The mixture was stirred over 5 days at 60° C. The solvent was removed in vacuo and the crude product was purified by chromatography silica gel (12 g cartridge, 0-20% MeOH/DCM) to afford the title compound (H-5) (14 mg, 27 μmol, 24%, 95% Purity) as a light yellow solid. m/z 493.1 (M+H)$^+$ (ES+). $^1$H NMR (400 MHz, Methanol-d$_4$) δ 8.54 (dd, J=2.2, 1.4 Hz, 1H), 8.46 (s, 1H), 8.13 (d, J=7.6 Hz, 1H), 8.05-7.99 (m, 2H), 7.85-7.79 (m, 3H), 7.77 (t, J=1.5 Hz, 1H), 7.73-7.69 (m, 2H), 5.15 (s, 2H), 3.97 (s, 3H), 3.34 (s, 3H).

Example 4: Synthesis of 2'-(4-Methyl-4H-1,2,4-triazol-3-yl)-5-(1-oxo-4-(trifluoromethyl)isoindolin-2-yl)-[1,1'-biphenyl]-3-carboxylic acid (I-1)

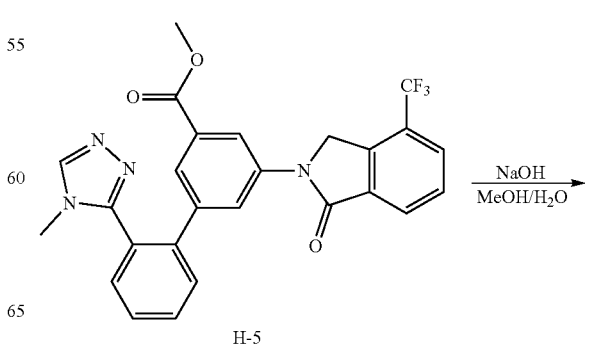

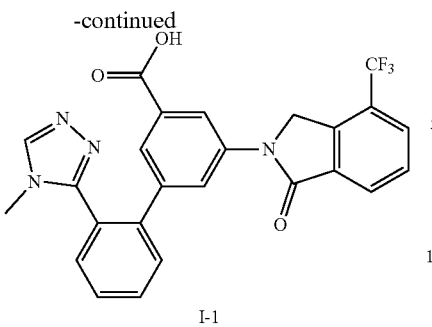

I-1

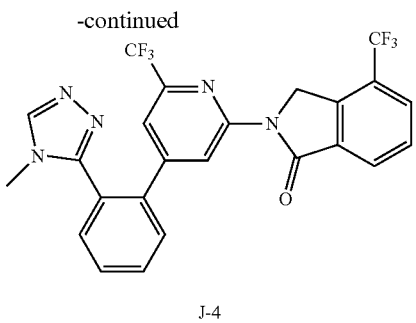

J-4

To a solution of methyl compound H-5 (10 mg, 1 Eq, 20 μmol) in MeOH (2 mL) was added NaOH (0.97 mg, 24 μL, 1 molar, 1.2 Eq, 24 μmol) and stirred at rt for 5 days. The reaction mixture was diluted with water (10 mL) and extracted with EtOAc (5 mL). The aqueous layers were combined, acidified with 1 M aqueous HCl and extracted with DCM (3×10 mL). The organic extracts were combined, washed with brine (10 mL), dried (MgSO4), and concentrated in vacuo to afford the title compound (I-1) (7 mg, 0.01 mmol, 70%) as a white solid. m/z 479.2 (M+H)$^+$ (ES+). $^1$H NMR (400 MHz, DMSO-d6) δ 13.15 (s, 1H), 8.59 (s, 1H), 8.40 (s, 1H), 8.08 (dd, J=16.7, 7.7 Hz, 2H), 7.85 (s, 1H), 7.81 (t, J=7.7 Hz, 1H), 7.73 (s, 2H), 7.68-7.59 (m, 2H), 7.49 (d, J=1.5 Hz, 1H), 5.16 (s, 2H), 3.14 (s, 3H).

Example 5: Synthesis of 2-(4-(2-(4-Methyl-4H-1,2,4-triazol-3-yl)phenyl)-6-(trifluoromethyl)pyridin-2-yl)-4-(trifluoromethyl)isoindolin-1-one (J-4)

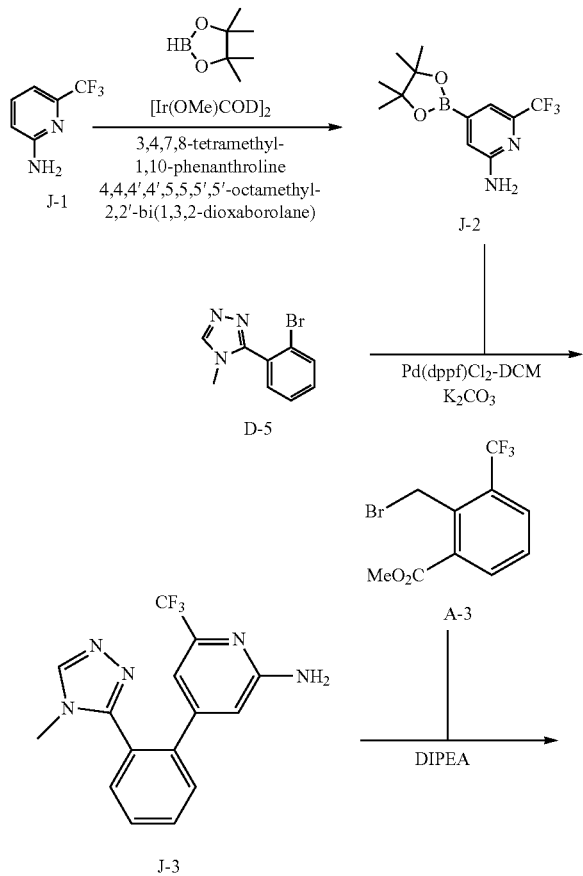

Step 1: Synthesis of 4-(4,4,5,5-Tetramethyl-1,3,2-dioxaborolan-2-yl)-6-(trifluoromethyl)pyridin-2-amine (J-2)

To a solution of 6-(trifluoromethyl)pyridin-2-amine (J-1) (162 mg, 1 Eq, 999 μmol) in THF (1 mL) was added 4,4,5,5-tetramethyl-1,3,2-dioxaborolane (153 mg, 174 μL, 1.2 Eq, 1.20 mmol), and stirred at rt for 1 h. [Ir(OMe)COD]2 (9.94 mg, 0.015 Eq, 15.0 μmol), 3,4,7,8-tetramethyl-1,10-phenanthroline (7.08 mg, 0.03 Eq, 30.0 μmol) and 4,4,4',4',5,5,5',5'-octamethyl-2,2'-bi(1,3,2-dioxaborolane) (127 mg, 0.5 Eq, 500 μmol) were added and the mixture was stirred 8 h at 80° C. The mixture was cooled to rt, diluted with MeOH (5 mL) and concentrated in vacuo. The residue was dissolved in DCM, passed through a silica gel plug, washing with DCM (350 mL). The washings were concentrated in vacuo to afford the sub-title compound (J-2) (80 mg, 0.27 mmol, 28%, 99% Purity) as a white solid. m/z 288.9 (M+H)$^+$ (ES+). $^1$H NMR (400 MHz, Chloroform-d) δ 7.34 (s, 1H), 7.05 (s, 1H), 1.35 (s, 12H). Exchangeable protons not observed.

Step 2: Synthesis of 4-(2-(4-Methyl-4H-1,2,4-triazol-3-yl)phenyl)-6-(trifluoromethyl)pyridin-2-amine (J-3)

To a solution of the product from step 1 (J-2) (70.0 mg, 1.0 Eq, 243 μmol) and intermediate D-5 (57.9 mg, 1.0 Eq, 243 μmol) in degassed 1,4-Dioxane (2 mL) and Water (0.5 mL) were successively added Pd(dppf)Cl$_2$.DCM (19.8 mg, 0.1 Eq, 24.3 μmol) and K$_2$CO$_3$ (101 mg, 3 Eq, 729 μmol) and stirred at 90° C. overnight. The reaction mixture was concentrated in vacuo and the crude product was purified by chromatography on silica gel (12 g cartridge, 0-30% MeOH/DCM) to afford the sub-title compound (J-3) (62 mg, 0.16 mmol, 64%, 80% Purity) as a pale green solid. m/z 320.3 (M+H)$^+$ (ES+). $^1$H NMR (400 MHz, Methanol-d4) δ 8.50 (s, 1H), 7.82-7.75 (m, 1H), 7.73-7.63 (m, 3H), 6.69 (d, J=1.3 Hz, 1H), 6.58 (d, J=0.7 Hz, 1H), 3.31 (s, 3H). Exchangeable proton not observed.

Step 3: Synthesis of 2-(4-(2-(4-Methyl-4H-1,2,4-triazol-3-yl)phenyl)-6-(trifluoromethyl)pyridin-2-yl)-4-(trifluoromethyl)isoindolin-1-one (J-4)

To a solution of the product from step 2 (J-3) (30 mg, 1 Eq, 94 μmol) and intermediate A-3 (33 mg, 1.2 Eq, 0.11 mmol) in MeOH (1 mL) was added DIPEA (18 mg, 21 μL, 1.5 Eq, 0.14 mmol) and the mixture was stirred at 60° C. for 3 days. The solvent was removed in vacuo and the crude product was purified by chromatography on silica gel (12 g cartridge, 0-40% MeOH/DCM) to afford a 90% pure product. The crude was purified by preparative HPLC (Waters, Basic (0.3% Ammonia), Basic water XBridge BEH C18 ODB prep column, 5 μm, 30 mm×100 mm, 0-100% MeCN in Water) to afford the title compound (J-4) (8 mg, 0.02 mmol, 20%, 99% Purity) as a pale yellow solid. m/z 504.5 (M+H)$^+$ (ES+). $^1$H NMR (400 MHz, DMSO-d6) δ 8.52 (d, J=8.5 Hz, 1H), 8.15 (d, J=2.0 Hz, 1H), 7.95 (d, J=7.0 Hz, 1H), 7.92-7.84 (m, 2H), 7.77 (ddd, J=9.1, 7.3, 1.5 Hz, 2H), 7.32 (dd, J=8.5, 7.1 Hz, 1H), 6.84 (d, J=1.4 Hz, 1H), 6.62 (s, 2H), 6.42 (s, 1H), 3.86 (s, 3H).

Example 6: Synthesis of 2-(2'-(4-Methyl-4H-1,2,4-triazol-3-yl)-5-(trifluoromethyl)-[1,1'-biphenyl]-3-yl)-4-(trifluoromethyl)isoindolin-1-one (K-3)

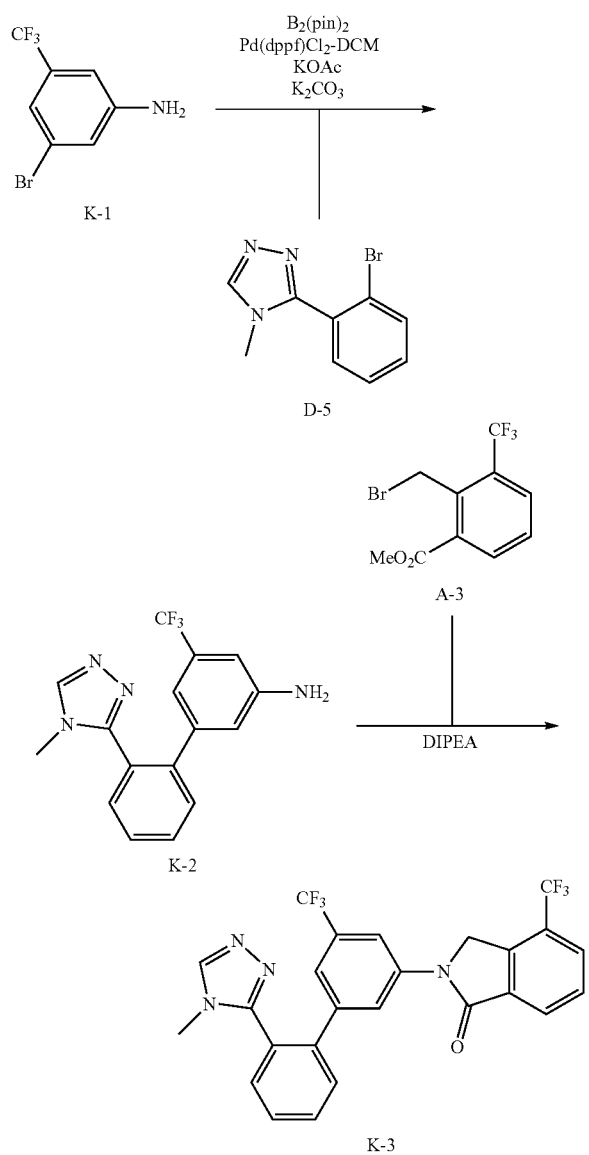

Step 1: Synthesis of 2'-(4-Methyl-4H-1,2,4-triazol-3-yl)-5-(trifluoromethyl)-[1,1'-biphenyl]-3-amine (K-2)

To a solution of 3-bromo-5-(trifluoromethyl)aniline (K-1) (100 mg, 58.9 μL, 1 Eq, 417 μmol) and B$_2$(pin)$_2$ (116 mg, 1.1 Eq, 458 μmol) in degassed 1,4-Dioxane (1.5 mL) was successively added Pd(dppf)Cl$_2$.DCM (34.0 mg, 0.1 Eq, 41.7 μmol) and KOAc (123 mg, 3 Eq, 1.25 mmol) and stirred at 100° C. for 2 h. The reaction mixture was cooled to rt and a solution of intermediate D-5 (99.2 mg, 1 Eq, 417 μmol) in 1,4-Dioxane (1.5 mL) and K$_2$CO$_3$ (173 mg, 3 Eq, 1.25 mmol) in water (0.75 mL) were added. The reaction mixture was stirred at 100° C. overnight. The reaction mixture was concentrated in vacuo and the crude product was purified by chromatography on silica gel (12 g cartridge, 0-30% MeOH/DCM) to afford the sub-title compound (K-2) (81 mg, 0.25 mmol, 60%, 98% Purity) as a pale green solid. m/z 319.3 (M+H)$^+$ (ES+). $^1$H NMR (400 MHz, DMSO-d6) δ 8.41 (s, 1H), 7.70-7.64 (m, 1H), 7.61-7.51 (m, 3H), 6.76 (s, 1H), 6.63 (t, J=1.9 Hz, 1H), 6.37 (s, 1H), 5.64 (s, 2H), 3.05 (s, 3H).

Step 2: Synthesis of 2-(2'-(4-Methyl-4H-1,2,4-triazol-3-yl)-5-(trifluoromethyl)-[1,1'-biphenyl]-3-yl)-4-(trifluoromethyl)isoindolin-1-one (K-3)

To a solution of the product from step 1 above (K-2) (32 mg, 1.5 Eq, 0.10 mmol) and intermediate A-3 (20 mg, 1 Eq, 67 μmol) in DMF (1 mL) was added DIPEA (13 mg, 15 μL, 1.5 Eq, 0.10 mmol) and stirred over 2 days at 60° C. The reaction mixture was concentrated in vacuo and the crude product was purified by chromatography on gold silica gel (12 g cartridge, 0-20% MeOH/DCM) followed by preparative HPLC (Waters, Acidic(0.1% Formic Acid), Acidic, Waters X-Select CSH C18 ODB, 5 μm, 30×100 mm column, 0-100% MeCN in water to afford the title compound (K-3) (3 mg, 4 μmol, 6%, 65% Purity) as a colourless oil. m/z 503.3 (M+H)$^+$ (ES+). $^1$H NMR (400 MHz, Methanol-d4) δ 8.45 (s, 1H), 8.40 (s, 1H), 8.15 (d, J=7.5 Hz, 1H), 8.03 (d, J=7.8 Hz, 1H), 7.95 (s, 1H), 7.82 (p, J=4.2 Hz, 3H), 7.73-7.65 (m, 2H), 7.36 (s, 1H), 5.18 (s, 2H), 3.31 (s, 3H).

Example 7: Synthesis of 2-(4-(2-(4-Methyl-4H-1,2,4-triazol-3-yl)phenyl)-1H-pyrrolo[2,3-b]pyridin-6-yl)-4-(trifluoromethyl)isoindolin-1-one (L-5)

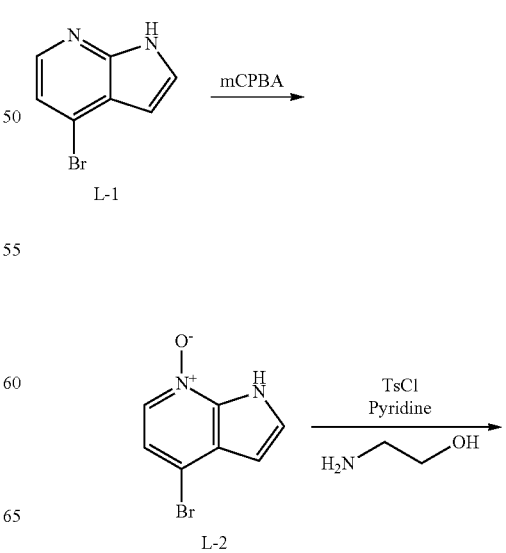

-continued

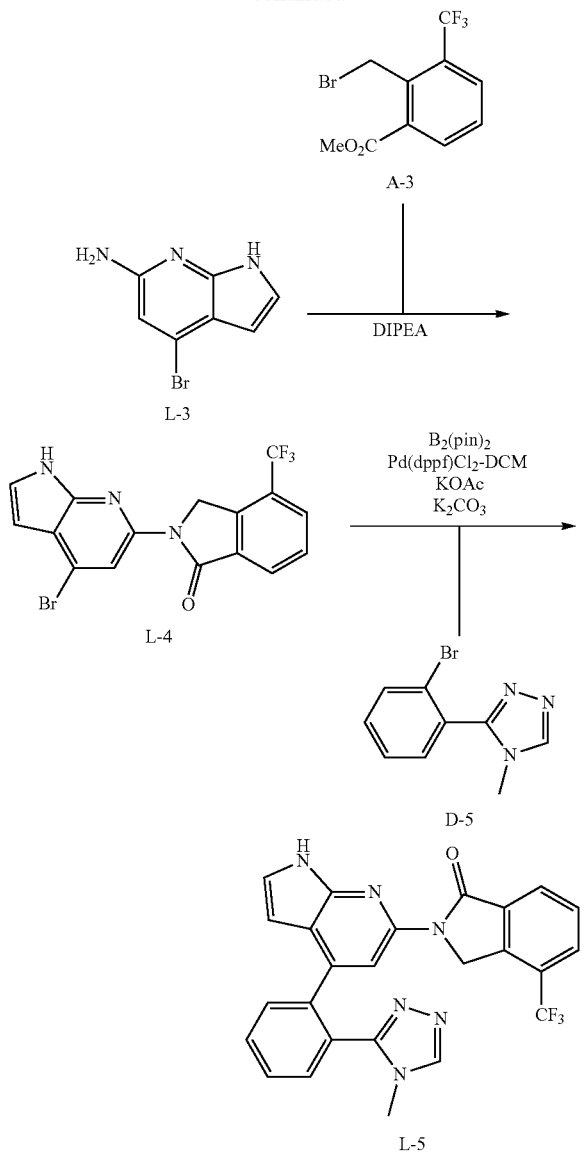

Step 1: Synthesis of 4-Bromo-1H-pyrrolo[2,3-b]pyridine 7-oxide (L-2)

To a solution of 4-bromo-1H-pyrrolo[2,3-b]pyridine (L-1) (1.00 g, 1 Eq, 5.08 mmol) in DCM (25 mL) was added 3-chlorobenzoperoxoic acid (1.88 g, 70% Wt, 1.5 Eq, 7.61 mmol) at 0° C. The mixture was slowly warmed to rt and stirred overnight. The reaction mixture was diluted with DCM (10 mL), washed with a 50/50 mix of sat. aq. sol. of NaHCO$_3$ and sat. aq. sol. of Na$_2$S$_2$O$_3$ (3×10 mL) and brine (10 mL). The combined organic layers were dried (MgSO$_4$), filtered and concentrated in vacuo to afford the sub-title compound (L-2) (520 mg, 2.4 mmol, 48%, 99% Purity) as a pale brown solid. m/z 213.1/215.1 (M+H)$^+$ (ES+). $^1$H NMR (400 MHz, Methanol-d4) δ 8.13 (d, J=6.6 Hz, 1H), 7.61 (d, J=3.5 Hz, 1H), 7.44 (d, J=6.6 Hz, 1H), 6.68 (d, J=3.5 Hz, 1H). Exchangeable proton not observed.

Step 2: Synthesis of 4-Bromo-1H-pyrrolo[2,3-b]pyridin-6-amine (L-3)

To a solution of the product from step 1 above (L-2) (519 mg, 1 Eq, 2.44 mmol) in pyridine (35 mL) was added 4-methylbenzenesulfonyl chloride (604 mg, 1.3 Eq, 3.17 mmol) and stirred at rt overnight. The pyridine was removed under vacuum and to the residue was added 2-aminoethan-1-ol (10.4 g, 10.3 mL, 70 Eq, 171 mmol) and stirred at rt for 1 h. The reaction mixture was diluted with DCM (25 mL) and water (25 mL) extracted with DCM (5×10 mL). The combined organic layers were dried (MgSO$_4$), filtered and concentrated in vacuo. The crude product was purified by chromatography on silica gel (40 g cartridge, 0-10% MeOH/DCM) to afford the sub-title compound (L-3) (300 mg, 1.4 mmol, 57%, 99% Purity) as a pale brown solid. m/z 212.1/214.1 (M+H)$^+$ (ES+). $^1$H NMR (400 MHz, DMSO-d6) δ 11.13 (s, 1H), 7.01 (dd, J=3.5, 2.4 Hz, 1H), 6.50 (s, 1H), 6.12 (dd, J=3.4, 2.1 Hz, 1H), 5.82 (s, 2H).

Step 3: Synthesis of 2-(4-Bromo-1H-pyrrolo[2,3-b]pyridin-6-yl)-4-(trifluoromethyl)isoindolin-1-one (L-4)

To a solution of the product from step 2 above (L-3) (50 mg, 1 Eq, 0.24 mmol) and intermediate A-3 (84 mg, 1.2 Eq, 0.28 mmol) in DMF (2 mL) was added DIPEA (61 mg, 72 μL, 2.0 Eq, 0.47 mmol) and stirred overnight at 60° C. The reaction mixture was cooled to rt and concentrated in vacuo. The solid was washed with a small amount of DCM, filtered and dried to afford the sub-title compound (L-4) (61 mg, 0.15 mmol, 65%, 99% Purity) as a pale brown solid. m/z 396.1/398.1 (M+H)$^+$ (ES+). $^1$H NMR (400 MHz, DMSO-d6) δ 12.14 (s, 1H), 8.63 (s, 1H), 8.14 (d, J=7.7 Hz, 1H), 8.07 (dd, J=8.0, 3.1 Hz, 1H), 7.81 (t, J=7.7 Hz, 1H), 7.53 (d, J=3.7 Hz, 1H), 6.42 (d, J=3.5 Hz, 1H), 5.32 (s, 2H).

Step 4: Synthesis of 2-(4-(2-(4-Methyl-4H-1,2,4-triazol-3-yl)phenyl)-1H-pyrrolo[2,3-b]pyridin-6-yl)-4-(trifluoromethyl)isoindolin-1-one (L-5)

To a solution of the product from step 3 above (L-4) (20 mg, 1.0 Eq, 50 μmol) and B$_2$(pin)$_2$ (14 mg, 1.1 Eq, 56 μmol) in degassed 1,4-Dioxane (1 mL) was successively added Pd(dppf)Cl$_2$.DCM (4.1 mg, 0.1 Eq, 5.0 μmol) and KOAc (15 mg, 3 Eq, 0.15 mmol). The mixture was stirred at 100° C. for 2 h. The reaction mixture was cooled to rt and a solution of intermediate D-5 (14 mg, 1.2 Eq, 61 μmol) in 1,4-Dioxane (1 mL) was added followed by a solution of K$_2$CO$_3$ (21 mg, 3 Eq, 0.15 mmol) in water (0.5 mL). The reaction mixture was stirred at 100° C. overnight. The reaction mixture was cooled to rt and concentrated in vacuo. The crude product was purified by chromatography on silica gel (12 g cartridge, 0-20% MeOH/DCM) followed by recrystallization in EtOH to afford the title compound (L-5) (7 mg, 0.01 mmol, 20%, 99% Purity) as a clear white solid. m/z 475.1 (M+H)$^+$ (ES+). $^1$H NMR (400 MHz, DMSO-d6) δ 11.84 (s, 1H), 8.33 (s, 1H), 8.13-8.00 (m, 3H), 7.84-7.65 (m, 5H), 7.37 (t, J=2.9 Hz, 1H), 6.17 (dd, J=3.6, 1.7 Hz, 1H), 5.32 (s, 2H), 3.30 (s, 3H).

Example 8: Synthesis of 2-(1-Ethyl-4-(2-(4-methyl-4H-1,2,4-triazol-3-yl)phenyl)-1H-pyrrolo[2,3-b]pyridin-6-yl)-4-(trifluoromethyl)isoindolin-1-one (M-2)

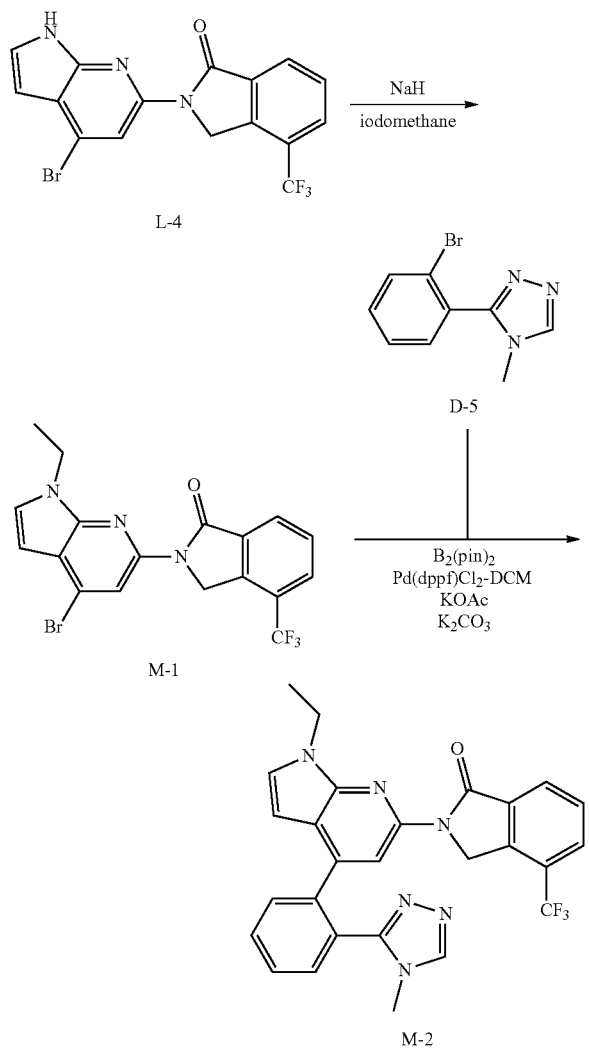

Step 1: Synthesis of 2-(4-Bromo-1-ethyl-1H-pyrrolo[2,3-b]pyridin-6-yl)-4-(trifluoromethyl)isoindolin-1-one (M-1)

To a solution of intermediate L-4 (30 mg, 1 Eq, 76 μmol) in DMF (1 mL) at 0° C. was added NaH (3.2 mg, 60% Wt, 1.05 Eq, 80 μmol) and the suspension stirred at 0° C. for 1 h. Iodoethane (12 mg, 6.4 μL, 1.05 Eq, 80 μmol) was added dropwise at 0° C. The resulting mixture was slowly warmed to rt and stirred for 1 h at this temperature. The solution was quenched with water and extracted with EtOAc (10 mL). The organic extract was washed with sat. aq. sol of NH$_4$Cl (5 mL), sat. aq. sol of NaHCO$_3$ (5 mL) and brine (5 mL). The combined organic extracts were dried (MgSO$_4$), filtered and concentrated in vacuo. The crude product was purified by chromatography on silica gel (12 g cartridge, 0-30% EtOAc/isohexane) to afford the sub-title compound (M-1) (21 mg, 47 μmol, 62%, 95% Purity) as a clear white solid. m/z 424.0 and 426.3 (M+H)$^+$ (ES+). $^1$H NMR (400 MHz, Chloroform-d) δ 8.71 (s, 1H), 8.14 (d, J=7.6 Hz, 1H), 7.87 (d, J=7.7 Hz, 1H), 7.66 (t, J=7.7 Hz, 1H), 7.23 (d, J=3.5 Hz, 1H), 6.49 (d, J=3.5 Hz, 1H), 5.33 (s, 2H), 4.32 (q, J=7.3 Hz, 2H), 1.52 (t, J=7.3 Hz, 3H).

Step 2: Synthesis of 2-(1-Ethyl-4-(2-(4-methyl-4H-1,2,4-triazol-3-yl)phenyl)-1H-pyrrolo[2,3-b]pyridin-6-yl)-4-(trifluoromethyl)isoindolin-1-one (M-2)

To a solution of the product from step 1 above (M-1) (21 mg, 1.0 Eq, 50 μmol) and B$_2$(pin)$_2$ (14 mg, 1.1 Eq, 54 μmol) in degassed 1,4-Dioxane (1 mL) was successively added Pd(dppf)Cl$_2$.DCM (4.0 mg, 0.1 Eq, 5.0 μmol) and KOAc (15 mg, 3 Eq, 0.15 mmol) and stirred at 100° C. for 2 h. The reaction mixture was cooled to rt and a solution of intermediate D-5 (14 mg, 1.2 Eq, 59 μmol) in 1,4-Dioxane (1 mL) was added followed by a solution of K$_2$CO$_3$ (21 mg, 3 Eq, 0.15 mmol) in water (0.5 mL). The reaction mixture was stirred at 100° C. overnight. The crude product was purified by chromatography on RP Flash C18 (12 g cartridge, 15-100% (0.1% Formic acid in MeCN)/(0.1% Formic Acid in Water)) to afford the title compound (M-2) (1.81 mg, 3.4 μmol, 5.1%, 95% Purity) as a pale yellow solid. m/z 503.3 (M+H)$^+$ (ES+). $^1$H NMR (400 MHz, Methanol-d4) δ 8.38 (s, 1H), 8.12 (d, J=7.7 Hz, 1H), 8.03 (s, 1H), 8.00 (d, J=7.7 Hz, 1H), 7.91-7.87 (m, 1H), 7.86-7.78 (m, 2H), 7.77-7.70 (m, 2H), 7.41 (d, J=3.6 Hz, 1H), 6.39 (d, J=3.6 Hz, 1H), 5.39 (s, 2H), 4.38 (q, J=7.2 Hz, 2H), 3.41 (s, 3H), 1.52 (t, J=7.3 Hz, 3H).

Example 9: Synthesis of 2-(5-(Hydroxymethyl)-2'-(4-methyl-4H-1,2,4-triazol-3-yl)-[1,1'-biphenyl]-3-yl)-4-(trifluoromethyl)isoindolin-1-one (N-5)

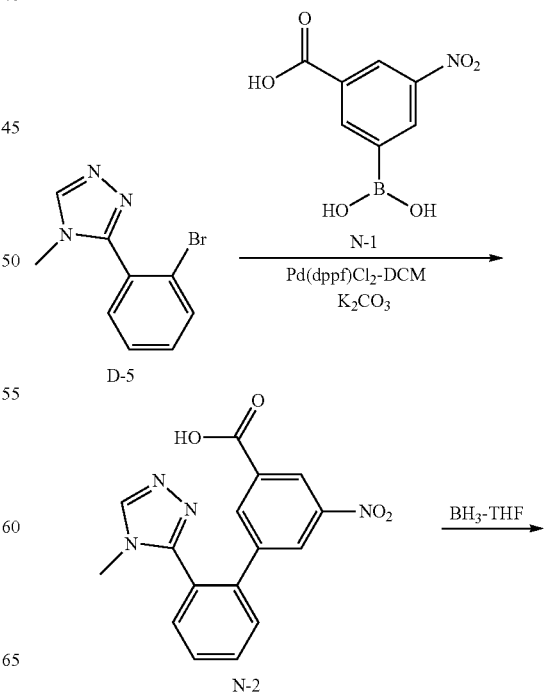

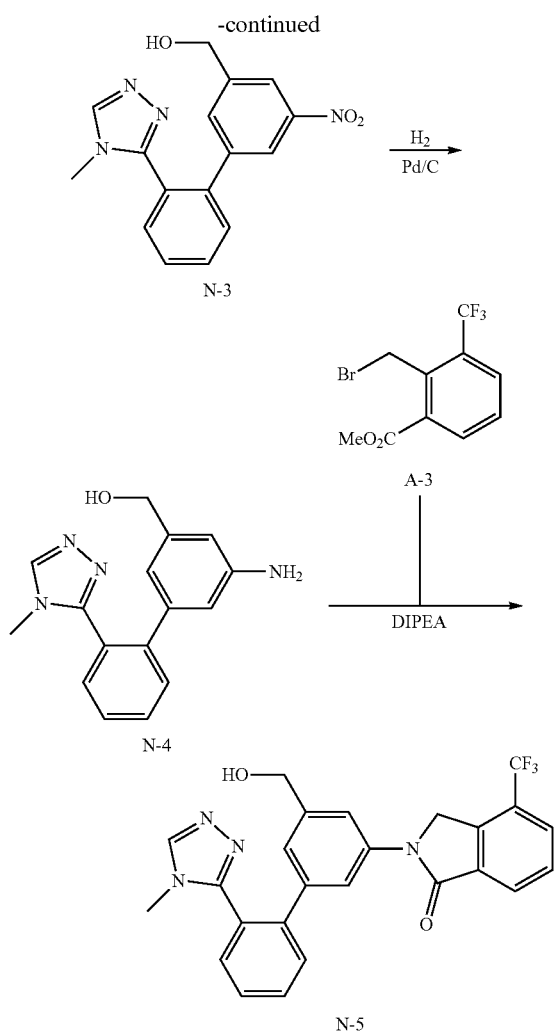

Step 1: Synthesis of 2'-(4-Methyl-4H-1,2,4-triazol-3-yl)-5-nitro-[1,1'-biphenyl]-3-carboxylic acid (N-2)

To a solution of (3-(methoxycarbonyl)-5-nitrophenyl)boronic acid (N-1) (227 mg, 1.2 Eq, 1.01 mmol) and intermediate D-5 (200 mg, 1.0 Eq, 840 μmol) in degassed 1,4-Dioxane (4 mL) and water (1 mL) were successively added Pd(dppf)Cl$_2$.DCM (68.6 mg, 0.1 Eq, 84.0 μmol) and K$_2$CO$_3$ (348 mg, 3 Eq, 2.52 mmol). The mixture was stirred at 90° C. overnight. The reaction mixture was diluted with DCM (5 mL) and 1 M NaOH (10 mL) and extracted with DCM (3×5 mL). The aqueous extracts were combined and acidified with concentrated HCl and extracted with DCM/IPA (70:30) (5×10 mL). The combined organic layers were dried (MgSO$_4$), filtered and concentrated in vacuo. The crude product was purified by chromatography on RP Flash C18 (12 g cartridge, 15-65% (0.1% Formic acid in MeCN)/(0.1% Formic Acid in Water)) to afford the sub-title compound (N-2) (255 mg, 0.72 mmol, 86%, 92% Purity) as a clear white solid. m/z 325.3 (M+H)$^+$ (ES+); 323.1 (M−H)$^−$ (ES−). $^1$H NMR (400 MHz, DMSO-d6) δ 13.74 (s, 1H), 8.52 (dd, J=2.2, 1.4 Hz, 1H), 8.43 (s, 1H), 8.15 (t, J=2.0 Hz, 1H), 8.02 (t, J=1.6 Hz, 1H), 7.78-7.73 (m, 2H), 7.69-7.63 (m, 2H), 3.19 (s, 3H).

Step 2: Synthesis of (2'-(4-Methyl-4H-1,2,4-triazol-3-yl)-5-nitro-[1,1'-biphenyl]-3-yl)methanol (N-3)

To a solution of the product from step 1 above (N-2) (235 mg, 1 Eq, 725 μmol) in anhydrous THF (25 mL) was added BH$_3$.THF (311 mg, 3.62 mL, 1 molar, 5 Eq, 3.62 mmol) at 0° C. The resulting mixture was slowly warmed to rt and stirred at this temperature under N$_2$ atmosphere for 16 h. The mixture was slowly quenched with MeOH and concentrated in vacuo. The crude product was purified by chromatography on RP Flash C18 (12 g cartridge, 15-75% (0.1% Formic acid in MeCN)/(0.1% Formic Acid in Water)) to afford the sub-title compound (N-3) (16 mg, 51 μmol, 7.0%, 98% Purity) as a clear white solid. m/z 311.2 (M+H)$^+$ (ES+). $^1$H NMR (400 MHz, Methanol-d4) δ 8.48-8.39 (m, 1H), 8.21 (s, 1H), 7.96-7.90 (m, 1H), 7.77 (ddt, J=17.5, 7.8, 2.9 Hz, 2H), 7.71-7.57 (m, 3H), 4.68 (s, 2H), 3.28-3.21 (m, 3H). One exchangeable proton not observed.

Step 3: Synthesis of (5-Amino-2'-(4-methyl-4H-1,2,4-triazol-3-yl)-[1,1'-biphenyl]-3-yl)methanol (N-4)

To a solution of the product from step 2 above (N-3) (15 mg, 1 Eq, 48 μmol) in EtOH (1 mL) was added Pd/C 39 (2 mg, 10% Wt, 0.04 Eq, 2 μmol). The reaction mixture was stirred at 45° C. with 5 atm of H$_2$ for 16 h. The catalyst was filtered, and the solvent removed in vacuo to afford the sub-title compound (N-4) (15 mg, 48 μmol, 100%, 90% Purity) as a pale yellow solid. m/z 281.6 (M+H)$^+$ (ES+). $^1$H NMR (400 MHz, Methanol-d4) δ 8.37 (s, 1H), 7.70 (ddd, J=8.5, 6.7, 2.0 Hz, 1H), 7.65-7.62 (m, 1H), 7.61-7.54 (m, 2H), 6.71 (t, J=1.8 Hz, 1H), 6.50 (d, J=1.6 Hz, 1H), 6.45 (t, J=2.0 Hz, 1H), 4.44 (s, 2H), 3.08 (s, 3H). Three exchangeable protons not observed.

Step 4: Synthesis of 2-(5-(Hydroxymethyl)-2'-(4-methyl-4H-1,2,4-triazol-3-yl)-[1,1'-biphenyl]-3-yl)-4-(trifluoromethyl)isoindolin-1-one (N-5)

To a solution of the product from step 3 above (N-4) (16 mg, 1 Eq, 57 μmol) and intermediate A-3 (20 mg, 1.2 Eq, 68 μmol) in DMF (1 mL) was added DIPEA (11 mg, 13 μL, 1.5 Eq, 86 μmol) and stirred at 60° C. for 3 days. The solvent was removed in vacuo and the crude product was purified by chromatography on RP Flash C18 (4 g cartridge, 15-65% (0.1% Formic acid in MeCN)/(0.1% Formic Acid in Water)) to afford the title compound (N-5) (1.96 mg, 3.8 μmol, 6.7%, 90% Purity) as a pale yellow solid. m/z 465.3 (M+H)$^+$ (ES+). $^1$H NMR (400 MHz, Methanol-d4) δ 8.40 (s, 1H), 8.12 (d, J=7.6 Hz, 1H), 8.00 (d, J=7.6 Hz, 1H), 7.89 (s, 1H), 7.81 (d, J=7.9 Hz, 1H), 7.79-7.74 (m, 2H), 7.66-7.63 (m, 3H), 7.15 (s, 1H), 5.10 (s, 2H), 4.65 (s, 2H), 3.24 (s, 3H). One exchangeable proton not observed.

Example 10: Synthesis of N-Methyl-2'-(4-methyl-4H-1,2,4-triazol-3-yl)-5-(1-oxo-4-(trifluoromethyl) isoindolin-2-yl)-[1,1'-biphenyl]-3-carboxamide (O-3)

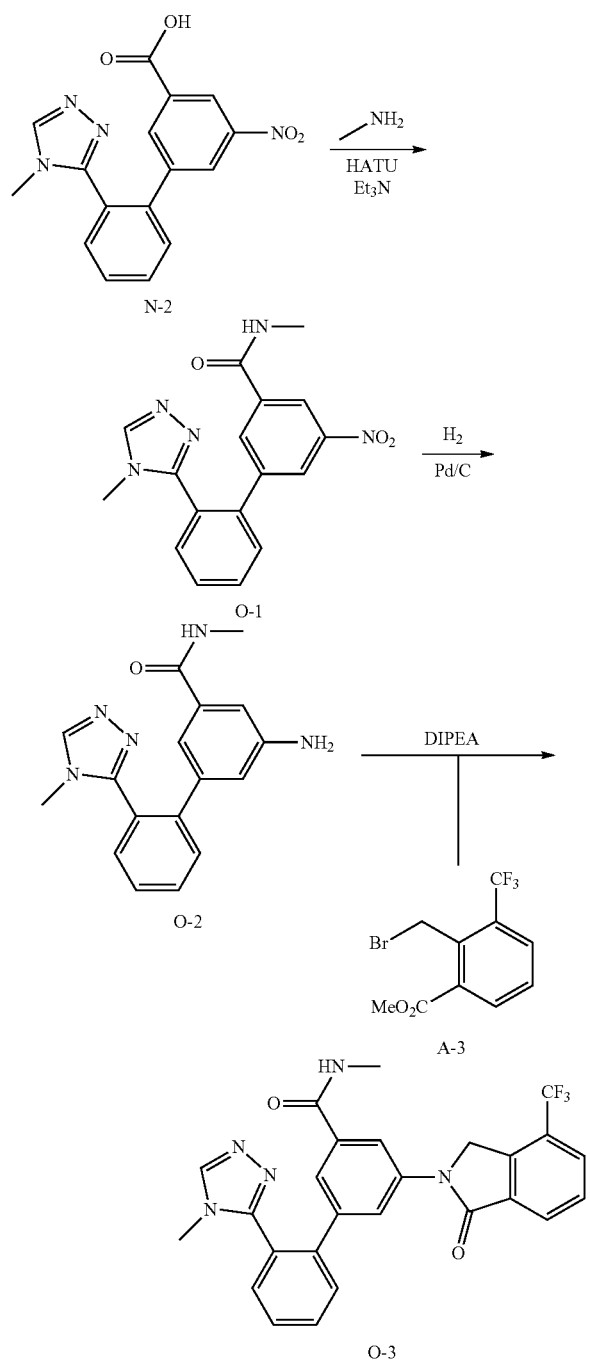

Step 1: Synthesis of N-Methyl-2'-(4-methyl-4H-1,2, 4-triazol-3-yl)-5-nitro-[1,1'-biphenyl]-3-carboxamide (O-1)

To a solution of intermediate N-2 (100 mg, 1 Eq, 308 μmol) in DMF (5 mL) were added HATU (129 mg, 1.1 Eq, 339 μmol) and NEt$_3$ (93.6 mg, 129 μL, 3 Eq, 925 μmol). The mixture was stirred 20 min at rt then methanamine (14.4 mg, 231 μL, 2 molar, 1.5 Eq, 463 μmol) was slowly added. The mixture was stirred at rt for 16 h. The solvent was removed in vacuo and the crude product was purified by chromatography on silica gel (12 g cartridge, 0-20% MeOH/DCM) to afford the sub-title compound (O-1) (55.3 mg, 0.16 mmol, 51%, 95% Purity) as a pale yellow solid. m/z 337.9 (M+H)$^+$ (ES+). $^1$H NMR (400 MHz, Methanol-d4) δ 8.64 (t, J=1.9 Hz, 1H), 8.45 (s, 1H), 8.13 (dt, J=4.3, 1.7 Hz, 2H), 7.86-7.77 (m, 2H), 7.76-7.68 (m, 2H), 3.01 (s, 3H), 2.96 (s, 3H). One exchangeable proton not observed.

Step 2: Synthesis of 5-Amino-N-methyl-2'-(4-methyl-4H-1,2,4-triazol-3-yl)-[1,1'-biphenyl]-3-carboxamide (O-2)

To a solution of the product from step 1 above (O-1) (76 mg, 90% Wt, 1 Eq, 0.20 mmol) in EtOH (3 mL) was added Pd/C 39 (8 mg, 10% Wt, 0.04 Eq, 8 μmol). The reaction mixture was stirred at 45° C. with 5 atm of H$_2$ for 16 h. The catalyst was filtered, and the solvent was removed in vacuo to afford the sub-title compound (O-2) (65 mg, 0.19 mmol, 94%, 90% Purity) as a pale yellow solid. m/z 308.4 (M+H)$^+$ (ES+). $^1$H NMR (400 MHz, Methanol-d4) δ 8.39 (s, 1H), 7.73 (ddd, J=7.8, 5.2, 3.4 Hz, 1H), 7.66 (dt, J=7.8, 1.0 Hz, 1H), 7.64-7.56 (m, 2H), 7.05 (t, J=1.9 Hz, 1H), 6.96 (t, J=1.6 Hz, 1H), 6.58 (t, J=1.9 Hz, 1H), 3.13 (s, 3H), 2.89 (s, 3H). Three exchangeable protons not observed.

Step 3: Synthesis of N-Methyl-2'-(4-methyl-4H-1,2, 4-triazol-3-yl)-5-(1-oxo-4-(trifluoromethyl)isoindolin-2-yl)-[1,1'-biphenyl]-3-carboxamide (O-3)

To a solution of the product from step 2 above (O-2) (65 mg, 1 Eq, 0.21 mmol) and intermediate A-3 (75 mg, 1.2 Eq, 0.25 mmol) in DMF (2.5 mL) was added DIPEA (41 mg, 48 μL, 1.5 Eq, 0.32 mmol). The mixture was stirred at 60° C. for 3 days. The solvent was removed in vacuo and the crude product was purified by chromatography on RP Flash C18 (12 g cartridge, 15-65% MeCN/10 mM ammonium bicarbonate) to afford the title compound (O-3) (7 mg, 0.01 mmol, 7%, 99% Purity) as a white solid. m/z 492.4 (M+H)$^+$ (ES+). $^1$H NMR (400 MHz, Methanol-d4) δ 8.43 (s, 1H), 8.22 (t, J=1.8 Hz, 1H), 8.12 (d, J=7.7 Hz, 1H), 8.01 (d, J=7.7 Hz, 1H), 7.94 (t, J=1.9 Hz, 1H), 7.83-7.77 (m, 3H), 7.67 (dd, J=3.8, 2.8 Hz, 2H), 7.64 (t, J=1.6 Hz, 1H), 5.13 (s, 2H), 3.36 (s, 3H), 2.97 (s, 3H). One exchangeable proton not observed.

Example 11: Synthesis of 6-(Hydroxymethyl)-2-(2'-(4-methyl-4H-1,2,4-triazol-3-yl)-[1,1'-biphenyl]-3-yl)-4-(trifluoromethyl)isoindolin-1-one (P-2)

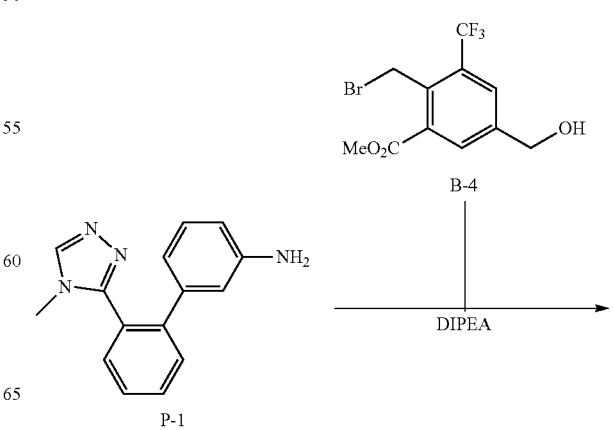

-continued

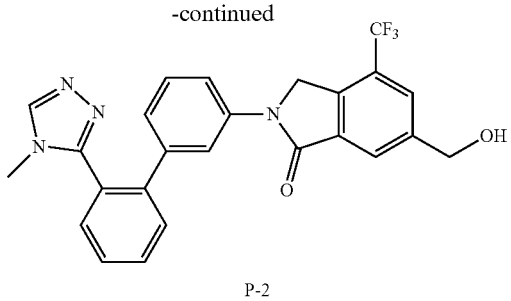

P-2

DIPEA (159 mg, 214 µL, 1.5 Eq, 1.38 mmol) was added to a solution of 2'-(4-methyl-4H-1,2,4-triazol-3-yl)-[1,1'-biphenyl]-3-amine (P-1) (230 mg, 1 Eq, 917 µmol) D-5 and intermediate B-4 (300 mg, 1 Eq, 917 µmol) in EtOH (16 mL) and stirred at 60° C. for 18 h and then at rt over 16 h. The reaction mixture was cooled down and the precipitate filtered to afford the title compound (P-2) (167 mg, 360 µmol, 39.2%) as a white solid. m/z 465.2 (M+H)+ (ES+). $^1$H NMR (400 MHz, DMSO-d6) δ 8.39 (s, 1H), 8.02-7.97 (m, 2H), 7.95 (s, 1H), 7.75-7.65 (m, 3H), 7.62-7.56 (m, 2H), 7.37 (t, J=8.0 Hz, 1H), 6.90 (d, J=7.7 Hz, 1H), 5.58 (t, J=5.8 Hz, 1H), 5.09 (s, 2H), 4.71 (d, J=5.8 Hz, 2H), 3.08 (s, 3H).

Example 12: Synthesis of (S)-2-(2'-(4-Methyl-4H-1,2,4-triazol-3-yl)-[1,1'-biphenyl]-3-yl)-6-((3-methylpiperidin-1-yl)methyl)-4-(trifluoromethyl)isoindolin-1-one (R-2)

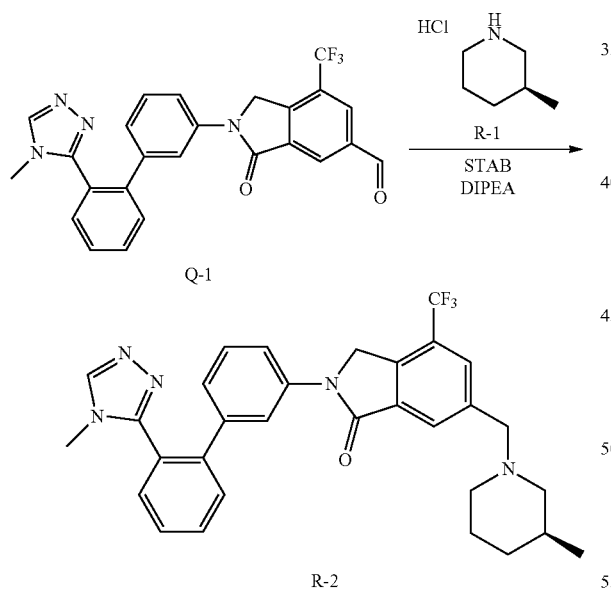

(S)-3-methylpiperidine, HCl (R-1) (7.1 mg, 1.1 Eq, 52 µmol) and DIPEA (18 mg, 25 µL, 3.0 Eq, 0.14 mmol) in DCM (1 mL) were added to intermediate Q-1 (22 mg, 1 Eq, 48 µmol) in DCM (1 mL) followed by NaBH(OAc)$_3$ (20 mg, 2.0 Eq, 95 µmol). The reaction mixture was stirred at rt overnight. The reaction mixture was diluted with DCM (10 mL) and washed with sat. aq. NaHCO$_3$ (10 mL). The organic extract was dried (phase separator) and concentrated in vacuo. The crude product was purified by preparative HPLC (Waters, Basic (0.3% Ammonia), Basic, Waters XBridge BEH C18 ODB, 5 µm, 30×100 mm column 0-100% MeCN in water to afford the title compound (R-2) (3.5 mg, 6.4 µmol, 13%, 99% Purity) as a white solid. m/z 546.2 (M+H)+ (ES+). $^1$H NMR (400 MHz, Methanol-d4) δ 8.40 (s, 1H), 8.07 (s, 1H), 7.99 (s, 1H), 7.89 (ddd, J=8.2, 2.3, 0.9 Hz, 1H), 7.80-7.73 (m, 3H), 7.67-7.61 (m, 2H), 7.46 (t, J=8.0 Hz, 1H), 7.13 (ddd, J=7.8, 1.8, 1.0 Hz, 1H), 5.08 (d, J=1.7 Hz, 2H), 3.72 (s, 2H), 3.22 (s, 3H), 2.91-2.80 (m, 2H), 2.08-1.97 (m, 1H), 1.82-1.57 (m, 5H), 1.00-0.87 (m, 4H).

Example 13: Synthesis of (R)-2-(2'-(4-Methyl-4H-1,2,4-triazol-3-yl)-[1,1'-biphenyl]-3-yl)-6-((3-methylpiperidin-1-yl)methyl)-4-(trifluoromethyl)isoindolin-1-one (S-2)

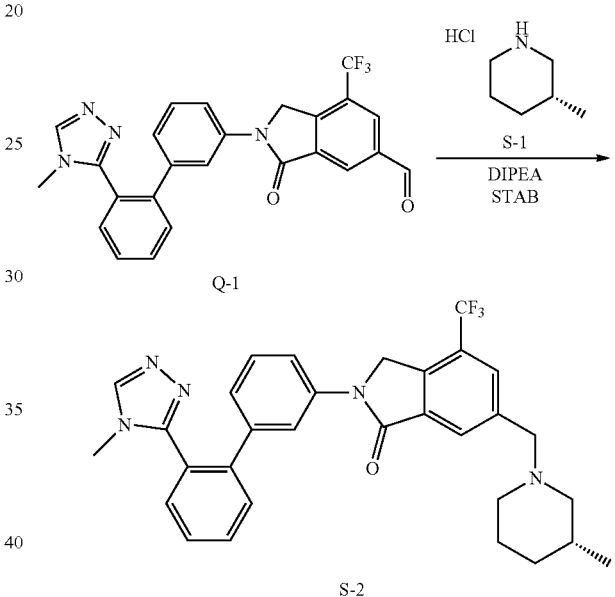

(R)-3-methylpiperidine, HCl (S-1) (7.1 mg, 1.1 Eq, 52 µmol) and DIPEA (18 mg, 25 µL, 3.0 Eq, 0.14 mmol) in DCM (1 mL) was added to intermediate Q-1 (22 mg, 1 Eq, 48 µmol) in DCM (1 mL) followed by NaBH(OAc)$_3$ (20 mg, 2.0 Eq, 95 µmol). The reaction mixture was stirred at rt overnight. The reaction mixture was diluted with DCM (10 mL) and washed with sat. aq. NaHCO$_3$ (10 mL). The organic extract was dried (phase separator) and concentrated in vacuo. The crude was purified by reversed phase preparative HPLC (Waters, Basic (0.3% Ammonia), Basic, Waters XBridge BEH C18 ODB, 5 µm, 30×100 mm column 0-100% MeCN in water to afford the title compound (S-2) (4 mg, 48 µmol, 20%, 99% Purity) as a white solid. m/z 546.2 (M+H)+ (ES+) at 2.58 min. $^1$H NMR (400 MHz, Methanol-d4) δ 8.40 (s, 1H), 8.07 (s, 1H), 7.99 (s, 1H), 7.89 (ddd, J=8.3, 2.3, 0.9 Hz, 1H), 7.80-7.73 (m, 3H), 7.67-7.62 (m, 2H), 7.46 (t, J=8.0 Hz, 1H), 7.13 (dt, J=7.9, 1.1 Hz, 1H), 5.08 (d, J=1.6 Hz, 2H), 3.72 (s, 2H), 3.22 (s, 3H), 2.91-2.79 (m, 2H), 2.08-1.97 (m, 1H), 1.80-1.57 (m, 5H), 1.01-0.87 (m, 4H).

Example 14: Synthesis of 6-((((1S,2S)-2-Hydroxy-cyclopentyl)amino)methyl)-2-(2'-(4-methyl-4H-1,2,4-triazol-3-yl)-[1,1'-biphenyl]-3-yl)-4-(trifluoromethyl)isoindolin-1-one (T-2)

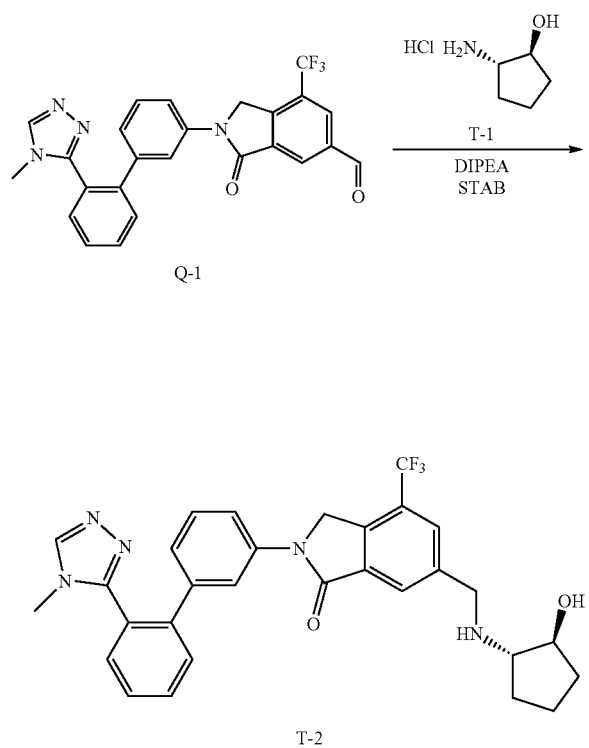

(1S,2S)-2-aminocyclopentan-1-ol, HCl (T-1) (10 mg, 1.1 Eq, 76 µmol) and DIPEA (27 mg, 36 µL, 3.0 Eq, 0.21 mmol) in DCM (1 mL) was added to intermediate Q-1 (40 mg, 80% Wt, 1 Eq, 69 µmol) in DCM (1 mL) followed by NaBH(OAc)₃ (29 mg, 2.0 Eq, 0.14 mmol). The reaction mixture was stirred at rt overnight. The reaction mixture was diluted with DCM (10 mL) and washed with sat. aq. NaHCO₃ (10 mL). The organic phase was dried (phase separator) and concentrated in vacuo. The crude product was purified by preparative HPLC (Waters, Basic (0.3% Ammonia), Basic, Waters XBridge BEH C18 ODB 5 µm, 30×100 mm column, 0-100% MeCN in water) to afford the title compound (T-2) (8 mg, 0.01 mmol, 20%, 99% Purity) as a white solid. m/z 548.2 (M+H)⁺ (ES+). ¹H NMR (400 MHz, DMSO-d6) δ 8.39 (s, 1H), 8.04 (s, 1H), 8.00 (d, J=7.9 Hz, 2H), 7.75-7.65 (m, 3H), 7.60-7.56 (m, 2H), 7.37 (t, J=8.0 Hz, 1H), 6.94-6.88 (m, 1H), 5.07 (s, 2H), 4.52 (d, J=4.2 Hz, 1H), 3.91 (s, 2H), 3.80 (dt, J=8.5, 4.3 Hz, 1H), 3.08 (s, 3H), 2.78-2.69 (m, 1H), 1.87-1.75 (m, 2H), 1.61-1.52 (m, 2H), 1.44-1.35 (m, 1H), 1.35-1.24 (m, 1H). One exchangeable proton not observed.

Example 15: Synthesis of ((3-Fluoroazetidin-1-yl)methyl)-2-(2'-(4-methyl-4H-1,2,4-triazol-3-yl)-[1,1'-biphenyl]-3-yl)-4-(trifluoromethyl)isoindolin-1-one (U-2)

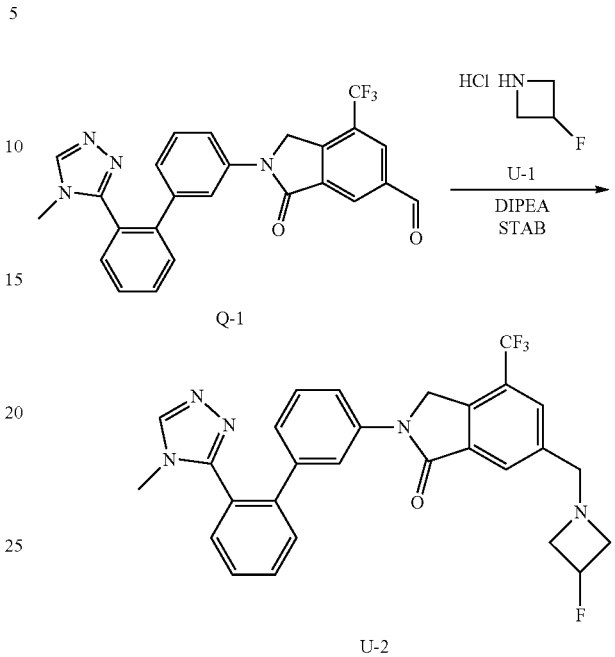

To a solution of 3-fluoroazetidine, HCl (U-1) (8.5 mg, 1.1 Eq, 76 µmol) and DIPEA (27 mg, 36 µL, 3.0 Eq, 0.21 mmol) in DCM (2 mL) was added intermediate Q-1 (40 mg, 80% Wt, 1 Eq, 69 µmol) followed by NaBH(OAc)₃ (29 mg, 2.0 Eq, 0.14 mmol). The reaction mixture was stirred at rt overnight. The reaction mixture was diluted with DCM (10 mL) and washed with sat. aq. NaHCO₃ (10 mL). The organic phase was dried (phase separator) and concentrated in vacuo. The crude product was purified by preparative HPLC (Waters, Basic (0.3% Ammonia), Basic Waters XBridge BEH C18 ODB, 5 µm, 30×100 mm column, 0-100% MeCN in water) to afford the title compound (U-2) (4.6 mg, 8.7 µmol, 13%, 99% Purity) as a white solid. m/z 522.2 (M+H)⁺ (ES+). ¹H NMR (400 MHz, DMSO-d6) δ 8.39 (s, 1H), 8.00-7.95 (m, 2H), 7.91 (s, 1H), 7.75-7.64 (m, 3H), 7.62-7.56 (m, 2H), 7.37 (t, J=8.0 Hz, 1H), 6.91 (d, J=7.4 Hz, 1H), 5.21 (dq, J=57.8, 5.2 Hz, 1H), 5.08 (s, 2H), 3.85 (s, 2H), 3.64-3.53 (m, 2H), 3.26-3.20 (m, 1H), 3.20-3.14 (m, 1H), 3.08 (s, 3H).

Example 16: Synthesis of (S)-6-((3-Fluoropyrrolidin-1-yl)methyl)-2-(2'-(4-methyl-4H-1,2,4-triazol-3-yl)-[1,1'-biphenyl]-3-yl)-4-(trifluoromethyl)isoindolin-1-one (V-2)

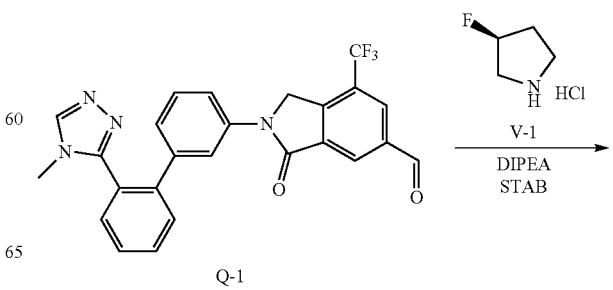

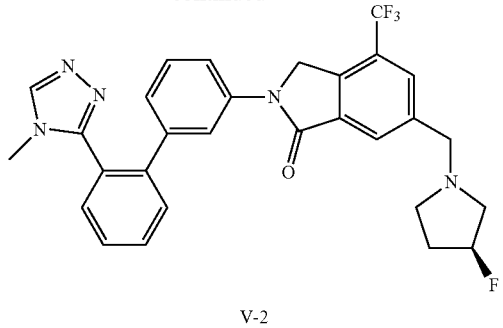

V-2

(S)-3-fluoropyrrolidine, HCl (V-1) (9.6 mg, 1.1 Eq, 76 µmol) and DIPEA (27 mg, 36 µL, 3.0 Eq, 0.21 mmol) in DCM (1 mL) was added to intermediate Q-1 (40 mg, 80% Wt, 1 Eq, 69 µmol) in DCM (1 mL) followed by NaBH(OAc)$_3$ (29 mg, 2.0 Eq, 0.14 mmol). The reaction mixture was stirred at rt overnight. The reaction mixture was diluted with DCM (10 mL) and washed with sat. aq. NaHCO$_3$ (10 mL). The organic phase was dried (phase separator) and concentrated in vacuo. The crude product was purified by reversed phase preparative HPLC (Waters, Basic (0.3% Ammonia), Basic, Waters XBridge BEH C18 ODB, 5 µm, 30×100 mm column, 0-100% MeCN in water) to afford the title compound (V-2) (7.2 mg, 13 µmol, 19%, 99% Purity) as a white solid. m/z 536.3 (M+H)$^+$ (ES+). $^1$H NMR (400 MHz, DMSO-d6) δ 8.39 (s, 1H), 8.02-7.97 (m, 2H), 7.95 (s, 1H), 7.76-7.65 (m, 3H), 7.62-7.56 (m, 2H), 7.38 (t, J=8.0 Hz, 1H), 6.91 (dd, J=7.7, 1.5 Hz, 1H), 5.32-5.12 (m, 1H), 5.09 (s, 2H), 3.84 (s, 2H), 3.08 (s, 3H), 2.87-2.76 (m, 2H), 2.74-2.59 (m, 1H), 2.42-2.34 (m, 1H), 2.25-2.07 (m, 1H), 1.99-1.81 (m, 1H).

Example 17: Synthesis of 6-((((1R,2R)-2-Hydroxycyclopentyl)amino)methyl)-2-(2'-(4-methyl-4H-1,2,4-triazol-3-yl)-[1,1'-biphenyl]-3-yl)-4-(trifluoromethyl)isoindolin-1-one (W-2)

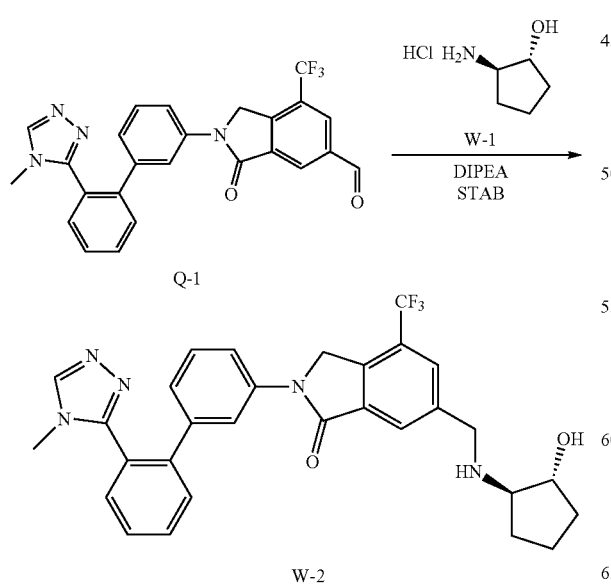

(1R,2R)-2-aminocyclopentan-1-ol, HCl (W-1) (10 mg, 1.1 Eq, 76 µmol) and DIPEA (27 mg, 36 µL, 3.0 Eq, 0.21 mmol) in DCM (1 mL) was added to intermediate Q-1 (40 mg, 80% Wt, 1 Eq, 69 µmol) in DCM (1 mL) followed by NaBH(OAc)$_3$ (29 mg, 2.0 Eq, 0.14 mmol). The reaction mixture was stirred at rt overnight. Additional NaBH(OAc)$_3$ (29 mg, 2.0 Eq, 0.14 mmol) was added and the reaction stirred for further 2 h. The reaction mixture was diluted with DCM (10 mL) and washed with sat. aq. sol. of NaHCO$_3$ (10 mL). The organic phase was dried (phase separator) and concentrated in vacuo. The crude product purified by preparative HPLC (Waters, Basic (0.3% Ammonia), Basic, Waters XBridge BEH C18 ODB, 5 µm, 30×100 mm column, 0-100% MeCN in water) to afford the title compound (W-2) (6.36 mg, 11 µmol, 17%, 99% Purity) as a white solid. m/z 548.2 (M+H)$^+$ (ES+). $^1$H NMR (400 MHz, DMSO-d6) δ 8.39 (s, 1H), 8.04 (s, 1H), 8.01-7.95 (m, 2H), 7.76-7.65 (m, 3H), 7.61-7.55 (m, 2H), 7.38 (t, J=8.0 Hz, 1H), 6.93-6.88 (m, 1H), 5.08 (s, 2H), 4.51 (d, J=4.1 Hz, 1H), 3.91 (s, 2H), 3.79 (q, J=5.2, 4.5 Hz, 1H), 3.08 (s, 3H), 2.73 (q, J=5.7 Hz, 1H), 1.87-1.75 (m, 2H), 1.57 (p, J=7.4 Hz, 2H), 1.45-1.35 (m, 1H), 1.36-1.25 (m, 1H). One exchangeable proton not observed.

Example 18: Synthesis of (R)-2-(2'-(4-Methyl-4H-1,2,4-triazol-3-yl)-[1,1'-biphenyl]-3-yl)-6-((2-methylmorpholino)methyl)-4-(trifluoromethyl)isoindolin-1-one (X-2)

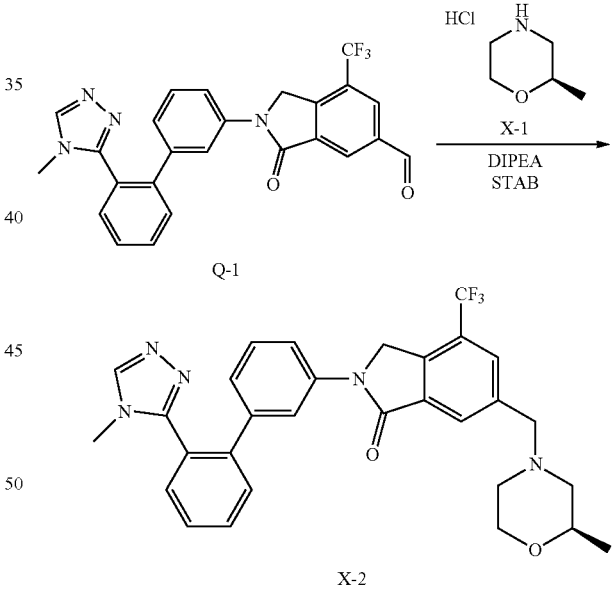

To a solution of (R)-2-methylmorpholine, HCl (X-1) (14 mg, 1.5 Eq, 0.10 mmol) and DIPEA (27 mg, 36 µL, 3.0 Eq, 0.21 mmol) in DCM (2 mL) was added intermediate Q-1 (40 mg, 80% Wt, 1 Eq, 69 µmol) and the reaction mixture stirred for 30 min. NaBH(OAc)$_3$ (29 mg, 2.0 Eq, 0.14 mmol) was added and the reaction mixture was stirred at 40° C. overnight. The reaction mixture was diluted with DCM (10 mL) and washed with sat. aq. sol. of NaHCO$_3$ (10 mL). The organic phase was dried (phase separator) and concentrated in vacuo. The crude was purified by preparative HPLC (Waters, Basic (0.3% Ammonia), Basic, Waters X-Bridge BEH C18 ODB, 5 µm, 30×100 mm column, 0-100% MeCN in water to afford the title compound (X-2) (4.8 mg, 8.3 µmol, 12%, 95% Purity) as a white solid. m/z 548.3 (M+H)+ (ES+). ¹H NMR (400 MHz, DMSO-d6) δ 8.39 (s, 1H), 7.99 (d, J=7.0 Hz, 2H), 7.94 (s, 1H), 7.75-7.64 (m, 3H), 7.63-7.56 (m, 2H), 7.38 (t, J=8.0 Hz, 1H), 6.91 (d, J=7.7 Hz, 1H), 5.08 (s, 2H), 3.79-3.70 (m, 1H), 3.68 (s, 2H), 3.57-3.46 (m, 2H), 3.08 (s, 3H), 2.66 (dd, J=27.2, 11.3 Hz, 2H), 2.14-2.05 (m, 1H), 1.84-1.74 (m, 1H), 1.03 (d, J=6.2 Hz, 3H).

Example 19: Synthesis of (R)-6-((3-Fluoropyrrolidin-1-yl)methyl)-2-(2'-(4-methyl-4H-1,2,4-triazol-3-yl)-[1,1'-biphenyl]-3-yl)-4-(trifluoromethyl)isoindolin-1-one (Y-2)

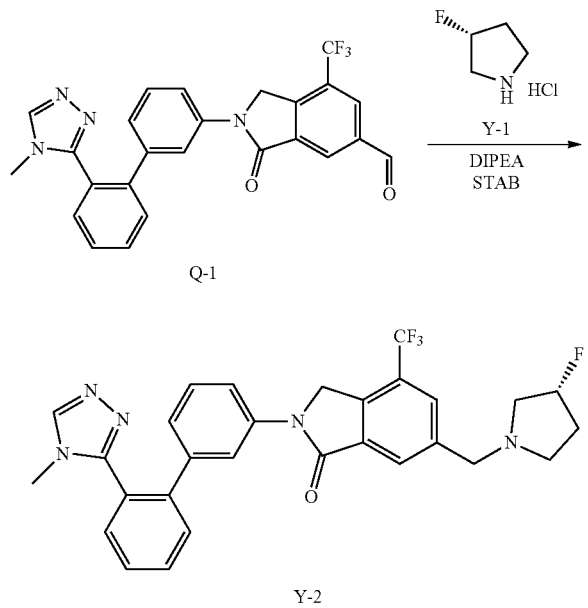

To a solution of (R)-3-fluoropyrrolidine-HCl (Y-1) (8.1 mg, 1.2 Eq, 65 µmol) and DIPEA (21 mg, 28 µL, 3.0 Eq, 0.16 mmol) in CHCl₃ (4 mL) was added intermediate Q-1 (25 mg, 1 Eq, 0.054 mmol) and the reaction mixture stirred for 30 min. NaBH(OAc)₃ (23 mg, 2 Eq, 0.11 mmol) was added and the reaction mixture was stirred at 40° C. overnight. The crude was quenched with NaHCO₃ (5 mL) and DCM (10 mL) was added. The organic phase was extracted, dried (phase separator) and concentrated in vacuo. The crude was purified by preparative HPLC (Waters, Basic (0.3% Ammonia), Basic, Waters XBridge BEH C18 ODB, 5 µm, 30×100 mm column, 0-100% MeCN in water) to afford the title compound (Y-2) (5 mg, 9 µmol, 20%, 99% Purity) as a tan solid. m/z 536.3 (M+H)+ (ES+). ¹H NMR (400 MHz, DMSO-d6) δ 8.39 (s, 1H), 8.11-7.88 (m, 3H), 7.77-7.64 (m, 3H), 7.63-7.54 (m, 2H), 7.38 (dd, J=9.4, 6.7 Hz, 1H), 6.91 (d, J=7.8 Hz, 1H), 5.32-5.13 (m, 1H), 5.09 (s, 2H), 3.84 (s, 2H), 3.09 (s, 3H), 2.89-2.74 (m, 2H), 2.74-2.60 (m, 1H), 2.42-2.30 (m, 1H), 2.25-2.11 (m, 1H), 1.98-1.83 (m, 1H).

Example 20: Synthesis of 6-((((1R,2S)-2-Hydroxycyclopentyl)amino)methyl)-2-(2'-(4-methyl-4H-1,2,4-triazol-3-yl)-[1,1'-biphenyl]-3-yl)-4-(trifluoromethyl)isoindolin-1-one (Z-2)

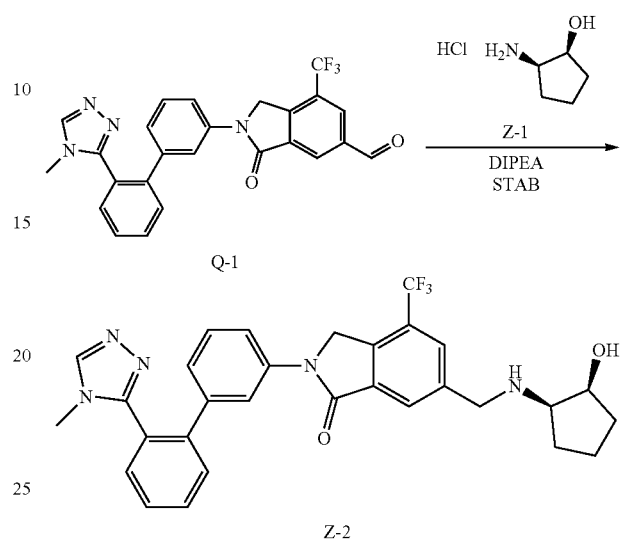

To a solution of (1S,2R)-2-aminocyclopentan-1-ol, HCl (Z-1) (8.9 mg, 1.2 Eq, 65 µmol) and DIPEA (21 mg, 28 µL, 3.0 Eq, 0.16 mmol) in CHCl₃ (4 mL) was added intermediate Q-1 (25 mg, 1 Eq, 0.054 mmol) and the reaction mixture stirred for 30 min. NaBH(OAc)₃ (23 mg, 2 Eq, 0.11 mmol) was added and the reaction mixture was stirred at 40° C. overnight. The crude was quenched with sat. aq. sol. of NaHCO₃ (5 mL) and DCM (10 mL) was added. The organics were extracted, dried (phase separator) and concentrated in vacuo. The crude product was purified by reversed phase preparative HPLC (Waters, Basic (0.3% Ammonia), Basic Waters XBridge BEH C18 ODB, 5 µm, 30×100 mm column, 0-100% MeCN in water) to afford the title compound (Z-2) (8 mg, 0.01 mmol, 30%, 99% Purity) as a white solid. m/z 548.2 (M+H)+ (ES+). ¹H NMR (400 MHz, DMSO-d6) δ 8.39 (s, 1H), 8.05 (s, 1H), 8.02-7.97 (m, 2H), 7.75-7.64 (m, 3H), 7.62-7.56 (m, 2H), 7.37 (t, J=8.0 Hz, 1H), 6.91 (dt, J=7.7, 1.3 Hz, 1H), 5.08 (s, 2H), 4.45-4.36 (m, 1H), 4.00-3.84 (m, 3H), 3.07 (s, 3H), 2.81-2.71 (m, 1H), 1.75-1.53 (m, 4H), 1.48-1.33 (m, 2H). One exchangeable proton not observed.

Example 21: Synthesis of 6-((((1S,2R)-2-Hydroxycyclopentyl)amino)methyl)-2-(2'-(4-methyl-4H-1,2,4-triazol-3-yl)-[1,1'-biphenyl]-3-yl)-4-(trifluoromethyl)isoindolin-1-one (AA-2)

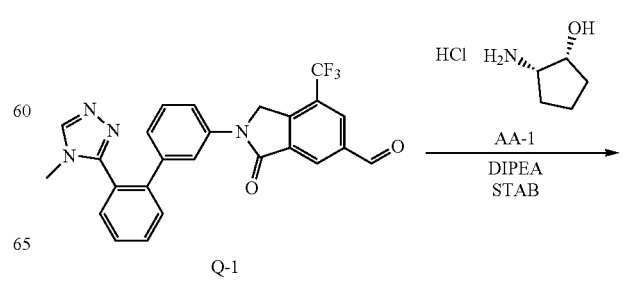

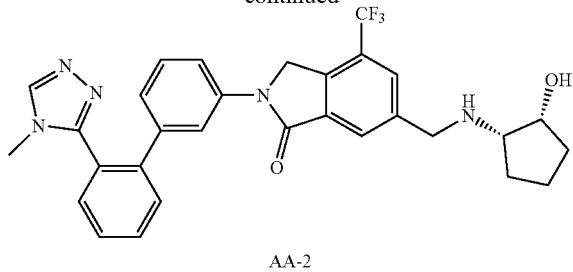

AA-2

To a solution of the (1R,2S)-2-aminocyclopentan-1-ol, HCl (AA-1) (8.9 mg, 1.2 Eq, 65 µmol) and DIPEA (21 mg, 28 µL, 3.0 Eq, 0.16 mmol) in CHCl₃ (4 mL) was added intermediate Q-1 (25 mg, 1 Eq, 0.054 mmol) and the reaction mixture stirred for 30 min. NaBH(OAc)₃ (23 mg, 2 Eq, 0.11 mmol) was added and the reaction mixture was stirred at 40° C. overnight. The crude was quenched with sat. aq. sol. of NaHCO₃ (5 mL) and DCM (10 mL) was added. The organics were extracted, dried (phase separator) and concentrated in vacuo. The crude product was purified by preparative HPLC (Waters, Basic (0.3% Ammonia), Waters XBridge BEH C18 ODB 1, 5 µm, 30×100 mm column, 0-100% MeCN in water) to afford the title compound (AA-2) (3 mg, 5 µmol, 10%, 95% Purity) as a white solid. m/z 548.2 (M+H)⁺ (ES+). ¹H NMR (400 MHz, DMSO-d6) δ 8.39 (s, 1H), 8.05 (s, 1H), 8.02-7.97 (m, 2H), 7.75-7.65 (m, 3H), 7.62-7.56 (m, 2H), 7.37 (t, J=8.0 Hz, 1H), 6.91 (d, J=7.6 Hz, 1H), 5.08 (s, 2H), 4.45-4.28 (m, 1H), 4.00-3.85 (m, 3H), 3.08 (s, 3H), 2.82-2.71 (m, 1H), 1.75-1.54 (m, 4H), 1.48-1.36 (m, 2H). One exchangeable proton not observed.

Example 22: Synthesis of (S)-2-(2'-(4-Methyl-4H-1,2,4-triazol-3-yl)-[1,1'-biphenyl]-3-yl)-6-((2-methylmorpholino)methyl)-4-(trifluoromethyl)isoindolin-1-one (AB-2)

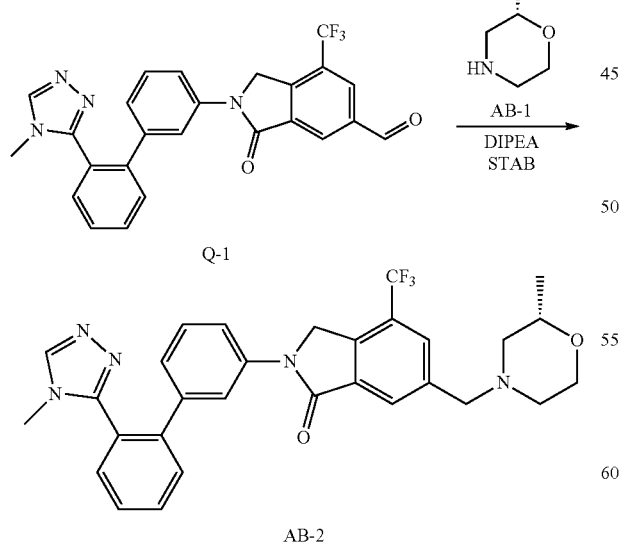

AB-2

To a solution of (S)-2-methylmorpholine (AB-1) (6.6 mg, 1.2 Eq, 65 µmol) and DIPEA (21 mg, 28 µL, 3.0 Eq, 0.16 mmol) in CHCl₃ (4 mL) was added intermediate Q-1 (25 mg, 1 Eq, 0.054 mmol) and the reaction mixture stirred for 30 min. NaBH(OAc)₃ (23 mg, 2 Eq, 0.11 mmol) was added and the reaction mixture was stirred at 40° C. overnight. The crude was quenched with sat. aq. sol. of NaHCO₃ (5 mL) and DCM (10 mL) was added. The organics were extracted, dried (phase separator) and concentrated in vacuo. The crude product was purified by preparative HPLC (Waters, Basic (0.3% Ammonia), Waters XBridge BEH C18 ODB 1, 5 µm, 30×100 mm column, 0-100% MeCN in water) to afford the title compound (9 mg, 0.02 mmol, 30%, 99% Purity) as a white solid. m/z 548.2 (M+H)⁺ (ES+). ¹H NMR (400 MHz, DMSO-d6) δ 8.39 (s, 1H), 7.99 (dd, J=8.1, 2.0 Hz, 2H), 7.94 (s, 1H), 7.75-7.65 (m, 3H), 7.63-7.56 (m, 2H), 7.38 (t, J=8.0 Hz, 1H), 6.94-6.88 (m, 1H), 5.08 (s, 2H), 3.78-3.70 (m, 1H), 3.68 (s, 2H), 3.58-3.47 (m, 2H), 2.73-2.59 (m, 2H), 2.10 (td, J=11.3, 3.2 Hz, 1H), 1.84-1.76 (m, 1H), 1.03 (d, J=6.3 Hz, 3H). Three protons masked by water peak.

Example 23: Synthesis of 2-Chloro-4-(2-(4-methyl-4H-1,2,4-triazol-3-yl)phenyl)-6-(pyrrolidin-1-yl)pyridine (AC-3)

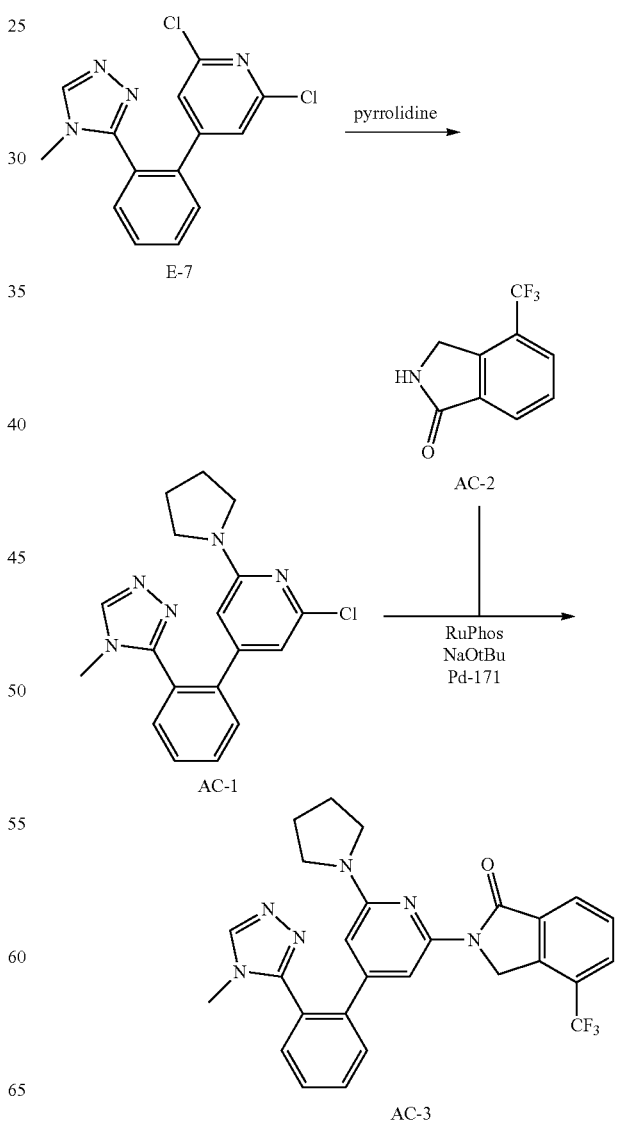

Step 1: Synthesis of 2-Chloro-4-(2-(4-methyl-4H-1,2,4-triazol-3-yl)phenyl)-6-(pyrrolidin-1-yl)pyridine (AC-1)

Intermediate E-7 (60.0 mg, 1 Eq, 197 μmol) was dissolved in pyrrolidine (0.43 g, 0.50 mL, 30 Eq, 6.0 mmol) and heated to 80° C. for 1 h. The reaction mixture was cooled to rt and concentrated in vacuo. The crude product was purified by chromatography on silica gel (12 g cartridge, 0-10% MeOH/DCM) to afford the sub-title compound (AC-1) (54.5 mg, 160 μmol, 81.6%) as a yellow oil. m/z 340.1 (M+H)⁺ (ES+). ¹H NMR (400 MHz, Methanol-d4) δ 8.48 (s, 1H), 7.80-7.73 (m, 1H), 7.73-7.60 (m, 3H), 6.51 (d, J=1.2 Hz, 1H), 5.99 (d, J=1.2 Hz, 1H), 3.31 (s, 4H), 3.27-3.23 (m, 3H), 2.02-1.97 (m, 4H).

Step 2: Synthesis of 2-Chloro-4-(2-(4-methyl-4H-1,2,4-triazol-3-yl)phenyl)-6-(pyrrolidin-1-yl)pyridine (AC-3)

A mixture of RuPhos (2.42 mg, 0.05 Eq, 5.18 μmol), NaOtBu (4.98 mg, 0.5 Eq, 51.8 μmol), the product from step 1 above (AC-1) (39.1 mg, 90% Wt, 1 Eq, 104 μmol), intermediate AC-2 (31.2 mg, 1.5 Eq, 155 μmol), and Pd-171 (RuPhos Pd(crotyl)Cl) (3.44 mg, 0.05 Eq, 5.18 μmol) were dissolved in 1,4-Dioxane (1.5 mL). The reaction mixture was purged with N₂ (×3) and heated to 100° C. overnight. The reaction mixture was concentrated in vacuo and the crude product was purified by reversed phase preparative HPLC (Basic (0.3% Ammonia), Basic, Waters XBridge BEH C18 ODB, 5 μm, 30×100 mm column 0-100% MeCN in water to afford the title compound (AC-3) (3.57 mg, 10 μmol, 9.6%, 95% Purity) as a white solid. m/z 505.4 (M+H)⁺ (ES+). ¹H NMR (400 MHz, Methanol-d4) δ 8.45 (s, 1H), 8.11 (d, J=7.7 Hz, 1H), 7.99 (d, J=7.7 Hz, 1H), 7.82-7.75 (m, 3H), 7.71-7.62 (m, 3H), 5.94 (s, 1H), 5.29 (s, 2H), 3.42-3.36 (m, 7H), 2.08-1.99 (m, 4H).

Example 24: Synthesis of 2-(6-(Ethylamino)-4-(2-(4-methyl-4H-1,2,4-triazol-3-yl)phenyl)pyridin-2-yl)-6-(hydroxymethyl)-4-(trifluoromethyl)isoindolin-1-one (AD-3) and 2-(6-(dimethylamino)-4-(2-(4-methyl-4H-1,2,4-triazol-3-yl)phenyl)pyridin-2-yl)-6-(hydroxymethyl)-4-(trifluoromethyl)isoindolin-1-one (AD-4)

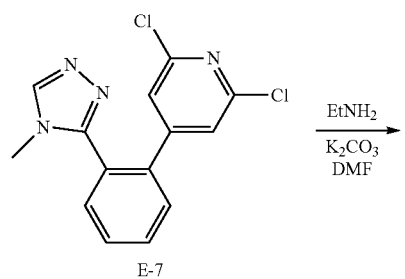

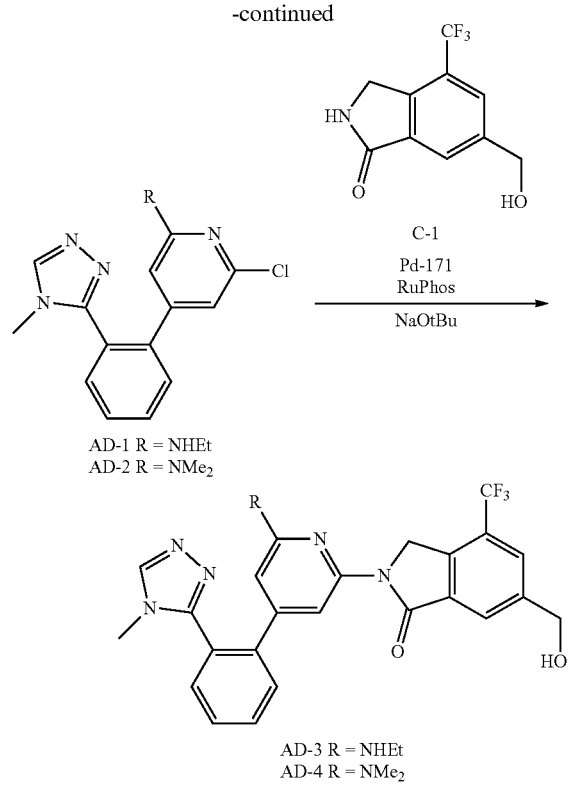

Step 1: Synthesis of 6-Chloro-N-ethyl-4-(2-(4-methyl-4H-1,2,4-triazol-3-yl)phenyl)pyridin-2-amine (AD-1) and 6-chloro-N,N-dimethyl-4-(2-(4-methyl-4H-1,2,4-triazol-3-yl)phenyl)pyridin-2-amine (AD-2)

To a solution of intermediate E-7 (33 mg, 1 Eq, 0.11 mmol) in DMF (2 mL) were successively added K₂CO₃ (23 mg, 1.5 Eq, 0.17 mmol) and ethanamine (75 mg, 0.84 mL, 2 molar, 15 Eq, 1.7 mmol). The reaction mixture was stirred at 100° C. overnight in sealed tube. The crude product was purified by chromatography on RP Flash C18 (12 g cartridge, 15-75% MeCN/10 mM ammonium bicarbonate) to afford an inseparable mixture of the sub-title compounds AD-1 (32 mg, 31 μmol, 27%, 30% Purity) and AD-2 (32 mg, 71 μmol, 64%, 70% Purity) as a pale brown gum. m/z 314.3 (M+H)⁺ (ES+), at 1.51 and 1.59 min, 30% and 70% purity (diode array). 6-chloro-N-ethyl-4-(2-(4-methyl-4H-1,2,4-triazol-3-yl)phenyl)pyridin-2-amine (AD-1) (30%): ¹H NMR (400 MHz, Methanol-d4) δ 8.46 (s, 1H), 7.76-7.56 (m, 4H), 6.33 (d, J=1.2 Hz, 1H), 6.08 (d, J=1.2 Hz, 1H), 3.25 (s, 3H), 3.17 (q, J=7.2 Hz, 2H), 1.13 (t, J=7.2 Hz, 3H). One exchangeable proton not observed. 6-chloro-N,N-dimethyl-4-(2-(4-methyl-4H-1,2,4-triazol-3-yl)phenyl)pyridin-2-amine (AD-2) (70%): ¹H NMR (400 MHz, Methanol-d4) δ 8.44 (s, 1H), 7.77-7.54 (m, 4H), 6.47 (d, J=1.0 Hz, 1H), 6.10 (d, J=1.1 Hz, 1H), 3.21 (s, 3H), 2.93 (s, 6H).

Step 2: Synthesis of 2-(6-(Ethylamino)-4-(2-(4-methyl-4H-1,2,4-triazol-3-yl)phenyl)pyridin-2-yl)-6-(hydroxymethyl)-4-(trifluoromethyl)isoindolin-1-one (AD-3) and 2-(6-(dimethylamino)-4-(2-(4-methyl-4H-1,2,4-triazol-3-yl)phenyl)pyridin-2-yl)-6-(hydroxymethyl)-4-(trifluoromethyl)isoindolin-1-one (AD-4)

To a solution of the products from step 1 above (AD-1) and (AD-2) (32 mg, 70% Wt, 2.3 Eq, 71 μmol) and intermediate C-1 (33 mg, 4.6 Eq, 0.14 mmol) in 1,4-Dioxane (1 mL) were added K₃PO₄ (42 mg, 6.5 Eq, 0.20 mmol), XantPhos (12 mg, 0.65 Eq, 0.020 mmol) and Pd(OAc)₂ (2 mg, 0.3 Eq, 0.01 mmol) at rt under an atmosphere of N₂. The mixture was stirred at 100° C. for 16 h. Additional Pd(OAc)₂ (2 mg, 0.3 Eq, 0.01 mmol) and dppf (11 mg, 0.6 eq., 0.02 mmol) were added and the reaction was stirred at 100° C. for 16 h. The reaction mixture was diluted with DCM and filtered over a silica plug. The silica plug was washed with 10% MeOH/DCM (50 mL) and the solvent was removed in vacuo. To the residue were added Pd-171 (662.62 g/mol, 3.3 mg, 0.15 Eq., 0.05 mmol), RuPhos (2.3 mg, 0.15 Eq., 0.05 mmol), NaOtBu (6 mg, 13 equiv., 0.6 mmol) and 1,4-Dioxane (1 mL) and the mixture was stirred at 100° C. for 16 h. The reaction mixture was diluted with DCM and filtered over a silica plug eluting with 10% MeOH/DCM (50 mL). The filtrate was concentrated in vacuo and the crude was purified by reversed phase preparative HPLC (Waters, Acidic (0.1% Formic Acid), Acidic Waters X-Select CSH C18 ODB, 5 μm, 30×100 mm column, 0-100% MeCN in Water to afford the title compounds (AD-3) and (AD-4): 2-(6-(Ethylamino)-4-(2-(4-methyl-4H-1,2,4-triazol-3-yl)phenyl)pyridin-2-yl)-6-(hydroxymethyl)-4-(trifluoromethyl)isoindolin-1-one (AD-3) (6 mg, 0.01 mmol, 10%, 99% Purity) as a white solid. m/z 509.5 (M+H)⁺ (ES+). ¹H NMR (400 MHz, Methanol-d4) δ 8.46 (s, 1H), 8.07 (s, 1H), 7.97 (s, 1H), 7.81-7.70 (m, 2H), 7.70-7.61 (m, 2H), 7.57 (s, 1H), 6.06 (s, 1H), 5.22 (s, 2H), 4.81 (s, 2H), 3.44 (s, 3H), 3.29 (q, J=7.2 Hz, 2H), 1.23 (t, J=7.2 Hz, 3H). Two exchangeable protons not observed. 2-(6-(Dimethylamino)-4-(2-(4-methyl-4H-1,2,4-triazol-3-yl)phenyl)pyridin-2-yl)-6-(hydroxymethyl)-4-(trifluoromethyl)isoindolin-1-one (AD-4) (15 mg, 29 μmol, 29%, 99% Purity) as white solid. m/z 509.2 (M+H)⁺ (ES+). ¹H NMR (400 MHz, Methanol-d4) δ 8.42 (s, 1H), 8.03 (s, 1H), 7.93 (s, 1H), 7.79-7.70 (m, 2H), 7.70-7.57 (m, 3H), 6.05 (s, 1H), 5.19 (s, 2H), 4.77 (s, 2H), 3.33-3.27 (m, 3H), 2.98 (s, 6H). One exchangeable proton not observed.

Example 25: Synthesis of (R)-2-(6-(Ethylamino)-4-(2-(4-methyl-4H-1,2,4-triazol-3-yl)phenyl)pyridin-2-yl)-6-((3-methylpiperidin-1-yl)methyl)-4-(trifluoromethyl)isoindolin-1-one (AE-2)

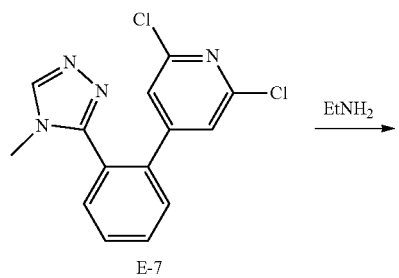

E-7

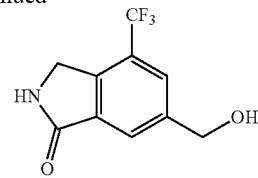

C-1

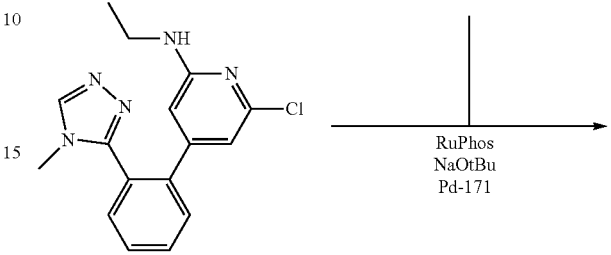

AD-1

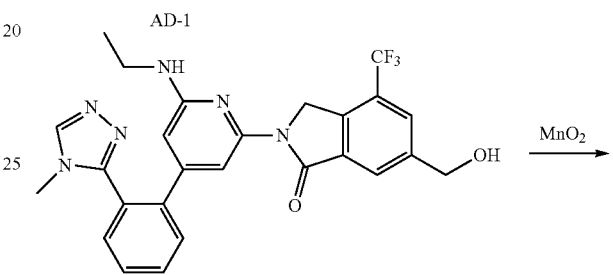

AD-3

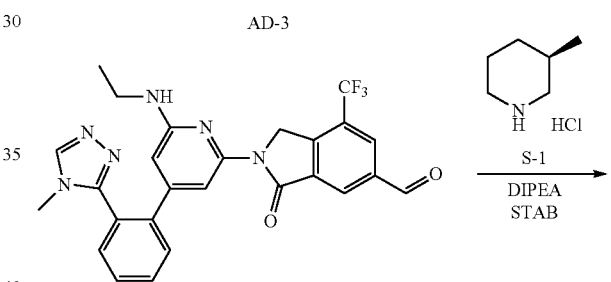

AE-1

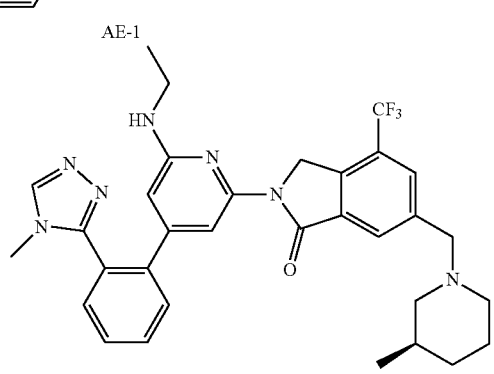

AE-2

Step 1: Synthesis of 6-Chloro-N-ethyl-4-(2-(4-methyl-4H-1,2,4-triazol-3-yl)phenyl)pyridin-2-amine (AD-1)

Intermediate E-7 (330 mg, 1 Eq, 1.08 mmol) and ethylamine (2.10 g, 23.3 mL, 2 molar, 43 Eq, 46.5 mmol) were added to a microwave vial and irradiated for 20 h at 100° C. The reaction mixture was concentrated in vacuo. The crude product was purified by chromatography on silica gel (24 g cartridge, 0-20% MeOH/DCM) to afford the sub-title compound (AD-1) (326 mg, 1.0 mmol, 92%, 96% Purity) as a pale yellow solid. m/z 313.9 (M+H)⁺ (ES+).

Step 2: Synthesis of 2-(6-(Ethylamino)-4-(2-(4-methyl-4H-1,2,4-triazol-3-yl)phenyl)pyridin-2-yl)-6-(hydroxymethyl)-4-(trifluoromethyl)isoindolin-1-one (AD-3)

To a solution of the product from step 1 above (AD-1) (226 mg, 85% Wt, 1 Eq, 612 μmol) and intermediate C-1 (212 mg, 1.5 Eq, 918 μmol) in 1,4-Dioxane (6 mL) were successively added RuPhos (14.3 mg, 0.05 Eq, 30.6 μmol), NaO$^t$Bu (64.7 mg, 1.1 Eq, 673 μmol) and Pd-171 (RuPhos Pd(crotyl)Cl) (20.3 mg, 0.05 Eq, 30.6 μmol). The resulting mixture was stirred at 100° C. under $N_2$ for 16 h. The solvent was removed in vacuo and the crude product was purified by chromatography on silica gel (12 g cartridge, 0-20% MeOH/DCM) to afford the sub-title compound (AD-3) (152 mg, 0.30 mmol, 48%, 99% Purity) as a clear white solid. m/z 509.2 (M+H)⁺ (ES+).

Step 3: Synthesis of 2-(6-(Ethylamino)-4-(2-(4-methyl-4H-1,2,4-triazol-3-yl)phenyl)pyridin-2-yl)-3-oxo-7-(trifluoromethyl)isoindoline-5-carbaldehyde (AE-1)

Manganese dioxide (1.18 g, 60 Eq, 13.6 mmol) was added to the product from step 2 above (AD-3) (116 mg, 99% Wt, 1 Eq, 226 μmol) in chloroform (25 mL) and stirred at 40° C. for 18 h. The reaction mixture was filtered through a Celite plug washing with 1,4-Dioxane (25 mL) and DCM (25 mL). The filtrate was concentrated in vacuo to afford the sub-title compound (AE-1) (79 mg, 0.15 mmol, 65%, 94% Purity) as a pale yellow solid. m/z 507.2 (M+H)⁺ (ES+). ¹H NMR (400 MHz, DMSO-d6) δ 10.21 (s, 1H), 8.52 (s, 1H), 8.47 (d, J=6.7 Hz, 2H), 7.72 (td, J=7.4, 1.6 Hz, 1H), 7.66-7.54 (m, 3H), 7.50 (d, J=1.2 Hz, 1H), 6.73 (t, J=5.5 Hz, 1H), 5.95 (d, J=1.2 Hz, 1H), 5.28 (s, 2H), 3.33 (s, 3H), 3.17 (q, J=6.4 Hz, 2H), 1.13 (t, J=7.1 Hz, 3H).

Step 4: Synthesis of (R)-2-(6-(Ethylamino)-4-(2-(4-methyl-4H-1,2,4-triazol-3-yl)phenyl)pyridin-2-yl)-6-((3-methylpiperidin-1-yl)methyl)-4-(trifluoromethyl)isoindolin-1-one (AE-2)

NaBH(OAc)₃ (65 mg, 6.0 Eq, 0.30 mmol) was added to a stirred solution of the product from step 3 above (AE-1) (26 mg, 99% Wt, 1 Eq, 51 μmol), (R)-3-methylpiperidine-HCl (S-1) (14 mg, 2.0 Eq, 0.10 mmol) and DIPEA (20 mg, 26 μL, 3.0 Eq, 0.15 mmol) in chloroform (2 mL) and stirred at rt for 3 days. The reaction mixture was diluted with DCM (5 mL) and washed with sat. aq. sol. of NaHCO₃ (6 mL). The organic layer was separated, dried (MgSO₄) and concentrated in vacuo. The crude product was purified by preparative HPLC (Waters, Basic (0.3% Ammonia), Basic Waters XBridge BEH C18 ODB, 5 μm, 30×100 mm column 0-100% MeCN in water) to afford the title compound (AE-2) (8 mg, 0.01 mmol, 30%, 100% Purity) as a flocculent white solid. m/z 590.6 (M+H)⁺ (ES+). ¹H NMR (400 MHz, DMSO-d6) δ 8.46 (s, 1H), 7.95 (s, 1H), 7.91 (s, 1H), 7.71 (td, J=7.5, 1.7 Hz, 1H), 7.66-7.53 (m, 3H), 7.48 (d, J=1.2 Hz, 1H), 6.69 (t, J=5.4 Hz, 1H), 5.93 (d, J=1.3 Hz, 1H), 5.16 (s, 2H), 3.63 (s, 2H), 3.23-3.11 (m, 2H), 2.76-2.67 (m, 2H), 1.93 (t, J=10.9 Hz, 1H), 1.68-1.56 (m, 4H), 1.51-1.43 (m, 1H), 1.12 (t, J=7.2 Hz, 3H), 0.89-0.85 (m, 1H), 0.82 (d, J=6.0 Hz, 3H). CH₃ masked by water peak.

Example 26: Synthesis of (S)-2-(6-(Ethylamino)-4-(2-(4-methyl-4H-1,2,4-triazol-3-yl)phenyl)pyridine-2-yl)6-((3-methylpiperidin-1-yl)methyl)-4-(trifluoromethyl)isoindolin-1-one (AF-1)

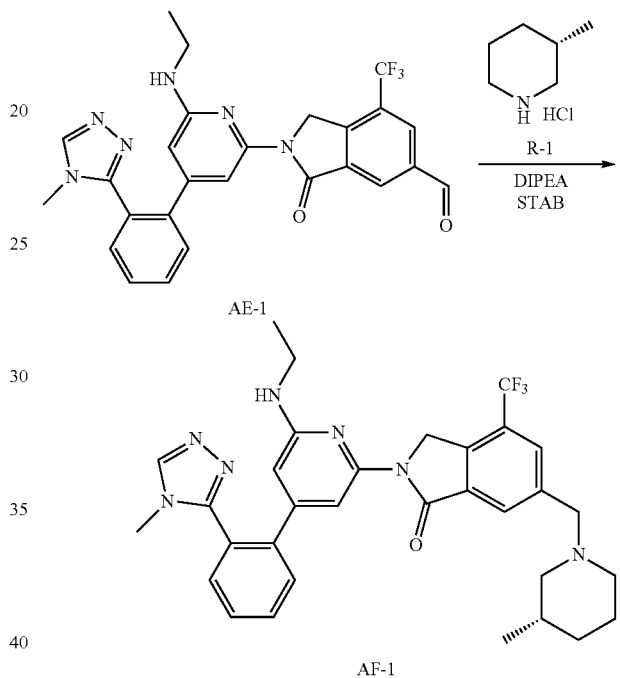

To a solution of intermediate AE-1 (30 mg, 99% Wt, 1 Eq, 59 μmol) and DIPEA (23 mg, 31 μL, 3.0 Eq, 0.18 mmol) in DCM (2 mL) was added (S)-3-methylpiperidine-HCl (R-1) (8.7 mg, 1.1 Eq, 65 μmol). The reaction was stirred for 1 h then NaBH(OAc)₃ (25 mg, 2.0 Eq, 0.12 mmol) was added and stirred at rt overnight. The reaction mixture was diluted with DCM (5 mL) washed with sat. aq. sol. of NaHCO₃ (5 mL) and brine (5 mL). The combined organic layers were dried (MgSO₄), filtered and concentrated in vacuo. The crude was purified by reversed phase preparative HPLC (Waters, Basic (0.3% Ammonia), Basic, Waters XBridge BEH C18 ODB, 5 μm, 30×100 mm column, 0-100% MeCN in water to afford the title compound (AF-1) (3 mg, 5 μmol, 9%, 98% Purity). m/z 590.2 (M+H)⁺ (ES+). ¹H NMR (400 MHz, Methanol-d4) δ 8.47 (s, 1H), 8.05 (s, 1H), 7.97 (s, 1H), 7.80-7.70 (m, 2H), 7.69-7.60 (m, 2H), 7.56 (d, J=1.2 Hz, 1H), 6.07 (d, J=1.2 Hz, 1H), 5.23 (s, 2H), 3.70 (s, 2H), 3.45 (s, 3H), 3.30 (q, J=7.2 Hz, 2H), 2.85 (dd, J=15.1, 8.9 Hz, 2H), 2.02 (td, J=11.3, 3.1 Hz, 1H), 1.83-1.57 (m, 5H), 1.24 (t, J=7.2 Hz, 3H), 0.90 (m, 4H). One exchangeable proton not observed.

Example 27: Synthesis of 2-(6-(Ethylamino)-4-(2-(4-methyl-4H-1,2,4-triazol-3-yl)phenyl)pyridin-2-yl)-6-((3-fluoroazetidin-1-yl)methyl)-4-(trifluoromethyl)isoindolin-1-one (AG-1)

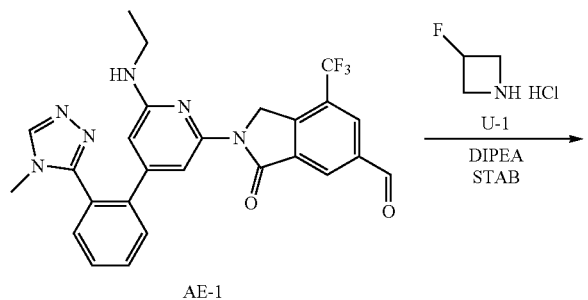

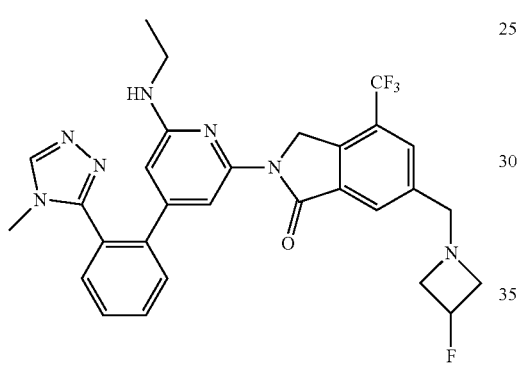

NaBH(OAc)$_3$ (52 mg, 6.0 Eq, 0.25 mmol) was added to a stirred solution of intermediate AE-1 (21 mg, 99% Wt, 1 Eq, 41 µmol), 3-fluoroazetidine-HCl (U-1) (9.2 mg, 2.0 Eq, 82 µmol) and DIPEA (16 mg, 21 µL, 3.0 Eq, 0.12 mmol) in chloroform (2 mL) and left at rt for 16 h. The reaction mixture was diluted with DCM (5 mL) and washed with sat. aq. sol. of NaHCO$_3$ (6 mL). The organic layer was extracted, dried (MgSO$_4$) and concentrated in vacuo. The crude product was purified by preparative HPLC (Waters, Basic (0.3% Ammonia), Basic, Waters XBridge BEH C18 ODB, 5 µm, 30×100 mm column, 0-100% MeCN in water to afford the title compound (AG-1) (9 mg, 0.02 mmol, 40%, 100% Purity) as a flocculent white solid. m/z 566.3 (M+H)$^+$ (ES+). $^1$H NMR (400 MHz, DMSO-d6) δ 8.46 (s, 1H), 7.95 (s, 1H), 7.90 (s, 1H), 7.75-7.67 (m, 1H), 7.65-7.54 (m, 3H), 7.48 (d, J=1.2 Hz, 1H), 6.69 (t, J=5.4 Hz, 1H), 5.93 (d, J=1.2 Hz, 1H), 5.33-5.10 (m, 3H), 3.84 (s, 2H), 3.65-3.53 (m, 2H), 3.28-3.13 (m, 4H), 1.12 (t, J=7.2 Hz, 3H). CH$_3$ masked by water peak.

Example 28: Synthesis of 2-(6-(Ethylamino)-4-(2-(4-methyl-4H-1,2,4-triazol-3-yl)phenyl)pyridin-2-yl)-3-oxo-7-(trifluoromethyl)isoindoline-5-carbaldehyde (AH-2)

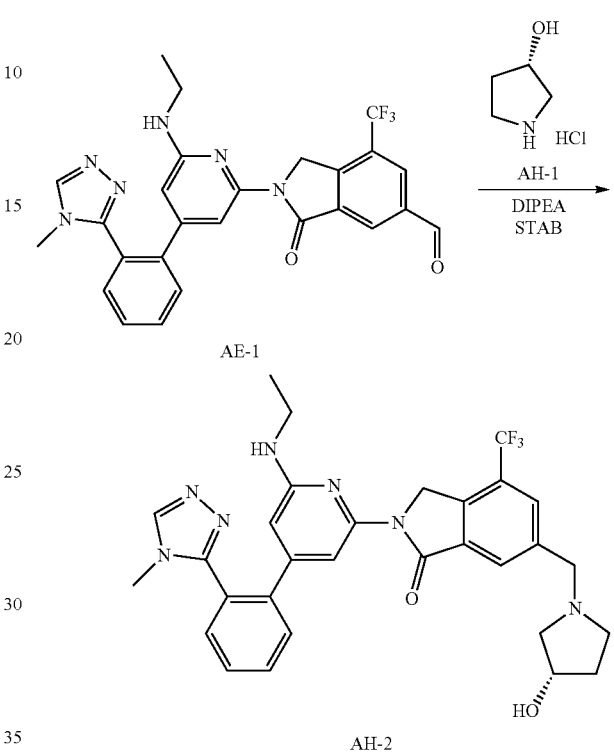

NaBH(OAc)$_3$ (52 mg, 6.0 Eq, 0.25 mmol) was added to a stirred solution of intermediate AE-1 (21 mg, 99% Wt, 1 Eq, 41 µmol), (S)-(+)-3-pyrrolidinol-HCl (AH-1) (10 mg, 2.0 Eq, 82 µmol) and DIPEA (16 mg, 21 µL, 3.0 Eq, 0.12 mmol) in chloroform (2 mL) and stirred at rt for 16 h. The reaction mixture was diluted with DCM (5 mL) and washed with sat. aq. sol. of NaHCO$_3$ (6 mL). The organic layer was extracted, dried (MgSO$_4$) and concentrated in vacuo. The crude product was purified by preparative HPLC (Waters, Basic (0.3% Ammonia), Basic Waters XBridge DEH C18 ODB, 5 µm, 30×100 mm, 0-100% MeCN in water) to afford the title compound (AH-2) (21 mg, 99% Wt, 1 Eq, 41 µmol) as a flocculent white solid. m/z 578.1 (M+H)$^+$ (ES+). $^1$H NMR (400 MHz, DMSO-d6) δ 8.46 (s, 1H), 7.97 (s, 1H), 7.92 (s, 1H), 7.75-7.67 (m, 1H), 7.65-7.53 (m, 3H), 7.48 (d, J=1.2 Hz, 1H), 6.69 (t, J=5.4 Hz, 1H), 5.94 (d, J=1.3 Hz, 1H), 5.16 (s, 2H), 4.72 (d, J=4.4 Hz, 1H), 4.21 (s, 1H), 3.82-3.72 (m, 2H), 3.23-3.12 (m, 2H), 2.73-2.58 (m, 2H), 2.48-2.39 (m, 1H), 2.36 (dd, J=9.6, 3.6 Hz, 1H), 2.08-1.95 (m, 1H), 1.63-1.51 (m, 1H), 1.13 (t, J=7.2 Hz, 3H). CH$_3$ masked by water peak.

Example 29: Synthesis of 6-((6-Azaspiro[2.5]octan-6-yl)methyl)-2-(6-(ethylamino)-4-(2-(4-methyl-4H-1,2,4-triazol-3-yl)phenyl)pyridin-2-yl)-4-(trifluoromethyl)isoindolin-1-one (AI-2)

Example 30: Synthesis of (S)-2-(6-(Ethylamino)-4-(2-(4-methyl-4H-1,2,4-triazol-3-yl)phenyl)pyridin-2-yl)-6-((3-fluoropyrrolidin-1-yl)methyl)-4-(trifluoromethyl)isoindolin-1-one (AJ-1)

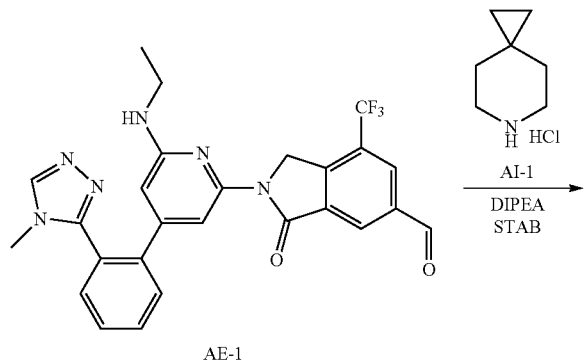

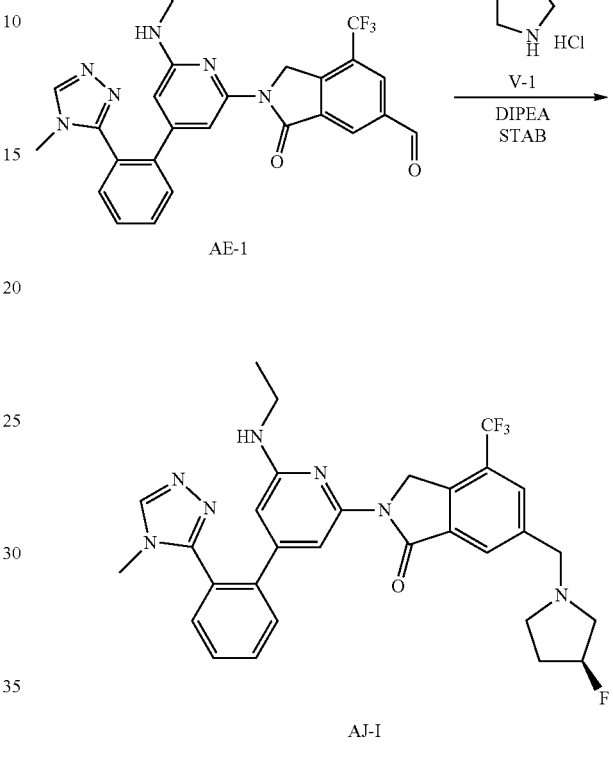

NaBH(OAc)₃ (65 mg, 6.0 Eq, 0.30 mmol) was added to a stirred solution of intermediate AE-1 (26 mg, 99% Wt, 1 Eq, 51 μmol), 6-azaspiro[2.5]octane-HCl (AI-1) (15 mg, 2.0 Eq, 0.10 mmol) and DIPEA (20 mg, 26 μL, 3.0 Eq, 0.15 mmol) in chloroform (2 mL) and stirred at rt for 3 days. The reaction mixture was diluted with DCM (5 mL) and washed with sat. aq. sol. of NaHCO₃ (6 mL). The organic layer was extracted, dried (MgSO₄) and concentrated in vacuo. The crude product was purified by preparative HPLC (Waters, Basic (0.3% Ammonia) Basic, Waters XBridge BEH C18 ODB, 5 μm, 30×100 mm column, 0-100% MeCN in water to afford the title compound (AI-2) (10 mg, 17 μmol, 33%, 100% Purity) as a flocculent white solid. m/z 602.5 (M+H)⁺ (ES+). ¹H NMR (400 MHz, DMSO-d6) δ 8.46 (s, 1H), 7.97 (s, 1H), 7.93 (s, 1H), 7.75-7.67 (m, 1H), 7.66-7.54 (m, 3H), 7.48 (d, J=1.2 Hz, 1H), 6.69 (t, J=5.4 Hz, 1H), 5.93 (d, J=1.2 Hz, 1H), 5.16 (s, 2H), 3.70 (s, 2H), 3.23-3.13 (m, 2H), 2.45-2.41 (m, 4H), 1.37-1.32 (m, 4H), 1.13 (t, J=7.2 Hz, 3H), 0.25 (s, 4H). CH₃ masked by water peak.

NaBH(OAc)₃ (52 mg, 6.0 Eq, 0.25 mmol) was added to a stirred solution of intermediate AE-1 (21 mg, 99% Wt, 1 Eq, 41 μmol), (S)-(+)-3-Fluoropyrrolidine-HCl (V-1) (10 mg, 2 Eq, 82 μmol) and DIPEA (16 mg, 21 μL, 3.0 Eq, 0.12 mmol) in chloroform (2 mL) and stirred at rt overnight. The reaction mixture was diluted with DCM (5 mL) and washed with sat. aq. sol. of NaHCO₃ (6 mL). The organic layer was extracted, dried (MgSO₄) and concentrated in vacuo. The crude product was purified by preparative HPLC (Waters, Basic (0.3% Ammonia), Basic, Waters XBridge BEH C18 ODB, 5 μm, 30×100 mm column, 0-100% MeCN in water) to afford the title compound (AJ-1) (9 mg, 0.02 mmol, 40%, 100% Purity) as a flocculent white solid. m/z 580.5 (M+H)⁺ (ES+). ¹H NMR (400 MHz, DMSO-d6) δ 8.46 (s, 1H), 7.98 (s, 1H), 7.94 (s, 1H), 7.75-7.67 (m, 1H), 7.65-7.53 (m, 3H), 7.48 (d, J=1.2 Hz, 1H), 6.69 (t, J=5.4 Hz, 1H), 5.94 (d, J=1.3 Hz, 1H), 5.22 (d, J=50.2 Hz, 3H), 3.83 (s, 2H), 3.23-3.12 (m, 2H), 2.88-2.79 (m, 1H), 2.82-2.75 (m, 1H), 2.74-2.57 (m, 1H), 2.43-2.32 (m, 1H), 2.27-2.07 (m, 1H), 1.98-1.82 (m, 1H), 1.13 (t, J=7.2 Hz, 3H). CH₃ masked by water peak.

Example 31: Synthesis of 6-((4,4-Difluoro-3-methylpiperidin-1-yl)methyl)-2-(6-(ethylamino)-4-(2-(4-methyl-4H-1,2,4-triazol-3-yl)phenyl)pyridin-2-yl)-4-(trifluoromethyl)isoindolin-1-one (AK-2)

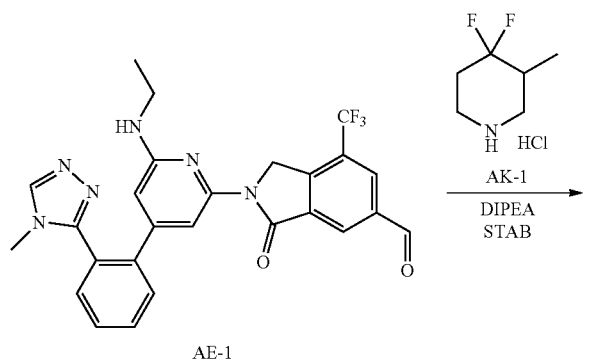

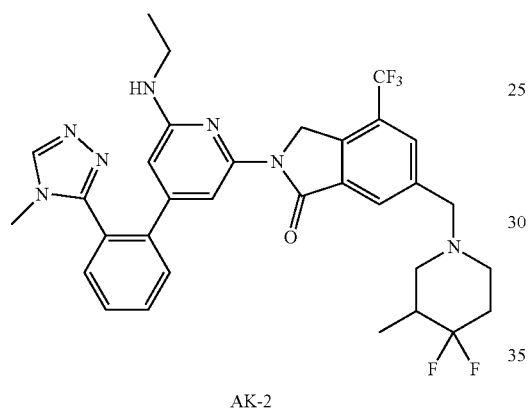

Example 32: Synthesis of (S)-2-(6-(Ethylamino)-4-(2-(4-methyl-4H-1,2,4-triazol-3-yl)phenyl)pyridin-2-yl)-6-((2-methylmorpholino)methyl)-4-(trifluoromethyl)isoindolin-1-one (AL-1)

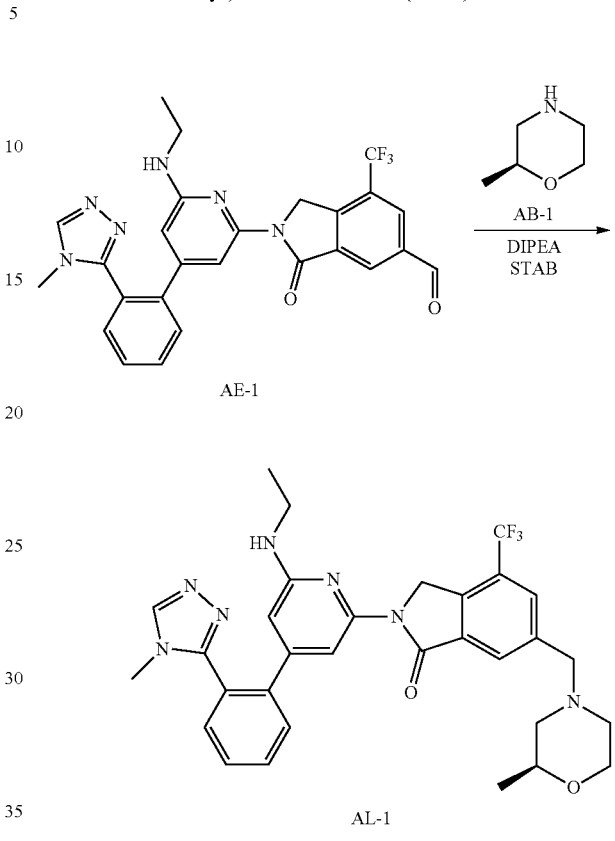

NaBH(OAc)$_3$ (65 mg, 6.0 Eq, 0.30 mmol) was added to a stirred solution of intermediate AE-1 (26 mg, 99% Wt, 1 Eq, 51 μmol), rac-4,4-difluoro-3-methylpiperidine-HCl (AK-1) (17 mg, 2.0 Eq, 0.10 mmol) and DIPEA (20 mg, 26 μL, 3.0 Eq, 0.15 mmol) in chloroform (2 mL) and stirred at rt for 3 days. The reaction mixture was diluted with DCM (5 mL) and washed with sat. aq. sol. of NaHCO$_3$ (6 mL). The organic layer was extracted, dried (MgSO$_4$) and concentrated in vacuo. The crude product was purified by preparative HPLC (waters, Basic (0.3% Ammonia), Basic, Waters XBridge BEH C18 ODB. 5 μm, 30-100 mm column, 0-100% MeCN in water) to afford the title compound (AK-2) (13 mg, 21 μmol, 41%, 100% Purity) as a white solid. m/z 626.6 (M+H)$^+$ (ES+). $^1$H NMR (400 MHz, DMSO-d6) δ 8.46 (s, 1H), 7.99 (s, 1H), 7.94 (s, 1H), 7.75-7.67 (m, 1H), 7.65-7.54 (m, 3H), 7.48 (d, J=1.1 Hz, 1H), 6.69 (t, J=5.3 Hz, 1H), 5.94 (s, 1H), 5.16 (s, 2H), 3.74 (s, 2H), 3.21-3.13 (m, 2H), 2.77-2.72 (m, 2H), 2.32 (s, 2H), 2.13 (s, 1H), 2.09-2.00 (m, 2H), 1.13 (t, J=7.2 Hz, 3H), 0.92 (d, J=6.4 Hz, 3H). CH$_3$ masked by water peak.

NaBH(OAc)$_3$ (68 mg, 6.0 Eq, 0.32 mmol) was added to a stirred solution of intermediate AE-1 (33 mg, 82% Wt, 1 Eq, 53 μmol), (2S)-2-methylmorpholine (AB-1) (11 mg, 2.0 Eq, 0.11 mmol) and DIPEA (6.9 mg, 9.2 μL, 1.0 Eq, 53 μmol) in chloroform (2 mL) and left at rt overnight. The reaction mixture was diluted with DCM (5 mL) and washed with sat. aq. sol. of NaHCO$_3$ (6 mL). The organic layer was separated, dried (phase separator) and concentrated in vacuo. The crude product was purified by preparative HPLC (Waters, Basic (0.3% Ammonia), Basic, Waters XBridge BEH C18 ODB, 5 μm, 30×100 mm column, 0-100% MeCN in water to afford the title compound (AL-1) (11 mg, 18 μmol, 34%, 99% Purity) as a flocculent white solid. m/z 592.5 (M+H)$^+$ (ES+). $^1$H NMR (400 MHz, DMSO-d6) δ 8.46 (s, 1H), 7.98 (s, 1H), 7.93 (s, 1H), 7.75-7.67 (m, 1H), 7.65-7.53 (m, 3H), 7.48 (d, J=1.3 Hz, 1H), 6.69 (t, J=5.4 Hz, 1H), 5.94 (s, 1H), 5.16 (s, 2H), 3.74 (d, J=11.2 Hz, 1H), 3.66 (s, 2H), 3.57-3.46 (m, 2H), 3.23-3.13 (m, 2H), 2.69 (d, J=11.1 Hz, 1H), 2.62 (d, J=11.3 Hz, 1H), 2.09 (td, J=11.4, 3.2 Hz, 1H), 1.79 (t, J=10.5 Hz, 1H), 1.13 (t, J=7.1 Hz, 3H), 1.02 (d, J=6.2 Hz, 3H). CH$_3$ signal masked by water peak.

Example 33: Synthesis of 2-(6-(Ethylamino)-4-(2-(4-methyl-4H-1,2,4-triazol-3-yl)phenyl)pyridin-2-yl)-6-(morpholinomethyl)-4-(trifluoromethyl)isoindolin-1-one (AM-2)

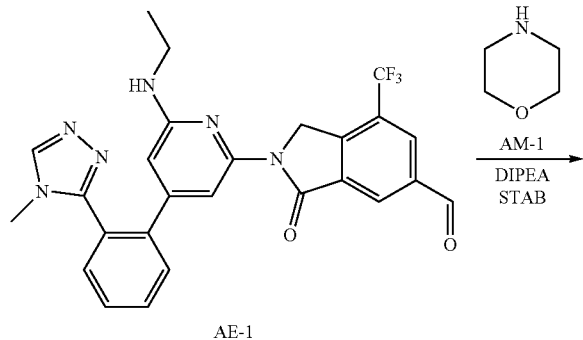

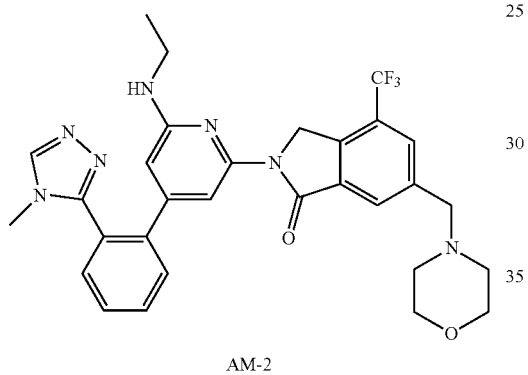

NaBH(OAc)₃ (68 mg, 6.0 Eq, 0.32 mmol) was added to a stirred solution of intermediate AE-1 (33 mg, 82% Wt, 1 Eq, 53 μmol), morpholine (AM-1) (9.3 mg, 2.0 Eq, 0.11 mmol) and DIPEA (6.9 mg, 9.2 μL, 1.0 Eq, 53 μmol) in chloroform (2 mL) and stirred at rt overnight. The reaction mixture was diluted with DCM (5 mL) and washed with sat. aq. sol. of NaHCO₃ (6 mL). The organic layer was separated, dried (phase separator) and concentrated in vacuo. The crude product was purified by preparative HPLC (Waters, Basic (0.3% Ammonia), Basic, Waters XBridge BEH C18 ODB, 5 μm, 30×100 mm column, 0-100% MeCN in water to afford the title compound (AM-2) (12 mg, 21 μmol, 39%, 100% Purity) as a flocculent white solid. m/z 578.5 (M+H)⁺ (ES+). ¹H NMR (400 MHz, DMSO-d6) δ 8.46 (s, 1H), 7.98 (s, 1H), 7.93 (s, 1H), 7.75-7.67 (m, 1H), 7.65-7.54 (m, 3H), 7.48 (s, 1H), 6.69 (t, J=5.4 Hz, 1H), 5.94 (s, 1H), 5.16 (s, 2H), 3.68 (s, 2H), 3.59 (t, J=4.6 Hz, 4H), 3.18 (q, J=6.7 Hz, 2H), 2.40 (s, 4H), 1.13 (t, J=7.2 Hz, 3H). CH₃ signal masked by water peak.

Example 34: Synthesis of (R)-2-(6-(Ethylamino)-4-(2-(4-methyl-4H-1,2,4-triazol-3-yl)phenyl)pyridin-2-yl)-6-((2-methylmorpholino)methyl)-4-(trifluoromethyl)isoindolin-1-one (AN-1)

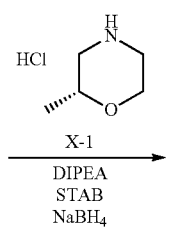

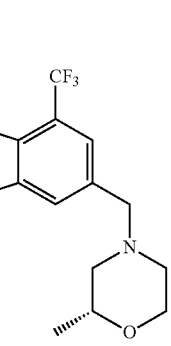

NaBH(OAc)₃ (63 mg, 6.0 Eq, 0.29 mmol) was added to a stirred solution of intermediate AE-1 (30 mg, 83% Wt, 1 Eq, 49 μmol), (R)-2-methyl-morpholine-HCl (X-1) (14 mg, 2.0 Eq, 98 μmol) and DIPEA (19 mg, 25 μL, 3.0 Eq, 0.15 mmol) in chloroform (2 mL) and stirred at rt for 3 days. Additional DIPEA (38 mg, 50 μL, 5.9 Eq, 0.29 mmol), chloroform (1.0 mL) and NaBH(OAc)₃ (30 mg, 2.9 Eq, 0.14 mmol) were added, and the reaction mixture was left to stir at rt overnight. NaBH₄ (10 mg, 5.4 Eq, 0.26 mmol) was added, and the reaction mixture stirred at rt overnight. The reaction mixture was diluted with DCM (4 mL) and washed with sat. aq. sol. of NaHCO₃ (10 mL). The organic phase was separated, dried (phase separator) and concentrated in vacuo. The crude product was purified by preparative HPLC (Waters, Basic (0.3% Ammonia), Basic, Waters XBridge BEH C18 ODB, 5 μm, 30×100 mm column, 0-100% MeCN in water) to afford the title compound (AN-1) (7 mg, 0.01 mmol, 20%, 99% Purity) as a flocculent white solid. m/z 592.5 (M+H)⁺ (ES+). ¹H NMR (400 MHz, DMSO-d6) δ 8.46 (s, 1H), 7.98 (s, 1H), 7.93 (s, 1H), 7.75-7.67 (m, 1H), 7.66-7.53 (m, 3H), 7.48 (d, J=1.2 Hz, 1H), 6.73-6.65 (m, 1H), 5.94 (s, 1H), 5.18-5.12 (m, 2H), 3.77-3.70 (m, 1H), 3.66 (s, 2H), 3.55-3.46 (m, 2H), 3.20-3.15 (m, 2H), 2.69 (d, J=11.1 Hz, 1H), 2.62 (d, J=11.3 Hz, 1H), 2.15-2.04 (m, 1H), 1.79 (dd, J=11.2, 9.9 Hz, 1H), 1.13 (t, J=7.1 Hz, 3H), 1.02 (d, J=6.3 Hz, 3H). CH₃ signal masked by water peak.

Example 35: Synthesis of 2-(6-(Ethylamino)-4-(2-(4-methyl-4H-1,2,4-triazol-3-yl)phenyl)pyridin-2-yl)-6-((((1R,2R)-2-hydroxycyclopentyl)amino)methyl)-4-(trifluoromethyl)isoindolin-1-one (AO-1)

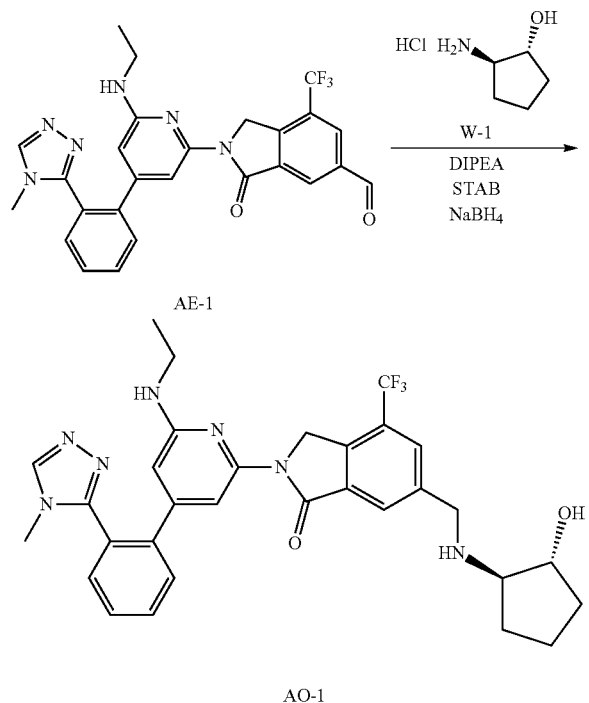

Example 36: Synthesis of 2-(6-(Ethylamino)-4-(2-(4-methyl-4H-1,2,4-triazol-3-yl)phenyl)pyridin-2-yl)-6-((((1S,2S)-2-hydroxycyclopentyl)amino)methyl)-4-(trifluoromethyl)isoindolin-1-one (AP-1)

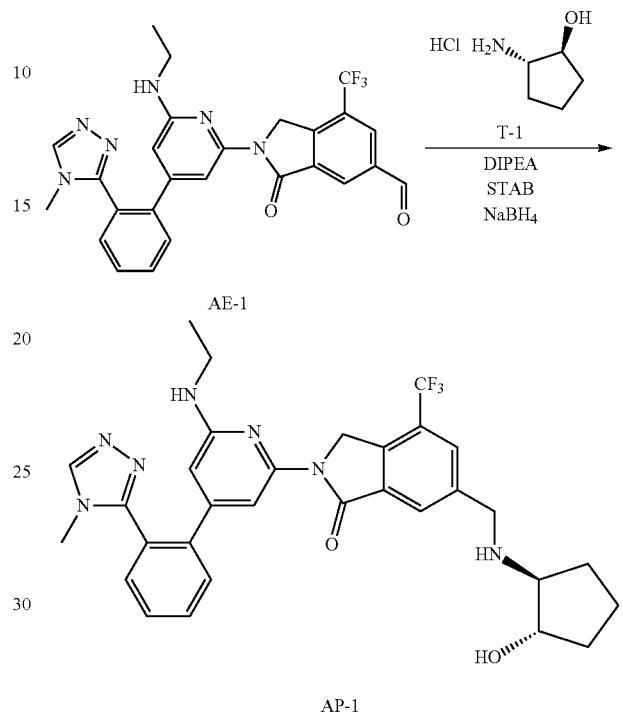

NaBH(OAc)$_3$ (63 mg, 6.0 Eq, 0.29 mmol) was added to a stirred solution of intermediate AE-1 (30 mg, 83% Wt, 1 Eq, 49 μmol), (1R,2R)-2-aminocyclopentan-1-ol-HCl (W-1) (14 mg, 2.0 Eq, 98 μmol) and DIPEA (19 mg, 25 μL, 3.0 Eq, 0.15 mmol) in chloroform (2 mL) and stirred at rt overnight. Additional DIPEA (38 mg, 50 μL, 5.9 Eq, 0.29 mmol), chloroform (1.0 mL) and NaBH(OAc)$_3$ (30 mg, 2.9 Eq, 0.14 mmol)) and stirred at rt overnight. NaBH$_4$ (10 mg, 5.4 Eq, 0.26 mmol) was added, and the reaction mixture stirred at rt overnight. The reaction mixture was diluted with DCM (4 mL) and washed with sat. aq. sol. of NaHCO$_3$ (10 mL). The organic phase was separated, dried (phase separator) and concentrated in vacuo. The crude product was purified by preparative HPLC (Waters, Basic (0.3% Ammonia), Basic, Water XBridge BEH C18 ODB, 5 μm, 30×100 mm column, 0-100% MeCN in water) to afford the title compound (AO-1) (8 mg, 0.01 mmol, 30%, 100% Purity) as a flocculent white solid. m/z 592.6 (M+H)$^+$ (ES+). $^1$H NMR (400 MHz, DMSO-d6) δ 8.46 (s, 1H), 8.02 (s, 1H), 7.98 (s, 1H), 7.75-7.67 (m, 1H), 7.65-7.53 (m, 3H), 7.48 (d, J=1.2 Hz, 1H), 6.68 (t, J=5.3 Hz, 1H), 5.94 (d, J=1.2 Hz, 1H), 5.15 (s, 2H), 4.51 (d, J=4.2 Hz, 1H), 3.92-3.87 (m, 2H), 3.83-3.76 (m, 1H), 3.23-3.14 (m, 2H), 2.75-2.71 (m, 1H), 2.38-2.34 (m, 1H), 1.88-1.74 (m, 2H), 1.63-1.51 (m, 2H), 1.46-1.36 (m, 1H), 1.36-1.23 (m, 1H), 1.13 (t, J=7.2 Hz, 3H). CH$_3$ masked by water peak.

NaBH(OAc)$_3$ (63 mg, 6.0 Eq, 0.29 mmol) was added to a stirred solution of intermediate AE-1 (30 mg, 83% Wt, 1 Eq, 49 μmol), trans-(1S,2S)-2-aminocyclopentanol-HCl (T-1) (14 mg, 2.0 Eq, 98 μmol) and DIPEA (19 mg, 25 μL, 3.0 Eq, 0.15 mmol) in chloroform (2 mL) and stirred at rt for 3 days. Additional DIPEA (38 mg, 50 μL, 5.9 Eq, 0.29 mmol), chloroform (1.0 mL) and NaBH(OAc)$_3$ (30 mg, 2.9 Eq, 0.14 mmol) were added, and the reaction stirred at rt overnight. NaBH$_4$ (10 mg, 5.4 Eq, 0.26 mmol) was added, and the reaction mixture stirred at rt overnight. The reaction mixture was diluted with DCM (4 mL) and washed with sat. aq. sol. of NaHCO$_3$ (10 mL). The organic phase was separated, dried (phase separator) and concentrated in vacuo. The crude product was purified by preparative HPLC (Waters, Basic (0.3% Ammonia), Basic, Waters XBridge BEH C18 ODB, 5 μm, 30×100 mm column, 0-100% MeCN in water) to afford the title compound (AP-1) (8 mg, 0.01 mmol, 30%, 100% Purity) as a flocculent white solid. m/z 592.4 (M+H)$^+$ (ES+). $^1$H NMR (400 MHz, DMSO-d6) δ 8.46 (s, 1H), 8.02 (s, 1H), 7.98 (s, 1H), 7.75-7.67 (m, 1H), 7.65-7.53 (m, 3H), 7.48 (d, J=1.2 Hz, 1H), 6.68 (t, J=5.4 Hz, 1H), 5.94 (d, J=1.2 Hz, 1H), 5.15 (s, 2H), 4.51 (d, J=4.2 Hz, 1H), 3.89 (s, 2H), 3.84-3.75 (m, 1H), 3.23-3.12 (m, 2H), 2.76-2.70 (m, 1H), 2.39-2.34 (m, 1H), 1.88-1.75 (m, 2H), 1.63-1.51 (m, 2H), 1.46-1.37 (m, 1H), 1.37-1.23 (m, 1H), 1.13 (t, J=7.2 Hz, 3H). CH$_3$ masked by water peak.

Example 37: Synthesis of 2-(6-(Ethylamino)-4-(2-(4-methyl-4H-1,2,4-triazol-3-yl)phenyl)pyridin-2-yl)-6-(((((1R,2S)-2-hydroxycyclopentyl)amino)methyl)-4-(trifluoromethyl)isoindolin-1-one (AQ-1)

Example 38: Synthesis of 2-(6-(Ethylamino)-4-(2-(4-methyl-4H-1,2,4-triazol-3-yl)phenyl)pyridin-2-yl)-6-(((((1S,2R)-2-hydroxycyclopentyl)amino)methyl)-4-(trifluoromethyl)isoindolin-1-one (AR-1)

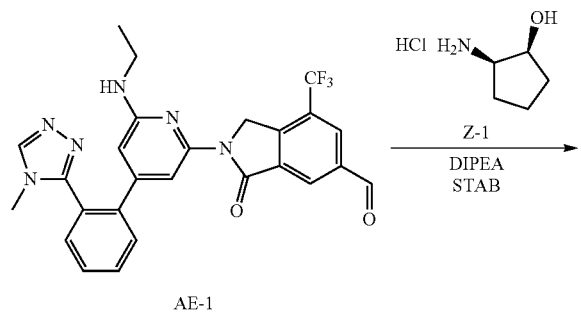

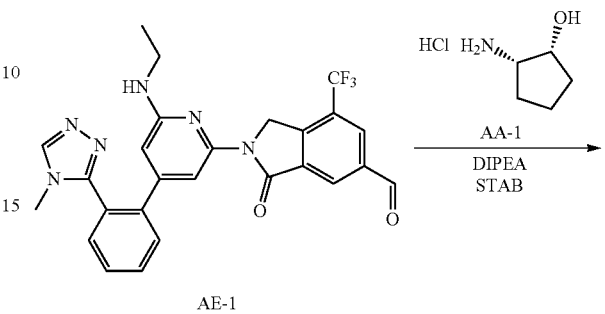

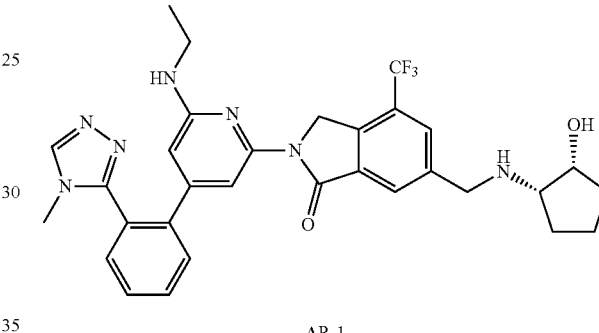

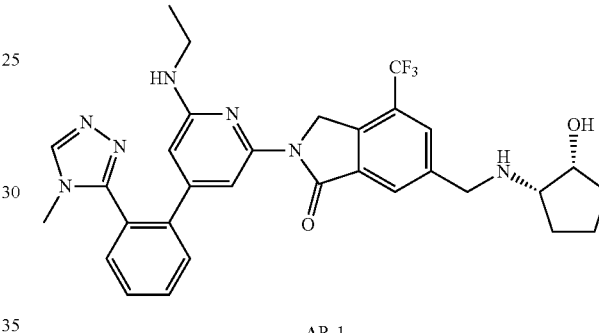

A mixture of intermediate AE-1 (30 mg, 99% Wt, 1 Eq, 59 μmol), (1S,2R)-2-aminocyclopentan-1-ol·HCl (Z-1) (16 mg, 2.0 Eq, 0.12 mmol) and DIPEA (23 mg, 30 μL, 3.0 Eq, 0.18 mmol) in CHCl₃ (2 mL) was stirred at 40° C. for 30 min. NaBH(OAc)₃ (75 mg, 6.0 Eq, 0.35 mmol) was then added and the resultant suspension stirred at rt overnight. The reaction mixture was diluted with DCM (4 mL) and washed with sat. aq. NaHCO₃ (10 mL). The organic phase was separated and concentrated in vacuo to afford the crude product which was purified by preparative HPLC (Waters, Basic (0.3% Ammonia), Basic, Waters XBridge BEH C18 ODB, 5 μm, 30×100 mm column, 0-100% MeCN in water) to afford the title compound (AQ-1) (14 mg, 23 μmol, 39%, 97% Purity) as a white solid. m/z 592.3 (M+H)⁺ (ES+). ¹H NMR (400 MHz, DMSO-d6) δ 8.46 (s, 1H), 8.01 (d, J=16.6 Hz, 2H), 7.71 (td, J=7.4, 1.7 Hz, 1H), 7.65-7.53 (m, 3H), 7.48 (d, J=1.2 Hz, 1H), 6.68 (t, J=5.4 Hz, 1H), 5.93 (d, J=1.4 Hz, 1H), 5.15 (s, 2H), 4.40 (d, J=3.6 Hz, 1H), 3.99-3.91 (m, 2H), 3.91-3.83 (m, 1H), 3.33 (s, 3H), 3.20-3.14 (m, 2H), 2.78-2.74 (m, 1H), 2.31-2.27 (m, 1H), 1.75-1.54 (m, 4H), 1.48-1.38 (m, 2H), 1.13 (t, J=7.1 Hz, 3H).

A mixture of intermediate AE-1 (30 mg, 99% Wt, 1 Eq, 59 μmol), (1R,2S)-2-aminocyclopentan-1-ol·HCl (AA-1) (16 mg, 2.0 Eq, 0.12 mmol) and DIPEA (23 mg, 30 μL, 3.0 Eq, 0.18 mmol) in CHCl₃ (2 mL) was stirred at 40° C. for 30 min. NaBH(OAc)₃ (75 mg, 6.0 Eq, 0.35 mmol) was then added and the resultant suspension stirred at rt overnight. The reaction mixture was diluted with DCM (4 mL) and washed with sat. aq. NaHCO₃ (10 mL). The organic phase was separated and concentrated in vacuo to afford the crude product which was purified by preparative HPLC (Waters, Basic (0.3% Ammonia), Basic, Waters XBridge BEH C18 ODB, 5 μm, 30×100 mm column, 0-100% MeCN in water) to afford the title compound (AR-1) (15 mg, 25 μmol, 42%, 98% Purity) as a white solid. m/z 591.9 (M+H)⁺ (ES+). ¹H NMR (400 MHz, DMSO-d6) δ 8.46 (s, 1H), 8.01 (d, J=16.6 Hz, 2H), 7.71 (td, J=7.4, 1.7 Hz, 1H), 7.65-7.53 (m, 3H), 7.48 (d, J=1.2 Hz, 1H), 6.68 (t, J=5.4 Hz, 1H), 5.93 (d, J=1.3 Hz, 1H), 5.15 (s, 2H), 4.40 (d, J=3.6 Hz, 1H), 3.99-3.91 (m, 2H), 3.91-3.83 (m, 1H), 3.33 (s, 3H), 3.20-3.14 (m, 2H), 2.78-2.74 (m, 1H), 2.32-2.27 (m, 1H), 1.73-1.54 (m, 4H), 1.48-1.34 (m, 2H), 1.13 (t, J=7.1 Hz, 3H).

Example 39: Synthesis of 2-(6-(Ethylamino)-4-(2-(4-methyl-4H-1,2,4-triazol-3-yl)phenyl)pyridin-2-yl)-6-(methoxymethyl)-4-(trifluoromethyl)isoindolin-1-one (AS-2)

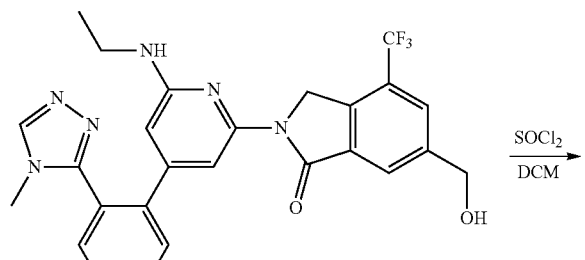

AD-3

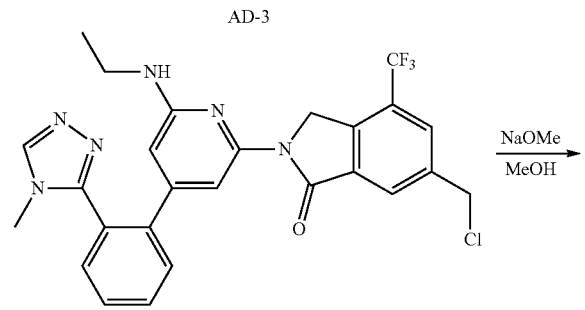

AS-1

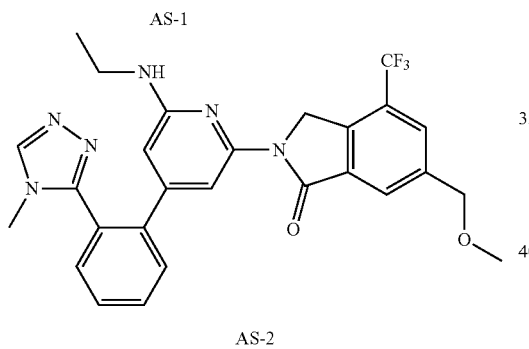

AS-2

Step 1: Synthesis of 6-(Chloromethyl)-2-(6-(ethylamino)-4-(2-(4-methyl-4H-1,2,4-triazol-3-yl)phenyl)pyridin-2-yl)-4-(trifluoromethyl)isoindolin-1-one (AS-1)

Thionyl chloride (7.1 mg, 4.4 μL, 1.1 Eq, 60 μmol) was added to a suspension of intermediate AD-3 (30 mg, 92% Wt, 1 Eq, 54 μmol) in DCM (2 mL) and the resulting mixture stirred at rt overnight. More thionyl chloride (65 mg, 40 μL, 10 Eq, 0.54 mmol) was added and stirring continued at rt overnight affording the sub-title compound (AS-1), which was used directly in the next step. m/z 527.2 (M+H)⁺ (ES+)

Step 2: Synthesis of 2-(6-(Ethylamino)-4-(2-(4-methyl-4H-1,2,4-triazol-3-yl)phenyl)pyridin-2-yl)-6-(methoxymethyl)-4-(trifluoromethyl)isoindolin-1-one (AS-2)

Sodium methoxide (0.11 g, 0.55 mL, 5.4 molar, 60 Eq, 3.3 mmol) was added to the product from step 1 above (AS-1) (30 mg, 1 Eq, 57 μmol) in DCM (0.8 mL) and MeOH (2 mL). The reaction mixture was stirred at rt overnight. The reaction mixture was brought to neutral pH by addition of 4M HCl in dioxane followed by addition of sat. aq. NaHCO₃. The bulk solvent was removed in vacuo and the residue partitioned between 1:1 DCM-EtOAc (10 mL) and water (10 mL). The organic layer was concentrated in vacuo affording an orange gum. The crude product was purified by preparative HPLC (Waters, Basic (0.3% Ammonia), Basic, Waters XBridge BEH C18 ODB, 5 μm, 30×100 mm column, 0-100% MeCN in water) to afford the title compound (AS-2) (10 mg, 19 μmol, 37%, 98% Purity) as a white solid. m/z 523.4 (M+H)⁺ (ES+). ¹H NMR (400 MHz, DMSO-d6) δ 8.46 (s, 1H), 7.99 (s, 1H), 7.94 (s, 1H), 7.75-7.67 (m, 1H), 7.66-7.53 (m, 3H), 7.49 (d, J=1.2 Hz, 1H), 6.69 (t, J=5.5 Hz, 1H), 5.93 (d, J=1.3 Hz, 1H), 5.17 (s, 2H), 4.62 (s, 2H), 3.36 (s, 3H), 3.29 (s, 3H), 3.21-3.13 (m, 2H), 1.12 (t, J=7.2 Hz, 3H).

Example 40: Synthesis of 2-[3-[2-(4-Methyl-1,2,4-triazol-3-yl) imidazol-1-yl]phenyl]-4-(trifluoromethyl)-3H-isoindol-1-one (AAA-8)

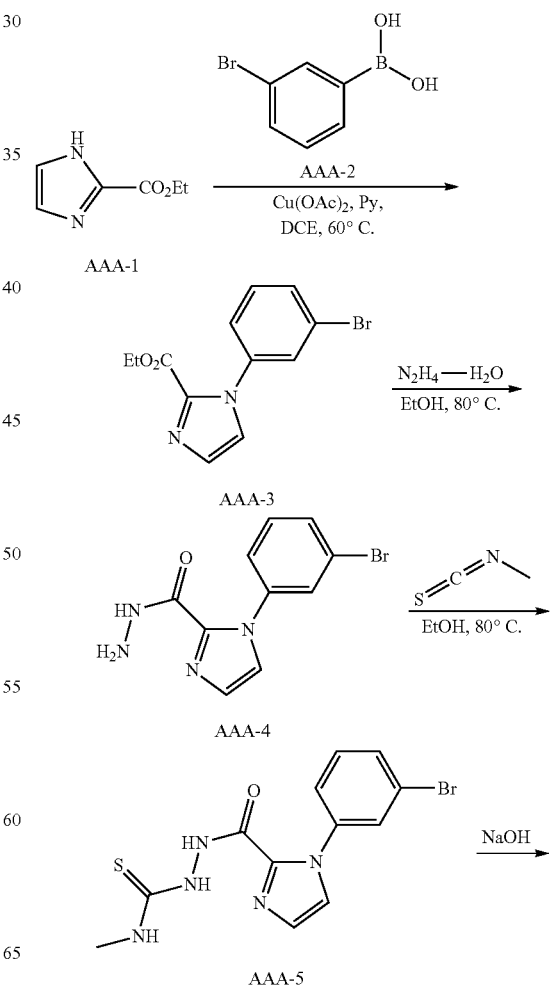

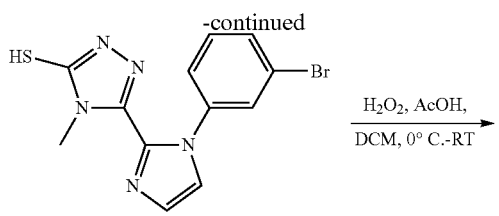

AAA-6

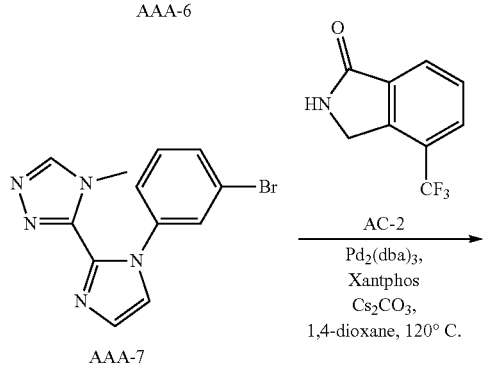

AAA-7

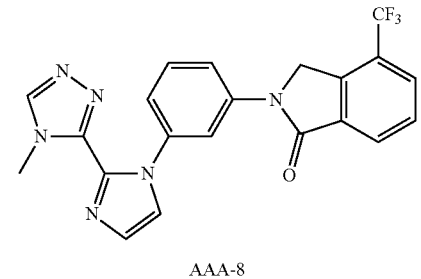

AAA-8

Step 1: Synthesis of Ethyl 1-(3-bromophenyl) imidazole-2-carboxylate (AAA-3)

To a stirred mixture of ethyl 1H-imidazole-2-carboxylate (AAA-1) (1.00 g, 1 Eq, 7.1 mmol) and 3-bromophenylboronic acid (AAA-2) (2.87 g, 2 Eq, 14.3 mmol) in 1,2-dichloroethane (20 mL) were added cupric acetate (1.94 g, 1.5 Eq, 10.7 mmol) and pyridine (1.13 g, 2 Eq, 14.3 mmol) at rt. The resulting mixture was stirred overnight at 60° C. The mixture was cooled to rt and concentrated in vacuo. The residue was purified by silica gel column chromatography, eluted with petroleum ether/EtOAc (1/1) to afford the sub-title compound (AAA-3) (500 mg, 1.7 mmol, 24%) as a white solid. m/z 295.1/297.1 (M+H)$^+$ (ES+)

Step 2: Synthesis of 1-(3-Bromophenyl)imidazole-2-carbohydrazide (AAA-4)

To a stirred mixture of the product from step 1 above (AAA-3) (400 mg, 1 Eq, 1.36 mmol) in EtOH (8 mL) was added hydrazine hydrate (678 mg, 80% Wt, 10 Eq, 13.6 mmol) drop-wise at rt. The resulting mixture was stirred for overnight at 80° C. The mixture was cooled to rt and concentrated in vacuo to afford the sub-title compound (AAA-4) (330 mg, 1.17 mmol, crude) as a white solid. m/z 281.1/283.1 (M+H)$^+$ (ES+).

Step 3: 1-(3-Bromophenyl)-N-[(methylcarbamothioyl)amino]imidazole-2-carboxamide (AAA-5)

To a stirred solution of the product from step 2 above (AAA-4) (320 mg, 1 Eq, 1.14 mmol) in EtOH (10 mL) was added methyl isothiocyanate (99.8 mg, 1.2 Eq, 1.37 mmol) at rt. The resulting mixture was stirred 6 h at 80° C. The mixture was cooled to rt and concentrated to afford the sub-title compound (AAA-5) (350 mg, 991 μmol, 87%) as a white solid. m/z 354.2/356.2 (M+H)$^+$ (ES+).

Step 4: Synthesis of 5-[1-(3-Bromophenyl)imidazol-2-yl]-4-methyl-1,2,4-triazole-3-thiol (AAA-6)

A mixture of the product from step 3 above (AAA-5) (330 mg, 1 Eq, 0.93 mmol) in NaOH (aq.) (10 mL, 1 molar, 10 Eq, 10 mmol) was stirred 3 h at 60° C. The resulting mixture was diluted with water, acidified to pH 6 with HCl (aq. 1M) and extracted with EtOAc (3×30 mL). The combined organic layers were washed with brine (2×30 mL), dried (Na$_2$SO$_4$), filtered and concentrated in vacuo to afford the sub-title compound (AAA-6) (300 mg, 895 μmol, 96%) as a white solid. m/z 336.2/338.2 (M+H)$^+$ (ES+).

Step 5: Synthesis of 3-[1-(3-Bromophenyl)imidazol-2-yl]-4-methyl-1,2,4-triazole (AAA-7)

To a stirred solution of the product from step 4 above (AAA-6) (300 mg, 1 Eq, 892 μmol) in DCM (20 mL) were added acetic acid (54 mg, 1 Eq, 892 μmol) and hydrogen peroxide (607 mg, 30% Wt, 6 Eq, 5.35 mmol,) drop-wise at 0° C. The resulting mixture was stirred for 3 h at rt. The resulting mixture was concentrated in vacuo. The residue was purified by silica gel column chromatography, eluted with DCM/MeOH (10/1) to afford the sub-title compound (AAA-7) (240 mg, 792 μmol, 88%) as a brown oil. m/z 304.2/306.2 (M+H)$^+$ (ES+).

Step 6: Synthesis of 2-[3-[2-(4-Methyl-1,2,4-triazol-3-yl)imidazol-1-yl]phenyl]-4-(trifluoromethyl)-3H-isoindol-1-one (AAA-8)

To a solution of the product from step 5 above (AAA-7) (50 mg, 1 Eq, 0.16 mmol), intermediate (AC-2) (36 mg, 1.1 Eq, 0.18 mmol) and Cs$_2$CO$_3$ (161 mg, 3 Eq, 493 μmol) in 1,4-dioxane (3 mL) were added tris(dibenzylideneacetone)dipalladium (30 mg, 0.2 Eq, 33 μmol) and Xantphos (19 mg, 0.2 Eq, 33 μmol) under nitrogen atmosphere. The resulting mixture was stirred overnight at 120° C. under nitrogen atmosphere. The mixture was allowed to cool to rt then diluted with water and extracted with EtOAc (3×20 mL). The combined organic layers were washed with brine (2×20 mL), dried (Na$_2$SO$_4$), filtered and concentrated in vacuo. The residue was purified by reverse flash chromatography with the following conditions: column, C18 silica gel; mobile phase, ACN in water (0.1% NH$_4$HCO$_3$), 10% to 80% gradient in 20 min; detector, UV 254/220 nm and Prep-HPLC with the following conditions (Column: XBridge Shield RP18 OBD Column, 30*150 mm, 5 μm; Mobile Phase A: Water(0.1% NH$_4$HCO$_3$+0.1% NH$_3$·H$_2$O), Mobile Phase B: ACN; Flow rate: 60 mL/min; Gradient: 26% B to 48% B in 7 min; UV detection at 254/210 nm; RT: 5.93). The product-containing fractions were combined and evaporated partially in vacuo and lyophilized overnight to afford the title compound (AAA-8) (20.9 mg, 49 μmol, 28%) as a white solid. m/z 425.2 (M+H)$^+$ (ES+). $^1$H NMR (300 MHz, MeOH-d4) δ 8.61 (s, 1H), 8.14-8.03 (m, 2H), 7.99 (d, J=7.7 Hz, 1H), 7.95-7.85 (m, 1H), 7.84-7.68 (m, 2H), 7.55 (t, J=8.2 Hz, 1H), 7.45 (d, J=1.3 Hz, 1H), 7.28-7.18 (m, 1H), 5.18 (s, 2H), 3.90 (s, 3H).

Example 41: Synthesis of 6-((5-Azaspiro [2.4] heptan-5-yl)methyl)-2-(3-(1-methyl-4-(4-methyl-4H-1,2,4-triazol-3-yl)-1H-pyrazol-5-yl) phenyl)-4-(trifluoromethyl)isoindolin-1-one (AAD-1)

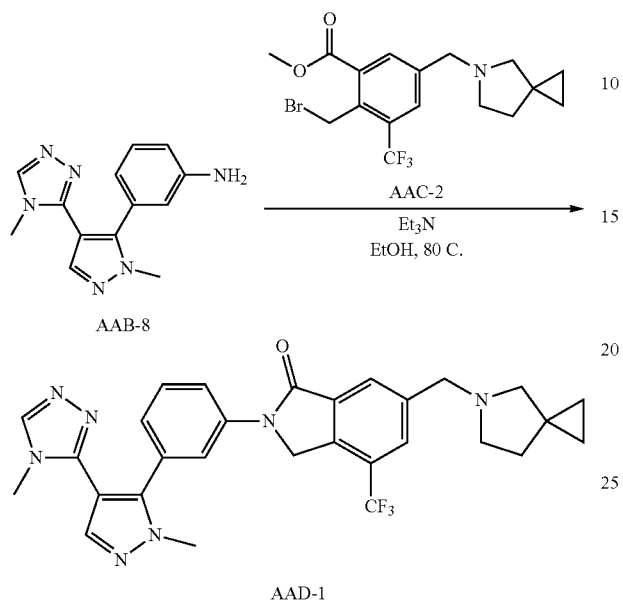

To a stirred mixture of intermediate (AAB-8) (50 mg, 1 Eq, 197 µmol) and intermediate (AAC-2) (160 mg, 2 Eq, 393 µmol) in EtOH (6 mL) was added Et₃N (100 mg, 5 Eq, 983 µmol) at rt. The resulting mixture was stirred overnight at 80° C. under nitrogen atmosphere. The resulting mixture was cooled to rt and concentrated in vacuo. The crude product was purified by Prep-HPLC with the following conditions: Column: XBridge Shield RP18 OBD Column, 19×250 mm, 10 µm; Mobile Phase A: Water (0.1% FA), Mobile Phase B: MeOH, Flow rate: 25 mL/min; Gradient: 10% B to 65% B in 7 min; Detector, UV 210/254 nm; RT: 6.15. The product-containing fractions were combined and evaporated partially in vacuo and lyophilized overnight to afford the title compound (AAD-1) (4.9 mg, 9.0 µmol, 4.5%) as a white solid. m/z 548.2 (M+H)⁺ (ES+). ¹H NMR (300 MHz, MeOH-d4) δ 8.45 (s, 1H), 8.12-7.93 (m, 4H), 7.89 (s, 1H), 7.59 (t, J=8.0 Hz, 1H), 7.30-7.20 (m, 1H), 5.17 (s, 2H), 4.00 (s, 3H), 3.87 (s, 2H), 3.43 (s, 3H), 2.83 (t, J=7.0 Hz, 2H), 2.58 (s, 2H), 1.89 (t, J=6.9 Hz, 2H), 0.59 (s, 4H).

Example 42: Synthesis of 2-Cyclopropyl-1-methyl-N-[3-[2-methyl-4-(4-methyl-1,2,4-triazol-3-yl) pyrazol-3-yl]phenyl]-6-oxopyrimidine-4-carboxamide (AAE-6)

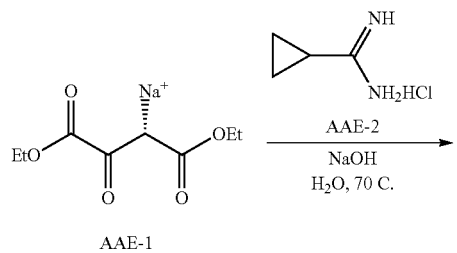

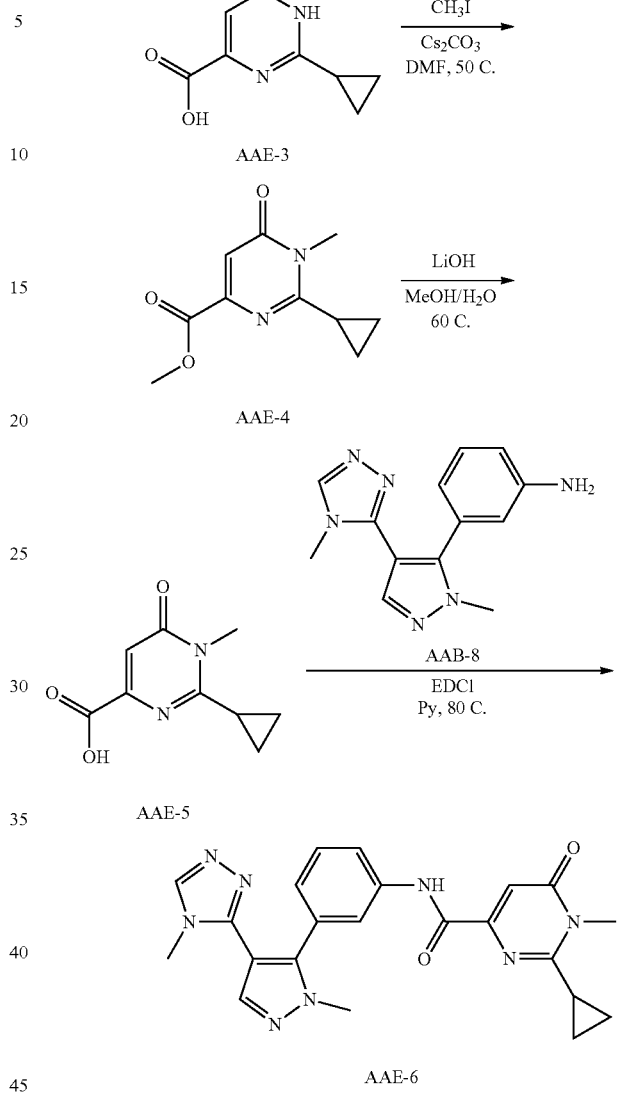

Step 1: Synthesis of 2-Cyclopropyl-6-oxo-1H-pyrimidine-4-carboxylic acid (AAE-3)

To a stirred mixture of sodium 1,4-diethoxy-1,3,4-trioxobutan-2-ide (AAE-1) (8.70 g, 1 Eq, 41.4 mmol) in water (50 mL) was added NaOH (2.85 g, 1.72 Eq, 71.3 mmol) and cyclopropanecarboximidamide, HCl (AAE2) (5.00 g, 1 Eq, 41.5 mmol) portion-wise at rt. The resulting mixture was stirred for overnight at 70° C. The residue was acidified to pH 1 with conc. HCl (aq.). The crude product was purified by reverse flash column chromatography with the following conditions: Column, C18; mobile phase, Water (0.1% FA) and ACN (10% ACN up to 50% in 10 min); Detector, UV 254/220 nm. The resulting mixture was concentrated in vacuo. This resulted in the sub-title compound (AAE-3) (4 g, 22.2 mmol, 54%) as a white solid. m/z 181.1 (M+H)⁺ (ES+).

Step 2: Synthesis of Methyl 2-cyclopropyl-1-methyl-6-oxopyrimidine-4-carboxylate (AAE-4)

To a stirred mixture of the product from step 1 above (AAE-3) (1.00 g, 1 Eq, 5.55 mmol) and in DMF (25 mL) was added methyl iodide (1.9 g, 2.5 Eq, 13.9 mmol) at rt. The resulting mixture was stirred for 16 h at 50° C. The mixture was cooled to rt and the resulting mixture extracted with EtOAc (3×150 mL). The combined organic layers were washed with brine (2×150 mL), dried ($Na_2SO_4$), filtered and concentrated in vacuo. The crude product was purified by reverse flash column chromatography with the following conditions: Column, C18; mobile phase, Water (0.1% $NH_4HCO_3$) and ACN (0% ACN up to 100% in 20 min); Detector, UV 254/220 nm. This resulted in the sub-title compound (AAE-4) (358 mg, 1.71 mmol, 31%) as a yellow solid. m/z 209.1 (M+H)$^+$ (ES+).

Step 3: Synthesis of 2-Cyclopropyl-1-methyl-6-oxopyrimidine-4-carboxylic acid (AAE-5)

To a stirred mixture of the product from step 2 above (AAE-4) (358 mg, 1 Eq, 1.72 mmol) in MeOH (8 mL) was added water (2 mL) and LiOH (206 mg, 5 Eq, 8.59 mmol) at rt. The resulting mixture was stirred for 4 h at 60° C. The mixture was cooled to rt and the residue acidified to pH 5 with conc. HCl (aq.). The resulting mixture was extracted with EtOAc (3×50 mL). The combined organic layers were washed with brine (2×50 mL), dried ($Na_2SO_4$), filtered and concentrated in vacuo. The crude product was purified by reverse flash column chromatography with the following conditions: Column, C18; mobile phase, Water (0.1% $NH_4HCO_3$) and ACN (0% ACN up to 100% in 20 min); Detector, UV 254/220 nm. This resulted in the sub-title compound (AAE-5) (300 mg, 759 μmol, 90%) as a white solid. m/z 195.1 (M+H)$^+$ (ES+).

Step 4: Synthesis of 2-Cyclopropyl-1-methyl-N-[3-[2-methyl-4-(4-methyl-1,2,4-triazol-3-yl)pyrazol-3-yl]phenyl]-6-oxopyrimidine-4-carboxamide (AAE-6)

To a stirred mixture of the product from step 3 above (AAE-5) (38.4 mg, 1 Eq, 120 μmol) and intermediate (AAB-8) (50.3 mg, 1 Eq, 120 μmol) in pyrazine (1 mL) was added EDCI (75.8 mg, 2 Eq, 0.4 mmol) at rt. The resulting mixture was stirred for 1 h at 80° C. The mixture was cooled to rt and concentrated in vacuo. The crude product was purified by reverse flash column chromatography with the following conditions: Column, C18; mobile phase, Water (0.1% FA) and ACN (0% ACN up to 100% in 20 min); Detector, UV 254/220 nm. The crude product was purified by Prep-HPLC with the following conditions (Column: XBridge Shield RP18 OBD Column, 19×250 mm, 10 μm; Mobile Phase A: Water (0.1% FA), Mobile Phase B: MeOH, Flow rate: 25 mL/min; Gradient: 10% B to 50% B in 7 min; Detector, UV 210/254 nm; RT: 6.15) to afford the title compound (AAE-6) (24.6 mg, 57.1 μmol, 29%) as a white solid. m/z 431.2 (M+H)$^+$ (ES+). $^1$H NMR (400 MHz, MeOH-d4) δ 8.45 (s, 1H), 7.90-7.83 (m, 2H), 7.78 (m, 1H), 7.51 (t, J=7.9 Hz, 1H), 7.18 (m, 1H), 7.00 (s, 1H), 3.97 (s, 3H), 3.78 (s, 3H), 3.39 (s, 3H), 2.30 (m, 1H), 1.44-1.36 (m, 2H), 1.25 (m, 2H).

Example 43: Synthesis of 2-[3-[1-Ethyl-4-(4-methyl-1,2,4-triazol-3-yl)pyrazol-3-yl]phenyl]-4-(trifluoromethyl)-3H-isoindol-1-one (AAF-9)

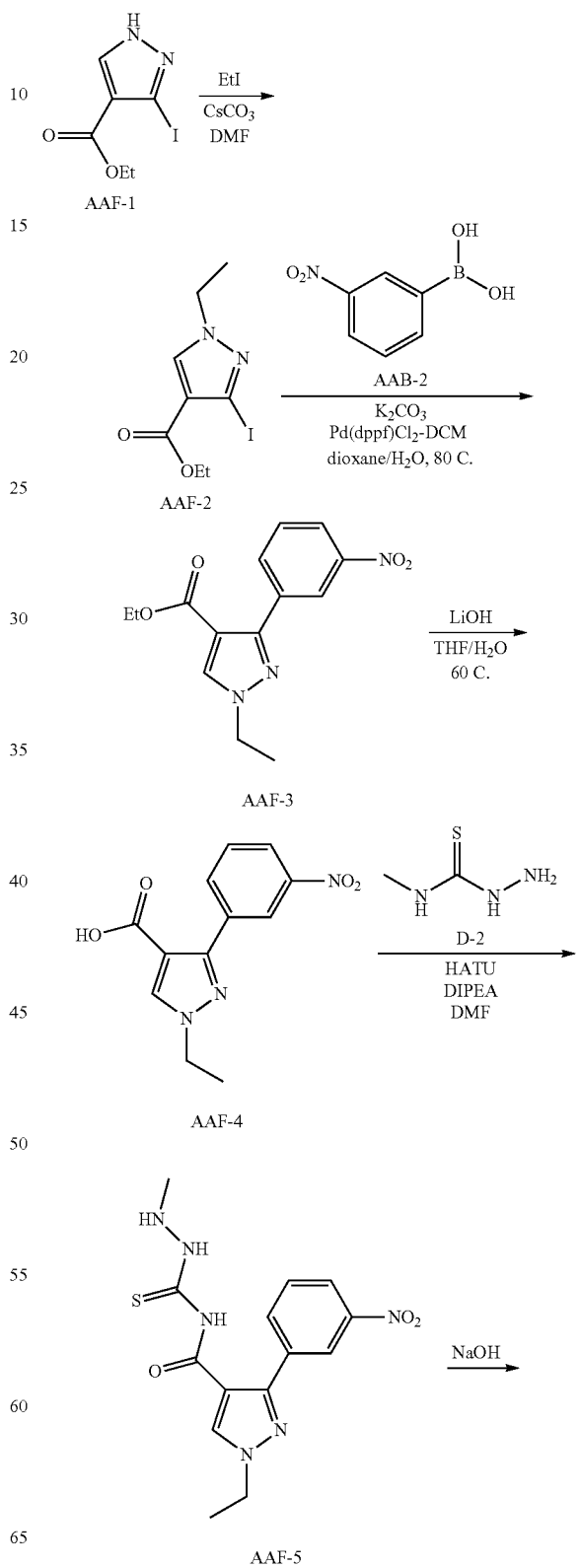

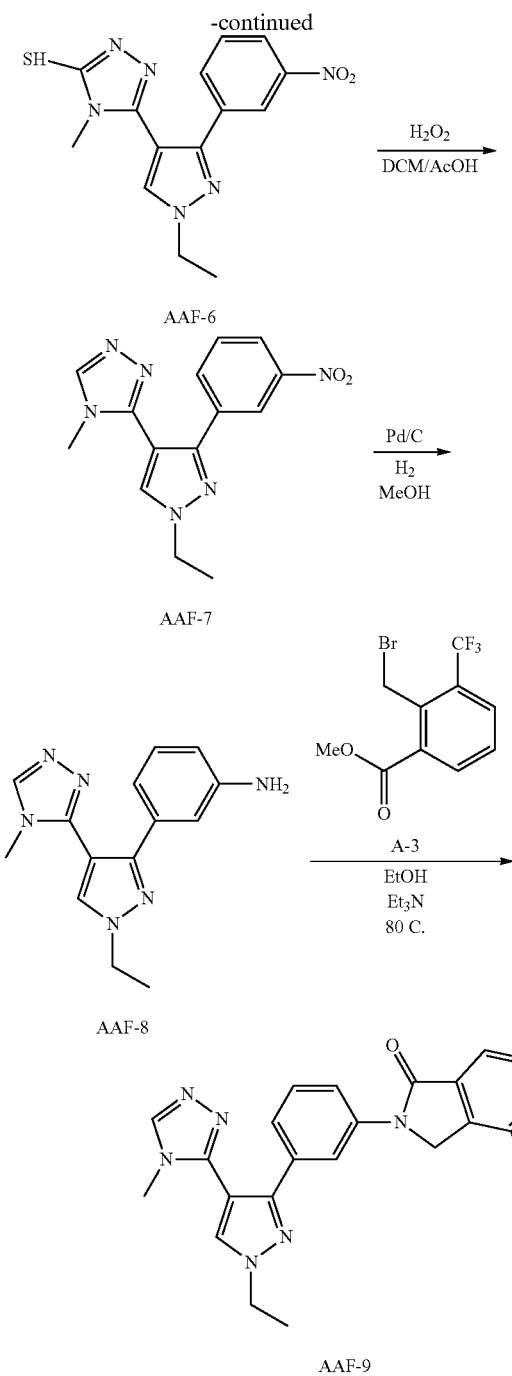

title compound (AAF-2) (340 mg, 1.15 mmol, 62%) as a yellow oil. m/z 295.0 (M+H)+ (ES+).

Step 2: Synthesis of Ethyl 1-ethyl-3-(3-nitrophenyl)-1H-pyrazole-4-carboxylate (AAF-3)

To a stirred solution of the product from step 1 above (AAF-2) (340 mg, 1 Eq, 1.16 mmol) and 3-nitrophenylboronic acid (AAB-2) (232 mg, 1.2 Eq, 1.39 mmol) in 1,4-dioxane (6 mL) were added $K_2CO_3$ (479 mg, 3 Eq, 3.47 mmol) and water (1.5 mL) at rt under nitrogen atmosphere. To the above mixture was added Pd(dppf)$Cl_2$.DCM (85 mg, 0.1 Eq, 116 µmol) at rt under nitrogen atmosphere. The resulting mixture was stirred for additional 2 h at 80° C. under nitrogen atmosphere. The mixture was allowed to cool to rt and was concentrated in vacuo. The resulting mixture was diluted with water and extracted with EtOAc (3×30 mL). The combined organic layers were washed with brine (2×30 mL), dried ($Na_2SO_4$), filtered and concentrated in vacuo. The residue was purified by Prep-TLC with petroleum ether:EtOAc 5/1 to afford the sub-title compound (AAF-3) (335 mg, 1.16 mmol, 100%) as a yellow oil. m/z 290.1 (M+H)+ (ES+).

Step 3: Synthesis of 1-Ethyl-3-(3-nitrophenyl)-1H-pyrazole-4-carboxylic acid (AAF-4)

To a stirred solution of the product from step 2 above (AAF-3) (335 mg, 1 Eq, 1.16 mmol) in THF (5 mL) were added LiOH (83 mg, 3 Eq, 3.47 mmol) and water (1 mL) portion-wise at rt. The resulting mixture was stirred for 16 h at 60° C. The mixture was allowed to cool to rt and was acidified to pH 3 with HCl (aq.). The precipitated solids were collected by filtration and washed with EtOAc (3×5 mL). The resulting solid was dried in an oven in vacuo affording sub-title compound (AAF-4) (300 mg, 1.15 mmol, 99%) as a white solid. m/z 262.1 (M+H)+ (ES+).

Step 4: Synthesis of 1-Ethyl -N-(2-methylhydrazine-1-carbonothioyl)-3-(3-nitrophenyl)-1H-pyrazole-4-carboxamide (AAF-5)

To a stirred solution of the product from step 3 above (AAF-4) (300 mg, 1 Eq, 1.15 mmol) and 4-methyl-3-thiosemicarbazide (D-2) (146 mg, 1.2 Eq, 1.39 mmol) in DMF (6 mL) were added HATU (480 mg, 1.1 Eq, 1.26 mmol) and DIPEA (1.48 g, 10 Eq, 11.5 mmol) at rt. The resulting mixture was stirred for 2 h at rt under nitrogen atmosphere. The resulting mixture was used in the next step directly without further purification. m/z 349.1 (M+H)+ (ES+).

Step 5: Synthesis of 5-(1-Ethyl-3-(3-nitrophenyl)-1H-pyrazol-4-yl)-4-methyl-4H-1,2,4-triazole-3-thiol (AAF-6)

To the reaction from step 4 above was added NaOH (aq., 10M) (6 mL). The resulting mixture was stirred for 16 h at rt under nitrogen atmosphere. The resulting mixture was extracted with EtOAc (3×50 mL). The combined organic layers were washed with brine (3×50 mL), dried ($Na_2SO_4$), filtered and concentrated in vacuo. The residue was dissolved in DMF (10 mL). The resulting mixture was concentrated in vacuo. This resulted in the sub-title compound (AAF-6) (350 mg, 1.06 mmol) as a yellow oil. m/z 331.1 (M+H)+ (ES+).

Step 1: Synthesis of Ethyl 1-ethyl-3-iodo-1H-pyrazole-4-carboxylate (AAF-2)

To a stirred solution of ethyl 3-iodo-1H-pyrazole-4-carboxylate (AAF-1) (500 mg, 1 Eq, 1.88 mmol) in DMF (10 mL) were added ethyl iodide (440 mg, 1.5 Eq, 2.82 mmol) and $Cs_2CO_3$ (1.53 g, 2.5 Eq, 4.70 mmol) at rt. The resulting mixture was diluted with water (50 mL). The resulting mixture was extracted with EtOAc (3×30 mL). The combined organic layers were washed with brine (3×30 mL), dried ($Na_2SO_4$), filtered and concentrated in vacuo. The residue was purified by silica gel column chromatography, eluted with petroleum ether/EtOAc 10/1 to afford the sub-

Step 6: Synthesis of 3-(1-Ethyl-3-(3-nitrophenyl)-1H-pyrazol-4-yl)-4-methyl-4H-1,2,4-triazole (AAF-7)

To a stirred solution of the product from step 5 above (AAF-6) (350 mg, 1 Eq, 1.06 mmol) in DCM (5 mL) were added acetic acid (7 mL) and water (7 mL) at 0° C. The resulting mixture was stirred for 16 h at rt. The mixture was basified to pH 10 with sat. NaHCO₃ (aq.). The resulting mixture was extracted with DCM (3×50 mL). The combined organic layers were washed with brine (3×50 mL), dried (Na₂SO₄), filtered and concentrated in vacuo affording the sub-title compound (AAF-7) (290 mg, 973 μmol, 77%) as a green oil. m/z 299.1 (M+H)⁺ (ES+).

Step 7: Synthesis of 3-(1-Ethyl-4-(4-methyl-4H-1,2,4-triazol-3-yl)-1H-pyrazol-3-yl)aniline (AAF-8)

To a stirred solution of the product from step 6 above (AAF-7) (290 mg, 1 Eq, 972 μmol) in MeOH was added Pd/C 39 (10.35 mg, 10% Wt, 0.1 Eq, 97 μmol) at rt under nitrogen atmosphere. The resulting mixture was stirred for 3 h at rt under hydrogen atmosphere. The resulting mixture was filtered; the filter cake was washed with MeOH (3×5 mL). The filtrate was concentrated in vacuo. The resulting oil was dried in an oven in vacuo affording the sub-title compound (AAF-8) (262 mg, 977 μmol, 57%) as an orange oil. m/z 269.1 (M+H)⁺ (ES+).

Step 8: 2-(3-(1-Ethyl-4-(4-methyl-4H-1,2,4-triazol-3-yl)-1H-pyrazol-3-yl)phenyl)-4-(trifluoromethyl)isoindolin-1-one (AAF-9)

To a stirred solution of the product from step 7 above (AAF-8) (262 mg, 1 Eq, 976 μmol) and EtOH (5 mL) were added Et₃N (296 mg, 3 Eq, 2.93 mmol) and intermediate (A-3) (290 mg, 1 Eq, 976 μmol) at rt. The residue was purified by Prep-TLC with petroleum ether/EtOAc (15/1). The crude product was purified by Prep-HPLC with the following conditions (Column: YMC-Triart Diol Hilic, 20*150 mm 5 um; Mobile Phase A: Water (0.1% NH₄HCO₃+0.1% NH₃·H₂O), Mobile Phase B: ACN; Flow rate:60 mL/min; Gradient:30 B to 50 B in 10 min; 254/210 nm) to afford the title compound (AAF-9) (40.6 mg, 90 μmol, 9%) as a white solid. m/z 453.1 (M+H)⁺ (ES+). ¹H NMR (300 MHz, MeOH-d4) δ 8.57 (s, 1H), 8.13-8.05 (m, 2H), 7.97 (d, J=7.7 Hz, 1H), 7.94-7.83 (m, 2H), 7.77 (t, J=7.7 Hz, 1H), 7.47 (t, J=8.0 Hz, 1H), 7.36-7.31 (m, 1H), 5.12 (s, 2H), 4.36 (q, J=7.3 Hz, 2H), 3.42 (s, 3H), 1.60 (t, J=7.3 Hz, 3H).

Example 44: Synthesis of 2-(2'-(4-Methyl-4H-1,2,4-triazol-3-yl)-5'-(trifluoromethyl)-[1,1'-biphenyl]-3-yl)-4-(trifluoromethyl)isoindolin-1-one (AAG-8)

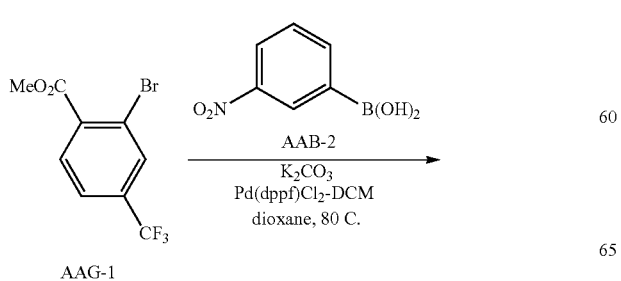

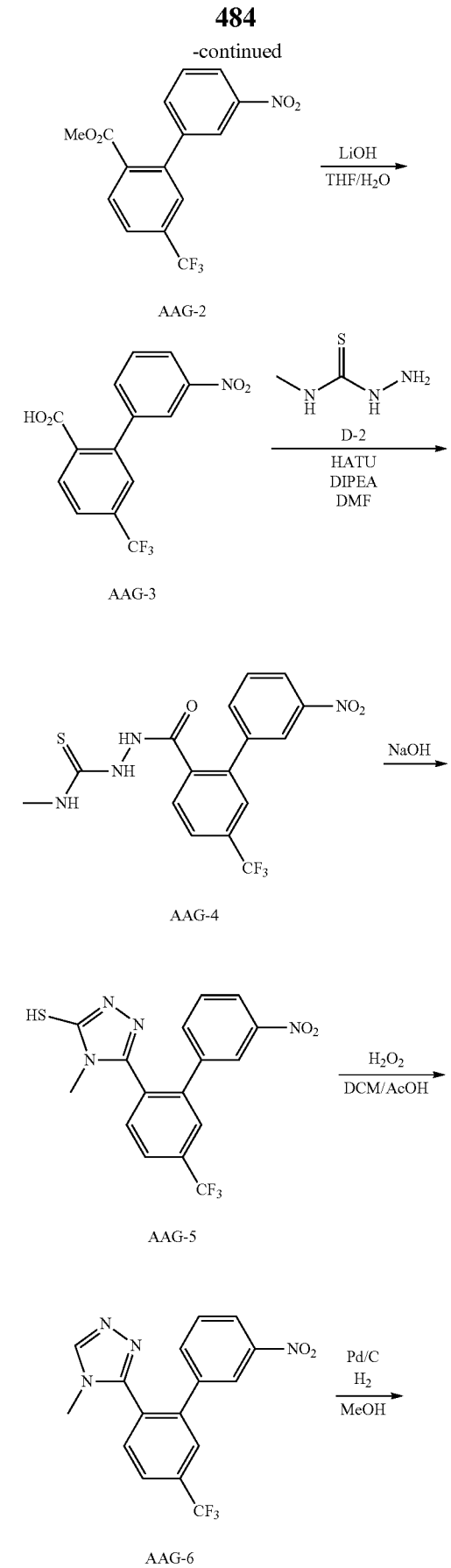

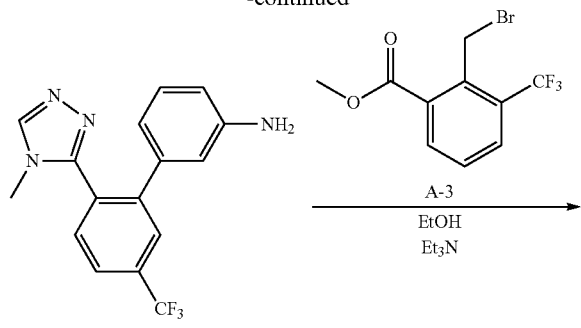

AAG-7

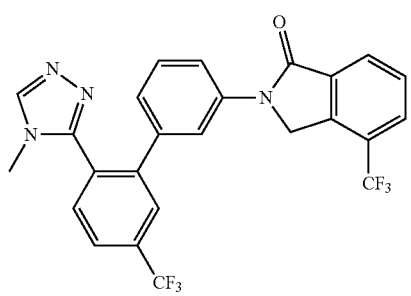

AAG-8

Step 1: Synthesis of Methyl 4'-nitro-5-(trifluoromethyl)-[1,1'-biphenyl]-2-carboxylate (AAG-2)

To a stirred mixture of methyl 2-bromo-4-(trifluoromethyl) benzoate (AAG-1) (2.5 g, 1 Eq, 9.00 mmol), intermediate (AAB-2) (2.3 g, 1.5 Eq, 13.6 mmol) and K$_2$CO$_3$ (3.7 g, 3 Eq, 27.0 mmol) in 1,4-dioxane (50 mL) was added and Pd(dppf)Cl$_2$.DCM (663 mg, 0.1 Eq, 910 µmol) under nitrogen atmosphere. The resulting mixture was stirred for 2 h at 80° C. under nitrogen atmosphere. The mixture was cooled to rt, diluted with water and extracted with EtOAc (3×200 mL). The combined organic layers were washed with brine (2×200 mL), dried (Na$_2$SO$_4$), filtered and concentrated in vacuo. The reaction was concentrated and purified by silica gel column chromatography, eluted with petroleum ether/EtOAc (5/1) to afford the sub-title compound (AAG-2) (2.3 g, 7.08 mmol, 78%) as a Brown yellow solid. m/z 326.1 (M+H)$^+$ (ES+).

Step 2: Synthesis of 3'-Nitro-5-(trifluoromethyl)-[1,1'-biphenyl]-2-carboxylic acid (AAG-3)

To a solution of the product from step 1 above (AAG-2) (500 mg, 1 Eq, 1.54 mmol) in THF (10 mL) and water (2 mL) was added LiOH (184 mg, 5 Eq, 7.70 mmol). The resulting solution was stirred for 4 h at 60° C. The mixture was cooled to rt and concentrated in vacuo. The residue was diluted with water. The pH value of the solution was adjusted to 3 with HCl (aq., 1 M). The solids were collected by filtration to afford the sub-title compound (AAG-3) (380 mg, 1.22 mmol, 79%) as a light yellow solid. m/z 312.0 (M+H)$^+$ (ES+).

Step 3: Synthesis of N-Methyl-2-(3'-nitro-5-(trifluoromethyl)-[1,1'-biphenyl]-2-carbonyl)hydrazine-1-carbothioamide (AAG-4)

To a stirred mixture of the product from step 2 above (AAG-3) (380 mg, 1 Eq, 1.22 mmol) and 4-methyl-3-thiosemicarbazide (D-2) (193 mg, 1.5 Eq, 1.83 mmol) and DIPEA (473 mg, 3 Eq, 3.66 mmol) in DMF (12 mL) was HATU (557 mg, 1.2 Eq, 1.47 mmol) at rt. The residue was purified by reverse flash chromatography with the following conditions: column, C18 silica gel; mobile phase, ACN in water (0.1% FA), 10% to 100% gradient in 20 min; detector, UV 254/220 nm. The product-containing fractions were combined and evaporated to afford the sub-title compound (AAG-4) (306 mg, 769 µmol, 63%) as a yellow solid. m/z 399.1 (M+H)$^+$ (ES+).

Step 4: Synthesis of 4-Methyl-5-(3'-nitro-5-(trifluoromethyl)-[1,1'-biphenyl]-2-yl)-4H-1,2,4-triazole-3-thiol (AAG-5)

To a stirred solution of the product from step 3 above (AAG-4) (559 mg, 1 Eq, 1.40 mmol) in DMF (10 mL) was added NaOH (aq., 1 M) (8 mL) at rt. The resulting mixture was stirred overnight at 50° C. The mixture was cooled to rt, diluted with water and extracted with EtOAc (3×50 mL). The combined organic layers were washed with brine (2×50 mL), dried (Na$_2$SO$_4$), filtered and concentrated in vacuo. The crude product was purified by reverse flash column chromatography with the following conditions: Column, C18; mobile phase, Water (0.1% NH$_4$HCO$_3$) and ACN (10% ACN up to 70% in 20 min); Detector, UV 254/220 nm. This resulted in the sub-title compound (AAG-5) (220 mg, 579 µmol, 41%) as a yellow solid. m/z 381.1 (M+H)$^+$ (ES+).

Step 5: Synthesis of 4-Methyl-3-(3'-nitro-5-(trifluoromethyl)-[1,1'-biphenyl]-2-yl)-4H-1,2,4-triazole (AAG-6)

To a stirred mixture of the product from step 4 above (AAG-5) (220 mg, 1 Eq, 580 µmol) in DCM (3 ml) were added acetic acid (0.93 mL) and hydrogen peroxide (0.72 mL, 30% Wt) at 0° C. The resulting mixture was stirred for 2 h at rt. The residue was basified to pH 8 with NaOH (aq., 1M). The resulting mixture was diluted with water and extracted with DCM (3×20 mL). The combined organic layers were washed with brine (2×20 mL), dried (Na$_2$SO$_4$), filtered and concentrated in vacuo. The reaction purified by reverse flash chromatography with the following conditions: column, C18 silica gel; mobile phase, ACN in water (0.1% NH$_4$HCO$_3$), 10% to 70% gradient in 20 min; detector, UV 254/220 nm. The product-containing fractions were combined and evaporated to afford the sub-title compound (AAG-6) (108 mg, 310 µmol, 54%) as a light yellow oil. m/z 349.1 (M+H)$^+$ (ES+).

Step 6: Synthesis of 2'-(4-Methyl-4H-1,2,4-triazol-3-yl)-5'-(trifluoromethyl)-[1,1'-biphenyl]-3-amine (AAG-7)

To a stirred solution of the product from step 5 above (AAG-6) (108 mg, 1 Eq, 310 µmol) in acetic acid (2 ml) was added Pd/C 39 (1 mg, 10% Wt, 0.03 Eq, 9.4 µmol) at rt under hydrogen atmosphere. The resulting mixture was stirred for 2 h at rt under hydrogen atmosphere. The resulting mixture was filtered; the filter cake was washed with acetic acid (2×2 mL). The residue was purified by reverse flash chromatography with the following conditions: column, C18 silica gel; mobile phase, ACN in water (0.1% NH$_4$HCO$_3$), 10% to 60% gradient in 20 min; detector, UV 254/220 nm. This resulted the sub-title compound (AAG-7) (65 mg, 200 µmol, 14.4%) as an off-white solid. m/z 319.1 (M+H)$^+$ (ES+).

Step 7: Synthesis of 2-(2'-(4-Methyl-4H-1,2,4-triazol-3-yl)-5'-(trifluoromethyl)-[1,1'-biphenyl]-3-yl)-4-(trifluoromethyl) isoindolin-1-one (AAG-8)

To a stirred solution of the product from step 6 above (AAG-7) (65 mg, 1 Eq, 200 μmol) in EtOH (10 ml) were added Et$_3$N (62 mg, 3 Eq, 620 μmol) and intermediate (A-3) (61 mg, 1 Eq, 200 μmol) at rt. The resulting mixture was stirred for 2 h at 80° C. under nitrogen atmosphere. The mixture was cooled to rt and concentrated in vacuo. The residue was purified by reverse flash chromatography with the following conditions: Column: Sun Fire Prep C18 OBD Column, 19*150 mm, 5 μm 10 nm; Mobile Phase A: Water(0.1% FA), Mobile Phase B: ACN; Flow rate: 60 mL/min; Gradient: 40% B to 68% B in 7 min; Wavelength: 254/210 nm; RT: 6.32 to afford the title compound (AAG-8) (20.9 mg, 42 μmol, 13%) as a white solid. m/z 503.1 (M+H)$^+$ (ES+). $^1$H NMR (400 MHz, MeOH-d4) δ 8.44 (s, 1H), 8.11 (d, J=7.6 Hz, 1H), 8.05-7.75 (m, 7H), 7.49 (t, J=8.0 Hz, 1H), 7.15-7.13 (m, 1H), 5.12 (s, 2H), 3.25 (s, 3H).

Example 45: Synthesis of 2-(3-Ethoxy-5-(1-methyl-4-(4-methyl-4H-1,2,4-triazol-3-yl)-1H-pyrazol-5-yl) phenyl)-4-(trifluoromethyl) isoindolin-1-one (AAI-7)

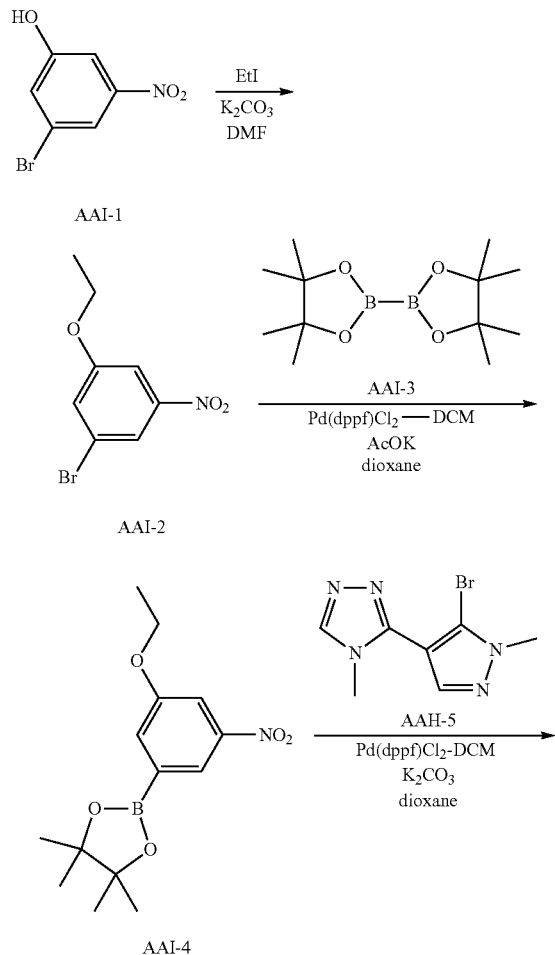

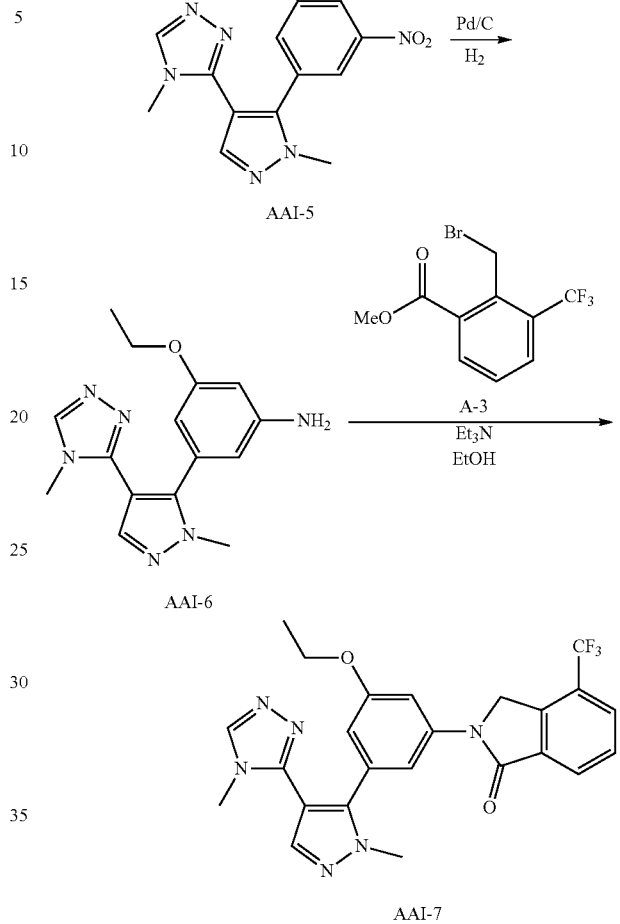

Step 1: Synthesis of 1-Bromo-3-ethoxy-5-nitrobenzene (AAI-2)

To a stirred solution of 3-bromo-5-nitrophenol (AAI-1) (1.09 g, 1 Eq, 5.00 mmol) in DMF (10 mL) was added K$_2$CO$_3$ (1.73 g, 2.50 Eq, 12.5 mmol) and ethyl iodide (1.60 g, 2 Eq, 10.0 mmol) at rt. The resulting mixture was stirred overnight at rt. The resulting mixture was diluted with water and extracted with EtOAc (3×100 mL). The combined organic layers were washed with brine (2×100 mL), dried (Na$_2$SO$_4$), filtered and concentrated in vacuo. This resulted in the sub-title compound (AAI-2) (1.08 g, 4.41 mmol, 88%) as a yellow solid. m/z 246.1/248.1 (M+H)$^+$ (ES+).

Step 2: Synthesis of 2-(3-Ethoxy-5-nitrophenyl)-4,4,5,5-tetramethyl-1,3,2-dioxaborolane (AAI-4)

Into a 250-mL round-bottom flask purged and maintained with an inert atmosphere of nitrogen, was placed the product from step 1 above (AAI-2) (2.46 g, 1 Eq, 10.0 mmol) and bis(pinacolato)diboron (AAI-3) (3.05 g, 1.2 Eq, 12.0 mmol) in dioxane (50 mL), then potassium acetate (2.45 g, 2.5 Eq, 25.0 mmol) and Pd(dppf)Cl$_2$.DCM (409 mg, 0.05 Eq, 501 μmol) were added at rt. The resulting solution was stirred 2h at 100° C. The mixture was cooled to rt, diluted with water and extracted with EtOAc (3×200 mL). The combined organic layers were washed with brine (2×200 mL), dried (Na₂SO₄), filtered and concentrated in vacuo. The residue was applied on a silica gel column chromatography with petroleum ether/EtOAc (50/1). This resulted in the sub-title compound (AAI-4) (2 g, 6.82 mmol, 68%) as a brown solid. m/z 294.1 (M+H)⁺ (ES+).

Step 3: 3-(5-(3-Ethoxy-5-nitrophenyl)-1-methyl-1H-pyrazol-4-yl)-4-methyl-4H-1,2,4-triazole (AAI-5)

Into a 25-mL round-bottom flask purged and maintained with an inert atmosphere of nitrogen, was placed the product from step 2 above (AAI-4) (145 mg, 1.2 Eq, 496 µmol), intermediate (AAH-5) (100 mg, 1 Eq, 413 µmol) and K₂CO₃ (171 mg, 3 Eq, 1.24 mmol) in dioxane (5 mL) and water (1 mL), then Pd(dppf)Cl₂.DCM (30 mg, 0.1 Eq, 41 µmol) was added at rt under nitrogen atmosphere. The resulting solution was stirred for 2 h at 100° C. under nitrogen atmosphere. The mixture was cooled to rt, diluted with water and extracted with EtOAc (3×20 mL). The combined organic layers were washed with brine (2×20 mL), dried (Na₂SO₄), filtered and concentrated in vacuo. The residue was purified by Prep-TLC with DCM/MeOH (10/1). This resulted in the sub-title compound (AAI-5) (96.3 mg, 294 µmol, 71%) as a brown solid. m/z 329.1 (M+H)⁺ (ES+).

Step 4: Synthesis of 3-Ethoxy-5-(1-methyl-4-(4-methyl-4H-1,2,4-triazol-3-yl)-1H-pyrazol-5-yl)aniline (AAI-6)

Into a 25-mL round-bottom flask and maintained with an inert atmosphere of hydrogen, was placed the product from step 3 above (AAI-5) (96 mg, 1 Eq, 293 µmol) in MeOH (5 mL) under nitrogen atmosphere, to the above mixture was added Pd/C 39 (31 mg, 10% Wt, 0.1 Eq, 29.3 µmol) under hydrogen atmosphere. The resulting solution was stirred for 3 h at rt. The resulting mixture was filtered the filter cake was washed with EtOAc (3×5 mL). The filtrate was concentrated in vacuo affording the sub-title compound (AAI-6) (71.7 mg, 240 µmol, 82%) as brown/yellow solid. m/z 299.2 (M+H)⁺ (ES+).

Step 5: Synthesis of 2-(3-Ethoxy-5-(1-methyl-4-(4-methyl-4H-1,2,4-triazol-3-yl)-1H-pyrazol-5-yl) phenyl)-4-(trifluoromethyl) isoindolin-1-one (AAI-7)

Into a 25-mL round-bottom flask, was placed the product from step 4 above (AAI-6) (71.7 mg, 1 Eq, 240 µmol) and intermediate (A-3) (107 mg, 1.5 Eq, 360 µmol) in EtOH (3 mL), then Et₃N (73 mg, 3 Eq, 720 µmol) was added at rt. The resulting solution was stirred 3h at 80° C. The resulting mixture was cooled to rt and concentrated. The crude product was purified by Prep-HPLC with the following conditions: Column: XBridge Prep C18 OBD Column, 20×150 mm, 5 µm; Mobile Phase A: Water (0.1% NH₄HCO₃), Mobile Phase B: ACN; Flow rate: 60 mL/min; Gradient: 30 B to 60 B in 7 min; Detector, UV 210/254 nm; RT: 6.32. This resulted in the title compound (AAI-7) (6.0 mg, 12 µmol, 5.1%) as a white solid. m/z 483.1 (M+H)⁺ (ES+). ¹H NMR (300 MHz, MeOH-d4) δ 8.45 (s, 1H), 8.10 (d, J=7.7 Hz, 1H), 7.98 (d, J=7.8 Hz, 1H), 7.86 (s, 1H), 7.78 (t, J=7.7 Hz, 1H), 7.64 (t, J=2.1 Hz, 1H), 7.49 (s, 1H), 6.82-6.75 (m, 1H), 5.15 (s, 2H), 4.14-3.95 (m, 5H), 3.41 (s, 3H), 1.39 (t, J=7.0 Hz, 3H).

Example 46: Synthesis of 2-(5'-Bromo-2'-(4-methyl-4H-1,2,4-triazol-3-yl)-[1,1'-biphenyl]-3-yl)-4-(trifluoromethyl)isoindolin-1-one (AAJ-9)

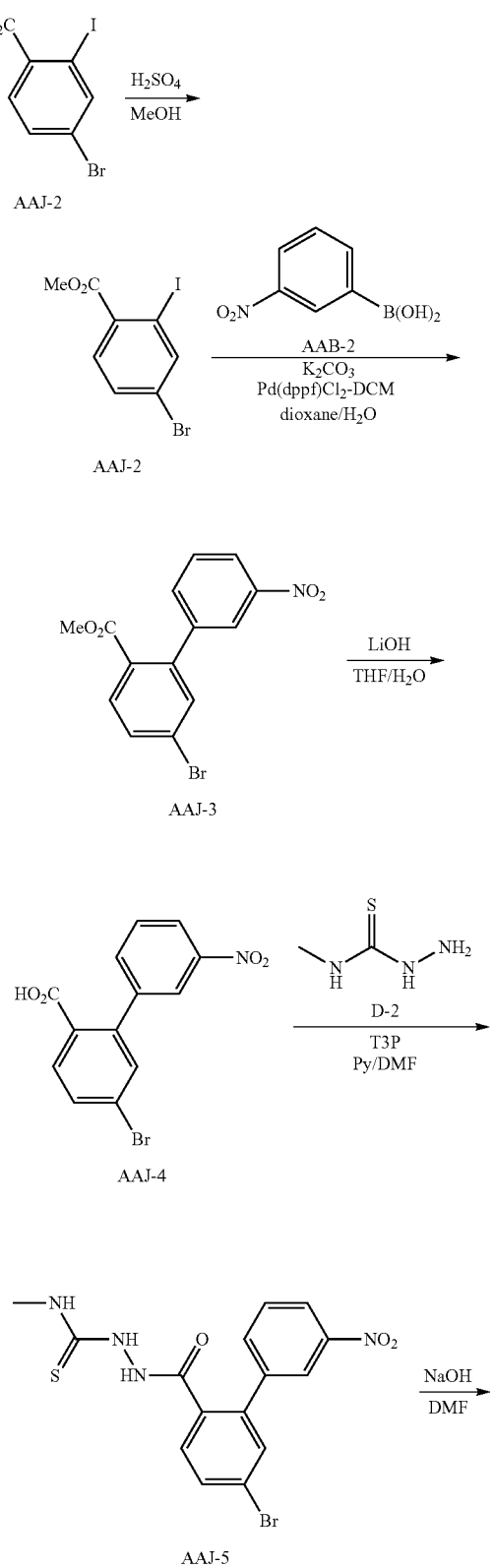

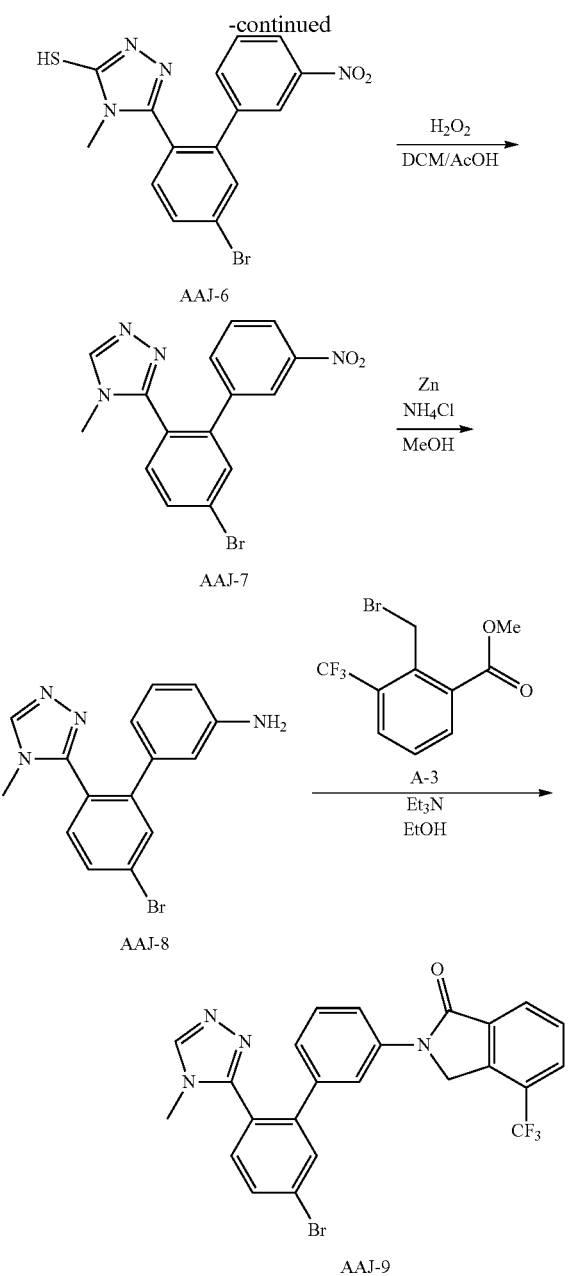

AAJ-6

AAJ-7

AAJ-8

AAJ-9

Step 1: Synthesis of Methyl 4-bromo-2-iodobenzoate (AAJ-2)

To a stirred solution of 4-bromo-2-iodobenzoic acid (AAJ-1) (5.00 g, 1 Eq, 15.3 mmol) in MeOH (30 mL) was added sulfuric acid (5 mL) at rt. The resulting mixture was stirred for 3 h at 80° C. then cooled to rt and concentrated in vacuo. The resulting mixture was diluted with water. The solution was basified to pH 8 with sat. sodium carbonate solution (aq.). The resulting mixture was extracted with DCM (3×300 mL). The combined organic layers were washed with brine (2×300 mL), dried (Na$_2$SO$_4$), filtered and concentrated in vacuo. This resulted in the sub-title compound (AAJ-2) (4.7 g, 13.8 mmol, 90%) as a yellow solid. m/z 340.9/342.9 (M+H)$^+$ (ES+).

Step 2: Synthesis of Methyl 5-bromo-3'-nitro-[1,1'-biphenyl]-2-carboxylate (AAJ-3)

To a solution of the product from step 1 above (AAJ-2) (1.7 g, 1 Eq, 5.00 mmol) and 3-nitrophenylboronic acid (AAB-2) (832 mg, 1 Eq, 4.98 mmol) in 1,4-dioxane (25 mL) and water (5 mL) were added K$_2$CO$_3$ (2.1 g, 3 Eq, 15.0 mmol) and Pd(dppf)Cl$_2$.DCM (365 mg, 0.1 Eq, 499 μmol) under nitrogen atmosphere. After stirring for 3 h at 80° C., the mixture was allowed to cool to rt. The resulting mixture was diluted with water and extracted with EtOAc (3×100 mL). The combined organic layers were washed with brine (2×100 mL), dried (Na$_2$SO$_4$), filtered and concentrated in vacuo. The residue was purified by silica gel column chromatography petroleum ether/EtOAc (3/1) to afford the sub-title compound (AAJ-3) (1.5 g, 4.48 mmol, 90%) as a yellow solid. m/z 336.0/338.0 (M+H)$^+$ (ES+).

Step 3: Synthesis of 5-Bromo-3'-nitro-[1,1'-biphenyl]-2-carboxylic acid (AAJ-4)

To a stirred solution of the product from step 2 above (AAJ-3) (830 mg, 1 Eq, 2.47 mmol) in THF (8 mL) and water (2 mL) were added and LiOH (177 mg, 3 Eq, 7.41 mmol) at rt. The resulting mixture was stirred for 2 h at 60° C. then cooled to rt and concentrated in vacuo. The residue was diluted with water. The pH value of the solution was adjusted to 3 with HCl (aq., 1M). The solids were collected by filtration to obtain the sub-title compound (AAJ-4) (750 mg, 2.34 mmol, 94%) as a brown solid. m/z 322.0/324.0 (M+H)$^+$ (ES+).

Step 4: Synthesis of 2-(5-Bromo-3'-nitro-[1,1'-biphenyl]-2-carbonyl)-N-methylhydrazine-1-carbothioamide (AAJ-5)

To a stirred solution of the product from step 3 above (AAJ-4) (1.1 g, 1 Eq, 3.42 mmol) and pyridine (1.6 g, 6 Eq, 20.5 mmol) in DMF (5 mL) was added T3P (4.4 g, 4 Eq, 13.7 mmol) and 4-methyl-3-thiosemicarbazide (D-2) (1.1 g, 3 Eq, 10.2 mmol) at 0° C. The resulting mixture was stirred overnight at rt. The crude product was purified by reverse flash column chromatography with the following conditions: Column, C18; mobile phase, Water (0.1% NH$_4$HCO$_3$) and ACN (30% ACN up to 70% in 10 min); Detector, UV 254/220 nm. The product-containing fractions were combined and concentrated in vacuo. This resulted in the sub-title compound (AAJ-5) (1 g, 2.44 mmol, 72%) as a yellow solid. m/z 409.0/411.0 (M+H)$^+$ (ES+).

Step 5: Synthesis of 5-(5-Bromo-3'-nitro-[1,1'-biphenyl]-2-yl)-4-methyl-4H-1,2,4-triazole-3-thiol (AAJ-6)

To a stirred solution of the product from step 4 above (AAJ-5) (1.0 g, 1 Eq, 2.44 mmol) in DMF (8 mL) were added NaOH (aq. 1M) (15 mL) at rt. The resulting mixture was stirred for overnight at 50° C. The mixture was cooled to rt. The crude product was purified by reverse flash column chromatography with the following conditions: Column, C18; mobile phase, Water (0.1% NH$_4$HCO$_3$) and ACN (30% ACN up to 50% in 7 min); Detector, UV 254/220 nm. The product-containing fractions were combined and concentrated in vacuo. This resulted in the sub-title compound (AAJ-6) (600 mg, 1.54 mmol, 63%) as a white solid. m/z 390.0392.0 (M+H)$^+$ (ES+).

Step 6: 3-(5-Bromo-3'-nitro-[1,1'-biphenyl]-2-yl)-4-methyl-4H-1,2,4-triazole (AAJ-7)

To a stirred solution of the product from step 5 above (AAJ-6) (140 mg, 1 Eq, 358 μmol) in DCM (5 mL) were added acetic acid (43 mg, 2 Eq, 716 μmol) and hydrogen peroxide solution (61 mg, 30% Wt, 5 Eq, 1.79 mmol) at 0° C. The resulting mixture was stirred for additional 2 h at rt. The resulting mixture was diluted with water. The solution was basified to pH 8 with sat. NaHCO$_3$ solution. The resulting mixture was extracted with DCM (3×80 mL). The combined organic layers were washed with brine (2×80 mL), dried (Na$_2$SO$_4$), filtered and concentrated in vacuo. This resulted in the sub-title compound (AAJ-7) (120 mg, 335 μmol, 93%) as a yellow solid. m/z 359.0/361.0 (M+H)$^+$ (ES+).

Step 7: Synthesis of 5'-Bromo-2'-(4-methyl-4H-1,2,4-triazol-3-yl)-[1,1'-biphenyl]-3-amine (AAJ-8)

To a stirred solution of the product from step 6 above (AAJ-7) (130 mg, 1 Eq, 362 μmol) and NH$_4$Cl (97 mg, 5 Eq, 1.81 mmol) in MeOH (5 mL) was added zinc powder (95 mg, 4 Eq, 1.45 mmol) at rt. The resulting mixture was stirred for 2 h at 70° C. The resulting mixture was cooled to rt and filtered. The filtrate was concentrated in vacuo affording the sub-title compound (AAJ-8) (100 mg, 305 μmol, 84%) as a yellow solid. m/z 329.2/331.2 (M+H)$^+$ (ES+).

Step 8: 2-(5'-Bromo-2'-(4-methyl-4H-1,2,4-triazol-3-yl)-[1,1'-biphenyl]-3-yl)-4-(trifluoromethyl) isoindolin-1-one (AAJ-9)

To a stirred solution of the product from step 7 above (AAJ-8) (50 mg, 1 Eq, 152 μmol) and intermediate (A-3) (50 mg, 1.1 Eq, 167 μmol) in EtOH (5 mL) was added Et$_3$N (46 mg, 3 Eq, 450 μmol) at rt. The resulting mixture was stirred for 3 h at 80° C. then cooled to rt. The crude product was purified by reverse flash column chromatography with the following conditions: Column, C18; mobile phase, Water (0.1% FA) and ACN (30% ACN up to 70% in 10 min); Detector, UV 254/220 nm. The product-containing fractions were combined and concentrated in vacuo. The crude product was purified by Prep-HPLC with the following conditions: Column: SunFire Prep C18 OBD Column, 19×150 mm 5 um; Mobile Phase A: Water (0.1% FA), Mobile Phase B: ACN; Flow rate:60 mL/min; Gradient:40 B to 60 B in 10 min; Detector, UV 254/210 nm; RT: 10.38. The product-containing fractions were combined and evaporated partially in vacuo and lyophilized overnight to afford the title compound (AAJ-9) (20.8 mg, 41 μmol, 27%) as a white solid. m/z 513.2 (M+H)$^+$ (ES+). $^1$H NMR (300 MHz, MeOH-d4) δ 8.39 (s, 1H), 8.10 (d, J=7.6 Hz, 1H), 8.05-7.82 (m, 3H), 7.86-7.75 (m, 3H), 7.55 (d, J=8.21 Hz, 1H), 7.45 (t, J=7.95 Hz, 1H), 7.10-7.07 (m, 1H), 5.10 (s, 2H), 3.21 (s, 3H).

Example 47: Synthesis of 2-(2'-(4-Methyl-4H-1,2,4-triazol-3-yl)-[1,1'-biphenyl]-3-yl)-4-(trifluoromethyl) isoindolin-1-one (AAK-2)

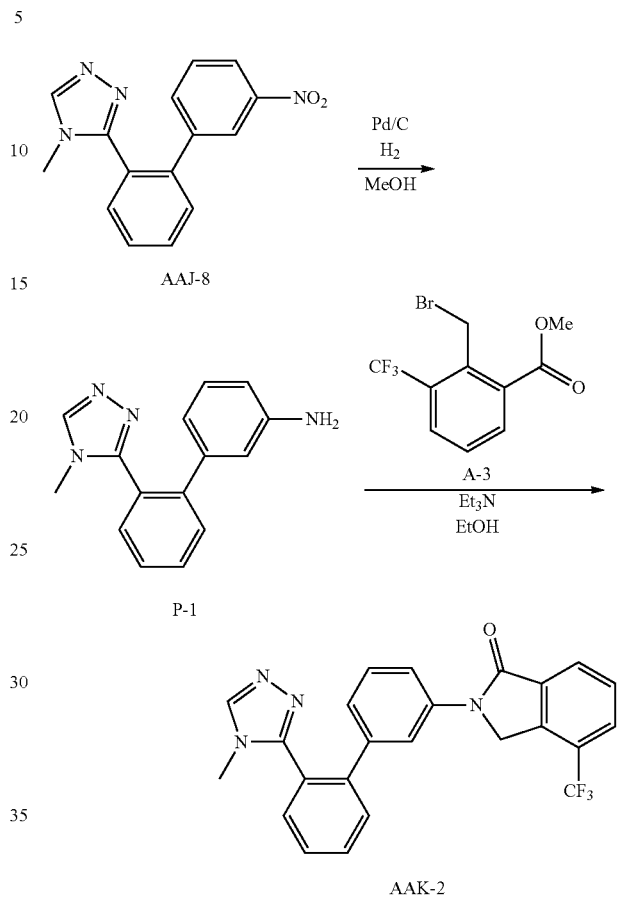

Step 1: Synthesis of 2'-(4-methyl-4H-1,2,4-triazol-3-yl)-[1,1'-biphenyl]-3-amine (P-1)

To a solution of intermediate (AAJ-8) (200 mg, 1 Eq, 559 μmol) in MeOH (10 mL) was added Pd/C 39 (30 mg, 10% Wt, 0.5 Eq, 283 μmol) under hydrogen atmosphere. The resulting mixture was stirred at rt for 3 h under hydrogen atmosphere. After the reaction was completed, the reaction mixture was filtered. The filtrate was evaporated in vacuo affording the sub-title compound (P-1) (135 mg, 540 μmol, 96%) as a yellow solid. m/z 251.1 (M+H)$^+$ (ES+).

Step 2: 2-(2'-(4-Methyl-4H-1,2,4-triazol-3-yl)-[1,1'-biphenyl]-3-yl)-4-(trifluoromethyl) isoindolin-1-one (AAK-2)

To a stirred solution of the product from step 1 above (P-1) (80 mg, 319 μmol, 1 Eq) and intermediate (A-3) (104 mg, 1.1 Eq, 351 μmol) in EtOH (5 mL) was added Et$_3$N (97.0 mg, 3 Eq, 962 μmol) at rt. The resulting mixture was stirred for 3 h at 80° C. and the resulting mixture cooled to rt. The crude product was purified by reverse flash column chromatography with the following conditions: Column, C18; mobile phase, Water (0.1% NH$_4$HCO$_3$) and ACN (30% ACN up to 70% in 10 min); Detector, UV 254/220 nm. The product-containing fractions were combined and concentrated in vacuo. The crude product was purified by Prep- HPLC with the following conditions: Column: YMC-Triart Diol Hilic, 20×150 mm, 5 μm; Mobile Phase A: Water (0.1% NH₄HCO₃+0.1% NH₃·H₂O), Mobile Phase B: ACN; Flow rate: 60 mL/min; Gradient: 34 B to 64 B in 7 min; Detector, UV 254/210 nm; RT: 6.32. The product-containing fractions were combined and evaporated partially in vacuo and lyophilized overnight to afford the sub-title compound (AAK-2) (16.9 mg, 39 μmol, 12%) as a white solid. m/z 435.0 (M+H)⁺ (ES+). ¹H NMR (400 MHz, DMSO-d6) δ 8.40 (s, 1H), 8.16-7.97 (m, 3H), 7.87-7.77 (m, 1H), 7.73-7.62 (m, 3H), 7.62-7.52 (m, 2H), 7.38 (t, J=8.0 Hz, 1H), 6.97-6.81 (m, 1H), 5.12 (s, 2H), 3.08 (s, 3H).

Example 48: Synthesis of 2-[3-[1-Methyl-4-(4-methyl-1,2,4-triazol-3-yl) pyrazol-3-yl]phenyl]-4-(trifluoromethyl)-3H-isoindol-1-one (AAL-8)

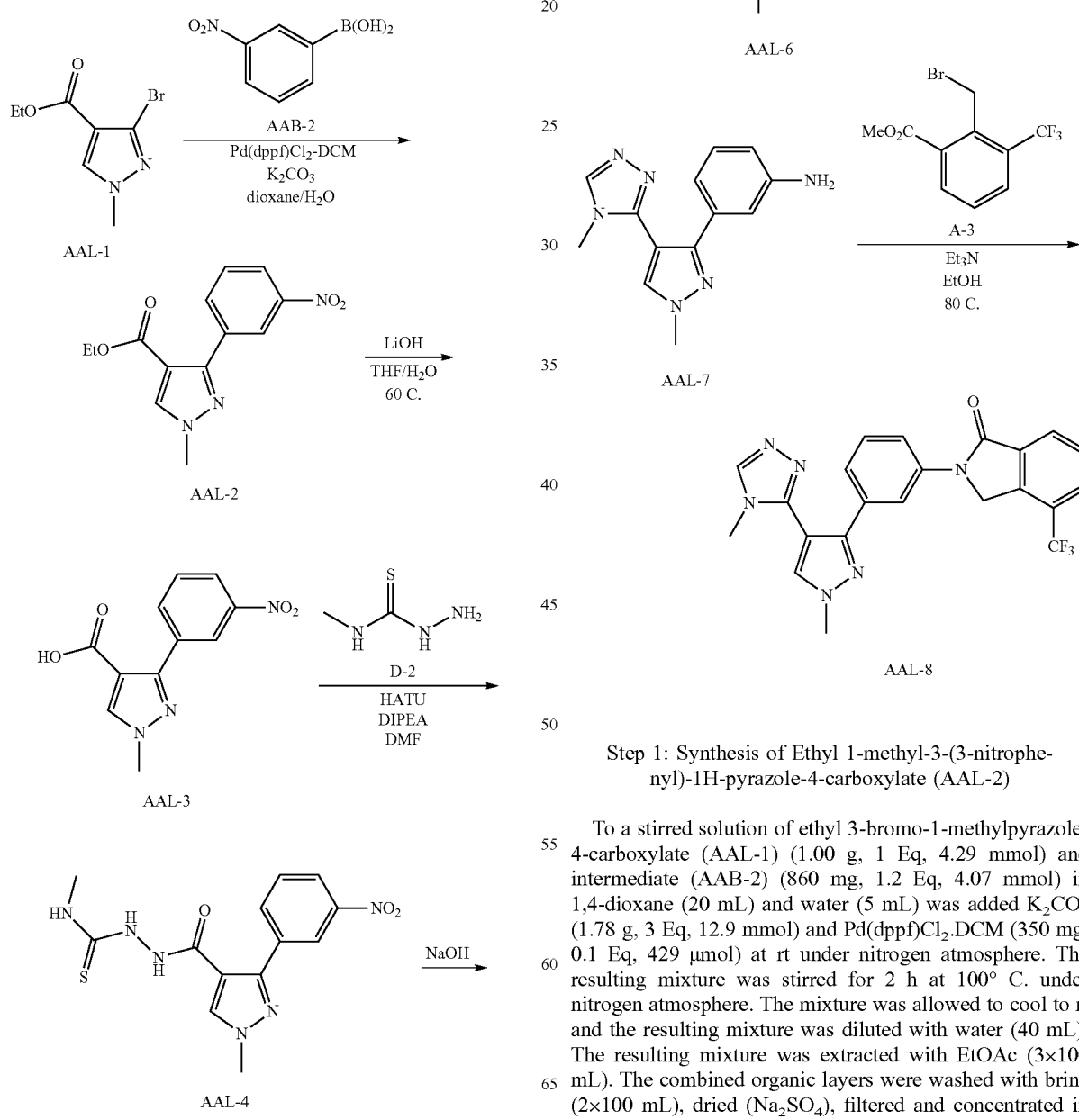

Step 1: Synthesis of Ethyl 1-methyl-3-(3-nitrophenyl)-1H-pyrazole-4-carboxylate (AAL-2)

To a stirred solution of ethyl 3-bromo-1-methylpyrazole-4-carboxylate (AAL-1) (1.00 g, 1 Eq, 4.29 mmol) and intermediate (AAB-2) (860 mg, 1.2 Eq, 4.07 mmol) in 1,4-dioxane (20 mL) and water (5 mL) was added K₂CO₃ (1.78 g, 3 Eq, 12.9 mmol) and Pd(dppf)Cl₂·DCM (350 mg, 0.1 Eq, 429 μmol) at rt under nitrogen atmosphere. The resulting mixture was stirred for 2 h at 100° C. under nitrogen atmosphere. The mixture was allowed to cool to rt and the resulting mixture was diluted with water (40 mL). The resulting mixture was extracted with EtOAc (3×100 mL). The combined organic layers were washed with brine (2×100 mL), dried (Na₂SO₄), filtered and concentrated in vacuo. The residue was purified by silica gel column chromatography, eluted with hexane/EtOAc (5/1) to afford the sub-title compound (AAL-2) (1 g, 3.63 mmol, 85%) as a white solid. m/z 276.1 (M+H)$^+$ (ES+).

Step 2: Synthesis of 1-Methyl-3-(3-nitrophenyl)-1H-pyrazole-4-carboxylic acid (AAL-3)

To a stirred solution of the product from step 1 above (AAL-2) (1.00 g, 1 Eq, 3.63 mmol) in THF (25 mL) and water (5 mL) was added LiOH (261 mg, 3 Eq, 10.9 mmol) at rt. The resulting mixture was stirred for overnight at 60° C. The mixture was allowed to cool to rt and the resulting mixture was diluted with water (50 mL). The mixture was acidified to pH 3 with HCl (aq., 1 M). The precipitated solids were collected by filtration and washed with water (3×5 mL). This resulted in the sub-title compound (AAL-3) (800 mg, 3.24 mmol, 89%) as a white solid. m/z 248.1 (M+H)$^+$ (ES+).

Step 3: Synthesis of N-Methyl-2-(1-methyl-3-(3-nitrophenyl)-1H-pyrazole-4-carbonyl)hydrazine-1-carbothioamide (AAL-4)

To a stirred solution of the product from step 1 above (AAL-3) (500 mg, 1 Eq, 2.02 mmol) and 4-methyl-3-thiosemicarbazide (D-2) (277 mg, 1.3 Eq, 2.63 mmol) in DMF (25 mL) was added DIPEA (784 mg, 3 Eq, 6.07 mmol) and HATU (923 mg, 1.2 Eq, 2.43 mmol) at rt. The resulting mixture was stirred for 3h at rt. The resulting mixture was used in the next step directly without further purification. m/z 335.1 (M+H)$^+$ (ES+).

Step 4: Synthesis of 4-Methyl-5-(1-methyl-3-(3-nitrophenyl)-1H-pyrazol-4-yl)-4H-1,2,4-triazole-3-thiol (AAL-5)

To the above product from step 3 above (AAL-4) was added NaOH (aq., 1M) (30 mL) at rt and the resulting mixture stirred for 2 days. The crude product was purified by reverse flash column chromatography with the following conditions: Column, C18; mobile phase, Water (0.1% NH$_4$HCO$_3$) and ACN (10% ACN up to 50% in 10 min); Detector, UV 254/220 nm. The product-containing fractions were combined and concentrated in vacuo. This resulted in the sub-title compound (AAL-5) (500 mg, 1.58 mmol, 88%) as a yellow oil. m/z 317.0 (M+H)$^+$ (ES+).

Step 5: Synthesis of 4-Methyl-3-(1-methyl-3-(3-nitrophenyl)-1H-pyrazol-4-yl)-4H-1,2,4-triazole (AAL-6)

To a stirred solution of the product from step 4 above (AAL-5) (560 mg, 1 Eq, 1.77 mmol) in DCM (20 mL) were added acetic acid (2.78 mL, 27.4 Eq, 48.5 mmol) and hydrogen peroxide (1.85 mL, 44.9 Eq, 79.4 mmol) at 0° C. and the resulting mixture stirred for 2 h at 0° C. The mixture was basified to pH 8 with sat. NaHCO$_3$ (aq.) solution. The resulting mixture was extracted with EtOAc (3×80 mL). The combined organic layers were washed with brine (2×80 mL), dried (Na$_2$SO$_4$), filtered and concentrated in vacuo. This resulted in the sub-title compound (AAL-6) (500 mg, 1.76 mmol, 99%) as a yellow oil. m/z 285.1 (M+H)$^+$ (ES+).

Step 6: Synthesis of 3-(1-Methyl-4-(4-methyl-4H-1,2,4-triazol-3-yl)-1H-pyrazol-3-yl) aniline (AAL-7)

To a solution of the product from step 5 above (AAL-6) (400 mg, 1 Eq, 1.41 mmol) in MeOH (20 mL) was added Pd/C 39 (30 mg, 10% Wt, 0.2 Eq, 281 µmol) under nitrogen atmosphere in a 50 mL round-bottom flask. The mixture was hydrogenated at rt overnight under hydrogen atmosphere using a hydrogen balloon, then filtered through a Celite pad and concentrated in vacuo. The residue was purified by Prep-TLC with DCM/MeOH (12/1) to afford the sub-title compound (AAL-7) (300 mg, 1.18 mmol, 84%) as an off-white solid. m/z 255.1 (M+H)$^+$ (ES+).

Step 7: Synthesis of 2-(3-(1-Methyl-4-(4-methyl-4H-1,2,4-triazol-3-yl)-1H-pyrazol-3-yl)phenyl)-4-(trifluoromethyl)isoindolin-1-one (AAL-8)

To a stirred solution of the product from step 6 above (AAL-7) (100 mg, 1 Eq, 393 µmol) and intermediate (A-3) (117 mg, 1 Eq, 338 µmol) in EtOH (4 mL) was added Et$_3$N (119 mg, 3 Eq, 1.18 mmol) at rt. The resulting mixture was stirred for 4 h at 80° C. The mixture was allowed to cool to rt and the crude product was purified by reverse flash column chromatography with the following conditions: Column, C18; mobile phase, Water (0.1% NH$_4$HCO$_3$) and ACN (10% ACN up to 50% in 10 min); Detector, UV 254/220 nm. The product-containing fractions were combined and concentrated in vacuo. The crude product was purified by Prep-HPLC with the following conditions (Column: XBridge Shield RP18 OBD Column, 30*150 mm, 5 µm; Mobile Phase A: Water (0.1% NH$_4$HCO$_3$+0.1% NH$_3$·H$_2$O), Mobile Phase B: ACN; Flow rate: 60 mL/min; Gradient: 22% B to 38% B in 10 min; Detector, UV 254 nm; RT: 9.72) to afford the sub-title compound (AAL-8) (31.4 mg, 72 µmol, 18%) as a white solid. m/z 439.0 (M+H)$^+$ (ES+). $^1$H NMR (300 MHz, CD3OD) δ 8.69 (s, 1H), 8.13-8.05 (m, 2H), 8.00-7.93 (m, 2H), 7.88-7.84 (m, 1H), 7.77 (t, J=7.7 Hz, 1H), 7.48 (t, J=8.0 Hz, 1H), 7.38-7.33 (m, 1H), 5.12 (s, 2H), 4.08 (s, 3H), 3.46 (s, 3H).

Example 49: Synthesis of 2-(4-(1-Methyl-4-(4-methyl-4H-1,2,4-triazol-3-yl)-1H-pyrazol-5-yl)pyridin-2-yl)-4-(trifluoromethyl)isoindolin-1-one (AAM-3)

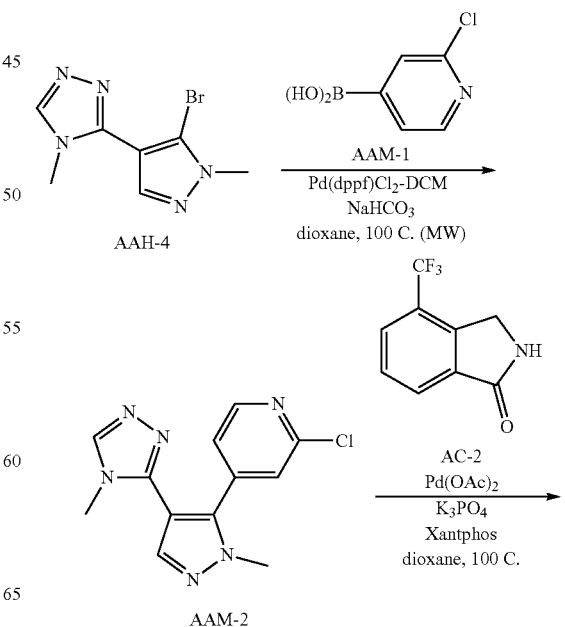

-continued

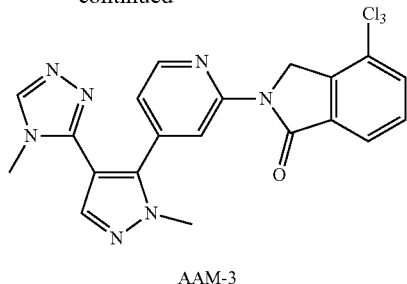

AAM-3

Step 1: Synthesis of 2-Chloro-4-(1-methyl-4-(4-methyl-4H-1,2,4-triazol-3-yl)-1H-pyrazol-5-yl)pyridine (AAM-2)

To a stirred solution of intermediate (AAH-4) (200 mg, 1 Eq, 826 μmol), 2-chloropyridin-4-ylboronic acid (AAM-1) (65 mg, 0.5 Eq, 413 μmol) and NaHCO$_3$ (aq., 1M) (2 mL) in 1,4-dioxane (2 mL) and was added Pd(dppf)Cl$_2$.DCM (68 mg, 0.1 Eq, 83 μmol) at rt under nitrogen atmosphere. The final reaction mixture was irradiated with microwave radiation for 30 min at 100° C. under nitrogen atmosphere. The mixture was allowed to cool to rt and the resulting mixture diluted with water (30 mL). The resulting mixture was extracted with EtOAc (3×30 mL) and the combined organic layers were washed with brine (2×30 mL), dried (Na$_2$SO$_4$) and concentrated in vacuo. The residue was purified by Prep-TLC with DCM/MeOH (30/1) to afford the sub-title compound (AAM-2) (34 mg, 124 μmol, 12%) as a yellow solid. m/z 275.1/277.1 (M+H)$^+$ (ES+).

Step 2: 2-(4-(1-Methyl-4-(4-methyl-4H-1,2,4-triazol-3-yl)-1H-pyrazol-5-yl)pyridin-2-yl)-4-(trifluoromethyl)isoindolin-1-one (AAM-3)

To a stirred solution of the product from step 1 above (AAM-2) (34 mg, 1 Eq, 124 μmol), intermediate (AC-2) (50 mg, 2 Eq, 248 μmol) and potassium phosphate (53 mg, 2 Eq, 248 μmol) in 1,4-dioxane (4 mL) was added Pd(OAc)$_2$ (3 mg, 0.1 Eq, 12 μmol) and Xantphos (14 mg, 0.2 Eq, 25 μmol) at rt under nitrogen atmosphere. The resulting mixture was stirred for 12h at 100° C. under nitrogen atmosphere. The mixture was allowed to cool to rt and the resulting mixture was diluted with water (30 mL). The resulting mixture was extracted with EtOAc (3×30 mL). The combined organic layers were washed with brine (30 mL), dried (Na$_2$SO$_4$) and concentrated in vacuo. The residue was purified by Prep-TLC with DCM/MeOH (15/1) and the crude product was purified by Prep-HPLC with the following conditions (Column: YMC-Triart Diol Hilic, 20*150 mm 5 um; Mobile Phase A: Water (0.1% NH$_4$HCO$_3$+0.1% NH$_3$·H$_2$O), Mobile Phase B: ACN; Flow rate:60 mL/min; Gradient:23 B to 43 B in 7 min; Detector, UV 210/254 nm; RT: 8.97) to afford the sub-title compound (AAM-3) (6.8 mg, 15 μmol, 12%) as a white solid. m/z 440.0 (M+H)$^+$ (ES+). $^1$H NMR (400 MHz, CD3OD) δ 8.57-8.51 (m, 3H), 8.13 (d, J=7.7 Hz, 1H), 8.02 (d, J=7.7 Hz, 1H), 7.94 (s, 1H), 7.79 (t, J=7.7 Hz, 1H), 7.24 (dd, J=5.1, 1.6 Hz, 1H), 5.34 (s, 2H), 4.06 (s, 3H), 3.60 (s, 3H).

Example 50: Synthesis of 2-(6-Chloro-4-(1-methyl-4-(4-methyl-4H-1,2,4-triazol-3-yl)-1H-pyrazol-5-yl)pyridin-2-yl)-4-(trifluoromethyl)isoindolin-1-one (AAN-7)

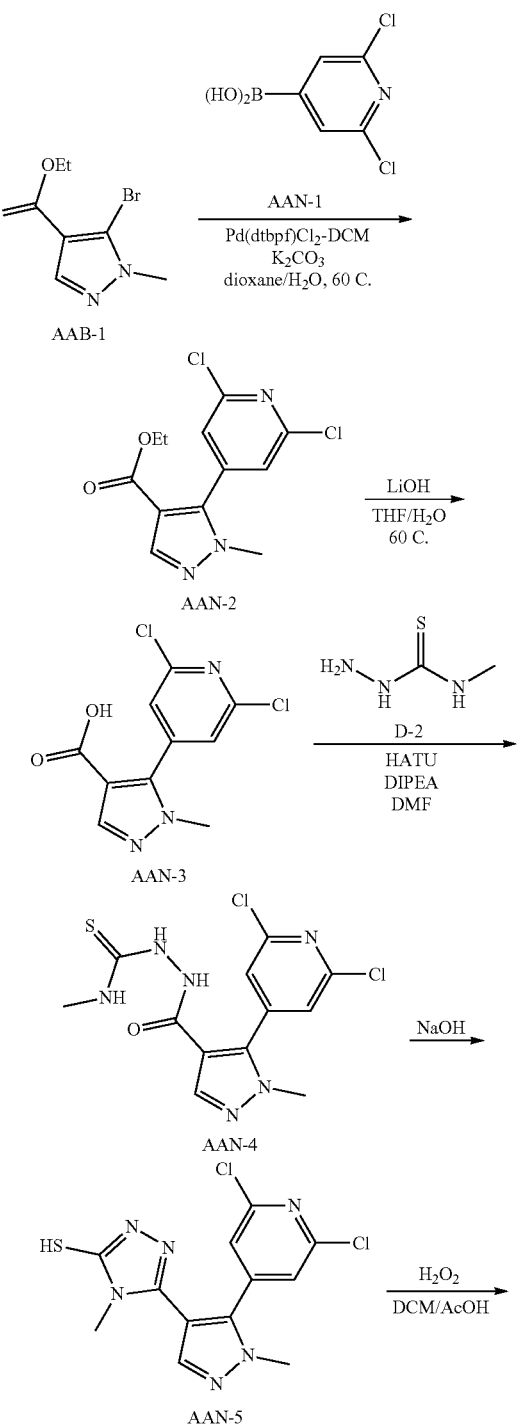

-continued

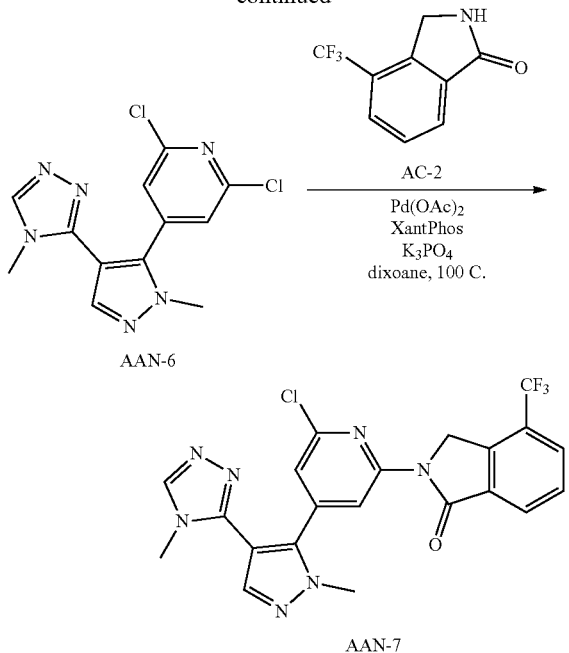

Step 1: Synthesis of Ethyl 5-(2,6-dichloropyridin-4-yl)-1-methyl-1H-pyrazole-4-carboxylate (AAN-2)

To a stirred solution of intermediate (AAB-1) (1.00 g, 1 Eq, 4.29 mmol) and 2,6-dichloropyridin-4-ylboronic acid (AAN-1) (823 mg, 1 Eq, 4.29 mmol) and $K_2CO_3$ (1.77 g, 3 Eq, 12.9 mmol) in 1,4-dioxane (37.5 mL) and water (7.5 mL) was added Pd(dtbpf)$Cl_2$.DCM (280 mg, 0.1 Eq, 420 μmol) at rt under nitrogen atmosphere. The resulting mixture was stirred overnight at 60° C. under nitrogen atmosphere. The mixture was cooled to rt and concentrated in vacuo. The residue was purified by silica gel column chromatography, eluted with petroleum ether/EtOAc (5/1) to afford the sub-title compound (AAN-2) (550 mg, 18.3 mmol, 55%) as a yellow solid. m/z 300.0/302.0 (M+H)$^+$ (ES+).

Step 2: Synthesis of 5-(2,6-Dichloropyridin-4-yl)-1-methyl-1H-pyrazole-4-carboxylic acid (AAN-3)

To a solution of the product from step 1 above (AAN-2) (550 mg, 1 Eq, 1.83 mmol) in THF (20 mL) and water (5 mL) was added LiOH (439 mg, 10 Eq, 18.3 mmol) at rt. The resulting mixture was stirred overnight at 60° C. then cooled to rt. The mixture was acidified to pH 3 with HCl (aq., 1 M). The resulting mixture was diluted with water and extracted with EtOAc (3×50 mL). The combined organic layers were washed with brine (2×50 mL), dried ($Na_2SO_4$), filtered and concentrated in vacuo. This resulted in the sub-title compound (AAN-3) (850 mg, 3.12 mmol, crude) as a yellow solid. m/z 272.1/274.1 (M+H)$^+$ (ES+).

Step 3: Synthesis of 2-(5-(2,6-Dichloropyridin-4-yl)-1-methyl-1H-pyrazole-4-carbonyl)-N-methylhydrazine-1-carbothioamide (AAN-4)

To a stirred solution of the product from step 2 above (AAN-3) (850 mg, 1 Eq, 3.12 mmol) and DIPEA (1.21 g, 3 Eq, 9.37 mmol) in DMF (10 mL) were added 4-methyl-3-thiosemicarbazide (D-2) (329 mg, 1 Eq, 3.12 mmol) and HATU (1.19 g, 1 Eq, 3.12 mmol) at 0° C. The resulting mixture was stirred for 2 h at rt and the crude product used directly in next step without any further purification. m/z 359.2/361.2 (M+H)$^+$ (ES+).

Step 4: Synthesis of 5-(5-(2,6-Dichloropyridin-4-yl)-1-methyl-1H-pyrazol-4-yl)-4-methyl-4H-1,2,4-triazole-3-thiol (AAN-5)

To the reaction mixture from step 3 above (AAN-4) was added NaOH (aq., 1M) (12.5 mL) at 0° C. The resulting mixture was stirred overnight at rt. The crude product was purified by reverse flash column chromatography with the following conditions: Column, C18; mobile phase, Water (0.1% $NH_4HCO_3$) and ACN (36% ACN up to 48% in 10 min); Detector, UV 254/220 nm. The product-containing fractions were combined and concentrated in vacuo. This resulted in the sub-title compound (AAN-5) (620 mg, 18.1 mmol, 92%) as a white solid. m/z 341.2/343.2 (M+H)$^+$ (ES+).

Step 5: Synthesis of 2,6-Dichloro-4-(1-methyl-4-(4-methyl-4H-1,2,4-triazol-3-yl)-1H-pyrazol-5-yl) pyridine (AAN-6)

To a solution of the product from step 4 above (AAN-5) (620 mg, 1 Eq, 1.81 mmol) in DCM (10 mL) was added acetic acid (218.24 mg, 2 Eq, 3.63 mmol) and hydrogen peroxide (309 mg, 30% Wt, 5 Eq, 9.08 mmol) at 0° C. The resulting mixture was stirred for 1 h at rt then the mixture basified to pH 8 with sat. $NaHCO_3$ (aq., 1M) solution. The resulting mixture was diluted with water and extracted with DCM (3×80 mL). The combined organic layers were washed with brine (2×80 mL), dried ($Na_2SO_4$), filtered and concentrated in vacuo. This resulted in the sub-title compound (AAN-6) (360 mg, 1.17 mmol, 58%) as a white solid. m/z 309.1/311.1 (M+H)$^+$ (ES+).

Step 6: Synthesis of 2-(6-Chloro-4-(1-methyl-4-(4-methyl-4H-1,2,4-triazol-3-yl)-1H-pyrazol-5-yl)pyridin-2-yl)-4-(trifluoromethyl)isoindolin-1-one (AAN-7)

To a stirred solution of the product from step 5 above (AAN-6) (31 mg, 1 Eq, 100 μmol) and intermediate (AC-2) (20 mg, 1 Eq, 100 μmol) and potassium phosphate (42 mg, 2 Eq, 200 μmol) in 1,4-dioxane (5 mL) were added Pd(OAc)$_2$ (2.24 mg, 0.1 Eq, 10 μmol) and XantPhos (12 mg, 0.2 Eq, 20 μmol) at rt under nitrogen atmosphere. The resulting mixture was stirred for 3 h at 100° C. under nitrogen atmosphere then cooled to rt and concentrated in vacuo. The crude product was purified by Prep-HPLC with the following conditions: Column: SunFire Prep C18 OBD Column, 19*150 mm, 5 μm 10 nm; Mobile Phase A: Water(0.1% FA), Mobile Phase B: ACN; Flow rate: 60 mL/min; Gradient: 30% B to 60% B in 7 min, 60% B; Wavelength: 254/210 nm; RT: 6.32. This resulted in the title compound (AAN-7) (8.3 mg, 18 mmol, 27%) as a white solid. m/z 474.0 (M+H)$^+$ (ES+). $^1$H NMR (400 MHz, MeOH-d4) δ 8.53 (s, 1H), 8.49 (d, J=1.2 Hz, 1H), 8.12 (d, J=7.7 Hz, 1H), 8.03 (d, J=7.7 Hz, 1H), 7.96 (s, 1H), 7.79 (t, J=7.7 Hz, 1H), 7.35 (d, J=1.2 Hz, 1H), 5.29 (s, 2H), 4.06 (s, 3H), 3.68 (s, 3H).

Example 51: Synthesis of 2-(6-Hydroxy-4-(1-methyl-4-(4-methyl-4H-1,2,4-triazol-3-yl)-1H-pyrazol-5-yl)pyridin-2-yl)-4-(trifluoromethyl)isoindolin-1-one (AAO-1)

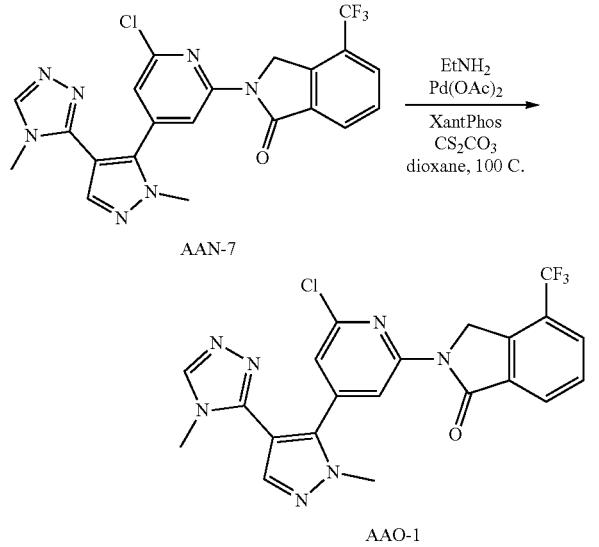

To a stirred mixture of the intermediate (AAN-7) (75 mg, 1 Eq, 150 μmol) and ethylamine (36 mg, 5 Eq, 10 μmol) and Cs$_2$CO$_3$ (206 mg, 4 Eq, 630 μmol) in 1,4-dioxane were added Pd(OAc)$_2$ (3.6 mg, 0.1 Eq, 20 μmol) and XantPhos (18 mg, 0.2 Eq, 30 mmol) at rt under nitrogen atmosphere. The resulting mixture was stirred overnight at 100° C. under nitrogen atmosphere then cooled to rt and concentrated in vacuo. The crude product was purified by Prep-HPLC with the following conditions: Column: SunFire Prep C18 OBD Column, 19×150 mm, 5 um; Mobile Phase A: Water (0.1% FA), Mobile Phase B: ACN; Flow rate: 60 mL/min; Gradient: 30 B to 60 B in 7 min; Detector, UV 254/210 nm; RT: 6.08. This resulted in the title compound (AAO-1) (9.1 mg, 20 μmol, 12.49%) as a white solid. m/z 456.0 (M+H)$^+$ (ES+). $^1$H NMR (400 MHz, MeOH-d4) δ 8.51 (s, 1H), 8.07 (d, J=7.7 Hz, 1H), 7.99 (d, J=7.7 Hz, 1H), 7.78-7.75 (s, 2H), 7.75 (t, J=7.7 Hz, 1H), 6.46 (d, J=1.2 Hz, 1H), 5.24 (s, 2H), 4.05 (s, 3H), 3.58 (s, 3H).

Example 52: Synthesis of 2-Cyclopropyl-N-(2'-(4-methyl-4H-1,2,4-triazol-3-yl)-[1,1'-biphenyl]-3-yl)-6-oxo-1,6-dihydropyrimidine-4-carboxamide (AAP-1)

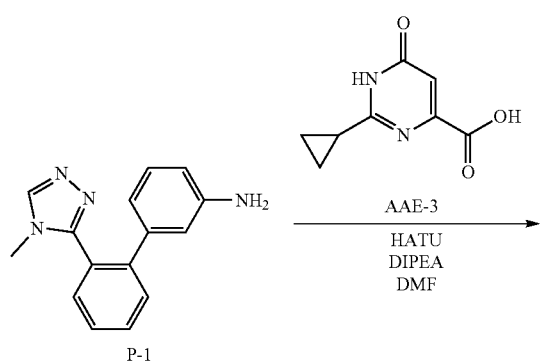

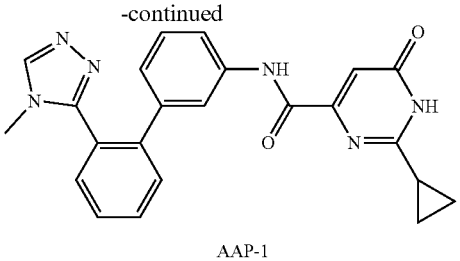

Into an 8 mL sealed tube were added intermediate (P-1) (50 mg, 1 Eq, 200 μmol), intermediate (AAE-3) (43 mg, 1.2 Eq, 240 μmol) and DIPEA (77 mg, 3 Eq, 599 μmol) in DMF (3 mL) was added HATU (114 mg, 1.5 Eq, 300 μmol) at 0° C. The resulting mixture was stirred overnight at rt. The crude product was purified by Prep-HPLC with the following conditions (Column: SunFire Prep C18 OBD Column, 19*150 mm, 5 μm 10 nm; Mobile Phase A: Water(0.1% FA), Mobile Phase B: ACN; Flow rate: 60 mL/min; Gradient: 15% B to 35% B in 10 min, 35% B; Wavelength: 254/210 nm; RT: 9.77) to afford the title compound (AAP-1) (22 mg, 70 μmol, 25%) as a white solid. m/z 413.3 (M+H)$^+$ (ES+). $^1$H NMR (400 MHz, MeOH-d4) δ 8.39 (s, 1H), 7.79-7.65 (m, 4H), 7.63-7.60 (m, 2H), 7.34 (t, J=7.9 Hz, 1H), 7.01-6.92 (m, 2H), 3.18 (s, 3H), 2.04-1.95 (m, 1H), 1.43-1.36 (m, 2H), 1.25-1.17 (m, 2H).

Example 53: Synthesis of 6-((5-Azaspiro[2.4]heptan-5-yl)methyl)-2-(2'-(4-methyl-4H-1,2,4-triazol-3-yl)-[1,1'-biphenyl]-3-yl)-4-(trifluoromethyl)isoindolin-1-one (AAQ-1)

Into a 20 mL sealed tube were added the intermediate (AAC-2) (100 mg, 1 Eq, 246 μmol), intermediate (P-1) (74 mg, 1.2 Eq, 295 μmol) and Et$_3$N (75 mg, 3 Eq, 738 μmol) in EtOH (3 mL) at rt. The resulting mixture was stirred for 16 h at 80° C. The resulting mixture was cooled to rt and concentrated in vacuo. The crude product was purified by Prep-HPLC with the following conditions (Column: YMC-Actus Triart C18 ExRS, 30*150 mm, 5 μm; Mobile Phase A:

Water (0.1% NH$_4$HCO$_3$), Mobile Phase B: ACN; Flow rate: 60 mL/min; Gradient: 43% B to 63% B in 9 min, 63% B; Wavelength: 254/220 nm; RT: 8.33) to afford the title compound (AAQ-1) (23 mg, 42 μmol, 18%) as a white solid. m/z 544.2 (M+H)$^+$ (ES+). $^1$H NMR (300 MHz, MeOH-d4) δ 8.39 (s, 1H), 8.08 (s, 1H), 8.01 (s, 1H), 7.89-7.83 (m, 1H), 7.78-7.70 (m, 3H), 7.67-7.60 (m, 2H), 7.44 (t, J=8.0 Hz, 1H), 7.15-7.08 (m, 1H), 5.07 (s, 2H), 3.87 (s, 2H), 3.21 (s, 3H), 2.84 (t, J=7.0 Hz, 2H), 2.58 (s, 2H), 1.89 (t, J=6.9 Hz, 2H), 0.66-0.53 (m, 4H).

Example 54: Synthesis of 2-(5-Ethoxy-2'-(4-methyl-4H-1,2,4-triazol-3-yl)-[1,1'-biphenyl]-3-yl)-4-(trifluoromethyl) isoindolin-1-one (AAR-5)

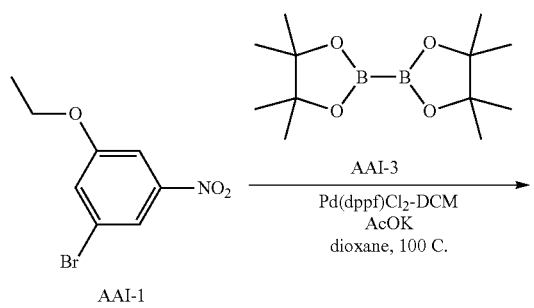

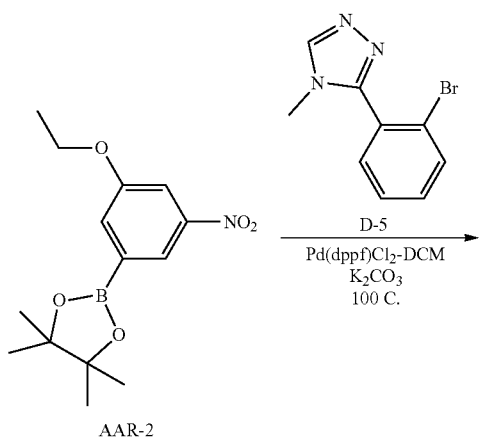

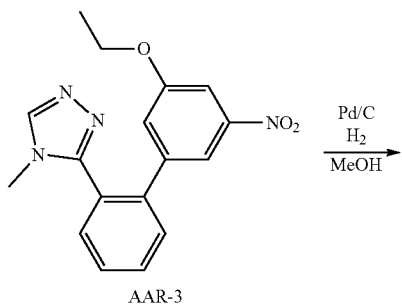

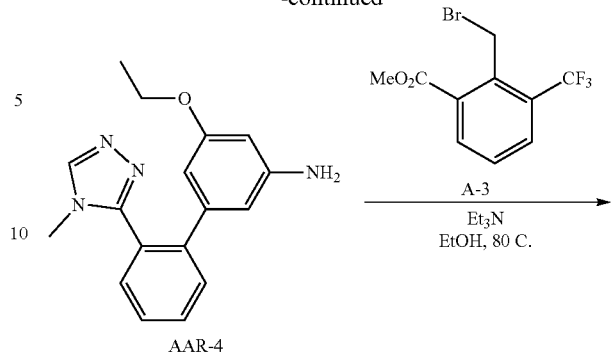

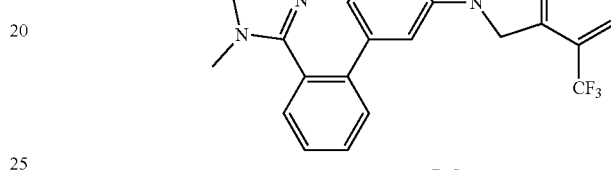

Step 1: Synthesis of 2-(3-Ethoxy-5-nitrophenyl)-4,4,5,5-tetramethyl-1,3,2-dioxaborolane (AAR-2)

To a solution of 1-bromo-3-ethoxy-5-nitrobenzene (AAI-1) (500 mg, 1 Eq, 2.03 mmol), intermediate (AAI-3) (1.55 mg, 3 Eq, 6.10 mmol) and potassium acetate (598 mg, 3 Eq, 6.10 mmol) in 1,4-dioxane (10 mL) was added Pd(dppf)Cl$_2$.DCM (297 mg, 0.2 Eq, 410 μmol) under a nitrogen atmosphere. After stirring for overnight at 100° C. under a nitrogen atmosphere, the resulting mixture was concentrated in vacuo. The crude product was purified by reverse flash column chromatography with the following conditions: Column, C18; mobile phase, Water (0.1% NH$_4$HCO$_3$) and ACN (10% ACN up to 50% in 10 min); Detector, UV 254/220 nm. The product-containing fractions were combined and evaporated to afford the sub-title compound (AAR-2) (445 mg, 1.52 mmol, 75%) as a light reddish brown solid. m/z 294.1 (M+H)$^+$ (ES+).

Step 2: Synthesis of 3-(3'-Ethoxy-5'-nitro-[1,1'-biphenyl]-2-yl)-4-methyl-4H-1,2,4-triazole (AAR-3)

To a solution of the product from step 1 above (AAR-2) (231 mg, 1 Eq, 790 μmol), intermediate (D-5) (225 mg, 1.2 Eq, 950 μmol) and K$_2$CO$_3$ (327 mg, 3 Eq, 2.36 mmol) in 1,4-dioxane (5 mL) was added Pd(dppf)Cl$_2$.DCM (115 mg, 0.2 Eq, 160 μmol) under a nitrogen atmosphere. After stirring for 2 h at 100° C. under a nitrogen atmosphere, the resulting mixture was concentrated in vacuo. The crude product was purified by reverse flash column chromatography with the following conditions: Column, C18; mobile phase, Water (0.1% NH$_4$HCO$_3$) and ACN (10% ACN up to 50% in 10 min); Detector, UV 254/220 nm. The product-containing fractions were combined and evaporated to afford the sub-title compound (AAR-3) (137 mg, 423 μmol, 62%) as a Light reddish brown solid. m/z 325.1 (M+H)$^+$ (ES+).

Step 3: Synthesis of 5-Ethoxy-2'-(4-methyl-4H-1,2,4-triazol-3-yl)-[1,1'-biphenyl]-3-amine (AAR-4)

To a solution of the product from step 2 above (AAR-3) (281 mg, 1 Eq, 870 μmol) in MeOH (10 ml) was added Pd/C 39 (9 mg 10% Wt, 0.1 Eq, 85 µmol) under nitrogen atmosphere in a 50 mL round-bottom flask. The mixture was hydrogenated at rt for 4h under hydrogen atmosphere. The resulting mixture was filtered; the filter cake was washed with MeOH (3×5 mL). The filtrate was concentrated in vacuo. This resulted in the sub-title compound (AAR-4) (230 mg, 782 µmol, 90%) as a light green solid. m/z 295.1 (M+H)$^+$ (ES+).

Step 4: Synthesis of 2-(5-Ethoxy-2'-(4-methyl-4H-1,2,4-triazol-3-yl)-[1,1'-biphenyl]-3-yl)-4-(trifluoromethyl)isoindolin-1-one (AAR-5)

To a stirred solution of the product from step 3 above (AAR-4) (50 mg, 1 Eq, 170 µmol) and intermediate (A-3) (61 mg, 1.2 Eq, 200 µmol) in EtOH (2 mL) was added Et$_3$N (26 mg, 1.5 Eq, 260 mmol) at rt. The resulting mixture was stirred for 12 h at 80° C. under nitrogen atmosphere. The resulting mixture was concentrated in vacuo. The crude product was purified by Prep-HPLC with the following conditions (Column: YMC-Actus Triart C18 ExRS, 30*250, 5 um; Mobile Phase A: Water (0.1% NH$_4$HCO$_3$+0.1% NH$_3$·H$_2$O), Mobile Phase B: ACN; Flow rate:60 mL/min; Gradient:35 B to 65 B in 7 min; Detector, UV 254/210 nm; RT:6.32) to afford the title compound (AAR-5) (20.6 mg, 43 µmol, 25%) as an off-white solid. m/z 479.1 (M+H)$^+$ (ES+). $^1$H NMR (400 MHz, MeOH-d4) δ 8.29 (s, 1H), 7.97 (d, J=7.6 Hz, 1H), 7.87-7.86 (m, 1H), 7.82-7.71 (m, 3H), 7.51-7.50 (m, 2H), 7.58 (t, J=2.2 Hz, 1H), 7.27 (t, J=1.7 Hz, 1H), 6.61 (dd, J=2.3, 1.4 Hz, 1H), 5.08 (d, J=1.7 Hz, 2H), 3.97 (q, J=7.0 Hz, 2H), 3.20 (s, 3H), 1.38 (t, J=7.0 Hz, 3H).

Example 55: Synthesis of 2-(6-Chloro-4-(2-(4-methyl-4H-1,2,4-triazol-3-yl)phenyl)pyridin-2-yl)-4-(trifluoromethyl)isoindolin-1-one (AAT-1)

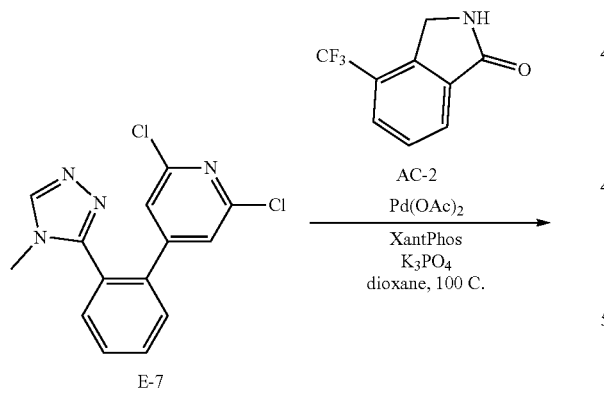

To a stirred solution of intermediate (E-7) (140 mg, 1 Eq, 450 µmol) and intermediate (AC-2) (92 mg, 1 Eq, 450 mmol) and potassium phosphate (195 mg, 2 Eq, 910 µmol) in 1,4-dioxane were added Pd(OAc)$_2$ (10 mg, 0.1 Eq, 40 µmol) and XantPhos (53 mg, 0.2 Eq, 90 µmol) at rt under nitrogen atmosphere. The resulting mixture was stirred for 3 h at 100° C. under nitrogen atmosphere. The mixture was cooled to rt and concentrated in vacuo. The crude product was purified by Prep-HPLC with the following conditions: Column: SunFire Prep C18 OBD Column, 19*150 mm, 5 µm 10 nm; Mobile Phase A: Water(0.1% FA), Mobile Phase B: ACN; Flow rate: 60 mL/min; Gradient: 30% B to 60% B in 7 min, Wavelength: 254/210 nm; RT: 6.32. This resulted in the title compound (AAT-1) (11 mg, 23 µmol, 5%) as a white solid. m/z 470.2 (M+H)$^+$ (ES+). $^1$H NMR (400 MHz, MeOH-d4) δ 8.52 (s, 1H), 8.21 (d, J=1.3 Hz, 1H), 8.11 (d, J=7.7 Hz, 1H), 8.01 (d, J=7.8 Hz, 1H), 7.85-7.67 (m, 5H), 7.18 (d, J=1.3 Hz, 1H), 5.23 (s, 2H), 3.59 (s, 3H).

Example 56: Synthesis of 2-(6-(Ethylamino)-4-(2-(4-methyl-4H-1,2,4-triazol-3-yl)phenyl)pyridin-2-yl)-4-(trifluoromethyl)isoindolin-1-one (AAU-1)

To a stirred mixture of intermediate (AAT-1) (60 mg, 1 Eq, 120 µmol) and ethylamine (52 mg, 5 Eq, 640 µmol) and Cs$_2$CO$_3$ (333 mg, 8 Eq, 1.02 mmol) in 1,4-dioxane (2 mL) were added Pd(OAc)$_2$ (3 mg, 0.1 Eq, 10 µmol) and XantPhos (15 mg, 0.2 Eq, 20 µmol) at rt under nitrogen atmosphere. The resulting mixture was stirred for overnight at 100° C. under nitrogen atmosphere. The mixture was cooled to rt and concentrated in vacuo. The crude product was purified by Prep-HPLC with the following conditions: Column: XBridge Shield RP18 OBD Column, 19*250 mm, 10 µm; Mobile Phase A: Water (0.1% NH$_4$HCO$_3$), Mobile Phase B: ACN; Flow rate: 25 mL/min; Gradient: 45% B to 59% B in 10 min; Wavelength: 254/210 nm; RT: 8.25. This resulted in the title compound (AAU-1) (2.1 mg, 4.4 µmol, 3.4%) as a white solid. m/z 479.1 (M+H)$^+$ (ES+) $^1$H NMR (400 MHz, MeOH-d4) δ 8.46 (s, 1H), 8.09 (d, J=7.7 Hz, 1H), 7.98 (d, J=7.7 Hz, 1H), 7.78-7.71 (m, 3H), 7.69-7.59 (m, 2H), 7.56 (d, J=1.3 Hz, 1H), 6.06 (d, J=1.3 Hz, 1H), 5.25 (s, 2H), 3.44 (s, 3H), 3.32-3.26 (m, 2H), 1.23 (t, J=7.2 Hz, 3H).

Example 57: Synthesis of 2-(2'-(4-Methyl-1H-imidazol-5-yl)-[1,1'-biphenyl]-3-yl)-4-(trifluoromethyl) isoindolin-1-one (AAV-6)

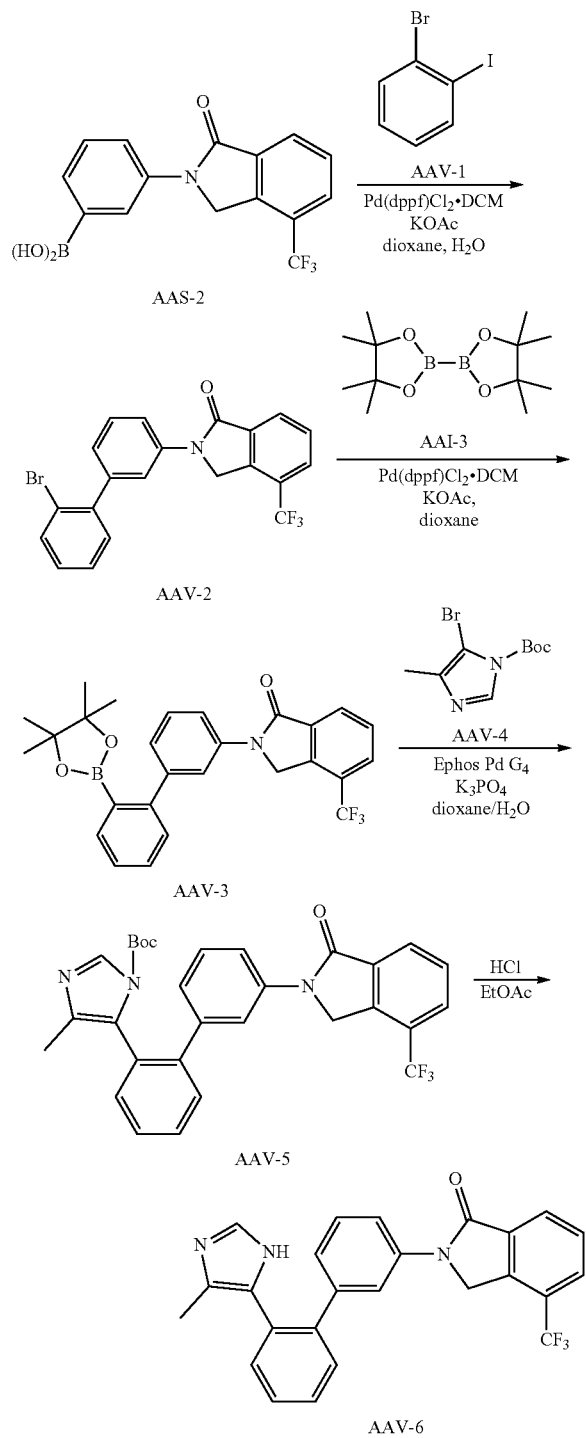

Step 1: Synthesis of 2-(2'-Bromo-[1,1'-biphenyl]-3-yl)-4-(trifluoromethyl) isoindolin-1-one (AAV-2)

To a stirred solution of intermediate (AAS-2) (1.00 g, 1 Eq, 3.11 mmol), 1-bromo-2-iodo-benzene (AAV-1) (1.7 g, 2 Eq, 6.23 mmol) and potassium acetate (610 mg, 2 Eq, 6.23 mmol) in 1,4-Dioxane (10 mL) and water (1 mL) under a nitrogen atmosphere at rt was added Pd(dppf)Cl$_2$·DCM (254 mg, 311 µmol). The resulting mixture was stirred for 1 h at 80° C. under nitrogen atmosphere then cooled to rt, concentrated in vacuo and purified by reverse flash column chromatography with the following conditions: Column, C18; mobile phase, Water (0.1% NH$_4$HCO$_3$) and ACN (10% ACN up to 50% in 10 min); Detector, UV 254/220 nm to afford the sub-title compound (AAV-2) (800 mg, 1.86 mmol, 59%) as a light yellow solid. m/z 432.2/434.2 (M+H)$^+$ (ES+).

Step 2: Synthesis of 2-(2'-(4,4,5,5-Tetramethyl-1,3,2-dioxaborolan-2-yl)-[1,1'-biphenyl]-3-yl)-4-(trifluoromethyl) isoindolin-1-one (AAV-3)

To a stirred solution of the product from step 1 above (AAV-2) (700 mg, 1 Eq, 1.62 mmol), intermediate (AAI-3) (777 mg, 2 Eq, 3.24 mmol) and potassium acetate (317 mg, 2 Eq, 3.24 mmol) in 1,4-Dioxane (10 mL) under a nitrogen atmosphere at rt was added Pd(dppf)Cl$_2$·DCM (132 mg, 0.1 Eq, 162 µmol) under a nitrogen atmosphere. The resulting mixture was stirred for 48 h at 90° C. under nitrogen atmosphere. The mixture was cooled to rt and concentrated in vacuo. The residue was purified by Prep-TLC with EtOAc/petroleum ether (1/1) to afford the sub-title compound (AAV-3) (300 mg, 626 µmol, 39%) as a light yellow solid. m/z 380.2 (M+H)$^+$ (ES+).

Step 3: tert-Butyl 4-methyl-5-(3'-(1-oxo-4-(trifluoromethyl) isoindolin-2-yl)-[1,1'-biphenyl]-2-yl)-1H-imidazole-1-carboxylate (AAV-5)

To a stirred solution of the product from step 2 above (AAV-3) (300 mg, 1 Eq, 626 µmol), tert-butyl 5-bromo-4-methyl-imidazole-1-carboxylate (AAV-4) (490 mg, 3 Eq, 1.88 mmol) and potassium phosphate (265 mg, 2 Eq, 1.25 mmol) in 1,4-Dioxane (3 mL) and water (0.3 mL) under a nitrogen atmosphere at rt was added Ephos Pd G4 (60 mg, 0.1 Eq, 0.06 mmol). The resulting mixture was stirred for 2 h at 100° C. under nitrogen atmosphere. The mixture was cooled to rt and concentrated in vacuo. The crude product was purified by reverse flash column chromatography with the following conditions: Column, C18; mobile phase, Water (0.1% NH$_4$HCO$_3$) and ACN (10% ACN up to 50% in 10 min); Detector, UV 254/220 nm to afford the sub-title compound (AAV-5) (40 mg, 75 µmol, 12%) as an off-white solid. m/z 534.2 (M+H)$^+$ (ES+).

Step 4: 2-[3-[2-(4-Methyl-1H-imidazol-5-yl)phenyl]phenyl]-4-(trifluoromethyl)isoindolin-1-one (AAV-6)

To a stirred solution of the product from step 3 above (AAV-5) (40 mg, 1 Eq, 75 µmol) in EtOAc (2 mL) was added HCl (aq., 2 M) (2 mL) under nitrogen atmosphere. The resulting mixture was stirred for 1 h at rt under nitrogen atmosphere. The mixture was concentrated in vacuo. The crude product was purified by Prep-HPLC with the following conditions: Column: XBridge Prep C18 OBD Column, 19*150 mm, 5 µm; Mobile Phase A: Water (0.05% TFA), Mobile Phase B: ACN; Flow rate: 20 mL/min; Gradient: 50% B to 65% B in 4.5 min, 65% B; Wavelength: 254/210 nm; RT: 4.35. The product-containing fractions were combined and evaporated partially in vacuo and lyophilized overnight to afford the title compound (AAV-6) (1.1 mg, 2.5 µmol, 3.4%) as a white solid. m/z 434.2 (M+H)$^+$ (ES+). $^1$H NMR (400 MHz, MeOH-d4) δ 8.10 (d, J=7.64 Hz, 1H), 7.98 (d, J=7.76 Hz, 1H), 7.91-7.86 (m, 1H), 7.78 (t, J=7.71 Hz, 1H), 7.59 (s, 1H), 7.58-7.46 (m, 5H), 7.40 (t, J=7.95 Hz, 1H), 7.15 (d, J=7.80 Hz, 1H), 4.98 (s, 2H), 2.05 (s, 1H), 1.74 (s, 3H).

Example 58: Synthesis of N-(4-(1-Methyl-4-(4-methyl-4H-1,2,4-triazol-3-yl)-1H-pyrazol-5-yl)-6-(1-oxo-4-(trifluoromethyl)isoindolin-2-yl)pyridin-2-yl)methanesulfonamide (AAW-2)

Example 59: Synthesis of 2-(2'-(1-Methyl-1H-1,2,4-triazol-5-yl)-[1,1'-biphenyl]-3-yl)-4-(trifluoromethyl)isoindolin-1-one (AAX-2)

m/z 533.1 (M+H)+ (ES+). ¹H NMR (300 MHz, MeOH-d4) δ 8.52 (s, 1H), 8.18-8.07 (m, 2H), 8.01 (d, J=7.7 Hz, 1H), 7.92 (s, 1H), 7.78 (t, J=7.7 Hz, 1H), 6.74 (d, J=1.2 Hz, 1H), 5.34 (s, 2H), 4.06 (s, 3H), 3.60 (s, 3H), 3.30 (s, 3H).

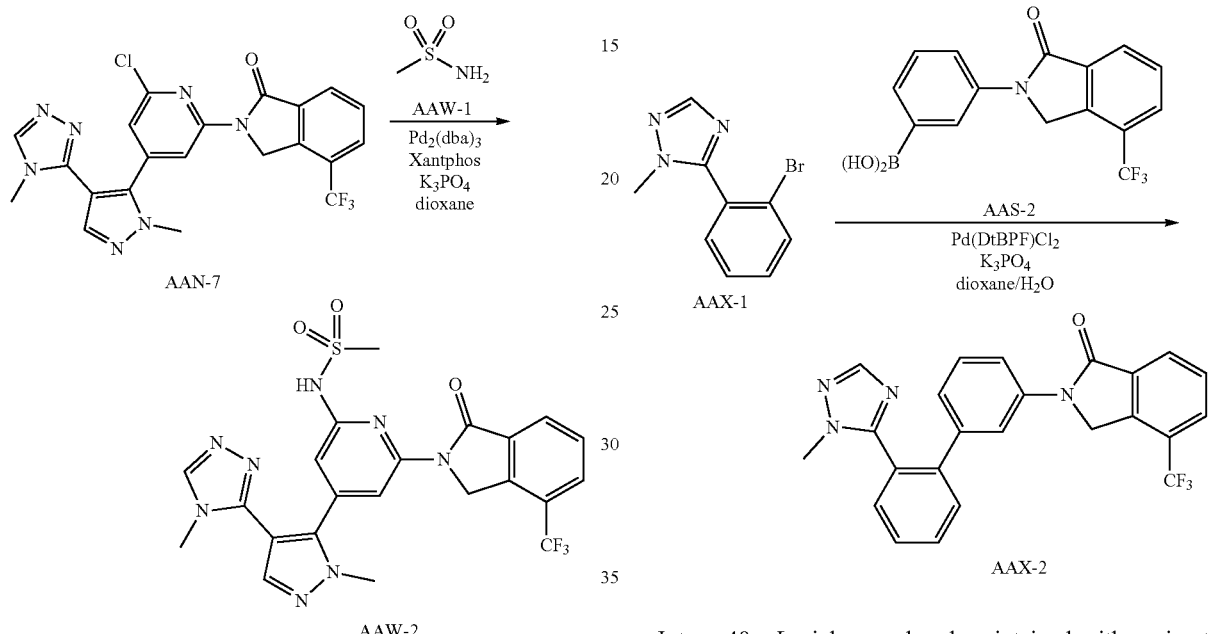

To a stirred mixture of the product from intermediate (AAN-7) (112 mg, 1 Eq, 237 μmol), methanesulfonamide (AAW-1) (45 mg, 2 Eq, 470 μmol) and potassium phosphate (125.4 mg, 2.5 Eq, 590 μmol) in 1,4-dioxane (8 mL) were added Pd₂(dba)₃ (22 mg, 0.1 Eq, 20 μmol) and XantPhos (27 mg, 0.2 Eq, 40 μmol) at rt under nitrogen atmosphere. The resulting mixture was stirred for 3 h at 100° C. under nitrogen atmosphere. The resulting mixture was cooled to rt and the crude product purified by reverse flash column chromatography with the following conditions: Column, C18; mobile phase, Water (0.1% NH₄HCO₃) and ACN (25% ACN up to 35% in 8 min); Detector, UV 254/220 nm. The product-containing fractions were combined and concentrated in vacuo. The crude product was purified by Prep-HPLC with the following conditions: Column: SunFire Prep C18 OBD Column, 30×250 mm 5 um; Mobile Phase A: Water (0.1% NH₄HCO₃+0.1% NH₃·H₂O), Mobile Phase B: ACN; Flow rate:60 mL/min; Gradient:10 B to 30 B in 10 min; Detector, UV 254/210 nm; RT: 7.53. The product-containing fractions were combined and evaporated partially in vacuo and lyophilized overnight to afford the title compound (AAW-2) (32.8 mg, 62 μmol, 25%) as a white solid.

Into a 40-mL vial purged and maintained with an inert atmosphere of nitrogen, was placed intermediate (AAX-1) (300 mg, 1 Eq, 1.26 mmol), intermediate (AAS-2) (445 mg, 1.1 Eq, 1.39 mmol) and potassium phosphate (801 mg, 3 Eq, 3.78 mmol) in water (3.5 mL) and 1,4-dioxane (16.5 mL) at rt under nitrogen atmosphere. Pd(DtBPF)Cl₂ (164 mg, 0.2 Eq, 252 μmol) was added at rt under nitrogen atmosphere and the resulting solution was stirred overnight at 100° C. The mixture was cooled to rt, diluted with water and extracted with EtOAc (3×30 mL). The combined organic layers were washed with brine (2×30 mL), dried (Na₂SO₄), filtered and concentrated in vacuo. The crude product was purified by Prep-HPLC with the following conditions: (Column: XBridge Prep C18 OBD Column, 30×100 mm, 5 μm; Mobile Phase A: Water (0.1% NH₄HCO₃+0.1% NH₃·H₂O), Mobile Phase B: ACN; Flow rate: 60 mL/min; Gradient: 39% B to 59% B in 10 min, 59% B; Wavelength: 254/220 nm; RT: 9.67). This resulted in the title compound (AAX-2) (45.5 mg, 104 μmol, 8%) as a white solid. m/z 435.0 (M+H)+ (ES+). ¹H NMR (400 MHz, Chloroform-d) δ 8.11 (d, J=6.6 Hz, 2H), 7.99 (s, 1H), 7.87 (d, J=7.7 Hz, 1H), 7.70-7.62 (m, 4H), 7.56 (d, J=7.9 Hz, 1H), 7.45 (t, J=8.0 Hz, 1H), 7.40 (s, 1H), 7.14 (d, J=7.7 Hz, 1H), 4.80 (s, 2H), 3.21 (s, 3H).

Example 60: Synthesis of 2-[3-[3-(4-Methyl-1,2,4-triazol-3-yl)-pyridin-4-yl]-phenyl]-4-(trifluoromethyl)-3H-isoindol-1-one (AAY-6)

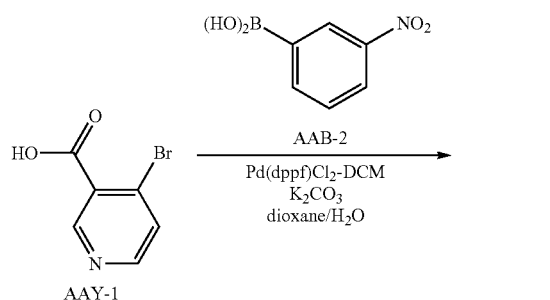

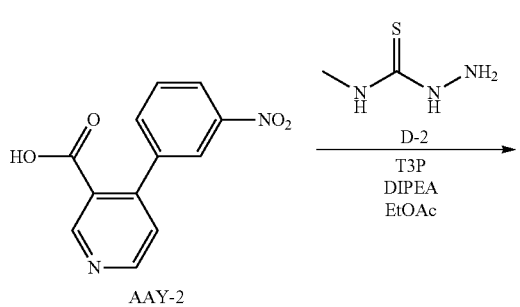

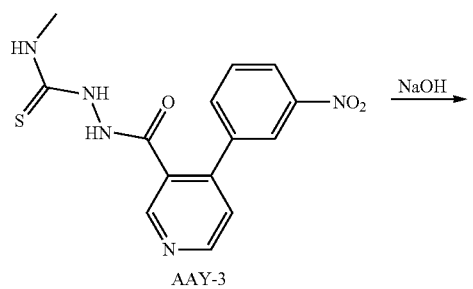

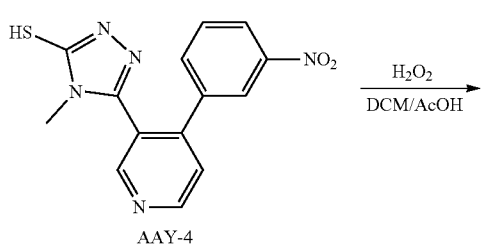

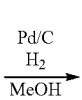

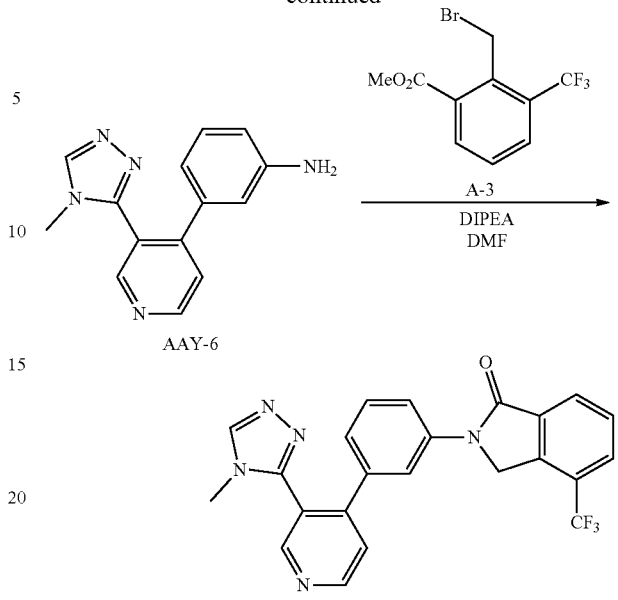

Step 1: Synthesis of 4-(3-Nitrophenyl)nicotinic acid (AAY-2)

To a stirred solution of 4-bromonicotinic acid (AAY-1) (200 mg, 1 Eq, 990 μmol), intermediate (AAB-2) (198 mg, 1.2 Eq, 1.18 mmol) and K$_2$CO$_3$ (411 mg, 3 Eq, 2.97 mmol) in 1,4-dioxane (8 mL) was added Pd(dppf)Cl$_2$.DCM (145 mg, 0.2 Eq, 190 μmol) at rt under nitrogen atmosphere. The resulting mixture was stirred for additional 4 h at 85° C. under nitrogen atmosphere. The mixture was cooled to rt and concentrated in vacuo. The crude product was purified by reverse flash column chromatography with the following conditions: Column, C18; mobile phase, Water (0.1% FA) and ACN (20% ACN up to 40% in 10 min); Detector, UV 254/220 nm. This resulted in the sub-title compound (AAY-2) (178 mg, 729 μmol, 73%) as a white solid. m/z 245.1 (M+H)$^+$ (ES+).

Step 2: Synthesis of N-Methyl-2-(4-(3-nitrophenyl)nicotinoyl)hydrazine-1-carbothioamide (AAY-3)

To a stirred solution of the product from step 1 above (AAY-2) (60 mg, 1 Eq, 240 μmol) and 1-amino-3-methyl-thiourea (D-2) (31 mg, 1.2 Eq, 29 μmol) in EtOAc (2 mL) were added T$_3$P (313 mg, 4 Eq, 980 μmol) and DIPEA (191 mg, 6 Eq, 1.47 mmol) at rt. The resulting mixture was stirred for 3 h at rt. The crude product was used in the next step directly without further purification. m/z 332.1 (M+H)$^+$ (ES+).

Step 3: Synthesis of 4-methyl-5-(4-(3-nitrophenyl)pyridin-3-yl)-4H-1,2,4-triazole-3-thiol (AAY-4)

To the reaction mixture from step 2 above (AAY-3) was added NaOH (aq., 1M) (10 mL) at 0° C. The resulting mixture was stirred for 2 h at 80° C. then cooled to rt. The residue was diluted with water and acidified to pH 4 with HCl (aq., 1 M). The resulting mixture was extracted with EtOAc (3×50 mL). The combined organic layers were washed with brine (50 mL), dried (Na$_2$SO$_4$), filtered and concentrated in vacuo. This resulted in the sub-title compound (AAY-4) (55 mg, 176 μmol, 71%) as a white solid. m/z 314.1 (M+H)⁺ (ES+).

Step 4: Synthesis of 3-(4-Methyl-4H-1,2,4-triazol-3-yl)-4-(3-nitrophenyl)pyridine (AAY-5)

To a stirred mixture of the product from step 3 above (AAY-4) (50 mg, 1 Eq, 160 μmol) and acetic acid (19 mg, 2 Eq, 320 μmol) in DCM (3 mL) was added hydrogen peroxide (27 mg, 30% Wt, 5 Eq, 800 μmol) at 0° C. and the resulting mixture stirred for 2 h at rt. The residue was diluted with water and basified to pH 8 with saturated NaHCO₃ (aq., 1M). The resulting mixture was extracted with DCM (3×50 mL) and the combined organic layers washed with brine (30 mL), dried (Na₂SO₄), filtered and concentrated in vacuo. This resulted in the sub-title compound (AAY-5) (40 mg, 142 μmol, 89%) as a white solid. m/z 282.1 (M+H)⁺ (ES+).

Step 5: Synthesis of 3-(3-(4-Methyl-4H-1,2,4-triazol-3-yl)pyridin-4-yl)aniline (AAY-6)

To a solution of the product from step 4 above (AAY-5) (40 mg, 1 Eq, 140 μmol) in MeOH (8 mL) was added palladium on carbon (1.5 mg, 10% Wt, 0.1 Eq, 14 μmol) under nitrogen atmosphere in a 10 mL pressure tank reactor. The mixture was hydrogenated at rt for 2 h under hydrogen atmosphere using a hydrogen balloon, then filtered through a Celite pad and concentrated in vacuo. This resulted in the sub-title compound (AAY-6) (31 mg, 123 μmol, 57%) as a white solid. m/z 252.1 (M+H)⁺ (ES+).

Step 6: 2-(3-(3-(4-Methyl-4H-1,2,4-triazol-3-yl)pyridin-4-yl)phenyl)-4-(trifluoromethyl) isoindolin-1-one (AAY-7)

To a stirred mixture of the product from step 5 above (AAY-6) (30 mg, 1 Eq, 110 μmol) and intermediate (A-3) (71 mg, 2 Eq, 230 μmol) in DMF (6 mL) was added DIPEA (60 mg, 5 Eq, 590 μmol) at rt under nitrogen atmosphere. The resulting mixture was stirred for 16 h at 80° C. under nitrogen atmosphere. The resulting mixture was cooled to rt and concentrated in vacuo. The crude product was purified by reverse flash column chromatography with the following conditions: Column, C18; mobile phase, Water (0.1% NH₄HCO₃) and ACN (30% ACN up to 45% in 10 min); Detector, UV 254/220 nm. The product-containing fractions were combined and concentrated in vacuo. The crude product was purified by Prep-HPLC with the following conditions: Column: SunFire Prep C18 OBD Column, 30*100 mm, 5 um; Mobile Phase A: Water (0.1% NH₄HCO₃), Mobile Phase B: ACN; Flow rate:60 mL/min; Gradient:21 B to 41 B in 10 min; Detector, UV 254/210 nm; RT: 10. The product-containing fractions were combined and evaporated partially in vacuo and lyophilized overnight to afford the title compound (AAY-7) (1.9 mg, 4.3 μmol, 3%) as a white solid. m/z 436.0 (M+H)⁺ (ES+). ¹H NMR (400 MHz, MeOH-d4) δ 8.88 (d, J=5.2 Hz, 1H), 8.80 (d, J=0.8 Hz, 1H), 8.49 (s, 1H), 8.12 (d, J=7.6 Hz, 1H), 8.03-7.94 (m, 2H), 7.88-7.75 (m, 3H), 7.53 (t, J=8.0 Hz, 1H), 7.20-7.13 (m, 1H), 5.12 (s, 2H), 3.23 (s, 3H).

Example 61: Synthesis of 2-(2'-(4-Methylisoxazol-3-yl)-[1,1'-biphenyl]-3-yl)-4-(trifluoromethyl)isoindolin-1-one (AAZ-7)

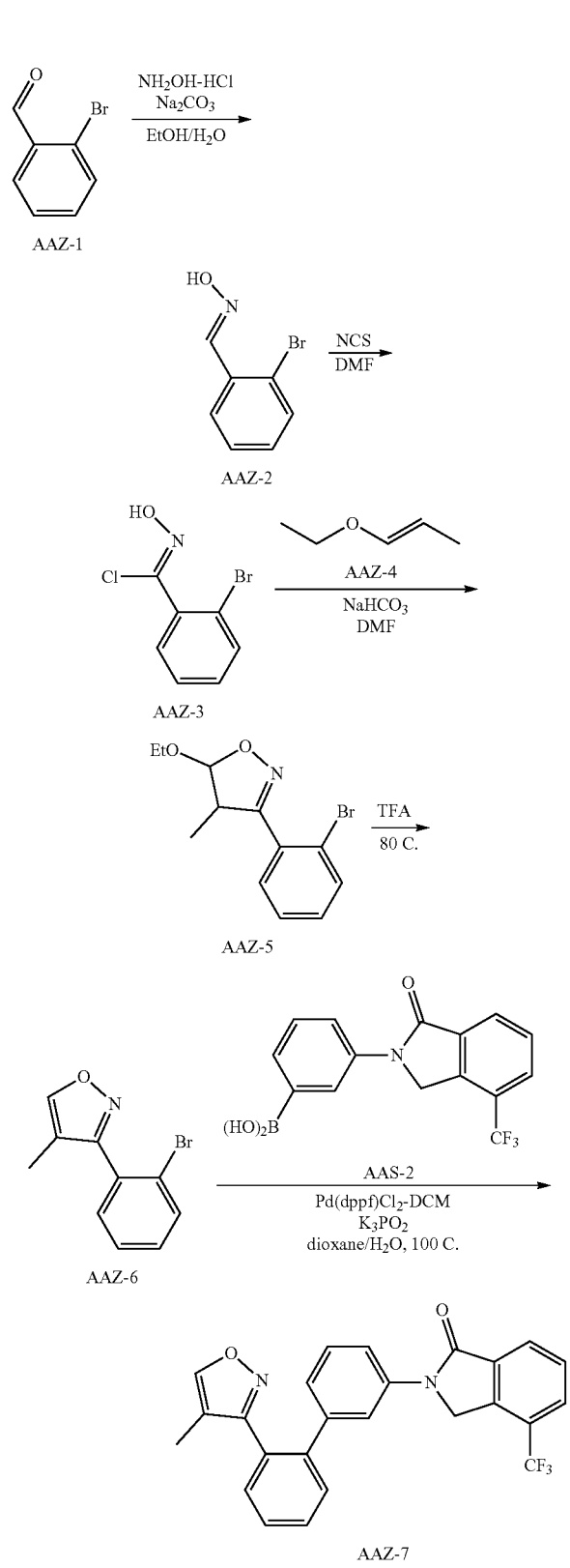

Step 1: Synthesis of (E)-2-Bromobenzaldehyde oxime (AAZ-2)

Into a 100-mL round-bottom flask, was placed 2-bromobenzaldehyde (AAZ-1) (1.00 g, 1 Eq, 5.40 mmol), hydroxylamine, HCl (751 mg, 2 Eq, 10.8 mmol) and sodium carbonate (2.86 g, 5 Eq, 27.0 mmol) in EtOH (24.00 mL) and water (6.00 mL). The resulting solution was stirred for 2 hr at rt. The resulting solution was diluted with water, extracted with EtOAc (3×50 mL) and the organic layers were combined and concentrated. This resulted in the sub-title compound (AAZ-2) (1.06 g, crude) as a white solid. m/z 200.0/202.0 $(M+H)^+$ (ES+).

Step 2: Synthesis of (Z)-2-Bromo-N-hydroxybenzimidoyl chloride (AAZ-3)

Into a 50-mL round-bottom flask, was placed the product from step 1 above (AAZ-2) (1.06 g, 1 Eq, 5.29 mmol) in DMF (20.00 mL), then 1-chloropyrrolidine-2,5-dione (707 mg, 1 Eq, 5.29 mmol) was added. The resulting solution was stirred for 2 hr at rt then diluted with water, extracted with EtOAc (3×50 mL) and the organic layers were combined and concentrated. This resulted in the sub-title compound (AAZ-3) (1.25 g, crude) as yellow oil. m/z 233.9/235.9 $(M+H)^+$ (ES+).

Step 3: Synthesis of 3-(2-Bromophenyl)-5-ethoxy-4-methyl-4,5-dihydroisoxazole (AAZ-5)

Into a 50-mL round-bottom flask, was placed the product from step 2 above (AAZ-3) (1.25 g, 1 Eq, 5.33 mmol) in DMF (20 mL) were added ether, ethyl propenyl (AAZ-4) (918 mg, 2 Eq, 10.7 mmol) and NaHCO$_3$ (896 mg, 2 Eq, 10.7 mmol) at rt and the resulting solution stirred overnight at rt. The resulting mixture was diluted with water and extracted with EtOAc (3×100 mL). The combined organic layers were washed with brine (2×100 mL), dried (Na$_2$SO$_4$), filtered and concentrated in vacuo. The residue was applied onto a silica gel column with EtOAc/petroleum ether (1/6). This resulted in the sub-title compound (AAZ-5) (800 mg, 2.83 mmol, 53%) as yellow oil. m/z 284.0/286.0 $(M+H)^+$ (ES+).

Step 4: Synthesis of 3-(2-bromophenyl)-4-methylisoxazole (AAZ-6)

Into a 25-mL round-bottom flask, was placed the product from step 3 above (AAZ-5) (800 mg, 1 Eq, 2.82 mmol) in TFA (3 mL) at rt. The resulting solution was stirred for 3 h at 80° C. then the resulting mixture cooled to rt and concentrated. The resulting mixture was diluted with water and extracted with EtOAc (3×80 mL). The combined organic layers were washed with brine (2×80 mL), dried (Na$_2$SO$_4$), filtered and concentrated in vacuo. The residue was applied onto a silica gel column with EtOAc/petroleum ether (1/4). This resulted in the sub-title compound (AAZ-6) (620 mg, 2.62 mmol, 93%) of as yellow oil. m/z 238.0/240.0 $(M+H)^+$ (ES+).

Step 5: 2-(2'-(4-Methylisoxazol-3-yl)-[1,1'-biphenyl]-3-yl)-4-(trifluoromethyl)isoindolin-1-one (AAZ-7)

Into a 25-mL round-bottom flask, was placed the product from step 1 (AAZ-6) (50 mg, 1 Eq, 210 µmol), intermediate (AAS-2) (67 mg, 1 Eq, 210 µmol) and K$_2$CO$_3$ (87 mg, 3 Eq, 630 µmol) in 1,4-dioxane (5 mL) and water (1 mL) Pd(dppf)Cl$_2$.DCM (15 mg, 0.1 Eq, 21 µmol) was added at rt under nitrogen atmosphere. The resulting solution was stirred overnight at 80° C. under nitrogen atmosphere then cooled to rt and concentrated in vacuo. The crude product was purified by Prep-HPLC with the following conditions: Column: XBridge Prep C18 OBD Column, 30×150 mm, 5 um; Mobile Phase A: Water (0.1% FA), Mobile Phase B: ACN; Flow rate: 60 mL/min; Gradient: 57 B to 82 B in 9 min; Detector, UV 220/254 nm; RT: 8.85. This resulted in the title compound (AAZ-7) (41.3 mg, 95 µmol, 45%) as a white solid. m/z 435.3 $(M+H)^+$ (ES+). $^1$H NMR (300 MHz, DMSO-d6) δ 8.60 (d, J=1.2 Hz, 1H), 8.11-8.04 (m, 2H), 8.01-7.93 (m, 1H), 7.85-7.73 (m, 2H), 7.72-7.62 (m, 2H), 7.60-7.47 (m, 2H), 7.42 (t, J=8.0 Hz, 1H), 7.09-7.00 (m, 1H), 5.12 (s, 2H), 1.46 (d, J=1.1 Hz, 3H).

Example 62: Synthesis of 2-(2'-(1,3,4-Oxadiazol-2-yl)-[1,1'-biphenyl]-3-yl)-4-(trifluoromethyl)isoindolin-1-one (ABA-4)

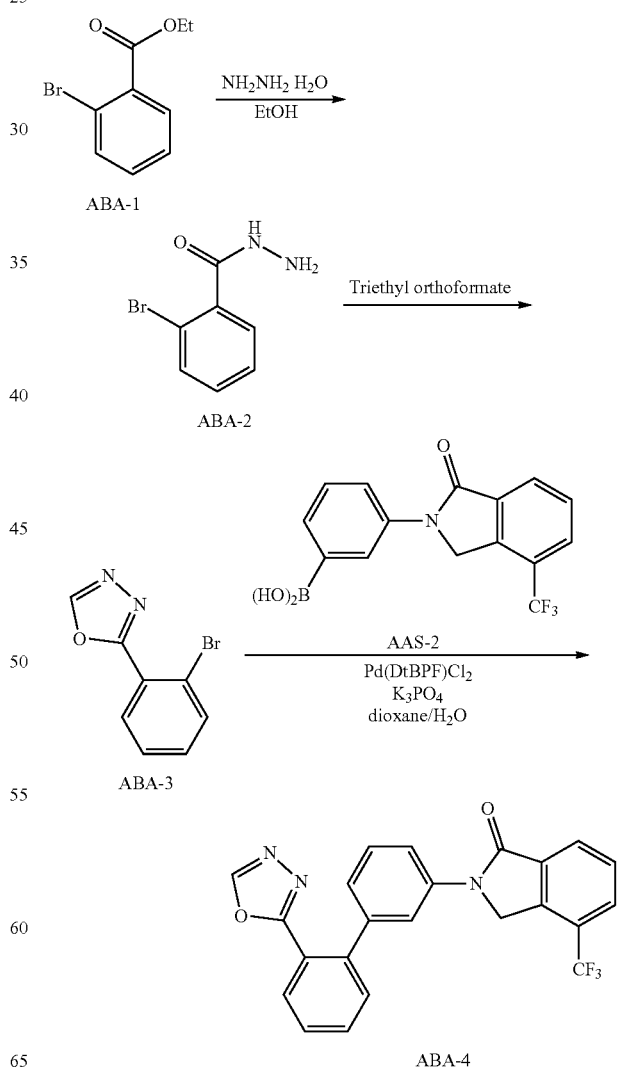

519

Step 1: Synthesis of 2-Bromobenzohydrazide (ABA-2)

Into a 100-mL round-bottom flask purged and maintained with an inert atmosphere of nitrogen, was placed ethyl 2-bromobenzoate (ABA-1) (1.00 g, 1 Eq, 4.37 mmol) and hydrazine hydrate (2.20 g, 80% Wt, 10 Eq, 43.7 mmol) in EtOH (40 mL) at rt under nitrogen atmosphere. The resulting mixture was stirred overnight at 60° C. under nitrogen atmosphere then cooled to rt The resulting mixture was diluted with water and extracted with EtOAc (3×100 mL). The combined organic layers were washed with brine (2×100 mL), dried ($Na_2SO_4$), filtered and concentrated in vacuo. The crude product used directly in next step without any further purification. This resulted in the sub-title compound (ABA-2) (800 mg, 3.72 mmol, 85%) as a yellow solid. m/z 215.0/217.0 $(M+H)^+$ (ES+).

Step 2: Synthesis of 2-(2-Bromophenyl)-1,3,4-oxadiazole (ABA-3)

Into a 50 mL round-bottom flask purged and maintained with an inert atmosphere of nitrogen, was placed the product from step 1 above (ABA-2) (800 mg, 1 Eq, 3.72 mmol) in (diethoxymethoxy)ethane (15 mL) at rt. The resulting mixture was stirred for 3 h at rt under nitrogen atmosphere. The resulting mixture was diluted with water and extracted with EtOAc (3×50 mL). The combined organic layers were washed with brine (2×50 mL), dried ($Na_2SO_4$), filtered and concentrated in vacuo. The crude product was purified by reverse flash column chromatography with the following conditions: Column, C18; mobile phase, Water (0.1% $NH_4HCO_3$) and ACN (10% ACN up to 50% in 8 min); Detector, UV 254/220 nm to afford the sub-title compound (ABA-3) (300 mg, 1.34 mmol, 36%) as a yellow solid. m/z 225.0/227.0 $(M+H)^+$ (ES+).

Step 3: 2-(2'-(1,3,4-Oxadiazol-2-yl)-[1,1'-biphenyl]-3-yl)-4-(trifluoromethyl)isoindolin-1-one (ABA-4)

Into a 40-mL vial purged and maintained with an inert atmosphere of nitrogen, was placed the product from step 2 above (ABA-3) (95 mg, 1 Eq, 424 μmol), intermediate (AAS-2) (136 mg, 1 Eq, 424 μmol) and potassium phosphate (225 mg, 2.5 Eq, 1.06 mmol) in 1,4-dioxane (6 mL) and water (1.5 mL). $Pd(DtBPF)Cl_2$ (55 mg, 0.2 Eq, 85 μmol) was added at rt under nitrogen atmosphere and the resulting mixture stirred for 6 h at 100° C. under nitrogen atmosphere. The mixture was cooled to rt and the resulting mixture was diluted with water and extracted with EtOAc (3×20 mL). The combined organic layers were washed with brine (2×20 mL), dried ($Na_2SO_4$), filtered and concentrated in vacuo. The crude product was purified by Prep-HPLC with the following conditions (Column: XBridge Prep C18 OBD Column, 30×100 mm, 5 μm; Mobile Phase A: Water (0.1% $NH_4HCO_3$), Mobile Phase B: ACN; Flow rate: 60 mL/min; Gradient: 40% B to 60% B in 10 min, 60% B; Wavelength: 254/220 nm; RT: 10.38) to afford the title compound (ABA-4) (64.1 mg, 152 μmol, 36%) as a white solid. m/z 422.0 $(M+H)^+$ (ES+). $^1H$ NMR (300 MHz, Chloroform-d) δ 8.28 (s, 1H), 8.14 (d, J=7.6 Hz, 1H), 8.05-8.02 (m, 1H), 7.94-87.86 (m, 2H), 7.83-7.82 (m, 1H), 7.71-7.64 (m, 2H), 7.60-7.54 (m, 2H), 7.45 (t, J=7.9 Hz, 1H), 7.08 (d, J=7.7 Hz, 1H), 5.03 (s, 2H).

520

Example 63: Synthesis of 2-[3-[4-(4-Methyl-1,2,4-triazol-3-yl) pyridin-3-yl]phenyl]-4-(trifluoromethyl)-3H-isoindol-1-one (ABB-5)

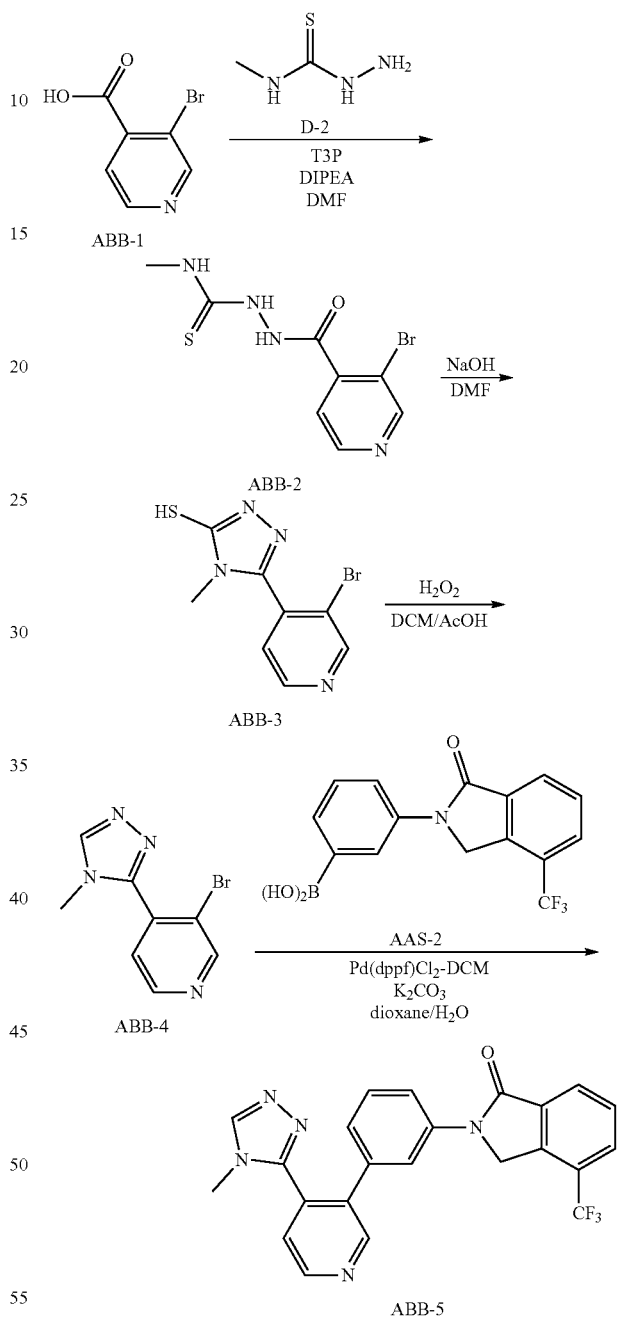

Step 1: Synthesis of 2-(3-Bromoisonicotinoyl)-N-methylhydrazine-1-carbothioamide (ABB-2)

Into a 40-mL vial purged and maintained with an inert atmosphere of nitrogen, was placed 3-bromoisonicotinic acid (ABB-1) (202 mg, 1 Eq, 1.00 mmol) and 4-methyl-3-thiosemicarbazide (D-2) (116 mg, 1.1 Eq, 1.10 mmol) in DMF (10 mL), then T3P (1.57 g, 4 Eq, 4.40 mmol) and DIPEA (1.09 mL, 98% Wt, 6 Eq, 6.60 mmol) was added at 0° C. under nitrogen atmosphere. The resulting solution was stirred overnight at rt. The resulting mixture was diluted with water and extracted with EtOAc (3×50 mL). The combined organic layers were washed with brine (2×50 mL), dried ($Na_2SO_4$), filtered and concentrated in vacuo to afford the sub-title compound (ABB-2) (220 mg, 761 μmol, 76%) as a yellow solid. m/z 289.2/291.2 $(M+H)^+$ (ES+).

Step 2: Synthesis of 5-(3-Bromopyridin-4-yl)-4-methyl-4H-1,2,4-triazole-3-thiol (ABB-3)

Into a 40-mL vial purged and maintained with an inert atmosphere of nitrogen, was placed the product from step 1 above (ABB-2) (220 mg, 1 Eq, 761 μmol) and NaOH (aq., 1M) (3.8 mL, 5 Eq, 3.81 mmol) in DMF (10 mL) at rt. The resulting mixture was stirred overnight at 50° C. under nitrogen atmosphere then cooled to. The resulting mixture was diluted with water and extracted with EtOAc (3×30 mL). The combined organic layers were washed with brine (2×30 mL), dried ($Na_2SO_4$), filtered and concentrated in vacuo. The residue was purified by Prep-TLC with DCM/MeOH (10/1) to afford the sub-title compound (ABB-3) (190 mg, 704 μmol, 92%) as a white solid. m/z 271.0/273.0 $(M+H)^+$ (ES+).

Step 3: Synthesis of 3-Bromo-4-(4-methyl-4H-1,2,4-triazol-3-yl)pyridine (ABB-4)

Into a 20-mL vial purged and maintained with an inert atmosphere of nitrogen, was placed the product from step 2 above (ABB-3) (123 mg, 1 Eq, 452 μmol) and acetic acid (54 mg, 2 Eq, 904 μmol) in DCM (4 mL) at rt. Then hydrogen peroxide (92 mg, 30% Wt, 6 Eq, 2.71 mmol) was added at 0° C. under nitrogen atmosphere. The resulting solution was stirred for 2 h at rt under nitrogen atmosphere. The mixture was diluted with water and extracted with EtOAc (3×30 mL). The combined organic layers were washed with brine (2×30 mL), dried ($Na_2SO_4$), filtered and concentrated in vacuo. The crude product was purified by reverse flash column chromatography with the following conditions: Column, C18; mobile phase, Water (0.1% $NH_4HCO_3$) and ACN (50% ACN up to 60% in 20 min); Detector, UV 254/220 nm to afford the sub-title compound (ABB-4) (80 mg, 336 μmol, 52%) as a white solid. m/z 239.1/241.1 $(M+H)^+$ (ES+).

Step 4: Synthesis of 2-(3-(4-(4-Methyl-4H-1,2,4-triazol-3-yl)pyridin-3-yl)phenyl)-4-(trifluoromethyl)isoindolin-1-one (ABB-5)

Into a 20-mL vial purged and maintained with an inert atmosphere of nitrogen, was placed the product from step 3 above (ABB-4) (80 mg, 1 Eq, 335 μmol), intermediate (AAS-2) (118 mg, 1.1 Eq, 369 μmol) and $K_2CO_3$ (139 mg, 3 Eq, 1.00 mmol) in 1,4-dioxane (5 mL) and water (1 mL) at rt. $Pd(dppf)Cl_2 \cdot DCM$ (49 mg, 0.2 Eq, 67 μmol) was added at rt under nitrogen atmosphere then the mixture stirred overnight at 80° C. The mixture was cooled to rt and the mixture diluted with water and extracted with EtOAc (3×20 mL). The combined organic layers were washed with brine (2×20 mL), dried ($Na_2SO_4$), filtered and concentrated in vacuo. The residue was purified by Prep-HPLC with the following conditions (Column: XBridge Prep C18 OBD Column, 30×100 mm, 5 μm; Mobile Phase A: Water (0.1% $NH_4HCO_3$+0.1% $NH_3 \cdot H_2O$), Mobile Phase B: ACN; Flow rate: 60 mL/min; Gradient: 23% B to 43% B in 10 min; Wavelength: 254/220 nm; RT: 9.67) to afford the title compound (ABB-5) (23.4 mg, 16%) as a white solid. m/z 436.0 $(M+H)^+$ (ES+). $^1H$ NMR (400 MHz, MeOH-d4) δ 8.94 (d, J=0.8 Hz, 1H), 8.82 (d, J=5.1 Hz, 1H), 8.47 (s, 1H), 8.11 (d, J=7.6 Hz, 1H), 8.03-7.91 (m, 2H), 7.84 (t, J=2.0 Hz, 1H), 7.83-7.75 (m, 1H), 7.72-7.71 (m, 1H), 7.52 (t, J=8.0 Hz, 1H), 7.16-7.14 (m, 1H), 5.12 (s, 2H), 3.26 (s, 3H).

Example 64: Synthesis of 6-((5-Azaspiro [2.4] heptan-5-yl)methyl)-2-(6-(ethylamino)-4-(1-methyl-4-(4-methyl-4H-1,2,4-triazol-3-yl)-1H-pyrazol-5-yl)pyridin-2-yl)-4-(trifluoromethyl)isoindolin-1-one (ABC-7)

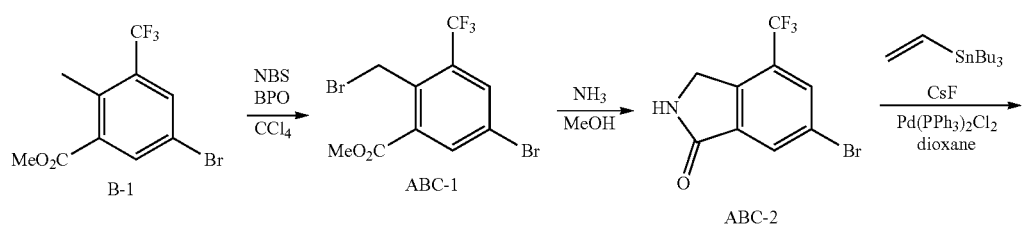

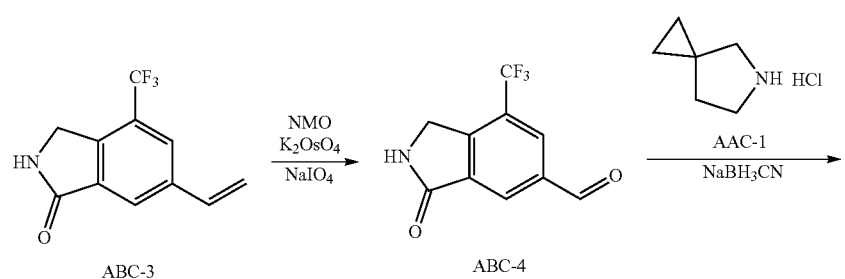

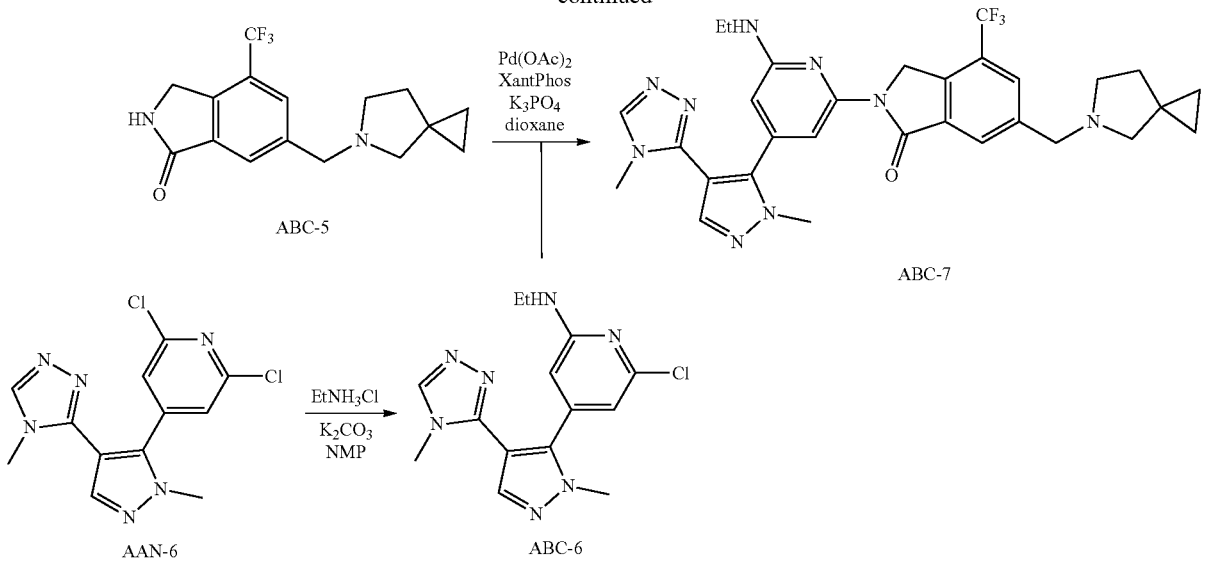

Step 1: Synthesis of Methyl 5-bromo-2-(bromomethyl)-3-(trifluoromethyl)benzoate (ABC-1)

To a stirred solution of intermediate (B-1) (2.70 g, 1 Eq, 9.09 mmol) in carbon tetrachloride (80 mL) were added NBS (2.43 g, 1.5 Eq, 13.6 mmol) and BPO (700 mg, 0.3 Eq, 2.73 mmol) at rt under nitrogen atmosphere. The resulting mixture was stirred for 16 h at 80° C. under nitrogen atmosphere then cooled to rt and concentrated in vacuo. The residue was applied on a silica gel column chromatography with petroleum ether/EtOAc (50/1) to afford the sub-title compound (ABC-1) (2.7 g, 7.18 mmol, 79%) as a yellow solid. m/z 377.0/379.0 (M+H)+ (ES+).

Step 2: Synthesis of 6-Bromo-4-(trifluoromethyl)isoindolin-1-one (ABC-2)

A solution of the product from step 1 above (ABC-1) (2.70 g, 1 Eq, 7.18 mmol) in ammonia MeOH solution (80 ml, 7 M) was stirred for 16 h at rt. The resulting mixture was concentrated in vacuo. The residue was applied on a silica gel column chromatography with petroleum ether/EtOAc (2/1) to afford the sub-title compound (ABC-2) (1.2 g, 4.32 mmol, 60%) as a yellow solid. m/z 279.0/281.0 (M+H)+ (ES+).

Step 3: Synthesis of 4-(Trifluoromethyl)-6-vinylisoindolin-1-one (ABC-3)

To a stirred solution of the product from step 2 above (ABC-2) (1.00 g, 1 Eq, 3.57 mmol), tri-tert-butyl(ethenyl)stannane (1.36 g, 1.2 Eq, 4.29 mmol) and cesium fluoride (1.08 g, 2 Eq, 7.14 mmol) in dioxane (30 mL) was added Pd(PPh$_3$)$_2$Cl$_2$ (501 mg, 714 μmol, 0.2 Eq) at rt under nitrogen atmosphere. The resulting mixture was stirred for 3 h at 100° C. under nitrogen atmosphere. The resulting mixture was diluted with water. The resulting mixture was extracted with EtOAc (3×100 mL). The combined organic layers were washed with brine (2×100 mL), dried (Na$_2$SO$_4$), filtered and concentrated in vacuo. The residue was purified by Prep-TLC with EtOAc/petroleum ether (2/1) to afford the sub-title compound (ABC-3) (620 mg, 2.73 mmol, 76%) as a yellow solid. m/z 228.1 (M+H)+ (ES+).

Step 4: Synthesis of 3-Oxo-7-(trifluoromethyl)isoindoline-5-carbaldehyde (ABC-4)

To a solution of the product from step 3 above (ABC-3) (620 mg, 1 Eq, 2.73 mmol), citric acid (682 mg, 1.3 Eq, 3.55 mmol) and NMO (416 mg, 1.3 Eq, 3.55 mmol) in water (10 mL) were added potassium osmate(VI) dihydrate (101 mg, 0.1 Eq, 273 μmol) in tBuOH (10 mL) and the mixture stirred for 2 h at rt. To the above mixture was added sodium periodate (1.17 mg, 2 Eq, 5.46 mmol) at rt and the resulting mixture stirred for additional 3 h at rt. The resulting mixture was diluted with water and extracted with EtOAc (3×80 mL). The combined organic layers were washed with brine (2×80 mL), dried (Na$_2$SO$_4$), filtered and concentrated in vacuo. The crude product was purified by reverse flash column chromatography with the following conditions: Column, C18; mobile phase, Water (0.1% NH$_4$HCO$_3$) and ACN (0% ACN up to 40% in 12 min); Detector, UV 254/220 nm. This resulted in the sub-title compound (ABC-4) (500 mg, 2.17 mmol, 80%) as a yellow solid. m/z 230.0 (M+H)+ (ES+).

Step 5: Synthesis of 6-((5-Azaspiro [2.4] heptan-5-yl) methyl)-4-(trifluoromethyl)isoindolin-1-one (ABC-5)

To a stirred solution of the product from step 4 above (ABC-4) (200 mg, 1 Eq, 873 μmol) and 5-azaspiro [2.4] heptane, HCl (AAC-1) (117 mg, 1 Eq, 873 μmol,) in MeOH (5 mL) was added NaBH$_3$CN (274 mg, 5 Eq, 4.37 mmol) at rt under nitrogen atmosphere. The resulting mixture was stirred for 6 h at rt under nitrogen atmosphere. The resulting mixture was diluted with water and extracted with EtOAc (3×50 mL). The combined organic layers were washed with brine (2×50 mL), dried (Na$_2$SO$_4$), filtered and concentrated in vacuo. The crude product was purified by reverse flash column chromatography with the following conditions: Column, C18; mobile phase, Water (0.1% FA) and ACN (10%

ACN up to 50% in 15 min); Detector, UV 254/220 nm. This resulted in the sub-title compound (ABC-5) (93 mg, 300 μmol, 34%) as a yellow oil. m/z 311.1 (M+H)+ (ES+).

Step 6: Synthesis of 6-Chloro-N-ethyl-4-(1-methyl-4-(4-methyl-4H-1,2,4-triazol-3-yl)-1H-pyrazol-5-yl)pyridin-2-amine (ABC-6)

To a stirred mixture of intermediate (AAN-6) (1.00 g, 1 Eq, 3.24 mmol) and ethylamine, HCl (2.64 g 10 Eq, 32.4 mmol) in NMP (25 mL) was added K$_2$CO$_3$ (4.47 g, 10 Eq, 32.4 mmol) at rt under nitrogen atmosphere. The resulting mixture was stirred for overnight at 100° C. under nitrogen atmosphere then cooled to rt. The crude product was purified by reverse flash column chromatography with the following conditions: Column, C18; mobile phase, Water (0.1% FA) and ACN (10% ACN up to 30% in 20 min); Detector, UV 254/220 nm to afford the sub-title compound (ABC-6) (800 mg, 2.52 mmol, 78%) as a brown solid. m/z 318.1/320.1 (M+H)+ (ES+).

Step 7: 6-((5-Azaspiro [2.4] heptan-5-yl)methyl)-2-(6-(ethylamino)-4-(1-methyl-4-(4-methyl-4H-1,2,4-triazol-3-yl)-1H-pyrazol-5-yl)pyridin-2-yl)-4-(trifluoromethyl) Above isoindolin-1-one (ABC-7)

Into a 25-mL round-bottom flask, was placed the product from step 6 (ABC-6) (50.00 mg, 1 Eq, 157 μmol), the product from step 5 above (ABC-5) (49 mg, 1 Eq, 157 μmol) and potassium phosphate (100 mg, 3 Eq, 471 μmol) in 1,4-dioxane (3 mL), then palladium acetate (7 mg, 0.2 Eq, 31 μmol) and XantPhos (36 mg, 0.4 Eq, 63 μmol) were added at rt. The resulting solution was stirred overnight at 80° C. then cooled to rt and concentrated. The crude product was purified by Prep-HPLC with the following conditions: Column: XBridge Prep C18 OBD Column, 30×100 mm, 5 μm; Mobile Phase A: Water (0.1% NH$_4$HCO$_3$), Mobile Phase B: ACN; Flow rate: 60 mL/min; Gradient: 40 B to 60 B in 10 min; Detector, UV 220/254 nm; RT: 9.67. This resulted in the title compound (ABC-7) (10.2 mg, 11%) as a white solid. m/z 592.2 (M+H)+ (ES+). $^1$H NMR (400 MHz, MeOH-d4) δ 8.49 (s, 1H), 8.08 (s, 1H), 8.02 (s, 1H), 7.87 (s, 1H), 7.65 (d, J=1.2 Hz, 1H), 6.20 (d, J=1.2 Hz, 1H), 5.26 (d, J=1.8 Hz, 2H), 4.04 (s, 3H), 3.91 (s, 2H), 3.50 (s, 3H), 3.42-3.34 (m, 2H), 2.88 (t, J=7.0 Hz, 2H), 2.62 (s, 2H), 1.90 (t, J=7.0 Hz, 2H), 1.25 (t, J=7.2 Hz, 3H), 0.65-0.55 (m, 4H).

Example 65: Synthesis of 6-((5-Azaspiro [2.4] heptan-5-yl)methyl)-2-(6-chloro-4-(1-methyl-4-(4-methyl-4H-1,2,4-triazol-3-yl)-1H-pyrazol-5-yl)pyridin-2-yl)-4-(trifluoromethyl)isoindolin-1-one (ABD-1)

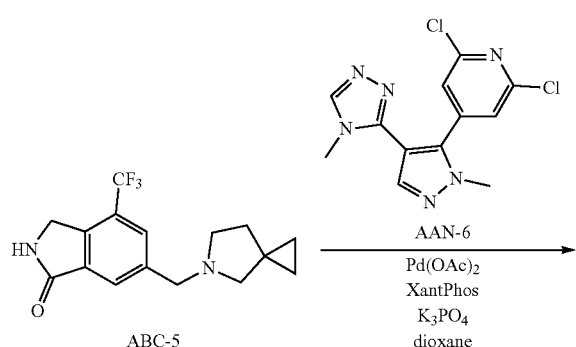

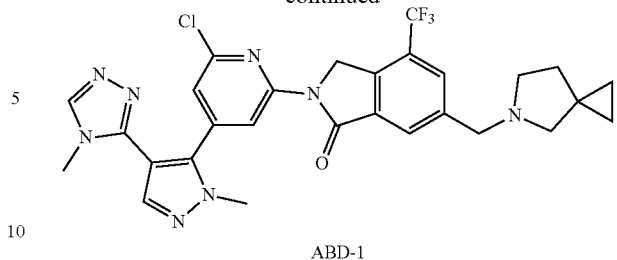

Into a 25-mL round-bottom flask, was placed intermediate (ABC-5) (20 mg, 1 Eq, 64 μmol), intermediate (AAN-6) (20 mg, 1 Eq, 64 μmol) and potassium phosphate (41 mg, 3 Eq, 193 μmol) in 1,4-dioxane (3 mL), then palladium acetate (3 mg, 0.2 Eq, 13 μmol) and XantPhos (15 mg, 0.4 Eq, 26 μmol) were added at rt under nitrogen atmosphere. The resulting solution was stirred overnight at 80° C. under nitrogen atmosphere. The resulting mixture was cooled to rt and concentrated. The crude product was purified by Prep-HPLC with the following conditions: Column: XBridge Prep C18 OBD Column, 30×150 mm, 5 μm; Mobile Phase A: Water (0.1% NH$_4$HCO$_3$), Mobile Phase B: ACN; Flow rate: 60 mL/min; Gradient: 45 B to 75 B in 7 min; Detector, UV 210/254 nm; RT: 4.85. This resulted in the title compound (ABD-1) (1.2 mg, 2.1 μmol, 3.2%) as a white solid. m/z 583.1 (M+H)+ (ES+). $^1$H NMR (400 MHz, MeOH-d4) δ 8.52 (s, 1H), 8.48 (d, J=1.17 Hz, 1H), 8.10 (s, 1H), 8.04 (s, 1H), 7.96 (s, 1H), 7.34 (d, J=1.2 Hz, 1H), 5.29-5.24 (m, 2H), 4.05 (s, 3H), 3.87 (s, 2H), 3.68 (s, 3H), 2.83 (t, J=7.0 Hz, 2H), 2.57 (s, 2H), 1.89 (t, J=7.0 Hz, 2H), 0.61-0.54 (m, 4H).

Example 66: Synthesis of 6-((5-Azaspiro [2.4] heptan-5-yl)methyl)-2-(6-hydroxy-4-(1-methyl-4-(4-methyl-4H-1,2,4-triazol-3-yl)-1H-pyrazol-5-yl)pyridin-2-yl)-4-(trifluoromethyl)isoindolin-1-one (ABE-1)

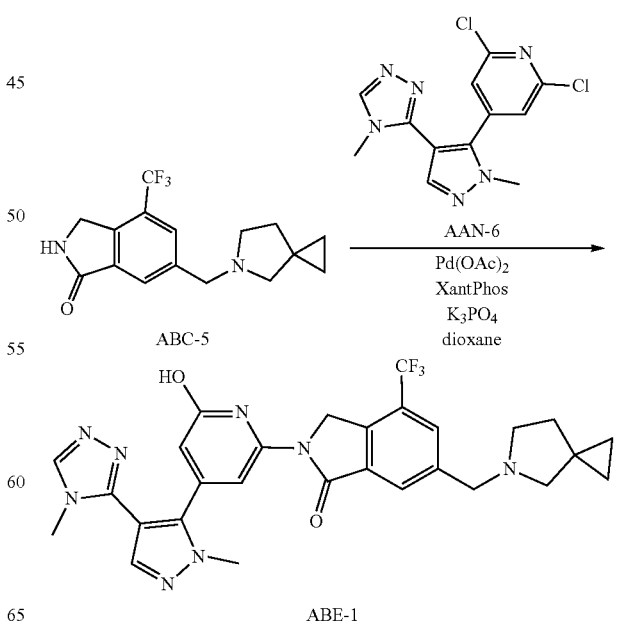

Into a 25-mL round-bottom flask, was placed intermediate (ABC-5) (60 mg, 1 Eq, 193 μmol), intermediate (AAN-6) (72 mg, 1.2 Eq, 232 μmol) and potassium phosphate (123 mg, 3 Eq, 579 μmol) in 1,4-dioxane (3 mL), then palladium acetate (9 mg, 0.2 Eq, 39 μmol) and XantPhos (45 mg, 0.4 Eq, 77 μmol) were added at rt under nitrogen atmosphere. The resulting solution was stirred overnight at 80° C. under nitrogen atmosphere then cooled to rt and concentrated. The crude product was purified by Prep-HPLC with the following conditions: Column: XBridge Prep C18 OBD Column, 30×150 mm, 5 μm; Mobile Phase A: Water (0.1% NH₄HCO₃), Mobile Phase B: ACN; Flow rate: 60 mL/min; Gradient: 45 B to 75 B in 7 min; Detector, UV 210/254 nm; RT: 4.85. This resulted in the title compound (ABE-1) (11.0 mg, 9.9%) as a white solid. m/z 565.2 (M+H)$^+$ (ES+). $^1$H NMR (400 MHz, MeOH-d4) δ 8.50 (s, 1H), 8.07 (s, 1H), 8.02 (s, 1H), 7.89 (s, 1H), 7.84 (s, 1H), 6.43 (s, 1H), 5.22 (s, 2H), 4.04 (s, 3H), 3.88 (s, 2H), 3.55 (s, 3H), 2.85 (t, J=7.0 Hz, 2H), 2.59 (s, 2H), 1.89 (t, J=6.9 Hz, 2H), 0.64-0.54 (m, 4H).

Example 67: Synthesis of 4-((5-Azaspiro [2.4] heptan-5-yl)methyl)-6-cyclopropyl-N-(6-(ethylamino)-4-(1-methyl-4-(4-methyl-4H-1,2,4-triazol-3-yl)-1H-pyrazol-5-yl)pyridin-2-yl)picolinamide (ABF-8)

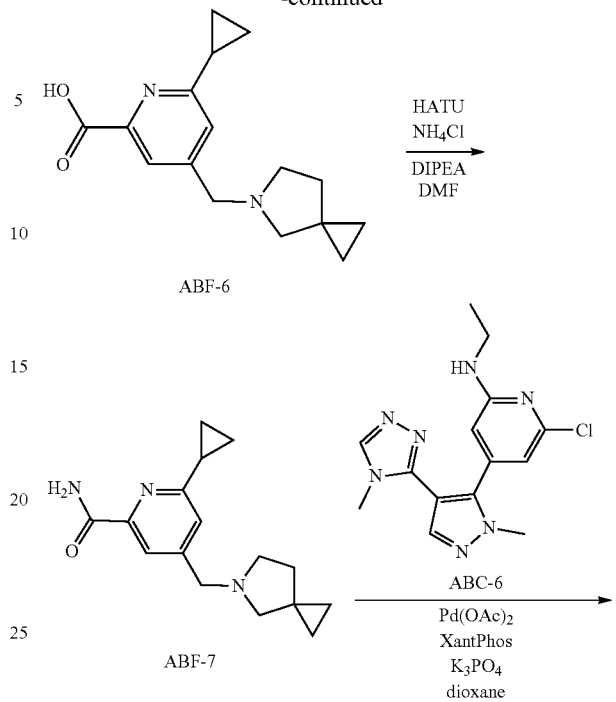

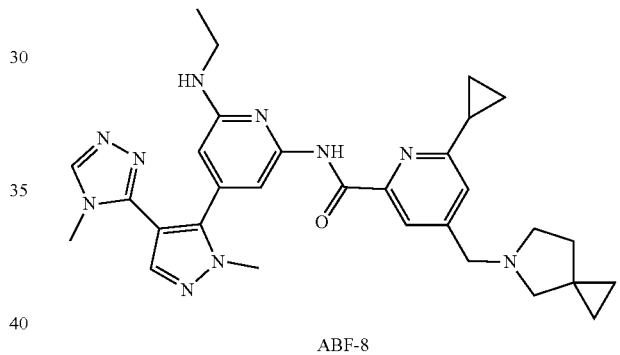

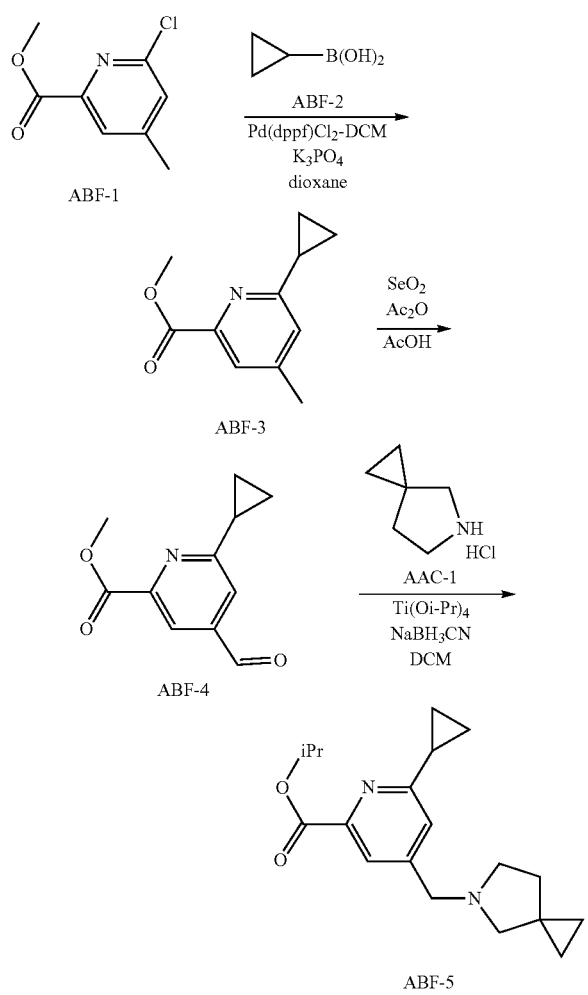

Step 1: Synthesis of methyl 6-cyclopropyl-4-methylpicolinate (ABF-3)

To a stirred solution of methyl 6-chloro-4-methylpyridine-2-carboxylate (ABF-1) (2.00 g, 1 Eq, 10.8 mmol), cyclopropylboronic acid (ABF-2) (1.39 g, 1.5 Eq, 16.2 mmol) and potassium phosphate (4.58 g, 2 Eq, 21.6 mmol) in dioxane (40 mL) was added Pd(dppf)Cl₂.DCM (788 mg, 0.1 Eq, 1.08 mmol) at rt under nitrogen atmosphere. The resulting mixture was stirred overnight at 100° C. under nitrogen atmosphere then cooled to rt, diluted with water and extracted with EtOAc (3×100 mL). The combined organic layers were washed with brine (2×100 mL), dried (Na₂SO₄), filtered and concentrated in vacuo. The residue was applied on a silica gel column chromatography with petroleum ether/EtOAc (10/1) to afford the sub-title compound (ABF-3) (750 mg, 3.92 mmol, 36%) as a yellow oil. m/z 192.1 (M+H)$^+$ (ES+).

Step 2: Synthesis of Methyl 6-cyclopropyl-4-formylpicolinate (ABF-4)

A solution of the product from step 1 above (ABF-3) (931 mg, 1 Eq, 4.87 mmol), selenium dioxide (810 mg, 1.5 Eq, 7.30 mmol) and acetic anhydride (1.99 g, 4 Eq, 19.5 mmol) in acetic acid (18.6 mL) was stirred for 8 h at 105° C. The mixture was cooled to rt, diluted with water and extracted with EtOAc (3×100 mL). The combined organic layers were washed with brine (2×200 mL), dried (Na$_2$SO$_4$), filtered and concentrated in vacuo. The residue was purified by Prep-TLC with EtOAc/petroleum ether (1/5) to afford the sub-title compound (ABF-4) (460 mg, 2.24 mmol, 86%) as light yellow oil. m/z 206.1 (M+H)$^+$ (ES+).

Step 3: Synthesis of Isopropyl 4-((5-azaspiro [2.4] heptan-5-yl) methyl)-6-cyclopropylpicolinate (ABF-5)

To a stirred mixture of the product from step 2 above (ABF-4) (600 mg, 1 Eq, 2.92 mmol) and 5-azaspiro [2.4] heptane, HCl (AAC-1) (781 mg, 2 Eq, 5.85 μmol) in DCM (30 mL) were added NaBH$_3$CN (735 mg, 4 Eq, 11.7 mmol) and Ti(OiPr)$_4$ (3.32 g, 4 Eq, 11.7 mmol) at 0° C. under nitrogen atmosphere and the resulting mixture was stirred. The resulting mixture was concentrated in vacuo and purified by Prep-TLC with EtOAc/petroleum ether (1/1) to afford the sub-title compound (ABF-5) (274 mg, 873 μmol, 26%) as a light brown oil. m/z 315.2 (M+H)$^+$ (ES+).

Step 4: Synthesis of 4-((5-Azaspiro [2.4] heptan-5-yl) methyl)-6-cyclopropylpicolinic acid (ABF-6)

To a stirred solution of the product from step 3 above (ABF-5) (300 mg, 1 Eq, 1.05 mmol) in a mixture of THF (10 mL) and water (2 mL) was added LiOH (125 mg, 5 Eq, 5.24 mmol) at rt. The resulting mixture was stirred for 2 h at 70° C. then the resulting mixture cooled to rt and concentrated in vacuo. The mixture was acidified to pH 6 with HCl (aq., 1M). The resulting mixture was extracted with (chloroform: isopropyl alcohol=3:1) (5×30 mL). The combined organic layers were washed with brine (2×30 mL), dried (Na$_2$SO$_4$) and concentrated in vacuo. This resulted in the sub-title compound (ABF-6) (170 mg, 625 μmol, 60%) as an off-white solid. m/z 273.2 (M+H)$^+$ (ES+).

Step 5: Synthesis of 4-((5-Azaspiro [2.4] heptan-5-yl) methyl)-6-cyclopropylpicolinamide (ABF-7)

To a stirred solution of the product from step 4 above (ABF-6) (50 mg, 1 Eq, 184 μmol) and DIPEA (71 mg, 3 Eq, 552 μmol) in DMF (1.5 mL) were added HATU (105 mg, 1.5 Eq, 276 μmol) and NH$_4$Cl (98 mg, 10 Eq, 1.84 mmol) at rt. The resulting mixture was stirred for 2 h at rt then concentrated in vacuo. The residue was purified by Prep-TLC with DCM/MeOH (10/1) to afford the sub-title compound (ABF-7) (39 mg, 144 μmol, 78%) as a light yellow oil. m/z 272.2 (M+H)$^+$ (ES+).

Step 6: Synthesis of 4-((5-Azaspiro [2.4] heptan-5-yl) methyl)-6-cyclopropyl-N-(6-(ethylamino)-4-(1-methyl-4-(4-methyl-4H-1,2,4-triazol-3-yl)-1H-pyrazol-5-yl)pyridin-2-yl)picolinamide (ABF-8)

To a solution of intermediate (ABC-6) (40 mg, 1 Eq, 126 μmol), the product from step 5 above (ABF-7) (34 mg, 1 Eq, 126 μmol) and potassium phosphate (53 mg, 252 μmol, 2 Eq) in 1,4-dioxane (1.5 mL) were added Pd(OAc)$_2$ (3 mg, 0.1 Eq, 13 μmol) and XantPhos (15 mg, 0.2 Eq, 25 μmol) at rt with stirring overnight at 100° C. under nitrogen atmosphere, the resulting mixture was cooled to rt, diluted with water and extracted with EtOAc (3×20 mL). The combined organic layers were washed with brine (2×20 mL), dried (Na$_2$SO$_4$), filtered and concentrated in vacuo. The crude product was purified by Prep-HPLC with the following conditions (Column: XBridge Prep C18 OBD Column, 30*100 mm, 5 μm; Mobile Phase A: Water (0.1% NH$_4$HCO$_3$), Mobile Phase B: ACN; Flow rate: 60 mL/min; Gradient: 40% B to 60% B in 9 min; Wavelength: 254/220 nm; RT: 8.85) to afford the title compound (ABF-8) (9.1 mg, 16 μmol, 13%) as a white solid. m/z 553.5 (M+H)$^+$ (ES+). $^1$H NMR (300 MHz, DMSO-d6) δ 10.01 (s, 1H), 8.47 (s, 1H), 7.87 (d, J=2.9 Hz, 2H), 7.51 (d, J=1.4 Hz, 1H), 7.31 (d, J=1.2 Hz, 1H), 6.86 (t, J=5.4 Hz, 1H), 6.24 (d, J=1.2 Hz, 1H), 3.89 (s, 3H), 3.68 (s, 2H), 3.44 (s, 3H), 3.22 (dd, J=7.3, 5.5 Hz, 2H), 2.69 (t, J=6.8 Hz, 2H), 2.45 (s, 2H), 2.29-2.24 (m, 1H), 1.77 (t, J=6.8 Hz, 2H), 1.19-0.95 (m, 7H), 0.55-0.47 (m, 4H).

Example 68: Synthesis of 2-(6-(Aminomethyl)-4-(1-methyl-4-(4-methyl-4H-1,2,4-triazol-3-yl)-1H-pyrazol-5-yl)pyridin-2-yl)-4-(trifluoromethyl)isoindolin-1-one (ABG-3)

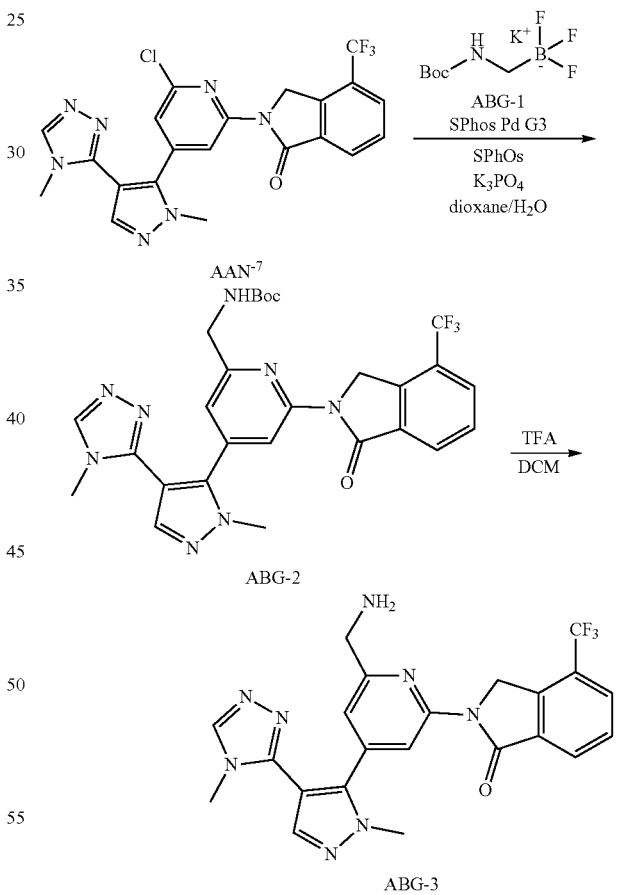

Step 1: Synthesis of tert-Butyl ((4-(1-methyl-4-(4-methyl-4H-1,2,4-triazol-3-yl)-1H-pyrazol-5-yl)-6-(1-oxo-4-(trifluoromethyl)isoindolin-2-yl)pyridin-2-yl) methyl)carbamate (ABG-2)

To a stirred mixture of intermediate (AAN-7) (150 mg, 1 Eq, 317 μmol), tert-butyl N-[(trifluoro-lambda4-boranyl)

methyl] carbamate (ABG-1) (125 mg, 2 Eq, 633 µmol), potassium (25 mg, 2 Eq, 633 µmol) and potassium phosphate (134 mg, 2 Eq, 633 µmol) in dioxane (10 mL) and water (2 mL) were added SPhos Pd Gen.3 (49 mg, 0.2 Eq, 63 µmol) and SPhOs (52 mg, 0.4 Eq, 127 µmol) at rt under nitrogen atmosphere. The mixture was stirred for 15 h at 90° C. under nitrogen atmosphere then cooled to rt and concentrated in vacuo. The crude product was purified by reverse flash column chromatography with the following conditions: Column, C18; mobile phase, Water (0.1% $NH_4HCO_3$) and ACN (10% ACN up to 60% in 20 min); Detector, UV 254/220 nm to afford the sub-title compound (ABG-2) (155 mg, 273 µmol, 86%) as a white solid. m/z 569.1 $(M+H)^+$ (ES+).

Step 2: Synthesis of 2-(6-(Aminomethyl)-4-(1-methyl-4-(4-methyl-4H-1,2,4-triazol-3-yl)-1H-pyrazol-5-yl)pyridin-2-yl)-4-(trifluoromethyl)isoindolin-1-one (ABG-3)

To a stirred mixture of the product from step 1 above (ABG-2) (30 mg, 1 Eq, 50 µmol) in DCM (2 mL) was added TFA (0.4 mL) at 0° C. under nitrogen atmosphere. The mixture was stirred for 2 h at rt then concentrated and purified by prep-HPLC with the following conditions: Column: XBridge Prep C18 OBD Column, 30*100 mm, 5 µm; Mobile Phase A: Water (0.11% $NH_4HCO_3$), Mobile Phase B: ACN; Flow rate: 60 mL/min; Gradient: 25 B to 50 B in 9 min; Detector, UV 254/220 nm; RT: 8.85 to afford the title compound (ABG-3) (10.4 mg, 22 µmol, 40%) as a white solid. m/z 469.1 $(M+H)^+$ (ES+). $^1H$ NMR (400 MHz, DMSO-d6) δ 8.48 (s, 1H), 8.30 (d, J=1.3 Hz, 1H), 8.10 (dd, J=15.6, 7.7 Hz, 2H), 7.97 (s, 1H), 7.81 (t, J=7.7 Hz, 1H), 7.38 (d, J=1.3 Hz, 1H), 5.30 (s, 2H), 3.92-3.90 (m, 5H), 3.54 (s, 3H).

Example 69: Synthesis of 2-(6-Ethoxy-4-(1-methyl-4-(4-methyl-4H-1,2,4-triazol-3-yl)-1H-pyrazol-5-yl)pyridin-2-yl)-4-(trifluoromethyl)isoindolin-1-one (ABH-2)

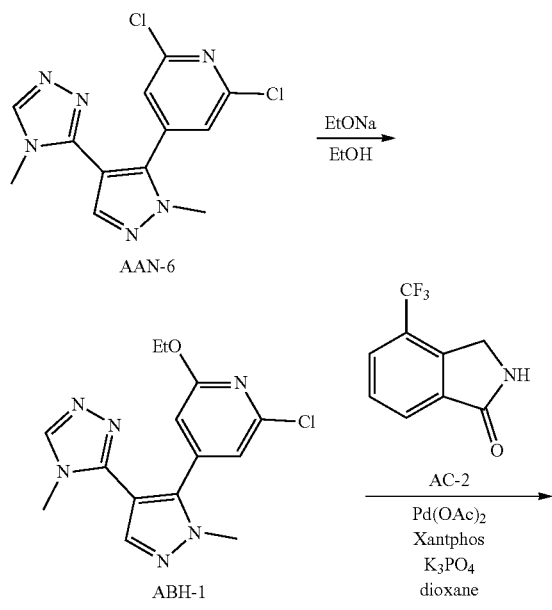

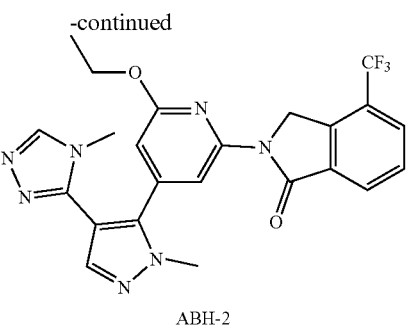

Step 1: Synthesis of 2-Chloro-6-ethoxy-4-[2-methyl-4-(4-methyl-1,2,4-triazol-3-yl)-pyrazol-3-yl]-pyridine (ABH-1)

To a stirred solution of intermediate (AAN-6) (100 mg, 1 Eq, 320 µmol) and NaOEt (44 mg, 2 Eq, 640 µmol) in EtOH (8 mL) at rt. The resulting mixture was stirred for 16 h at 60° C. The mixture was cooled to rt, diluted with water and extracted with EtOAc (3×20 mL). The combined organic layers were washed with brine (2×20 mL), dried ($Na_2SO_4$), filtered and concentrated in vacuo. This resulted in the sub-title compound (ABH-1) (80 mg, 251 µmol, 77%) as a white solid. m/z 319.1/321.1 $(M+H)^+$ (ES+).

Step 2: Synthesis of 2-(6-Ethoxy-4-(1-methyl-4-(4-methyl-4H-1,2,4-triazol-3-yl)-1H-pyrazol-5-yl)pyridin-2-yl)-4-(trifluoromethyl)isoindolin-1-one (ABH-2)

To a stirred mixture of the product from step 1 above (ABH-1) (80 mg, 1 Eq, 251 µmol), intermediate (AC-2) (60 mg, 1.2 Eq, 300 µmol) and potassium phosphate (106.5 mg, 0.50 mmol, 2.0 Eq) in dioxane (8 mL) were added Xantphos (29 mg, 0.2 Eq, 50 µmol) and $Pd(OAc)_2$ (6 mg, 0.1 Eq, 20 µmol) at rt under nitrogen atmosphere. The resulting mixture was stirred for 16 h at 100° C. under nitrogen atmosphere. The resulting mixture was cooled to rt and the crude product purified by reverse flash column chromatography with the following conditions: Column, C18; mobile phase, Water (0.1% $NH_4HCO_3$) and ACN (30% ACN up to 40% in 8 min); Detector, UV 254/220 nm. The product-containing fractions were combined and concentrated in vacuo. The crude product was purified by Prep-HPLC with the following conditions: Column: SunFire Prep C18 OBD Column, 19×150 mm 5 um; Mobile Phase A: Water (0.1% $NH_4HCO_3$), Mobile Phase B: ACN; Flow rate:60 mL/min; Gradient:31 B to 51 B in 10 min; Detector, UV 254/210 nm; RT: 9.67. The product-containing fractions were combined and evaporated partially in vacuo and lyophilized overnight to afford the title compound (ABH-2) (54.7 mg, 113 µmol, 44%) as a white solid. m/z 484.1 $(M+H)^+$ (ES+). $^1H$ NMR (300 MHz, MeOH-d4) δ 8.50 (s, 1H), 8.10-7.96 (m, 3H), 7.91 (s, 1H), 7.78 (t, J=7.7 Hz, 1H), 6.62 (d, J=1.2 Hz, 1H), 5.31 (s, 2H), 4.53-4.39 (m, 2H), 4.04 (s, 3H), 3.58 (s, 3H), 1.45 (t, J=7.1 Hz, 3H).

Example 70: Synthesis of 2-(6-(Isopropylamino)-4-(1-methyl-4-(4-methyl-4H-1,2,4-triazol-3-yl)-1H-pyrazol-5-yl)pyridin-2-yl)-4-(trifluoromethyl)isoindolin-1-one (ABI-1)

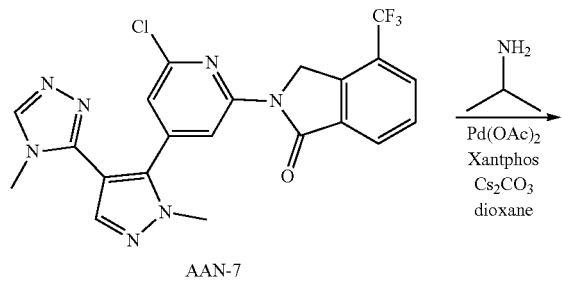

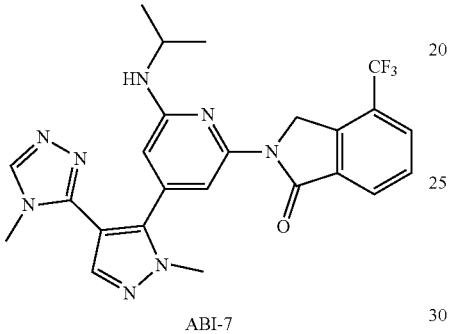

To a stirred mixture of intermediate (AAN-7) (95 mg, 1 Eq, 200 μmol), isopropylamine (59 mg, 5 Eq, 1.00 mmol) and Cs₂CO₃ (523 mg, 8 Eq, 1.60 mmol) in dioxane (8 mL) were added and Pd(OAc)₂ (5 mg, 0.1 Eq, 20 μmol) and Xantphos (23 mg, 0.2 Eq, 40 μmol) at rt under nitrogen atmosphere. The resulting mixture was stirred for 16 h at 100° C. under nitrogen atmosphere then cooled to rt. The crude product was purified by reverse flash column chromatography with the following conditions: Column, C18; mobile phase, Water (0.1% NH₄HCO₃) and ACN (40% ACN up to 70% in 10 min); Detector, UV 254/220 nm. The product-containing fractions were combined and concentrated in vacuo. The crude product was purified by Prep-HPLC with the following conditions: Column: SunFire Prep C18 OBD Column, 30×150 mm 5 um; Mobile Phase A: Water (0.1% NH₄HCO₃), Mobile Phase B: ACN; Flow rate:60 mL/min; Gradient:33 B to 58 B in 9 min; Detector, UV 254/210 nm; RT: 8.85. The product-containing fractions were combined and evaporated partially in vacuo and lyophilized overnight to afford the title compound (ABI-1) (10.6 mg, 21 μmol, 10%) as a white solid. m/z 497.1 (M+H)⁺ (ES+) ¹H NMR (300 MHz, MeOH-d4) δ 8.49 (s, 1H), 8.09 (d, J=7.7 Hz, 1H), 7.99 (d, J=7.7 Hz, 1H), 7.86 (s, 1H), 7.77 (t, J=7.7 Hz, 1H), 7.64 (d, J=1.2 Hz, 1H), 6.20 (d, J=1.2 Hz, 1H), 5.27 (s, 2H), 4.12-3.97 (m, 4H), 3.51 (s, 3H), 1.25 (d, J=6.4 Hz, 6H).

Example 71: Synthesis of 2-Cyclopropyl-N-(6-(ethylamino)-4-(1-methyl-4-(4-methyl-4H-1,2,4-triazol-3-yl)-1H-pyrazol-5-yl)pyridin-2-yl)-6-methylpyrimidine-4-carboxamide (ABJ-4)

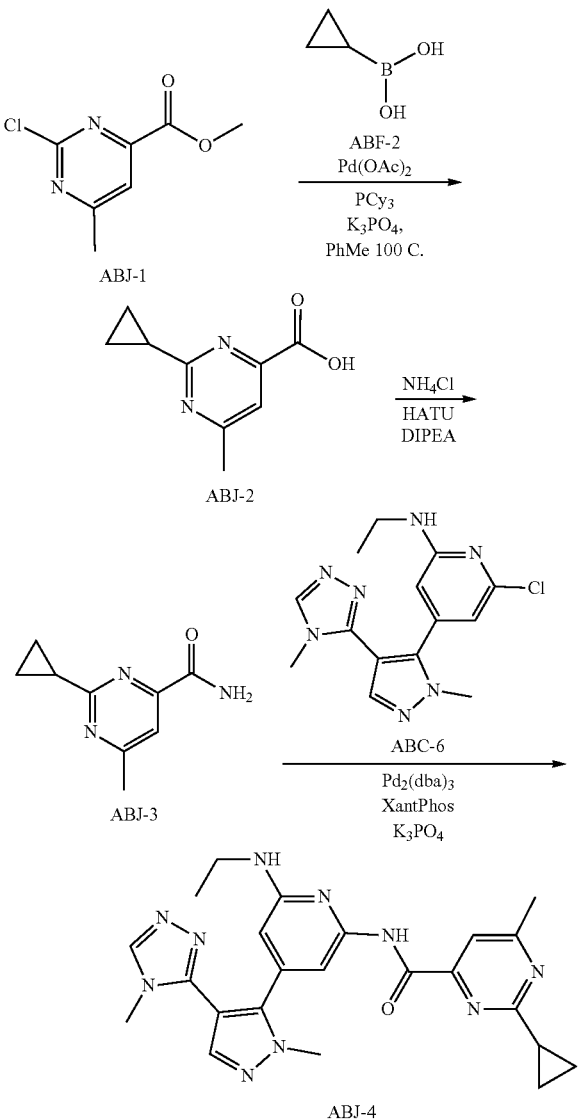

Step 1: Synthesis of 2-Cyclopropyl-6-methylpyrimidine-4-carboxylic acid (ABJ-2)

Into a 40 mL sealed tube were added methyl 2-chloro-6-methylpyrimidine-4-carboxylate (ABJ-1) (1.00 g, 1 Eq, 5.36 mmol), cyclopropylboronic acid (ABF-2) (921 mg, 2 Eq, 10.7 mmol) and potassium phosphate (4.55 g, 4 Eq, 21.4 mmol) in Toluene (15 mL) at rt under nitrogen atmosphere. To the above mixture was added Pd(OAc)₂ (60 mg, 0.05 Eq, 268 μmol) and PCy3 (150 mg, 0.1 Eq, 536 μmol) over 3 min at rt under nitrogen atmosphere. The resulting mixture was stirred for overnight at 110° C. under nitrogen atmosphere then cooled to rt, diluted with water and extracted with EtOAc (3×80 mL). The combined organic layers were washed with brine (2×80 mL), dried (Na$_2$SO$_4$), filtered and concentrated in vacuo. The crude product was purified by reverse flash column chromatography with the following conditions: Column, C18; mobile phase, Water (0.1% NH$_4$HCO$_3$) and ACN (36% ACN up to 48% in 10 min); Detector, UV 254/220 nm. The product-containing fractions were combined and concentrated in vacuo. This resulted in the sub-title compound (ABJ-2) (660 mg, 3.71 mmol, 69%) as a yellow oil. m/z 179.1 (M+H)$^+$ (ES+).

Step 2: Synthesis of 2-Cyclopropyl-6-methylpyrimidine-4-carboxamide (ABJ-3)

Into a 40 mL sealed tube were added the product from step 1 above (ABJ-2) (534 mg, 1 Eq, 3.00 mmol), NH$_4$Cl (802 mg, 5 Eq, 15.0 mmol) and DIPEA (3.87 g, 10 Eq, 30.0 mmol) in THF (10 mL) at rt. To the above mixture was added HATU (2.28 g, 2 Eq, 5.99 mmol) over 3 min at 0° C.a and the resulting mixture stirred for 3 h at rt. The resulting mixture was concentrated in vacuo to afford the sub-title compound (ABJ-3) (310 mg, 1.75 mmol, 58%) as a white solid. m/z 178.1 (M+H)$^+$ (ES+).

Step 3: Synthesis of 2-Cyclopropyl-N-(6-(ethyl-amino)-4-(1-methyl-4-(4-methyl-4H-1,2,4-triazol-3-yl)-1H-pyrazol-5-yl)pyridin-2-yl)-6-methylpyrimidine-4-carboxamide (ABJ-4)

Into an 8 mL sealed tube were added intermediate (ABC-6) (55 mg, 1 Eq, 173 μmol), potassium phosphate (110 mg, 3 Eq, 519 μmol) and the product from step 2 above (ABJ-3) (37 mg, 1.2 Eq, 208 μmol) in 1,4-dioxane (4 mL) at rt under nitrogen atmosphere. To the above mixture was added Pd$_2$(dba)$_3$ (32 mg, 0.2 Eq, 35 μmol) and XantPhos (40 mg, 0.4 Eq, 69 μmol) over 3 min under nitrogen atmosphere and the resulting mixture stirred for 3 h at 100° C. The mixture was cooled to rt and concentrated in vacuo. The residue was purified by Prep-TLC with DCM/MeOH (10/1). The crude product was purified by Prep-HPLC with the following conditions (Column: XBridge Prep C18 OBD Column, 30*100 mm, 5 μm; Mobile Phase A: Water (0.1% NH$_4$HCO$_3$+0.1% NH$_3$·H$_2$O), Mobile Phase B: ACN; Flow rate: 60 mL/min; Gradient: 25% B to 50% B in 9 min; Wavelength: 254/220 nm; RT: 7.53;) to afford the title compound (ABJ-4) (31.8 mg, 69 μmol, 40%) as a white solid. m/z 459.2 (M+H)$^+$ (ES+). $^1$H NMR (400 MHz, DMSO-d6) δ 9.97 (s, 1H), 8.47 (s, 1H), 7.88 (s, 1H), 7.75 (s, 1H), 7.29 (d, J=1.3 Hz, 1H), 6.90 (t, J=5.4 Hz, 1H), 6.28 (d, J=1.3 Hz, 1H), 3.89 (s, 3H), 3.44 (s, 3H), 3.30-3.19 (m, 2H), 2.53 (s, 3H), 2.37-2.26 (m, 1H), 1.18-1.05 (m, 7H).

Example 72: Synthesis of 2-Cyclopropyl-N-(2'-(4-methyl-4H-1,2,4-triazol-3-yl)-[1,1'-biphenyl]-3-yl)-6-(2-(pyrrolidin-1-yl)ethoxy)pyrimidine-4-carboxamide (ABK-7)

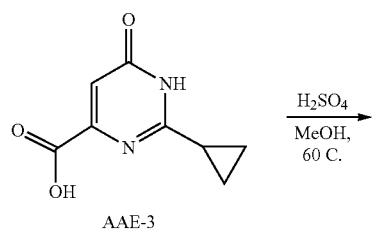

Step 1: Synthesis of Methyl 2-cyclopropyl-6-oxo-1H-pyrimidine-4-carboxylate (ABK-1)

To a stirred mixture of intermediate (AAE-3) (5.00 g, 1 Eq, 27.8 mmol) in MeOH (150 mL) was added sulfuric acid (5 mL) drop-wise at 0° C. The mixture was stirred for 2 h at 60° C. then allowed to cool to rt. The resulting mixture was concentrated in vacuo and the crude product purified by reverse flash column chromatography with the following conditions: Column, C18; mobile phase, Water (0.1% NH$_4$HCO$_3$) and ACN (0% ACN up to 30% in 10 min);

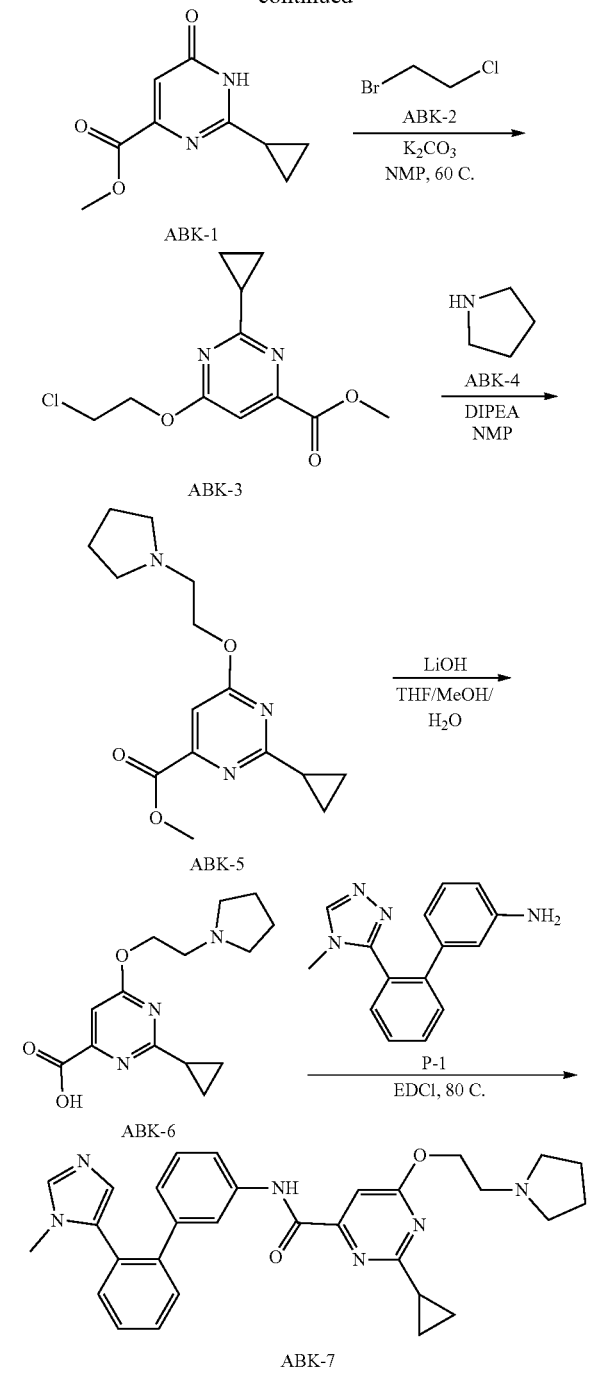

Detector, UV 254/220 nm. The reaction was concentrated in vacuo to afford the sub-title compound (ABK-1) (3.78 g, 19.5 mmol, 70%) as a brown solid. m/z 195.1 (M+H)$^+$ (ES+).

Step 2: Synthesis of Methyl 6-(2-chloroethoxy)-2-cyclopropylpyrimidine-4-carboxylate (ABK-3)

To a stirred mixture of the product from step 1 above (ABK-1) (140 mg, 1 Eq, 721 µmol) and K$_2$CO$_3$ (498 mg, 5 Eq, 3.61 mmol) in NMP (8 mL) was added 1-bromo-2-chloroethane (ABK-2) (517 mg, 5 Eq, 3.61 mmol) at rt under nitrogen atmosphere. The mixture was stirred for 1 h at 60° C. then cooled to rt. The mixture was concentrated and purified by prep-TLC with petroleum ether/EtOAc (10/1)) to afford the sub-title compound (ABK-3) (115 mg, 448 µmol, 62%) as a light yellow oil. m/z 257.1/259.1 (M+H)$^+$ (ES+).

Step 3: Synthesis of Methyl 2-cyclopropyl-6-(2-(pyrrolidin-1-yl)ethoxy)pyrimidine-4-carboxylate (ABK-5)

To a stirred mixture of the product from step 2 above (ABK-3) (115 mg, 1 Eq, 448 mmol) and DIPEA (173 mg, 3 Eq, 1.34 mmol) in NMP (5 mL) was added pyrrolidine (ABK-4) (127 mg, 4 Eq, 1.79 mmol) at rt under nitrogen atmosphere. The mixture was stirred for 3 h at 80° C. then the mixture was cooled to rt. The resulting mixture was diluted with water and extracted with EtOAc (3×20 mL). The combined organic layers were washed with brine (2×20 mL), dried (Na$_2$SO$_4$), filtered and concentrated in vacuo. The crude product was purified by reverse flash column chromatography with the following conditions: Column, C18; mobile phase, Water (0.1% NH$_4$HCO$_3$) and ACN (0% ACN up to 45% in 25 min); Detector, UV 254/220 nm. The reaction was concentrated in vacuo to afford the sub-title compound (ABK-5) (37 mg, 127 µmol, 28%) as a white solid. m/z 292.2 (M+H)$^+$ (ES+).

Step 4: Synthesis of 2-Cyclopropyl-6-(2-(pyrrolidin-1-yl)ethoxy)pyrimidine-4-carboxylic acid (ABK-6)

To a stirred mixture of the product from step 3 above (ABK-5) (37 mg, 1 Eq, 127 µmol) and LiOH (15 mg, 5 Eq, 636 µmol) in MeOH (2 mL), THF (2 mL) and water (1 mL) at rt under nitrogen atmosphere. The mixture was stirred for 2 h at rt then concentrated to afford the sub-title compound (ABK-6) (30 mg, 108 µmol, 86%) as a white solid. m/z 278.1 (M+H)$^+$ (ES+).

Step 5: Synthesis of 2-Cyclopropyl-N-(2'-(4-methyl-4H-1,2,4-triazol-3-yl)-[1,1'-biphenyl]-3-yl)-6-(2-(pyrrolidin-1-yl)ethoxy) pyrimidine-4-carboxamide (ABK-7)

To a stirred mixture of the product from step 4 above (ABK-6) (30 mg, 1 Eq, 108 µmol) and intermediate (P-1) (27 mg, 1 Eq, 108 µmol) in pyridine (2 mL) was added EDCI (41 mg, 2 Eq, 216 µmol) at rt under nitrogen atmosphere. The mixture was stirred for 2 h at 80° C. under nitrogen atmosphere. The mixture was allowed to cool down to rt. The mixture was concentrated and purified by prep-TLC with DCM/MeOH (15/1). And then the mixture was purified by prep-HPLC with the following conditions: (Column: Sunfire prep C18 column, 30*150 mm, 5 µm; Mobile Phase A: Water (0.1% FA), Mobile Phase B: ACN; Flow rate: 60 mL/min; Gradient: 10% B to 35% B in 7 min; Wavelength: 254/220 nm; RT: 6.45) to afford the title compound (ABK-7) (4.7 mg, 9.2 µmol, 8.5%) as a white solid. m/z 510.4 (M+H)$^+$ (ES+). $^1$H NMR (400 MHz, MeOH-d4) δ 8.38 (s, 1H), 7.81-7.67 (m, 4H), 7.66-7.57 (m, 2H), 7.36 (t, J=7.9 Hz, 1H), 7.33 (s, 1H), 7.02-6.70 (m, 1H), 4.67-4.70 (m, 2H), 3.36 (s, 2H), 3.19 (s, 3H), 3.13 (s, 4H), 2.38-2.32 (m, 1H), 2.05-1.96 (m, 4H), 1.26-1.23 (m, 1H), 1.18-1.13 (m, 2H).

Example 73: Synthesis of 2-Cyclopropyl-N-(6-(ethylamino)-4-(1-methyl-4-(4-methyl-4H-1,2,4-triazol-3-yl)-1H-pyrazol-5-yl)pyridin-2-yl)-6-oxo-1-(2-(pyrrolidin-1-yl)ethyl)-1,6-dihydropyrimidine-4-carboxamide (ABL-4)

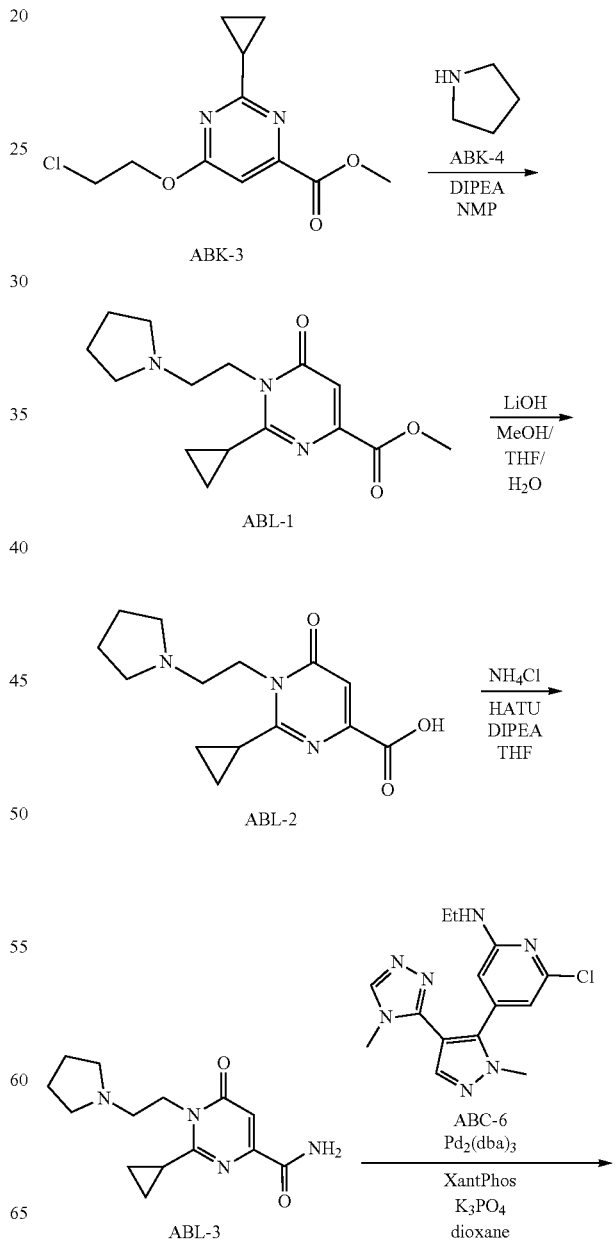

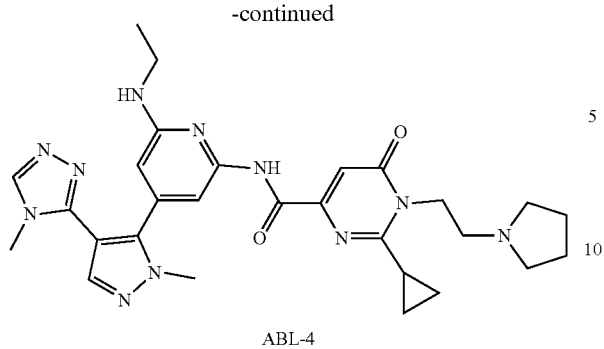

ABL-4

Step 1: Synthesis of Methyl 2-cyclopropyl-6-oxo-1-(2-(pyrrolidin-1-yl)ethyl)-1,6-dihydropyrimidine-4-carboxylate (ABL-1)

To a stirred mixture of intermediate (ABK-3) (800 mg, 1 Eq, 3.12 mmol) and pyrrolidine (ABK-4) (887 mg, 4 Eq, 12.5 mmol) in NMP (20 mL) was added DIPEA (1.21 mg, 3 Eq, 9.35 mmol) at rt under nitrogen atmosphere and the mixture stirred for 3h at 80° C. The mixture was cooled to rt, diluted with water and extracted with EtOAc (3×80 mL). The combined organic layers were washed with brine (2×80 mL), dried ($Na_2SO_4$), filtered and concentrated in vacuo. The crude product was purified by reverse flash column chromatography with the following conditions: Column, C18; mobile phase, Water (0.1% $NH_4HCO_3$) and ACN (10% ACN up to 50% in 10 min); Detector, UV 254/220 nm to afford the sub-title compound (ABL-1) (370 mg, 1.27 mmol, 41%) as a brown/yellow oil. m/z 292.2 $(M+H)^+$ (ES+).

Step 2: Synthesis of 2-Cyclopropyl-6-oxo-1-(2-(pyrrolidin-1-yl)ethyl)-1,6-dihydropyrimidine-4-carboxylic acid (ABL-2)

A solution of the product from step 1 above (ABL-1) (120 mg, 1 Eq, 410 µmol) and LiOH (49 mg, 5 Eq, 2.06 mmol) in MeOH (3 mL), THF (3 mL) and water (1.5 mL) at rt was stirred for 2 h at rt. The crude product was purified by reverse flash column chromatography with the following conditions: Column, C18; mobile phase, Water (0.1% FA) and ACN (0% ACN up to 10% in 10 min); Detector, UV 254/220 nm. The product-containing fractions were combined and concentrated in vacuo. This resulted in the sub-title compound (ABL-2) (40 mg, 144 µmol, 35%) as a white solid. m/z 278.1 $(M+H)^+$ (ES+).

Step 3: 2-Cyclopropyl-6-oxo-1-(2-(pyrrolidin-1-yl)ethyl)-1,6-dihydropyrimidine-4-carboxamide (ABL-3)

To a stirred solution of the product from step 2 above (ABL-2) (40 mg, 1 Eq, 144 µmol) and $NH_4Cl$ (39 mg, 5 Eq, 720 µmol) in DMF (10 mL) were added HATU (110 mg, 2 Eq, 288 mmol) and DIPEA (186 mg, 10 Eq, 1.44 mmol) at rt. The resulting mixture was stirred for 2 h at rt. The crude product was purified by reverse flash column chromatography with the following conditions: Column, C18; mobile phase, Water (0.1% $NH_4HCO_3$) and ACN (30% ACN up to 50% in 10 min); Detector, UV 254/220 nm. The product-containing fractions were combined and concentrated in vacuo. This resulted in the sub-title compound (ABL-3) (35 mg, 126 µmol, 87%) as a white solid. m/z 277.2 $(M+H)^+$ (ES+).

Step 4: 2-Cyclopropyl-N-(6-(ethylamino)-4-(1-methyl-4-(4-methyl-4H-1,2,4-triazol-3-yl)-1H-pyrazol-5-yl)pyridin-2-yl)-6-oxo-1-(2-(pyrrolidin-1-yl)ethyl)-1,6-dihydropyrimidine-4-carboxamide (ABK-4)

To a stirred mixture of the product from step 3 above (ABL-3) (40 mg, 1 Eq, 144 mmol) and intermediate (ABC-6) (69 mg, 1.5 Eq, 216 µmol) and potassium phosphate (61 mg, 2 Eq, 288 µmol) in 1,4-dioxane (8 mL) were added $Pd_2(dba)_3$ (26 mg, 0.2 Eq, 28 µmol) and XantPhos (34 mg, 0.4 Eq, 57 µmol) at rt under nitrogen atmosphere. The resulting mixture was stirred for 3 h at 120° C. under nitrogen atmosphere then cooled to rt. The crude product was purified by reverse flash column chromatography with the following conditions: Column, C18; mobile phase, Water (0.1% $NH_4HCO_3$) and ACN (20% ACN up to 30% in 10 min); Detector, UV 254/220 nm. The product-containing fractions were combined and concentrated in vacuo. The crude product was purified by Prep-HPLC with the following conditions: Column: SunFire Prep C18 OBD Column, 30×100 mm 5 um; Mobile Phase A: Water (0.1% $NH_4HCO_3$), Mobile Phase B: ACN; Flow rate:60 mL/min; Gradient:16 B to 36 B in 10 min; Detector, UV 254/210 nm; RT: 10.58. The product-containing fractions were combined and evaporated partially in vacuo and lyophilized overnight to afford the title compound (ABL-4) (8.1 mg, 14 µmol, 9%) as a yellow solid. m/z 558.2 $(M+H)^+$ (ES+). $^1$H NMR (400 MHz, MeOH-d4) δ 8.49 (s, 1H), 7.86 (s, 1H), 7.39 (d, J=1.2 Hz, 1H), 6.99 (s, 1H), 6.22 (d, J=1.2 Hz, 1H), 4.55-4.41 (m, 2H), 4.01 (s, 3H), 3.49 (s, 3H), 3.32-3.28 (m, 2H), 2.94-2.82 (m, 2H), 2.75-2.68 (m, 4H), 2.40-2.29 (m, 1H), 1.90-1.82 (m, 4H), 1.43-1.33 (m, 2H), 1.36-1.25 (m, 2H), 1.22 (t, J=7.2 Hz, 3H).

Example 74: Synthesis of 2-Cyclopropyl-N-(2'-(4-methyl-4H-1,2,4-triazol-3-yl)-[1,1'-biphenyl]-3-yl)-6-oxo-1-(2-(pyrrolidin-1-yl)ethyl)-1,6-dihydropyrimidine-4-carboxamide (ABM-1)

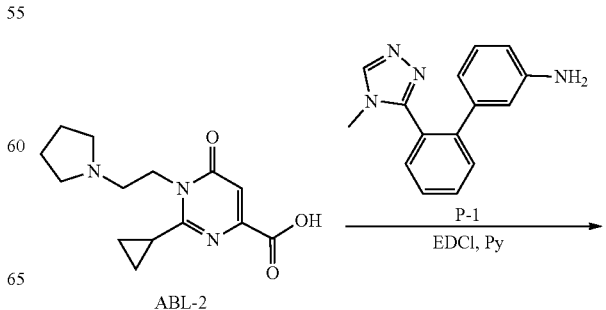

541
-continued

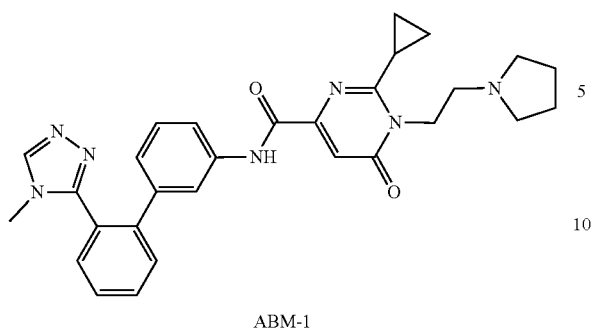

ABM-1

To a stirred mixture of intermediate (ABL-2) (40 mg, 1 Eq, 144 μmol) and intermediate (P-1) (36 mg, 1 Eq, 144 mmol) in pyrazine (6 mL) was added EDCI (55 mg, 2 Eq, 288 μmol) at rt under nitrogen atmosphere. The resulting mixture was stirred for 16 h at 80° C. under nitrogen atmosphere then cooled to rt. The crude product was purified by reverse flash column chromatography with the following conditions: Column, C18; mobile phase, Water (0.1% NH$_4$HCO$_3$) and ACN (50% ACN up to 65% in 10 min); Detector, UV 254/220 nm. The product-containing fractions were combined and concentrated in vacuo. The crude product was purified by Prep-HPLC with the following conditions: Column: SunFire Prep C18 OBD Column, 30×100 mm 5 um; Mobile Phase A: Water (0.1% NH$_4$HCO$_3$), Mobile Phase B: ACN; Flow rate:60 mL/min; Gradient:20 B to 45 B in 10 min; Detector, UV 254/210 nm; RT: 7.53. The product-containing fractions were combined and evaporated partially in vacuo and lyophilized overnight to afford the title compound (ABM-1) (9.2 mg, 18 μmol, 12%) as a white solid. m/z 510.2 (M+H)$^+$ (ES+). $^1$H NMR (400 MHz, MeOH-d4) δ 8.39 (s, 1H), 7.79-7.57 (m, 6H), 7.35 (t, J=7.9 Hz, 1H), 7.03-6.96 (m, 2H), 4.56-4.47 (m, 2H), 3.19 (s, 3H), 2.94-2.86 (m, 2H), 2.76-2.68 (m, 4H), 2.38-2.28 (m, 1H), 1.92-1.81 (m, 4H), 1.48-1.39 (m, 2H), 1.32-1.23 (m, 2H).

Example 75: Synthesis of 2-(6-(Ethylamino)-4-(1-methyl-4-(4-methyl-4H-1,2,4-triazol-3-yl)-1H-pyrazol-5-yl)pyridin-2-yl)-6-((3-fluoroazetidin-1-yl)methyl)-4-(trifluoromethyl)isoindolin-1-one (ABN-2)

542
-continued

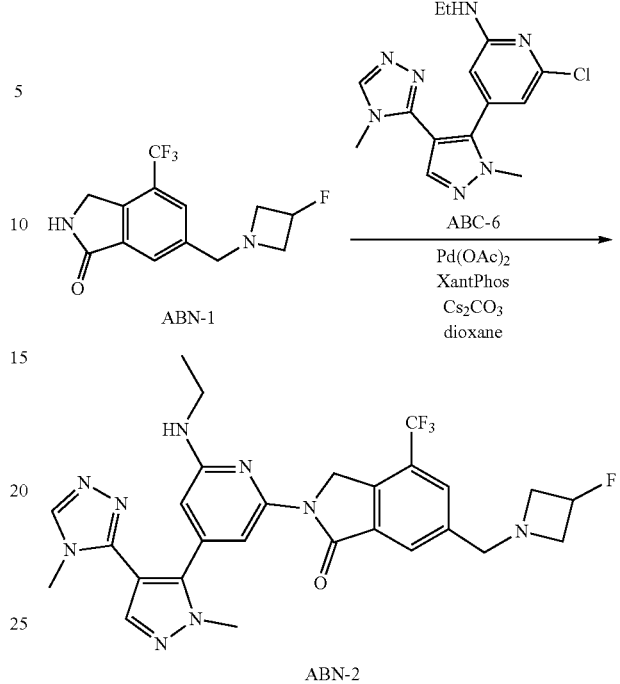

Step 1: Synthesis of 6-((3-Fluoroazetidin-1-yl)methyl)-4-(trifluoromethyl)isoindolin-1-one (ABN-1)

To a stirred solution of intermediate (ABC-4) (100 mg, 1 Eq, 436 μmol) and 3-fluoroazetidine, HCl (U-1) (131 mg, 4 Eq, 1.74 mmol) in MeOH (5 mL) was added NaBH$_3$CN (137 mg, 5 Eq, 2.18 mmol) at rt. The resulting mixture was stirred overnight at rt under nitrogen atmosphere. The crude product was purified by reverse flash column chromatography with the following conditions: Column, C18; mobile phase, Water (0.1% NH$_4$HCO$_3$) and ACN (35% ACN up to 65% in 8 min); Detector, UV 254/220 nm. The product-containing fractions were combined and concentrated in vacuo. This resulted in the sub-title compound (ABN-1) (70 mg, 243 μmol, 56%) as a white solid. m/z 289.1 (M+H)$^+$ (ES+).

Step 2: Synthesis of 2-(6-(Ethylamino)-4-(1-methyl-4-(4-methyl-4H-1,2,4-triazol-3-yl)-1H-pyrazol-5-yl)pyridin-2-yl)-6-((3-fluoroazetidin-1-yl)methyl)-4-(trifluoromethyl)isoindolin-1-one (ABN-2)

To a stirred solution of the product from step 1 above (ABN-1) (30 mg, 1 Eq, 104 μmol), intermediate (ABC-6) (33 mg, 1 Eq, 104 μmol) and potassium phosphate (44 mg, 2 Eq, 208 μmol) in 1,4-dioxane (2 mL) were added XantPhos (12 mg, 0.2 Eq, 21 μmol) and Pd(OAc)$_2$ (2.3 mg, 0.1 Eq, 10 μmol) at rt under nitrogen atmosphere. The resulting mixture was stirred for 2 h at 100° C. under nitrogen atmosphere. The resulting mixture was cooled to rt, diluted with water and extracted with EtOAc (3×10 mL). The combined organic layers were washed with brine (2×10 mL), dried (Na$_2$SO$_4$), filtered and concentrated in vacuo. The residue was purified by Prep-TLC with petroleum ether/EtOAc (2/1). The crude product was purified by Prep-HPLC with the following conditions: Column: Sunfire prep C18 column, 30×150 mm 5 um; Mobile Phase A: Water (0.1% FA), Mobile Phase B: ACN; Flow rate: 60 mL/min; Gradient: 8% B to 32% B in 10 min; Detector, UV 254/210 nm; RT: 9.67. The product-containing fractions were combined and evaporated partially in vacuo and lyophilized overnight to afford the title compound (ABN-2) (16.5 mg, 29 µmol, 28%) as a white solid. m/z 570.2 (M+H)$^+$ (ES+). $^1$H NMR (400 MHz, MeOH-d4) δ 8.49 (s, 1H), 8.04 (s, 1H), 7.95 (s, 1H), 7.87 (s, 1H), 7.65 (d, J=1.2 Hz, 1H), 6.20 (d, J=1.2 Hz, 1H), 5.31-5.19 (m, 3H), 4.04 (s, 3H), 3.96 (s, 2H), 3.82-3.71 (m, 2H), 3.50 (s, 3H), 3.41-3.34 (m, 4H), 1.25 (t, J=7.2 Hz, 3H).

Example 76: Synthesis of 2-[4-Fluoro-2-(4-methyl-1,2,4-triazol-3-yl)-[1,1-biphenyl]-3-yl]-4-(trifluoromethyl)-3H-isoindol-1-one (ABO-5)

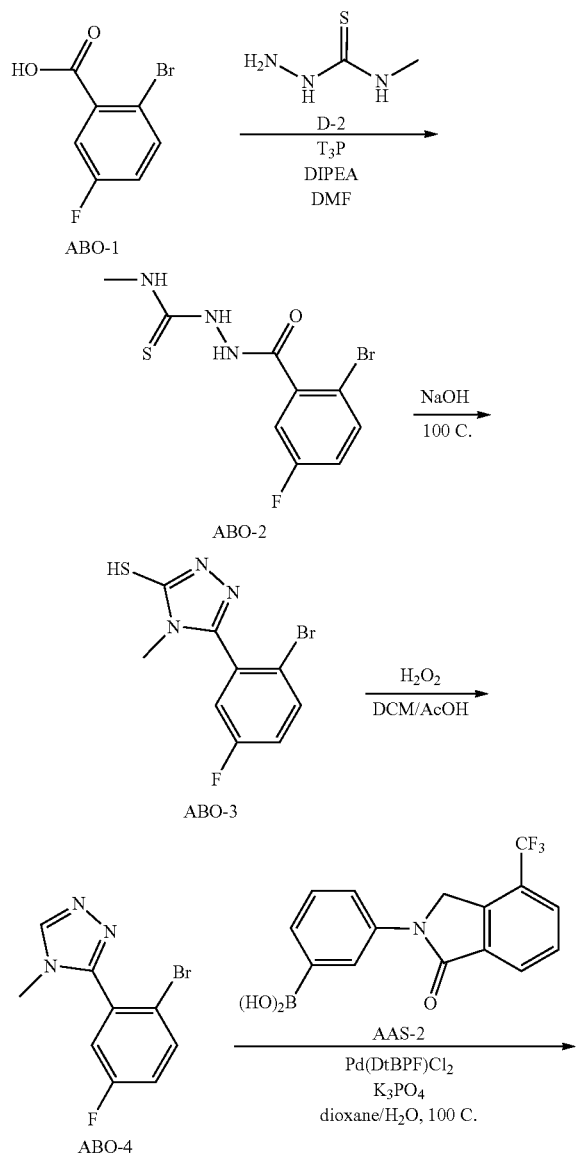

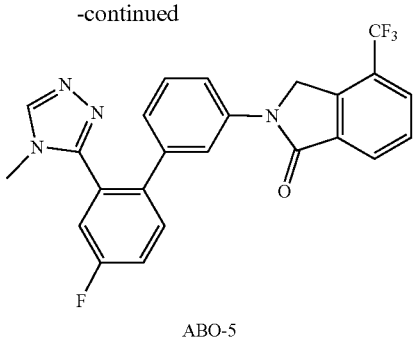

ABO-5

Step 1: Synthesis of 2-(2-Bromo-5-fluorobenzoyl)-N-methylhydrazine-1-carbothioamide (ABO-2)

To a stirred mixture of 2-bromo-5-fluorobenzoic acid (ABO-1) (2.19 g, 1 Eq, 10.0 mmol) and 4-methyl-3-thiosemicarbazide (D-2) (1.05 g, 1 Eq, 10.0 mmol) in DMF (40 mL) was added DIPEA (7.75 g, 6 Eq, 60.0 mmol) and T$_3$P (12.7 g, 4 Eq, 40.0 mmol) at rt. The resulting mixture was stirred overnight at rt. The resulting mixture was concentrated in vacuo. The crude resulting mixture was used in the next step directly without further purification. m/z 306.0/308.0 (M+H)$^+$ (ES+).

Step 2: Synthesis 5-(2-Bromo-5-fluorophenyl)-4-methyl-4H-1,2,4-triazole-3-thiol (ABO-3)

To a stirred mixture of the product from step 1 above (ABO-2) was added NaOH (aq., 1 M) at rt and the resulting mixture stirred overnight at 100° C. The residue was neutralized to pH 5 with HCl (aq., 1 M). The resulting mixture was diluted with water and extracted with EtOAc (3×100 mL). The combined organic layers were washed with brine (2×100 mL), dried (Na$_2$SO$_4$), filtered and concentrated in vacuo. The crude product was purified by reverse flash column chromatography with the following conditions: Column, C18; mobile phase, Water (0.1% NH$_4$HCO$_3$) and ACN (35% ACN up to 50% in 10 min); Detector, UV 254/220 nm. The product-containing fractions were combined and concentrated in vacuo. This resulted in the sub-title compound (ABO-3) (1 g, 3.48 mmol, 45%) as a white solid. m/z 288.0/290.0 (M+H)$^+$ (ES+).

Step 3: Synthesis 3-(2-Bromo-5-fluorophenyl)-4-methyl-4H-1,2,4-triazole (ABO-4)

To a stirred mixture of the product from step 2 above (ABO-3) (230 mg, 1 Eq, 798 µmol) in DCM (4 mL) were added acetic acid (96 mg, 2 Eq, 1.60 mmol) and hydrogen peroxide (136 mg, 5 Eq, 4.00 mmol) at 0° C. The resulting mixture was stirred for 2 h at rt then basified to pH 9 with sat. NaHCO$_3$ solution (aq.). The resulting mixture was diluted with water and extracted with EtOAc (3×50 mL). The combined organic layers were washed with brine (2×50 mL), dried (Na$_2$SO$_4$), filtered and concentrated in vacuo. The crude product was purified by reverse flash column chromatography with the following conditions: Column, C18; mobile phase, Water (0.1% NH$_4$HCO$_3$) and ACN (36% ACN up to 48% in 10 min); Detector, UV 254/220 nm. The product-containing fractions were combined and concentrated in vacuo. This resulted in the sub-title compound (ABO-4) (145 mg, 568 µmol, 71%) as a white solid. m/z 256.0/258.0 (M+H)⁺ (ES+).

Step 4: Synthesis of 2-(4'-Fluoro-2'-(4-methyl-4H-1,2,4-triazol-3-yl)-[1,1'-biphenyl]-3-yl)-4-(trifluoromethyl)isoindolin-1-one (ABO-5)

To a stirred mixture of the product from step 3 above (ABO-4) (232 mg, 1 Eq, 906 µmol), intermediate (AAS-2) (291 mg, 1 Eq, 906 µmol) and potassium phosphate (577 mg, 3 Eq, 2.72 mmol) in dioxane (5 ml) and water (1 ml) was added Pd(DtBPF)Cl₂ (59 mg, 0.1 Eq, 91 µmol) at rt under nitrogen atmosphere. The resulting mixture was stirred overnight at 100° C. under nitrogen atmosphere then cooled to rt and concentrated in vacuo. The crude product was purified by reverse flash column chromatography with the following conditions: Column, C18; mobile phase, Water (0.1% NH₄HCO₃) and ACN (10% ACN up to 50% in 10 min); Detector, UV 254/220 nm. The crude product was purified by Prep-HPLC with the following conditions (Column: XBridge Prep C18 OBD Column, 30*100 mm, 5 um; Mobile Phase A: Water (0.1% NH₄HCO₃), Mobile Phase B: ACN; Flow rate: 60 mL/min; Gradient: 35% B to 55% B in 10 min; Wavelength: 254/220 nm; RT: 7.13) to afford the title compound (ABO-5) (10.8 mg, 24 µmol, 2.6%) as a white solid. m/z 453.0 (M+H)⁺ (ES+). ¹H NMR (400 MHz, DMSO-d6) δ 8.43 (s, 1H), 8.12-8.02 (m, 2H), 8.02-7.96 (m, 1H), 7.80 (t, J=7.7 Hz, 1H), 7.77-7.69 (m, 1H), 7.67 (t, J=2.0 Hz, 1H), 7.64-7.54 (m, 1H), 7.54-7.46 (m, 1H), 7.38 (t, J=8.0 Hz, 1H), 6.92-6.85 (m, 1H), 5.12 (d, J=1.8 Hz, 2H), 3.14 (s, 3H).

Example 77: Synthesis of 2-(6-(Ethylamino)-4-(1-methyl-4-(4-methyl-4H-1,2,4-triazol-3-yl)-1H-pyrazol-5-yl) pyridin-2-yl)-6-((3-fluoropyrrolidin-1-yl) methyl)-4-(trifluoromethyl)isoindolin-1-one (ABP-3)

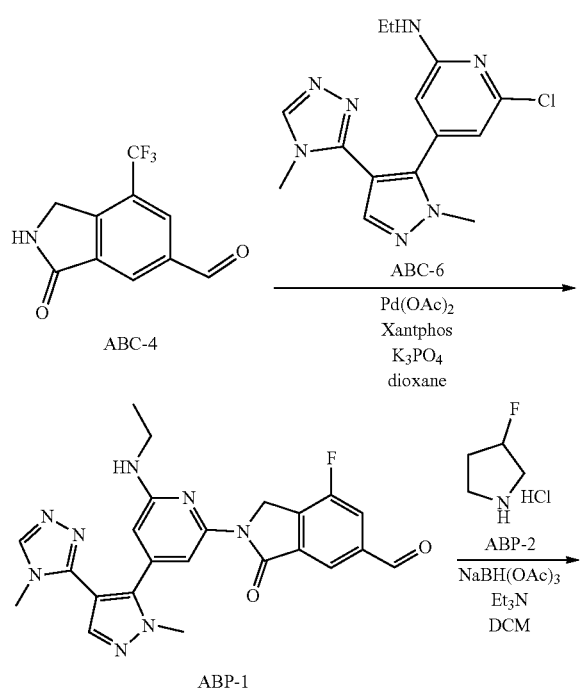

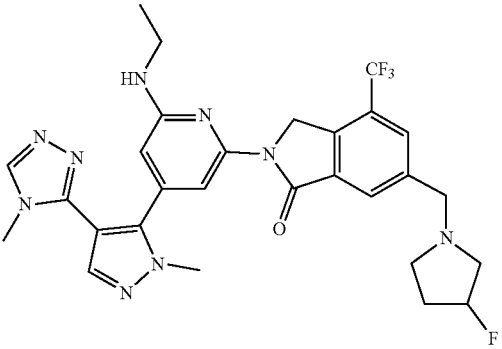

ABP-3

Step 1: Synthesis of 2-(6-(Ethylamino)-4-(1-methyl-4-(4-methyl-4H-1,2,4-triazol-3-yl)-1H-pyrazol-5-yl) pyridin-2-yl)-3-oxo-7-(trifluoromethyl)isoindoline-5-carbaldehyde (ABP-1)

To a stirred solution of intermediate (ABC-4) (150 mg, 1 Eq, 650 µmol), intermediate (ABC-6) (146 mg, 0.7 Eq, 450 µmol) and potassium phosphate (278 mg, 2 Eq, 1.31 mmol) in dioxane (10 mL) were added XantPhos (76 mg, 0.2 Eq, 130 mol) and Pd(OAc)₂ (15 mg, 0.1 Eq, 60 mol) at rt under nitrogen atmosphere. The resulting mixture was stirred for 2 h at 100° C. under nitrogen atmosphere then cooled to rt and concentrated in vacuo. The crude product was purified by reverse flash column chromatography with the following conditions: Column, C18; mobile phase, Water (0.1% NH₄HCO₃) and ACN (60% ACN up to 70% in 10 min); Detector, UV 254/220 nm. The product-containing fractions were combined and concentrated in vacuo. This resulted in the sub-title compound (ABP-1) (180 mg, 353 µmol, 53%) as a yellow solid. m/z 511.2 (M+H)⁺ (ES+).

Step 2: Synthesis of 2-(6-(Ethylamino)-4-(1-methyl-4-(4-methyl-4H-1,2,4-triazol-3-yl)-1H-pyrazol-5-yl) pyridin-2-yl)-6-((3-fluoropyrrolidin-1-yl) methyl)-4-(trifluoromethyl) isoindolin-1-one (ABP-3)

To a stirred mixture of the product from step 1 (ABP-1) (20 mg, 1 Eq, 30 µmol) and 3-fluoropyrrolidine, HCl (ABP-2) (20 mg, 4 Eq, 150 mmol) in DCM (2 mL) were added NaBH(OAc)₃ (17 mg, 2 Eq, 70 µmol) and Et₃N (12 mg, 3 Eq, 110 µmol) at rt under nitrogen atmosphere. The resulting mixture was stirred for 1 h at rt under nitrogen atmosphere and the resulting mixture concentrated in vacuo. The crude product was purified by reverse flash column chromatography with the following conditions: Column, C18; mobile phase, Water (0.1% FA) and ACN (20% ACN up to 30% in 10 min); Detector, UV 254/220 nm. The product-containing fractions were combined and concentrated in vacuo. The crude product was purified by Prep-HPLC with the following conditions: Column: SunFire Prep Cl18 OBD Column, 30×150 mm Sum; Mobile Phase A: Water (0.1% FA), Mobile Phase B: ACN; Flow rate: 60 mL/min; Gradient:40 B to 60 B in 10 min; Detector, UV 254/210 nm; RT: 6.97. The product-containing fractions were combined and evaporated partially in vacuo and lyophilized overnight to afford the title compound (ABP-3) (2.3 mg, 4 µmol, 10%) as a white solid. m/z 584.1 (M+H)⁺ (ES+). ¹H NMR (400 MHz, MeOH-d4) δ 8.49 (s, 1H), 8.07 (s, 1H), 8.00 (s, 1H), 7.87 (s, 1H), 7.66 (d, J=1.2 Hz, 1H), 6.20 (d, J=1.2 Hz, 1H), 5.26-5.14 (m, 3H), 4.04 (s, 3H), 3.95-3.82 (m, 2H), 3.50 (s, 3H), 3.40-3.36 (m, 2H), 2.99-2.85 (m, 2H), 2.85-2.68 (m, 1H), 2.57-2.46 (m, 1H), 2.35-2.15 (m, 1H), 2.14-1.95 (m, 1H), 1.25 (t, J=7.2 Hz, 3H).

Example 78: Synthesis of 6-(Ethylamino)-4-(1-methyl-4-(4-methyl-4H-1,2,4-triazol-3-yl)-1H-pyrazol-5-yl)picolinic acid (ABQ-1)

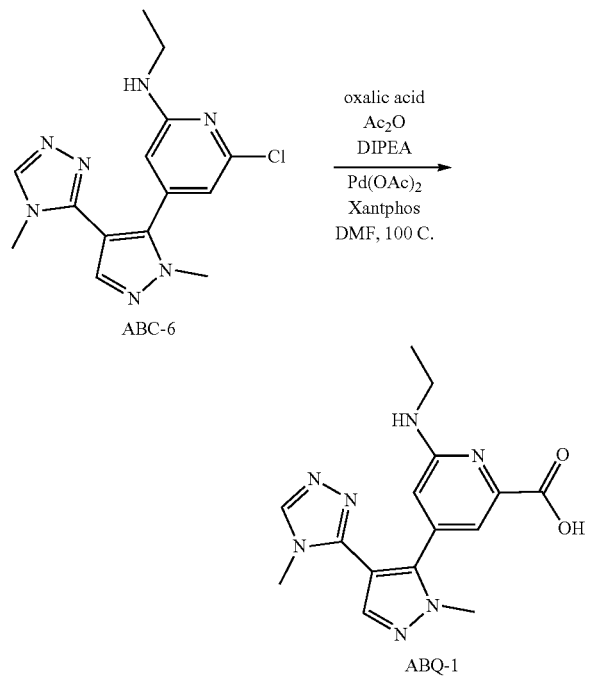

Into an 8 mL sealed tube were added intermediate (ABC-6) (30 mg, 1 Eq, 94 μmol), oxalic acid (13 mg, 1.5 Eq, 141 μmol), DIPEA (18.3 mg, 1.5 Eq, 140 μmol) and acetic anhydride (14 mg, 1.5 Eq, 141 μmol) in DMF (2 mL) at rt under nitrogen atmosphere. To the above mixture were added Pd(OAc)$_2$ (2 mg, 0.1 Eq, 10 μmol) and XantPhos (11 mg, 0.2 Eq, 20 μmol) at rt under nitrogen atmosphere. The resulting mixture was stirred for overnight at 100° C. under nitrogen atmosphere then the mixture allowed to cool to rt and concentrated in vacuo. The crude product was purified by Prep-HPLC with the following conditions (Column: Sunfire prep C18 column, 30*150 mm, 5 μm; Mobile Phase A: Water(0.1% FA), Mobile Phase B: ACN; Flow rate: 60 mL/min; Gradient: 2% B to 20% B in 9 min; Wavelength: 254/220 nm; RT: 6.32) to afford the title compound (ABQ-1) (5.2 mg, 16 μmol, 17%) as a white solid. m/z 328.1 (M+H)$^+$ (ES+). $^1$H NMR (400 MHz, MeOH-d4) δ 8.50 (s, 1H), 7.92 (s, 1H), 7.26 (d, J=1.4 Hz, 1H), 6.78 (s, 1H), 4.00 (s, 3H), 3.55 (s, 3H), 3.34 (s, 1H), 3.32 (s, 1H), 1.23 (t, J=7.2 Hz, 3H).

Example 79: Synthesis of 6-((5-Azaspiro [2.4] heptan-5-yl)methyl)-2-(6-(ethylamino)-4-(2-(4-methyl-4H-1,2,4-triazol-3-yl)phenyl)pyridin-2-yl)-4-(trifluoromethyl)isoindolin-1-one (ABR-1)

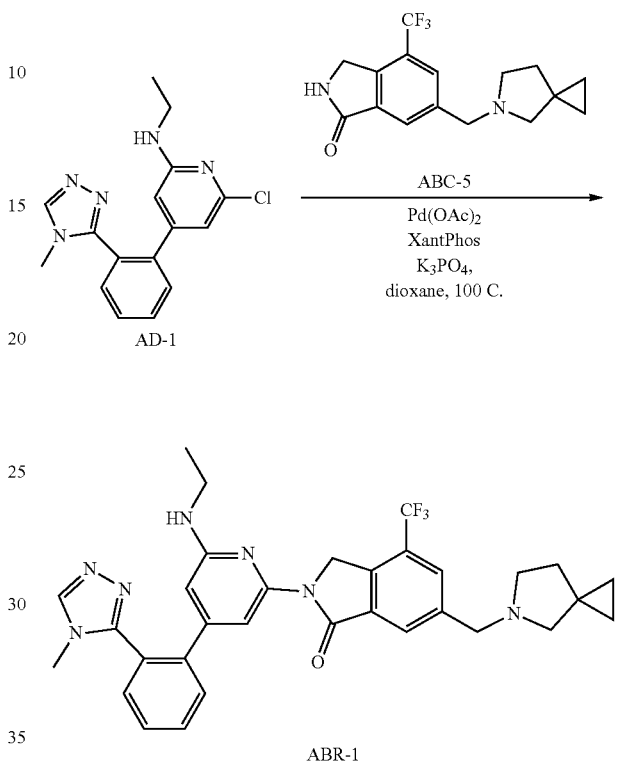

To a stirred mixture of intermediate (AD-1) (30 mg, 1 Eq, 90 μmol), intermediate (ABC-5) (30 mg, 90 μmol, 1 Eq) and potassium phosphate (41 mg, 2 Eq, 190 μmol) in 1,4-dioxane (1.5 mL) was added XantPhos (11 mg, 0.2 Eq, 20 μmol) and Pd(OAc)$_2$ (2 mg, 0.1 Eq, 10 mmol) at rt under nitrogen atmosphere. The resulting mixture was stirred for 5 h at 100° C. under nitrogen atmosphere then cooled to rt and concentrated in vacuo. The crude product was purified by Prep-HPLC with the following conditions: Column: XBridge Prep C18 OBD Column, 30*100 mm, 5 μm; Mobile Phase A: Water (0.1% NH$_4$HCO$_3$), Mobile Phase B: ACN; Flow rate: 60 mL/min; Gradient: 48% B to 72% B in 10 min; Wavelength: 254/220 nm; RT: 9.67. This resulted in the title compound (ABR-1) (2.7 mg, 4.6 μmol, 3.6%) as a white solid. m/z 588.4 (M+H)$^+$ (ES+). $^1$H NMR (400 MHz, MeOH-d4) δ 8.45 (s, 1H), 8.07 (s, 1H), 8.00 (s, 1H), 7.80-7.69 (m, 2H), 7.69-7.58 (m, 2H), 7.56 (d, J=1.3 Hz, 1H), 6.05 (d, J=1.2 Hz, 1H), 5.22 (s, 2H), 3.86 (s, 2H), 3.44 (s, 3H), 3.32-3.26 (m, 2H), 2.83 (t, J=6.9 Hz, 2H), 2.57 (s, 2H), 1.89 (t, J=7.0 Hz, 2H), 1.22 (t, J=7.2 Hz, 3H), 0.59 (d, J=4.6 Hz, 4H).

Example 80: Synthesis of 2-(6-Cyclopropyl-5-(2-(4-methyl-4H-1,2,4-triazol-3-yl) phenyl)pyridin-2-yl)-4-(trifluoromethyl)isoindolin-1-one (ABS-1)

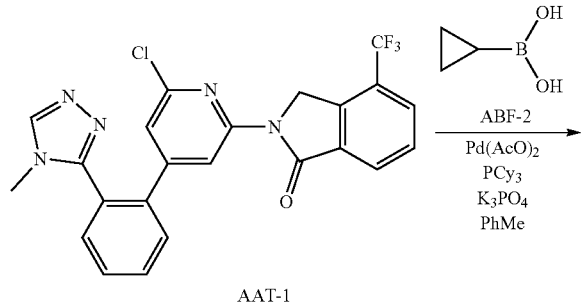

Example 81: Synthesis of 2-(6-((2-Hydroxyethyl)amino)-4-(2-(4-methyl-4H-1,2,4-triazol-3-yl)phenyl)pyridin-2-yl)-4-(trifluoromethyl)isoindolin-1-one (ABT-2)

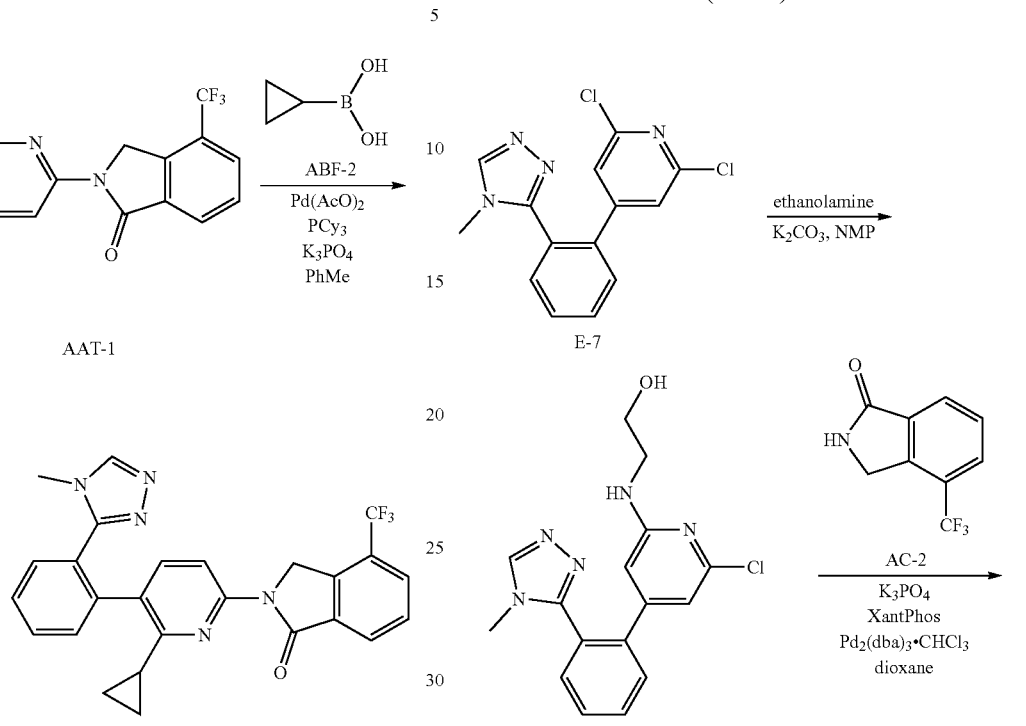

Into a 40-mL vial purged and maintained with an inert atmosphere of nitrogen, was placed intermediate (AAT-1) (100 mg, 1 Eq, 213 µmol), intermediate (ABF-2) (73 mg, 4 Eq, 851 µmol) and potassium phosphate (136 mg, 3 Eq, 639 µmol) in PhMe (8 mL) were added tricyclohexylphosphane (6 mg, 0.1 Eq, 21 µmol) and Pd(OAc)$_2$ (5 mg, 0.1 Eq, 21 µmol) at rt under nitrogen atmosphere and the resulting mixture stirred overnight at 100° C. under nitrogen atmosphere. The mixture was cooled to rt and the resulting mixture was diluted with water and extracted with EtOAc (3×50 mL). The combined organic layers were washed with brine (2×50 mL), dried (Na$_2$SO$_4$), filtered and concentrated in vacuo. The crude product was purified by Prep-HPLC with the following conditions (Column: Sunfire prep C18 column, 30×150 mm, 5 µm; Mobile Phase A: Water (0.1% FA), Mobile Phase B: ACN; Flow rate: 60 mL/min; Gradient: 45% B to 75% B in 7 min; Wavelength: 254/220 nm; RT: 6.32) to afford the title compound (ABS-1) (37.8 mg, 79 µmol, 36%) as a white solid. m/z 476.0 (M+H)$^+$ (ES+). $^1$H NMR (300 MHz, MeOH-d4) δ 8.47 (s, 1H), 8.12-8.02 (m, 2H), 7.97 (d, J=7.7 Hz, 1H), 7.85-7.60 (m, 5H), 6.91 (d, J=1.4 Hz, 1H), 5.23-5.16 (m, 2H), 3.46 (s, 3H), 2.09-2.00 (m, 1H), 1.02-1.00 (m, 4H).

Step 1: Synthesis of 2-((6-Chloro-4-(2-(4-methyl-4H-1,2,4-triazol-3-yl)phenyl)pyridin-2-yl)amino)ethan-1-ol (ABT-1)

Into a 40-mL vial purged and maintained with an inert atmosphere of nitrogen, was placed intermediate (E-7) (100 mg, 1 Eq, 328 µmol), K$_2$CO$_3$ (453 mg, 10 Eq, 3.28 mmol) and ethanolamine (200 mg, 10 Eq, 3.28 mmol) in NMP (1.5 mL) at rt under nitrogen atmosphere. The resulting mixture was stirred overnight at 100° C. under nitrogen atmosphere. The mixture was cooled to rt and the resulting mixture was diluted with water and extracted with EtOAc (3×50 mL). The combined organic layers were washed with brine (2×50 mL), dried (Na$_2$SO$_4$), filtered and concentrated in vacuo. The crude product was purified by reverse flash column chromatography with the following conditions: Column, C18; mobile phase, Water (0.1% NH$_4$HCO$_3$) and ACN (30% ACN up to 40% in 25 min); Detector, UV 254/220 nm to afford the sub-title compound (ABT-1) (70 mg, 212 µmol, 65%) as a white solid. m/z 330.1/332.1 (M+H)⁺ (ES+).

Step 2: Synthesis of 2-(6-((2-Hydroxyethyl)amino)-4-(2-(4-methyl-4H-1,2,4-triazol-3-yl)phenyl)pyridin-2-yl)-4-(trifluoromethyl)isoindolin-1-one (ABT-2)

Into a 40-mL vial purged and maintained with an inert atmosphere of nitrogen, was placed the product from step 1 above (ABT-1) (69 mg, 1 Eq, 209 µmol), intermediate (AC-2) (63 mg, 1.5 Eq, 314 µmol) and potassium phosphate (89 mg, 2 Eq, 418 µmol) in 1,4-dioxane (8 mL) were added XantPhos (24 mg, 0.2 Eq, 42 µmol) and Pd₂(dba)₃-CHCl₃ (22 mg, 0.1 Eq, 21 µmol) at rt under nitrogen atmosphere. The resulting mixture was stirred for overnight at 100° C. under nitrogen atmosphere. The mixture was cooled to rt and the resulting mixture was diluted with water and extracted with EtOAc (3×20 mL). The combined organic layers were washed with brine (2×20 mL), dried (Na₂SO₄), filtered and concentrated in vacuo. The crude product was purified by Prep-HPLC with the following conditions (Column: XBridge Prep C18 OBD Column, 30×100 mm, 5 µm; Mobile Phase A: Water (0.1% NH₄HCO₃+0.1% NH₃·H₂O), Mobile Phase B: ACN; Flow rate: 60 mL/min; Gradient: 23% B to 43% B in 10 min; Wavelength: 254/220 nm; RT: 9.67) to afford the title compound (ABT-2) (30.7 mg, 62 µmol, 29%) as a white solid. m/z 495.2 (M+H)⁺ (ES+). ¹H NMR (400 MHz, MeOH-d4) δ 8.46 (s, 1H), 8.08 (d, J=7.6 Hz, 1H), 7.97 (d, J=7.7 Hz, 1H), 7.79-7.60 (m, 5H), 7.55 (d, J=1.2 Hz, 1H), 6.14 (d, J=1.3 Hz, 1H), 5.24 (s, 2H), 3.73 (t, J=5.8 Hz, 2H), 3.46-3.43 (m, 5H).

Example 82: Synthesis of 2-Cyclopropyl-N-(6-(ethylamino)-4-(1-methyl-4-(4-methyl-4H-1,2,4-triazol-3-yl)-1H-pyrazol-5-yl)pyridin-2-yl)-6-(2-(pyrrolidin-1-yl)ethoxy)pyrimidine-4-carboxamide (ABU-2)

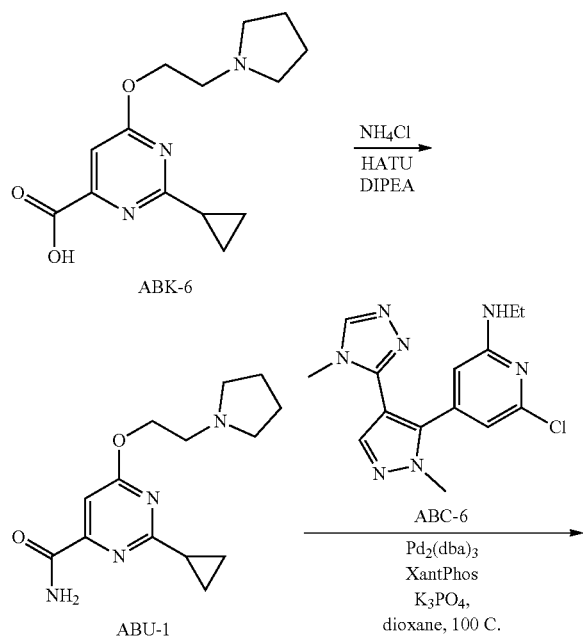

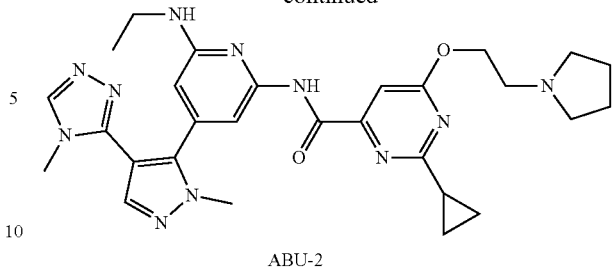

Step 1: Synthesis of 2-Cyclopropyl-6-(2-(pyrrolidin-1-yl)ethoxy)pyrimidine-4-carboxamide (ABU-1)

To a stirred mixture of intermediate (ABK-6) (100 mg, 1 Eq, 361 µmol), HATU (274 mg, 2 Eq, 721 µmol) and NH₄Cl (96 mg, 5 Eq, 1.80 mmol) in THF (20 mL) was added DIPEA (466 mg, 10 Eq, 3.61 mmol) at rt. The mixture was stirred for 2 h at rt. The mixture was concentrated and purified by prep-TLC with DCM/MeOH (10/1) to afford the sub-title compound (ABU-1) (75 mg, 253 µmol, 75%) as a brown/yellow solid. m/z 277.2 (M+H)⁺ (ES+).

Step 2: Synthesis of 2-Cyclopropyl-N-(6-(ethylamino)-4-(1-methyl-4-(4-methyl-4H-1,2,4-triazol-3-yl)-1H-pyrazol-5-yl)pyridin-2-yl)-6-(2-(pyrrolidin-1-yl)ethoxy)pyrimidine-4-carboxamide (ABU-2)

To a stirred mixture of the product from step 1 above (ABU-1) (70 mg, 1 Eq, 253 µmol) and intermediate (ABC-6) (97 mg, 1.2 Eq, 304 µmol) and potassium phosphate (161 mg, 760 µmol, 3 Eq) in dioxane (5 mL) were added Pd₂(dba)₃ (46 mg, 0.2 Eq, 51 µmol) and XantPhos (59 mg, 0.4 Eq, 101 µmol) at rt under nitrogen atmosphere. The mixture was stirred for 15 h at 100° C. under nitrogen atmosphere. The mixture was allowed to cool to rt and the resulting mixture was concentrated in vacuo. The crude product was purified by reverse flash column chromatography with the following conditions: Column, C18; mobile phase, Water (0.1% NH₄HCO₃) and ACN (0% ACN up to 70% in 40 min) Detector, UV 254/220 nm. The reaction was concentrated in vacuo. The crude product was purified by prep-HPLC with the following conditions: (Column: XBridge Prep OBD C18 Column, 30*150 mm, 5 µm; Mobile Phase A: Water (0.1% NH₄HCO₃), Mobile Phase B: ACN; Flow rate: 60 mL/min; Gradient: 33% B to 42% B in 9 min; Wavelength: 254/220 nm; RT: 8.2) to afford the title compound (ABU-2) (21.2 mg, 38 µmol, 15%) as a light yellow solid, m/z 558.2 (M+H)⁺ (ES+). ¹H NMR (400 MHz, MeOH-d4) δ 8.49 (s, 1H), 7.86 (s, 1H), 7.44 (d, J=1.2 Hz, 1H), 7.26 (s, 1H), 6.22 (d, J=1.2 Hz, 1H), 4.59 (t, J=5.7 Hz, 2H), 4.02 (s, 3H), 3.49 (s, 3H), 3.36 (s, 1H), 3.31 (s, 1H), 2.95 (t, J=5.8 Hz, 2H), 2.69-2.68 (m, 4H), 2.35-2.28 (m, 1H), 1.89-1.84 (m, 4H), 1.28-1.10 (m, 7H).

Example 83: Synthesis of tert-Butyl ((6-(ethyl-amino)-4-(1-methyl-4-(4-methyl-4H-1,2,4-triazol-3-yl)-1H-pyrazol-5-yl) pyridin-2-yl)methyl)carbamate (Intermediate ABV-1)

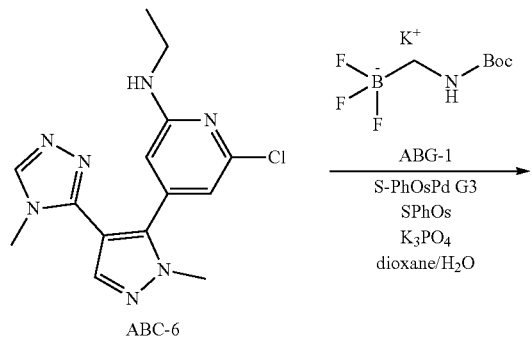

Into a 40-mL vial purged and maintained with an inert atmosphere of nitrogen, was placed intermediate (ABC-6) (30 mg, 1 Eq, 94 μmol), intermediate (ABG-1) (90 mg, 4 Eq, 378 μmol) and potassium phosphate (40 mg, 2 Eq, 189 μmol) in 1,4-dioxane (3.33 mL) and water (0.66 mL). S-PHOSPDG₃ (8 mg, 0.1 Eq, 9 μmol) and SPhOs (8 mg, 0.2 Eq, 19 μmol) were added at rt under nitrogen atmosphere. The resulting mixture was stirred for overnight at 100° C. under nitrogen atmosphere then cooled to rt, diluted with water and extracted with EtOAc (3×20 mL). The combined organic layers were washed with brine (2×20 mL), dried (Na₂SO₄), filtered and concentrated in vacuo. The crude product was purified by Prep-HPLC with the following conditions (Column: XBridge Prep OBD C18 Column, 30×150 mm, 5 μm; Mobile Phase A: Water (0.1% NH₄HCO₃), Mobile Phase B: ACN; Flow rate: 60 mL/min; Gradient: 25% B to 50% B in 8 min; Wavelength: 254/220 nm; RT: 6.27) to afford the title compound (ABV-1) (5.1 mg, 12 μmol, 12%) as a white solid. m/z 413.2 (M+H)⁺ (ES+). ¹H NMR (400 MHz, MeOH-d4) δ 8.46 (s, 1H), 7.84 (s, 1H), 6.43 (s, 1H), 6.22 (s, 1H), 4.17 (s, 2H), 3.94 (s, 3H), 3.37 (s, 3H), 3.30-3.27 (m, 2H), 1.46 (s, 9H), 1.18 (t, J=7.2 Hz, 3H).

Example 84: Synthesis of 6-Cyclopropyl-N-(6-(ethylamino)-4-(1-methyl-4-(4-methyl-4H-1,2,4-triazol-3-yl)-1H-pyrazol-5-yl)pyridin-2-yl)-4-methylpicolinamide (ABW-3)

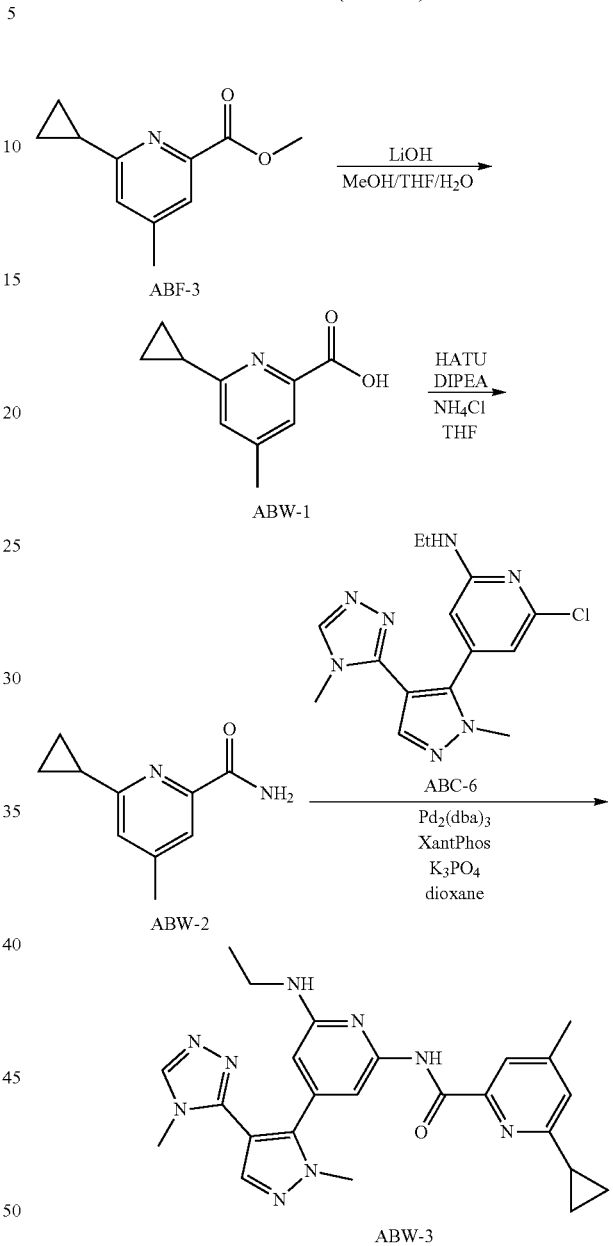

Step 1: Synthesis of 6-Cyclopropyl-4-methylpicolinic acid (ABW-1)

To a stirred solution of intermediate (ABF-3) (200 mg, 1 Eq, 1.04 mmol) in THF (2 mL), MeOH (2 mL) and water (1 mL) was added and LiOH (125 mg, 5 Eq, 5.20 mmol) at rt. The resulting mixture was stirred for 2 h at rt. The mixture was concentrated in vacuo. The residue was diluted with water and the solution acidified to pH 3 with HCl (aq., 1M). The solids were collected by filtration to obtain the sub-title compound (ABW-1) (180 mg, 1.02 mmol, 97%) as a yellow solid. m/z 178.1 (M+H)⁺ (ES+).

Step 2: Synthesis of 6-Cyclopropyl-4-methylpicolinamide (ABW-2)

To a stirred solution of the product from step 1 above (ABW-1) (110 mg, 1 Eq, 620 μmol) and NH$_4$Cl (166 mg, 5 Eq, 3.10 mmol) in THF (5 mL) were added HATU (708 mg, 3 Eq, 1.86 mmol) and DIPEA (802 mg, 10 Eq, 6.20 mmol) at rt. The resulting mixture was stirred for 3 h at rt then concentrated in vacuo. The residue was purified by Prep-TLC with petroleum ether/EtOAc (1/1). This resulted in the sub-title compound (ABW-2) (80 mg, 454 μmol, 73%) as a white solid. m/z 177.1 (M+H)$^+$ (ES+).

Step 3: Synthesis of 6-Cyclopropyl-N-[6-(ethyl-amino)-4-[2-methyl-4-(4-methyl-1,2,4-triazol-3-yl)-pyrazol-3-yl]-pyridine-2-yl]-4-methylpyridine-2-carboxamide (ABW-3)

To a stirred solution of the product from step 2 above (ABW-2) (32 mg, 1 Eq, 180 μmol), intermediate (ABC-6) (58 mg, 1 Eq, 180 μmol) and potassium phosphate (77 mg, 2 Eq, 360 μmol) in 1,4-dioxane (8 mL) were added Xant-Phos (21 mg, 0.2 Eq, 36 μmol) and Pd$_2$(dba)$_3$ (17 mg, 0.1 Eq, 18 μmol) at rt under nitrogen atmosphere. The resulting mixture was stirred for 3 h at 80° C. under nitrogen atmosphere then cooled to rt and concentrated in vacuo. The residue was purified by Prep-TLC with DCM/MeOH (10/1) and concentrated in vacuo. The crude product was purified by Prep-HPLC with the following conditions: Column: XBridge Prep OBD C18 Column, 30×150 mm 5 um; Mobile Phase A: Water (0.1% NH$_4$HCO$_3$), Mobile Phase B: ACN; Flow rate: 60 mL/min; Gradient: 42% B to 67% B in 8 min; Detector, UV 254/210 nm; RT: 6.92. The product-containing fractions were combined and evaporated partially in vacuo and lyophilized overnight to afford the title compound (ABW-3) (19.9 mg, 43 μmol, 23%) as a white solid. m/z 458.2 (M+H)$^+$ (ES+). $^1$H NMR (400 MHz, MeOH-d4) δ 8.49 (s, 1H), 7.86 (s, 1H), 7.79 (s, 1H), 7.45 (d, J=1.3 Hz, 1H), 7.34 (s, 1H), 6.18 (d, J=1.3 Hz, 1H), 4.03 (s, 3H), 3.48 (s, 3H), 3.32-3.29 (m, 2H), 2.44 (s, 3H), 2.21-2.15 (m, 1H), 1.22 (t, J=7.2 Hz, 3H), 1.17-1.04 (m, 4H).

Example 85: Synthesis of 2-[3-(Ethylamino)-5-[2-methyl-4-(4-methyl-1,2,4-triazol-3-yl) pyrazol-3-yl] phenyl]-4-(trifluoromethyl)-3H-isoindol-1-one (ABX-6)

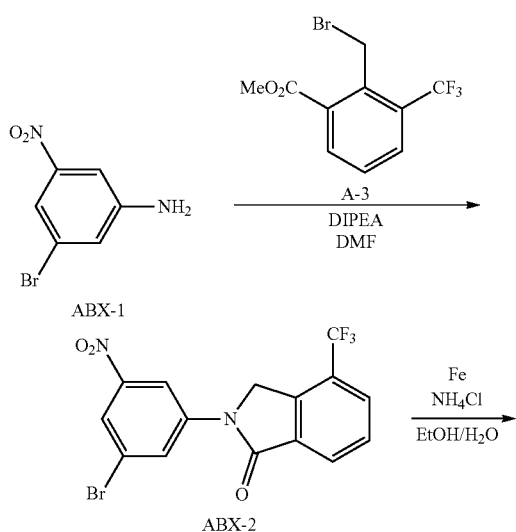

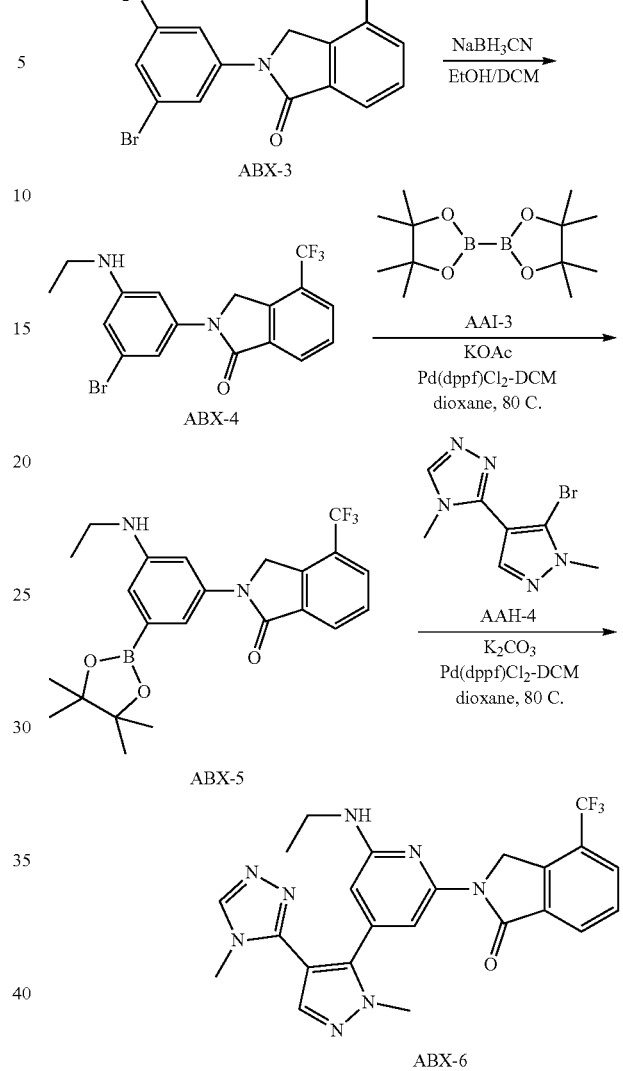

Step 1: Synthesis of 2-(3-Bromo-5-nitrophenyl)-4-(trifluoromethyl)isoindolin-1-one (ABX-2)

Into a 250-mL round-bottom flask purged and maintained with an inert atmosphere of nitrogen, was placed 3-bromo-5-nitroaniline (ABX-1) (2.17 g, 1 Eq, 10.0 mmol) in DMF (50 mL), then intermediate (A-3) (5.94 g, 2 Eq, 20.0 mmol) and DIPEA (12.9 g, 10 Eq, 100.0 mmol) were added at rt. The resulting solution was stirred overnight at 80° C. The resulting mixture was diluted with water and extracted with EtOAc (3×200 mL). The combined organic layers were washed with brine (2×200 mL), dried (Na$_2$SO$_4$), filtered and concentrated in vacuo. The crude product was purified by reverse flash column chromatography with the following conditions: Column, C18; mobile phase, Water (0.1% NH$_4$HCO$_3$) and ACN (65% ACN up to 80% in 10 min); Detector, UV 254/220 nm. The product-containing fractions were combined and concentrated in vacuo. This resulted in the sub-title compound (ABX-2) (2 g, 4.99 mmol, 50%) as a yellow solid. m/z 401.1/403.1 (M+H)$^+$ (ES+).

Step 2: Synthesis of 2-(3-Amino-5-bromophenyl)-4-(trifluoromethyl)isoindolin-1-one (ABX-3)

Into a 250-mL round-bottom flask purged and maintained with an inert atmosphere of nitrogen, was placed the product from step 1 above (ABX-2) (2.00 g, 1 Eq, 4.99 mmol) in EtOH (80 mL) and water (20 mL) at rt, then iron powder (1.39 g, 5 Eq, 24.9 mmol) and NH$_4$Cl (2.67 g, 10 Eq, 49.9 mmol) was added at rt under nitrogen atmosphere. The resulting solution was stirred for 16 h at 80° C. under nitrogen atmosphere. The mixture was cooled to rt and concentrated in vacuo. The residue was applied on a silica gel column chromatography with petroleum ether/EtOAc (5/1). This resulted in (1.5 g, 4.05 mmol, 81%) of the sub-title compound (ABX-3) as a yellow solid. m/z 371.2/373.2 (M+H)$^+$ (ES+).

Step 3: 2-(3-Bromo-5-(ethylamino) phenyl)-4-(trifluoromethyl)isoindolin-1-one (ABX-4)

Into a 100-mL round-bottom flask, was placed the product from step 2 above (ABX-3) (1.30 g, 1 Eq, 3.50 mmol) and acetaldehyde (123 mg, 0.8 Eq, 2.80 mmol) in DCM (30 mL). The mixture was stirred for 30 min at rt and then NaBH(OAc)$_3$ (123 mg, 0.8 Eq, 2.80 mmol) was added at 0° C. The resulting solution was stirred for 16 h at rt and the resulting mixture diluted with water and extracted with DCM (3×100 mL). The combined organic layers were washed with brine (2×100 mL), dried (Na$_2$SO$_4$), filtered and concentrated in vacuo. The crude product was purified by Prep-TLC with DCM/MeOH (10/1). This resulted in the sub-title compound (ABX-4) (800 mg, 2.01 mmol, 57%) as a yellow solid. m/z 399.2/401.2 (M+H)$^+$ (ES+).

Step 4: Synthesis of 2-(3-(Ethylamino)-5-(4,4,5,5-tetramethyl-1,3,2-dioxaborolan-2-yl) phenyl)-4-(trifluoromethyl)isoindolin-1-one (ABX-5)

Into a 100-mL round-bottom flask purged and maintained with an inert atmosphere of nitrogen, was placed the product from step 3 above (ABX-4) (3.00 g, 1 Eq, 8.39 mmol), bis(pinacolato)diboron (AAI-3) (1.02 g, 2 Eq, 4.00 mmol) and potassium acetate (590 mg, 3 Eq, 6.01 mmol) in 1,4-dioxane (20 mL) at rt. Pd(dppf)Cl$_2$.DCM (147 mg, 0.1 Eq, 200 µmol) was added at rt under nitrogen atmosphere and the resulting solution stirred for 4 h at 80° C. under nitrogen atmosphere. The mixture was cooled to rt, diluted with water and extracted with EtOAc (3×200 mL). The combined organic layers were washed with brine (2×200 mL), dried (Na$_2$SO$_4$), filtered and concentrated in vacuo. The crude product was purified by reverse flash column chromatography with the following conditions: Column, C18; mobile phase, Water (0.1% NH$_4$HCO$_3$) and ACN (22% ACN up to 45% in 8 min); Detector, UV 254/220 nm. The product-containing fractions were combined and concentrated in vacuo. This resulted in the sub-title compound (ABX-5) (550 mg, 1.23 mmol, 16%) as brown/yellow solid. m/z 447.2 (M+H)$^+$ (ES+).

Step 5: 2-(3-(Ethylamino)-5-(1-methyl-4-(4-methyl-4H-1,2,4-triazol-3-yl)-1H-pyrazol-5-yl) phenyl)-4-(trifluoromethyl)isoindolin-1-one (ABX-6)

Into a 25-mL round-bottom flask, was placed the product from step 4 (ABX-5) (100 mg, 1 Eq, 224 µmol), intermediate (AAH-4) (54 mg, 1 Eq, 224 µmol) and K$_2$CO$_3$ (93 mg, 3 Eq, 672 µmol) in 1,4-dioxane (4 mL) and water (1 mL), then Pd(dppf)Cl$_2$.DCM (18 mg, 0.1 Eq, 22 µmol) was added at rt under nitrogen atmosphere. The resulting solution was stirred overnight at 80° C. under nitrogen atmosphere. The mixture was cooled to rt and concentrated in vacuo. The crude product was purified by Prep-HPLC with the following conditions: Column: XBridge Prep C18 OBD Column, 19×150 mm, 5 µm; Mobile Phase A: Water (0.1% NH$_4$HCO$_3$), Mobile Phase B: ACN; Flow rate: 60 mL/min; Gradient: 24 B to 49 B in 9 min; Detector, UV 210/254 nm; RT: 8.9. This resulted in the title compound (ABX-6) (34.6 mg, 72 µmol, 32%) as a white solid. m/z 482.1 (M+H)$^+$ (ES+). $^1$H NMR (400 MHz, MeOH-d4) δ 8.45 (s, 1H), 8.10 (d, J=7.6 Hz, 1H), 8.01-7.95 (m, 1H), 7.84 (s, 1H), 7.82-7.74 (m, 1H), 7.23 (t, J=2.1 Hz, 1H), 7.14 (t, J=1.7 Hz, 1H), 6.39 (dd, J=2.1, 1.4 Hz, 1H), 5.12 (s, 2H), 4.01 (s, 3H), 3.36 (s, 3H), 3.11 (q, J=7.2 Hz, 2H), 1.22 (t, J=7.2 Hz, 3H).

Example 86: Synthesis of 2-[5-(Ethylamino)-2-(4-methyl-1,2,4-triazol-3-yl)-[1,1-biphenyl]-3-yl]-4-(trifluoromethyl)-3H-isoindol-1-one (ABY-1)

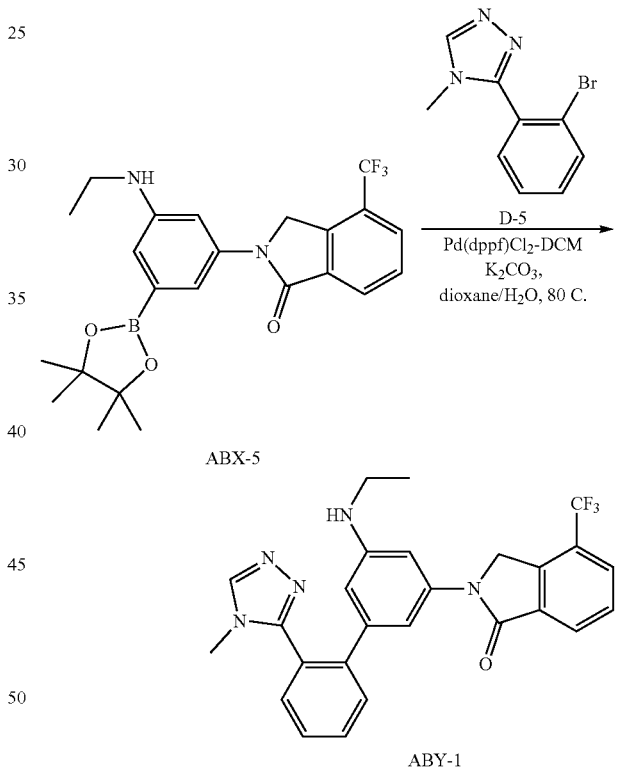

ABX-5

ABY-1

Into a 25-mL round-bottom flask, was placed intermediate (ABX-5) (80 mg, 179 µmol, 1 Eq), intermediate (D-5) (43 mg, 1 Eq, 179 µmol) and K$_2$CO$_3$ (74 mg, 3 Eq, 538 µmol) in 1,4-dioxane (4 mL) and water (1 mL), then Pd(dppf)Cl$_2$.DCM (15 mg, 0.1 Eq, 18 µmol) was added at rt under nitrogen atmosphere. The resulting solution was stirred overnight at 80° C. under nitrogen atmosphere then cooled to rt and concentrated in vacuo. The crude product was purified by Prep-HPLC with the following conditions: Column: XBridge Prep C18 OBD Column, 30×150 mm, 5 µm; Mobile Phase A: Water (0.1% NH$_4$HCO$_3$), Mobile Phase B: ACN; Flow rate: 60 mL/min; Gradient: 48 B to 66 B in 8 min; Detector, UV 210/254 nm; RT: 6.05. This resulted in 1.1 (20.3 mg, 42 μmol, 24%) as a white solid. m/z 478.1 (M+H)⁺ (ES+). ¹H NMR (400 MHz, MeOH-d4) δ 8.39 (s, 1H), 8.09 (d, J=7.6 Hz, 1H), 7.97 (d, J=7.7 Hz, 1H), 7.82-7.68 (m, 3H), 7.64-7.54 (m, 2H), 7.20 (t, J=2.1 Hz, 1H), 6.92 (t, J=1.8 Hz, 1H), 6.30 (t, J=1.8 Hz, 1H), 5.04 (s, 2H), 3.19 (s, 3H), 3.04 (q, J=7.2 Hz, 2H), 1.21 (t, J=7.2 Hz, 3H).

Example 87: Synthesis of 6-Cyclopropyl-N-(6-(ethylamino)-4-(1-methyl-4-(4-methyl-4H-1,2,4-triazol-3-yl)-1H-pyrazol-5-yl)pyridin-2-yl)-4-(hydroxymethyl) picolinamide (ABZ-7)

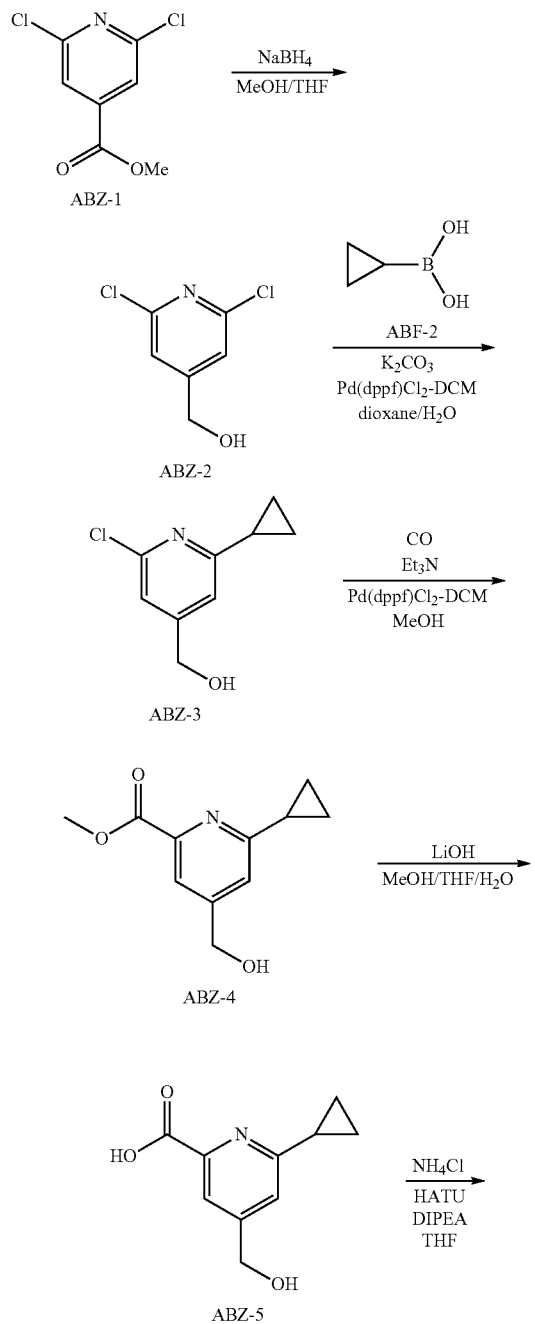

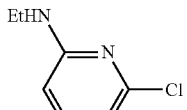

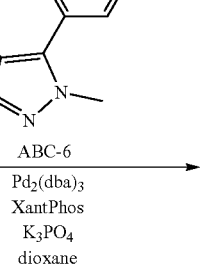

Step 1: Synthesis of (2,6-Dichloropyridin-4-yl)methanol (ABZ-2)

To a stirred solution of methyl 2,6-dichloropyridine-4-carboxylate (ABZ-1) (8.20 g, 1 Eq, 39.8 mmol) in the mixture of MeOH (100 mL) and THF (20 mL) was added NaBH₄ (7.53 g, 199 mmol, 5 Eq) at 0° C. The resulting mixture was stirred for 1 h at rt then quenched by the addition of sat. NH₄Cl solution (aq.) (60 mL) at 0° C. The resulting mixture was diluted with water and extracted with EtOAc (3×500 mL). The combined organic layers were washed with brine (2×500 mL), dried (Na₂SO₄), filtered and concentrated in vacuo. This resulted in the sub-title compound (ABZ-2) (7 g, 39.5 mmol, 99%) as a white solid. m/z 178.0/180.0 (M+H)⁺ (ES+).

Step 2: Synthesis of (2-Chloro-6-cyclopropylpyridin-4-yl)methanol (ABZ-3)

To a stirred solution of the product from step 1 above (ABZ-2) (3.56 g, 1 Eq, 20.0 mmol), cyclopropylboronic acid (ABF-2) (1.89 g, 1.1 Eq, 22.0 mmol) and K₂CO₃ (8.29 g, 3 Eq, 60.0 mmol) in the mixture of dioxane (20 mL) and water (1 mL) was added Pd(dppf)Cl₂.DCM (1.46 g, 0.1 Eq, 2.00 mmol) at rt under nitrogen atmosphere. The resulting mixture was stirred overnight at 90° C. under nitrogen atmosphere. The mixture was cooled to rt and concentrated in vacuo. The residue was applied on a silica gel column chromatography with petroleum ether/EtOAc (5/1) to afford the sub-title compound (ABZ-3) (2.1 g, 11.5 mmol, 57%) as a yellow solid. m/z 184.0/186.0 (M+H)⁺ (ES+).

Step 3: Synthesis of Methyl 6-cyclopropyl-4-(hydroxymethyl)picolinate (ABZ-4)

To a stirred solution of the product from step 2 above (ABZ-3) (2.10 g, 1 Eq, 11.4 mmol) and Et₃N (3.47 g, 3 Eq, 34.3 mmol) in MeOH (40 mL) was added Pd(dppf)Cl$_2$.DCM (418 mg, 0.05 Eq, 572 µmol) at rt under nitrogen atmosphere. The resulting mixture was stirred overnight at 70° C. under carbon monoxide atmosphere. The resulting mixture was cooled to rt and concentrated in vacuo. The residue was applied on a silica gel column chromatography with petroleum ether/EtOAc (2/1) to afford the sub-title compound (ABZ-4) (1.82 g, 8.79 mmol, 77%)) as a light yellow oil. m/z 208.0 (M+H)$^+$ (ES+).

Step 4: Synthesis of 6-Cyclopropyl-4-(hydroxymethyl)picolinic acid (ABZ-5)

To a stirred solution of the product from step 3 above (ABZ-4) (200 mg, 1 Eq, 965 µmol) in THF (2 mL), MeOH (2 mL) and water (1 mL) was added and LiOH (116 mg, 5 Eq, 4.83 mmol) at rt. The resulting mixture was stirred for 2 h at rt then concentrated in vacuo. The residue was diluted with water and acidified to pH 3 with HCl (aq., 1M). The solids were collected by filtration to obtain the sub-title compound (ABZ-5) (180 mg, 932 µmol, 97%) as a white solid. m/z 194.1 (M+H)$^+$ (ES+).

Step 5: Synthesis of 6-Cyclopropyl-4-(hydroxymethyl)picolinamide (ABZ-6)

To a stirred solution of the product from step 4 above (ABZ-5) (160 mg, 1 Eq, 820 µmol) and NH$_4$Cl (222 mg, 5 Eq, 4.14 mmol) in THF (5 mL) were added HATU (945 mg, 3 Eq, 2.48 mmol) and DIPEA (1.00 g, 10 Eq, 8.28 mmol) at 0° C. and the resulting mixture stirred overnight at rt. The crude product was purified by reverse flash column chromatography with the following conditions: Column, C18; mobile phase, Water (0.1% NH$_4$HCO$_3$) and ACN (40% ACN up to 80% in 8 min); Detector, UV 254/220 nm. The product-containing fractions were combined and concentrated in vacuo. This resulted in the sub-title compound (ABZ-6) (120 mg, 625 µmol, 75%) as a white solid. m/z 193.1 (M+H)$^+$ (ES+).

Step 6: Synthesis of 6-Cyclopropyl-N-(6-(ethylamino)-4-(1-methyl-4-(4-methyl-4H-1,2,4-triazol-3-yl)-1H-pyrazol-5-yl) pyridin-2-yl)-4-(hydroxymethyl)picolinamide (ABZ-7)

To a stirred of the product from step 5 above (ABZ-6) (48 mg, 1 Eq, 250 µmol), intermediate (ABC-6) (79 mg, 1 Eq, 250 µmol) and potassium phosphate (159 mg, 3 Eq, 749 µmol) in 1,4-dioxane (4 mL) were added XantPhos (29 mg, 0.2 Eq, 50 µmol) and Pd$_2$(dba)$_3$ (23 mg, 0.1 Eq, 25 µmol) at rt under nitrogen atmosphere and the resulting mixture stirred for 2 h at 100° C. under nitrogen atmosphere. The resulting mixture was cooled to rt and diluted with water and extracted with EtOAc (3×20 mL). The combined organic layers were washed with brine (2×20 mL), dried (Na$_2$SO$_4$), filtered and concentrated in vacuo. The residue was purified by Prep-TLC with petroleum ether/EtOAc (1/1). The crude product was purified by Prep-HPLC with the following conditions: Column: XBridge Prep OBD C18 Column, 30×150 mm 5 um; Mobile Phase A: Water (10% NH$_4$HCO$_3$), Mobile Phase B: ACN; Flow rate: 60 mL/min; Gradient: 29% B to 54% B in 8 min; Detector, UV 254/210 nm; RT: 6.6. The product-containing fractions were combined and evaporated partially in vacuo and lyophilized overnight to afford the title compound (ABZ-7) (17.6 mg, 37 µmol, 14.88%) as a white solid. m/z 474.4 (M+H)$^+$ (ES+). $^1$H NMR (400 MHz, MeOH-d4) δ 8.49 (s, 1H), 7.96 (d, J=1.4 Hz, 1H), 7.86 (s, 1H), 7.47 (m, 2H), 6.19 (d, J=1.2 Hz, 1H), 4.72 (s, 2H), 4.03 (s, 3H), 3.48 (s, 3H), 3.31-3.19 (m, 2H), 2.26-2.20 (m, 1H), 1.22 (t, J=7.2 Hz, 3H), 1.16-1.06 (m, 4H).

Example 88: Synthesis of (R)-2-(6-(Ethylamino)-4-(1-methyl-4-(4-methyl-4H-1,2,4-triazol-3-yl)-1H-pyrazol-5-yl) pyridin-2-yl)-6-((3-fluoropyrrolidin-1-yl) methyl)-4-(trifluoromethyl)isoindolin-1-one (ACA-1)

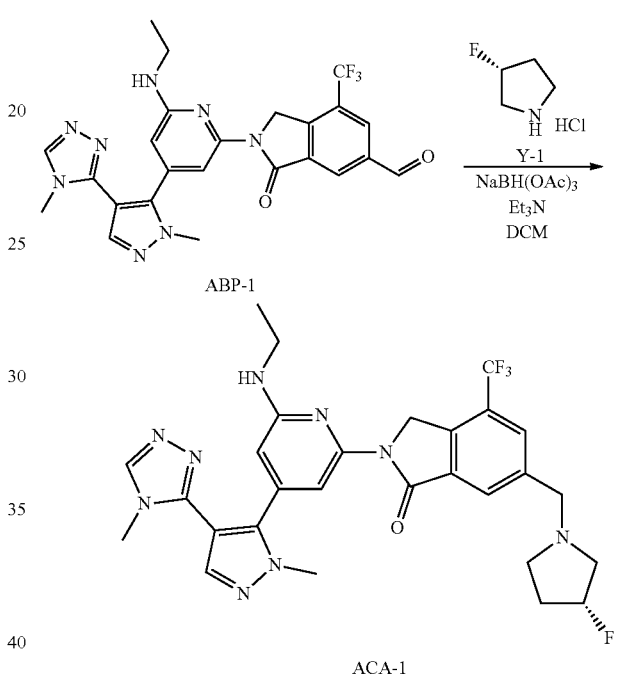

To a stirred solution of intermediate (ABP-1) (30 mg, 1 Eq, 50 µmol) and (3R)-3-fluoropyrrolidine, HCl (Y-1) (21 mg, 4 Eq, 230 µmol) in DCM (5 mL) were added Et$_3$N (18 mg, 3 Eq, 170 µmol) and NaBH(OAc)$_3$ (25 mg, 2 Eq, 110 µmol) at rt. The resulting mixture was stirred for 1 h at rt then concentrated in vacuo. The residue was purified by Prep-TLC with DCM/MeOH (15/1). The product-containing fractions were combined and concentrated in vacuo. The crude product was purified by Prep-HPLC with the following conditions: Column: SunFire Prep C18 OBD Column, 30×150 mm 5 um; Mobile Phase A: Water (0.1% NH$_4$HCO$_3$), Mobile Phase B: ACN; Flow rate:60 mL/min; Gradient:43 B to 68 B in 8 min; Detector, UV 254/210 nm; RT: 6.53. The product-containing fractions were combined and evaporated partially in vacuo and lyophilized overnight to afford the title compound (ACA-1) (5.2 mg, 8.9 µmol, 15%) as a white solid. m/z 584.3 (M+H)$^+$ (ES+). $^1$H NMR (400 MHz, MeOH-d4) δ 8.49 (s, 1H), 8.07 (s, 1H), 8.00 (s, 1H), 7.86 (s, 1H), 7.66 (s, 1H), 6.20 (s, 1H), 5.31-5.09 (m, 3H), 4.04 (s, 3H), 3.94-3.82 (m, 2H), 3.50 (s, 3H), 3.50-3.36 (t, J=7.2 Hz, 2H), 2.99-2.85 (m, 2H), 2.84-2.68 (m, 1H), 2.56-2.46 (m, 1H), 2.33-2.16 (m, 1H), 2.14-1.96 (m, 1H), 1.25 (t, J=7.2 Hz, 3H).

Example 89: Synthesis of (S)-2-(6-(Ethylamino)-4-(1-methyl-4-(4-methyl-4H-1,2,4-triazol-3-yl)-1H-pyrazol-5-yl) pyridin-2-yl)-6-((3-fluoropyrrolidin-1-yl) methyl)-4-(trifluoromethyl)isoindolin-1-one (ACB-1)

Example 90: Synthesis of 2-(4-Methyl-4H-1,2,4-triazol-3-yl)-3'-(1-oxo-4-(trifluoromethyl)isoindolin-2-yl)-[1,1'-biphenyl]-4-carbonitrile (ACC-8)

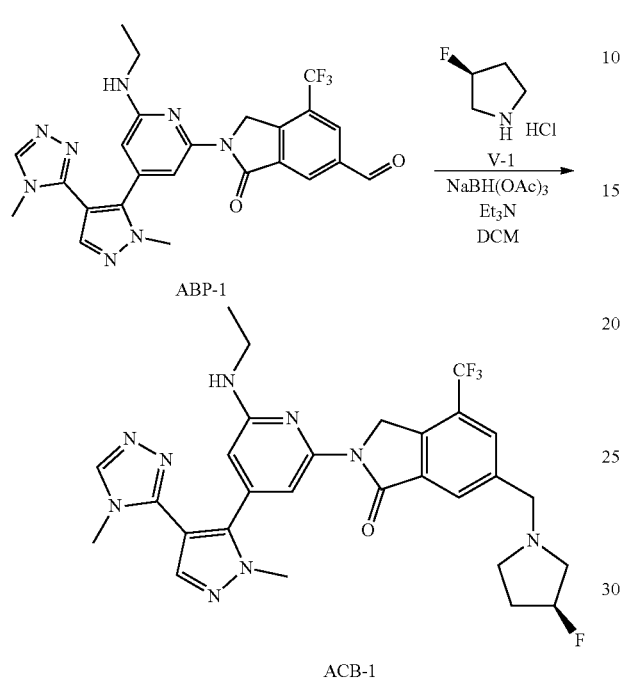

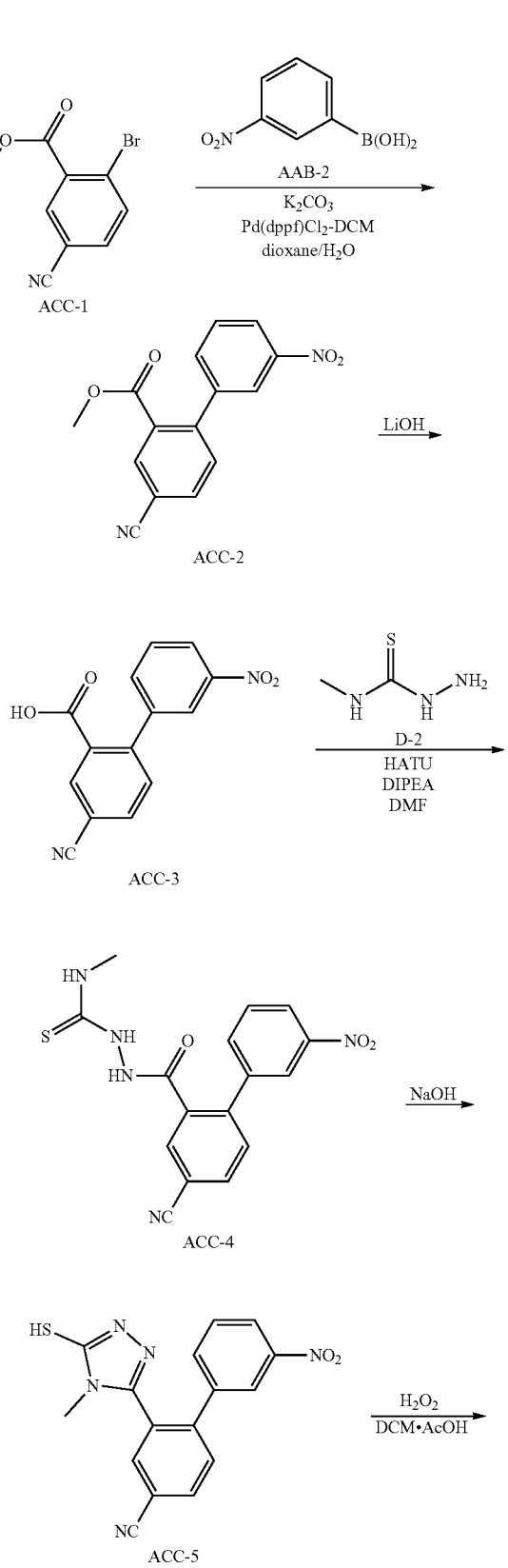

To a stirred solution of intermediate (ABP-1) (30 mg, 1 Eq, 50 µmol) and (S)-3-fluoropyrrolidine, HCl (V-1) (21 mg, 4 Eq, 230 µmol) in DCM (5 mL) were added Et$_3$N (18 mg, 3 Eq, 170 µmol) and NaBH(OAc)$_3$ (25 mg, 2 Eq, 110 µmol) at rt and the resulting mixture stirred for 1 h at rt. The mixture was concentrated in vacuo and the residue purified by Prep-TLC with DCM/MeOH (15/1). The product-containing fractions were combined and concentrated in vacuo. The crude product was purified by Prep-HPLC with the following conditions: Column: SunFire Prep C18 OBD Column, 30×150 mm 5 um; Mobile Phase A: Water (0.1% NH$_4$HCO$_3$), Mobile Phase B: ACN; Flow rate:60 mL/min; Gradient:37 B to 54 B in 10 min; Detector, UV 254/210 nm; RT: 8.2. The product-containing fractions were combined and evaporated partially in vacuo and lyophilized overnight to afford the title compound (ACB-1) (8.2 mg, 14 µmol, 23%) as a white solid. m/z 584.3 (M+H)$^+$ (ES+). $^1$H NMR (400 MHz, MeOH-d4) δ 8.49 (s, 1H), 8.07 (s, 1H), 8.00 (s, 1H), 7.87 (s, 1H), 7.66 (d, J=1.2 Hz, 1H), 6.20 (d, J=1.2 Hz, 1H), 5.31-5.24 (m, 3H), 4.04 (s, 3H), 3.94-3.82 (m, 2H), 3.50 (s, 3H), 3.40-3.34 (m, 2H), 2.96-2.87 (m, 2H), 2.92-2.76 (m, 1H), 2.56-2.45 (m, 1H), 2.35-2.15 (m, 1H), 2.14-1.95 (m, 1H), 1.25 (t, J=7.2 Hz, 3H).

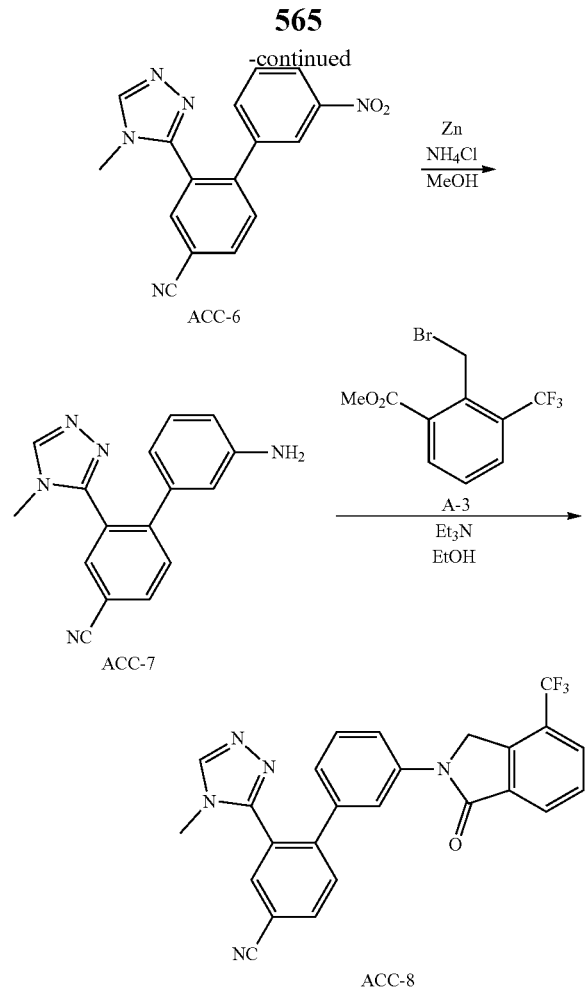

Step 1: Synthesis of Methyl 4-cyano-3'-nitro-[1,1'-biphenyl]-2-carboxylate (ACC-2)

Into a 250 mL round-bottom flask were added methyl 2-bromo-5-cyanobenzoate (ACC-1) (3.00 g, 10.5 mmol, 1 Eq), intermediate (AAB-2) (2.09 g, 12.5 mmol, 1.2 Eq) and potassium phosphate (2.89 g, 20.9 mmol, 2 Eq) in 1,4-dioxane (40 mL) at rt under nitrogen atmosphere. To the above mixture was added Pd(dppf)Cl$_2$.DCM (760 mg, 0.1 Eq, 1.05 mmol) at rt under nitrogen atmosphere and the resulting mixture stirred for 3 h at 80° C. under nitrogen atmosphere. The mixture was allowed to cool to rt and was diluted with water and extracted with EtOAc (3×100 mL). The combined organic layers were washed with brine (2×100 mL), dried (Na$_2$SO$_4$), filtered and concentrated in vacuo. The residue was purified by silica gel column chromatography Petroleum ether/EtOAc (4/1) to afford the sub-title compound (ACC-2) (2.2 g, 7.79 mmol, 75%) as a yellow oil. m/z 283.1 (M+H)$^+$ (ES+).

Step 2: Synthesis of 4-Cyano-3'-nitro-[1,1'-biphenyl]-2-carboxylic acid (ACC-3)

Into a 20 mL sealed tube were added the product from step 1 above (ACC-2) (846 mg, 1 Eq, 3.00 mmol) in THF (8 mL) and water (2 mL) at rt. To the above mixture was added LiOH (215 mg, 3 Eq, 8.99 mmol) over 3 min at rt and the resulting mixture was stirred for 3 h at 60° C. The mixture was cooled to rt and concentrated in vacuo. The residue was diluted with water and the solution acidified to pH 3 with HCl (aq., 1 M). The solids were collected by filtration to obtain the sub-title compound (ACC-3) (650 mg, 2.42 mmol, 81%) as a yellow oil. m/z 269.1 (M+H)$^+$ (ES+).

Step 3: 2-(4-Cyano-3'-nitro-[1,1'-biphenyl]-2-carbonyl)-N-methylhydrazine-1-carbothioamide (ACC-4)

Into a 20 mL sealed tube were added the product from step 2 above (ACC-3) (600 mg, 1 Eq, 2.24 mmol), 1-amino-3-methylthiourea (D-2) (705 mg, 3 Eq, 6.71 mmol) and DIPEA (867 mg, 6.71 mmol, 3 Eq) in DMF (10 mL) at rt. To the above mixture was added HATU (851 mg, 1 Eq, 2.24 mmol) over 3 min at 0° C. and the resulting mixture stirred overnight at rt. The crude product was purified by reverse flash column chromatography with the following conditions: Column, C18; mobile phase, Water (0.1% NH$_4$HCO$_3$) and ACN (30% ACN up to 70% in 10 min); Detector, UV 254/220 nm. The product-containing fractions were combined and concentrated in vacuo. This resulted in the sub-title compound (ACC-4) (450 mg, 1.27 mmol, 57%) as a white solid. m/z 356.1 (M+H)$^+$ (ES+).

Step 4: 2-(5-Mercapto-4-methyl-4H-1,2,4-triazol-3-yl)-3'-nitro-[1,1'-biphenyl]-4-carbonitrile (ACC-5)

To a stirred solution of the product from step 3 above (ACC-4) (430 mg, 1 Eq, 1.21 mmol) in DMF (8 mL) was added NaOH (aq., 1M) (15 mL) at rt. The resulting mixture was stirred overnight at 50° C. The mixture was cooled to rt and the crude product purified by reverse flash column chromatography with the following conditions: Column, C18; mobile phase, Water (0.1% NH$_4$HCO$_3$) and ACN (30% ACN up to 50% in 7 min); Detector, UV 254/220 nm. The product-containing fractions were combined and concentrated in vacuo. This resulted in the sub-title compound (ACC-5) (120 mg, 356 μmol, 29%) as a yellow solid. m/z 338.1 (M+H)$^+$ (ES+).

Step 5: 2-(4-Methyl-4H-1,2,4-triazol-3-yl)-3'-nitro-[1,1'-biphenyl]-4-carbonitrile (ACC-6)

To a stirred solution of the product from step 4 above (ACC-5) (100 mg, 1 Eq, 296 μmol) in DCM (5 mL) were added acetic acid (53 mg, 3 Eq, 888 μmol) and hydrogen peroxide solution (168 mg, 30% Wt, 5 Eq, 1.48 mmol) at 0° C. The resulting mixture was stirred for 2 h at rt. The resulting mixture was diluted with water. The solution was basified to pH 8 with sat. NaHCO$_3$ solution (aq.). The resulting mixture was extracted with DCM (3×50 mL) and the combined organic layers washed with brine (2×50 mL), dried (Na$_2$SO$_4$), filtered and concentrated in vacuo. This resulted in the sub-title compound (ACC-6) (85 mg, 278 μmol, 94%) as a yellow solid. m/z 306.1 (M+H)$^+$ (ES+).

Step 6: 3'-Amino-2-(4-methyl-4H-1,2,4-triazol-3-yl)-[1,1'-biphenyl]-4-carbonitrile (ACC-7)

Into a 20 mL sealed tube were added the product from step 5 above (ACC-6) (80 mg, 1 Eq, 262 μmol) in MeOH (5 mL) at rt under nitrogen atmosphere. To the above mixture was added Pd/C 39 (3 mg, 10% Wt, 0.1 Eq, 26 μmol) at rt under nitrogen atmosphere. The resulting mixture was stirred for 3 h at rt under hydrogen atmosphere. The resulting mixture was filtered; the filter cake was washed with MeOH (3×2 mL). The filtrate was concentrated in vacuo to afford the sub-title compound (ACC-7) (50 mg, 182 μmol, 69%) as a colorless oil. m/z 276.1 (M+H)+ (ES+).

Step 7: 2-(4-Methyl-4H-1,2,4-triazol-3-yl)-3'-(1-oxo-4-(trifluoromethyl)isoindolin-2-yl)-[1,1'-biphenyl]-4-carbonitrile (ACC-8)

Into an 8 mL sealed tube were added the product from step 6 above (ACC-7) (20 mg, 1 Eq, 73 μmol) and intermediate (A-3) (24 mg, 1.1 Eq, 80 μmol) in EtOH (2 mL) at rt. To the above mixture was added Et₃N (30 uL, 3 Eq, 219 μmol) over 5 min at rt. The resulting mixture was stirred for overnight at 80° C. The mixture was allowed to cool to rt and the resulting mixture concentrated in vacuo. The crude product was purified by reverse flash column chromatography with the following conditions: Column, C18; mobile phase, Water (0.1% NH₄HCO₃) and ACN (10% ACN up to 50% in 10 min); Detector, UV 254/220 nm. The product-containing fractions were combined and concentrated in vacuo. The crude product was purified by Prep-HPLC with the following conditions (Column: XBridge Prep OBD C18 Column, 30*150 mm, 5 μm; Mobile Phase A: Water (0.1% NH₄HCO₃), Mobile Phase B: ACN; Flow rate: 60 mL/min; Gradient: 34% B to 48% B in 10 min; Wavelength: 254/220 nm; RT: 9.8) to afford the title compound (ACC-8) (2.0 mg, 4.3 μmol, 6%) as a white solid. m/z 460.1 (M+H)+ (ES+). ¹H NMR (400 MHz, MeOH-d4) δ 8.44 (s, 1H), 8.14-7.91 (m, 6H), 7.85-7.76 (m, 2H), 7.50 (t, J=8.0 Hz, 1H), 7.13 (d, J=8.0 Hz, 1H), 5.11 (s, 2H), 3.24 (s, 3H).

Example 91: Synthesis of 2-(4-Methyl-4H-1,2,4-triazol-3-yl)-3'-(1-oxo-4-(trifluoromethyl)isoindolin-2-yl)-[1,1'-biphenyl]-4-carboxamide (ACD-1)

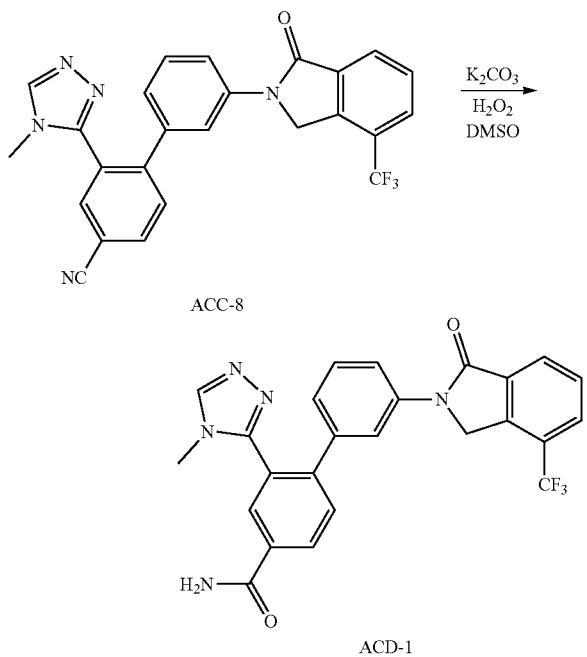

To a stirred mixture of compound (ACC-8) (10 mg, 1 Eq, 22 μmol) and K₂CO₃ (9 mg, 3 Eq, 66 μmol) in DMSO (1 mL) was added hydrogen peroxide (0.3 mL, 30% Wt) at 0° C. The resulting mixture was stirred for 20 min at rt before quenching with sodium thiosulfate aq. solution (2 mL) at 0° C. The mixture was extracted with EtOAc (3×10 mL) and the combined organic layers washed with brine (2×10 mL), dried (Na₂SO₄), filtered and concentrated in vacuo. The crude product was purified by Prep-HPLC with the following conditions (Column: XBridge Prep OBD C18 Column, 30*150 mm, 5 μm; Mobile Phase A: Water (0.1% NH₄HCO₃), Mobile Phase B: ACN; Flow rate: 60 mL/min; Gradient: 25% B to 45% B in 9 min; Wavelength: 254/220 nm; RT: 8.5) to afford the title compound (ACD-1) (6 mg, 13 μmol, 58%) as a white solid. m/z 478.0 (M+H)+ (ES+). ¹H NMR (400 MHz, DMSO-d6) δ 8.43 (s, 1H), 8.23-8.16 (m, 2H), 8.11-8.01 (m, 4H), 7.84-7.70 (m, 3H), 7.55 (s, 1H), 7.41 (t, J=8.0 Hz, 1H), 6.95-6.93 (m, 1H), 5.13 (s, 2H), 3.10 (s, 3H).

Example 92: Synthesis of (R)-2-(6-(Ethylamino)-4-(1-methyl-4-(4-methyl-4H-1,2,4-triazol-3-yl)-1H-pyrazol-5-yl)pyridin-2-yl)-6-((3-methylpiperidin-1-yl)methyl)-4-(trifluoromethyl) isoindolin-1-one (ACE-1)

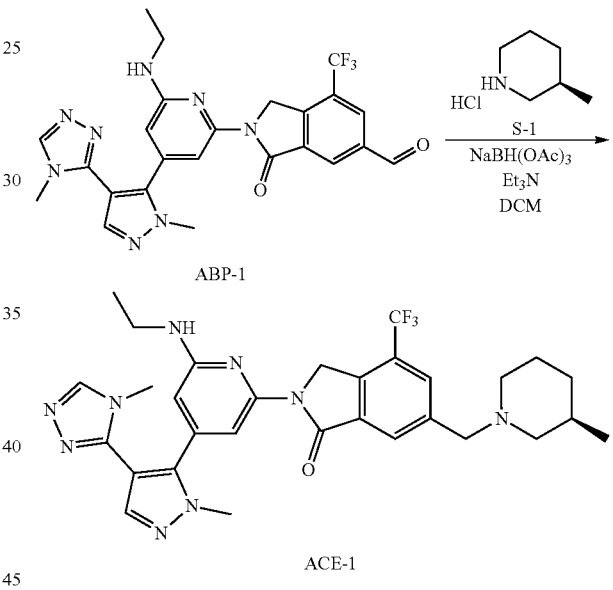

Into a 40-mL vial purged and maintained with an inert atmosphere of nitrogen, was placed intermediate (ABP-1) (50 mg, 1 Eq, 98 μmol), (R)-3-methyplperidine, HCl (53 mg, 4 Eq, 392 μmol) and Et₃N (30 mg, 3 Eq, 294 μmol) in DCM (4 mL) at rt. The resulting mixture was stirred for 1 h at rt under nitrogen atmosphere. To the above mixture was added NaBH(OAc)₃ (42 mg, 2 Eq, 196 μmol) at rt and the resulting mixture stirred for 2 h at rt. The resulting mixture was diluted with water and extracted with EtOAc (3×20 mL). The combined organic layers were washed with brine (2×00 mL), dried (Na₂SO₄), filtered and concentrated in vacuo. The crude product was purified by Prep-HPLC with the following conditions (Column: XBridge Prep OBD C18 Column, 30×150 mm, 5 μm; Mobile Phase A: Water (0.1% NH₄HCO₃), Mobile Phase B: ACN; Flow rate: 60 mL/min; Gradient: 58% B to 83% B in 8 min; Wavelength: 254/210 nm; RT: 7.08) to afford the title compound (ACE-1) (18.8 mg, 31 μmol, 32%) as a white liquid. m/z 594.4 (M+H)+ (ES+). ¹H NMR (400 MHz, DMSO-d6) δ 8.47 (s, 1H), 7.97 (s, 1H), 7.92 (s, 1H), 7.88 (s, 1H), 7.57 (d, J=1.2 Hz, 1H), 6.92 (t, J=5.4 Hz, 1H), 6.25 (d, J=1.2 Hz, 1H), 5.20 (s, 2H), 3.90 (s, 3H), 3.64 (s, 2H), 3.47 (s, 3H), 3.29-3.24 (m, 2H), 2.74-2.70 (m, 2H), 1.96-1.91 (m, 1H), 1.71-1.40 (m, 5H), 1.17 (t, J=7.1 Hz, 3H), 0.90-0.81 (m, 4H).

Example 93: Synthesis of (S)-2-(6-(Ethylamino)-4-(1-methyl-4-(4-methyl-4H-1,2,4-triazol-3-yl)-1H-pyrazol-5-yl)pyridin-2-yl)-6-((3-methylpiperidin-1-yl)methyl)-4-(trifluoromethyl)isoindolin-1-one (ACF-1)

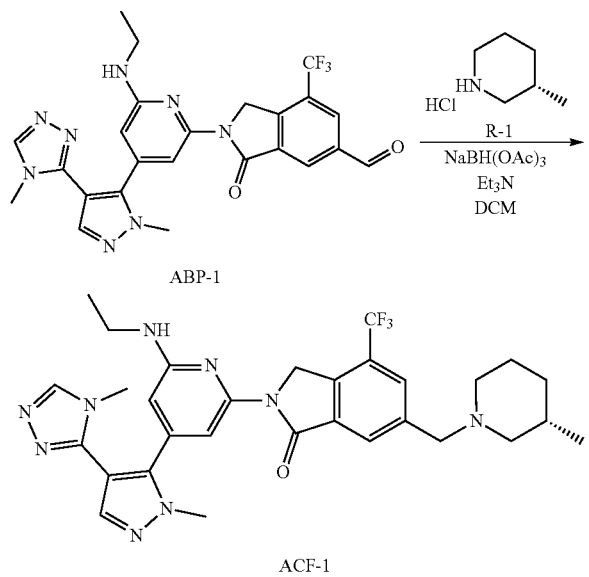

Into a 40-mL vial purged and maintained with an inert atmosphere of nitrogen, was placed intermediate (ABP-1) (50 mg, 98 µmol, 1.0 Eq), (S)-3-methyplperidine, HCl (R-1) (53 mg, 4 Eq, 392 µmol) and Et₃N (30 mg, 3 Eq, 294 µmol) in DCM (4 mL) at rt. The resulting mixture was stirred for 1h at rt under nitrogen atmosphere. To the above mixture was added NaBH(OAc)₃ (42 mg, 2 Eq, 196 µmol) at rt and the resulting mixture stirred for 2 h at rt. The resulting mixture was diluted with water and extracted with EtOAc (3×20 mL). The combined organic layers were washed with brine (2×20 mL), dried (Na₂SO₄), filtered and concentrated in vacuo. The crude product was purified by Prep-HPLC with the following conditions (Column: XBridge Prep OBD C18 Column, 30×150 mm, 5 µm; Mobile Phase A: Water (0.1% NH₄HCO₃), Mobile Phase B: ACN; Flow rate: 60 mL/min; Gradient: 50% B to 70% B in 9 min; Wavelength: 254/220 nm; RT: 8.83) to afford the title compound (ACF-1) (18.8 mg, 32 µmol, 32%) as a white liquid. m/z 594.4 (M+H)⁺ (ES+). ¹H NMR (400 MHz, MeOH-d4) δ 8.49 (s, 1H), 8.04 (s, 1H), 7.97 (s, 1H), 7.86 (s, 1H), 7.66 (d, J=1.2 Hz, 1H), 6.20 (d, J=1.2 Hz, 1H), 5.26 (s, 2H), 4.04 (s, 3H), 3.70 (s, 2H), 3.51 (s, 3H), 3.41-3.34 (m, 2H), 2.87-2.81 (m, 2H), 2.05-1.98 (m, 1H), 1.82-1.55 (m, 5H), 1.25 (t, J=7.2 Hz, 3H), 0.99-0.77 (m, 4H).

Example 94: Synthesis of 6-(Aminomethyl)-2-(6-(ethylamino)-4-(1-methyl-4-(4-methyl-4H-1,2,4-triazol-3-yl)-1H-pyrazol-5-yl) pyridin-2-yl)-4-(trifluoromethyl)isoindolin-1-one (ACG-3)

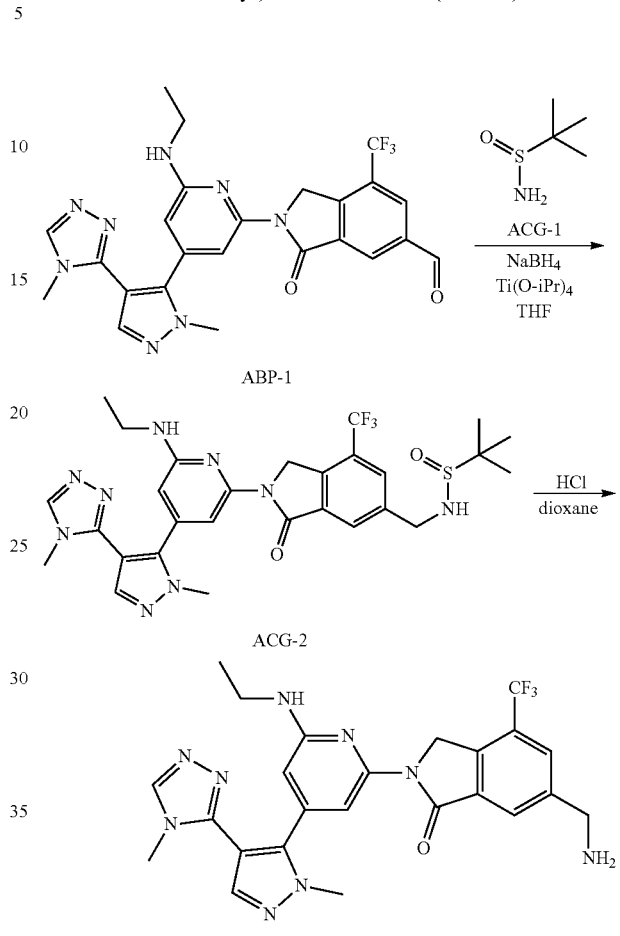

Step 1: Synthesis of N-((2-(6-(Ethylamino)-4-(1-methyl-4-(4-methyl-4H-1,2,4-triazol-3-yl)-1H-pyrazol-5-yl)pyridin-2-yl)-3-oxo-7-(trifluoromethyl) isoindolin-5-yl)methyl)-2-methylpropane-2-sulfinamide (ACG-2)

To a stirred mixture of intermediate (ABP-1) (50 mg, 1 Eq, 98 µmol) and tert-butanesulfinamide (ACG-1) (36 mg, 3 Eq, 294 µmol) in THF (2 mL) were added Ti(OiPr)₄ (139 mg, 5 Eq, 490 µmol) and NaBH₄ (11 mg, 3 Eq, 294 µmol) at rt under nitrogen atmosphere. The resulting mixture was stirred for 1 h at 60° C. under nitrogen atmosphere. The mixture was allowed to cool to rt and the resulting mixture diluted with water. The resulting mixture was extracted with EtOAc (3×20 mL) and the combined organic layers washed with water (3×20 mL), dried (Na₂SO₄), filtered and concentrated in vacuo. The residue was purified by Prep-TLC with DCM/MeOH (10/1) to afford the sub-title compound (ACG-2) (50 mg, 81 µmol, 83%) as a yellow solid. m/z 616.2 (M+H)⁺ (ES+).

Step 2: 6-(Aminomethyl)-2-(6-(ethylamino)-4-(1-methyl-4-(4-methyl-4H-1,2,4-triazol-3-yl)-1H-pyrazol-5-yl)pyridin-2-yl)-4-(trifluoromethyl)isoindolin-1-one (ACG-3)

A mixture of the product from step 1 above (ACG-2) (50 mg, 1 Eq, 81 μmol) in 1,4-dioxane and HCl in 1,4-dioxane (1 mL, 4 M) at rt was stirred for 1 h at rt. The resulting mixture was diluted with water. The resulting mixture was extracted with EtOAc (3×20 mL) and the combined organic layers washed with water (2×20 mL), dried ($Na_2SO_4$), filtered and concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: Water (0.1% $NH_4HCO_3$), Mobile Phase B: ACN; Flow rate: 60 mL/min; Gradient: 30% B to 43% B in 9 min; Wavelength: 254/220 nm; RT: 8.72) to afford the title compound (ACG-3) (21 mg, 41 μmol, 51%) as a white solid. m/z 512.3 $(M+H)^+$ (ES+). $^1$H NMR (400 MHz, DMSO-d6) δ 8.47 (s, 1H), 8.03 (d, J=15.6 Hz, 2H), 7.89 (s, 1H), 7.58 (d, J=1.2 Hz, 1H), 6.91 (t, J=5.4 Hz, 1H), 6.25 (d, J=1.2 Hz, 1H), 5.19 (s, 2H), 3.94-3.90 (m, 5H), 3.48 (s, 3H), 3.29-3.21 (m, 2H), 1.17 (t, J=7.1 Hz, 3H).

Example 95: Synthesis of 2-(6-(Ethylamino)-4-(1-methyl-4-(4-methyl-4H-1,2,4-triazol-3-yl)-1H-pyrazol-5-yl)pyridin-2-yl)-6-(hydroxymethyl)-4-(trifluoromethyl)isoindolin-1-one (ACH-1)

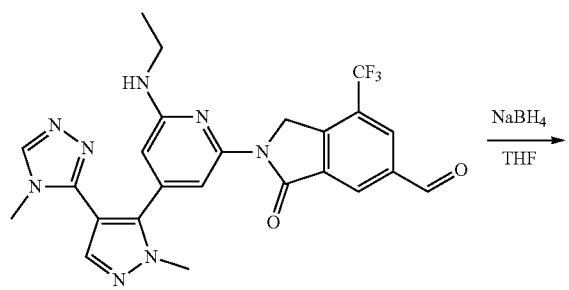

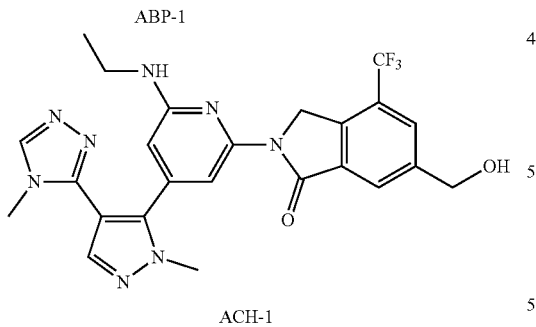

To a stirred mixture of intermediate (ABP-1) (40 mg, 1 Eq, 78 μmol) in THF (5 ml) was added $NaBH_4$ (6 mg, 2 Eq, 156 μmol) at rt. The resulting mixture was stirred for 2 h at rt. The resulting mixture was diluted with water. The resulting mixture was extracted with EtOAc (3×30 mL) and the combined organic layers washed with brine (3×30 mL), dried ($Na_2SO_4$), filtered and concentrated in vacuo. The residue was purified by Prep-TLC with DCM/MeOH (8/1). The crude product was purified by Prep-HPLC with the following conditions: (Column: XBridge Prep OBD C18 Column, 30*150 mm, 5 μm; Mobile Phase A: Water (0.1% $NH_4HCO_3$), Mobile Phase B: ACN; Flow rate: 60 mL/min; Gradient: 40% B to 60% B in 8 min, 60% B; Wavelength: 254/220 nm; RT: 7.83) to afford the title compound (ACH-1) (20 mg, 39 μmol, 5%) as a white solid. m/z 513.2 $(M+H)^+$ (ES+). $^1$H NMR (400 MHz, DMSO-d6) δ 8.47 (s, 1H), 7.98 (d, J=18.3 Hz, 2H), 7.89 (s, 1H), 7.58 (d, J=1.2 Hz, 1H), 6.92 (t, J=5.4 Hz, 1H), 6.25 (d, J=1.2 Hz, 1H), 5.57 (t, J=5.8 Hz, 1H), 5.20 (s, 2H), 4.70 (d, J=5.8 Hz, 2H), 3.90 (s, 3H), 3.47 (s, 3H), 3.30-3.23 (m, 2H), 1.17 (t, J=7.1 Hz, 3H).

Example 96: Synthesis of 2-(6-(Ethylamino)-4-(1-methyl-4-(4-methyl-4H-1,2,4-triazol-3-yl)-1H-pyrazol-5-yl)pyridin-2-yl)-6-(((2-hydroxyethyl) amino)methyl)-4-(trifluoromethyl)isoindolin-1-one (ACI-1)

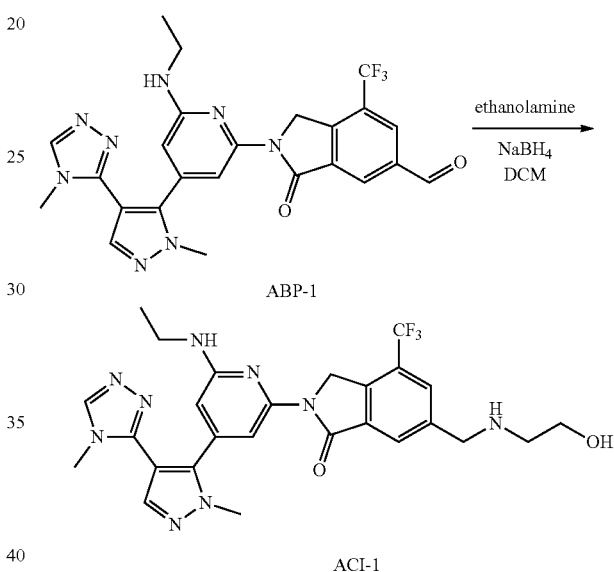

A solution of intermediate (ABP-1) (20 mg, 1 Eq, 39 μmol) and ethanolamine (12 mg, 5 Eq, 195 μmol) in DCM (5 mL) was stirred for 1 h at rt. To the above mixture was added $NaBH_4$ (3 mg, 2 Eq, 78 μmol) over 0.5 h at 0° C. and the resulting mixture stirred for 1 h at rt. The reaction was quenched with MeOH (2 mL) at 0° C., the resulting mixture diluted with DCM (30 mL) and concentrated in vacuo. The residue was purified by TLC with DCM/MeOH (5/1). The crude product was purified by Prep-HPLC with the following conditions Column: XBridge Prep OBD C18 Column, 30*150 mm, 5 μm; Mobile Phase A: Water (0.1% $NH_4HCO_3$), Mobile Phase B: ACN; Flow rate: 60 mL/min; Gradient: 17% B to 42% B in 10 min; Wavelength: 254/220 nm to afford the title compound (ACI-1) (19.7 mg, 35 μmol, 87%) as a white solid. m/z 556.1 $(M+H)^+$ (ES+). $^1$H NMR (400 MHz, DMSO-d6) δ 8.47 (s, 1H), 8.01 (d, J=15.6 Hz, 2H), 7.89 (s, 1H), 7.58 (d, J=1.2 Hz, 1H), 6.91 (t, J=5.4 Hz, 1H), 6.25 (d, J=1.2 Hz, 1H), 5.19 (s, 2H), 4.49 (t, J=5.4 Hz, 1H), 3.95-3.85 (m, 5H), 3.52-3.47 (m, 5H), 3.31-3.22 (m, 2H), 2.57 (t, J=5.8 Hz, 2H), 1.17 (t, J=7.1 Hz, 3H).

Example 97: Synthesis of Methyl 1-(4-(2-(4-methyl-4H-1,2,4-triazol-3-yl) phenyl)-6-(1-oxo-4-(trifluoromethyl)isoindolin-2-yl)pyridin-2-yl) cyclopropane-1-carboxylate (ACJ-6)

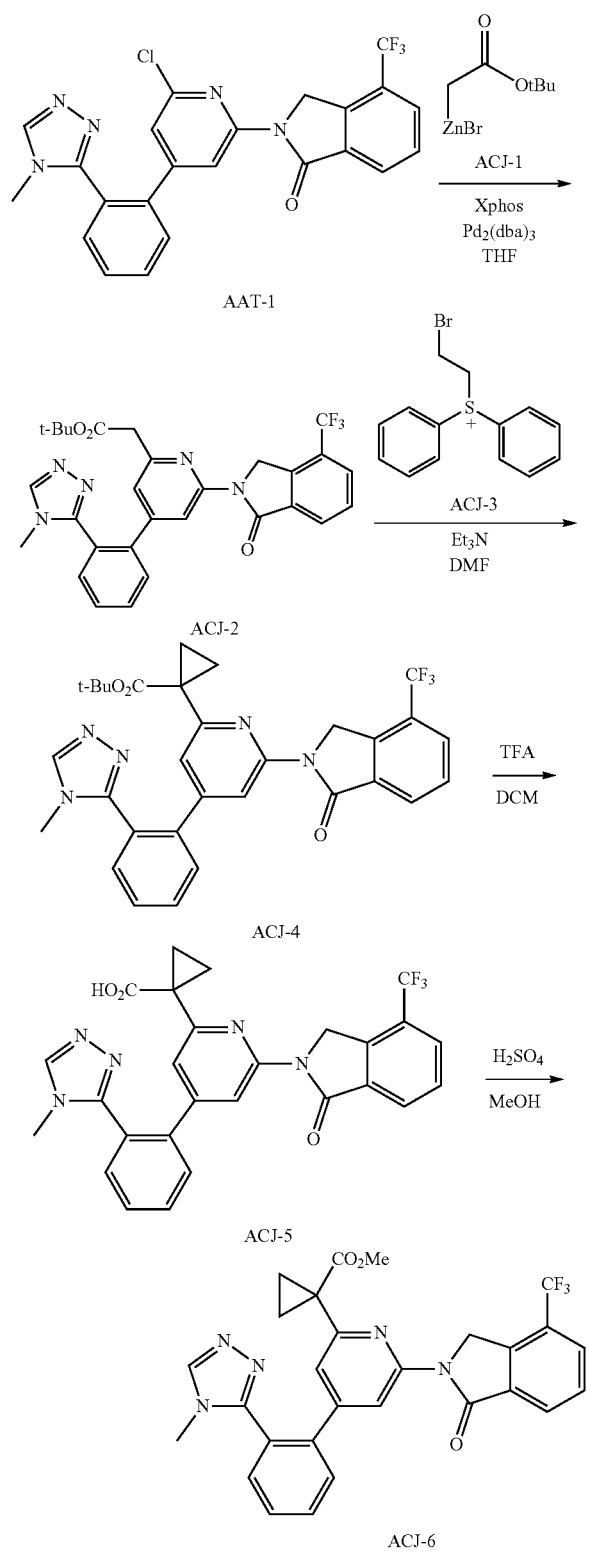

Step 1: Synthesis of tert-Butyl 2-(4-(2-(4-methyl-4H-1,2,4-triazol-3-yl)phenyl)-6-(1-oxo-4-(trifluoromethyl)isoindolin-2-yl)pyridin-2-yl)acetate (ACJ-2)

To a stirred solution of intermediate (AAT-1) (50 mg, 106 μmol, 1 Eq) in THF (5 mL) were added XPhos (10. mg, 0.2 Eq, 21 μmol) and Pd$_2$(dba)$_3$ (9.74 mg, 0.1 Eq, 11 μmol) drop-wise at rt under nitrogen atmosphere. The resulting mixture was stirred for 10 min at 60° C. under nitrogen atmosphere. Tert-butyl 2-(bromozincio) acetate (ACJ-1) (139 mg, 5 Eq, 530 μmol) was added in the system at 60° C. under nitrogen atmosphere. The resulting mixture was stirred for 5 h at 60° C. under nitrogen atmosphere then allowed to cool to rt. The residue was purified by Prep-TLC with DCM/MeOH (10/1) to afford the sub-title compound (ACJ-2) (52 mg, 94 μmol, 80%) as an off-white solid. m/z 550.2 (M+H)$^+$ (ES+).

Step 2: Synthesis of tert-Butyl 1-(4-(2-(4-methyl-4H-1,2,4-triazol-3-yl)phenyl)-6-(1-oxo-4-(trifluoromethyl)isoindolin-2-yl)pyridin-2-yl)cyclopropane-1-carboxylate (ACJ-4)

A solution of the product from step 1 above (ACJ-2) (60 mg, 1 Eq, 109 μmol) and (2-bromoethyl) diphenylsulfanium triflate (ACJ-3) (145 mg, 3 Eq, 327 μmol) in DMF (12 mL) was stirred for 10 min at rt. Then Et$_3$N (55 mg, 5 Eq, 545 μmol) was added in the system at rt. The resulting mixture was stirred for 48 h at rt. The reaction was then quenched by the addition of ice water (3 mL) 0° C. and the resulting mixture extracted with EtOH (3×20 mL). The combined organic layers were washed with water (2×20 mL), dried (Na$_2$SO$_4$), filtered and concentrated in vacuo. The residue was purified by Prep-TLC with DCM/MeOH (10/1) to afford the sub-title compound (ACJ-4) (40 mg, 69 μmol, 57%) as a white solid. m/z 576.2 (M+H)$^+$ (ES+).

Step 3: 1-(4-(2-(4-Methyl-4H-1,2,4-triazol-3-yl) phenyl)-6-(1-oxo-4-(trifluoromethyl)isoindolin-2-yl) pyridin-2-yl)cyclopropane-1-carboxylic acid (ACJ-5)

A solution of the product from step 2 above (ACJ-4) (30 mg, 1 Eq, 52 μmol) in DCM (3 mL) and TFA (1 mL) was stirred for 2 h at rt. The crude product was used in the next step directly without further purification. m/z 520.2 (M+H)$^+$ (ES+).

Step 4: Methyl 1-(4-(2-(4-methyl-4H-1,2,4-triazol-3-yl)phenyl)-6-(1-oxo-4-(trifluoromethyl) isoindolin-2-yl)pyridin-2-yl)cyclopropane-1-carboxylate (ACJ-6)

Into a 10 mL vial were added the product from step 3 above (ACJ-5) (10 mg, 1 Eq, 19 μmol) and MeOH (3 mL) at rt. To the above mixture was added sulfuric acid (0.2 mL) at 0° C. The resulting mixture was stirred for additional 2h at 60° C. The mixture was allowed to cool to rt. The reaction was then quenched by the addition of ice water (2 mL) at 0° C. The resulting mixture was extracted with EtOAc (3×10 mL). The combined organic layers were washed with water (2×10 mL), dried (Na$_2$SO$_4$), filtered and concentrated in vacuo. The residue was purified by Prep-TLC with DCM/MeOH (10/1). The crude product was purified by Prep-HPLC with the following conditions (Column: Xselect CSH OBD Column 30*150 mm 5 um; Mobile Phase A: Water (0.1% FA), Mobile Phase B: ACN; Flow rate: 60 mL/min; Gradient: 2% B to 23% B in 7 min; Wavelength: 254/220 nm) to afford the title compound (ACJ-6) (0.8 mg, 1.50 μmol, 7.4%) as a white solid. m/z 534.1 (M+H)+ (ES+). $^1$H NMR (400 MHz, DMSO-d6) δ 8.49 (s, 1H), 8.26 (d, J=1.5 Hz, 1H), 8.10 (dd, J=17.0, 7.6 Hz, 2H), 7.85-7.74 (m, 2H), 7.72-7.57 (m, 3H), 7.02 (d, J=1.4 Hz, 1H), 5.23 (s, 2H), 3.63 (s, 3H), 3.32 (s, 3H), 1.53 (q, J=4.0, 3.5 Hz, 2H), 1.40 (q, J=4.6, 4.1 Hz, 2H).

Example 98: Synthesis of 2-(6-Cyclopropyl-4-(2-(4-methyl-4H-1,2,4-triazol-3-yl) phenyl)pyridin-2-yl)-6-(hydroxymethyl)-4-(trifluoromethyl)isoindolin-1-one (ACK-3)

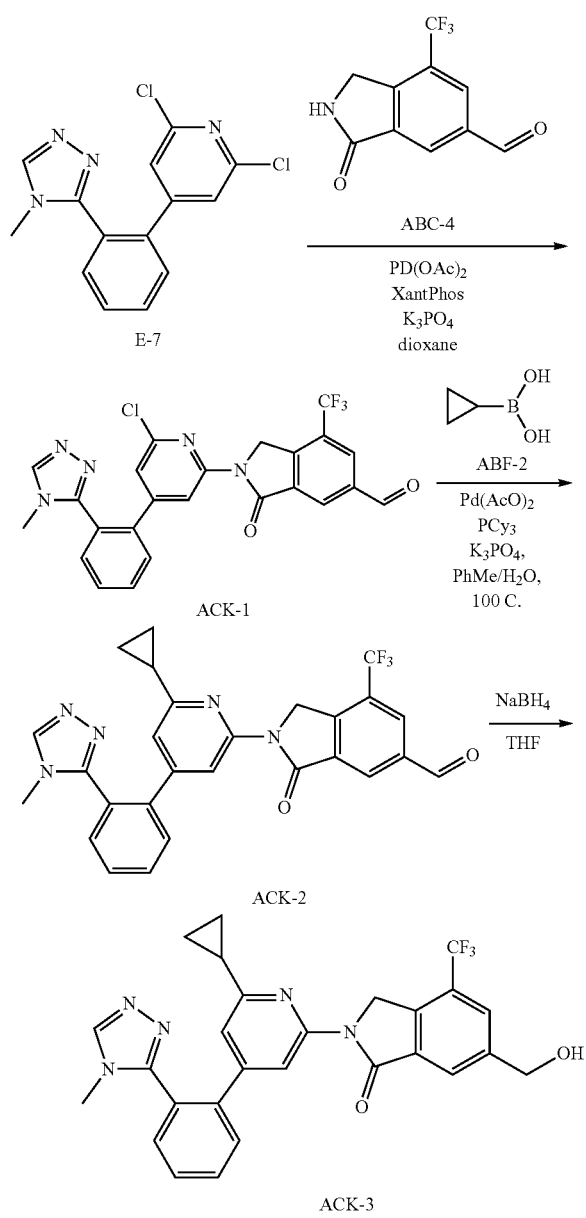

Step 1: Synthesis of 2-(6-Chloro-4-(2-(4-methyl-4H-1,2,4-triazol-3-yl)phenyl)pyridin-2-yl)-3-oxo-7-(trifluoromethyl)isoindoline-5-carbaldehyde (ACK-1)

To a stirred mixture of 2,6-dichloro-4-[2-(4-methyl-1,2,4-triazol-3-yl) phenyl] pyridine (E-7) (100 mg, 1 Eq, 328 μmol), intermediate (ABC-4) (68 mg, 0.9 Eq, 295 μmol) and potassium phosphate (209 mg, 3 Eq, 984 μmol) in dioxane (4 mL) were added XantPhos (19 mg, 0.1 Eq, 33 μmol) and Pd(OAc)$_2$ (7 mg, 0.1 Eq, 33 μmol) at rt under nitrogen atmosphere. The resulting mixture was stirred for 2 h at 100° C. under nitrogen atmosphere. The mixture was cooled to rt, diluted with water and extracted with EtOAc (3×20 mL). The combined organic layers were washed with brine (2×20 mL), dried (Na$_2$SO$_4$), filtered and concentrated in vacuo. The resulting mixture was concentrated in vacuo and the residue was purified by Prep-TLC with DCM/MeOH (10/1) to afford the sub-title compound (ACK-1) (60 mg, 120 μmol, 37%) as a yellow oil. m/z 498.1 (M+H)+ (ES+).

Step 2: 2-(6-Cyclopropyl-4-(2-(4-methyl-4H-1,2,4-triazol-3-yl)phenyl)pyridin-2-yl)-3-oxo-7-(trifluoromethyl)isoindoline-5-carbaldehyde (ACK-2)

To a stirred mixture of the product from step 1 above (ACK-1) (150 mg, 1 Eq, 301 μmol), intermediate (ABF-2) (52 mg, 2 Eq, 602 μmol) and potassium phosphate (192 mg, 3 Eq, 904 μmol) in toluene (3 mL) were added tricyclohexylphosphine (8 mg, 0.1 Eq, 30 μmol) and Pd(AcO)$_2$ (7 mg, 0.1 Eq, 30 mmol) at rt under nitrogen atmosphere. The resulting mixture was stirred for 3 h at 110° C. under nitrogen atmosphere. The mixture was cooled to rt and concentrated in vacuo. The precipitated solids were collected by filtration and washed with EtOAc (3×5 mL). The resulting mixture was concentrated in vacuo. The residue was purified by Prep-TLC with DCM/MeOH (10/1) to afford the sub-title compound (ACK-2) (80 mg, 159 μmol, 53%) as a yellow oil. m/z 504.2 (M+H)+ (ES+).

Step 3: 2-(6-Cyclopropyl-4-(2-(4-methyl-4H-1,2,4-triazol-3-yl)phenyl)pyridin-2-yl)-6-(hydroxymethyl)-4-(trifluoromethyl)isoindolin-1-one (ACK-3)

To a stirred solution of the product from step 2 above (ACK-2) (30 mg, 1 Eq, 60 μmol) in THF (5 mL) was added NaBH$_4$ (4.51 mg, 2 Eq, 119 μmol) at rt. The resulting mixture was stirred for 1h at rt. The reaction was then quenched by the addition of ice water (2 mL) at 0° C. The resulting mixture was concentrated in vacuo. The crude product was purified by Prep-HPLC with the following conditions (Column: XBridge Prep OBD C18 Column, 30*150 mm, 5 μm; Mobile Phase A: Water (0.1% NH$_4$HCO$_3$), Mobile Phase B: ACN; Flow rate: 60 mL/min; Gradient: 40% B to 60% B in 8 min; Wavelength: 254/220 nm; RT: 7.83) to afford the title compound (ACK-3) (2.9 mg, 5.74 μmol, 10%) as a white solid. m/z 506.1 (M+H)+ (ES+). $^1$H NMR (400 MHz, DMSO-d6) δ 8.49 (s, 1H), 8.06-7.93 (m, 3H), 7.79-7.73 (m, 1H), 7.71-7.61 (m, 3H), 6.81 (d, J=1.4 Hz, 1H), 5.59 (t, J=5.8 Hz, 1H), 5.18 (s, 2H), 4.71 (d, J=5.8 Hz, 2H), 3.38 (s, 3H), 2.09-2.00 (m, 1H), 1.02-0.95 (m, 2H), 0.95-0.88 (m, 2H).

Example 99: Synthesis of 6-((5-Azaspiro [2.4] heptan-5-yl)methyl)-2-(6-cyclopropyl-4-(2-(4-methyl-4H-1,2,4-triazol-3-yl)phenyl)pyridin-2-yl)-4-(trifluoromethyl)isoindolin-1-one (ACL-1)

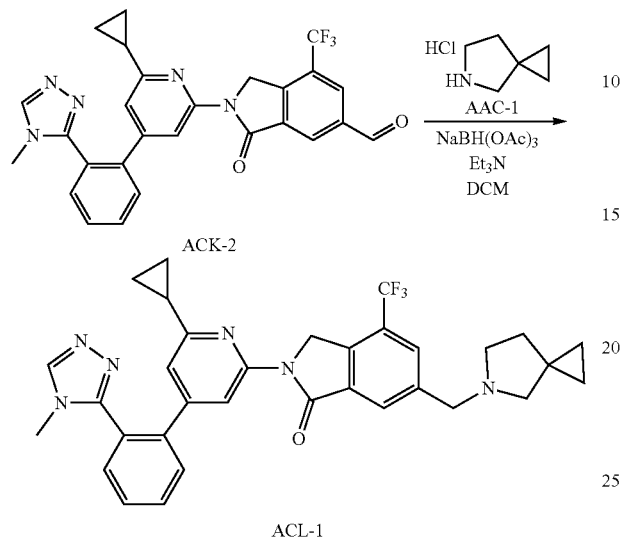

To a stirred mixture of intermediate (ACK-2) (30 mg, 1 Eq, 60 µmol) and 5-azaspiro [2.4] heptane (AAC-1) (9 mg, 1.5 Eq, 90 µmol) in DCM (5 mL) were added Et₃N (18 mg, 3 Eq, 180 µmol) and NaBH(OAc)₃ (63 mg, 5 Eq, 300 µmol) at rt under nitrogen atmosphere. The resulting mixture was stirred for 2 h at 40° C. under nitrogen atmosphere. The resulting mixture was concentrated in vacuo. The crude product was purified by Prep-HPLC with the following conditions (Column: XBridge Prep OBD C18 Column, 30*150 mm, 5 µm; Mobile Phase A: Water (0.1% NH4HCO3), Mobile Phase B: ACN; Flow rate: 60 mL/min; Gradient: 62% B to 82% B in 8 min; Wavelength: 254/220 nm; RT: 7.66) to afford the title compound (ACL-1) (2.9 mg, 4.96 µmol, 8%) as a white solid. m/z 585.0 (M+H)⁺ (ES+). ¹H NMR (400 MHz, DMSO-d6) δ 8.49 (s, 1H), 8.04-7.99 (m, 2H), 7.96 (s, 1H), 7.78-7.73 (m, 1H), 7.70-7.61 (m, 3H), 6.82 (d, J=1.4 Hz, 1H), 5.17 (s, 2H), 3.80 (s, 2H), 3.38 (s, 3H), 2.70 (t, J=6.8 Hz, 2H), 2.46 (s, 2H), 2.10-2.02 (m, 1H), 1.77 (t, J=6.8 Hz, 2H), 1.01-0.95 (m, 2H), 0.95-0.89 (m, 2H), 0.55-0.47 (m, 4H).

Example 100: Synthesis of 2-(6-(Ethylamino)-4-(4-fluoro-2-(4-methyl-4H-1,2,4-triazol-3-yl)phenyl)pyridin-2-yl)-4-(trifluoromethyl)isoindolin-1-one (ACM-8)

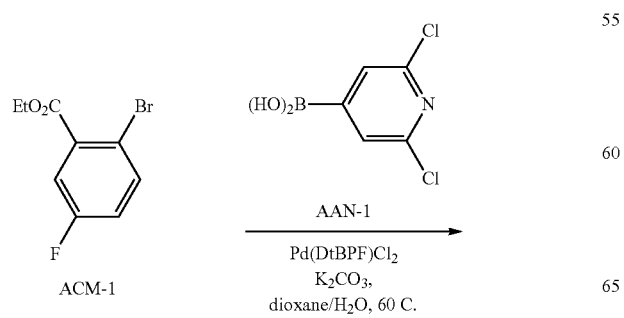

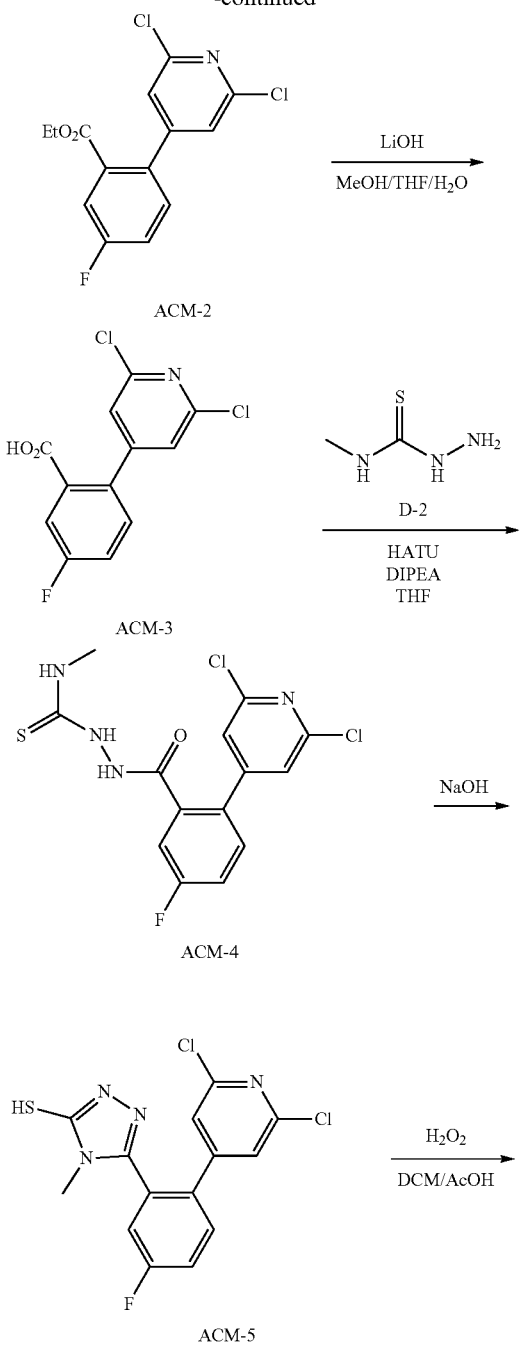

-continued

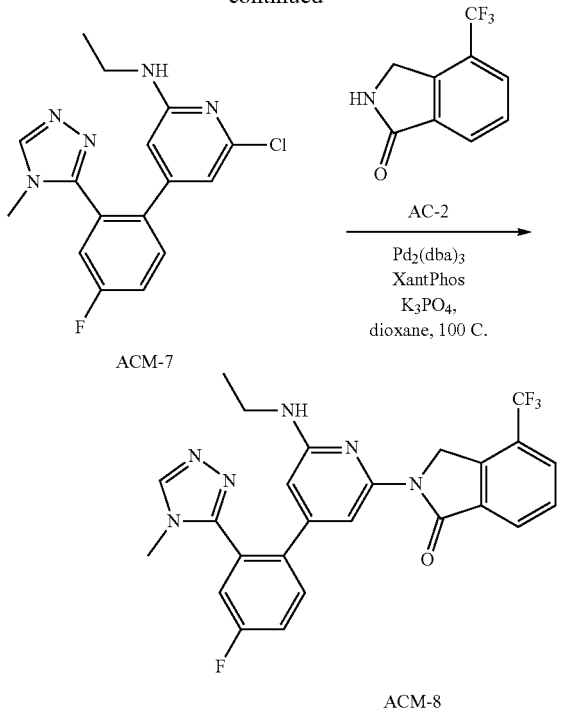

Step 1: Synthesis of Ethyl 2-(2,6-dichloropyridin-4-yl)-5-fluorobenzoate (ACM-2)

To a stirred mixture of ethyl 2-bromo-5-fluorobenzoate (ACM-1) (4.94 g, 1 Eq, 20.0 mmol), intermediate (AAN-1) (4.60 g, 1.2 Eq, 24.0 mmol) and K$_2$CO$_3$ (8.29 g, 3 Eq, 60.0 mmol) in 1,4-dioxane (80 mL) were added Pd(DtBPF)Cl$_2$ (1.30 g, 0.1 Eq, 2.00 mmol) at rt under nitrogen atmosphere. The resulting mixture was stirred for 5 h at 60° C. under nitrogen atmosphere. The resulting mixture was cooled to rt and diluted with water. The resulting mixture was extracted with EtOAc (3×300 mL). The combined organic layers were washed with brine (2×300 mL), dried (Na$_2$SO$_4$), filtered and concentrated in vacuo. The crude product was purified by reverse flash column chromatography with the following conditions: Column, C18; mobile phase, Water (0.1% NH$_4$HCO$_3$) and ACN (36% ACN up to 48% in 10 min); Detector, UV 254/220 nm. The product-containing fractions were combined and concentrated in vacuo. This resulted in the sub-title compound (ACM-2) (4.6 g, 14.7 mmol, 73%) as a brown solid. m/z 314.0/316.0 (M+H)$^+$ (ES+).

Step 2: Synthesis of 2-(2,6-Dichloropyridin-4-yl)-5-fluorobenzoic acid (ACM-3)

To a stirred mixture of the product from step 1 above (ACM-2) (2.3 g, 1 Eq, 7.32 mmol) in THF (30 mL) was added LiOH (700 mg, 4 Eq, 29.3 mmol) over 3 min at rt. The resulting mixture was stirred for additional 3 h at 60° C. The resulting mixture was cooled to rt. The residue was neutralized to pH 5 with HCl (aq., 1 M). The resulting mixture was diluted with water and extracted with EtOAc (3×200 mL). The combined organic layers were washed with brine (2×200 mL), dried (Na$_2$SO$_4$), filtered and concentrated in vacuo. The crude resulting mixture was used in the next step directly without further purification. m/z 286.0/288.0 (M+H)$^+$ (ES+).

Step 3: Synthesis of 2-(2-(2,6-Dichloropyridin-4-yl)-5-fluorobenzoyl)-N-methylhydrazine-1-carbothioamide (ACM-4)

To a stirred mixture of the product from step 2 above (ACM-3) (2.00 g, 1 Eq, 6.99 mmol) and 4-methyl-3-thiosemicarbazide (D-2) (740 mg, 1 Eq, 6.99 mmol) in THF (30 mL) were added DIPEA (2.71 g, 3 Eq, 21.0 mmol) and HATU (2.66 g, 1 Eq, 6.99 mmol) at rt. The resulting mixture was stirred for 2 h at rt. The crude resulting mixture was used in the next step directly without further purification. m/z 373.0/375.0 (M+H)$^+$ (ES+).

Step 4: Synthesis of 5-(2-(2,6-Dichloropyridin-4-yl)-5-fluorophenyl)-4-methyl-4H-1,2,4-triazole-3-thiol (ACM-5)

To a stirred mixture of the product from step 3 above (ACM-4) was added NaOH (aq., 10M) at rt. The resulting mixture was stirred for overnight at 100° C. The residue was cooled to rt and acidified to pH 5 with HCl (aq., 1M). The resulting mixture was diluted with water and extracted with EtOAc (3×100 mL). The combined organic layers were washed with brine (2×100 mL), dried (Na$_2$SO$_4$), filtered and concentrated in vacuo. The crude resulting mixture was used in the next step directly without further purification. m/z 355.0/357.0 (M+H)$^+$ (ES+).

Step 5: Synthesis of 2,6-Dichloro-4-(4-fluoro-2-(4-methyl-4H-1,2,4-triazol-3-yl)phenyl)pyridine (ACM-6)

To a stirred mixture of the product from step 4 above (ACM-5) (1 g, 1 Eq, 2.81 mmol) in DCM (10 mL) was added acetic acid (340 mg, 2 Eq, 5.63 mmol) and hydrogen peroxide (480 g, 5 Eq, 14.1 mmol) at rt. The resulting mixture was stirred for 2 h at rt. The mixture was neutralized to pH 9 with saturated NaHCO$_3$ (aq.). The resulting mixture was diluted with water and extracted with EtOAc (3×100 mL). The combined organic layers were washed with brine (2×100 mL), dried (Na$_2$SO$_4$), filtered and concentrated in vacuo. The crude product was purified by reverse flash column chromatography with the following conditions: Column, C18; mobile phase, Water (0.1% NH$_4$HCO$_3$) and ACN (50% ACN up to 70% in 15 min); Detector, UV 254/220 nm. The product-containing fractions were combined and concentrated in vacuo. This resulted in the sub-title compound (ACM-6) (800 mg, 2.48 mmol, 88%) as a white solid. m/z 323.0/325.0 (M+H)$^+$ (ES+).

Step 6: Synthesis of 6-Chloro-N-ethyl-4-(4-fluoro-2-(4-methyl-4H-1,2,4-triazol-3-yl)phenyl)pyridin-2-amine (ACM-7)

To a stirred mixture of the product from step 5 above (ACM-6) (400 mg, 1 Eq, 1.24 mmol) and ethanamine, HCl (558 mg, 10 Eq, 12.4 mmol) in NMP (5 mL) were added K$_2$CO$_3$ (1.71 g, 10 Eq, 12.3 mmol) at rt. The resulting mixture was stirred for overnight at 100° C. The mixture was purified by reverse flash column chromatography with the following conditions: Column, C18; mobile phase, Water (0.1% NH$_4$HCO$_3$) and ACN (36% ACN up to 48% in 10 min); Detector, UV 254/220 nm. The product-containing fractions were combined and concentrated in vacuo affording the sub-title compound (ACM-7) (300 mg, 906 μmol, 73%) as a white solid. m/z 332.1/334.1 (M+H)$^+$ (ES+).

Step 7: Synthesis of 2-(6-(Ethylamino)-4-(4-fluoro-2-(4-methyl-4H-1,2,4-triazol-3-yl)phenyl)pyridin-2-yl)-4-(trifluoromethyl)isoindolin-1-one (ACM-8)

To a stirred mixture of the product from step 6 above (ACM-7) (150 mg, 1 Eq, 452 μmol), intermediate (AC-2) (91 mg, 1 Eq, 452 mmol) and potassium phosphate (287 mg, 3 Eq, 1.36 mmol) in 1,4-dioxane (2 mL) were added XantPhos (52 mg, 0.2 Eq, 90 μmol) and Pd$_2$(dba)$_3$ (41 mg, 0.1 Eq, 45 μmol) at rt under nitrogen atmosphere. The resulting mixture was stirred for overnight at 100° C. under nitrogen atmosphere. The resulting mixture was cooled to rt. The crude product was purified by reverse flash column chromatography with the following conditions: Column, C18; mobile phase, Water (0.1% NH$_4$HCO$_3$) and ACN (20% ACN up to 60% in 25 min); Detector, UV 254/220 nm. The resulting mixture was concentrated in vacuo. The crude product was purified by Prep-HPLC with the following conditions (Column: XBridge Prep OBD C18 Column, 30*150 mm, 5 μm; Mobile Phase A: Water (0.1% NH$_4$HCO$_3$), Mobile Phase B: ACN; Flow rate: 60 mL/min; Gradient: 41% B to 59% B in 10 min; Wavelength: 254/220 nm; RT: 9.5) to afford the title compound (ACM-8) (12 mg, 24 μmol, 5.3%) as a white solid. m/z 497.2 (M+H)$^+$ (ES+). $^1$H NMR (400 MHz, MeOH-d4) δ 8.47 (s, 1H), 8.08 (d, J=7.7 Hz, 1H), 7.97 (d, J=7.7 Hz, 1H), 7.80-7.71 (m, 2H), 7.56-7.47 (m, 2H), 7.45-7.42 (m, 1H), 6.03 (d, J=1.3 Hz, 1H), 5.23 (s, 2H), 3.45 (s, 3H), 3.32-3.26 (m, 2H), 1.22 (t, J=7.2 Hz, 3H).

Example 101: Synthesis of 2-(6-(Ethylamino)-4-(1-methyl-4-(4-methyl-4H-1,2,4-triazol-3-yl)-1H-pyrazol-5-yl)pyridin-2-yl)-6-(2-(pyrrolidin-1-yl)ethoxy)-4-(trifluoromethyl)isoindolin-1-one (ACN-5)

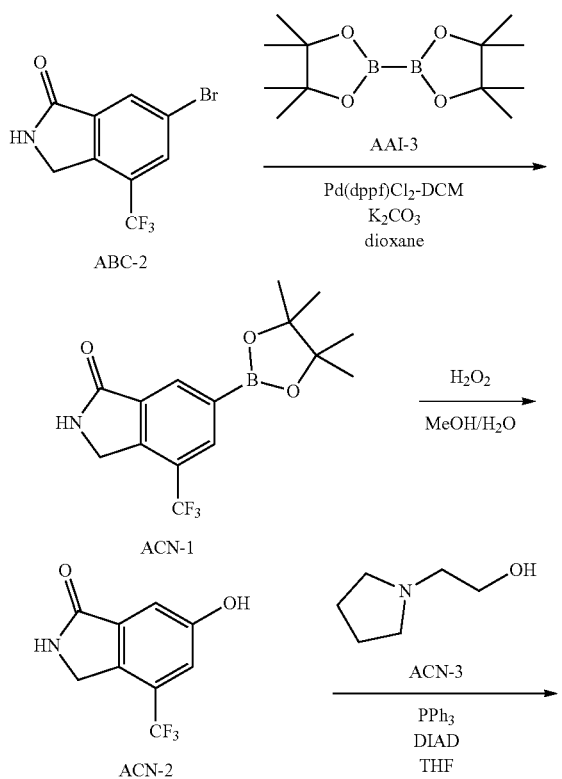

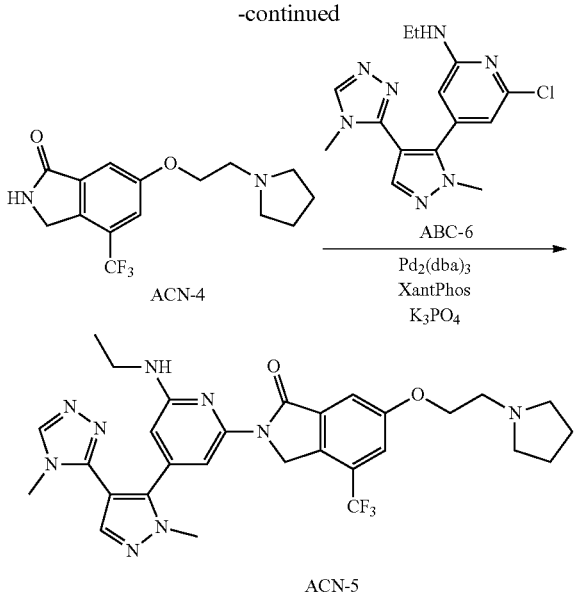

Step 1: Synthesis of 6-(4,4,5,5-Tetramethyl-1,3,2-dioxaborolan-2-yl)-4-(trifluoromethyl)isoindolin-1-one (ACN-1)

To a stirred solution of intermediate (ABC-2) (200 mg, 1 Eq, 714 μmol), intermediate (AAI-3) (5.44 g, 30 Eq, 21.4 mmol) and potassium acetate (210 mg, 3 Eq, 2.14 mmol) in 1,4-dioxane (20 mL) was added Pd(dppf)Cl$_2$.DCM (116 mg, 0.2 Eq, 143 μmol) at rt under nitrogen atmosphere. The resulting mixture was stirred for 2 h at 80° C. under nitrogen atmosphere. The mixture was cooled to rt and concentrated in vacuo. The residue was purified by silica gel column chromatography, eluted with DCM/MeOH (15:1) to afford the sub-title compound (ACN-1) (180 mg, 550 μmol, 69%) as a brown/yellow solid. m/z 328.1 (M+H)$^+$ (ES+).

Step 2: Synthesis of 6-Hydroxy-4-(trifluoromethyl)isoindolin-1-one (ACN-2)

A solution of the product from step 1 above (ACN-1) (400 mg, 1 Eq, 1.22 mmol) in THF (3 mL) and hydrogen peroxide (1 mL, 30% Wt) was added acetic acid (1 mL) at rt. The resulting mixture was stirred for 2 h at rt. The mixture was concentrated in vacuo. The residue was purified by silica gel column chromatography, eluted with DCM/MeOH (15:1) to afford the sub-title compound (ACN-2) (100 mg, 460 μmol, 34%) as an off-white solid. m/z 218.0 (M+H)$^+$ (ES+).

Step 3: Synthesis of 6-(2-(Pyrrolidin-1-yl)ethoxy)-4-(trifluoromethyl)isoindolin-1-one (ACN-4)

To a stirred solution mixture of the product from step 2 above (ACN-2) (100 mg, 1 Eq, 461 μmol), epolamine (ACN-3) (265 mg, 5 Eq, 2.31 mmol) and triphenylphosphine (362 mg, 1.38 mmol, 3 Eq) in THF (15 mL) was added DIAD (186 mg, 2 Eq, 922 μmol) at rt under nitrogen atmosphere. The resulting mixture was stirred for 2 h at rt under nitrogen atmosphere. The mixture was acidified to pH 5 with HCl (aq., 1 M). The resulting mixture was extracted with DCM (2×40 mL). The combined water layers were spin dry. The crude product was purified by Prep-HPLC with the following conditions (Column: Xselect CSH OBD Column 30*150 mm 5 um, n; Mobile Phase A: Water(0.1% FA), Mobile Phase B: ACN; Flow rate: 60 mL/min; Gradient: 2% B to 23% B in 7 min; Wavelength: 254/220 nm) to afford the sub-title compound (ACN-4) (70 mg, 223 μmol, 44%) as an off-white solid. m/z 315.1 (M+H)$^+$ (ES+).

Step 4: Synthesis of 2-(6-(Ethylamino)-4-(1-methyl-4-(4-methyl-4H-1,2,4-triazol-3-yl)-1H-pyrazol-5-yl)pyridin-2-yl)-6-(2-(pyrrolidin-1-yl)ethoxy)-4-(trifluoromethyl)isoindolin-1-one (ACN-5)

To a stirred solution of the product from step 3 above (ACN-4) (40 mg, 127 μmol, 1 Eq), potassium phosphate (81 mg, 3 Eq, 381 μmol) and intermediate (ABC-6) (40 mg, 1 Eq, 127 μmol) in 1,4-dioxane (5 ml) were added XantPhos (15 mg, 0.2 Eq, 25 μmol) and Pd$_2$(dba)$_3$ (12 mg, 0.1 Eq, 13 μmol) at rt under nitrogen atmosphere. The final reaction mixture was irradiated with microwave radiation overnight at 100° C. under nitrogen atmosphere. The mixture was allowed to cool to rt and was acidified to pH 5 with HCl (aq., 1 M). The mixture was concentrated in vacuo. The crude product was purified by Prep-HPLC with the following conditions (Column: Xselect CSH OBD Column 30*150 mm 5 um, n; Mobile Phase A: Water (0.1% FA), Mobile Phase B: ACN; Flow rate: 60 mL/min; Gradient: 2% B to 23% B in 7 min; Wavelength: 254/220 nm) to afford the title compound (ACN-5) (13.2 mg, 22 μmol, 17%) as a light yellow solid. m/z 596.3 (M+H)$^+$ (ES+). $^1$H NMR (400 MHz, DMSO-d6) δ 8.47 (s, 1H), 7.89 (s, 1H), 7.56 (s, 3H), 6.92 (t, J=5.4 Hz, 1H), 6.25 (d, J=1.2 Hz, 1H), 5.13 (d, J=1.8 Hz, 2H), 4.27 (t, J=5.7 Hz, 2H), 3.90 (s, 3H), 3.46 (s, 3H), 3.32-3.19 (m, 2H), 2.85 (t, J=5.7 Hz, 2H), 2.62-2.53 (m, 4H), 1.83-1.54 (m, 4H), 1.17 (t, J=7.1 Hz, 3H).

Example 102: Synthesis of 2-(6-(Ethylamino)-4-(1-methyl-4-(4-methyl-4H-1,2,4-triazol-3-yl)-1H-pyrazol-5-yl)pyridin-2-yl)-4-(trifluoromethyl)isoindolin-1-one (ACO-1)

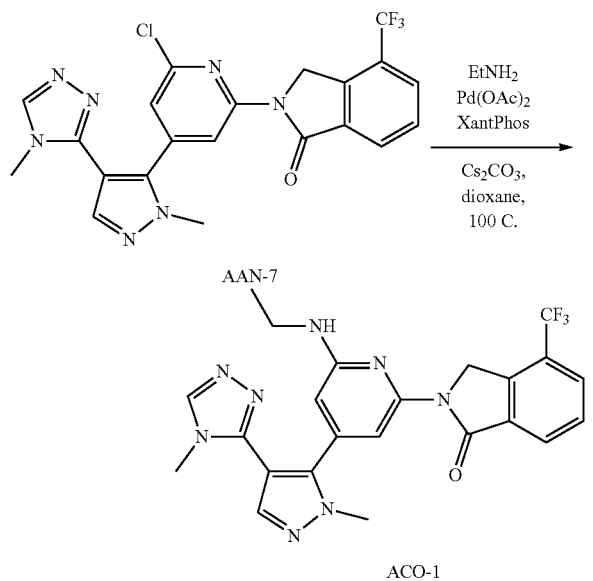

To a solution of intermediate (AAN-7) (80 mg, 1 Eq, 169 μmol), ethylamine solution in THF (422 uL, 2 M, 5 Eq, 845 μmol) and Cs$_2$CO$_3$ (165 mg, 3 Eq, 500 μmol) in 1,4-dioxane (5 mL) were added Pd$_2$(dba)$_3$ (31 mg, 34 μmol, 0.2 Eq) and XantPhos (39 mg, 0.4 Eq, 68 μmol) at rt under nitrogen atmosphere. After stirring for overnight at 80° C. under nitrogen atmosphere, the resulting mixture was cooled to rt and concentrated in vacuo. The residue was purified by silica gel column chromatography, eluted with DCM/MeOH (10/1) and Prep-HPLC with the following conditions: Column: Sunfire prep C18 column, 30*150 mm, 5 μm; Mobile Phase A: Water (0.1% FA), Mobile Phase B: ACN; Flow rate: 60 mL/min; Gradient: 30% B to 50% B in 9 min; Detector, 254/220 nm; RT: 8.77. The product-containing fractions were combined and evaporated partially in vacuo and lyophilized overnight to afford to afford the title compound (ACO-1) (5.5 mg, 11 μmol, 6.5%) as a white solid. m/z 483.1 (M+H)$^+$ (ES+). $^1$H NMR (400 MHz, MeOH-d4) δ 8.50 (s, 1H), 8.09 (d, J=7.6 Hz, 1H), 7.99 (d, J=7.6 Hz, 1H), 7.87 (s, 1H), 7.79-7.75 (m, 1H), 7.66 (d, J=1.2 Hz, 1H), 6.20 (d, J=1.3 Hz, 1H), 5.28 (s, 2H), 4.04 (s, 3H), 3.50 (s, 3H), 3.40-3.36 (m, 2H), 1.25 (t, J=7.2 Hz, 3H).

Example 103: Synthesis of 2-(6-(Ethylamino)-4-(1-methyl-4-(4-methyl-4H-1,2,4-triazol-3-yl)-1H-pyrazol-5-yl)pyridin-2-yl)-6-((2-hydroxyethoxy)methyl)-4-(trifluoromethyl)isoindolin-1-one (ACP-3)

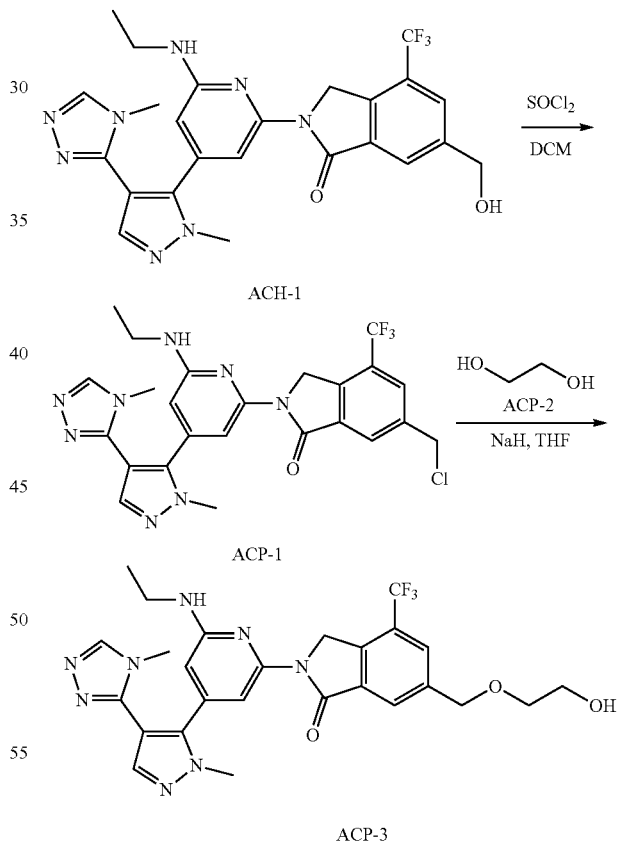

Step 1: Synthesis of 6-(Chloromethyl)-2-(6-(ethylamino)-4-(1-methyl-4-(4-methyl-4H-1,2,4-triazol-3-yl)-1H-pyrazol-5-yl)pyridin-2-yl)-4-(trifluoromethyl)isoindolin-1-one (ACP-1)

To a stirred solution of intermediate (ACH-1) (50 mg, 1 Eq, 98 μmol) in DCM (10 mL) was added thionyl chloride (35 mg, 3 Eq, 294 µmol) at 0° C. under nitrogen atmosphere. The resulting mixture was stirred for 1 h at rt under nitrogen atmosphere. The reaction was quenched with MeOH (3 mL) at 0° C. and concentrated in vacuo. The residue was purified by TLC with DCM/MeOH (8/1) to afford the sub-title compound (ACP-1) (31 mg, 58 µmol, 60%) as an off-white solid. m/z 531.2/533.2 (M+H)⁺ (ES+).

Step 2: Synthesis of 2-(6-(Ethylamino)-4-(1-methyl-4-(4-methyl-4H-1,2,4-triazol-3-yl)-1H-pyrazol-5-yl)pyridin-2-yl)-6-((2-hydroxyethoxy)methyl)-4-(trifluoromethyl)isoindolin-1-one (ACP-3)

A solution of ethylene glycol (ACP-2) (18 mg, 5 Eq, 290 µmol) and sodium hydride (0.5 mg, 60% Wt, 20 µmol, 0.2 equiv) in THF (10 mL) was stirred for 30 mins at 0° C. under nitrogen atmosphere. To the above mixture was added the product from step 1 a above (ACP-1) (31 mg, 1 Eq, 58 µmol) over 30 mins at 0° C. and the resulting mixture was stirred for additional 1 h. The reaction was then quenched by the addition of ice water (2 mL) at 0° C. The resulting mixture was diluted with water and extracted with EtOAc (3×10 mL). The combined organic layers were washed with brine (2×10 mL), dried (Na₂SO₄), filtered and concentrated in vacuo. The residue was purified by Prep-TLC with DCM/MeOH (6/1). The crude product was purified by reverse flash column chromatography with the following conditions: Column, C18; mobile phase, Water (0.1% NH₄HCO₃) and ACN (10% ACN up to 35% in 20 min); Detector, UV 254/220 nm. The crude product was purified by Prep-HPLC with the following conditions Column: XBridge Prep OBD C18 Column, 30*150 mm, 5 µm; Mobile Phase A: Water (0.1% NH₄HCO₃), Mobile Phase B: ACN; Flow rate: 60 mL/min; Gradient: 30% B to 38% B in 10 min; Wavelength: 254/220 nm to afford the title compound (ACP-3) (4.5 mg, 7.8 µmol, 13%) as a white solid. m/z 577.0 (M+H)⁺ (ES+). ¹H NMR (400 MHz, DMSO-d6) δ 8.48 (s, 1H), 8.02 (d, J=16.4 Hz, 2H), 7.89 (s, 1H), 7.58 (d, J=1.2 Hz, 1H), 6.93 (t, J=5.5 Hz, 1H), 6.25 (d, J=1.2 Hz, 1H), 5.21 (s, 2H), 4.73-4.71 (m, 3H), 3.90 (s, 3H), 3.63-3.49 (m, 4H), 3.47 (s, 3H), 3.32-3.22 (m, 2H), 1.17 (t, J=7.1 Hz, 3H).

Example 104: Synthesis of 2-(6-(Ethylamino)-4-(1-methyl-4-(4-methyl-4H-1,2,4-triazol-3-yl)-1H-pyrazol-5-yl)pyridin-2-yl)-6-hydroxy-4-(trifluoromethyl)isoindolin-1-one (ACQ-7)

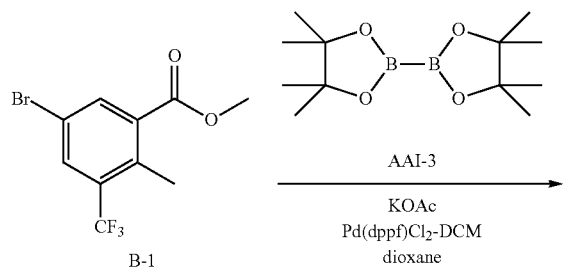

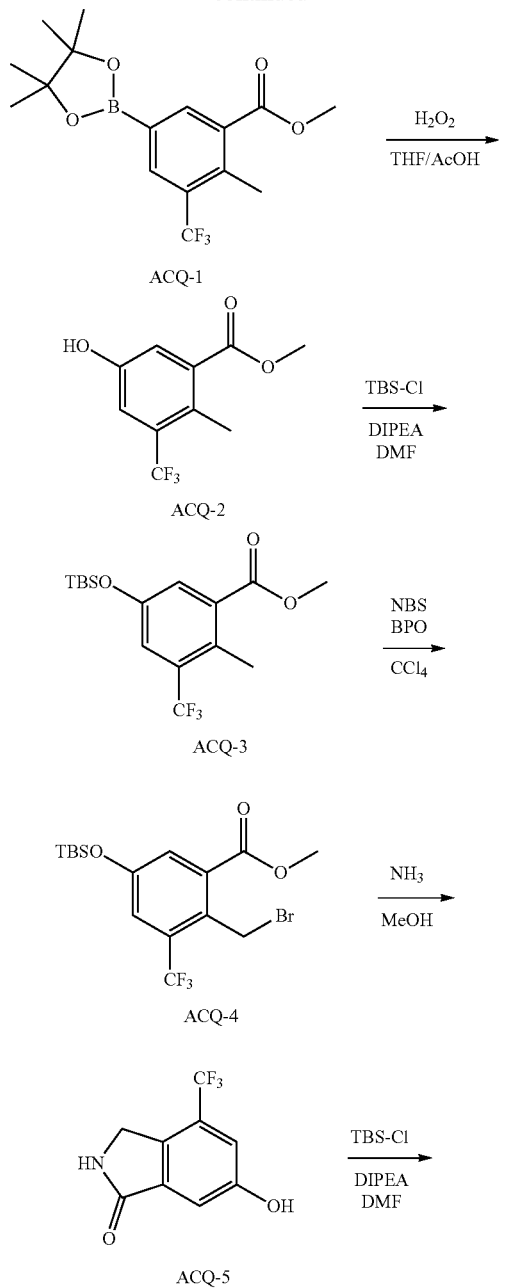

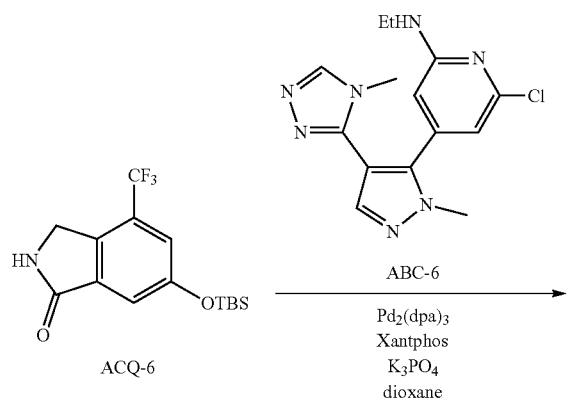

-continued

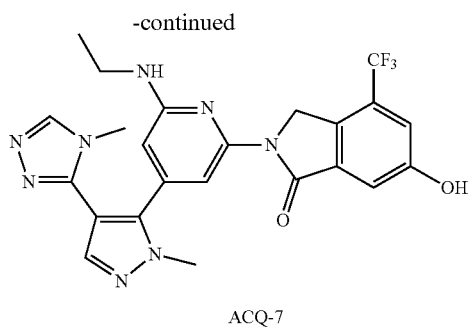

ACQ-7

Step 1: Synthesis of Methyl 2-methyl-5-(4,4,5,5-tetramethyl-1,3,2-dioxaborolan-2-yl)-3-(trifluoromethyl)benzoate (ACQ-1)

To a stirred solution of intermediate (B-1) (800 mg, 1 Eq, 2.69 mmol), intermediate (AAI-3) (752 mg, 1.1 Eq, 2.96 mmol) and potassium acetate (793 mg, 3 Eq, 8.08 mmol) in dioxane (15 mL) was added Pd(dppf)Cl$_2$.DCM (219 mg, 0.1 Eq, 269 μmol) at rt under nitrogen atmosphere. The resulting mixture was stirred for 16 h at 100° C. under nitrogen atmosphere. The mixture was allowed to cool to rt and the resulting mixture was filtered; the filter cake was washed with petroleum ether (3×5 mL). The filtrate was concentrated in vacuo affording crude sub-title compound (ACQ-1) (900 mg, 2.61 mmol, 96%) which was used in the next step directly without further purification. m/z 345.1 (M+H)$^+$ (ES+).

Step 2: Synthesis of Methyl 5-hydroxy-2-methyl-3-(trifluoromethyl)benzoate (ACQ-2)

Into a 25 mL round-bottom flask were added the product from step 1 above (ACQ-1) (890 mg, 1 Eq, 2.59 mmol) and acetic acid (6 mL) at rt. To the above mixture were added hydrogen peroxide (3 mL, 30% Wt) and THF (6 mL) at 0° C. The resulting mixture was stirred for additional 2 h at rt. The resulting mixture was extracted with EtOAc (3×80 mL). The combined organic layers were washed with brine (2×80 mL), dried (Na$_2$SO$_4$), filtered and concentrated in vacuo. The residue was purified by Prep-TLC with petroleum ether/EtOAc (10/1) to afford the sub-title compound (ACQ-2) (480 mg, 2.05 mmol, 79%) as an off-white solid. m/z 235.1 (M+H)$^+$ (ES+).

Step 3: Synthesis of Methyl 5-((tert-butyldimethylsilyl)oxy)-2-methyl-3-(trifluoromethyl)benzoate (ACQ-3)

A solution of the product from step 2 above (ACQ-2) (200 mg, 1 Eq, 854 μmol), TBSCl (154 mg, 1.2 Eq, 1.03 mmol) and imidazole (140 mg, 2.4 Eq, 2.05 mmol) in DMF (10 mL) at rt was stirred overnight at rt. The resulting mixture was diluted with water and extracted with EtOAc (3×50 mL). The combined organic layers were washed with brine (2×50 mL), dried (Na$_2$SO$_4$), filtered and concentrated in vacuo. The residue was purified by Prep-TLC with petroleum ether/EtOAc (20/1) to afford the sub-title compound (ACQ-3) (210 mg, 603 μmol, 71%) as a colorless oil. m/z 349.1 (M+H)$^+$ (ES+).

Step 4: Synthesis of Methyl 2-(bromomethyl)-5-((tert-butyldimethylsilyl)oxy)-3-(trifluoromethyl)benzoate (ACQ-4)

A solution of the product from step 3 above (ACQ-3) (100 mg, 287 μmol, 1 Eq), NBS (77 mg, 1.5 Eq, 430 μmol) and benzoyl peroxide (22 mg, 0.3 Eq, 86 μmol) in carbon tetrachloride (5 mL) was stirred overnight at 80° C. The mixture was allowed to cool to rt and was concentrated in vacuo. The residue was purified by Prep-TLC with petroleum ether/EtOAc (20/1) to afford the sub-title compound (ACQ-4) (100 mg, 234 μmol, 82%) as a brown/yellow solid. m/z 427.0/429.0 (M+H)$^+$ (ES+).

Step 5: Synthesis of 6-Hydroxy-4-(trifluoromethyl)isoindolin-1-one (ACQ-5)

A solution of the product from step 4 above (ACQ-4) (100 mg, 1 Eq, 234 μmol) in ammonia in MeOH (5 mL, 7 M) at rt was stirred for 2 h. The resulting mixture was concentrated in vacuo. The residue was purified by Prep-TLC with DCM/MeOH (15/1) to afford the sub-title compound (ACQ-5) (50 mg, 230 μmol, 98%) as an off-white solid. m/z 218.0 (M+H)$^+$ (ES+).

Step 6: Synthesis of 6-((tert-Butyldimethylsilyl)oxy)-4-(trifluoromethyl)isoindolin-1-one (ACQ-6)

A solution of the product from step 5 above (ACQ-5) (50 mg, 1 Eq, 230 μmol), TBSCl (42 mg, 1.2 Eq, 276 μmol) and imidazole (38 mg, 2.4 Eq, 552 μmol) in DMF (5 mL) at rt was stirred overnight. The resulting mixture was diluted with water and extracted with EtOAc (3×20 mL). The combined organic layers were washed with brine (2×20 mL), dried (Na$_2$SO$_4$), filtered and concentrated in vacuo. The crude product was purified by reverse flash column chromatography with the following conditions: Column, C18; mobile phase, Water (0.1% NH$_4$HCO$_3$) and ACN (0% ACN up to 100% in 24 min); Detector, UV 254/220 nm. This resulted in the sub-title compound (ACQ-6) (60 mg, 181 μmol, 79%) as a colorless oil. m/z 332.1 (M+H)$^+$ (ES+).

Step 7: Synthesis of 2-(6-(Ethylamino)-4-(1-methyl-4-(4-methyl-4H-1,2,4-triazol-3-yl)-1H-pyrazol-5-yl)pyridin-2-yl)-6-hydroxy-4-(trifluoromethyl)isoindolin-1-one (ACQ-7)

To a solution of the product from step 6 above (ACQ-6) (50 mg, 0.151 mmol, 1.0 Eq.) and intermediate (ABC-6) (43 mg, 0.9 Eq, 136 μmol) and potassium phosphate (19 mg, 3 Eq, 90 μmol) in dioxane (10 mL) were added Pd$_2$(dba)$_3$ (3 mg, 0.1 Eq, 3 μmol) and XantPhos (17 mg, 0.2 Eq, 30 μmol) at rt under nitrogen atmosphere. The resulting mixture was stirred for 4 h at 100° C. under nitrogen atmosphere. The mixture was allowed to cool to rt. The crude product was purified by reverse flash column chromatography with the following conditions: Column, C18; mobile phase, Water (0.1% NH$_4$HCO$_3$) and ACN (0% ACN up to 50% in 24 min); Detector, UV 254/220 nm. The crude product was purified by Prep-HPLC with the following conditions: Column: XBridge Prep OBD C18 Column, 30*150 mm, 5 μm; Mobile Phase A: Water (0.1% NH$_4$HCO$_3$), Mobile Phase B: ACN; Flow rate: 60 mL/min; Gradient: 35% B to 60% B in 8 min; Wavelength: 254/220 nm to afford the title compound (ACQ-7) (5.4 mg, 10.8 μmol, 7.1%) as a white solid. m/z 499.2 (M+H)$^+$ (ES+). $^1$H NMR (400 MHz, DMSO-d6) δ

10.64 (s, 1H), 8.48 (s, 1H), 7.88 (s, 1H), 7.56 (s, 1H), 7.35 (s, 2H), 6.91 (t, J=5.5 Hz, 1H), 6.23 (s, 1H), 5.09 (s, 2H), 3.89 (s, 3H), 3.46 (s, 3H), 3.31-3.25 (m, 2H), 1.16 (t, J=7.1 Hz, 3H).

Example 105: Synthesis of 2-(4-(4-Chloro-2-(4-methyl-4H-1,2,4-triazol-3-yl)phenyl)-6-(ethylamino)pyridin-2-yl)-4-(trifluoromethyl)isoindolin-1-one (ACR-7)

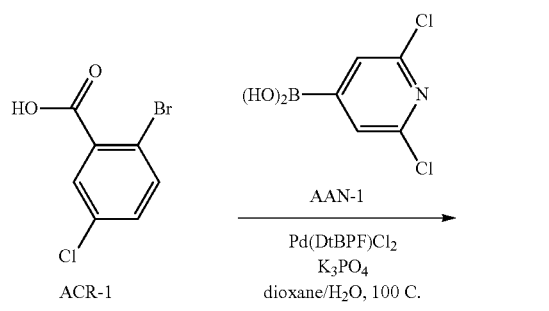

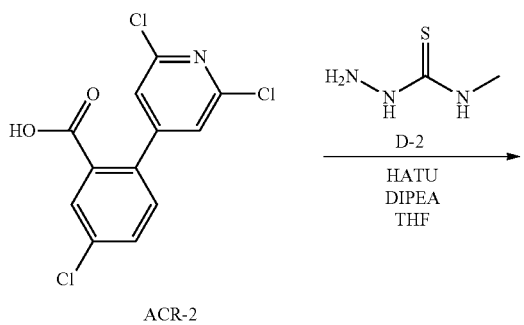

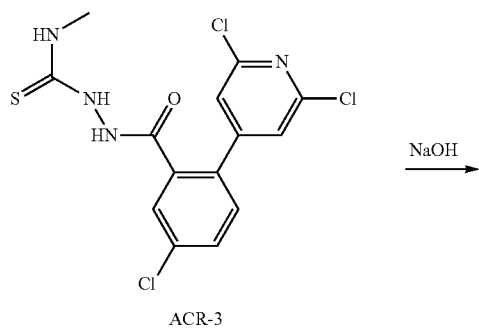

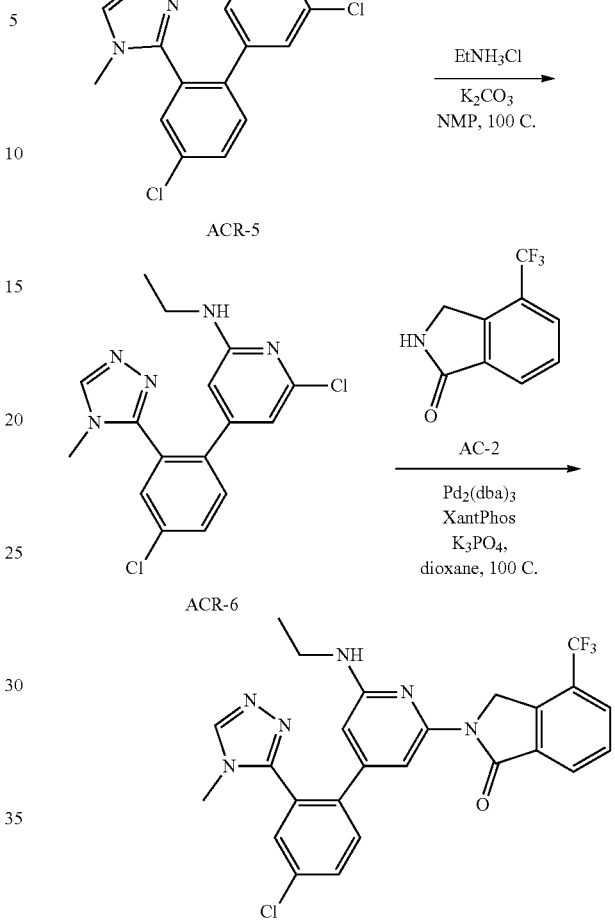

Step 1: Synthesis of 5-chloro-2-(2,6-dichloropyridin-4-yl) benzoic acid (ACR-2)

Into a 250-mL round-bottom flask purged and maintained with an inert atmosphere of nitrogen, was placed 2-bromo-5-chlorobenzoic acid (ACR-1) (5.00 g, 1 Eq, 21.2 mmol), intermediate (AAN-1) (4.07 g, 1 Eq, 21.2 mmol) and potassium phosphate (13.52 g, 3 Eq, 63.7 mmol) in dioxane (50 mL) and water (10 mL), then Pd(DtBPF)Cl$_2$ (1.38 g, 0.1 Eq, 2.12 mmol) was added at rt under nitrogen atmosphere. The resulting solution was stirred overnight at 60° C. under nitrogen atmosphere. The mixture was cooled to rt, diluted with water and extracted with EtOAc (3×200 mL). The combined organic layers were washed with brine (2×200 mL), dried (Na$_2$SO$_4$), filtered and concentrated in vacuo. The crude product was purified by reverse flash column chromatography with the following conditions: Column, C18; mobile phase, Water (0.1% NH$_4$HCO$_3$) and ACN (36% ACN up to 48% in 10 min); Detector, UV 254/220 nm. The product-containing fractions were combined and concentrated in vacuo. This resulted in the sub-title compound (ACR-2) (1.8 g, 5.95 mmol, 28%) as a brown solid. m/z 302.9/304.9 (M+H)$^+$ (ES+).

Step 2: Synthesis of 2-(5-Chloro-2-(2,6-dichloro-pyridin-4-yl)benzoyl)-N-methylhydrazine-1-carbothioamide (ACR-3)

Into a 100-mL round-bottom flask purged and maintained with an inert atmosphere of nitrogen, was placed the product from step 1 above (ACR-2) (1.80 g, 1 Eq, 5.95 mmol) and DIPEA (2.31 g, 3 Eq, 17.9 mmol) in DMF (40 mL) at rt, then 4-methyl-3-thiosemicarbazide (D-2) (630 mg, 1 Eq, 5.95 mmol) and T3P (4.73 g, 2.5 Eq, 14.9 mmol) were added at rt. The resulting solution was stirred for 6 h at rt and the resulting mixture was diluted with water and extracted with EtOAc (3×100 mL). The combined organic layers were washed with brine (2×100 mL), dried (Na$_2$SO$_4$), filtered and concentrated in vacuo. The crude product was purified by reverse flash column chromatography with the following conditions: Column, C18; mobile phase, Water (0.1% NH$_4$HCO$_3$) and ACN (60% ACN up to 85% in 10 min); Detector, UV 254/220 nm. The product-containing fractions were combined and concentrated in vacuo. This resulted in the sub-title compound (ACR-3) (720 mg, 1.85 mmol, 30%) as a brown/yellow solid. m/z 389.0/391.0 (M+H)$^+$ (ES+).

Step 3: Synthesis of 5-(5-Chloro-2-(2,6-dichloro-pyridin-4-yl)phenyl)-4-methyl-4H-1,2,4-triazole-3-thiol (ACR-4)

Into a 50-mL round-bottom flask, was placed the product from step 2 above (ACR-3) (650 mg, 1.67 mmol, 1 Eq) in NaOH solution (aq., 1 M) (20 mL) at rt. The resulting solution was stirred for 4 h at rt. The resulting solution was concentrated in vacuo affording the sub-title compound (ACR-4) (620 mg, 1.61 mmol, 96%) as brown/yellow solid which was used directly in next step without any further purification. m/z 371.0/373.0 (M+H)$^+$ (ES+).

Step 4: Synthesis of 2,6-Dichloro-4-(4-chloro-2-(4-methyl-4H-1,2,4-triazol-3-yl)phenyl)pyridine (ACR-5)

Into a 50-mL round-bottom flask purged and maintained with an inert atmosphere of nitrogen, was placed the product from step 3 above (ACR-4) (600 mg, 1 Eq, 1.61 mmol) in DCM (20 mL) at rt. Acetic acid (194 mg, 2 Eq, 3.23 mmol) and hydrogen peroxide solution (290 mg, 30% Wt, 5 Eq, 8.05 mmol) were added at rt and the resulting solution was stirred for 4 h. The resulting mixture was diluted with water and extracted with DCM (3×80 mL). The combined organic layers were washed with brine (2×80 mL), dried (Na$_2$SO$_4$), filtered and concentrated in vacuo. This resulted in the sub-title compound (ACR-5) (500 mg, 1.47 mmol, 91%) as a brown/yellow solid. m/z 339.0/341.0 (M+H)$^+$ (ES+).

Step 5: Synthesis of 6-Chloro-4-(4-chloro-2-(4-methyl-4H-1,2,4-triazol-3-yl)phenyl)-N-ethylpyridin-2-amine (ACR-6)

Into a 100-mL round-bottom flask, was placed the product from step 4 above (ACR-5) (500 mg, 1 Eq, 1.47 mmol) and ethanamine, HCl (664 mg, 10 Eq, 14.7 mmol) in NMP (10 mL) at rt, then K$_2$CO$_3$ (2.03 g, 10 Eq, 14.7 mmol) was added at rt under nitrogen atmosphere. The resulting solution was stirred for 16 h at 100° C. under nitrogen atmosphere. The mixture was cooled to rt and the crude product purified by reverse flash column chromatography with the following conditions: Column, C18; mobile phase, Water (0.1% NH$_4$HCO$_3$) and ACN (20% ACN up to 43% in 10 min); Detector, UV 254/220 nm. The product-containing fractions were combined and concentrated in vacuo. This resulted in the sub-title compound (ACR-6) (480 mg, 1.38 mmol, 94%) as white solid. m/z 348.1/350.1 (M+H)$^+$ (ES+).

Step 6: 2-(4-(4-Chloro-2-(4-methyl-4H-1,2,4-triazol-3-yl)phenyl)-6-(ethylamino)pyridin-2-yl)-4-(trifluoromethyl)isoindolin-1-one (ACR-7)

Into a 25-mL round-bottom flask, was placed the product from step 5 above (ACR-6) (70 mg, 1 Eq, 201 μmol), intermediate (AC-2) (40 mg, 1 Eq, 201 μmol) and potassium phosphate (128 mg, 3 Eq, 603 μmol) in 1,4-dioxane (3 mL), then Pd$_2$(dba)$_3$-CHCl$_3$ (42 mg, 0.2 Eq, 40 μmol) and Xant-Phos (47 mg, 0.4 Eq, 80 μmol) were added at rt under nitrogen atmosphere. The resulting solution was stirred overnight at 100° C. under nitrogen atmosphere. The resulting mixture was cooled to rt and concentrated. The crude product was purified by Prep-HPLC with the following conditions: Column: XBridge Prep C18 OBD Column, 19×150 mm, 5 μm; Mobile Phase A: Water (0.1% NH$_4$HCO$_3$), Mobile Phase B: ACN; Flow rate: 25 mL/min; Gradient: 50 B to 65 B in 9 min; Detector, UV 210/254 nm; RT: 6.67. This resulted in the title compound (ACR-7) (10.6 mg, 21 μmol, 10%) as a white solid. m/z 513.1 (M+H)$^+$ (ES+). $^1$H NMR (400 MHz, MeOH-d4) δ 8.47 (s, 1H), 8.08 (d, J=7.7 Hz, 1H), 7.97 (d, J=7.8 Hz, 1H), 7.81-7.66 (m, 4H), 7.52 (d, J=1.3 Hz, 1H), 6.03 (d, J=1.3 Hz, 1H), 5.23 (s, 2H), 3.44 (s, 3H), 3.29-3.26 (m, 2H), 1.22 (t, J=7.2 Hz, 3H).

Example 106: Synthesis of (S)-2-(6-(Ethylamino)-4-(1-methyl-4-(4-methyl-4H-1,2,4-triazol-3-yl)-1H-pyrazol-5-yl)pyridin-2-yl)-6-(3-hydroxypyrrolidine-1-carbonyl)-4-(trifluoromethyl)isoindolin-1-one (ACS-4)

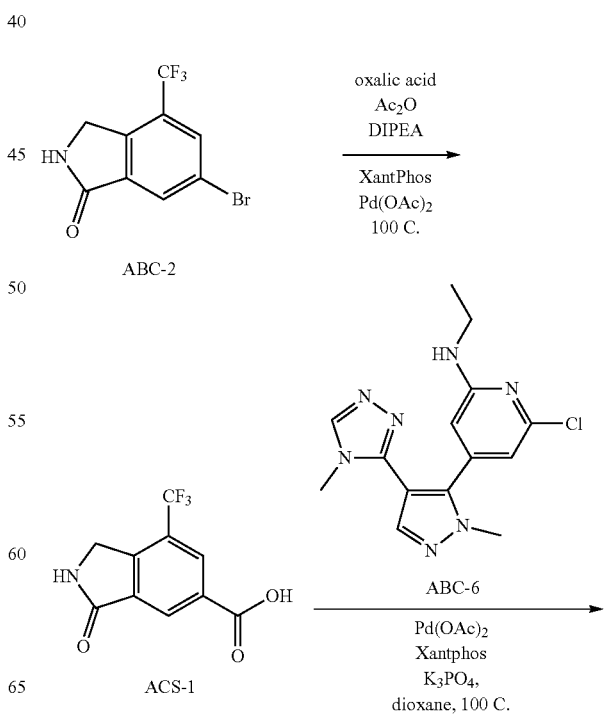

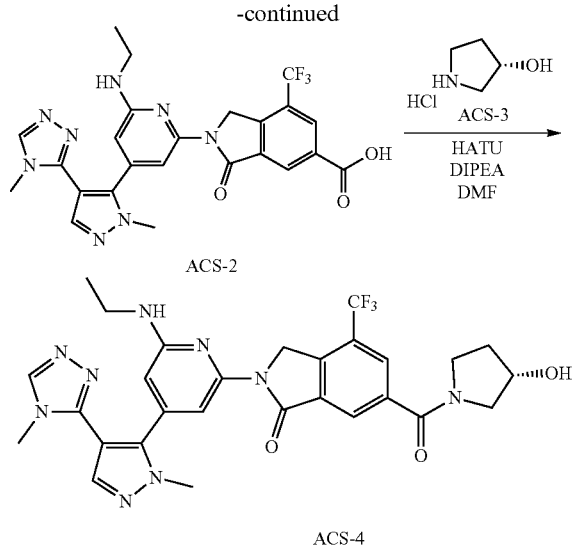

Step 1: Synthesis of 3-Oxo-7-(trifluoromethyl)isoindoline-5-carboxylic acid (ACS-1)

Into a 40 mL sealed tube were added intermediate (ABC-2) (300 mg, 1 Eq, 1.07 mmol), oxalic acid (145 mg, 1.5 Eq, 1.60 mmol), DIPEA (208 mg, 1.5 Eq, 1.61 mmol) and acetic anhydride (164 mg, 1.5 Eq, 1.60 mmol) in DMF (10 mL) at rt. To the above mixture was added Pd(OAc)$_2$ (24 mg, 0.1 Eq, 107 μmol) and XantPhos (124 mg, 0.2 Eq, 210 μmol) over 3 min at rt under nitrogen atmosphere. The resulting mixture was stirred overnight at 100° C. under nitrogen atmosphere before being allowed to cool to rt. The crude product was purified by reverse flash column chromatography with the following conditions: Column, C18; mobile phase, Water (0.1% FA) and ACN (36% ACN up to 48% in 10 min); Detector, UV 254/220 nm. The product-containing fractions were combined and concentrated in vacuo. This resulted in the sub-title compound (ACS-1) (120 mg, 489 μmol, 46%) as a yellow oil. m/z 246.0 (M+H)$^+$ (ES+).

Step 2: Synthesis of 2-(6-(Ethylamino)-4-(1-methyl-4-(4-methyl-4H-1,2,4-triazol-3-yl)-1H-pyrazol-5-yl)pyridin-2-yl)-3-oxo-7-(trifluoromethyl)isoindoline-5-carboxylic acid (ACS-2)

Into a 20 mL sealed tube were added the product from step 1 above (ACS-1) (100 mg, 1 Eq, 408 μmol), intermediate (ABC-6) (143 mg, 1.1 Eq, 449 μmol), and potassium phosphate (260 mg, 3 Eq, 1.22 mmol) in 1,4-dioxane (5 mL) at rt. To the above mixture was added Pd(OAc)$_2$ (9 mg, 0.1 Eq, 41 μmol) and XantPhos (47 mg, 82 μmol, 0.2 Eq) over 3 min at rt under nitrogen atmosphere and the resulting mixture stirred for 3 h at 100° C. under nitrogen atmosphere. The mixture was allowed to cool to rt and the crude product was purified by reverse flash column chromatography with the following conditions: Column, C18; mobile phase, Water (0.1% NH$_4$HCO$_3$) and ACN (36% ACN up to 48% in 10 min); Detector, UV 254/220 nm. The product-containing fractions were combined and concentrated in vacuo. This resulted in the sub-title compound (ACS-2) (60 mg, 114 μmol, 28%) as a yellow oil. m/z 527.2 (M+H)$^+$ (ES+).

Step 3: 2-[6-(Ethylamino)-4-[2-methyl-4-(4-methyl-1,2,4-triazol-3-yl)pyrazol-3-yl]pyridin-2-yl]-6-[(3S)-3-hydroxypyrrolidine-1-carbonyl]-4-(trifluoromethyl)-3H-isoindol-1-one (ACS-4)

Into an 8 mL sealed tube were added the product from step 2 above (ACS-2) (50 mg, 1 Eq, 95 μmol), (3S)-pyrrolidin-3-ol (ACS-3) (10 mg, 1.2 Eq, 114 μmol) and DIPEA (37 mg, 3 Eq, 285 μmol) in DMF (2 mL) at rt. To the above mixture was added HATU (54 mg, 1.5 Eq, 143 μmol) over 5 min at 0° C. and the resulting mixture stirred for 3 h at rt. The mixture was concentrated in vacuo and the crude product purified by Prep-HPLC with the following conditions (Column: XBridge Prep OBD C18 Column, 30*150 mm, 5 μm; Mobile Phase A: Water (0.1% NH$_4$HCO$_3$), Mobile Phase B: ACN; Flow rate: 60 mL/min; Gradient: 25% B to 36% B in 9 min; Wavelength: 254/220 nm; RT: 8.9) to afford the title compound (ACS-4) (19.2 mg, 32 μmol, 34%) as a white solid. m/z 596.4 (M+H)$^+$ (ES+). $^1$H NMR (400 MHz, MeOH-d4) δ 8.49 (s, 1H), 8.23 (d, J=7.7 Hz, 1H), 8.15 (d, J=4.5 Hz, 1H), 7.87 (s, 1H), 7.65 (d, J=1.2 Hz, 1H), 6.22 (d, J=1.3 Hz, 1H), 5.33 (s, 2H), 4.54-4.42 (m, 1H), 4.04 (s, 3H), 3.88-3.52 (m, 4H), 3.51 (s, 3H), 3.42-3.35 (m, 3H), 2.21-1.94 (m, 2H), 1.25 (t, J=7.2 Hz, 3H).

Example 107: Synthesis of (R)-2-(6-(Ethylamino)-4-(1-methyl-4-(4-methyl-4H-1,2,4-triazol-3-yl)-1H-pyrazol-5-yl)pyridin-2-yl)-6-(3-hydroxypyrrolidine-1-carbonyl)-4-(trifluoromethyl)isoindolin-1-one (ACT-2)

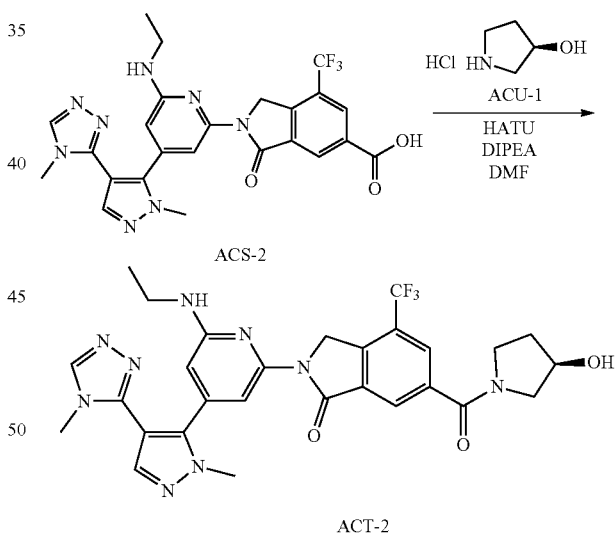

Into an 8 mL sealed tube were added intermediate (ACS-2) (50 mg, 1 Eq, 95 μmol), (3R)-pyrrolidin-3-ol (ACT-1) (10 mg, 1.2 Eq, 114 μmol) and DIPEA (37 mg, 3 Eq, 285 μmol) in DMF (2 mL) at rt. To the above mixture was added HATU (54 mg, 143 μmol, 1.5 Eq) over 5 min at 0° C. and the resulting mixture stirred for 3 h at rt. The mixture was concentrated in vacuo and the crude product purified by Prep-HPLC with the following conditions (Column: XBridge Prep OBD C18 Column, 30*150 mm, 5 μm; Mobile Phase A: Water (0.1% NH$_4$HCO$_3$), Mobile Phase B: ACN; Flow rate: 60 mL/min; Gradient: 25% B to 36% B in 9 min; Wavelength: 254/220 nm; RT: 8.8) to afford the title compound (ACT-2) (18.4 mg, 31 µmol, 33%) as a white solid. m/z 596.4 (M+H)⁺ (ES+). ¹H NMR (400 MHz, MeOH-d4) δ 8.49 (s, 1H), 8.23 (d, J=7.6 Hz, 1H), 8.16 (d, J=4.5 Hz, 1H), 7.87 (s, 1H), 7.66 (d, J=1.3 Hz, 1H), 6.22 (d, J=1.2 Hz, 1H), 5.34 (d, J=1.7 Hz, 2H), 4.54-4.43 (m, 1H), 4.04 (s, 3H), 3.86-3.52 (m, 4H), 3.51 (s, 3H), 3.43-3.35 (m, 3H), 2.22-1.97 (m, 2H), 1.25 (t, J=7.2 Hz, 3H).

Example 108: Synthesis of 2-(6-(1-(Hydroxymethyl)cyclopropyl)-4-(2-(4-methyl-4H-1,2,4-triazol-3-yl)phenyl)pyridin-2-yl)-4-(trifluoromethyl)isoindolin-1-one (ACU-2)

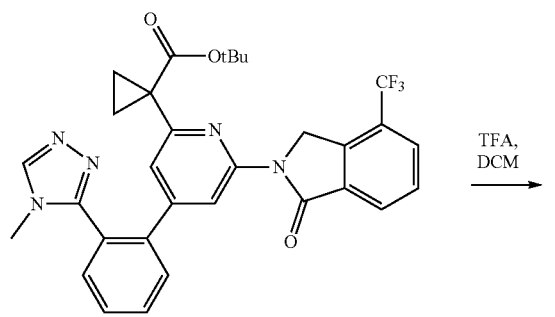
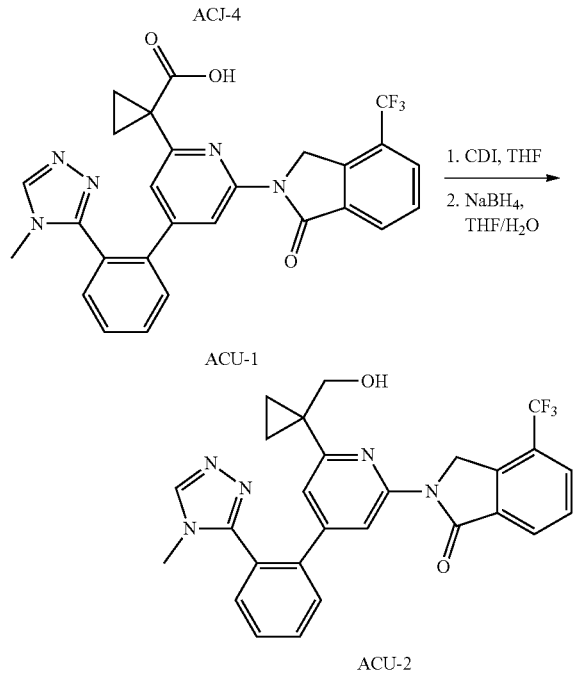

Step 1: Synthesis of 1-(4-(2-(4-Methyl-4H-1,2,4-triazol-3-yl)phenyl)-6-(1-oxo-4-(trifluoromethyl)isoindolin-2-yl)pyridin-2-yl)cyclopropane-1-carboxylic acid (ACU-1)

A solution of intermediate (ACJ-4) (60 mg, 1 Eq, 104 µmol) in DCM (3 mL) and TFA (1 mL) was stirred for 2 h at rt. The resulting mixture was concentrated in vacuo. The crude product was used in the next step directly without further purification. m/z 520.2 (M+H)⁺ (ES+).

Step 2: 2-(6-(1-(Hydroxymethyl)cyclopropyl)-4-(2-(4-methyl-4H-1,2,4-triazol-3-yl)phenyl)pyridin-2-yl)-4-(trifluoromethyl)isoindolin-1-one (ACU-2)

To a stirred solution of the product from step 1 above (ACU-1) (20 mg, 1 Eq, 35 µmol) in THF (1 mL) was added CDI (7 mg, 1.3 Eq, 46 µmol) at rt. After 30 min, the mixture was added into a solution of NaBH₄ (7 mg, 175 µmol, 5 Eq) in THF (1 mL) and water (0.5 mL) at 0° C. under nitrogen atmosphere. The resulting mixture was stirred for 2 h at rt then concentrated in vacuo. The crude product was purified by Prep-HPLC with the following conditions (Column: XBridge Prep OBD C18 Column, 30*150 mm, 5 µm; Mobile Phase A: Water (0.1% NH₄HCO₃), Mobile Phase B: ACN; Flow rate: 60 mL/min; Gradient: 42% B to 67% B in 8 min; Wavelength: 254/220 nm; RT: 6.62) to afford the title compound (ACU-2) (3 mg, 5.9 µmol, 17%) as a white solid. m/z 506.0 (M+H)⁺ (ES+). ¹H NMR (400 MHz, MeOH-d4) δ 8.47 (s, 1H), 8.18 (d, J=1.3 Hz, 1H), 8.11 (d, J=7.7 Hz, 1H), 8.00 (d, J=7.7 Hz, 1H), 7.85-7.76 (m, 3H), 7.73-7.64 (m, 2H), 7.08 (d, J=1.4 Hz, 1H), 5.30-5.25 (m, 2H), 3.87 (s, 2H), 3.45 (s, 3H), 1.22 (m, 2H), 1.01 (m, 2H).

Example 109: Synthesis of 2-(6-(Ethylamino)-4-(1-methyl-4-(4-methyl-4H-1,2,4-triazol-3-yl)-1H-pyrazol-5-yl)pyridin-2-yl)-6-((1-methylazetidin-3-yl)oxy)-4-(trifluoromethyl)isoindolin-1-one (ACV-2)

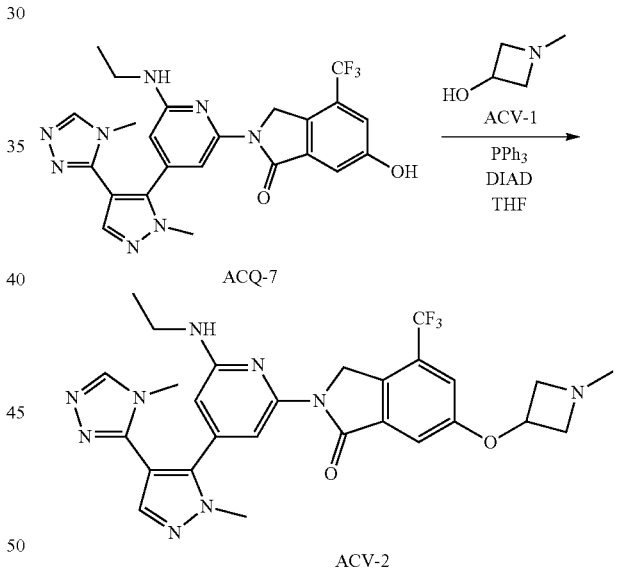

To a stirred solution of intermediate (ACQ-7) (40 mg, 1 Eq, 80 µmol) and 1-methylazetidin-3-ol (ACV-1) (28 mg, 4 Eq, 320 µmol) in THF (10 mL) was added triphenylphosphine (105 mg, 5 Eq, 400 µmol) and DIAD (81 mg, 5 Eq, 400 µmol) at rt. The resulting mixture was stirred overnight at rt then acidified to pH 3 with HCl (aq., 4 M). The resulting mixture was diluted with water and extracted with DCM (3×10 mL). The combined organic layers were washed with brine (2×10 mL), dried (Na₂SO₄), filtered and concentrated in vacuo. The crude product was purified by Prep-HPLC with the following conditions (Column: XBridge Prep OBD C18 Column, 30*150 mm, 5 µm; Mobile Phase A: Water (0.1% NH₄HCO₃), Mobile Phase B: ACN; Flow rate: 60 mL/min; Gradient: 37% B to 44% B in 9 min; Wavelength: 254/220 nm) to afford the title compound (ACV-2) (3.3 mg, 5.8 µmol, 7%) as an off-white solid. m/z 568.4 (M+H)⁺ (ES+). ¹H NMR (400 MHz, DMSO-d6) δ 8.46 (s, 1H), 7.87 (s, 1H), 7.52 (d, J=1.2 Hz, 1H), 7.48 (d, J=2.3 Hz, 1H), 7.35 (d, J=2.3 Hz, 1H), 6.24 (d, J=1.2 Hz, 1H), 5.16-5.07 (m, 2H), 5.06-4.94 (m, 1H), 3.89 (s, 3H), 3.81-3.72 (m, 2H), 3.43 (s, 3H), 3.25 (q, J=7.2 Hz, 2H), 3.19-3.07 (m, 2H), 2.33 (s, 3H), 1.15 (t, J=7.2 Hz, 3H).

Example 110: Synthesis of 2-(6-(Ethylamino)-4-(1-methyl-4-(4-methyl-4H-1,2,4-triazol-3-yl)-1H-pyrazol-5-yl)pyridin-2-yl)-6-(isopropoxymethyl)-4-(trifluoromethyl)isoindolin-1-one (ACW-1)

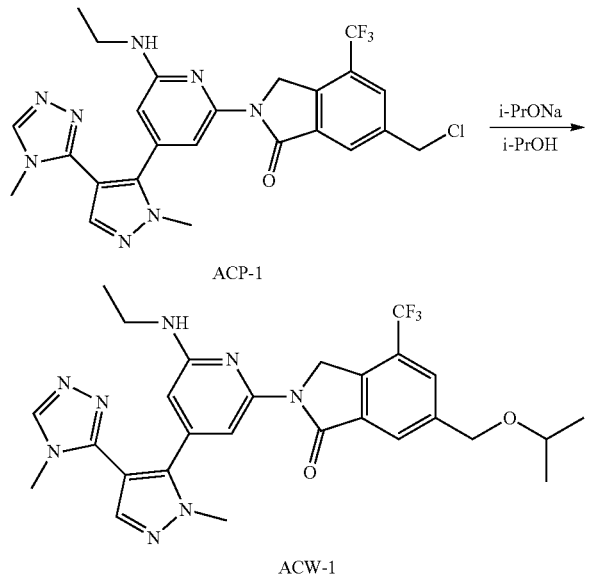

To a stirred solution of intermediate (ACP-1) (42 mg, 79 µmol, 1 Eq) in iPrOH (5 mL) was added NaOiPr (32 mg, 395 µmol, 5 Eq) at rt. The resulting mixture was stirred for 1 h at rt. The reaction was then quenched by the addition of ice water (3 mL) at 0° C. The mixture was concentrated in vacuo and the residue purified by TLC with DCM/MeOH (10/1). The crude product was purified by Prep-HPLC with the following conditions (Column: XBridge Prep OBD C18 Column, 30*150 mm, 5 µm; Mobile Phase A: Water (0.1% NH₄HCO₃), Mobile Phase B: ACN; Flow rate: 60 mL/min; Gradient: 52% B to 62% B in 8 min; Wavelength: 254/220 nm) to afford the title compound (ACW-1) (16.8 mg, 30 µmol, 38%) as a white solid. m/z 555.3 (M+H)⁺ (ES+). ¹H NMR (400 MHz, DMSO-d6) δ 8.47 (s, 1H), 8.00-7.95 (m, 2H), 7.89 (s, 1H), 7.57 (d, J=1.2 Hz, 1H), 6.93 (t, J=5.3 Hz, 1H), 6.25 (d, J=1.3 Hz, 1H), 5.21 (s, 2H), 4.67 (s, 2H), 3.90 (s, 3H), 3.75-3.66 (m, 1H), 3.47 (s, 3H), 3.31-3.23 (m, 2H), 1.22-1.13 (m, 9H).

Example 111: Synthesis of (R)-2-(6-(Ethylamino)-4-(2-(4-methyl-4H-1,2,4-triazol-3-yl)phenyl)pyridin-2-yl)-6-((3-hydroxypyrrolidin-1-yl)methyl)-4-(trifluoromethyl)isoindolin-1-one (AT-1)

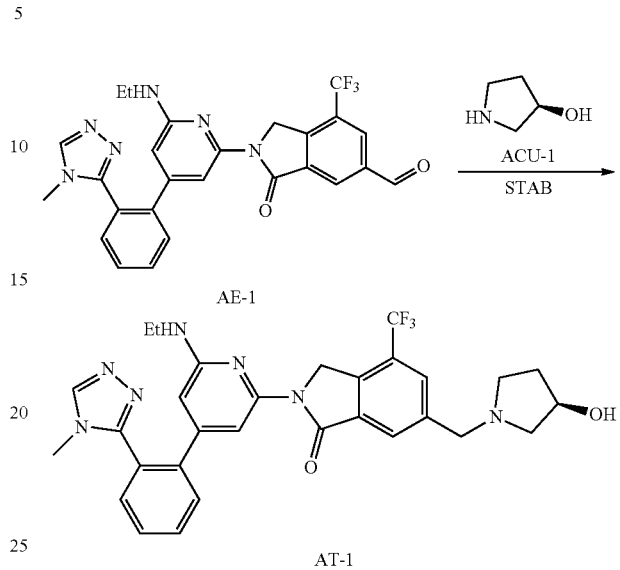

NaBH(OAc)₃ (75 mg, 6.0 Eq, 0.35 mmol) was added to a stirred solution of intermediate AE-1 (30 mg, 99% Wt, 1 Eq, 59 µmol) and (R)-pyrrolidin-3-ol (ACU-1) (20 mg, 4.0 Eq, 0.23 mmol) in CHCl₃ (2 mL) and stirred at rt overnight. The reaction mixture was diluted with DCM (4 mL) and washed with sat. aq. sol. of NaHCO₃ (10 mL). The organic extract was dried (phase separator) and concentrated in vacuo. The crude product was purified by preparative HPLC (Waters, Basic (0.3% ammonia), Basic, Waters XBridge BEH C18 ODB, 5 µm, 30×100 mm column 0-100% MeCN in water to afford the title compound (AT-1) (16 mg, 26 µmol, 44%, 94% Purity) as a pale yellow solid. m/z 576.3 (M−H)⁻ (ES−). ¹H NMR (400 MHz, DMSO-d6) δ 8.46 (s, 1H), 7.97 (s, 1H), 7.92 (s, 1H), 7.71 (td, J=7.4, 1.6 Hz, 1H), 7.65-7.53 (m, 3H), 7.48 (d, J=1.2 Hz, 1H), 6.69 (t, J=5.5 Hz, 1H), 5.94 (d, J=1.2 Hz, 1H), 5.16 (s, 2H), 4.72 (d, J=4.3 Hz, 1H), 4.23-4.19 (m, 1H), 3.82-3.72 (m, 2H), 3.33 (s, 3H), 3.21-3.12 (m, 2H), 2.73-2.58 (m, 2H), 2.48-2.39 (m, 1H), 2.39-2.32 (m, 1H), 2.08-1.95 (m, 1H), 1.61-1.53 (m, 1H), 1.13 (t, J=7.1 Hz, 3H).

Example 112: Synthesis of (R)-6-((4,4-Difluoro-3-methylpiperidin-1-yl)methyl)-2-(6-(ethylamino)-4-(2-(4-methyl-4H-1,2,4-triazol-3-yl)phenyl)pyridin-2-yl)-4-(trifluoromethyl)isoindolin-1-one (AU-2)

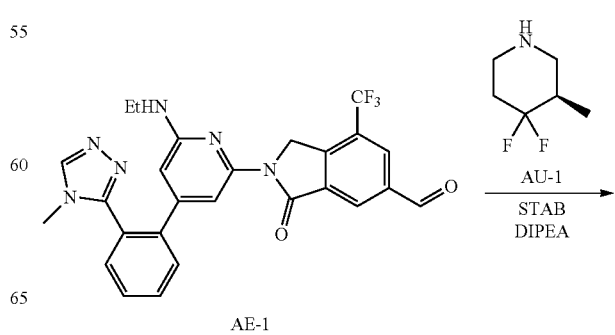

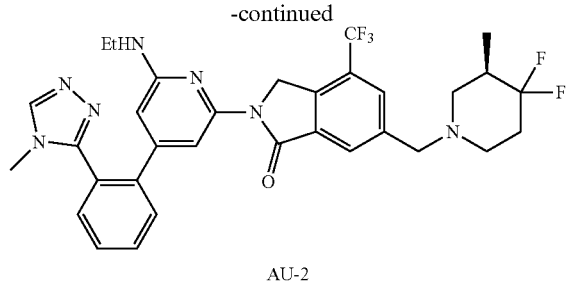

AU-2

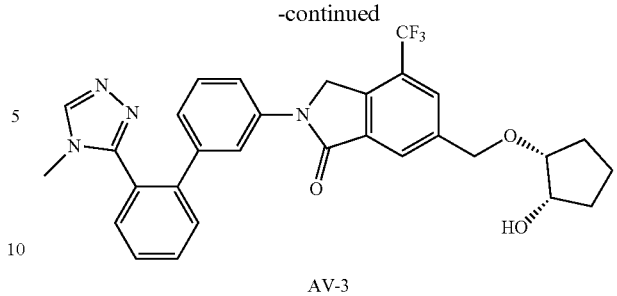

AV-3

NaBH(OAc)₃ (94 mg, 6.0 Eq, 0.44 mmol) was added to a stirred solution intermediate AE-1 (30 mg, 99% Wt, 0.79 Eq, 59 µmol), (R)-4,4-difluoro-3-methylpiperidine (AU-1) (10 mg, 1 Eq, 74 µmol) and DIPEA (29 mg, 38 µL, 3.0 Eq, 0.22 mmol) in DCM (2 mL) and stirred at rt overnight. The reaction mixture was diluted with DCM (5 mL) and washed with sat. aq. sol. of NaHCO₃ (6 mL). The organic layer was separated and concentrated in vacuo. The crude product was purified by chromatography on RP Flash C18 (12 g cartridge, 15-80% MeCN/10 mM ammonium bicarbonate) to afford the title compound (AU-2) (4.5 mg, 7.1 µmol, 9.6%, 99% Purity) as a white solid. m/z 626.3 (M+H)⁺ (ES+). ¹H NMR (400 MHz, DMSO-d6) δ 8.46 (s, 1H), 7.99 (s, 1H), 7.94 (s, 1H), 7.71 (td, J=7.5, 1.7 Hz, 1H), 7.64-7.54 (m, 3H), 7.48 (d, J=1.2 Hz, 1H), 6.69 (t, J=5.5 Hz, 1H), 5.94 (d, J=1.2 Hz, 1H), 5.16 (s, 2H), 3.74 (d, J=2.5 Hz, 2H), 3.29 (s, 3H), 3.22-3.12 (m, 2H), 2.80-2.68 (m, 2H), 2.36-1.84 (m, 5H), 1.13 (t, J=7.2 Hz, 3H), 0.92 (d, J=6.4 Hz, 3H).

Example 113: Synthesis of 6-((((1R,2S)-2-Hydroxycyclopentyl)oxy)methyl)-2-(2'-(4-methyl-4H-1,2,4-triazol-3-yl)-[1,1'-biphenyl]-3-yl)-4-(trifluoromethyl)isoindolin-1-one (AV-3)

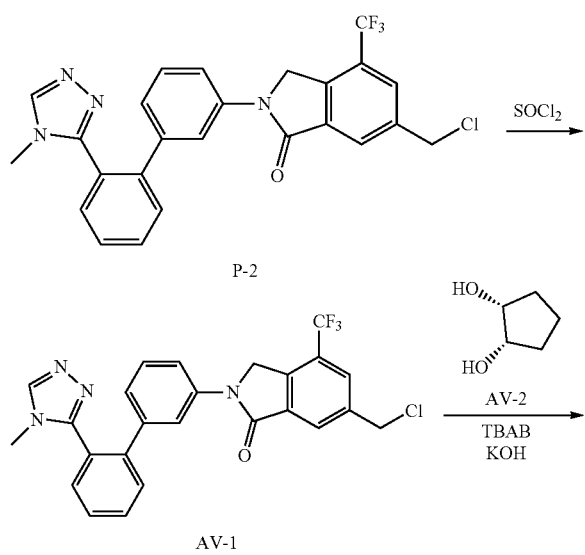

Step 1: Synthesis of 6-(Chloromethyl)-2-(2'-(4-methyl-4H-1,2,4-triazol-3-yl)-[1,1'-biphenyl]3-yl)-4-(trifluoromethyl)isoindolin-1-one (AV-1)

A stirred solution of intermediate (P-2) (35 mg, 1 Eq, 75 µmol) in DCM (2 mL) was treated with SOCl₂ (22 mg, 14 µL, 2.5 Eq, 0.19 mmol) dropwise. The resultant suspension was stirred at rt for 30 min. The volatiles were removed in vacuo and the resulting crude sub-title compound (AV-1) was used as a solution without further purification. ¹H NMR (400 MHz, DMSO-d6) δ 9.05 (s, 1H), 8.15 (d, J=4.9 Hz, 2H), 7.96-7.89 (m, 1H), 7.85-7.78 (m, 1H), 7.76-7.64 (m, 4H), 7.44 (t, J=8.0 Hz, 1H), 7.01 (d, J=7.7 Hz, 1H), 5.17 (s, 2H), 5.02 (s, 2H), 3.29 (s, 3H).

Step 2: Synthesis of 6-((((1R,2S)-2-Hydroxycyclopentyl)oxy)methyl)-2-(2'-(4-methyl-4H-1,2,4-triazol-3-yl)-[1,1'-biphenyl]-3-yl)-4-(trifluoromethyl)isoindolin-1-one (AV-3)

To a vial containing the product from step 1 above (AV-1) (20 mg, 1 Eq, 41 µmol), TBAB (6.7 mg, 0.5 Eq, 21 µmol) and (1R,2S)-cyclopentane-1,2-diol (AV-2) (21 mg, 5 Eq, 0.21 mmol) was added DCM (2 mL). A solution of KOH (aq) (12 mg, 1 mL, 20% Wt, 1 Eq, 41 µmol) was added and the reaction left at rt for 2 h without stirring. The reaction was diluted with water (10 mL) and extracted with EtOAc (3×10 mL). The organics were combined, dried (MgSO₄), filtered and evaporated. The crude product was purified by chromatography on RP Flash C18 (12 g cartridge, 15-65% MeCN/10 mM ammonium bicarbonate) to afford the title compound (AV-3) (3 mg, 5 µmol, 10%, 99% Purity) as a white solid. m/z 549.3 (M+H)⁺ (ES+). ¹H NMR (400 MHz, DMSO-d6) δ 8.39 (s, 1H), 8.05 (d, J=17.9 Hz, 2H), 8.00 (dd, J=8.1, 2.3 Hz, 1H), 7.75-7.65 (m, 3H), 7.60-7.56 (m, 2H), 7.38 (t, J=8.0 Hz, 1H), 6.93-6.88 (m, 1H), 5.10 (s, 2H), 4.80 (d, J=12.7 Hz, 1H), 4.70 (d, J=12.8 Hz, 1H), 4.49 (d, J=4.8 Hz, 1H), 4.05-3.98 (m, 1H), 3.72 (td, J=6.2, 3.8 Hz, 1H), 3.08 (s, 3H), 1.82-1.65 (m, 4H), 1.62-1.53 (m, 1H), 1.48-1.40 (m, 1H).

Example 114: Synthesis of 6-((((1-Hydroxycyclobutyl)methyl)amino)methyl)-2-(2'-(4-methyl-4H-1,2,4-triazol-3-yl)-[1,1'-biphenyl]-3-yl)-4-(trifluoromethyl)isoindolin-1-one (AW-2)

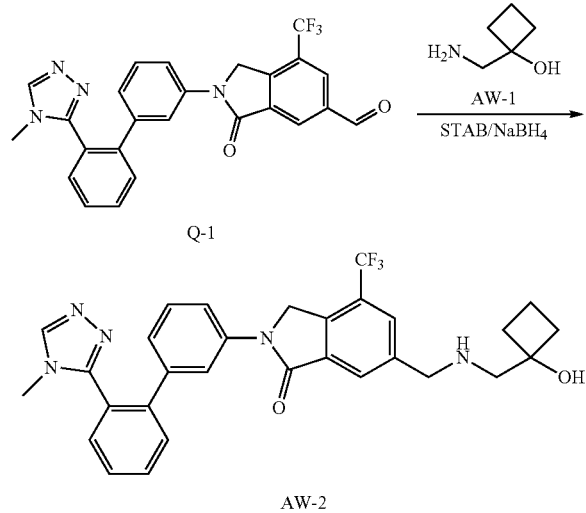

NaBH(OAc)₃ (82 mg, 6.0 Eq, 0.39 mmol) was added to a stirred solution of intermediate (Q-1) (30 mg, 99% Wt, 1 Eq, 64 µmol), 1-(aminomethyl)cyclobutan-1-ol (AW-1) (7.8 mg, 1.2 Eq, 77 µmol) and DIPEA (25 mg, 34 µL, 3 Eq, 0.19 mmol) in DCM (5 mL) and stirred at rt overnight. NaBH₄ (7.3 mg, 3 Eq, 0.19 mmol) was added and the reaction mixtures stirred at rt overnight. The reaction mixture was diluted with DCM (5 mL) and washed with sat. aq. sol. of NaHCO₃ (6 mL). The organic layer was separated, dried (phase separator), and concentrated in vacuo. The crude product was purified by chromatography on RP Flash C18 (12 g cartridge, 25-55% MeCN/10 mM ammonium bicarbonate) to afford the title compound (AW-2) (5 mg, 9 µmol, 10%, 95% Purity) as a white solid. m/z 548.2 (M+H)⁺ (ES+). ¹H NMR (400 MHz, DMSO-d6) δ 8.39 (s, 1H), 8.05 (s, 1H), 8.03-7.97 (m, 2H), 7.75-7.65 (m, 3H), 7.61-7.55 (m, 2H), 7.37 (t, J=8.0 Hz, 1H), 6.90 (dt, J=7.7, 1.3 Hz, 1H), 5.08 (s, 2H), 4.93 (s, 1H), 3.96 (s, 2H), 3.08 (s, 3H), 2.04-1.96 (m, 2H), 1.96-1.85 (m, 2H), 1.67-1.55 (m, 1H), 1.44-1.32 (m, 1H). Three protons masked by DMSO peak.

Example 115: Synthesis of 6-((((1-Hydroxycyclobutyl)methyl)amino)methyl)-2-phenyl-4-(trifluoromethyl)isoindolin-1-one (AX-3)

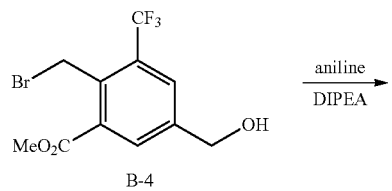

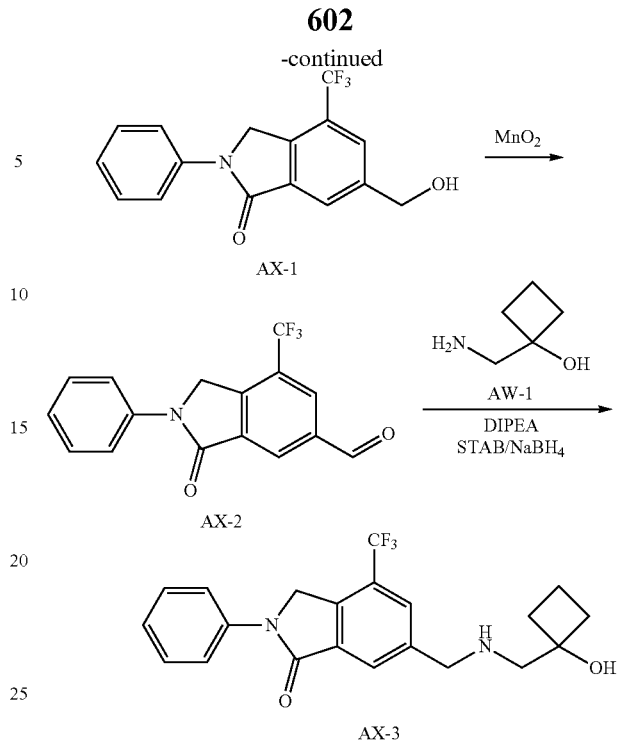

Step 1: Synthesis of 6-(Hydroxymethyl)-2-phenyl-4-(trifluoromethyl)isoindolin-1-one (AX-1)

Intermediate (B-4) (135 mg, 1 Eq, 413 µmol) in aniline (500 mg, 489 µL, 13 Eq, 5.37 mmol) was stirred at 100° C. for 30 min (microwave). The reaction mixture was then allowed to stand at rt overnight. The reaction mixture was dilute with EtOAc (10 mL) and washed with 1 M HCl (aq.) (2×10 mL). The organic layer was diluted with DCM (10 mL), passed through a phase separator and concentrated in vacuo to afford the sub-title compound (AX-1) (84 mg, 0.26 mmol, 63%, 95% Purity) as a flocculent beige solid. m/z 305.7 & 307.2 (M−H)⁻ (ES−). ¹H NMR (400 MHz, DMSO-d6) δ 8.02 (s, 1H), 7.98-7.88 (m, 3H), 7.50-7.41 (m, 2H), 7.26-7.17 (m, 1H), 5.59 (t, J=5.8 Hz, 1H), 5.20 (d, J=1.8 Hz, 2H), 4.71 (d, J=5.8 Hz, 2H).

Step 2: Synthesis of 3-Oxo-2-phenyl-7-(trifluoromethyl)isoindoline-5-carbaldehyde (AX-2)

Manganese dioxide (0.68 g, 30 Eq, 7.8 mmol) was added to the product from step 1 above (AX-1) (84 mg, 95% Wt, 1 Eq, 0.26 mmol) in CHCl₃ (10 mL) and stirred at rt over the weekend. The reaction mixture was filtered through a Celite plug (chased with 10 mL MeOH). The filtrate was evaporated to afford the sub-title compound (AX-2) (74 mg, 0.22 mmol, 86%, 92% Purity) as a pale yellow solid. ¹H NMR (400 MHz, DMSO-d6) δ 10.22 (s, 1H), 8.56 (s, 1H), 8.49 (s, 1H), 8.00-7.92 (m, 2H), 7.52-7.43 (m, 2H), 7.29-7.19 (m, 1H), 5.35 (s, 2H).

Step 3: Synthesis of 6-((((1-Hydroxycyclobutyl)methyl)amino)methyl)-2-phenyl-4-(trifluoromethyl)isoindolin-1-one (AX-3)

A mixture of the product from step 2 above (AX-2) (20 mg, 99% Wt, 1 Eq, 65 µmol), 1-aminomethyl-cyclobutanol (AW-1) (6.6 mg, 1 Eq, 65 µmol) and DIPEA (25 mg, 33 µL, 3.0 Eq, 0.19 mmol) in CHCl₃ (2 mL) was stirred at rt for 5 min. NaBH(OAc)₃ (82 mg, 6.0 Eq, 0.39 mmol) was then added and the resultant suspension stirred at rt overnight. The reaction temperature was raised to 40° C. and stirring continued overnight. NaBH₄ (10 mg, 4.1 Eq, 0.26 mmol) was added and stirring continued at rt overnight. The reaction mixture was diluted with DCM (4 mL) and washed with sat. aq. NaHCO₃ (10 mL). The organic phase was separated and evaporated to afford the crude product. The crude product was purified by preparative HPLC (Waters, Basic (0.3% ammonia), basic, Waters XBridge BEH C18 ODB column, 130A, 5 μm, 30×100 mm column, 30-100% MeCN in Water) to afford the title compound (AX-3) (6 mg, 0.01 mmol, 20%, 94% Purity) as a white solid. m/z 391.3 (M+H)⁺ (ES+). ¹H NMR (400 MHz, DMSO-d6) δ 8.06 (s, 1H), 8.01 (s, 1H), 7.97-7.90 (m, 2H), 7.51-7.42 (m, 2H), 7.26-7.17 (m, 1H), 5.20 (s, 2H), 4.93 (s, 1H), 3.96 (s, 2H), 3.29 (s, 1H), 2.53 (s, 2H), 2.05-1.84 (m, 4H), 1.65-1.55 (m, 1H), 1.44-1.33 (m, 1H).

Example 116: Synthesis of 6-Bromo-2-(2'-(4-methyl-4H-1,2,4-triazol-3-yl)-[1,1'-biphenyl]-3-yl)-4-(trifluoromethyl)isoindolin-1-one (AY-1)

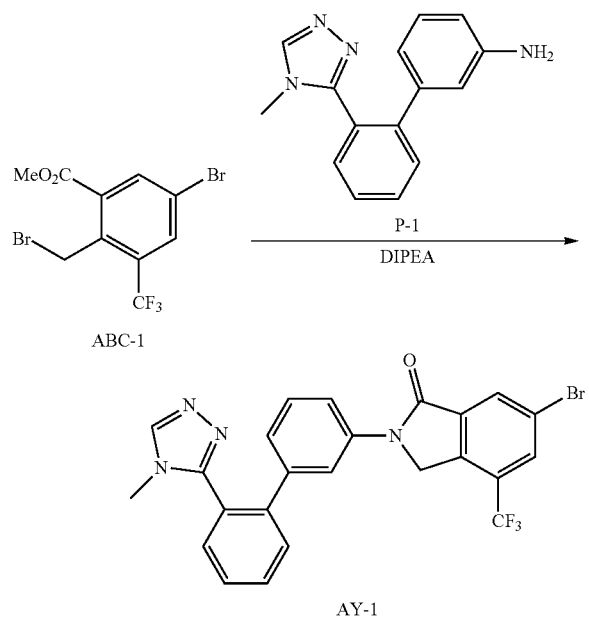

DIPEA (258 mg, 347 μL, 1.5 Eq, 1.99 mmol) was added to a solution of intermediate P-1 (366 mg, 1.1 Eq, 1.46 mmol) and intermediate ABC-1 (500 mg, 1 Eq, 1.33 mmol) in benzotrifluoride (3 mL) and the reaction stirred at 60° C. for 16 h. Volatiles were evaporated and the crude dissolved in EtOH (20 mL) and stirred at 60° C. for 16 h. The reaction mixture was concentrated in vacuo and the crude product was purified by chromatography on RP Flash C18 (40 g cartridge, 15-80% MeCN/10 mM ammonium hydroxide) to afford the title compound (AY-1) (161 mg, 0.30 mmol, 23%, 96% Purity) as a yellow solid. m/z 513/515 (M+H)⁺ (ES+). ¹H NMR (400 MHz, DMSO-d6) δ 8.39 (s, 1H), 8.27 (s, 1H), 8.23 (d, J=1.7 Hz, 1H), 7.98 (dd, J=8.0, 2.2 Hz, 1H), 7.74-7.70 (m, 1H), 7.69-7.66 (m, 2H), 7.62-7.57 (m, 2H), 7.38 (t, J=7.9 Hz, 1H), 6.91 (d, J=7.8 Hz, 1H), 5.08 (s, 2H), 3.08 (s, 3H).

Example 117: Synthesis of 6-(((2-Hydroxy-2-methylpropyl)amino)methyl)-2-(2'-(4-methyl-4H-1,2,4-triazol-3-yl)-[1,1'-biphenyl]-3-yl)-4-(trifluoromethyl)isoindolin-1-one (AZ-2)

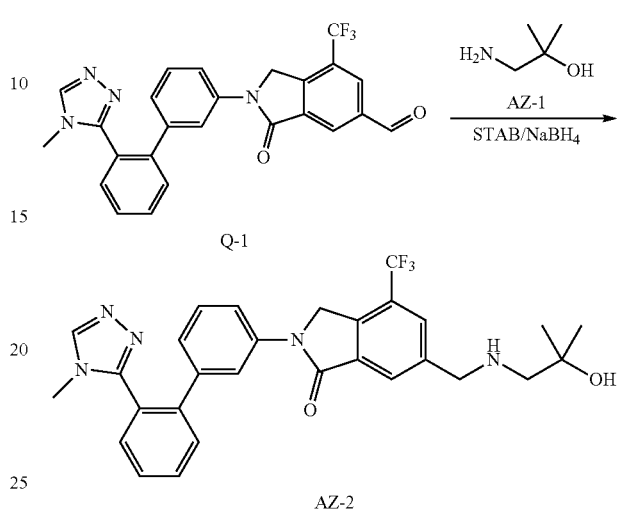

NaBH(OAc)₃ (82 mg, 6.0 Eq, 0.39 mmol) was added to a stirred solution of intermediate Q-1 (30 mg, 99% Wt, 1 Eq, 64 μmol), 1-amino-2-methylpropan-2-ol (AZ-1) (6.9 mg, 1.2 Eq, 77 μmol) and DIPEA (25 mg, 34 μL, 3 Eq, 0.19 mmol) in DCM (5 mL) and stirred at rt overnight. NaBH₄ (7.3 mg, 3 Eq, 0.19 mmol) was added and the reaction mixtures stirred at rt overnight. The reaction mixture was diluted with DCM (5 mL) and washed with sat. aq. sol. of NaHCO₃ (6 mL). The organic layer was separated, dried (phase separator), and concentrated in vacuo. The crude product was purified by chromatography on RP Flash C18 (12 g cartridge, 25-55% MeCN/10 mM ammonium bicarbonate) to afford the title compound (AZ-2) (10 mg, 18 μmol, 28%, 97% Purity) as a white solid. m/z 536.1 (M+H)⁺ (ES+). ¹H NMR (400 MHz, DMSO-d6) δ 8.39 (s, 1H), 8.04 (s, 1H), 8.02-7.96 (m, 2H), 7.75-7.65 (m, 3H), 7.62-7.55 (m, 2H), 7.37 (t, J=8.0 Hz, 1H), 6.91 (dt, J=7.7, 1.2 Hz, 1H), 5.08 (s, 2H), 4.23 (s, 1H), 3.93 (s, 2H), 3.08 (s, 3H), 2.36 (s, 2H), 1.11 (s, 6H). One exchangeable proton not observed.

Example 118: Synthesis of 2-(6-(Ethylamino)-4-(2-(4-methyl-4H-1,2,4-triazol-3-yl)phenyl)pyridin-2-yl)-6-((piperidin-4-yloxy)methyl)-4-(trifluoromethyl)isoindolin-1-one, HCl (BA-4)

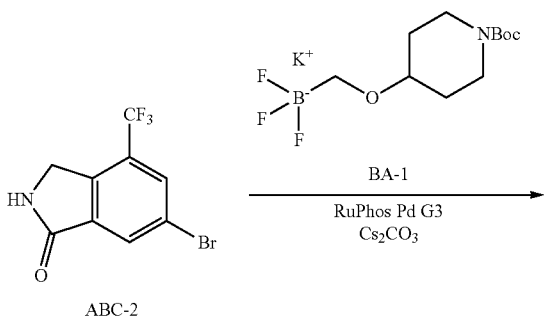

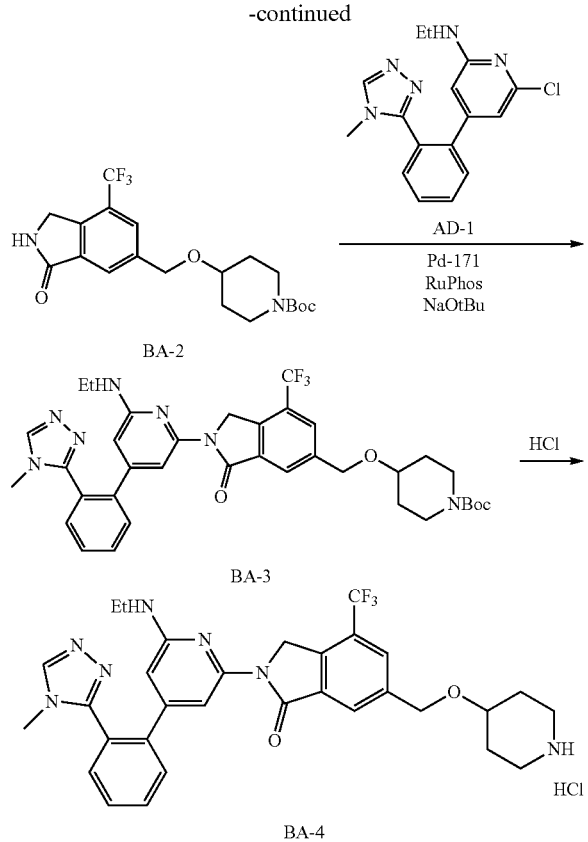

Step 1: Synthesis of tert-Butyl 4-((3-oxo-7-(trifluoromethyl)isoindolin-5-yl)methoxy)piperidine-1-carboxylate (BA-2)

Cs$_2$CO$_3$ (0.26 g, 4.5 Eq, 0.82 mmol) in water (0.4 mL) was added to intermediate ABC-2 (54 mg, 95% Wt, 1 Eq, 184 μmol), potassium (((1-(tert-butoxycarbonyl)piperidin-4-yl)oxy)methyl)trifluoroborate (BA-1) (88 mg, 1.5 Eq, 0.28 mmol) and RuPhos Pd G3 (15.4 mg, 0.1 Eq, 18.4 μmol) in toluene (3 mL). The reaction mixture was sparged with nitrogen for 1 min. and stirred at 100° C. for 30 min (microwave). The reaction mixture was filtered through a Celite plug washing with MeOH (10 mL). The filtrate was evaporated under reduced pressure and the crude product was purified by chromatography on RP Flash C18 (24 g cartridge, 0-100% MeCN/10 mM ammonium bicarbonate) to afford the sub-title compound (BA-2) (14 mg, 33 μmol, 18%, 99% Purity) as a colourless gum. m/z 359.2 (M-tBu+H)$^+$ (ES+).

Step 2: Synthesis of tert-Butyl 4-((2-(6-(ethylamino)-4-(2-(4-methyl-4H-1,2,4-triazol-3-yl)phenyl)pyridin-2-yl)-3-oxo-7-(trifluoromethyl)isoindolin-5-yl)methoxy)piperidine-1-carboxylate (BA-3)

Pd-171 (RuPhos Pd(crotyl)Cl) (2.1 mg, 0.10 Eq, 3.2 μmol) and RuPhos (1.5 mg, 0.10 Eq, 3.2 μmol) were added to a mixture of NaOtBu (3.0 mg, 1 Eq, 32 μmol), intermediate AD-1 (10 mg, 99% Wt, 1 Eq, 32 μmol and the product from step 1 above (BA-2) (14 mg, 99% Wt, 1.05 Eq, 33 μmol) in 1,4-dioxane (1.2 mL) and NMP (0.3 mL). The reaction mixture was sparged with nitrogen for 2 min and then stirred at 120° C. for 3 h (microwave). Additional RuPhos (1.5 mg, 0.10 Eq, 3.2 μmol) and Pd-171 (RuPhos Pd(crotyl)Cl) (2.1 mg, 0.10 Eq, 3.2 μmol) were added to the reaction mixture which was sparged with nitrogen for 2 min and then stirred at 120° C. for a further 1 h (microwave). The reaction mixture was filtered and concentrated in vacuo. The crude product was purified by preparative HPLC (Waters, Basic (0.3% ammonia), Basic, Waters XBridge BEH C18 ODB, 5 μm, 30×100 mm column, 0-100% MeCN in water) to afford the sub-title compound (BA-3) (10 mg, 14 μmol, 44%, 97% Purity) as a colourless solid. m/z 692.2 (M+H)$^+$ (ES+). $^1$H NMR (400 MHz, DMSO-d6) δ 8.46 (s, 1H), 8.00 (s, 1H), 7.95 (s, 1H), 7.75-7.67 (m, 1H), 7.66-7.53 (m, 3H), 7.49 (d, J=1.2 Hz, 1H), 6.69 (t, J=5.4 Hz, 1H), 5.93 (d, J=1.3 Hz, 1H), 5.17 (s, 2H), 4.73 (s, 2H), 3.71-3.58 (m, 2H), 3.33 (s, 3H), 3.23-3.13 (m, 2H), 3.07-3.03 (m, 3H), 1.90-1.83 (m, 2H), 1.45 (ddd, J=13.0, 8.7, 4.1 Hz, 2H), 1.39 (s, 9H), 1.13 (t, J=7.2 Hz, 3H).

Step 3: Synthesis of 2-(6-(Ethylamino)-4-(2-(4-methyl-4H-1,2,4-triazol-3-yl)phenyl)pyridin-2-yl)-6-((piperidin-4-yloxy)methyl)-4-(trifluoromethyl)isoindolin-1-one, HCl (BA-4)

HCl (4 M in 1,4-dioxane) (13 mg, 88 μL, 4 molar, 25 Eq, 0.35 mmol) was added to the product from step 2 above (BA-3) (10 mg, 97% Wt, 1 Eq, 14 μmol) in 1,4-dioxane (1 mL) and the mixture stirred at rt overnight. The reaction mixture was concentrated in vacuo to afford the title compound (BA-4) (9.0 mg, 13 μmol, 92%, 90% Purity) as a pale yellow glass. m/z 592.2 (M+H)$^+$ (ES+). $^1$H NMR (400 MHz, Methanol-d4) δ 9.37 (s, 1H), 8.16 (s, 1H), 8.05 (s, 1H), 7.99-7.92 (m, 1H), 7.91-7.87 (m, 1H), 7.84-7.81 (m, 1H), 7.05 (s, 1H), 6.43 (s, 1H), 5.26 (s, 2H), 4.83 (s, 2H), 3.96-3.88 (m, 1H), 3.80-3.75 (m, 1H), 3.73 (s, 3H), 3.71-3.67 (m, 1H), 3.65-3.58 (m, 1H), 3.49-3.36 (m, 4H), 3.26-3.15 (m, 2H), 2.22-2.11 (m, 2H), 2.09-1.96 (m, 2H), 1.34 (t, J=7.2 Hz, 3H).

Example 119: Synthesis of tert-Butyl 4-((2-(2'-(4-methyl-4H-1,2,4-triazol-3-yl)-[1,1'-biphenyl]-3-yl)-3-oxo-7-(trifluoromethyl)isoindolin-5-yl)methoxy)piperidine-1-carboxylate (BB-1)

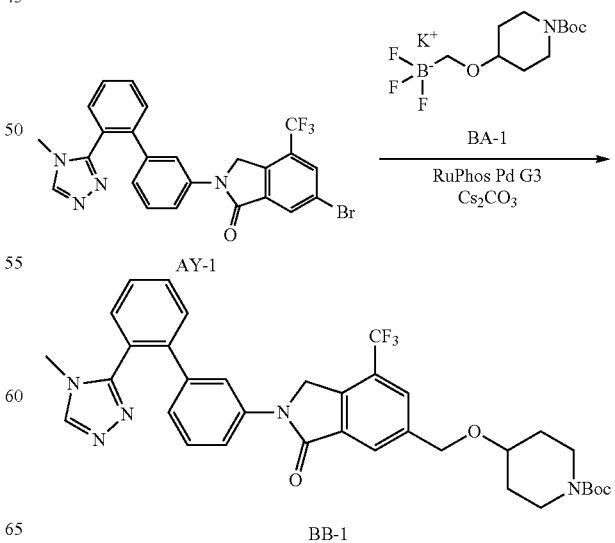

Cs₂CO₃ (85 mg, 4.5 Eq, 0.26 mmol) in water (0.2 mL) was added to compound (AY-1) (30 mg, 99% Wt, 1 Eq, 58 µmol), potassium (((1-(tert-butoxycarbonyl)piperidin-4-yl)oxy)methyl)trifluoroborate (BA-1) (28 mg, 1.5 Eq, 87 µmol) and RuPhos Pd G3 (4.8 mg, 0.1 Eq, 5.8 µmol) in toluene (1.5 mL). The reaction mixture was sparged with nitrogen for 1 min. and then stirred at 100° C. for 2 h (microwave). Additional RuPhos Pd G3 (4.8 mg, 0.1 Eq, 5.8 µmol) was added and stirred at 120° C. for 2 h (microwave). The reaction mixture was dissolved with EtOAc (10 mL) and sat. aq. sol. of NaHCO₃ (10 mL) added. The organic layer was separated and aqueous extracted with EtOAc (2×10 mL). The organic layers were combined, dried (MgSO₄), filtered and evaporated. The crude product was purified by chromatography on RP Flash C18 (12 g cartridge, 10-60% MeCN/10 mM ammonium bicarbonate) followed by preparative HPLC (Waters, Basic (0.3% ammonia), Basic, Waters XBridge BEH C18 ODB, 5 µm, 30×100 mm column, 0-100% MeCN in water) to afford the title compound (BB-1) (5 mg, 8 µmol, 10%, 99% Purity) as a tan solid. m/z 648.3 (M+H)⁺ (ES+). ¹H NMR (400 MHz, DMSO-d6) δ 8.39 (s, 1H), 8.02 (s, 1H), 8.02-7.98 (m, 1H), 7.96 (s, 1H), 7.72 (ddd, J=8.4, 5.6, 3.0 Hz, 1H), 7.68 (dd, J=4.8, 2.6 Hz, 2H), 7.61-7.57 (m, 2H), 7.38 (t, J=8.0 Hz, 1H), 6.91 (dt, J=7.7, 1.2 Hz, 1H), 5.10 (s, 2H), 4.74 (s, 2H), 3.64 (tt, J=8.4, 4.6 Hz, 3H), 3.08 (s, 3H), 3.05 (s, 2H), 1.90-1.82 (m, 2H), 1.45 (ddd, J=12.9, 8.6, 4.0 Hz, 2H), 1.40 (s, 9H).

Example 120: Synthesis of 2-(2'-(4-Methyl-4H-1,2,4-triazol-3-yl)-[1,1'-biphenyl]-3-yl)-6-(((1-methylpiperidin-4-yl)oxy)methyl)-4-(trifluoromethyl)isoindolin-1-one (BC-4)

Step 2: Synthesis of 2-(2'-(4-Methyl-4H-1,2,4-triazol-3-yl)-[1,1'-biphenyl]-3-yl)-6-(((1-methylpiperidin-4-yl)oxy)methyl)-4-(trifluoromethyl)isoindolin-1-one (BC-4)

Cs₂CO₃ (0.14 g, 4.5 Eq, 0.43 mmol) in water (0.2 mL) was added to compound (AY-1) (50 mg, 99% Wt, 1 Eq, 96 µmol), the product from step 1 above (BC-3) (34 mg, 1.5 Eq, 0.14 mmol) and RuPhos Pd G3 (8.1 mg, 0.1 Eq, 9.6 µmol) in toluene (1.5 mL). The reaction mixture was sparged with nitrogen for 1 min. and stirred at 100° C. for 2 h (microwave). The reaction mixture was dissolved with EtOAc (10 mL) and washed with sat. aq. sol. of NaHCO₃ (10 mL). The organic layer was separated and the aqueous extracted with EtOAc (2×10 mL). The organics were combined, dried (MgSO₄), filtered and evaporated. The crude was purified by preparative HPLC (Waters, Basic (0.3% ammonia), Basic, Waters X-Select CSH C18 ODB, 5 µm, 30×100 mm,

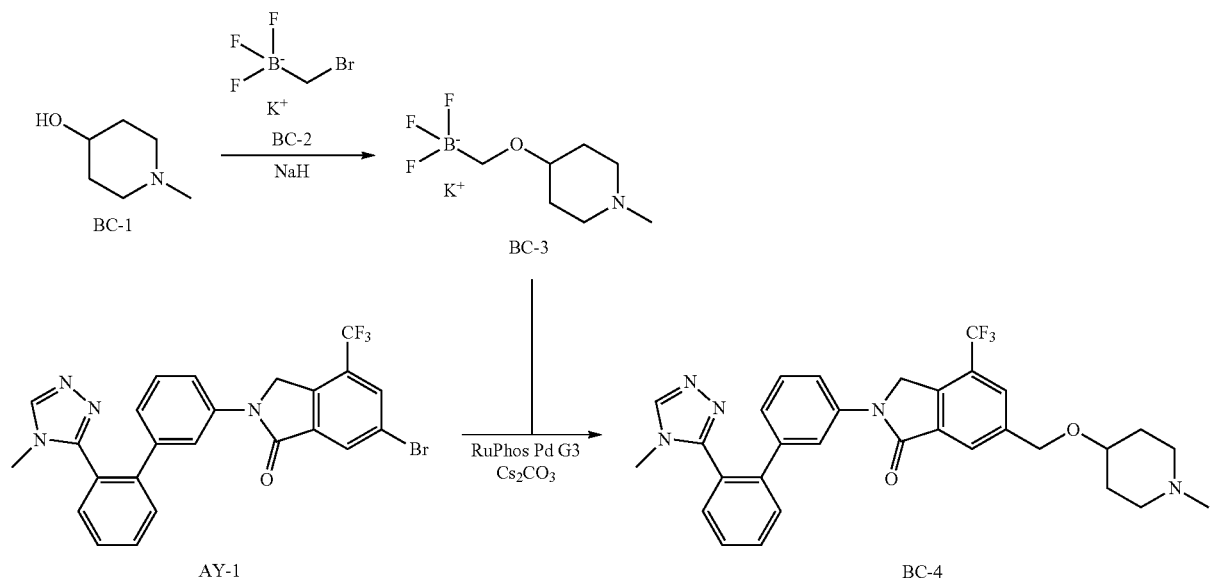

Step 1: Synthesis of Potassium trifluoro(((1-methylpiperidin-4-yl)oxy)methyl)borate (BC-3)

To a stirred solution of NaH (174 mg, 60% Wt, 3 Eq, 4.34 mmol) in THF (3 mL) was added 1-methylpiperidin-4-ol (BC-1) (500 mg, 3 Eq, 4.34 mmol) at 0° C. The mixture was stirred at 0° C. for 15 min and at rt for 30 min. Potassium (bromomethyl)trifluoroborate (BC-2) (291 mg, 1 Eq, 1.45 mmol) was then added at 0° C. and the mixture stirred at rt for 20 h. The reaction mixture was then quenched with 4.5 M potassium bifluoride (1.02 g, 2.89 mL, 4.5 molar, 9 Eq, 13.0 mmol) and the solution was stirred for 30 min. The mixture was evaporated under reduced pressure and dried in vacuo. The crude product was suspended in Et₂O (10 mL) and filtered to remove organic impurities. The resulting solid was suspended in acetone (10 mL) and filtered to remove further inorganic impurities. The organic phase was then evaporated to afford the sub-title compound (BC-3) (140 mg, 0.12 mmol, 8.2%, 20% Purity) as a yellow gum, which was used crude in the next step without further purification or analysis.

0-100% MeCN in water to afford the title compound (BC-4) (4 mg, 7 µmol, 7%, 99% Purity). m/z 562.3 (M+H)⁺ (ES+). ¹H NMR (400 MHz, DMSO-d6) δ 8.39 (s, 1H), 8.03-7.97 (m, 2H), 7.95 (s, 1H), 7.72 (ddd, J=8.3, 5.5, 2.9 Hz, 1H), 7.68 (dd, J=4.5, 2.5 Hz, 2H), 7.61-7.57 (m, 2H), 7.38 (t, J=8.0 Hz, 1H), 6.91 (d, J=8.0 Hz, 1H), 5.10 (s, 2H), 4.71 (s, 2H), 3.08 (s, 3H), 2.64-2.56 (m, 2H), 2.15 (s, 3H), 2.04 (t, J=10.7 Hz, 2H), 1.89 (d, J=12.7 Hz, 2H), 1.55 (d, J=9.8 Hz, 2H). One proton masked by water peak.

Example 121: Synthesis of 2-(2'-(4-Methyl-4H-1,2,4-triazol-3-yl)-[1,1'-biphenyl]-3-yl)-6-(((tetrahydro-2H-pyran-4-yl)oxy)methyl)-4-(trifluoromethyl)isoindolin-1-one (BD-3)

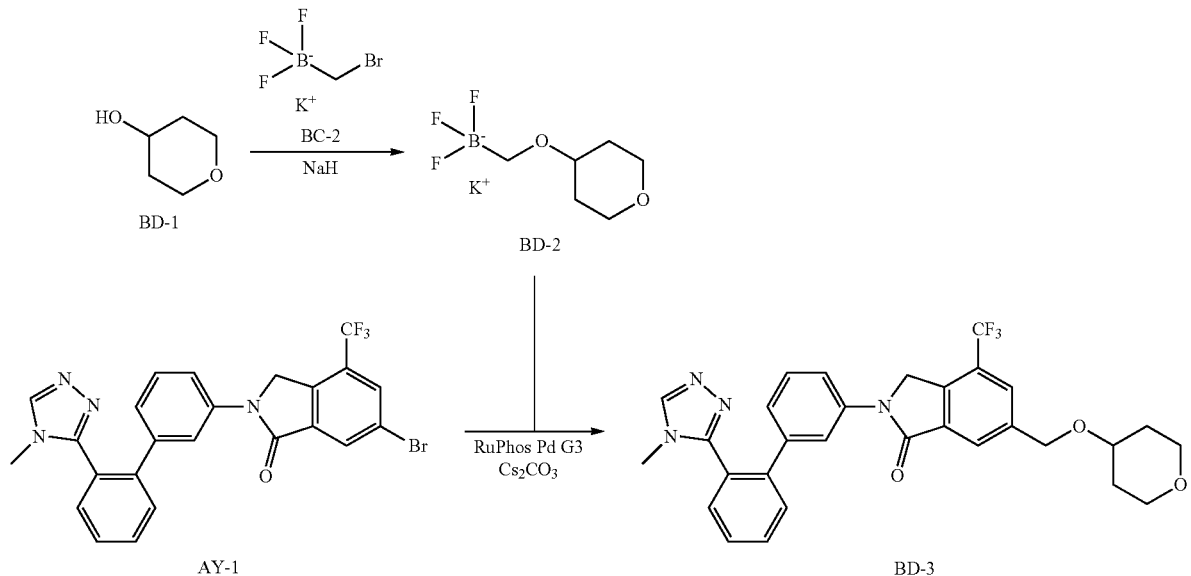

Step 1: Synthesis of Potassium trifluoro(((tetrahydro-2H-pyran-4-yl)oxy)methyl)borate (BD-2)

To a stirred solution of NaH (196 mg, 60% Wt, 3 Eq, 4.90 mmol) in THF (3 mL) was added tetrahydro-2H-pyran-4-ol (BD-1) (500 mg, 3 Eq, 4.90 mmol) at 0° C. The mixture was stirred at 0° C. for 15 min and at rt for 30 min. Potassium (bromomethyl)trifluoroborate (BC-2) (328 mg, 1 Eq, 1.63 mmol) was then added at 0° C. and the mixture stirred at rt for 20 h. The reaction mixture was quenched with 4.5 M potassium bifluoride (1.15 g, 3.26 mL, 4.5 molar, 9 Eq, 14.7 mmol) and the solution was stirred for 30 min. The mixture was evaporated under reduced pressure and dried in vacuo. The crude product was suspended in Et$_2$O (10 mL) and filtered to remove organic impurities. The resulting solid was suspended in acetone (10 mL) and filtered to remove further inorganic impurities. The organic phase was then evaporated to afford the sub-title compound (BD-2) (45 mg, 0.20 mmol, 12%).

Step 2: Synthesis of 2-(2'-(4-Methyl-4H-1,2,4-triazol-3-yl)-[1,1'-biphenyl]-3-yl)-6-(((tetrahydro-2H-pyran-4-yl)oxy)methyl)-4-(trifluoromethyl)isoindolin-1-one (BD-3)

Cs$_2$CO$_3$ (0.14 g, 4.5 Eq, 0.43 mmol) in water (0.2 mL) was added to compound (AY-1) (50 mg, 99% Wt, 1 Eq, 96 μmol), the product from step 1 above (BD-2) (28 mg, 1.3 Eq, 0.13 mmol) and RuPhos Pd G3 (8.1 mg, 0.1 Eq, 9.6 μmol) in toluene (1.5 mL). The reaction mixture was sparged with nitrogen for 1 min. and then stirred at 100° C. for 2 h (microwave). The reaction mixture was dissolved with EtOAc (10 mL) and sat. aq. sol. of NaHCO$_3$ (10 mL). The organic layer was separated and the aqueous extracted with EtOAc (2×10 mL). The organic extracts were combined, dried (MgSO$_4$), filtered and evaporated. The crude purified preparative HPLC (Waters, Basic (0.1% ammonia), Basic, Waters XBridge BEH C18 ODB, 5 μm, 30×100 mm column, 0-100% MeCN in water) to afford the title compound (BD-3) (5 mg, 9 μmol, 9%, 99% Purity) as a white solid. m/z 549.2 (M+H)$^+$ (ES+). $^1$H NMR (400 MHz, DMSO-d6) δ 8.39 (s, 1H), 8.03 (s, 1H), 7.99 (dd, J=7.9, 2.2 Hz, 1H), 7.97 (s, 1H), 7.74-7.69 (m, 1H), 7.69-7.66 (m, 2H), 7.61-7.56 (m, 2H), 7.38 (t, J=8.0 Hz, 1H), 6.93-6.88 (m, 1H), 5.10 (s, 2H), 4.75 (s, 2H), 3.83 (dt, J=11.7, 4.2 Hz, 2H), 3.65 (tt, J=8.8, 4.0 Hz, 1H), 3.36 (ddd, J=11.9, 9.9, 2.7 Hz, 2H), 3.08 (s, 3H), 1.94-1.87 (m, 2H), 1.50 (dtd, J=13.3, 9.5, 4.1 Hz, 2H).

Example 122: Synthesis of 3'-(6-((((1R,2S)-2-Hydroxycyclopentyl)amino)methyl)-1-oxo-4-(trifluoromethyl)isoindolin-2-yl)-2-(4-methyl-4H-1,2,4-triazol-3-yl)-[1,1'-biphenyl]-4-carbonitrile (BE-3)

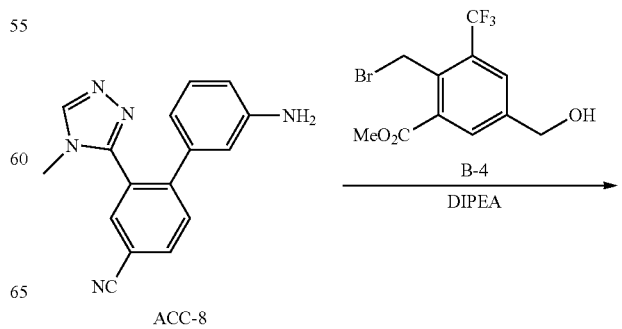

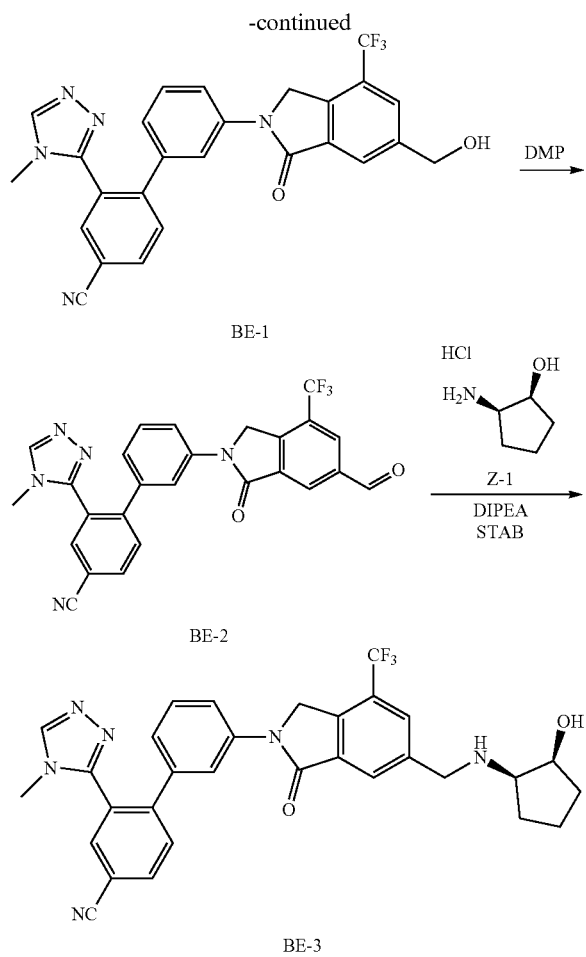

BE-1

BE-2

BE-3

Step 1: Synthesis of 3'-(6-(Hydroxymethyl)-1-oxo-4-(trifluoromethyl)isoindolin-2-yl)-2-(4-methyl-4H-1,2,4-triazol-3-yl)-[1,1'-biphenyl]-4-carbonitrile (BE-1)

DIPEA (105 mg, 141 µL, 1.5 Eq, 908 µmol) was added to a solution of intermediate ACC-8 (200 mg, 1.2 Eq, 726 µmol) and intermediate B-4 (198 mg, 1 Eq, 605 µmol) in EtOH (20 mL) and stirred at 60° C. for 16 h. Additional intermediate B-4 (99.0 mg, 0.5 Eq, 303 µmol) was added and the reaction stirred at 60° C. for 16 h. Volatiles were evaporated and the crude product was purified by chromatography on RP Flash C18 (24 g cartridge, 25-55% MeCN/10 mM ammonium bicarbonate) to afford the sub-title compound (BE-1) (257 mg, 0.25 mmol, 42%, 48% Purity) as a white solid. m/z 490.2 (M+H)⁺ (ES+).

Step 2: Synthesis of 3'-(6-Formyl-1-oxo-4-(trifluoromethyl)isoindolin-2-yl)-2-(4-methyl-4H-1,2,4-triazol-3-yl)-[1,1'-biphenyl]-4-carbonitrile (BE-2)

The product from step 1 above (BE-1) (257 mg, 1 Eq, 525 µmol) and Dess-Martin periodinane (334 mg, 1.5 Eq, 788 µmol) were stirred in DCM (25 mL) at 40° C. for 16 h. The reaction mixture was diluted with DCM (10 mL) and washed with sat. aq. NaHCO₃ (10 mL). Organics were separated, dried (MgSO₄), filtered and evaporated to afford the crude product. The crude product was purified by preparative HPLC (Waters, Basic (0.3% ammonia), Waters XBridge BEH C18 ODB 1, 5 µm, 30×100 mm column, 20-100% MeCN in water) to afford the sub-title compound (BE-2) (11 mg, 22 µmol, 4.3%, 99% Purity) as a white solid. m/z 488.1 (M+H)⁺ (ES+).

Step 3: Synthesis of 3'-(6-((((1R,2S)-2-Hydroxycyclopentyl)amino)methyl)-1-oxo-4-(trifluoromethyl)isoindolin-2-yl)-2-(4-methyl-4H-1,2,4-triazol-3-yl)-[1,1'-biphenyl]-4-carbonitrile (BE-3)

NaBH(OAc)₃ (34 mg, 6.0 Eq, 0.16 mmol) was added to a stirred solution of the product from step 2 above (BE-2) (13 mg, 99% Wt, 1 Eq, 26 µmol), (1S,2R)-2-aminocyclopentan-1-ol, HCl (Z-1) (11 mg, 3 Eq, 79 µmol) and DIPEA (17 mg, 23 µL, 5 Eq, 0.13 mmol) in DCM (2 mL) and left at rt overnight. The reaction mixture was diluted with DCM (5 mL) and washed with sat. at. NaHCO₃ (6 mL). The organic layer was separated and evaporated to dryness affording the crude product. The crude product was purified by preparative HPLC (Waters, Basic (0.1% ammonia), Waters XBridge BEH C18 ODB 1, 5 µm, 30×100 mm column, 25-100% MeCN in water) to afford the title compound (BE-3) (4 mg, 7 µmol, 30%, 99% Purity) as a white solid. m/z 573.3 (M+H)⁺ (ES+). ¹H NMR (400 MHz, DMSO-d6) δ 8.46 (s, 1H), 8.19 (dd, J=8.1, 1.8 Hz, 1H), 8.12 (d, J=1.8 Hz, 1H), 8.07-7.99 (m, 3H), 7.89 (d, J=8.0 Hz, 1H), 7.72 (t, J=2.0 Hz, 1H), 7.41 (t, J=8.0 Hz, 1H), 6.93 (d, J=7.7 Hz, 1H), 5.09 (s, 2H), 4.40 (d, J=3.5 Hz, 1H), 4.01-3.82 (m, 3H), 3.16 (s, 3H), 2.80-2.70 (m, 1H), 2.34-2.24 (m, 1H), 1.75-1.54 (m, 4H), 1.47-1.34 (m, 2H).

Example 123: Synthesis of 6-(Hydroxymethyl)-2-{6-[6-(hydroxymethyl)-1-oxo-4-(trifluoromethyl)-3H-isoindol-2-yl]-4-[2-(4-methyl-1,2,4-triazol-3-yl)phenyl]pyridin-2-yl}-4-(trifluoromethyl)-3H-isoindol-1-one (ACX-2)

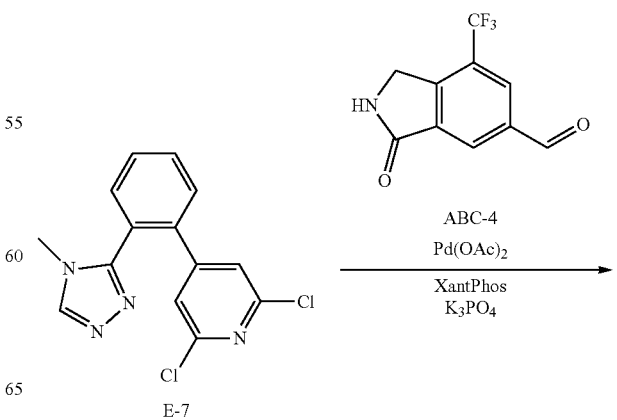

E-7

ABC-4

Pd(OAc)₂
XantPhos
K₃PO₄

-continued

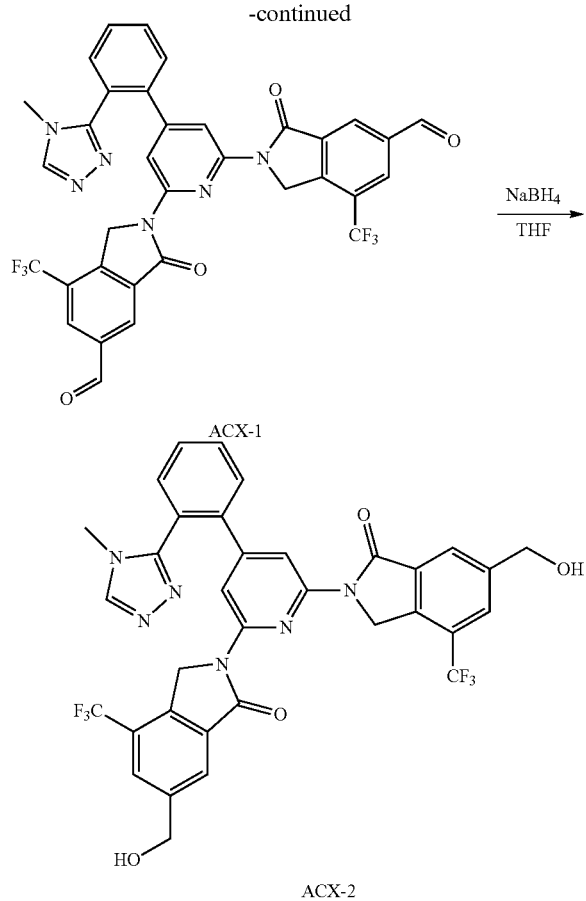

Step 1: Synthesis of 2-{6-[6-Formyl-1-oxo-4-(trifluoromethyl)-3H-isoindol-2-yl]-4-[2-(4-methyl-1,2,4-triazol-3-yl)phenyl]pyridin-2-yl}-3-oxo-7-(trifluoromethyl)-1H-isoindole-5-carbaldehyde (ACX-1)

To a stirred mixture of intermediate (E-7) (100 mg, 1.0 eq, 328 μmol) and intermediate (ABC-4) (113 mg, 1.5 eq, 492 μmol) in 1,4-dioxane (5 mL) was added potassium phosphate and Pd(OAc)$_2$ (7.4 mg, 0.1 eq, 33 μmol) and XantPhos (19 mg, 0.1 eq, 33 μmol) at rt under nitrogen atmosphere. The resulting mixture was stirred for 3 h at 100° C. under nitrogen atmosphere. The resulting mixture was extracted with EtOAc (3×30 mL). The combined organic layers were washed with water (2×30 mL), dried (Na$_2$SO$_4$). After filtration, the filtrate was concentrated in vacuo. The residue was purified by Prep-TLC with DCM/MeOH (10/1) to afford the sub-title compound (ACX-1) (50 mg, 65 μmol, 22%, 90% Purity) as a yellow solid. m/z 691.1 (M+H)$^+$ (ES+).

Step 2: Synthesis of 6-(Hydroxymethyl)-2-{6-[6-(hydroxymethyl)-1-oxo-4-(trifluoromethyl)-3H-isoindol-2-yl]-4-[2-(4-methyl-1,2,4-triazol-3-yl)phenyl]pyridin-2-yl}-4-(trifluoromethyl)-3H-isoindol-1-one (ACX-2)

To a stirred solution of the product from step 1 above (ACX-1) (30 mg, 1 eq, 43 μmol) in THF (5 mL) was added NaBH$_4$ (3.3 mg, 2 eq, 86 μmol) at rt under nitrogen atmosphere. The resulting mixture was stirred for 1 h at rt under nitrogen atmosphere. The reaction was quenched with MeOH (1 mL) at rt. The resulting mixture was concentrated in vacuo. The crude product (25 mg) was purified by Prep-HPLC with the following conditions (Column: XBridge Prep OBD C18 Column, 30*150 mm, 5 μm; Mobile Phase A: Water (0.1% NH$_4$HCO$_3$), Mobile Phase B: MeCN; Flow rate: 60 mL/min; Gradient: 30% B to 55% B in 10 min; Wave Length: 254/220 nm; RT: 9.07) to afford the title compound (ACX-2) (3.1 mg, 4.4 μmol, 9.3%, 91% Purity) as a white solid. m/z 695.0 (M+H)$^+$ (ES+). $^1$H NMR (400 MHz, DMSO-d6) δ 8.50 (s, 1H), 8.05 (d, J=1.7 Hz, 4H), 7.99 (s, 2H), 7.81-7.76 (m, 1H), 7.75-7.66 (m, 3H), 5.61 (s, 2H), 5.29 (s, 4H), 4.72 (s, 4H), 3.58 (s, 3H).

Example 124: Synthesis of 2-[6-(Ethylamino)-4-[2-(4-methyl-1,2,4-triazol-3-yl)phenyl]pyridin-2-yl]-6-{[(3S)-3-methylpiperidin-1-yl]methyl}-3H-isoindol-1-one (ACY-4)

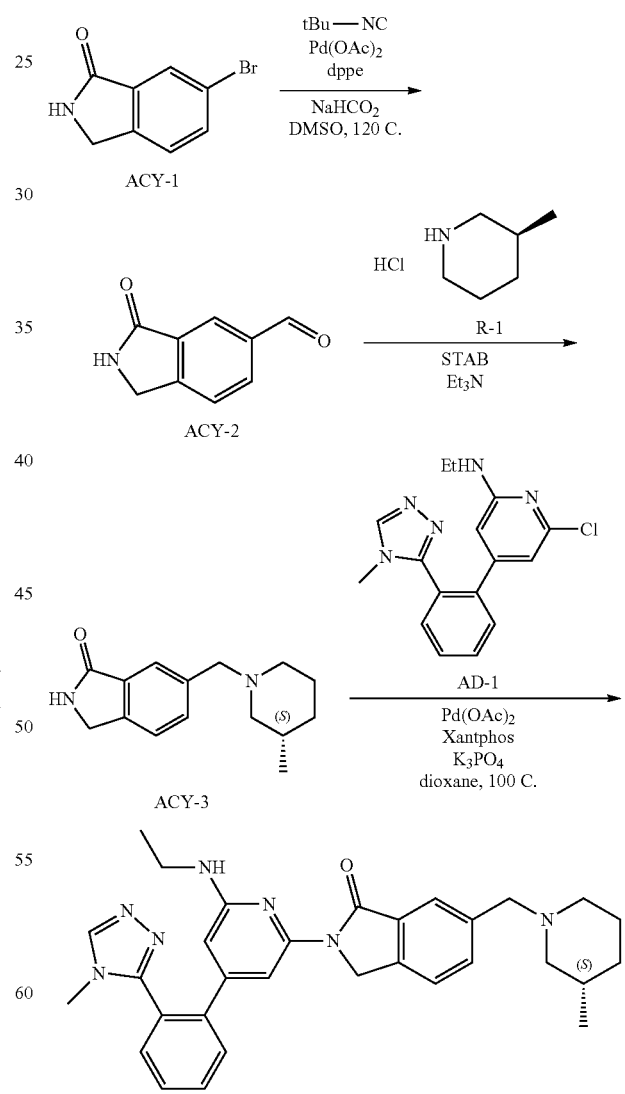

Step 1: Synthesis of 3-Oxoisoindoline-5-carbaldehyde (ACY-2)

Into a 50-mL round-bottom flask purged and maintained with an inert atmosphere of nitrogen, was placed 6-bromo-2,3-dihydroisoindol-1-one (ACY-1) (424 mg, 1 eq, 2.00 mmol), tert-butyl isocyanide (199 mg, 1.2 eq, 2.40 mmol) and sodium formate (272 mg, 2 eq, 4.00 mmol) in DMSO (20 mL), then Pd(OAc)$_2$ (45 mg, 0.1 eq, 200 μmol) and DPPE (159 mg, 0.2 eq, 400 μmol) were added at rt under nitrogen atmosphere. The resulting solution was stirred overnight at 120° C. under nitrogen atmosphere. The mixture was cooled to rt and purified by reverse flash column chromatography with the following conditions: Column, C18; mobile phase, water (0.1% NH$_4$HCO$_3$) and MeCN (10% MeCN up to 48% in 15 min); Detector, UV 254/220 nm. The product-containing fractions were combined and concentrated in vacuo. This resulted in the sub-title compound (ACY-2) (150 mg, 0.87 mmol, 47%, 93% Purity) as a yellow solid. m/z 162.0 (M+H)$^+$ (ES+).

Step 2: Synthesis of (S)-6-((3-Methylpiperidin-1-yl)methyl)isoindolin-1-one (ACY-3)

Into a 250-mL round-bottom flask purged and maintained with an inert atmosphere of nitrogen, was placed the product from step 1 above (ACY-2) (150 mg, 1 eq, 931 μmol) and (3S)-3-methylpiperidine (R-1) (185 mg, 2 eq, 1.86 mmol) in DCM (15 mL) at rt, then Et$_3$N (188 mg, 2 eq, 1.86 mmol) was added at rt. To the above mixture was added NaBH(OAc)$_3$ (395 mg, 2 eq, 1.86 mmol) over 4 h at 0° C. The resulting mixture was stirred for additional 2 h at rt. The resulting mixture was diluted with water and extracted with DCM (3×50 mL). The combined organic layers were washed with brine (2×50 mL), dried (Na2SO4). After filtration, the filtrate was concentrated in vacuo. This resulted in the sub-title compound (ACY-3) (90 mg, 295 μmol, 39%, 80% Purity) as a yellow solid. m/z 245.2 (M+H)$^+$ (ES+).

Step 3: Synthesis of (S)-2-(6-(Ethylamino)-4-(2-(4-methyl-4H-1,2,4-triazol-3-yl)phenyl)pyridin-2-yl)-6-((3-methylpiperidin-1-yl)methyl)isoindolin-1-one (ACY-4)

Into a 25-mL round-bottom flask purged and maintained with an inert atmosphere of nitrogen, was placed the product from step 2 above (ACY-3) (45 mg, 1 eq, 184 μmol), intermediate (AD-1) (58 mg, 184 μmol, 1 eq) and K$_3$PO$_4$ (117 mg, 3 eq, 552 μmol) in 1,4-dioxane (3 mL) at rt, then Pd(OAc)$_2$ (8.3 mg, 0.2 eq, 37 μmol) and XantPhos (43 mg, 0.4 eq, 74 μmol) were added at rt under nitrogen atmosphere. The resulting mixture was stirred for additional overnight at 100° C. under nitrogen atmosphere. The resulting mixture was cooled to rt, diluted with water and extracted with DCM (3×20 mL). The combined organic layers were washed with brine (2×20 mL), dried over (Na$_2$SO$_4$). After filtration, the filtrate was concentrated in vacuo. The crude product was purified by Prep-HPLC with the following conditions: Column: SunFire Prep C18 Column, 30*150 mm, 5 μm; Mobile Phase A: Water (0.1% FA), Mobile Phase B: MeCN; Flow rate: 60 mL/min; Gradient: 11% B to 25% B in 10 min; Wave Length: 254/210 nm; RT: 6.32. This resulted in the title compound (ACY-4) (15.3 mg, 28 μmol, 15%, 96% Purity) as a white solid. m/z 522.2 (M+H)$^+$ (ES+). $^1$H NMR (400 MHz, MeOH-d4) δ 8.45 (s, 1H), 7.89 (s, 1H), 7.82-7.63 (m, 4H), 7.68-7.60 (m, 2H), 7.54 (d, J=1.3 Hz, 1H), 6.06 (d, J=1.2 Hz, 1H), 5.11 (s, 2H), 4.10 (s, 2H), 3.44 (s, 3H), 3.34 (s, 1H), 3.32 (s, 1H), 3.26-3.11 (m, 2H), 2.53 (t, J=11.9 Hz, 1H), 2.25 (t, J=12.1 Hz, 1H), 1.83 (s, 3H), 1.71 (d, J=12.9 Hz, 1H), 1.23 (t, J=7.2 Hz, 3H), 1.09 (d, J=11.2 Hz, 1H), 0.95 (d, J=6.4 Hz, 3H).

Example 125: Synthesis of 4-{2-[(1-{2-[6-(Ethylamino)-4-[2-methyl-4-(4-methyl-1,2,4-triazol-3-yl)pyrazol-3-yl]pyridin-2-yl]-3-oxo-7-(trifluoromethyl)-1H-isoindol-5-yl]-5,8,11-trioxa-2-azatridecan-13-yl) carbamoyl]ethyl}-2,2-difluoro-12-(1H-pyrrol-2-yl)-11lambda5,3-diaza-2-boratricyclo [7.3.0.0^{3,7}] dodeca-1(12),4,6,8,10-pentaen-1-ylium-2-uide) (ACZ-5)

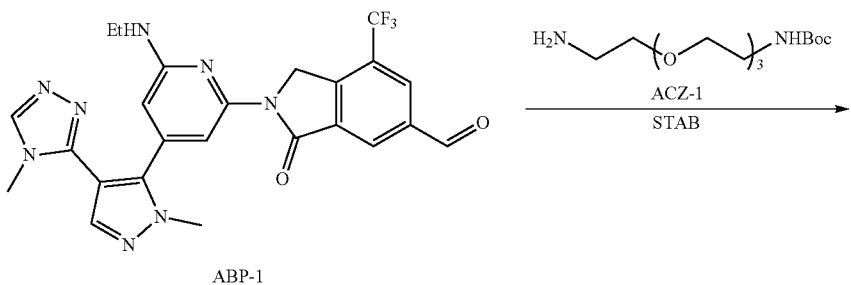

ABP-1

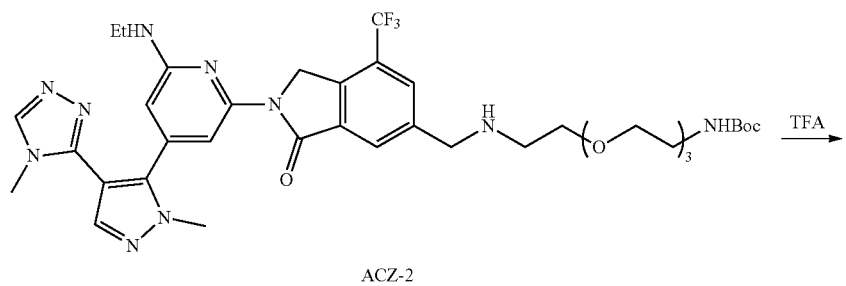

ACZ-2

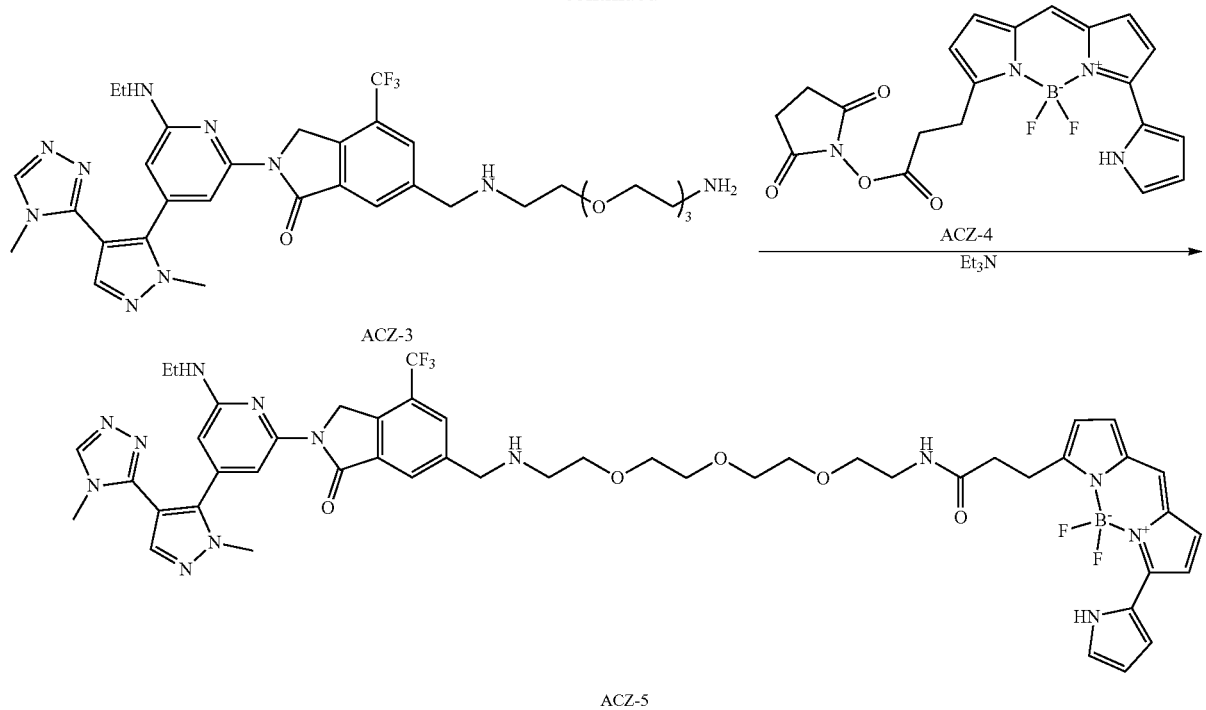

Step 1: Synthesis of tert-Butyl N-(1-{2-[6-(ethyl-amino)-4-[2-methyl-4-(4-methyl-1,2,4-triazol-3-yl) pyrazol-3-yl]pyridin-2-yl]-3-oxo-7-(trifluorom-ethyl)-1H-isoindol-5-yl}-5,8,11-trioxa-2-azatride-can-13-yl) carbamate (ACZ-2)

To a stirred solution of intermediate (ABP-1) (70 mg, 1 eq, 137 μmol) and tert-butyl N-(2-{2-[2-(2-aminoethoxy) ethoxy]ethoxy}ethyl)carbamate (ACZ-1) (52 mg, 1.3 eq, 178 μmol) in DCM (2 mL) was added NaBH(OAc)$_3$ (87 mg, 3 eq, 411 μmol) at rt. The resulting mixture was stirred for 3 h at 40° C. The resulting mixture was concentrated in vacuo. The residue was purified by Prep-TLC with DCM/MeOH (8/1) to afford the sub-title compound (ACZ-2) (93 mg, 123 μmol, 85%, 92% Purity) as a yellow solid. m/z 699.3 (M+H)$^+$ (ES+).

Step 2: Synthesis of 6-(13-Amino-5,8,11-trioxa-2-azatridecan-1-yl)-2-[6-(ethylamino)-4-[2-methyl-4-(4-methyl-1,2,4-triazol-3-yl) pyrazol-3-yl] pyridin-2-yl]-4-(trifluoromethyl)-3H-isoindol-1-one) (ACZ-3)

To a stirred solution of the product from step 1 above (ACZ-2) (88 mg, 1 eq, 112 μmol) in DCM (1 mL) was added TFA (0.3 mL) dropwise at rt. The resulting mixture was stirred for 2 h at rt. The resulting mixture was concentrated in vacuo. The crude product was purified by Prep-HPLC with the following conditions (Column: Sunfire prep C18 column, 30*150 mm, 5 μm; Mobile Phase A: water (0.1% FA), Mobile Phase B: MeCN; Flow rate: 60 mL/min; Gradient: 2% B to 17% B in 10 min; Wave Length: 254/220 nm; RT: 9.67) to afford the sub-title compound (ACZ-3) (65 mg, 103 μmol, 86%, 95% Purity) as a light yellow solid. m/z 599.3 (M+H)$^+$ (ES+)

Step 3: Synthesis of 4-{2-[(1-{2-[6-(Ethylamino)-4-[2-methyl-4-(4-methyl-1,2,4-triazol-3-yl) pyrazol-3-yl] pyridin-2-yl]-3-oxo-7-(trifluoromethyl)-1H-isoindol-5-yl}-5,8,11-trioxa-2-azatridecan-13-yl) carbamoyl]ethyl}-2,2-difluoro-12-(1H-pyrrol-2-yl)-11lambda5,3-diaza-2-boratricyclo [7.3.0.0ˆ{3,7}] dodeca-1(12),4,6,8,10-pentaen-1-ylium-2-uide) (ACZ-5)

To a stirred solution of the product from step 2 above (ACZ-3) (13 mg, 1 eq, 22 μmol) and Et$_3$N (6 mg, 3 eq, 57 μmol) in DMF (1 mL) were added 4-{3-[(2,5-dioxopyrroli-din-1-yl)oxy]-3-oxopropyl}-2,2-difluoro-12-(1H-pyrrol-2-yl)-1lambda5,3-diaza-2-boratricyclo[7.3.0.0ˆ{3,7}] dodeca-1(12),4,6,8,10-pentaen-1-ylium-2-uide (ACZ-4) (6.5 mg, 0.8 eq, 15 μmol) at rt. The resulting mixture was stirred for 1 h at rt. The resulting mixture was concentrated in vacuo. The residue was purified by Prep-HPLC with following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 40% B to 50% B in 9 min; Wave Length: 254/220 nm; RT: 8.77) to afford the title compound (ACZ-5) (7.2 mg, 7.2 μmol, 38%, 98% Purity) as a purple solid. m/z 998.4 (M+H)$^+$ (ES+). $^1$H NMR (400 MHz, MeOH-d4) δ 8.49 (d, J=1.0 Hz, 1H), 8.00-7.84 (m, 3H), 7.62 (d, J=1.3 Hz, 1H), 7.19-7.07 (m, 4H), 6.94-6.79 (m, 2H), 6.34-6.15 (m, 3H), 5.14 (s, 2H), 4.02 (d, J=1.1 Hz, 3H), 3.90 (s, 2H), 3.68-3.57 (m, 10H), 3.54 (t, J=5.3 Hz, 2H), 3.50 (d, J=1.0 Hz, 3H), 3.37 (d, J=5.2 Hz, 2H), 3.35 (d, J=6.0 Hz, 2H), 3.22 (t, J=7.8 Hz, 2H), 2.76 (t, J=5.1 Hz, 2H), 2.60 (t, J=7.8 Hz, 2H), 1.25-1.19 (m, 3H).

Example 126: Synthesis of 2-[6-(Ethylamino)-4-[2-methyl-4-(4-methyl-1,2,4-triazol-3-yl)pyrazol-3-yl]pyridin-2-yl]-6-{1[(1-methylpiperidin-4-yl) oxy]methyl}-4-(trifluoromethyl)-3H-isoindol-1-one (ADA-2)

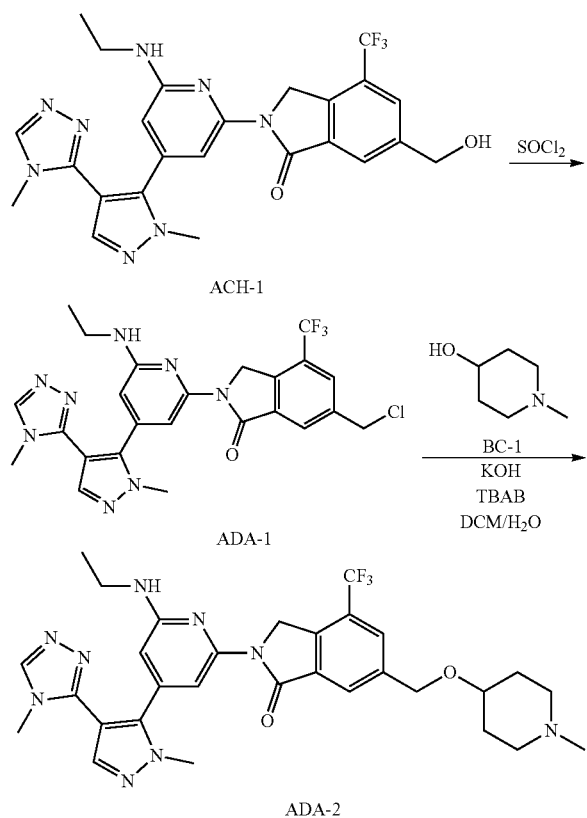

Step 1: Synthesis of 6-(Chloromethyl)-2-[6-(ethylamino)-4-[2-methyl-4-(4-methyl-1,2,4-triazol-3-yl)pyrazol-3-yl]pyridin-2-yl]-4-(trifluoromethyl)-3H-isoindol-1-one (ADA-1)

To a stirred solution of intermediate (ACH-1) (197 mg, 1 eq, 384 µmol) in DCM (39 mL) was added SOCl₂ (137 mg, 3 eq, 1.15 mmol) dropwise at 0° C. under nitrogen atmosphere. The resulting mixture was stirred for 1 h at rt under nitrogen atmosphere. The reaction was quenched with MeOH (5 mL) at 0° C. and concentrated in vacuo. The residue was purified by Prep-TLC with DCM/MeOH (8/1) to afford the sub-title compound (ADA-1) (171 mg, 271 µmol, 84%, 84% Purity) as a yellow solid. m/z 531.2/533.2 (M+H)⁺ (ES+).

Step 2: Synthesis of 2-[6-(Ethylamino)-4-[2-methyl-4-(4-methyl-1,2,4-triazol-3-yl) pyrazol-3-yl]pyridin-2-yl]-6-{[(1-methylpiperidin-4-yl) oxy] methyl}-4-(trifluoromethyl)-3H-isoindol-1-one (ADA-2)

To a stirred solution of the product from step 1 above (ADA-1) (23 mg, 43 µmol, 1 eq) and 1-methylpiperidin-4-ol (BC-1) (25 mg, 5 eq, 215 µmol) in DCM (2 mL) were added TBAB (7 mg, 0.5 eq, 21 µmol) and 1 mL 20% KOH aq. solution at rt. The resulting mixture was stirred slowly for 1 h at rt. The resulting mixture was diluted with water (20 mL), extracted with DCM (3×20 mL) and dried over (Na₂SO₄). After filtration, the filtrate was concentrated in vacuo. The residue was purified by Prep-TLC with DCM/MeOH (6/1) and Prep-HPLC with the following conditions (Column: XBridge Prep OBD C18 Column, 30*150 mm, 5 µm; Mobile Phase A: water (0.1% NH₄HCO₃), Mobile Phase B: MeCN; Flow rate: 60 mL/min; Gradient: 32% B to 42% B in 9 min; Wave Length: 254/220 nm; RT: 8.58) to afford the title compound (ADA-2) (2.3 mg, 4.4 µmol, 8.5%, 97% Purity) as a white solid. m/z 522.2 (M+H)⁺ (ES+). ¹H NMR (400 MHz, MeOH-d4) δ 8.50 (s, 1H), 8.07 (s, 1H), 7.95 (s, 1H), 7.87 (s, 1H), 7.65 (d, J=1.2 Hz, 1H), 6.20 (d, J=1.2 Hz, 1H), 5.26 (s, 2H), 4.75 (s, 2H), 4.04 (s, 3H), 3.59 (s, 1H), 3.51 (s, 3H), 3.41-3.36 (m, 2H), 2.76 (s, 2H), 2.30 (s, 5H), 2.01 (s, 2H), 1.76 (s, 2H), 1.25 (t, J=7.2 Hz, 3H).

Example 127: Synthesis of (rac)-2-[6-(ethylamino)-4-[2-methyl-4-(4-methyl-1,2,4-triazol-3-yl)pyrazol-3-yl]pyridin-2-yl]-6-({[(1R,2S)-2-hydroxycyclopentyl]oxy}methyl)-4-(trifluoromethyl)-3H-isoindol-1-one (ADB-1)

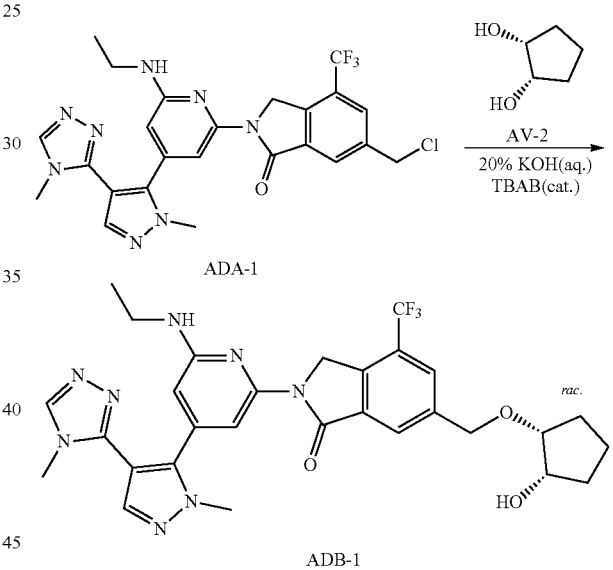

To a stirred solution of intermediate (ADA-1) (88 mg, 1 eq, 166 µmol) and (1R,2S)-cyclopentane-1,2-diol (AV-2) (85 mg, 5 eq, 830 µmol) in DCM (2 mL) was added TBAB (27 mg, 0.5 eq, 83 µmol) and 1 mL 20% KOH aq. at rt. The resulting mixture was stirred slowly for 1 h at rt. The resulting mixture was diluted with water and extracted with DCM (3×30 mL). The combined organic layers were washed with brine (3×30 mL), dried (Na₂SO₄) and concentrated in vacuo. The residue was purified by Prep-TLC with DCM/MeOH (8/1). The crude product was purified by Prep-HPLC with the following conditions (Column: XBridge Prep OBD C18 Column, 30*150 mm, 5 µm; Mobile Phase A: water (0.1% NH₄HCO₃), Mobile Phase B: MeCN; Flow rate: 60 mL/min; Gradient: 41% B to 51% B in 8 min; Wave Length: 254/220 nm) to afford the title compound (ADB-1) (3.9 mg, 6.5 µmol, 3.9%, 98% Purity) as a white solid. m/z 597.0 (M+H)⁺ (ES+). ¹H NMR (400 MHz, DMSO-d6) δ 8.48 (s, 1H), 8.06 (d, J=15.2 Hz, 2H), 7.89 (s, 1H), 7.58 (d, J=1.2 Hz, 1H), 6.94 (t, J=5.4 Hz, 1H), 6.25 (d, J=1.2 Hz, 1H), 5.21 (s, 2H), 4.80 (d, J=12.8 Hz, 1H), 4.69 (d, J=12.8 Hz, 1H), 4.50 (d, J=4.8 Hz, 1H), 4.05-3.89 (m, 1H), 3.90 (s, 3H), 3.75-3.68 (td, J=6.1, 3.7 Hz, 1H), 3.47 (s, 3H), 3.32-3.23 (m, 2H), 1.82-1.64 (m, 4H), 1.62-1.52 (m, 1H), 1.52-1.40 (m, 1H), 1.17 (t, J=7.1 Hz, 3H).

Example 128: Synthesis of 2-[6-(Ethylamino)-4-[2-methyl-4-(4-methyl-1,2,4-triazol-3-yl) pyrazol-3-yl] pyridin-2-yl]-6-[(oxetan-3-yloxy)methyl]-4-(trifluoromethyl)-3H-isoindol-1-one (ADC-2)

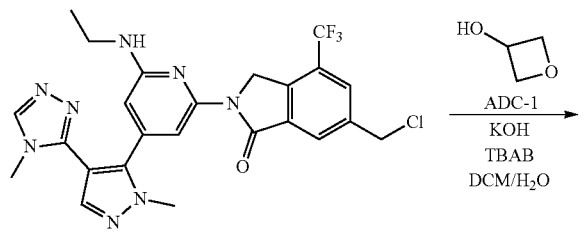

To a stirred solution of intermediate (ADA-1) (35 mg, 1 eq, 66 μmol) and oxetan-3-ol (ADC-1) (50 mg, 10 eq, 660 μmol) in DCM (1 mL) was added TBAB (11 mg, 0.5 eq, 33 μmol) and 1 mL 20% KOH aq. solution at rt. The resulting mixture was stirred for 2 h at rt. The resulting mixture was diluted with water. The aq. layer was extracted with DCM (3×20 mL). The combined organic layers were washed with brine (2×20 mL), dried (Na$_2$SO$_4$). After filtration, the filtrate was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 35% B to 45% B in 9 min; Wave Length: 254/220 nm; RT: 8.63) to afford the title compound (ADC-2) (4.2 mg, 7.4 μmol, 11%, 98% Purity) as a white solid. m/z 569.0 (M+H)$^+$ (ES+). $^1$H NMR (400 MHz, MeOH-d4) δ 8.50 (s, 1H), 8.08 (s, 1H), 7.98 (s, 1H), 7.87 (s, 1H), 7.66 (d, J=1.2 Hz, 1H), 6.21 (d, J=1.2 Hz, 1H), 5.27 (s, 2H), 4.87-4.82 (m, 2H), 4.81-4.75 (m, 1H), 4.72-4.62 (m, 4H), 4.04 (s, 3H), 3.51 (s, 3H), 3.37 (d, J=7.2 Hz, 2H), 1.25 (t, J=7.2 Hz, 3H).

Example 129: Synthesis of 4-{2-[(1-{2-[6-(Ethylamino)-4-[2-methyl-4-(4-methyl-1,2,4-triazol-3-yl) pyrazol-3-yl]pyridin-2-yl]-3-oxo-7-(trifluoromethyl)-1H-isoindol-5-yl}-5,8,11-trioxa-2-azatridecan-13-yl)carbamoyl]ethyl}-2,2-difluoro-10,12-dimethyl-1lambda5,3-diaza-2-boratricyclo[7.3.0.0^{3,7}]dodeca-1(12),4,6,8,10-pentaen-1-ylium-2-uide (ADD-2)

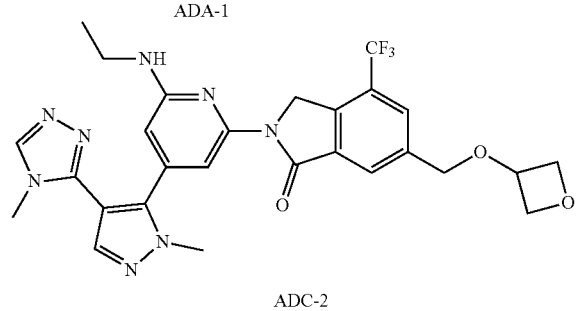

To a stirred solution of intermediate (ACZ-3) (7.8 mg, 0.8 eq, 26 μmol) and Et₃N (10 mg, 3 eq, 99 μmol) in DMF (1.5 mL) were added HATU (17 mg, 1.3 eq, 43 mmol) and 6-({[2-(2-aminoethoxy)ethyl]amino}methyl)-2-[6-(ethylamino)-4-[2-methyl-4-(4-methyl-1,2,4-triazol-3-yl)pyrazol-3-yl]pyridin-2-yl]-4-(trifluoromethyl)-3H-isoindol-1-one (ADD-1) (20 mg, 1 eq, 33 μmol) at rt. The resulting mixture was stirred for 2 h at rt. The resulting mixture was concentrated in vacuo. The residue was purified by Prep-TLC with DCM/MeOH (8/1) and Prep-HPLC with the following conditions (Column: XBridge Prep OBD C18 Column, 30*150 mm, 5 μm; Mobile Phase A: water (0.1% NH₄HCO₃), Mobile Phase B: MeCN; Flow rate: 60 mL/min; Gradient: 40% B to 50% B in 9 min; Wave Length: 254/220 nm; RT: 8.73) to afford the title compound (ADD-2) (13.4 mg, 14 μmol, 41%, 98% Purity) as an orange solid. m/z 961.0 (M+H)⁺ (ES+). ¹H NMR (400 MHz, MeOH-d4) δ 8.49 (s, 1H), 8.01 (s, 1H), 7.95 (s, 1H), 7.87 (s, 1H), 7.65 (d, J=1.2 Hz, 1H), 7.32 (s, 1H), 6.92 (d, J=4.0 Hz, 1H), 6.26 (d, J=4.0 Hz, 1H), 6.20 (d, J=1.2 Hz, 1H), 6.15 (s, 1H), 5.18 (s, 2H), 4.03 (s, 3H), 3.93 (s, 2H), 3.70-3.58 (m, 10H), 3.52 (d, J=9.4 Hz, 5H), 3.38-3.35 (m, 4H), 3.16 (t, J=7.7 Hz, 2H), 2.78 (t, J=5.2 Hz, 2H), 2.58 (t, J=7.7 Hz, 2H), 2.45 (s, 3H), 2.23 (s, 3H), 1.24 (t, J=7.2 Hz, 3H).

Example 130: Synthesis of 2-[6-(Ethylamino)-4-[2-methyl-4-(4-methyl-1,2,4-triazol-3-yl)pyrazol-3-yl]pyridin-2-yl]-6-[(1,2-oxazol-4-yloxy)methyl]-4-(trifluoromethyl)-3H-isoindol-1-one (ADE-2)

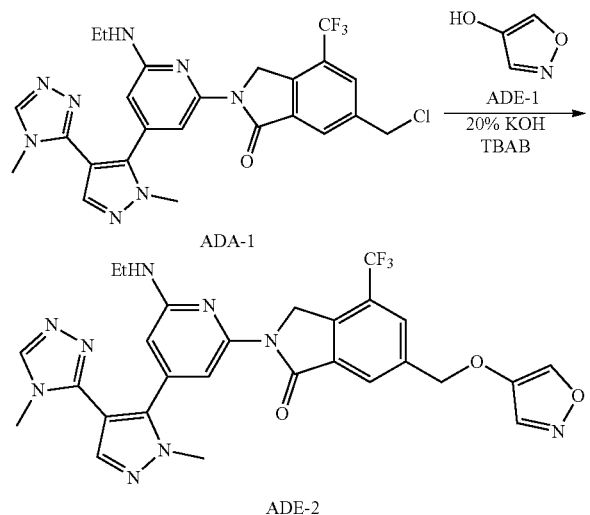

To a stirred solution of intermediate (ADA-1) (25 mg, 1 eq, 47 μmol) and 1,2-oxazol-4-ol (ADE-1) (0 (20 mg, 5 eq, 235 μmol) in DCM (2 mL) were added TABA (8 mg, 0.5 eq, 24 μmol) and 1 mL 20% KOH aq. dropwise at rt. The resulting mixture was stirred slowly for 1 h at rt. The resulting mixture was diluted with water and extracted with DCM (3×20 mL). The combined organic layers were washed with brine (2×20 mL), dried (Na₂SO₄). After filtration, the filtrate was concentrated in vacuo. The residue was purified by Prep-TLC with DCM/MeOH (8/1). The crude product was purified by Prep-HPLC with the following conditions (Column: XBridge Prep C18 OBD Column, 30*100 mm, 5 μm; Mobile Phase A: water (0.1% NH₄HCO₃), Mobile Phase B: MeCN; Flow rate: 60 mL/min; Gradient: 24% B to 54% B in 7 min; Wave Length: 254/220 nm) to afford the title compound (ADE-2) (2.6 mg, 8.9%, 93% Purity) as a white solid. m/z 580.0 (M+H)⁺ (ES+). ¹H NMR (400 MHz, DMSO-d6) δ 9.26 (s, 1H), 8.47 (s, 1H), 8.37 (s, 1H), 8.00-7.82 (m, 3H), 7.55 (d, J=1.2 Hz, 1H), 6.93 (t, J=5.3 Hz, 1H), 6.25 (d, J=1.2 Hz, 1H), 5.19 (s, 2H), 4.33 (s, 2H), 3.89 (s, 3H), 3.47 (s, 3H), 3.30-3.21 (m, 2H), 1.17 (t, J=7.1 Hz, 3H).

Example 131: Synthesis of 2-[6-(Ethylamino)-4-[2-methyl-4-(4-methyl-1,2,4-triazol-3-yl)pyrazol-3-yl]pyridin-2-yl]-6-({[(1R,2S)-2-hydroxycyclopentyl]amino}methyl)-4-(trifluoromethyl)-3H-isoindol-1-one (ADF-2)

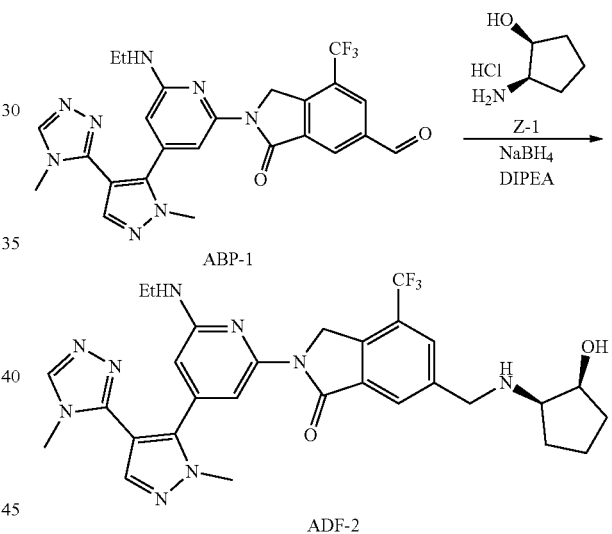

To a stirred solution of intermediate (ABP-1) (50 mg, 1 eq, 98 μmol) and (1S,2R)-2-aminocyclopentan-1-ol (Z-1) (20 mg, 2 eq, 196 μmol) in MeOH (2 mL) was added DIPEA (38 mg, 3 eq, 294 μmol) dropwise at rt. The resulting mixture was stirred for 3 h at rt. To the above mixture was added NaBH₄ (15 mg, 4 eq, 392 μmol) at rt. The resulting mixture was stirred for additional 2 h at rt. The mixture was concentrated in vacuo. The crude product was purified by Prep-HPLC with the following conditions (Column: Sunfire prep C18 column, 30*150 mm, 5 μm; Mobile Phase A: water (0.1% FA), Mobile Phase B: MeCN; Flow rate: 60 mL/min; Gradient: 7% B to 31% B in 7 min; Wave Length: 254/220 nm; RT: 6.81) to afford the title compound (ADF-2) (15.1 mg, 25 μmol, 25%, 98% Purity) as a yellow solid. m/z 596.4 (M+H)⁺ (ES+). ¹H NMR (400 MHz, DMSO-d6) δ 8.45 (s, 1H), 8.10 (d, J=15.4 Hz, 2H), 7.86 (s, 1H), 7.49 (d, J=1.2 Hz, 1H), 6.24 (d, J=1.2 Hz, 1H), 5.20 (s, 2H), 4.14-4.07 (m, 3H), 3.87 (s, 3H), 3.45 (s, 3H), 3.25 (q, J=7.2 Hz, 2H), 3.14-3.04 (m, 1H), 1.90-1.79 (m, 1H), 1.78-1.65 (m, 2H), 1.63-1.40 (m, 3H), 1.15 (t, J=7.2 Hz, 3H).

Example 132: Synthesis of 3'-[6-(Hydroxymethyl)-1-oxo-4-(trifluoromethyl)-3H-isoindol-2-yl]-2-(4-methyl-1,2,4-triazol-3-yl)-[1,1'-biphenyl]-4-carbonitrile (ADG-3)

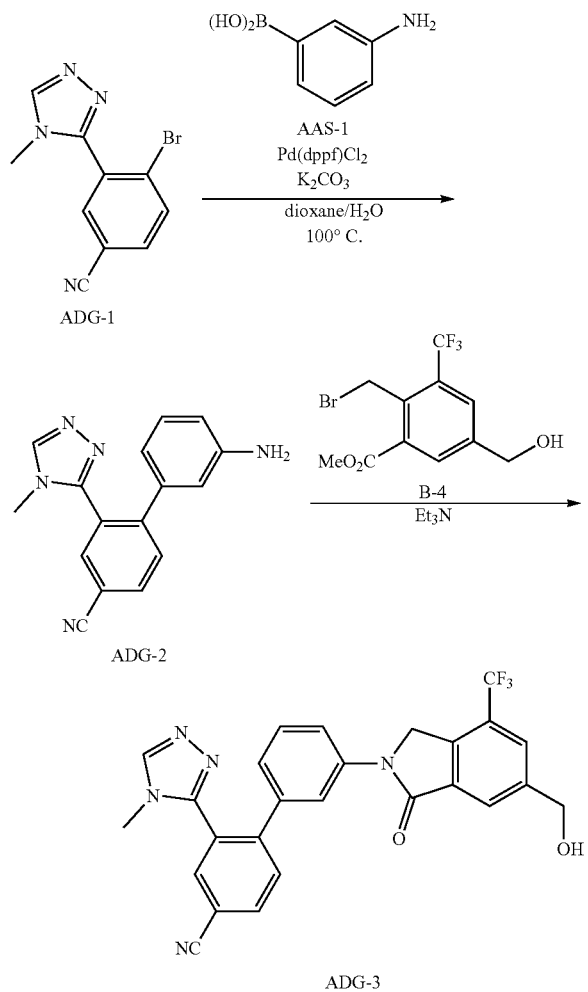

Step 1: Synthesis of 3'-amino-2-(4-methyl-1,2,4-triazol-3-yl)-[1,1'-biphenyl]-4-carbonitrile (ADG-2)

Into a 8 mL sealed tube were added 4-bromo-3-(4-methyl-1,2,4-triazol-3-yl)benzonitrile (ADG-1) (60 mg, 1 eq, 228 μmol), 3-aminophenylboronic acid (AAS-1) (31 mg, 1 eq, 228 μmol) and $K_2CO_3$ (95 mg, 3 eq, 684 μmol) in 1,4-dioxane (2 mL) water (0.2 mL) at rt. To the above mixture was added Pd(dppf)$Cl_2$·DCM (17 mg, 0.1 eq, 23 μmol) at rt under nitrogen atmosphere. The resulting mixture was stirred for additional 3 h at 100° C. under nitrogen atmosphere. The mixture was allowed to cool down to rt and concentrated in vacuo. The crude product was purified by reverse flash column chromatography with the following conditions: Column, C18; mobile phase, Water (0.1% $NH_4HCO_3$) and MeCN (36% MeCN up to 48% in 10 min); Detector, UV 254/220 nm. The product-containing fractions were combined and concentrated in vacuo. This resulted in the sub-title compound (ADG-2) (35 mg, 114 μmol, 56%, 90% Purity) as a white solid. m/z 276.1 (M+H)⁺ (ES+).

Step 2: Synthesis of 3'-[6-(Hydroxymethyl)-1-oxo-4-(trifluoromethyl)-3H-isoindol-2-yl]-2-(4-methyl-1,2,4-triazol-3-yl)-[1,1'-biphenyl]-4-carbonitrile (ADG-3)

Into an 8 mL sealed tube were added the product from step 1 above (ADG-2) (20 mg, 1 eq, 73 μmol) and intermediate (B-4) (36 mg, 1.5 eq, 109 μmol) in EtOH (1 mL) at rt. To the above mixture was added Et$_3$N (22 mg, 3 eq, 219 μmol) dropwise over 3 min at rt. The resulting mixture was stirred for additional overnight at 80° C. The mixture was allowed to cool down to rt and concentrated in vacuo. The crude product was purified by Prep-HPLC with the following conditions: Column: SunFire Prep C18 OBD Column, 19×150 mm, 5 μm; Mobile Phase A: water (0.1% $NH_4HCO_3$+0.1% $NH_3$·$H_2O$), Mobile Phase B: MeCN; Flow rate: 60 mL/min; Gradient: 30 B to 60 B in 7 min; Detector, UV 254/210 nm; RT: 6.08 to afford the title compound (ADG-3) (1.7 mg, 3.5 μmol, 4.7%, 98% Purity) as a white solid. m/z 490.1 (M+H)⁺ (ES+). $^1$H NMR (400 MHz, DMSO-d6) δ 8.47 (s, 1H), 8.25-8.10 (m, 1H), 8.13 (d, J=1.8 Hz, 1H), 8.08-7.87 (m, 4H), 7.74 (s, 1H), 7.42 (t, J=8.0 Hz, 1H), 6.93 (d, J=7.7 Hz, 1H), 5.60 (t, J=5.8 Hz, 1H), 5.11 (s, 2H), 4.71 (d, J=5.7 Hz, 2H), 3.17 (s, 3H).

Example 133: Synthesis of 2-[6-(Ethylamino)-4-[2-methyl-4-(4-methyl-1,2,4-triazol-3-yl)pyrazol-3-yl]pyridin-2-yl]-6-({[(1R,2S)-2-hydroxycyclopentyl]oxy}methyl)-4-(trifluoromethyl)-3H-isoindol-1-one (ADH-1)

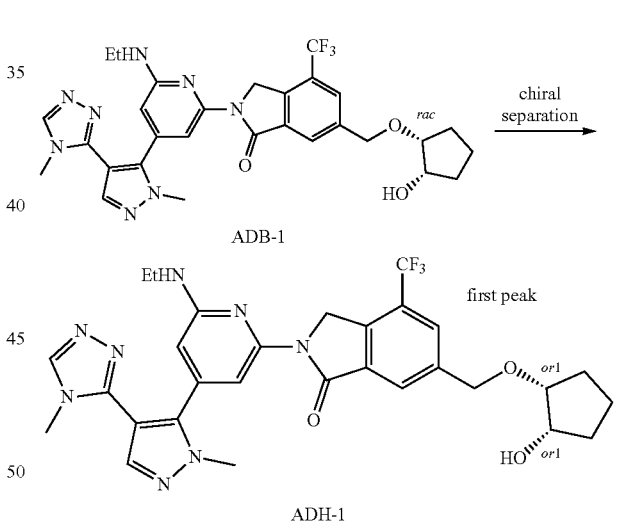

The racemic compound (ADB-1) (25 mg, 1 eq, 42 μmol) was separated by chiral Prep-HPLC with the following conditions (Column: CHIRAL ART Cellulose-SB, 2*25 cm, 5 μm; Mobile Phase A: MTBE:MEOH=2:1, Mobile Phase B: Hex (0.5% 2M NH3-MeOH)-HPLC; Flow rate: 45 mL/min; Gradient: 55% B to 55% B in 30 min; Wave Length: 220/254 nm; RT1(min): 23.4; RT2(min): 26.9) to afford the title compound (ADH-1) (10.8 mg, 18 μmol, 43%, 99% Purity) as a white solid. m/z 597.0 (M+H)⁺ (ES+). $^1$H NMR (400 MHz, DMSO-d6) δ 8.48 (s, 1H), 8.05 (d, J=15.2 Hz, 2H), 7.89 (s, 1H), 7.58 (d, J=1.2 Hz, 1H), 6.94 (t, J=5.4 Hz, 1H), 6.25 (d, J=1.2 Hz, 1H), 5.21 (s, 2H), 4.80 (d, J=12.8 Hz, 1H), 4.69 (d, J=12.8 Hz, 1H), 4.50 (d, J=4.8 Hz, 1H), 4.07-3.96 (m, 1H), 3.90 (s, 3H), 3.78-3.64 (m, 1H), 3.47 (s, Example 134: Synthesis of 2-[6-(Ethylamino)-4-[2-methyl-4-(4-methyl-1,2,4-triazol-3-yl)pyrazol-3-yl]pyridin-2-yl]-6-({[(1S,2R)-2-hydroxycyclopentyl]oxy}methyl)-4-(trifluoromethyl)-3H-isoindol-1-one (ADI-1)

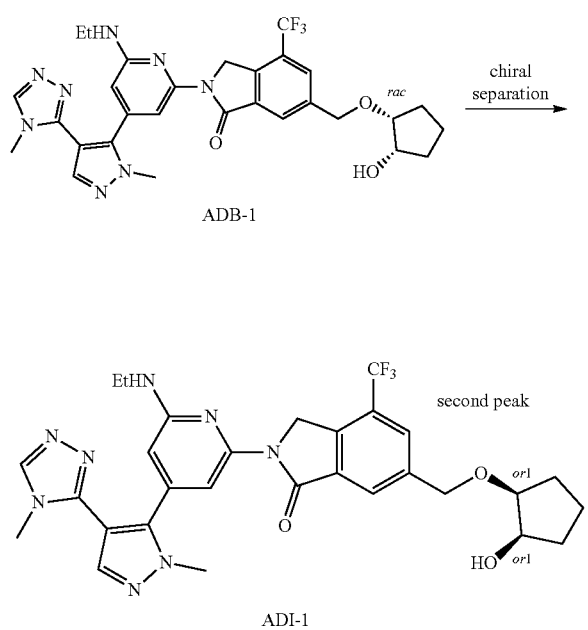

The racemic compound (ADB-1) (25 mg, 1 eq, 42 µmol) was separated by chiral Prep-HPLC with the following conditions (Column: CHIRAL ART Cellulose-SB, 2*25 cm, 5 µm; Mobile Phase A: MTBE:MEOH=2:1, Mobile Phase B: Hex (0.5% 2M NH3-MeOH)-HPLC; Flow rate: 45 mL/min; Gradient: 55% B to 55% B in 30 min; Wave Length: 220/254 nm; RT1(min): 23.4; RT2(min): 26.9) to afford the title compound (ADI-1) (10.4 mg, 17 µmol, 41%, 98% Purity) as a white solid. m/z 597.0 (M+H)$^+$ (ES+). $^1$H NMR (400 MHz, DMSO-d6) δ 8.48 (s, 1H), 8.05 (d, J=15.2 Hz, 2H), 7.89 (s, 1H), 7.57 (d, J=1.2 Hz, 1H), 6.94 (t, J=5.4 Hz, 1H), 6.25 (d, J=1.2 Hz, 1H), 5.21 (s, 2H), 4.80 (d, J=12.8 Hz, 1H), 4.69 (d, J=12.8 Hz, 1H), 4.50 (d, J=4.8 Hz, 1H), 4.06-3.95 (m, 1H), 3.90 (s, 3H), 3.77-3.63 (m, 1H), 3.47 (s, 3H), 3.30-3.20 (m, 2H), 1.86-1.62 (m, 4H), 1.62-1.51 (m, 1H), 1.51-1.38 (m, 1H), 1.26-1.08 (m, 3H). Column: CHIRAL ART Cellulose-SB, 4.6*100 mm, 3 µm; Mobile Phase A: MTBE(0.1% DEA):Hex:MeOH=30:55:15; Flow rate: 1 mL/min; RT: 9.545.

Example 135: Synthesis of 2-[6-(Ethylamino)-4-[2-methyl-4-(4-methyl-1,2,4-triazol-3-yl)pyrazol-3-yl]pyridin-2-yl]-6-({[(1-hydroxycyclobutyl)methyl]amino}methyl)-4-(trifluoromethyl)-3H-isoindol-1-one (ADJ-1)

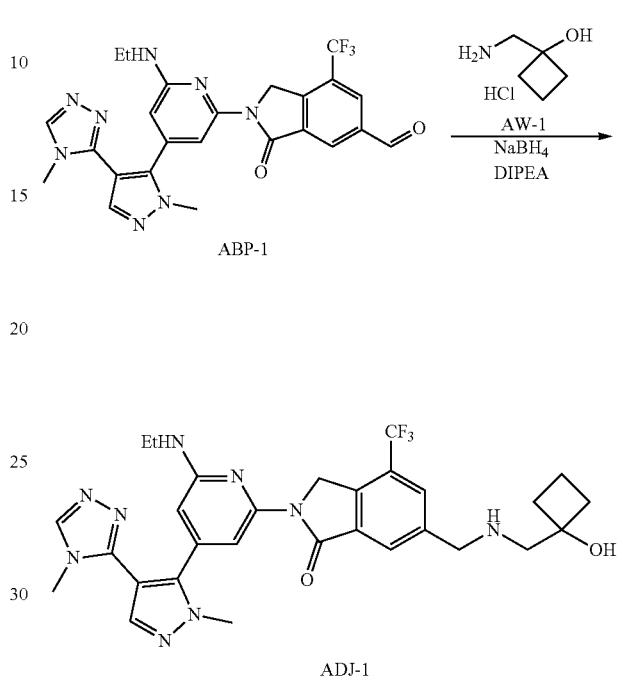

To a stirred solution of intermediate (ABP-1) (100 mg, 1 eq, 196 µmol) and 1-(aminomethyl)cyclobutan-1-ol, HCl (AW-1) (40 mg, 2 eq, 392 µmol) in MeOH (15 mL) was added DIPEA (51 mg, 2 eq, 392 µmol) dropwise at rt. The resulting mixture was stirred for 2 h at rt. To the above mixture was added NaBH$_4$ (30 mg, 4 eq, 784 µmol) dropwise at 0° C. The resulting mixture was stirred for additional 2 h at rt. The reaction was then quenched by the addition of 5 mL of ice water at 0° C. The resulting mixture was concentrated in vacuo. The crude product was purified by Prep-HPLC with the following conditions (Column: Sunfire prep C18 column, 30*150 mm, 5 µm; Mobile Phase A: water (0.1% FA), Mobile Phase B: MeCN; Flow rate: 60 mL/min; Gradient: 8% B to 32% B in 7 min; Wave Length: 254/220 nm; RT: 6.12) to afford the title compound (ADJ-1) (50.1 mg, 84 µmol, 43%, 99% Purity) as an off-white solid. m/z 596.4 (M+H)$^+$ (ES+). $^1$H NMR (400 MHz, MeOH-d4) δ 8.49 (s, 1H), 8.14 (d, J=4.6 Hz, 1H), 8.09 (s, 1H), 7.87 (s, 1H), 7.65 (t, J=1.2 Hz, 1H), 6.21 (d, J=1.2 Hz, 1H), 5.28 (d, J=2.5 Hz, 2H), 4.25-4.19 (m, 2H), 4.04 (s, 3H), 3.51 (s, 3H), 3.42-3.34 (m, 2H), 2.94 (d, J=1.5 Hz, 2H), 2.18-2.05 (m, 4H), 1.84-1.71 (m, 1H), 1.60-1.48 (m, 1H), 1.25 (t, J=7.2 Hz, 3H).

Example 136: Synthesis of 3'-[6-(Hydroxymethyl)-1-oxo-4-(trifluoromethyl)-3H-isoindol-2-yl]-2-(4-methyl-1,2,4-triazol-3-yl)-[1,1'-biphenyl]-4-carboxamide (ADK-1)

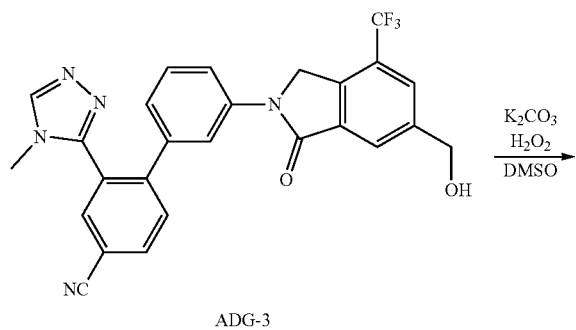

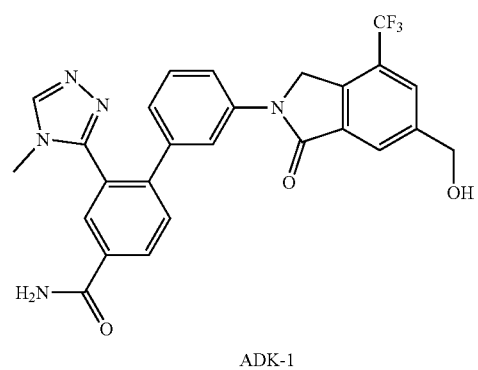

To a stirred solution of compound (ADG-3) (30 mg, 1 eq, 60 μmol) and K$_2$CO$_3$ (25 mg, 3 eq, 180 μmol) in DMSO (1 mL) was added hydrogen peroxide solution (0.5 mL, 30% Wt) at 0° C. The resulting mixture was stirred for additional 3 h at rt. The crude product was purified by reverse flash column chromatography with the following conditions: Column, C18; mobile phase, water (0.1% FA) and MeCN (0% MeCN up to 50% in 15 min); Detector, UV 254/220 nm. The product-containing fractions were combined and concentrated in vacuo. The crude product was purified by Prep-HPLC with the following conditions: Column: Sunfire prep C18 column, 30*150 mm, 5 μm; Mobile Phase A: water (0.1% FA), Mobile Phase B: MeCN; Flow rate: 60 mL/min; Gradient: 15% B to 35% B in 10 min, Detector, UV 254/220 nm; RT: 9.4. The product-containing fractions were combined and evaporated partially in vacuo and lyophilized overnight to afford the title compound (ADK-1) (1.2 mg, 2.3 μmol, 3.9%, 95% Purity) as a white solid. m/z 508.1 (M+H)$^+$ (ES+). $^1$H NMR (400 MHz, MeOH-d4) δ 8.44 (s, 1H), 8.28-8.20 (m, 1H), 8.16-8.07 (m, 2H), 7.98 (s, 1H), 7.95-7.79 (m, 1H), 7.70 (s, 2H), 7.48 (t, J=8.0 Hz, 1H), 7.14 (d, J=7.7 Hz, 1H), 5.09 (s, 2H), 4.82 (s, 2H), 3.24 (s, 3H).

Example 137: Synthesis of 6-({[(1R,2R)-2-Hydroxycyclopentyl]oxy}methyl)-2-[2'-(4-methyl-1,2,4-triazol-3-yl)-[1,1'-biphenyl]-3-yl]-4-(trifluoromethyl)-3H-isoindol-1-one (ADL-4)

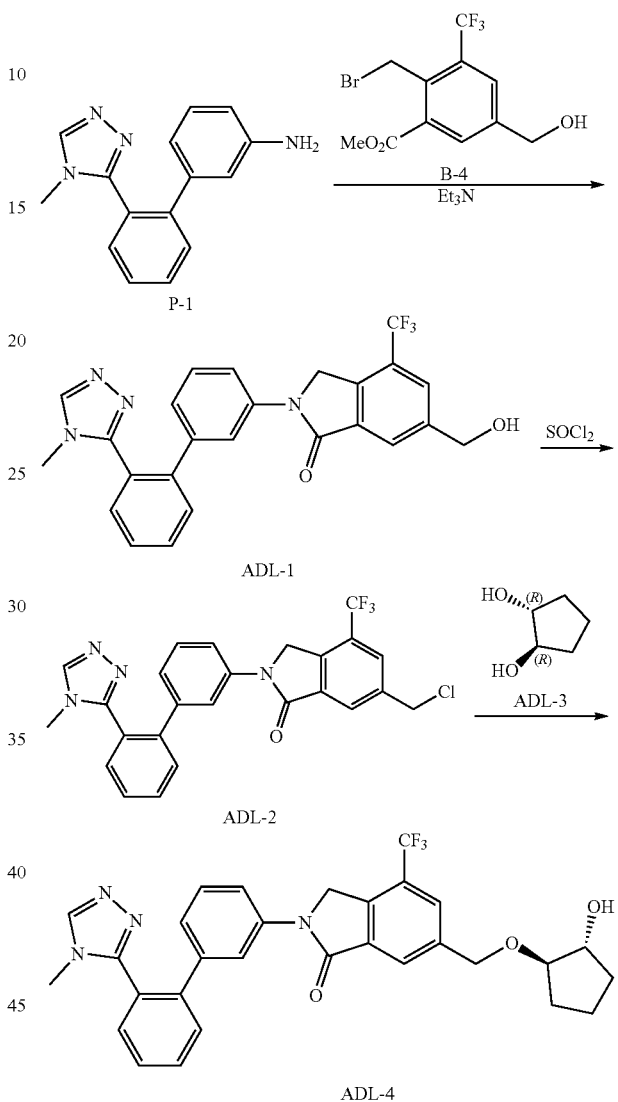

Step 1: Synthesis of 6-(Hydroxymethyl)-2-(2'-(4-methyl-4H-1,2,4-triazol-3-yl)-[1,1'-biphenyl]-3-yl)-4-(trifluoromethyl)isoindolin-1-one (ADL-1)

To a stirred mixture of intermediate (P-1) (104 mg, 0.42 mmol, 1 eq) and intermediate (B-4) (136 mg, 1 eq, 0.42 mmol) in EtOH (5 mL) was added Et$_3$N (126 mg, 3 eq, 1.25 mmol) at rt under nitrogen atmosphere. The resulting mixture was stirred for overnight at 60° C. under nitrogen atmosphere. The crude product was purified by reverse flash column chromatography with the following conditions: Column, C18; mobile phase, water (0.1% NH$_4$HCO$_3$) and MeCN (0% MeCN up to 30% in 20 min); Detector, UV 254/220 nm to afford the sub-title compound (ADL-1) (70 mg, 0.14 mmol, 36%, 91% Purity) as a yellow solid. m/z 465.1 (M+H)$^+$ (ES+).

Step 2: Synthesis of 6-(Chloromethyl)-4-(1,1-difluoroethyl)-2-(2'-(4-methyl-4H-1,2,4-triazol-3-yl)-[1,1'-biphenyl]-3-yl)isoindolin-1-one (ADL-2)

Into a 25 mL round-bottom flask were added the product from step 1 above (ADL-1) (40 mg, 1 eq, 86 μmol) and SOCl$_2$ (31 mg, 3 eq, 0.26 mmol) in DCM (3 mL) at 0° C. The resulting mixture was stirred for overnight at rt. The crude product was purified by reverse flash column chromatography with the following conditions: Column, C18; mobile phase, water (0.1% NH$_4$HCO$_3$) and MeCN (0% MeCN up to 30% in 20 min); Detector, UV 254/220 nm. This resulted in the sub-title compound (ADL-2) (25 mg, 47 μmol, 60%, 90% Purity) as a yellow solid. m/z 479.1/481.1 (M+H)$^+$ (ES+).

Step 3: Synthesis of 6-((((1R,2R)-2-Hydroxycyclopentyl)oxy)methyl)-2-(2'-(4-methyl-4H-1,2,4-triazol-3-yl)-[1,1'-biphenyl]-3-yl)-4-(trifluoromethyl)isoindolin-1-one (ADL-4)

To a stirred mixture of the product from step 2 above (ADL-2) (20 mg, 1 eq, 41 μmol) and (1R,2R)-cyclopentane-1,2-diol (ADL-3) (8.5 mg, 2 eq, 82 μmol) in DCM (1.5 mL) and H$_2$O (1.5 mL) were added NaOH (5 mg, 3 eq, 0.12 mmol) and TBAHS (14 mg, 1 eq, 41 μmol) at rt under nitrogen atmosphere. The resulting mixture was stirred for overnight at 60° C. under nitrogen atmosphere. The mixture was cooled to rt and concentrated in vacuo. The crude product was purified by Prep-HPLC with the following conditions (Column: XBridge Prep C18 OBD Column, 30*100 mm, 5 μm; Mobile Phase A: water (0.1% NH$_4$HCO$_3$), Mobile Phase B: MeCN; Flow rate: 60 mL/min; Gradient: 28% B to 53% B in 9 min; Wave Length: 254/220 nm; RT: 8.87) to afford the title compound (ADL-4) (2.1 mg, 3.8 μmol, 9.2%, 99% Purity) as a white solid. m/z 549.3 (M+H)$^+$ (ES+). $^1$H NMR (400 MHz, MeOH-d4) δ 8.40 (s, 1H), 8.09 (s, 1H), 7.96 (s, 1H), 7.92-7.85 (m, 1H), 7.81-7.71 (m, 3H), 7.67-7.59 (m, 2H), 7.45 (t, J=8.0 Hz, 1H), 7.15-7.08 (m, 1H), 5.08 (s, 2H), 4.77 (s, 2H), 4.23-4.15 (m, 1H), 3.89-3.82 (m, 1H), 3.21 (s, 3H), 2.10-1.94 (m, 2H), 1.83-1.66 (m, 3H), 1.66-1.54 (m, 1H).

Example 138: Synthesis 3'-[6-(Hydroxymethyl)-1-oxo-4-(trifluoromethyl)-3H-isoindol-2-yl]-6-(4-methyl-1,2,4-triazol-3-yl)-[1,1'-biphenyl]-3-carbonitrile (ADM-6)

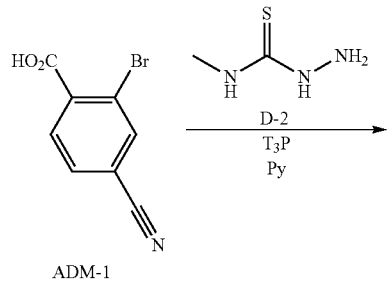

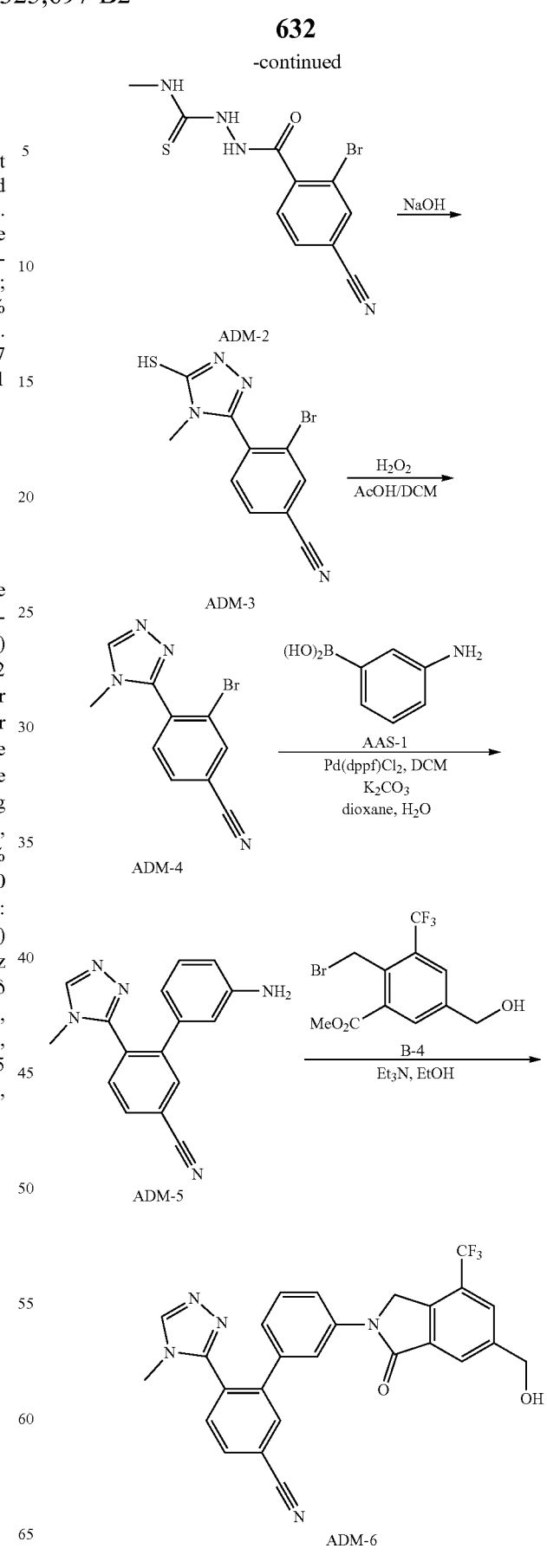

Step 1: Synthesis of 2-Bromo-4-cyano-N-[(methyl-carbamothioyl)-amino]-benzamide (ADM-2)

To a stirred solution of 2-bromo-4-cyanobenzoic acid (ADM-1) (500 mg, 1 eq, 2.21 mmol) and 4-methyl-3-thiosemicarbazide (D-2) (698 mg, 3 eq, 6.63 mmol) in DMF (15 mL) were added T$_3$P (2.82 g, 4 eq, 8.84 mmol) and pyridine (1.05 g, 6 eq, 13.3 mmol) at 0° C. The resulting mixture was stirred for 16 h at rt. The crude resulting mixture was used in the next step directly without further purification. m/z 313.0/315.0 (M+H)$^+$ (ES+).

Step 2: Synthesis of 3-Bromo-4-(4-methyl-5-sulfa-nyl-1,2,4-triazol-3-yl)-benzonitrile (ADM-3)

The resulting mixture from step 1 above (ADM-2) and aq. NaOH (22 mL, 1 M, 10 eq, 22.1 mmol) was stirred for 2 h at 80° C. The mixture was cooled to rt. The residue was diluted with water. The pH value of the solution was adjusted to 4 with 1N HCl. The resulting mixture was extracted with EtOAc (3×50 mL). The combined organic layers were washed with brine (2×50 mL), dried (Na$_2$SO$_4$). After filtration, the filtrate was concentrated in vacuo. This resulted in the sub-title compound (ADM-3) (140 mg, 0.43 mmol, 21%, 90% Purity) as a white solid. m/z 295.0/297.0 (M+H)$^+$ (ES+).

Step 3: Synthesis of 3-Bromo-4-(4-methyl-1,2,4-triazol-3-yl)-benzonitrile (ADM-4)

To a stirred solution of the product from step 2 above (ADM-3) (50 mg, 1 eq, 160 µmol) and hydrogen peroxide (12 mg, 2 eq, 330 µmol) in DCM (10 mL) was added AcOH (51 mg, 5 eq, 840 µmol) at 0° C. The resulting mixture was stirred for 16 h at rt. The mixture was basified to pH 9 with saturated NaHCO$_3$ (aq.). The resulting mixture was extracted with DCM (3×50 mL). The combined organic layers were washed with brine (2×30 mL), dried (Na$_2$SO$_4$). After filtration, the filtrate was concentrated in vacuo. This resulted in the sub-title compound (ADM-4) (40 mg, 146 µmol, 89%, 96% Purity) as a white solid. m/z 263.0/265.0 (M+H)$^+$ (ES+).

Step 4: Synthesis of 3'-Amino-6-(4-methyl-1,2,4-triazol-3-yl)-[1,1'-biphenyl]-3-carbonitrile (ADM-5)

To a stirred solution of the product from step 3 above (ADM-4) (40 mg, 1 eq, 152 µmol) and 3-aminophenylboronic acid (AAS-1) (23 mg, 1.1 eq, 160 µmol) in 1,4-dioxane (4 mL) and water (1 mL) were added K$_2$CO$_3$ (63 mg, 3 eq, 450 µmol) and Pd(dppf)Cl$_2$.DCM (22 mg, 0.2 eq, 30 µmol) at rt under nitrogen atmosphere. The resulting mixture was stirred for 2 h at 80° C. under nitrogen atmosphere. The mixture was allowed to cool down to rt and concentrated in vacuo. The residue was purified by Prep-TLC with DCM/MeOH (12/1) to afford the sub-title compound (ADM-5) (30 mg, 101 µmol, 71%, 93% Purity) as a white solid. m/z 276.1 (M+H)$^+$ (ES+).

Step 5: Synthesis of 3'-[6-(Hydroxymethyl)-1-oxo-4-(trifluoromethyl)-3H-isoindol-2-yl]-6-(4-methyl-1,2,4-triazol-3-yl)-[1,1'-biphenyl]-3-carbonitrile (ADM-6)

To a stirred solution of the product from step 4 above (ADM-5) (30 mg, 1 eq, 100 µmol) and intermediate (B-4) (89 mg, 2.5 eq, 270 µmol) in EtOH (2 mL) was added Et$_3$N (55 mg, 5 eq, 540 µmol) at rt. The resulting mixture was stirred for 16 h at 80° C. The resulting mixture was concentrated in vacuo. The crude product was purified by reverse flash column chromatography with the following conditions: Column, C18; mobile phase, water (0.1% FA) and MeCN (30% MeCN up to 45% in 10 min); Detector, UV 254/220 nm. The product-containing fractions were combined and concentrated in vacuo. The crude product was purified by Prep-HPLC with the following conditions: Column: SunFire Prep C18 OBD Column, 30*100 mm, 5 µm; Mobile Phase A: water (0.05% TFA), Mobile Phase B: MeCN; Flow rate:60 mL/min; Gradient:24 B to 46 B in 7 min; Detector, UV 254/210 nm; RT: 6.75. The product-containing fractions were combined and evaporated partially in vacuo and lyophilized overnight to afford the title compound (ADM-6) (4.6 mg, 8.9 µmol, 8%, 95% Purity) as a white solid. m/z 490.0 (M+H)$^+$ (ES+). $^1$H NMR (400 MHz, MeOH-d4) δ 8.45 (s, 1H), 8.17-8.07 (m, 2H), 8.03-7.92 (m, 3H), 7.87-7.78 (m, 2H), 7.53-7.44 (m, 1H), 7.15-7.07 (m, 1H), 5.10 (s, 2H), 4.82 (s, 2H), 3.23 (s, 3H).

Example 139: Synthesis of 2-{6-Cyclopropyl-4-[4-fluoro-2-(4-methyl-1,2,4-triazol-3-yl)phenyl]pyridin-2-yl}-4-(trifluoromethyl)-3H-isoindol-1-one (ADN-2)

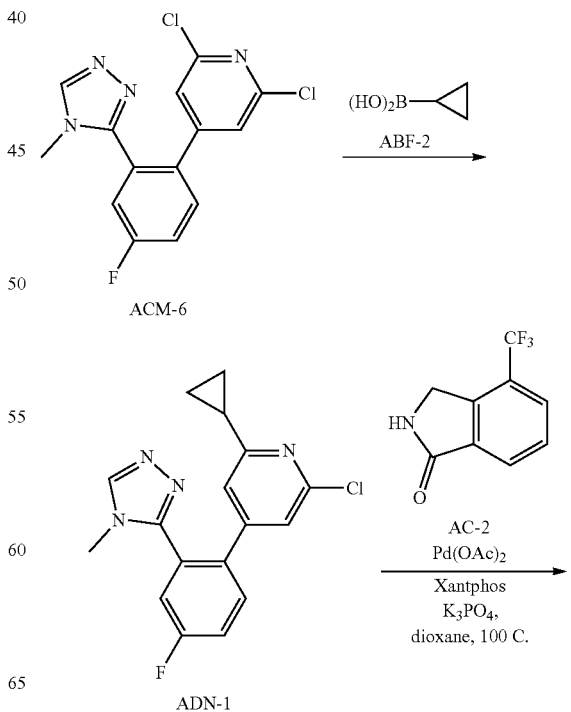

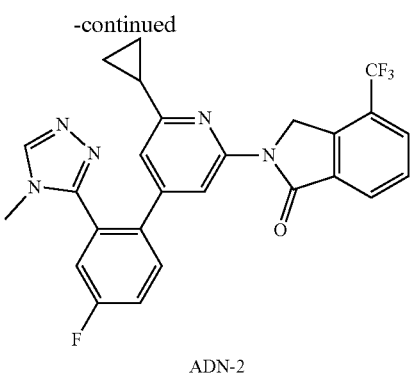

ADN-2

Step 1: Synthesis of 2-Chloro-6-cyclopropyl-4-(4-fluoro-2-(4-methyl-4H-1,2,4-triazol-3-yl)phenyl)pyridine (ADN-1)

Into a 50-mL round-bottom flask purged and maintained with an inert atmosphere of nitrogen, was placed intermediate (ACM-6) (650 mg, 1 Eq, 2.01 mmol), cyclopropylboronic acid (ABF-2) (207 mg, 1.2 Eq, 2.41 mmol) and potassium phosphate (1.28 g, 3 Eq, 6.03 mmol) in toluene (15 mL) at rt under nitrogen atmosphere. Then Pd(OAc)$_2$ (59 mg, 0.13 Eq, 261 µmol) and tricyclohexylphosphane (73 mg, 0.13 Eq, 261 µmol) were added at rt under nitrogen atmosphere. The resulting solution was stirred for 3 h at 110° C. under nitrogen atmosphere. The mixture was cooled to rt and concentrated in vacuo. The residue was purified by Prep-TLC with DCM/MeOH (10/1). This resulted in the sub-title compound (AND-1) (310 mg, 945 µmol, 47%) as a brown yellow solid. m/z 329.1/331.1 (M+H)$^+$ (ES+).

Step 2: Synthesis of 2-{6-Cyclopropyl-4-[4-fluoro-2-(4-methyl-1,2,4-triazol-3-yl)phenyl]pyridin-2-yl}-4-(trifluoromethyl)-3H-isoindol-1-one (ADN-2)

To a stirred mixture of the product from step 1 anpve (ADN-1) (16 mg, 1 eq, 49 µmol), intermediate (AC-2) (10 mg, 1 eq, 49 µmol) and K$_3$PO$_4$ (31 mg, 3 eq, 147 µmol) in 1,4-dioxane (2 mL) were added Pd(OAc)$_2$ (2.2 mg, 0.2 eq, 10 µmol) and XantPhos (11 mg, 0.4 eq, 20 µmol) at rt under nitrogen atmosphere. The resulting mixture was stirred for 3 h at 100° C. under nitrogen atmosphere. The mixture was cooled to rt and concentrated in vacuo. The crude product was purified by Prep-HPLC with the following conditions (Column: XBridge Prep OBD C18 Column, 30*150 mm, 5 µm; Mobile Phase A: water (0.1% NH$_4$HCO$_3$), Mobile Phase B: MeCN; Flow rate: 60 mL/min; Gradient: 45% B to 60% B in 10 min; Wave Length: 254/220 nm; RT: 9.9) to afford the title compound (ADN-2) (6.2 mg, 12 µmol, 25%, 97% Purity) as a white solid. m/z 494.0 (M+H)$^+$ (ES+). $^1$H NMR (400 MHz, MeOH-d4) δ 8.50 (s, 1H), 8.10 (d, J=7.7 Hz, 1H), 8.04 (d, J=1.4 Hz, 1H), 7.99 (d, J=7.7 Hz, 1H), 7.84-7.73 (m, 2H), 7.61-7.33 (m, 2H), 6.91 (d, J=1.4 Hz, 1H), 5.21 (s, 2H), 3.49 (s, 3H), 2.10-2.00 (m, 1H), 1.05-0.98 (m, 4H).

Example 140: Synthesis of 6-({[(1R,2S)-2-Hydroxycyclopentyl]amino}methyl)-2-{3-[2-methyl-4-(4-methyl-1,2,4-triazol-3-yl)pyrazol-3-yl]phenyl}-4-(trifluoromethyl)-3H-isoindol-1-one (ADO-2)

Step 1: Synthesis of 2-{3-[2-Methyl-4-(4-methyl-1,2,4-triazol-3-yl)pyrazol-3-yl]phenyl}-3-oxo-7-(trifluoromethyl)-1H-isoindole-5-carbaldehyde (ADO-1)

To a stirred solution of intermediate (B-5) (150 mg, 1 eq, 461 µmol), intermediate (AAB-8) (129 mg, 507 µmol, 1.1 eq) and silver nitrate (235 mg, 3 eq, 1.38 mmol) in MeCN (6 mL) and H$_2$O (3 mL) at rt. The resulting mixture was stirred for overnight at 60° C. The mixture was allowed to cool down to rt. The crude product was purified by reverse flash column chromatography with the following conditions: Column, C18; mobile phase, water (0.1% NH$_4$HCO$_3$) and MeCN (0% MeCN up to 50% in 24 min); Detector, UV 254/220 nm. This resulted in the sub-title compound (ADO-1) (90 mg, 177 µmol, 42%, 92% Purity) as an off-white solid. m/z 467.1 (M+H)$^+$ (ES+).

Step 2: Synthesis of 6-({[(1R,2S)-2-Hydroxycyclopentyl]amino}methyl)-2-{3-[2-methyl-4-(4-methyl-1,2,4-triazol-3-yl)pyrazol-3-yl]phenyl}-4-(trifluoromethyl)-3H-isoindol-1-one (ADO-2)

To a stirred solution of the product from step 1 above (ADO-1) (80 mg, 1 eq, 172 µmol) and (1S,2R)-2-aminocyclopentan-1-ol, HCl (Z-1) (35 mg, 1.5 eq, 258 µmol) and Et$_3$N (52 mg, 3 eq, 516 µmol) in MeOH (10 mL) at rt. The resulting mixture was stirred for overnight at rt. To the above mixture was added NaBH$_4$ (97 mg, 15 eq, 2.58 mmol) at 0°

C. The resulting mixture was stirred for additional 2 days at 30° C. The mixture was allowed to cool down to rt. The reaction was then quenched by the addition of 2 mL of ice water at 0° C. and concentrated in vacuo. The crude product was purified by Prep-HPLC with the following conditions (Column: XBridge Prep OBD C18 Column, 30*150 mm, 5 µm; Mobile Phase A: water (0.1% NH$_4$HCO$_3$), Mobile Phase B: MeCN; Flow rate: 60 mL/min; Gradient: 30% B to 50% B in 8 min; Wave Length: 254/220 nm) to afford the title compound (ADO-2) (19.4 mg, 35 µmol, 21%, 98% Purity) as a white solid. m/z 552.0 (M+H)$^+$ (ES+). 1H NMR (400 MHz, MeOH-d4) δ 8.46 (s, 1H), 8.12 (s, 1H), 8.07-8.02 (m, 2H), 7.98-7.94 (m, 1H), 7.89 (s, 1H), 7.59 (t, J=8.0 Hz, 1H), 7.28-7.22 (m, 1H), 5.17 (s, 2H), 4.20-4.14 (m, 1H), 4.10-3.95 (m, 5H), 3.43 (s, 3H), 3.01-2.93 (m, 1H), 1.98-1.68 (m, 4H), 1.63-1.49 (m, 2H).

Example 141: Synthesis of 4-[2-(Ethylamino)-6-[1-oxo-4-(trifluoromethyl)-3H-isoindol-2-yl]pyridin-4-yl]-3-(4-methyl-1,2,4-triazol-3-yl)benzonitrile (ADP-8)

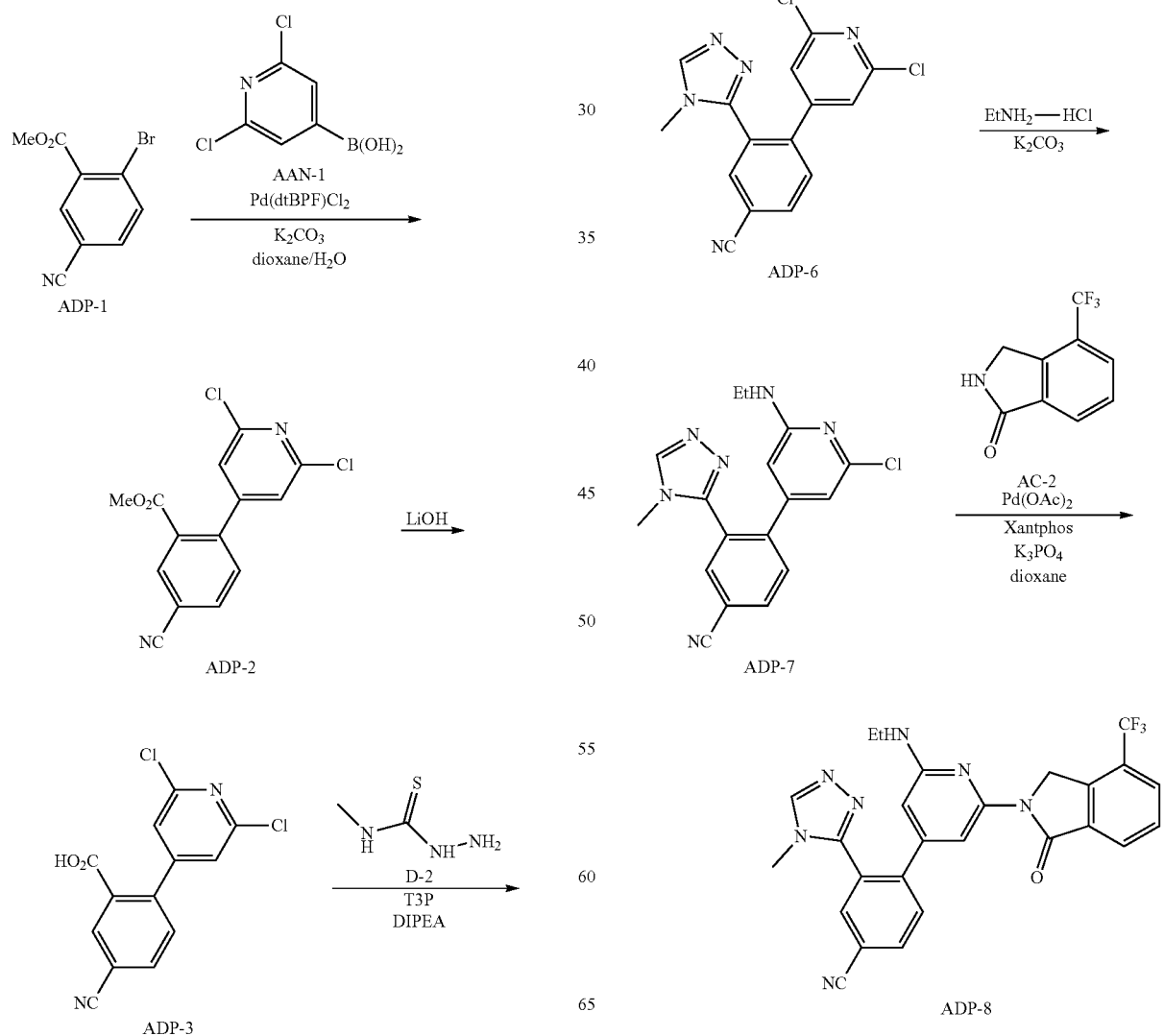

Step 1: Synthesis of Methyl 5-cyano-2-(2,6-dichloropyridin-4-yl) benzoate (ADP-2)

To a stirred solution of methyl 2-bromo-5-cyanobenzoate (ADP-1) (2.40 g, 1 eq, 10.0 mmol), 2,6-dichloropyridin-4-ylboronic acid (AAN-1) (1.92 g, 1 eq, 10.0 mmol) and $K_2CO_3$ (4.15 g, 3 eq, 30 mmol) in 1,4-dioxane (30 mL) and $H_2O$ (3 mL) was added $Pd(dtBPF)Cl_2$ (652 mg, 0.1 eq, 1.00 mmol) at rt under nitrogen atmosphere. The resulting mixture was stirred for 3 h at 60° C. under nitrogen atmosphere. The mixture was allowed to cool down to rt. The resulting mixture was diluted with water and extracted with EtOAc (3×200 mL). The combined organic layers were washed with brine (2×200 mL), dried ($Na_2SO_4$). After filtration, the filtrate was concentrated in vacuo. The residue was applied on a silica gel column chromatography with petroleum ether/EtOAc (4/1) to afford the sub-title compound (ADP-2) (2.2 g, 5.96 mmol, 72%, 83% Purity) as an off-white solid. m/z 307.0/309.0 $(M+H)^+$ (ES+).

Step 2: Synthesis of 5-Cyano-2-(2,6-dichloropyridin-4-yl) benzoic acid (ADP-3)

To a stirred solution of the product from step 1 above (ADP-2) (2.20 g, 1 eq, 7.16 mmol) and LiOH (860 mg, 5 eq, 35.8 mmol) in THF (30 mL) and $H_2O$ (10 mL) at rt. The resulting mixture was stirred for 3 h at rt. The mixture was acidified to pH3 with aq. HCl (4M) at 0° C. The resulting mixture was diluted with water and extracted with EtOAc (3×200 mL). The combined organic layers were washed with brine (2×200 mL), dried (Na2SO4). After filtration, the filtrate was concentrated in vacuo to afford the sub-title compound (ADP-3) (2.1 g, 6.11 mmol, 95%, 85% Purity) as an off-white solid. m/z 293.0/295.0 (M+H)+ (ES+).

Step 3: Synthesis of 5-Cyano-2-(2,6-dichloropyridin-4-yl)-N-[(methylcarbamothioyl) amino]benzamide (ADP-4)

To a stirred solution of the product from step 2 above (ADP-3) (2.10 g, 1 eq, 7.17 mmol), 4-methyl-3-thiosemicarbazide (D-2) (753 mg, 1 eq, 7.17 mmol), $T_3P$ (50% in DMF) (9.12 g, 50% Wt, 4 eq, 28.7 mmol) and DIPEA (5.56 g, 6 eq, 43.0 mmol) in DMF (20 mL) at rt. The resulting mixture was stirred for 3 h at rt. The crude product was purified by reverse flash column chromatography with the following conditions: Column, C18; mobile phase, water (0.1% $NH_4HCO_3$) and MeCN (0% MeCN up to 40% in 24 min); Detector, UV 254/220 nm. This resulted in the sub-title compound (ADP-4) (1.9 g, 4.51 mmol, 70%, 90% Purity) as an off-white solid. m/z 380.0/382.0 $(M+H)^+$ (ES+).

Step 4: Synthesis of 4-(2,6-Dichloropyridin-4-yl)-3-(4-methyl-5-sulfanyl-1,2,4-triazol-3-yl)benzonitrile (ADP-5)

A solution of the product from step 3 above (ADP-4) (1.90 g, 1 eq, 5.00 mmol) in aq. of $NaHCO_3$ (20 mL, 1 M) was stirred for 1 h at 80° C. The mixture was allowed to cool down to rt. The crude product was purified by reverse flash column chromatography with the following conditions: Column, C18; mobile phase, water (0.1% $NH_4HCO_3$) and MeCN (0% MeCN up to 40% in 25 min); Detector, UV 254/220 nm. This resulted in the sub-title compound (ADP-5) (1.3 g, 3.42 mmol, 61%, 95% Purity) as an off-white solid. m/z 362.0/364.0 $(M+H)^+$ (ES+).

Step 5: Synthesis of 4-(2,6-Dichloropyridin-4-yl)-3-(4-methyl-1,2,4-triazol-3-yl)benzonitrile (ADP-6)

To a stirred solution of the product from step 4 above (ADP-5) (1.30 g, 1 eq, 3.59 mmol), $H_2O_2$ (610 mg, 30% Wt, 5 eq, 17.9 mmol), AcOH (431 mg, 2 eq, 7.18 mmol) in DCM (20 mL) at rt. The resulting mixture was stirred for 2 h at rt. The crude product was purified by reverse flash column chromatography with the following conditions: Column, C18; mobile phase, water (0.1% $NH_4HCO_3$) and MeCN (0% MeCN up to 45% in 25 min); Detector, UV 254/220 nm. This resulted in the sub-title compound (ADP-6) (750 mg, 2.05 mmol, 63%, 90% Purity) as an off-white solid. m/z 330.0/332.0 $(M+H)^+$ (ES+).

Step 6: Synthesis of 4-[2-Chloro-6-(ethylamino)pyridin-4-yl]-3-(4-methyl-1,2,4-triazol-3-yl)benzonitrile (ADP-7)

To a stirred solution of the product from step 5 above (ADP-6) (350 mg, 1 eq, 1.06 mmol), $EtNH_2$—HCl (864 mg, 10 eq, 10.6 mmol) and $K_2CO_3$ (1.46 g, 10 eq, 10.6 mmol) in NMP (20 mL) at rt. The resulting mixture was stirred for 6 h at 120° C. The mixture was allowed to cool down to rt. The crude product was purified by reverse flash column chromatography with the following conditions: Column, C18; mobile phase, water (0.1% $NH_4HCO_3$) and MeCN (0% MeCN up to 50% in 27 min); Detector, UV 254/220 nm. This resulted in the sub-title compound (ADP-7) (260 mg, 0.71 mmol, 72%, 92% Purity) as an off-white solid. m/z 339.1/341.1 $(M+H)^+$ (ES+).

Step 7: Synthesis of 4-[2-(Ethylamino)-6-[1-oxo-4-(trifluoromethyl)-3H-isoindol-2-yl]pyridin-4-yl]-3-(4-methyl-1,2,4-triazol-3-yl)benzonitrile (ADP-8)

To a stirred solution of the product from step 6 above (ADP-7) (40 mg, 1 eq, 118 µmol), 4-(trifluoromethyl)-2,3-dihydroisoindol-1-one (AC-2) (29 mg, 1.2 eq, 142 µmol) and $K_3PO_4$ (75 mg, 3 eq, 354 µmol) in 1,4-dioxane (5 mL) were added $Pd(OAc)_2$ (2.65 mg, 0.1 eq, 12 µmol) and Xantphos (14 mg, 0.2 eq, 24 µmol) at rt under nitrogen atmosphere. The resulting mixture was stirred for 3 h at 100° C. under nitrogen atmosphere. The mixture was allowed to cool down to rt. The crude product was purified by reverse flash column chromatography with the following conditions: Column, C18; mobile phase, water (0.1% $NH_4HCO_3$) and MeCN (40% MeCN up to 80% in 20 min); Detector, UV 254/220 nm. The crude product was purified by Prep-HPLC with the following conditions (Column: XBridge Prep OBD C18 Column, 30*150 mm, 5 µm; Mobile Phase A: water (0.1% $NH_4HCO_3$), Mobile Phase B: MeCN; Flow rate: 60 mL/min; Gradient: 46% B to 62% B in 8 min; Wave Length: 254/220 nm) to afford the title compound (ADP-8) (7.7 mg, 15 µmol, 13%, 98% Purity) as an off-white solid. m/z 504.2 $(M+H)^+$ (ES+). $^1$H NMR (400 MHz, MeOH-d4) δ 8.51 (s, 1H), 8.17-8.04 (m, 3H), 7.98 (d, J=7.8 Hz, 1H), 7.90 (d, J=8.1 Hz, 1H), 7.76 (t, J=7.7 Hz, 1H), 7.53 (s, 1H), 6.08 (s, 1H), 5.24 (s, 2H), 3.48 (s, 3H), 3.31-3.25 (m, 2H), 1.23 (t, J=7.2 Hz, 3H).

Example 142: Synthesis of 2-(4-methyl-1,2,4-triazol-3-yl)-3'-(6-{[(3S)-3-methyl piperidin-1-yl]methyl}-1-oxo-4-(trifluoromethyl)-3H-isoindol-2-yl)-[1,1'-biphenyl]-4-carbonitrile (ADQ-2)

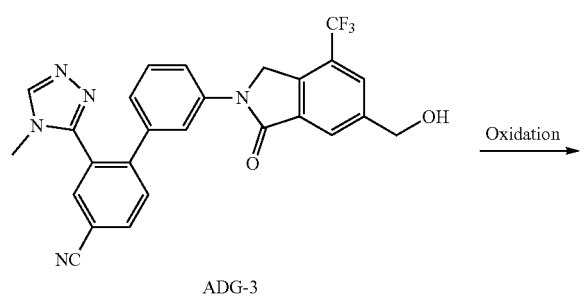

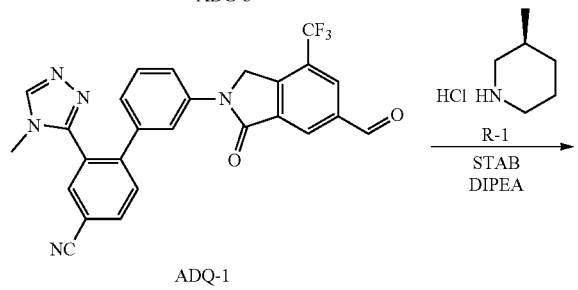

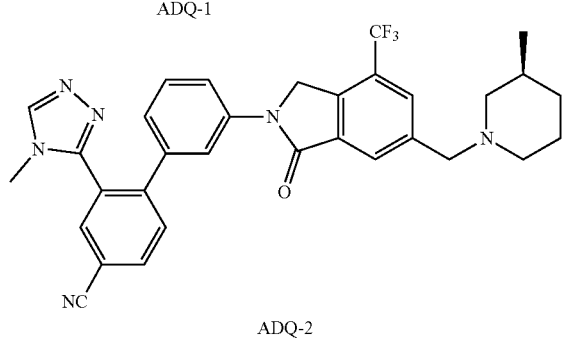

Step 1: 3'-(6-formyl-1-oxo-4-(trifluoromethyl)isoindolin-2-yl)-2-(4-methyl-4H-1,2,4-triazol-3-yl)-[1,1'-biphenyl]-4-carbonitrile The reaction was carried out in a manner similar to Step 2 for the synthesis of BE-3 (Example 122).

Step 2: Synthesis of 2-(4-methyl-1,2,4-triazol-3-yl)-3'-(6-{[(3S)-3-methylpiperidin-1-yl]methyl}-1-oxo-4-(trifluoromethyl)-3H-isoindol-2-yl)-[1,1'-biphenyl]-4-carbonitrile (ADQ-2)

To a stirred solution of intermediate (ADQ-1) (50 mg, 1 eq, 103 μmol) and (S)-3-methylpiperidine, HCl (R-1) (31 mg, 3 eq, 309 μmol) in DCM (10 mL) was added DIPEA (16 mg, 124 μmol, 1.2 eq) and NaBH(OAc)$_3$ (44 mg, 2 eq, 206 μmol) at rt. The resulting mixture was stirred for 2 h at rt. The reaction was quenched with MeOH (1 mL) at 0° C. and concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 50% B to 65% B in 9 min; Wave Length: 254/220 nm) to afford the title compound (ADQ-2) (23.5 mg, 41 μmol, 40%, 99% Purity) as a white solid. m/z 571.4 (M+H)$^+$ (ES+). $^1$H NMR (400 MHz, DMSO-d6) δ 8.47 (s, 1H), 8.24-8.17 (m, 1H), 8.13 (d, J=1.7 Hz, 1H), 8.08-8.01 (m, 1H), 7.98 (s, 1H), 7.96-7.86 (m, 2H), 7.72 (t, J=2.0 Hz, 1H), 7.42 (t, J=8.0 Hz, 1H), 6.97-6.90 (m, 1H), 5.11 (s, 2H), 3.65 (s, 2H), 3.17 (s, 3H), 2.77-2.68 (m, 2H), 1.99-1.89 (m, 1H), 1.70-1.56 (m, 4H), 1.52-1.44 (m, 1H), 0.92-0.80 (m, 4H).

Example 143: Synthesis of 2-{6-Cyclopropyl-4-[2-methyl-4-(4-methyl-1,2,4-triazol-3-yl)pyrazol-3-yl]pyridin-2-yl}-6-({[(1-hydroxycyclobutyl)methyl]amino}methyl)-4-(trifluoromethyl)-3H-isoindol-1-one) (ADR-3)

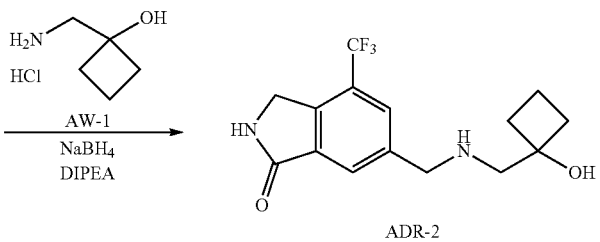

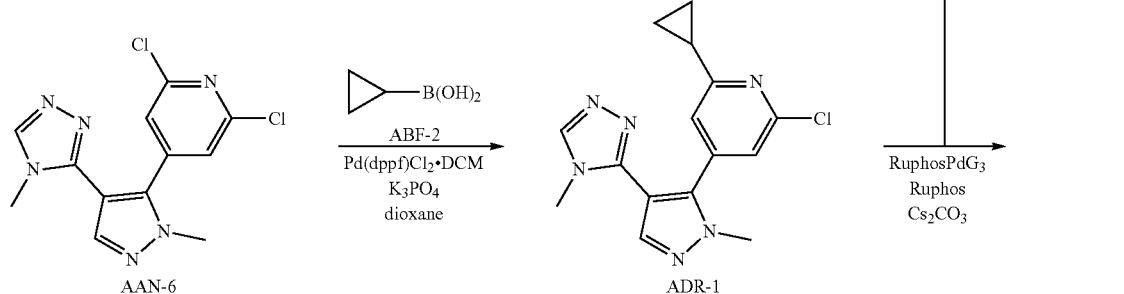

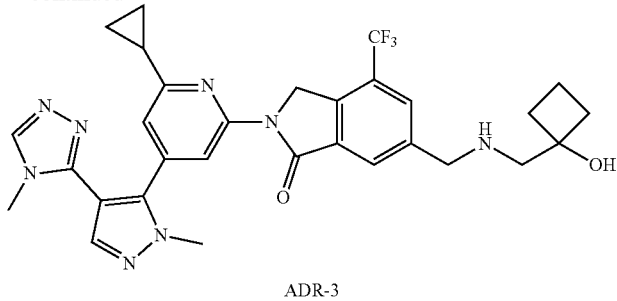

ADR-3

Step 1: Synthesis of 2-Chloro-6-cyclopropyl-4-(1-methyl-4-(4-methyl-4H-1,2,4-triazol-3-yl)-1H-pyrazol-5-yl)pyridine (ADR-1)

To a stirred mixture of intermediate (AAN-6) (30 mg, 1 eq, 97 µmol), cyclopropylboronic acid (ABF-2) (14 mg, 1.7 eq, 165 µmol) and $K_3PO_4$ (41 mg, 2 eq, 194 µmol) in 1,4-dioxane (1 mL) were added Pd(dppf)$Cl_2$.DCM (7.1 mg, 0.1 eq, 10 µmol) at rt under nitrogen atmosphere. The resulting mixture was stirred for overnight at 100° C. under nitrogen atmosphere. The mixture was allowed to cool down to rt. The resulting mixture was concentrated in vacuo. The crude product was purified by reverse flash column chromatography with the following conditions: Column, C18; mobile phase, Water (0.1% $NH_4HCO_3$) and MeCN (10% MeCN up to 50% in 10 min); Detector, UV 254/220 nm. This resulted in the sub-title compound (ADR-1) (20 mg, 57 µmol, 65%, 90% Purity) as a white solid. m/z 315.1/317.1 $(M+H)^+$ (ES+).

Step 2: Synthesis of 6-((((1-Hydroxycyclobutyl)methyl)amino)methyl)-4-(trifluoromethyl)isoindolin-1-one (ADR-2)

A solution of 1-(aminomethyl)cyclobutan-1-ol (AW-1) (33 mg, 1.5 eq, 327 µmol) and DIPEA (85 mg, 3 eq, 654 µmol) in MeOH (6 mL) was stirred for 30 min at rt. To the above mixture was added intermediate (ABC-4) (50 mg, 1 eq, 218 µmol) at rt. To the above mixture was added $NaBH_4$ (41 mg, 5 eq, 1.09 mmol) over 2 h at rt. The resulting mixture was stirred for additional 2 h at rt. The reaction was then quenched by the addition of 2 mL of ice water at 0° C. The resulting mixture was diluted with water and extracted with EtOAc (3×10 mL). The combined organic layers were washed with brine (2×10 mL), dried ($Na_2SO_4$). The residue was purified by Prep-TLC with DCM/petroleum ether (1/1) to afford the sub-title compound (ADR-2) (36 mg, 105 µmol, 51%, 92% Purity) as an off-white solid. m/z 315.1 $(M+H)^+$ (ES+).

Step 3: Synthesis of 2-{6-Cyclopropyl-4-[2-methyl-4-(4-methyl-1,2,4-triazol-3-yl)pyrazol-3-yl]pyridin-2-yl}-6-({[(1-hydroxycyclobutyl)methyl]amino}methyl)-4-(trifluoromethyl)-3H-isoindol-1-one) (ADR-3)

To a stirred solution of the product from step 2 above (ADR-2) (100 mg, 1 eq, 318 µmol), the product from step 1 above (ADR-1) (100 mg, 1 eq, 318 µmol) and $Cs_2CO_3$ (207 mg, 2 eq, 636 µmol) in 1,4-dioxane (15 mL) were added RuPhos palladacycle Gen.3 (53 mg, 0.2 eq, 64 µmol) and RuPhos (59 mg, 0.4 eq, 127 µmol) at rt under nitrogen atmosphere. The resulting mixture was stirred for 2 h at 100° C. under nitrogen atmosphere. The mixture was allowed to cool down to rt. The resulting mixture was diluted with water and extracted with EtOAc (3×20 mL). The combined organic layers were washed with brine (2×20 mL), dried ($Na_2SO_4$). After filtration, the filtrate was concentrated in vacuo. The residue was purified by Prep-TLC with DCM/MeOH (10/1). The crude product was purified by Prep-HPLC with the following conditions (Column: Sunfire prep C18 column, 30*150 mm, 5 µm; Mobile Phase A: water (0.1% FA), Mobile Phase B: MeCN; Flow rate: 60 mL/min; Gradient: 12% B to 23% B in 11 min; Wave Length: 254/220 nm; RT: 13.1) to afford the title compound (ADR-3) (64.1 mg, 106 µmol, 34%, 98% Purity) as a white solid. m/z 593.4 $(M+H)^+$ (ES+). $^1$H NMR (400 MHz, DMSO-d6) δ 8.49 (s, 1H), 8.26-8.15 (m, 2H), 8.07 (d, J=10.7 Hz, 2H), 7.97 (s, 1H), 7.23 (d, J=1.4 Hz, 1H), 5.21 (s, 2H), 3.98 (s, 2H), 3.91 (s, 3H), 3.55 (s, 3H), 2.58-2.53 (m, 2H), 2.15 (p, J=6.4 Hz, 1H), 2.04-1.97 (m, 2H), 1.96-1.85 (m, 2H), 1.69-1.57 (m, 1H), 1.44-1.32 (m, 1H), 1.03 (d, J=6.3 Hz, 4H).

Example 144: Synthesis of 3-[2-(Ethylamino)-6-[1-oxo-4-(trifluoromethyl)-3H-isoindol-2-yl]pyridin-4-yl]-4-(4-methyl-1,2,4-triazol-3-yl)benzonitrile (ADS-6)

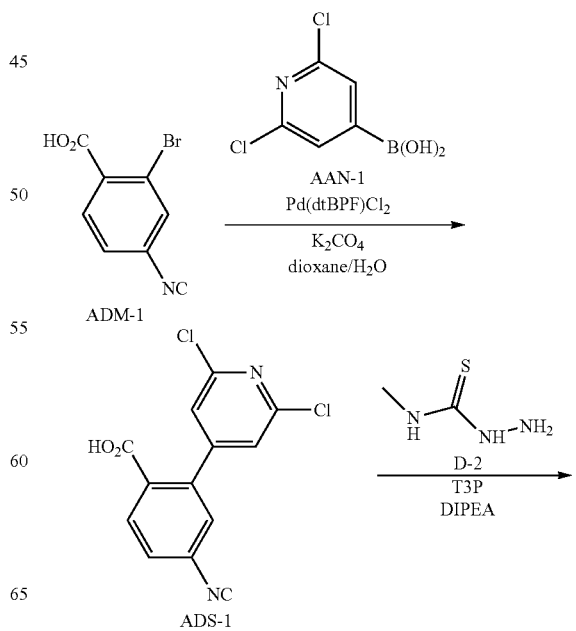

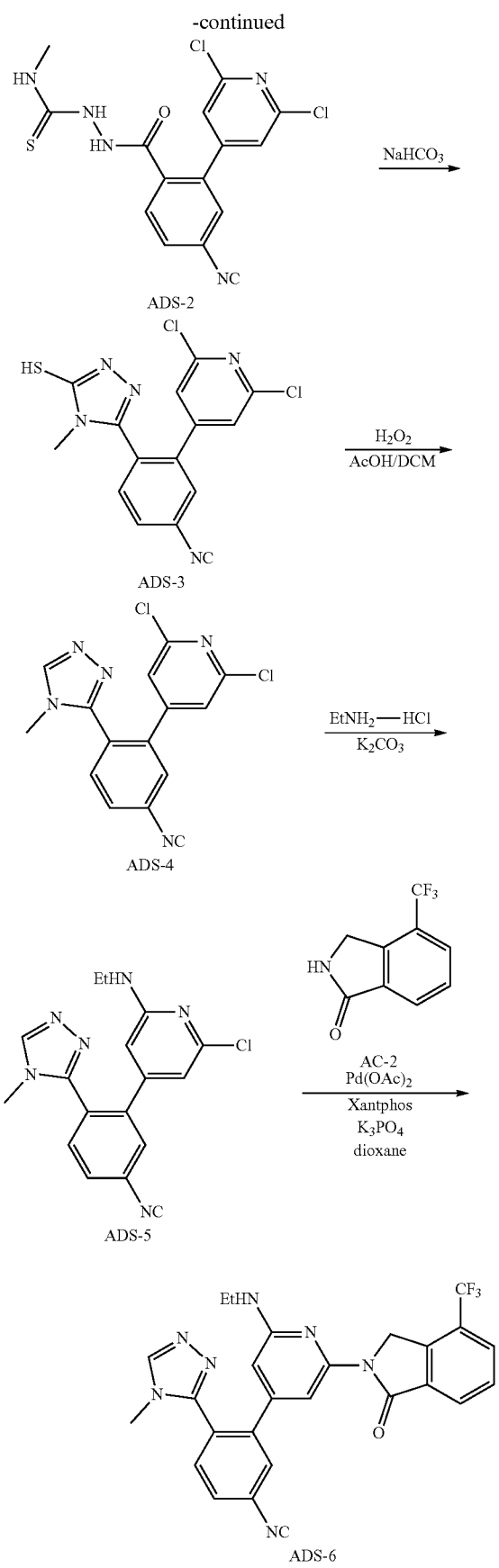

Step 1: Synthesis of 4-Cyano-2-(2,6-dichloropyridin-4-yl)benzoic acid (ADS-1)

To a stirred solution of 2-bromo-4-cyanobenzoic acid (ADM-1) (2.00 g, 1 eq, 8.85 mmol), 2,6-dichloropyridin-4-ylboronic acid (AAN-1) (1.19 g, 0.7 eq, 6.19 mmol) and K$_3$PO$_4$ (3.67 g, 3 eq, 26.5 mmol) in 1,4-dioxane (20 mL) and water (1 mL) was added Pd(dtBPF)Cl$_2$ (577 mg, 0.1 eq, 0.89 mmol) at rt under nitrogen atmosphere. The resulting mixture was stirred for 2 h at 60° C. under nitrogen atmosphere. The mixture was cooled to rt, diluted with water and extracted with EtOAc (3×100 mL). The combined organic layers were washed with brine (2×100 mL), dried (Na$_2$SO$_4$). After filtration, the filtrate was concentrated in vacuo. The crude product was purified by reverse flash column chromatography with the following conditions: Column, C18; mobile phase, water (0.1% FA) and MeCN (50% MeCN up to 70% in 10 min); Detector, UV 254/220 nm. The product-containing fractions were combined and concentrated in vacuo. This resulted in the sub-title compound (ADS-1) (350 mg, 1.08 mmol, 14%, 90% Purity) as a yellow solid. m/z 293.0/295.0 (M+H)$^+$ (ES+).

Step 2: 4-Cyano-2-(2,6-dichloropyridin-4-yl)-N-[(methylcarbamothioyl)amino]benzamide (ADS-2)

To a stirred solution of the product from step 1 above (ADS-1) (350 mg, 1 eq, 1.19 mmol) and 4-methyl-3-thiosemicarbazide (D-2) (151 mg, 1.2 eq, 1.43 mmol) in DMF (5 mL) was added T$_3$P (50% in EA) (2.28 g, 50% Wt, 6 eq, 7.16 mmol) at rt. The resulting mixture was stirred for 2 h at rt. The crude product was purified by reverse flash column chromatography with the following conditions: Column, C18; mobile phase, Water (0.1% FA) and MeCN (52% MeCN up to 73% in 10 min); Detector, UV 254/220 nm. The product-containing fractions were combined and concentrated in vacuo. This resulted in the sub-title compound (ADS-2) (330 mg, 0.80 mmol, 73%, 92% Purity) as a yellow solid. m/z 380.0/382.0 (M+H)$^+$ (ES+).

Step 3: Synthesis of 3-(2,6-Dichloropyridin-4-yl)-4-(4-methyl-5-sulfanyl-1,2,4-triazol-3-yl)benzonitrile (ADS-3)

Into an 8 mL vial were added the product from step 2 above (ADS-2) (330 mg, 1 eq, 0.87 mmol) and aq. of NaHCO$_3$ (6 mL, 1 M) at rt. The resulting mixture was stirred for 1 h at 80° C. The mixture was allowed to cool down to rt. The crude product was purified by reverse flash column chromatography with the following conditions: Column, C18; mobile phase, water (0.1% NH$_4$HCO$_3$) and MeCN (44% MeCN up to 65% in 10 min); Detector, UV 254/220 nm. The product-containing fractions were combined and concentrated in vacuo. This resulted in the sub-title compound (ADS-3) (300 mg, 0.79 mmol, 95%, 95% Purity) as a yellow solid. m/z 362.0/364.0 (M+H)$^+$ (ES+).

Step 4: Synthesis of 3-(2,6-Dichloropyridin-4-yl)-4-(4-methyl-1,2,4-triazol-3-yl)benzonitrile (ADS-4)

To a stirred solution of the product from step 3 above (ADS-3) (300 mg, 1 eq, 0.83 mmol) and AcOH (100 mg, 2 eq, 1.66 mmol) in DCM (10 mL) was added H$_2$O$_2$ (469.7 mg, 30% Wt, 5 eq, 4.15 mmol) at 0° C. The resulting mixture was stirred for 2 h at rt. The resulting mixture was concentrated in vacuo. The crude product was purified by reverse flash column chromatography with the following conditions: Column, C18; mobile phase, water (0.1% FA) and MeCN (56% MeCN up to 83% in 10 min); Detector, UV 254/220 nm. The product-containing fractions were combined and concentrated in vacuo. This resulted in the sub-title compound (ADS-4) (150 mg, 0.41 mmol, 50%, 91% Purity) as a yellow solid. m/z 330.0/332.0 (M+H)+ (ES+).

Step 5: Synthesis of 3-[2-Chloro-6-(ethylamino) pyridin-4-yl]-4-(4-methyl-1,2,4-triazol-3-yl)benzonitrile (ADS-5)

To a stirred solution of the product from step 4 above (ADS-4) (100 mg, 1 eq, 0.30 mmol) and EtNH$_2$—HCl (741 mg, 30 eq, 9.09 mmol) in NMP (10 mL) was added K$_2$CO$_3$ (1.26 g, 30 eq, 9.09 mmol) at rt under nitrogen atmosphere. The resulting mixture was stirred for overnight at 110° C. under nitrogen atmosphere. The mixture was allowed to cool down to rt. The crude product was purified by reverse flash column chromatography with the following conditions: Column, C18; mobile phase, Water (0.1% FA) and MeCN (60% MeCN up to 80% in 10 min); Detector, UV 254/220 nm. The product-containing fractions were combined and concentrated in vacuo. This resulted in the sub-title compound (ADS-5) (80 mg, 0.21 mmol, 78%, 90% Purity) as a yellow oil. m/z 339.1/341.1 (M+H)+ (ES+)

Step 6: Synthesis of 3-[2-(Ethylamino)-6-[1-oxo-4-(trifluoromethyl)-3H-isoindol-2-yl]pyridin-4-yl]-4-(4-methyl-1,2,4-triazol-3-yl)benzonitrile (ADS-6)

To a stirred solution of the product from step 5 above (ADS-5) (80 mg, 1 eq, 0.24 mmol), intermediate (AC-2) (57 mg, 1.2 eq, 0.28 mmol) and K$_3$PO$_4$ (150 mg, 3 eq, 0.71 mmol) in 1,4-dioxane (3 mL) were added Pd(OAc)$_2$ (5.3 mg, 0.1 eq, 24 μmol) and XantPhos (27 mg, 0.2 eq, 47 μmol) at rt under nitrogen atmosphere. The resulting mixture was stirred for overnight at 100° C. under nitrogen atmosphere. The mixture was cooled to rt, diluted with water and extracted with EtOAc (3×20 mL). The combined organic layers were washed with brine (2×20 mL), dried (Na$_2$SO$_4$). After filtration, the filtrate was concentrated in vacuo. The crude product was purified by reverse flash column chromatography with the following conditions: Column, C18; mobile phase, Water (0.1% NH$_4$HCO$_3$) and MeCN (36% MeCN up to 70% in 10 min); Detector, UV 254/220 nm. The product-containing fractions were combined and concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 38% B to 65% B in 9 min; Wave Length: 254/220 nm; RT: 8.48) to afford the title compound (ADS-6) (19.8 mg, 39 μmol, 17%, 99% Purity) as a white solid. m/z 504.0 (M+H)+ (ES+) $^1$H NMR (400 MHz, MeOH-d4) δ 8.51 (s, 1H), 8.11-8.07 (m, 2H), 8.04-7.96 (m, 2H), 7.86-7.73 (m, 2H), 7.51 (d, J=1.3 Hz, 1H), 6.09 (d, J=1.3 Hz, 1H), 5.24 (s, 2H), 3.48 (s, 3H), 3.29 (d, J=7.2 Hz, 2H), 1.24 (t, J=7.2 Hz, 3H).

Example 145: Synthesis of 4-[2-(Ethylamino)-6-(6-{1[(3S)-3-methylpiperidin-1-yl]methyl}-1-oxo-4-(trifluoromethyl)-3H-isoindol-2-yl)pyridin-4-yl]-3-(4-methyl-1,2,4-triazol-3-yl) benzonitrile (ADT-2)

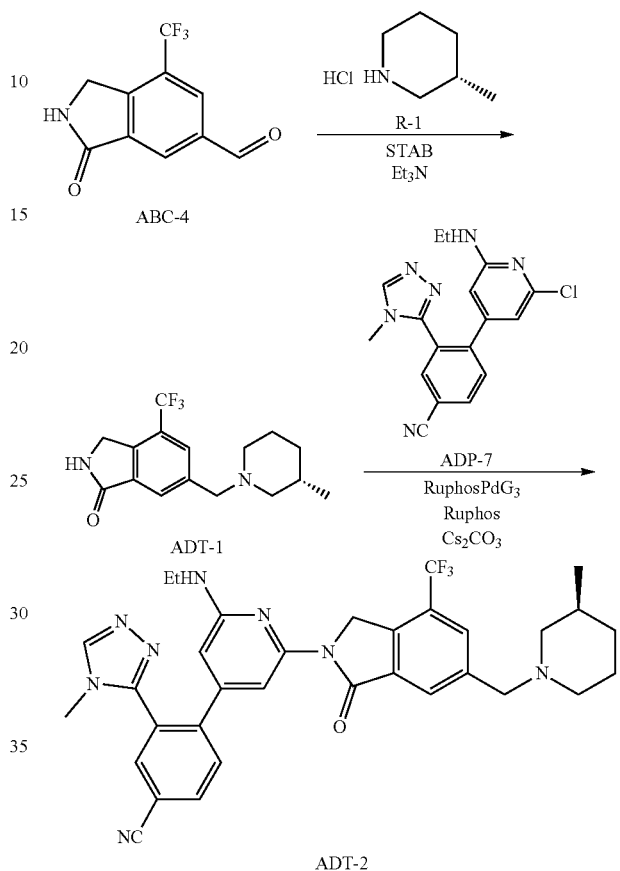

Step 1: Synthesis of 6-{[(3S)-3-Methylpiperidin-1-yl]methyl}-4-(trifluoromethyl)-2,3-dihydroisoindol-1-one (ADT-1)

Into an 8 mL sealed tube were added intermediate (ABC-4) (100 mg, 1 eq, 0.44 mmol), Et$_3$N (265 mg, 6 eq, 2.62 mmol) and (S)-3-methylpiperidine, HCl (R-1) (43 mg, 1 eq, 0.44 mmol) in DCM (3 mL) at rt. To the above mixture was added NaBH(OAc)$_3$ (555 mg, 6 eq, 2.62 mmol) over 10 min at 0° C. The resulting mixture was stirred for additional overnight at rt. The resulting mixture was concentrated in vacuo. The crude product was purified by reverse flash column chromatography with the following conditions: Column, C18; mobile phase, water (0.1% NH$_4$HCO$_3$) and MeCN (10% MeCN up to 50% in 15 min); Detector, UV 254/220 nm to afford the sub-title compound (ADT-1) (41 mg, 0.12 mmol, 30%, 90% Purity) as a yellow oil. m/z 313.1 (M+H)+ (ES+).

Step 2: Synthesis 4-[2-(Ethylamino)-6-(6-{[(3S)-3-methylpiperidin-1-yl]methyl}-1-oxo-4-(trifluoromethyl)-3H-isoindol-2-yl) pyridin-4-yl]-3-(4-methyl-1,2,4-triazol-3-yl)benzonitrile (ADT-2)

To a stirred solution of the product from step 1 above (ADT-1) (70 mg, 1 eq, 0.22 mmol), intermediate (ADP-7)

(75.93 mg, 1 eq, 0.22 mmol) and Cs$_2$CO$_3$ (146 mg, 2 eq, 0.45 mmol) in 1,4-dioxane (8 mL) were added RuPhos (42 mg, 0.4 eq, 90 μmol) and RuPhos palladacycle Gen.3 (37 mg, 0.2 eq, 45 μmol) at rt under nitrogen atmosphere. The final reaction mixture was irradiated with microwave radiation for 1 h at 100° C. under nitrogen atmosphere. The mixture was allowed to cool down to rt. The resulting mixture was diluted with water and extracted with EtOAc (3×20 mL). The combined organic layers were washed with brine (2×20 mL), dried (Na$_2$SO$_4$). After filtration, the filtrate was concentrated in vacuo. The residue was purified by Prep-TLC with EtOAc/petroleum ether (1/1) to afford the crude product. The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 2% B to 10% B in 7 min; Wave Length: 254/220 nm; RT: 6.2) to afford the title compound (ADT-2) (9.9 mg, 16 μmol, 7.1%, 99% Purity) as a yellow solid. m/z 615.4 (M+H)$^+$ (ES+). $^1$H NMR (400 MHz, Methanol-d4) δ 8.51 (s, 1H), 8.11-8.02 (m, 3H), 7.96 (s, 1H), 7.90 (d, J=8.1 Hz, 1H), 7.52 (d, J=1.2 Hz, 1H), 6.08 (d, J=1.3 Hz, 1H), 5.23-5.19 (m, 2H), 3.69 (s, 2H), 3.48 (s, 3H), 3.29 (t, J=7.2 Hz, 2H), 2.90-2.78 (m, 2H), 2.07-1.98 (m, 1H), 1.81-1.56 (m, 5H), 1.23 (t, J=7.2 Hz, 3H), 0.95-0.89 (m, 4H).

Example 146: Synthesis of 4-[2-(Ethylamino)-6-(6-{1[(3R)-3-methylpiperidin-1-yl]methyl}-1-oxo-4-(trifluoromethyl)-3H-isoindol-2-yl)pyridin-4-yl]-3-(4-methyl-1,2,4-triazol-3-yl)benzonitrile (ADU-2)

Step 1: Synthesis of 6-{1[(3R)-3-Methylpiperidin-1-yl]methyl}-4-(trifluoromethyl)-2,3-dihydroisoindol-1-one (ADU-1)

To a stirred solution of (3R)-3-methylpiperidine,HCl (S-1) (57 mg, 1.2 eq, 0.42 mmol) and DIPEA (68 mg, 1.5 eq, 0.52 mmol) in DCM (10 mL) at rt. The resulting mixture was stirred for 20 min at rt. To the above mixture was added intermediate (ABC-4) (80 mg, 1 eq, 0.35 mmol) at rt. The resulting mixture was stirred for additional 1 h at rt. To the above mixture was added NaBH(OAc)$_3$ (370 mg, 5 eq, 1.75 mmol) at rt. The resulting mixture was stirred for overnight at rt. The crude product was purified by reverse flash column chromatography with the following conditions: Column, C18; mobile phase, Water (0.1% NH$_4$HCO$_3$) and MeCN (0% MeCN up to 60% in 24 min); Detector, UV 254/220 nm. This resulted in the sub-title compound (ADU-1) (60 mg, 0.18 mmol, 55%, 92% Purity) as an off-white solid. m/z 313.1 (M+H)$^+$ (ES+).

Step 2: Synthesis of 4-[2-(Ethylamino)-6-(6-{[(3R)-3-methylpiperidin-1-yl]methyl}-1-oxo-4-(trifluoromethyl)-3H-isoindol-2-yl) pyridin-4-yl]-3-(4-methyl-1,2,4-triazol-3-yl) benzonitrile (ADU-2)

To a stirred solution of the product from step 1 above (ADU-1) (60 mg, 1 eq, 0.19 mmol), intermediate (ADP-7) (72 mg, 1.1 eq, 0.21 mmol) and Cs$_2$CO$_3$ (125 mg, 2 eq, 0.38 mmol) in 1,4-dioxane (10 mL) were added RuPhos palladacycle Gen.3 (32 mg, 0.2 eq, 38 μmol) and RuPhos (36 mg, 0.4 eq, 77 μmol) at rt under nitrogen atmosphere. The resulting mixture was stirred for 3 h at 100° C. under nitrogen atmosphere. The mixture was allowed to cool down to rt. The crude product was purified by reverse flash column chromatography with the following conditions: Column, C18; mobile phase, water (0.1% NH$_4$HCO$_3$) and MeCN (20% MeCN up to 100% in 25 min); Detector, UV 254/220 nm. The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 65% B to 78% B in 8 min; Wave Length: 254/220 nm) to afford the title compound (ADU-2) (27.3 mg, 44 μmol, 23%, 99% Purity) as a light yellow solid. m/z 615.0 (M+H)$^+$ (ES+). $^1$H NMR (400 MHz, MeOH-d4) δ 8.50 (s, 1H), 8.13-7.87 (m, 5H), 7.52 (d, J=1.3 Hz, 1H), 6.08 (d, J=1.3 Hz, 1H), 5.21 (s, 2H), 3.70 (s, 2H), 3.48 (s, 3H), 3.29 (t, J=7.2 Hz, 2H), 2.84 (t, J=12.1 Hz, 2H), 2.06-1.92 (m, 1H), 1.86-1.51 (m, 5H), 1.23 (t, J=7.2 Hz, 3H), 0.89 (d, J=5.4 Hz, 4H).

Example 147: Synthesis of 3'-[6-({[(1-Hydroxycyclobutyl)methyl]amino}methyl)-1-oxo-4-(trifluoromethyl)-3H-isoindol-2-yl]-2-(4-methyl-1,2,4-triazol-3-yl)-[1,1'-biphenyl]-4-carbonitrile (ADV-1)

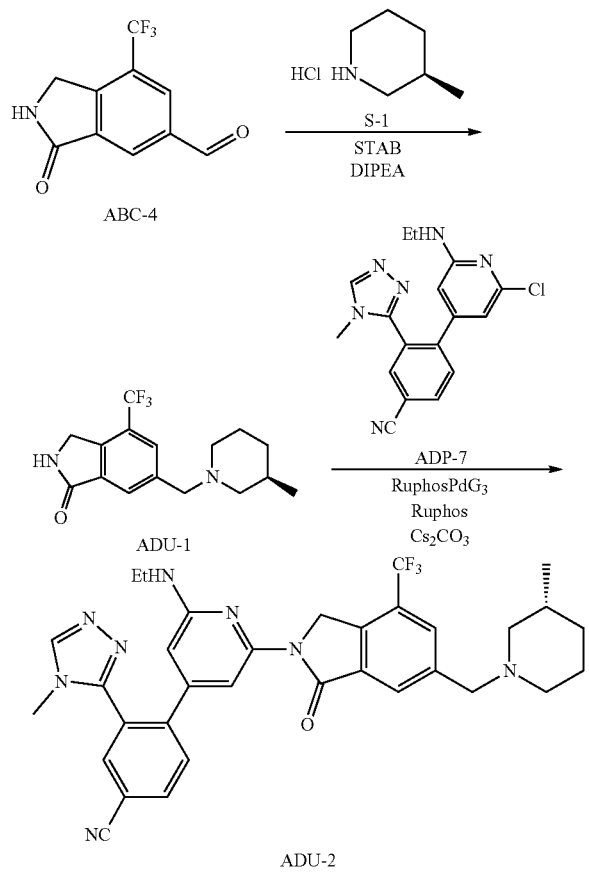

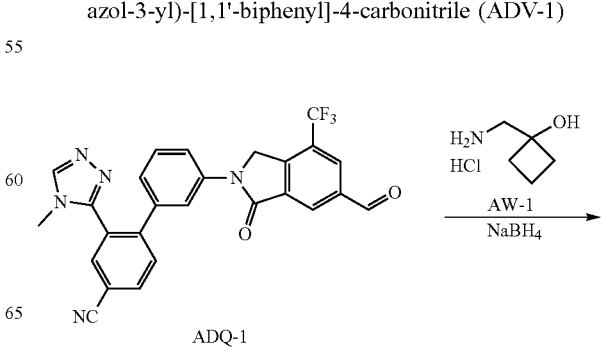

-continued

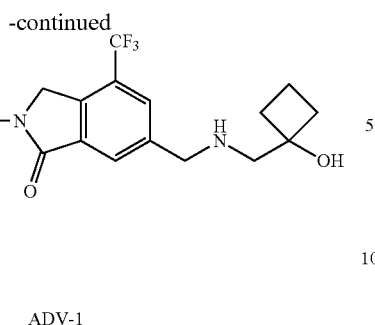

ADV-1

A solution of intermediate (ADQ-1) mg, 1 eq, 0.10 mmol) and 1-(aminomethyl) cyclobutan-1-ol (AW-1) (31 mg, 3 eq, 0.31 mmol) in MeOH (10 mL) was stirred for 1 h at 60° C. To the above mixture was added NaBH$_4$ (8 mg, 2 eq, 0.21 mmol) at 0° C. The resulting mixture was stirred for 1 h at rt. The reaction was quenched with H$_2$O (1 mL) at 0° C. and concentrated in vacuo. The residue was purified by Prep-TLC with DCM/MeOH (8/1). The crude product was purified by Prep-HPLC with the following conditions (Column: Sunfire prep C18 column, 30*150 mm, 5 μm; Mobile Phase A: water (0.1% FA), Mobile Phase B: MeCN; Flow rate: 60 mL/min; Gradient: 5% B to 25% B in 10 min; Wave Length: 254/220 nm) to afford the title compound (ADV-1) (17.5 mg, 30 μmol, 30%, 99% Purity) as a white solid. m/z 573.0 (M+H)$^+$ (ES+). $^1$H NMR (400 MHz, DMSO-d6) δ 8.46 (s, 1H), 8.21 (d, J=1.8 Hz, 1H), 8.19 (d, J=1.9 Hz, 1H), 8.13 (d, J=1.8 Hz, 1H), 8.05 (d, J=12.6 Hz, 3H), 7.90 (d, J=8.1 Hz, 1H), 7.73 (d, J=2.4 Hz, 1H), 7.42 (t, J=8.0 Hz, 1H), 6.93 (d, J=7.7 Hz, 1H), 5.10 (s, 2H), 4.97 (s, 1H), 3.98 (s, 2H), 3.17 (s, 3H), 2.55 (s, 2H), 2.06-1.86 (m, 4H), 1.66-1.59 (m, 1H), 1.48-1.34 (m, 1H).

Example 148: Synthesis of N-[2-Amino-5-({[(1R, 2S)-2-hydroxycyclopentyl] amino} methyl)-3-(trifluoromethyl)phenyl]-4'-cyano-2'-(4-methyl-1,2,4-triazol-3-yl)-[1,1'-biphenyl]-3-carboxamide (ADW-5)

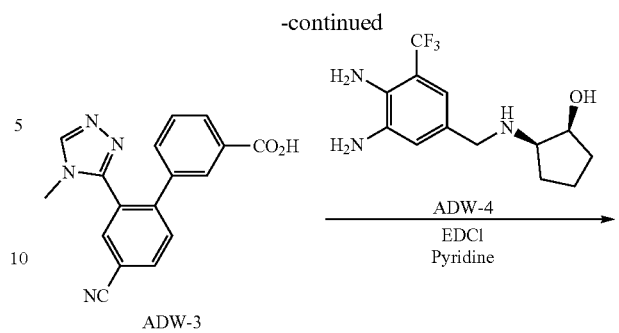

Step 1: Synthesis of tert-Butyl 4'-cyano-2'-(4-methyl-1,2,4-triazol-3-yl)-[1,1'-biphenyl]-3-carboxylate (ADW-2)

To a solution of intermediate (ADG-1) (160 mg, 1 Eq, 608 μmol) and (3-(tert-butoxycarbonyl)phenyl)boronic acid (ADW-1) (135 mg, 1 Eq, 608 μmol) in dioxane (5 mL) and water (1 mL) were added K$_2$CO$_3$ (252 mg, 3 Eq, 1.82 mmol) and Pd(dppf)Cl$_2$-DCM (45 mg, 0.1 Eq, 61 μmol) at rt under nitrogen atmosphere. After stirring for 3 hours at 80° C. under nitrogen atmosphere, the mixture was allowed to cool down to rt. The resulting mixture was diluted with water and extracted with EtOAc (3×20 mL). The combined organic layers were washed with brine (2×20 mL), dried (Na$_2$SO$_4$). After filtration, the filtrate was concentrated in vacuo. The residue was purified by TLC with DCM/MeOH (12/1) to afford the sub-title compound (ADW-2) (150 mg, 417 μmol, 68%) as a yellow solid. m/z 361.2 (M+H)$^+$ (ES+).

Step 2: Synthesis of 4'-Cyano-2'-(4-methyl-1,2,4-triazol-3-yl)-[1,1'-biphenyl]-3-carboxylic acid (ADW-3)

To a stirred solution of the product from step 1 above (ADW-2) (145 mg, 1 Eq, 402 μmol) in DCM (3 mL) was added TFA (1 mL) dropwise at rt. The resulting mixture was stirred for 1 hour at rt. The resulting mixture was concentrated in vacuo. The crude product was used in the next step directly without further purification. m/z 305.1 (M+H)$^+$ (ES+).

Step 3: Synthesis of N-[2-Amino-5-({[(1R,2S)-2-Hydroxycyclopentyl]amino}methyl)-3-(trifluoromethyl)phenyl]-4'-cyano-2'-(4-methyl-1,2,4-triazol-3-yl)-[1,1'-biphenyl]-3-carboxamide (ADW-5)

To a stirred solution of the product from step 2 above (ADW-3) (20 mg, 1 eq, 66 μmol) and (1S,2R)-2-({[3,4-diamino-5-(trifluoromethyl)phenyl]methyl}amino)cyclopentan-1-ol (ADW-4) (19 mg, 1 eq, 66 μmol) in pyridine (1.5 mL) was added EDCI (26 mg, 2 eq, 0.13 mmol) at rt. The resulting mixture was stirred for 2 h at 60° C. The mixture was allowed to cool down to rt and concentrated in vacuo. The crude product was purified by Prep-HPLC with the following conditions (Column: XBridge Prep OBD C18 Column, 30*150 mm, 5 μm; Mobile Phase A: Water (0.1% NH$_4$HCO$_3$), Mobile Phase B: MECN; Flow rate: 60 mL/min; Gradient: 28% B to 38% B in 8 min; Wave Length: 254/220 nm) to afford the title compound (ADW-5) (2.9 mg, 5.0 μmol, 7.7%, 99% Purity) as a white solid. m/z 576.0 (M+H)$^+$ (ES+) $^1$H NMR (400 MHz, DMSO-d6) δ 9.84 (s, 1H), 8.49 (s, 1H), 8.24-8.17 (m, 1H), 8.14 (d, J=1.7 Hz, 1H), 8.03-7.91 (m, 3H), 7.48-7.30 (m, 3H), 7.16 (d, J=7.7 Hz, 1H), 5.19 (s, 2H), 4.39 (s, 1H), 3.99-3.91 (m, 1H), 3.70-3.54 (m, 2H), 3.16 (s, 3H), 2.77 (d, J=5.8 Hz, 1H), 1.74-1.48 (m, 4H), 1.46-1.31 (m, 2H).

Example 149: Synthesis of 4-[2-(Ethylamino)-6-[6-(hydroxymethyl)-1-oxo-4-(trifluoromethyl)-3H-isoindol-2-yl] pyridin-4-yl]-3-(4-methyl-1,2,4-triazol-3-yl) benzonitrile (ADX-2)

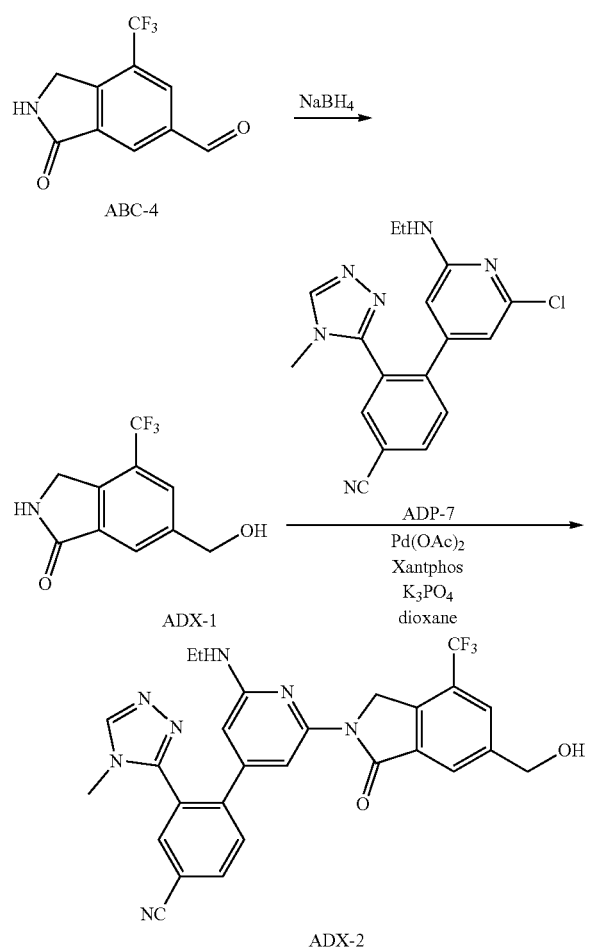

Step 1: Synthesis of 6-(Hydroxymethyl)-4-(trifluoromethyl)-2,3-dihydroisoindol-1-one (ADX-1)

To a stirred solution of intermediate (ABC-4) (90 mg, 1 eq, 0.39 mmol) and NaBH$_4$ (45 mg, 3 eq, 1.18 mmol) in MeOH (10 mL) at rt. The resulting mixture was stirred for 2 h at rt. The crude product was purified by reverse flash column chromatography with the following conditions: Column, C18; mobile phase, water (0.1% NH$_4$HCO$_3$) and MeCN (0% MeCN up to 40% in 24 min); Detector, UV 254/220 nm. This resulted in the sub-title compound (ADX-1) (70 mg, 0.29 mmol, 77%, 95% Purity) as an off-white solid. m/z 232.1 (M+H)$^+$ (ES+).

Step 2: Synthesis of 4-[2-(Ethylamino)-6-[6-(hydroxymethyl)-1-oxo-4-(trifluoromethyl)-3H-isoindol-2-yl] pyridin-4-yl]-3-(4-methyl-1,2,4-triazol-3-yl)benzonitrile (ADX-2)

To a stirred solution of the product from step 1 above (ADX-1) (50 mg, 1 eq, 0.22 mmol), intermediate (ADP-7) (88 mg, 1.2 eq, 0.26 mmol) and K$_3$PO$_4$ (138 mg, 3 eq, 0.65 mmol) in 1,4-dioxane (5 mL) were added Xantphos (25 mg, 0.2 eq, 43 μmol) and Pd(OAc)$_2$ (5 mg, 0.1 eq, 22 μmol) at rt under nitrogen atmosphere. The resulting mixture was stirred for 6 h at 100° C. under nitrogen atmosphere. The crude product was purified by reverse flash column chromatography with the following conditions: Column, C18; mobile phase, water (0.1% NH$_4$HCO$_3$) and MeCN (0% MeCN up to 50% in 25 min); Detector, UV 254/220 nm. The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 33% B to 44% B in 11 min; Wave Length: 254/220 nm) to afford the title compound (ADX-2) (7.2 mg, 13 μmol, 6.2%, 99% Purity) as a light yellow solid. m/z 534.2 (M+H)$^+$ (ES+). $^1$H NMR (400 MHz, MeOH-d4) δ 8.50 (s, 1H), 8.16-8.04 (m, 3H), 7.98-7.87 (m, 2H), 7.53 (d, J=1.3 Hz, 1H), 6.08 (d, J=1.3 Hz, 1H), 5.22 (s, 2H), 4.81 (s, 2H), 3.48 (s, 3H), 3.29 (t, J=7.2 Hz, 2H), 1.23 (t, J=7.2 Hz, 3H).

Example 150: Synthesis of 2-[6-(Ethylamino)-4-[2-methyl-4-(4-methyl-1,2,4-triazol-3-yl)pyrazol-3-yl] pyridin-2-yl]-6-[(2-hydroxy-2-methylpropoxy) methyl]-4-(trifluoromethyl)-3H-isoindol-1-one (ADY-2)

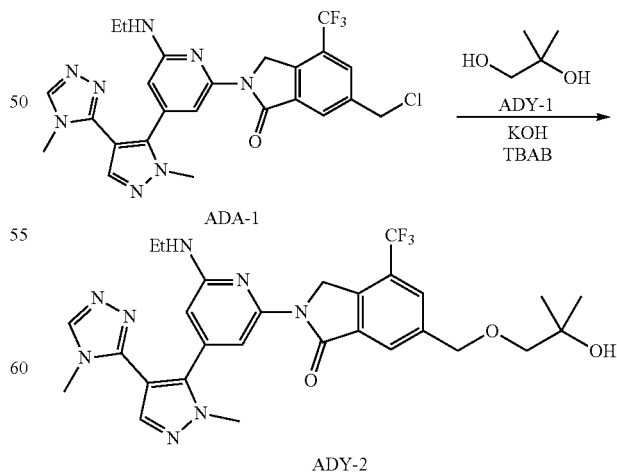

To a stirred solution of intermediate (ADA-1) (40 mg, 1 eq, 75 μmol) and 2-methyl-propane-1,2-diol (ADY-1) (68 mg, 10 eq, 0.75 mmol) in DCM (5 mL) were added TBAB (13 mg, 0.5 eq, 37 μmol) and aq. KOH (5 mL, 20% Wt) at rt. The resulting mixture was stirred slowly for 1 h at rt. The resulting mixture was diluted with water and extracted with EtOAc (3×10 mL). The combined organic layers were washed with brine (2×10 mL), dried (Na$_2$SO$_4$). After filtration, the filtrate was concentrated in vacuo. The residue was purified by TLC with DCM/MeOH (8/1). The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 35% B to 46% B in 9 min; Wave Length: 254/220 nm) to afford the title compound (ADY-2) (3.6 mg, 6.1 μmol, 8.2%, 99% Purity) as a white solid. m/z 585.0 (M+H)$^+$ (ES+). $^1$H NMR (400 MHz, MeOH-d4) δ 8.49 (s, 1H), 8.09 (s, 1H), 8.00 (s, 1H), 7.87 (s, 1H), 7.66 (d, J=1.2 Hz, 1H), 6.20 (d, J=1.2 Hz, 1H), 5.27 (s, 2H), 4.77 (s, 2H), 4.04 (s, 3H), 3.50 (s, 3H), 3.43-3.32 (m, 4H), 1.33-1.20 (m, 9H).

Example 151: Synthesis of 2-{6-Cyclopropyl-4-[2-(4-methyl-1,2,4-triazol-3-yl)phenyl]pyridin-2-yl}-6-({[(1-hydroxycyclobutyl)methyl]amino}methyl)-4-(trifluoromethyl)-3H-isoindol-1-one (ADZ-2)

Step 1: Synthesis of 2-Chloro-6-cyclopropyl-4-[2-(4-methyl-1,2,4-triazol-3-yl)-phenyl]-pyridine (ADZ-1)

To a stirred solution of intermediate (E-7) (450 mg, 1 Eq, 1.47 mmol) and cyclopropylboronic acid (ABF-2) (177 mg, 1.4 Eq, 2.06 mmol) in toluene (15 mL) were added potassium phosphate (939 mg, 3 Eq, 4.45 mmol), PCy$_3$ (62 mg, 0.1 Eq, 220 μmol) and Pd(AcO)$_2$ (50 mg, 0.1 Eq, 220 μmol) at rt under nitrogen atmosphere. The resulting mixture was stirred for 16 hours at 110° C. under nitrogen atmosphere. The mixture was cooled to rt and concentrated in vacuo. The crude product was purified by reverse flash column chromatography with the following conditions: C18 silica gel; mobile phase, Water (0.1% NH$_4$HCO$_3$) and MeCN (20% MeCN up to 40% in 10 min); Detector, UV 254 nm. This resulted in the sub-title compound (ADZ-1) (120 mg, 387 μmol, 26%) as a white solid. m/z 311.1/313.1 (M+H)$^+$ (ES+).

Step 2: Synthesis of 2-(6-Cyclopropyl-4-(2-(4-methyl-4H-1,2,4-triazol-3-yl)phenyl)pyridin-2-yl)-6-((((1-hydroxycyclobutyl)methyl)amino)methyl)-4-(trifluoromethyl)isoindolin-1-one (ADZ-2)

To a stirred solution of intermediate (ADR-2) (40 mg, 1 eq, 0.13 mmol), the product from step 1 above (ADZ-1) (40 mg, 1 eq, 0.13 mmol) and Cs$_2$CO$_3$ (83 mg, 0.25 mmol, 2 eq) in 1,4-dioxane (1 mL) were added RuPhos (24 mg, 0.4 eq, 51 μmol) and RuPhos palladacycle Gen.3 (21 mg, 0.2 eq, 25 μmol) at rt under nitrogen atmosphere. The resulting mixture was stirred for 2 h at 100° C. under nitrogen atmosphere. The mixture was cooled to rt and concentrated in vacuo. The crude product was purified by Prep-HPLC with the following conditions: Column: SunFire Prep C18 OBD Column, 19×150 mm, 5 μm; Mobile Phase A: water (0.1% FA), Mobile Phase B: MeCN; Flow rate: 60 mL/min; Gradient: 30 B to 60 B in 7 min; Detector, UV 254/210 nm; RT: 6.08. This resulted in the title compound (ADZ-2) (17.3 mg, 29 μmol, 23%, 98% Purity) as a white solid. m/z 589.4 (M+H)$^+$ (ES+). $^1$H NMR (400 MHz, MeOH-d4) δ 8.20 (s, 1H), 8.14 (s, 1H), 8.08 (d, J=1.4 Hz, 1H), 7.84-7.76 (m, 1H), 7.80-7.70 (m, 2H), 7.73-7.63 (m, 2H), 6.94 (d, J=1.4 Hz, 1H), 5.24 (s, 2H), 4.33 (s, 2H), 3.45 (s, 3H), 3.06 (s, 2H), 2.22-2.12 (m, 4H), 2.12-2.01 (m, 1H), 1.85-1.73 (m, 1H), 1.65-1.53 (m, 1H), 1.02 (d, J=6.4 Hz, 4H).

Example 152: Synthesis of 3'-(6-{[(2-Hydroxyethyl)amino]methyl}-1-oxo-4-(trifluoromethyl)-3H-isoindol-2-yl)-2-(4-methyl-1,2,4-triazol-3-yl)-[1,1'-biphenyl]-4-carbonitrile (AEA-2)

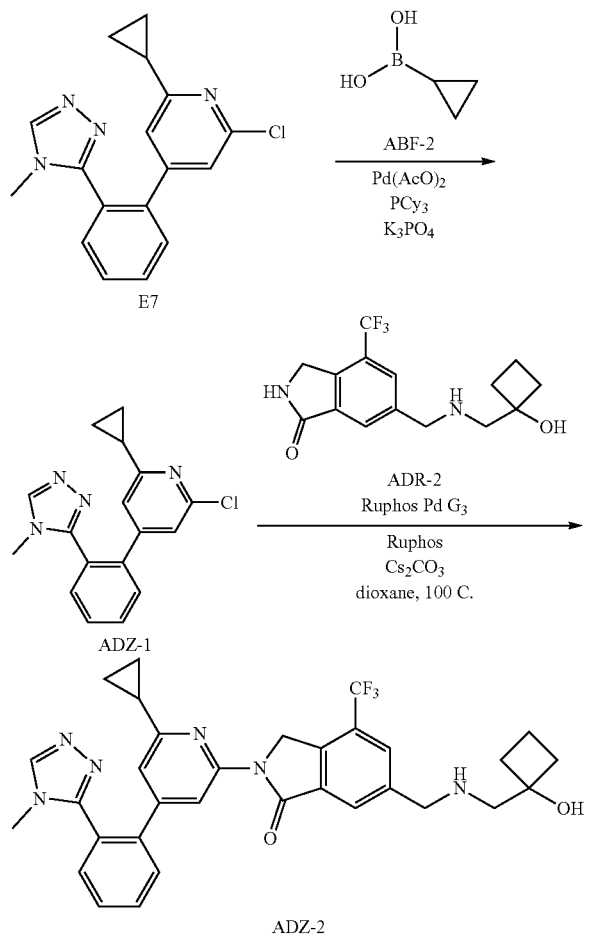

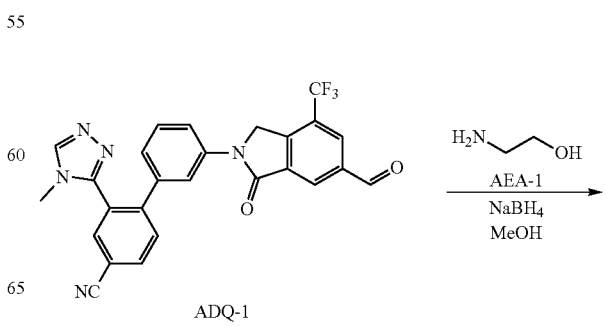

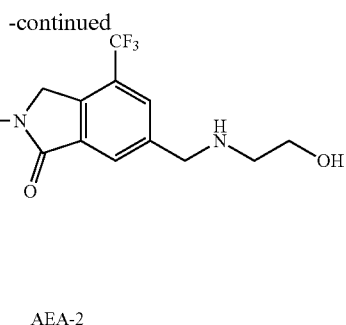

AEA-2

A solution of intermediate (ADQ-1) (20 mg, 1 eq, 41 μmol) and ethanolamine (AEA-1) (26 mg, 10 eq, 0.41 mmol) in MeOH (5 mL) was stirred for 0.5 h at 60° C. To the above mixture was added NaBH$_4$ (4 mg, 2 eq, 82 μmol) at 0° C. The resulting mixture was stirred for additional 1 h at rt. The reaction was quenched with H$_2$O (1 mL) at 0° C. and concentrated in vacuo. The residue was purified by TLC with DCM/MeOH (8/1). The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 28% B to 37% B in 9 min; Wave Length: 254/220 nm) to afford the title compound (AEA-2) (10.0 mg, 18 μmol, 45%, 97% Purity) as a white solid. m/z 533.0 (M+H)$^+$ (ES+). $^1$H NMR (400 MHz, MeOH-d4) δ 8.44 (s, 1H), 8.15-8.08 (m, 2H), 8.08-8.00 (m, 2H), 7.97-7.90 (m, 2H), 7.85-7.79 (m, 1H), 7.49 (t, J=8.0 Hz, 1H), 7.16-7.08 (m, 1H), 5.08 (s, 2H), 4.01 (s, 2H), 3.71 (t, J=5.6 Hz, 2H), 3.24 (s, 3H), 2.77 (t, J=5.6 Hz, 2H).

Example 153: Synthesis of 3'-(6-(((2-Methoxyethyl)amino)methyl)-1-oxo-4-(trifluoromethyl)isoindolin-2-yl)-2-(4-methyl-4H-1,2,4-triazol-3-yl)-[1,1'-biphenyl]-4-carbonitrile (AEB-2)

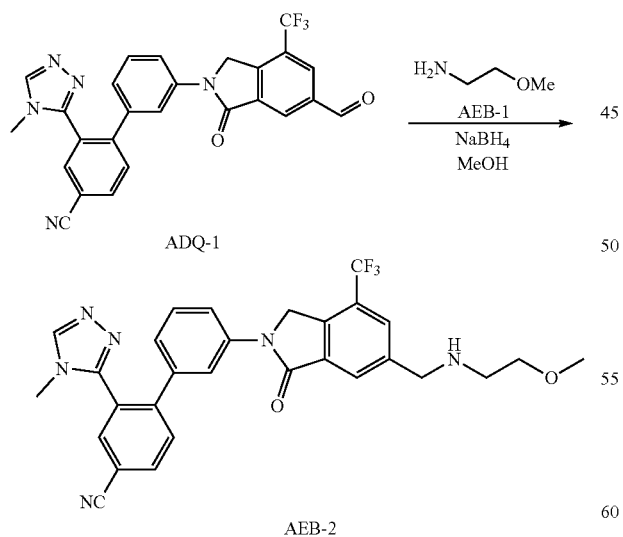

A solution of intermediate (ADQ-1) (20 mg, 1 eq, 41 μmol) and 2-methoxyethylamine (AEB-1) (31 mg, 10 eq, 0.41 mmol) in MeOH (5 mL) was stirred for 0.5 h at 60° C. To the above mixture was added NaBH$_4$ (4 mg, 2 eq, 82 μmol) at 0° C. The resulting mixture was stirred for 1 h at rt. The reaction was quenched with H$_2$O at 0° C. and concentrated in vacuo. The residue was purified by TLC with DCM/MeOH (8/1). The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 34% B to 44% B in 8 min; Wave Length: 254/220 nm) to afford the title compound (AEB-2) (5.4 mg, 9.4 μmol, 23%, 95% Purity) as a white solid. m/z 547.0 (M+H)$^+$ (ES+). $^1$H NMR (400 MHz, MeOH-d4) δ 8.44 (s, 1H), 8.14-8.08 (m, 2H), 8.07-8.00 (m, 2H) 7.97-7.90 (m, 2H), 7.83 (t, J=2.0 Hz, 1H), 7.49 (t, J=8.0 Hz, 1H), 7.12 (d, J=7.6 Hz, 1H), 5.09 (s, 2H), 4.00 (s, 2H), 3.55 (t, J=5.3 Hz, 2H), 3.38 (s, 3H), 3.24 (s, 3H), 2.80 (t, J=5.3 Hz, 2H).

Example 154: Synthesis of 4-[2-(Ethylamino)-6-(6-{1[(2-methoxyethyl)amino] methyl}-1-oxo-4-(trifluoromethyl)-3H-isoindol-2-yl)pyridin-4-yl]-3-(4-methyl-1,2,4-triazol-3-yl)benzonitrile (AEC-2)

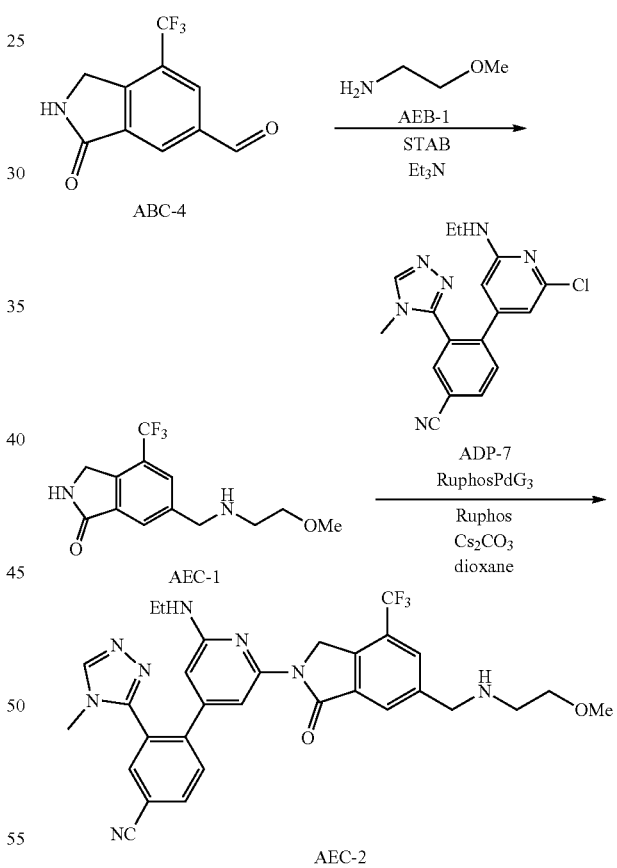

Step 1: Synthesis of 6-{[(2-Methoxyethyl)amino]methyl}-4-(trifluoromethyl)-2,3-dihydroisoindol-1-one (AEC-1)

A stirred solution of 2-methoxyethan-1-amine (AEB-1) (52 mg, 0.52 μmol, 1.2 eq) and Et$_3$N (66 mg, 1.5 eq, 0.65 mmol) in DCM (5 mL) was stirred for 10 min at rt. To the above mixture was added intermediate (ABC-4) (100 mg, 1 eq, 0.44 mmol) at rt. The resulting mixture was stirred for 2 h at rt. To the above mixture was added NaBH(OAc)₃ (462 mg, 5 eq, 2.18 mmol) at rt. The resulting mixture was stirred for overnight at rt. The crude product was purified by reverse flash column chromatography with the following conditions: Column, C18; mobile phase, water (0.1% NH₄HCO₃) and MeCN (0% MeCN up to 50% in 20 min); Detector, UV 254/220 nm. This resulted in the sub-title compound (AEC-1) (80 mg, 0.26 mmol, 64%, 94% Purity) as an off-white solid. m/z 289.1 (M+H)⁺ (ES+).

Step 2: 4-[2-(Ethylamino)-6-(6-{[(2-methoxyethyl) amino]methyl}-1-oxo-4-(trifluoromethyl)-3H-isoindol-2-yl)pyridin-4-yl]-3-(4-methyl-1,2,4-triazol-3-yl) benzonitrile (AEC-2)

To a stirred solution of intermediate (ADP-7) (40 mg, 1 eq, 0.12 mmol), the product from step 1 above (AEC-1) (41 mg, 1.2 eq, 0.14 µmol) and Cs₂CO₃ (77 mg, 2 eq, 0.24 mmol) in 1,4-dioxane (5 mL) was added RuPhos palladacycle Gen.3 (20 mg, 0.2 eq, 24 µmol) and RuPhos (22 mg, 0.4 eq, 47 µmol) at rt under nitrogen atmosphere. The resulting mixture was stirred for 3 h at 100° C. under nitrogen atmosphere. The mixture was allowed to cool down to rt. The crude product was purified by reverse flash column chromatography with the following conditions: Column, C18; mobile phase, water (0.1% NH₄HCO₃) and MeCN (0% MeCN up to 50% in 20 min); Detector, UV 254/220 nm. The crude product was purified by Prep-HPLC with the following conditions (Column: XBridge Prep OBD C18 Column, 30*150 mm, 5 µm; Mobile Phase A: water (0.1% NH₄HCO₃), Mobile Phase B: MeCN; Flow rate: 60 mL/min; Gradient: 40% B to 50% B in 9 min; Wave Length: 254/220 nm) to afford the title compound (AEC-2) (10 mg, 16 µmol, 14%, 96% Purity) as a light yellow solid. m/z 591.5 (M+H)⁺ (ES+). ¹H NMR (400 MHz, MeOH-d4) δ 8.49 (s, 1H), 8.13-8.01 (m, 4H), 7.90 (d, J=8.1 Hz, 1H), 7.53 (d, J=1.3 Hz, 1H), 6.08 (d, J=1.3 Hz, 1H), 5.22 (s, 2H), 4.07 (s, 2H), 3.58 (t, J=5.3 Hz, 2H), 3.47 (s, 3H), 3.39 (s, 3H), 3.29 (t, J=7.2 Hz, 2H), 2.89 (t, J=5.3 Hz, 2H), 1.23 (t, J=7.2 Hz, 3H).

Example 155: Synthesis of 2-[6-(Ethylamino)-4-[2-methyl-4-(4-methyl-1,2,4-triazol-3-yl)pyrazol-3-yl] pyridin-2-yl]-6-{[(1-hydroxycyclobutyl) methoxy]methyl}-4-(trifluoromethyl)-3H-isoindol-1-one (AED-2)

To a stirred solution of intermediate (ADA-1) (46 mg, 1 eq, 87 µmol) and 1-(hydroxymethyl) cyclobutan-1-ol (AED-1) (89 mg, 10 eq, 0.87 mmol) in DCM (5 mL) were added TBAB (14 mg, 0.5 eq, 43 µmol) and aq. KOH (5 mL, 20% Wt) at rt. The resulting mixture was stirred slowly for 1 h at rt. The resulting mixture was diluted with water and extracted with EtOAc (3×20 mL). The combined organic layers were washed with brine (2×20 mL), dried (Na₂SO₄). After filtration, the filtrate was concentrated in vacuo. The residue was purified by TLC with DCM/MeOH (8/1). The crude product was purified by Prep-HPLC with the following conditions (Column: XBridge Prep OBD C18 Column, 30*150 mm, 5 µm; Mobile Phase A: water (0.1% NH₄HCO₃), Mobile Phase B: MeCN; Flow rate: 60 mL/min; Gradient: 41% B to 51% B in 8 min; Wave Length: 254/220 nm) to afford the title compound (AED-2) (4.8 mg, 8.0 µmol, 9.3%, 99% Purity) as a white solid. m/z 597.1 (M+H)⁺ (ES+). ¹H NMR (400 MHz, MeOH-d4) δ 8.50-8.44 (m, 1H), 8.08 (s, 1H), 8.00 (s, 1H), 7.84 (s, 1H), 7.64 (d, J=1.2 Hz, 1H), 6.18 (d, J=1.2 Hz, 1H), 5.25 (s, 2H), 4.78 (s, 2H), 4.01 (s, 3H), 3.57 (s, 2H), 3.48 (s, 3H), 3.40-3.32 (m, 2H), 2.21-2.11 (m, 2H), 2.11-1.99 (m, 2H), 1.84-1.70 (m, 1H), 1.63-1.51 (m, 1H), 1.23 (t, J=7.2 Hz, 3H).

Example 156: Synthesis of 2-[6-(Ethylamino)-4-[2-methyl-4-(4-methyl-1,2,4-triazol-3-yl)pyrazol-3-yl] pyridin-2-yl]-6-({[(1-hydroxycyclobutyl)methyl] amino}methyl)-3H-isoindol-1-one (AEE-2)

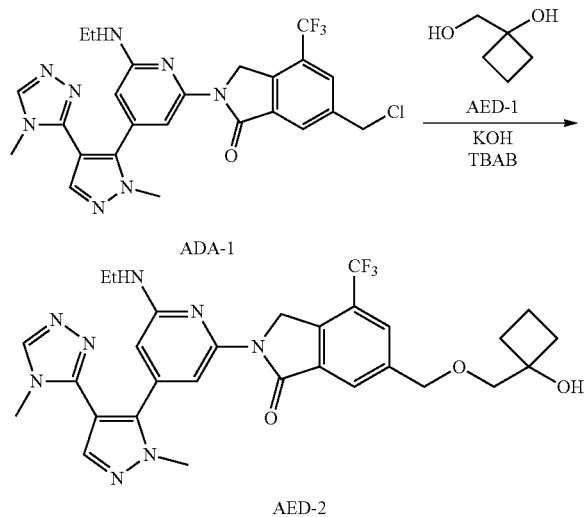

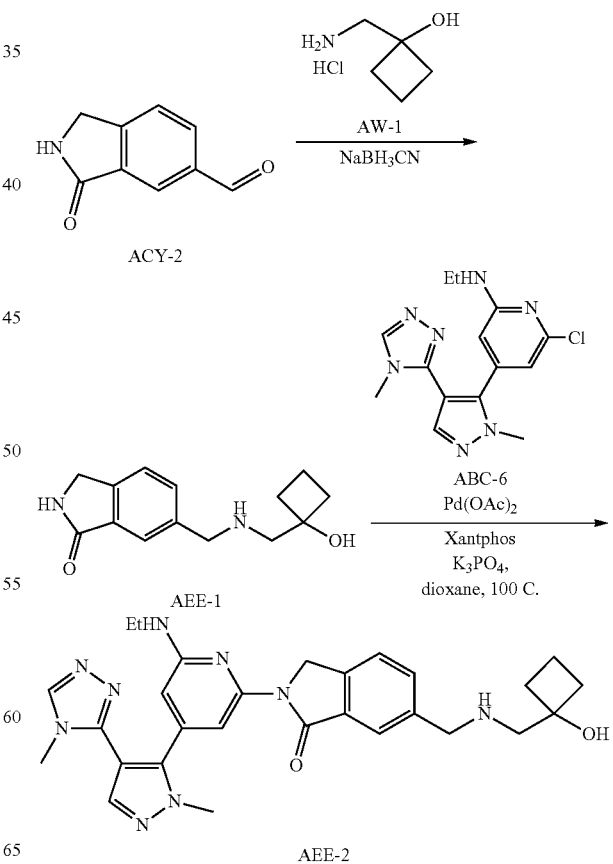

Step 1: Synthesis of 6-({[(1-Hydroxycyclobutyl)methyl]amino}methyl)-2,3-dihydroisoindol-1-one (AEE-1)

To a stirred solution of intermediate (ACY-2) (170 mg, 1 eq, 1.06 mmol) and 1-(aminomethyl)cyclobutan-1-ol (AW-1) (213 mg, 2 eq, 2.11 mmol) in MeOH (10 mL) was added NaBH$_3$CN (265 mg, 4 eq, 4.22 mmol) and AcOH (63 mg, 1 eq, 1.06 mmol) at rt under nitrogen atmosphere. The resulting mixture was stirred for 2 h at rt under nitrogen atmosphere. The crude product was purified by reverse flash column chromatography with the following conditions: Column, C18; mobile phase, water (0.1% NH$_4$HCO$_3$) and MeCN (0% MeCN up to 40% in 15 min); Detector, UV 254/220 nm. This resulted in the sub-title compound (AEE-1) (120 mg, 0.46 mmol, 46%, 95% Purity) as a white solid. m/z 247.1 (M+H)$^+$ (ES+).

Step 2: Synthesis of 2-[6-(Ethylamino)-4-[2-methyl-4-(4-methyl-1,2,4-triazol-3-yl)pyrazol-3-yl]pyridin-2-yl]-6-({[(1-hydroxycyclobutyl)methyl]amino}methyl)-3H-isoindol-1-one (AEE-2))

To a stirred solution of intermediate (ABC-6) (50 mg, 1 eq, 0.16 mmol), the product from step 1 above (AEE-1) (39 mg, 1 eq, 0.16 mmol) and K$_3$PO$_4$ (67 mg, 0.31 mmol, 2 eq) in 1,4-dioxane (5 mL) were added XantPhos (18 mg, 0.2 eq, 31 µmol) and Pd(OAc)$_2$ (3.5 mg, 0.1 eq, 16 µmol) at rt under nitrogen atmosphere. The resulting mixture was stirred for 2 h at 100° C. under nitrogen atmosphere. The mixture was cooled to rt and concentrated in vacuo. The crude product was purified by reverse flash column chromatography with the following conditions: Column, C18; mobile phase, water (0.1% FA) and MeCN (5% MeCN up to 50% in 15 min); Detector, UV 254/220 nm. The product-containing fractions were combined and concentrated in vacuo. The crude product was purified by Prep-HPLC with the following conditions: Column: Sunfire prep C18 column 30*150 mm, 5 µm; Mobile Phase A: water (0.1% FA), Mobile Phase B: MeCN; Flow rate: 60 mL/min; Gradient: 10% B to 35% B in 10 min; Detector, UV 254/220 nm; RT:6.7. The product-containing fractions were combined and evaporated partially in vacuo and lyophilized overnight to afford the title compound (AEE-2) (10.3 mg, 19 µmol, 12%, 98 Purity) as a white solid. m/z 528.3 (M+H)$^+$ (ES+). $^1$H NMR (400 MHz, DMSO-d6) δ 8.47 (s, 1H), 8.24 (s, 2H), 7.88 (s, 1H), 7.76 (s, 1H), 7.66 (d, J=1.2 Hz, 2H), 7.57 (d, J=1.2 Hz, 1H), 6.86 (t, J=5.4 Hz, 1H), 6.20 (d, J=1.2 Hz, 1H), 5.05 (s, 2H), 3.89 (s, 5H), 3.53-3.42 (m, 4H), 2.55 (s, 3H), 2.45 (s, 2H), 2.05-1.83 (m, 2H), 1.64-1.57 (m, 1H), 1.44-1.32 (m, 1H), 1.26-1.10 (m, 3H).

Example 157: Synthesis of 2-(6-(Ethylamino)-4-(4-fluoro-2-(4-methyl-4H-1,2,4-triazol-3-yl)phenyl)pyridin-2-yl)-6-(hydroxymethyl)-4-(trifluoromethyl)isoindolin-1-one (AEF-1)

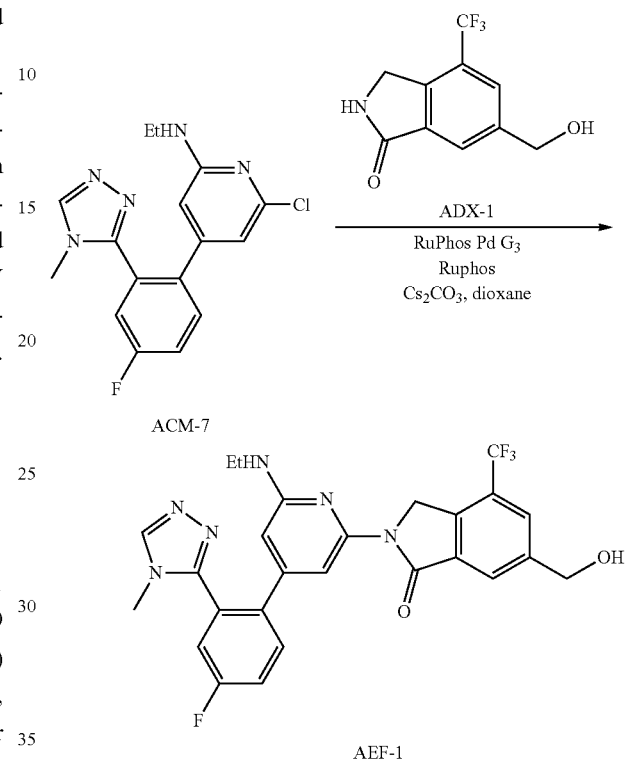

To a stirred mixture of intermediate (ACM-7) (50 mg, 1 eq, 0.15 mmol), intermediate (ADX-1) (35 mg, 1 eq, 0.15 mmol) and Cs$_2$CO$_3$ (98 mg, 2 eq, 0.30 mmol) in 1,4-dioxane (3 mL) were added Ruphos (28 mg, 0.4 eq, 60 µmol) and RuPhos palladacycle Gen.3 (25 mg, 0.2 eq, 30 µmol) at rt under nitrogen atmosphere. The resulting mixture was stirred for 2 h at 100° C. under nitrogen atmosphere. The mixture was allowed to cool down to rt. The resulting mixture was diluted with water. The resulting mixture was extracted with EtOAc (3×10 mL). The combined organic layers were washed with brine (2×10 mL), dried (Na$_2$SO$_4$). After filtration, the filtrate was concentrated in vacuo. The crude product was purified by Prep-HPLC with the following conditions: Column: XBridge Prep OBD C18 Column, 30*150 mm, 5 µm; Mobile Phase A: water (0.1% NH$_4$HCO$_3$), Mobile Phase B: MeCN; Flow rate: 60 mL/min; Gradient: 42% B to 52% B in 8 min, UV 254/220 nm; RT: 7.07. This resulted in the title compound (AEF-1) (29.6 mg, 56 µmol, 37%, 99% Purity) as a off-white solid. m/z 527.0 (M+H)$^+$ (ES+) $^1$H NMR (400 MHz, DMSO-d6) δ 8.50 (s, 1H), 7.97 (d, J=20.4 Hz, 2H), 7.65 (d, J=8.6, 5.8 Hz, 1H), 7.57 (td, J=8.5, 2.7 Hz, 1H), 7.53-7.50 (m, 1H), 7.46 (d, J=1.2 Hz, 1H), 6.71 (t, J=5.4 Hz, 1H), 5.92 (d, J=1.2 Hz, 1H), 5.59 (t, J=5.8 Hz, 1H), 5.16 (s, 2H), 4.70 (d, J=5.4 Hz, 2H), 3.38 (s, 3H), 3.21-3.14 (m, 2H), 1.13 (t, J=7.2 Hz, 3H).

Example 158: Synthesis of 4-{2-Cyclopropyl-6-[1-oxo-4-(trifluoromethyl)-3H-isoindol-2-yl]pyridin-4-yl}-3-(4-methyl-1,2,4-triazol-3-yl)benzonitrile (AEG-3)

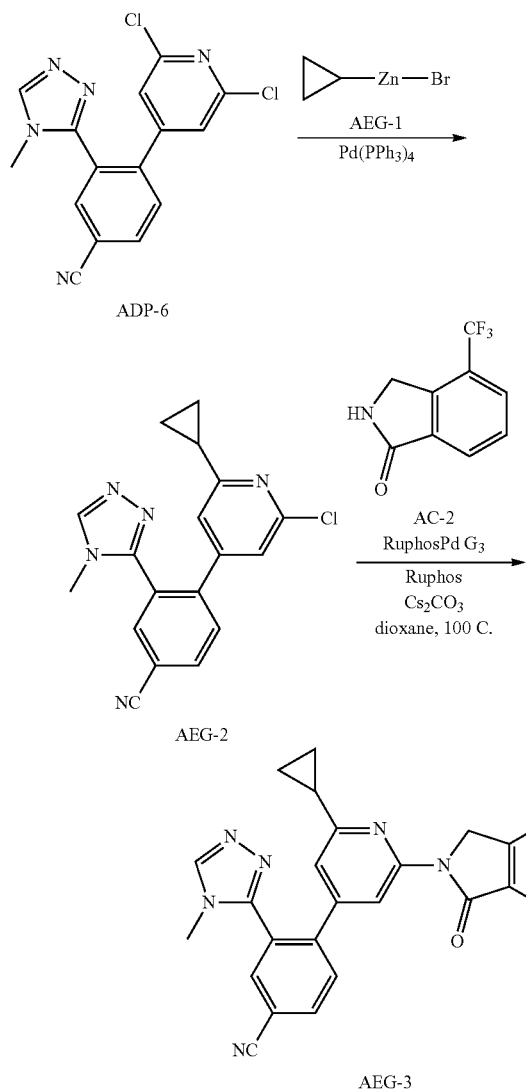

Step 1: Synthesis of 4-(2-Chloro-6-cyclopropylpyridin-4-yl)-3-(4-methyl-1,2,4-triazol-3-yl)benzonitrile (AEG-2)

To a stirred mixture of intermediate (ADP-6) (80 mg, 1 eq, 0.24 mmol) and bromo(cyclopropyl)zinc (AEG-1) (226 mg, 5 eq, 1.21 mmol) in THF (3 mL) were added Pd(PPh$_3$)$_4$ (56 mg, 0.2 eq, 48 μmol) at rt under nitrogen atmosphere. The resulting mixture was stirred for 2 h at 100° C. under nitrogen atmosphere. The mixture was allowed to cool down to rt. The reaction was then quenched by the addition of 2 mL of ice water at 0° C. The crude product was purified by reverse flash column chromatography with the following conditions: Column, C18; mobile phase, water (0.1% NH$_4$HCO$_3$) and MeCN (10% MeCN up to 60% in 25 min); Detector, UV 254/220 nm to afford the sub-title compound (AEG-2) (25 mg, 69 μmol, 31%, 93% Purity) as a white solid. m/z 336.1/338.1 (M+H)$^+$ (ES+).

Step 2: Synthesis of 4-{2-Cyclopropyl-6-[1-oxo-4-(trifluoromethyl)-3H-isoindol-2-yl]pyridin-4-yl}-3-(4-methyl-1,2,4-triazol-3-yl)benzonitrile (AEG-3)

To a stirred solution of the product from step 1 above (AEG-2) (13 mg, 1 eq, 39 μmol), intermediate (AC-2) (9.3 mg, 1.2 eq, 47 μmol) and Cs$_2$CO$_3$ (25 mg, 2 eq, 78 μmol) in 1,4-dioxane (2 mL) were added RuPhos (7.2 mg, 0.4 eq, 16 μmol) and RuPhos palladacycle Gen.3 (6.5 mg, 0.2 eq, 8 μmol) at rt under nitrogen atmosphere. The resulting mixture was stirred for 1 h at 100° C. under nitrogen atmosphere. The mixture was cooled to rt and concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MECN; Flow rate: 60 mL/min; Gradient: 50% B to 60% B in 9 min; Wave Length: 254/220 nm; RT: 8.25) to afford the title compound (AEG-3) (3.1 mg, 6 μmol, 16%, 98% Purity) as a white solid. m/z 501.0 (M+H)$^+$ (ES+). $^1$H NMR (300 MHz, DMSO-d6) δ 8.54 (s, 1H), 8.26-8.17 (m, 2H), 8.15-7.96 (m, 3H), 7.91-7.75 (m, 2H), 6.89 (s, 1H), 5.19 (s, 2H), 3.46 (s, 3H), 2.06 (d, J=8.6 Hz, 1H), 1.04-1.88 (m, 4H).

Example 159: Synthesis of 2-{6-Cyclopropyl-4-[2-(4-methyl-1,2,4-triazol-3-yl)phenyl]pyridin-2-yl}-6-({[(1-hydroxycyclobutyl)methyl]amino}methyl)-3H-isoindol-1-one (AEH-1)

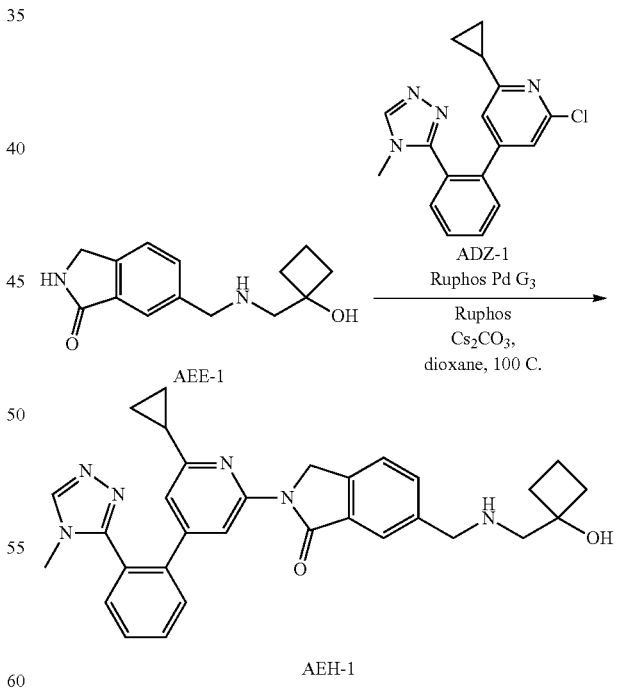

To a stirred solution of intermediate (AEE-1) (40 mg, 1 eq, 0.16 mmol), intermediate (ADZ-1) (50 mg, 1 eq, 0.16 mmol) and Cs$_2$CO$_3$ (106 mg, 0.32 mmol, 2 eq) in 1,4-dioxane (5 mL) were added RuPhos (30 mg, 0.4 eq, 0.06 mmol) and RuPhos palladacycle Gen.3 (27 mg, 0.2 eq, 0.03 mmol) at rt under nitrogen atmosphere. The resulting mixture was stirred for 2 h at 100° C. under nitrogen atmosphere. The mixture was cooled to rt and concentrated in vacuo. The crude product was purified by reverse flash column chromatography with the following conditions: Column, C18; mobile phase, Water (0.1% NH$_4$HCO$_3$) and MeCN (50% MeCN up to 80% in 15 min); Detector, UV 254/220 nm. The product-containing fractions were combined and concentrated in vacuo. The crude product was purified by Prep-HPLC with the following conditions: Column: XBridge Prep OBD C18 Column, 30×150 mm 5 um; Mobile Phase A: water (0.1% NH$_4$HCO$_3$), Mobile Phase B: MeCN; Flow rate:60 mL/min; Gradient:72 B to 82 B in 8 min; Detector, UV 254/210 nm; RT: 5.68. The product-containing fractions were combined and evaporated partially in vacuo and lyophilized overnight to afford the title compound (AEH-1) (20.8 mg, 39 μmol, 25%, 99% Purity) as a white solid. m/z 521.4 (M+H)$^+$ (ES+). $^1$H NMR (400 MHz, DMSO-d6) δ 8.48 (s, 1H), 8.21 (s, 1H), 8.03 (d, J=1.4 Hz, 1H), 7.81-7.73 (m, 2H), 7.74-7.59 (m, 5H), 6.79 (d, J=1.4 Hz, 1H), 5.01 (s, 2H), 3.89 (s, 2H), 3.38 (s, 3H), 2.57 (s, 2H), 2.08-1.97 (m, 3H), 1.93-1.84 (m, 2H), 1.63-1.51 (m, 1H), 1.42-1.28 (m, 1H), 0.95 (d, J=6.3 Hz, 4H).

Example 160: Synthesis of 2-{6-Cyclopropyl-4-[2-(4-methyl-1,2,4-triazol-3-yl)phenyl]pyridin-2-yl}-5-fluoro-6-({[(1-hydroxycyclobutyl)methyl]amino}methyl)-3H-isoindol-1-one (AEI-5)

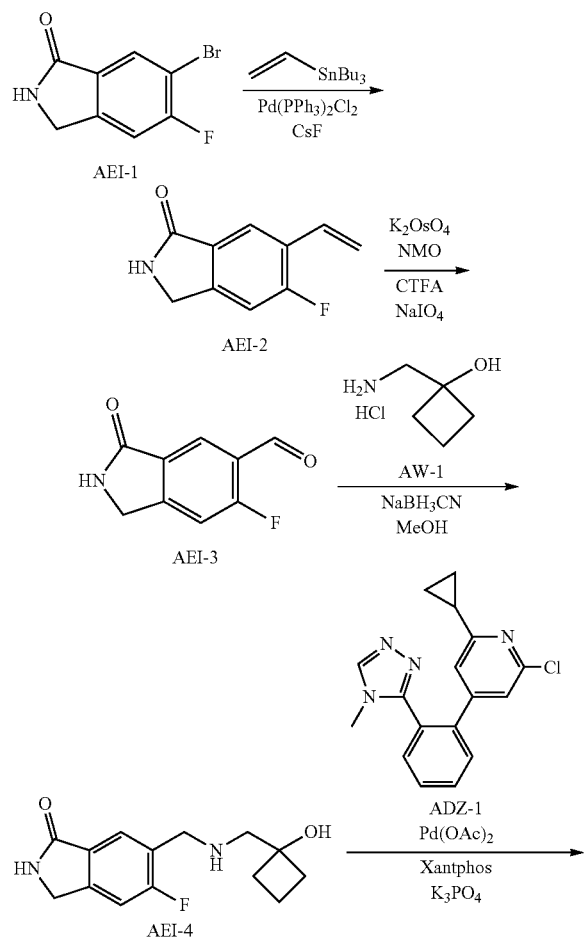

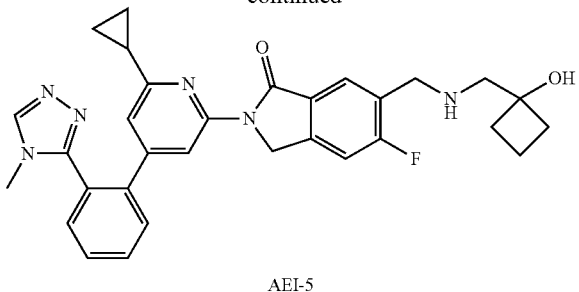

AEI-5

Step 1: Synthesis of 6-Ethenyl-5-fluoro-2,3-dihydroisoindol-1-one (AEI-2)

To a stirred solution of 6-bromo-5-fluoro-2,3-dihydroisoindol-1-one (AEI-1) (200 mg, 1 eq, 0.87 mmol), tributyl (ethenyl)stannane (331 mg, 1.2 eq, 1.04 mmol) and CsF (265 mg, 2 eq, 1.74 mmol) in 1,4-dioxane (3 mL) was added Pd(PPh$_3$)$_2$Cl$_2$ (61 mg, 0.1 eq, 87 μmol) at rt under nitrogen atmosphere. The resulting mixture was stirred for 2 h at 100° C. under nitrogen atmosphere. The mixture was allowed to cool down to rt. The crude product was purified by reverse flash column chromatography with the following conditions: Column, C18; mobile phase, water (0.1% NH$_4$HCO$_3$) and MeCN (30% MeCN up to 50% in 10 min); Detector, UV 254/220 nm. The product-containing fractions were combined and concentrated in vacuo. This resulted in This resulted in the sub-title compound (AEI-2) (120 mg, 0.62 mmol, 78%, 92% Purity) as a white solid. m/z 178.1 (M+H)$^+$ (ES+).

Step 2: Synthesis of 6-Fluoro-3-oxo-1,2-dihydroisoindole-5-carbaldehyde (AEI-3)

To a stirred solution of the product from step 1 above (AEI-2) (120 mg, 1 eq, 0.67 mmol) and NMO (106 mg, 1.3 eq 0.90 mmol,) in tBuOH (3 mL) and water (3 mL) were added K$_2$OsO$_4$.2H$_2$O (13 mg, 0.06 eq, 0.04 mmol) and 2-hydroxypropane-1,2,3-tricarboxylic acid (173 mg, 1.3 eq, 0.90 mmol) at rt. After 2 h, to the above mixture was added sodium periodate (289 mg, 2 eq, 1.35 mmol) at rt. The resulting mixture was stirred for additional 1 h at rt. The crude product was purified by reverse flash column chromatography with the following conditions: Column, C18; mobile phase, water (0.1% NH$_4$HCO$_3$) and MeCN (20% MeCN up to 30% in 10 min); Detector, UV 254/220 nm. The product-containing fractions were combined and concentrated in vacuo. This resulted in the sub-title compound (AEI-3) (100 mg, 0.50 mmol, 83%, 90% Purity) as a white solid. m/z 180.0 (M+H)$^+$ (ES+).

Step 3: Synthesis of 5-Fluoro-6-({[(1-hydroxycyclobutyl)methyl]amino}methyl)-2,3-dihydroisoindol-1-one (AEI-4)

To a stirred solution of the product from step 2 above (AEI-3) (100 mg, 1 eq, 0.56 mmol) and 1-(aminomethyl) cyclobutan-1-ol (AW-1) (153 mg, 2 eq, 1.12 mmol) in MeOH (5 mL) was added NaBH$_3$CN (105 mg, 3 eq, 1.67 mmol) and AcOH (3.4 mg, 0.1 eq, 56 μmol) at rt. The resulting mixture was stirred for overnight at rt. The residue was purified by Prep-TLC with DCM/MeOH (12/1) to afford the sub-title compound (AEI-4) (100 mg, 0.34 mmol, 68%, 91% Purity) as a yellow solid. m/z 265.1 (M+H)+ (ES+).

Step 4: 2-{6-Cyclopropyl-4-[2-(4-methyl-1,2,4-triazol-3-yl)phenyl]pyridin-2-yl}-5-fluoro-6-({[(1-hydroxycyclobutyl)methyl]amino}methyl)-3H-isoindol-1-one (AEI-5)

To a stirred solution of the product from step 3 above (AEI-4) (50 mg, 1 eq, 0.19 mmol), intermediate (ADZ-1) (65 mg, 1.1 eq, 0.21 mmol) and $Cs_2CO_3$ (185 mg, 0.57 mmol, 3 eq) in DMF (3 mL) were added, $Pd(OAc)_2$ (8.5 mg, 0.2 eq, 38 μmol) and XantPhos (44 mg, 0.4 eq, 76 μmol) at rt under nitrogen atmosphere. The resulting mixture was stirred for 2 h at 100° C. under nitrogen atmosphere. The mixture was allowed to cool down to rt. The crude product was purified by reverse flash column chromatography with the following conditions: Column, C18; mobile phase, water (0.1% $NH_4HCO_3$) and MeCN (70% MeCN up to 90% in 10 min); Detector, UV 254/220 nm. The product-containing fractions were combined and concentrated in vacuo. The crude product was purified by Prep-HPLC with the following conditions (Column: Sunfire prep C18 column, 30*150 mm, 5 μm; Mobile Phase A: water(0.1% FA), Mobile Phase B: MeCN; Flow rate: 60 mL/min; Gradient: 10% B to 40% B in 7 min; Wave Length: 254/220 nm; RT: 6.3) to afford the title compound (AEI-5) (5.0 mg, 9.1 μmol, 4.9%, 99% Purity) as a white solid. m/z 539.4 (M+H)+ (ES+). $^1$H NMR (400 MHz, DMSO-d6) δ 8.48 (s, 1H), 8.31 (s, 1H), 8.00 (d, J=1.4 Hz, 1H), 7.90 (d, J=6.7 Hz, 1H), 7.76-7.72 (m, 1H), 7.67-7.61 (m, 3H), 7.54 (d, J=9.5 Hz, 1H), 6.80 (d, J=1.5 Hz, 1H), 5.01 (s, 2H), 3.87 (s, 2H), 3.37 (s, 3H), 2.57 (s, 2H), 2.05-1.97 (m, 3H), 1.94-1.86 (m, 2H), 1.62 (d, J=10.7 Hz, 1H), 1.47-1.35 (m, 1H), 0.96-0.83 (m, 4H).

Example 161: Synthesis of 2-(6-(Ethylamino)-4-(1-methyl-4-(4-methyl-4H-1,2,4-triazol-3-yl)-1H-pyrazol-5-yl)pyridin-2-yl)-6-((((1-hydroxycyclobutyl)methyl)(methyl)amino)methyl)-4-(trifluoromethyl)isoindolin-1-one (AEJ-3)

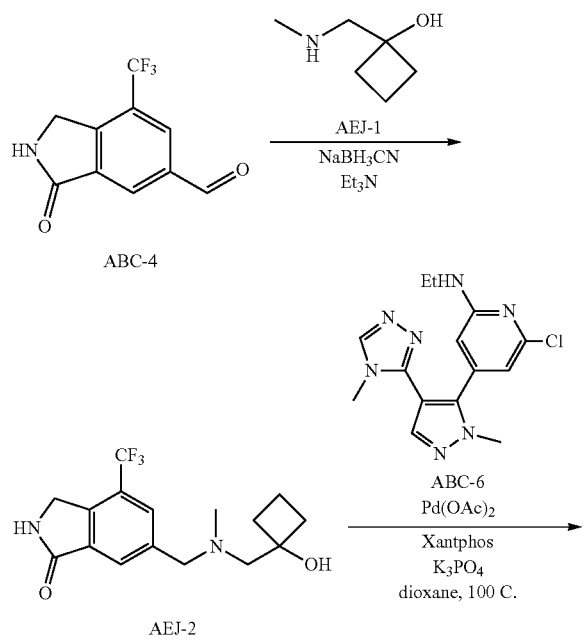

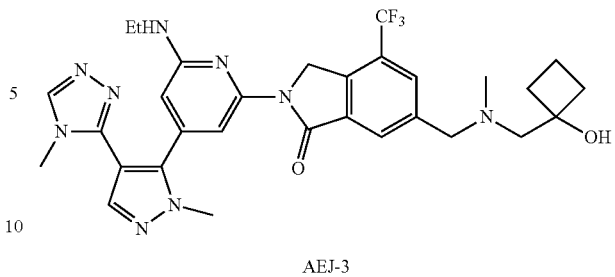

Step 1: 6-((((1-Hydroxycyclobutyl)methyl)(methyl)amino)methyl)-4-(trifluoromethyl)isoindolin-1-one (AEJ-2)

To a stirred mixture of intermediate (ABC-4) (75 mg, 0.327 mmol, 1.00 eq) and 1-[(methylamino)methyl]cyclobutan-1-ol (AEJ-1) (75 mg, 2 eq, 0.65 mmol) in MeOH (5 mL) was added $Et_3N$ (66 mg, 2 eq, 0.65 mmol) at rt under nitrogen atmosphere. The resulting mixture was stirred for 2 h at 60° C. under nitrogen atmosphere. To the above mixture was added $NaBH_3CN$ (82 mg, 4 eq, 1.31 mmol) at 0° C. The resulting mixture was stirred for additional overnight at rt. The crude product was purified by reverse flash column chromatography with the following conditions: Column, C18; mobile phase, water (0.1% $NH_4HCO_3$) and MeCN (10% MeCN up to 60% in 10 min); Detector, UV 254/220 nm to afford the sub-title compound (AEJ-2) (86 mg, 0.23 mmol, 80%, 89% Purity) as a yellow solid. m/z 329.1 (M+H)+ (ES+).

Step 2: Synthesis of 2-(6-(Ethylamino)-4-(1-methyl-4-(4-methyl-4H-1,2,4-triazol-3-yl)-1H-pyrazol-5-yl)pyridin-2-yl)-6-((((1-hydroxycyclobutyl)methyl)(methyl)amino)methyl)-4-(trifluoromethyl)isoindolin-1-one (AEJ-3)

To a stirred mixture of the product from step 1 above (AEJ-2) (50 mg, 1 eq, 0.15 mmol), intermediate (ABC-6) (48 mg, 1 eq, 0.15 mmol) and $Cs_2CO_3$ (99 mg, 2 eq, 0.30 mmol) in dioxane (5 mL) were added RuPhos palladacycle Gen.3 (25 mg, 0.2 eq, 30 μmol) and RuPhos (28 mg, 0.4 eq, 61 μmol) at rt under nitrogen atmosphere. The resulting mixture was stirred for 2 h at 100° C. under nitrogen atmosphere. The mixture was cooled to rt and concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: water (0.1% $NH_4HCO_3$), Mobile Phase B: MeCN; Flow rate: 60 mL/min; Gradient: 34% B to 42% B in 9 min; Wave Length: 254/220 nm; RT: 8.35) to afford the title compound (AEJ-3) (36.1 mg, 58 μmol, 35%, 98% Purity) as a white solid. m/z 610.0 (M+H)+ (ES+). $^1$H NMR (400 MHz, MeOH-d4) δ 8.46 (s, 1H), 8.08 (d, J=21.3 Hz, 2H), 7.85 (s, 1H), 7.62 (d, J=1.2 Hz, 1H), 6.19 (d, J=1.2 Hz, 1H), 5.25 (d, J=1.8 Hz, 2H), 4.03 (d, J=17.0 Hz, 5H), 3.48 (s, 3H), 3.36 (t, J=7.2 Hz, 2H), 2.85 (s, 2H), 2.51 (s, 3H), 2.20-2.01 (m, 4H), 1.85-1.73 (m, 1H), 1.59-1.43 (m, 1H), 1.23 (t, J=7.2 Hz, 3H).

Example 162: Synthesis of 2-[6-(Ethylamino)-4-[2-methyl-4-(4-methyl-1,2,4-triazol-3-yl)pyrazol-3-yl]pyridin-2-yl]-6-({[(1-hydroxycyclobutyl)methyl](methyl)amino}methyl)-4-(trifluoromethyl)-3H-isoindol-1-one (AEK-3)

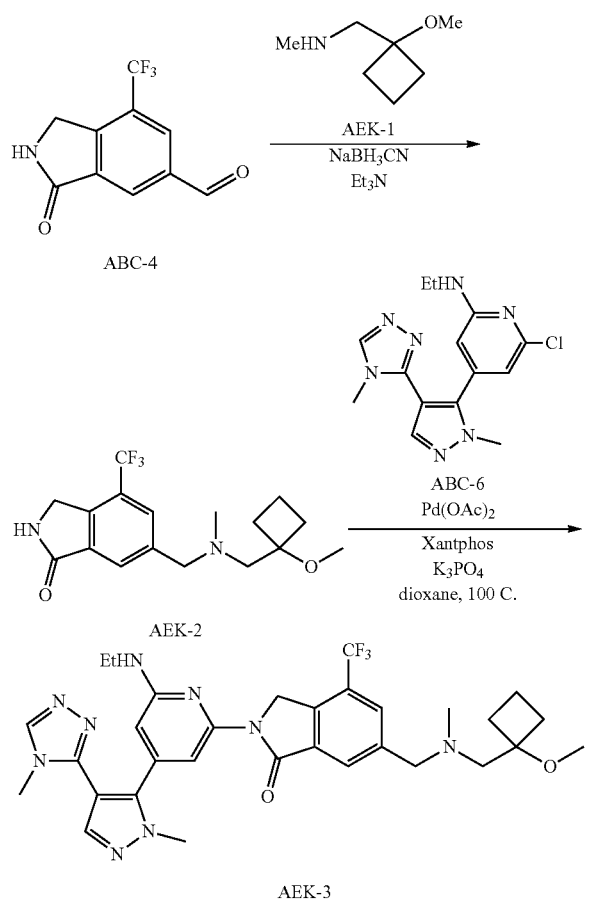

Step 1: Synthesis of 6-((((1-Methoxycyclobutyl)methyl)(methyl)amino)methyl)-4-(trifluoromethyl)isoindolin-1-one (AEK-2)

To a stirred mixture of intermediate (ABC-4) (50 mg, 1 eq, 0.22 mmol) and [(1-methoxycyclobutyl)methyl](methyl)amine (AEK-1) (56 mg, 2 eq, 0.45 mmol) in MeOH (5 mL) was added Et₃N (44 mg, 2 eq, 0.44 mmol) at rt under nitrogen atmosphere. The resulting mixture was stirred for 2 h at 60° C. under nitrogen atmosphere. To the above mixture was added NaBH₃CN (55 mg, 4 eq, 0.87 mmol) at 0° C. The resulting mixture was stirred for additional overnight at rt. The crude product was purified by reverse flash column chromatography with the following conditions: Column, C18; mobile phase, water (0.1% NH₄HCO₃) and MeCN (10% MeCN up to 40% in 15 min); Detector, UV 254/220 nm to afford the sub-title compound (AEK-2) (65 mg, 0.17 mmol, 87%, 90% Purity) as a yellow solid. m/z 343.2 (M+H)⁺ (ES+).

Step 2: Synthesis of 2-(6-(Ethylamino)-4-(1-methyl-4-(4-methyl-4H-1,2,4-triazol-3-yl)-1H-pyrazol-5-yl)pyridin-2-yl)-6-((((1-methoxycyclobutyl)methyl)(methyl)amino)methyl)-4-(trifluoromethyl)isoindolin-1-one (AEK-3)

To a stirred mixture of the product from step 1 above (AEK-2) (60 mg, 1 eq, 0.18 mmol), intermediate (ABC-6) (56 mg, 1 eq, 0.18 mmol) and Cs₂CO₃ (99 mg, 0.30 mmol, 2 eq) in 1,4-dioxane (5 mL) were added RuPhos palladacycle Gen.3 (29 mg, 0.2 eq, 35 μmol), and RuPhos (33 mg, 0.4 eq, 70 μmol) at rt under nitrogen atmosphere. The resulting mixture was stirred for 2 h at 80° C. under nitrogen atmosphere. The mixture was allowed to cool down to rt. The crude product was purified by reverse flash column chromatography with the following conditions: Column, C18; mobile phase, water (0.1% FA) and MeCN (0% MeCN up to 30% in 10 min); Detector, UV 254/220 nm. The crude product was purified by Prep-HPLC with the following conditions (Column: Sunfire prep C18 column, 30*150 mm, 5 μm; Mobile Phase A: water (0.1% FA), Mobile Phase B: MeCN; Flow rate: 60 mL/min; Gradient: 11% B to 26% B in 10 min; Wave Length: 254/220 nm; RT: 11.5) to afford the title compound (AEK-3) (11.0 mg, 17 μmol, 10%, 99% Purity) as a white solid. m/z 624.4 (M+H)⁺ (ES+). ¹H NMR (400 MHz, MeOH-d4) δ 8.47 (s, 1H), 8.02 (d, J=19.3 Hz, 2H), 7.84 (s, 1H), 7.63 (d, J=1.2 Hz, 1H), 6.17 (d, J=1.2 Hz, 1H), 5.23 (d, J=1.8 Hz, 2H), 4.01 (s, 3H), 3.78 (s, 2H), 3.48 (s, 3H), 3.35 (t, J=7.2 Hz, 2H), 3.20 (s, 3H), 2.66 (s, 2H), 2.32 (s, 3H), 2.17-2.06 (m, 2H), 2.02-1.92 (m, 2H), 1.79-1.68 (m, 1H), 1.59-1.43 (m, 1H), 1.22 (t, J=7.2 Hz, 3H).

Example 163: Synthesis of 4-[2-(Ethylamino)-6-[6-({[(1R,2S)-2-hydroxycyclopentyl]amino}methyl)-1-oxo-4-(trifluoromethyl)-3H-isoindol-2-yl]pyridin-4-yl]-3-(4-methyl-1,2,4-triazol-3-yl) benzonitrile (AEL-2)

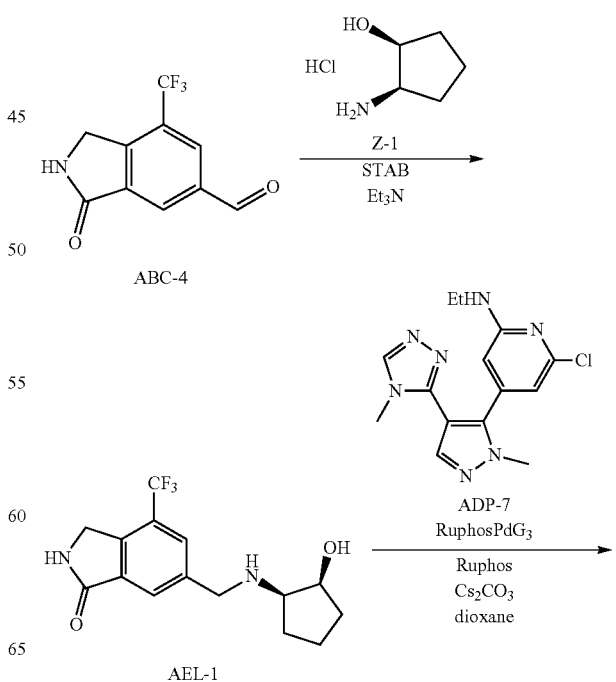

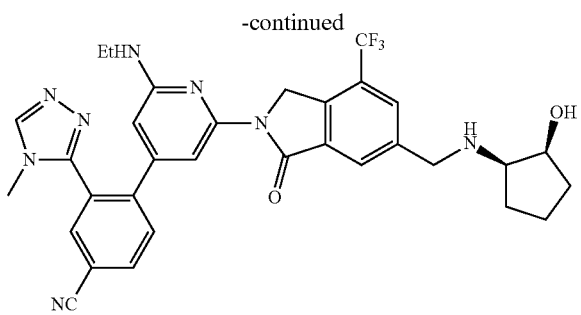

AEL-2

Step 1: Synthesis of 6-({[(1R,2S)-2-Hydroxycyclopentyl]amino}methyl)-4-(trifluoromethyl)-2,3-dihydroisoindol-1-one (AEL-1)

To a stirred solution of (1S,2R)-2-aminocyclopentan-1-ol, HCl (Z-1) (144 mg, 1.2 eq, 1.05 mmol) and Et₃N (339 mg, 3 eq, 2.62 mmol) in DCM (3 mL) at rt. The resulting mixture was stirred for 30 min at rt. To the above mixture was added intermediate (ABC-4) (200 mg, 1 eq, 0.87 mmol) at rt. The resulting mixture was stirred for additional 1 h at rt. To the above mixture was added NaBH(OAc)₂ (925 mg, 5 eq, 4.37 mmol) at rt. The resulting mixture was stirred for overnight at rt. The crude product was purified by reverse flash column chromatography with the following conditions: Column, C18; mobile phase, water (0.1% NH₄HCO₃) and MeCN (10% MeCN up to 50% in 10 min); Detector, UV 254/220 nm. This resulted in the sub-title compound (AEL-1) (200 mg, 0.60 mmol, 73%, 94% Purity) as an off-white solid. m/z 315.1 (M+H)⁺ (ES+).

Step 2: Synthesis of 4-[2-(Ethylamino)-6-[6-({[(1R, 2S)-2-hydroxycyclopentyl]amino}methyl)-1-oxo-4-(trifluoromethyl)-3H-isoindol-2-yl]pyridin-4-yl]-3-(4-methyl-1,2,4-triazol-3-yl)benzonitrile (AEL-2)

To a stirred solution of intermediate (ADP-7) (40 mg, 1 eq, 0.12 mmol), the product from step 1 above (AEL-1) (41 mg, 1.1 eq, 0.13 mmol) and Cs₂CO₃ (115 mg, 3 eq, 0.35 mmol) in 1,4-dioxane (10 mL) was added RuPhos palladacycle Gen.3 (20 mg, 0.2 eq, 24 µmol) and RuPhos (22 mg, 0.4 eq, 47 µmol) at rt under nitrogen atmosphere. The resulting mixture was stirred for 3 h at 100° C. under nitrogen atmosphere. The mixture was allowed to cool down to rt. The residue was purified by Prep-TLC with DCM/MeOH (10/1). The crude product was purified by Prep-HPLC with the following conditions (Column: XBridge Prep OBD C18 Column, 30*150 mm, 5 µm; Mobile Phase A: water (0.1% NH₄HCO₃), Mobile Phase B: MeCN; Flow rate: 60 mL/min; Gradient: 40% B to 50% B in 9 min; Wave Length: 254/220 nm) to afford the title compound (AEL-2) (19.6 mg, 31 µmol, 27%, 98% Purity) as a light yellow solid. m/z 617.4 (M+H)⁺ (ES+). ¹H NMR (400 MHz, MeOH-d4) δ 8.47 (s, 1H), 8.12-7.97 (m, 4H), 7.87 (d, J=8.1 Hz, 1H), 7.51 (d, J=1.3 Hz, 1H), 6.05 (d, J=1.2 Hz, 1H), 5.18 (s, 2H), 4.17-4.12 (m, 1H), 4.04-3.88 (m, 2H), 3.45 (s, 3H), 3.27 (t, J=7.2 Hz, 2H), 2.99-2.90 (m, 1H), 1.93-1.66 (m, 4H), 1.65-1.46 (m, 2H), 1.20 (t, J=7.2 Hz, 3H).

Example 164: Synthesis of 2-(6-Cyclopropyl-4-(2-(4-methyl-4H-1,2,4-triazol-3-yl) phenyl)pyridin-2-yl)-6-((((1-hydroxycyclobutyl)methyl)amino) methyl)-5-methoxyisoindolin-1-one (AEM-9)

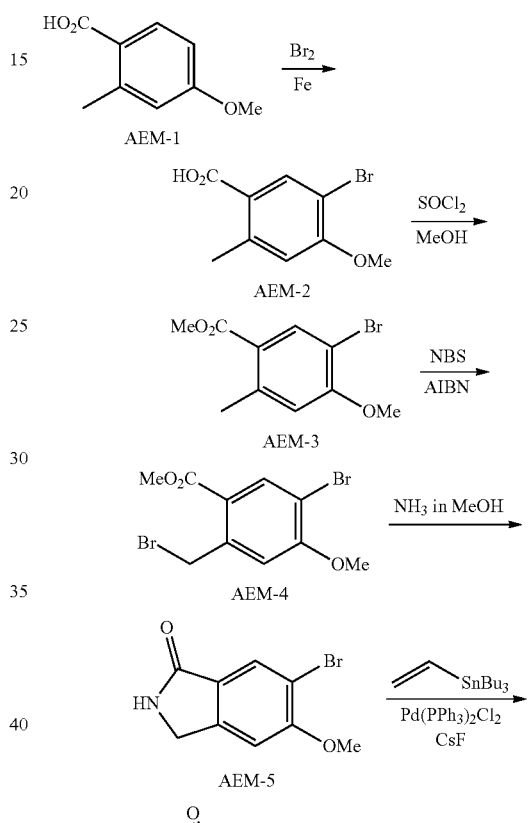

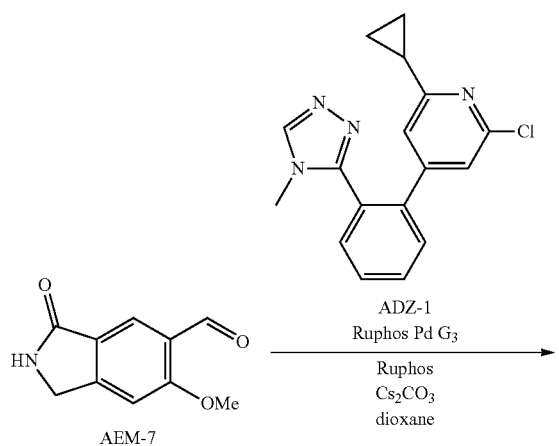

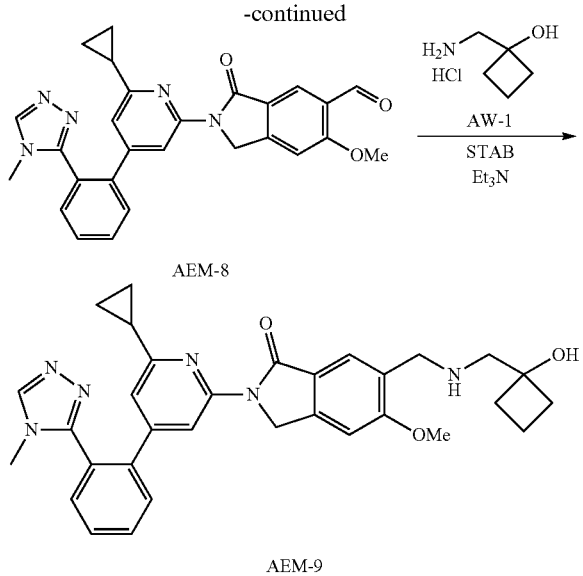

AEM-8

AEM-9

Step 1: Synthesis of
5-Bromo-4-methoxy-2-methylbenzoic acid
(AEM-2)

To a stirred mixture of 4-methoxy-2-methylbenzoic acid (AEM-1) (3.00 g, 1 eq, 18.1 mmol) and Fe (710 mg, 0.7 eq, 12.6 mmol) in CHCl₃ (40 mL) were added Br₂ (2.89 g, 1 eq, 18.1 mmol) at rt under nitrogen atmosphere. The resulting mixture was stirred for overnight at rt under nitrogen atmosphere. The resulting mixture was diluted with water. The resulting mixture was extracted with DCM (3×200 mL). The combined organic layers were washed with brine (2×200 mL), dried (Na₂SO₄). After filtration, the filtrate was concentrated in vacuo. The crude product was purified by reverse flash column chromatography with the following conditions: Column, C18; mobile phase, water (0.1% NH₄HCO₃) and MeCN (0% MeCN up to 30% in 10 min); Detector, UV 254/220 nm. This resulted in the sub-title compound (AEM-2) (2.85 g, 10.4 mmol, 64%, 89% Purity) as a white solid. m/z 245.0/247.0 (M+H)⁺ (ES+).

Step 2: Synthesis of Methyl
5-bromo-4-methoxy-2-methylbenzoate (AEM-3)

To a stirred mixture of the product from step 1 above (AEM-2) (2.83 g, 1 eq, 11.5 mmol) in MeOH (30 mL) was added thionyl chloride (962 mg, 0.7 eq, 8.08 mmol) dropwise at rt. The resulting mixture was stirred for 3 h at 70° C. The mixture was allowed to cool down to rt. The resulting mixture was diluted with water. The resulting mixture was extracted with DCM (3×150 mL). The combined organic layers were washed with brine (2×150 mL), dried (Na₂SO₄). After filtration, the filtrate was concentrated in vacuo. The residue was applied on a silica gel column chromatography with petroleum ether/EtOAc (3/1) to afford the sub-title compound (AEM-3) (2.46 g, 8.58 mmol, 82%, 90% Purity) as a white solid. m/z 259.0/261.0 (M+H)⁺ (ES+).

Step 3: Synthesis of Methyl
5-bromo-2-(bromomethyl)-4-methoxybenzoate
(AEM-4)

To a stirred mixture of the product from step 2 above (AEM-3) (2.44 g, 1 eq, 9.42 mmol) and AIBN (1.55 g, 1 eq, 9.42 mmol) in CHCl₃ (30 mL) were added NBS (1.76 g, 1.05 eq, 10.0 mmol) at 0° C. under nitrogen atmosphere. The resulting mixture was stirred for 4 h at 90° C. under nitrogen atmosphere. The mixture was allowed to cool down to rt. The resulting mixture was diluted with water. The resulting mixture was extracted with DCM (3×100 mL). The combined organic layers were washed with brine (2×100 mL), dried (Na₂SO₄). After filtration, the filtrate was concentrated in vacuo. The residue was applied on a silica gel column chromatography with petroleum ether/EtOAc (1/1) to afford the sub-title compound (AEM-4) (1.64 g, 4.27 mmol, 52%, 88% Purity) as an off-white solid. m/z 338.9/340.9 (M+H)⁺ (ES+).

Step 4: Synthesis of
6-Bromo-5-methoxyisoindolin-1-one (AEM-5)

To a stirred mixture of the product from step 3 above (AEM-4) (1.44 g, 1 eq, 4.26 mmol) in NH₃ in MeOH (30 mL, 7 M) at rt under nitrogen atmosphere. The resulting mixture was stirred for 2 h at 120° C. under nitrogen atmosphere. The mixture was allowed to cool down to rt. The resulting mixture was diluted with water. The resulting mixture was extracted with DCM (3×100 mL). The combined organic layers were washed with brine (2×100 mL), dried (Na₂SO₄). After filtration, the filtrate was concentrated in vacuo. The residue was applied on a silica gel column chromatography with DCM/MeOH (20/1) to afford the sub-title compound (AEM-5) (760 mg, 2.9 mmol, 74%, 92% Purity) as a white solid. m/z 242.0/244.0 (M+H)⁺ (ES+).

Step 5: Synthesis of
5-Methoxy-6-vinylisoindolin-1-one (AEM-6)

To a stirred mixture of the product from step 4 above (AEM-5) (750 mg, 1 eq, 3.10 mmol), tributyl(ethenyl)stannane (1.18 g, 1.2 eq, 3.72 mmol) and CsF (941 mg, 2 eq, 6.20 mmol) in 1,4-dioxane (10 mL) was added Pd(PPh₃)₂Cl₂ (435 mg, 0.2 eq, 0.62 mmol) at rt under nitrogen atmosphere. The resulting mixture was stirred for 2 h at 100° C. under nitrogen atmosphere. The mixture was allowed to cool down to rt. The resulting mixture was diluted with water. The resulting mixture was extracted with DCM (3×80 mL). The combined organic layers were washed with brine (2×80 mL), dried (Na₂SO₄). After filtration, the filtrate was concentrated in vacuo. The residue was purified by Prep-TLC with DCM/MeOH (20/1) to afford the sub-title compound (AEM-6) (550 mg, 2.62 mmol, 94%, 90% Purity) as a white solid. m/z 190.1 (M+H)⁺ (ES+).

Step 6: Synthesis of
6-Methoxy-3-oxoisoindoline-5-carbaldehyde
(AEM-7)

To a stirred mixture of the product from step 5 above (AEM-6) (550 mg, 1 eq, 2.91 mmol) and NMO (443 mg, 1.3 eq, 3.78 mmol) in tBuOH (3 mL) and water (3 mL) were added citric acid (726 mg, 1.3 eq, 3.78 mmol) and K₂OsO₄ (97 mg, 0.1 eq, 0.29 mmol) and sodium periodate (1.24 g, 2 eq, 5.81 mmol) at rt. The resulting mixture was stirred for 3 h at rt. The resulting mixture was diluted with water. The resulting mixture was extracted with DCM (3×80 mL). The combined organic layers were washed with brine (2×80 mL), dried (Na₂SO₄). After filtration, the filtrate was concentrated in vacuo. The crude product was purified by reverse flash column chromatography with the following conditions: Column, C18; mobile phase, water (0.1%

NH₄HCO₃) and MeCN (25% MeCN up to 35% in 9 min); Detector, UV 254/220 nm. This resulted in the sub-title compound (AEM-7) (130 mg, 0.65 mmol, 23%, 95% Purity) as a white solid. m/z 192.1 (M+H)⁺ (ES+).

Step 7: Synthesis of 2-(6-Cyclopropyl-4-(2-(4-methyl-4H-1,2,4-triazol-3-yl)phenyl)pyridin-2-yl)-6-methoxy-3-oxoisoindoline-5-carbaldehyde (AEM-8)

To a stirred mixture of the product from step 6 above (AEM-7) (100 mg, 1 eq, 0.52 mmol), intermediate (ADZ-1) (163 mg, 1 eq, 0.52 mmol) and Cs₂CO₃ (342 mg, 2 eq, 1.05 mmol) in 1,4-dioxane (3 mL) were added Ruphos (98 mg, 0.4 eq, 0.21 mmol) and RuPhos palladacycle Gen.3 (87 mg, 0.2 eq, 0.11 mmol) at rt under nitrogen atmosphere. The resulting mixture was stirred for 2 h at 100° C. under nitrogen atmosphere. The mixture was allowed to cool down to rt. The resulting mixture was diluted with water. The resulting mixture was extracted with DCM (3×50 mL). The combined organic layers were washed with brine (2×50 mL), dried (Na₂SO₄). After filtration, the filtrate was concentrated in vacuo. The residue was purified by Prep-TLC with DCM/MeOH (15/1) to afford the sub-title compound (AEM-8) (70 mg, 0.14 mmol, 29%, 95% Purity) as a white solid. m/z 466.2 (M+H)⁺ (ES+).

Step 8: Synthesis of 2-(6-Cyclopropyl-4-(2-(4-methyl-4H-1,2,4-triazol-3-yl)phenyl)pyridin-2-yl)-6-((((1-hydroxycyclobutyl) methyl) amino) methyl)-5-methoxyisoindolin-1-one (AEM-9)

To a stirred mixture of the product from step 7 above (AEM-8) (40 mg, 1 eq, 86 μmol) and 1-(aminomethyl)cyclobutan-1-ol (AW-1) (26 mg, 3 eq, 0.26 mmol) in DCM (3 mL) were added Et₃N (17 mg, 2 eq, 0.17 mmol) and NaBH(OAc)₃ (73 mg, 4 eq, 0.34 mmol) at rt under nitrogen atmosphere. The resulting mixture was stirred for overnight at rt under nitrogen atmosphere. The resulting mixture was diluted with water. The resulting mixture was extracted with DCM (3×10 mL). The combined organic layers were washed with brine (2×10 mL), dried (Na₂SO₄). After filtration, the filtrate was concentrated in vacuo. The crude product was purified by Prep-HPLC with the following conditions: Column: XBridge Prep OBD C18 Column, 30*150 mm, 5 μm; Mobile Phase A: water (0.1% NH₄HCO₃), Mobile Phase B: MeCN; Flow rate: 60 mL/min; Gradient: 33% B to 45% B in 9 min; Wave Length: 254/220 nm; RT: 8.2. This resulted in the title compound (AEM-9) (13.4 mg, 24 μmol, 28%, 98% Purity) as a white solid. m/z 551.2 (M+H)⁺ (ES+). ¹H NMR (400 MHz, DMSO-d6) δ 8.48 (s, 1H), 8.00 (d, J=1.4 Hz, 1H), 7.79-7.58 (m, 5H), 7.32 (s, 1H), 6.76 (d, J=1.4 Hz, 1H), 4.97 (s, 2H), 4.91 (s, 1H), 3.84 (d, J=51.3 Hz, 5H), 3.38 (s, 3H), 2.56 (s, 2H), 2.03-1.98 (m, 3H), 1.98-1.86 (m, 2H), 1.68-1.58 (m, 1H), 1.50-1.37 (m, 1H), 0.94 (d, J=6.4 Hz, 4H).

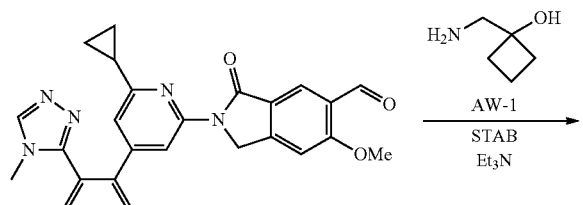

AEM-8

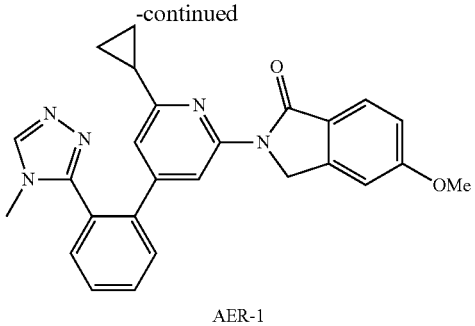

AER-1

A byproduct was isolated from the purification and this resulted in compound (AER-1) (6.3 mg, 14 μmol, 22%, 98% Purity) as a white solid. m/z 438.0 (M+H)⁺ (ES+). ¹H NMR (400 MHz, DMSO-d6) δ 8.48 (s, 1H), 8.01 (d, J=1.4 Hz, 1H), 7.79-7.57 (m, 5H), 7.28 (d, J=2.2 Hz, 1H), 7.07 (d, J=8.5, 2.3 Hz, 1H), 6.76 (d, J=1.4 Hz, 1H), 4.98 (s, 2H), 3.87 (s, 3H), 3.36 (s, 3H), 2.10-1.94 (m, 1H), 0.98-0.91 (m, 4H).

Example 165: Synthesis of 4-[2-Cyclopropyl-6-(6-{[(2-methoxyethyl)amino] methyl}-1-oxo-4-(trifluoromethyl)-3H-isoindol-2-yl)pyridin-4-yl]-3-(4-methyl-1,2,4-triazol-3-yl)benzonitrile (AEN-1)

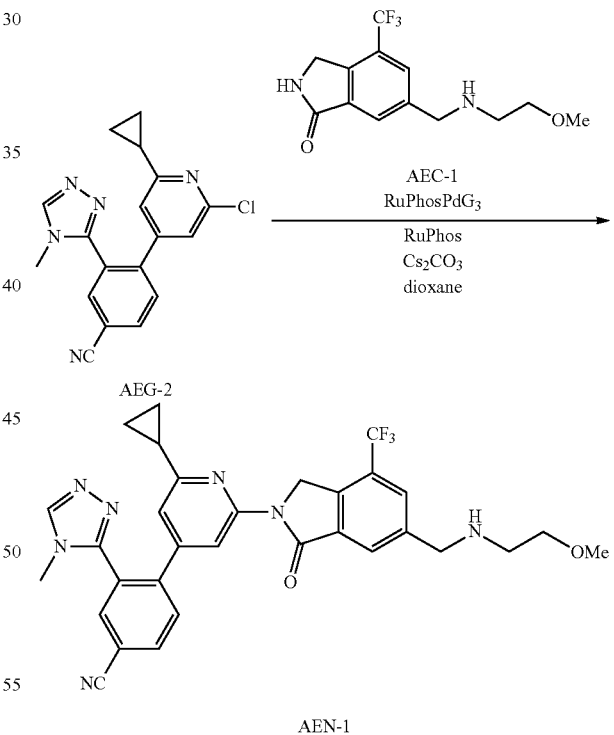

To a stirred solution of intermediate (AEG-2) (30 mg, 1 eq, 89 μmol), intermediate (AEC-1) (31 mg, 1.2 eq, 0.11 mmol) and Cs₂CO₃ (58 mg, 2 eq, 0.18 mmol) in 1,4-dioxane (4 mL) were added RuPhos (17 mg, 0.4 eq, 36 μmol) and RuPhos palladacycle Gen.3 (15 mg, 0.2 eq, 18 μmol) at rt under nitrogen atmosphere. The resulting mixture was stirred for 2 h at 100° C. under nitrogen atmosphere. The mixture was cooled to rt and concentrated in vacuo. The residue was purified by Prep-TLC with DCM/MeOH (10/1).

The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 30% B to 60% B in 9 min; Wave Length: 254/220 nm; RT: 8.83) to afford the title compound (AEN-1) (7.8 mg, 13 μmol, 15%, 98% Purity) as a white solid. m/z 588.4 (M+H)$^+$ (ES+). $^1$H NMR (300 MHz, DMSO-d6) δ 8.54 (s, 1H), 8.25-8.16 (m, 2H), 8.05-7.96 (m, 3H), 7.87 (d, J=8.5 Hz, 1H), 6.89 (d, J=1.4 Hz, 1H), 5.15 (s, 2H), 3.90 (s, 2H), 3.47 (s, 3H), 3.40 (t, J=5.6 Hz, 2H), 3.25-3.22 (m, 3H), 2.64 (t, J=5.7 Hz, 2H), 2.11-2.00 (m, 1H), 1.04-0.87 (m, 4H).

Example 166: Synthesis of 4-[2-Cyclopropyl-6-(6-{[(2-hydroxyethyl)amino]methyl}-1-oxo-4-(trifluoromethyl)-3H-isoindol-2-yl)pyridin-4-yl]-3-(4-methyl-1,2,4-triazol-3-yl) benzonitrile (AEO-2)

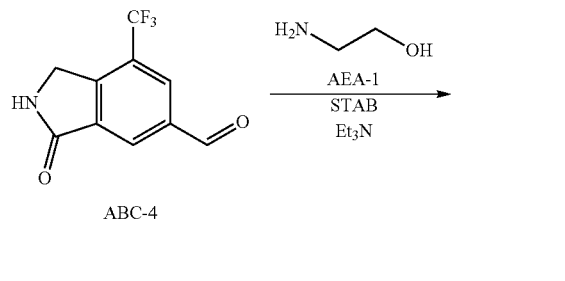

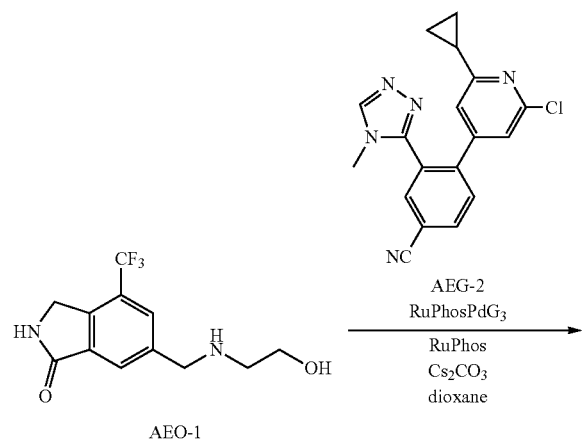

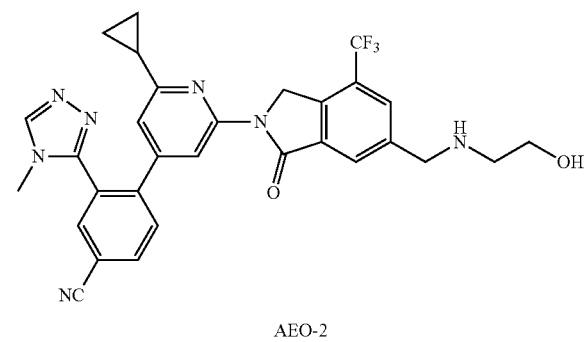

Step 1: Synthesis of 6-(((2-Hydroxyethyl)amino)methyl)-4-(trifluoromethyl)isoindolin-1-one (AEO-1)

To a stirred solution of intermediate (ABC-4) (150 mg, 1 eq, 0.66 mmol) and ethanolamine (AEA-1) (48 mg, 1.2 eq, 0.79 mmol) in DCM (20 mL) were added NaBH(OAc)$_3$ (694 mg, 5 eq, 3.28 mmol) and Et$_3$N (99 mg, 1.5 eq, 0.98 mmol) at rt. The resulting mixture was stirred for overnight at rt under nitrogen atmosphere. The resulting mixture was concentrated in vacuo. The residue was purified by Prep-TLC with DCM/MeOH (5/1). This resulted in the sub-title compound (AEO-1) (180 mg, 0.56 mmol, 99%, 85% Purity) as a white solid. m/z 275.1 (M+H)$^+$ (ES+).

Step 2: Synthesis of 4-[2-Cyclopropyl-6-(6-{[(2-hydroxyethyl)amino]methyl}-1-oxo-4-(trifluoromethyl)-3H-isoindol-2-yl)pyridin-4-yl]-3-(4-methyl-1,2,4-triazol-3-yl)benzonitrile (AEO-2)

To a stirred solution of intermediate (AEG-2) (40 mg, 1 eq, 0.12 mmol), the product from step 1 above (AEO-1) (39 mg, 1.2 eq, 0.14 mmol) and Cs$_2$CO$_3$ (78 mg, 2 eq, 0.24 mmol) in 1,4-dioxane (5 mL) were added RuPhos palladacycle Gen.3 (20 mg, 0.2 eq, 24 μmol) and RuPhos (22 mg, 0.4 eq, 48 μmol) at rt under nitrogen atmosphere. The resulting mixture was stirred for 2 h at 100° C. under nitrogen atmosphere. The mixture was cooled to rt and concentrated in vacuo. The residue was purified by Prep-TLC with DCM/MeOH (5/1). The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 38% B to 52% B in 8 min; Wave Length: 254/220 nm; RT: 7.33) to afford the title compound (AEO-2) (12.9 mg, 22 μmol, 19%, 99% Purity) as a white solid. m/z 574.3 (M+H)$^+$ (ES+). $^1$H NMR (400 MHz, DMSO-d6) δ 8.54 (s, 1H), 8.24-7.95 (m, 5H), 7.87 (d, J=8.5 Hz, 1H), 6.90 (d, J=1.4 Hz, 1H), 5.16 (s, 2H), 4.55 (s, 1H), 3.94 (s, 2H), 3.48 (d, J=9.7 Hz, 5H), 2.60 (t, J=5.8 Hz, 2H), 2.11-2.01 (m, 1H), 1.02-0.89 (m, 4H).

Example 167: Synthesis of 4-[2-(Ethylamino)-6-[1-oxo-6-(pyrrolidin-1-yl)-4-(trifluoromethyl)-3H-isoindol-2-yl]pyridin-4-yl]-3-(4-methyl-1,2,4-triazol-3-yl)benzonitrile (AEP-2)

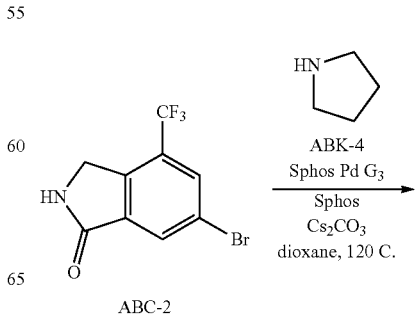

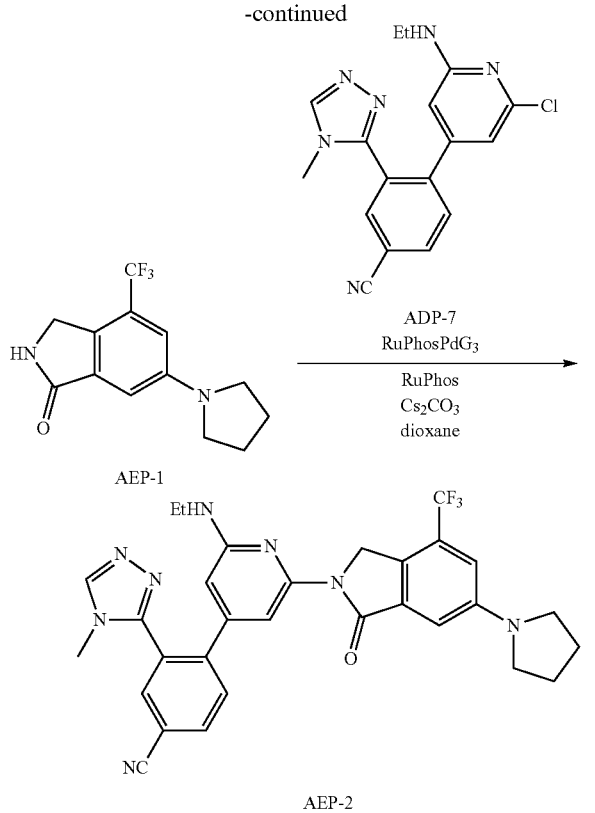

Prep C18 OBD Column, 19×150 mm, 5 μm; Mobile Phase A: water (0.1% NH₄HCO₃), Mobile Phase B: MeCN; Flow rate: 60 mL/min; Gradient: 30 B to 60 B in 7 min; Detector, UV 254/210 nm; RT: 6.08. This resulted in the title compound (AEP-2) (15.7 mg, 26 μmol, 20%, 95% Purity) as a white solid. m/z 573.2 (M+H)⁺ (ES+). ¹H NMR (400 MHz, DMSO-d6) δ 8.52 (s, 1H), 8.20-8.11 (m, 2H), 7.78 (d, J=8.0 Hz, 1H), 7.41 (d, J=1.2 Hz, 1H), 7.04-6.97 (m, 2H), 6.77 (t, J=5.4 Hz, 1H), 5.97 (d, J=1.4 Hz, 1H), 5.00 (s, 2H), 3.40 (s, 3H), 3.38-3.32 (m, 4H), 3.23-3.15 (m, 2H), 2.05-1.96 (m, 4H), 1.13 (t, J=7.2 Hz, 3H).

Example 168: Synthesis of 2-[6-(Ethylamino)-4-[2-methyl-4-(4-methyl-1,2,4-triazol-3-yl)pyrazol-3-yl]pyridin-2-yl]-6-({[(1-methoxycyclobutyl) methyl]amino}methyl)-4-(trifluoromethyl)-3H-isoindol-1-one (AEQ-3)

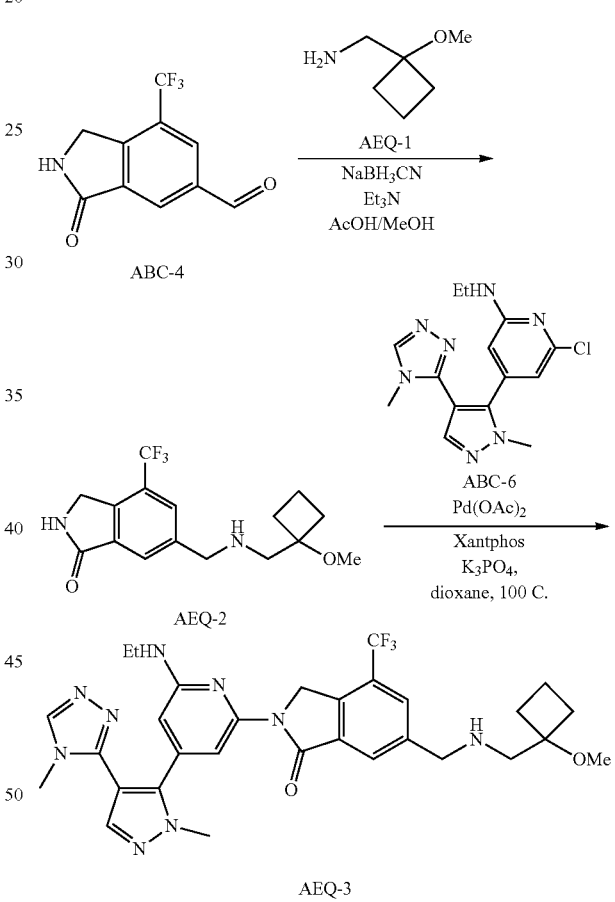

Step 1: Synthesis of 6-(Pyrrolidin-1-yl)-4-(trifluoromethyl)isoindolin-1-one (AEP-1)

To a stirred mixture of intermediate (ABC-2) (140 mg, 1 eq, 0.50 mmol) and pyrrolidine (ABK-4) (356 mg, 10 eq, 5.00 mmol) in 1,4-dioxane (5 mL) was added Cs₂CO₃ (407 mg, 2.5 eq, 1.25 mmol) and SPhos Pd Gen.3 (41 mg, 0.2 eq, 0.10 mmol) and SPhos (82 mg, 0.4 eq, 0.20 mmol) at rt under nitrogen atmosphere. The resulting mixture was stirred for overnight at 100° C. under nitrogen atmosphere. The mixture was allowed to cool down to rt. The resulting mixture was concentrated in vacuo. The crude product was purified by reverse flash column chromatography with the following conditions: Column, C18; mobile phase, water (0.1% NH₄HCO₃) and MeCN (36% MeCN up to 48% in 10 min); Detector, UV 254/220 nm. This resulted in the subtitle compound (AEP-1) (40 mg, 0.13 mmol, 30%, 90% Purity) as a white solid. m/z 271.1 (M+H)⁺ (ES+).

Step 2: Synthesis of 4-(2-(Ethylamino)-6-(1-oxo-6-(pyrrolidin-1-yl)-4-(trifluoromethyl)isoindolin-2-yl)pyridin-4-yl)-3-(4-methyl-4H-1,2,4-triazol-3-yl)benzonitrile (AEP-2)

To a stirred solution of intermediate (ADP-7) (35 mg, 1 eq, 0.13 mmol), the product from step 1 above (AEP-1) (44 mg, 1.0 eq, 0.13 mmol) and Cs₂CO₃ (84 mg, 2 eq, 0.26 mmol) in 1,4-dioxane (5 mL) were added RuPhos palladacycle Gen.3 (22 mg, 0.2 eq, 26 μmol) and RuPhos (24 mg, 0.4 eq, 52 μmol) at rt under nitrogen atmosphere. The resulting mixture was stirred for overnight at 120° C. under nitrogen atmosphere. The mixture was cooled to rt and concentrated in vacuo. The crude product was purified by Prep-HPLC with the following conditions: Column: SunFire Step 1: Synthesis of 6-({[(1-Methoxycyclobutyl)methyl]amino}methyl)-4-(trifluoromethyl)-2,3-dihydroisoindol-1-one (AEQ-2)

To a stirred mixture of intermediate (ABC-4) (60 mg, 1 eq, 0.26 mmol) and 1-(1-methoxycyclobutyl)methanamine (AEQ-1) (60 mg, 2 eq, 0.52 mmol) in MeOH (1 mL) were added Et₃N (53 mg, 2 eq, 0.52 mmol) and AcOH (16 mg, 1 eq, 0.26 mmol) at rt under nitrogen atmosphere. To the above mixture was added NaBH₃CN (66 mg, 4 eq, 1.05 mmol) over 30 min at 0° C. The resulting mixture was stirred for overnight at 60° C. The resulting mixture was diluted with water and extracted with EtOAc (3×20 mL). The combined organic layers were washed with brine (2×20 mL), dried (Na₂SO₄). After filtration, the filtrate was concentrated in vacuo. The crude product was purified by reverse flash column chromatography with the following conditions: Column, C18; mobile phase, Water (0.1% NH₄HCO₃) and MeCN (0% MeCN up to 30% in 15 min); Detector, UV 254/220 nm to afford the sub-title compound (AEQ-2) (40 mg, 0.14 mmol, 47%, 95% Purity) as a yellow solid. m/z 271.1 (M+H)⁺ (ES+).

Step 2: Synthesis of 2-[6-(Ethylamino)-4-[2-methyl-4-(4-methyl-1,2,4-triazol-3-yl)pyrazol-3-yl]pyridin-2-yl]-6-({[(1-methoxycyclobutyl)methyl]amino}methyl)-4-(trifluoromethyl)-3H-isoindol-1-one (AEQ-3)

To a stirred mixture of the product from step 1 above (AEQ-2) (40 mg, 1 eq, 0.12 mmol), 6-intermediate (ABC-6) (39 mg, 1 eq, 0.12 mmol) and Cs₂CO₃ (79 mg, 0.24 mmol, 2 eq) in 1,4-dioxane (5 mL) were added RuPhos palladacycle Gen.3 (11 mg, 0.2 eq, 24 μmol) and RuPhos (23 mg, 0.4 eq, 49 μmol) at rt under nitrogen atmosphere. The resulting mixture was stirred for overnight at 100° C. under nitrogen atmosphere. The mixture was cooled to rt and concentrated in vacuo. The residue was purified by Prep-TLC with DCM/MeOH (10/1). The crude product was purified by Prep-HPLC with the following conditions (Column: Sunfire prep C18 column, 30*150 mm, 5 μm; Mobile Phase A: water (0.1% FA), Mobile Phase B: MeCN; Flow rate: 60 mL/min; Gradient: 10% B to 30% B in 10 min; Wave Length: 254/220 nm; RT: 9.3) to afford the title compound (AEQ-3) (3.2 mg, 5.1 μmol, 4.2%, 98% Purity) as a white solid. m/z 610.3 (M+H)⁺ (ES+). ¹H NMR (400 MHz, MeOH-d4) δ 8.46 (s, 1H), 8.07 (d, J=18.9 Hz, 2H), 7.84 (s, 1H), 7.64 (d, J=1.2 Hz, 1H), 6.18 (d, J=1.2 Hz, 1H), 5.25 (s, 2H), 4.07 (s, 2H), 4.01 (s, 3H), 3.48 (s, 3H), 3.36 (t, J=7.2 Hz, 2H), 3.15 (s, 3H), 2.84 (s, 2H), 2.25-2.12 (m, 2H), 1.98-1.88 (m, 2H), 1.78-1.71 (m, 1H), 1.62-1.48 (m, 1H), 1.23 (t, J=7.2 Hz, 3H).

Example 170: Synthesis of 4-(2-Cyclopropyl-6-(6-(hydroxymethyl)-1-oxo-4-(trifluoromethyl)isoindolin-2-yl)pyridin-4-yl)-3-(4-methyl-4H-1,2,4-triazol-3-yl)benzonitrile (AES-1)

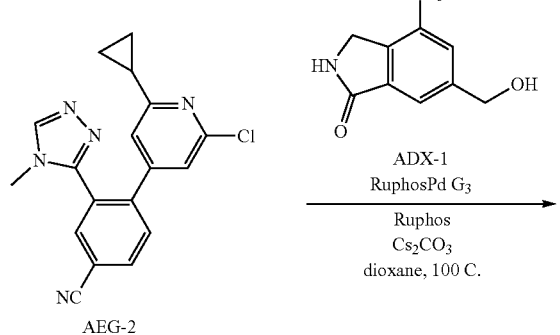

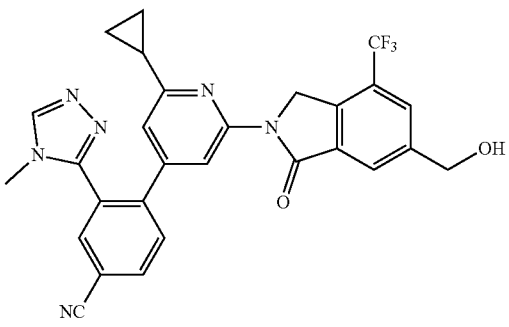

To a stirred mixture of intermediate (AEG-2) (25 mg, 74 μmol, 1 eq), intermediate (ADX-1) (17 mg, 1 eq, 74 μmol) and Cs₂CO₃ (49 mg, 0.15 mmol, 2 eq) in 1,4-dioxane (2 mL) were added Ruphos (14 mg, 0.4 eq, 30 μmol) and RuPhos palladacycle Gen.3 (12 mg, 0.2 eq, 15 μmol) at rt under nitrogen atmosphere. The resulting mixture was stirred for 2 h at 100° C. under nitrogen atmosphere. The mixture was allowed to cool down to rt. The resulting mixture was diluted with water. The resulting mixture was extracted with DCM (3×5 mL). The combined organic layers were washed with brine (2×5 mL), dried (Na₂SO₄). After filtration, the filtrate was concentrated in vacuo. The crude product was purified by Prep-HPLC with the following conditions: Column: XBridge Prep OBD C18 Column, 30*150 mm, 5 μm; Mobile Phase A: water (0.1% NH₄HCO₃), Mobile Phase B: MeCN; Flow rate: 60 mL/min; Gradient: 30% B to 50% B in 10 min, UV 254/220 nm; RT: 10.17. This resulted in the title compound (AES-1) (4.7 mg, 8.8 μmol, 12%, 99% Purity) as a white solid. m/z 531.3 (M+H)⁺ (ES+). ¹H NMR (400 MHz, DMSO-d6) δ 8.54 (s, 1H), 8.25-8.18 (m, 2H), 8.04-7.94 (m, 3H), 7.88 (d, J=8.5 Hz, 1H), 6.89 (d, J=1.4 Hz, 1H), 5.58 (t, J=5.8 Hz, 1H), 5.17 (s, 2H), 4.70 (d, J=5.8 Hz, 2H), 3.47 (s, 3H), 2.12-2.01 (m, 1H), 1.00-0.91 (m, 4H).

Example 171: Synthesis of 4-[2-(Ethylamino)-6-[6-({[(1R,2S)-2-fluorocyclopentyl] amino} methyl)-1-oxo-4-(trifluoromethyl)-3H-isoindol-2-yl] pyridin-4-yl]-3-(4-methyl-1,2,4-triazol-3-yl) benzonitrile (AET-6)

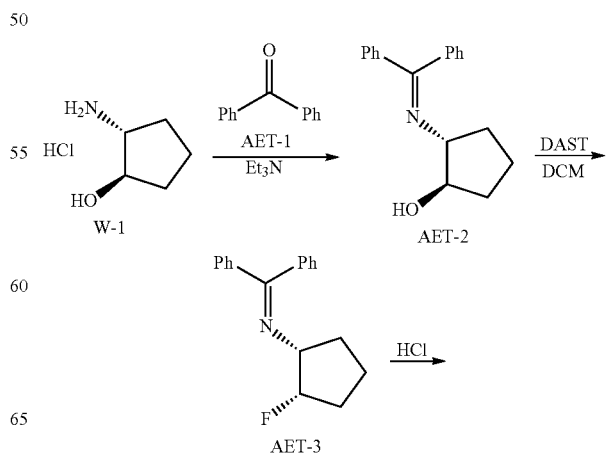

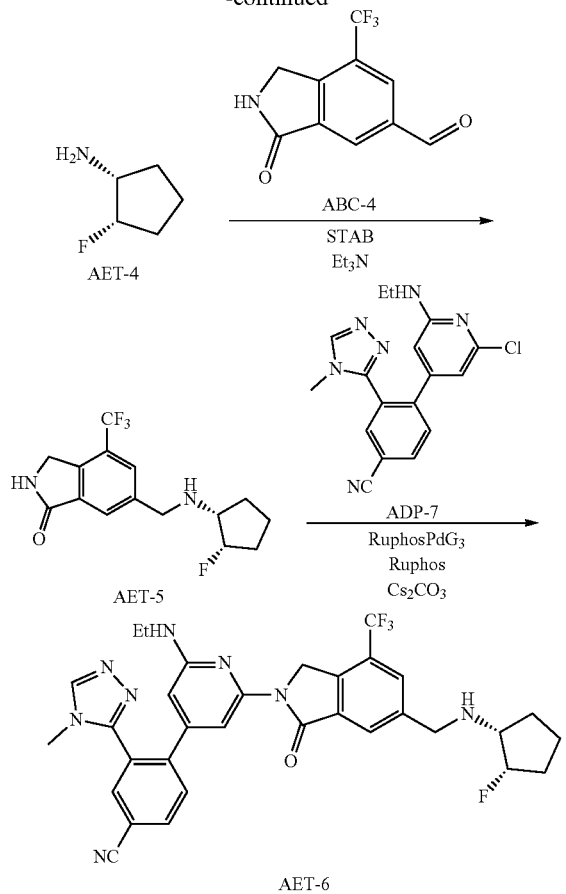

Step 1: Synthesis of (1R,2R)-2-[(Diphenylmethylidene)amino] cyclopentan-1-ol (AET-2)

A stirred solution of (1R,2R)-2-aminocyclopentan-1-ol, HCl (W-1) (500 mg, 1 eq, 3.63 mmol), benzophenone (AET-1) (659 mg, 1 eq, 3.63 mmol) and $Et_3N$ (735 mg, 2 eq, 7.27 mmol) in DCM (20 mL) was stirred overnight at rt. The resulting mixture was extracted with EtOAc (3×20 mL). The combined organic layers were washed with water (2×20 mL), dried ($Na_2SO_4$). After filtration, the filtrate was concentrated in vacuo. The residue was purified by Prep-TLC with EtOAc/petroleum ether (1/5) to afford the sub-title compound (AET-2) (400 mg, 1.39 mmol, 41%, 92% Purity) as a brown oil. m/z 266.2 $(M+H)^+$ (ES+).

Step 2: Synthesis of N-[(1R,2S)-2-Fuorocyclopentyl]-1,1-diphenylmethanimine (AET-3)

To a stirred solution of the product from step 1 above (AET-2) (500 mg, 1 eq, 1.88 mmol) in DCM (10 mL) was added DAST (607 mg, 2 eq, 3.78 mmol) dropwise at −20° C. The reaction liquid was concentrated in vacuo. This resulted in the sub-title compound (AET-3) (500 mg, 1.78 mmol, 99%, 95% Purity) as a brown oil. m/z 268.1 $(M+H)^+$ (ES+).

Step 3: Synthesis of (1R,2S)-2-Fluorocyclopentan-1-amine (AET-4)

To a stirred solution of the product from step 2 above (AET-3) (500 mg, 1 eq, 1.87 mmol) in dioxane (10 mL) was added HCl (gas) at rt. The resulting mixture was stirred for 3 h at 80° C. The mixture was allowed to cool down to rt. The resulting mixture was concentrated in vacuo. This resulted in the sub-title compound (AET-4) (180 mg, 1.55 mmol, 93%, 89% Purity) as a brown oil. m/z 104.1 $(M+H)^+$ (ES+).

Step 4: Synthesis of 6-({[(1R,2S)-2-Fluorocyclopentyl] amino} methyl)-4-(trifluoromethyl)-2,3-dihydroisoindol-1-one (AET-5)

A stirred solution of the product from step 3 above (AET-4) (81 mg, 1.2 eq, 0.79 mmol), $Et_3N$ (338 mg, 4 eq, 2.62 mmol) in DCM (10 mL) at rt was stirred for 30 min at rt. To the above mixture was added intermediate (ABC-4) (150 mg, 1 eq, 0.66 mmol) at rt. The resulting mixture was stirred for overnight at rt. To the above mixture was added $NaBH(OAc)_3$ (124 mg, 5 eq, 3.28 mmol) at rt. The resulting mixture was stirred for 2 h at rt. The reaction was then quenched by the addition of 2 mL of ice water at 0° C. The crude product was purified by reverse flash column chromatography with the following conditions: Column, C18; mobile phase, water (0.1% $NH_4HCO_3$) and MeCN (0% MeCN up to 40% in 18 min); Detector, UV 254/220 nm. This resulted in the sub-title compound (AET-5) (70 mg, 0.21 mmol, 34%, 93% Purity) as a brown oil. m/z 317.1 $(M+H)^+$ (ES+).

Step 5: Synthesis of 4-[2-(Ethylamino)-6-[6-({[(1R,2S)-2-fluorocyclopentyl] amino} methyl)-1-oxo-4-(trifluoromethyl)-3H-isoindol-2-yl] pyridin-4-yl]-3-(4-methyl-1,2,4-triazol-3-yl)benzonitrile (AET-6)

To a stirred solution of the product from step 5 above (AET-5) (50 mg, 1 eq, 0.16 mmol), intermediate (ADP-7) (59 mg, 0.17 mmol, 1.1 eq) and $Cs_2CO_3$ (103 mg, 2 eq, 0.32 mmol) in 1,4-dioxane (10 mL) were added RuPhos palladacycle Gen.3 (26 mg, 0.2 eq, 32 μmol) and RuPhos (30 mg, 0.4 eq, 63 μmol) at rt under nitrogen atmosphere. The resulting mixture was stirred for 2 h at 100° C. under nitrogen atmosphere. The mixture was allowed to cool down to rt. The crude product was purified by reverse flash column chromatography with the following conditions: Column, C18; mobile phase, water (0.1% $NH_4HCO_3$) and MeCN (30% MeCN up to 60% in 20 min); Detector, UV 254/220 nm. The product was purified by Prep-HPLC with the following conditions (Column: XBridge Prep OBD C18 Column, 30*150 mm, 5 μm; Mobile Phase A: Water (0.1% $NH_4HCO_3$), Mobile Phase B: MeCN; Flow rate: 60 mL/min; Gradient: 50% B to 55% B in 10 min; Wave Length: 254/220 nm) to afford the title compound (AET-6) (8.3 mg, 13 μmol, 8.5%, 98% Purity) as a light yellow solid. m/z 619.3 $(M+H)^+$ (ES+). $^1H$ NMR (400 MHz, MeOH-d4) δ 8.47 (s, 1H), 8.16-8.03 (m, 3H), 7.98 (s, 1H), 7.87 (d, J=8.1 Hz, 1H), 7.51 (d, J=1.3 Hz, 1H), 6.05 (d, J=1.3 Hz, 1H), 5.18 (d, J=1.9 Hz, 2H), 4.99-4.78 (m, 1H), 3.99 (s, 2H), 3.45 (s, 3H), 3.27 (t, J=7.2 Hz, 2H), 3.22-3.10 (m, 1H), 2.11-1.84 (m, 3H), 1.81-1.69 (m, 2H), 1.49-1.39 (m, 1H), 1.20 (t, J=7.2 Hz, 3H).

Example 172: Synthesis of 6-{1[(1-Aminocyclobutyl)methoxy]methyl}-2-{4-[4-fluoro-2-(4-methyl-1,2,4-triazol-3-yl)phenyl]-6-(methylamino)pyridin-2-yl}-4-(trifluoromethyl)-3H-isoindol-1-one (AEU-8)

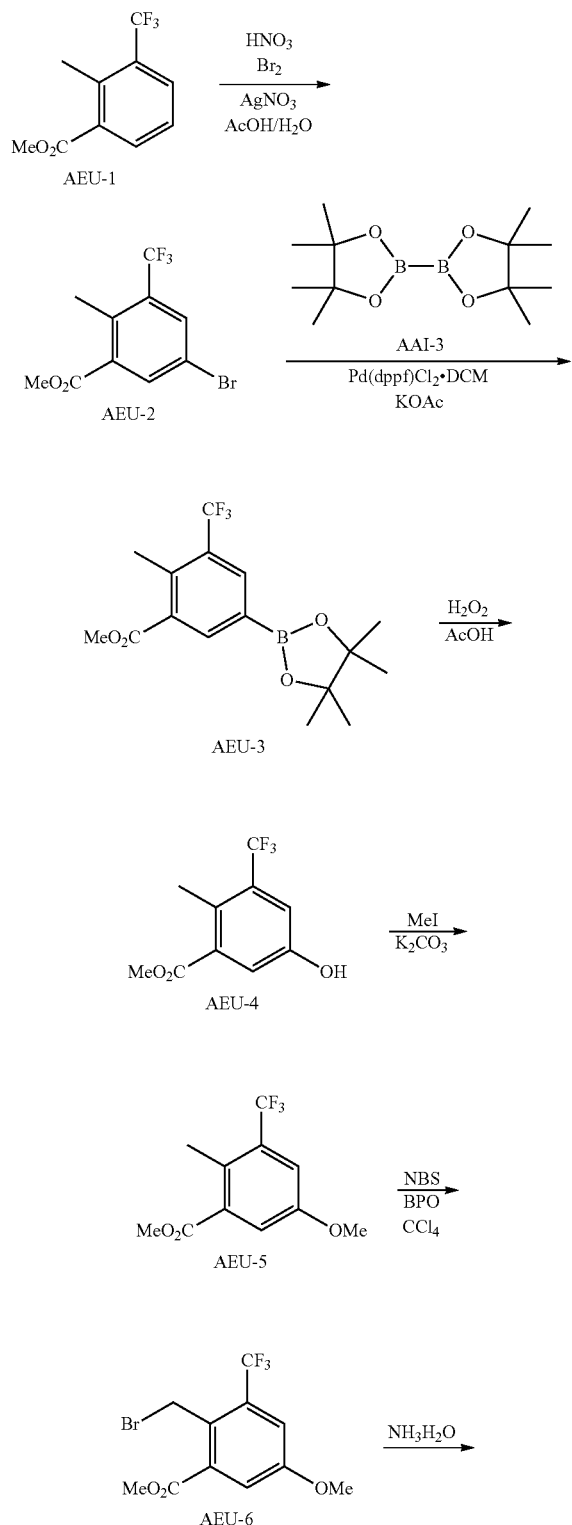

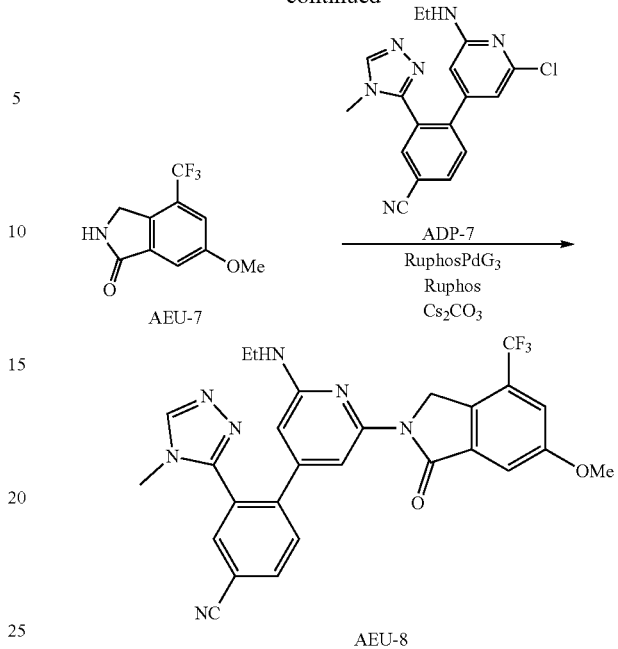

Step 1: Synthesis of Methyl 5-bromo-2-methyl-3-(trifluoromethyl)benzoate (AEU-2)

To a stirred mixture of methyl 2-methyl-3-(trifluoromethyl)benzoate (AEU-1) (1.00 g, 1 eq, 4.58 mmol) in AcOH (20 mL) were added HNO$_3$ (2.89 g, 10 eq, 45.8 mmol) and Br$_2$ (952 mg, 1.3 eq, 5.96 mmol) at rt. To the above mixture was added AgNO$_3$ (1.01 mg, 1.3 eq, 5.96 mmol) in H$_2$O (1 mg) over 10 min at 0° C. The resulting mixture was stirred for 2 h at rt. The resulting mixture was diluted with water and extracted with EtOAc (3×100 mL). The combined organic layers were washed with brine (2×100 mL), dried (Na$_2$SO$_4$). After filtration, the filtrate was concentrated in vacuo. The residue was purified by Prep-TLC with EtOAc/petroleum ether (1/5) to afford methyl the sub-title compound (AEU-2) (1.25 g, 3.80 mmol, 92%, 90% Purity) as a yellow solid. m/z 297.0/299.0 (M+H)$^+$ (ES+).

Step 2: Synthesis of Methyl 2-methyl-5-(4,4,5,5-tetramethyl-1,3,2-dioxaborolan-2-yl)-3-(trifluoromethyl) benzoate (AEU-3)

To a stirred mixture of the product from step 1 above (AEU-2) (2.40 g, 1 eq, 6.06 mmol), bis(pinacolato)diboron (AAI-3) (1.69 g, 1.1 eq, 6.67 mmol) and KOAc (1.78 g, 18.2 mmol, 3 eq) in 1,4-dioxane (20 mL) was added Pd(dppf)Cl$_2$.DCM (490 mg, 0.1 eq, 0.61 mmol) at rt under nitrogen atmosphere. The resulting mixture was stirred for additional 12 h at 100° C. under nitrogen atmosphere. The mixture was allowed to cool down to rt. The resulting mixture was filtered; the filter cake was washed with EtOAc (15 mL). The filtrate was concentrated in vacuo. The crude product was used in the next step directly without further purification. m/z 343.1 (M+H)$^+$ (ES+).

Step 3: Synthesis of Methyl 5-hydroxy-2-methyl-3-(trifluoromethyl)benzoate (AEU-4)

To a stirred mixture of the product from step 2 above (AEU-3) (2.40 g, 1 eq, 6.97 mmol) in AcOH (20 mL) was added $H_2O_2$ (5 mL, 30% Wt): THF (5 mL)=1:1 at rt. The resulting mixture was stirred for 1 h at rt. The resulting mixture was diluted with water and extracted with EtOAc (3×200 mL). The combined organic layers were washed with brine (2×200 mL), dried ($Na_2SO_4$). After filtration, the filtrate was concentrated in vacuo. The residue was applied on a silica gel column chromatography with petroleum ether/EtOAc (5/1) to afford the sub-title compound (AEU-4) (1.3 g, 5.27 mmol, 76%, 95% Purity) as a yellow solid. m/z 235.1 $(M+H)^+$ (ES+).

Step 4: Synthesis of Methyl 5-hydroxy-2-methyl-3-(trifluoromethyl)benzoate (AEU-5)

To a stirred mixture of the product from step 3 above (AEU-4) (1.30 g, 1 eq, 5.27 mmol) and $CH_3I$ (898 mg, 1.2 eq, 6.33 mmol) in DMF (10 mL) was added $K_2CO_3$ (2.19 g, 3 eq, 15.8 mmol) at rt. The resulting mixture was stirred for 12 h at rt. The resulting mixture was concentrated in vacuo. The resulting mixture was diluted with water and extracted with EtOAc (3×100 mL). The combined organic layers were washed with brine (2×100 mL), dried ($Na_2SO_4$). After filtration, the filtrate was concentrated in vacuo. The residue was applied on a silica gel column chromatography with petroleum ether/EtOAc (1/1) to afford the sub-title compound (AEU-5) (1.1 g, 3.99 mmol, 76%, 90% Purity) as a yellow solid. m/z 249.1 $(M+H)^+$ (ES+).

Step 5: Synthesis of Methyl 2-(bromomethyl)-5-methoxy-3-(trifluoromethyl)benzoate (AEU-6)

To a stirred mixture of the product from step 4 above (AEU-5) (1.10 g, 1 eq, 4.43 mmol) and NBS (1.18 g, 1.5 eq, 6.65 mmol) in $CHCl_3$ (20 mL) was added BPO (341 mg, 0.3 eq, 1.33 mmol) at rt. The resulting mixture was stirred for 12 h at 80° C. under nitrogen atmosphere. The mixture was allowed to cool down to rt. The resulting mixture was used in the next step directly without further purification. m/z 327.0/329.0 $(M+H)^+$ (ES+).

Step 6: Synthesis of 6-Methoxy-4-(trifluoromethyl)-2,3-dihydroisoindol-1-one (AEU-7)

To a stirred mixture of $NH_3$ in MeOH (20 mL) was added the product from step 5 above (AEU-6) (1.1 g, 1 eq, 3.36 mmol) at rt. The resulting mixture was stirred for 30 min at rt. The resulting mixture was concentrated in vacuo. The residue was applied on a silica gel column chromatography with petroleum ether/EtOAc (1/1) to afford the sub-title compound (AEU-7) (1.0 g, 3.98 mmol, 90%, 92% Purity) as a white solid. m/z 232.1 $(M+H)^+$ (ES+).

Step 7: Synthesis of 4-[2-(Ethylamino)-6-[6-methoxy-1-oxo-4-(trifluoromethyl)-3H-isoindol-2-yl]pyridin-4-yl]-3-(4-methyl-1,2,4-triazol-3-yl)benzonitrile (AEU-8)

To a stirred mixture of the product from step 6 above (AEU-7) (500 mg, 14.7 eq, 2.17 mmol), intermediate (ADP-7) (50 mg, 1 eq, 0.15 mmol) and $Cs_2CO_3$ (144 mg, 3 eq, 0.44 mmol) in 1,4-dioxane (20 mL) were added RuPhos palladacycle Gen.3 (23 mg, 0.2 eq, 30 µmol) and RuPhos (28 mg, 0.4 eq, 59 µmol) at 100° C. under nitrogen atmosphere. The resulting mixture was stirred for 2 h at 100° C. under nitrogen atmosphere. The mixture was allowed to cool down to rt. The resulting mixture was diluted with water and extracted with EtOAc (3×50 mL). The combined organic layers were washed with brine (2×50 mL), dried ($Na_2SO_4$). After filtration, the filtrate was concentrated in vacuo. The residue was purified by Prep-TLC with DCM/MeOH (8/1). The crude product was purified by Prep-HPLC with the following conditions (Column: XBridge Prep OBD C18 Column, 30*150 mm, 5 µm; Mobile Phase A: water (0.1% $NH_4HCO_3$), Mobile Phase B: MeCN; Flow rate: 60 mL/min; Gradient: 45% B to 65% B in 9 min; Wave Length: 254/220 nm) to afford the title compound (AEU-8) (25.7 mg, 48 µmol, 33%, 99% Purity) as a green solid. m/z 534.0 $(M+H)^+$ (ES+). $^1H$ NMR (400 MHz, DMSO-d6) δ 8.51 (s, 1H), 8.23-8.09 (m, 2H), 7.78 (d, J=8.0 Hz, 1H), 7.60-7.51 (m, 2H), 7.41 (d, J=1.2 Hz, 1H), 6.79 (t, J=5.4 Hz, 1H), 5.99 (d, J=1.3 Hz, 1H), 5.14-5.05 (m, 2H), 3.93 (s, 3H), 3.41 (s, 3H), 3.26-3.14 (m, 2H), 1.13 (t, J=7.1 Hz, 3H).

Example 173: Synthesis of 4-{2-[6-(Cyclopropoxymethyl)-1-oxo-4-(trifluoromethyl)-3H-isoindol-2-yl]-6-(ethylamino)pyridin-4-yl}-3-(4-methyl-1,2,4-triazol-3-yl) benzonitrile (AEV-3)

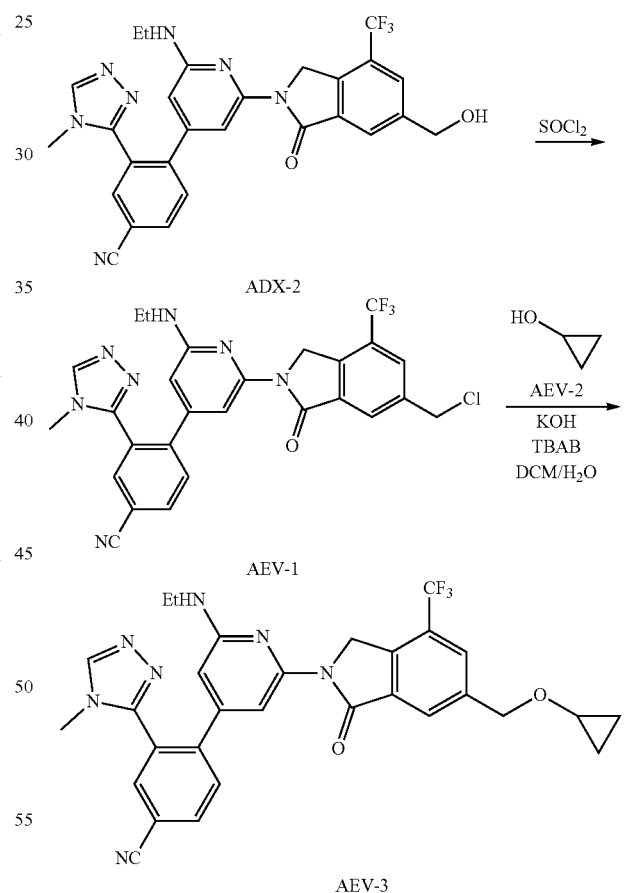

Step 1: Synthesis of 4-{2-[6-(Chloromethyl)-1-oxo-4-(trifluoromethyl)-3H-isoindol-2-yl]-6-(ethyl amino) pyridin-4-yl}-3-(4-methyl-1,2,4-triazol-3-yl) benzonitrile (AEV-1)

To a stirred solution of intermediate (ADX-2) (89 mg, 1 eq, 0.17 mmol) in DCM (8 mL) was added $SOCl_2$ (60 mg, 3 eq, 0.50 mmol) at 0° C. The resulting mixture was stirred for 1 h at rt. The reaction was quenched with MeOH (2 mL) at 0° C. and concentrated in vacuo. The residue was purified by TLC with DCM/MeOH (10/1) to afford the sub-title compound (AEV-1) (50 mg, 86 μmol, 54%, 95% Purity) as a yellow solid. m/z 552.1/554.1 (M+H)+ (ES+).

Step 2: Synthesis of 4-{2-[6-(Cyclopropoxymethyl)-1-oxo-4-(trifluoromethyl)-3H-isoindol-2-yl]-6-(ethylamino) pyridin-4-yl}-3-(4-methyl-1,2,4-triazol-3-yl) benzonitrile (AEV-3)

To a stirred solution of the product from step 1 above (AEV-1) (43 mg, 1 eq, 78 μmol) and cyclopropanol (AEV-2) (45 mg, 10 eq, 0.78 mmol) in DCM (5 mL) were added TBAB (13 mg, 0.5 eq, 39 μmol) and aq. KOH (5 mL, 20% Wt) at rt. The resulting mixture was stirred slowly for 1 h at rt. The resulting mixture was diluted with water and extracted with EtOAc (3×10 mL). The combined organic layers were washed with brine (2×10 mL), dried (Na$_2$SO$_4$). After filtration, the filtrate was concentrated in vacuo. The residue was purified by TLC with DCM/MeOH (8/1). The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 50% B to 65% B in 10 min; Wave Length: 254/220 nm) to afford the title compound (AEV-3) (6.9 mg, 12 μmol, 15%, 99% Purity) as a yellow solid. m/z 574.0 (M+H)+ (ES+) $^1$H NMR (400 MHz, DMSO-d6) δ 8.52 (s, 1H), 8.20-8.11 (m, 2H), 7.96 (d, J=15.3 Hz, 2H), 7.79 (d, J=8.0 Hz, 1H), 7.43 (d, J=1.3 Hz, 1H), 6.80 (t, J=5.4 Hz, 1H), 5.98 (d, J=1.3 Hz, 1H), 5.16 (s, 2H), 4.70 (s, 2H), 3.47-3.38 (m, 4H), 3.25-3.15 (m, 2H), 1.13 (t, J=7.1 Hz, 3H), 0.66-0.57 (m, 2H), 0.54-0.46 (m, 2H).

Example 174: Synthesis of 4-{2-Ethoxy-6-[6-(hydroxymethyl)-1-oxo-4-(trifluoromethyl)-3H-isoindol-2-yl]pyridin-4-yl}-3-(4-methyl-1,2,4-triazol-3-yl)benzonitrile (AEW-2)

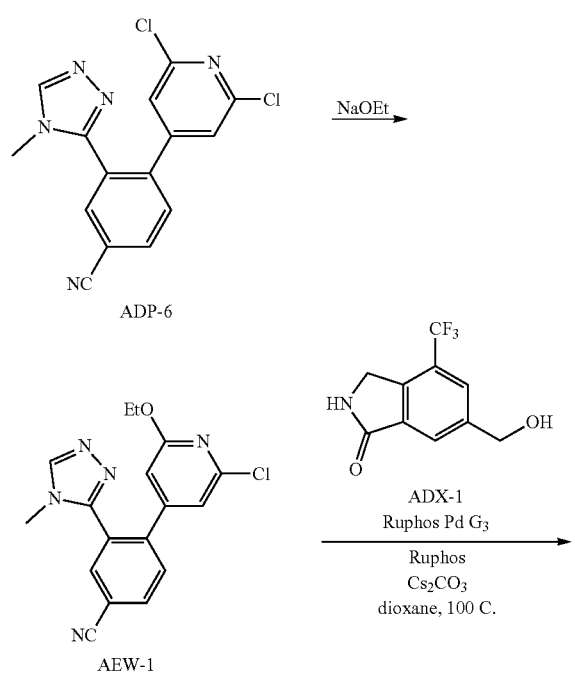

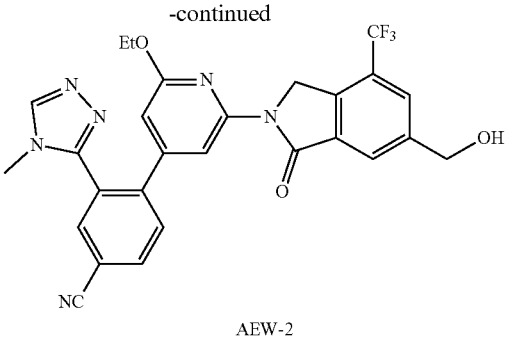

AEW-2

Step 1: Synthesis of 4-(2-Chloro-6-ethoxypyridin-4-yl)-3-(4-methyl-1,2,4-triazol-3-yl)benzonitrile (AEW-1)

To a stirred solution of intermediate (ADP-6) (68 mg, 1 eq, 0.21 mmol) in EtOH (4 mL) was added EtONa (17 mg, 1.2 eq, 0.25 mmol) at rt. The resulting mixture was stirred for overnight at 60° C. The mixture was cooled to rt and purified by Prep-TLC with EtOAc/petroleum ether (1/1). This resulted in the sub-title compound (AEW-1) (60 mg, 0.15 mmol, 86%, 85% Purity) as a white oil. m/z 340.1/342.1 (M+H)+ (ES+).

Step 2: Synthesis of 4-{2-Ethoxy-6-[6-(hydroxymethyl)-1-oxo-4-(trifluoromethyl)-3H-isoindol-2-yl]pyridin-4-yl}-3-(4-methyl-1,2,4-triazol-3-yl)benzonitrile (AEW-2)

To a stirred solution of the product from step 1 above (AEW-1) (50 mg, 1 eq, 0.14 mmol), intermediate (ADX-1) (68 mg, 2 eq, 0.29 mmol) and Cs$_2$CO$_3$ (96 mg, 0.29 mmol, 2.0 eq) in 1,4-dioxane (3 mL) were added RuPhos (27 mg, 0.4 eq, 59 μmol) and RuPhos palladacycle Gen.3 (25 mg, 0.2 eq, 29 μmol) at rt under nitrogen atmosphere. The resulting mixture was stirred for overnight at 100° C. under nitrogen atmosphere. The mixture was cooled to rt, diluted with water and extracted with EtOAc (3×30 mL). The combined organic layers were washed with brine (2×30 mL), dried (Na$_2$SO$_4$). After filtration, the filtrate was concentrated in vacuo. The residue was purified by Prep-TLC with EtOAc/petroleum ether (1/1). The crude product was purified by Prep-HPLC with the following conditions: Column: XBridge Prep OBD C18 Column, 30×150 mm, 5 μm; Mobile Phase A: water (0.1% NH$_4$HCO$_3$) Mobile Phase B: MeCN; Flow rate: 60 mL/min; Gradient: 72 B to 82 B in 8 min; Detector, UV 254/210 nm; RT: 5.68. The product-containing fractions were combined and evaporated partially in vacuo and lyophilized overnight to afford the title compound (AEW-2) (7.1 mg, 13 μmol, 9%, 98% Purity) as a white solid. m/z 535.0 (M+H)+ (ES+). $^1$H NMR (400 MHz, MeOH-d4) δ 8.49 (s, 1H), 8.15-8.04 (m, 3H), 7.96 (s, 1H), 7.90 (d, J=8.0 Hz, 1H), 7.84 (d, J=1.2 Hz, 1H), 6.48 (d, J=1.2 Hz, 1H), 5.22 (s, 2H), 4.79 (s, 2H), 4.45-4.35 (m, 2H), 3.53 (s, 3H), 1.40 (t, J=7.1 Hz, 3H).

Example 175: Synthesis of 4-{2-[6-(Hydroxymethyl)-1-oxo-4-(trifluoromethyl)-3H-isoindol-2-yl] pyridin-4-yl}-3-(4-methyl-1,2,4-triazol-3-yl) benzonitrile (AEX-2)

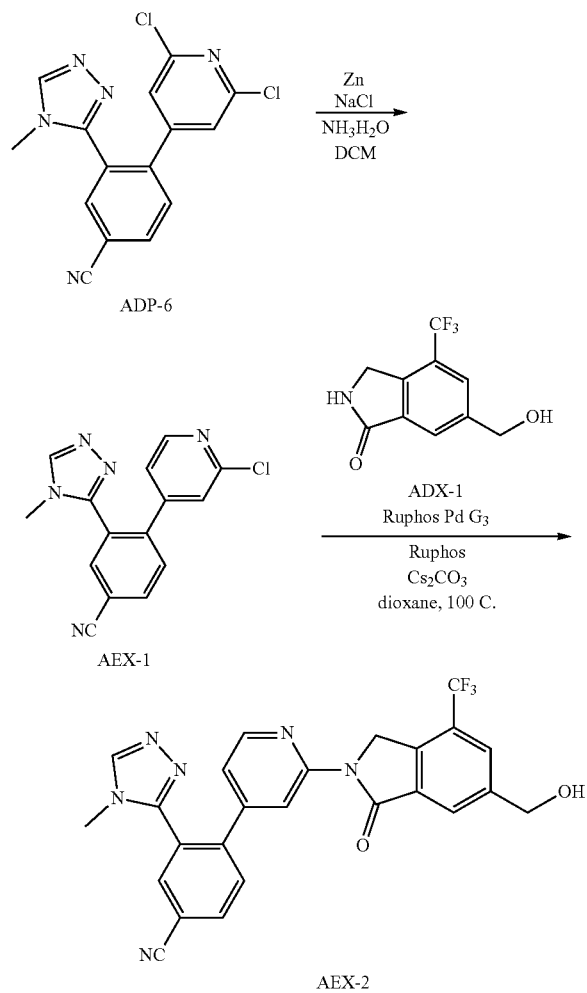

Step 1: Synthesis of 4-(2-Chloropyridin-4-yl)-3-(4-methyl-1,2,4-triazol-3-yl) benzonitrile (AEX-1)

To a stirred solution of intermediate (ADP-6) (200 mg, 1 eq, 0.61 mmol) and Zn (396 mg, 10 eq, 6.06 mmol), aq. NaCl (1.2 mL, 12 M), NH$_3$H$_2$O (0.2 mL, 25% Wt) in DCM (2 mL) was stirred for overnight at 50° C. The mixture was allowed to cool down to rt. The crude product was purified by reverse flash column chromatography with the following conditions: Column, C18; mobile phase, Water (0.1% NH$_4$HCO$_3$) and MeCN (10% MeCN up to 60% in 20 min); Detector, UV 254/220 nm. This resulted in the sub-title compound (AEX-1) (60 mg, 0.18 mmol, 33%, 90% Purity) as a white solid. m/z 296.1/298.1 (M+H)$^+$ (ES+).

Step 2: 4-{2-[6-(Hydroxymethyl)-1-oxo-4-(trifluoromethyl)-3H-isoindol-2-yl] pyridin-4-yl}-3-(4-methyl-1,2,4-triazol-3-yl)benzonitrile (AEX-2)

To a stirred solution of the product from step 1 above (AEX-1) (60 mg, 1 eq, 0.20 mmol), intermediate (ADX-1) (52 mg, 1.1 eq, 0.22 mmol) and Cs$_2$CO$_3$ (132 mg, 2 eq, 0.41 mmol) in 1,4-dioxane (10 mL) was added RuPhos palladacycle Gen.3 (34 mg, 0.2 eq, 41 µmol) and RuPhos (38 mg, 0.4 eq, 81 µmol) at rt under nitrogen atmosphere. The resulting mixture was stirred for 2 h at 100° C. under nitrogen atmosphere. The mixture was allowed to cool down to rt. The crude product was purified by reverse flash column chromatography with the following conditions: Column, C18; mobile phase, water (0.1% NH$_4$HCO$_3$) and MeCN (30% MeCN up to 50% in 15 min); Detector, UV 254/220 nm. The product was purified by Prep-HPLC with the following conditions (Column: XBridge Prep OBD C18 Column, 30*150 mm, 5 µm; Mobile Phase A: Water (0.1% NH$_4$HCO$_3$), Mobile Phase B: MeCN; Flow rate: 60 mL/min; Gradient: 33% B to 44% B in 11 min; Wave Length: 254/220 nm) to afford the title compound (AEX-2) (25.3 mg, 51 µmol, 25%, 98% Purity) as a white solid. m/z 491.2 (M+H)$^+$ (ES+). $^1$H NMR (400 MHz, MeOH-d4) δ 8.56-8.40 (m, 2H), 8.34-8.30 (m, 1H), 8.18-8.03 (m, 3H), 8.00-7.90 (m, 2H), 7.11-7.05 (m, 1H), 5.23 (s, 2H), 4.79 (s, 2H), 3.53 (s, 3H).

Example 176: Synthesis of 2-{6-Cyclopropyl-4-[4-fluoro-2-(4-methyl-1,2,4-triazol-3-yl)phenyl]pyridin-2-yl}-6-({[(1-hydroxycyclobutyl)methyl]amino}methyl)-4-(trifluoromethyl)-3H-isoindol-1-one (AEY-1)

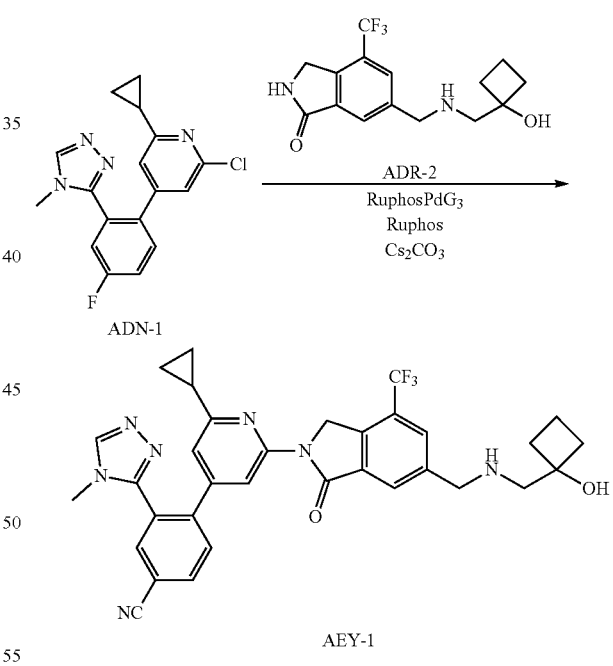

To a stirred mixture of intermediate (ADN-1) (50 mg, 0.15 mmol, 1 eq), intermediate (ADR-2) (48 mg, 1 eq, 0.15 mmol) and Cs$_2$CO$_3$ (99 mg, 0.304 mmol, 2.0 eq) in 1,4-dioxane (3 mL) were added RuPhos (28 mg, 0.4 eq, 61 µmol) and RuPhos palladacycle Gen.3 (25 mg, 0.2 eq, 30 µmol) at rt under nitrogen atmosphere. The resulting mixture was stirred for overnight at 100° C. under nitrogen atmosphere. The mixture was cooled to rt and concentrated in vacuo. The crude product was purified by Prep-HPLC with the following conditions: Column: SunFire Prep C18 OBD Column, 19×150 mm, 5 µm; Mobile Phase A: water (0.1%

NH₄HCO₃+0.1% NH₃·H₂O), Mobile Phase B: MeCN; Flow rate: 60 mL/min; Gradient: 30 B to 60 B in 7 min; Detector, UV 254/210 nm; RT: 6.08. This resulted in the title compound (AEY-1) (30.8 mg, 49 μmol, 92%, 97% Purity) as a white solid. m/z 607.3 (M+H)⁺ (ES+). ¹H NMR (400 MHz, MeOH-d4) δ 8.45 (s, 1H), 8.10 (s, 1H), 8.06-8.00 (m, 2H), 7.82-7.73 (m, 1H), 7.58-7.49 (m, 1H), 7.49-7.43 (m, 1H), 6.88 (d, J=1.4 Hz, 1H), 5.18 (s, 2H), 4.09 (s, 2H), 3.45 (s, 3H), 2.80 (s, 2H), 2.17-1.98 (m, 5H), 1.81-1.68 ((m, 1H), 1.59-1.45 (m, 1H), 0.99 (d, J=6.5 Hz, 4H).

Example 177: Synthesis of 4-[2-(ethylamino)-6-(6-{[(1-hydroxycyclobutyl) methoxy]methyl}-1-oxo-4-(trifluoromethyl)-3H-isoindol-2-yl) pyridin-4-yl]-3-(4-methyl-1,2,4-triazol-3-yl) benzonitrile (AEZ-1)

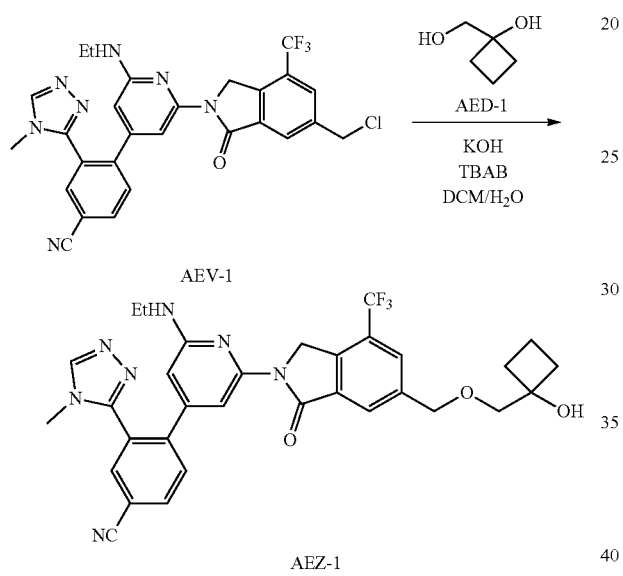

To a stirred solution of intermediate (AEV-1) (40 mg, 1 eq, 74 μmol) and 1-(hydroxymethyl) cyclobutan-1-ol (AED-1) (76 mg, 10 eq, 0.74 mmol) in DCM (5 mL) were added TBAB (12 mg, 0.5 eq, 37 μmol) and aq. KOH (5 m, 20% Wt) at rt. The resulting mixture was stirred slowly for 1 h at rt. The resulting mixture was diluted with water and extracted with EtOAc (3×10 mL). The combined organic layers were washed with brine (2×10 mL), dried (Na₂SO₄). After filtration, the filtrate was concentrated in vacuo. The residue was purified by TLC with DCM/MeOH (12/1). The crude product was purified by Prep-HPLC with the following conditions (Column: XBridge Prep OBD C18 Column, 30*150 mm, 5 μm; Mobile Phase A: water (0.1% NH₄HCO₃), Mobile Phase B: MeCN; Flow rate: 60 mL/min; Gradient: 40% B to 60% B in 9 min; Wave Length: 254/220 nm) to afford the title compound (AEZ-1) (9.6 mg, 15 μmol, 21%, 99% Purity) as a white solid. m/z 618.0 (M+H)⁺ (ES+). ¹H NMR (400 MHz, DMSO-d6) δ 8.52 (s, 1H), 8.23-8.08 (m, 2H), 8.01 (d, J=14.1 Hz, 2H), 7.79 (d, J=8.0 Hz, 1H), 7.44 (d, J=1.2 Hz, 1H), 6.81 (t, J=5.4 Hz, 1H), 5.98 (d, J=1.3 Hz, 1H), 5.22-5.08 (m, 3H), 4.76 (s, 2H), 3.45 (s, 2H), 3.41 (s, 3H), 3.25-3.15 (m, 2H), 2.09-2.00 (m, 2H), 1.99-1.88 (m, 2H), 1.73-1.58 (m, 1H), 1.55-1.39 (m, 1H), 1.13 (t, J=7.1 Hz, 3H).

Example 178: Synthesis of 4-[2-(ethylamino)-6-[6-(methylamino)-1-oxo-4-(trifluoromethyl)-3H-isoindol-2-yl]pyridin-4-yl]-3-(4-methyl-1,2,4-triazol-3-yl) benzonitrile (AFA-2)

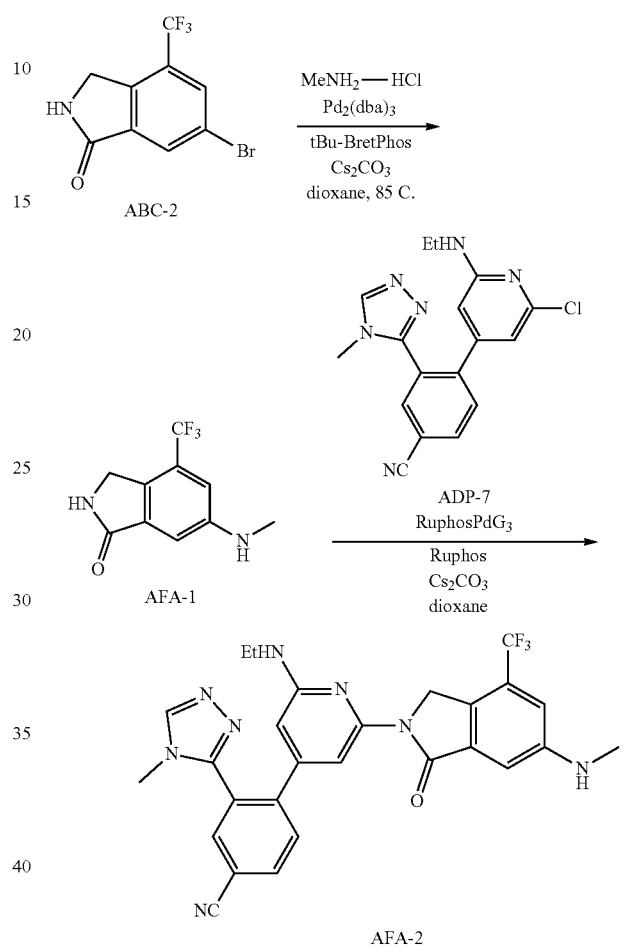

Step 1: Synthesis of 6-(Methylamino)-4-(trifluoromethyl)isoindolin-1-one (AFA-1)

To a stirred mixture of intermediate (ABC-2) (280 mg, 1 eq, 1.00 mmol) and methylamine, HCl (155 mg, 5 eq, 5.00 mmol) and Cs₂CO₃ (2.28 g, 7.00 mmol, 7 eq) in 1,4-dioxane (20 mL) were added Pd₂(dba)₃ (92 mg, 0.1 eq, 0.10 mmol) and t-BuBrettPhos (48 mg, 0.1 eq, 0.10 mmol) at rt under nitrogen atmosphere. The resulting mixture was stirred for 2 h at 100° C. under nitrogen atmosphere. The mixture was cooled to rt, diluted with water and extracted with EtOAc (3×50 mL). The combined organic layers were washed with brine (2×50 mL), dried (Na₂SO₄). After filtration, the filtrate was concentrated in vacuo. The crude product was purified by reverse flash column chromatography with the following conditions: Column, C18; mobile phase, water (0.1% NH₄HCO₃) and MeCN (10% MeCN up to 60% in 20 min); Detector, UV 254/220 nm to afford the sub-title compound (AFA-1) (39 mg, 0.16 mmol, 17%, 93% Purity) as a yellow solid. m/z 231.1 (M+H)⁺ (ES+).

Step 2: Synthesis of 4-[2-(Ethylamino)-6-[6-(methylamino)-1-oxo-4-(trifluoromethyl)-3H-isoindol-2-yl]pyridin-4-yl]-3-(4-methyl-1,2,4-triazol-3-yl)benzonitrile (AFA-2)

To a stirred mixture of the product from step 1 above (AFA-1) (35 mg, 1 eq, 0.15 mmol) and intermediate (ADP-7) (52 mg, 1 eq, 0.15 mmol) in 1,4-dioxane (5 mL) were added RuPhos palladacycle Gen.3 (13 mg, 0.1 eq, 15 μmol) and RuPhos (14 mg, 0.2 eq, 30 μmol) at rt under nitrogen atmosphere. The resulting mixture was stirred for overnight at 100° C. under nitrogen atmosphere. The mixture was cooled to rt, diluted with water and extracted with EtOAc (3×10 mL). The combined organic layers were washed with brine (2×10 mL), dried ($Na_2SO_4$). After filtration, the filtrate was concentrated in vacuo. The crude product was purified by Prep-HPLC with the following conditions (Column: XBridge Shield RP18 OBD Column, 19*250 mm, 10 μm; Mobile Phase A: water (0.1% $NH_4HCO_3$+0.1% $NH_3·H_2O$), Mobile Phase B: MeCN; Flow rate: 25 mL/min; Gradient: 48% B to 60% B in 9 min; Wave Length: 254/220 nm; RT: 8.03) to afford the title compound (AFA-2) (11.7 mg, 22 μmol, 14%, 99% Purity) as a white solid. m/z 533.0 $(M+H)^+$ (ES+). $^1$H NMR (300 MHz, DMSO-d6) δ 8.52 (s, 1H), 8.22-8.10 (m, 2H), 7.80-7.74 (m, 1H), 7.42 (d, J=1.2 Hz, 1H), 7.12 (d, J=2.1 Hz, 1H), 7.02 (d, J=2.2 Hz, 1H), 6.77 (t, J=5.4 Hz, 1H), 6.51 (d, J=5.3 Hz, 1H), 5.96 (d, J=1.3 Hz, 1H), 4.98 (s, 2H), 3.40 (s, 3H), 3.23-3.13 (m, 2H), 2.78 (d, J=4.9 Hz, 3H), 1.12 (t, J=7.1 Hz, 3H).

Example 179: Synthesis of 2-[6-(Ethylamino)-4-[4-methoxy-2-(4-methyl-1,2,4-triazol-3-yl)phenyl]pyridin-2-yl]-4-(trifluoromethyl)-3H-isoindol-1-one (AFB-8)

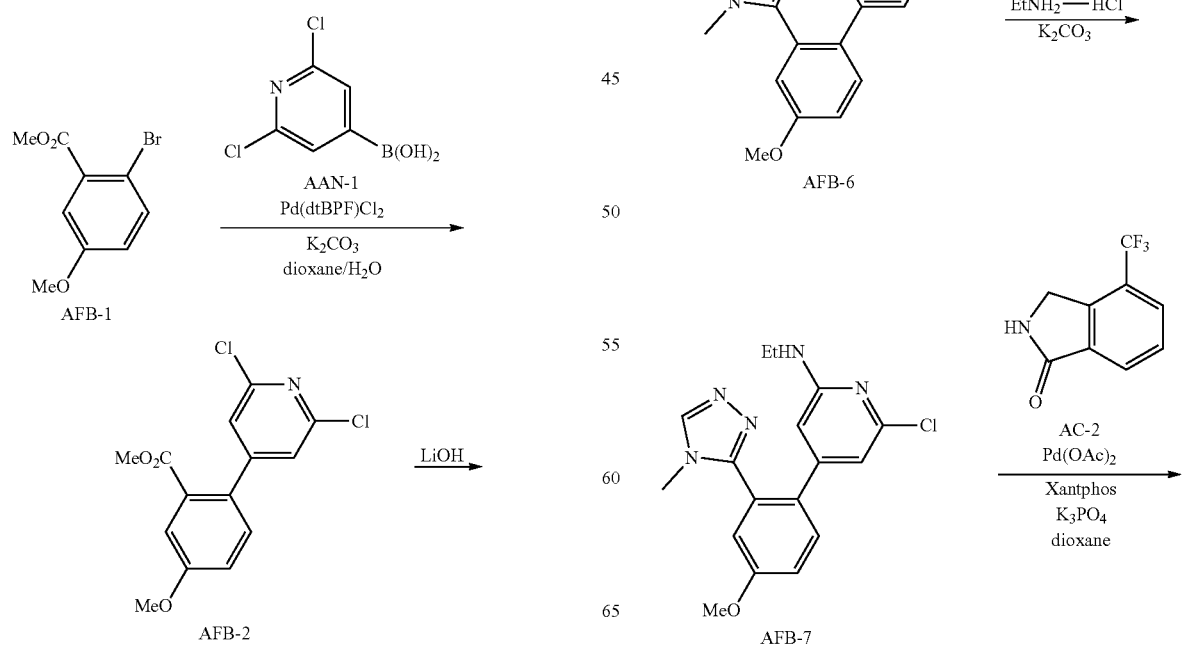

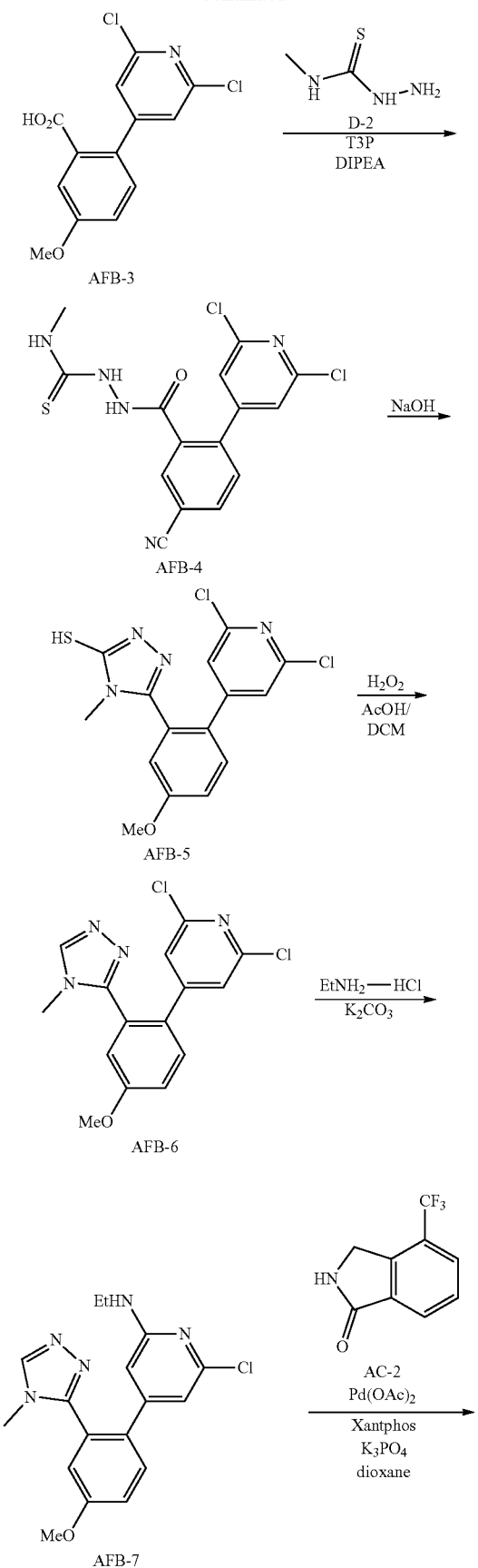

-continued

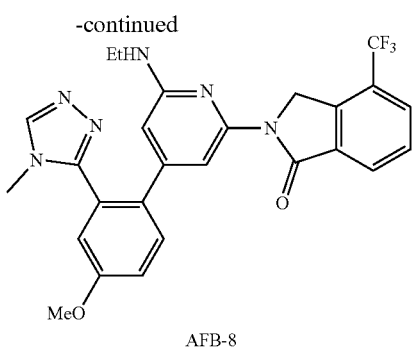

AFB-8

Step 1: Synthesis of 2-(2,6-Dichloropyridin-4-yl)-5-methoxybenzoate (AFB-2)

To a stirred mixture of methyl 2-bromo-5-methoxybenzoate (AFB-1) (1.00 g, 1 eq, 4.08 mmol), 2,6-dichloropyridin-4-ylboronic acid (AAN-1) (860 mg, 1.1 eq, 4.49 mmol) and $K_2CO_3$ (1.69 g, 12.2 mmol, 3 eq) in 1,4-dioxane (15 ml) and $H_2O$ (1.5 mL) was added Pd(dtBPF)Cl$_2$ (530 mg, 0.2 eq, 0.82 mmol) at rt under nitrogen atmosphere. The resulting mixture was stirred for 6 h at 60° C. under nitrogen atmosphere. The mixture was cooled to rt, diluted with water and extracted with EtOAc (3×100 mL). The combined organic layers were washed with brine (2×100 mL), dried ($Na_2SO_4$). After filtration, the filtrate was concentrated in vacuo. The crude product was purified by reverse flash column chromatography with the following conditions: Column, C18; mobile phase, water (0.1% $NH_4HCO_3$) and MeCN (20% MeCN up to 80% in 20 min); Detector, UV 254/220 nm to afford the sub-title compound (AFB-2) (871 mg, 2.58 mmol, 66%, 92% Purity) as a yellow solid. m/z 312.0/314.0 (M+H)$^+$ (ES+).

Step 2: Synthesis of 2-(2,6-Dichloropyridin-4-yl)-5-methoxybenzoic acid (AFB-3)

A solution of the product from step 1 above (AFB-2) (821 mg, 1 eq, 2.63 mmol) in THF (12 mL) and $H_2O$ (4 mL) was treated with LiOH (310 g, 5 eq, 13.2 mmol). The resulting mixture was stirred for 3 h at 70° C. The mixture was cooled to rt. The mixture was acidified to pH 2 with conc. HCl. The resulting mixture was diluted with water and extracted with EtOAc (3×80 mL). The combined organic layers were washed with brine (2×80 mL), dried ($Na_2SO_4$). After filtration, the filtrate was concentrated in vacuo. The crude product was used in the next step directly without further purification. m/z 298.0/230.0 (M+H)$^+$ (ES+).

Step 3: Synthesis of 2-(2,6-Dichloropyridin-4-yl)-5-methoxy-N-[(methylcarbamothioyl)amino]benzamide (AFB-4)

To a stirred mixture of the product from step 2 above (AFB-3) (583 mg, 1 eq, 2.63 mmol) in DMF (15 ml) were added DIPEA (2.03 g, 6 eq, 15.8 mmol) and $T_3P$ (50% in EA) (5.01 g, 50% Wt, 6 eq, 15.8 mmol) at 0° C. To the above mixture was added 4-methyl-3-thiosemicarbazide (D-2) (206 mg, 1 eq, 1.96 mmol) at 0° C. The resulting mixture was stirred for 1.5 h at rt. The resulting mixture was concentrated in vacuo. The crude product was purified by reverse flash column chromatography with the following conditions: Column, C18; mobile phase, water (0.1% $NH_4HCO_3$) and MeCN (10% MeCN up to 50% in 10 min); Detector, UV 254/220 nm. This resulted in the sub-title compound (AFB-4) (500 mg, 1.24 mmol, 49%, 90% Purity) as a white solid. m/z 365.0/367.0 (M+H)$^+$ (ES+).

Step 4: Synthesis of 5-[2-(2,6-Dichloropyridin-4-yl)-5-methoxyphenyl]-4-methyl-1,2,4-triazole-3-thiol (AFB-5)

To a stirred mixture of the product from step 3 above (AFB-4) (500 mg, 1 eq, 1.30 mmol) in DMF (10 ml) was added aq. NaOH (5.2 mL, 10 M, 4 eq, 5.20 mmol). The resulting mixture was stirred for 1.5 h at 80° C. The mixture was allowed to cool down to rt. The resulting mixture was diluted with water. The mixture was acidified to pH 4 with conc. HCl. The resulting mixture was diluted with water and extracted with EtOAc (3×80 mL). The combined organic layers were washed with brine (2×80 mL), dried ($Na_2SO_4$). After filtration, the filtrate was concentrated in vacuo. The crude product was purified by reverse flash column chromatography with the following conditions: Column, C18; mobile phase, water (0.1% $NH_4HCO_3$) and MeCN (10% MeCN up to 70% in 15 min); Detector, UV 254/220 nm to afford the sub-title compound (AFB-5) (225 mg, 0.57 mmol, 77%, 93% Purity) as a white solid. m/z 367.0/369.0 (M+H)$^+$ (ES+).

Step 5: Synthesis of 2,6-Dichloro-4-[4-methoxy-2-(4-methyl-1,2,4-triazol-3-yl)phenyl]pyridine (AFB-6)

To a stirred mixture of the product from step 4 above (AFB-5) (225 mg, 1 eq, 0.62 mmol) in DCM (10 ml) were added AcOH (184 mg, 5 eq, 3.07 mmol) and $H_2O_2$ (347 mg, 30% Wt, 15 eq, 10.2 mmol) dropwise at 0° C. The resulting mixture was stirred for 45 min at rt. The resulting mixture was diluted with water. The mixture was basified to pH 8 with sat. aq. sol. of $NaHCO_3$. The resulting mixture was filtered; the filter cake was washed with brine (3×3 mL). The filtrate was concentrated in vacuo. The crude product was purified by reverse flash column chromatography with the following conditions: Column, C18; mobile phase, water (0.1% $NH_4HCO_3$) and MeCN (10% MeCN up to 40% in 10 min); Detector, UV 254/220 nm. This resulted in the sub-title compound (AFB-6) (92 mg, 0.27 mmol, 70%, 97% Purity) as a white solid. m/z 335.0/337.0 (M+H)$^+$ (ES+).

Step 6: Synthesis of 6-Chloro-N-ethyl-4-[4-methoxy-2-(4-methyl-1,2,4-triazol-3-yl)phenyl]pyridin-2-amine (AFB-7)

To a stirred mixture of the product from step 5 above (AFB-6) (168 mg, 1 eq 0.50, mmol) in NMP (15 ml) were added $K_2CO_3$ (2.08 g, 15.0 mmol, 30 eq) and $EtNH_2$—HCl (123 mg, 3 eq, 1.50 mmol) at rt. The resulting mixture was stirred for 7 h at 120° C. The mixture was allowed to cool down to rt. The crude product was purified by reverse flash column chromatography with the following conditions: Column, C18; mobile phase, water (0.1% $NH_4HCO_3$) and MeCN (10% MeCN up to 50% in 10 min); Detector, UV 254/220 nm. This resulted in the sub-title compound (AFB-7) (126 mg, 0.33 mmol, 67%, 90% Purity) as a white solid. m/z 344.1/346.1 (M+H)$^+$ (ES+).

Step 7: Synthesis of 2-[6-(Ethylamino)-4-[4-methoxy-2-(4-methyl-1,2,4-triazol-3-yl)phenyl]pyridin-2-yl]-4-(trifluoromethyl)-3H-isoindol-1-one (AFB-8)

To a stirred mixture of the product from step 6 above (AFB-7) (120 mg, 1 eq, 0.35 mmol) and intermediate (AC-2) (78 mg, 1.1 eq, 0.39 mmol) in 1,4-dioxane (10 mL) was added $Cs_2CO_3$ (227 mg, 2 eq, 0.70 mmol). To the above mixture were added RuPhos (67 mg, 0.4 eq, 0.14 mmol) and RuPhos palladacycle Gen.3 (58 mg, 0.2 eq, 0.07 mmol) at rt under nitrogen atmosphere. The resulting mixture was stirred for 1 h at 100° C. under nitrogen atmosphere. The mixture was allowed to cool down to rt. The resulting mixture was diluted with water. The resulting mixture was diluted with water and extracted with EtOAc (3×20 mL). The combined organic layers were washed with brine (2×20 mL), dried ($Na_2SO_4$). After filtration, the filtrate was concentrated in vacuo. The residue was purified by Prep-TLC with DCM/MeOH (12/1). The crude product was purified by Prep-HPLC with the following conditions (Column: XBridge Prep OBD C18 Column, 30*150 mm, 5 μm; Mobile Phase A: water (0.1% $NH_4HCO_3$), Mobile Phase B: MeCN; Flow rate: 60 mL/min; Gradient: 45% B to 65% B in 9 min; Wave Length: 254/220 nm) to afford the title compound (AFB-8) (58.8 mg, 0.11 mmol, 33%, 99% Purity) as a green solid. m/z 509.0 (M+H)$^+$ (ES+). $^1$H NMR (400 MHz, DMSO-d6) δ 8.46 (s, 1H), 8.05 (m, 2H), 7.78 (t, J=7.7 Hz, 1H), 7.56-7.43 (m, 2H), 7.27 (d, J=8.6, 2.7 Hz, 1H), 7.11 (d, J=2.7 Hz, 1H), 6.64 (t, J=5.4 Hz, 1H), 5.87 (s, 1H), 5.18 (s, 2H), 3.87 (s, 3H), 3.32 (s, 3H), 3.23-3.09 (m, 2H), 1.12 (t, J=7.1 Hz, 3H).

Example 180: Synthesis of Methyl 4-[2-(ethyl-amino)-6-[1-oxo-4-(trifluoromethyl)-3H-isoindol-2-yl]pyridin-4-yl]-3-(4-methyl-1,2,4-triazol-3-yl) benzoate (AFC-1)

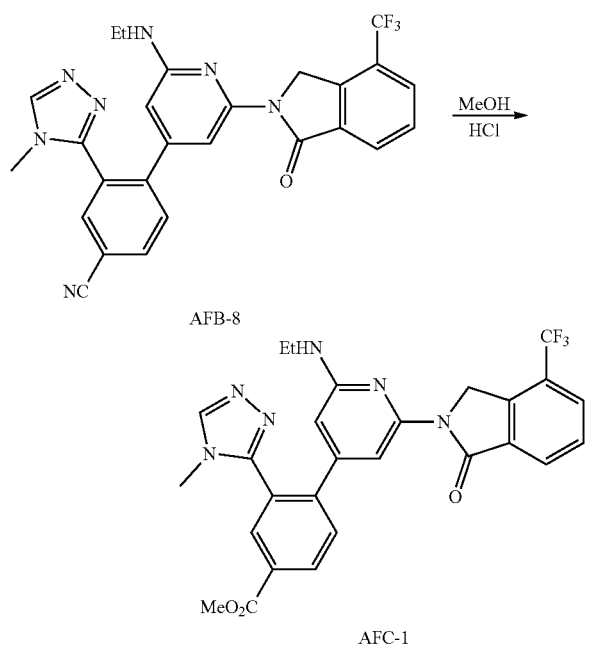

AFC-1

To a stirred solution of compound (ADP-8) (10 mg, 1 eq, 20 μmol) in MeOH (1 mL) was added HCl (gas) in 1,4-dioxane (1 mL, 4 M) at rt under nitrogen atmosphere. The resulting mixture was stirred for 2 days at 60° C. under nitrogen atmosphere. The mixture was allowed to cool down to rt. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% $NH_4HCO_3$), Mobile Phase B: MeCN; Flow rate: 60 mL/min; Gradient: 40% B to 51% B in 9 min; Wave Length: 254/220 nm; RT: 8.05) to afford the title compound (AFC-1) (2.7 mg, 4.8 μmol, 24%, 96% Purity) as a light yellow solid. m/z 537.3 (M+H)$^+$ (ES+). $^1$H NMR (400 MHz, DMSO-d6) δ 8.49 (s, 1H), 8.28-8.23 (m, 1H), 8.13-8.00 (m, 3H), 7.81-7.74 (m, 2H), 7.53 (s, 1H), 6.79 (t, J=5.4 Hz, 1H), 5.96 (s, 1H), 5.19 (s, 2H), 3.92 (s, 3H), 3.31 (s, 3H) 3.21-3.12 (m, 2H), 1.13 (t, J=7.2 Hz, 3H).

Example 181: Synthesis of 2-[6-(ethylamino)-4-[4-(hydroxymethyl)-2-(4-methyl-1,2,4-triazol-3-yl) phenyl]pyridin-2-yl]-4-(trifluoromethyl)-3H-isoindol-1-one (AFD-1)

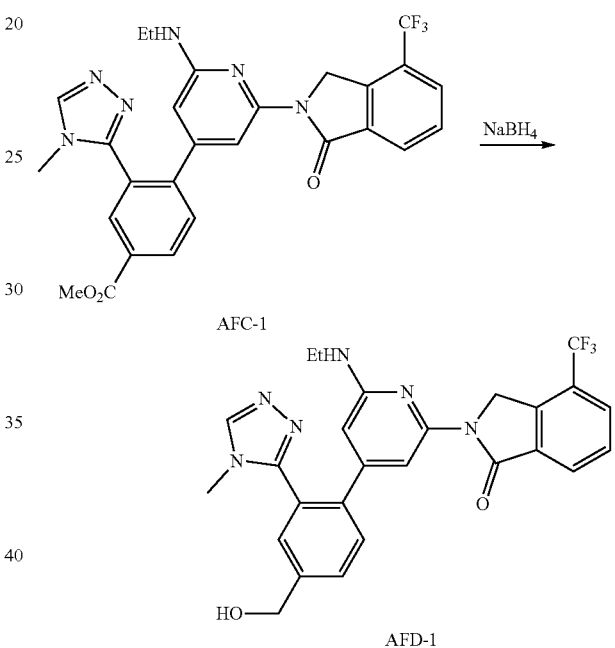

To a stirred solution of compound (AFC-1) (40 mg, 1 eq, 75 μmol) in MeOH (5 mL) was added $NaBH_4$ (28 mg, 10 eq, 0.75 mmol) at 0° C. under nitrogen atmosphere. The resulting mixture was stirred for 2 days at rt under nitrogen atmosphere. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% $NH_4HCO_3$), Mobile Phase B: MeCN; Flow rate: 60 mL/min; Gradient: 40% B to 51% B in 9 min; Wave Length: 254/220 nm; RT: 8.05) to afford the title compound (AFD-1) (5.4 mg, 11 μmol, 14%, 99% Purity) as a white solid. m/z 509.0 (M+H)$^+$ (ES+). $^1$H NMR (400 MHz, DMSO-d6) δ 8.46 (s, 1H), 8.09-8.01 (m, 2H), 7.78 (t, J=7.7 Hz, 1H), 7.66-7.61 (m, 1H), 7.56 (d, J=7.9 Hz, 1H), 7.53-7.47 (m, 2H), 6.69 (t, J=5.4 Hz, 1H), 5.91 (d, J=1.3 Hz, 1H), 5.40 (t, J=5.7 Hz, 1H), 5.19 (s, 2H), 4.63 (d, J=5.2 Hz, 2H), 3.29 (s, 3H), 3.22-3.07 (m, 2H), 1.12 (t, J=7.1 Hz, 3H).

Example 182: Synthesis of 4-[2-(ethylamino)-6-{6-[(2-hydroxy-2-methylpropoxy) methyl]-1-oxo-4-(trifluoromethyl)-3H-isoindol-2-yl}pyridin-4-yl]-3-(4-methyl-1,2,4-triazol-3-yl)benzonitrile (AFE-1)

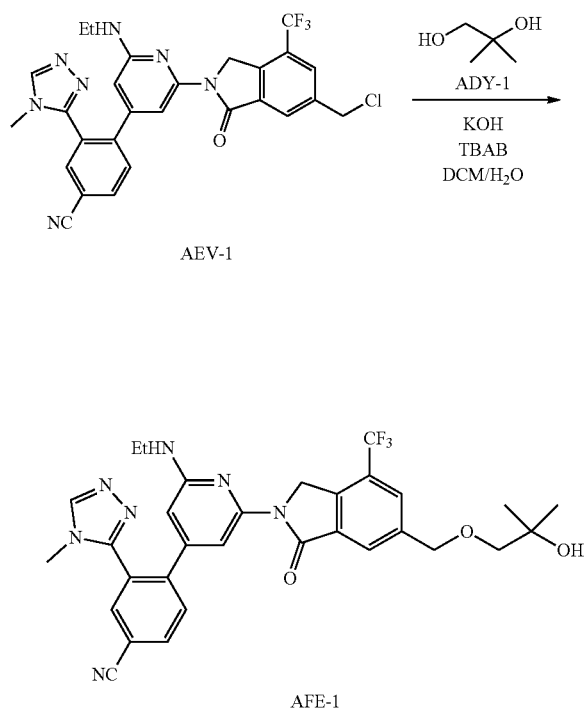

To a stirred solution of intermediate (AEV-1) (40 mg, 1 eq, 72 μmol) and 2-methyl-propane-1,2-diol (ADY-1) (65 mg, 10 eq, 0.72 mmol) in DCM (5 mL) were added TBAB (12 mg, 0.5 eq, 36 μmol) and aq. KOH (5 mL, 20% Wt) at rt. The resulting mixture was stirred slowly for 1 h at rt. The resulting mixture was diluted with water and extracted with EtOAc (3×20 mL). The combined organic layers were washed with brine (2×20 mL), dried (Na$_2$SO$_4$). After filtration, the filtrate was concentrated in vacuo. The residue was purified by TLC with DCM/MeOH (12/1). The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 42% B to 62% B in 8 min; Wave Length: 254/220 nm) to afford the title compound (AFE-1) (3.4 mg, 5.6 μmol, 7.7%, 99% Purity) as a yellow solid. m/z 606.0 (M+H)$^+$ (ES+). $^1$H NMR (400 MHz, DMSO-d6) δ 8.52 (s, 1H), 8.22-8.11 (m, 2H), 8.00 (d, J=15.0 Hz, 2H), 7.79 (d, J=8.0 Hz, 1H), 7.48-7.39 (m, 1H), 6.81 (t, J=5.4 Hz, 1H), 6.01-5.93 (m, 1H), 5.17 (s, 2H), 4.73 (s, 2H), 4.47 (s, 1H), 3.41 (s, 3H), 3.26 (s, 2H), 3.22-3.15 (m, 2H), 1.19-1.05 (m, 9H).

Example 183: Synthesis of 2-[6-(Ethylamino)-4-[4-fluoro-2-(4-methyl-1,2,4-triazol-3-yl) phenyl]pyridin-2-yl]-6-{1[(1-hydroxycyclobutyl) methoxy] methyl}-4-(trifluoromethyl)-3H-isoindol-1-one (AFF-2)

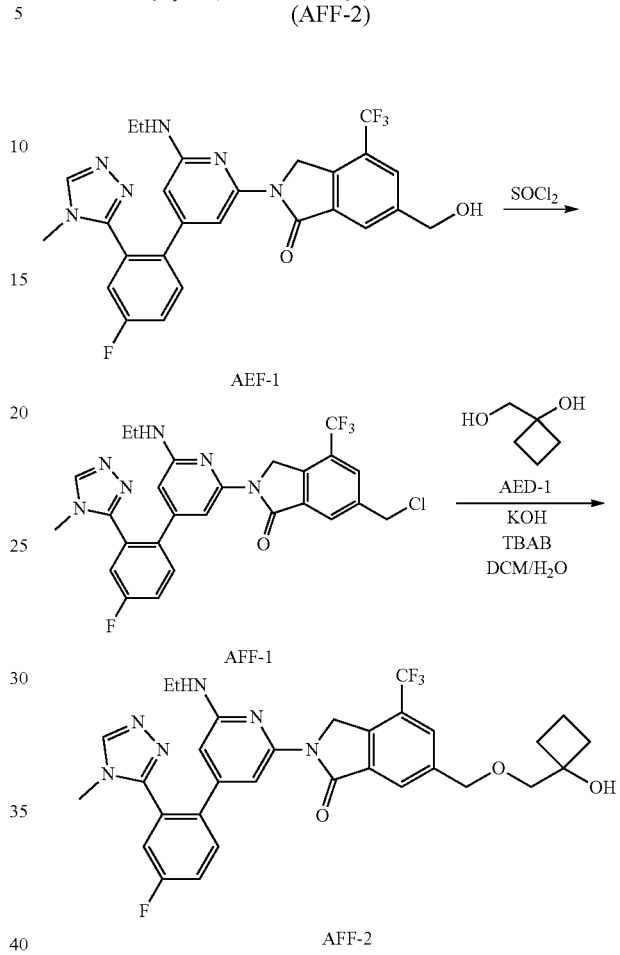

Step 1: Synthesis of 6-(Chloromethyl)-2-[6-(ethylamino)-4-[4-fluoro-2-(4-methyl-1,2,4-triazol-3-yl) phenyl] pyridin-2-yl]-4-(trifluoromethyl)-3H-isoindol-1-one (AFF-1)

To a stirred solution of compound (AEF-1) (417 mg, 1 eq, 0.79 mmol) in DCM (15 mL) was added SOCl$_2$ (283 mg, 3 eq, 2.38 mmol) at 0° C. The resulting mixture was stirred for 1 h at rt. The reaction was quenched with MeOH (1 mL) at 0° C. and concentrated in vacuo. The residue was purified by TLC with DCM/MeOH (10/1) to afford the sub-title compound (AFF-1) (351 mg, 0.59 mmol, 81%, 92% Purity) as a yellow solid. m/z 545.1/547.1 (M+H)$^+$ (ES+).

Step 2: Synthesis of 2-[6-(Ethylamino)-4-[4-fluoro-2-(4-methyl-1,2,4-triazol-3-yl)phenyl] pyridin-2-yl]-6-{1[(1-hydroxycyclobutyl)methoxy]methyl}-4-(trifluoromethyl)-3H-isoindol-1-one (AFF-2)

To a stirred solution of the product from step 1 above (AFF-1) (40 mg, 1 eq, 73 μmol) and 1-(hydroxymethyl) cyclobutan-1-ol (AED-1) (75 mg, 10 eq, 0.73 mmol) in DCM (5 mL) were added TBAB (12 mg, 0.5 eq, 36 μmol) and aq. KOH (5 mL, 20% Wt) at rt. The resulting mixture was stirred slowly for 1 h at rt. The resulting mixture was diluted with water and extracted with EtOAc (3×10 mL). The combined organic layers were washed with brine (2×10 mL), dried (Na$_2$SO$_4$). After filtration, the filtrate was concentrated in vacuo The residue was purified by TLC with DCM/MeOH (10/1). The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 52% B to 64% B in 9 min; Wave Length: 254/220 nm) to afford the title compound (AFF-2) (5.8 mg, 9.4 μmol, 13%, 99% Purity) as a white solid. m/z 611.0 (M+H)$^+$ (ES+). $^1$H NMR (400 MHz, DMSO-d6) δ 8.49 (s, 1H), 8.01 (d, J=14.7 Hz, 2H), 7.68-7.50 (m, 3H), 7.47-7.43 (m, 1H), 6.72 (t, J=5.4 Hz, 1H), 5.97-5.88 (m, 1H), 5.16 (s, 2H), 5.10 (s, 1H), 4.83-4.74 (m, 2H), 3.45 (s, 2H), 3.38 (d, J=2.9 Hz, 3H), 3.24-3.14 (m, 2H), 2.08-2.00 (m, 2H), 1.99-1.89 (m, 2H), 1.72-1.58 (m, 1H), 1.55-1.40 (m, 1H), 1.13 (t, J=7.1 Hz, 3H).

Example 184: Synthesis of 2-[6-(Ethylamino)-4-[4-fluoro-2-(4-methyl-1,2,4-triazol-3-yl)phenyl]pyridin-2-yl]-6-[(2-hydroxy-2-methylpropoxy)methyl]-4-(trifluoromethyl)-3H-isoindol-1-one (AFG-1)

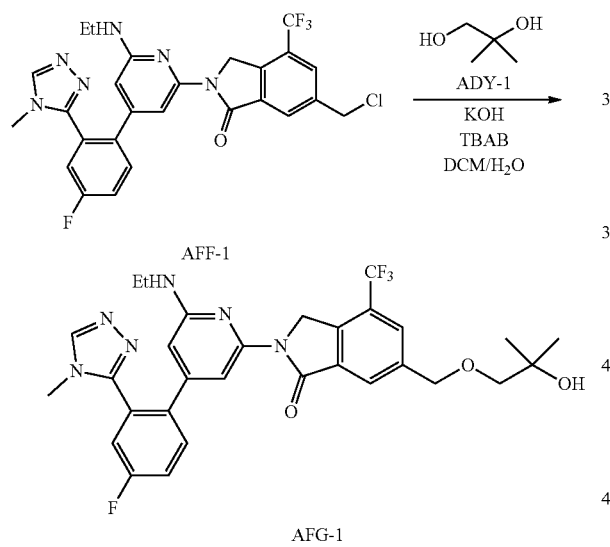

To a stirred solution of intermediate (AFF-1) (35 mg, 1 eq, 64 μmol) and 2-methyl-propane-1,2-diol (ADY-1) (58 mg, 10 eq, 0.64 μmol) in DCM (5 mL) were added TBAB (11 mg, 0.5 eq, 32 μmol) and aq. KOH (5 mL, 20% Wt) at rt. The resulting mixture was stirred slowly for 1 h at rt. The resulting mixture was diluted with water and extracted with EtOAc (3×10 mL). The combined organic layers were washed with brine (2×10 mL), dried (Na$_2$SO$_4$). After filtration, the filtrate was concentrated in vacuo. The residue was purified by TLC with DCM/MeOH (10/1). The crude product was purified by Prep-HPLC with the following conditions (Column: XBridge Prep OBD C18 Column, 30*150 mm, 5 μm; Mobile Phase A: Water (0.1% NH$_4$HCO$_3$), Mobile Phase B: MeCN; Flow rate: 60 mL/min; Gradient: 40% B to 60% B in 9 min; Wave Length: 254/220 nm) to afford the title compound (AFG-1) (3.3 mg, 5.4 μmol, 8.5%, 98% Purity) as a off-white solid. m/z 599.1 (M+H)$^+$ (ES+). $^1$H NMR (400 MHz, DMSO-d6) δ 8.49 (s, 1H), 7.99 (d, J=16.2 Hz, 2H), 7.68-7.41 (m, 4H), 6.71 (t, J=5.4 Hz, 1H), 5.92 (s, 1H), 5.17 (s, 2H), 4.73 (s, 2H), 4.46 (s, 1H), 3.37 (s, 3H), 3.26 (s, 2H), 3.23-3.10 (m, 2H), 1.21-1.06 (m, 9H).

Example 185: Synthesis of 2-{6-Cyclopropyl-4-[4-fluoro-2-(4-methyl-1,2,4-triazol-3-yl)phenyl]pyridin-2-yl}-6-({[(1-hydroxycyclobutyl)methyl]amino}methyl)-3H-isoindol-1-one (AFH-1)

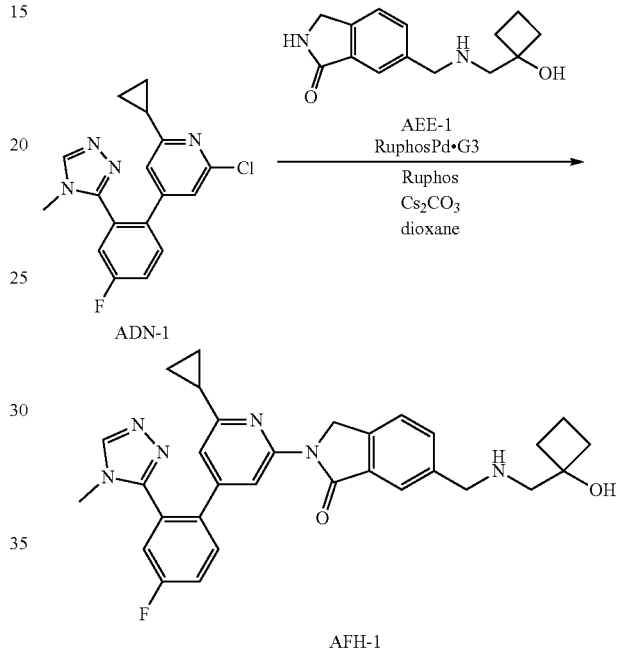

To a stirred solution of intermediate (ADN-1) (60 mg, 1 eq, 0.18 mmol), intermediate (AEE-1) (54 mg, 1.2 eq, 0.22 mmol) and Cs$_2$CO$_3$ (119 mg, 2 eq, 0.36 mmol) in 1,4-dioxane (8 mL) were added RuPhos (34 mg, 0.4 eq, 73 μmol) and RuPhos palladacycle Gen.3 (31 mg, 0.2 eq, 36 μmol) at rt under nitrogen atmosphere. The resulting mixture was stirred for 2 h at 100° C. under nitrogen atmosphere. The mixture was cooled to rt and concentrated in vacuo. The residue was purified by Prep-TLC with DCM/MeOH (12/1). The crude product was purified by Prep-HPLC with the following conditions (Column: Sunfire prep C18 column, 30*150 mm, 5 μm; Mobile Phase A: water (0.1% FA), Mobile Phase B: MeCN; Flow rate: 60 mL/min; Gradient: 10% B to 40% B in 7 min; Wave Length: 254/220 nm; RT: 6.6) to afford the title compound (AFH-1) (22.8 mg, 42 μmol, 23%, 99% Purity) as a white solid. m/z 539.6 (M+H)$^+$ (ES+). $^1$H NMR (400 MHz, DMSO-d6) δ 8.51 (s, 1H), 7.98 (d, J=1.4 Hz, 1H), 7.77-7.68 (m, 2H), 7.65 (d, J=1.8 Hz, 2H), 7.60 (t, J=8.6 Hz, 2H), 6.80 (d, J=1.5 Hz, 1H), 4.96 (d, J=35.4 Hz, 3H), 3.86 (s, 2H), 3.43 (s, 3H), 2.53 (s, 2H), 1.99 (t, J=8.8 Hz, 3H), 1.94-1.84 (m, 2H), 1.60 (d, J=10.6 Hz, 1H), 1.46-1.32 (m, 1H), 0.95 (d, J=6.4 Hz, 4H).

Example 186: Synthesis of 2-{6-Cyclopropyl-4-[2-methyl-4-(4-methyl-1,2,4-triazol-3-yl)pyrazol-3-yl]pyridin-2-yl}-6-({[(1-hydroxycyclobutyl)methyl]amino}methyl)-3H-isoindol-1-one (AFI-1)

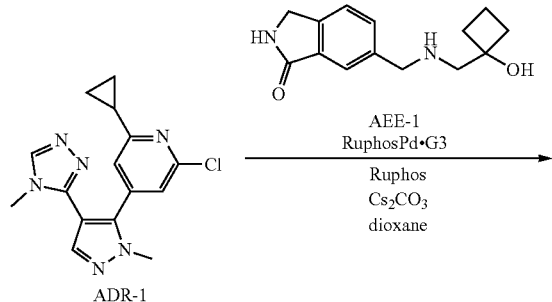

To a stirred mixture of intermediate (ADR-1) (50 mg, 1 eq, 0.16 mmol), intermediate (AEE-1) (39 mg, 1 eq, 0.16 mmol) and Cs$_2$CO$_3$ (104 mg, 0.32 mmol, 2 eq) in 1,4-dioxane (5 mL) were added RuPhos (30 mg, 0.4 eq, 64 µmol) and RuPhos palladacycle Gen.3 (27 mg, 0.2 eq, 32 µmol) at rt under nitrogen atmosphere. The resulting mixture was stirred for overnight at 80° C. under nitrogen atmosphere. The mixture was allowed to cool down to rt. The resulting mixture was concentrated in vacuo. The crude product was purified by Prep-HPLC with the following conditions: Column: XBridge Prep OBD C18 Column, 30*150 mm, 5 µm; Mobile Phase A: water (0.1% NH$_4$HCO$_3$), Mobile Phase B: MeCN; Flow rate: 60 mL/min; Gradient: 27% B to 37% B in 9 min; Wave Length: 254/220 nm; RT: 8.9 to afford the title compound (AFI-1) (19 mg, 35 µmol, 22%, 96% Purity) as a white solid. m/z 525.5 (M+H)$^+$ (ES+). $^1$H NMR (400 MHz, MeOH-d4) δ 8.48 (s, 1H), 8.23 (d, J=1.3 Hz, 1H), 7.90 (s, 1H), 7.83 (s, 1H), 7.70 (d, J=7.4 Hz, 1H), 7.64 (d, J=7.8 Hz, 1H), 7.07 (d, J=1.4 Hz, 1H), 5.07 (s, 2H), 4.02 (s, 3H), 3.95 (s, 2H), 3.55 (s, 3H), 2.72 (s, 2H), 2.14-2.00 (m, 5H), 1.73 (s, 1H), 1.56-1.44 (m, 1H), 1.15-1.06 (m, 2H), 1.06-0.97 (m, 2H).

Example 187: Synthesis of 4-{2-Cyclopropyl-6-[6-({[(1-hydroxycyclobutyl)methyl]amino}methyl)-1-oxo-3H-isoindol-2-yl]pyridin-4-yl}-3-(4-methyl-1,2,4-triazol-3-yl)benzonitrile (AFJ-1)

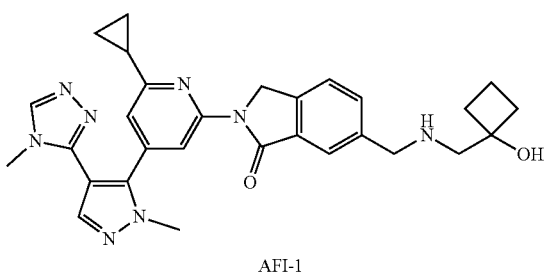

To a stirred solution of intermediate (AEG-2) (60 mg, 1 eq, 0.18 mmol), intermediate (AEE-1) (57 mg, 1.3 eq, 0.23 mmol) and Cs$_2$CO$_3$ (116 mg, 2 eq, 0.36 mmol) in 1,4-dioxane (8 mL) were added RuPhos (33 mg, 0.4 eq, 72 µmol) and RuPhos palladacycle Gen.3 (30 mg, 0.2 eq, 36 µmol) at rt under nitrogen atmosphere. The resulting mixture was stirred for 2 h at 100° C. under nitrogen atmosphere. The mixture was cooled to rt and concentrated in vacuo. The residue was purified by Prep-TLC with DCM/MeOH (15/1). The crude product was purified by Prep-HPLC with the following conditions (Column: XBridge Prep OBD C18 Column, 30*150 mm, 5 µm; Mobile Phase A: water (0.1% NH$_4$HCO$_3$), Mobile Phase B: MeCN; Flow rate: 60 mL/min; Gradient: 38% B to 48% B in 8 min; Wave Length: 254/220 nm; RT: 7.3) to afford the title compound (AFJ-1) (3.7 mg, 6.6 µmol, 3.8%, 97% Purity) as a white solid. m/z 546.5 (M+H)$^+$ (ES+). $^1$H NMR (400 MHz, DMSO-d6) δ 8.54 (s, 1H), 8.25-8.18 (m, 2H), 7.99 (d, J=1.4 Hz, 1H), 7.87 (d, J=8.5 Hz, 1H), 7.75 (s, 1H), 7.65 (t, J=1.3 Hz, 2H), 6.88 (d, J=1.4 Hz, 1H), 5.00 (s, 2H), 4.91 (s, 1H), 3.86 (s, 2H), 3.48 (s, 3H), 2.53 (s, 2H), 2.09-1.95 (m, 3H), 1.89 (d, J=12.1, 9.4 Hz, 2H), 1.64-1.57 (m, 1H), 1.40 (d, J=10.9, 8.9 Hz, 1H), 1.00-0.93 (m, 4H).

Example 188: Synthesis of 2-{6-Cyclopropyl-4-[4-fluoro-2-(4-methyl-1,2,4-triazol-3-yl)phenyl]pyridin-2-yl}-6-(hydroxymethyl)-4-(trifluoromethyl)-3H-isoindol-1-one (AFK-1)

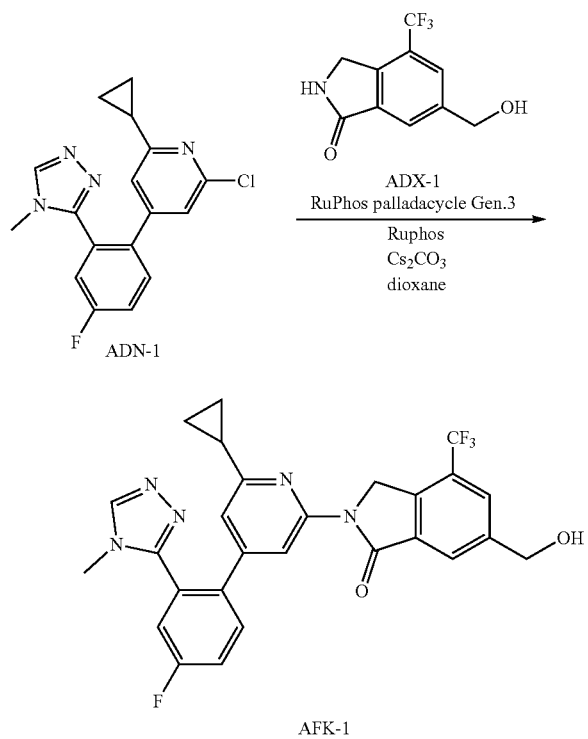

Example 189: Synthesis of 2-{6-Cyclopropyl-4-[4-fluoro-2-(4-methyl-1,2,4-triazol-3-yl) phenyl]pyridin-2-yl}-6-{[(1-hydroxycyclobutyl)methoxy]methyl}-4-(trifluoromethyl)-3H-isoindol-1-one (AFL-2)

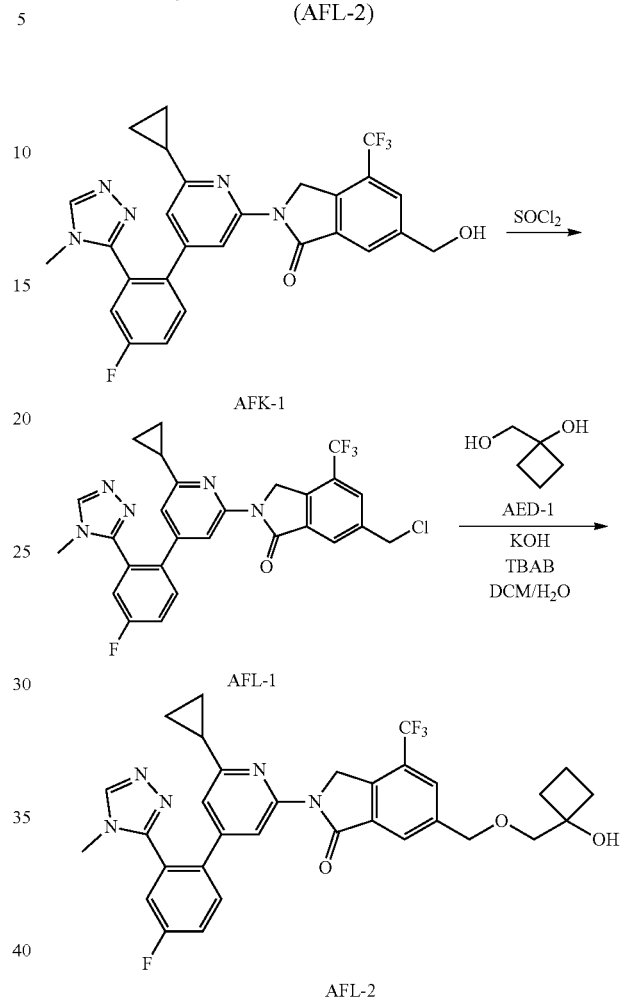

To a stirred solution of intermediate (ADN-1) (45 mg, 1 eq, 0.14 mmol), intermediate (ADX-1) (38 mg, 1.2 eq, 0.16 mmol) and Cs$_2$CO$_3$ (134 mg, 3 eq, 0.41 mmol) in 1,4-dioxane (3 mL) were added RuPhos palladacycle Gen.3 (23 mg, 0.2 eq, 27 μmol) and Ruphos (26 mg, 0.4 eq, 55 μmol) at rt under nitrogen atmosphere. The resulting mixture was stirred for 2 h at 100° C. under nitrogen atmosphere. The mixture was cooled to rt, diluted with water and extracted with EtOAc (3×10 mL). The combined organic layers were washed with brine (2×10 mL), dried (Na$_2$SO$_4$). After filtration, the filtrate was concentrated in vacuo. The residue was purified by Prep-TLC with DCM/MeOH (15/1). The crude product was purified by Prep-HPLC with the following conditions (Column: Sunfire prep C18 column, 30*150 mm, 5 μm; Mobile Phase A: mater (0.1% FA), Mobile Phase B: MeCN; Flow rate: 60 mL/min; Gradient: 34% B to 64% B in 7 min; Wave Length: 254/220 nm; RT: 6.3) to afford the title compound (AFK-1) (19.4 mg, 37 μmol, 27%, 99% Purity) as a white solid. m/z 524.0 (M+H)$^+$ (ES+). $^1$H NMR (400 MHz, DMSO-d6) δ 8.51 (s, 1H), 8.01-7.96 (m, 3H), 7.74-7.71 (m, 1H), 7.64-7.53 (m, 2H), 6.81 (d, J=1.5 Hz, 1H), 5.59 (t, J=5.8 Hz, 1H), 5.16 (s, 2H), 4.70 (d, J=5.8 Hz, 2H), 3.43 (s, 3H), 2.07-2.01 (m, 1H), 0.99-0.93 (m, 4H).

Step 1: Synthesis of 6-(Chloromethyl)-2-{6-cyclopropyl-4-[4-fluoro-2-(4-methyl-1,2,4-triazol-3-yl) phenyl] pyridin-2-yl}-4-(trifluoromethyl)-3H-isoindol-1-one (AFL-1)

To a stirred solution of compound (AFK-1) (40 mg, 1 eq, 76 μmol) in DCM (3 mL) was added SOCl$_2$ (14 mg, 1.5 eq, 0.11 mmol) at 0° C. The resulting mixture was stirred for 2 h at rt. The resulting mixture was diluted with water. The resulting mixture was extracted with EtOAc (3×20 mL). The combined organic layers were washed with brine (20 mL), dried (Na$_2$SO$_4$). After filtration, the filtrate was concentrated in vacuo. The residue was purified by Prep-TLC (DCM/MeOH 15:1) to afford the sub-title compound (AFL-1) (25 mg, 44 μmol, 60%, 95% Purity) as a yellow solid. m/z 542.1/544.1 (M+H)$^+$ (ES+).

Step 2: Synthesis of 2-{6-Cyclopropyl-4-[4-fluoro-2-(4-methyl-1,2,4-triazol-3-yl)phenyl]pyridin-2-yl}-6-{[(1-hydroxycyclobutyl)methoxy]methyl}-4-(trifluoromethyl)-3H-isoindol-1-one (AFL-2)

To a stirred solution of the product from step 1 above (AFL-1) (25 mg, 1 eq, 46 μmol) and 1-(hydroxymethyl)

cyclobutan-1-ol (AED-1) (47 mg, 10 eq, 0.46 mmol) in DCM (5 mL) was added TBAB (7.4 mg, 0.5 eq, 23 µmol) at rt. To the above mixture was added aq. KOH (5 mL, 20% Wt) at rt. The resulting mixture was stirred for 1 h at rt. The resulting mixture was diluted with water. The resulting mixture was extracted with EtOAc (3×10 mL). The combined organic layers were washed with brine (10 mL), dried ($Na_2SO_4$). After filtration, the filtrate was concentrated in vacuo. The residue was purified by Prep-TLC with DCM/MeOH (12/1). The crude product was purified by Prep-HPLC with the following conditions (Column: Sunfire prep C18 column, 30*150 mm, 5 µm; Mobile Phase A: water (0.1% FA), Mobile Phase B: MeCN; Flow rate: 60 mL/min; Gradient: 20% B to 50% B in 7 min; Wave Length: 254/220 nm; RT: 6.3) to afford the title compound (AFL-2) (4.8 mg, 7.5 µmol, 16%, 95% Purity) as a white solid. m/z 608.1 $(M+H)^+$ (ES+). $^1$H NMR (400 MHz, MeOH-d4) δ 8.47 (s, 1H), 8.08 (s, 1H), 8.01-8.00 (m, 2H), 7.79-7.77 (m, 1H), 7.57-7.45 (m, 2H), 6.88 (d, J=1.5 Hz, 1H), 5.17 (s, 2H), 4.77 (s, 2H), 3.57 (s, 2H), 3.46 (s, 3H), 2.19-2.13 (m, 2H), 2.09-2.01 (m, 3H), 1.79-1.76 (m, 1H), 1.61-1.54 (m, 1H), 1.00-0.98 (m, 4H).

Example 190: Synthesis of 2-[6-(Ethylamino)-4-[4-fluoro-2-(4-methyl-1,2,4-triazol-3-yl)phenyl]pyridin-2-yl]-6-[(methoxymethoxy)methyl]-4-(trifluoromethyl)-3H-isoindol-1-one (AFM-2)

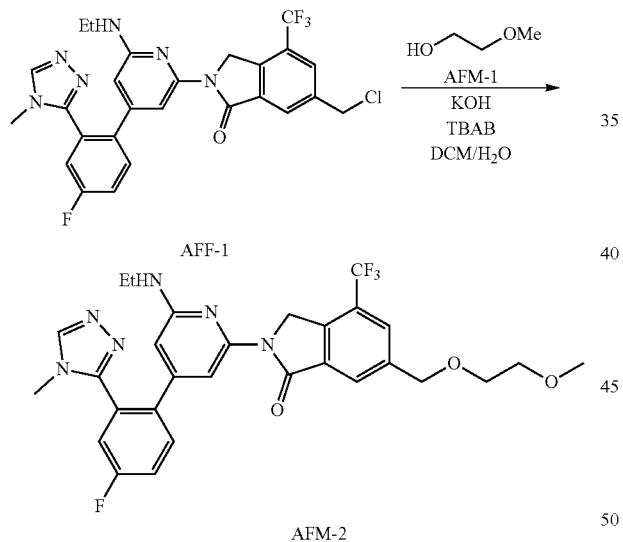

To a stirred solution of intermediate (AFF-1) (35 mg, 1 eq, 64 µmol) and 2-methoxyethanol (AFM-1) (49 mg, 10 eq, 0.64 mmol) in DCM (5 mL) were added TBAB (11 mg, 0.5 eq, 32 µmol) and aq. KOH (5 mL, 20% Wt) at rt. The resulting mixture was stirred slowly for 1 h at rt. The resulting mixture was diluted with water and extracted with EtOAc (3×10 mL). The combined organic layers were washed with brine (2×10 mL), dried ($Na_2SO_4$). After filtration, the filtrate was concentrated in vacuo. The residue was purified by TLC with DCM/MeOH (10/1). The crude product was purified by Prep-HPLC with the following conditions (Column: XBridge Prep OBD C18 Column, 30*150 mm, 5 µm; Mobile Phase A: water (0.1% $NH_4HCO_3$), Mobile Phase B: MeCN; Flow rate: 60 mL/min; Gradient: 55% B to 65% B in 9 min; Wave Length: 254/220 nm) to afford the title compound (AFM-2) (3.5 mg, 5.9 µmol, 9.5%, 99% Purity) as a white solid. m/z 585.5 $(M+H)^+$ (ES+). $^1$H NMR (400 MHz, DMSO-d6) δ 8.52 (s, 1H), 7.98 (d, J=14.8 Hz, 2H), 7.67-7.50 (m, 3H), 7.43 (s, 1H), 6.71 (s, 1H), 5.93 (s, 1H), 5.16 (s, 2H), 4.70 (s, 2H), 3.65-3.62 (m, 2H), 3.53-3.51 (m, 2H), 3.38 (s, 3H), 3.27 (s, 3H), 3.22-3.15 (m, 2H), 1.13 (t, J=7.2 Hz, 3H).

Example 191: Synthesis of 2-[4'-Fluoro-2'-(4-methyl-1,2,4-triazol-3-yl)-[1,1'-biphenyl]-3-yl]-6-({[(1-hydroxycyclobutyl)methyl]amino}methyl)-4-(trifluoromethyl)-3H-isoindol-1-one (AFN-3)

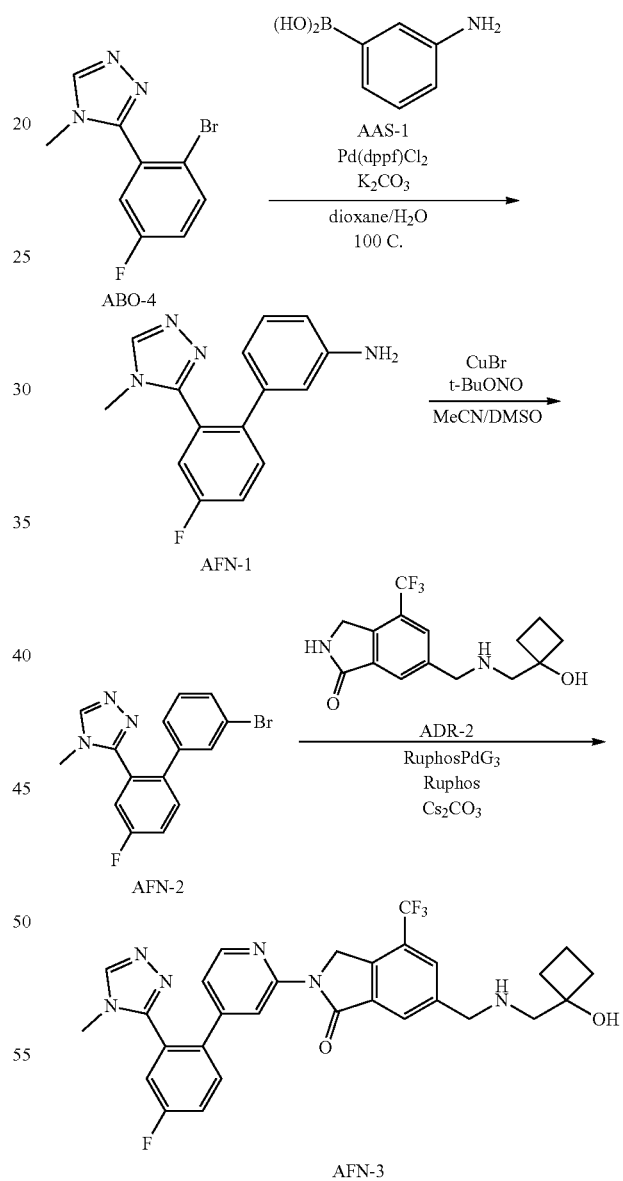

Step 1: Synthesis of 4'-Fluoro-2'-(4-methyl-1,2,4-triazol-3-yl)-[1,1'-biphenyl]-3-amine) (AFN-1)

To a stirred mixture of intermediate (ABO-4) (400 mg, 1 eq, 1.56 mmol), 3-aminophenylboronic acid (AAS-1) (235 mg, 1.1 eq, 1.72 mmol) and K₂CO₃ (649 mg, 3 eq, 4.68 mmol) in 1,4-dioxane (15 mL) and H₂O (1.5 mL) was added Pd(dppf)Cl₂.DCM (127 mg, 0.1 eq, 0.16 mmol) at rt under nitrogen atmosphere. The resulting mixture was stirred for 6 h at 100° C. under nitrogen atmosphere. The mixture was cooled to rt, diluted with water and extracted with EtOAc (3×80 mL). The combined organic layers were washed with brine (2×80 mL), dried (Na₂SO₄). After filtration, the filtrate was concentrated in vacuo. The residue was purified by Prep-TLC with DCM/MeOH (12/1) to afford the sub-title compound (AFN-1) (283 mg, 0.97 mmol, 67%, 92% Purity) as a white solid. m/z 269.1 (M+H)⁺ (ES+).

Step 2: Synthesis of 3-{3'-Bromo-4-fluoro-[1,1'-biphenyl]-2-yl}-4-methyl-1,2,4-triazole (AFN-2)

To a stirred mixture of t-BuNO₂ (231 mg, 6 eq, 2.24 mmol) in MeCN (8 mL) was added CuBr (80 mg, 1.5 eq, 0.56 mmol) at 0° C. under nitrogen atmosphere. The resulting mixture was stirred for 1 h at 0° C. under nitrogen atmosphere. To the above mixture was added the product from step 1 above (AFN-1) (100 mg, 1 eq, 0.37 mmol) in MeCN (1 mL) at rt. The resulting mixture was stirred for 10 min at rt. Then the resulting mixture was stirred for 1.5 h at 50° C. The mixture was allowed to cool down to rt. The resulting mixture was concentrated in vacuo. The residue was purified by Prep-TLC with DCM/MeOH (12/1) to afford the sub-title compound (AFN-2) (64 mg, 0.18 mmol, 52%, 95% Purity) as a white solid. m/z 332.0/334.0 (M+H)⁺ (ES+).

Step 3: Synthesis of 2-[4'-Fluoro-2'-(4-methyl-1,2,4-triazol-3-yl)-[1,1'-biphenyl]-3-yl]-6-({[(1-hydroxycyclobutyl)methyl]amino}methyl)-4-(trifluoromethyl)-3H-isoindol-1-one (AFN-3)

To a stirred mixture of the product from step 2 above (AFN-2) (46 mg, 1 eq, 0.14 mmol) and intermediate (ADR-2) (48 mg, 1.1 eq, 0.15 mmol) in 1,4-dioxane (15 mL) was added Cs₂CO₃ (90 mg, 2 eq, 0.28 mmol) at rt. To the above mixture were added RuPhos (26 mg, 0.4 eq, 55 μmol) and RuPhos palladacycle Gen.3 (24 mg, 0.2 eq, 29 μmol) at rt under nitrogen atmosphere. The resulting mixture was stirred for 1 h at 100° C. under nitrogen atmosphere. The mixture was cooled to rt, diluted with water and extracted with EtOAc (3×20 mL). The combined organic layers were washed with brine (2×20 mL), dried (Na₂SO₄). After filtration, the filtrate was concentrated in vacuo. The residue was purified by Prep-TLC with DCM/MeOH (12/1). The crude product was purified by Prep-HPLC with the following conditions (Column, XBridge Prep OBD C18 Column, 30*150 mm, 5 μm; Mobile phase A: water (0.1% NH₄HCO₃); Mobile phase B: MeCN; Gradient: 38% MeCN up to 48% in 9 min; Wave Length: 254/220 nm) to afford the title compound (AFN-3) (6.2 mg, 11 μmol, 7.7%, 96% Purity) as a white solid. m/z 566.1 (M+H)⁺ (ES+). ¹H NMR (300 MHz, DMSO-d6) δ 8.42 (s, 1H), 8.01 (m, 3H), 7.76-7.33 (m, 5H), 6.88 (d, J=7.7 Hz, 1H), 5.08 (s, 2H), 4.94 (s, 1H), 3.96 (s, 2H), 3.13 (s, 3H), 2.53 (s, 2H), 2.05-1.86 (m, 4H), 1.61 (m, 1H), 1.44-1.34 (m, 1H).

Example 192: Synthesis of 2-{6-Cyclopropyl-4-[4-fluoro-2-(4-methyl-1,2,4-triazol-3-yl)phenyl]pyridin-2-yl}-6-({[(1R,2S)-2-hydroxycyclopentyl]amino}methyl)-3H-isoindol-1-one (AFO-2)

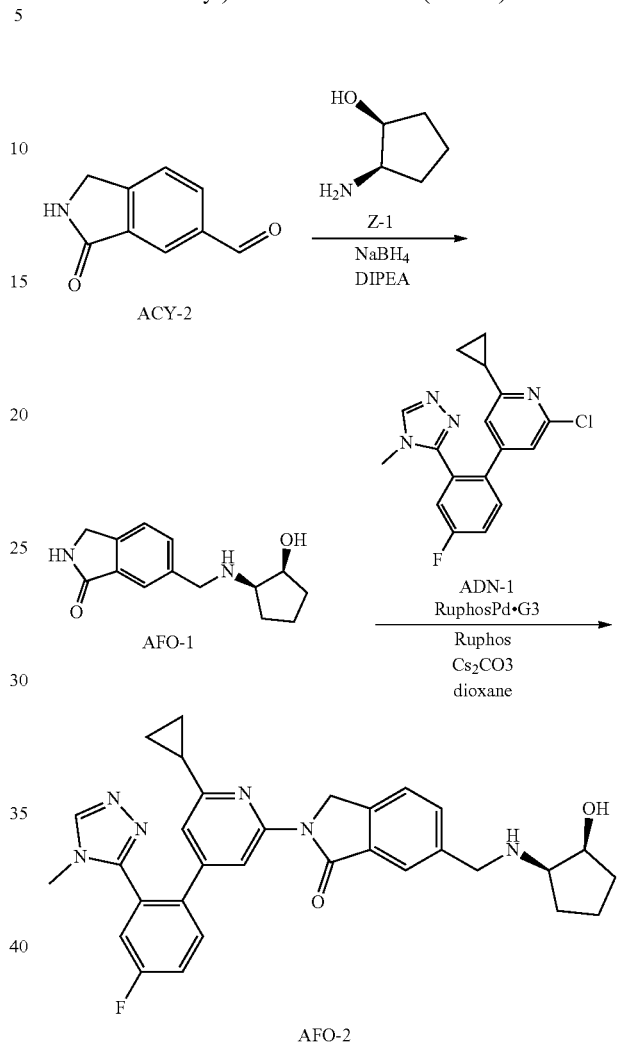

Step 1: Synthesis of 6-((((1R,2S)-2-Hydroxycyclopentyl)amino)methyl)isoindolin-1-one (AFO-1)

To a stirred solution (1S,2R)-2-aminocyclopentan-1-ol (Z-1) (151 mg, 1.2 eq, 1.49 mmol) in MeOH (10 mL) were added DIPEA (642 mg, 4 eq, 5.00 mmol) at rt. The resulting mixture was stirred for 10 min at 60° C. Then intermediate (ACY-2) (200 mg, 1 eq, 1.24 mmol) was added at rt. The resulting mixture was stirred for 2 h at 60° C. To the above mixture was added NaBH₄ (235 mg, 5 eq, 6.21 mmol) at 0° C. The resulting was stirred for 1 h at rt. The crude product was purified by reverse flash column chromatography with the following conditions: Column, C18; mobile phase, water (0.1% NH₄HCO₃) and MeCN (0% MeCN up to 20% in 20 min); Detector, UV 254/220 nm to afford the sub-title compound (AFO-1) (144 mg, 0.51 mmol, 47%, 88% Purity) as a white solid. m/z 247.1 (M+H)⁺ (ES+).

Step 2: Synthesis of 2-{6-Cyclopropyl-4-[4-fluoro-2-(4-methyl-1,2,4-triazol-3-yl) phenyl] pyridin-2-yl}-6-({[(1R,2S)-2-hydroxycyclopentyl] amino} methyl)-3H-isoindol-1-one (AFO-2)

To a stirred solution of intermediate (ADN-1) (50 mg, 1 eq, 0.15 mmol), the product from step 1 above (AFO-1) (37 mg, 1 eq, 0.15 mmol) and Cs$_2$CO$_3$ (99 mg, 2 eq, 0.30 mmol) in 1,4-dioxane (6 mL) were added RuPhos (28 mg, 0.4 eq, 61 μmol) and RuPhos palladacycle Gen.3 (25 mg, 0.2 eq, 30 μmol) at rt under nitrogen atmosphere. The resulting mixture was stirred for 2 h at 100° C. under nitrogen atmosphere. The mixture was cooled to rt and concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 35% B to 52% B in 9 min; Wave Length: 254/220 nm; RT: 8.03) to afford the title compound (AFO-2) (23.0 mg, 42 μmol, 28%, 99% Purity) as a white solid. m/z 539.2 (M+H)$^+$ (ES+). $^1$H NMR (300 MHz, DMSO-d6) δ 8.51 (s, 1H), 7.97 (d, J=1.4 Hz, 1H), 7.80-7.68 (m, 2H), 7.68-7.53 (m, 4H), 6.81 (d, J=1.4 Hz, 1H), 5.00 (s, 2H), 4.39 (s, 1H), 4.00-3.90 (m, 1H), 3.91-3.73 (m, 2H), 3.44 (s, 3H), 2.83-2.69 (m, 1H), 2.26 (s, 1H), 2.08-1.95 (m, 1H), 1.77-1.47 (m, 4H), 1.48-1.31 (m, 2H), 0.95 (d, J=6.4 Hz, 4H).

Example 193: Synthesis of 2-[6-(Ethylamino)-4-[2-methyl-4-(4-methyl-1,2,4-triazol-3-yl)pyrazol-3-yl] pyridin-2-yl]-6-{[(1-fluorocyclobutyl) methoxy] methyl}-4-(trifluoromethyl)-3H-isoindol-1-one (AFP-2)

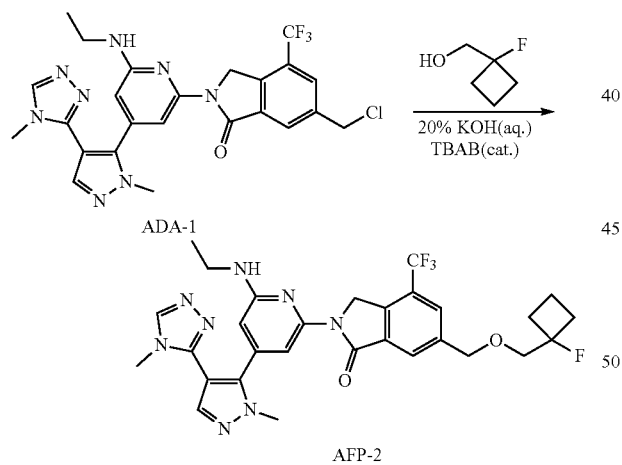

To a stirred solution of intermediate (ADA-1) (40 mg, 1 eq, 75 μmol) and (1-fluorocyclobutyl) MeOH (78 mg, 10 eq, 0.75 mmol) in DCM (3 mL) were added TBAB (49 mg, 2 eq, 0.15 mmol) and aq. KOH (3 mL, 20% Wt) at rt. The resulting mixture was stirred for 1 h at rt. The resulting mixture was diluted with water and extracted with EtOAc (3×20 mL). The combined organic layers were washed with brine (2×20 mL), dried (Na$_2$SO$_4$). After filtration, the filtrate was concentrated in vacuo. The residue was purified by Prep-TLC with DCM/MeOH (10/1). The crude product was purified by Prep-HPLC with the following conditions (Column: Sunfire prep C18 column, 30*150 mm, 5 m; Mobile Phase A: water (0.1% FA), Mobile Phase B: MeCN; Flow rate: 60 mL/min; Gradient: 43% B to 67% B in 7 min; Wave Length: 254/220 nm; RT: 6.8) to afford the title compound (AFP-2) (14.9 mg, 25 μmol, 33%, 99% Purity) as a white solid. m/z 599.2 (M+H)$^+$ (ES+). $^1$H NMR (400 MHz, DMSO-d6) δ 8.47 (s, 1H), 8.00 (d, J=16.4 Hz, 2H), 7.89 (s, 1H), 7.57 (d, J=1.2 Hz, 1H), 6.93 (t, J=5.4 Hz, 1H), 6.25 (d, J=1.3 Hz, 1H), 5.21 (s, 2H), 4.77 (s, 2H), 3.89 (s, 3H), 3.69 (d, J=24.6 Hz, 2H), 3.47 (s, 3H), 3.29-3.20 (m, 2H), 2.28-2.15 (m, 4H), 1.82-1.72 (m, 1H), 1.56-1.45 (m, 1H), 1.17 (t, J=7.2 Hz, 3H).

Example 194: Synthesis of 2-{6-Cyclopropyl-4-[2-methyl-4-(4-methyl-1,2,4-triazol-3-yl)pyrazol-3-yl] pyridin-2-yl}-6-({[(1-hydroxycyclopentyl)methyl] amino}methyl)-3H-isoindol-1-one (AFQ-3)

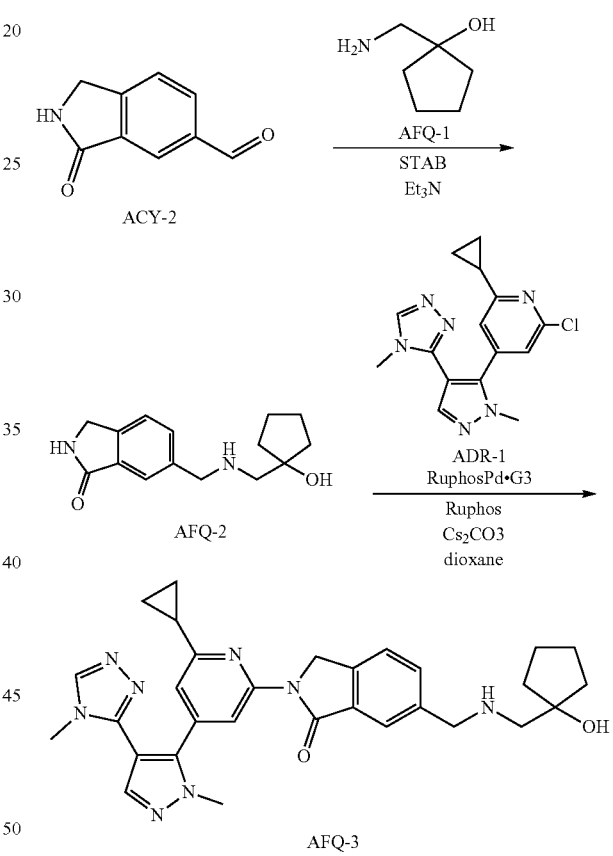

Step 1: Synthesis of 6-((((1-Hydroxycyclopentyl) methyl)amino)methyl)isoindolin-1-one (AFQ-2)

To a stirred solution 1-(aminomethyl)cyclopentan-1-ol (AFQ-1) (172 mg, 1.2 eq, 1.49 mmol) in MeOH (10 mL) and were added DIPEA (642 mg, 4 eq, 4.96 mmol) and intermediate (ACY-2) (200 mg, 1 eq, 1.24 mmol) at rt. The resulting mixture was stirred for 2 h at 60° C. Then NaBH$_4$ (235 mg, 5 eq, 6.21 mmol) was added at 0° C. The resulting mixture was stirred for 1 h at rt. The reaction was then quenched by the addition of 2 mL of ice water at 0° C. The crude product was purified by reverse flash column chromatography with the following conditions: Column, C18; mobile phase, water (0.1% NH$_4$HCO$_3$) and MeCN (0%

MeCN up to 30% in 20 min); Detector, UV 254/220 nm to afford the sub-title compound (AFQ-2) (131 mg, 0.45 mmol, 40%, 90% Purity) as a white solid. m/z 261.2 (M+H)+ (ES+).

Step 2: Synthesis of 2-{6-Cyclopropyl-4-[2-methyl-4-(4-methyl-1,2,4-triazol-3-yl)pyrazol-3-yl]pyridin-2-yl}-6-({[(1-hydroxycyclopentyl)methyl]amino}methyl)-3H-isoindol-1-one (AFQ-3)

To a stirred mixture of intermediate (ADR-1) (60 mg, 1 eq, 0.19 mmol), the product from step 1 above (AFQ-2) (50 mg, 1 eq, 0.19 mmol) and Cs$_2$CO$_3$ (124 mg, 2 eq, 0.38 mmol) in 1,4-dioxane (5 mL) were added RuPhos (36 mg, 0.4 eq, 76 μmol) and RuPhos palladacycle Gen.3 (32 mg, 0.2 eq, 38 μmol) at rt under nitrogen atmosphere. The resulting mixture was stirred for overnight at 80° C. under nitrogen atmosphere. The mixture was allowed to cool down to rt. The resulting mixture was concentrated in vacuo. The crude product was purified by Prep-HPLC with the following conditions: Column: SunFire Prep C18 OBD Column, 19×150 mm, 5 μm; Mobile Phase A: water (0.1% FA), Mobile Phase B: MeCN; Flow rate: 60 mL/min; Gradient: 30 B to 60 B in 7 min; Detector, UV 254/210 nm; RT: 6.08. This resulted in the title compound (AFQ-3) (24.5 mg, 45 μmol, 24%, 99% Purity) as a white solid. m/z 539.5 (M+H)+ (ES+). $^1$H NMR (300 MHz, MeOH-d4) δ 8.49 (d, J=4.5 Hz, 1H), 8.22 (d, J=1.3 Hz, 1H), 7.92 (d, J=7.7 Hz, 2H), 7.83-7.69 (m, 2H), 7.10 (d, J=1.3 Hz, 1H), 5.11 (s, 2H), 4.29 (s, 2H), 4.02 (s, 3H), 3.56 (s, 3H), 2.99 (s, 2H), 2.17-2.03 (m, 1H), 1.70 (t, J=7.8 Hz, 8H), 1.64 (s, 2H), 1.16-1.07 (m, 2H).

Example 195: Synthesis of 4-(2-{6-[2-(Dimethylamino)-1-hydroxyethyl]-1-oxo-4-(trifluoromethyl)-3H-isoindol-2-yl}-6-(ethylamino)pyridin-4-yl)-3-(4-methyl-1,2,4-triazol-3-yl)benzonitrile (AFR-7)

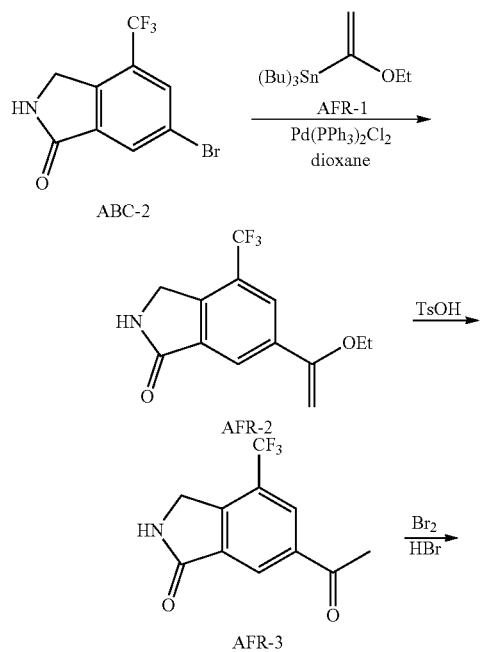

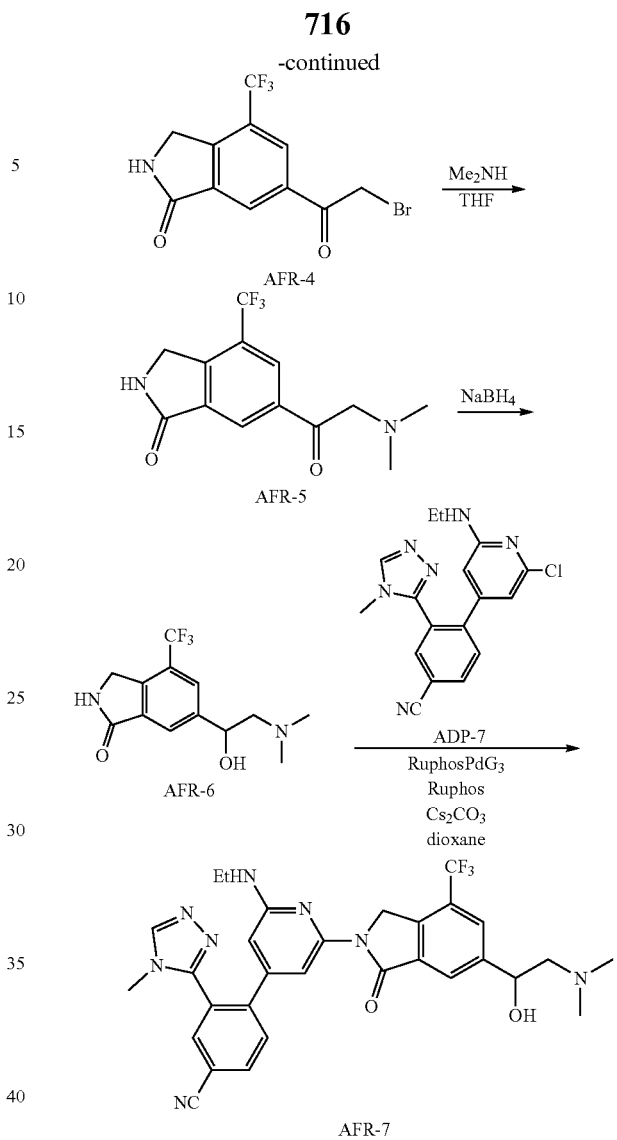

Step 1: Synthesis of 6-(1-Ethoxyethenyl)-4-(trifluoromethyl)-2,3-dihydroisoindol-1-one (AFR-2)

To a stirred solution of intermediate (ABC-2) (1.5 g, 1 eq, 5.36 mmol) and tributyl(1-ethoxyethenyl) stannane (AFR-1) (2.32 g, 1.2 eq, 6.43 mmol) in 1,4-dioxane (15 mL) was added Pd(PPh$_3$)$_2$Cl$_2$ (376 mg, 0.1 eq, 0.54 mmol) at rt under nitrogen atmosphere. The resulting mixture was stirred for overnight at 80° C. under nitrogen atmosphere. The mixture was allowed to cool down to rt. The resulting mixture was concentrated in vacuo. The residue was applied on a silica gel column chromatography with petroleum ether/EtOAc (1/3) to afford the sub-title compound (AFR-2) (1.2 g, 3.76 mmol, 83%, 85% Purity) as a Brown yellow solid. m/z 272.1 (M+H)+ (ES+).

Step 2: Synthesis of 6-Acetyl-4-(trifluoromethyl)-2,3-dihydroisoindol-1-one (AFR-3)

To a stirred solution of the product from step 1 above (AFR-2) (600 mg, 1 eq, 2.21 mmol) and TsOH (1.90 g, 5 eq, 11.1 mmol) in DCM (20 mL) at rt. The resulting mixture was stirred for 2 h at rt. The resulting mixture was diluted with water and extracted with EtOAc (3×80 mL). The combined organic layers were washed with brine (2×80 mL), dried (Na$_2$SO$_4$). After filtration, the filtrate was concentrated in vacuo. The residue was purified by Prep-TLC with EtOAc/petroleum ether (3/1) to afford the sub-title compound (AFR-3) (420 mg, 1.59 mmol, 78%, 92% Purity) as an off-white solid. m/z 244.1 (M+H)$^+$ (ES+).

Step 3: Synthesis of 6-(2-Bromoacetyl)-4-(trifluoromethyl)-2,3-dihydroisoindol-1-one (AFR-4)

A stirred solution of the product from step 2 above (AFR-3) (300 mg, 1 eq, 1.23 mmol) and bromine (197 mg, 1 eq, 1.23 mmol) in HBr (10 mL) at rt was stirred for 1 h at 70° C. The mixture was allowed to cool down to rt. The residue was purified by Prep-TLC with DCM/MeOH (15/1) to afford the sub-title compound (AFR-4) (170 mg, 0.48 mmol, 43%, 90% Purity) as an off-white solid. m/z 322.0/324.0 (M+H)$^+$ (ES+).

Step 4: Synthesis of 6-[2-(Dimethylamino) acetyl]-4-(trifluoromethyl)-2,3-dihydroisoindol-1-one (AFR-5)

A solution of the product from step 3 above (AFR-4) (230 mg, 1 eq, 0.71 mmol) and dimethylamine (2 M in THF) (0.02 mL, 10 eq, 0.31 mmol) in THF (3 mL) at rt was stirred for 2 h at rt. The crude product was used in the next step directly without further purification. m/z 287.1 (M+H)$^+$ (ES+).

Step 5: Synthesis of 6-[2-(Dimethylamino)-1-hydroxyethyl]-4-(trifluoromethyl)-2,3-dihydroisoindol-1-one (AFR-6)

To the above mixture was added NaBH$_4$ (152 mg, 5 eq, 4.02 mmol) at 0° C. The resulting mixture was stirred for additional 2 h at rt. The reaction was then quenched by the addition of 2 mL of MeOH at 0° C. The residue was purified by Prep-TLC with DCM/MeOH (15/1) to afford the sub-title compound (AFR-6) (130 mg, 0.40 mmol, 56%, 89% Purity) as an off-white solid. m/z 289.1 (M+H)$^+$ (ES+).

Step 6: Synthesis of 4-(2-{6-[2-(Dimethylamino)-1-hydroxyethyl]-1-oxo-4-(trifluoromethyl)-3H-isoindol-2-yl}-6-(ethylamino) pyridin-4-yl)-3-(4-methyl-1,2,4-triazol-3-yl) benzonitrile (AFR-7)

To a stirred solution of intermediate (ADP-7) (130 mg, 1 eq, 0.38 mmol), the product from step 5 above (AFR-6) (122 mg, 1.1 eq, 0.42 mmol) and Cs$_2$CO$_3$ (250 mg, 2 eq, 0.77 mmol) in 1,4-dioxane (10 mL) were added RuPhos (72 mg, 0.4 eq, 0.15 mmol) and RuPhos palladacycle Gen.3 (64 mg, 0.2 eq, 77 μmol) at rt under nitrogen atmosphere. The resulting mixture was stirred for 2 h at 100° C. under nitrogen atmosphere. The mixture was allowed to cool down to rt. The residue was purified by Prep-TLC with DCM/MeOH (15/1). The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 20% B to 30% B in 7 min; Wave Length: 254/220 nm) to afford the title compound (AFR-7) (55 mg, 92 μmol, 24%, 99% Purity) as a yellow solid. m/z 591.6 (M+H)$^+$ (ES+). $^1$H NMR (400 MHz, MeOH-d4) δ 8.48 (s, 1H), 8.12-7.96 (m, 4H), 7.87 (d, J=8.1 Hz, 1H), 7.50 (d, J=1.4 Hz, 1H), 6.06 (d, J=1.2 Hz, 1H), 5.20-5.15 (m, 2H), 5.02-4.98 (m, 1H), 3.46 (s, 3H), 3.27 (t, J=7.2 Hz, 2H), 2.71-2.63 (m, 1H), 2.55-2.49 (m, 1H), 2.38 (s, 6H), 1.20 (t, J=7.2 Hz, 3H).

Example 196: Synthesis of 6-Acetyl-2-{6-cyclopropyl-4-[2-(4-methyl-1,2,4-triazol-3-yl)phenyl]pyridin-2-yl}-4-(trifluoromethyl)-3H-isoindol-1-one (AFS-1)

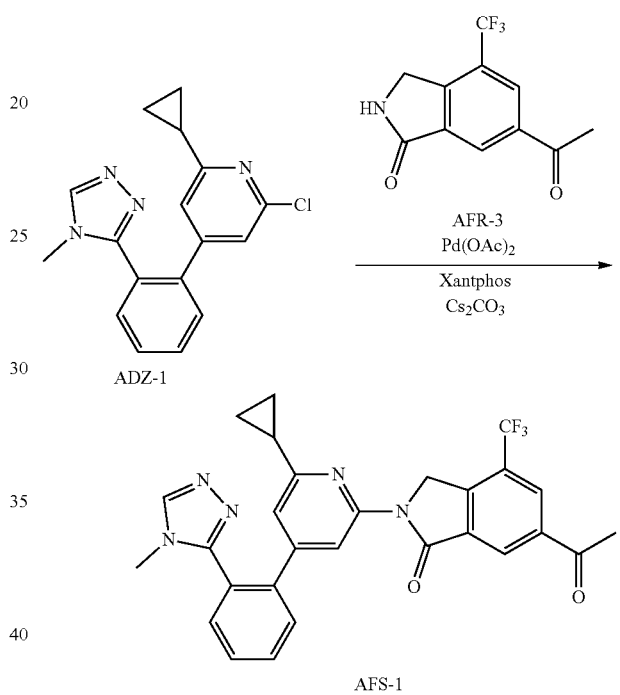

Into a 8 mL sealed tube were added intermediate (ADZ-1) (30 mg, 1 eq, 97 μmol), intermediate (AFR-3) (35 mg, 1.5 eq, 0.15 mmol) and Cs$_2$CO$_3$ (94 mg, 3 eq, 0.29 mmol) in 1,4-dioxane (1 mL) at rt under nitrogen atmosphere. To the above mixture were added Pd(OAc)$_2$ (2.2 mg, 0.1 eq, 10 μmol) and XantPhos (11 mg, 0.2 eq, 19 μmol) over 2 min at rt under nitrogen atmosphere. The resulting mixture was stirred for additional 3 h at 100° C. under nitrogen atmosphere. The mixture was cooled to rt and concentrated in vacuo. The crude product was purified by Prep-HPLC with the following conditions: Column: SunFire Prep C18 OBD Column, 19×150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 30 B to 60 B in 7 min; Detector, UV 254/210 nm; RT: 6.08 to afford the title compound (AFS-1) (5.0 mg, 9.5 μmol, 9.8%, 98% Purity) as a white solid. m/z 518.1 (M+H)$^+$ (ES+). $^1$H NMR (400 MHz, MeOH-d4) δ 8.61 (d, J=1.3 Hz, 1H), 8.47 (d, J=9.2 Hz, 2H), 8.03 (d, J=1.4 Hz, 1H), 7.85-7.73 (m, 2H), 7.73-7.61 (m, 2H), 6.93 (d, J=1.4 Hz, 1H), 5.25 (d, J=1.6 Hz, 2H), 3.46 (s, 3H), 2.73 (s, 3H), 2.10-2.00 (m, 1H), 1.07-0.92 (m, 4H).

Example 197: Synthesis of 2-{6-Cyclopropyl-4-[2-(4-methyl-1,2,4-triazol-3-yl)phenyl]pyridin-2-yl}-6-[(1S)-1-{[(1-hydroxycyclobutyl)methyl]amino}ethyl]-4-(trifluoromethyl)-3H-isoindol-1-one (AFT-2). Stereochemistry Arbitrarily Assigned

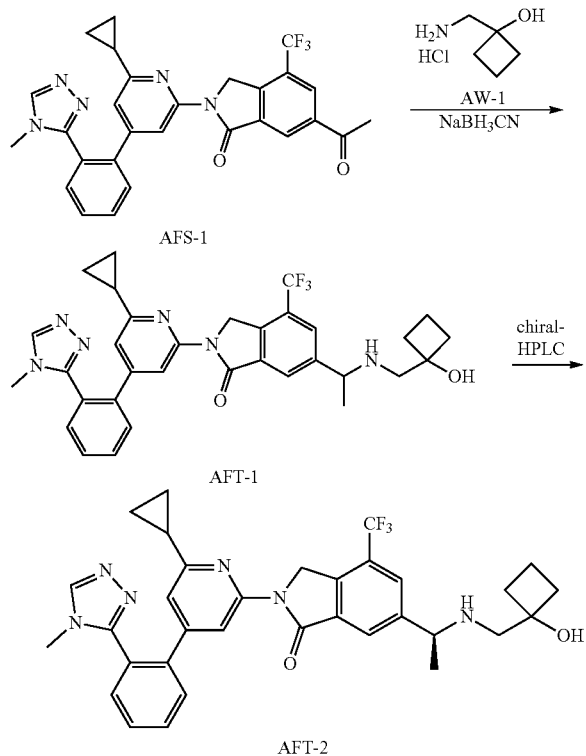

Step 1: Synthesis of 2-{6-Cyclopropyl-4-[2-(4-methyl-1,2,4-triazol-3-yl)phenyl]pyridin-2-yl}-6-(1-{[(1-hydroxycyclobutyl)methyl]amino}ethyl)-4-(trifluoromethyl)-3H-isoindol-1-one (AFT-1)

Into a 8 mL sealed tube were added compound (AFS-1) (40 mg, 1 eq, 77 µmol), 1-(aminomethyl)cyclobutan-1-ol, HCl (AW-1) (16 mg, 2 eq, 0.15 mmol) and AcOH (14 mg, 3 eq, 0.23 mmol) in MeOH (1 mL) at rt. To the above mixture was added NaBH₃CN (24 mg, 5 eq, 0.39 mmol) over 2 min at rt. The resulting mixture was stirred for additional overnight at rt. The resulting mixture was filtered; the filter cake was washed with MeOH (2×2 mL). The filtrate was concentrated in vacuo. The crude product was purified by reverse flash column chromatography with the following conditions: Column, C18; mobile phase, water (0.1% NH₄HCO₃) and MeCN (10% MeCN up to 48% in 20 min); Detector, UV 254/220 nm. The product-containing fractions were combined and concentrated in vacuo. This resulted in the sub-title compound (AFT-1) (11 mg, 17 µmol, 24%, 95% Purity) as a white solid. m/z 603.4 (M+H)⁺ (ES+).

Step 2: Synthesis of 2-{6-Cyclopropyl-4-[2-(4-methyl-1,2,4-triazol-3-yl)phenyl]pyridin-2-yl}-6-[(1S)-1-{[(1-hydroxycyclobutyl)methyl]amino}ethyl]-4-(trifluoromethyl)-3H-isoindol-1-one (AFT-2)

The product from step 1 above (AFT-1) (40 mg, 1 eq, 77 µmol) was separated by chiral Prep-HPLC with the following conditions: Column: CHIRALPAK IG, 2*25 cm, 5 µm; Mobile Phase A: Hex:DCM=3:1 (0.5% 2M NH₃-MeOH)-HPLC, Mobile Phase B: EtOH-HPLC; Flow rate: 20 mL/min; Gradient: 30% B to 30% B in 30 min; Wave Length: 220/254 nm; RT1(min): 14.24; RT2(min): 21.388; Sample Solvent: EtOH-HPLC; Injection Volume: 4 mL. This resulted in the title compound (AFT-2) (2.0 mg, 3.2 µmol, 18%, 98% Purity) as a white solid. m/z 603.4 (M+H)⁺ (ES+). ¹H NMR (400 MHz, MeOH-d4) δ 8.45 (s, 1H), 8.14-7.98 (m, 3H), 7.83-7.73 (m, 2H), 7.73-7.60 (m, 2H), 6.89 (d, J=1.4 Hz, 1H), 5.18 (d, J=1.8 Hz, 2H), 4.10-3.95 (m, J=6.6 Hz, 1H), 3.44 (s, 3H), 2.65 (d, J=11.8 Hz, 1H), 2.45 (d, J=11.8 Hz, 1H), 2.15-1.92 (m, 5H), 1.82-1.63 (m, 1H), 1.53-1.35 (m, 4H), 1.05-0.83 (m, 4H). Column: CHIRALPAK IG-3, 4.6*50 mm 3 um; Mobile Phase A: Hex:DCM=3:1) (0.1% DEA):EtOH=70:30; Flow rate: 1 mL/min; RT: 2.712.

Example 198: Synthesis of 2-{6-Cyclopropyl-4-[2-(4-methyl-1,2,4-triazol-3-yl)phenyl]pyridin-2-yl}-6-[(1R)-1-{[(1-hydroxycyclobutyl)methyl]amino}ethyl]-4-(trifluoromethyl)-3H-isoindol-1-one (AFU-1). Stereochemistry Arbitrarily Assigned

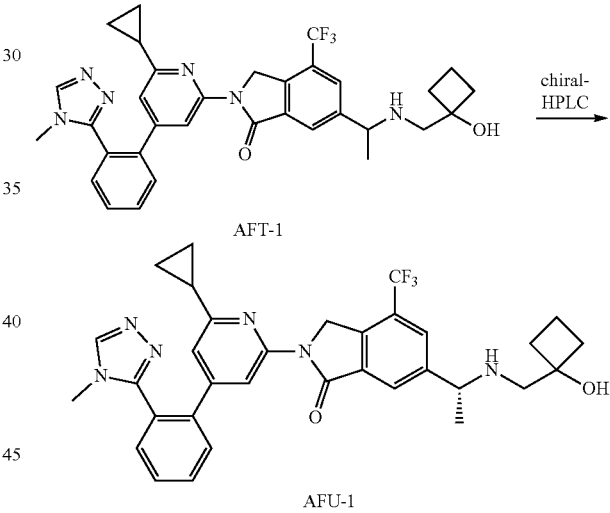

Racemic product (AFT-1) (40 mg, 1 eq, 77 µmol) was separated by chiral Prep-HPLC with the following conditions: Column: CHIRALPAK IG, 2*25 cm, 5 µm; Mobile Phase A: Hex:DCM=3:1 (0.5% 2M NH₃-MeOH)-HPLC, Mobile Phase B: EtOH-HPLC; Flow rate: 20 mL/min; Gradient: 30% B to 30% B in 30 min; Wave Length: 220/254 nm; RT1(min): 14.24; RT2(min): 21.388; Sample Solvent: EtOH-HPLC; Injection Volume: 4 mL. This resulted in the title compound (AFU-1) (2.5 mg, 4.0 µmol, 23%, 97% Purity) as a white solid. m/z 603.4 (M+H)⁺ (ES+). ¹H NMR (400 MHz, MeOH-d4) δ 8.45 (s, 1H), 8.14-7.99 (m, 3H), 7.84-7.72 (m, 2H), 7.72-7.60 (m, 2H), 6.90 (d, J=1.4 Hz, 1H), 5.18 (d, J=1.6 Hz, 2H), 4.10-3.97 (m, 1H), 3.44 (s, 3H), 2.65 (d, J=11.8 Hz, 1H), 2.45 (d, J=11.9 Hz, 1H), 2.15-1.96 (m, 5H), 1.79-1.63 (m, 1H), 1.52-1.35 (m, 4H), 1.06-0.94 (m, 4H). Column: CHIRALPAK IG-3, 4.6*50 mm, 3 µm; Mobile Phase A: Hex:DCM=3:1) (0.1% DEA):EtOH=70:30; Flow rate: 1 mL/min; RT: 4.162.

Example 199: Synthesis of 2-{6-Cyclopropyl-4-[2-methyl-4-(4-methyl-1,2,4-triazol-3-yl)pyrazol-3-yl]pyridin-2-yl}-6-{[(1-hydroxycyclobutyl)methoxy]methyl}-4-(trifluoromethyl)-3H-isoindol-1-one (AFV-3)

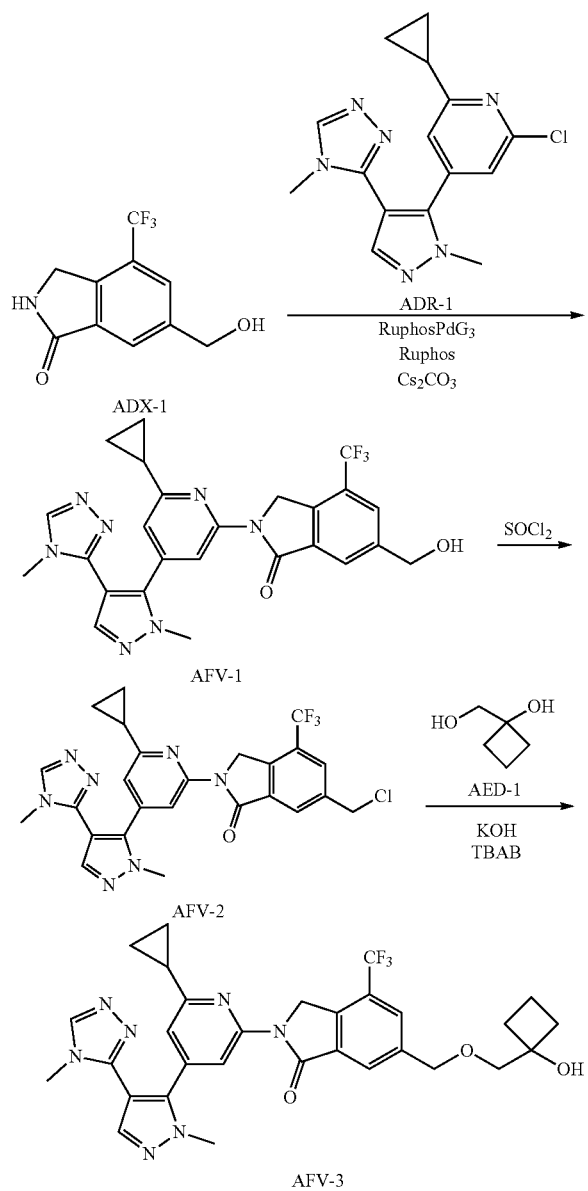

Step 1: Synthesis of 2-{6-Cyclopropyl-4-[2-methyl-4-(4-methyl-1,2,4-triazol-3-yl)pyrazol-3-yl]pyridin-2-yl}-6-(hydroxymethyl)-4-(trifluoromethyl)-3H-isoindol-1-one (AFV-1)

To a stirred solution of intermediate (ADX-1) (100 mg, 1 eq, 0.43 mmol), intermediate (ADR-1) (150 mg, 1.1 eq, 0.48 mmol) and $Cs_2CO_3$ (423 mg, 3 eq, 1.30 mmol) in 1,4-dioxane (4 mL) were added RuPhos palladacycle Gen.3 (72 mg, 0.2 eq, 87 μmol) and RuPhos (81 mg, 0.4 eq, 0.17 mmol) at rt under nitrogen atmosphere. The resulting mixture was stirred for 2 h at 100° C. under nitrogen atmosphere. The mixture was cooled to rt, diluted with water and extracted with EtOAc (3×50 mL). The combined organic layers were washed with brine (2×50 mL), dried ($Na_2SO_4$). After filtration, the filtrate was concentrated in vacuo. The residue was purified by Prep-TLC with DCM/MeOH (10/1) to afford the sub-title compound (AFV-1) (150 mg, 0.26 mmol, 68%, 90% Purity) as a yellow solid. m/z 510.2 $(M+H)^+$ (ES+).

Step 2: Synthesis of 6-(Chloromethyl)-2-{6-cyclopropyl-4-[2-methyl-4-(4-methyl-1,2,4-triazol-3-yl)pyrazol-3-yl]pyridin-2-yl}-4-(trifluoromethyl)-3H-isoindol-1-one (AFV-2)

To a stirred solution of the product from step 1 above (AFV-1) (100 mg, 1 eq, 0.20 mmol) in DCM (5 mL) was added $SOCl_2$ (35 mg, 1.5 eq, 0.29 mmol) dropwise at 0° C. under nitrogen atmosphere. The resulting mixture was stirred for 2 h at 0° C. under nitrogen atmosphere. The reaction was quenched with MeOH (2 mL) at 0° C. and concentrated in vacuo. The residue was purified by Prep-TLC with DCM/MeOH (10/1) to afford the sub-title compound (AFV-2) (80 mg, 0.14 mmol, 77%, 92% Purity) as an off-white solid. m/z 528.1/530.1 $(M+H)^+$ (ES+).

Step 3: Synthesis of 2-{6-Cyclopropyl-4-[2-methyl-4-(4-methyl-1,2,4-triazol-3-yl)pyrazol-3-yl]pyridin-2-yl}-6-{1[(1-hydroxycyclobutyl)methoxy]methyl}-4-(trifluoromethyl)-3H-isoindol-1-one (AFV-3)

To a stirred solution of the product from step 2 above (AFV-2) (40 mg, 1 eq, 76 μmol) and 1-(hydroxymethyl)cyclobutan-1-ol (AED-1) (77 mg, 10 eq, 0.76 mmol) in DCM (3 mL) was added TBAB (12 mg, 0.5 eq, 38 μmol) and aq. KOH (5 mL, 20% Wt) at rt. The resulting mixture was stirred for 1 h at rt. The resulting mixture was diluted with water and extracted with EtOAc (3×20 mL). The combined organic layers were washed with brine (2×20 mL), dried ($Na_2SO_4$). After filtration, the filtrate was concentrated in vacuo. The residue was purified by Prep-TLC with DCM/MeOH (15/1). The crude product was purified by Prep-HPLC with the following conditions (Column: XBridge Prep OBD C18 Column, 30*150 mm, 5 μm; Mobile Phase A: water (0.1% $NH_4HCO_3$), Mobile Phase B: MeCN; Flow rate: 60 mL/min; Gradient: 15% B to 75% B in 8 min; Wave Length: 254/220 nm; RT: 6.48) to afford the title compound (AFV-3) (9.3 mg, 15 μmol, 21%, 99% Purity) as a white solid. m/z 594.1 $(M+H)^+$ (ES+) $^1H$ NMR (400 MHz, CD3OD) δ 8.48 (s, 1H), 8.23 (d, J=1.3 Hz, 1H), 8.09 (s, 1H), 8.02 (s, 1H), 7.90 (s, 1H), 7.10 (d, J=1.3 Hz, 1H), 5.22 (s, 2H), 4.78 (s, 2H), 4.02 (s, 3H), 3.56 (d, J=4.8 Hz, 5H), 2.19-2.01 (m, 5H), 1.78-1.72 (m, 1H), 1.61-1.53 (m, 1H), 1.11-1.01 (m, 4H).

Example 200: Synthesis of 2-{4-[4-Fluoro-2-(4-methyl-1,2,4-triazol-3-yl)phenyl]-6-(prop-1-en-2-yl)pyridin-2-yl}-6-({[(1-hydroxycyclobutyl)methyl]amino}methyl)-3H-isoindol-1-one (AFW-3)

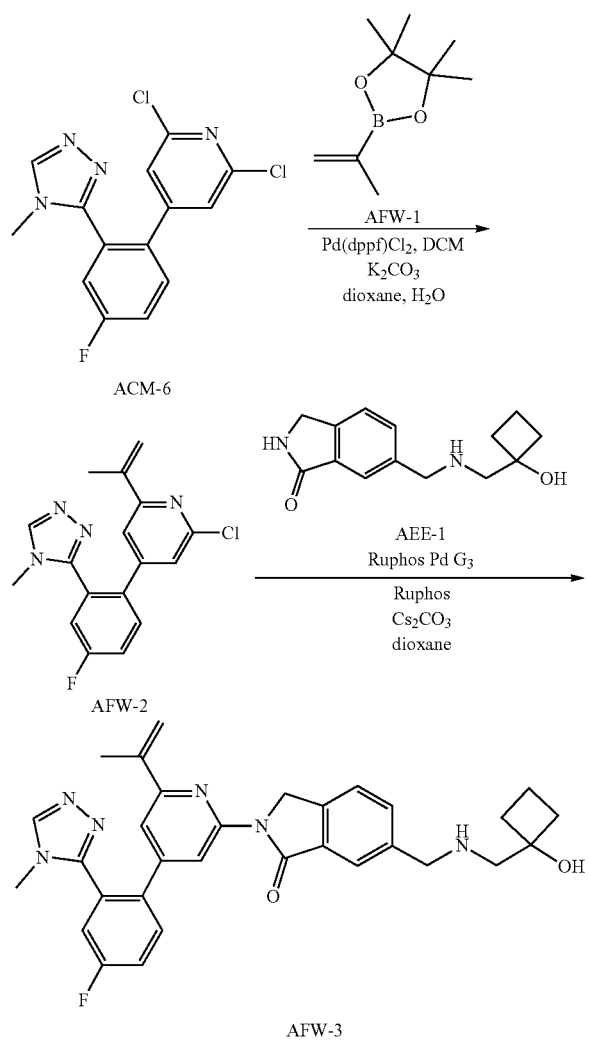

Step 1: Synthesis of 2-Chloro-4-[4-fluoro-2-(4-methyl-1,2,4-triazol-3-yl) phenyl]-6-(prop-1-en-2-yl) pyridine (AFW-2)

To a stirred solution of intermediate (ACM-6) (200 mg, 1 eq, 0.62 mmol) and 4,4,5,5-tetramethyl-2-(prop-1-en-2-yl)-1,3,2-dioxaborolane (AFW-1) (62 mg, 0.6 eq, 0.37 mmol) and $K_2CO_3$ (257 mg, 3 eq, 1.86 mmol) in 1,4-dioxane (10 mL) and $H_2O$ (1 mL) was added Pd(dppf)$Cl_2$.DCM (101 mg, 0.2 eq, 0.12 mmol) at rt under nitrogen atmosphere. The resulting mixture was stirred for overnight at 100° C. under nitrogen atmosphere. The mixture was allowed to cool down to rt. The resulting mixture was concentrated in vacuo. The crude product was purified by reverse flash column chromatography with the following conditions: Column, C18; mobile phase, water (0.1% $NH_4HCO_3$) and MeCN (0% MeCN up to 50% in 27 min); Detector, UV 254/220 nm. This resulted in the sub-title compound (AFW-2) (50 mg, 0.14 mmol, 25%, 95% Purity) as a brown solid. m/z 329.1/331.1 $(M+H)^+$ (ES+).

Step 2: Synthesis of 2-{4-[4-Fluoro-2-(4-methyl-1,2,4-triazol-3-yl)phenyl]-6-(prop-1-en-2-yl)pyridin-2-yl}-6-({[(1-hydroxycyclobutyl)methyl]amino}methyl)-3H-isoindol-1-one (AFW-3)

To a stirred solution of the product from step 1 above (AFW-2) (40 mg, 1 eq, 0.12 mmol), intermediate (AEE-1) (33 mg, 1.1 eq, 0.13 mmol) and $Cs_2CO_3$ (79 mg, 2 eq, 0.24 mmol) in 1,4-dioxane (5 mL) were added RuPhos (23 mg, 0.4 eq, 49 μmol) and RuPhos palladacycle Gen.3 (20 mg, 0.2 eq, 24 μmol) at rt under nitrogen atmosphere. The resulting mixture was stirred for 2 h at 100° C. under nitrogen atmosphere. The mixture was allowed to cool down to rt. The crude product was purified by reverse flash column chromatography with the following conditions: Column, C18; mobile phase, water (0.1% $NH_4HCO_3$) and MeCN (10% MeCN up to 50% in 15 min); Detector, UV 254/220 nm. The crude product was purified by Prep-HPLC with the following conditions (Column: XBridge Prep OBD C18 Column, 30*150 mm, 5 μm; Mobile Phase A: water (0.1% $NH_4HCO_3$), Mobile Phase B: MeCN; Flow rate: 60 mL/min; Gradient: 38% B to 48% B in 8 min; Wave Length: 254/220 nm) to afford the title compound (AFW-3) (9.6 mg, 17 μmol, 15%, 98% Purity) as a white solid. m/z 539.4 $(M+H)^+$ (ES+). $^1H$ NMR (400 MHz, DMSO-d6) δ 8.51 (s, 1H), 8.25 (d, J=1.3 Hz, 1H), 7.87-7.76 (m, 2H), 7.74-7.56 (m, 4H), 7.00 (d, J=1.3 Hz, 1H), 5.94 (t, J=1.4 Hz, 1H), 5.32 (t, J=1.8 Hz, 1H), 5.11 (s, 2H), 4.92 (s, 1H), 3.87 (s, 2H), 3.40 (s, 3H), 2.54 (s, 2H), 2.07 (s, 3H), 2.04-1.95 (m, 2H), 1.95-1.84 (m, 2H), 1.66-1.55 (m, 1H), 1.45-1.32 (m, 1H).

Example 201: Synthesis of 2-{4-[4-Fluoro-2-(4-methyl-1,2,4-triazol-3-yl)phenyl]-6-isopropylpyridin-2-yl}-6-({[(1-hydroxycyclobutyl)methyl]amino}methyl)-3H-isoindol-1-one (AFX-1)

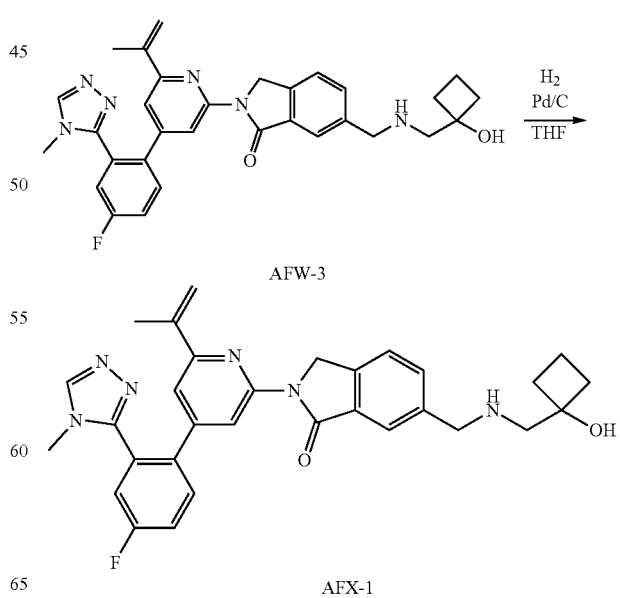

To a stirred solution of compound (AFW-3) (65 mg, 1 eq, 0.12 mmol) and Pd/C type 87 L (10 mg, 0.78 eq, 94 µmol) in THF (10 mL) at rt under nitrogen atmosphere. The resulting mixture was stirred for 2 h at rt under hydrogen atmosphere. The resulting mixture was filtered; the filter cake was washed with MeOH (3×5 mL). The filtrate was concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 µm; Mobile Phase A: water (0.1% NH$_4$HCO$_3$), Mobile Phase B: MeCN; Flow rate: 60 mL/min; Gradient: 31% B to 48% B in 10 min; Wave Length: 254/220 nm) to afford the title compound (AFX-1) (2.2 mg, 3.5 µmol, 3.4%, 95% Purity) as a white solid. m/z 541.5 (M+H)$^+$ (ES+). $^1$H NMR (400 MHz, Methanol-d4) δ 8.49 (d, J=15.2 Hz, 1H), 8.22 (d, J=1.5 Hz, 1H), 7.86 (d, J=1.6 Hz, 1H), 7.82-7.76 (m, 1H), 7.72-7.68 (m, 1H), 7.65 (d, J=7.9 Hz, 1H), 7.57-7.50 (m, 1H), 7.50-7.44 (m, 1H), 6.77 (d, J=1.5 Hz, 1H), 5.12 (s, 2H), 3.98 (s, 2H), 3.40 (s, 3H), 2.99-2.88 (m, 1H), 2.75 (s, 2H), 2.15-1.97 (m, 4H), 1.78-1.68 (m, 1H), 1.58-1.44 (m, 1H), 1.24 (d, J=6.8 Hz, 6H).

Example 202: Synthesis of 2-(4-(4-fluoro-2-(4-methyl-4H-1,2,4-triazol-3-yl)phenyl)-6-isopropylpyridin-2-yl)-6-methylisoindolin-1-one (AFY-1)

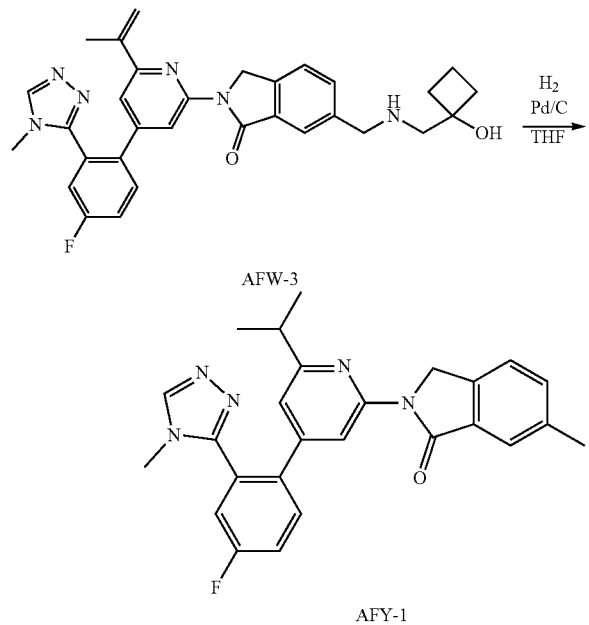

A byproduct of Example 201 was afforded as compound (AFY-1) (2 mg, 4.5 µmol, 3.8%, 99% Purity) as a white solid. m/z 442.4 (M+H)$^+$ (ES+). $^1$H NMR (400 MHz, MeOH-d4) δ 8.47 (s, 1H), 8.20 (d, J=1.4 Hz, 1H), 7.83-7.75 (m, 1H), 7.64 (s, 1H), 7.58-7.42 (m, 4H), 6.75 (d, J=1.4 Hz, 1H), 5.07 (s, 2H), 3.39 (s, 3H), 3.00-2.90 (m, 1H), 2.46 (s, 3H), 1.23 (d, J=6.9 Hz, 6H).

Example 203: Synthesis of 2-[6-(Ethylamino)-4-[4-fluoro-2-(4-methyl-1,2,4-triazol-3-yl)phenyl]pyridin-2-yl]-6-({[(1R,2S)-2-hydroxycyclopentyl]oxy}methyl)-4-(trifluoromethyl)-3H-isoindol-1-one (AFZ-1)

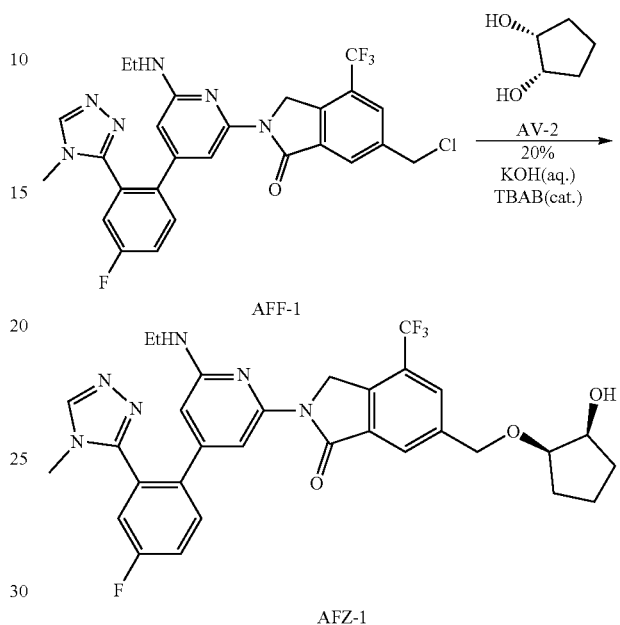

To a stirred solution of intermediate (AFF-1) (40 mg, 1 eq, 75 µmol) and (1R,2S)-cyclopentane-1,2-diol (AV-2) (38 mg, 5 eq, 0.38 mmol) in DCM (2 mL) was added TBAB (12 mg, 0.5 eq, 37 µmol) and aq. KOH (2 mL, 20% Wt) at rt. The resulting mixture was stirred for 1 h at rt. The resulting mixture was diluted with water and extracted with DCM (3×20 mL). The combined organic layers were washed with brine (2×20 mL), dried (Na$_2$SO$_4$). After filtration, the filtrate was concentrated in vacuo. The residue was purified by Prep-TLC with DCM/MeOH (20/1). The crude product was purified by Prep-HPLC with the following conditions (Column: XBridge Prep OBD C18 Column, 30*150 mm, 5 µm; Mobile Phase A: water (0.1% NH$_4$HCO$_3$), Mobile Phase B: MeCN; Flow rate: 60 mL/min; Gradient: 35% B to 68% B in 9 min; Wave Length: 254/220 nm; RT: 8.73) to afford the title compound (AFZ-1) (10.2 mg, 16 µmol, 22%, 98% Purity) as a white solid. m/z 611.3 (M+H)$^+$ (ES+). $^1$H NMR (400 MHz, DMSO-d6) δ 8.49 (s, 1H), 8.04 (d, J=14.0 Hz, 2H), 7.66-7.61 (m, 1H), 7.60-7.56 (m, 1H), 7.56-7.49 (m, 1H), 7.44 (d, J=1.2 Hz, 1H), 6.72 (t, J=5.4 Hz, 1H), 5.93 (d, J=1.3 Hz, 1H), 5.16 (s, 2H), 4.79 (d, J=12.8 Hz, 1H), 4.69 (d, J=12.8 Hz, 1H), 4.49 (d, J=4.8 Hz, 1H), 4.05-3.98 (m, 1H), 3.39-3.34 (s, 3H), 3.74-3.68 (m, 1H), 3.22-3.11 (m, 2H), 1.84-1.64 (m, 4H), 1.62-1.53 (m, 1H), 1.48-1.38 (m, 1H), 1.13 (t, J=7.2 Hz, 3H).

Example 204: Synthesis of 2-{6-Cyclopropyl-4-[2-methyl-4-(4-methyl-1,2,4-triazol-3-yl)pyrazol-3-yl]pyridin-2-yl}-6-({1[(1R,2S)-2-hydroxycyclopentyl]oxy}methyl)-4-(trifluoromethyl)-3H-isoindol-1-one (AGA-1)

Example 205: Synthesis of 2-[6-(Ethylamino)-4-[4-fluoro-2-(4-methyl-1,2,4-triazol-3-yl)phenyl]pyridin-2-yl]-6-{1[(1-fluorocyclobutyl)methoxy]methyl}-4-(trifluoromethyl)-3H-isoindol-1-one (AGB-1)

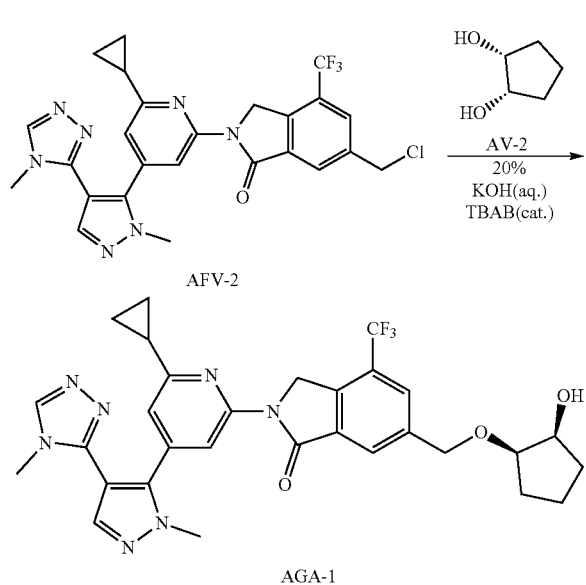

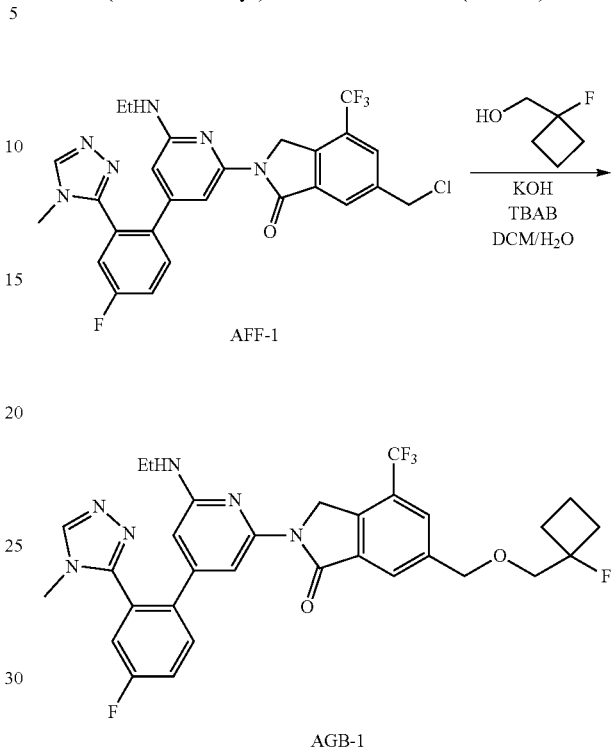

To a stirred solution of 6-(chloromethyl)-2-{6-cyclopropyl-4-[2-methyl-4-(4-methyl-1,2,4-triazol-3-yl)pyrazol-3-yl]pyridin-2-yl}-4-(trifluoromethyl)-3H-isoindol-1-one (AFV-2) (40 mg, 1 eq, 76 μmol) and (1R,2S)-cyclopentane-1,2-diol (AV-2) (77 mg, 10 eq, 0.76 mmol) in DCM (3 mL) was added TBAB (12 mg, 0.5 eq, 38 μmol), aq. KOH (3 mL, 20% Wt) at rt. The resulting mixture was stirred for 1 h at rt. The resulting mixture was diluted with water and extracted with EtOAc (3×20 mL). The combined organic layers were washed with brine (2×20 mL), dried (Na$_2$SO$_4$). After filtration, the filtrate was concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 5% B to 95% B in 8 min; Wave Length: 254/220 nm; RT: 5.75) to afford the title compound (AGA-1) (13.1 mg, 22 μmol, 29%, 98% Purity) as a white solid. m/z 594.3 (M+H)$^+$ (ES+). $^1$H NMR (400 MHz, CD3OD) δ 8.49 (s, 1H), 8.22 (d, J=1.3 Hz, 1H), 8.10 (s, 1H), 8.03 (s, 1H), 7.90 (s, 1H), 7.10 (d, J=1.3 Hz, 1H), 5.22 (s, 2H), 4.84-4.72 (m, 2H), 4.19-4.10 (m, 1H), 4.02 (s, 3H), 3.86-3.82 (m, 1H), 3.56 (s, 3H), 2.16-2.05 (m, 1H), 1.90-1.79 (m, 4H), 1.73-1.70 (m, 1H), 1.59-1.55 (m, 1H), 1.10-1.01 (m, 4H).

To a stirred solution of intermediate (AFF-1) (40 mg, 1 eq, 75 μmol) and (1-fluorocyclobutyl) MeOH (39 mg, 5 eq, 0.38 mmol) in DCM (2 mL) were added TBAB (12 mg, 0.5 eq, 37 μmol) and aq. KOH (2 mL, 20% Wt) at rt. The resulting mixture was stirred slowly for 1 h at rt. The resulting mixture was diluted with water and extracted with DCM (3×20 mL). The combined organic layers were washed with brine (2×20 mL), dried (Na$_2$SO$_4$). After filtration, the filtrate was concentrated in vacuo. The residue was purified by Prep-TLC with DCM/MeOH (20/1). The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 49% B to 69% B in 10 min; Wave Length: 254/220 nm; RT: 9.22) to afford the title compound (AGB-1) (9.0 mg, 15 μmol, 19%, 99% Purity) as a white solid. m/z 614.2 (M+H)$^+$ (ES+). $^1$H NMR (400 MHz, DMSO-d6) δ 8.49 (s, 1H), 7.99 (d, J=16.7 Hz, 2H), 7.67-7.42 (m, 4H), 6.72 (t, J=5.4 Hz, 1H), 5.92 (d, J=1.3 Hz, 1H), 5.21-5.11 (m, 2H), 4.77 (s, 2H), 3.73 (s, 1H), 3.67 (s, 1H), 3.38 (s, 3H), 3.21-3.12 (m, 2H), 2.29-2.11 (m, 4H), 1.82-1.69 (m, 1H), 1.57-1.43 (m, 1H), 1.13 (t, J=7.2 Hz, 3H).

Example 206: Synthesis of 4-[2-(Ethylamino)-6-(1-oxo-6-{[(2-oxocyclopentyl) amino]methyl}-4-(trifluoromethyl)-3H-isoindol-2-yl)pyridin-4-yl]-3-(4-methyl-1,2,4-triazol-3-yl)benzonitrile (AGC-5)

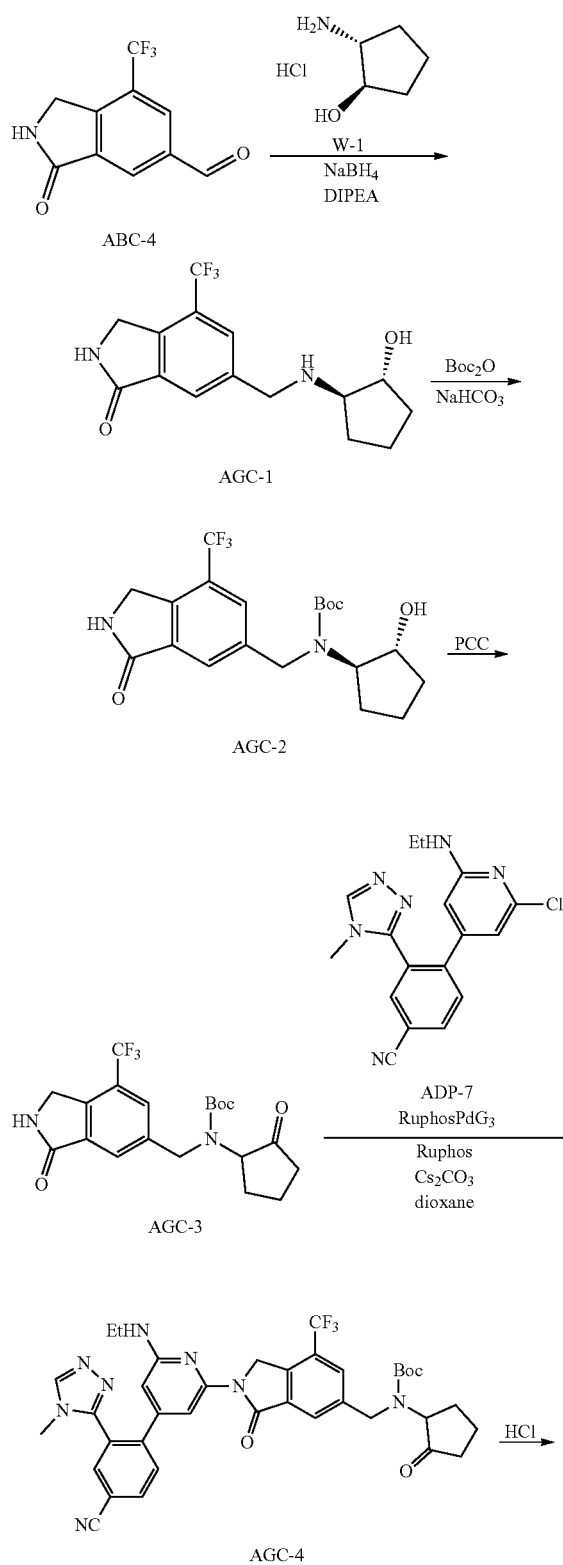

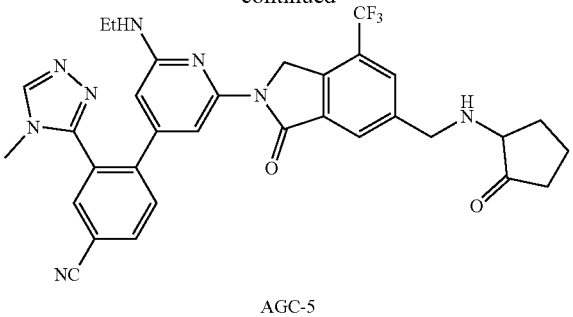

Step 1: Synthesis of 6-({[(1R,2R)-2-Hydroxycyclopentyl]amino}methyl)-4-(trifluoromethyl)-2,3-dihydroisoindol-1-one (AGC-1)

A solution of intermediate (ABC-4) (200 mg, 1 eq, 0.87 mmol) and (1R,2R)-2-aminocyclopentan-1-ol, HCl (W-1) (132 mg, 1.5 eq, 1.31 mmol) in MeOH (20 mL) was stirred for 2 h at 60° C. To the above mixture was added NaBH$_4$ (132 mg, 4 eq, 3.49 mmol) at 0° C. The resulting mixture was stirred for additional 2 h at rt. The reaction was then quenched by the addition of 5 mL of ice water at 0° C. The residue was purified by Prep-TLC with EtOAc/petroleum ether (1/1) to afford the sub-title compound (AGC-1) (210 mg, 0.60 mmol, 69%, 90% Purity) as a white solid. m/z 315.1 (M+H)$^+$ (ES+).

Step 2: Synthesis of tert-Butyl N-[(1R,2R)-2-hydroxycyclopentyl]-N-{[3-oxo-7-(trifluoromethyl)-1,2-dihydroisoindol-5-yl]methyl}carbamate (AGC-2)

To a stirred solution of the product from step 1 above (AGC-1) (200 mg, 1 eq, 0.64 mmol) and (Boc)$_2$O (153 mg, 1.1 eq, 0.70 mmol) in THF (15 mL) was added NaHCO$_3$ (160 mg, 3 eq 1.91, mmol) at rt. The resulting mixture was stirred for 2 h at 60° C. The mixture was cooled to rt and concentrated in vacuo. The resulting mixture was diluted with water and extracted with EtOAc (3×80 mL). The combined organic layers were washed with brine (2×80 mL), dried (Na$_2$SO$_4$). After filtration, the filtrate was concentrated in vacuo. The residue was purified by Prep-TLC with EtOAc/petroleum ether (1/5) to afford the sub-title compound (AGC-2) (100 mg, 0.21 mmol, 34%, 88% Purity) as a yellow oil. m/z 415.2 (M+H)$^+$ (ES+).

Step 3: Synthesis of tert-Butyl N-{[3-oxo-7-(trifluoromethyl)-1,2-dihydroisoindol-5-yl]methyl}-N-(2-oxocyclopentyl)carbamate (AGC-3)

A solution of the product from step 2 above (AGC-2) (100 mg, 1 eq, 0.24 mmol) and PCC (156 mg, 3 eq, 0.72 mmol) in DCM (15 mL) was stirred for overnight at rt. The resulting mixture was filtered; the filter cake was washed with DCM (3×5 mL). The filtrate was concentrated in vacuo. This resulted in the sub-title compound (AGC-3) (70 mg, 0.15 mmol, 63%, 90% Purity) as a Brown yellow oil. m/z 413.2 (M+H)$^+$ (ES+).

Step 4: Synthesis of tert-Butyl N-[(2-{4-[4-cyano-2-(4-methyl-1,2,4-triazol-3-yl)phenyl]-6-(ethylamino) pyridin-2-yl}-3-oxo-7-(trifluoromethyl)-1H-isoindol-5-yl)methyl]-N-(2-oxocyclopentyl) carbamate (AGC-4)

To a stirred solution of intermediate (ADP-7) (40 mg, 1 eq, 0.12 mmol), the product from step 3 above (AGC-3) (54 mg, 1.1 eq, 0.13 mmol) and Cs₂CO₃ (18 mg, 2 eq, 0.24 mmol) in 1,4-dioxane(10 mL) were added RuPhos (22 mg, 0.4 eq, 47 µmol) and RuPhos palladacycle Gen.3 (20 mg, 0.2 eq, 24 µmol) at rt under nitrogen atmosphere. The resulting mixture was stirred for 2 h at 100° C. under nitrogen atmosphere. The mixture was cooled to rt. The resulting mixture was filtered; the filter cake was washed with MeOH (2×2 mL). The filtrate was concentrated in vacuo. The residue was purified by Prep-TLC with DCM/MeOH (10/1) to afford the sub-title compound (AGC-4) (35 mg, 47 µmol, 37%, 96% Purity) as a yellow solid. m/z 715.2 (M+H)⁺ (ES+).

Step 5: Synthesis of 4-[2-(Ethylamino)-6-(1-oxo-6-{[(2-oxocyclopentyl)amino]methyl}-4-(trifluoromethyl)-3H-isoindol-2-yl)pyridin-4-yl]-3-(4-methyl-1,2,4-triazol-3-yl)benzonitrile (AGC-5)

Into a 25 mL round-bottom flask were added the product from step 4 above (AGC-4) (30 mg, 1 eq, 42 µmol) and HCl(gas) in 1,4-dioxane (5 mL) at rt. The resulting mixture was stirred for 2 h at rt. The mixture was concentrated in vacuo. The crude product was purified by Prep-HPLC with the following conditions (Column: XBridge Prep OBD C18 Column, 30*150 mm, 5 µm; Mobile Phase A: water (0.1% NH₄HCO₃), Mobile Phase B: MeCN; Flow rate: 60 mL/min; Gradient: 45% B to 55% B in 8 min, 55% B; Wave Length: 254/220 nm; RT: 7.2) to afford the title compound (AGC-5) (2.4 mg, 3.8 µmol, 9.0%, 96% Purity) as a white solid. m/z 615.2 (M+H)⁺ (ES+). ¹H NMR (300 MHz, CHCl3-d) δ 8.43 (d, J=4.1 Hz, 1H), 8.10-7.97 (m, 4H), 7.83 (d, J=8.1 Hz, 1H), 7.48-7.39 (m, 1H), 6.09-6.00 (m, 1H), 5.23-5.09 (m, 2H), 4.44-4.11 (m, 2H), 3.50 (t, J=9.8 Hz, 1H), 3.41 (d, J=3.0 Hz, 3H), 3.22 (d, J=7.2 Hz, 2H), 2.49-2.37 (m, 2H), 2.30-1.96 (m, 2H), 1.89-1.55 (m, 2H), 1.17 (t, J=7.1 Hz, 3H).

Example 207: Synthesis of 4-[2-(6-{[(2-Cyclopropoxyethyl)amino]methyl}-1-oxo-4-(trifluoromethyl)-3H-isoindol-2-yl)-6-(ethylamino)pyridin-4-yl]-3-(4-methyl-1,2,4-triazol-3-yl)benzonitrile (AGD-2)

To a stirred solution of intermediate (AEV-1) (50 mg, 1 eq, 91 µmol) and 2-cyclopropoxyethan-1-amine, HCl (AGD-1) (92 mg, 10 eq, 0.91 mmol) in DCM (5 mL) was added TBAB (12 mg, 0.5 eq, 36 µmol) and aq. KOH (5 mL, 20% Wt) at rt. The resulting mixture was stirred slowly for 1 h at rt. The resulting mixture was extracted with EtOAc (3×10 mL). The combined organic layers were washed with water (2×10 mL), dried (Na₂SO₄). After filtration, the filtrate was concentrated in vacuo. The residue was purified by Prep-TLC with DCM/MeOH (10/1). The crude product was purified by Prep-HPLC with the following conditions: (Column: XBridge Prep OBD C18 Column, 30*150 mm, 5 µm; Mobile Phase A: Water (0.1% NH₄HCO₃), Mobile Phase B: MeCN; Flow rate: 60 mL/min; Gradient: 44% B to 54% B in 9 min; Wave Length: 254/220 nm; RT: 8.9) to afford the title compound (AGD-2) (6.5 mg, 10 µmol, 12%, 99% Purity) as an off-white solid. m/z 617.2 (M+H)⁺ (ES+). ¹H NMR (400 MHz, MeOH-d4) δ 8.47 (s, 1H), 8.17-8.06 (m, 1H), 8.05-8.00 (m, 2H), 7.96 (s, 1H), 7.87 (d, J=8.0 Hz, 1H), 7.50 (d, J=1.2 Hz, 1H), 6.04 (d, J=1.2 Hz, 1H), 5.17 (s, 2H), 3.95 (s, 2H), 3.64 (t, J=5.4 Hz, 2H), 3.45 (s, 3H), 3.34 (s, 1H), 3.26 (t, J=7.2 Hz, 2H), 2.75 (t, J=5.3 Hz, 2H), 1.20 (t, J=7.2 Hz, 3H), 0.58-0.48 (m, 2H), 0.47-0.42 (m, 2H).

Example 208: Synthesis of 2-[6-(Ethylamino)-4-[4-fluoro-2-(4-methyl-1,2,4-triazol-3-yl)phenyl]pyridin-2-yl]-6-[(2-hydroxyethoxy)methyl]-4-(trifluoromethyl)-3H-isoindol-1-one (AGE-3)

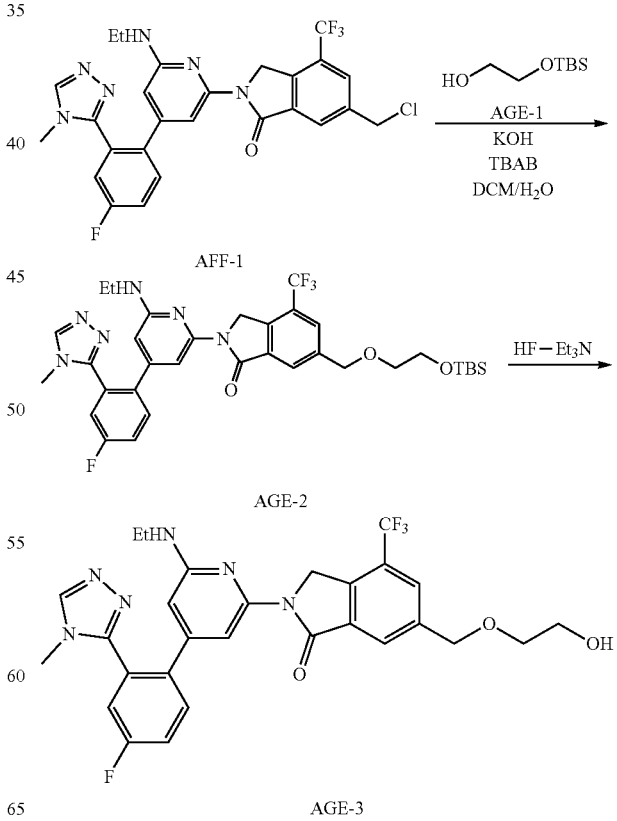

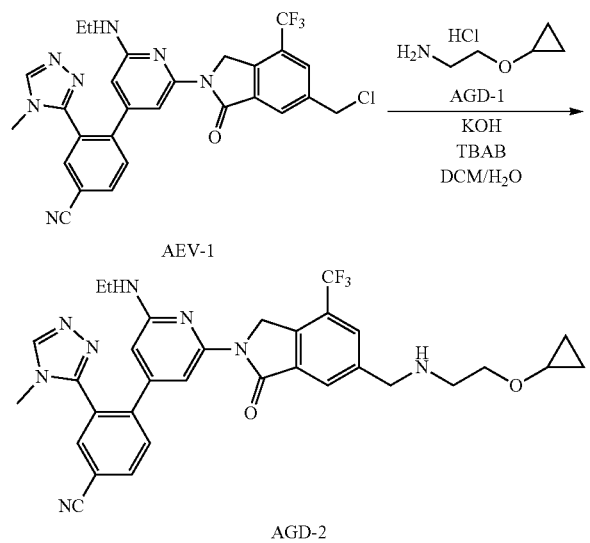

Step 1: Synthesis of 6-({2-[(tert-Butyldimethylsilyl)oxy]ethoxy}methyl)-2-[6-(ethylamino)-4-[4-fluoro-2-(4-methyl-1,2,4-triazol-3-yl)phenyl]pyridin-2-yl]-4-(trifluoromethyl)-3H-isoindol-1-one (AGE-2)

To a stirred solution of intermediate (AFF-1) (40 mg, 1 eq, 73 μmol) and 2-[(tert-butyldimethylsilyl)oxy]ethanol (AGE-1) (129 mg, 10 eq, 0.73 mmol) in DCM (5 mL) were added TBAB (12 mg, 0.5 eq, 36 μmol) and aq. KOH (5 mL, 20% Wt) at rt. The resulting mixture was stirred slowly for 1 h at rt. The resulting mixture was extracted with EtOAc (3×10 mL). The combined organic layers were washed with water (2×10 mL), dried (Na$_2$SO$_4$). After filtration, the filtrate was concentrated in vacuo. The residue was purified by Prep-TLC with DCM/MeOH (10/1) to afford the sub-title compound (AGE-2) (26 mg, 36 μmol, 47%, 95% Purity) as a yellow oil. m/z 685.3 (M+H)$^+$ (ES+).

Step 2: Synthesis of 2-[6-(Ethylamino)-4-[4-fluoro-2-(4-methyl-1,2,4-triazol-3-yl)phenyl]pyridin-2-yl]-6-[(2-hydroxyethoxy)methyl]-4-(trifluoromethyl)-3H-isoindol-1-one (AGE-3)

Into a 25 mL round-bottom flask were added the product from step 1 above (AGE-2) (30 mg, 1 eq, 44 μmol) and TEA.3HF (0.5 mL) in THF (5 ml) at rt. The resulting mixture was stirred for overnight at rt. The mixture was concentrated in vacuo. The crude product was purified by Prep-HPLC with the following conditions (Column: Xselect CSH F-Phenyl OBD column, 19*250 mm, 5 μm; Mobile Phase A: water (0.1% NH$_4$HCO$_3$), Mobile Phase B: MeOH-HPLC; Flow rate: 25 mL/min; Gradient: 65% B to 70% B in 9 min; Wave Length: 254/220 nm; RT: 8.67) to afford the title compound (AGE-3) (10.5 mg, 18 μmol, 42%, 98% Purity) as a white solid. m/z 571.1 (M+H)$^+$ (ES+). $^1$H NMR (300 MHz, DMSO-d6) δ 8.49 (s, 1H), 8.00 (d, J=11.1 Hz, 2H), 7.70-7.45 (m, 3H), 7.42 (d, J=1.2 Hz, 1H), 5.94 (d, J=1.3 Hz, 1H), 5.17 (s, 2H), 4.70 (s, 2H), 3.60-3.51 (m, 4H), 3.39 (s, 3H), 3.28-3.01 (m, 2H), 1.17-1.08 (m, 3H).

Example 209: Synthesis of 6-{[(1-Aminocyclobutyl)methoxy]methyl}-2-[6-(ethylamino)-4-[2-methyl-4-(4-methyl-1,2,4-triazol-3-yl)pyrazol-3-yl]pyridin-2-yl]-4-(trifluoromethyl)-3H-isoindol-1-one (AGF-3)

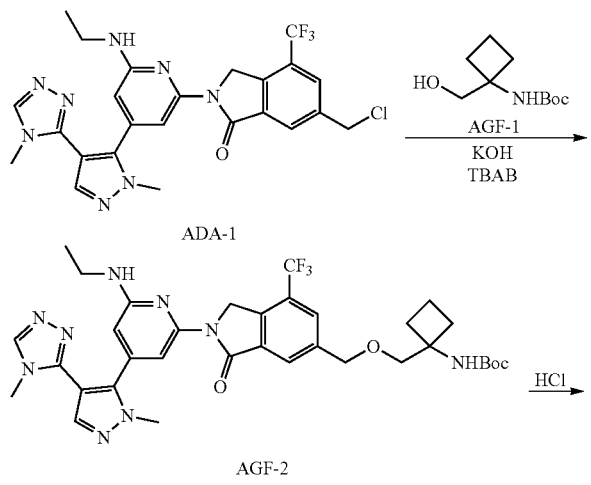

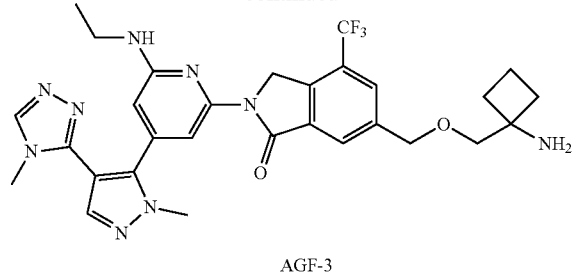

Step 1: Synthesis of tert-Butyl N-{1-[({2-[6-(ethylamino)-4-[2-methyl-4-(4-methyl-1,2,4-triazol-3-yl)pyrazol-3-yl]pyridin-2-yl]-3-oxo-7-(trifluoromethyl)-1H-isoindol-5-yl}methoxy)methyl]cyclobutyl}carbamate (AGF-2)

To a stirred solution of intermediate (ADA-1) (30 mg, 1 eq, 57 μmol) and tert-butyl N-[1-(hydroxymethyl)cyclobutyl]carbamate (AGF-1) (114 mg, 10 eq, 0.57 mmol) in DCM (3 mL) were added TBAB (9 mg, 0.5 eq, 29 μmol) and aq. KOH (3 mL, 20% Wt) at rt. The resulting mixture was diluted with water and extracted with EtOAc (3×10 mL). The combined organic layers were washed with brine (2×10 mL), dried (Na$_2$SO$_4$). After filtration, the filtrate was concentrated in vacuo. The residue was purified by Prep-TLC with DCM/MeOH (10/1) to afford the sub-title compound (AGF-2) (25 mg, 34 μmol, 64%, 95% Purity) as a yellow solid. m/z 696.2 (M+H)$^+$ (ES+).

Step 2: Synthesis of 6-{[(1-Aminocyclobutyl)methoxy]methyl}-2-[6-(ethylamino)-4-[2-methyl-4-(4-methyl-1,2,4-triazol-3-yl)pyrazol-3-yl]pyridin-2-yl]-4-(trifluoromethyl)-3H-isoindol-1-one (AGF-3)

To a stirred solution of the product from step 1 above (AGF-2) (25 mg, 1 eq, 36 μmol) in DCM (4 mL) was added HCl (gas) in 1,4-dioxane (2 mL, 4 M) at rt. The resulting mixture was stirred for 2 h at rt. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 30% B to 40% B in 10 min; Wave Length: 254/220 nm; RT: 9.09) to afford the title compound (AGF-3) (12.6 mg, 20 μmol, 59%, 96% Purity) as a white solid. m/z 596.2 (M+H)$^+$ (ES+). $^1$H NMR (400 MHz, DMSO-d6) δ 8.47 (s, 1H), 8.02 (d, J=16.3 Hz, 2H), 7.88 (s, 1H), 7.57 (d, J=1.1 Hz, 1H), 6.93 (t, J=5.4 Hz, 1H), 6.25 (d, J=1.2 Hz, 1H), 5.21 (s, 2H), 4.74 (s, 2H), 3.89 (s, 3H), 3.46 (s, 3H), 3.40 (s, 2H), 3.29-3.05 (m, 2H), 2.00-1.94 (m, 2H), 1.81-1.75 (m, 2H), 1.73-1.63 (m, 1H), 1.62-1.52 (m, 1H), 1.17 (t, J=7.2 Hz, 3H).

Example 210: Synthesis of 6-{1[(1-Aminocyclobutyl)methoxy]methyl}-2-{6-cyclopropyl-4-[4-fluoro-2-(4-methyl-1,2,4-triazol-3-yl)phenyl]pyridin-2-yl}-4-(trifluoromethyl)-3H-isoindol-1-one (AGG-2)

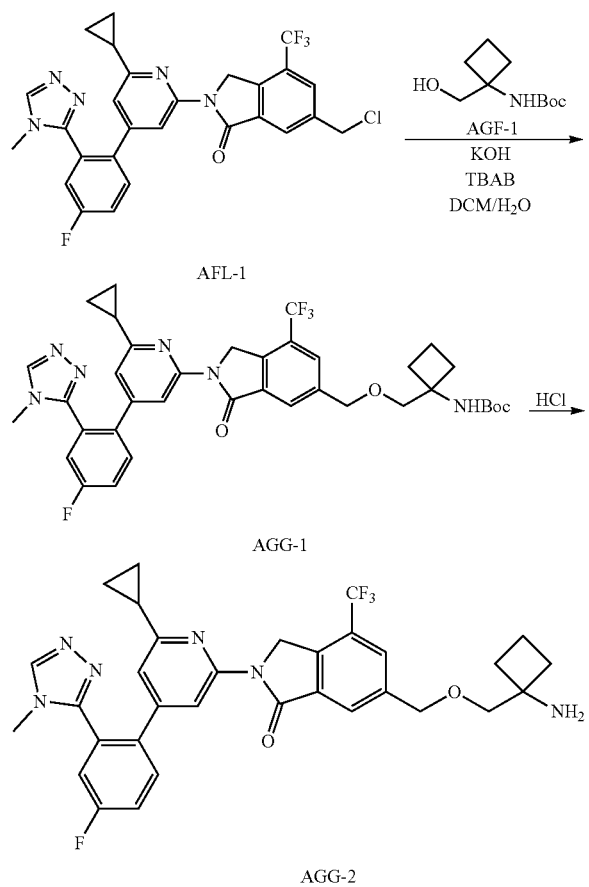

Step 1: Synthesis of tert-Butyl N-(1-{[(2-{6-cyclopropyl-4-[4-fluoro-2-(4-methyl-1,2,4-triazol-3-yl)phenyl] pyridin-2-yl}-3-oxo-7-(trifluoromethyl)-1H-isoindol-5-yl)methoxy]methyl}cyclobutyl)carbamate (AGG-1)

To a stirred solution of intermediate (AFL-1) (50 mg, 1 eq, 92 μmol) and tert-butyl N-[1-(hydroxymethyl)cyclobutyl]carbamate (AGF-1) (279 mg, 15 eq, 1.38 mmol) in DCM (8 mL) was added TBAB (15 mg, 0.5 eq, 46 μmol) at at rt. To the above mixture was added aq. KOH (8 mL, 20% Wt) at at rt. The resulting mixture was stirred for 1 h at at rt. The resulting mixture was diluted with water. The resulting mixture was extracted with EtOAc (3×20 mL). The combined organic layers were washed with brine (2×20 mL), dried (Na₂SO₄). After filtration, the filtrate was concentrated in vacuo. The residue was purified by Prep-TLC (DCM/MeOH 12:1) to afford the sub-title compound (AGG-1) (35 mg, 45 μmol, 54%, 90% Purity). m/z 707.1 (M+H)⁺ (ES+).

Step 2: Synthesis of 6-{[(1-Aminocyclobutyl)methoxy]methyl}-2-{6-cyclopropyl-4-[4-fluoro-2-(4-methyl-1,2,4-triazol-3-yl)phenyl]pyridin-2-yl}-4-(trifluoromethyl)-3H-isoindol-1-one (AGG-2)

To a stirred solution of the product from step 1 above (AGG-1) (35 mg, 1 eq, 50 μmol) in DCM (2 mL) was added HCl (gas) in 1,4-dioxane (1 mL, 4 M) dropwise at 0° C. The resulting mixture was stirred for 2 h at rt. The resulting mixture was diluted with water. The mixture was neutralized to pH 7 with sat. ammonium bicarbonate. The resulting mixture was extracted with EtOAc (3×10 mL). The combined organic layers were washed with brine (2×10 mL), dried (Na₂SO₄). After filtration, the filtrate was concentrated in vacuo. The crude product was purified by Prep-HPLC with the following conditions (Column: XBridge Prep OBD C18 Column, 30*150 mm, 5 μm; Mobile Phase A: water (0.1% NH₄HCO₃), Mobile Phase B: MeCN; Flow rate: 60 mL/min; Gradient: 44% B to 54% B in 8 min; Wave Length: 254/220 nm; RT: 7.93) to afford the title compound (AGG-2) (3.2 mg, 5.2 μmol, 11%, 99% Purity) as a white solid. m/z 607.1 (M+H)⁺ (ES+). ¹H NMR (400 MHz, MeOH-d4) δ 8.46 (s, 1H), 8.11-7.96 (m, 3H), 7.79-7.73 (m, 1H), 7.58-7.43 (m, 2H), 6.90 (d, J=1.4 Hz, 1H), 5.18 (s, 2H), 4.78 (s, 2H), 3.60 (d, J=2.0 Hz, 2H), 3.46 (s, 3H), 2.14-1.99 (m, 5H), 1.92-1.70 (m, 2H), 1.00 (d, J=6.6 Hz, 4H).

Example 211: Synthesis of 2-{6-Cyclopropyl-4-[4-fluoro-2-(4-methyl-1,2,4-triazol-3-yl)phenyl]pyridin-2-yl}-6-(hydroxymethyl)-3H-isoindol-1-one (AGH-2)

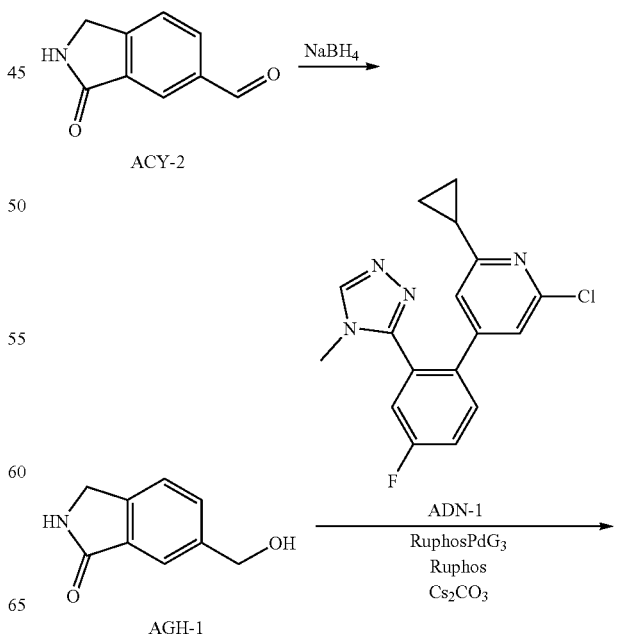

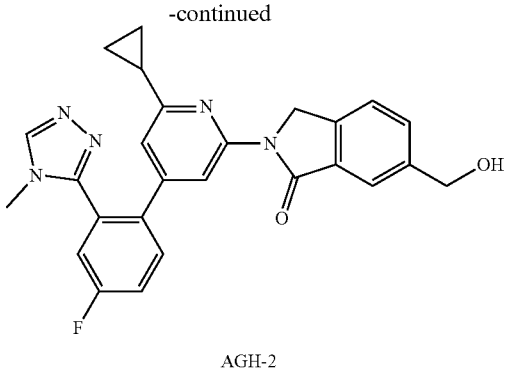

AGH-2

Step 1: Synthesis of 6-(Hydroxymethyl)-2,3-dihydroisoindol-1-one (AGH-1)

To a stirred mixture of intermediate (ACY-2) (150 mg, 1 eq, 0.93 mmol) in THF (20 mL) were added NaBH$_4$ (70 mg, 2 eq, 1.86 mmol) at 0° C. The resulting mixture was stirred for 1 h at rt. The reaction was quenched with MeOH (2 mL) at 0° C. The crude product was purified by reverse flash column chromatography with the following conditions: Column, C18; mobile phase, water (0.1% NH$_4$HCO$_3$) and MeCN (10% MeCN up to 50% in 12 min); Detector, UV 254/220 nm to afford the sub-title compound (AGH-1) (95 mg, 0.54 mmol, 63%, 92% Purity) as a white solid. m/z 164.1 (M+H)$^+$ (ES+).

Step 2: Synthesis of 2-{6-Cyclopropyl-4-[4-fluoro-2-(4-methyl-1,2,4-triazol-3-yl)phenyl]pyridin-2-yl}-6-(hydroxymethyl) (AGH-2)

To a stirred mixture of the product from step 1 above (AGH-1) (89 mg, 1.5 eq, 0.55 mmol), intermediate (ADN-1) (120 mg, 1 eq, 0.37 mmol) and Cs$_2$CO$_3$ (357 mg, 1.10 mmol, 3 eq) in 1,4-dioxane (2 mL) were added RuPhos palladacycle Gen.3 (57 mg, 0.2 eq, 73 μmol) and RuPhos (68 mg, 0.4 eq, 0.15 mmol) at rt under nitrogen atmosphere. The resulting mixture was stirred for 2 h at 100° C. under nitrogen atmosphere. The mixture was allowed to cool down to rt. The resulting mixture was diluted with water and extracted with EtOAc (3×20 mL). The combined organic layers were washed with brine (2×20 mL), dried (Na$_2$SO$_4$). After filtration, the filtrate was concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 33% B to 47% B in 9 min; Wave Length: 254/220 nm) to afford the title compound (AGH-2) (7 mg, 15 μmol, 4.1%, 96% Purity) as a white solid. m/z 456.1 (M+H)$^+$ (ES+). $^1$H NMR (400 MHz, DMSO-d6) δ 8.51 (s, 1H), 7.99 (d, J=1.3 Hz, 1H), 7.82-7.46 (m, 6H), 6.79 (d, J=1.3 Hz, 1H), 5.37 (t, J=5.8 Hz, 1H), 5.01 (s, 2H), 4.61 (d, J=5.7 Hz, 2H), 3.43 (s, 3H), 2.01 (m, 1H), 0.95 (d, J=6.4 Hz, 4H).

Example 212: Synthesis of 6-{1[(1-Aminocyclobutyl)methoxy]methyl}-2-{6-cyclopropyl-4-[4-fluoro-2-(4-methyl-1,2,4-triazol-3-yl)phenyl]pyridin-2-yl}-3H-isoindol-1-one (AGI-3)

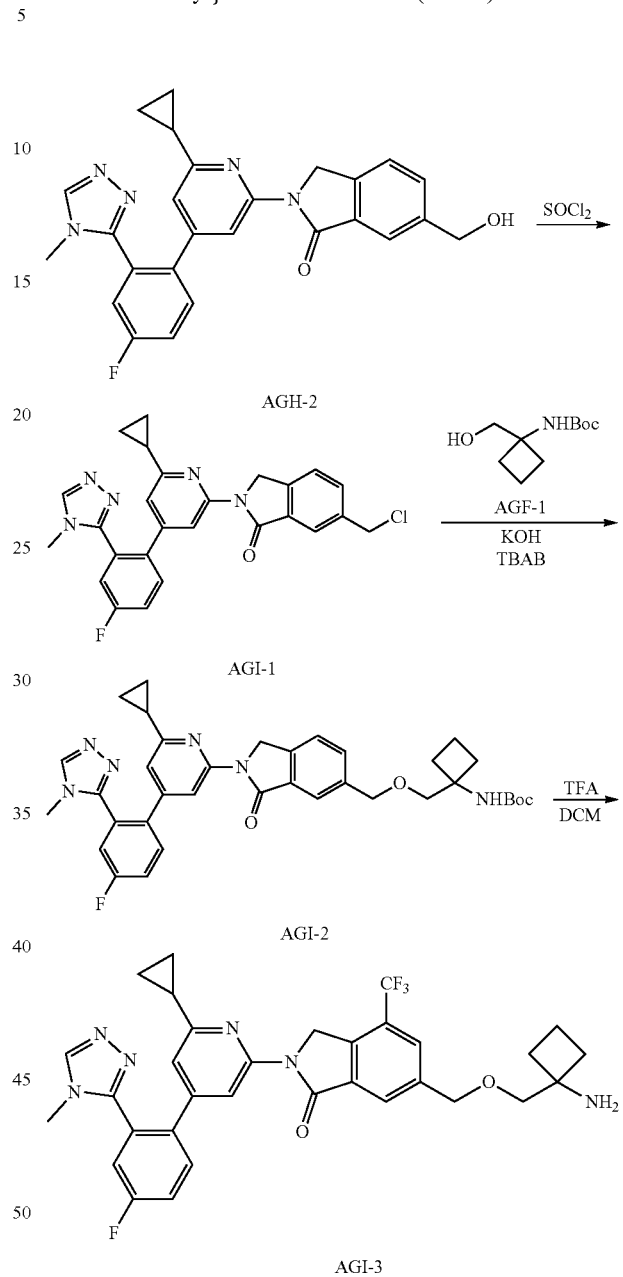

Step 1: Synthesis of 6-(Chloromethyl)-2-(6-cyclopropyl-4-(4-fluoro-2-(4-methyl-4H-1,2,4-triazol-3-yl)phenyl)pyridin-2-yl)isoindolin-1-one (AGI-1)

To a stirred mixture of intermediate (AGH-2) (115 mg, 1 eq, 0.25 mmol) in DCM (10 mL) was added SOCl$_2$ (0.15 mL) at 0° C. The resulting mixture was stirred for 0.5 h at rt. The residue was purified by Prep-TLC with DCM/MeOH (10/1) to afford the sub-title compound (AGI-1) (80 mg, 0.16 mmol, 53%, 92% Purity) as a white solid. m/z 474.1/476.1 (M+H)$^+$ (ES+).

Step 2: Synthesis of tert-Butyl (1-(((2-(6-cyclopropyl-4-(4-fluoro-2-(4-methyl-4H-1,2,4-triazol-3-yl)phenyl)pyridin-2-yl)-3-oxoisoindolin-5-yl)methoxy)methyl)cyclobutyl)carbamate (AGI-2)

To a stirred mixture of the product from step 1 above (AGI-1) (30 mg, 1 eq, 32 μmol) and tert-butyl N-[1-(hydroxymethyl)cyclobutyl] carbamate (AGF-1) (127 mg, 10 eq, 0.32 mmol) in DCM (5 mL) was added TBAB (10 mg, 0.5 eq, 16 μmol) at rt. To the above mixture was added aq. KOH (5 mL, 20% Wt) over 1 min at rt. The resulting mixture was stirred for additional 0.5 h at rt. The resulting mixture was diluted with water and extracted with EtOAc (3×10 mL). The combined organic layers were washed with brine (2×10 mL), dried (Na$_2$SO$_4$). After filtration, the filtrate was concentrated in vacuo. The residue was purified by Prep-TLC with DCM/MeOH (10/1) to afford the sub-title compound (AGI-2) (30 mg, 43 μmol, 74%, 92% Purity) as a white solid. m/z 639.1 (M+H)$^+$ (ES+).

Step 3: Synthesis of 6-(((1-Aminocyclobutyl)methoxy)methyl)-2-(6-cyclopropyl-4-(4-fluoro-2-(4-methyl-4H-1,2,4-triazol-3-yl)phenyl)pyridin-2-yl)isoindolin-1-one (AGI-3)

To a stirred solution of the product from step 2 above (AGI-2) (30 mg, 1 eq, 47 μmol) in DCM (3 mL) was added HCl(gas) in 1,4-dioxane (1 mL, 4 M) at 0° C. The resulting mixture was stirred for 2 h at rt. The mixture was concentrated in vacuo. The crude product was purified by Prep-HPLC with the following conditions (Column: XBridge Shield RP18 OBD Column, 30*150 mm, 5 μm; Mobile Phase A: water (0.1% NH$_4$HCO$_3$), Mobile Phase B: MeCN; Flow rate: 60 mL/min; Gradient: 26% B to 42% B in 10 min; Wave Length: 254/220 nm) to afford the title compound (AGI-3) (3.1 mg, 5.6 μmol, 12%, 98% Purity) as a white solid. m/z 539.1 (M+H)$^+$ (ES+). $^1$H NMR (400 MHz, DMSO-d6) δ 8.51 (s, 1H), 7.98 (d, J=1.3 Hz, 1H), 7.79-7.50 (m, 6H), 6.80 (d, J=1.4 Hz, 1H), 5.03 (s, 2H), 4.65 (s, 2H), 3.43 (s, 3H), 3.36-3.35 (m, 2H), 2.05-1.92 (m, 3H), 1.83-1.63 (m, 3H), 1.61-1.51 (m, 1H), 0.96 (d, J=6.4 Hz, 4H).

Example 213: Synthesis of 4-[2-(6-{[(1-aminocyclobutyl) methoxy] methyl}-1-oxo-4-(trifluoromethyl)-3H-isoindol-2-yl)-6-(ethylamino)pyridin-4-yl]-3-(4-methyl-1,2,4-triazol-3-yl)benzonitrile (AGJ-2)

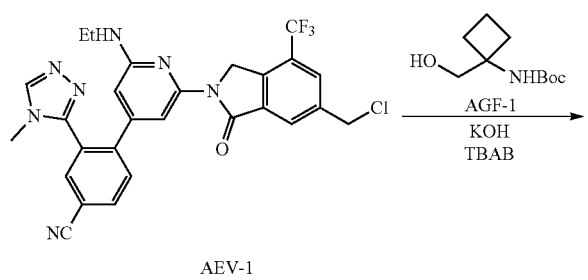

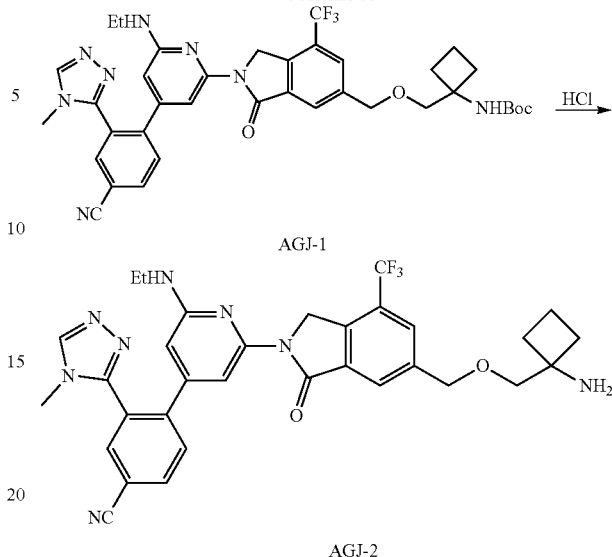

Step 1: Synthesis of tert-Butyl N-(1-{[(2-{4-[4-cyano-2-(4-methyl-1,2,4-triazol-3-yl)phenyl]-6-(ethylamino)pyridin-2-yl}-3-oxo-7-(trifluoromethyl)-1H-isoindol-5-yl)methoxy]methyl}cyclobutyl)carbamate (AGJ-1)

To a stirred mixture of intermediate (AEV-1) (60 mg, 1 eq, 0.11 mmol) and tert-butyl N-[1-(hydroxymethyl)cyclobutyl] carbamate (AGF-1) (219 mg, 10 eq, 1.09 mmol) in DCM (10 mL) was added TBAB (18 mg, 0.5 eq, 54 μmol) at rt. To the above mixture was added aq. KOH (8 mL, 20% Wt) over 2 min at rt. The resulting mixture was stirred for additional 0.5 h at rt. The resulting mixture was diluted with water and extracted with EtOAc (3×20 mL). The combined organic layers were washed with brine (2×20 mL), dried (Na$_2$SO$_4$). After filtration, the filtrate was concentrated in vacuo. The residue was purified by Prep-TLC with DCM/MeOH (10/1) to afford the sub-title compound (AGJ-1) (40 mg, 52 μmol, 51%, 94% Purity) as a white solid. m/z 717.2 (M+H)$^+$ (ES+).

Step 2: Synthesis of 4-[2-(6-{[(1-Aminocyclobutyl)methoxy]methyl}-1-oxo-4-(trifluoromethyl)-3H-isoindol-2-yl)-6-(ethylamino)pyridin-4-yl]-3-(4-methyl-1,2,4-triazol-3-yl)benzonitrile (AGJ-2)

To a stirred mixture of the product from step 1 above (AGJ-1) (50 mg, 1 eq, 70 μmol) in DCM (6 mL) was added HCl (gas) in 1,4-dioxane (2 mL, 4 M) at rt. The resulting mixture was stirred for 0.5 h at rt. The mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 30% B to 70% B in 9 min; Wave Length: 254/220 nm) to afford the title compound (AGJ-2) (3.4 mg, 5.3 μmol, 7.7%, 97% Purity) as a yellow solid. m/z 617.2 (M+H)$^+$ (ES+). $^1$H NMR (300 MHz, DMSO-d6) δ 8.52 (s, 1H), 8.22-8.12 (m, 2H), 8.01 (d, J=11.3 Hz, 2H), 7.79 (d, J=8.0 Hz, 1H), 7.45 (d, J=1.2 Hz, 1H), 6.82 (t, J=5.5 Hz, 1H), 5.97 (d, J=1.3 Hz, 1H), 5.17 (s, 2H), 4.75 (s, 2H), 3.43-3.39 (m, 5H), 3.25-3.14 (m, 2H), 2.05-1.92 (m, 2H), 1.80 (m, 2H), 1.72-1.53 (m, 2H), 1.13 (t, J=7.1 Hz, 3H).

Example 214: Synthesis of 4-(2-{6-[(1R)-2-(Dimethylamino)-1-hydroxyethyl]-1-oxo-4-(trifluoromethyl)-3H-isoindol-2-yl}-6-(ethylamino)pyridin-4-yl)-3-(4-methyl-1,2,4-triazol-3-yl)benzonitrile (AGK-1). Stereochemistry Arbitrarily Assigned

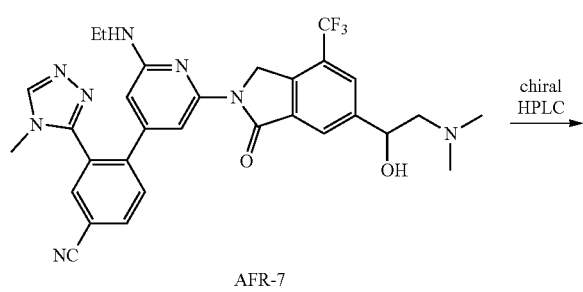

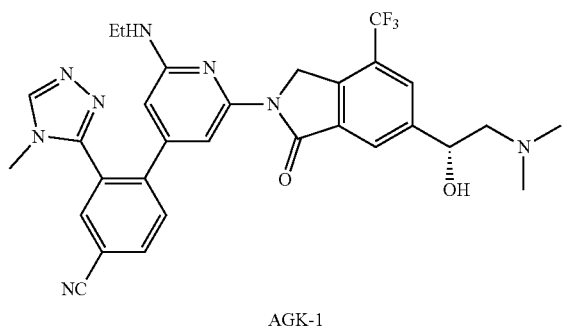

AGK-1

The compound (AFR-7) (50 mg, 1 eq, 85 µmol) was purified by CHIRAL-HPLC with the following conditions (Column: CHIRALPAK IG, 2*25 cm, 5 µm; Mobile Phase A: Hex:DCM=3:1 (0.5% 2M NH$_3$-MeOH)-HPLC, Mobile Phase B: EtOH-HPLC; Flow rate: 20 mL/min; Gradient: 30% B to 30% B in 20 min; Wave Length: 220/254 nm; RT1(min): 11.51; RT2(min): 17.34) to afford the title compound (AGK-1) (14.9 mg, 24 µmol, 30%, 97% Purity) as a yellow solid. m/z 591.2 (M+H)$^+$ (ES+). $^1$H NMR (400 MHz, MeOH-d4) δ 8.48 (s, 1H), 8.11-8.07 (m, 2H), 8.03 (d, J=1.7 Hz, 1H), 7.99 (s, 1H), 7.87 (d, J=8.1 Hz, 1H), 7.51-7.46 (m, 1H), 6.08-6.03 (m, 1H), 5.19 (s, 2H), 5.08-5.00 (m, 1H), 3.46 (s, 3H), 3.27 (t, J=7.2 Hz, 2H), 2.77-2.68 (m, 1H), 2.62-2.54 (m, 1H), 2.44 (s, 6H), 1.20 (t, J=7.2 Hz, 3H).

Column: CHIRALPAK IG-3, 4.6*50 mm, 3 um; Mobile Phase A: (Hex:DCM=3:1) (0.1% DEA):EtOH=70:30; Flow rate: 1 mL/min; RT: 2.745.

Example 215: Synthesis of 4-(2-{6-[(1S)-2-(Dimethylamino)-1-hydroxyethyl]-1-oxo-4-(trifluoromethyl)-3H-isoindol-2-yl}-6-(ethylamino)pyridin-4-yl)-3-(4-methyl-1,2,4-triazol-3-yl)benzonitrile (AGL-1). Stereochemistry Arbitrarily Assigned

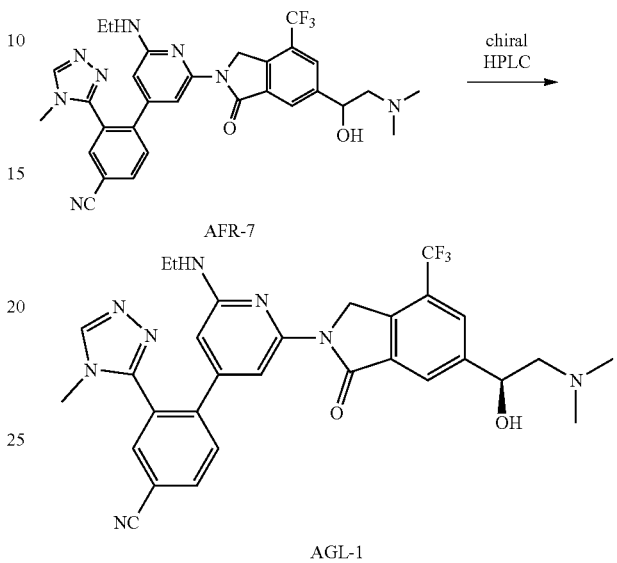

The compound (AFR-7) (50 mg, 1 eq, 85 µmol) was purified by CHIRAL-HPLC with the following conditions (Column: CHIRALPAK IG, 2*25 cm, 5 µm; Mobile Phase A: Hex:DCM=3:1 (0.5% 2M NH$_3$-MeOH)-HPLC, Mobile Phase B: EtOH-HPLC; Flow rate: 20 mL/min; Gradient: 30% B to 30% B in 20 min; Wave Length: 220/254 nm; RT1(min): 11.51; RT2(min): 17.34) to afford the title compound (AGL-1) (4.1 mg, 6.7 µmol, 8.2%, 97% Purity) as a yellow solid. m/z 591.2 (M+H)$^+$ (ES+). $^1$H NMR (400 MHz, MeOH-d4) δ 8.48 (s, 1H), 8.15-7.98 (m, 4H), 7.87 (d, J=8.1 Hz, 1H), 7.53-7.46 (m, 1H), 6.11-6.00 (m, 1H), 5.19 (s, 2H), 5.09-5.00 (m, 1H), 3.46 (s, 3H), 3.29-3.23 (m, 2H), 2.82-2.69 (m, 1H), 2.69-2.59 (m, 1H), 2.47 (s, 6H), 1.21 (t, J=7.2 Hz, 3H). Column: CHIRALPAK IG-3, 4.6*50 mm, 3 µm; Mobile Phase A: (Hex:DCM=3:1) (0.1% DEA):EtOH=70:30; Flow rate: 1 mL/min; RT: 4.004.

Example 216: Synthesis of 4-{2-Cyclopropyl-6-[6-(1-hydroxycyclobutyl)-1-oxo-4-(trifluoromethyl)-3H-isoindol-2-yl]pyridin-4-yl}-3-(4-methyl-1,2,4-triazol-3-yl)benzonitrile (AGM-5)

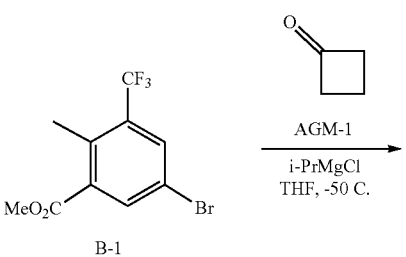

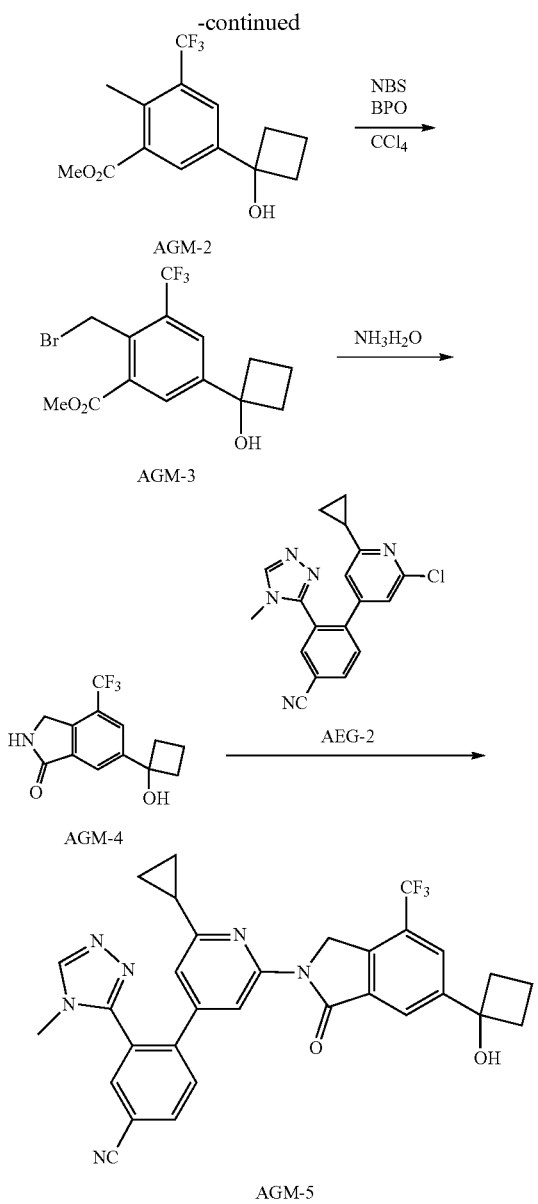

NH$_4$HCO$_3$) and MeCN (10% MeCN up to 50% in 15 min); Detector, UV 254/220 nm to afford the sub-title compound (AGM-2) (120 mg, 0.37 mmol, 31%, 90% Purity) as a white solid. m/z 289.1 (M+H)$^+$ (ES+).

Step 2: Synthesis of Methyl 2-(bromomethyl)-5-(1-hydroxycyclobutyl)-3-(trifluoromethyl)benzoate (AGM-3)

Into a 250-mL round-bottom flask and maintained with an inert atmosphere of nitrogen, was placed the product from step 1 above (AGM-2) (270 mg, 1 eq, 0.94 mmol) in CCl$_4$ (15 mL) at rt, then NBS (250 mg, 1.5 eq, 1.41 mmol) and BPO (72 mg, 0.3 eq, 0.28 mmol) were added at 0° C. The resulting mixture was stirred for overnight at 80° C. The mixture was cooled to rt. The resulting mixture was concentrated in vacuo. The crude product mixture was used in the next step directly without further purification. m/z 267.0/269.0 (M+H)$^+$ (ES+).

Step 3: Synthesis of 6-(1-Hydroxycyclobutyl)-4-(trifluoromethyl)isoindolin-1-one (AGM-4)

Into a 40-mL vial purged and maintained with an inert atmosphere of nitrogen, was placed the product from step 2 above (AGM-3) (150 mg, 1 eq, 0.41 mmol) in NH$_3$/MeOH solution (10 mL, 25%). The resulting mixture was stirred for 3 h at rt under nitrogen atmosphere. The mixture was cooled to rt. The resulting mixture was diluted with water and extracted with DCM (3×50 mL). The combined organic layers were washed with brine (2×50 mL), dried (Na$_2$SO$_4$). After filtration, the filtrate was concentrated in vacuo. The crude product was purified by reverse flash column chromatography with the following conditions: Column, C18; mobile phase, water (0.1% NH$_4$HCO$_3$) and MeCN (10% MeCN up to 70% in 15 min); Detector, UV 254/220 nm. This resulted in the sub-title compound (AGM-4) (100 mg, 0.34 mmol, 90%, 92% Purity) as a white solid. m/z 272.1 (M+H)$^+$ (ES+).

Step 4: Synthesis of 4-(2-Cyclopropyl-6-(6-(1-hydroxycyclobutyl)-1-oxo-4-(trifluoromethyl)isoindolin-2-yl)pyridin-4-yl)-3-(4-methyl-4H-1,2,4-triazol-3-yl)benzonitrile (AGM-5)

Into a 20-mL vial purged and maintained with an inert atmosphere of nitrogen, was placed the product from step 3 above (AGM-4) (30 mg, 1 eq, 0.11 mmol), intermediate (AEG-2) (37 mg, 1 eq, 0.11 mmol) and Cs$_2$CO$_3$ (72 mg, 2 eq, 0.22 mmol) in 1,4-dioxane (6 mL), then RuPhos palladacycle Gen.3 (19 mg, 0.2 eq, 22 µmol) and RuPhos (21 mg, 0.4 eq, 44 µmol) were added at rt under nitrogen atmosphere. The resulting mixture was stirred for 2 h at 100° C. under nitrogen atmosphere. The mixture was cooled to rt. The aq. layer was extracted with DCM (3×30 mL). The combined organic layers were washed with brine (2×30 mL), dried (Na$_2$SO$_4$). After filtration, the filtrate was concentrated in vacuo. The crude product was purified by Prep-HPLC with the following conditions (Column: XBridge Prep OBD C18 Column, 30*150 mm, 5 µm; Mobile Phase A: water (0.1% NH$_4$HCO$_3$), Mobile Phase B: MeCN; Flow rate: 60 mL/min; Gradient: 48% B to 58% B in 9 min; Wave Length: 571 nm; RT: 8.63;) to afford the title compound (AGM-5) (13.2 mg, 23 µmol, 21%, 99% Purity) as a white solid.

m/z 571.3 (M+H)$^+$ (ES+). $^1$H NMR (300 MHz, DMSO-d6) δ 8.55 (s, 1H), 8.22 (h, J=1.8 Hz, 2H), 8.08 (d, J=12.4

Step 1: Synthesis of Methyl 5-(1-hydroxycyclobutyl)-2-methyl-3-(trifluoromethyl)benzoate (AGM-2)

Into a 40-mL vial purged and maintained with an inert atmosphere of nitrogen, was placed methyl 5-bromo-2-methyl-3-(trifluoromethyl)benzoate (B-1) (400 mg, 1 eq, 1.35 mmol) in THF (10 mL), then i-PrMgCl (554 mg, 4 eq, 5.38 mmol) was added at 0° C. The resulting mixture was stirred for 2 h at 0° C. under nitrogen atmosphere, then cyclobutanone (AGM-1) (566 mg, 6 eq, 8.08 mmol) was added at 0° C. The resulting mixture was stirred for 2 h at rt under nitrogen atmosphere. The resulting mixture was diluted with water and extracted with DCM (3×50 mL). The combined organic layers were washed with brine (2×50 mL), dried (Na$_2$SO$_4$). After filtration, the filtrate was concentrated in vacuo. The crude product was purified by reverse flash column chromatography with the following conditions: Column, C18; mobile phase, water (0.1%

Hz, 2H), 7.98 (d, J=1.3 Hz, 1H), 7.88 (d, J=8.5 Hz, 1H), 6.91 (d, J=1.4 Hz, 1H), 5.98 (s, 1H), 5.17 (s, 2H), 3.48 (s, 3H), 2.49-2.42 (m, 2H), 2.41-2.26 (m, 2H), 2.14-1.95 (m, 2H), 1.83-1.67 (m, 1H), 1.03-0.87 (m, 4H).

Example 217: Synthesis of 4-{2-Cyclopropyl-6-[1-oxo-6-({[2-(trifluoromethoxy) ethyl]amino}methyl)-4-(trifluoromethyl)-3H-isoindol-2-yl] pyridin-4-yl}-3-(4-methyl-1,2,4-triazol-3-yl)benzonitrile (AGN-3)

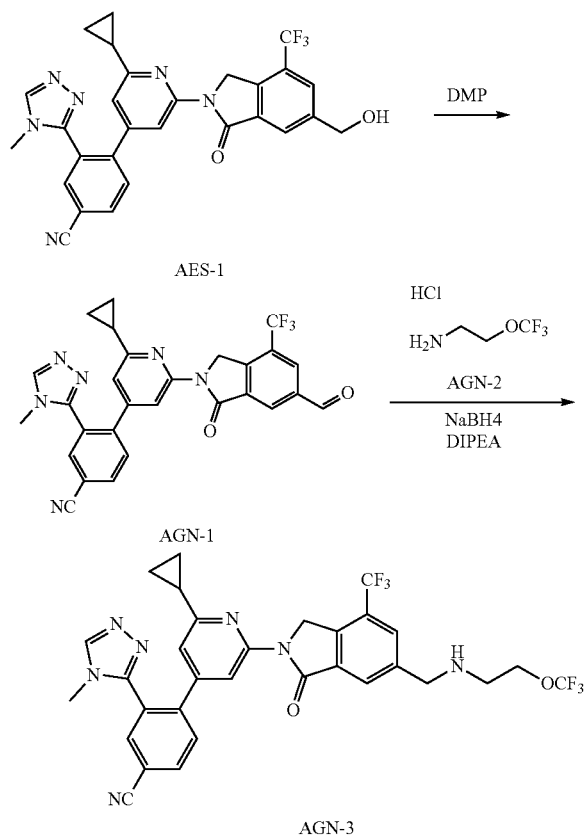

Step 1: Synthesis of 4-{2-Cyclopropyl-6-[6-formyl-1-oxo-4-(trifluoromethyl)-3H-isoindol-2-yl]pyridin-4-yl}-3-(4-methyl-1,2,4-triazol-3-yl)benzonitrile (AGN-1)

A solution of intermediate (AES-1) (60 mg, 1 eq, 0.11 mmol) and Dess-Martin periodinane (72 mg, 1.5 eq, 0.17 mmol) in DCM (15 mL) was stirred for 1 h at rt. The resulting mixture was filtered; the filter cake was washed with DCM (3×3 mL). The filtrate was concentrated in vacuo to afford the sub-title compound (AGN-1) (40 mg, 72 μmol, 60%, 95% Purity) as a yellow solid. m/z 529.2 (M+H)$^+$ (ES+).

Step 2: Synthesis of 4-{2-Cyclopropyl-6-[1-oxo-6-({[2-(trifluoromethoxy)ethyl]amino}methyl)-4-(trifluoromethyl)-3H-isoindol-2-yl]pyridin-4-yl}-3-(4-methyl-1,2,4-triazol-3-yl)benzonitrile (AGN-3)

To a stirred solution of the product from step 1 above (AGN-1) (20 mg, 1 eq, 36 μmol) and 2-(trifluoromethoxy) ethan-1-amine, HCl (AGN-2) (9.4 mg, 2 eq, 72 μmol) in MeOH (15 mL) was added DIPEA (19 mg, 4 eq, 0.14 mmol) at rt. The resulting mixture was stirred for 2 h at rt. To the above mixture was added NaBH$_4$ (7 mg, 5 eq, 0.18 mmol) at 0° C. The resulting mixture was stirred for additional 2 h at rt. The reaction was then quenched by the addition of 2 mL of ice water at 0° C. The mixture was concentrated in vacuo. The crude product was purified by Prep-HPLC with the following conditions (Column: Sunfire prep C18 column, 30*150 mm, 5 μm; Mobile Phase A: water (0.1% FA), Mobile Phase B: MeCN; Flow rate: 60 mL/min; Gradient: 8% B to 32% B in 7 min; Wave Length: 254/220 nm; RT: 6.12) to afford the title compound (AGN-3) (1.7 mg, 2.6 μmol, 7.2%, 98 Purity) as an off-white solid. m/z 642.1 (M+H)$^+$ (ES+).

6.95 (d, J=1.5 Hz, 1H), 5.17 (s, 2H), 4.15 (t, J=5.4 Hz, 2H), 4.01 (s, 2H), 3.49 (s, 3H), 2.93 (t, J=5.4 Hz, 2H), 2.12-1.98 (m, 1H), 1.04-0.97 (m, 4H).

Example 218: Synthesis of 4-(2-Cyclopropyl-6-(6-(((2-methoxyethyl)amino)methyl)-1-oxoisoindolin-2-yl)pyridin-4-yl)-3-(4-methyl-4H-1,2,4-triazol-3-yl) benzonitrile (AGO-2)

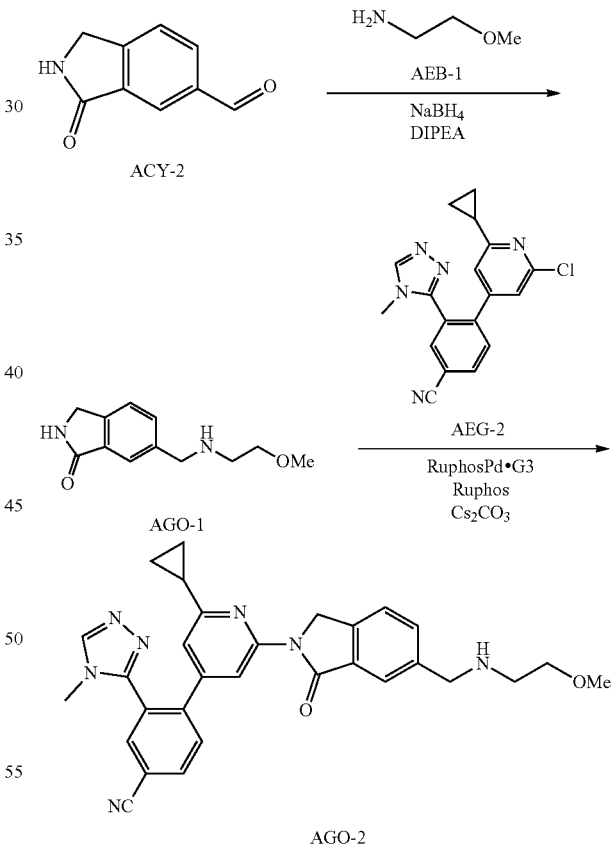

Step 1: Synthesis of 6-(((2-Methoxyethyl)amino) methyl)isoindolin-1-one (AGO-1)

To a stirred solution of intermediate (ACY-2) (60 mg, 1 eq, 0.37 mmol) in DCM (8 mL) were added DIPEA (192 mg, 4 eq, 1.49 mmol) at rt. The resulting mixture was stirred for 10 min at 60° C. Than 2-methoxyethan-1-amine (39 mg, 1.4 eq, 0.52 mmol) was added at rt. The resulting mixture was stirred for 2 h at 60° C. Finally, NaBH$_4$ (395 mg, 5 eq, 1.86 mmol) was added at 0° C. The resulting was stirred for 1 h at rt. The mixture was concentrated in vacuo. The crude product was purified by reverse flash column chromatography with the following conditions: Column, C18; mobile phase, water (0.1% NH$_4$HCO$_3$) and MeCN (0% MeCN up to 20% in 20 min); Detector, UV 254/220 nm. This resulted in the sub-title compound (AGO-1) (45 mg, 0.19 mmol, 55%, 95% Purity) as a yellow crude solid. m/z 221.1 (M+H)$^+$ (ES+).

Step 2: Synthesis of 4-(2-Cyclopropyl-6-(6-(((2-methoxyethyl)amino)methyl)-1-oxoisoindolin-2-yl)pyridin-4-yl)-3-(4-methyl-4H-1,2,4-triazol-3-yl)benzonitrile (AGO-2)

To a stirred solution of intermediate (AEG-2) (60 mg, 0.18 mmol, 1 eq), the product from step 1 above (AGO-1) (43 mg, 1.1 eq, 0.20 mmol) and Cs$_2$CO$_3$ (175 mg, 3 eq, 0.54 mmol) in 1,4-dioxane (8 mL) were added RuPhos (33 mg, 0.4 eq, 72 µmol) and RuPhos palladacycle Gen.3 (30 mg, 0.2 eq, 36 µmol) at rt under nitrogen atmosphere. The resulting mixture was stirred for 2 h at 100° C. under nitrogen atmosphere. The mixture was cooled to rt and concentrated in vacuo. The residue was purified by Prep-TLC with DCM/MeOH (12/1). The crude product was purified by Prep-HPLC with the following conditions (Column: XBridge Prep OBD C18 Column, 19*250 mm, 5 µm; Mobile Phase A: water (0.1% NH$_4$HCO$_3$), Mobile Phase B: MeCN; Flow rate: 25 mL/min; Gradient: 25% B to 70% B in 8 min; Wave Length: 254/220 nm; RT: 7.67) to afford the title compound (AGO-2) (34.1 mg, 64 µmol, 36%, 98% Purity) as a white solid. m/z 520.2 (M+H)$^+$ (ES+). $^1$H NMR (400 MHz, DMSO-d6) δ 8.54 (s, 1H), 8.25-8.18 (m, 2H), 7.98 (d, J=1.4 Hz, 1H), 7.87 (d, J=8.5 Hz, 1H), 7.74 (s, 1H), 7.63 (d, J=1.2 Hz, 2H), 6.89 (d, J=1.4 Hz, 1H), 5.00 (s, 2H), 3.82 (s, 2H), 3.48 (s, 3H), 3.40 (t, J=5.7 Hz, 2H), 3.24 (s, 3H), 2.64 (t, J=5.7 Hz, 2H), 2.08-2.02 (m, 1H), 1.00-0.93 (m, 4H).

Example 219: Synthesis of 2-{6-Cyclopropyl-4-[4-fluoro-2-(4-methyl-1,2,4-triazol-3-yl)phenyl]pyridin-2-yl}-6-({[(1-hydroxycyclopentyl)methyl]amino}methyl)-3H-isoindol-1-one (AGP-1)

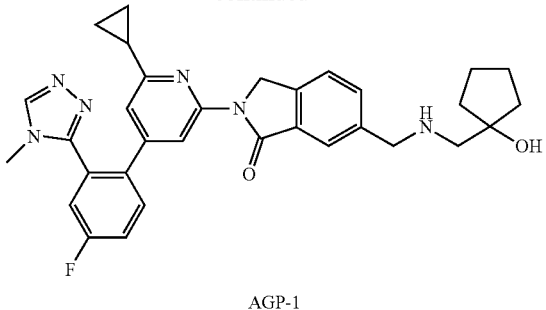

AGP-1

To a stirred solution of intermediate (ADN-1) (70 mg, 0.21 mmol, 1 eq), intermediate (AFQ-2) (67 mg, 1.2 eq, 0.26 mmol) and Cs$_2$CO$_3$ (208 mg, 0.64 mmol, 3 eq) in 1,4-dioxane were added Ruphos (10 mg, 0.1 eq, 21 µmol) and Ruphos palladacycle Gen.3 (18 mg, 0.1 eq, 21 µmol) at rt under nitrogen atmosphere. The resulting mixture was stirred for 2 h at 100° C. under nitrogen atmosphere. The mixture was cooled to rt, diluted with water and extracted with EtOAc (3×20 mL). The combined organic layers were washed with brine (2×20 mL), dried (Na$_2$SO$_4$). After filtration, the filtrate was concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 µm; Mobile Phase A: water (0.1% NH$_4$HCO$_3$), Mobile Phase B: MeCN; Flow rate: 60 mL/min; Gradient: 40% B to 50% B in 9 min; Wave Length: 254/220 nm) to afford the title compound (AGP-1) (51.9 mg, 93 µmol, 44%, 99% Purity) as a white solid. m/z 553.4 (M+H)$^+$ (ES+). $^1$H NMR (400 MHz, DMSO-d6) δ 8.50 (s, 1H), 7.94 (d, J=1.4 Hz, 1H), 7.80-7.70 (m, 2H), 7.67-7.51 (m, 4H), 6.81 (d, J=1.4 Hz, 1H), 5.00 (s, 2H), 3.83 (s, 2H), 3.43 (s, 3H), 2.50 (s, 2H), 2.03 (m, 1H), 1.70-1.45 (m, 8H), 0.96 (m, 4H).

Example 220: Synthesis of 2-{6-Ethoxy-4-[4-fluoro-2-(4-methyl-1,2,4-triazol-3-yl)phenyl]pyridin-2-yl}-6-({[(1-hydroxycyclobutyl)methyl]amino}methyl)-4-(trifluoromethyl)-3H-isoindol-1-one (AGQ-2)

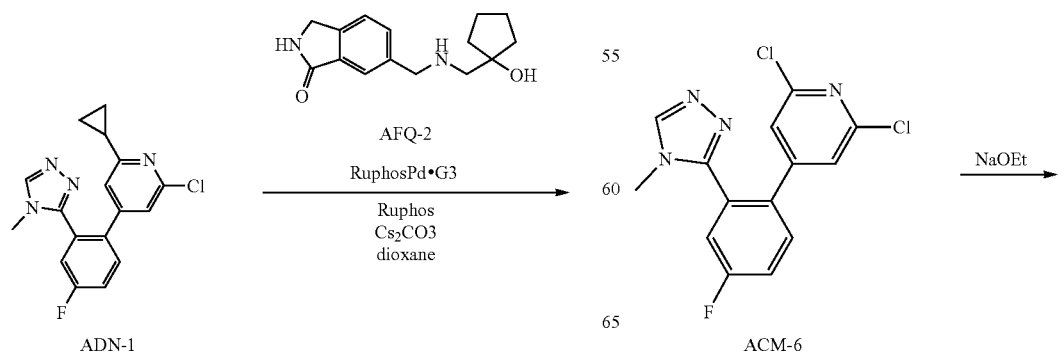

-continued

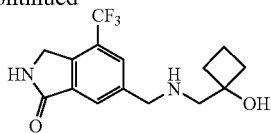

ADR-2

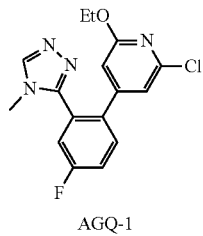

AGQ-1

Ruphos Pd G₃
───────────→
Ruphos
Cs₂CO₃
dioxane

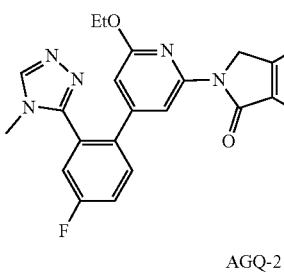

AGQ-2

Step 1: Synthesis 2-Chloro-6-ethoxy-4-[4-fluoro-2-(4-methyl-1,2,4-triazol-3-yl)phenyl]pyridine (AGQ-1)

Into a 20 mL sealed tube were added intermediate (ACM-6) (300 mg, 1 eq, 0.93 mmol) in EtOH (10 mL) at rt. To the above mixture was added EtONa (94.76 mg, 1.5 eq, 1.39 mmol) over 1 min at rt. The resulting mixture was stirred for overnight at 60° C. The mixture was allowed to cool down to rt. The crude product was purified by reverse flash column chromatography with the following conditions: Column, C18; mobile phase, water (0.1% NH₄HCO₃) and MeCN (10% MeCN up to 70% in 15 min); Detector, UV 254/220 nm to afford the sub-title compound (AGQ-1) (135 mg, 0.39 mmol, 44%, 95% Purity) as a yellow solid. m/z 333.1/335.1 (M+H)⁺ (ES+).

Step 2: Synthesis 2-{6-Ethoxy-4-[4-fluoro-2-(4-methyl-1,2,4-triazol-3-yl)phenyl]pyridin-2-yl}-6-({[(1-hydroxycyclobutyl)methyl]amino}methyl)-4-(trifluoromethyl)-3H-isoindol-1-one (AGQ-2)

To a stirred solution of the product from step 1 above (AGQ-1) (70 mg, 1 eq, 0.21 mmol), intermediate (ADR-2) (79 mg, 1.2 eq, 0.25 mmol) and Cs₂CO₃ (137 mg, 2 eq, 0.42 mmol) in 1,4-dioxane (10 mL) were added RuPhos (39 mg, 0.4 eq, 84 μmol) and RuPhos palladacycle Gen.3 (35 mg, 0.2 eq, 42 μmol) at rt under nitrogen atmosphere. The resulting mixture was stirred for 1 h at 100° C. under nitrogen atmosphere. The mixture was cooled to rt and concentrated in vacuo. The residue was purified by Prep-TLC with DCM/MeOH (10/1) and Prep-HPLC with the following conditions (Column: XBridge Prep OBD C18 Column, 30*150 mm, 5 μm; Mobile Phase A: water (0.1% NH₄HCO₃), Mobile Phase B: MeCN; Flow rate: 60 mL/min; Gradient: 50% B to 70% B in 8 min; Wave Length: 254/220 nm; RT: 6.62) to afford the title compound (AGQ-2) (37.5 mg, 60 μmol, 29%, 99% Purity) as a white solid. m/z 611.4 (M+H)⁺ (ES+). ¹H NMR (400 MHz, DMSO-d6) δ 8.51 (s, 1H), 8.04 (d, J=10.2 Hz, 2H), 7.81 (d, J=1.2 Hz, 1H), 7.74-7.68 (m, 1H), 7.63-7.55 (m, 2H), 6.33 (d, J=1.2 Hz, 1H), 5.19 (s, 2H), 4.94 (s, 1H), 4.34-4.26 (m, 2H), 3.95 (s, 2H), 3.43 (s, 3H), 2.53 (s, 2H), 2.05-1.94 (m, 2H), 1.94-1.84 (m, 2H), 1.66-1.57 (m, 1H), 1.44-1.32 (m, 4H).

Example 221: Synthesis of 2-{6-Ethoxy-4-[4-fluoro-2-(4-methyl-1,2,4-triazol-3-yl)phenyl]pyridin-2-yl}-6-({[(1-hydroxycyclobutyl)methyl]amino}methyl)-3H-isoindol-1-one (AGR-1)

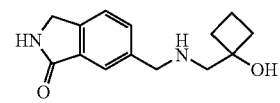

AEE-1

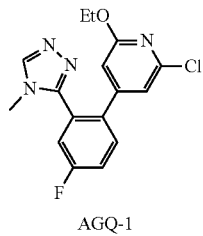

AGQ-1

Ruphos Pd G₃
───────────→
Ruphos
Cs₂CO₃
dioxane

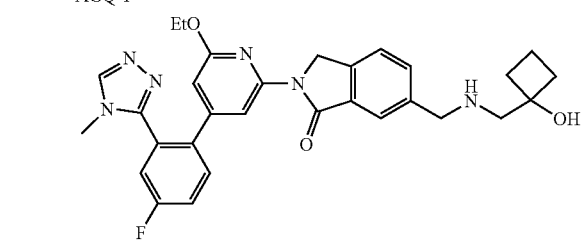

AGR-1

To a stirred mixture of intermediate (AGQ-1) (60 mg, 1 eq, 0.18 mmol), intermediate (AEE-1) (49 mg, 1.1 eq, 0.20 mmol) and Cs₂CO₃ (118 mg, 2 eq, 0.36 mmol) in 1,4-dioxane (8 mL) were added RuPhos (34 mg, 0.4 eq, 72 μmol) and RuPhos palladacycle Gen.3 (30 mg, 0.2 eq, 36 μmol) at rt under nitrogen atmosphere. The resulting mixture was stirred for 1 h at 100° C. under nitrogen atmosphere. The mixture was cooled to rt and concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: water (0.1% NH₄HCO₃), Mobile Phase B: MeCN; Flow rate: 60 mL/min; Gradient: 27% B to 42% B in 10 min; Wave Length: 254/220 nm; RT: 9.2) to afford the title compound (AGR-1) (25.2 mg, 0.45 mmol, 25%, 96% Purity) as a white solid. m/z 543.3 (M+H)⁺ (ES+). ¹H NMR (400 MHz, DMSO-d6) δ 8.51 (s, 1H), 7.83-7.55 (m, 7H), 6.28 (d, J=1.2 Hz, 1H), 5.05 (s, 2H), 4.91 (s, 1H), 4.33 (q, J=7.0 Hz, 2H), 3.86 (s, 2H), 3.44 (s, 3H), 2.53 (s, 2H), 2.00 (t, J=8.8, 3.1 Hz, 2H), 1.89 (d, J=12.2, 9.5 Hz, 2H), 1.64-1.54 (m, 1H), 1.47-1.30 (m, 4H).-

Example 222: Synthesis of 6-{1[(1-Aminocyclobutyl)methoxy]methyl}-2-{4-[4-fluoro-2-(4-methyl-1,2,4-triazol-3-yl)phenyl]-6-(methylamino)pyridin-2-yl}-4-(trifluoromethyl)-3H-isoindol-1-one (AGS-2)

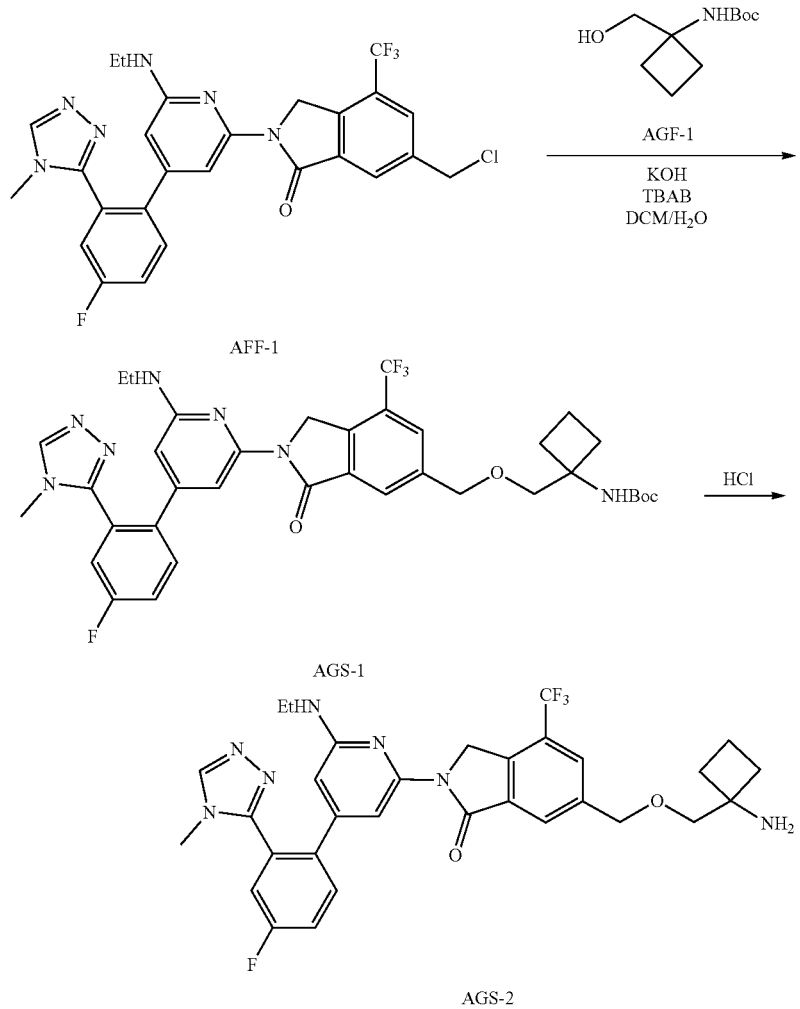

Step 1: Synthesis of tert-Butyl N-{1-[({2-[6-(ethylamino)-4-[4-fluoro-2-(4-methyl-1,2,4-triazol-3-yl)phenyl]pyridin-2-yl]-3-oxo-1-(trifluoromethyl)-1H-isoindol-5-yl}methoxy)methyl]cyclobutyl}carbamate (AGS-1)

To a stirred mixture of intermediate (AFF-1) (40 mg, 1 eq, 73 μmol) and tert-butyl N-[1-(hydroxymethyl)cyclobutyl]carbamate (AGF-1) (148 mg, 10 eq, 0.73 mmol) in DCM (2 mL) was added aq. KOH (2 mL, 20% Wt) at rt. To the above mixture was added TBAB (12 mg, 0.5 eq, 36 μmol) over 2 min at rt. The resulting mixture was stirred for 30 min at rt. The resulting mixture was diluted with water and extracted with EtOAc (3×10 mL). The combined organic layers were washed with brine (2×10 mL), dried (Na$_2$SO$_4$). After filtration, the filtrate was concentrated in vacuo. The residue was purified by Prep-TLC with DCM/MeOH (10/1) to afford the sub-title compound (AGS-1) (20 mg, 27 μmol, 38%, 96% Purity) as a white solid. m/z 710.4 (M+H)$^+$ (ES+).

Step 2: Synthesis of 6-{1[(1-Aminocyclobutyl)methoxy]methyl}-2-{4-[4-fluoro-2-(4-methyl-1,2,4-triazol-3-yl) phenyl]-6-(methylamino) pyridin-2-yl}-4-(trifluoromethyl)-3H-isoindol-1-one (AGS-2)

To a stirred mixture of the product from step 1 above (AGS-1) (18 mg, 1 eq, 25 μmol) in DCM (5 mL) was added HCl (gas) in 1,4-dioxane (1 mL, 4 M) at rt. The resulting mixture was stirred for 0.5 h at rt. The mixture was concentrated in vacuo. The crude product was purified by Prep-HPLC with the following conditions (Column: XBridge Shield RP18 OBD Column, 19*250 mm, 10 μm; Mobile Phase A: water (0.1% NH$_4$HCO$_3$), Mobile Phase B: MeCN; Flow rate: 25 mL/min; Gradient: 40% B to 70% B in 8 min; Wave Length: 254/220 nm) to afford the title compound (AGS-2) (3.3 mg, 5.1 μmol, 21%, 95% Purity) as a white solid. m/z 610.4 (M+H)$^+$ (ES+). $^1$H NMR (400 MHz, DMSO-d6) δ 8.48 (s, 1H), 8.02 (d, J=18.6 Hz, 2H), 7.70-7.47 (m, 3H), 7.45 (s, 1H), 6.71 (t, J=5.4 Hz, 1H), 5.92 (s, 1H), 5.17 (s, 2H), 4.75 (s, 2H), 3.47 (s, 3H), 3.17 (m, 4H), 2.05-1.84 (m, 4H), 1.77-1.62 (m, 2H), 1.13 (t, J=7.1 Hz, 3H).

Example 223: Synthesis of 4-{2-Cyclopropyl-6-[1-oxo-6-({[2-(trifluoromethoxy) ethyl]amino}methyl)-3H-isoindol-2-yl]pyridin-4-yl}-3-(4-methyl-1,2,4-triazol-3-yl)benzonitrile (AGT-3)

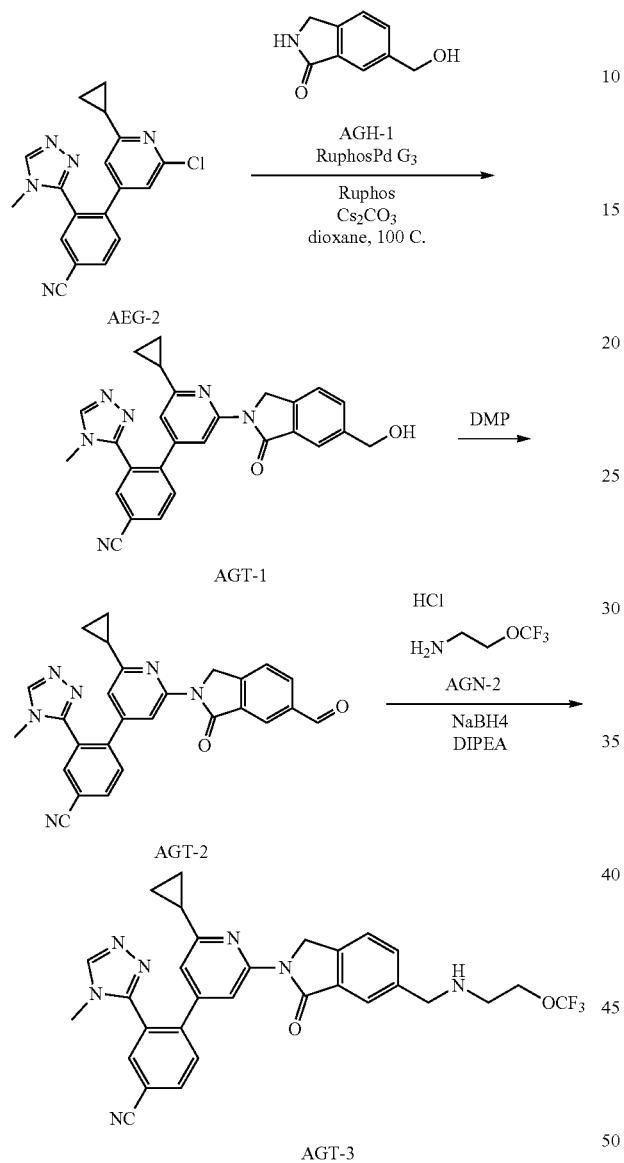

Step 1: Synthesis of 4-(2-Cyclopropyl-6-(6-(hydroxymethyl)-1-oxoisoindolin-2-yl)pyridin-4-yl)-3-(4-methyl-4H-1,2,4-triazol-3-yl)benzonitrile (AGT-1)

To a stirred mixture of intermediate (AEG-2) (60 mg, 1 eq, 0.18 mmol), intermediate (AGH-1) (38 mg, 1.3 eq, 0.23 mmol) and $Cs_2CO_3$ (116 mg, 0.36 mmol, 2 eq) in 1,4-dioxane (10 mL) were added RuPhos palladacycle Gen.3 (30 mg, 0.2 eq, 36 µmol) and RuPhos (33 mg, 0.4 eq, 72 µmol) at rt under nitrogen atmosphere. The resulting mixture was stirred for 2 h at 100° C. under nitrogen atmosphere. The mixture was cooled to rt and concentrated in vacuo. The residue was purified by Prep-TLC with DCM/MeOH (8/1) to afford the sub-title compound (AGT-1) (55 mg, 0.12 mmol, 66%, 90% Purity) as a white solid. m/z 463.2 $(M+H)^+$ (ES+).

Step 2: Synthesis of 4-(2-Cyclopropyl-6-(6-formyl-1-oxoisoindolin-2-yl)pyridin-4-yl)-3-(4-methyl-4H-1,2,4-triazol-3-yl)benzonitrile (AGT-2)

A solution of the product from step 1 above (AGT-1) (20 mg, 1 eq, 43 µmol) and DMP (24 mg, 1.3 eq, 56 µmol) in DCM (6 mL) was stirred for 1 h at rt. The resulting mixture was filtered; the filter cake was washed with MeOH (3×2 mL). The filtrate was concentrated in vacuo. The crude product was used in the next step directly without further purification. m/z 461.2 $(M+H)^+$ (ES+).

Step 3: Synthesis of 4-{2-Cyclopropyl-6-[1-oxo-6-({[2-(trifluoromethoxy)ethyl]amino}methyl)-3H-isoindol-2-yl] pyridin-4-yl}-3-(4-methyl-1,2,4-triazol-3-yl)benzonitrile (AGT-3)

To a stirred solution of the product from step 2 above (AGT-2) (30 mg, 1 eq, 65 µmol) and 2-(trifluoromethoxy)ethan-1-amine, HCl (13 mg, 1.5 eq, 98 µmol) in MeOH (15 mL) was added DIPEA (51 mg, 2 eq, 0.39 mmol) at rt. The resulting mixture was stirred for 2 h at rt. To the above mixture was added $NaBH_4$ (30 mg, 4 eq, 0.78 mmol) at 0° C. The resulting mixture was stirred for additional 2 h at rt. The reaction was then quenched by the addition of 2 mL of ice water at 0° C. and concentrated in vacuo. The crude product was purified by Prep-HPLC with the following conditions (Column: Sunfire prep C18 column, 30*150 mm, 5 µm; Mobile Phase A: water (0.1% FA), Mobile Phase B: MeCN; Flow rate: 60 mL/min; Gradient: 8% B to 32% B in 7 min; Wave Length: 254/220 nm; RT: 6.12) to afford the title compound (AGT-3) (10.4 mg, 17 µmol, 27%, 95% Purity) as a white solid. m/z 574.1 $(M+H)^+$ (ES+). $^1H$ NMR (400 MHz, MeOH-d4) δ 8.48 (s, 1H), 8.15-8.03 (m, 3H), 7.96-7.77 (m, 2H), 7.73-7.56 (m, 2H), 6.92 (s, 1H), 5.03 (s, 2H), 4.17 (t, J=5.3 Hz, 2H), 3.97 (s, 2H), 3.49 (s, 3H), 2.96 (t, J=5.4 Hz, 2H), 2.08-1.97 (m, 1H), 1.08-0.94 (m, 4H).

Example 224: Synthesis of 2-[4'-Chloro-2'-(4-methyl-1,2,4-triazol-3-yl)-[1,1'-biphenyl]-3-yl]-6-({[[(1-hydroxycyclopentyl) methyl]amino} methyl)-3H-isoindol-1-one (AGU-10)

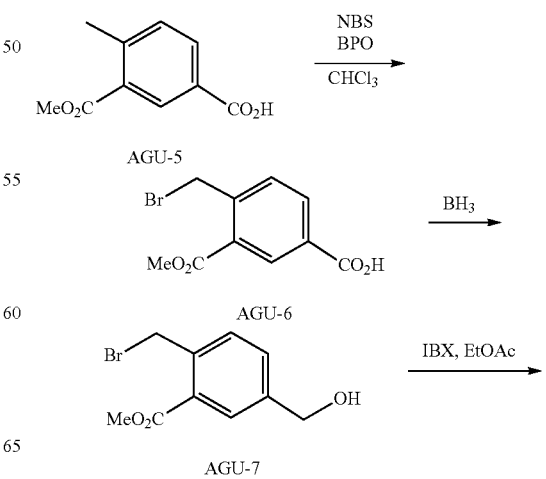

-continued

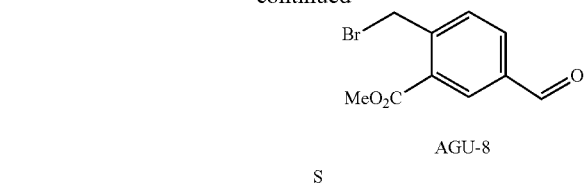

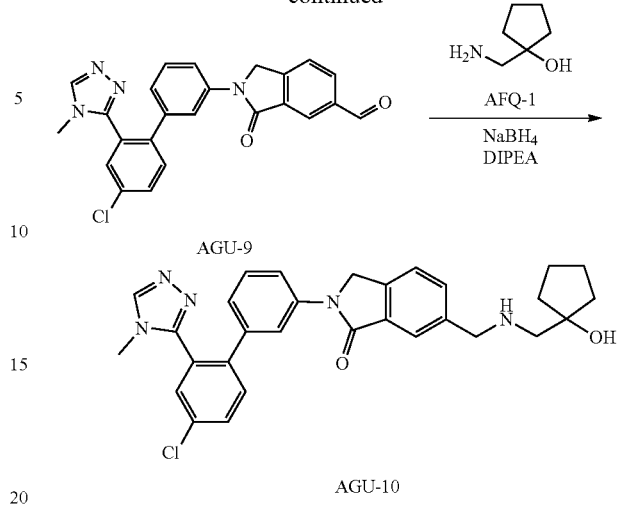

Step 1: Synthesis of 2-Bromo-5-chloro-N-[(methyl-carbamothioyl)amino]benzamide (AGU-1)

To a stirred mixture of 2-bromo-5-chlorobenzoic acid (ACR-1) (4.90 g, 1 eq, 20.8 mmol) and DIPEA (8.07 g, 3 eq, 62.4 mmol) in DMF (50 mL) was added 4-methyl-3-thiosemicarbazide (D-2) (2.63 g, 1.2 eq, 25.0 mmol) and $T_3P$ in EtOAc (26.5 g, 50% Wt, 4 eq, 83.2 mmol) at 0° C. The resulting mixture was stirred for overnight at rt. The resulting mixture was concentrated in vacuo. The crude product was purified by reverse flash column chromatography with the following conditions: Column, C18; mobile phase, water (0.1% FA) and MeCN (0% MeCN up to 60% in 30 min); Detector, UV 254/220 nm to afford the sub-title compound (AGU-1) (4.5 g, 11.5 mmol, 67%, 82% Purity) as a yellow solid. m/z 321.9/323.9 $(M+H)^+$ (ES+).

Step 2: Synthesis of 5-(2-Bromo-5-chlorophenyl)-4-methyl-1,2,4-triazole-3-thiol (AGU-2)

To a stirred mixture of NaOH (2.79 g, 69.745 mmol, 5 eq) in $H_2O$ (200 g) was added the product from step 1 above (AGU-1) (4.50 g, 1 eq, 14.0 mmol) at 0° C. The resulting mixture was stirred for 2 h at 60° C. The mixture was acidified to pH 4 with HCl (aq., 1 M) at 0° C. The resulting mixture was diluted with water and extracted with DCM (3×300 mL). The combined organic layers were washed with brine (2×300 mL), dried ($Na_2SO_4$). After filtration, the filtrate was concentrated in vacuo. This resulted in the sub-title compound (AGU-2) (4.3 g, 10.6 mmol, crude, 75% Purity) as a yellow solid. m/z 303.9/305.9 $(M+H)^+$ (ES+).

Step 3: Synthesis of 3-(2-Bromo-5-chlorophenyl)-4-methyl-1,2,4-triazole (AGU-3)

To a stirred mixture of the product from step 2 above (AGU-2) (4.3 g, 1 eq, 14.1 mmol) in DCM (50 mL) was added AcOH (1.70 g, 2 eq, 28.2 mmol) dropwise at 0° C. To the above mixture was added $H_2O_2$ (2.40 g, 30% Wt, 5 eq, 70.6 mmol) dropwise at 0° C. The resulting mixture was stirred for 2 h at rt. The mixture was acidified to pH 7 with saturated $NaHCO_3$ (aq., 1 M). The resulting mixture was diluted with water and extracted with DCM (3×300 mL). The combined organic layers were washed with brine (2×300 mL), dried ($Na_2SO_4$). After filtration, the filtrate was concentrated in vacuo. This resulted in the sub-title compound (AGU-3) (2.8 g, 8.30 mmol, 73%, 80% Purity) as a yellow solid. m/z 271.0/273.0 (M+H)$^+$ (ES+).

Step 4: Synthesis of 4'-Chloro-2'-(4-methyl-1,2,4-triazol-3-yl)-[1,1'-biphenyl]-3-amine (AGU-4)

To a stirred solution of the product from step 3 above (AGU-3) (600 mg, 1 eq, 2.20 mmol), 3-aminophenylboronic acid (AAS-1) (332 mg, 1.1 eq, 2.42 mmol) and K$_2$CO$_3$ (913 mg, 3 eq, 6.61 mmol) in 1,4-dioxane (10 mL) and water (1 mL) was added Pd(dppf)Cl$_2$.DCM (179 mg, 0.1 eq, 0.22 mmol) at rt under nitrogen atmosphere. The resulting mixture was stirred for 3 h at 100° C. under nitrogen atmosphere. The mixture was allowed to cool down to rt. The resulting mixture was concentrated in vacuo. The residue was purified by Prep-TLC with DCM/MeOH (15/1) to afford the sub-title compound (AGU-4) (500 mg, 1.58 mmol, 80%, 90% Purity) as a Brown yellow solid. m/z 285.1/287.1 (M+H)$^+$ (ES+).

Step 5: Synthesis of 4-(Bromomethyl)-3-(methoxycarbonyl) benzoic acid (AGU-6)

To a stirred solution of 3-(methoxycarbonyl)-4-methylbenzoic acid (AGU-5) (2.00 g, 1 eq, 10.3 mmol) and NBS (2.20 g, 1.2 eq, 12.4 mmol) in CHCl$_3$ (60 mL) was added BPO (792 mg, 0.3 eq, 3.09 mmol) at rt. The resulting mixture was stirred for overnight at 80° C. The mixture was allowed to cool down to rt. The resulting mixture was concentrated in vacuo. The residue was applied on a silica gel column chromatography with petroleum ether/EtOAc (1/6) to afford the sub-title compound (AGU-6) (2.4 g, 7.68 mmol, 85%, 87% Purity) as an off-white solid. m/z 273.0/275.0 (M+H)$^+$ (ES+).

Step 6: Synthesis of Methyl 2-(bromomethyl)-5-(hydroxymethyl) benzoate (AGU-7)

To a stirred solution of the product from step 1 above (AGU-6) (2.00 g, 1 eq, 7.32 mmol) in THF (40 mL) was added BH$_3$-THF (18 mL, 1 M, 2.5 eq, 18.3 mmol) dropwise at 0° C. under nitrogen atmosphere. The resulting mixture was stirred for 2 h at rt under nitrogen atmosphere. The reaction was quenched with MeOH (10 mL) at 0° C. The resulting mixture was concentrated in vacuo. The residue was applied on a silica gel column chromatography with petroleum ether/EtOAc (3/1) to afford the sub-title compound (AGU-7) (1.1 g, 3.75 mmol, 58%, 88% Purity) as an off-white solid. m/z 259.0/261.0 (M+H)$^+$ (ES+).

Step 7: Synthesis of Methyl 2-(bromomethyl)-5-formylbenzoate (AGU-8)

To a stirred solution of the product from step 6 above (AGU-7) (1.20 g, 1 eq, 4.63 mmol) and IBX (1.95 g, 1.5 eq, 6.95 mmol) in EtOAc (20 mL) at rt. The resulting mixture was stirred for 3 h at 70° C. The mixture was allowed to cool down to rt. The resulting mixture was diluted with water and extracted with EtOAc (3×100 mL). The combined organic layers were washed with brine (2×100 mL), dried (Na$_2$SO$_4$). After filtration, the filtrate was concentrated in vacuo. The residue was purified by Prep-TLC with EtOAc/petroleum ether (1/3) to afford the sub-title compound (AGU-8) (700 mg, 2.46 mmol, 59%, 90% Purity) as a brown yellow oil. m/z 257.0/259.0 (M+H)$^+$ (ES+).

Step 8: Synthesis of 2-[4'-Chloro-2'-(4-methyl-1,2,4-triazol-3-yl)-[1,1'-biphenyl]-3-yl]-3-oxo-1H-isoindole-5-carbaldehyde (AGU-9)

To a stirred solution of the product from step 4 above (AGU-4) (400 mg, 1 eq, 1.41 mmol) and the product from step 7 above (AGU-8) (433 mg, 1.2 eq, 1.69 mmol) in MeCN (10 mL) and water (5 mL) was added AgNO$_3$ (358 mg, 1.5 eq, 2.11 mmol) at 0° C. The resulting mixture was stirred for overnight at rt. The resulting mixture was concentrated in vacuo. The crude product was purified by reverse flash column chromatography with the following conditions: Column, C18; mobile phase, water (0.1% NH$_4$HCO$_3$) and MeCN (0% MeCN up to 50% in 25 min); Detector, UV 254/220 nm. This resulted in the sub-title compound (AGU-9) (260 mg, 0.57 mmol, 43%, 94% Purity) as a brown yellow solid. m/z 429.1/431.1 (M+H)$^+$ (ES+).

Step 9: Synthesis of 2-[4'-chloro-2'-(4-methyl-1,2,4-triazol-3-yl)-[1,1'-biphenyl]-3-yl]-6-({[(1-hydroxycyclopentyl)methyl]amino}methyl)-3H-isoindol-1-one (AGU-10)

To a stirred solution of the product from step 8 above (AGU-9) (70 mg, 1 eq, 0.16 mmol), 1-(aminomethyl) cyclopentan-1-ol (AFQ-1) (23 mg, 1.2 eq, 0.20 mmol) and DIPEA (63 mg, 3 eq, 0.49 mmol) in MeOH (10 mL) at rt. The resulting mixture was stirred for 2 h at 60° C. The mixture was allowed to cool down to rt. To the above mixture was added NaBH$_4$ (31 mg, 5 eq, 0.82 mmol) at 0° C. The resulting mixture was stirred for additional 2 h at rt. The reaction was then quenched by the addition of 2 mL of ice water at 0° C. and concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 31% B to 48% B in 10 min; Wave Length: 254/220 nm) to afford the title compound (AGU-10) (24.4 mg, 45 μmol, 28%, 98% Purity) as a white solid. m/z 528.4/530.4 (M+H)$^+$ (ES+). $^1$H NMR (400 MHz, DMSO-d6) δ 8.43 (s, 1H), 8.01-7.92 (m, 1H), 7.85-7.55 (m, 7H), 7.39 (t, J=8.0 Hz, 1H), 6.94-6.86 (m, 1H), 4.86 (s, 2H), 3.84 (s, 2H), 3.11 (s, 3H), 2.49 (s, 2H), 1.75-1.62 (m, 2H), 1.60-1.36 (m, 6H).

Example 225: Synthesis of 2-[4'-Chloro-2'-(4-methyl-1,2,4-triazol-3-yl)-[1,1'-biphenyl]-3-yl]-6-({[(1-hydroxycyclobutyl)methyl]amino}methyl)-3H-isoindol-1-one (AGV-1)

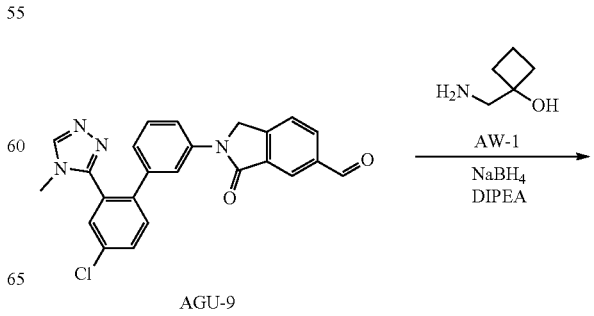

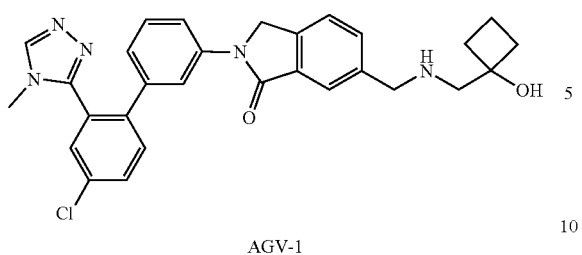

AGV-1

To a stirred solution of intermediate (AGU-9) (70 mg, 1 eq, 0.16 mmol), 1-(aminomethyl)cyclobutan-1-ol, HCl (AW-1) (20 mg, 1.2 eq, 0.20 mmol) and DIPEA (63 mg, 3 eq, 0.49 mmol) in MeOH (10 mL) at rt. The resulting mixture was stirred for 2 h at 60° C. The mixture was allowed to cool down to rt. To the above mixture was added NaBH$_4$ (31 mg, 5 eq, 0.82 mmol) at 0° C. The resulting mixture was stirred for additional 2 h at rt. The reaction was then quenched by the addition of 2 mL of ice water at 0° C. and concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 31% B to 48% B in 10 min; Wave Length: 254/220 nm) to afford the title compound (AGV-1) (29.3 mg, 56 μmol, 35%, 98% Purity) as a white solid. m/z 514.4/516.4 (M+H)$^+$ (ES+). $^1$H NMR (400 MHz, DMSO-d6) δ 8.43 (s, 1H), 8.03-7.96 (m, 1H), 7.84-7.73 (m, 2H), 7.72-7.63 (m, 4H), 7.59 (d, J=7.8 Hz, 1H), 7.37 (t, J=8.0 Hz, 1H), 6.92-6.82 (m, 1H), 4.89 (d, J=14.0 Hz, 3H), 3.87 (s, 2H), 3.10 (s, 3H), 2.53 (s, 2H), 2.06-1.95 (m, 2H), 1.95-1.81 (m, 2H), 1.70-1.53 (m, 1H), 1.45-1.31 (m, 1H).

Example 226: Synthesis of 2-{4-[4-Chloro-2-(4-methyl-1,2,4-triazol-3-yl)phenyl]-6-cyclopropylpyridin-2-yl}-6-({[(1-hydroxycyclobutyl)methyl]amino}methyl)-3H-isoindol-1-one (AGW-6)

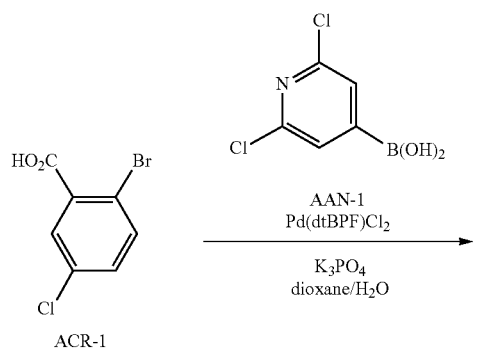

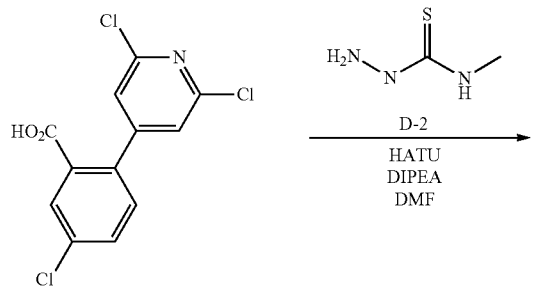

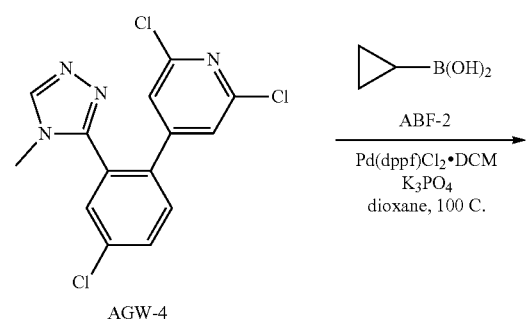

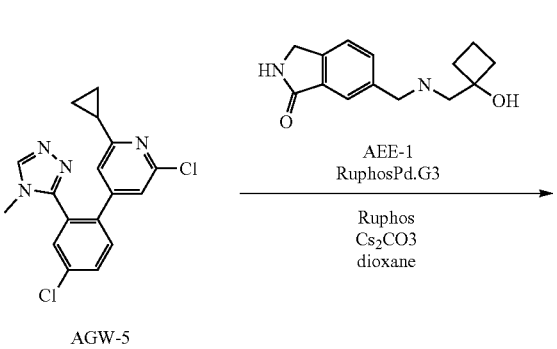

-continued

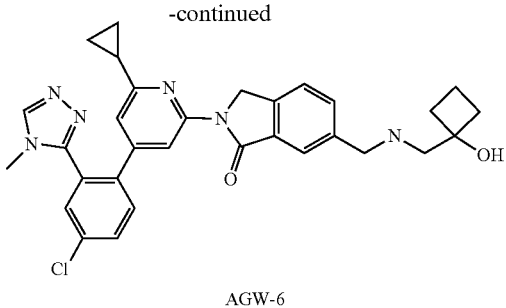

AGW-6

Step 1: Synthesis of 5-Chloro-2-(2,6-dichloropyridin-4-yl)benzoic acid (AGW-1)

Into a 250-mL round-bottom flask purged and maintained with an inert atmosphere of nitrogen, was placed 2-bromo-5-chlorobenzoic acid (ACR-1) (5.00 g, 1 eq, 21.2 mmol), 2,6-dichloropyridin-4-ylboronic acid (AAN-1) (4.07 g, 1 eq, 21.2 mmol) and $K_3PO_4$ (13.5 g, 3 eq, 63.7 mmol) in 1,4-dioxane (50 mL) and water (10 mL), then $Pd(DtBPF)Cl_2$ (1.38 g, 0.1 eq, 2.12 mmol) was added at rt under nitrogen atmosphere. The resulting solution was stirred overnight at 60° C. under nitrogen atmosphere. The mixture was cooled to rt, diluted with water and extracted with EtOAc (3×300 mL). The combined organic layers were washed with brine (2×300 mL), dried ($Na_2SO_4$). After filtration, the filtrate was concentrated in vacuo. The crude product was purified by reverse flash column chromatography with the following conditions: Column, C18; mobile phase, Water (0.1% $NH_4HCO_3$) and MeCN (10% MeCN up to 70% in 20 min); Detector, UV 254/220 nm. The product-containing fractions were combined and concentrated in vacuo. This resulted in of the sub-title compound (AGW-1) (1.8 g, 5.32 mmol, 28%, 89% Purity) as a brown solid. m/z 301.9/303.9 $(M+H)^+$ (ES+).

Step 2: Synthesis of 2-(5-Chloro-2-(2,6-dichloropyridin-4-yl)benzoyl)-N-methylhydrazine-1-carbothioamide (AGW-2)

Into a 100-mL round-bottom flask purged and maintained with an inert atmosphere of nitrogen, was placed the product from step 1 above (AGW-1) (1.80 g, 1 eq, 5.95 mmol) and DIPEA (2.31 g, 3 eq, 17.9 mmol) in DMF (40 mL) at rt, then 4-methyl-3-thiosemicarbazide (D-2) (630 mg, 1 eq, 5.95 mmol) and HATU (4.73 g, 2.5 eq, 14.9 mmol) were added at rt. The resulting solution was stirred for 6 h at rt. The resulting mixture was diluted with water and extracted with EtOAc (3×100 mL). The combined organic layers were washed with brine (2×100 mL), dried ($Na_2SO_4$). After filtration, the filtrate was concentrated in vacuo. The crude product was purified by reverse flash column chromatography with the following conditions: Column, C18; mobile phase, water (0.1% $NH_4HCO_3$) and MeCN (60% MeCN up to 85% in 10 min); Detector, UV 254/220 nm. The product-containing fractions were combined and concentrated in vacuo. This resulted in the sub-title compound (AGW-2) (720 mg, 1.70 mmol, 30%, 92% Purity) as a brown yellow solid. m/z 389.0/391.0 $(M+H)^+$ (ES+).

Step 3: Synthesis of 5-(5-Chloro-2-(2,6-dichloropyridin-4-yl)phenyl)-4-methyl-4H-1,2,4-triazole-3-thiol (AGW-3)

Into a 50-mL round-bottom flask, was placed the product from step 2 above (AGW-2) (650 mg, 1 eq, 1.67 mmol) in aq. NaOH (20 mL, 1 M). The resulting solution was stirred for 4 h at rt. The resulting solution was concentrated in vacuo. The crude product used directly in next step without any further purification. This resulted in the sub-title compound (AGW-3) (620 mg, 1.37 mmol, crude, 82% Purity) as brown yellow solid. m/z 371.0/373.0 $(M+H)^+$ (ES+).

Step 4: Synthesis of 2,6-Dichloro-4-(4-chloro-2-(4-methyl-4H-1,2,4-triazol-3-yl)phenyl)pyridine (AGW-4)

Into a 50-mL round-bottom flask purged and maintained with an inert atmosphere of nitrogen, was placed the product from step 3 above (AGW-3) (600 mg, 1 eq, 1.61 mmol) in DCM (20 mL) at rt. Then AcOH (194 mg, 2 eq, 3.23 mmol) and $H_2O_2$ (912 mg, 30% Wt, 5 eq, 8.05 mmol) was added at rt. The resulting solution was stirred for 4 h at rt. The resulting mixture was diluted with water and extracted with DCM (3×80 mL). The combined organic layers were washed with brine (2×80 mL), dried ($Na_2SO_4$). After filtration, the filtrate was concentrated in vacuo. This resulted in the sub-title compound (AGW-4) (500 mg, 1.18 mmol, crude, 80%) as a brown yellow solid. m/z 339.0/341.0 $(M+H)^+$ (ES+).

Step 5: Synthesis of 2-Chloro-4-[4-chloro-2-(4-methyl-1,2,4-triazol-3-yl)phenyl]-6-cyclopropylpyridine (AGW-5)

To a stirred solution of the product from step 4 above (AGW-4) (200 mg, 1 eq, 0.58 mmol), cyclopropylboronic acid (ABF-2) (75.8 mg, 1.5 eq, 0.88 mmol) and $K_3PO_4$ (250 mg, 2 eq, 1.17 mmol) in 1,4-dioxane (5 mL) was added $Pd(dppf)Cl_2 \cdot DCM$ (43 mg, 0.05 mmol, 0.1 eq) at rt under nitrogen atmosphere. The resulting mixture was stirred for overnight at 100° C. under nitrogen atmosphere. The mixture was cooled to rt and diluted with water and extracted with EtOAc (3×50 mL). The combined organic layers were washed with brine (2×50 mL), dried ($Na_2SO_4$). After filtration, the filtrate was concentrated in vacuo. The crude product was purified by reverse flash column chromatography with the following conditions: Column, C18; mobile phase, water (0.1% FA) and MeCN (20% MeCN up to 70% in 10 min); Detector, UV 254/220 nm. The product-containing fractions were combined and concentrated in vacuo. This resulted in the sub-title compound (AGW-5) (110 mg, 0.29 mmol, 54%, 90% Purity) as a white solid. m/z 345.1/347.1 $(M+H)^+$ (ES+).

Step 6: Synthesis of 2-{4-[4-Chloro-2-(4-methyl-1,2,4-triazol-3-yl)phenyl]-6-cyclopropylpyridin-2-yl}-6-({[(1-hydroxycyclobutyl)methyl]amino}methyl)-3H-isoindol-1-one (AGW-6)

To a stirred solution of the product from step 5 above (AGW-5) (80 mg, 1 eq, 0.23 mmol), intermediate (AEE-1) (57 mg, 1 eq, 0.23 mmol) and $Cs_2CO_3$ (151 mg, 2 eq, 0.46 mmol) in 1,4-dioxane (5 mL) were added RuPhos palladacycle Gen.3 (39 mg, 0.2 eq, 0.04 mmol) and RuPhos (43 mg, 0.4 eq, 0.09 mmol) at rt under nitrogen atmosphere. The resulting mixture was stirred for 2 h at 100° C. under nitrogen atmosphere. The mixture was cooled to rt, diluted with water and extracted with EtOAc (3×30 mL). The combined organic layers were washed with brine (2×30 mL), dried ($Na_2SO_4$). After filtration, the filtrate was concentrated in vacuo. The crude product was purified by reverse flash column chromatography with the following conditions: Column, C18; mobile phase, water (0.10% NH₄HCO₃) and MeCN (20% MeCN up to 60% in 10 min); Detector, UV 254/220 nm. The product-containing fractions were combined and concentrated in vacuo. The crude product was purified by Prep-HPLC with the following conditions: Column: XBridge Prep OBD C18 Column, 30×150, 5 μm; Mobile Phase A: water (0.1% NH₄HCO₃) Mobile Phase B: MeCN; Flow rate: 60 mL/min; Gradient: 43 B to 49 B in 8 min; Detector, UV 254/210 nm; RT: 7.70. The product-containing fractions were combined and evaporated partially in vacuo and lyophilized overnight to afford the title compound (AGW-6) (5.3 mg, 9.2 μmol, 4.1%, 97% Purity) as a white solid. m/z 555.3/557.3 (M+H)⁺ (ES+). ¹H NMR (400 MHz, MeOH-d4) δ 8.47 (s, 1H), 8.05 (d, J=1.4 Hz, 1H), 7.85-7.77 (m, 2H), 7.77-7.66 (m, 3H), 7.65-7.59 (m, 1H), 6.85 (d, J=1.5 Hz, 1H), 5.03 (s, 2H), 3.94 (s, 2H), 3.46 (s, 3H), 2.71 (s, 2H), 2.15-2.05 (m, 2H), 1.99-2.00 (m, 3H), 1.75-1.72 (m, 1H), 1.54-1.47 (m, 1H), 1.05-0.91 (m, 4H).

Example 227: Synthesis of 2-[6-(Ethylamino)-4-[4-(4-methyl-1,2,4-triazol-3-yl)-1-(2-methylpropyl)pyrazol-3-yl]pyridin-2-yl]-4-(trifluoromethyl)-3H-isoindol-1-one (AGX-8)

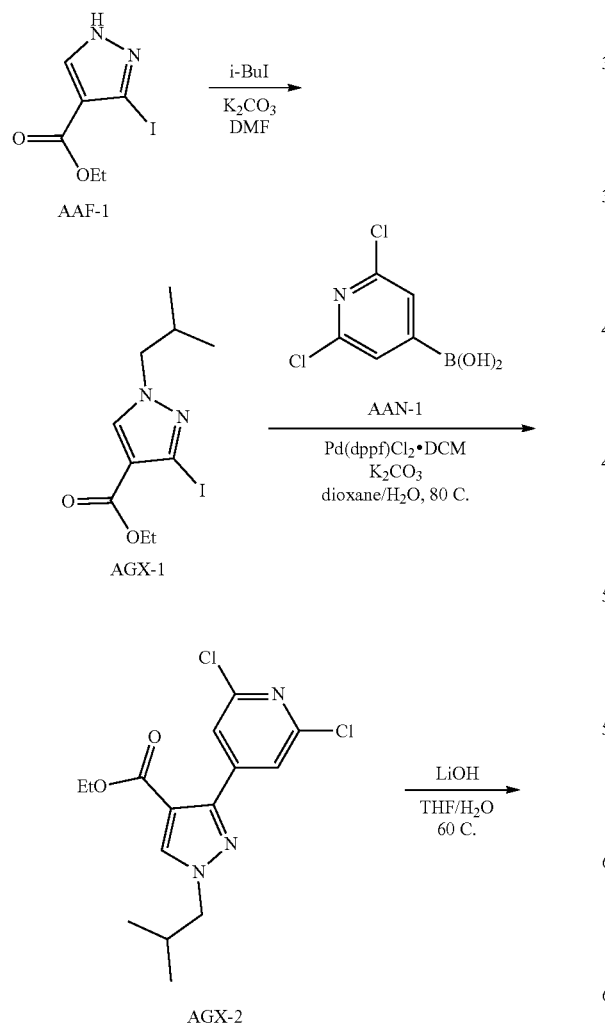

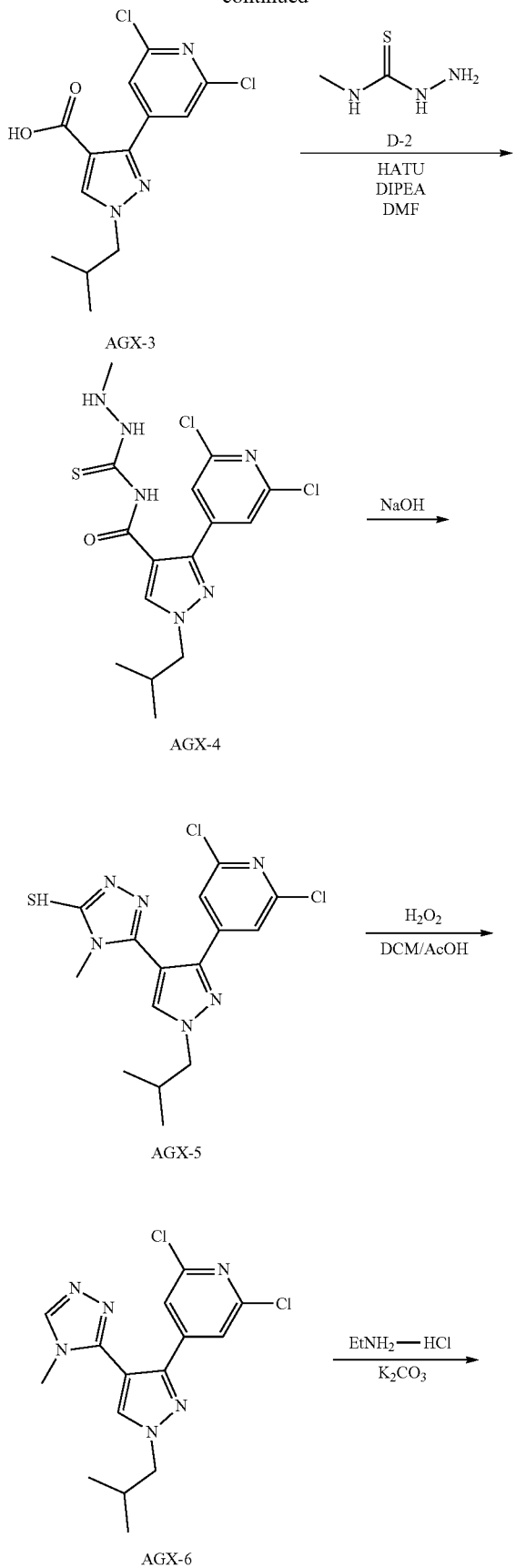

-continued

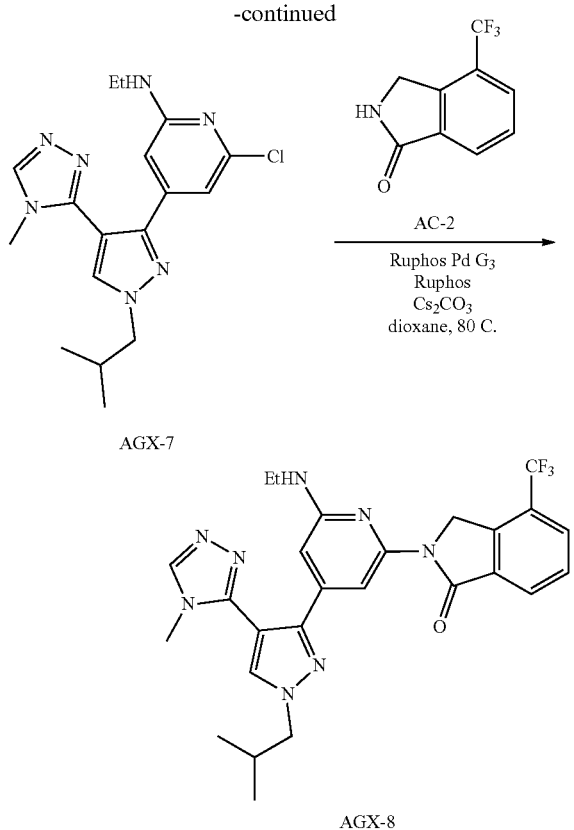

Step 1: Synthesis of Ethyl 3-iodo-1-(2-methylpropyl)pyrazole-4-carboxylate (AGX-1)

To a stirred mixture of ethyl 3-iodo-1H-pyrazole-4-carboxylate (AAF-1) (2.66 g, 1 eq, 10.0 mmol) in DMF (50 mL) was added 1-iodo-2-methylpropane (2.76 g, 1.5 eq, 15.0 mmol) and $K_2CO_3$ (4.15 g, 3 eq, 30.0 mmol) at rt under nitrogen atmosphere. The resulting mixture was stirred for overnight at rt under nitrogen atmosphere. The crude product was purified by reverse flash column chromatography with the following conditions: Column, C18; mobile phase, water (0.1% $NH_4HCO_3$) and MeCN (20% MeCN up to 80% in 20 min); Detector, UV 254/220 nm. This resulted in the sub-title compound (AGX-1) (1.5 g, 4.19 mmol, 47%, 90% Purity) as a white solid. m/z 323.0 (M+H)+ (ES+).

Step 2: Synthesis of Ethyl 3-(2,6-dichloropyridin-4-yl)-1-(2-methylpropyl)pyrazole-4-carboxylate (AGX-2)

To a stirred mixture of the product from step 1 above (AGX-1) (640 mg, 1 eq, 1.99 mmol), 2,6-dichloropyridin-4-ylboronic acid (AAN-1) (381 mg, 1 eq, 1.99 mmol) and $K_2CO_3$ (824 mg, 3 eq, 5.96 mmol) in 1,4-dioxane (25 mL) and $H_2O$ (5 mL) was added Pd(DtBPF)Cl$_2$ (129 mg, 0.1 eq, 0.20 mmol) at rt under nitrogen atmosphere. The resulting mixture was stirred for overnight at 60° C. under nitrogen atmosphere. The mixture was allowed to cool down to rt. The resulting mixture was concentrated in vacuo. The crude product was purified by reverse flash column chromatography with the following conditions: Column, C18; mobile phase, water (0.1% $NH_4HCO_3$) and MeCN (10% MeCN up to 50% in 10 min); Detector, UV 254/220 nm. This resulted in the sub-title compound (AGX-2) (540 mg, 1.46 mmol, 79%, 92% Purity) as a white solid. m/z 342.1/344.1 (M+H)+ (ES+).

Step 3: Synthesis of 3-(2,6-Dichloropyridin-4-yl)-1-isobutyl-1H-pyrazole-4-carboxylic acid (AGX-3)

To a stirred mixture of the product from step 2 above (AGX-2) (530 mg, 1 eq, 1.55 mmol) in THF (8 mL) and $H_2O$ (2 mL) were added LiOH (185 mg, 5 eq, 7.75 mmol) at rt. The resulting mixture was stirred for overnight at 60° C. The mixture was allowed to cool down to rt. The resulting mixture was concentrated in vacuo. The resulting mixture was diluted with water and extracted with EtOAc (3×80 mL). The combined organic layers were washed with brine (2×80 mL), dried ($Na_2SO_4$). After filtration, the filtrate was concentrated in vacuo. This resulted in the sub-title compound (AGX-3) (470 mg, 1.34 mmol, 96%, 89% Purity) as a white solid. m/z 314.0/316.0 (M+H)+ (ES+).

Step 4: Synthesis of 2-(3-(2,6-Dichloropyridin-4-yl)-1-isobutyl-1H-pyrazole-4-carbonyl)-N-methylhydrazine-1-carbothioamide (AGX-4)

To a stirred mixture of the product from step 3 above (AGX-3) (460 mg, 1 eq, 1.46 mmol) and 1-amino-3-methylthiourea (D-2) (185 mg, 1.2 eq, 1.76 mmol) in THF (5 mL) were added HATU (557 mg, 1 eq, 1.46 mmol) and DIPEA (568 mg, 3 eq, 4.39 mmol) at 0° C. The resulting mixture was stirred for overnight at rt under air atmosphere. The resulting mixture was concentrated in vacuo. The crude product used directly in next step without any further purification. m/z 401.1/403.1 (M+H)+ (ES+).

Step 5: Synthesis of 5-(3-(2,6-Dichloropyridin-4-yl)-1-isobutyl-1H-pyrazol-4-yl)-4-methyl-4H-1,2,4-triazole-3-thiol (AGX-5)

To the reaction mixture from the product from step 4 above (AGX-4) was added aq. NaOH (12.5 mL, 1 M) dropwise at 0° C. The resulting mixture was stirred for overnight at rt. The resulting mixture was concentrated in vacuo. The crude product was purified by reverse flash column chromatography with the following conditions: Column, C18; mobile phase, water (0.1% $NH_4HCO_3$) and MeCN (10% MeCN up to 48% in 20 min); Detector, UV 254/220 nm. The product-containing fractions were combined and concentrated in vacuo. This resulted in the sub-title compound (AGX-5) (400 mg, 0.97 mmol, 70%, 93% Purity) as a white solid. m/z 383.1/385.1 (M+H)+ (ES+).

Step 6: Synthesis of 2,6-Dichloro-4-[4-(4-methyl-1,2,4-triazol-3-yl)-1-(2-methylpropyl)pyrazol-3-yl]pyridine (AGX-6)

To a stirred mixture of the product from step 5 above (AGX-5) (400 mg, 1 eq, 1.04 mmol) in DCM (5 mL) were added AcOH (125 mg, 2 eq, 2.09 mmol) and $H_2O_2$ (177 mg, 30% Wt, 5 eq, 5.22 mmol) at 0° C. The resulting mixture was stirred for 1 h at rt. The resulting mixture was concentrated in vacuo. The crude product was purified by reverse flash column chromatography with the following conditions: Column, C18; mobile phase, water (0.1% $NH_4HCO_3$) and MeCN (20% MeCN up to 60% in 20 min); Detector, UV 254/220 nm. This resulted in the sub-title compound (AGX- 6) (360 mg, 0.97 mmol, 98%, 94% Purity) as a white solid. m/z 351.1/353.1 (M+H)⁺ (ES+).

Step 7: Synthesis of 6-Chloro-N-ethyl-4-[4-(4-methyl-1,2,4-triazol-3-yl)-1-(2-methylpropyl)pyrazol-3-yl]pyridin-2-amine (AGX-7)

To a stirred mixture of the product from step 6 above (AGX-6) (100 mg, 1 eq, 0.29 mmol) and ethylamine (128 mg, 10 eq, 2.85 mmol) in NMP (2 mL) was added K₂CO₃ (393 mg, 10 eq, 2.85 mmol) at rt under nitrogen atmosphere. The resulting mixture was stirred for overnight at 120° C. under nitrogen atmosphere. The mixture was allowed to cool down to rt. The crude product was purified by reverse flash column chromatography with the following conditions: Column, C18; mobile phase, water (0.1% NH₄HCO₃) and MeCN (10% MeCN up to 50% in 20 min); Detector, UV 254/220 nm. This resulted in the sub-title compound (AGX-7) (90 mg, 0.23 mmol, 88%, 90% Purity) as a white solid. m/z 360.2/362.2 (M+H)⁺ (ES+).

Step 8: Synthesis of 2-[6-(Ethylamino)-4-[4-(4-methyl-1,2,4-triazol-3-yl)-1-(2-methylpropyl)pyrazol-3-yl]pyridin-2-yl]-4-(trifluoromethyl)-3H-isoindol-1-one (AGX-8)

To a stirred mixture of the product from step 7 above (AGX-7) (40 mg, 1 eq, 0.11 mmol), intermediate (AC-2) (22 mg, 1 eq, 0.11 mmol) and Cs₂CO₃ (72 mg, 2 eq, 0.22 mmol) in 1,4-dioxane (2 mL) were added RuPhos (21 mg, 0.4 eq, 44 μmol) and RuPhos palladacycle Gen.3 (19 mg, 0.2 eq, 22 μmol) at rt under nitrogen atmosphere. The resulting mixture was stirred for overnight at 80° C. under nitrogen atmosphere. The mixture was allowed to cool down to rt. The resulting mixture was concentrated in vacuo. The crude product was purified by Prep-HPLC with the following conditions: Column: SunFire Prep C18 OBD Column, 19×150 mm, 5 μm; Mobile Phase A: water (0.1% NH₄HCO₃+0.1% NH₃·H₂O), Mobile Phase B: MeCN; Flow rate: 60 mL/min; Gradient: 30 B to 60 B in 7 min; Detector, UV 254/210 nm; RT: 6.08. This resulted in the title compound (AGX-8) (11.9 mg, 22 μmol, 20%, 99% Purity) as a white solid. m/z 525.2 (M+H)⁺ (ES+). ¹H NMR (400 MHz, MeOH-d4) δ 8.59 (s, 1H), 8.06 (d, J=7.6 Hz, 2H), 7.98-7.91 (m, 1H), 7.78-7.69 (m, 1H), 7.61 (d, J=1.2 Hz, 1H), 6.41 (d, J=1.2 Hz, 1H), 5.23 (d, J=1.7 Hz, 2H), 4.11 (d, J=7.3 Hz, 2H), 3.50 (s, 3H), 3.37-3.27 (m, 2H), 2.40-2.25 (m, 1H), 1.23 (t, J=7.2 Hz, 3H), 1.00 (d, J=6.7 Hz, 6H).

Example 228: Synthesis of tert-Butyl N-[(2-{4-[4-cyano-2-(4-methyl-1,2,4-triazol-3-yl)phenyl]-6-cyclopropylpyridin-2-yl}-3-oxo-7-(trifluoromethyl)-1H-isoindol-5-yl)methyl]-N-methylcarbamate (AGY-3)

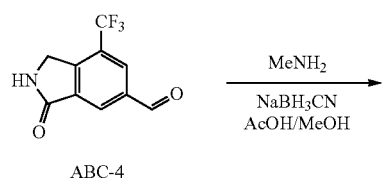

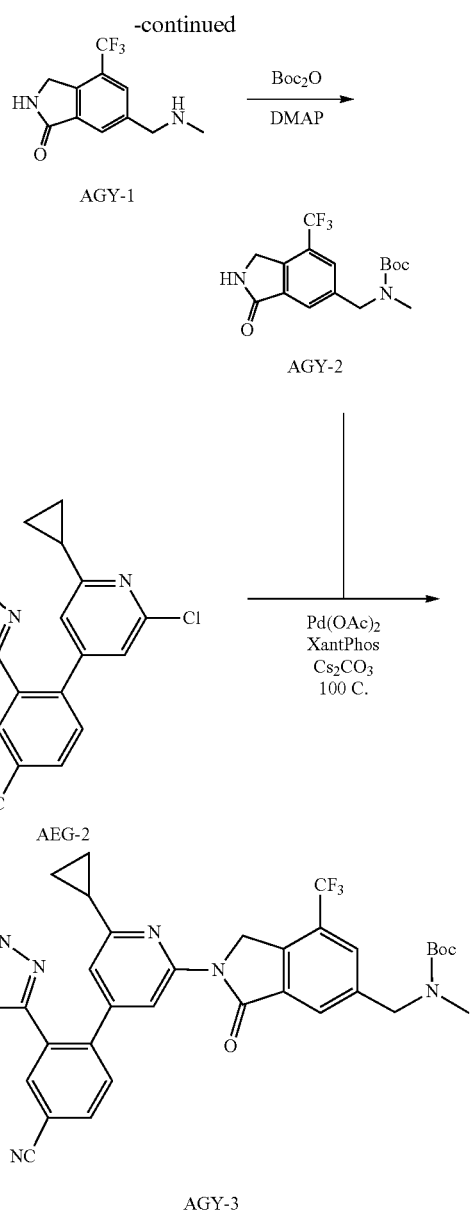

Step 1: Synthesis of 6-[(Methylamino)methyl]-4-(trifluoromethyl)-2,3-dihydroisoindol-1-one (AGY-1)

Into a 20 mL sealed tube were added intermediate (ABC-4) (200 mg, 1 eq, 0.87 mmol), methylamine (136 mg, 5 eq, 4.37 mmol) and AcOH (524 mg, 10 eq, 8.73 mmol) in MeOH (5 mL) at rt. To the above mixture was added NaBH₃CN (274 mg, 5 eq, 4.37 mmol) over 2 days at rt. The resulting mixture was stirred for overnight at rt. The resulting mixture was filtered; the filter cake was washed with MeOH (3 mL). The filtrate was concentrated in vacuo. The crude product was purified by reverse flash column chromatography with the following conditions: Column, C18; mobile phase, water (0.1% NH₄HCO₃) and MeCN (30% MeCN up to 60% in 15 min); Detector, UV 254/220 nm. The product-containing fractions were combined and concentrated in vacuo. This resulted in the sub-title compound (AGY-1) (112 mg, 0.42 mmol, 53%, 92% Purity) as a yellow oil. m/z 245.1 (M+H)+ (ES+).

Step 2: Synthesis of tert-Butyl N-methyl-N-{[3-oxo-7-(trifluoromethyl)-1,2-dihydroisoindol-5-yl]methyl}carbamate (AGY-2)

Into an 8 mL sealed tube were added the product from step 1 above (AGY-1) (80 mg, 1 eq, 0.33 mmol) and Boc₂O (143 mg, 2 eq, 0.66 mmol) in methyl (2 mL) at rt. To the above mixture was added DMAP (4 mg, 0.1 eq, 33 µmol) over 3 min at rt. The resulting mixture was stirred for 3 h at rt. The resulting mixture was concentrated in vacuo. The crude product was purified by reverse flash column chromatography with the following conditions: Column, C18; mobile phase, water (0.1% NH₄HCO₃) and MeCN (36% MeCN up to 48% in 10 min); Detector, UV 254/220 nm. The product-containing fractions were combined and concentrated in vacuo. This resulted in the sub-title compound (AGY-2) (68 mg, 0.19 mmol, 60%, 95% Purity) as a yellow oil. m/z 345.1 (M+H)+ (ES+).

Step 3: Synthesis of tert-Butyl N-[(2-{4-[4-cyano-2-(4-methyl-1,2,4-triazol-3-yl)phenyl]-6-cyclopropyl-pyridin-2-yl}-3-oxo-7-(trifluoromethyl)-1H-isoindol-5-yl)methyl]-N-methylcarbamate (AGY-3)

Into a 8 mL sealed tube were added the product from step 2 above (AGY-2) (50 mg, 1 eq, 0.15 mmol), intermediate (AEG-2) (54 mg, 0.16 mmol, 1.1 eq) and Cs₂CO₃ (95 mg, 2 eq, 0.29 mmol) in 1,4-dioxane (1 mL) at rt. To the above mixture was added Pd(OAc)₂ (3.3 mg, 0.1 eq, 14 µmol) XantPhos (17 mg, 0.2 eq, 29 µmol) over 3 min at rt under nitrogen atmosphere. The resulting mixture was stirred for additional 2 h at 100° C. under nitrogen atmosphere. The mixture was cooled to rt and concentrated in vacuo. The crude product was purified by Prep-HPLC with the following conditions: Column: SunFire Prep C18 OBD Column, 19×150 mm, 5 µm; Mobile Phase A: water (0.1% NH₄HCO₃+0.1% NH₃·H₂O), Mobile Phase B: MeCN; Flow rate: 60 mL/min; Gradient: 30 B to 60 B in 7 min; Detector, UV 254/210 nm; RT: 6.08 to afford the title compound (AGY-3) (4.8 mg, 7.2 µmol, 5.1%, 97% Purity) as a white solid. m/z 644.2 (M+H)+ (ES+). ¹H NMR (400 MHz, MeOH-d4) δ 8.49 (s, 1H), 8.18-8.01 (m, 3H), 7.99-7.90 (m, 2H), 7.85 (s, 1H), 6.95 (d, J=1.4 Hz, 1H), 5.19 (s, 2H), 4.59 (d, J=15.8 Hz, 2H), 3.49 (s, 3H), 2.92 (s, 3H), 2.12-2.02 (m 1H), 1.48 (d, J=17.9 Hz, 9H), 1.08-0.96 (m, 4H).

Example 229: Synthesis of 4-(2-Cyclopropyl-6-{6-[(methylamino)methyl]-1-oxo-4-(trifluoromethyl)-3H-isoindol-2-yl}pyridin-4-yl)-3-(4-methyl-1,2,4-triazol-3-yl)benzonitrile (AGZ-1)

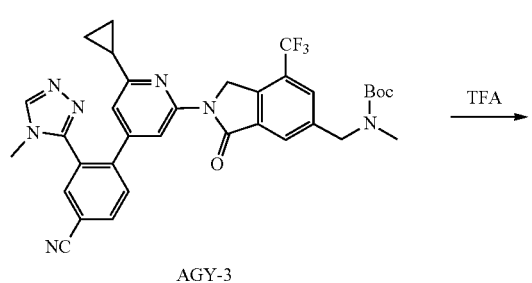

AGY-3

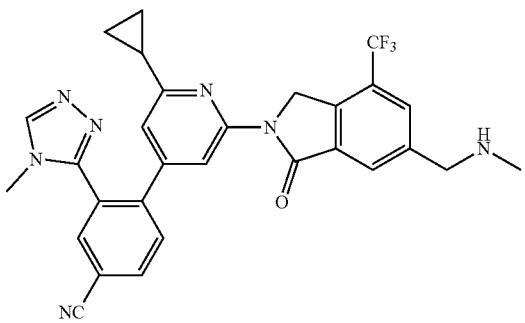

AGZ-1

Into a 8 mL sealed tube were added compound (AGY-3) (30 mg, 1 eq, 47 µmol) in DCM (1 mL) at rt. To the above mixture was added TFA (53 mg, 10 eq, 0.47 mmol) dropwise over 1 min at rt. The resulting mixture was stirred for additional 2 h at rt. The mixture was concentrated in vacuo. The crude product was purified by Prep-HPLC with the following conditions: Column: SunFire Prep C18 OBD Column, 19×150 mm, 5 µm; Mobile Phase A: water (0.1% NH₄HCO₃+0.1% NH₃·H₂O), Mobile Phase B: MeCN; Flow rate: 60 mL/min; Gradient: 30 B to 60 B in 7 min; Detector, UV 254/210 nm; RT: 6.08 to afford the title compound (AGZ-1) (9.7 mg, 17 µmol, 38%, 97% Purity) as a white solid. m/z 544.2 (M+H)+ (ES+). ¹H NMR (400 MHz, MeOH-d4) δ 8.48 (s, 1H), 8.18-7.98 (m, 5H), 7.92 (d, J=8.1 Hz, 1H), 6.95 (d, J=1.5 Hz, 1H), 5.19 (s, 2H), 4.01 (s, 2H), 3.48 (s, 3H), 2.49 (s, 3H), 2.13-2.02 (m, 1H), 1.09-0.96 (m, 4H).

Example 230: Synthesis of 2-(4'-Fluoro-2'-(4-methyl-4H-1,2,4-triazol-3-yl)-[1,1'-biphenyl]-3-yl)-6-((((1-hydroxycyclobutyl)methyl)amino)methyl)isoindolin-1-one (AHA-2)

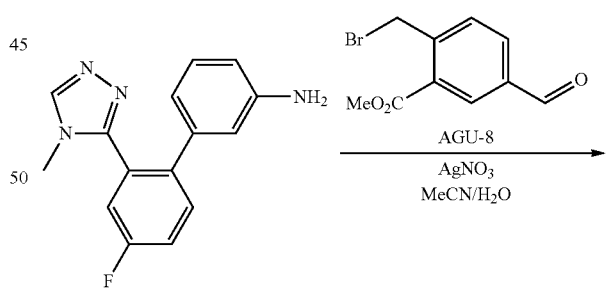

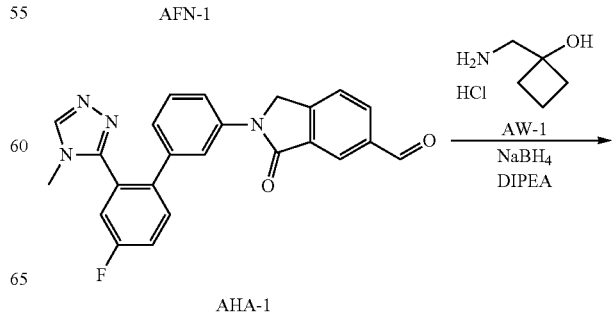

AHA-1

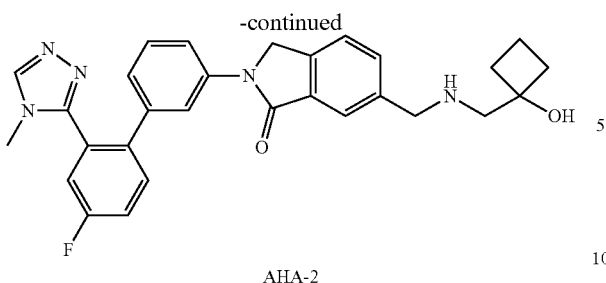

AHA-2

Step 1: Synthesis of 2-(4'-Fluoro-2'-(4-methyl-4H-1,2,4-triazol-3-yl)-[1,1'-biphenyl]-3-yl)-3-oxoisoindoline-5-carbaldehyde (AHA-1)

A solution of intermediate (AFN-1) (300 mg, 1 eq, 1.12 mmol) and intermediate (AGU-8) (431 mg, 1.5 eq, 1.68 mmol) in MeCN (6 mL) and H₂O (3 mL) was treated with AgNO₃ (285 mg, 1.5 eq, 1.68 mmol) at rt overnight. The precipitated solids were collected by filtration and washed with MeCN (2×5 mL). The crude product was purified by reverse flash column chromatography with the following conditions: Column, C18; mobile phase, water (0.1% NH₄HCO₃) and MeCN (20% MeCN up to 60% in 20 min); Detector, UV 254/220 nm. This resulted in the sub-title compound (AHA-1) (120 mg, 0.27 mmol, 26%, 92% Purity) as a yellow solid. m/z 413.1 (M+H)⁺ (ES+).

Step 2: 2-(4'-Fluoro-2'-(4-methyl-4H-1,2,4-triazol-3-yl)-[1,1'-biphenyl]-3-yl)-6-((((1-hydroxycyclobutyl)methyl)amino)methyl)isoindolin-1-one (AHA-2)

To a stirred mixture of the product from step 1 above (AHA-1) (50 mg, 1 eq, 0.12 mmol) and 1-(aminomethyl)cyclobutan-1-ol, HCl (15 mg, 1.2 eq, 0.15 mmol) in MeOH (5 mL) were added DIPEA (31 mg, 2 eq, 0.24 mmol) at 60° C. for 1 h. To the above mixture was added NaBH₄ (9 mg, 2 eq, 0.24 mmol) over 0.5 min at rt. The resulting mixture was stirred for 1 h at rt. The reaction was quenched with aq. sat. of NH₄Cl (1 mL) at 0° C. The resulting mixture was concentrated in vacuo. The crude product was purified by Prep-HPLC with the following conditions (Column: Sunfire prep C18 column, 30*150 mm, 5 μm; Mobile Phase A: water (0.1% FA), Mobile Phase B: MeCN; Flow rate: 60 mL/min; Gradient: 5% B to 30% B in 7 min; Wave Length: 254/220 nm; RT: 6.4) to afford the title compound (AHA-2) (18.8 mg, 37 μmol, 31%, 98% Purity) as an off-white solid. m/z 498.4 (M+H)⁺ (ES+). ¹H NMR (300 MHz, DMSO-d6) δ 8.43 (s, 1H), 8.22 (s, 1H), 8.01-7.91 (m, 1H), 7.78 (s, 1H), 7.73-7.54 (m, 4H), 7.49 (m, 1H), 7.39-7.30 (t, J=8.0 Hz, 1H), 6.90-6.81 (m, 1H), 4.88 (s, 2H), 3.91 (s, 2H), 3.12 (s, 3H), 2.57 (s, 2H), 2.11-1.80 (m, 4H), 1.71-1.56 (m, 1H), 1.49-1.29 (m, 1H).

Example 231: Synthesis of 2-(4'-Fluoro-2'-(4-methyl-4H-1,2,4-triazol-3-yl)-[1,1'-biphenyl]-3-yl)-6-((((1-hydroxycyclopentyl)methyl)amino)methyl)isoindolin-1-one (AHB-1)

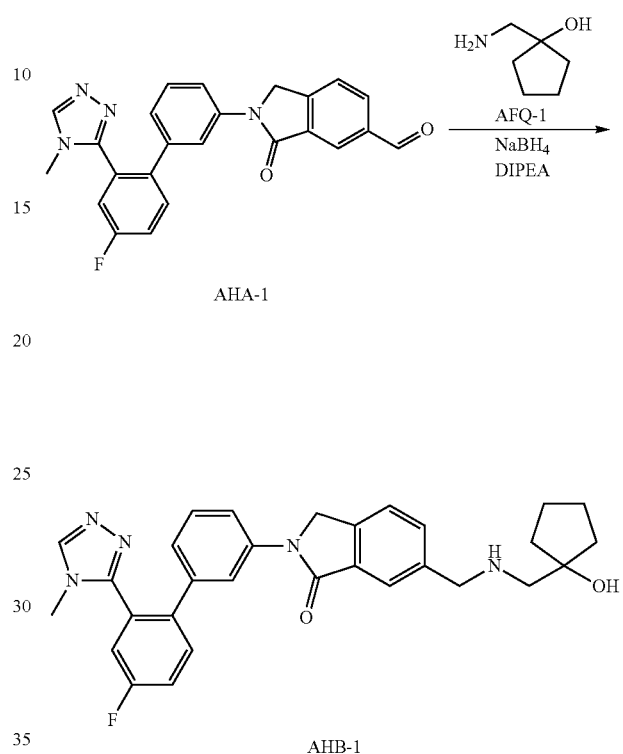

AHA-1

AHB-1

To a stirred mixture of intermediate (AHA-1) (50 mg, 1 eq, 0.12 mmol) and 1-(aminomethyl)cyclopentan-1-ol (AFQ-1) (14 mg, 1 eq, 0.12 mmol) in MeOH (3 mL) were added DIPEA (47 mg, 3 eq, 0.36 mmol) dropwise at 60° C. for 1 h. To the above mixture was added NaBH₄ (14 mg, 3 eq, 0.36 mmol) over 0.5 min at rt. The resulting mixture was stirred for 1 h at rt. The reaction was quenched with aq. sat. of NH₄Cl (1 mL) at 0° C. The mixture was concentrated in vacuo. The crude product was purified by Prep-HPLC with the following conditions (Column: Sunfire prep C18 column, 30*150 mm, 5 μm; Mobile Phase A: water (0.1% FA), Mobile Phase B: MeCN; Flow rate: 60 mL/min; Gradient: 8% B to 23% B in 10 min; Wave Length: 254/220 nm; RT: 10.5) to afford the title compound (AHB-1) (17.8 mg, 33 μmol, 26%, 95% Purity) as an off-white solid. m/z 512.5 (M+H)⁺ (ES+). ¹H NMR (300 MHz, DMSO-d6) δ 8.43 (s, 1H), 8.20-8.16 (d, J=3.0 Hz, 1H), 8.00-7.93 (m, 1H), 7.80 (s, 1H), 7.74-7.54 (m, 5H), 7.52-7.43 (m, 1H), 7.37 (t, J=8.0 Hz, 1H), 6.91-6.84 (m, 1H), 4.88 (s, 2H), 3.93 (s, 2H), 3.12 (s, 3H), 2.57 (d, J=2.2 Hz, 2H), 1.75-1.62 (m, 2H), 1.58-1.44 (m, 6H).

Example 232: Synthesis of 4-{2-cyclopropyl-6-[6-({[(1R,2S)-2-hydroxycyclopentyl] amino}methyl)-1-oxo-3H-isoindol-2-yl]pyridin-4-yl}-3-(4-methyl-1,2,4-triazol-3-yl)benzonitrile (AHC-1)

Example 233: Synthesis of 2-[6-(Ethylamino)-4-[4-(4-methyl-1,2,4-triazol-3-yl)-1-propylpyrazol-3-yl]pyridin-2-yl]-4-(trifluoromethyl)-3H-isoindol-1-one (AHD-9)

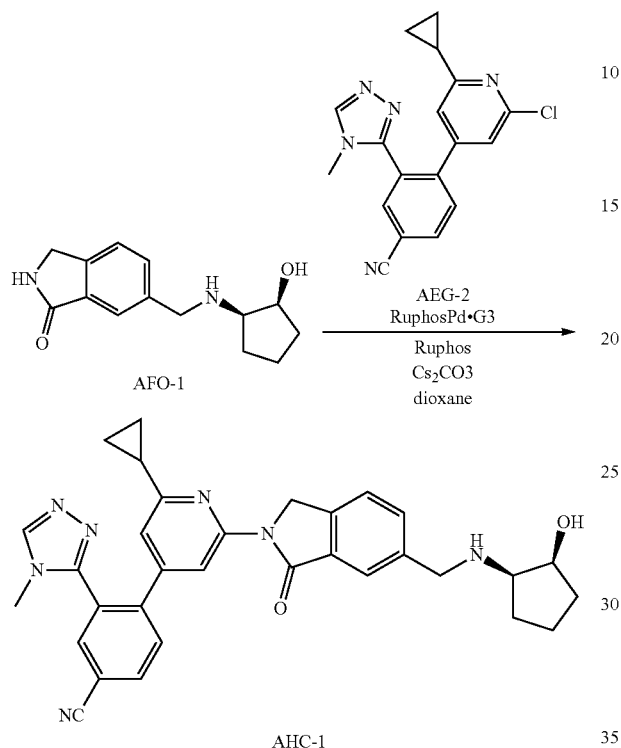

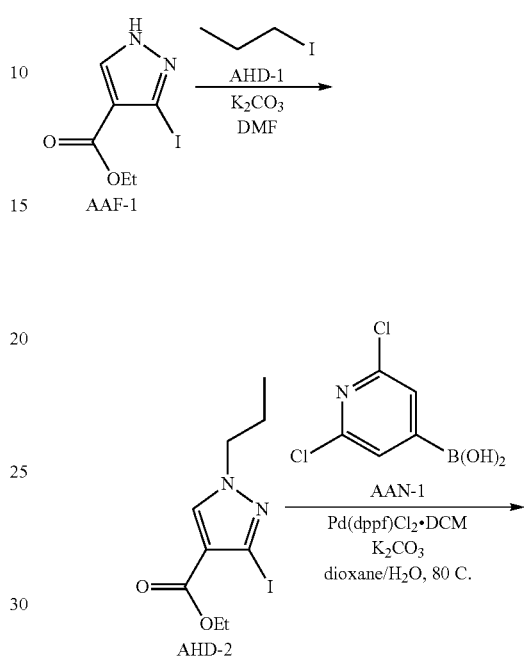

To a stirred solution of intermediate (AFO-1) (70 mg, 1 eq, 0.28 mmol), intermediate (AEG-2) (115 mg, 1.2 eq, 0.34 mmol) and Cs$_2$CO$_3$ (185 mg, 2 eq, 0.57 mmol) in 1,4-dioxane (5 mL) were added RuPhos (53 mg, 0.4 eq, 0.11 mmol) and RuPhos palladacycle Gen.3 (48 mg, 0.2 eq, 57 μmol) at rt under nitrogen atmosphere. The resulting mixture was stirred for 1 h at 100° C. under nitrogen atmosphere. The mixture was allowed to cool down to rt. The resulting mixture was concentrated in vacuo. The residue was purified by Prep-TLC with DCM/MeOH (20/1). The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 40% B to 60% B in 8 min; Wave Length: 254/220 nm; RT: 7.8) to afford the title compound (AHC-1) (18.2 mg, 33 μmol, 12%, 99% Purity) as a white solid. m/z 546.3 (M+H)$^+$ (ES+). $^1$H NMR (400 MHz, DMSO-d6) δ 8.54 (s, 1H), 8.24-8.19 (m, 2H), 7.98 (d, J=1.4 Hz, 1H), 7.90-7.74 (m, 2H), 7.69-7.61 (m, 2H), 6.89 (d, J=1.4 Hz, 1H), 5.00 (s, 2H), 4.39 (s, 1H), 3.96-3.76 (m, 3H), 3.48 (s, 3H), 2.80-2.72 (m, 1H), 2.09-1.99 (m, 1H), 1.70-1.50 (m, 4H), 1.44-1.33 (m, 2H), 1.01-0.92 (m, 4H).

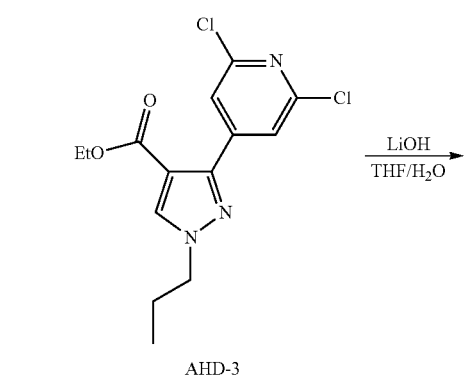

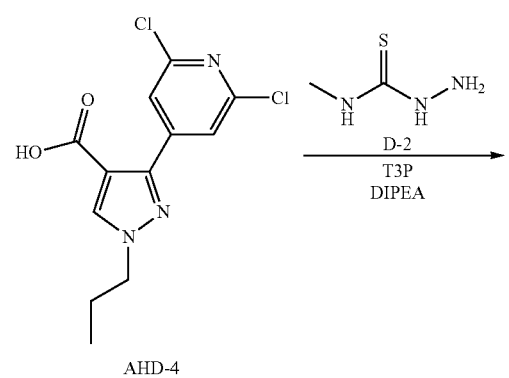

-continued

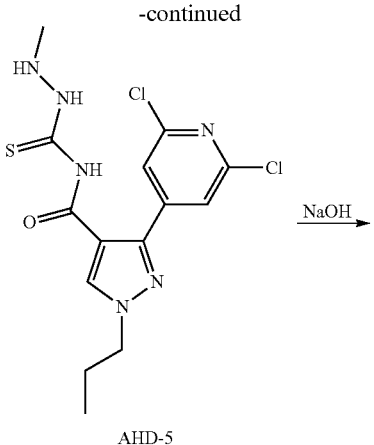

AHD-5

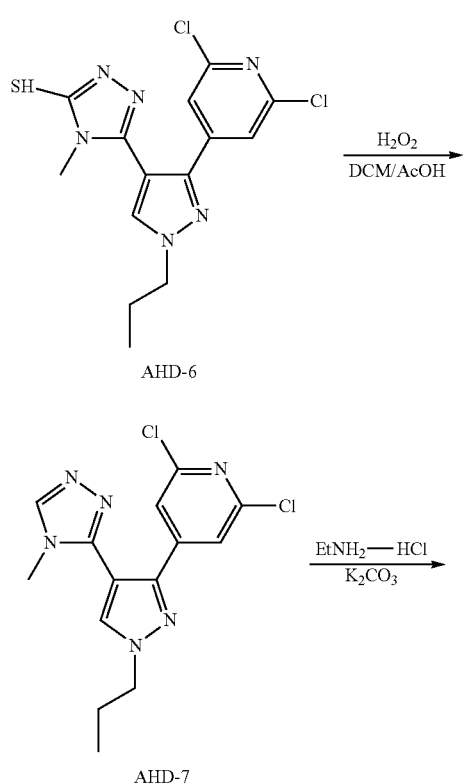

AHD-6

AHD-7

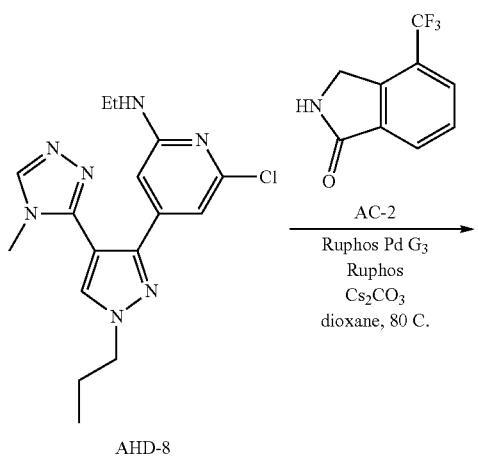

AHD-8

-continued

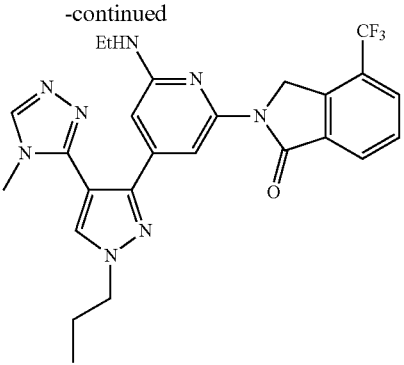

AHD-9

Step 1: Synthesis of Ethyl 3-iodo-1-propyl-1H-pyrazole-4-carboxylate (AHD-2)

Into a 500-mL round-bottom flask, to a stirred mixture of ethyl 3-iodo-1H-pyrazole-4-carboxylate (AAF-1) (2.60 g, 1 eq, 9.77 mmol) and iodopropane (AHD-1) (2.49 g, 1.5 eq, 14.6 mmol) in DMF (20 mL) was added $K_2CO_3$ (4.05 g, 3 eq, 29.3 mmol) at rt. The resulting mixture was stirred for overnight at rt. The mixture was acidified to pH 4 with HCl (aq., 1 M). The resulting mixture was diluted with water and extracted with EtOAc (3×300 mL). The combined organic layers were washed with brine (2×300 mL), dried ($Na_2SO_4$). After filtration, the filtrate was concentrated in vacuo. The crude product was purified by reverse flash column chromatography with the following conditions: Column, C18; mobile phase, Water (0.1% $NH_4HCO_3$) and MeCN (10% MeCN up to 80% in 20 min); Detector, UV 254/220 nm. The product-containing fractions were combined and concentrated in vacuo. This resulted in the sub-title compound (AHD-2) (1.3 g, 3.80 mmol, 43%, 90% Purity) as a colorless oil. m/z 309.0 $(M+H)^+$ (ES+).

Step 2: Synthesis of Ethyl 3-(2,6-dichloropyridin-4-yl)-1-propyl-1H-pyrazole-4-carboxylate (AHD-3)

To a stirred mixture of the product from step 1 above (AHD-2) (600 mg, 1 eq, 1.95 mmol) and 2,6-dichloropyridin-4-ylboronic acid (AAN-1) (373 mg, 1 eq, 1.95 mmol) in 1,4-dioxane (5 mL) and water (1 mL) was added $K_2CO_3$ (807 mg, 3 eq, 5.84 mmol) at rt under nitrogen atmosphere. To the above mixture was added $Pd(DtBPF)Cl_2$ (127 mg, 0.1 eq, 0.20 mmol) at rt under nitrogen atmosphere. The resulting mixture was stirred for overnight at 60° C. under nitrogen atmosphere. The mixture was cooled to rt and concentrated in vacuo. The crude product was purified by reverse flash column chromatography with the following conditions: Column, C18; mobile phase, water (0.1% $NH_4HCO_3$) and MeCN (10% MeCN up to 60% in 15 min); Detector, UV 254/220 nm to afford the sub-title compound (AHD-3) (400 mg, 1.09 mmol, 63%, 89% Purity) as a white solid. m/z 328.1/330.1 $(M+H)^+$ (ES+).

Step 3: Synthesis of 3-(2,6-Dichloropyridin-4-yl)-1-propyl-1H-pyrazole-4-carboxylic acid (AHD-4)

To a stirred mixture of the product from step 2 above (AHD-3) (400 mg, 1 eq, 1.22 mmol) and LiOH (88 mg, 3 eq, 3.65 mmol) in THF (16 mL) was added water (4 mL) at rt.

The resulting mixture was stirred for 2 h at 60° C. The mixture was acidified to pH 4 with HCl (aq., 1 M). The resulting mixture was diluted with water and extracted with EtOAc (3×80 mL). The combined organic layers were washed with brine (2×80 mL), dried (Na$_2$SO$_4$). After filtration, the filtrate was concentrated in vacuo. This resulted in the sub-title compound (AHD-4) (340 mg, 0.91 mmol, 93%, 80% Purity) as a white solid. m/z 300.0/302.0 (M+H)$^+$ (ES+).

Step 4: Synthesis of 2-(3-(2,6-Dichloropyridin-4-yl)-1-propyl-1H-pyrazole-4-carbonyl)-N-methylhydrazine-1-carbothioamide (AHD-5)

To a stirred mixture of the product from step 3 above (AHD-4) (294 mg, 1 eq, 0.98 mmol) in THF (20 mL) was added T$_3$P in EtOAc (1.25 g, 50% Wt, 4 eq, 3.92 mmol) dropwise at 0° C. To the above mixture was added DIPEA (380 mg, 3 eq, 2.94 mmol) and 1-amino-3-methylthiourea (D-2) (124 mg, 1.2 eq, 1.18 mmol) at 0° C. The resulting mixture was stirred for 2 h at rt. The crude product was purified by reverse flash column chromatography with the following conditions: Column, C18; mobile phase, water (0.1% NH$_4$HCO$_3$) and MeCN (0% MeCN up to 50% in 30 min); Detector, UV 254/220 nm to afford the sub-title compound (AHD-5) (300 mg, 0.72 mmol, 79%, 92% Purity) as a yellow solid. m/z 387.0/389.0 (M+H)$^+$ (ES+).

Step 5: Synthesis of 5-(3-(2,6-Dichloropyridin-4-yl)-1-propyl-1H-pyrazol-4-yl)-4-methyl-4H-1,2,4-triazole-3-thiol (AHD-6)

Into a 50 mL vial were added the product from step 4 above (AHD-5) (300 mg, 1 eq, 0.78 mmol) in aq. NaOH (20 mL) at rt. The resulting mixture was stirred for 2 h at 60° C. The mixture was acidified to pH 4 with HCl (aq., 1 M). The resulting mixture was diluted with water and extracted with EtOAc (3×50 mL). The combined organic layers were washed with brine (2×50 mL), dried (Na$_2$SO$_4$). After filtration, the filtrate was concentrated in vacuo. This resulted in the sub-title compound (AHD-6) (300 mg, 0.61 mmol, crude, 75% Purity) as a yellow solid. m/z 369.0/371.0 (M+H)$^+$ (ES+).

Step 6: Synthesis of 2,6-Dichloro-4-(4-(4-methyl-4H-1,2,4-triazol-3-yl)-1-propyl-1H-pyrazol-3-yl)pyridine (AHD-7)

To a stirred solution of the product from step 5 above (AHD-6) (760 mg, 1 eq, 2.06 mmol) and H$_2$O$_2$ (350 mg, 30% Wt, 5 eq, 10.3 mmol) in DCM (20 mL) was added AcOH (247 mg, 2 eq, 4.12 mmol) at 0° C. The resulting mixture was stirred for 2 h at rt. The resulting mixture was concentrated in vacuo. The crude product was purified by reverse flash column chromatography with the following conditions: Column, C18; mobile phase, water (0.1% NH$_4$HCO$_3$) and MeCN (0% MeCN up to 40% in 15 min); Detector, UV 254/220 nm to afford the sub-title compound (AHD-7) (560 mg, 1.50 mmol, 81%, 90% Purity) as a yellow solid. m/z 337.1/339.1 (M+H)$^+$ (ES+).

Step 7: Synthesis of 6-Chloro-N-ethyl-4-(4-(4-methyl-4H-1,2,4-triazol-3-yl)-1-propyl-1H-pyrazol-3-yl)pyridin-2-amine (AHD-8)

To a stirred solution the product from step 6 above (AHD-7) (150 mg, 1 eq, 0.30 mmol) and ethanamine, HCl (242 mg, 10 eq, 2.97 mmol) in NMP (3 mL) was added K$_2$CO$_3$ (410 mg, 10 eq, 2.97 mmol) at rt under nitrogen atmosphere. The resulting mixture was stirred for overnight at 120° C. under nitrogen atmosphere. The mixture was cooled to rt. The crude product was purified by reverse flash column chromatography with the following conditions: Column, C18; mobile phase, Water (0.1% NH$_4$HCO$_3$) and MeCN (0% MeCN up to 38% in 20 min); Detector, UV 254/220 nm to afford the sub-title compound (AHD-8) (110 mg, 0.29 mmol, 80%, 92% Purity) as a colorless solid. m/z 346.1/348.1 (M+H)$^+$ (ES+).

Step 8: Synthesis of 2-(6-(Ethylamino)-4-(4-(4-methyl-4H-1,2,4-triazol-3-yl)-1-propyl-1H-pyrazol-3-yl)pyridin-2-yl)-4-(trifluoromethyl)isoindolin-1-one (AHD-9)

To a stirred solution of the product from step 7 above (AHD-8) (50 mg, 1 eq, 0.15 mmol) and intermediate (AC-2) (29 mg, 1 eq, 0.15 mmol) in 1,4-dioxane (5 mL) was added Cs$_2$CO$_3$ (94 mg, 2 eq, 0.29 mmol) at rt under nitrogen atmosphere. To the above mixture was added RuPhos (27 mg, 0.4 eq, 58 μmol) and RuPhos palladacycle Gen.3 (24 mg, 0.2 eq, 29 μmol) at rt under nitrogen atmosphere. The resulting mixture was stirred for overnight at 100° C. under nitrogen atmosphere. The mixture was cooled to rt, diluted with water and extracted with EtOAc (3×10 mL). The combined organic layers were washed with brine (2×10 mL), dried (Na$_2$SO$_4$). After filtration, the filtrate was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 38% B to 60% B in 9 min; Wave Length: 254/220 nm; RT: 8.88) to afford the title compound (AHD-9) (13.8 mg, 27 μmol, 19%, 99% Purity) as a white solid. m/z 511.2 (M+H)$^+$ (ES+). $^1$H NMR (400 MHz, MeOH-d4) δ 8.59 (s, 1H), 8.09-8.03 (m, 2H), 7.98-7.91 (m, 1H), 7.78-7.69 (m, 1H), 7.61 (d, J=1.2 Hz, 1H), 6.41 (d, J=1.2 Hz, 1H), 5.25-5.21 (m, 2H), 4.27 (t, J=7.0 Hz, 2H), 3.49 (s, 3H), 3.34 (d, J=7.2 Hz, 2H), 2.07-1.94 (m, 2H), 1.23 (t, J=7.2 Hz, 3H), 1.00 (t, J=7.4 Hz, 3H).

Example 234: Synthesis of 4-{2-Ethoxy-6-[6-(hydroxymethyl)-1-oxo-4-(trifluoromethyl)-3H-isoindol-2-yl]pyridin-4-yl}-3-(4-methyl-1,2,4-triazol-3-yl)benzonitrile (AHE-4)

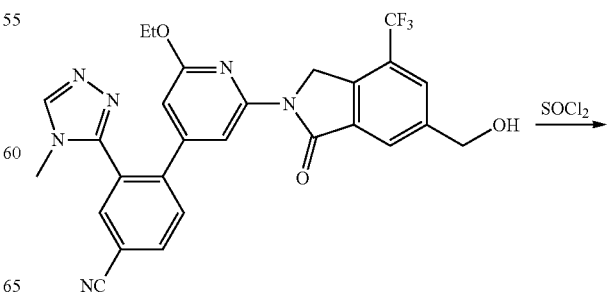

AEW-2

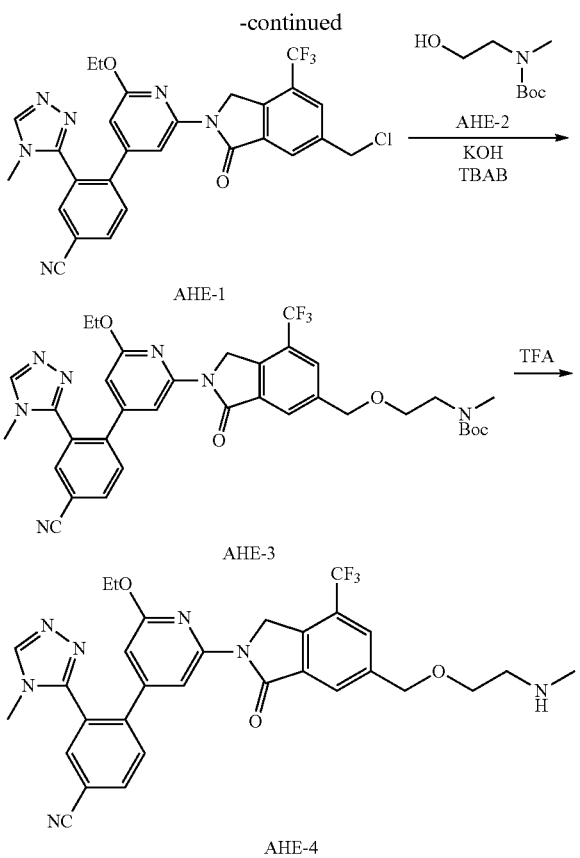

Step 1: Synthesis of 4-{2-[6-(Chloromethyl)-1-oxo-4-(trifluoromethyl)-3H-isoindol-2-yl]-6-ethoxypyridin-4-yl}-3-(4-methyl-1,2,4-triazol-3-yl) benzonitrile (AHE-1)

To a stirred solution of intermediate (AEW-2) (80 mg, 1 eq, 0.15 mmol) in DCM (10 mL) was added SOCl$_2$ (0.4 mL, 22.5 eq, 3.36 mmol) dropwise at 0° C. The resulting mixture was stirred for 1 h at rt. The reaction was quenched with MeOH (1 mL) at 0° C. The resulting mixture was concentrated in vacuo. The residue was purified by Prep-TLC with DCM/MeOH (15/1) to afford the sub-title compound (AHE-1) (61.5 mg, 0.11 mmol, 67%, 95% Purity) as a yellow solid. m/z 553.1/555.1 (M+H)$^+$ (ES+).

Step 2: Synthesis of tert-Butyl N-{2-[(2-{4-[4-cyano-2-(4-methyl-1,2,4-triazol-3-yl)phenyl]-6-ethoxypyridin-2-yl}-3-oxo-7-(trifluoromethyl)-1H-isoindol-5-yl)methoxy]ethyl}-N-methylcarbamate (AHE-3)

To a stirred solution of the product from step 1 above (AHE-1) (60 mg, 1 eq, 54 μmol) and tert-butyl N-(2-hydroxyethyl)-N-methylcarbamate (AHE-2) (190 mg, 10 eq, 0.54 mmol) in DCM (2 mL) was added TBAB (18 mg, 0.5 eq, 27 μmol) and aq. KOH (2 mL, 20% Wt) at rt. The resulting mixture was stirred slowly for 1 h at rt. The resulting mixture was diluted with water and extracted with EtOAc (3×20 mL). The combined organic layers were washed with brine (2×20 mL), dried (Na$_2$SO$_4$). After filtration, the filtrate was concentrated in vacuo. The residue was purified by Prep-TLC with DCM/MeOH (10/1) to afford the sub-title compound (AHE-3) (40 mg, 52 μmol, 96%, 90% Purity) as a yellow solid. m/z 692.2 (M+H)$^+$ (ES+).

Step 3: Synthesis of 4-{2-Ethoxy-6-[6-(hydroxymethyl)-1-oxo-4-(trifluoromethyl)-3H-isoindol-2-yl]pyridin-4-yl}-3-(4-methyl-1,2,4-triazol-3-yl) benzonitrile (AHE-4)

To a stirred solution of the product from step 2 above (AHE-3) (30 mg, 1 eq, 43 μmol) in DCM (9 mL) was added TFA (3 mL) at rt. The resulting mixture was stirred for 1 h at rt. The resulting mixture was concentrated in vacuo. The crude product was purified by Prep-HPLC with the following conditions (Column: Sunfire prep C18 column, 30*150 mm, 5 μm; Mobile Phase A: water (0.05% TFA), Mobile Phase B: MeCN; Flow rate: 60 mL/min; Gradient: 10% B to 20% B in 7 min; Wave Length: 254/220 nm; RT: 5.2) to afford the title compound (AHE-4) (8.3 mg, 14 μmol, 35%, 98% Purity) as a yellow solid. m/z 592.2 (M+H)$^+$ (ES+). $^1$H NMR (400 MHz, DMSO-d6) δ 8.53 (s, 1H), 8.24-8.15 (m, 2H), 8.03 (d, J=16.4 Hz, 2H), 7.89-7.83 (m, 1H), 7.81 (d, J=1.2 Hz, 1H), 6.43 (d, J=1.2 Hz, 1H), 5.22 (s, 2H), 4.70 (s, 2H), 4.33 (q, J=7.0 Hz, 2H), 3.59 (t, J=5.5 Hz, 2H), 3.48 (s, 3H), 2.76 (t, J=5.5 Hz, 2H), 2.34 (s, 3H), 1.36 (t, J=7.0 Hz, 3H).

Example 235: Synthesis of 4-(2-Cyclopropyl-6-{6-[(2-hydroxyethoxy)methyl]-1-oxo-4-(trifluoromethyl)-3H-isoindol-2-yl}pyridin-4-yl)-3-(4-methyl-1,2,4-triazol-3-yl)benzonitrile (AHF-4)

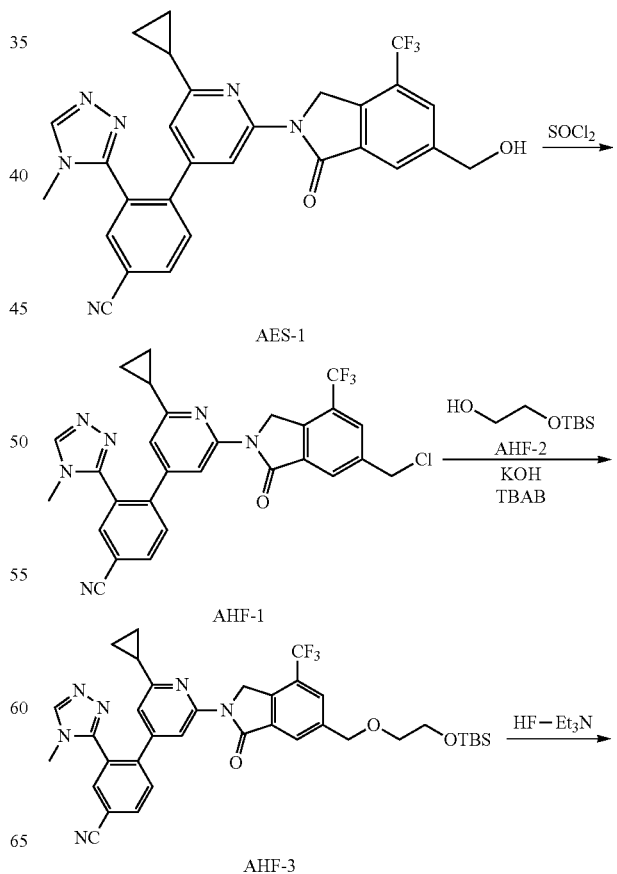

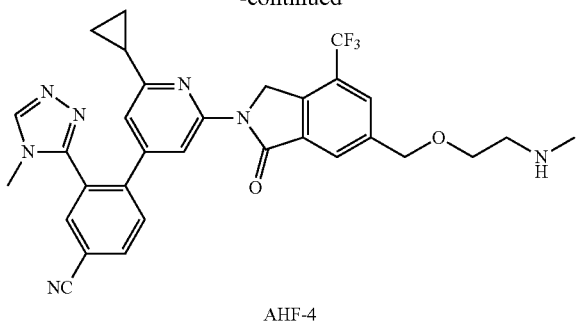

AHF-4

Step 1: Synthesis of 4-{2-[6-(Chloromethyl)-1-oxo-4-(trifluoromethyl)-3H-isoindol-2-yl]-6-cyclopropylpyridin-4-yl}-3-(4-methyl-1,2,4-triazol-3-yl)benzonitrile (AHF-1)

To a stirred solution of intermediate (AES-1) (60 mg, 1 eq, 0.11 mmol) in DCM (10 mL) was added $SOCl_2$ (0.4 mL, 29.7 eq, 3.36 mmol) dropwise at 0° C. The resulting mixture was stirred for 1 h at rt. The reaction was quenched by the addition of MeOH (4 mL) at 0° C. The resulting mixture was concentrated in vacuo. The residue was purified by Prep-TLC with DCM/MeOH (20/1) to afford the sub-title compound (AHF-1) (46 mg, 76 μmol, 67%, 91% Purity) as a yellow solid. m/z 549.1/551.1 (M+H)+ (ES+).

Step 2: Synthesis of 4-[2-(6-{2-[(tert-Butyldimethylsilyl)oxy]ethoxy}-1-oxo-4-(trifluoromethyl)-3H-isoindol-2-yl)-6-cyclopropylpyridin-4-yl]-3-(4-methyl-1,2,4-triazol-3-yl)benzonitrile (AHF-3)

To a stirred solution of the product from step 1 above (AHF-1) (40 mg, 1 eq, 36 μmol) and 2-[(tert-butyldimethylsilyl)oxy]ethanol (AHF-2) (128 mg, 10 eq, 0.36 mmol) in DCM (2 mL) was added TBAB (12 mg, 0.5 eq, 18 μmol) and aq. KOH (2 mL, 20% Wt) at rt. The resulting mixture was stirred slowly for 1 h at rt. The resulting mixture was diluted with water and extracted with EtOAc (3×20 mL). The combined organic layers were washed with brine (2×20 mL), dried ($Na_2SO_4$). After filtration, the filtrate was concentrated in vacuo. The residue was purified by Prep-TLC with DCM/MeOH (15/1) to afford the sub-title compound (AHF-3) (11 mg, 15 μmol, 40%, 96% Purity) as a yellow solid. m/z 689.3 (M+H)+ (ES+).

Step 3: Synthesis of 4-(2-Cyclopropyl-6-{6-[(2-hydroxyethoxy) methyl]-1-oxo-4-(trifluoromethyl)-3H-isoindol-2-yl} pyridin-4-yl)-3-(4-methyl-1,2,4-triazol-3-yl) benzonitrile (AHF-4)

To a stirred solution of the product from step 2 above (AHF-3) (10 mg, 1 eq, 15 μmol) in THF (7 mL) was added TEA.3HF (0.5 mL) dropwise at rt. The resulting mixture was stirred for 5 h at rt. The resulting mixture was concentrated in vacuo. The crude product was purified by Prep-HPLC with the following conditions (Column: Sunfire prep C18 column, 30*150 mm, 5 μm; Mobile Phase A: water (0.1% FA), Mobile Phase B: MeCN; Flow rate: 60 mL/min; Gradient: 35% B to 60% B in 7 min; Wave Length: 254/220 nm; RT: 6.8) to afford the title compound (AHF-4) (0.9 mg, 1.5 μmol, 11%, 98% Purity) as a white solid. m/z 575.0 (M+H)+ (ES+). 1H NMR (400 MHz, MeOH-d4) δ 8.49 (s, 1H), 8.14-7.90 (m, 6H), 6.95 (s, 1H), 5.16 (s, 2H), 4.74 (s, 2H), 3.76 (t, J=4.7 Hz, 2H), 3.66 (t, J=4.8 Hz, 2H), 3.49 (s, 3H), 2.09-2.02 (m, 1H), 1.31 (s, 2H), 1.01 (d, J=6.4 Hz, 2H).

Example 236: Synthesis of 2-{6-Cyclopropyl-4-[4-fluoro-2-(4-methyl-1,2,4-triazol-3-yl)phenyl]pyridin-2-yl}-6-{[(2-hydroxy-2-methylpropyl) amino] methyl}-3H-isoindol-1-one (AHG-2)

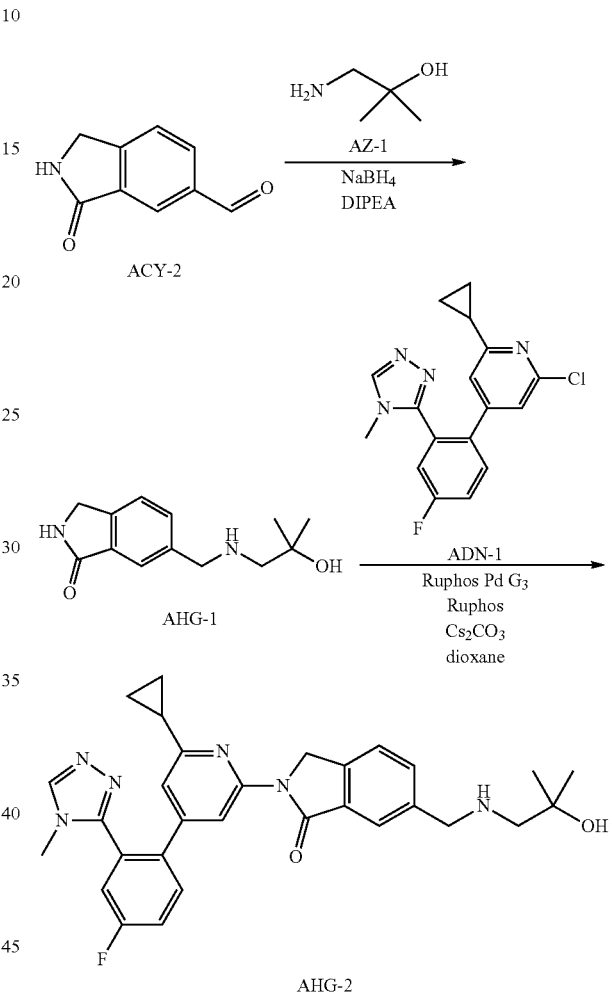

Step 1: Synthesis of 6-{[(2-Hydroxy-2-methylpropyl)amino]methyl}-2,3-dihydroisoindol-1-one (AHG-1)

To a stirred mixture of intermediate (ACY-2) (130 mg, 1 eq 0.81, mmol) and 1-amino-2-methylpropan-2-ol (AZ-1) (144 mg, 2 eq, 1.61 mmol) in MeOH (13 mL) was added DIPEA (209 mg, 2 eq, 1.61 mmol) at rt under nitrogen atmosphere. To the above mixture was added $NaBH_4$ (61 mg, 2 eq, 1.61 mmol) over 2 h at 60° C. The resulting mixture was stirred for 2 h at rt. The reaction was then quenched by the addition of 5 mL of ice water at 0° C. The resulting mixture was diluted with water and extracted with EtOAc (3×50 mL). The combined organic layers were washed with brine (2×50 mL), dried ($Na_2SO_4$). After filtration, the filtrate was concentrated in vacuo to afford the sub-title compound (AHG-1) (120 mg, 0.37 mmol, crude, 73% Purity) as a yellow solid. m/z 235.1 (M+H)+ (ES+).

Step 2: Synthesis of 2-{6-Cyclopropyl-4-[4-fluoro-2-(4-methyl-1,2,4-triazol-3-yl)phenyl]pyridin-2-yl}-6-{[(2-hydroxy-2-methylpropyl)amino]methyl}-3H-isoindol-1-one (AHG-2)

To a stirred mixture of the product from step 1 above (AHG-1) (60 mg, 1 eq, 0.26 mmol), intermediate (ADN-1) (84 mg, 1 eq, 0.26 mmol) and $Cs_2CO_3$ (167 mg, 2 eq, 0.51 mmol) in 1,4-dioxane (6 mL) were added RuPhos palladacycle Gen.3 (43 mg, 0.2 eq, 51 μmol) and RuPhos (48 mg, 0.4 eq, 102 μmol) at rt under nitrogen atmosphere. The resulting mixture was stirred for 2 h at 80° C. under nitrogen atmosphere. The mixture was cooled to rt, diluted with water and extracted with EtOAc (3×20 mL). The combined organic layers were washed with brine (2×20 mL), dried ($Na_2SO_4$). After filtration, the filtrate was concentrated in vacuo. The crude product was purified by Prep-HPLC with the following conditions (Column: Sunfire prep C18 column, 30*150 mm, 5 μm; Mobile Phase A: water (0.1% FA), Mobile Phase B: MeCN; Flow rate: 60 mL/min; Gradient: 13% B to 28% B in 10 min; Wave Length: 254/220 nm; RT: 9.7) to afford the title compound (AHG-2) (19.8 mg, 37 μmol, 15%, 99% Purity) as a white solid. m/z 527.3 $(M+H)^+$ (ES+). $^1$H NMR (400 MHz, MeOH-d4) δ 8.46 (s, 1H), 8.03 (d, J=1.4 Hz, 1H), 7.85 (d, J=1.4 Hz, 1H), 7.82-7.74 (m, 1H), 7.74-7.67 (m, 1H), 7.64 (d, J=7.8 Hz, 1H), 7.58-7.49 (m, 1H), 7.49-7.43 (m, 1H), 6.86 (d, J=1.4 Hz, 1H), 5.04 (s, 2H), 3.99 (s, 2H), 3.46 (s, 3H), 2.61 (s, 2H), 2.06-1.95 (m, 1H), 1.22 (s, 6H), 1.06-0.92 (m, 4H).

Example 237: Synthesis of 6-{[(Cyclopentylmethyl)amino]methyl}-2-{6-cyclopropyl-4-[4-fluoro-2-(4-methyl-1,2,4-triazol-3-yl)phenyl]pyridin-2-yl}-3H-isoindol-1-one (AHH-3)

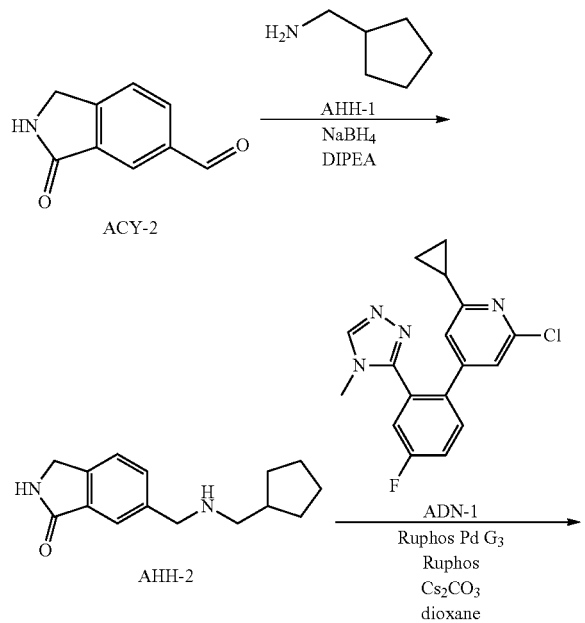

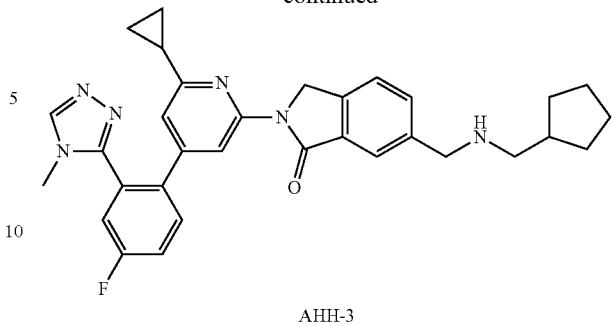

AHH-3

Step 1: Synthesis of 6-{[(Cyclopentylmethyl)amino]methyl}-2,3-dihydroisoindol-1-one (AHH-2)

To a stirred mixture of intermediate (ACY-2) (120 mg, 1 eq, 0.75 mmol), 1-cyclopentylmethanamine (AHH-1) (111 mg, 1.5 eq, 1.12 mmol) and AcOH (22 mg, 0.5 eq, 0.37 mmol) in MeOH (24 mL) was added DIPEA (115 mg, 1.2 eq, 0.89 mmol) at rt under nitrogen atmosphere. To the above mixture was added NaBH4 (56 mg, 2 eq, 1.49 mmol) over 2 h at 60° C. The resulting mixture was stirred for additional 2 h at rt. The resulting mixture was diluted with water and extracted with EtOAc (3×50 mL). The combined organic layers were washed with brine (2×50 mL), dried ($Na_2SO_4$). After filtration, the filtrate was concentrated in vacuo to afford the sub-title compound (AHH-2) (100 mg, 0.37 mmol, 55%, 90% Purity) as a yellow solid. m/z 245.2 $(M+H)^+$ (ES+).

Step 2: Synthesis of 6-{[(Cyclopentylmethyl)amino]methyl}-2-{6-cyclopropyl-4-[4-fluoro-2-(4-methyl-1,2,4-triazol-3-yl)phenyl]pyridin-2-yl}-3H-isoindol-1-one (AHH-3)

To a stirred mixture of the product from step 1 above (AHH-2) (50 mg, 1 eq, 0.21 mmol), intermediate (ADN-1) (67 mg, 1 eq, 0.21 mmol) and $Cs_2CO_3$ (31 mg, 2 eq, 0.41 mmol) in 1,4-dioxane (6 mL) were added RuPhos palladacycle Gen.3 (34 mg, 0.2 eq, 41 μmol) and RuPhos (38 mg, 0.4 eq, 82 μmol) at rt under nitrogen atmosphere. The resulting mixture was stirred for 2 h at 100° C. under nitrogen atmosphere. The mixture was cooled to rt, diluted with water and extracted with EtOAc (3×20 mL). The combined organic layers were washed with brine (2×20 mL), dried ($Na_2SO_4$). After filtration, the filtrate was concentrated in vacuo. The crude product was purified by Prep-HPLC with the following conditions (Column: Sunfire prep C18 column, 30*150 mm, 5 μm; Mobile Phase A: water (0.05% FA), Mobile Phase B: MeCN; Flow rate: 60 mL/min; Gradient: 15% B to 31% B in 10 min; Wave Length: 254/220 nm; RT: 10.4) to afford the title compound (AHH-3) (21.1 mg, 37 μmol, 18%, 95% Purity) as a white solid. m/z 537.6 $(M+H)^+$ (ES+). $^1$H NMR (400 MHz, MeOH-d4) δ 8.46 (s, 1H), 8.04 (d, J=1.4 Hz, 1H), 7.83 (s, 1H), 7.81-7.73 (m, 1H), 7.72-7.61 (m, 2H), 7.58-7.49 (m, 1H), 7.49-7.43 (m, 1H), 6.86 (d, J=1.4 Hz, 1H), 5.04 (s, 2H), 3.96 (s, 2H), 3.46 (s, 3H), 2.62 (d, J=7.2 Hz, 2H), 2.14-1.95 (m, 2H), 1.89-1.80 (m, 2H), 1.70-1.50 (m, 4H), 1.19 (s, 2H), 1.06-0.92 (m, 4H).

Example 238: Synthesis of 2-{6-Cyclopropyl-4-[4-fluoro-2-(4-methyl-1,2,4-triazol-3-yl)phenyl]pyridin-2-yl}-6-({[(3R)-1-methylpyrrolidin-3-yl]methoxy}methyl)-4-(trifluoromethyl)-3H-isoindol-1-one (AHI-4)

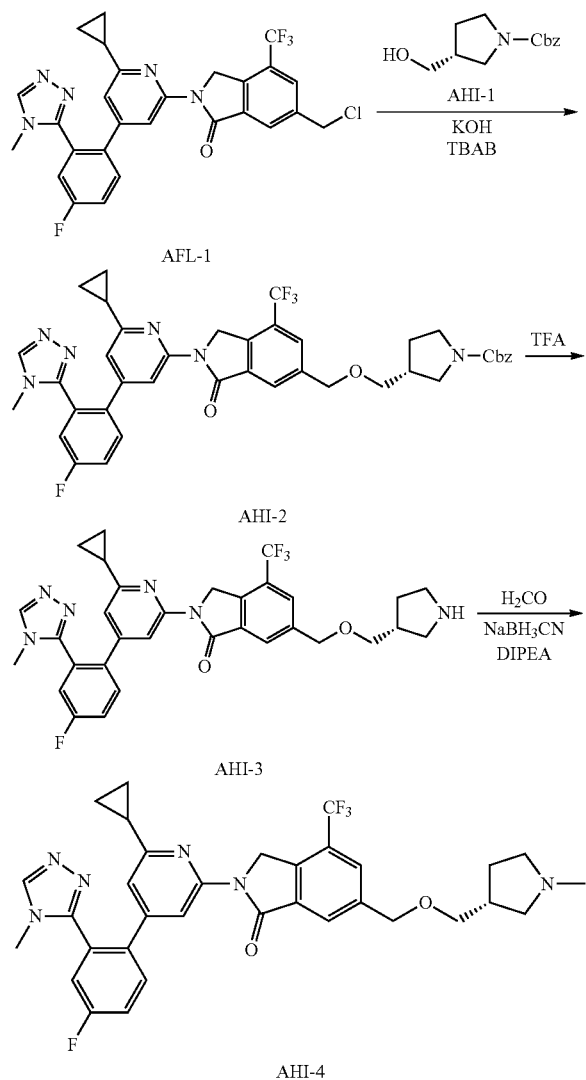

Step 1: Synthesis of Benzyl (3R)-3-{[(2-{6-cyclopropyl-4-[4-fluoro-2-(4-methyl-1,2,4-triazol-3-yl)phenyl] pyridin-2-yl}-3-oxo-7-(trifluoromethyl)-1H-isoindol-5-yl)methoxy]methyl}pyrrolidine-1-carboxylate (AHI-2)

To a stirred solution of intermediate (AFL-1) (120 mg, 1 eq, 0.22 mmol) and benzyl (3R)-3-(hydroxymethyl)pyrrolidine-1-carboxylate (AHI-1) (130 mg, 10 eq, 0.55 mmol) in DCM (5 mL) was added TBAB (36 mg, 0.5 eq, 0.11 mmol) and aq. KOH (5 mL, 20% Wt) at rt. The resulting mixture was stirred for 1 h at rt. The resulting mixture was diluted with water and extracted with EtOAc (3×50 mL). The combined organic layers were washed with brine (2×50 mL), dried (Na$_2$SO$_4$). After filtration, the filtrate was concentrated in vacuo. The crude product was purified by reverse flash column chromatography with the following conditions: Column, C18; mobile phase, Water (0.1% NH$_4$HCO$_3$) and MeCN (60% MeCN up to 75% in 10 min); Detector, UV 254/220 nm. This resulted in the sub-title compound (AHI-2) (77 mg, 96 μmol, 47%, 92% Purity) as a white solid. m/z 741.3 (M+H)$^+$ (ES+).

Step 2: Synthesis of (R)-2-(6-Cyclopropyl-4-(4-fluoro-2-(4-methyl-4H-1,2,4-triazol-3-yl)phenyl)pyridin-2-yl)-6-((pyrrolidin-3-ylmethoxy)methyl)-4-(trifluoromethyl)isoindolin-1-one (AHI-3)

A solution of the product from step 1 above (AHI-2) (77 mg, 1 eq, 104 μmol) and TFA (5 mL) in DCM (5 mL) was stirred for 2 h at 60° C. The mixture was allowed to cool down to rt and then concentrated in vacuo. The crude product was used in the next step directly without further purification. m/z 607.2 (M+H)$^+$ (ES+).

Step 3: 2-{6-Cyclopropyl-4-[4-fluoro-2-(4-methyl-1,2,4-triazol-3-yl)phenyl]pyridin-2-yl}-6-({[(3R)-1-methylpyrrolidin-3-yl]methoxy}methyl)-4-(trifluoromethyl)-3H-isoindol-1-one (AHI-4)

To a stirred solution of the product from step 2 above (AHI-3) (63 mg, 1 eq, 104 μmol) and formaldehyde (9.4 mg, 1.2 eq, 125 μmol) in MeOH (5 mL) were added DIPEA (41 mg, 3 eq, 0.31 mmol) at rt. The resulting mixture was stirred for 1 h at 60° C. The mixture was allowed to cool down to rt. To the above mixture was added NaBH$_3$CN (13 mg, 2 eq, 0.21 mmol) at rt. The resulting mixture was stirred for additional 1 h at rt. The reaction was then quenched by the addition of 2 mL of ice water at 0° C. and concentrated in vacuo. The residue was purified by TLC with DCM/MeOH (10/1). The crude product was purified by Prep-HPLC with the following conditions (Column: Sunfire prep C18 column, 30*150 mm, 5 μm; Mobile Phase A: Water (0.1% FA), Mobile Phase B: MeCN; Flow rate: 60 mL/min; Gradient: 12% B to 42% B in 7 min; Wave Length: 254/220 nm) to afford the title compound (AHI-4) (11.0 mg, 18 μmol, 17%, 99% Purity) as a white solid. m/z 621.2 (M+H)$^+$ (ES+). $^1$H NMR (400 MHz, DMSO-d6) δ 8.50 (s, 1H), 8.03-7.92 (m, 3H), 7.76-7.68 (m, 1H), 7.66-7.56 (m, 2H), 6.80 (s, 1H), 5.17 (s, 2H), 4.67 (s, 2H), 3.42-3.37 (m, 5H), 2.48-2.32 (m, 4H), 2.32-2.19 (m, 4H), 2.09-2.01 (m, 1H), 1.94-1.80 (m, 1H), 1.47-1.33 (m, 1H), 1.04-0.94 (m, 2H), 0.94-0.84 (m, 2H).

Example 239: Synthesis of (R)-2-(6-Chloro-4-(1-(4-methyl-4H-1,2,4-triazol-3-yl)propan-2-yl)pyridin-2-yl)-4-(trifluoromethyl)isoindolin-1-one (AHJ-11)

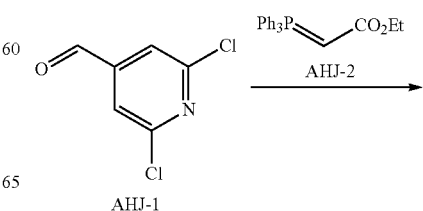

787
-continued

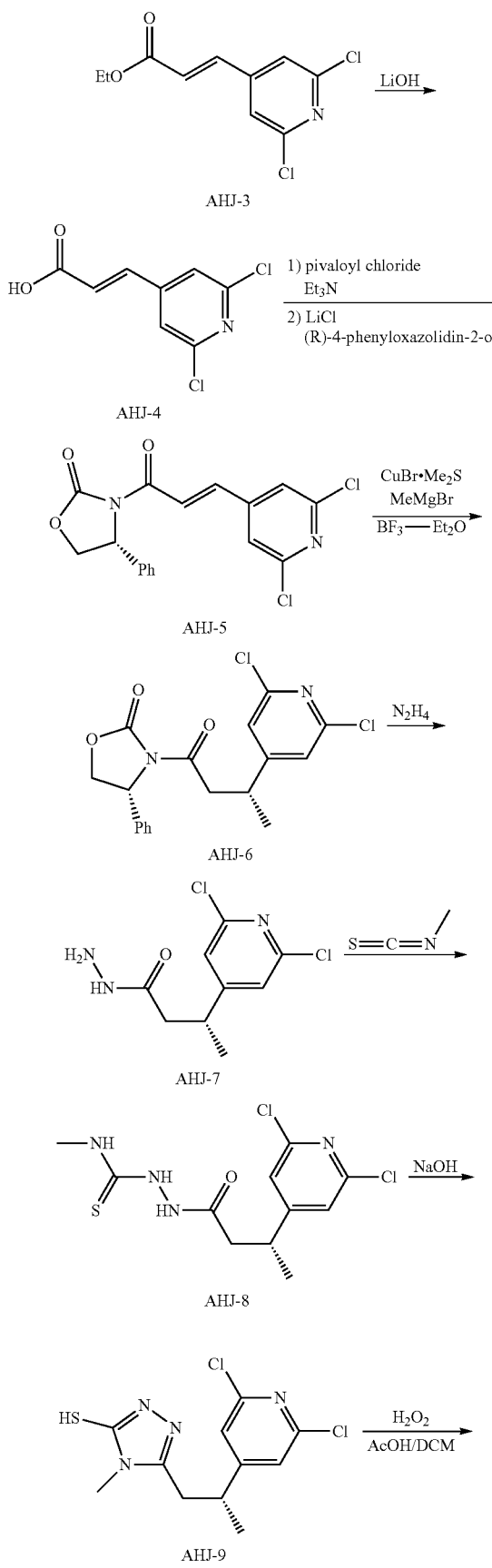

788
-continued

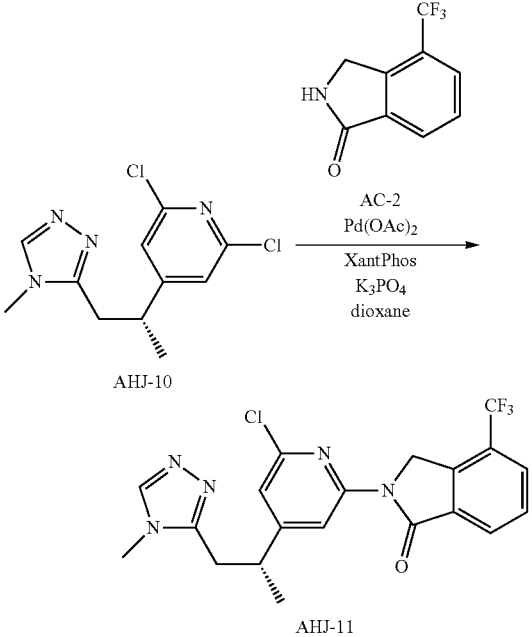

Step 1: Synthesis of Ethyl (E)-3-(2,6-dichloropyridin-4-yl)acrylate (AHJ-3)

To a stirred solution of 2,6-dichloropyridine-4-carbaldehyde (AHJ-1) (8.00 g, 1 eq, 45.5 mmol) in DCM (50 mL) was added ethyl 2-(triphenyl-lambda5-phosphanylidene)acetate (AHJ-2) (1.58 g, 1 eq, 45.5 mmol) at 0° C. The resulting mixture was stirred for 1 h at rt. The mixture was concentrated in vacuo. The residue was applied on a silica gel column chromatography with petroleum ether/EtOAc (5/1) to afford the sub-title compound (AHJ-3) (7.5 g, 26.3 mmol, 72%, 86% Purity) as a white solid. m/z 246.0/248.0 $(M+H)^+$ (ES+).

Step 2: Synthesis (2E)-3-(2,6-Dichloropyridin-4-yl)prop-2-enoic acid (AHJ-4)

To a stirred solution of the product from step 1 above (AHJ-3) (9.20 g, 1 eq, 37.4 mmol) in THF (160 mL) and water (160 mL), was added LiOH (4.50 g, 5 eq, 187 mmol) at 0° C. The resulting mixture was stirred for overnight at rt. The mixture was concentrated in vacuo and diluted with water. The pH value of the solution was adjusted to 3 with aq. HCl (1 M). The solids were collected by filtration to obtain the sub-title compound (AHJ-4) (7.3 g, 27.2 mmol, 90%, 82% Purity) as a yellow solid. m/z 218.0/220.0 $(M+H)^+$ (ES+).

Step 3: Synthesis of (4R)-3-[(2E)-3-(2,6-Dichloropyridin-4-yl)prop-2-enoyl]-4-phenyl-1,3-oxazolidin-2-one (AHJ-5)

A solution of the product from step 2 above (AHJ-4) (4.40 g, 1 eq, 20.2 mmol) and Et₃N (4.50 g, 2.2 eq, 44.4 mmol) in THF (80 mL) were added 2,2-dimethylpropanoyl chloride (2.40 g, 1 eq, 20.2 mmol) at 0° C. After stirred 1 h, to the above mixture was added LiCl (800 g, 1 eq, 20.2 mmol) and (4R)-4-phenyl-1,3-oxazolidin-2-one (3.30 g, 1 eq, 20.2 mmol) in THF (20 mL) dropwise over 10 min at 0° C. The resulting mixture was stirred for overnight at rt. The reaction was quenched with aq. of NH$_4$Cl (5 mL, 1 M) at 0° C. The resulting mixture was diluted with water and extracted with EtOAc (3×200 mL). The combined organic layers were washed with brine (2×200 mL), dried (Na$_2$SO$_4$). After filtration, the filtrate was concentrated in vacuo. The residue was applied on a silica gel column chromatography with petroleum ether/EtOAc (5/1). This resulted in the sub-title compound (AHJ-5) (5.8 g, 14.0 mmol, 79%, 88% Purity) as a white solid. m/z 363.0/365.0 (M+H)$^+$ (ES+).

Step 4: Synthesis of (4R)-3-[(3R)-3-(2,6-Dichloro-pyridin-4-yl)butanoyl]-4-phenyl-1,3-oxazolidin-2-one (AHJ-6)

Into a 500 mL 3-necked round-bottom flask were added copper(I) bromide; dimethyl sulfide (4.90 g, 1.5 eq, 24.0 mmol) in THF (100 mL) was added MeMgBr (16 mL, 3 M, 8.68 eq, 134 mmol) dropwise at −40° C. under nitrogen atmosphere. After stirred 40 min, to the above mixture was added BF$_3$·Et$_2$O (3.40 g, 1.5 eq, 24.0 mmol) dropwise over 5 min at −40° C. The resulting mixture was stirred for 40 min at −40° C. To the above mixture was added the product from step 3 above (AHJ-5) (5.80 g, 1 eq, 16.0 mmol) in THF (20 mL) dropwise over 10 min at −40° C. The resulting mixture was stirred for 30 min at −40° C. The reaction was quenched with aq. of NH$_4$Cl (5 mL, 1 M) at 0° C. The resulting mixture was diluted with water and extracted with EtOAc (3×200 mL). The combined organic layers were washed with brine (2×200 mL), dried (Na$_2$SO$_4$). After filtration, the filtrate was concentrated in vacuo. The residue was applied on a silica gel column chromatography with petroleum ether/EtOAc (6/1). This resulted in the sub-title compound (AHJ-6) (1.6 g, 3.81 mmol, 26%, 90% Purity) as a colorless solid. m/z 379.1/381.1 (M+H)$^+$ (ES+).

Step 5: Synthesis of (3R)-3-(2,6-Dichloropyridin-4-yl)butanehydrazide (AHJ-7)

To a solution of the product from step 4 above (AHJ-6) (1.50 g, 1 eq, 4.00 mmol) in THF (30 mL) was added hydrazine hydrate (64% hydrazine) (246 mg, 64% Wt, 2 eq, 7.91 mmol) at rt. The resulting mixture was stirred for overnight at rt. The resulting mixture was concentrated in vacuo. The crude product used directly in next step without any further purification. This resulted in the sub-title compound (AHJ-7) (950 mg, 3.07 mmol, crude, 80% Purity) as a white solid. m/z 248.0/250.0 (M+H)$^+$ (ES+).

Step 6: Synthesis of (3R)-3-(2,6-dichloropyridin-4-yl)-N-[(methylcarbamothioyl)amino]butanamide (AHJ-8)

To a stirred solution of the product from step 5 above (AHJ-7) (1.50 g, 1 eq, 6.05 mmol) in THF (15 mL) was added methyl isothiocyanate (530 mg, 1.2 eq, 7.26 mmol) at rt. The resulting mixture was stirred for overnight at rt. The resulting mixture was concentrated in vacuo. The crude product used directly in next step without any further purification. This resulted in the sub-title compound (AHJ-8) (1.5 g, 4.08 mmol, 77%, 87% Purity) as a white solid. m/z 321.0/323.0 (M+H)$^+$ (ES+).

Step 7: Synthesis of 5-[(2R)-2-(2,6-Dichloropyridin-4-yl)propyl]-4-methyl-1,2,4-triazole-3-thiol (AHJ-9)

To a stirred solution of the product from step 6 above (AHJ-8) (1.50 g, 1 eq, 4.67 mmol) in THF (15 mL) was added aq. NaOH (16 mL, 1M) at 0° C. The resulting mixture was stirred for overnight at rt. The mixture was concentrated in vacuo and diluted with water. The pH value of the solution was adjusted to 3 with aq. HCl (1 M) at 0° C. The resulting mixture was diluted with water and extracted with EtOAc (3×100 mL). The combined organic layers were washed with brine (1×100 mL), dried (Na$_2$SO$_4$). After filtration, the filtrate was concentrated in vacuo. This resulted in the sub-title compound (AHJ-9) (1.0 g, 2.81 mmol, 71%, 85% Purity) as a white solid. m/z 303.0/305.0 (M+H)$^+$ (ES+).

Step 8: Synthesis of 2,6-Dichloro-4-[(2R)-1-(4-methyl-1,2,4-triazol-3-yl)propan-2-yl]pyridine (AHJ-10)

To a stirred solution of the product from step 7 above (AHJ-9) (1.00 g, 1 eq, 3.30 mmol) in DCM (10 mL) was added H$_2$O$_2$ (224 mg, 30% Wt, 2 eq, 6.60 mmol) and AcOH (396 mg, 2 eq, 6.60 mmol) at 0° C. The resulting mixture was stirred for 3 h at rt. The mixture was basified to pH 8 with saturated aq. of Na$_2$CO$_3$ (1 M). The resulting mixture was diluted with water and extracted with DCM (3×100 mL). The combined organic layers were washed with brine (2×100 mL), dried (Na$_2$SO$_4$). After filtration, the filtrate was concentrated in vacuo. This resulted in the sub-title compound (AHJ-10) (800 g, 2.73 mmol, 89%, 92% Purity) as a yellow solid. m/z 271.0/273.0 (M+H)$^+$ (ES+).

Step 9: Synthesis of (R)-2-(6-Chloro-4-(1-(4-methyl-4H-1,2,4-triazol-3-yl)propan-2-yl)pyridin-2-yl)-4-(trifluoromethyl)isoindolin-1-one (AHJ-11)

To a stirred solution of the product from step 8 above (AHJ-10) (150 mg, 1 eq, 0.55 mmol), intermediate (AC-2) (45 mg, 0.4 eq, 0.22 mmol) and K$_3$PO$_4$ (235 mg, 2 eq, 1.10 mmol) in 1,4-dioxane (5 mL) were added XantPhos (64 mg, 0.2 eq, 0.11 mmol) and Pd(OAc)$_2$ (12 mg, 0.1 eq, 0.05 mmol) at rt under nitrogen atmosphere. The resulting mixture was stirred for 16 h at 100° C. under nitrogen atmosphere. The mixture was cooled to rt and concentrated in vacuo. The residue was purified by reverse phase flash with the following conditions: Column, C18 Column; Mobile Phase, water (0.1% FA) and MeCN (20% MeCN up to 70% in 20 min); UV detection at 254/220 nm. The product-containing fractions were combined and concentrated in vacuo. The residue was purified by Prep-HPLC with the following conditions: Column: SunFire Prep C18 OBD Column 5 µm, 19*150 mm; Mobile Phase, water (0.1% FA) and MeCN (35% MeCN up to 55% in 10 min); UV detection at 254/220 nm. The product-containing fractions were combined and evaporated partially in vacuo and lyophilized overnight to afford the title compound (AHJ-11) (6.5 mg, 15 µmol, 2.6%, 99% Purity) as a white solid. m/z 436.3/438.3 (M+H)$^+$ (ES+). $^1$H NMR (400 MHz, MeOH-d4) δ 8.44 (d, J=1.2 Hz, 1H), 8.35 (s, 1H), 8.13 (d, J=7.7 Hz, 1H), 8.04-7.98 (m, 1H), 7.83-7.74 (m, 1H), 7.19 (d, J=1.2 Hz, 1H), 5.24 (d, J=2.0 Hz, 2H), 3.69 (s, 3H), 3.52-3.41 (m, 1H), 3.19 (d, J=7.6 Hz, 2H), 1.45 (d, J=6.9 Hz, 3H).

Example 240: Synthesis of N-[4-[(2R)-1-(4-Methyl-1,2,4-triazol-3-yl)propan-2-yl]-6-[1-oxo-4-(trifluoromethyl)-3H-isoindol-2-yl]pyridin-2-yl]methanesulfonamide (AHK-1)

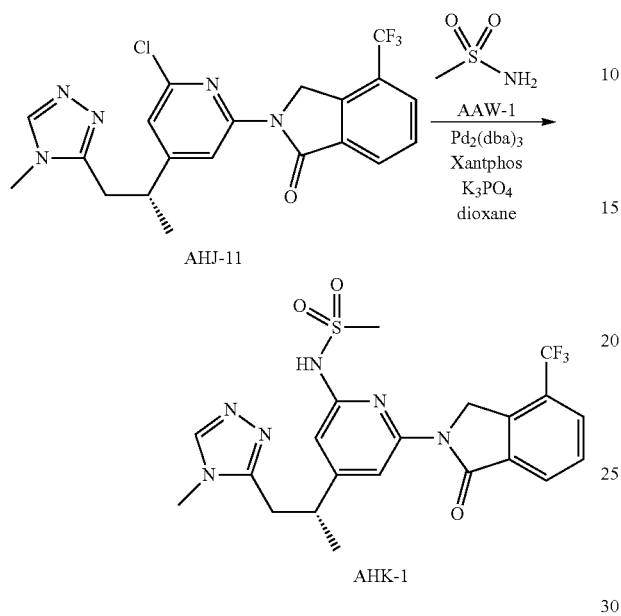

To a stirred solution of compound (AHJ-11) (60 mg, 1 eq, 0.14 mmol), methanesulfonamide (AAW-1) (26 mg, 2 eq, 0.28 mmol) and K₃PO₄ (58 mg, 2 eq, 0.28 mmol) in 1,4-dioxane (4 mL) were added XantPhos (16 mg, 0.2 eq, 28 μmol) and Pd(OAc)₂ (3 mg, 0.1 eq, 14 μmol) at rt under nitrogen atmosphere. The resulting mixture was stirred for overnight at 100° C. under nitrogen atmosphere. The mixture was cooled to rt, diluted with water and extracted with EtOAc (3×20 mL). The combined organic layers were washed with brine (2×20 mL), dried (Na₂SO₄). After filtration, the filtrate was concentrated in vacuo. The crude product was purified by reverse flash column chromatography with the following conditions: Column, C18; mobile phase, water (0.1% NH₄HCO₃) and MeCN (10% MeCN up to 50% in 15 min); Detector, UV 254/220 nm. The product-containing fractions were combined and concentrated in vacuo. The crude product was purified by Prep-HPLC with the following conditions (Column: YMC-Actus Triart C18, 30×250 mm, 5 μm; Mobile Phase A: water (0.1% NH₄HCO₃+0.1% NH₃·H2O), Mobile Phase B: MeCN; Flow rate:60 mL/min; Gradient:5 B to 35 B in 7 min; UV 254/210 nm; RT:6.32). The product-containing fractions were combined and evaporated partially in vacuo and lyophilized overnight to afford the title compound (AHK-1) (21.7 mg, 43 μmol, 32%, 99% Purity) as a white solid. m/z 495.0 (M+H)⁺ (ES+). ¹H NMR (300 MHz, MeOH-d4) δ 8.31 (s, 1H), 8.19-8.08 (m, 2H), 7.99 (d, J=7.7 Hz, 1H), 7.77 (t, J=7.7 Hz, 1H), 6.66 (d, J=1.2 Hz, 1H), 5.29 (s, 2H), 3.64 (s, 3H), 3.44-3.39 (m, 1H), 3.34 (s, 3H), 3.16 (d, J=7.6 Hz, 2H), 1.44 (d, J=6.9 Hz, 3H).

Example 241: Synthesis of N-[4-[(2S)-1-(4-Methyl-1,2,4-triazol-3-yl)propan-2-yl]-6-[1-oxo-4-(trifluoromethyl)-3H-isoindol-2-yl]pyridin-2-yl]methanesulfonamide (AHL-8)

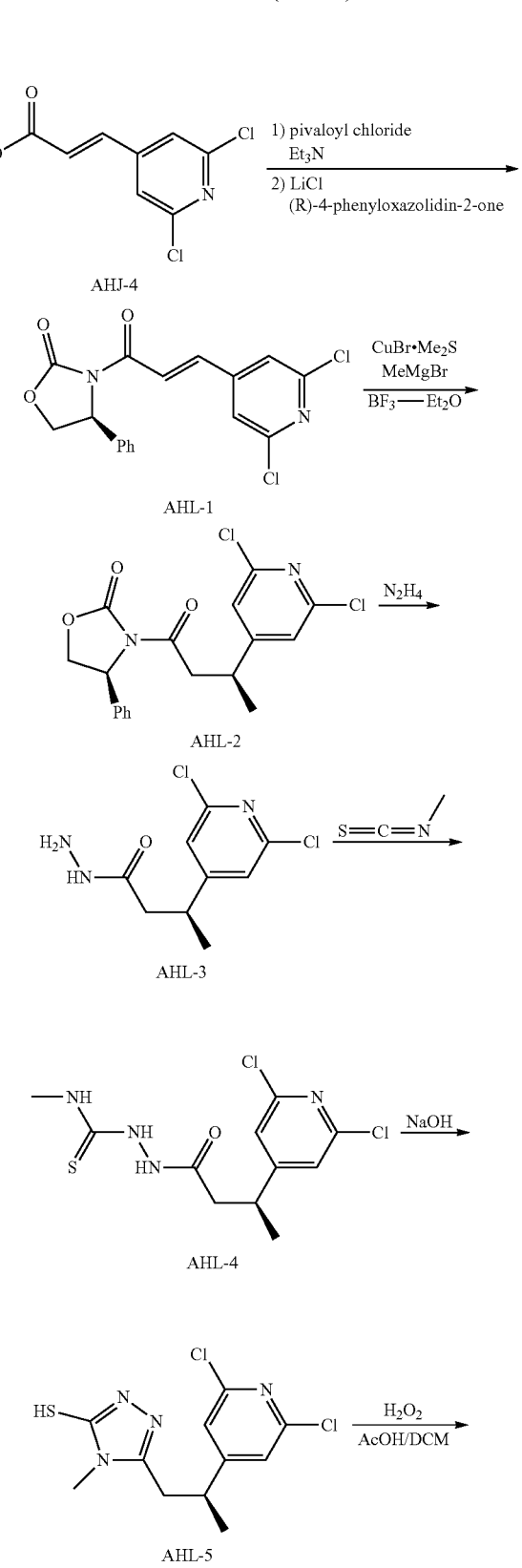

-continued

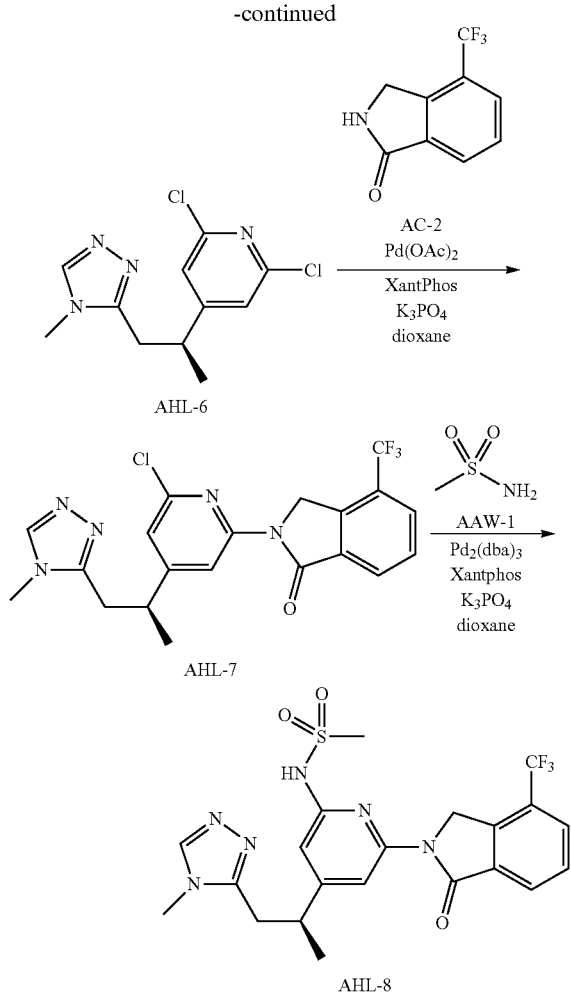

Step 1: Synthesis of (S,E)-3-(3-(2,6-Dichloropyridin-4-yl)acryloyl)-4-phenyloxazolidin-2-one (AHL-1)

To a stirred solution of intermediate (AHJ-4) (4.40 g, 1 eq, 20.2 mmol) and Et₃N (4.49 g, 2.2 eq, 44.4 mmol) in THF (80 mL) were added 2,2-dimethylpropanoyl chloride (2.43 g, 1 eq, 20.2 mmol) at 0° C. After 1 h, to the above mixture was added LiCl (860 mg, 1 eq, 20.2 mmol) and (4S)-4-phenyl-1,3-oxazolidin-2-one (3.29 g, 1 eq, 20.2 mmol) in THF (20 mL) dropwise over 10 min at 0° C. The resulting mixture was stirred for overnight at rt. The reaction was quenched with aq. sat. of NH₄Cl (10 mL) at rt. The resulting mixture was diluted with water and extracted with EtOAc (3×500 mL). The combined organic layers were washed with brine (2×500 mL), dried (Na₂SO₄). After filtration, the filtrate was concentrated in vacuo. The residue was applied on a silica gel column chromatography with petroleum ether/EtOAc (5/1) to afford the sub-title compound (AHL-1) (5.8 g, 13.6 mmol, 79%, 85% Purity) as a white solid. m/z 363.0/365.0 (M+H)⁺ (ES+).

Step 2: Synthesis of (4S)-3-[(3S)-3-(2,6-Dichloropyridin-4-yl)butanoyl]-4-phenyl-1,3-oxazolidin-2-one (AHL-2)

To a stirred solution of copper(I) bromide; dimethyl sulphide (4.92 g, 1.5 eq, 24.0 mmol) in THF (100 mL) was added MeMgBr (15.97 mL, 3M, 8.68 eq, 134 mmol) dropwise at −40° C. under nitrogen atmosphere. After 40 min, to the above mixture was added BF₃·Et₂O (3.40 g, 1.5 eq, 24.0 mmol) dropwise over 5 min at −40° C. The resulting mixture was stirred for 40 min at −40° C. To the above mixture was added the product from step 1 above (AHL-1) (5.80 g, 1 eq, 16.0 mmol) in THF (20 mL) dropwise over 10 min at −40° C. The resulting mixture was stirred for 30 min at −40° C. The reaction was quenched by the addition of aq. sat. of NH₄Cl (20 mL) at −40° C. The resulting mixture was diluted with water and extracted with EtOAc (3×400 mL). The combined organic layers were washed with brine (2×400 mL), dried (Na₂SO₄). After filtration, the filtrate was concentrated in vacuo. The residue was applied on a silica gel column chromatography with petroleum ether/EtOAc (6/1) to afford the sub-title compound (AHL-2) (1.6 g, 3.68 mmol, 26%, 87% Purity) as a colorless solid. m/z 379.1/381.1 (M+H)⁺ (ES+)

Step 3: Synthesis of (3S)-3-(2,6-Dichloropyridin-4-yl)butanehydrazide (AHL-3)

To a stirred solution of the product from step 2 above (AHL-2) (770 mg, 1 eq, 2.03 mmol) in THF (15 mL) was added hydrazine hydrate (64% hydrazine) (126 mg, 64% Wt, 4.06 mmol, 2 eq) at rt. The resulting mixture was stirred for overnight at rt. The resulting mixture was concentrated in vacuo. This resulted in the sub-title compound (AHL-3) (500 mg, 1.14 mmol, 99%, 79% Purity) as a yellow oil. m/z 348.0/350.0 (M+H)⁺ (ES+).

Step 4: Synthesis of (3S)-3-(2,6-Dichloropyridin-4-yl)-N-[(methylcarbamothioyl)amino]butanamide (AHL-4)

To a stirred solution of the product from step 3 above (AHL-3) (1.00 g, 1 eq, 4.03 mmol) in THF (30 mL) was added methyl isothiocyanate (354 mg, 1.2 eq, 4.84 mmol) at rt. The resulting mixture was stirred for overnight at rt. The resulting mixture was concentrated in vacuo. This resulted in the sub-title compound (AHL-4) (1.2 g, 2.73 mmol, 92%, 78% Purity) as a yellow oil. m/z 321.0/323.0 (M+H)⁺ (ES+).

Step 5: Synthesis of 5-[(2S)-2-(2,6-Dichloropyridin-4-yl)propyl]-4-methyl-1,2,4-triazole-3-thiol (AHL-5)

To a stirred solution of the product from step 4 above (AHL-4) (1.20 g, 1 eq, 3.74 mmol) in THF (30 mL) was added aq. NaOH (11 mL, 1M) dropwise at rt. The mixture was acidified to pH 3 with aq. HCl (1 M) at 0° C. The resulting mixture was diluted with water (40 mL). The resulting mixture was diluted with water and extracted with EtOAc (3×100 mL). The combined organic layers were washed with brine (2×100 mL), dried (Na₂SO₄). After filtration, the filtrate was concentrated in vacuo. This resulted in the sub-title compound (AHL-5) (1.0 g, 2.58 mmol, 88%, 78% Purity) as a yellow oil. m/z 303.0/305.0 (M+H)⁺ (ES+).

Step 6: Synthesis of 2,6-Dichloro-4-[(2S)-1-(4-methyl-1,2,4-triazol-3-yl)propan-2-yl]pyridine (AHL-6)

To a stirred solution of the product from step 5 above (AHL-5) (1.96 g, 1 eq, 6.46 mmol) in DCM (30 mL) was added AcOH (10 mL, 0.03 eq, 0.17 mmol) and H₂O₂ (6.80 mL, 30% Wt, 0.03 eq, 0.20 mmol) dropwise at 0° C. The resulting mixture was stirred for 2 h at 0° C. The mixture was basified to pH 8 with saturated aq. of NaHCO₃ (1 M). The resulting mixture was diluted with water and extracted with DCM (3×100 mL). The combined organic layers were washed with brine (2×100 mL), dried (Na₂SO₄). After filtration, the filtrate was concentrated in vacuo. The crude product was purified by reverse flash column chromatography with the following conditions: Column, C18; mobile phase, water (0.1% NH₄HCO₃) and MeCN (10% MeCN up to 70% in 20 min); Detector, UV 254/220 nm. This resulted in the sub-title compound (AHL-6) (1.4 g, 4.67 mmol, 80%, 90% Purity) as a yellow oil. m/z 271.0/273.0 (M+H)⁺ (ES+).

Step 7: Synthesis of 2-[6-Chloro-4-[(2S)-1-(4-methyl-1,2,4-triazol-3-yl)propan-2-yl]pyridin-2-yl]-4-(trifluoromethyl)-3H-isoindol-1-one (AHL-7)

To a stirred solution of the product from step 6 above (AHL-6) (150 mg, 1 eq, 0.55 mmol), intermediate (AC-2) (45 mg, 0.4 eq, 0.22 mmol) and K₃PO₄ (235 mg, 2 eq, 1.11 mmol) in 1,4-dioxane (5 mL) were added Pd(OAc)₂ (12 mg, 0.1 eq, 55 µmol) and XantPhos (64 mg, 0.2 eq, 0.11 mmol) at rt under nitrogen atmosphere. The resulting mixture was stirred for 1 h at 80° C. under nitrogen atmosphere. The mixture was cooled to rt, diluted with water and extracted with EtOAc (3×20 mL). The combined organic layers were washed with brine (2×20 mL), dried (Na₂SO₄). After filtration, the filtrate was concentrated in vacuo. The crude product was purified by reverse flash column chromatography with the following conditions: Column, C18; mobile phase, water (0.1% NH₄HCO₃) and MeCN (30% MeCN up to 70% in 15 min); Detector, UV 254/220 nm. This resulted in the sub-title compound (AHL-7) (120 mg, 0.25 mmol, 50%, 92% Purity) as a yellow oil. m/z 436.1/438.1 (M+H)⁺ (ES+).

Step 8: Synthesis of N-[4-[(2S)-1-(4-Methyl-1,2,4-triazol-3-yl)propan-2-yl]-6-[1-oxo-4-(trifluoromethyl)-3H-isoindol-2-yl]pyridin-2-yl]methanesulfonamide (AHL-8)

To a stirred solution of the product from step 7 above (AHL-7) (40 mg, 1 eq, 92 µmol), methanesulfonamide (AAW-1) (17 mg, 2 eq, 0.18 mmol) and K₃PO₄ (39 mg, 2 eq, 0.18 mmol) in 1,4-dioxane (3 mL) were added Pd(OAc)₂ (2.1 mg, 0.1 eq, 9 µmol) and Xantphos (11 mg, 0.2 eq, 18 µmol) at rt under nitrogen atmosphere. The resulting mixture was stirred for overnight at 100° C. under nitrogen atmosphere. The mixture was cooled to rt, diluted with water and extracted with EtOAc (3×10 mL). The combined organic layers were washed with brine (2×10 mL), dried (Na₂SO₄). After filtration, the filtrate was concentrated in vacuo. The crude product was purified by reverse flash column chromatography with the following conditions: Column, C18; mobile phase, water (0.1% NH₄HCO₃) and MeCN (50% MeCN up to 70% in 10 min); Detector, UV 254/220 nm. The product-containing fractions were combined and concentrated in vacuo. The crude product was purified by Prep-HPLC with the following conditions (Column: YMC-Actus Triart C18, 30*250 mm, 5 µm; Mobile Phase A: water (0.1% NH₄HCO₃+0.1% NH₃·H₂O), Mobile Phase B: MeCN; Flow rate:60 mL/min; Gradient: 15 B to 45 B in 7 min; 254/210 nm, RT: 6.03) to afford the title compound (AHL-8) (31.5 mg, 63 µmol, 69%, 99% Purity) as a white solid. m/z 495.1 (M+H)⁺ (ES+). ¹H NMR (400 MHz, CD3OD) δ 8.33 (s, 1H), 8.21-8.11 (m, 2H), 8.00 (d, J=7.7 Hz, 1H), 7.79 (t, J=7.7 Hz, 1H), 6.67 (d, J=1.2 Hz, 1H), 5.30 (s, 2H), 3.66 (s, 3H), 3.47-3.38 (m, 1H), 3.35 (s, 3H), 3.17 (d, J=7.7 Hz, 2H), 1.45 (d, J=6.9 Hz, 3H).

Example 242: Synthesis of 2-(3-Ethoxy-5-[3-[(4-methyl-1,2,4-triazol-3-yl)methyl] oxetan-3-yl]phenyl)-4-(trifluoromethyl)-3H-isoindol-1-one (AHM-12)

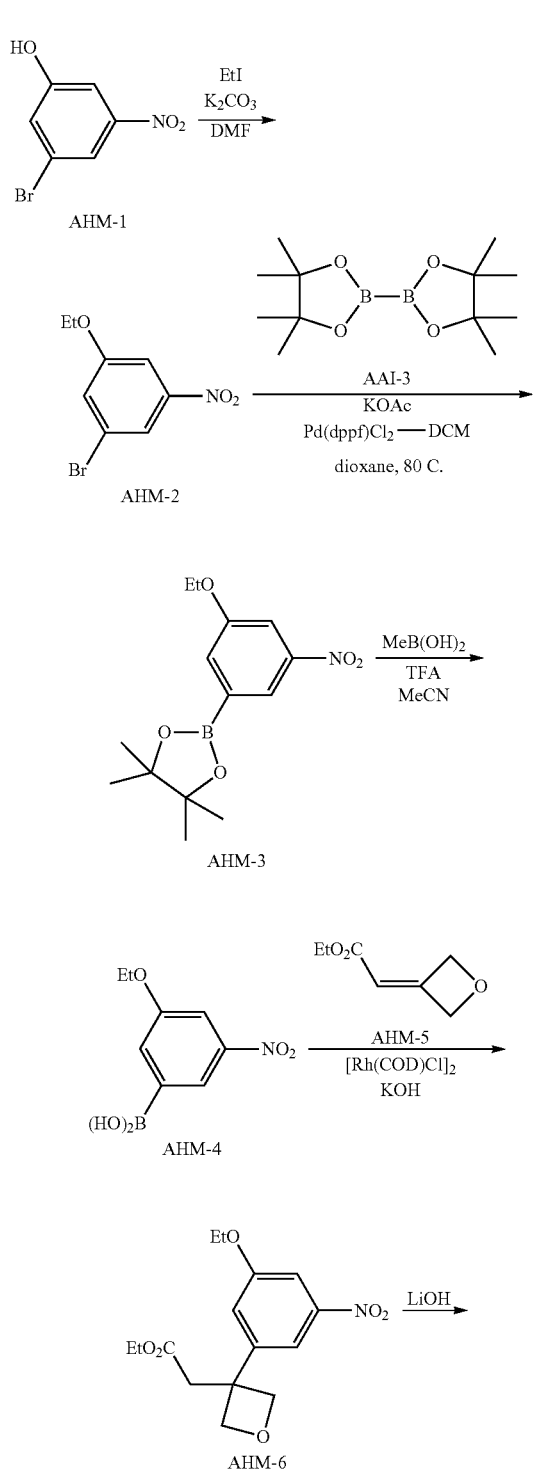

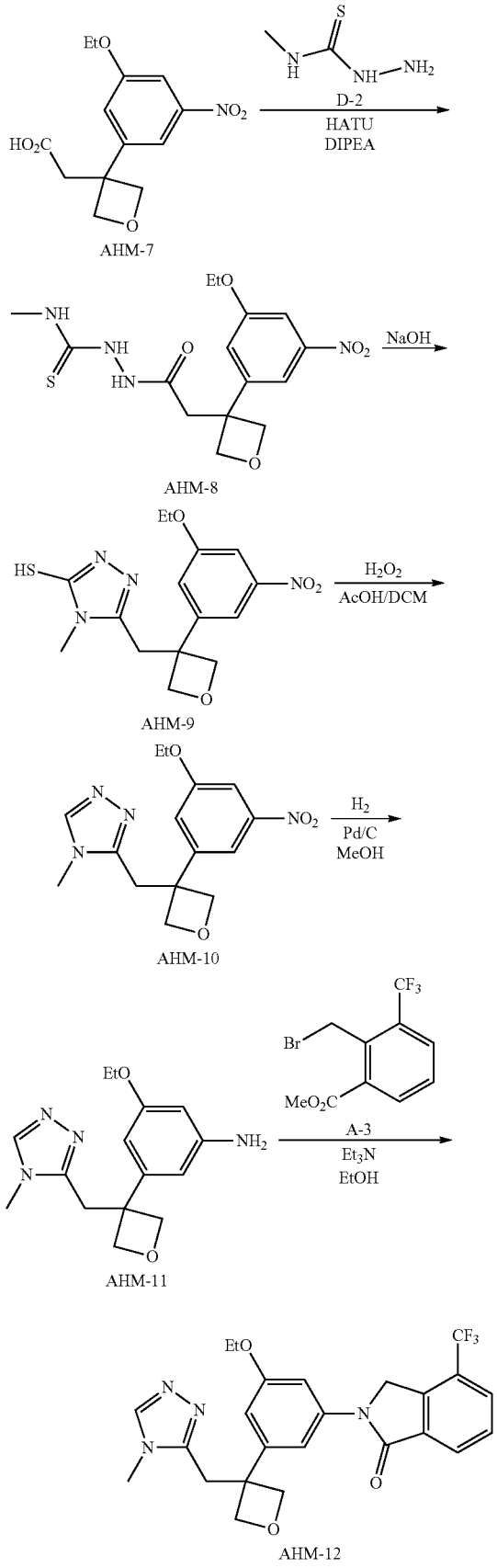

Step 1: Synthesis of
1-Bromo-3-ethoxy-5-nitrobenzene (AHM-2)

To a stirred solution of 3-bromo-5-nitrophenol (AHM-1) (6.00 g, 1 eq, 27.5 mmol) and $K_2CO_3$ (9.51 g, 2.5 eq, 68.7 mmol) in DMF (40 mL) were added ethyl iodide (8.59 g, 2 eq, 55 mmol) dropwise at 0° C. The resulting mixture was stirred for overnight at rt. The resulting mixture was diluted with water and extracted with EtOAc (3×300 mL). The combined organic layers were washed with brine (2×300 mL), dried ($Na_2SO_4$). After filtration, the filtrate was concentrated in vacuo. The crude product was purified by reverse phase flash to afford the sub-title compound (AHM-2) (6.5 g, 23.9 mmol, 96%, 90% Purity) as a yellow solid. m/z 246.0/248.0 $(M+H)^+$ (ES+).

Step 2: Synthesis of 2-(3-Ethoxy-5-nitrophenyl)-4,4,5,5-tetramethyl-1,3,2-dioxaborolane (AHM-3)

To a stirred mixture of the product from step 1 above (AHM-2) (6.00 g, 1 eq, 24.4 mmol), bis(pinacolato)diboron (AAI-3) (7.43 g, 1.2 eq, 29.3 mmol) and AcOK (5.98 g, 2.5 eq, 61.0 mmol) in 1,4-dioxane (20 mL) was added Pd(dppf)Cl$_2$.DCM (890 mg, 0.05 eq, 1.22 mmol) at rt under nitrogen atmosphere. The resulting mixture was stirred for 2 h at 100° C. under nitrogen atmosphere. The mixture was cooled to rt and concentrated in vacuo. The residue was applied on a silica gel column chromatography with petroleum ether/EtOAc (10/1) to afford the sub-title compound (AHM-3) (8.49 g, 25.0 mmol, crude, 73% Purity) as a white solid. m/z 294.1 $(M+H)^+$ (ES+).

Step 3: 3-Ethoxy-5-nitrophenylboronic acid (AHM-4)

To a stirred solution of the product from step 2 above (AHM-3) (5.80 g, 1 eq, 20.0 mmol) in MeCN (60 mL) were added methylboronic acid (10.66 g, 9 eq, 178 mmol) and TFA (4.06 mL, 2.76 eq, 54.7 mmol) dropwise at 80° C. The resulting mixture was stirred for 4 h at 80° C. The mixture was cooled to rt, diluted with water and extracted with EtOAc (3×500 mL). The combined organic layers were washed with brine (2×500 mL), dried ($Na_2SO_4$). After filtration, the filtrate was concentrated in vacuo. This resulted in the sub-title compound (AHM-4) (7.1 g, 24.2 mmol, crude, 72% Purity) as a pink solid. m/z 212.1 $(M+H)^+$ (ES+).

Step 4: Synthesis of Ethyl 2-[3-(3-ethoxy-5-nitrophenyl)oxetan-3-yl]acetate (AHM-6)

To a stirred mixture of the product from step 3 above (AHM-4) (2.84 g, 1 eq, 13.5 mmol) and Pd(COD)Cl$_2$ (380 mg, 0.1 eq, 1.35 mmol) in 1,4-dioxane (100 mL) were added KOH (2.27 g, 3 eq, 40.4 mmol) in $H_2O$ (20 mL) and ethyl 2-(oxetan-3-ylidene)acetate (AHM-5) (2.30 g, 1.2 eq, 16.2 mmol) at rt under nitrogen atmosphere. The resulting mixture was stirred for overnight at 40° C. under nitrogen atmosphere. The mixture was cooled to rt, diluted with water and extracted with EtOAc (3×100 mL). The combined organic layers were washed with brine (2×200 mL), dried ($Na_2SO_4$). After filtration, the filtrate was concentrated in vacuo. The residue was applied on a silica gel column chromatography with petroleum ether/EtOAc (15/1) to afford the sub-title compound (AHM-6) (2.28 g, 6.42 mmol, 55%, 87% Purity) as a brown solid. m/z 310.1 $(M+H)^+$ (ES+).

Step 5: Synthesis of [3-(3-Ethoxy-5-nitrophenyl) oxetan-3-yl]acetic acid (AHM-7)

To a stirred solution of the product from step 4 above (AHM-6) (830 mg, 1 eq, 2.68 mmol) in THF (15 mL) and H₂O (5 mL) was added LiOH (321 mg, 5 eq, 13.4 mmol) at 0° C. under nitrogen atmosphere. The resulting mixture was stirred for overnight at rt under nitrogen atmosphere. The resulting mixture was diluted with water (50 mL). The residue was acidified to pH 4 with aq. HCl (1 M). The precipitated solids were collected by filtration and washed with DCM (3×10 mL). This resulted in the sub-title compound (AHM-7) (705 mg, 2.13 mmol, 93%, 85% Purity) as a yellow solid. m/z 282.1 (M+H)⁺ (ES+).

Step 6: Synthesis of 2-[3-(3-Ethoxy-5-nitrophenyl) oxetan-3-yl]-N-[(methylcarbamothioyl)amino]acetamide (AHM-8)

To a stirred solution of the product from step 6 above (AHM-7) (705 mg, 1 eq, 2.51 mmol) and 4-methyl-3-thiosemicarbazide (D-2) (316 mg, 1.2 eq, 5.02 mmol) in DMF (15 mL) were added HATU (1.05 g, 1.1 eq, 2.8 mmol) and DIPEA (1.62 g, 5 eq, 12.5 mmol) at rt. The resulting mixture was stirred for 3 h at rt. The crude product was purified by reverse flash column chromatography with the following conditions: Column, C18; mobile phase, water (0.1% NH₄HCO₃) and MeCN (20% MeCN up to 60% in 20 min); Detector, UV 254/220 nm to afford the sub-title compound (AHM-8) (700 mg, 1.75 mmol, 76%, 92% Purity) as a yellow solid. m/z 369.1 (M+H)⁺ (ES+).

Step 7: Synthesis of 5-[[3-(3-Ethoxy-5-nitrophenyl) oxetan-3-yl]methyl]-4-methyl-1,2,4-triazole-3-thiol (AHM-9)

To a stirred mixture of the product from step 6 above (AHM-8) (700 mg, 1 eq, 1.90 mmol) in DMF (15 mL) were added NaOH (152 mg, 2 eq, 3.80 mmol) at 0° C. The resulting mixture was stirred for overnight at rt. The mixture was acidified to pH 4 with conc. HCl at 0° C. The resulting mixture was diluted with water and extracted with EtOAc (3×80 mL). The combined organic layers were washed with brine (2×80 mL), dried (Na₂SO₄). After filtration, the filtrate was concentrated in vacuo. This resulted in the sub-title compound (AHM-9) (609 mg, 1.55 mmol, 91%, 89% Purity) as a white solid. m/z 351.1 (M+H)⁺ (ES+).

Step 8: Synthesis of 3-[[3-(3-Ethoxy-5-nitrophenyl) oxetan-3-yl]methyl]-4-methyl-1,2,4-triazole (AHM-10)

To a stirred mixture of the product from step 7 above (AHM-9) (550 mg, 1 eq, 1.57 mmol) and H₂O₂ (0.22 mL, 30% Wt, 6 eq, 9.42 mmol) in DCM (10 mL) were added AcOH (189 mg, 2 eq, 3.14 mmol) dropwise at 0° C. The resulting mixture was stirred for 2 h at rt. The mixture was concentrated in vacuo. The residue was purified by Prep-TLC with DCM/MeOH (30/1) to afford the sub-title compound (AHM-10) (460 mg, 1.30 mmol, 92%, 90% Purity) as a brown yellow solid. m/z 319.1 (M+H)⁺ (ES+).

Step 9: Synthesis of 3-[[3-(3-Ethoxy-5-nitrophenyl) oxetan-3-yl]methyl]-4-methyl-1,2,4-triazole (AHM-11)

A mixture of the product from step 8 above (AHM-10) (400 mg, 1 eq, 1.26 mmol) and Pd/C type 87L (148 mg, 1 eq, 1.26 mmol) in MeOH (30 mL) was stirred for overnight at rt under hydrogen atmosphere. The resulting mixture was filtered; the filter cake was washed with MeOH (3×3 mL). The filtrate was concentrated in vacuo. This resulted in the sub-title compound (AHM-11) (290 mg, 0.86 mmol, 80%, 85% Purity) as a brown yellow solid. m/z 289.2 (M+H)⁺ (ES+).

Step 10: Synthesis of 2-(3-ethoxy-5-[3-[(4-methyl-1,2,4-triazol-3-yl)methyl]oxetan-3-yl]phenyl)-4-(trifluoromethyl)-3H-isoindol-1-one (AHM-12)

Into a 25-mL round-bottom flask, was placed the product from step 9 above (AHM-11) (50 mg, 1 eq, 0.17 mmol) and intermediate (A-3) (52 mg, 1 eq, 0.17 mmol) in EtOH (10 mL), then Et₃N (88 mg, 5 eq, 0.87 mmol) was added at rt. The resulting solution was stirred 2 h at 80° C. The mixture was cooled to rt and concentrated in vacuo. The crude product was purified by Prep-HPLC with the following conditions: Column: SunFire Prep C18 OBD Column, 19*150 mm, 5 µm; Mobile Phase A: water (0.1% FA), Mobile Phase B: MeCN; Flow rate: 60 mL/min; Gradient: 30% B to 60% B in 7 min; Wave Length: 254/210 nm; RT: 6.32. This resulted in the title compound (AHM-12) (24.7 mg, 51 µmol, 30%, 98% Purity) as a white solid. m/z 473.1 (M+H)⁺ (ES+). ¹H NMR (300 MHz, MeOH-d4) δ 8.22 (s, 1H), 8.08 (d, J=7.7 Hz, 1H), 8.01-7.92 (m, 1H), 7.82-7.71 (m, 1H), 7.48 (t, J=2.1 Hz, 1H), 6.85 (t, J=1.7 Hz, 1H), 6.26-6.19 (m, 1H), 5.11-4.99 (m, 6H), 4.04-3.91 (m, 2H), 3.64 (s, 2H), 2.95 (s, 3H), 1.36 (t, J=7.0 Hz, 3H).

Example 243: Synthesis of 2-(5-(Ethylamino)-4-(4-fluoro-2-(4-methyl-4H-1,2,4-triazol-3-yl)phenyl) pyridin-2-yl)-6-(hydroxymethyl)-4-(trifluoromethyl) isoindolin-1-one (AHN-9)

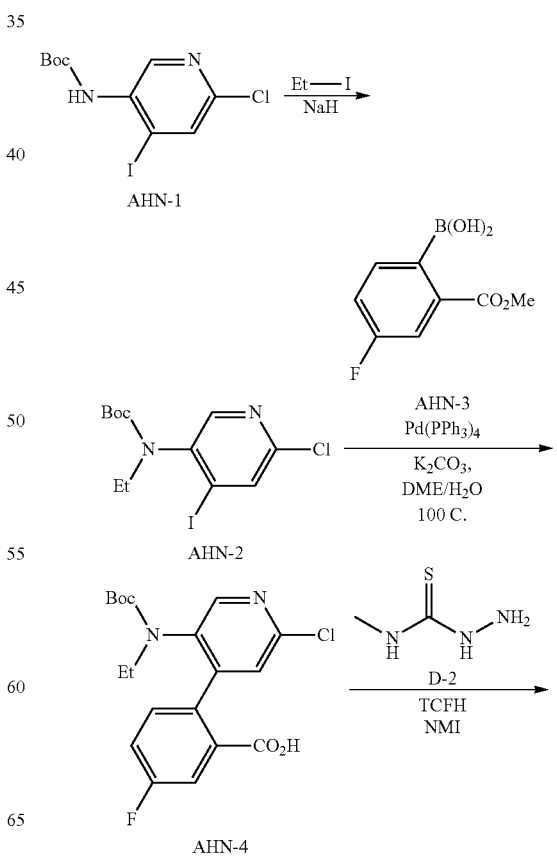

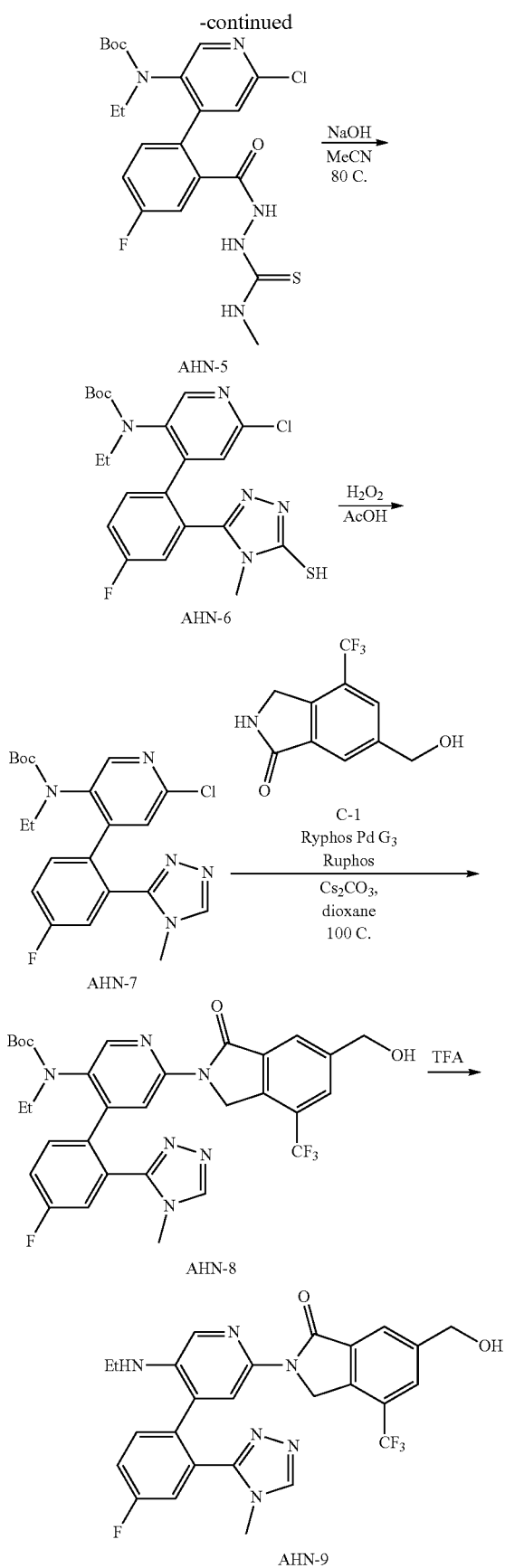

Step 1: tert-Butyl (6-chloro-4-iodopyridin-3-yl)(ethyl)carbamate (AHN-2)

To a stirred solution of tert-butyl N-(6-chloro-4-iodopyridin-3-yl)carbamate (AHN-1) (3.55 g, 1 Eq, 10.0 mmol) in DMF (50 mL) was added NaH (601 mg, 60% Wt, 1.5 Eq, 15.0 mmol) in portions at 0° C. under nitrogen atmosphere. The resulting mixture was stirred for 0.5 h at rt under nitrogen atmosphere. To the above mixture was added ethyl iodide (2.34 g, 1.5 Eq, 15.0 mmol) dropwise at 0° C. The resulting mixture was stirred overnight at rt. The reaction was then quenched by the addition of 5 mL of ice water at 0° C. The resulting mixture was diluted with water and extracted with EtOAc (3×100 mL). The combined organic layers were washed with brine (2×200 mL), dried ($Na_2SO_4$). After filtration, the filtrate was concentrated in vacuo. The crude product was purified by reverse flash column chromatography with the following conditions: Column, C18; mobile phase, water (0.10% $NH_4HCO_3$) and MeCN (10% MeCN up to 80% in 20 min); Detector, UV 254/220 nm. The product-containing fractions were combined and evaporated to afford the sub-title compound (AHN-2) (3.0 g, 7.07 mmol, 78%, 90% Purity) as a brown solid. m/z 383.0/385.0 $(M+H)^+$ (ES+).

Step 2: 2-(5-((tert-Butoxycarbonyl)(ethyl)amino)-2-chloropyridin-4-yl)-5-fluorobenzoic acid (AHN-4)

A solution of the product from step 1 above (AHN-2) (1.52 g, 1 Eq, 3.97 mmol), 4-fluoro-2-(methoxycarbonyl)phenylboronic acid (AHN-3) (1.18 g, 1.5 Eq, 5.96 mmol) and $K_2CO_3$ (220 mg, 0.4 Eq, 1.59 mmol) in DME (32 mL) and water (8 mL) at rt was placed under nitrogen atmosphere. Then $Pd(PPh_3)_4$ (918 mg, 0.2 Eq, 0.80 mmol) was added at rt under nitrogen atmosphere. The resulting mixture was stirred overnight at 100° C. under nitrogen atmosphere. The mixture was allowed to cool down to rt. The crude product was purified by reverse flash column chromatography with the following conditions: Column, C18; mobile phase, water (0.1% $NH_4HCO_3$) and MeCN (10% MeCN up to 80% in 20 min); Detector, UV 254/220 nm. The product-containing fractions were combined and evaporated to afford the sub-title compound (AHN-4) (520 mg, 1.05 mmol, 32%, 92% Purity) as a brown solid. m/z 495.1/497.1 $(M+H)^+$ (ES+).

Step 3: tert-Butyl (6-chloro-4-(4-fluoro-2-(2-(methylcarbamothioyl)hydrazine-1-carbonyl)phenyl)pyridin-3-yl)(ethyl)carbamate (AHN-5)

To a stirred solution of the product from step 2 above (AHN-4) (265 mg, 1 Eq, 0.67 mmol) and 1-amino-3-methylthiourea (D-2) (106 mg, 1.5 Eq, 1.01 mmol) in MeCN (10 mL) were added TCFH (377 mg, 2 Eq, 1.34 mmol) and NMI (441 mg, 8 Eq, 5.37 mmol) at 0° C. The resulting mixture was stirred for 3 h at rt. The mixture was concentrated in vacuo. The resulting mixture was used in the next step directly without further purification. m/z 482.1/484.1 $(M+H)^+$ (ES+)

Step 4: tert-Butyl (6-chloro-4-(4-fluoro-2-(5-mercapto-4-methyl-4H-1,2,4-triazol-3-yl)phenyl)pyridin-3-yl)(ethyl)carbamate (AHN-6)

To a stirred solution of the product from step 3 above (AHN-5) (324 mg, 1 Eq, 0.67 mmol) in MeCN (10 mL) was added NaOH (403 mg, 15 Eq, 10.1 mmol) in water (10 mL)

at rt. The resulting mixture was stirred overnight at 80° C. The mixture was cooled to rt and concentrated in vacuo. The resulting mixture was diluted with water and extracted with EtOAc (3×80 mL). The combined organic layers were washed with brine (2×80 mL), dried (Na$_2$SO$_4$). After filtration, the filtrate was concentrated in vacuo to afford the sub-title compound (AHN-6) (320 mg, crude) as a brown solid. m/z 464.1/466.1 (M+H)$^+$ (ES+).

Step 5: tert-butyl (6-chloro-4-(4-fluoro-2-(4-methyl-4H-1,2,4-triazol-3-yl)phenyl)pyridin-3-yl)(ethyl)carbamate (AHN-7)

To a stirred solution of the product from step 4 above (AHN-6) (290 mg, 1 Eq, 0.63 mmol) in DCM (20 mL) were added AcOH (75 mg, 2 Eq, 1.25 mmol) and hydrogen peroxide (284 mg, 30% Wt, 4 Eq, 2.50 mmol) at 0° C. The resulting mixture was stirred overnight at rt. The resulting mixture was concentrated in vacuo. The crude product was purified by reverse flash column chromatography with the following conditions: Column, C18; mobile phase, Water (0.1% NH$_4$HCO$_3$) and ACN (10% ACN up to 80% in 20 min); Detector, UV 254/220 nm. The product-containing fractions were combined and evaporated to afford the sub-title compound (AHN-7) (80 mg, 0.19 mmol, 30%, 95% Purity) as a brown solid. m/z 432.2/434.2 (M+H)$^+$ (ES+).

Step 6: tert-Butyl ethyl(4-(4-fluoro-2-(4-methyl-4H-1,2,4-triazol-3-yl)phenyl)-6-(6-(hydroxymethyl)-1-oxo-4-(trifluoromethyl)isoindolin-2-yl)pyridin-3-yl)carbamate (AHN-8)

To a solution of the product from step 5 above (AHN-7) (40 mg, 1 Eq, 0.09 mmol), intermediate (C-1) (26 mg, 1.2 Eq, 0.11 mmol) and Cs$_2$CO$_3$ (91 mg, 3 Eq, 0.28 mmol) in 1,4-dioxane (4 mL) were added RuPhos Palladacycle Gen.3 (16 mg, 0.2 Eq, 19 µmol) and RuPhos (17 mg, 0.4 Eq, 37 µmol) at rt under nitrogen atmosphere. The resulting mixture was stirred for 3 h at 100° C. under nitrogen atmosphere. The mixture was cooled to rt and concentrated in vacuo. The crude product was purified by reverse flash column chromatography with the following conditions: Column, C18; mobile phase, water (0.1% FA) and MeCN (10% MeCN up to 80% in 20 min); Detector, UV 254/220 nm. The product-containing fractions were combined and evaporated to afford the sub-title compound (AHN-8) (35 mg, 56 µmol, 60%, 96% Purity) as a brown solid. m/z 627.2 (M+H)$^+$ (ES+).

Step 7: 2-(5-(Ethylamino)-4-(4-fluoro-2-(4-methyl-4H-1,2,4-triazol-3-yl)phenyl)pyridin-2-yl)-6-(hydroxymethyl)-4-(trifluoromethyl)isoindolin-1-one (AHN-9)

To a stirred solution of the product from step 6 above (AHN-8) (35 mg, 1 Eq, 56 µmol,) in DCM (2 mL) was added TFA (0.4 mL) at 0° C. The resulting mixture was stirred overnight at rt. The resulting mixture was concentrated in vacuo. The crude product was purified by Prep-HPLC with the following conditions (Column: XBridge Prep OBD C18 Column, 30*150 mm, 5 µm; Mobile Phase A: water (0.1% NH$_4$HCO$_3$), Mobile Phase B: MeCN; Flow rate: 60 mL/min; Gradient: 36% B to 46% B in 9 min; Wave Length: 254/220 nm; RT: 8.05). The product-containing fractions were combined and evaporated partially in vacuo and lyophilized overnight to afford the title compound (AHN-9) (10.9 mg, 21 µmol, 36%, 97.2% Purity) as a white solid. m/z 527.2 (M+H)$^+$ (ES+). $^1$H NMR (300 MHz, Methanol-d4) δ 8.39 (s, 1H), 7.97 (t, J=14.5 Hz, 3H), 7.79 (s, 1H), 7.71-7.63 (m, 1H), 7.55-7.45 (m, 2H), 5.16 (s, 2H), 4.77 (s, 2H), 3.57 (s, 3H), 3.20-3.01 (m, 2H), 1.16 (t, J=7.1 Hz, 3H).

Example 244: Synthesis of 2-{6-Cyclopropyl-4-[4-fluoro-2-(4-methyl-1,2,4-triazol-3-yl)phenyl]pyridin-2-yl}-6-({[(2R)-1-methylpyrrolidin-2-yl]methoxy}methyl)-4-(trifluoromethyl)-3H-isoindol-1-one (AHO-4)

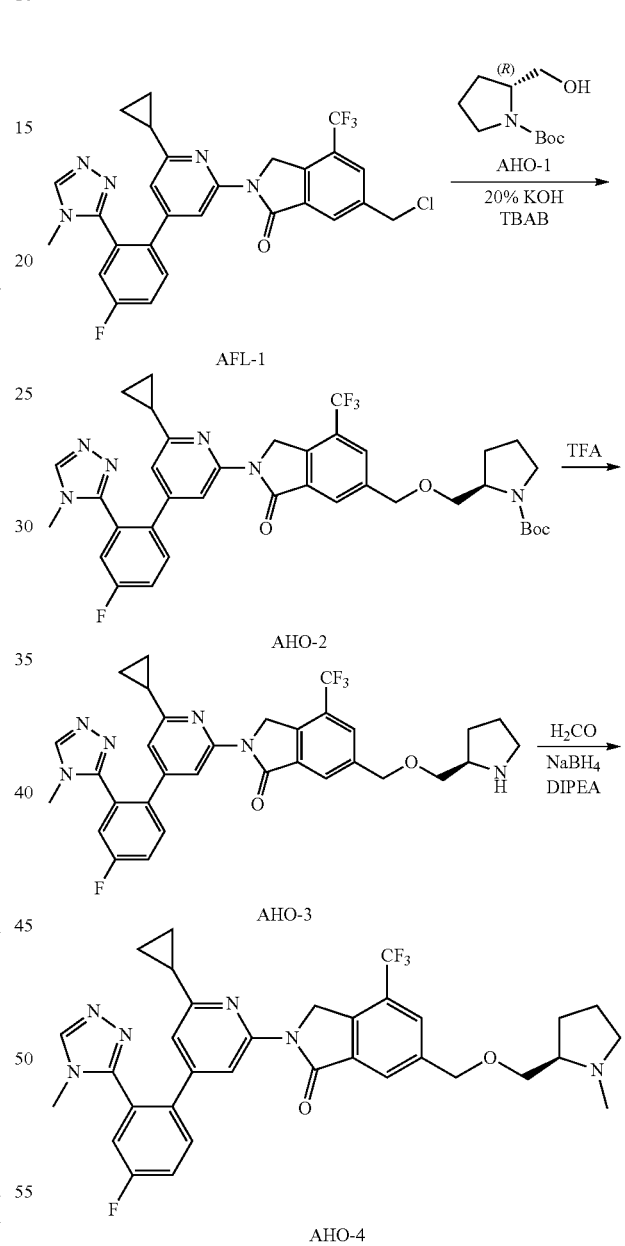

Step 1: tert-Butyl (2R)-2-{[(2-{6-cyclopropyl-4-[4-fluoro-2-(4-methyl-1,2,4-triazol-3-yl)phenyl]pyridin-2-yl}-3-oxo-7-(trifluoromethyl)-1H-isoindol-5-yl)methoxy]methyl}pyrrolidine-1-carboxylate (AHO-2)

To a stirred solution of intermediate (AFL-1) (100 mg, 1 Eq, 0.18 mmol) and tert-butyl (2R)-2-(hydroxymethyl)pyrrolidine-1-carboxylate (AHO-1) (371 mg, 10 Eq, 1.85 mmol) in DCM (5 mL) were added TBAB (30 mg, 0.5 Eq, 92 µmol) and aq. KOH (5 mL, 20% Wt) at rt. The resulting mixture was stirred for 1 h at rt. The resulting mixture was diluted with water and extracted with EtOAc (3×10 mL). The combined organic layers were washed with brine (2×10 mL), dried (Na$_2$SO$_4$). After filtration, the filtrate was concentrated in vacuo The combined organic layer was washed with brine, dried (Na$_2$SO$_4$) and concentrated in vacuo. The crude product was purified by reverse flash column chromatography with the following conditions: Column, C18; mobile phase, water (0.1% NH$_4$HCO$_3$) and MeCN (50% MeCN up to 75% in 10 min); Detector, UV 254/220 nm. This resulted in the sub-title compound (AHO-2) (64 mg, 91 µmol, 49%, 92% Purity) as a white solid. m/z 707.3 (M+H)$^+$ (ES+).

Step 2: 2-{6-Cyclopropyl-4-[4-fluoro-2-(4-methyl-1,2,4-triazol-3-yl)phenyl]pyridin-2-yl}-6-{[(2R)-pyrrolidin-2-ylmethoxy]methyl}-4-(trifluoromethyl)-3H-isoindol-1-one (AHO-3)

A solution of the product from step 1 above (AHO-2) (60 mg, 1 Eq, 85 µmol) and TFA (4 mL) in DCM (4 mL) was stirred for 2 h at 60° C. The mixture was allowed to cool down to rt and concentrated in vacuo. The crude product was used in the next step directly without further purification. m/z 607.2 (M+H)$^+$ (ES+).

Step 3: 2-{6-Cyclopropyl-4-[4-fluoro-2-(4-methyl-1,2,4-triazol-3-yl) phenyl] pyridin-2-yl}-6-({[(2R)-1-methylpyrrolidin-2-yl]methoxy}methyl)-4-(trifluoromethyl)-3H-isoindol-1-one (AHO-4)

To a stirred solution of the product from step 2 above (AHO-3) (58 mg, 1 Eq, 96 µmol) and formaldehyde (9 mg, 1.2 Eq, 0.12 mmol) in MeOH (5 mL) were added DIPEA (37 mg, 3 Eq, 0.29 mmol) and NaBH$_4$ (12 mg, 2 Eq, 0.19 mmol) at rt. The resulting mixture was stirred for 1 h at rt. The reaction was then quenched by the addition of 2 mL of MeOH at 0° C. and then concentrated in vacuo. The residue was purified by Prep-TLC with DCM/MeOH (12/1). The crude product was purified by Prep-HPLC with the following conditions (Column: Sunfire prep C18 column, 30*150 mm, 5 µm; Mobile Phase A: water (0.1% FA), Mobile Phase B: MeCN; Flow rate: 60 mL/min; Gradient: 14% B to 34% B in 10 min; Wave Length: 254/220 nm) to afford the title compound (AHO-4) (2.5 mg, 4.0 µmol, 4.2%, 99.3% Purity) as a white solid. m/z 621.2 (M+H)$^+$ (ES+). $^1$H NMR (400 MHz, DMSO-d6) δ 8.50 (s, 1H), 8.06-7.92 (m, 3H), 7.75-7.68 (m, 1H), 7.65-7.51 (m, 2H), 6.79 (s, 1H), 5.17 (s, 2H), 4.70 (s, 2H), 3.57-3.49 (m, 1H), 3.41 (s, 4H), 2.96-2.88 (m, 1H), 2.40 (t, J=7.0 Hz, 1H), 2.31 (s, 3H), 2.18-2.09 (m, 1H), 2.08-1.99 (m, 1H), 1.95-1.82 (m, 1H), 1.69-1.58 (m, 2H), 1.56-1.45 (m, 1H), 1.01-0.86 (m, 4H).

Example 245: Synthesis of 4-(2-Cyclopropyl-6-(6-(((1-hydroxycyclobutyl)methoxy)methyl)-1-oxo-4-(trifluoromethyl)isoindolin-2-yl)pyridin-4-yl)-3-(4-methyl-4H-1,2,4-triazol-3-yl)benzonitrile (AHP-1)

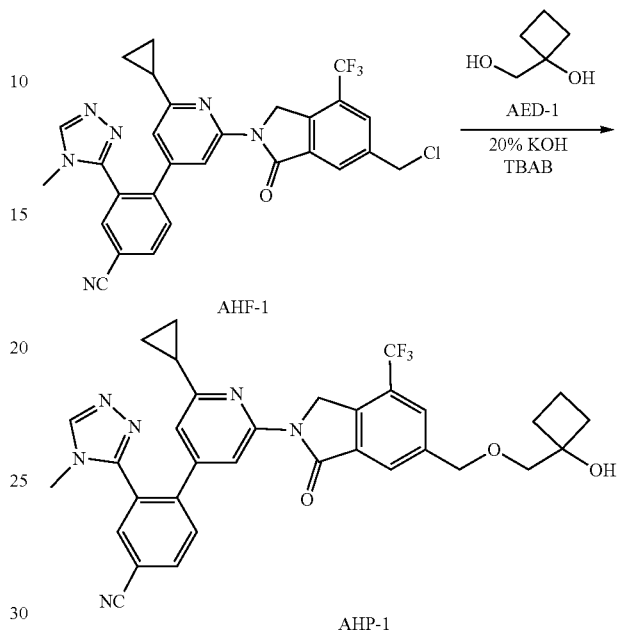

To a stirred solution of intermediate (AHF-1) (60 mg, 1 Eq, 0.11 mmol) and 1-(hydroxymethyl) cyclobutan-1-ol (AED-1) (112 mg, 10 Eq, 1.09 mmol) in DCM (5 mL) were added TBAB (18 mg, 0.5 Eq, 54 µmol) and aq. KOH (5 mL, 20% Wt) at rt. The resulting mixture was stirred slowly for 1 h at rt. The mixture was diluted with water and extracted with EtOAc. The resulting mixture was diluted with water and extracted with EtOAc (3×10 mL). The combined organic layers were washed with brine (2×10 mL), dried (Na$_2$SO$_4$). After filtration, the filtrate was concentrated in vacuo. The crude product was purified by reverse flash column chromatography with the following conditions: Column, C18; mobile phase, water (0.1% NH$_4$HCO$_3$) and MeCN (60% MeCN up to 75% in 10 min); Detector, UV 254/220 nm. The crude product was purified by Prep-HPLC with the following conditions (Column: XBridge Prep OBD C18 Column, 30*150 mm, 5 µm; Mobile Phase A: water (0.1% NH$_4$HCO$_3$), Mobile Phase B: MeCN; Flow rate: 60 mL/min; Gradient: 52% B to 57% B in 8 min; Wave Length: 254/220 nm) to afford the title compound (AHP-1) (11.3 mg, 18 µmol, 16.7%, 99.3%) as a white solid. m/z 615.2 (M+H)$^+$ (ES+). $^1$H NMR (400 MHz, DMSO-d6) δ 8.53 (s, 1H), 8.25-8.20 (m, 2H), 8.09-7.96 (m, 3H), 7.87 (d, J=8.4 Hz, 1H), 6.89 (s, 1H), 5.18-5.08 (m, 3H), 4.76 (s, 2H), 3.53-3.42 (m, 5H), 2.11-2.01 (m, 3H), 1.99-1.88 (m, 2H), 1.73-1.61 (m, 1H), 1.56-1.42 (m, 1H), 1.06-0.90 (m, 4H).

Example 246: Synthesis of 2-(6-Ethoxy-4-(4-fluoro-2-(4-methyl-4H-1,2,4-triazol-3-yl)phenyl)pyridin-2-yl)-6-((2-hydroxyethoxy)methyl)-4-(trifluoromethyl)isoindolin-1-one (AHQ-4)
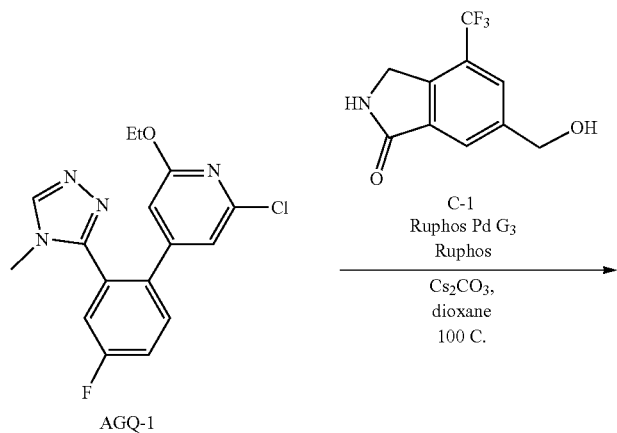
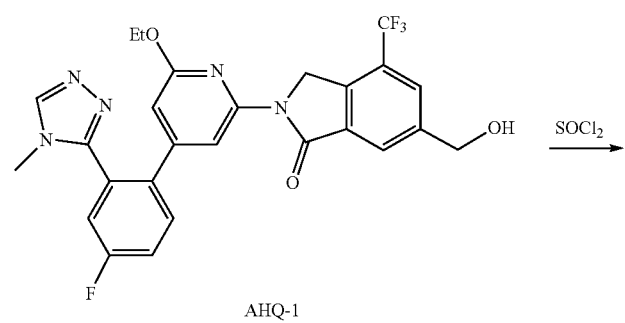
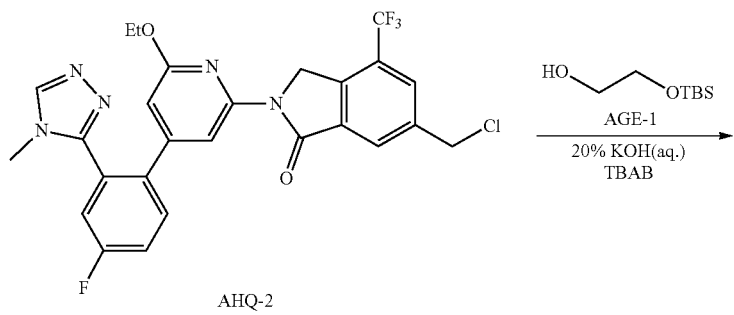
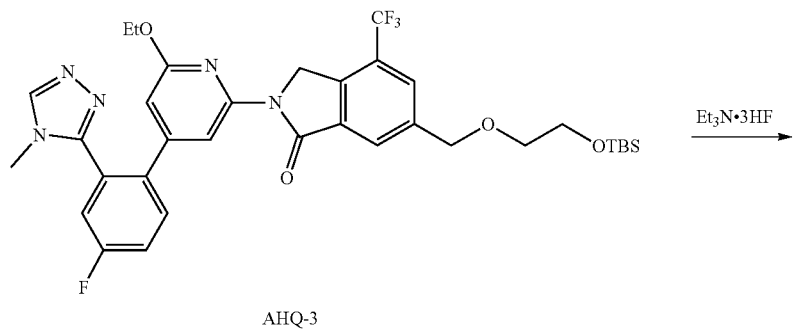

-continued

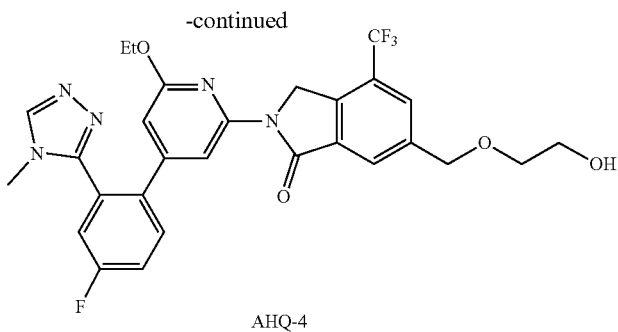

AHQ-4

Step 1: 2-(6-Ethoxy-4-(4-fluoro-2-(4-methyl-4H-1,2,4-triazol-3-yl)phenyl)pyridin-2-yl)-6-(hydroxymethyl)-4-(trifluoromethyl)isoindolin-1-one (AHQ-1)

A stirred solution of intermediate (AGQ-1) (100 mg, 1 Eq, 0.30 mmol), intermediate (C-1) (76 mg, 1.1 Eq, 0.33 mmol) and $Cs_2CO_3$ (196 mg, 2 Eq, 0.60 mmol) in dioxane (10 mL) at rt was placed under nitrogen atmosphere. To the above mixture was added RuPhos (56 mg, 0.4 Eq, 0.12 mmol) and RuPhos Palladacycle Gen.3 (50 mg, 0.2 Eq, 0.06 mmol) at rt under nitrogen atmosphere. The resulting mixture was stirred for 1 h at 100° C. under nitrogen atmosphere. The mixture was cooled to rt and concentrated in vacuo. T The residue was purified by Prep-TLC with DCM/MeOH (10/1) to afford the sub-title compound (AHQ-1) (80 mg, 0.15 mmol, 45%, 92% Purity) as an off-white solid. m/z 528.2 $(M+H)^+$ (ES+).

Step 2: 6-(Chloromethyl)-2-(6-ethoxy-4-(4-fluoro-2-(4-methyl-4H-1,2,4-triazol-3-yl)phenyl)pyridin-2-yl)-4-(trifluoromethyl)isoindolin-1-one (AHQ-2)

To a stirred solution of the product from step 1 above (AHQ-1) (30 mg, 1 Eq, 57 µmol) in DCM (6 mL) was added $SOCl_2$ (10 mg, 1.5 Eq, 86 µmol) dropwise at 0° C. The resulting mixture was stirred for 1 h at rt. The reaction was then quenched by the addition of 2 mL of MeOH at 0° C. The mixture was concentrated in vacuo. The residue was purified by Prep-TLC with DCM/MeOH (10/1) to afford the sub-title compound (AHQ-2) (27 mg, 5.0 µmol, 87%, 95% Purity) as a yellow solid. m/z 546.1/548.1 $(M+H)^+$ (ES+).

Step 3: 6-((2-((tert-Butyldimethylsilyl)oxy)ethoxy)methyl)-2-(6-ethoxy-4-(4-fluoro-2-(4-methyl-4H-1,2,4-triazol-3-yl)phenyl)pyridin-2-yl)-4-(trifluoromethyl)isoindolin-1-one (AHQ-3)

A stirred solution of the product from step 2 above (AHQ-2) (70 mg, 1 Eq, 0.13 mmol) and 2-[(tert-butyldimethylsilyl)oxy]ethanol (AGE-1) (27 mg, 1.2 Eq, 0.15 mmol) in DCM (6 mL) were added TBAB (21 mg, 0.5 Eq, 64 µmol) and aq. KOH (6 mL, 20% Wt) and the resulting mixture was stirred for 2 h at rt under nitrogen atmosphere. The resulting mixture was diluted with water and extracted with EtOAc (3×10 mL). The combined organic layers were washed with brine (2×10 mL), dried ($Na_2SO_4$). After filtration, the filtrate was concentrated in vacuo the crude product was purified by reverse flash column chromatography with the following conditions: Column, C18; mobile phase, water (0.1% $NH_4HCO_3$) and MeCN (10% MeCN up to 50% in 10 min); Detector, UV 254/220 nm to afford the sub-title compound (AHQ-3) (22 mg, 32 µmol, 25%, 96% Purity) as a white solid. m/z 686.3 $(M+H)^+$ (ES+).

Step 4: 2-(6-Ethoxy-4-(4-fluoro-2-(4-methyl-4H-1,2,4-triazol-3-yl)phenyl)pyridin-2-yl)-6-((2-hydroxyethoxy)methyl)-4-(trifluoromethyl)isoindolin-1-one (AHQ-4)

To a stirred solution of the product from step 3 (AHQ-3) (22 mg, 1 Eq, 32 µmol) in THF (3 mL) was added $Et_3N.3HF$ (6 mg, 1.2 Eq, 38 µmol) dropwise at rt. The resulting mixture was stirred for 2 h at rt under nitrogen atmosphere. The resulting mixture was diluted with water and extracted with EtOAc (3×10 mL). The combined organic layers were washed with brine (2×10 mL), dried ($Na_2SO_4$). After filtration, the filtrate was concentrated in vacuo. The residue was purified by Prep-HPLC with the following conditions (Column: XBridge Prep OBD C18 Column, 30*150 mm, 5 µm; Mobile Phase A: water (0.1% $NH_4HCO_3$), Mobile Phase B: MeCN; Flow rate: 60 mL/min; Gradient: 40% B to 60% B in 8 min; Wave Length: 254/220 nm; RT: 7.8) to afford the title compound (AHQ-4) (3.7 mg, 6.5 µmol, 6.3%, 98.5% Purity) as a white solid. m/z 572.2 $(M+H)^+$ (ES+). $^1$H NMR (400 MHz, DMSO-d6) δ 8.51 (s, 1H), 8.05 (s, 1H), 8.00 (s, 1H), 7.80 (s, 1H), 7.71 (s, 1H), 7.64-7.55 (m, 2H), 6.34 (s, 1H), 5.22 (s, 2H), 4.77-4.69 (m, 3H), 4.32-4.29 (m, 2H), 3.63-3.51 (m, 4H), 3.44 (s, 3H), 1.35-1.41 (m, 3H).

Example 247: Synthesis of (S)-2-(6-Cyclopropyl-4-(4-fluoro-2-(4-methyl-4H-1,2,4-triazol-3-yl)phenyl)pyridin-2-yl)-6-(((1-methylpyrrolidin-2-yl)methoxy)methyl)-4-(trifluoromethyl)isoindolin-1-one (AHR-4)

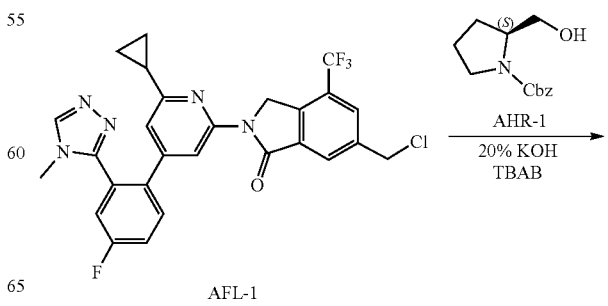

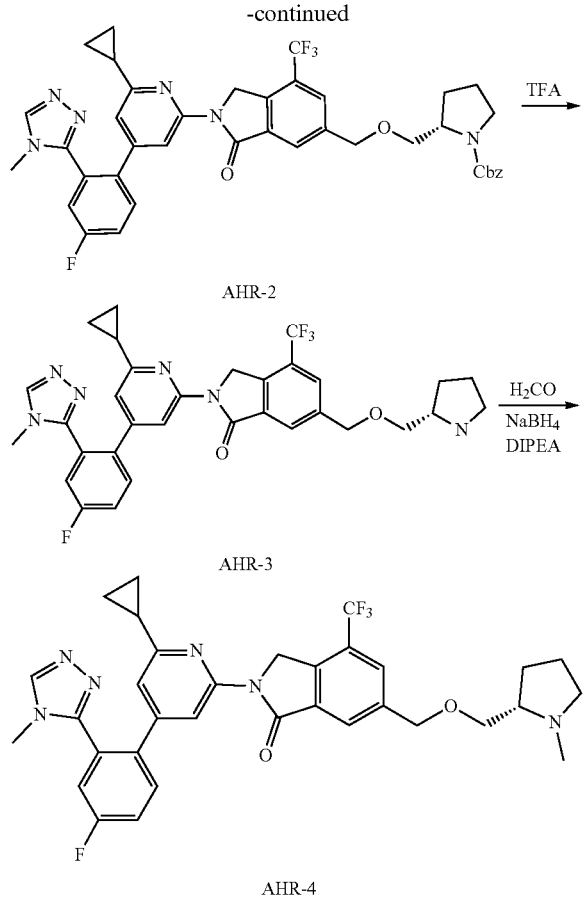

AHR-2

AHR-3

AHR-4

Step 1: Benzyl (S)-2-(((2-(6-cyclopropyl-4-(4-fluoro-2-(4-methyl-4H-1,2,4-triazol-3-yl)phenyl)pyridin-2-yl)-3-oxo-7-(trifluoromethyl)isoindolin-5-yl)methoxy)methyl)pyrrolidine-1-carboxylate (AHR-2)

To a stirred solution of Intermediate (AFL-1) (60 mg, 1 Eq, 0.11 mmol) and benzyl (2S)-2-(hydroxymethyl) pyrrolidine-1-carboxylate (AHR-1) (261 mg, 10 Eq, 1.11 mmol) in DCM (5 mL) were added TBAB (18 mg, 0.5 Eq, 56 μmol) and aq. KOH (5 mL, 20% Wt) and the resulting mixture was stirred for 1 h at rt. The mixture was then diluted with water and extracted with EtOAc (3×20 mL). The combined organic layers were washed with brine (2×20 mL), dried (Na$_2$SO$_4$). After filtration, the filtrate was concentrated in vacuo. The crude product was purified by reverse flash column chromatography with the following conditions: Column, C18; mobile phase, water (0.1% NH$_4$HCO$_3$) and MeCN (55% MeCN up to 60% in 20 min); Detector, UV 254/220 nm. This resulted in the sub-title compound (AHR-2) (45 mg, 61 μmol, 55%, 95% Purity) as a yellow solid. m/z 741.3 (M+H)$^+$ (ES+).

Step 2: (S)-2-(6-cyclopropyl-4-(4-fluoro-2-(4-methyl-4H-1,2,4-triazol-3-yl)phenyl)pyridin-2-yl)-6-((pyrrolidin-2-ylmethoxy)methyl)-4-(trifluoromethyl)isoindolin-1-one (AHR-3)

A solution of the product from step 1 above (AHR-2) (40 mg, 1 Eq, 54 μmol) and TFA (5 mL) in DCM (5 mL) was stirred for 4 h at 60° C. The mixture was allowed to cool down to rt and then concentrated in vacuo. The crude product was used in the next step directly without further purification. m/z 607.2 (M+H)$^+$ (ES+).

Step 3: (S)-2-(6-Cyclopropyl-4-(4-fluoro-2-(4-methyl-4H-1,2,4-triazol-3-yl)phenyl)pyridin-2-yl)-6-(((1-methylpyrrolidin-2-yl)methoxy)methyl)-4-(trifluoromethyl)isoindolin-1-one (AHR-4)

To a stirred solution of the product from step 2 above (AHR-3) (40 mg, 1 Eq, 66 μmol) and formaldehyde (5.9 mg, 1.2 Eq, 79 μmol) in MeOH (5 mL) were added DIPEA (26 mg, 3 Eq, 0.20 mmol) and NaBH$_4$ (8.3 mg, 2 Eq, 0.13 mmol) at rt and the resulting mixture was stirred for 1 h at rt. The reaction was then quenched by the addition of 2 mL of MeOH at 0° C. and then concentrated in vacuo. The residue was purified by Prep-TLC with DCM/MeOH (12/1). The crude product was purified by Prep-HPLC with the following conditions (Column: XBridge Shield RP18 OBD Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 35% B to 53% B in 10 min, 53% B; Wave Length: 254/220 nm) to afford the title compound (AHR-4) (7.1 mg, 11 μmol, 17%, 99.4% Purity) as a white solid. m/z 621.2 (M+H)$^+$ (ES+). $^1$H NMR (400 MHz, DMSO-d6) δ 8.50 (s, 1H), 8.05-7.93 (m, 3H), 7.76-7.69 (m, 1H), 7.66-7.55 (m, 2H), 6.79 (d, J=1.4 Hz, 1H), 5.17 (s, 2H), 4.70 (s, 2H), 3.57-3.52 (m, 1H), 3.41 (s, 3H), 3.40-3.36 (m, 1H), 2.98-2.88 (m, 1H), 2.46-2.37 m, 1H), 2.31 (s, 3H), 2.21-2.10 (m, 1H), 2.10-1.99 (m, 1H), 1.95-1.85 (m, 1H), 1.72-1.60 (m, 2H), 1.57-1.47 (m, 1H), 1.02-0.83 (m, 4H).

Example 248: Synthesis of 4-(2-Ethoxy-6-(6-(((2-methoxyethyl)amino)methyl)-1-oxoisoindolin-2-yl)pyridin-4-yl)-3-(4-methyl-4H-1,2,4-triazol-3-yl)benzonitrile (AHS-2)

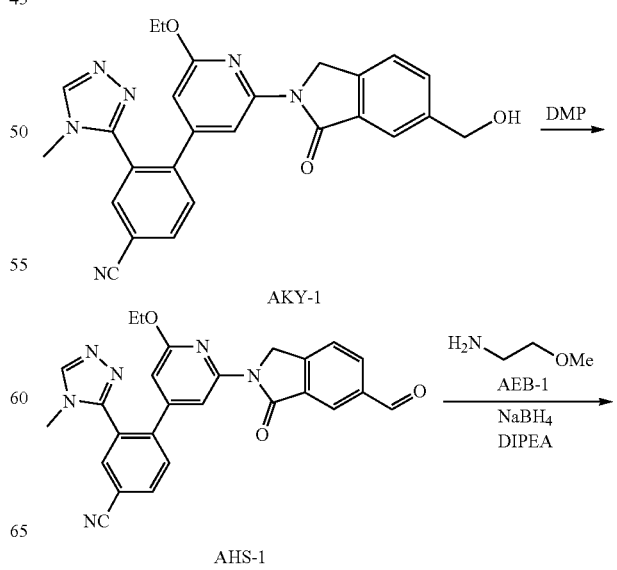

AKY-1

AHS-1

-continued

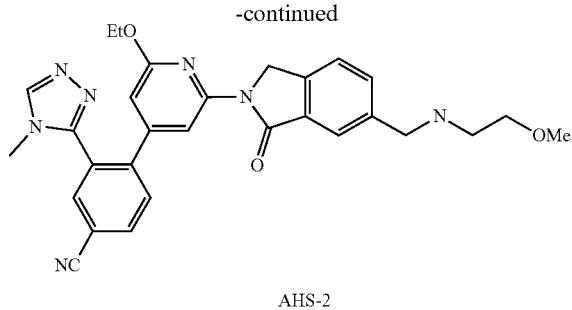

AHS-2

Step 1: 4-(2-ethoxy-6-(6-formyl-1-oxoisoindolin-2-yl)pyridin-4-yl)-3-(4-methyl-4H-1,2,4-triazol-3-yl)benzonitrile (AHS-1)

A solution of intermediate (AKY-1) (20 mg, 1 Eq, 43 μmol) and DMP (27 mg, 1.5 Eq, 65 μmol) in DCM (8 mL) was stirred for 1 h at rt. The crude product used directly in next step without any further purification. m/z 465.2 (M+H)$^+$ (ES+).

Step 2: 4-(2-Ethoxy-6-(6-(((2-methoxyethyl)amino)methyl)-1-oxoisoindolin-2-yl)pyridin-4-yl)-3-(4-methyl-4H-1,2,4-triazol-3-yl)benzonitrile (AHS-2)

A solution of the product from step 1 above (AHS-1) (20 mg, 1 Eq, 43 μmol), 2-methoxyethan-1-amine (AEB-1) (5 mg, 1.5 Eq, 65 μmol) and DIPEA (17 mg, 3 Eq, 0.13 mmol) in DCM (8 mL) was stirred for 2 h at rt. To the above mixture was added NaBH$_4$ (8 mg, 5 Eq, 0.22 mmol) at 0° C. The resulting mixture was stirred overnight at rt. The reaction was then quenched by the addition of 2 mL of MeOH at 0° C. The mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 33% B to 43% B in 9 min; Wave Length: 254/220 nm; RT: 8.28) to afford the title compound (AHS-2) (4.0 mg, 7.6 μmol, 17%, 97.2% Purity) as a white solid. m/z 524.1 (M+H)$^+$ (ES+). $^1$H NMR (400 MHz, DMSO-d6) δ 8.54 (s, 1H), 8.23-8.14 (m, 2H), 7.85 (d, J=8.5 Hz, 1H), 7.81 (d, J=1.2 Hz, 1H), 7.75 (s, 1H), 7.64 (d, J=1.2 Hz, 2H), 6.37 (d, J=1.2 Hz, 1H), 5.05 (s, 2H), 4.39-4.31 (m, 2H), 3.82 (s, 2H), 3.48 (s, 3H), 3.40 (t, J=5.7 Hz, 2H), 3.24 (s, 3H), 2.63 (t, J=5.7 Hz, 2H), 1.35 (t, J=7.0 Hz, 3H).

Example 249: Synthesis of 2-(4-(4-Chloro-2-(4-methyl-4H-1,2,4-triazol-3-yl)phenyl)-6-ethoxypyridin-2-yl)-6-((((1-hydroxycyclobutyl)methyl)amino)methyl)isoindolin-1-one (AHT-2)

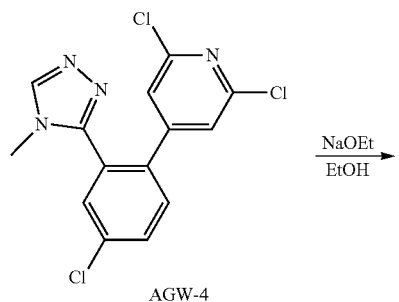

AGW-4

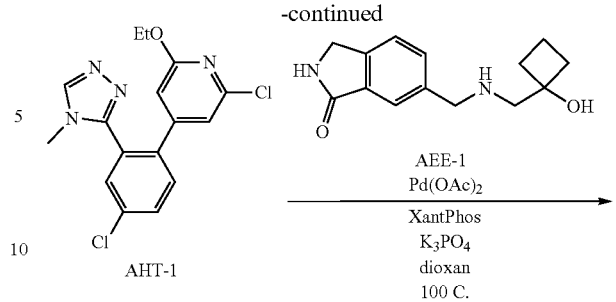

AHT-1

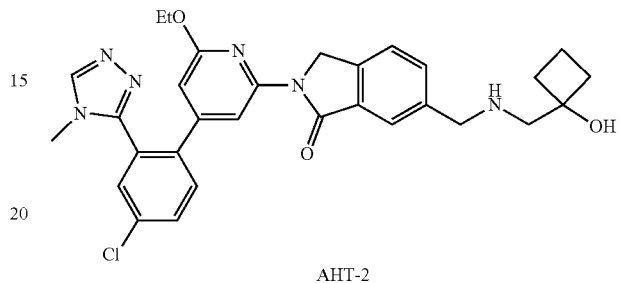

AHT-2

Step 1: 2-Chloro-4-[4-chloro-2-(4-methyl-1,2,4-triazol-3-yl)phenyl]-6-ethoxypyridine (AHT-1)

Into a 25 mL round-bottom flask were added intermediate (AGW-4) (200 mg, 1 Eq, 0.59 mmol) in EtOH (10 mL) at rt. To the above stirred solution was added EtONa (60 mg, 1.5 Eq, 0.88 mmol) at rt. The resulting mixture was stirred for additional 2 h at rt. The precipitated solids were collected by filtration and washed with toluene (3×10 mL) to afford the sub-title compound (AHT-1) (120 mg, 0.13 mmol, 58%, 95% Purity) as a light yellow solid. m/z 349.1/351.1 (M+H)$^+$ (ES+)

Step 2: 2-(4-(4-Chloro-2-(4-methyl-4H-1,2,4-triazol-3-yl)phenyl)-6-ethoxypyridin-2-yl)-6-((((1-hydroxycyclobutyl)methyl)amino)methyl)isoindolin-1-one (AHT-2)

To a stirred mixture of the product from step 1 above (AHT-1) (100 mg, 1 Eq, 0.29 mmol), intermediate (AEE-1) (85 mg, 1.2 Eq, 0.34 mmol) and K$_2$CO$_3$ (119 mg, 3 Eq, 0.86 mmol) in dioxane (10 mL) were added XantPhos (331 mg, 2 Eq, 0.57 mmol) at rt under nitrogen atmosphere. The resulting mixture was stirred for 2 h at 60° C. under nitrogen atmosphere. The mixture was cooled to rt, diluted with water and extracted with EtOAc (3×50 mL). The combined organic layers were washed with brine (2×50 mL), dried (Na$_2$SO$_4$). After filtration, the filtrate was concentrated in vacuo. The residue was purified by Prep-TLC with EtOAc/petroleum ether (5/1). The crude product was purified by Prep-HPLC with the following conditions (Column: Sunfire prep C18 column, 30*150 mm, 5 μm; Mobile Phase A: water (0.1% FA), Mobile Phase B: MeCN; Flow rate: 60 mL/min; Gradient: 20% B to 50% B in 7 min; Wave Length: 254/220 nm; RT: 6.63) to afford the title compound (AHT-2) (24 mg, 4.3 μmol, 14%, 98.7% Purity) as a white solid. m/z 559.1/561.1 (M+H)$^+$ (ES+). $^1$H NMR (400 MHz, Methanol-d4) δ 8.53 (s, 0.858H), 8.45 (s, 1H), 7.98-7.65 (m, 7H), 6.40 (d, J=1.3 Hz, 1H), 5.10 (s, 2H), 4.43-4.33 (m, 2H), 4.23 (s, 2H), 3.47 (s, 3H), 3.00 (s, 2H), 2.16-2.08 (m, 4H), 1.81-1.69 (m, 1H), 1.61-1.50 (m, 1H), 1.38 (t, J=7.0 Hz, 3H).

Example 250: Synthesis of 2-[6-(Ethylamino)-4-[2-(4-methyl-1,2,4-triazol-3-yl)-4-(prop-2-yn-1-yloxy)phenyl]pyridin-2-yl]-4-(trifluoromethyl)-3H-isoindol-1-one (AHU-12)
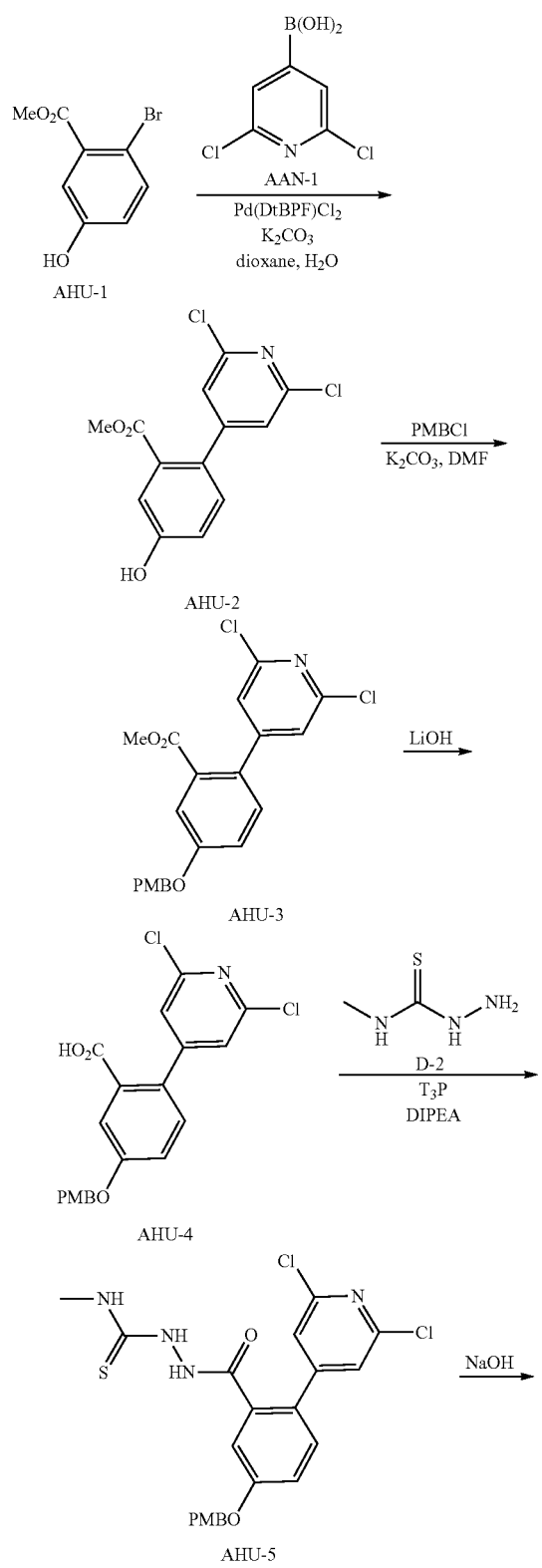
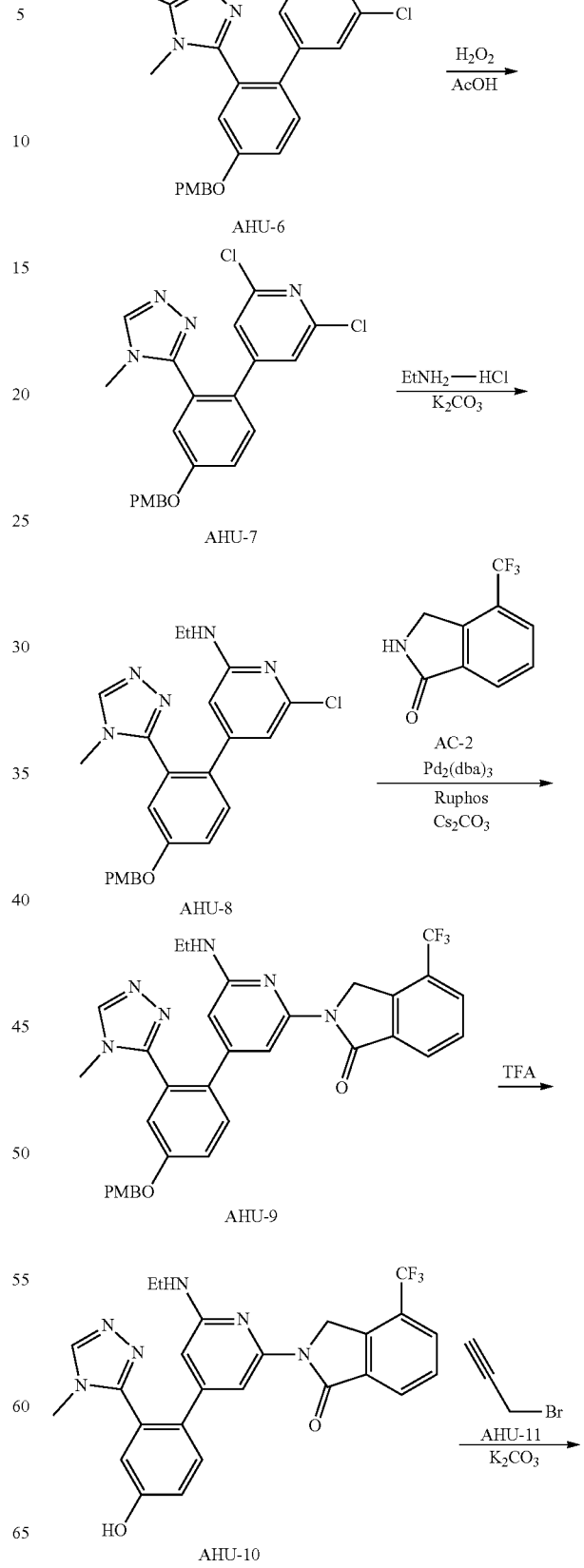

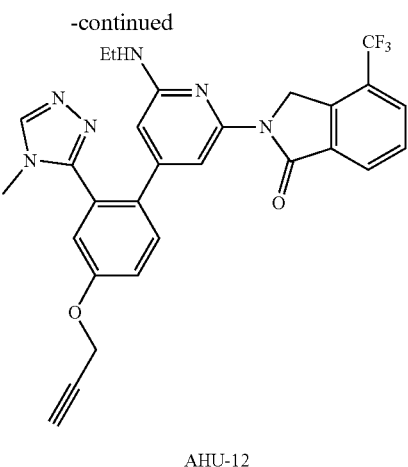

AHU-12

Step 1: Methyl 2-(2,6-dichloropyridin-4-yl)-5-hydroxybenzoate (AHU-2)

To a stirred solution of methyl 2-bromo-5-hydroxybenzoate (AHU-1) (1.4 g, 1 Eq, 6.06 mmol), 2,6-dichloropyridin-4-ylboronic acid (AAN-1) (1.74 g, 1.5 Eq, 9.09 mmol) and $K_2CO_3$ (2.51 g, 3 Eq, 18.2 mmol) in dioxane (20 mL) and water (2 mL) was added Pd(DtBPF)Cl$_2$ (395 mg, 0.1 Eq, 0.61 mmol) at rt under nitrogen atmosphere. The resulting mixture was stirred for 3 h at 100° C. under nitrogen atmosphere. The mixture was allowed to cool down to rt. The resulting mixture was concentrated in vacuo. The residue was applied on a silica gel column chromatography with petroleum ether/EtOAc (3/1) to afford the sub-title compound (AHU-2) (1.2 g, 4.04 mmol, 66%, 92% Purity) as a brown-yellow solid. m/z 298.0/300.0 (M+H)$^+$ (ES+)

Step 2: Methyl 2-(2,6-dichloropyridin-4-yl)-5-[(4-methoxyphenyl)methoxy]benzoate (AHU-3)

To a stirred solution of the product from step 1 above (AHU-2) (1.2 g, 1 Eq, 4.03 mmol) and $K_2CO_3$ (1.67 g, 3 Eq, 12.1 mmol) in DMF (20 mL) was added PMB-Cl (0.95 g, 1.5 Eq, 6.04 mmol) and the resulting mixture was stirred overnight at rt. The resulting mixture was diluted with water and extracted with EtOAc (3×100 mL). The combined organic layers were washed with brine (2×100 mL), dried ($Na_2SO_4$). After filtration, the filtrate was concentrated in vacuo. The residue was applied on a silica gel column chromatography with petroleum ether/EtOAc (4/1) to afford the sub-title compound (AHU-3) (1.3 g, 3.12 mmol, 77%, 92% Purity) as a yellow oil. m/z 418.1/420.1 (M+H)$^+$ (ES+)

Step 3: 2-(2,6-Dichloropyridin-4-yl)-5-[(4-methoxyphenyl)methoxy]benzoic acid (AHU-4)

To a stirred solution of the product from step 2 above (AHU-3) (1.3 g, 1 Eq, 3.11 mmol) and LiOH (372 mg, 5 Eq, 15.5 mmol) in THF (15 mL) and water (5 mL) and the resulting mixture was stirred overnight at 60° C. The mixture was allowed to cool down to rt. The resulting mixture was concentrated in vacuo. The crude product was purified by reverse flash column chromatography with the following conditions: Column, C18; mobile phase, water (0.1% $NH_4HCO_3$) and MeCN (0% MeCN up to 50% in 10 min); Detector, UV 254/220 nm. This resulted in the sub-title compound (AHU-4) (1.1 g, 2.72 mmol, 88%, 91% Purity) as an off-white solid. m/z 404.0/406.0 (M+H)$^+$ (ES+)

Step 4: 2-(2,6-Dichloropyridin-4-yl)-5-[(4-methoxyphenyl)methoxy]-N-[(methylcarbamothioyl)amino]benzamide (AHU-5)

To a stirred solution of the product from step 3 above (AHU-4) (1.1 g, 1 Eq, 2.72 mmol) and 4-methyl-3-thiosemicarbazide (D-2) (315 mg, 1.1 Eq, 2.99 mmol) in DMF (15 mL) was added $T_3P$ (6.93 g, 8 Eq, 21.8 mmol) and DIPEA (2.11 g, 6 Eq, 16.3 mmol) and the resulting mixture was stirred for 2 h at rt. The crude product was purified by reverse flash column chromatography with the following conditions: Column, C18; mobile phase, water (0.1% $NH_4HCO_3$) and MeCN (0% MeCN up to 50% in 15 min); Detector, UV 254/220 nm. This resulted in the sub-title compound (AHU-5) (480 mg, 0.98 mmol, 36%, 89% Purity) as an off-white solid. m/z 491.1/493.1 (M+H)$^+$ (ES+)

Step 5: 5-[2-(2,6-Dichloropyridin-4-yl)-5-[(4-methoxyphenyl)methoxy]phenyl]-4-methyl-1,2,4-triazole-3-thiol (AHU-6)

A solution of the product from step 4 above (AHU-5) (480 mg, 1 Eq, 0.98 mmol) in aq. NaOH (10 mL, 1 M) was stirred at rt for 2 h at 80° C. The mixture was allowed to cool down to rt and concentrated in vacuo. The crude product was purified by reverse flash column chromatography with the following conditions: Column, C18; mobile phase, water (0.1% $NH_4HCO_3$) and MeCN (0% MeCN up to 50% in 30 min); Detector, UV 254/220 nm. This resulted in the sub-title compound (AHU-6) (360 mg, 0.76 mmol, 78%, 90% Purity) as an off-white solid. m/z 473.1/475.1 (M+H)$^+$ (ES+)

Step 6: 2,6-Dichloro-4-{4-[(4-methoxyphenyl)methoxy]-2-(4-methyl-1,2,4-triazol-3-yl)phenyl}pyridine (AHU-7)

A solution of the product from step 5 above (AHU-6) (350 mg, 1 Eq, 0.74 mmol) and AcOH (89 mg, 2 Eq, 1.48 mmol), $H_2O_2$ (126 mg, 30% Wt, 5 Eq, 3.70 mmol) in DCM (10 mL) was stirred for 2 h at rt. The crude product was purified by reverse flash column chromatography with the following conditions: Column, C18; mobile phase, water (0.1% $NH_4HCO_3$) and MeCN (0% MeCN up to 50% in 20 min); Detector, UV 254/220 nm. This resulted in the sub-title compound (AHU-7) (230 mg, 0.52 mmol, 70%, 95% Purity) as an off-white solid. m/z 441.1/443.1 (M+H)$^+$ (ES+)

Step 7: 6-Chloro-N-ethyl-4-{4-[(4-methoxyphenyl)methoxy]-2-(4-methyl-1,2,4-triazol-3-yl)phenyl}pyridin-2-amine (AHU-8)

A solution of the product from step 6 above (AHU-7) (220 mg, 1 Eq, 0.50 mmol) and ethylamine, HCl (31 mg, 30 Eq, 0.69 mmol), $K_2CO_3$ (2.07 g, 30 Eq, 150 mmol) in NMP (15 mL) was stirred for 3 h at 120° C. The mixture was allowed to cool down to rt. The crude product was purified by reverse flash column chromatography with the following conditions: Column, C18; mobile phase, water (0.1% $NH_4HCO_3$) and MeCN (0% MeCN up to 50% in 20 min); Detector, UV 254/220 nm. This resulted in the sub-title compound (AHU-8) (170 mg, 0.38 mmol, 76%, 95% Purity) as an off-white solid. m/z 450.2/452.2 (M+H)$^+$ (ES+)

Step 8: 2-[6-(Ethylamino)-4-{4-[(4-methoxyphenyl)methoxy]-2-(4-methyl-1,2,4-triazol-3-yl)phenyl}pyridin-2-yl]-4-(trifluoromethyl)-3H-isoindol-1-one (AHU-9)

To a stirred solution of the product from step 7 above (AHU-8) (120 mg, 0.27 mmol, 1 Eq), intermediate (AC-2) (59 mg, 1.1 Eq, 0.29 mmol) and $Cs_2CO_3$ (261 mg, 3 Eq, 0.80 mmol) in DMF (10 mL) were added $Pd_2(dba)_3$ (24 mg, 0.1 Eq, 27 μmol) and RuPhos (12 mg, 0.1 Eq, 27 μmol) at rt under nitrogen atmosphere. The resulting mixture was stirred for 3 h at 100° C. under nitrogen atmosphere. The mixture was allowed to cool down to rt and concentrated in vacuo. The residue was purified by Prep-TLC with DCM/MeOH (30/1) to afford the sub-title compound (AHU-9) (90 mg, 0.15 mmol, 55%, 92% Purity) as an off-white solid. m/z 615.2 $(M+H)^+$ (ES+)

Step 9: 2-[6-(Ethylamino)-4-[4-hydroxy-2-(4-methyl-1,2,4-triazol-3-yl)phenyl]pyridin-2-yl]-4-(trifluoromethyl)-3H-isoindol-1-one (AHU-10)

A solution of the product from step 8 above (AHU-9) (90 mg, 1 Eq, 0.15 mmol) and TFA (1 mL) in DCM (3 mL) was stirred for 2 h at rt and concentrated in vacuo. The residue was purified by Prep-TLC with DCM/MeOH (15/1) to afford the sub-title compound (AHU-10) (50 mg, 0.10 mmol, 69%, 90% Purity) as an off-white solid. m/z 495.2 $(M+H)^+$ (ES+)

Step 10: 2-[6-(Ethylamino)-4-[2-(4-methyl-1,2,4-triazol-3-yl)-4-(prop-2-yn-1-yloxy)phenyl] pyridin-2-yl]-4-(trifluoromethyl)-3H-isoindol-1-one (AHU-12)

To a stirred solution of the product from step 9 above (AHU-10) (50 mg, 1 Eq, 0.10 mmol) and $K_2CO_3$ (42 mg, 3 Eq, 0.30 mmol) in DMF (5 mL) was added propargyl bromide (AHU-11) (18 mg, 1.5 Eq, 0.15 mmol) at rt. The resulting mixture was stirred overnight at rt. The resulting mixture was diluted with water and extracted with DCM/MeOH (10/1) (3×20 mL). The combined organic layers were washed with brine (2×20 mL), dried ($Na_2SO_4$). After filtration, the filtrate was concentrated in vacuo. The residue was purified by Prep-TLC with DCM/MeOH (15/1). The product was purified by Prep-HPLC with the following conditions (Column: XBridge Prep OBD C18 Column, 30*150 mm, 5 μm; Mobile Phase A: water (0.1% $NH_4HCO_3$), Mobile Phase B: MeCN; Flow rate: 60 mL/min; Gradient: 54% B to 58% B in 8 min; Wave Length: 254/220 nm) to afford the title compound (AHU-12) (7.0 mg, 13 μmol, 13%, 99.5% Purity) as an off-white solid. m/z 533.1 $(M+H)^+$ (ES+). $^1$H NMR (400 MHz, DMSO-d6) δ 8.47 (s, 1H), 8.10-8.00 (m, 2H), 7.79 (d, J=7.7 Hz, 1H), 7.57-7.44 (m, 2H), 7.34-7.28 (m, 1H), 7.17 (d, J=2.7 Hz, 1H), 6.65 (t, J=5.4 Hz, 1H), 5.89 (d, J=1.3 Hz, 1H), 5.18 (s, 2H), 4.94 (d, J=2.4 Hz, 2H), 3.65 (t, J=2.3 Hz, 1H), 3.35 (s, 3H), 3.20-3.12 (m, 2H), 1.12 (t, J=7.2 Hz, 3H).

Example 251: Synthesis of 4-{2-Cyclopropyl-6-[6-(hydroxymethyl)-1-oxo-3H-isoindol-2-yl]pyridin-4-yl}-3-(4-methyl-1,2,4-triazol-3-yl)benzonitrile (AHV-1)

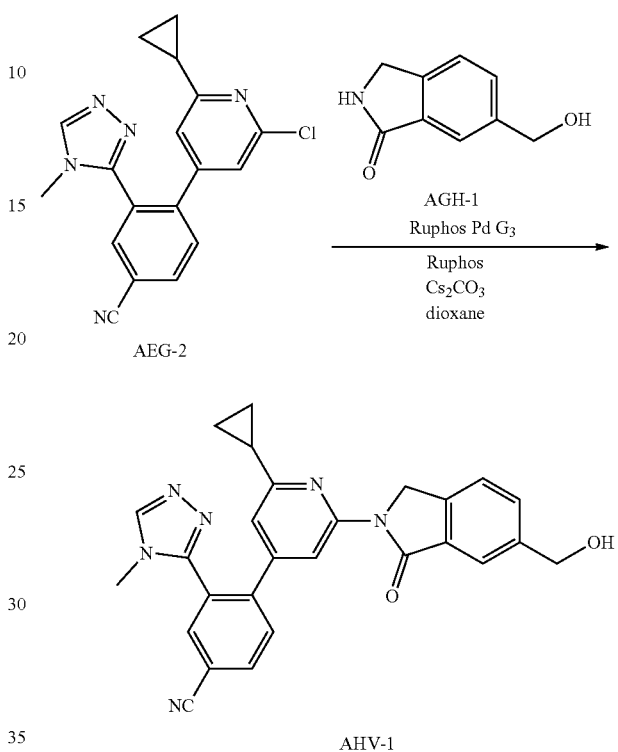

To a stirred mixture of intermediate (AEG-2) (60 mg, 1 Eq, 0.18 mmol), intermediate (AGH-1) (38 mg, 1.3 Eq, 0.23 mmol) and $Cs_2CO_3$ (116 mg, 2 Eq, 0.36 mmol) in 1,4-dioxane were added RuPhos Palladacycle Gen.3 (30 mg, 0.2 Eq, 36 μmol) and RuPhos (33 mg, 0.4 Eq, 72 μmol) at rt under nitrogen atmosphere. The resulting mixture was stirred for 2 h at 100° C. under nitrogen atmosphere. The mixture was cooled to rt and concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: water (0.1% $NH_4HCO_3$), Mobile Phase B: MeCN; Flow rate: 60 mL/min; Gradient: 30% B to 40% B in 10 min; Wave Length: 254/220 nm; RT: 9.67) to afford the title compound (AHV-1) (2.4 mg, 2.84%, 99.0% Purity) as a white solid. m/z 463.3 $(M+H)^+$ (ES+). $^1$H NMR (400 MHz, Methanol-d4) δ 8.50 (s, 1H), 8.15-8.02 (m, 3H), 7.92 (d, J=8.1 Hz, 1H), 7.83 (s, 1H), 7.70-7.57 (m, 2H), 6.92 (d, J=1.4 Hz, 1H), 5.03 (s, 2H), 4.71 (s, 2H), 3.50 (s, 3H), 2.07-1.99 (m, 1H), 1.07-0.89 (m, 4H).

Example 252: Synthesis of 2-{4-[4-Chloro-2-(4-methyl-1,2,4-triazol-3-yl)phenyl]-6-ethoxypyridin-2-yl}-6-({[(1-hydroxycyclobutyl)methyl]amino}methyl)-4-(trifluoromethyl)-3H-isoindol-1-one (AHW-1)

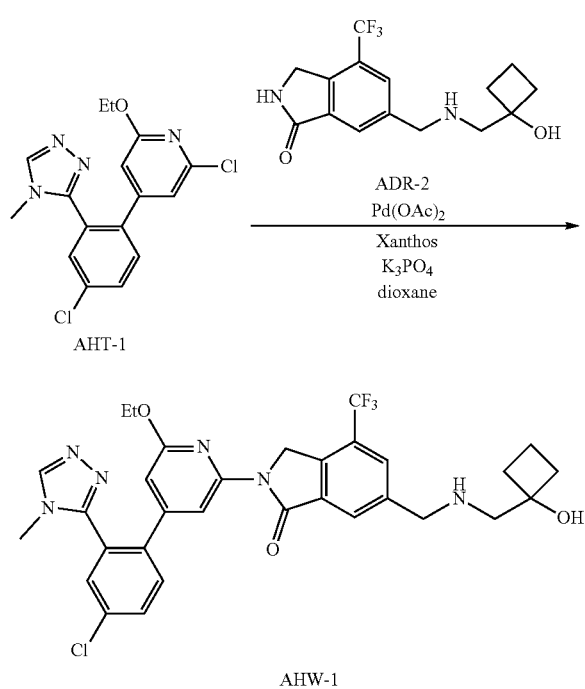

To a stirred mixture of intermediate (AHT-1) (50 mg, 1 Eq, 0.14 mmol), intermediate (ADR-2) (54 mg, 1.2 Eq, 0.17 mmol) and K$_3$PO$_4$ (61 mg, 2 Eq, 0.29 mmol) in dioxane (3 mL) were added Pd(OAc)$_2$ (3 mg, 0.1 Eq, 14 µmol) and XantPhos (17 mg, 0.2 Eq, 29 µmol) in portions at rt under nitrogen atmosphere. The resulting mixture was stirred for 2 h at 100° C. under nitrogen atmosphere. The mixture was cooled to rt and concentrated in vacuo. The residue was purified by Prep-TLC with DCM/MeOH (10/1). The crude product was purified by Prep-HPLC with the following conditions (Column: Sunfire prep C18 column, 30*150 mm, 5 µm; Mobile Phase A: water (0.1% FA), Mobile Phase B: MeCN; Flow rate: 60 mL/min; Gradient: 11% B to 31% B in 10 min, 31% B; Wave Length: 254/220 nm; RT: 11.3) to afford the title compound (AHW-1) (17.4 mg, 28 µmol, 19%, 99.8% Purity) as a white solid. m/z 627.2/629.2 (M+H)$^+$ (ES+). $^1$H NMR (400 MHz, Methanol-d4) δ 8.45 (s, 1H), 8.13 (d, J=26.3 Hz, 2H), 7.85-7.68 (m, 4H), 6.47-6.41 (m, 1H), 5.25 (d, J=3.2 Hz, 2H), 4.43-4.33 (m, 2H), 4.24 (d, J=6.4 Hz, 2H), 3.47 (s, 3H), 2.96 (d, J=5.8 Hz, 2H), 2.12 (t, J=9.6 Hz, 4H), 1.81-1.71 (m, 1H), 1.62-1.50 (m, 1H), 1.40 (t, J=7.0 Hz, 3H).

Example 253: Synthesis of 2-(6-Cyclopropyl-4-(4-fluoro-2-(4-methyl-4H-1,2,4-triazol-3-yl)phenyl)pyridin-2-yl)-6-((2-hydroxyethoxy)methyl)-4-(trifluoromethyl)isoindolin-1-one (AHX-2)

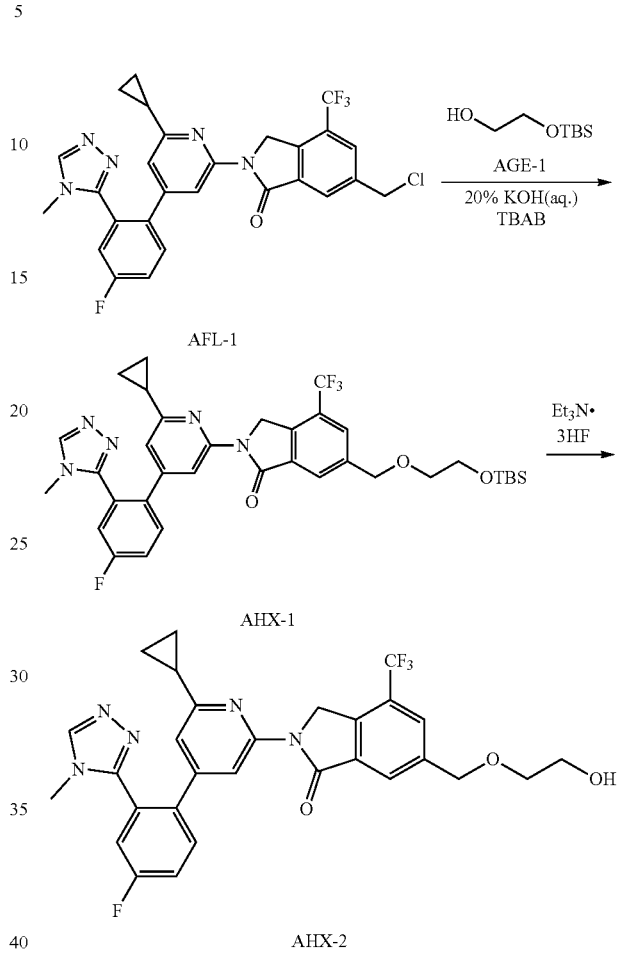

Step 1: 6-((2-((tert-Butyldimethylsilyl)oxy)ethoxy)methyl)-2-(6-cyclopropyl-4-(4-fluoro-2-(4-methyl-4H-1,2,4-triazol-3-yl)phenyl)pyridin-2-yl)-4-(trifluoromethyl)isoindolin-1-one (AHX-1)

To a solution of intermediate (AFL-1) (20 mg, 1 Eq, 37 µmol) 2-((tert-butyldimethylsilyl)oxy)ethan-1-ol (AGE-1) (8 mg, 1.2 Eq, 44 µmol) in DCM (2 mL) were added TBAB (6 mg, 0.5 Eq, 18 µmol) and aq. KOH (2 mL, 20% Wt) at rt. The resulting mixture was stirred for 1 h at rt under nitrogen atmosphere. The resulting mixture was diluted with water and extracted with EtOAc (3×10 mL). The combined organic layers were washed with brine (2×10 mL), dried (Na$_2$SO$_4$). After filtration, the filtrate was concentrated in vacuo. The residue was purified by Prep-TLC with DCM/MeOH (12/1) to afford the sub-title compound (AHX-1) (12 mg, 18 µmol, 48%, 95% Purity) as a white solid. m/z 682.3 (M+H)$^+$ (ES+).

Example 254: Synthesis of 2-(6-Cyclopropyl-4-(4-fluoro-2-(4-methyl-4H-1,2,4-triazol-3-yl)phenyl)pyridin-2-yl)-6-((2-hydroxyethoxy)methyl)-4-(trifluoromethyl)isoindolin-1-one (AHX-2)

To a stirred solution of the product from step 1 above (AHX-1) (23 mg, 1 Eq, 34 µmol) in THF (3 mL) was added Et₃N·3HF (7 mg, 1.2 Eq, 41 μmol) dropwise at rt. The resulting mixture was stirred for 2 h at rt. The resulting mixture was diluted with water and extracted with EtOAc (3×10 mL). The combined organic layers were washed with brine (2×10 mL), dried (Na₂SO₄). After filtration, the filtrate was concentrated in vacuo. The crude product was purified by Prep-HPLC with the following conditions (Column: Sunfire prep C18 column, 30*150 mm, 5 μm; Mobile Phase A: water (0.1% FA), Mobile Phase B: MeCN; Flow rate: 60 mL/min; Gradient: 35% B to 62% B in 10 min; Wave Length: 254/220 nm; RT: 10.58) to afford the title compound (AHX-2) (2.8 mg, 4.9 μmol, 15%, 97.9% Purity) as a white solid. m/z 568.2 (M+H)⁺ (ES+). ¹H NMR (300 MHz, Methanol-d4) δ 8.48 (s, 1H), 8.12-7.97 (m, 3H), 7.81-7.74 (m, 1H), 7.58-7.41 (m, 2H), 6.89 (d, J=1.4 Hz, 1H), 5.18 (s, 2H), 4.75 (s, 2H), 3.78-3.72 (m, 2H), 3.69-3.62 (m, 2H), 3.47 (s, 3H), 2.09-1.97 (m, 1H), 1.00 (d, J=6.4 Hz, 4H).

Example 255: Synthesis of 2-{7-[2-(4-Methyl-1,2,4-triazol-3-yl)phenyl]-1H-indol-5-yl}-4-(trifluoromethyl)-3H-isoindol-1-one (AHY-5)

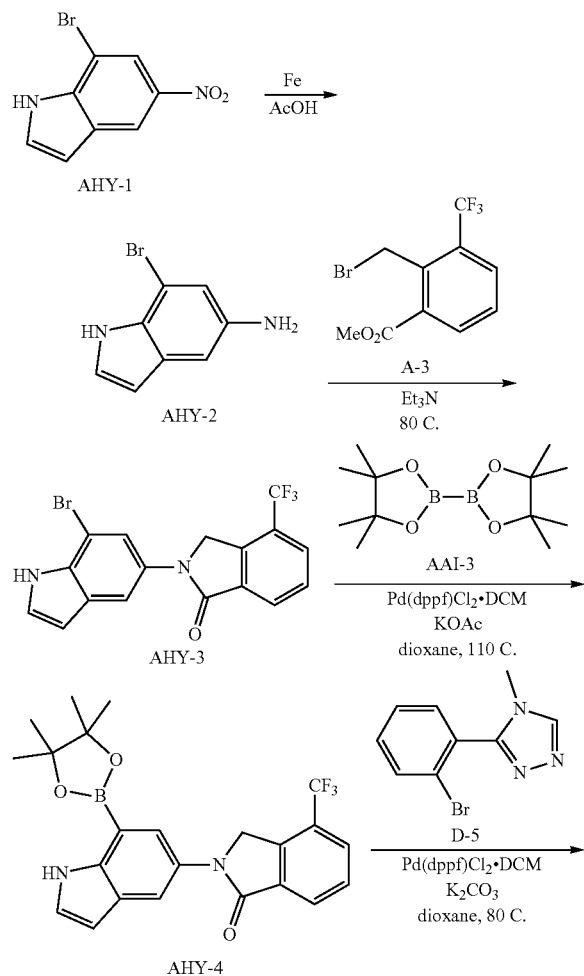

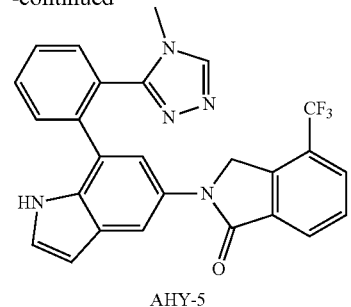

AHY-5

Step 1: 7-Bromo-1H-indol-5-amine (AHY-2)

Into a 40 mL sealed tube were added 7-bromo-5-nitro-1H-indole (AHY-1) (1.00 g, 1 Eq, 4.15 mmol) and AcOH (2.49 g, 10 Eq, 41.5 mmol) in THF (8 mL) at rt was added iron power (1.16 g, 5 Eq, 20.7 mmol) at 0° C. The resulting mixture was stirred overnight at rt. The resulting mixture was filtered the filter cake was washed with EtOAc (3×15 mL). The filtrate was concentrated in vacuo. The crude product was purified by reverse flash column chromatography with the following conditions: Column, C18; mobile phase, water (0.1% NH₄HCO₃) and MeCN (0% MeCN up to 50% in 10 min); Detector, UV 254/220 nm to afford the sub-title compound (AHY-2) (670 mg, 3.19 mmol, 77%, 92% Purity) as a yellow oil. m/z 211.0/213.0 (M+H)⁺ (ES+)

Step 2: 2-(7-Bromo-1H-indol-5-yl)-4-(trifluoromethyl)-3H-isoindol-1-one (AHY-3)

Into an 8 mL sealed tube were added the product from step 1 above (AHY-2) (100 mg, 1 Eq, 0.47 mmol) and Et₃N (144 mg, 3 Eq, 1.42 mmol) in EtOH (6 mL) at rt. To the above mixture was added intermediate (A-3) (211 mg, 1.5 Eq, 0.71 mmol) at rt. The resulting mixture was stirred overnight at 80° C. The mixture was allowed to cool down to rt. The resulting mixture was concentrated in vacuo. The crude product was purified by reverse flash column chromatography with the following conditions: Column, C18; mobile phase, water (0.1% NH₄HCO₃) and MeCN (0% MeCN up to 60% in 15 min); Detector, UV 254/220 nm. The product-containing fractions were combined and concentrated in vacuo. This resulted in to afford the sub-title compound (AHY-3) (86 mg, 0.22 mmol, 46%, 95% Purity) as a yellow solid. m/z 395.0/397.0 (M+H)⁺ (ES+)

Step 3: 2-[7-(4,4,5,5-Tetramethyl-1,3,2-dioxaborolan-2-yl)-1H-indol-5-yl]-4-(trifluoromethyl)-3H-isoindol-1-one (AHY-4)

Into an 8 mL sealed tube were added the product from step 2 above (AHY-3) (50 mg, 1 Eq, 0.13 mmol), bis(pinacolato)diboron (AAI-3) (64 mg, 2 Eq, 0.25 mmol) and KOAc (25 mg, 2 Eq, 0.25 mmol) in 1,4-dioxane (2 mL) at rt under nitrogen atmosphere. To the above mixture was added Pd(dppf)Cl₂.DCM (19 mg, 0.2 Eq, 25 μmol) at rt under nitrogen atmosphere. The resulting mixture was stirred for additional 2 h at 110° C. under nitrogen atmosphere. The mixture was allowed to cool down to rt. The resulting mixture was concentrated in vacuo. The crude product was purified by reverse flash column chromatography with the following conditions: Column, C18; mobile phase, water (0.1% NH₄HCO₃) and MeCN (10% MeCN up to 50% in 12 min); Detector, UV 254/220 nm. The product-containing fractions were combined and concentrated in vacuo. This resulted in to afford the sub-title compound (AHY-4) (35 mg, 79 μmol, 63%, 95% Purity) as a white solid. m/z 443.2 (M+H)⁺ (ES+)

Step 4: 2-{7-[2-(4-Methyl-1,2,4-triazol-3-yl)phenyl]-1H-indol-5-yl}-4-(trifluoromethyl)-3H-isoindol-1-one (AHY-5)

Into an 8 mL sealed tube were added the product from step 3 above (AHY-4) (30 mg, 1 Eq, 68 μmol), intermediate (D-5) (24 mg, 1.5 Eq, 0.10 mmol) and K₂CO₃ (13 mg, 2 Eq, 0.14 mmol) in 1,4-dioxane (5 mL) at rt under nitrogen atmosphere. To the above mixture was added Pd(dppf)Cl₂·DCM (10 mg, 0.2 Eq, 14 μmol) at rt under nitrogen atmosphere. The resulting mixture was stirred for additional 2 h at 80° C. under nitrogen atmosphere. The mixture was allowed to cool down to rt and concentrated in vacuo. The crude product was purified by Prep-HPLC with the following conditions: Column: SunFire Prep C18 OBD Column, 19×150 mm, 5 μm; Mobile Phase A: water (0.1% NH₄HCO₃+0.1% NH₃·H₂O), Mobile Phase B: MeCN; Flow rate: 60 mL/min; Gradient: 30 B to 60 B in 7 min; Detector, UV 254/210 nm; RT: 6.08 to afford the title compound (AHY-5) (3.0 mg, 6.3 μmol, 9.3%, 99.4% Purity) as a white solid. m/z 474.1 (M+H)⁺ (ES+). ¹H NMR (400 MHz, Methanol-d4) δ 8.24 (s, 1H), 8.07 (d, J=7.6 Hz, 1H), 7.97-7.90 (m, 2H), 7.86-7.63 (m, 5H), 7.31 (d, J=3.2 Hz, 1H), 7.03 (d, J=2.0 Hz, 1H), 6.57 (d, J=3.2 Hz, 1H), 5.00 (s, 2H), 3.01 (s, 3H).

Example 256: Synthesis of 4-[2-Cyclopropyl-6-(6-{1[(oxetan-3-ylmethyl)amino] methyl}-1-oxo-3H-isoindol-2-yl)pyridin-4-yl]-3-(4-methyl-1,2,4-triazol-3-yl)benzonitrile (AHZ-2)

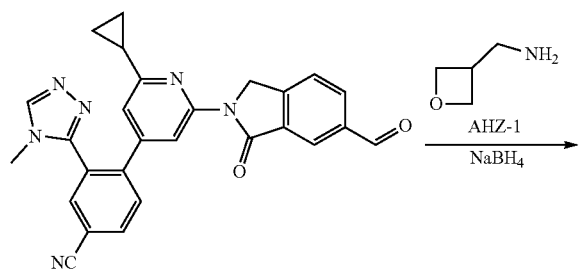

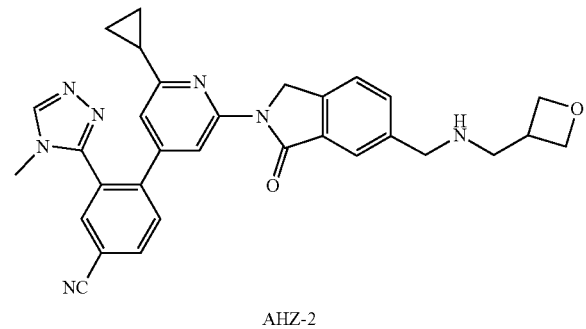

A solution of intermediate (AGT-2) (20 mg, 1 Eq, 43 μmol) and 1-(oxetan-3-yl)methanamine (AHZ-1) (6 mg, 1.5 Eq, 65 μmol) in MeOH (6 mL) was stirred for 1 h at rt. To the above mixture was added NaBH₄ (4 mg, 2 Eq, 86 μmol) at 0° C. The resulting mixture was stirred for 1 h at rt. The reaction was then quenched by the addition of 2 mL of MeOH at 0° C. The mixture was acidified to pH 6 with FA and then concentrated in vacuo. The crude product was purified by Prep-HPLC with the following conditions (Column: Sunfire prep C18 column, 30*150 mm, 5 μm; Mobile Phase A: water (0.1% FA), Mobile Phase B: MeCN; Flow rate: 60 mL/min; Gradient: 11% B to 25% B in 10 min; Wave Length: 254/220 nm) to afford the title compound (AHZ-2) (3.2 mg, 6.0 μmol, 14%, 98.7% Purity) as a white solid. m/z 532.1 (M+H)⁺ (ES+). ¹H NMR (400 MHz, DMSO-d6) δ 8.53 (s, 1H), 8.31-8.19 (m, 2H), 8.06-7.99 (m, 1H), 7.95-7.85 (m, 1H), 7.74-7.63 (m, 3H), 6.87 (d, J=1.4 Hz, 1H), 5.00 (s, 2H), 4.66-4.56 (m, 2H), 4.24 (t, J=5.9 Hz, 2H), 3.79 (s, 2H), 3.47 (s, 3H), 3.09-3.00 (m, 1H), 2.76 (d, J=7.4 Hz, 2H), 2.11-2.01 (m, 1H), 1.03-0.92 (m, 4H).

Example 257: Synthesis of 4-[2-(6-{[(Cyclobutylmethyl)amino]methyl}-1-oxo-3H-isoindol-2-yl)-6-cyclopropylpyridin-4-yl]-3-(4-methyl-1,2,4-triazol-3-yl)benzonitrile (AIA-2)

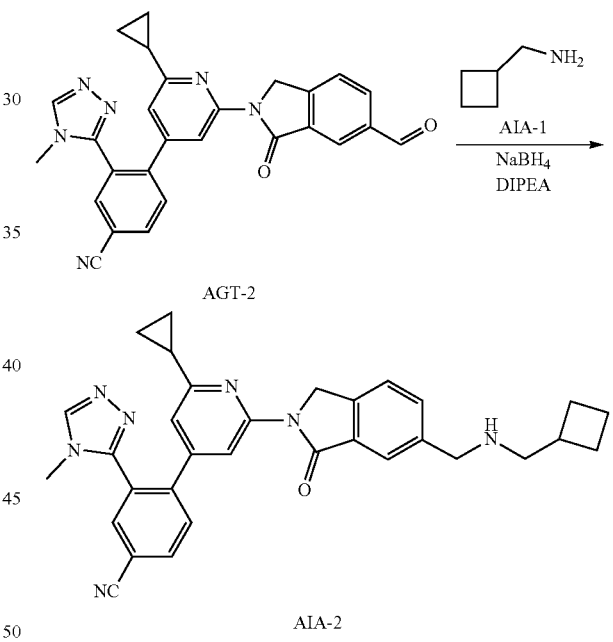

A solution of 1-cyclobutylmethanamine, HCl (AIA-1) (7 mg, 1.5 Eq, 58 μmol) and DIPEA (6 mg, 1.2 Eq, 47 μmol) in MeOH (5 mL) was stirred for 10 min at rt. To the above mixture was added intermediate (AGT-2) (18 mg, 1 Eq, 39 μmol) at rt. The resulting mixture was stirred overnight at rt. To the above mixture was added NaBH₄ (3 mg, 2 Eq, 78 μmol) at 0° C. The resulting mixture was stirred for 1 h at rt. The reaction was then quenched by the addition of 2 mL of MeOH at 0° C. The mixture was concentrated in vacuo. The crude product was purified by Prep-HPLC with the following conditions (Column: Sunfire prep C18 column, 30*150 mm, 5 μm; Mobile Phase A: water (0.1% FA), Mobile Phase B: MeCN; Flow rate: 60 mL/min; Gradient: 14% B to 34% B in 7 min; Wave Length: 254/220 nm) to afford the title compound (AIA-2) (6.3 mg, 12 μmol, 30%, 99.6% Purity) as a white solid. m/z 530.2 (M+H)⁺ (ES+). ¹H NMR (400 MHz, DMSO-d6) δ 8.53 (s, 1H), 8.23-8.19 (m, 2H), 7.99 (d, J=1.4 Hz, 1H), 7.87 (d, J=8.5 Hz, 1H), 7.75 (s, 1H), 7.64 (d, J=1.2 Hz, 2H), 6.87 (d, J=1.4 Hz, 2H), 5.00 (s, 2H), 3.81 (s, 2H), 3.47 (s, 3H), 2.54 (d, J=7.1 Hz, 2H), 2.45-2.40 (m, 1H), 2.06-1.96 (m, 3H), 1.86-1.76 (m, 2H), 1.69-1.60 (m, 2H), 1.01-0.93 (m, 4H).

Example 258: Synthesis of 4-(2-Cyclopropyl-6-(6-((((cyclopropylmethyl)amino) methyl)-1-oxoisoindolin-2-yl)pyridin-4-yl)-3-(4-methyl-4H-1,2,4-triazol-3-yl)benzonitrile (AIB-2)

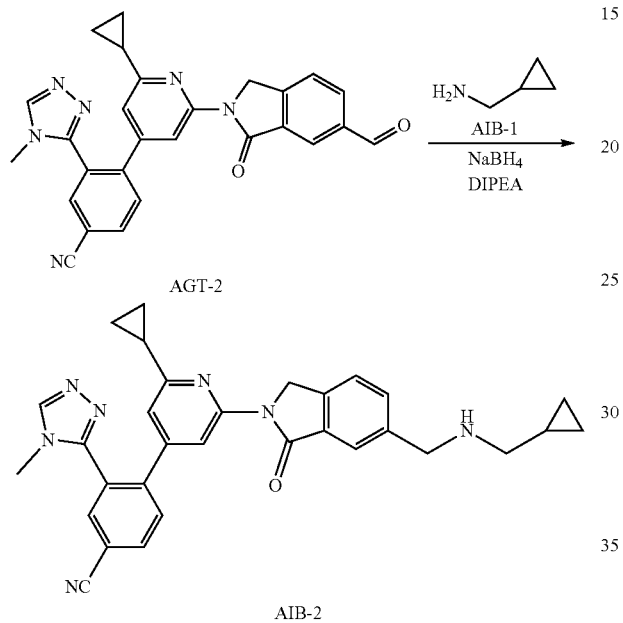

A solution of intermediate (AGT-2) (20 mg, 1 Eq, 43 µmol) and 1-cyclopropylmethanamine (AIB-1) (4.6 mg, 1.5 Eq, 65 µmol) in MeOH (8 mL) was stirred for 1 h at 60° C. To the above mixture was added NaBH₄ (3.3 mg, 2 Eq, 86 µmol) at 0° C. The resulting mixture was stirred for 1 h at rt. The reaction was then quenched by the addition of 2 mL of MeOH at 0° C. The mixture was concentrated in vacuo. The residue was purified by Prep-TLC with DCM/MeOH (9/1). The crude product was purified by Prep-HPLC with the following conditions (Column: XBridge Prep OBD C18 Column, 30*150 mm, 5 µm; Mobile Phase A: water (0.1% NH₄HCO₃+0.1% NH₃·H₂O), Mobile Phase B: MeCN; Flow rate: 60 mL/min; Gradient: 40% B to 47% B in 8 min; Wave Length: 254/220 nm) to afford the title compound (AIB-2) (0.9 mg, 1.7 µmol, 3.9%, 97.8% Purity) as a white solid. m/z 516.2 (M+H)⁺ (ES+). ¹H NMR (400 MHz, Methanol-d4) δ 8.48 (s, 1H), 8.14-8.05 (m, 3H), 7.92 (d, J=8.1 Hz, 1H), 7.80 (s, 1H), 7.69-7.60 (m, 2H), 6.90 (d, J=1.4 Hz, 1H), 5.03 (s, 2H), 3.90 (s, 2H), 3.49 (s, 3H), 2.46 (d, J=6.9 Hz, 2H), 2.05-1.99 (m, 1H), 1.06-0.96 (m, 5H), 0.53-0.49 (m, 2H), 0.16-0.12 (m, 2H).

Example 259: Synthesis of 2-{6-Cyclopropyl-4-[4-fluoro-2-(4-methyl-1,2,4-triazol-3-yl)phenyl]pyridin-2-yl}-6-{[(1-hydroxycyclobutyl)methoxy]methyl}-4-methoxy-3H-isoindol-1-one (AIC-11)

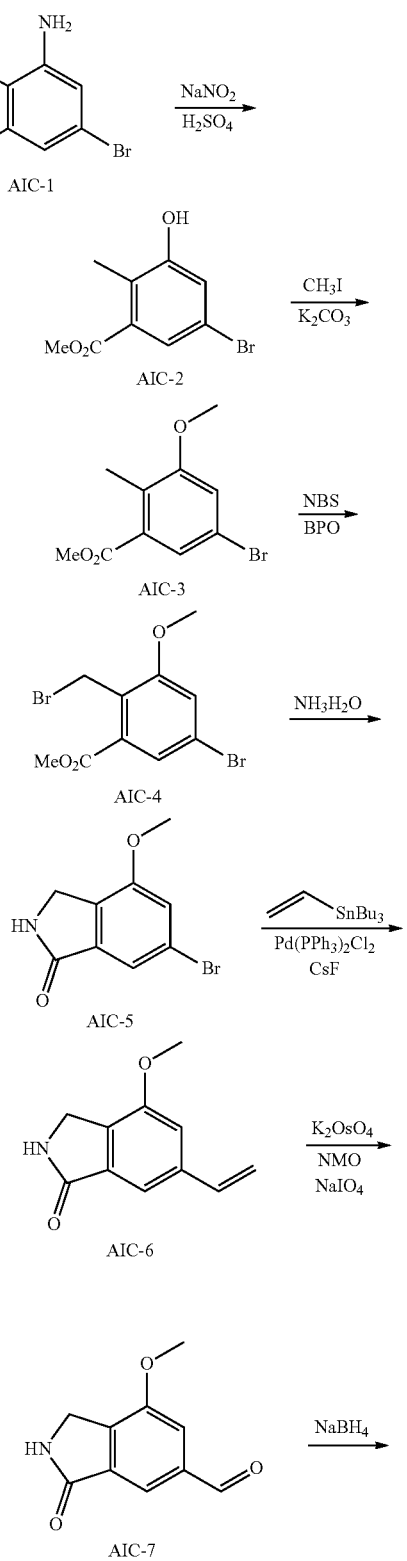

-continued

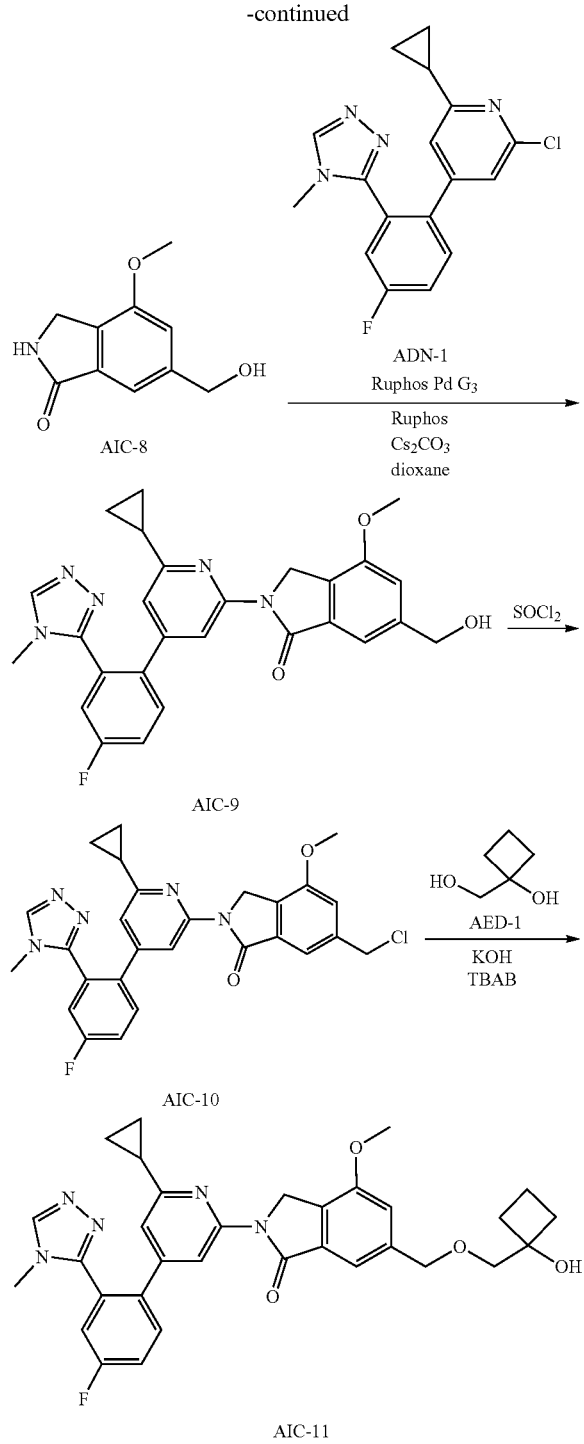

Step 1: Methyl 5-bromo-3-hydroxy-2-methylbenzoate (AIC-2)

To a stirred solution of methyl 3-amino-5-bromo-2-methylbenzoate (AIC-1) (10.0 g, 1 Eq, 41.0 mmol) in conc. $H_2SO_4$ (30 mL) was added $NaNO_2$ (3.39 g, 1.2 Eq, 49.2 mmol) in portions at 0° C. The resulting mixture was stirred for overnight at rt. The resulting mixture was diluted with water and extracted with EtOAc (3×100 mL). The combined organic layers were washed with brine (2×100 mL), dried ($Na_2SO_4$). After filtration, the filtrate was concentrated in vacuo. The residue was applied on a silica gel column chromatography with petroleum ether/EtOAc (8/1) to afford the sub-title compound (AIC-2) (6.0 g, 23.7 mmol, 54%, 90% Purity) as a brown-yellow oil. m/z 245.0/247.0 $(M+H)^+$ (ES+).

Step 2: Methyl 5-bromo-3-methoxy-2-methylbenzoate (AIC-3)

To a stirred solution of the product from step 1 above (AIC-2) (6.00 g, 1 Eq, 24.5 mmol) and $K_2CO_3$ (10.2 g, 3 Eq, 73.4 mmol) in DMF (20 mL) was added $CH_3I$ (5.21 g, 1.5 Eq, 36.7 mmol) dropwise at rt under nitrogen atmosphere. The resulting mixture was stirred for overnight at 60° C. under nitrogen atmosphere. The mixture was allowed to cool down to rt. The resulting mixture was diluted with water and extracted with EtOAc (3×100 mL). The combined organic layers were washed with brine (2×100 mL), dried ($Na_2SO_4$). After filtration, the filtrate was concentrated in vacuo. The residue was applied on a silica gel column chromatography with petroleum ether/EtOAc (5/1) to afford the sub-title compound (AIC-3) (5.0 g, 19.4 mmol, 73%, 92% Purity) as a light brown oil. m/z 259.0/261.0 $(M+H)^+$ (ES+)

Step 3: Methyl 5-bromo-2-(bromomethyl)-3-methoxybenzoate (AIC-4)

To a stirred solution of the product from step 2 above (AIC-3) (5.00 g, 1 Eq, 19.3 mmol) and NBS (3.78 g, 1.1 Eq, 21.2 mmol) in $CCl_4$ (20 mL) was added BPO (495 mg, 0.1 Eq, 1.93 mmol) at rt under nitrogen atmosphere. The resulting mixture was stirred for overnight at 80° C. under nitrogen atmosphere. The mixture was allowed to cool down to rt. The resulting mixture was diluted with water and extracted with EtOAc (3×100 mL). The combined organic layers were washed with brine (2×100 mL), dried ($Na_2SO_4$). After filtration, the filtrate was concentrated in vacuo. The crude product was used in the next step directly without further purification. m/z 338.9/340.9 $(M+H)^+$ (ES+)

Step 4: 6-Bromo-4-methoxy-2,3-dihydroisoindol-1-one (AIC-5)

A solution of the product from step 3 above (AIC-4) (5.00 g, 1 Eq, 14.8 mmol) in $NH_3$/MeOH (20 mL, 7 M) at rt was stirred for 3 h. The resulting mixture was concentrated in vacuo. The resulting mixture was diluted with water and extracted with EtOAc (3×100 mL). The combined organic layers were washed with brine (2×100 mL), dried ($Na_2SO_4$). After filtration, the filtrate was concentrated in vacuo. The crude product was used in the next step directly without further purification. m/z 242.0/244.0 $(M+H)^+$ (ES+)

Step 5: 6-Ethenyl-4-methoxy-2,3-dihydroisoindol-1-one (AIC-6)

To a stirred solution of the product from step 4 above (AIC-5) (6.50 g, 1 Eq, 26.9 mmol) and tributyl(ethenyl)stannane (10.2 g, 1.2 Eq, 32.2 mmol) in dioxane (30 mL) was added CsF (12.2 g, 3 Eq, 80.6 mmol) at rt under nitrogen atmosphere. To the above mixture was added $Pd(PPh_3)_2Cl_2$ (1.88 g, 0.1 Eq, 2.69 mmol) at rt under nitrogen atmosphere. The resulting mixture was stirred for 3 h at 100° C. under nitrogen atmosphere. The mixture was allowed to cool down to rt. The resulting mixture was concentrated in vacuo. The residue was applied on a silica gel column chromatography with petroleum ether/EtOAc (1/1) to afford the sub-title compound (AIC-6) (3.1 g, 16.4 mmol, 56%, 91% Purity) as an off-white solid. m/z 190.1 (M+H)$^+$ (ES+)

Step 6: 7-Methoxy-3-oxo-1,2-dihydroisoindole-5-carbaldehyde (AIC-7)

To a stirred solution of the product from step 5 above (AIC-6) (3.00 g, 1 Eq, 15.9 mmol) and citric acid (3.96 g, 1.3 Eq, 20.6 mmol) in t-BuOH (20 mL) were added NMO (2.41 g, 1.3 Eq, 20.6 mmol) and $K_2OsO_4.2H_2O$ (584 mg, 0.1 Eq, 1.59 mmol) at rt. The resulting mixture was stirred for 2 h at rt. To the above mixture was added $NaIO_4$ (4.75 g, 2 Eq, 31.7 mmol) at 0° C. The resulting mixture was stirred for 1 h at rt. The resulting mixture was diluted with water and extracted with EtOAc (3×100 mL). The combined organic layers were washed with brine (2×100 mL), dried ($Na_2SO_4$). After filtration, the filtrate was concentrated in vacuo. The residue was applied on a silica gel column chromatography with petroleum ether/EtOAc (1/1) to afford the sub-title compound (AIC-7) (1.8 g, 9.42 mmol, 53%, 95% Purity) as an off-white solid. m/z 192.1 (M+H)$^+$ (ES+)

Step 7: 6-(Hydroxymethyl)-4-methoxy-2,3-dihydroisoindol-1-one (AIC-8)

To a stirred solution of the product from step 6 above (AIC-7) (1.8 g, 9.42 mmol, 1 Eq) in MeOH (20 mL) was added $NaBH_4$ (1.07 g, 3 Eq, 28.2 mmol) in portions at 0° C. under nitrogen atmosphere. The resulting mixture was stirred for 2 h at rt under nitrogen atmosphere. The reaction was then quenched by the addition of 10 mL of MeOH at 0° C. The resulting mixture was concentrated in vacuo. The crude product was purified by reverse flash column chromatography with the following conditions: Column, C18; mobile phase, water (0.1% $NH_4HCO_3$) and MeCN (0% MeCN up to 30% in 15 min); Detector, UV 254/220 nm. This resulted in the sub-title compound (AIC-8) (980 mg, 5.08 mmol, 51%, 95% Purity) as an off-white solid. m/z 194.1 (M+H)$^+$ (ES+)

Step 8: 2-{6-Cyclopropyl-4-[4-fluoro-2-(4-methyl-1,2,4-triazol-3-yl)phenyl]pyridin-2-yl}-6-(hydroxymethyl)-4-methoxy-3H-isoindol-1-one (AIC-9)

To a stirred solution of the product from step 7 above (AIC-8) (107 mg, 1.1 Eq, 0.55 mmol), intermediate (ADN-1) (165 mg, 1 Eq, 0.50 mmol) and $Cs_2CO_3$ (327 mg, 2 Eq, 1.00 mmol) in dioxane (10 mL) at rt under nitrogen atmosphere were added Ruphos (94 mg, 0.4 Eq, 0.20 mmol) and RuPhos Palladacycle Gen.3 (84 mg, 0.2 Eq, 0.10 mmol). The resulting mixture was stirred for 2 h at 100° C. under nitrogen atmosphere. The mixture was allowed to cool down to rt. The resulting mixture was diluted with water and extracted with EtOAc (3×20 mL). The combined organic layers were washed with brine (2×20 mL), dried ($Na_2SO_4$). After filtration, the filtrate was concentrated in vacuo. The residue was purified by Prep-TLC with DCM/MeOH (12/1) to afford the sub-title compound (AIC-9) (101 mg, 0.21 mmol, 41%, 90% Purity) as a yellow solid. m/z 486.2 (M+H)$^+$ (ES+).

Step 9: 6-(Chloromethyl)-2-{6-cyclopropyl-4-[4-fluoro-2-(4-methyl-1,2,4-triazol-3-yl) phenyl]pyridin-2-yl}-4-methoxy-3H-isoindol-1-one (AIC-10)

To a stirred solution of the product from step 8 above (AIC-9) (98 mg, 1 Eq, 0.20 mmol) in DCM (10 mL) was added $SOCl_2$ (72 mg, 3 Eq, 0.61 mmol) dropwise at 0° C. The resulting mixture was stirred for 1 h at rt. The reaction was then quenched by the addition of 2 mL of MeOH at 0° C. and concentrated in vacuo. The residue was purified by Prep-TLC with DCM/MeOH (15/1) to afford the sub-title compound (AIC-10) (76 mg, 0.15 mmol, 75%, 95% Purity) as a yellow solid. m/z 504.2/506.2 (M+H)$^+$ (ES+).

Step 10: 2-{6-Cyclopropyl-4-[4-fluoro-2-(4-methyl-1,2,4-triazol-3-yl)phenyl]pyridin-2-yl}-6-{[(1-hydroxycyclobutyl)methoxy]methyl}-4-methoxy-3H-isoindol-1-one (AIC-11)

To a stirred solution of the product from step 8 above (AIC-10) (50 mg, 1 Eq, 99 μmol) and 1-(hydroxymethyl)cyclobutan-1-ol (AED-1) (101 mg, 10 Eq, 0.99 mmol) in DCM (5 mL) were added TBAB (16 mg, 0.5 Eq, 0.05 mmol) and aq. KOH (5 mL, 20% Wt) at rt. The resulting mixture was stirred slowly for 1 h at rt. The resulting mixture was diluted with water and extracted with EtOAc (3×20 mL). The combined organic layers were washed with brine (2×20 mL), dried ($Na_2SO_4$). After filtration, the filtrate was concentrated in vacuo. The residue was purified by Prep-TLC with DCM/MeOH (12/1). The crude product was purified by Prep-HPLC with the following conditions (Column: XBridge Shield RP18 OBD Column, 19*250 mm, 10 μm; Mobile Phase A: water (0.1% $NH_4HCO_3$), Mobile Phase B: MeOH-HPLC; Flow rate: 25 mL/min; Gradient: 63% B to 65% B in 17 min; Wave Length: 254/220 nm) to afford the title compound (AIC-11) (3.1 mg, 5.4 μmol, 5.4%, 98.2% Purity) as a white solid. m/z 570.2 (M+H)$^+$ (ES+). $^1$H NMR (400 MHz, DMSO-d6) δ 8.50 (s, 1H), 7.96 (d, J=1.4 Hz, 1H), 7.73-7.68 (m, 1H), 7.64-7.56 (m, 2H), 7.38-7.27 (m, 2H), 6.80 (d, J=1.4 Hz, 1H), 5.02 (s, 1H), 4.90 (s, 2H), 4.66 (s, 2H), 3.93 (s, 3H), 3.42 (d, J=5.6 Hz, 5H), 2.09-2.00 (m, 3H), 1.98-1.87 (m, 2H), 1.72-1.62 (m, 1H), 1.53-1.43 (m, 1H), 0.95 (d, J=6.4 Hz, 4H).

Example 260: Synthesis of 4-{2-Cyclopropyl-6-[6-({[(2R)-2-methoxypropyl]amino}methyl)-1-oxo-3H-isoindol-2-yl]pyridin-4-yl}-3-(4-methyl-1,2,4-triazol-3-yl)benzonitrile (AID-2)

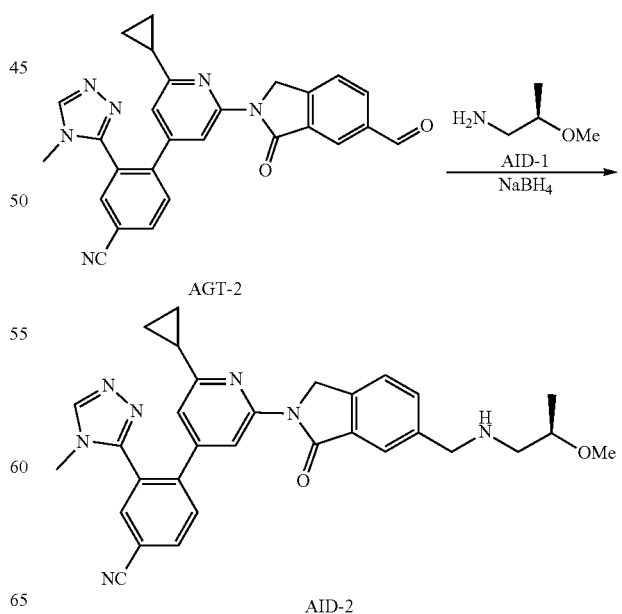

A solution of intermediate (AGT-2) (30 mg, 1 Eq, 65 µmol) and (2R)-2-methoxypropan-1-amine (AID-1) (8.7 mg, 1.5 Eq, 98 µmol) in MeOH (5 mL) was stirred for 1 h at 60° C. To the above mixture was added NaBH₄ (4.9 mg, 2 Eq, 0.13 mmol) at 0° C. The resulting mixture was stirred for 1 h at rt. The reaction was then quenched by the addition MeOH (2 mL) at 0° C. and concentrated in vacuo. The residue was purified by Prep-TLC with DCM/MeOH (12/1). The crude product was purified by Prep-HPLC with the following conditions (Column: Sunfire prep C18 column, 30*150 mm, 5 µm; Mobile Phase A: water (0.1% FA), Mobile Phase B: MeCN; Flow rate: 60 mL/min; Gradient: 5% B to 35% B in 7 min; Wave Length: 254/220 nm) to afford the title compound (AID-2) (14.7 mg, 28 µmol, 42%, 99.8% Purity) as a white solid. m/z 534.3 (M+H)⁺ (ES+). ¹H NMR (400 MHz, DMSO-d6) δ 8.54 (d, J=2.0 Hz, 1H), 8.24-8.19 (m, 2H), 7.99 (d, J=2.0 Hz, 1H), 7.92-7.84 (m, 1H), 7.73 (s, 1H), 7.63 (s, 2H), 6.88 (d, J=2.0 Hz, 1H), 5.00 (s, 2H), 3.81 (s, 2H), 3.48 (d, J=1.9 Hz, 3H), 3.42-3.38 (m, 1H), 3.23 (d, J=2.0 Hz, 3H) 2.49-2.42 (m, 2H), 2.08-2.00 (m, 1H), 1.13-1.06 (m, 3H), 1.00-0.95 (m, 4H).

Example 261: Synthesis of 4-[2-Cyclopropyl-6-(6-{[(2-hydroxy-2-methylpropyl)amino]methyl}-1-oxo-3H-isoindol-2-yl)pyridin-4-yl]-3-(4-methyl-1,2,4-triazol-3-yl)benzonitrile (AIE-1)

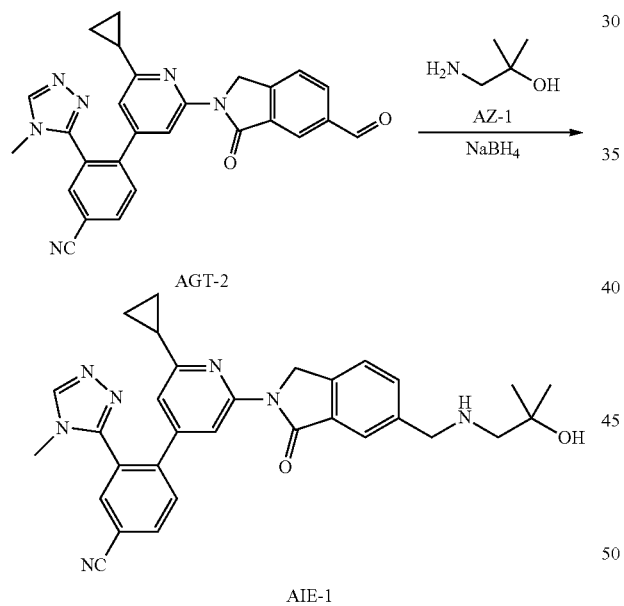

To a stirred solution of intermediate (AGT-2) (30 mg, 1 Eq, 0.06 mmol) and 1-amino-2-methylpropan-2-ol (AZ-1) (5.81 mg, 1 Eq, 0.06 mmol) in MeOH (5 mL) was added Et₃N (37 mg, 5 Eq, 0.33 mmol) for 2 h at 60° C. under nitrogen atmosphere. To the above mixture was added NaBH₄ (25 mg, 10 Eq, 0.65 mmol) at 0° C. The resulting mixture was stirred for 2 h at rt. The reaction was then quenched by the addition of MeOH (2 mL) at 0° C. The resulting mixture was diluted with water and extracted with DCM (3×20 mL). The combined organic layers were washed with brine (2×20 mL), dried (Na₂SO₄). After filtration, the filtrate was concentrated in vacuo. The crude product was purified by Prep-HPLC with the following conditions: Column: XBridge Prep OBD C18 Column, 19×250 mm, 5 µm; Mobile Phase A: water (0.1% NH₄HCO₃+0.1% NH₃·H₂O) Mobile Phase B: MeCN; Flow rate: 25 mL/min; Gradient: 32 B to 42 B in 10 min; Detector, UV 254/210 nm; RT: 9.12. The product-containing fractions were combined and evaporated partially in vacuo and lyophilized overnight to afford the title compound (AIE-1) (13.6 mg, 26 µmol, 39%, 98.6% Purity) as a white solid. m/z 534.3 (M+H)⁺ (ES+). ¹H NMR (400 MHz, Methanol-d4) δ 8.50 (s, 1H), 8.15-8.07 (m, 2H), 8.06 (d, J=1.4 Hz, 1H), 7.94-7.82 (m, 2H), 7.72-7.66 (m, 1H), 7.61 (d, J=7.8 Hz, 1H), 6.92 (d, J=1.4 Hz, 1H), 5.03 (s, 2H), 3.91 (s, 2H), 3.50 (s, 3H), 2.54 (s, 2H), 2.06-2.01 (m, 1H), 1.21 (s, 6H), 1.07-1.01 (m, 2H), 1.01-0.95 (m, 2H).

Example 262: Synthesis of 4-{2-Cyclopropyl-6-[6-({[(1-hydroxycyclopentyl)methyl]amino}methyl)-1-oxo-3H-isoindol-2-yl]pyridin-4-yl}-3-(4-methyl-1,2,4-triazol-3-yl)benzonitrile (AIF-1)

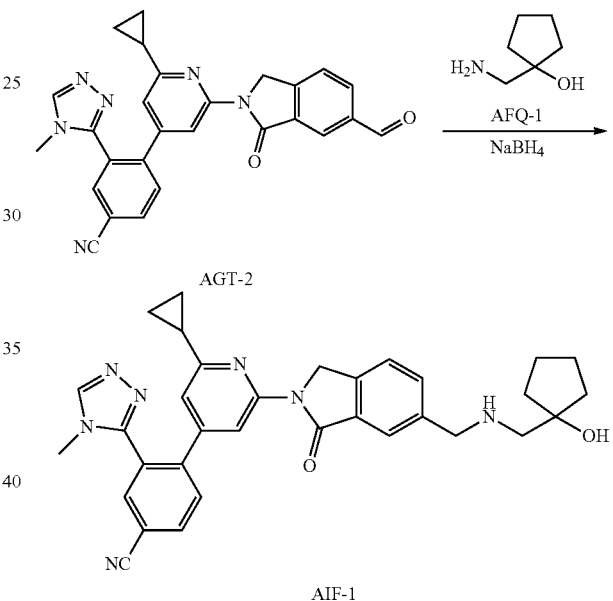

A solution of intermediate (AIG-1) (30 mg, 1 Eq, 65 µmol) and 1-(aminomethyl)cyclopentan-1-ol (AFQ-1) (11 mg, 1.5 Eq, 98 µmol) in MeOH (6 mL) was stirred overnight at rt under nitrogen atmosphere. To the above mixture was added NaBH₄ (12.32 mg, 0.325 mmol, 5 Eq) at 0° C. under nitrogen atmosphere. The resulting mixture was stirred for 2 h at rt under nitrogen atmosphere. The reaction was then quenched by the addition of MeOH (2 mL) at 0° C. The mixture was concentrated in vacuo. The crude product was purified by Prep-HPLC with the following conditions (Column: Sunfire prep C18 column, 30*150 mm, 5 µm; Mobile Phase A: water (0.1% FA), Mobile Phase B: MeCN; Flow rate: 60 mL/min; Gradient: 16% B to 30% B in 10 min; Wave Length: 254/220 nm; RT: 9.4) to afford the title compound (AIF-1) (9.1 mg, 16 µmol, 24%, 98.0% Purity) as a white solid. m/z 560.2 (M+H)⁺ (ES+). ¹H NMR (400 MHz, DMSO-d6) δ 8.54 (s, 1H), 8.28-8.19 (m, 2H), 7.99 (d, J=1.4 Hz, 1H), 7.87 (d, J=8.5 Hz, 1H), 7.75 (s, 1H), 7.65 (d, J=1.8 Hz, 2H), 6.88 (d, J=1.4 Hz, 1H), 5.00 (s, 2H), 3.85 (s, 3H), 3.48 (s, 4H), 2.09-2.00 (m, 1H), 1.71-1.61 (m, 2H), 1.61-1.29 (m, 6H), 1.03-0.79 (m, 4H).

Example 263: Synthesis of 4-[2-(6-{[(Cyclopentyl-methyl)amino]methyl}-1-oxo-3H-isoindol-2-yl)-6-cyclopropylpyridin-4-yl]-3-(4-methyl-1,2,4-triazol-3-yl)benzonitrile (AIG-1)

Example 264: Synthesis of 4-(2-Cyclopropyl-6-(5-fluoro-6-(((2-methoxyethyl)amino)methyl)-1-oxoi-soindolin-2-yl)pyridin-4-yl)-3-(4-methyl-4H-1,2,4-triazol-3-yl)benzonitrile (AIH-2)

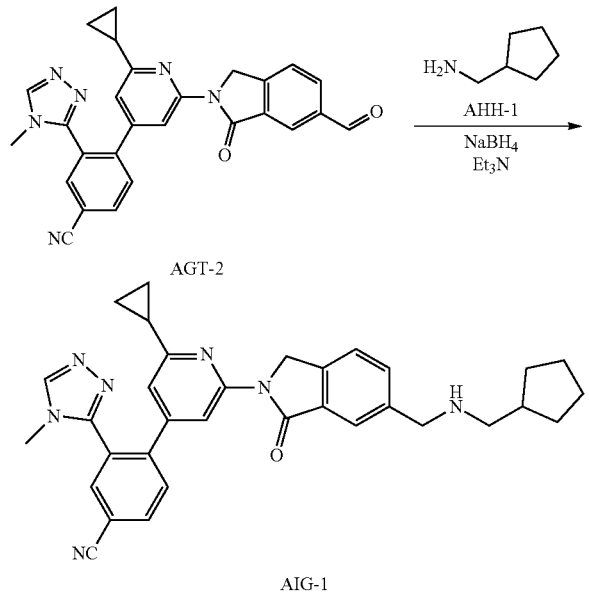

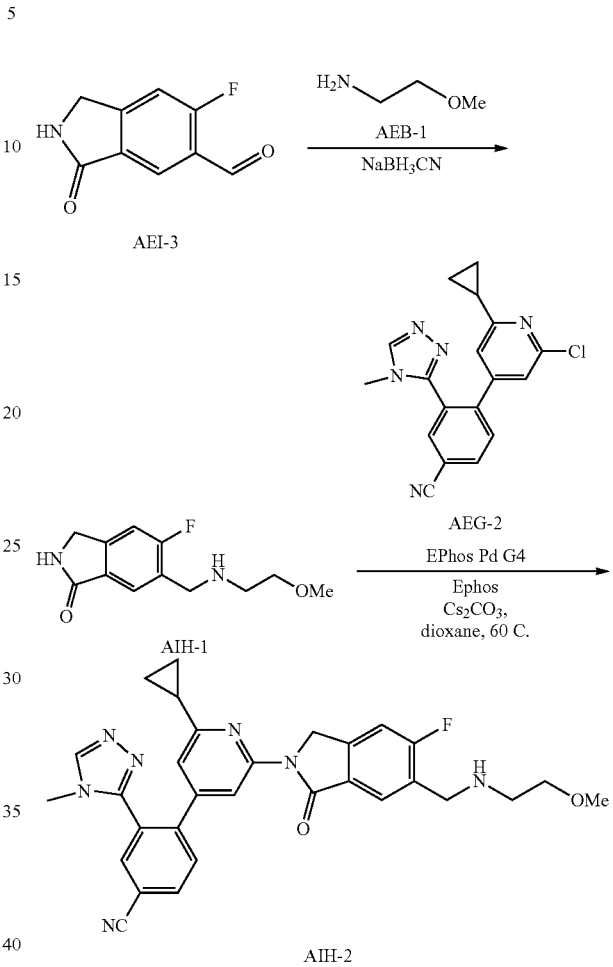

To a stirred solution of intermediate (AGT-2) (30 mg, 1 Eq, 65 μmol) and 1-cyclopentylmethanamine (AHH-1) (6.5 mg, 1 Eq, 65 μmol) in MeOH (5 mL) was added Et$_3$N (33 mg, 5 Eq, 0.33 mmol) for 2 h at 60° C. under nitrogen atmosphere. To the above mixture was added NaBH$_4$ (25 mg, 10 Eq, 0.65 mmol) at 0° C. The resulting mixture was stirred for 2 h at rt. The reaction was then quenched by the addition of MeOH (2 mL) at 0° C. The resulting mixture was diluted with water and extracted with DCM (3×20 mL). The combined organic layers were washed with brine (2×20 mL), dried (Na$_2$SO$_4$). After filtration, the filtrate was concentrated in vacuo. The crude product was purified by Prep-HPLC with the following conditions: Column: XBridge Prep OBD C18 Column, 19×250 mm, 5 μm; Mobile Phase A: water (0.1% NH$_4$HCO$_3$+0.1% NH$_3$·H$_2$O) Mobile Phase B: MeCN; Flow rate: 60 mL/min; Gradient: 48 B to 58 B in 9 min; Detector, UV 254/210 nm; RT: 8.6. The product-containing fractions were combined and evaporated partially in vacuo and lyophilized overnight to afford the title compound (AIG-1) (13.5 mg, 25 μmol, 38%, 99.7% Purity) as a white solid. m/z 544.4 (M+H)$^+$ (ES+). $^1$H NMR (400 MHz, Methanol-d4) δ 8.49 (s, 1H), 8.15-8.03 (m, 3H), 7.92-7.81 (m, 2H), 7.70-7.60 (m, 2H), 6.92 (d, J=1.5 Hz, 1H), 5.03 (s, 2H), 3.89 (s, 2H), 3.50 (s, 3H), 2.54 (d, J=7.3 Hz, 2H), 2.12-2.00 (m, 2H), 1.87-1.77 (m, 2H), 1.67-1.49 (m, 4H), 1.22-1.13 (m, 2H), 1.09-0.92 (m, 4H).

Step 1: 5-Fluoro-6-{[(2-methoxyethyl)amino]methyl}-2,3-dihydroisoindol-1-one (AIH-1)

To a solution of intermediate (AEI-3) (200 mg, 1.12 mmol, 1 Eq) and 2-methoxyethan-1-amine (AEB-1) (101 mg, 1.2 Eq, 1.34 mmol) in MeOH (10 mL) was added AcOH (134 mg, 2 Eq, 2.23 mmol) at rt. The resulting mixture was stirred for 1 h at rt. Then NaBH$_3$CN (140 mg, 2 Eq, 2.23 mmol) was added at rt. The resulting mixture was stirred for 1 h at rt. The resulting mixture was concentrated in vacuo. The resulting mixture was extracted with DCM (3×50 mL). The combined organic layers were washed with brine (2×50 mL), dried (Na$_2$SO$_4$). After filtration, the filtrate was concentrated in vacuo. The residue was purified by Prep-TLC with DCM/MeOH (10/1) to afford the sub-title compound (AIH-1) (200 mg, 0.84 mmol, 63%, 95% Purity) as a yellow oil. m/z 239.1 (M+H)$^+$ (ES+).

Step 2: 4-(2-Cyclopropyl-6-(5-fluoro-6-(((2-methoxyethyl)amino)methyl)-1-oxoisoindolin-2-yl)pyridin-4-yl)-3-(4-methyl-4H-1,2,4-triazol-3-yl)benzonitrile (AIH-2)

A solution of intermediate (AEG-2) (59 mg, 1 Eq, 0.18 mmol), the product from step 1 above (AIH-1) (50 mg, 1.2

Eq, 0.21 mmol) and Cs$_2$CO$_3$ (171 mg, 3 Eq, 0.53 mmol) in 1,4-dioxane (10 mL) was stirred at rt under nitrogen atmosphere. To the above mixture were added Ephos (9.4 mg, 0.1 Eq, 18 μmol) and Ephos Pd G4 (16 mg, 0.1 Eq, 18 μmol) at rt under nitrogen atmosphere. The resulting mixture was stirred for additional 2 h at 60° C. under nitrogen atmosphere. The mixture was cooled to rt and concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: water (0.1% NH4HCO3+0.1% NH3·H2O), Mobile Phase B: MeCN; Flow rate: 60 mL/min; Gradient: 37% B to 47% B in 8 min, 47% B; Wave Length: 254/220 nm) to afford the title compound (AIH-2) (3.1 mg, 5.8 μmol, 3.2%, 96.1% Purity) as a white solid. m/z 538.1 (M+H)$^+$ (ES+). $^1$H NMR (400 MHz, DMSO-d6) δ 8.53 (s, 1H), 8.22-8.19 (m, 2H), 7.95 (d, J=1.4 Hz, 1H), 7.88-7.85 (m, 2H), 7.53 (d, J=9.5 Hz, 1H), 6.89 (d, J=1.4 Hz, 1H), 5.00 (s, 2H), 3.82 (s, 2H), 3.48 (s, 3H), 3.40 (t, J=5.6 Hz, 2H), 3.24 (s, 3H), 2.67 (t, J=5.6 Hz, 2H), 2.07-2.01 (m, 1H), 0.97 (d, J=6.4 Hz, 4H).

Example 265: Synthesis of 2-{6-Cyclopropyl-4-[2,4-difluoro-6-(4-methyl-1,2,4-triazol-3-yl)phenyl]pyridin-2-yl}-6-({[(1-hydroxycyclobutyl)methyl]amino}methyl)-3H-isoindol-1-one (AII-9)

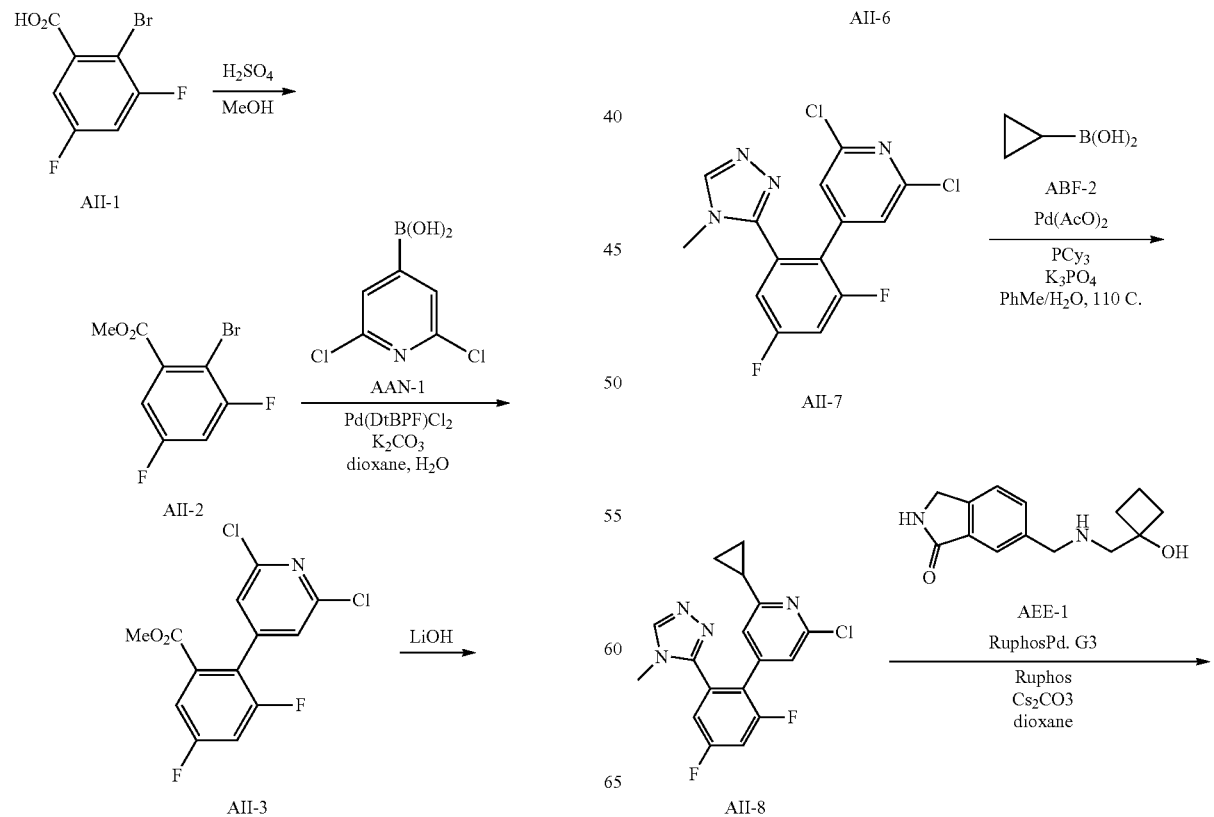

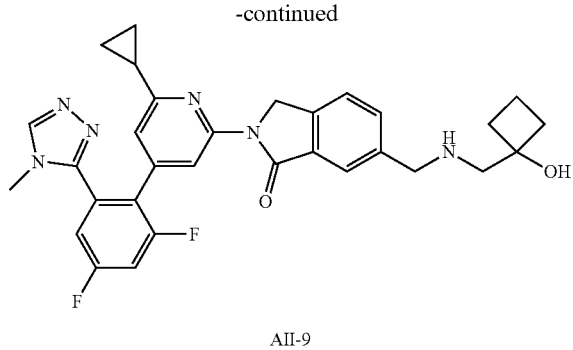

AII-9

Step 1: Methyl 2-bromo-3,5-difluorobenzoate (AII-2)

To a stirred mixture of 2-bromo-3,5-difluorobenzoic acid (AII-1) (2.00 g, 1 Eq, 8.44 mmol) in MeOH (30 mL) was added conc. $H_2SO_4$ (10 mL) at 0° C. The resulting mixture was stirred for 12 h at 70° C. The mixture was cooled to rt. The reaction was then quenched by the addition of 50 mL of ice water at 0° C. The residue was basified to pH 7 with sat. aq. of $NaHCO_3$. The resulting mixture was diluted with water and extracted with EtOAc (3×100 mL). The combined organic layers were washed with brine (2×100 mL), dried ($Na_2SO_4$). After filtration, the filtrate was concentrated in vacuo. The residue was applied on a silica gel column chromatography with petroleum ether/EtOAc (5/1) to afford the sub-title compound (AII-2) (1.1 g, 4.4 mmol, 52%, 90% Purity) as a yellow solid. m/z 250.9/252.9 (M+H)$^+$ (ES+)

Step 2: Methyl 2-(2,6-dichloropyridin-4-yl)-3,5-difluorobenzoate (AII-3)

To a stirred mixture of the product from step 1 above (AII-2) (600 mg, 1 Eq, 2.39 mmol), 2,6-dichloropyridin-4-ylboronic acid (AAN-1) (550 mg, 1.2 Eq, 2.87 mmol) and $K_2CO_3$ (991 mg, 7.17 mmol, 3 Eq) in dioxane (20 mL) was added Pd(DtBPF)Cl$_2$ (156 mg, 0.1 Eq, 0.24 mmol) at rt under nitrogen atmosphere. The resulting mixture was stirred for 4 h at 80° C. under nitrogen atmosphere. The mixture was cooled to rt and concentrated in vacuo. The resulting mixture was diluted with water and extracted with EtOAc (3×80 mL). The combined organic layers were washed with brine (2×80 mL), dried ($Na_2SO_4$). After filtration, the filtrate was concentrated in vacuo. The crude product was purified by reverse flash column chromatography with the following conditions: Column, C18; mobile phase, water (0.1% $NH_4HCO_3$) and MeCN (10% ACN up to 80% in 10 min); Detector, UV 254/220 nm. This resulted in the sub-title compound (AII-3) (300 mg, 0.95 mmol, 39%, 92% Purity) as a yellow solid. m/z 318.0/320.0 (M+H)$^+$ (ES+)

Step 3: 2-(2,6-Dichloropyridin-4-yl)-3,5-difluorobenzoic acid (AII-4)

To a stirred mixture of the product from step 2 above (AII-3) (990 mg, 1 Eq, 3.11 mmol) in THF (10 mL) and $H_2O$ (2 mL) was added LiOH (2.98 g, 40 Eq, 124 mmol) at rt. The resulting mixture was stirred for 12 h at 80° C. The mixture was cooled to rt. The residue was acidified to pH 4 with conc. HCl. The mixture was concentrated in vacuo. The resulting mixture was diluted with water and extracted with EtOAc (3×80 mL). The combined organic layers were washed with brine (2×80 mL), dried ($Na_2SO_4$). After filtration, the filtrate was concentrated in vacuo. The resulting mixture was used in the next step directly without further purification. m/z 304.0/306.0 (M+H)$^+$ (ES+)

Step 4: 2-(2,6-Dichloropyridin-4-yl)-3,5-difluoro-N-[(methylcarbamothioyl)amino]benzamide (AII-5)

To a stirred mixture of the product from step 3 above (AII-4) (573 mg, 1 Eq, 1.88 mmol) and 1-amino-3-methylthiourea (D-2) (238 mg, 2.26 mmol, 1.2 Eq) in DMF (20 mL) were added DIPEA (731 mg, 3 Eq, 5.65 mmol) and T$_3$P (899 mg, 1.5 Eq, 2.83 mmol) at rt. The resulting mixture was stirred for 2 h at rt under air atmosphere. The resulting mixture was diluted with water and extracted with EtOAc (3×80 mL). The combined organic layers were washed with brine (2×80 mL), dried ($Na_2SO_4$). After filtration, the filtrate was concentrated in vacuo. The crude product was purified by reverse flash column chromatography with the following conditions: Column, C18; mobile phase, water (0.1% $NH_4HCO_3$) and MeCN (10% MeCN up to 60% in 15 min); Detector, UV 254/220 nm. This resulted in the sub-title compound (AII-5) (500 mg, 1.28 mmol, 68%, 90% Purity) as a yellow solid. m/z 391.0/393.0 (M+H)$^+$ (ES+)

Step 5: 5-[2-(2,6-Dichloropyridin-4-yl)-3,5-difluorophenyl]-4-methyl-1,2,4-triazole-3-thiol (AII-6)

A mixture of the product from step 4 above (AII-5) (490 mg, 1 Eq, 1.25 mmol) in aq. NaOH (10 mL, 1 M) was stirred for 12 h at 60° C. The mixture was allowed to cool down to rt. The residue was acidified to pH 4 with conc. HCl. The resulting mixture was diluted with water and extracted with EtOAc (3×50 mL). The combined organic layers were washed with brine (2×50 mL), dried ($Na_2SO_4$). After filtration, the filtrate was concentrated in vacuo. The crude product was purified by reverse flash column chromatography with the following conditions: Column, C18; mobile phase, water (0.1% $NH_4HCO_3$) and MeCN (10% MeCN up to 65% in 15 min); Detector, UV 254/220 nm. This resulted in the sub-title compound (AII-6) (230 mg, 0.62 mmol, 49%, 92% Purity) as a yellow solid. m/z 373.0/375.0 (M+H)$^+$ (ES+)

Step 6: 2,6-Dichloro-4-[2,4-difluoro-6-(4-methyl-1,2,4-triazol-3-yl) phenyl]pyridine (AII-7)

To a stirred mixture of the product from step 5 above (AII-6) (275 mg, 1 Eq, 0.74 mmol) and AcOH (89 mg, 2 Eq, 1.47 mmol) in DCM (20 mL) was added $H_2O_2$ (66 mg, 30% Wt, 5 Eq, 3.69 mmol) at 0° C. The resulting mixture was stirred for 2 h at rt. The residue was basified to pH 8 with sat. aq. of $NaHCO_3$. The resulting mixture was diluted with water and extracted with EtOAc (3×50 mL). The combined organic layers were washed with brine (2×50 mL), dried ($Na_2SO_4$). After filtration, the filtrate was concentrated in vacuo. The crude product was purified by reverse flash column chromatography with the following conditions: Column, C18; mobile phase, water (0.1% $NH_4HCO_3$) and MeCN (10% ACN up to 50% in 15 min); Detector, UV 254/220 nm. This resulted in the sub-title compound (AII-7) (173 mg, 0.51 mmol, 69%, 95% Purity) as a yellow solid. m/z 341.0/343.0 (M+H)$^+$ (ES+)

Step 7: 2-Chloro-6-cyclopropyl-4-[2,4-difluoro-6-(4-methyl-1,2,4-triazol-3-yl)phenyl]pyridine (AII-8)

To a stirred mixture of the product from step 6 above (AII-7) (168 mg, 1 Eq, 0.49 mmol), cyclopropyl boronic acid (ABF-2) (63 mg, 1.5 Eq, 0.74 mmol) in dioxane (10 mL) were added KOAc (97 mg, 2 Eq, 0.98 mmol) and PCy3 (14 mg, 0.1 Eq, 49 μmol) at rt under nitrogen atmosphere. To the above mixture was added Pd(OAc)$_2$ (11 mg, 0.1 Eq, 49 μmol) at rt under nitrogen atmosphere. The resulting mixture was stirred for 2 h at 100° C. under nitrogen atmosphere. The mixture was cooled to rt and concentrated in vacuo. The resulting mixture was diluted with water and extracted with EtOAc (3×20 mL). The combined organic layers were washed with brine (2×20 mL), dried (Na$_2$SO$_4$). After filtration, the filtrate was concentrated in vacuo. The residue was purified by Prep-TLC with DCM/MeOH (10/1) to afford the sub-title compound (AII-8) (130 mg, 0.38 mmol, 76%, 91% Purity) as a yellow solid. m/z 347.1/349.1 (M+H)$^+$ (ES+)

Step 8: 2-{6-Cyclopropyl-4-[2,4-difluoro-6-(4-methyl-1,2,4-triazol-3-yl) phenyl]pyridin-2-yl}-6-({[(1-hydroxycyclobutyl)methyl]amino}methyl)-3H-isoindol-1-one (AII-9)

To a stirred mixture the product from step 7 above (AII-8) (107 mg, 1.2 Eq, 0.31 mmol), intermediate (AEE-1) (60 mg, 1 Eq, 0.26 mmol) and Cs$_2$CO$_3$ (252 mg, 3 Eq, 0.77 mmol) in dioxane (10 mL) were added RuPhos Palladacycle Gen.3 (43 mg, 0.2 Eq, 52 μmol) and RuPhos (48 mg, 0.4 Eq, 0.10 mmol) at rt under nitrogen atmosphere. The resulting mixture was stirred for 2 h at 100° C. under nitrogen atmosphere. The mixture was allowed to cool down to rt. The resulting mixture was diluted with water and extracted with EtOAc (3×20 mL). The combined organic layers were washed with brine (2×20 mL), dried (Na$_2$SO$_4$). After filtration, the filtrate was concentrated in vacuo. The residue was purified by Prep-TLC with DCM/MeOH (6/1). The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: MeCN; Flow rate: 60 mL/min; Gradient: 30% B to 55% B in 10 min; Wave Length: 254/220 nm; RT: 9) to afford the title compound (AII-9) (19.6 mg, 35 μmol, 14%, 99.1% Purity) as a white solid. m/z 557.2 (M+H)$^+$ (ES+). $^1$H NMR (400 MHz, DMSO-d6) δ 8.48 (s, 1H), 8.00 (d, J=1.1 Hz, 1H), 7.74 (d, J=4.9 Hz, 1H), 7.72-7.66 (m, 1H), 7.66-7.61 (m, 2H), 7.51 (d, J=8.8, 2.7, 1.2 Hz, 1H), 6.87 (t, J=1.3 Hz, 1H), 5.00 (s, 2H), 3.85 (s, 2H), 3.50 (s, 3H), 2.53 (s, 2H), 2.04-1.87 (m, 5H), 1.60 (t, J=13.1, 6.6, 3.4 Hz, 1H), 1.39 (d, J=11.1, 8.9 Hz, 1H), 1.00-0.93 (m, 4H).

Example 266: Synthesis of 2-{6-Ethoxy-4-[4-fluoro-2-(4-methyl-1,2,4-triazol-3-yl)phenyl]pyridin-2-yl}-6-({[(1-hydroxycyclobutyl)methyl]amino}methyl)-4-methoxy-3H-isoindol-1-one (AIJ-2)

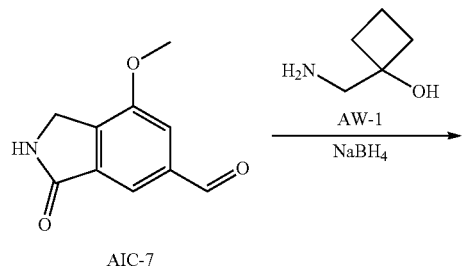

AIC-7

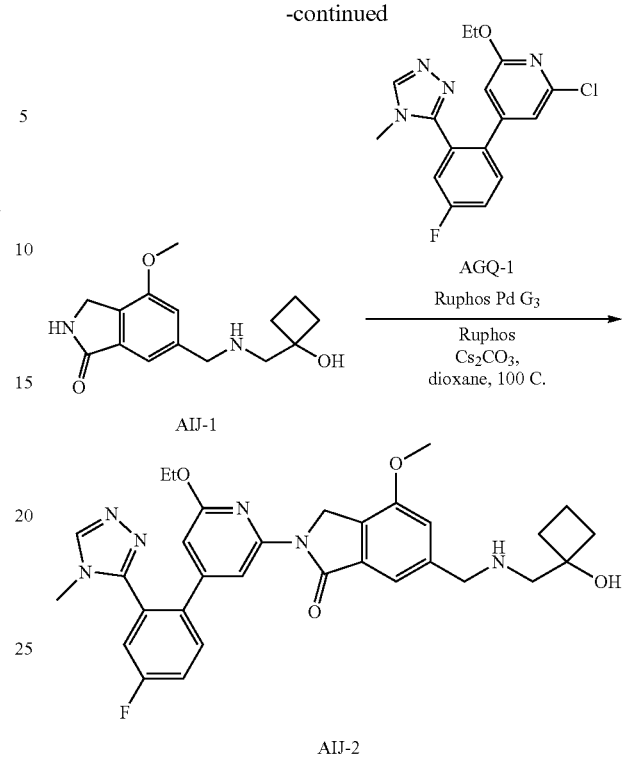

Step 1: 6-({[(1-Hydroxycyclobutyl)methyl]amino}methyl)-4-methoxy-2,3-dihydroisoindol-1-one (AIJ-1)

A mixture of 7-methoxy-3-oxo-1,2-dihydroisoindole-5-carbaldehyde (AIC-7) (180 mg, 1 Eq, 0.94 mmol) and 1-(aminomethyl)cyclobutan-1-ol (AW-1) (114 mg, 1.2 Eq, 1.13 mmol) in MeOH (10 mL) was stirred for 2 h at rt. To the above mixture was added NaBH$_4$ (71 mg, 2 Eq, 1.88 mmol) at 0° C. The resulting mixture was stirred for 1 h at rt. The reaction was then quenched by the addition of MeOH (2 mL) at 0° C. The resulting mixture was concentrated in vacuo. The residue was purified by Prep-TLC with DCM/MeOH (10/1) to afford the sub-title compound (AIJ-1) (150 mg, 0.54 mmol, 58%, 92% Purity) as a white solid. m/z 277.2 (M+H)$^+$ (ES+)

Step 2: 2-{6-Ethoxy-4-[4-fluoro-2-(4-methyl-1,2,4-triazol-3-yl)phenyl]pyridin-2-yl}-6-({[(1-hydroxycyclobutyl)methyl]amino}methyl)-4-methoxy-3H-isoindol-1-one (AIJ-2)

To a stirred mixture of the product from step 1 above (AIJ-1) (50 mg, 1 Eq, 0.18 mmol), intermediate (AGQ-1) (72 mg, 1.2 Eq, 0.22 mmol) and Cs$_2$CO$_3$ (177 mg, 3 Eq, 0.54 mmol) in dioxane (10 mL) were added RuPhos Palladacycle Gen.3 (30 mg, 0.2 Eq, 36 μmol) and RuPhos (34 mg, 0.4 Eq, 72 μmol) at rt under nitrogen atmosphere. The resulting mixture was stirred for 2 h at 100° C. under nitrogen atmosphere. The mixture was cooled to rt and concentrated in vacuo. The resulting mixture was diluted with water and extracted with EtOAc (3×20 mL). The combined organic layers were washed with brine (2×20 mL), dried (Na$_2$SO$_4$). After filtration, the filtrate was concentrated in vacuo. The residue was purified by Prep-TLC with DCM/MeOH (12/1).

The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 42% B to 52% B in 9 min; Wave Length: 254/220 nm; RT: 8.2) to afford the title compound (AIJ-2) (20.6 mg, 36 μmol, 20%, 99.7% Purity) as a white solid. m/z 573.2 (M+H)⁺ (ES+). ¹H NMR (400 MHz, DMSO-d6) δ 8.49 (s, 1H), 7.80 (d, J=1.2 Hz, 1H), 7.69 (d, J=8.4, 5.6 Hz, 1H), 7.62-7.52 (m, 2H), 7.40 (d, J=25.0 Hz, 2H), 6.28 (d, J=1.3 Hz, 1H), 5.21 (s, 1H), 4.96 (s, 2H), 4.33 (m, 2H), 4.00 (s, 2H), 3.93 (s, 3H), 3.43 (s, 3H), 2.69 (s, 2H), 2.07-1.90 (m, 4H), 1.62 (d, J=10.8 Hz, 1H), 1.46-1.39 (m, 1H), 1.34 (t, J=7.0 Hz, 3H).

Example 267: Synthesis of 4-{2-Cyclopropyl-6-[6-({[(2R)-1-methoxypropan-2-yl]amino}methyl)-1-oxo-3H-isoindol-2-yl]pyridin-4-yl}-3-(4-methyl-1,2,4-triazol-3-yl) (AIK-2)

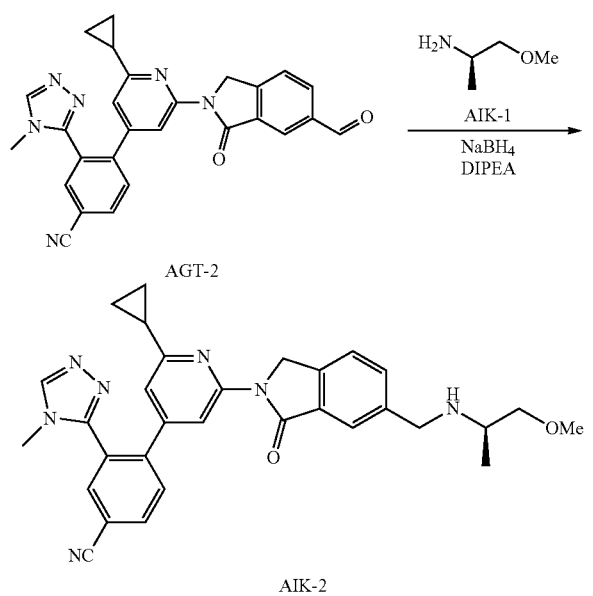

A solution of intermediate (AGT-2) (30 mg, 1 Eq, 65 μmol) in MeOH (10 mL) was treated with (2R)-1-methoxypropan-2-amine (AIK-1) (7 mg, 1.2 Eq, 78 μmol) for 1 h at 60° C. under nitrogen atmosphere. To the above mixture was added NaBH₄ (7 mg, 3 Eq, 0.20 mmol) at 0° C. The resulting mixture was stirred for 1 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 37% B to 47% B in 9 min; Wave Length: 254/220 nm; RT: 8.25) to afford the title compound (AIK-2) (3.4 mg, 6.4 μmol, 9.6%, 98.3% Purity) as a white solid. m/z 534.3 (M+H)⁺ (ES+). ¹H NMR (400 MHz, DMSO-d6) δ 8.53 (s, 1H), 8.21 (d, J=4.2, 1.8 Hz, 2H), 7.99 (d, J=1.4 Hz, 1H), 7.91-7.84 (m, 1H), 7.75 (s, 1H), 7.63 (d, J=1.5 Hz, 2H), 6.88 (d, J=1.4 Hz, 1H), 5.00 (s, 2H), 3.84 (m, 2H), 3.48 (s, 3H), 3.35 (s, 2H), 3.25 (s, 2H), 3.21-3.17 (m, 1H), 2.76 (m, 1H), 2.07-2.01 (m, 2H), 0.97 (d, J=6.9, 1.8 Hz, 7H).

Example 268: Synthesis of 4-[2-Cyclopropyl-6-(6-{[(2-isopropoxyethyl)amino]methyl}-1-oxo-3H-isoindol-2-yl)pyridin-4-yl]-3-(4-methyl-1,2,4-triazol-3-yl)benzonitrile (AIL-3)

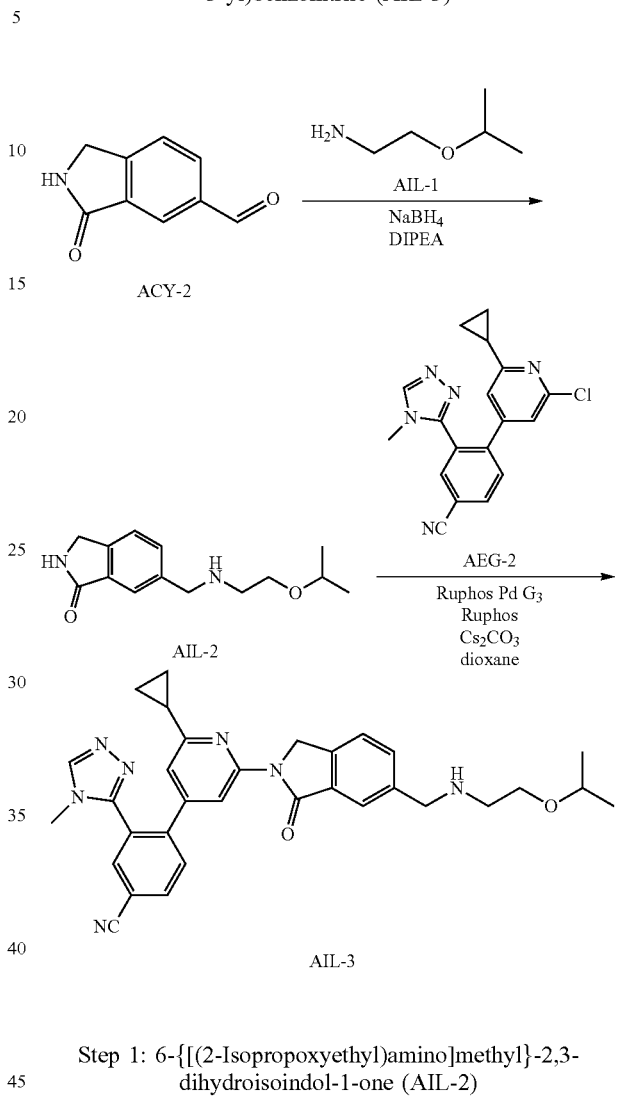

Step 1: 6-{[(2-Isopropoxyethyl)amino]methyl}-2,3-dihydroisoindol-1-one (AIL-2)

A solution of intermediate (ACY-2) (60 mg, 1 Eq, 0.37 mmol) and 2-isopropoxyethanamine (AIL-1) (46 mg, 1.2 Eq, 0.45 mmol) in MeOH (4 mL) was stirred for 2 h at 60° C. The mixture was allowed to cool down to rt. To the above mixture was added NaBH₄ (28 mg, 2 Eq, 0.74 mmol) at 0° C. The resulting mixture was stirred for additional 1 h at rt. The reaction was then quenched by the addition of MeOH (2 mL) at 0° C. The mixture was concentrated in vacuo. The residue was purified by Prep-TLC with DCM/MeOH (10/1) to afford the sub-title compound (AIL-2) (40 mg, 0.16 mmol, 43%, 95% Purity) as a white solid. m/z 248.1 (M+H)⁺ (ES+)

Step 2: 4-[2-Cyclopropyl-6-(6-{[(2-isopropoxyethyl)amino]methyl}-1-oxo-3H-isoindol-2-yl)pyridin-4-yl]-3-(4-methyl-1,2,4-triazol-3-yl)benzonitrile (AIL-3)

To a stirred mixture of intermediate (AEG-2) (50 mg, 1 Eq, 0.15 mmol), the product from step 1 above (AIL-2) (44 mg, 1.2 Eq, 0.18 mmol) and Cs₂CO₃ (34 mg, 3 Eq, 0.45 mmol) in dioxane (10 mL) were added RuPhos Palladacycle Gen.3 (23 mg, 0.2 Eq, 30 µmol) and RuPhos (28 mg, 0.4 Eq, 60 µmol) at rt under nitrogen atmosphere. The resulting mixture was stirred for 2 h at 100° C. under nitrogen atmosphere. The mixture was allowed to cool down to rt. The resulting mixture was diluted with water and extracted with EtOAc (3×20 mL). The combined organic layers were washed with brine (2×20 mL), dried ($Na_2SO_4$). After filtration, the filtrate was concentrated in vacuo. The residue was purified by Prep-TLC with DCM/MeOH (12/1). The crude product was purified by Prep-HPLC with the following conditions (Column: XBridge Prep OBD C18 Column, 30*150 mm, 5 µm; Mobile Phase A: water (0.1% $NH_4HCO_3$), Mobile Phase B: MeCN; Flow rate: 60 mL/min; Gradient: 37% B to 44% B in 12 min; Wave Length: 254/220 nm; RT: 10.75) to afford the title compound (AIL-3) (15.8 mg, 29 µmol, 19%, 99.4% Purity) as a white solid. m/z 548.1 $(M+H)^+$ (ES+). $^1$H NMR (400 MHz, DMSO-d6) δ 8.53 (s, 1H), 8.21 (d, J=3.5, 1.8 Hz, 2H), 7.99 (s, 1H), 7.87 (d, J=8.5 Hz, 1H), 7.73 (s, 1H), 7.63 (s, 2H), 6.88 (d, J=1.5 Hz, 1H), 5.00 (s, 2H), 3.82 (s, 2H), 3.56-3.41 (m, 6H), 2.61 (t, J=5.8 Hz, 2H), 2.05 (m, 1H), 1.08 (d, J=6.0 Hz, 6H), 0.97 (d, J=6.4 Hz, 4H).

Example 269: Synthesis of 4-{2-cyclopropyl-6-[6-({[(2S)-2-methoxypropyl] amino} methyl)-1-oxo-3H-isoindol-2-yl]pyridin-4-yl}-3-(4-methyl-1,2,4-triazol-3-yl) benzonitrile (AIN-2)

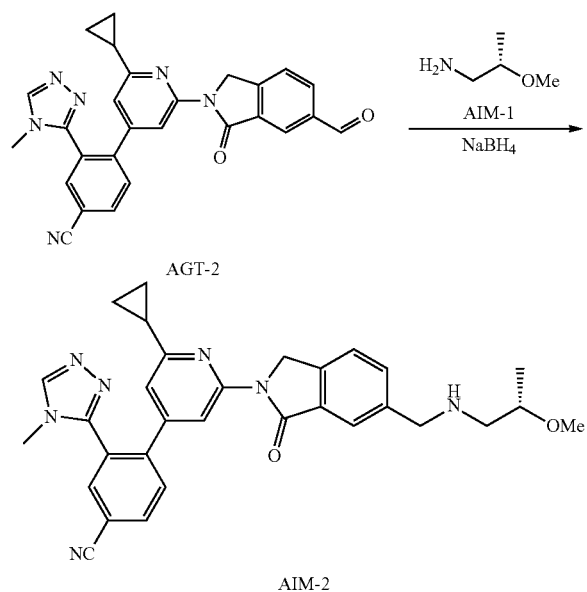

A solution of intermediate (AGT-2) (30 mg, 1 Eq, 65 µmol) and (2S)-2-methoxypropan-1-amine (AIM-1) (9 mg, 1.5 Eq, 98 µmol) in MeOH (5 mL) was stirred for 1 h at 60° C. To the above mixture was added $NaBH_4$ (5 mg, 2 Eq, 0.13 mmol) at 0° C. The resulting mixture was stirred for additional 1 h at rt. The reaction was then quenched by the addition of MeOH (2 mL) at 0° C. and then concentrated in vacuo. The crude product was purified by Prep-HPLC with the following conditions (Column: Sunfire prep C18 column, 30*150 mm, 5 µm; Mobile Phase A: water (0.1% FA), Mobile Phase B: MeCN; Flow rate: 60 mL/min; Gradient: 10% B to 32% B in 7 min; Wave Length: 254/220 nm) to afford the title compound (AIM-2) (14.2 mg, 26 µmol, 41%, 99.5% Purity) as a white solid. m/z 534.2 $(M+H)^+$ (ES+). $^1$H NMR (400 MHz, DMSO-d6) δ 8.54 (d, J=1.7 Hz, 1H), 8.28-8.17 (m, 2H), 8.02-7.96 (m, 1H), 7.93-7.81 (m, 1H), 7.75 (s, 1H), 7.65 (d, J=6.3 Hz, 2H), 6.93-6.82 (m, 1H), 5.09-4.93 (m, 2H), 3.84 (d, J=5.5 Hz, 2H), 3.48 (t, J=3.4 Hz, 3H), 3.43-3.37 (m, 1H), 3.25 (d, J=4.6 Hz, 3H), 2.55-2.52 (m, 2H), 2.09-1.99 (m, 1H), 1.12-1.04 (m, 3H), 1.05-0.84 (m, 4H).

Example 270: Synthesis of 4-[2-cyclopropyl-6-(6-{[(2-ethoxyethyl)amino]methyl}-1-oxo-3H-isoindol-2-yl)pyridin-4-yl]-3-(4-methyl-1,2,4-triazol-3-yl) benzonitrile (AIN-2)

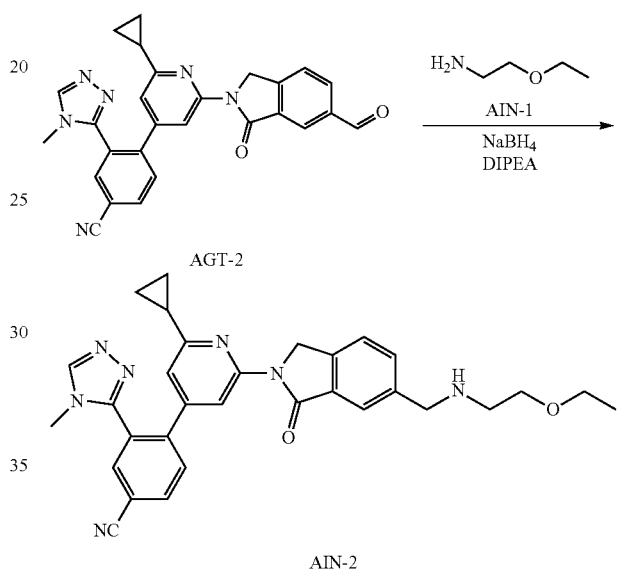

A solution of intermediate (AGT-2) (30 mg, 1 Eq, 65 µmol), DIPEA (25 mg, 3 Eq, 0.20 mmol) and 2-ethoxyethan-1-amine (AIN-1) (7 mg, 1.2 Eq, 78 µmol) in MeOH (8 mL) was stirred for 2 h at 60° C. The mixture was allowed to cool down to rt. To the above mixture was added $NaBH_4$ (12 mg, 5 Eq, 0.33 mmol) at 0° C. The resulting mixture was stirred for 1 h at rt. The reaction was then quenched by the addition of MeOH (2 mL) at 0° C. and concentrated in vacuo. The crude product was purified by Prep-HPLC with the following conditions (Column: Sunfire prep C18 column, 30*150 mm, 5 µm; Mobile Phase A: water (0.1% FA), Mobile Phase B: MeCN; Flow rate: 60 mL/min; Gradient: 18% B to 30% B in 10 min; Wave Length: 254/220 nm; RT: 10.07) to afford the title compound (AIN-2) (9.4 mg, 18 µmol, 26%, 97.6% Purity) as a white solid. m/z 534.3 $(M+H)^+$ (ES+). $^1$H NMR (400 MHz, Methanol-d4) δ 8.50 (s, 1H), 8.14-8.10 (m, 1H), 8.09 (d, J=1.5 Hz, 1H), 8.05 (d, J=1.4 Hz, 1H), 7.94-7.90 (m, 1H), 7.80 (t, J=1.1 Hz, 1H), 7.69-7.64 (m, 1H), 7.63-7.59 (m, 1H), 6.91 (d, J=1.4 Hz, 1H), 5.02 (s, 2H), 3.89 (s, 2H), 3.56 (t, J=5.4 Hz, 2H), 3.51 (d, J=7.0 Hz, 5H), 2.76 (t, J=5.4 Hz, 2H), 2.07-1.98 (m, 1H), 1.19 (t, J=7.0 Hz, 3H), 1.06-1.01 (m, 2H), 1.01-0.95 (m, 2H).

Example 271: Synthesis of 4-[2-Cyclopropyl-6-(4-fluoro-6-{[(2-methoxyethyl)amino]methyl}-1-oxo-3H-isoindol-2-yl)pyridin-4-yl]-3-(4-methyl-1,2,4-triazol-3-yl)benzonitrile (AIO-9)

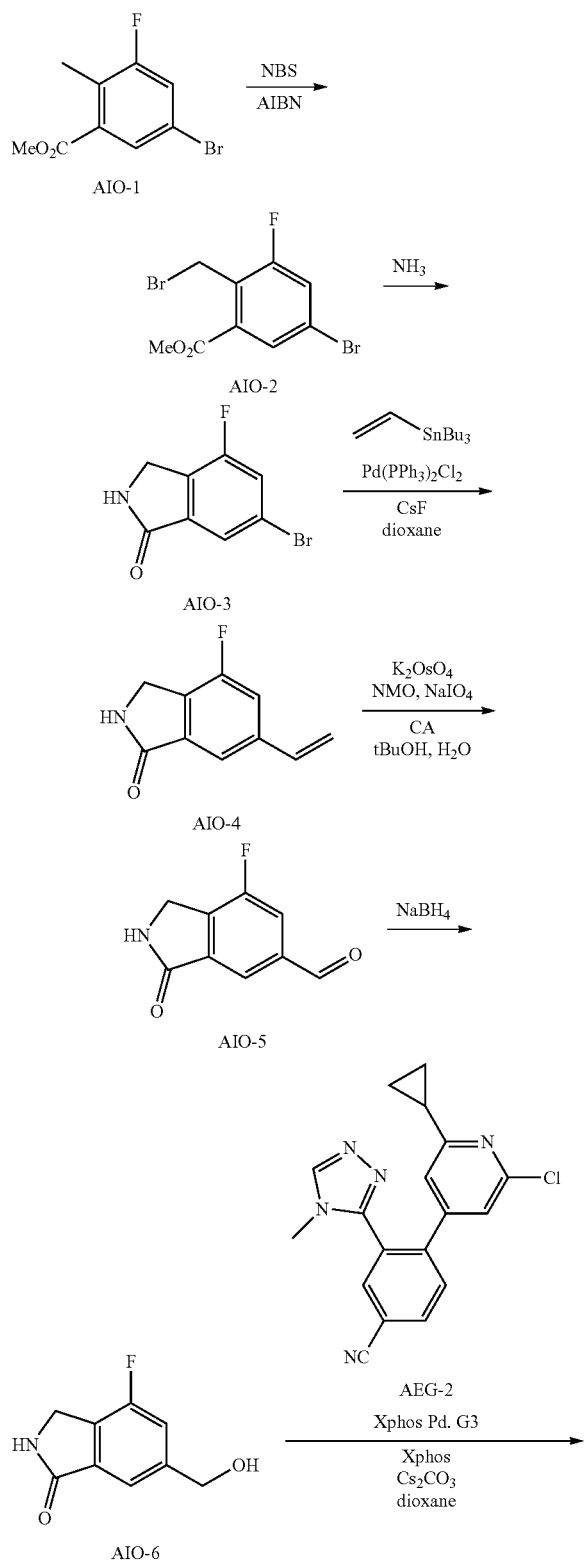

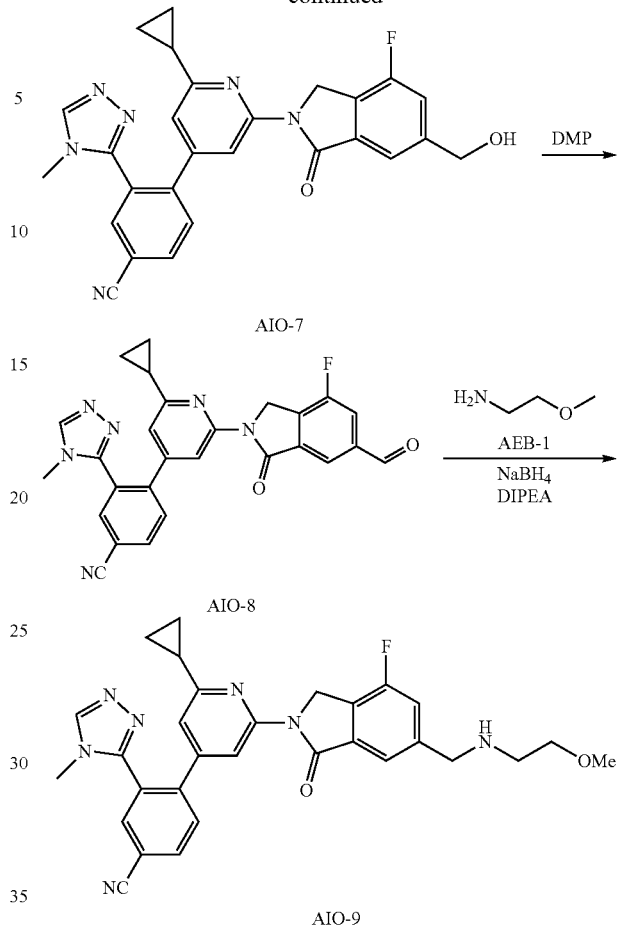

Step 1: Methyl 5-bromo-2-(bromomethyl)-3-fluorobenzoate (AIO-2)

To a stirred solution of methyl 5-bromo-3-fluoro-2-methylbenzoate (AIO-1) (1.50 g, 1 Eq, 6.07 mmol) and NBS (1.30 g, 1.2 Eq, 7.29 mmol) in benzotrifluoride (20 mL) was added AIBN (299 mg, 0.3 Eq, 1.82 mmol) at rt. The resulting mixture was stirred overnight at 110° C. The mixture was allowed to cool down to rt. The resulting mixture was concentrated in vacuo to afford the sub-title compound (AIO-2) (1.7 g, 5.21 mmol, 86%, 83% Purity) as a brown-yellow oil. m/z 326.9/328.9 (M+H)$^+$ (ES+)

Step 2: 6-Bromo-4-fluoro-2,3-dihydroisoindol-1-one (AIO-3)

A stirred solution of the product from step 1 above (AIO-2) (1.70 g, 1 Eq, 5.22 mmol) in NH$_3$/MeOH (30 mL, 7 M) was stirred for 2 h at rt. The resulting mixture was concentrated in vacuo. The residue was purified by Prep-TLC with EtOAc/petroleum ether (3/1) to afford the sub-title compound (AIO-3) (1.1 g, 3.34 mmol, 92%, 92% Purity) as a yellow solid. m/z 330.0/332.0 (M+H)$^+$ (ES+)

Step 3: 6-Ethenyl-4-fluoro-2,3-dihydroisoindol-1-one (AIO-4)

To a stirred solution of the product from step 2 above (AIO-3) (1.10 g, 1 Eq, 4.78 mmol), tributyl(ethenyl)stannane (1.82 g, 1.2 Eq, 5.74 mmol) and CsF (2.18 g, 3 Eq, 14.3 mmol) in dioxane (35 mL) was added Pd(PPh$_3$)$_2$Cl$_2$ (336 mg, 0.1 Eq, 0.48 mmol) at rt under nitrogen atmosphere. The resulting mixture was stirred for 3 h at 100° C. under nitrogen atmosphere. The mixture was allowed to cool down to rt and concentrated in vacuo. The residue was purified by Prep-TLC with EtOAc/petroleum ether (3/1) to afford the sub-title compound (AIO-4) (629 mg, 3.55 mmol, 74%, 90% Purity) as an off-white solid. m/z 178.1 (M+H)$^+$ (ES+)

Step 4:
7-Fluoro-3-oxo-1,2-dihydroisoindole-5-carbaldehyde (AIO-5)

A solution of the product from step 3 above (AIO-4) (629 mg, 1 Eq, 3.53 mmol) and CA (887 mg, 1.3 Eq, 4.61 mmol), NMO (541 mg, 1.3 Eq, 4.61 mmol), K$_2$OsO$_4$.2H$_2$O (131 mg, 0.1 Eq, 0.36 mmol) in t-BuOH (20 mL) and water (20 mL) was stirred for 2 h at rt. To the above mixture was added NaIO$_4$ (1.52 g, 2 Eq, 7.10 mmol) at rt. The resulting mixture was stirred for 1 h at rt. The resulting mixture was diluted with water and extracted with EtOAc (3×100 mL). The combined organic layers were washed with brine (2×200 mL), dried (Na$_2$SO$_4$). After filtration, the filtrate was concentrated in vacuo. The residue was purified by Prep-TLC with EtOAc/petroleum ether (3/1) to afford the sub-title compound (AIO-5) (314 mg, 1.75 mmol, 49%, 92% Purity) as an off-white solid. m/z 180.0 (M+H)$^+$ (ES+)

Step 5: 4-Fluoro-6-(hydroxymethyl)-2,3-dihydroisoindol-1-one (AIO-6)

To a stirred solution of the product from step 4 above (AIO-5) (314 mg, 1 Eq, 1.75 mmol) in MeOH (20 mL) was added NaBH$_4$ (333 mg, 5 Eq, 8.78 mmol) in portions at 0° C. The resulting mixture was stirred for 2 h at rt. The reaction was then quenched by the addition of MeOH (2 mL) at 0° C. The mixture was concentrated in vacuo. The residue was purified by Prep-TLC with DCM/MeOH (20/1) to afford the sub-title compound (AIO-6) (173 mg, 0.96 mmol, 55%, 95% Purity) as an off-white solid. m/z 182.1 (M+H)$^+$ (ES+)

Step 6: 4-{2-Cyclopropyl-6-[4-fluoro-6-(hydroxymethyl)-1-oxo-3H-isoindol-2-yl]pyridin-4-yl}-3-(4-methyl-1,2,4-triazol-3-yl)benzonitrile (AIO-7)

To a stirred solution of intermediate (AEG-2) (200 mg, 1 Eq, 0.60 mmol), the product from step 5 above (AIO-6) (108 mg, 1 Eq, 0.60 mmol) and Cs$_2$CO$_3$ (582 mg, 3 Eq, 1.79 mmol) in dioxane (10 mL) were added X-Phos (114 mg, 0.4 Eq, 0.24 mmol) and XPhos Pd G3 (101 mg, 0.2 Eq, 0.12 mmol) at rt under nitrogen atmosphere. The resulting mixture was stirred for 2 h at 100° C. under nitrogen atmosphere. The mixture was cooled to rt and concentrated in vacuo. The residue was purified by Prep-TLC with DCM/MeOH (10/1) to afford the sub-title compound (AIO-7) (200 mg, 0.42 mmol, 70%, 95% Purity) as a yellow solid. m/z 481.2 (M+H)$^+$ (ES+)

Step 7: 4-[2-Cyclopropyl-6-(4-fluoro-6-formyl-1-oxo-3H-isoindol-2-yl) pyridin-4-yl]-3-(4-methyl-1,2,4-triazol-3-yl)benzonitrile (AIO-8)

A solution of the product from step 6 above (AIO-7) (35 mg, 1 Eq, 73 µmol) and DMP (46 mg, 1.5 Eq, 0.11 mmol) in DCM (10 mL) was stirred for 1 h at rt. The resulting mixture was filtered the filter cake was washed with DCM (3×5 mL). The filtrate was concentrated in vacuo. The crude product used directly in next step without any further purification. m/z 479.2 (M+H)$^+$ (ES+)

Step 8: 4-[2-Cyclopropyl-6-(4-fluoro-6-{[(2-methoxyethyl)amino]methyl}-1-oxo-3H-isoindol-2-yl)pyridin-4-yl]-3-(4-methyl-1,2,4-triazol-3-yl)benzonitrile (AIO-9)

To a stirred solution of the product from step 7 above (AIO-8) (35 mg, 1 Eq, 73 µmol) and 2-methoxyethan-1-amine (AEB-1) (10 mg, 1.8 Eq, 0.13 mmol) in MeOH (5 mL) were added DIPEA (38 mg, 4 Eq, 0.29 mmol). The resulting mixture was stirred overnight at rt under nitrogen atmosphere. To the above mixture was added NaBH$_4$ (14 mg, 5 Eq, 0.37 mmol) at 0° C. The resulting mixture was stirred for 2 h at rt under nitrogen atmosphere. The reaction was then quenched by the addition of MeOH (2 mL) at 0° C. The resulting mixture was concentrated in vacuo. The crude product was purified by reverse phase flash with the following conditions (Column: XBridge Prep C18 OBD Column, 30*100 mm, 5 µm; Mobile Phase A: water (0.1% NH$_4$HCO$_3$+0.1% NH$_3$·H$_2$O), Mobile Phase B: MeCN; Flow rate: 60 mL/min; Gradient: 32% B to 62% B in 25 min; Wave Length: 254/220 nm) to afford the title compound (AIO-9) (14.8 mg, 28 µmol, 37%, 99.7% Purity) as a white solid. m/z 538.1 (M+H)$^+$ (ES+). $^1$H NMR (400 MHz, Methanol-d4) δ 8.49 (s, 1H), 8.17-7.89 (m, 4H), 7.65 (s, 1H), 7.47-7.40 (m, 1H), 6.94 (d, J=1.4 Hz, 1H), 5.06 (s, 2H), 3.91 (s, 2H), 3.59-3.44 (m, 5H), 3.35 (s, 3H), 2.77 (t, J=5.3 Hz, 2H), 2.09-2.00 (m, 1H), 1.10-0.96 (m, 4H).

Example 272: Synthesis of 4-{2-Cyclopropyl-6-[6-({[(2R)-2-hydroxybutyl]amino} methyl)-1-oxo-3H-isoindol-2-yl]pyridin-4-yl}-3-(4-methyl-1,2,4-triazol-3-yl)benzonitrile (AIP-2)

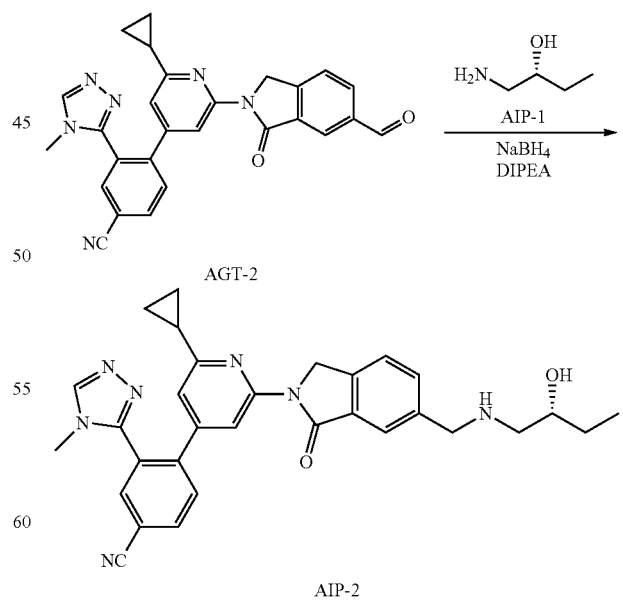

A solution of intermediate (AGT-2) (30 mg, 1 Eq, 65 µmol), (2R)-1-aminobutan-2-ol (AIP-1) (7 mg, 1.2 Eq, 78 µmol) and DIPEA (25 mg, 3 Eq, 0.20 mmol) in MeOH (8 mL) was stirred for 2 h at 60° C. The mixture was allowed to cool down to rt. To the above mixture was added NaBH$_4$ (12 mg, 5 Eq, 0.33 mmol) at 0° C. The resulting mixture was stirred for 1 h at rt. The reaction was then quenched by the addition of MeOH (2 mL) at 0° C. The mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 35% B to 52% B in 9 min; Wave Length: 254/220 nm) to afford the title compound (AIP-2) (11.6 mg, 22 μmol, 33%, 98.4% Purity) as a white solid. m/z 534.2 (M+H)$^+$ (ES+). $^1$H NMR (400 MHz, Methanol-d4) δ 8.49 (s, 1H), 8.16-8.06 (m, 2H), 8.05 (d, J=1.4 Hz, 1H), 7.92 (d, J=8.0 Hz, 1H), 7.82 (s, 1H), 7.83-7.80 (m, 1H), 7.63 (d, J=7.9 Hz, 1H), 6.92 (d, J=1.5 Hz, 1H), 5.02 (s, 2H), 4.03-3.88 (m, 2H), 3.68-3.61 (m, 1H), 3.49 (s, 3H), 2.74-2.68 (m, 1H), 2.61-2.54 (m, 1H), 2.06-1.99 (m, 1H), 1.59-1.37 (m, 2H), 1.10-0.88 (m, 7H).

Example 273: Synthesis of 4-(2-Cyclopropyl-6-(6-((2-methoxyethoxy)methyl)-1-oxoisoindolin-2-yl)pyridin-4-yl)-3-(4-methyl-4H-1,2,4-triazol-3-yl)benzonitrile (AIQ-2)

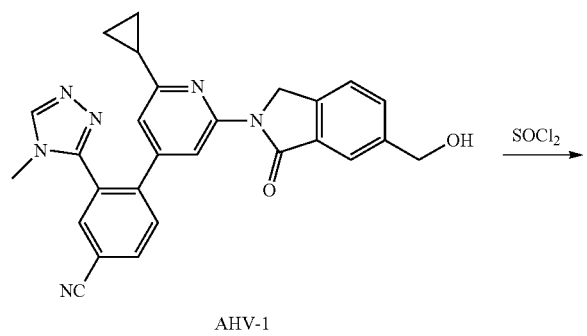

AHV-1

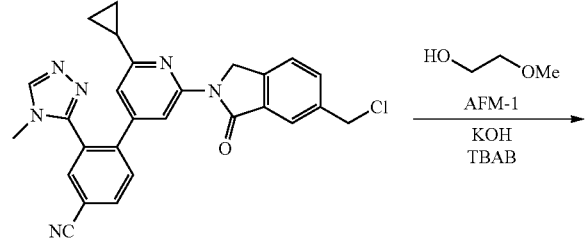

AIQ-1

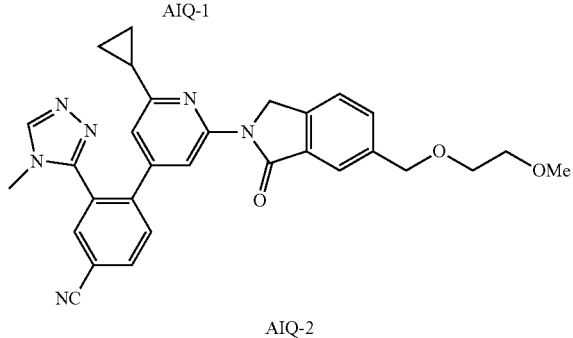

AIQ-2

Step 1: 4-(2-(6-(chloromethyl)-1-oxoisoindolin-2-yl)-6-cyclopropylpyridin-4-yl)-3-(4-methyl-4H-1,2,4-triazol-3-yl)benzonitrile (AIQ-1)

To a stirred solution of compound (AHV-1) (60 mg, 1 Eq, 0.13 mmol) in DCM (5 mL) at 0° C. was added SOCl$_2$ (46 mg, 3 Eq, 0.39 mmol). The resulting mixture was stirred for 1 h at rt. The reaction was then quenched by the addition of MeOH (2 mL) at 0° C. The resulting mixture was concentrated in vacuo. The residue was purified by Prep-TLC with DCM/MeOH (15/1) to afford the sub-title compound (AIQ-1) (58 mg, 0.12 mmol, 93%, 92% Purity) as a yellow solid. m/z 481.1/483.1 (M+H)$^+$ (ES+)

Step 2: 4-(2-Cyclopropyl-6-(6-((2-methoxyethoxy)methyl)-1-oxoisoindolin-2-yl)pyridin-4-yl)-3-(4-methyl-4H-1,2,4-triazol-3-yl)benzonitrile (AIQ-2)

To a stirred solution of the product from step 1 above (AIQ-1) (50 mg, 1 Eq, 0.10 mmol), 2-methoxyethanol (AFM-1) (40 mg, 5 Eq, 0.52 mmol) and TBAB (16.76 mg, 52 μmol, 0.5 Eq) in DCM (2 mL) was added aq. KOH (2 mL, 20% Wt) at rt. The resulting mixture was stirred for 1 h at rt. The resulting mixture was diluted with water and extracted with EtOAc (3×10 mL). The combined organic layers were washed with brine (2×10 mL), dried (Na$_2$SO$_4$). After filtration, the filtrate was concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 45% B to 54% B in 8 min; Wave Length: 254/220 nm) to afford the title compound (AIQ-2) (9.2 mg, 18 μmol, 17%, 99.4% Purity) as a white solid. m/z 521.1 (M+H)$^+$ (ES+). $^1$H NMR (400 MHz, Methanol-d4) δ 8.50 (s, 1H), 8.15-8.07 (m, 2H), 8.04 (d, J=1.4 Hz, 1H), 7.95-7.89 (m, 1H), 7.83-7.79 (m, 1H), 7.70-7.59 (m, 2H), 6.92 (d, J=1.4 Hz, 1H), 5.02 (s, 2H), 4.65 (s, 2H), 3.73-3.65 (m, 2H), 3.63-3.59 (m, 2H), 3.51 (s, 3H), 3.38 (s, 3H), 2.13-2.01 (m, 1H), 1.07-1.01 (m, 2H), 1.01-0.94 (m, 2H).

Example 274: Synthesis of (S)-4-(2-cyclopropyl-6-(6-(((1-methoxypropan-2-yl)amino)methyl)-1-oxoisoindolin-2-yl)pyridin-4-yl)-3-(4-methyl-4H-1,2,4-triazol-3-yl)benzonitrile (AIR-2)

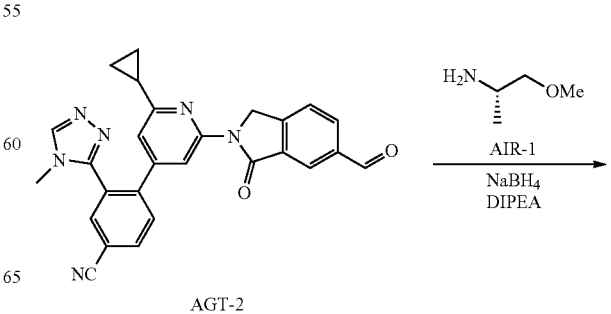

AGT-2

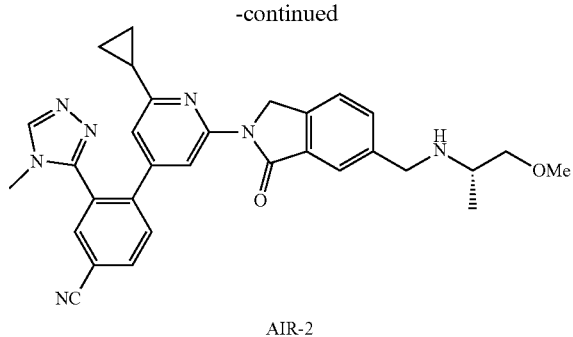

AIR-2

To a stirred mixture of intermediate (AGT-2) (30 mg, 1 Eq, 65 μmol) in MeOH (10 mL) was added (2S)-1-methoxypropan-2-amine (AIR-1) (9 mg, 1.5 Eq, 98 μmol at 60° C. The resulting mixture was stirred for 2 h at 60° C. To the above mixture was added NaBH₄ (5 mg, 2 Eq, 0.13 μmol) at 0° C. The resulting mixture was stirred for 1 h at rt. The reaction was then quenched by the addition of MeOH (2 mL) at 0° C. The mixture was concentrated in vacuo. The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 45% B to 58% B in 8 min; Wave Length: 254/220 nm; RT: 7.17) to afford the title compound (AIR-2) (11.9 mg, 22 μmol, 34%, 99.7% Purity) as a white solid. m/z 534.3 (M+H)⁺ (ES+). ¹H NMR (400 MHz, DMSO-d6) δ 8.53 (s, 1H), 8.27-8.18 (m, 2H), 7.99 (d, J=1.4 Hz, 1H), 7.87 (d, J=8.5 Hz, 1H), 7.75 (s, 1H), 7.63 (s, 2H), 6.88 (d, J=1.4 Hz, 1H), 5.00 (s, 2H), 3.93-3.77 (m, 2H), 3.48 (s, 3H), 3.23 (s, 4H), 3.22-3.16 (m, 1H), 2.81-2.72 (m, 1H), 2.08-1.98 (m, 1H), 1.06-0.89 (m, 7H).

Example 275: Synthesis of 4-(2-{6-[(cyclopentylmethoxy)methyl]-1-oxo-3H-isoindol-2-yl}-6-cyclopropylpyridin-4-yl)-3-(4-methyl-1,2,4-triazol-3-yl)benzonitrile (AIS-2)

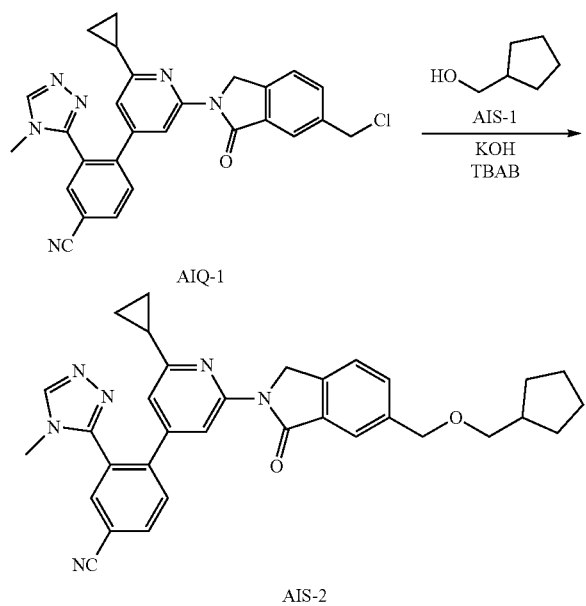

To a stirred mixture of intermediate (AIQ-1) (40 mg, 1 Eq, 83 μmol) and cyclopentanemethanol (AIT-1) (83 mg, 10 Eq, 0.83 mmol) in DCM (4 mL) was added TBAB (2.68 mg, 8 μmol, 0.1 Eq) at rt. To the above mixture was added aq. KOH (4 mL, 20% Wt) at rt. The resulting mixture was stirred for additional 0.5 h at rt. The resulting mixture was diluted with water and extracted with EtOAc (3×20 mL). The combined organic layers were washed with brine (2×20 mL), dried (Na₂SO₄). After filtration, the filtrate was concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 65% B to 75% B in 8 min; Wave Length: 254/220 nm; RT: 7.98) to afford the title compound (AIS-2) (2.1 mg, 3.9 μmol, 4.6%, 99.4% Purity) as a white solid. m/z 545.2 (M+H)⁺ (ES+). ¹H NMR (400 MHz, DMSO-d6) δ 8.53 (s, 1H), 8.23-8.19 (m, 2H), 8.00 (d, J=1.4 Hz, 1H), 7.87 (d, J=8.5 Hz, 1H), 7.73-7.60 (m, 3H), 6.87 (d, J=1.4 Hz, 1H), 5.02 (s, 2H), 4.58 (s, 2H), 3.47 (s, 3H), 3.33 (d, J=7.0 Hz, 2H), 2.20-2.10 (m, 1H), 2.08-1.99 (m, 1H), 1.76-1.61 (m, 2H), 1.59-1.44 (m, 4H), 1.26-1.17 (m, 2H), 1.03-0.91 (m, 4H).

Example 276: Synthesis of 4-(2-cyclopropyl-6-{6-[(methylamino)methyl]-1-oxo-3H-isoindol-2-yl}pyridin-4-yl)-3-(4-methyl-1,2,4-triazol-3-yl)benzonitrile (AIT-1)

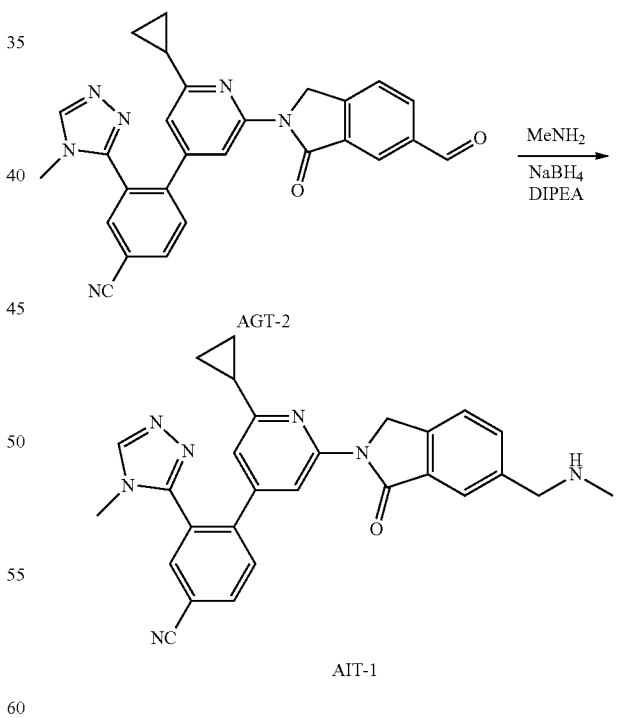

A solution of methylamine (3.1 mg, 1.5 Eq, 98 μmol) and DIPEA (10 mg, 1.2 Eq, 78 μmol) in MeOH (3 mL) was stirred for 10 min at rt. To the above mixture was added intermediate (AGT-2) (30 mg, 1 Eq, 65 μmol) at rt. The resulting mixture was stirred for 2 h at 60° C. The mixture was allowed to cool down to rt. To the above mixture was added NaBH₄ (5 mg, 2 Eq, 0.13 mmol) at 0° C. The resulting mixture was stirred for 1 h at rt. The reaction was then quenched by the addition of MeOH (2 mL) at 0° C. The mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 40% B to 50% B in 7 min; Wave Length: 254/220 nm) to afford the title compound (AIT-1) (3.7 mg, 7.8 μmol, 12%, 99.6% Purity) as a white solid. m/z 476.2 (M+H)$^+$ (ES+). $^1$H NMR (400 MHz, DMSO-d6) δ 8.53 (s, 1H), 8.22-8.19 (m, 2H), 7.99 (d, J=1.4 Hz, 1H), 7.87 (d, J=8.5 Hz, 1H), 7.73 (s, 1H), 7.63 (s, 2H), 6.87 (d, J=1.4 Hz, 1H), 5.00 (s, 2H), 3.75 (s, 2H), 3.47 (s, 3H), 2.27 (s, 3H), 2.07-2.01 (m, 1H), 0.97 (d, J=5.9 Hz, 4H).

Example 277: Synthesis of 2-(4-(4-Chloro-2-(4-methyl-4H-1,2,4-triazol-3-yl)phenyl)-6-cyclopropylpyridin-2-yl)-6-(hydroxymethyl)isoindolin-1-one (AIU-1)

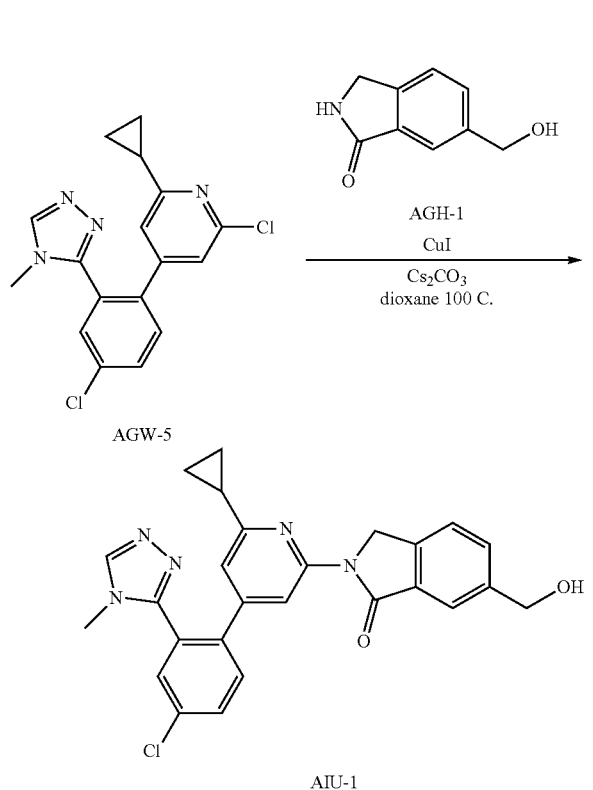

Into a 25 mL round-bottom flask were added intermediate (AGW-5) (100 mg, 1 Eq, 0.29 mmol), intermediate (AGH-1) (57 mg, 1.2 Eq, 0.35 mmol) and Cs$_2$CO$_3$ (283 mg, 3 Eq, 0.87 mmol) in 1,4-dioxane (15 ml) at rt under nitrogen atmosphere. To the above stirred solution were added CuI (11 mg, 0.2 Eq, 58 μmol) and (1S,2S)-1-N,2-N-dimethylcyclohexane-1,2-diamine (16 mg, 0.4 Eq, 0.12 mmol) at rt under nitrogen atmosphere. The resulting mixture was stirred for additional 2 h at 100° C. under nitrogen atmosphere. The mixture was allowed to cool down to rt. The resulting mixture was diluted with water and extracted with EtOAc (3×20 mL). The combined organic layers were washed with brine (2×20 mL), dried (Na$_2$SO$_4$). After filtration, the filtrate was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 28% B to 38% B in 9 min; Wave Length: 254 nm) to afford the title compound (AIU-1) (7.4 mg, 16 μmol, 5.4%, 99.6% Purity) as a white solid. m/z 472.0/474.0 (M+H)$^+$ (ES+). $^1$H NMR (400 MHz, DMSO-d6) δ 8.51 (s, 1H), 8.00 (d, J=1.4 Hz, 1H), 7.85-7.77 (m, 2H), 7.75-7.60 (m, 4H), 6.80 (d, J=1.5 Hz, 1H), 5.40-5.35 (m, 1H), 5.01 (s, 2H), 4.61 (d, J=5.8 Hz, 2H), 3.42 (s, 3H) 2.06-1.99 (m, 1H), 0.95 (d, J=6.4 Hz, 4H).

Example 278: Synthesis of 2-(4-(4-Chloro-2-(4-methyl-4H-1,2,4-triazol-3-yl)phenyl) -6-cyclopropylpyridin-2-yl)-6-(((cyclobutylmethyl)amino)methyl) isoindolin-1-one (AIV-2)

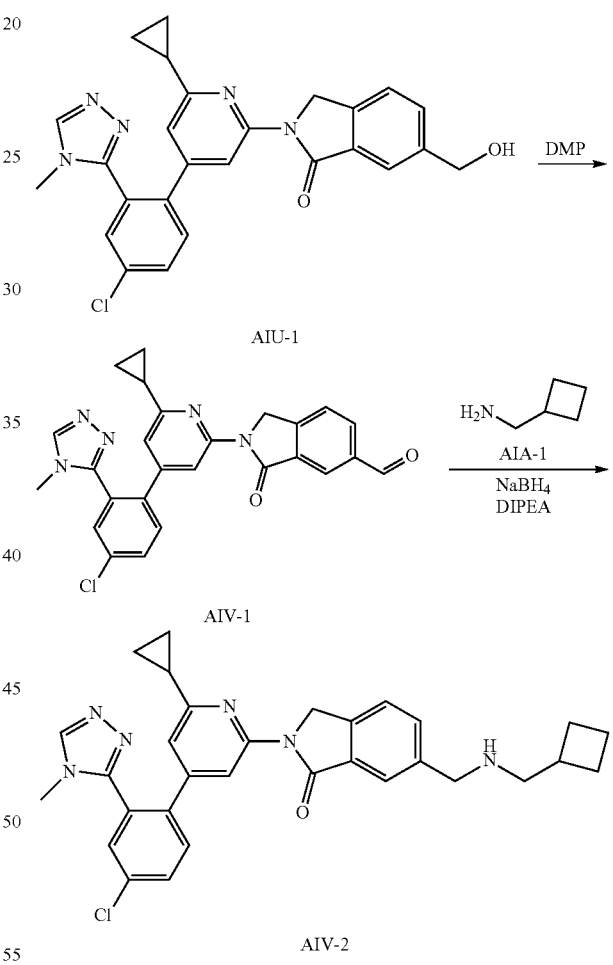

Step 1: 2-(4-(4-Chloro-2-(4-methyl-4H-1,2,4-triazol-3-yl)phenyl)-6-cyclopropylpyridin-2-yl)-3-oxoisoindoline-5-carbaldehyde (AIV-1)

To a stirred solution of compound (AIU-1) (100 mg, 1 Eq, 0.21 mmol) in DCM (5 mL) was added DMP (179 mg, 2 Eq, 0.42 mmol) at rt under nitrogen atmosphere. The resulting mixture was stirred for 2 h at rt under nitrogen atmosphere. The resulting mixture was filtered; the filter cake was washed with DCM (3×5 mL). The filtrate was concentrated in vacuo. The crude product used directly in next step without any further purification. m/z 470.1/472.1 (M+H)+ (ES+)

Step 2: 2-(4-(4-Chloro-2-(4-methyl-4H-1,2,4-triazol-3-yl)phenyl)-6-cyclopropylpyridin-2-yl)-6-((((cyclobutylmethyl)amino)methyl)isoindolin-1-one (AIV-2)

To a stirred mixture of the product from step 1 above (AIV-1) (50 mg, 1 Eq, 0.11 mmol) and 1-cyclobutylmethanamine (AIA-1) (14 mg, 1.5 Eq, 0.16 mmol) in DCM (5 mL) was added DIPEA (17 mg, 1.2 Eq, 0.13 mmol) at rt. The resulting mixture was stirred for 2 h at 60° C. The mixture was allowed to cool down to rt. To the above mixture was added NaBH$_4$ (8 mg, 2 Eq, 0.21 mmol). The resulting mixture was stirred for 1 h at rt. The reaction was then quenched by the addition of MeOH (2 mL) at 0° C. The resulting mixture was concentrated in vacuo. The crude product was purified by Prep-HPLC with the following conditions (Column: Xselect CSH F-Phenyl OBD column, 19*250 mm, 5 μm; Mobile Phase A: water (0.1% NH$_4$HCO$_3$+0.1% NH$_3$·H$_2$O), Mobile Phase B: MeCN; Flow rate: 25 mL/min; Gradient: 70% B to 85% B in 9 min; Wave Length: 254/220 nm; RT: 8.3) to afford the title compound (AIV-2) (6.8 mg, 13 μmol, 12%, 98.0% Purity) as a white solid. m/z 539.2/541.2 (M+H)+ (ES+). $^1$H NMR (400 MHz, Methanol-d4) δ 8.47 (s, 1H), 8.05 (d, J=1.4 Hz, 1H), 7.79 (d, J=1.5 Hz, 1H), 7.78 (d, J=2.2 Hz, 1H), 7.74 (s, 1H), 7.73-7.69 (m, 1H), 7.67-7.58 (m, 2H), 6.85 (d, J=1.5 Hz, 1H), 5.02 (s, 2H), 3.85 (s, 2H), 3.45 (s, 3H), 2.62 (d, J=7.3 Hz, 2H), 2.60-2.47 (m, 1H), 2.15-2.08 (m, 2H), 2.09-1.95 (m, 1H), 1.94-1.78 (m, 2H), 1.76-1.62 (m, 2H), 1.05-0.99 (m, 2H), 0.99-0.93 (m, 2H).

Example 279: Synthesis of 4-[2-Cyclopropyl-6-(6-{[(2-methoxy-2-methylpropyl) amino]methyl}-1-oxo-3H-isoindol-2-yl)pyridin-4-yl]-3-(4-methyl-1,2,4-triazol-3-yl)benzonitrile (AIW-2)

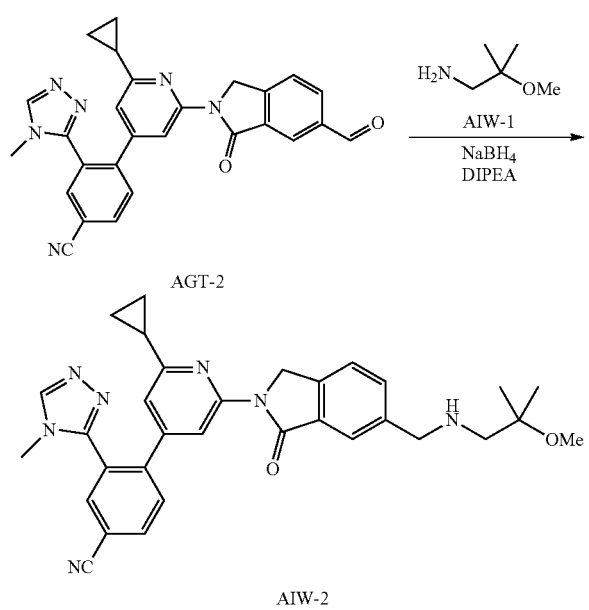

A solution of 2-methoxy-2-methylpropan-1-amine (AIW-1) (8 mg, 1.2 Eq, 78 μmol) and DIPEA (34 mg, 4 Eq, 0.26 mmol) in MeOH (8 mL) was stirred for 10 min at rt. To the above mixture was added intermediate (AGT-2) (30 mg, 1 Eq, 65 μmol). The resulting mixture was stirred for additional 4 h at 60° C. To the above mixture was added NaBH$_4$ (12 mg, 5 Eq, 0.33 mmol) at 0° C. The resulting mixture was stirred for 1 h at rt. The reaction was then quenched by the addition of MeOH (2 mL) at 0° C. The mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 42% B to 52% B in 8 min; Wave Length: 254/220 nm; RT: 7.58) to afford the title compound (AIW-2) (13.7 mg, 25 μmol, 38%, 99.1% Purity) as a white solid. m/z 549.1 (M+H)+ (ES+). $^1$H NMR (400 MHz, Methanol-d4) δ 8.49 (d, J=1.5 Hz, 1H), 8.14-8.03 (m, 3H), 7.95-7.88 (m, 1H), 7.81 (s, 1H), 7.71-7.64 (m, 1H), 7.61 (d, J=7.7 Hz, 1H), 6.91 (d, J=1.6 Hz, 1H), 5.02 (s, 2H), 3.89 (s, 2H), 3.50 (d, J=1.6 Hz, 3H), 3.15 (d, J=1.5 Hz, 3H), 2.56 (d, J=1.6 Hz, 2H), 2.07-1.97 (m, 1H), 1.18 (d, J=1.6 Hz, 6H), 1.04-0.97 (m, 4H).

Example 280: Synthesis of 4-[2-Cyclopropyl-6-(6-{[(cyclopropylmethyl)(methyl)amino]methyl}-1-oxo-3H-isoindol-2-yl)pyridin-4-yl]-3-(4-methyl-1,2,4-triazol-3-yl)benzonitrile (AIX-2)

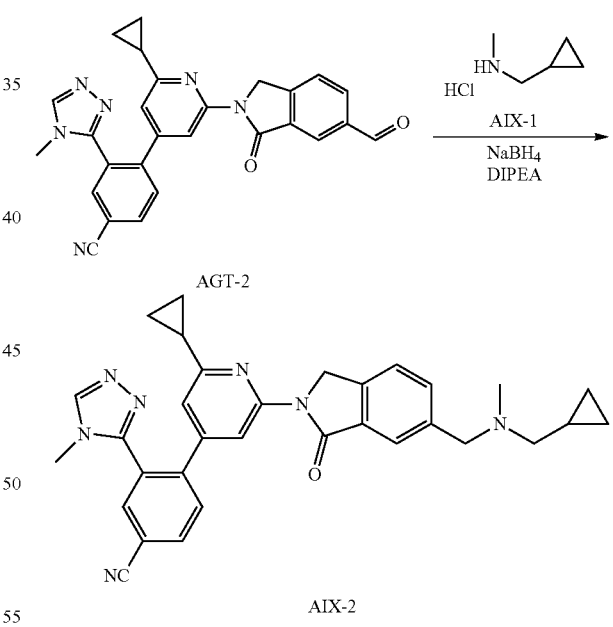

A solution of 1-cyclopropyl-N-methylmethanamine, HCl (AIX-1) (7 mg, 1.2 Eq, 78 μmol) and DIPEA (34 mg, 4 Eq, 0.26 μmol) in MeOH (8 mL) was stirred for 10 min at rt. To the above mixture was added intermediate (AGT-2) (30 mg, 1 Eq, 65 μmol) at rt. The resulting mixture was stirred overnight at rt. To the above mixture was added NaBH$_4$ (12 mg, 5 Eq, 0.33 mmol) at 0° C. The resulting mixture was stirred for additional 1 h at rt. The reaction was then quenched by the addition of MeOH (2 mL) at 0° C. The mixture was concentrated in vacuo. The crude product was purified by Prep-HPLC with the following conditions (Column: Xselect CSH C18 OBD Column 30*150 mm, 5 µm; Mobile Phase A: water (0.1% NH₄HCO₃), Mobile Phase B: MeCN; Flow rate: 60 mL/min; Gradient: 32% B to 62% B in 7 min; Wave Length: 254 nm; RT: 8.65) to afford the title compound (AIX-2) (3.4 mg, 6.4 µmol, 9.4%, 95.6% Purity) as a white solid. m/z 530.2 (M+H)⁺ (ES+). ¹H NMR (400 MHz, Methanol-d4) δ 8.50 (s, 1H), 8.15-8.07 (m, 2H), 8.05 (d, J=1.4 Hz, 1H), 7.92 (d, J=8.0 Hz, 1H), 7.79 (d, J=1.5 Hz, 1H), 7.68-7.59 (m, 2H), 6.92 (d, J=1.5 Hz, 1H), 5.03 (s, 2H), 3.70 (s, 2H), 3.50 (s, 4H), 2.37-2.26 (m, 5H), 2.07-1.99 (m, 1H), 1.06-1.02 (m, 2H), 1.01-0.96 (m, 2H), 0.58-0.51 (m, 2H), 0.15-0.09 (m, 2H).

Example 281: Synthesis of 4-[2-Cyclopropyl-6-(6-{[2-(methylamino)ethoxy]methyl}-1-oxo-3H-isoindol-2-yl)pyridin-4-yl]-3-(4-methyl-1,2,4-triazol-3-yl)benzonitrile (AIY-2)

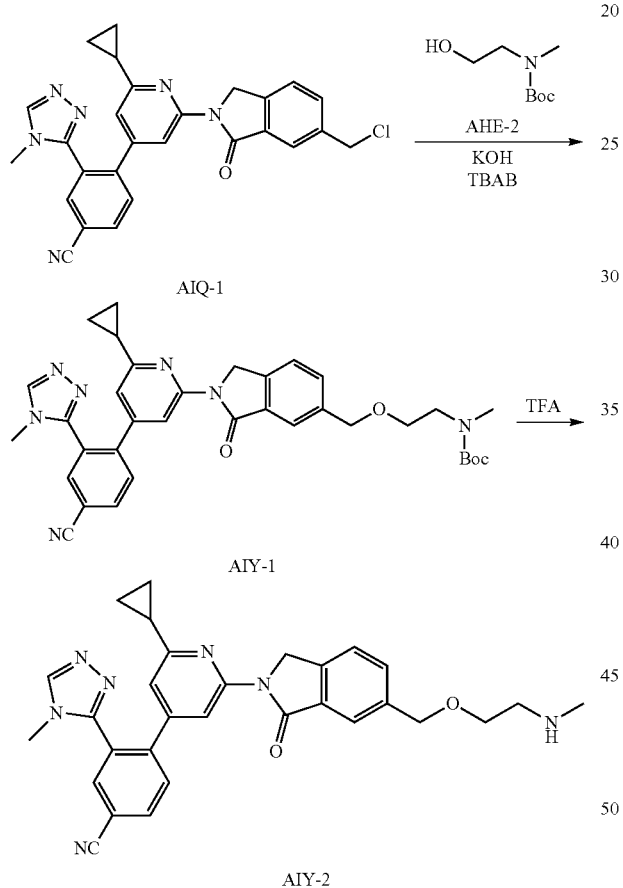

Step 1: tert-Butyl N-{2-[(2-{4-[4-cyano-2-(4-methyl-1,2,4-triazol-3-yl)phenyl]-6-cyclopropylpyridin-2-yl}-3-oxo-1H-isoindol-5-yl)methoxy]ethyl}-N-methylcarbamate (AIY-1)

To a stirred solution of intermediate (AIQ-1) (50 mg, 1 Eq, 0.10 mmol), tert-butyl N-(2-hydroxyethyl)-N-methylcarbamate (AHE-2) (18 mg, 1 Eq, 0.10 mmol) and TBAB (17 mg, 0.5 Eq, 52 µmol) in DCM (3 mL) was added aq. KOH (3 mL, 20% Wt) at rt. The resulting mixture was stirred for 1 h at rt. The resulting mixture was diluted with water and extracted with EtOAc (3×10 mL). The combined organic layers were washed with brine (2×10 mL), dried (Na₂SO₄). After filtration, the filtrate was concentrated in vacuo. The residue was purified by Prep-TLC with DCM/MeOH (15/1) to afford the title compound (AIY-1) (40 mg, 64 µmol, 62%, 95% Purity) as a brown-yellow solid. m/z 620.3 (M+H)⁺ (ES+)

Step 2: 4-[2-Cyclopropyl-6-(6-{[2-(methylamino)ethoxy]methyl}-1-oxo-3H-isoindol-2-yl) pyridin-4-yl]-3-(4-methyl-1,2,4-triazol-3-yl)benzonitrile (AIY-2)

To a stirred solution of the product from step 1 above (AIY-1) (40 mg, 1 Eq, 65 µmol) in DCM (6 mL) was added TFA (2 mL) at rt. The resulting mixture was stirred for 2 h at rt. The resulting mixture was concentrated in vacuo. The crude product was purified by Prep-HPLC with the following conditions (Column: XBridge Prep OBD C18 Column, 30*150 mm, 5 µm; Mobile Phase A: water (0.1% NH₄HCO₃+0.1% NH₃·H₂O), Mobile Phase B: MeCN; Flow rate: 60 mL/min; Gradient: 45% B to 54% B in 8 min; Wave Length: 254/220 nm) to afford the title compound (AIY-2) (6.9 mg, 13 µmol, 20%, 98.3% Purity) as a white solid. m/z 520.1 (M+H)⁺ (ES+). ¹H NMR (400 MHz, Methanol-d4) δ 8.50 (s, 1H), 8.15-8.08 (m, 2H), 8.04 (d, J=1.4 Hz, 1H), 7.92 (d, J=8.0 Hz, 1H), 7.85-7.79 (m, 1H), 7.71-7.62 (m, 2H), 6.93 (d, J=1.4 Hz, 1H), 5.03 (s, 2H), 4.65 (s, 2H), 3.66 (d, J=5.0 Hz, 2H), 3.50 (s, 3H), 2.87-2.80 (m, 2H), 2.44 (s, 3H), 2.09-1.99 (m, 1H), 1.08-0.95 (m, 4H).

Example 282: Synthesis of 4-{2-Cyclopropyl-6-[6-({[(3R)-1-methyl-2-oxopyrrolidin-3-yl]amino}methyl)-1-oxo-3H-isoindol-2-yl]pyridin-4-yl}-3-(4-methyl-1,2,4-triazol-3-yl)benzonitrile (AIZ-2)

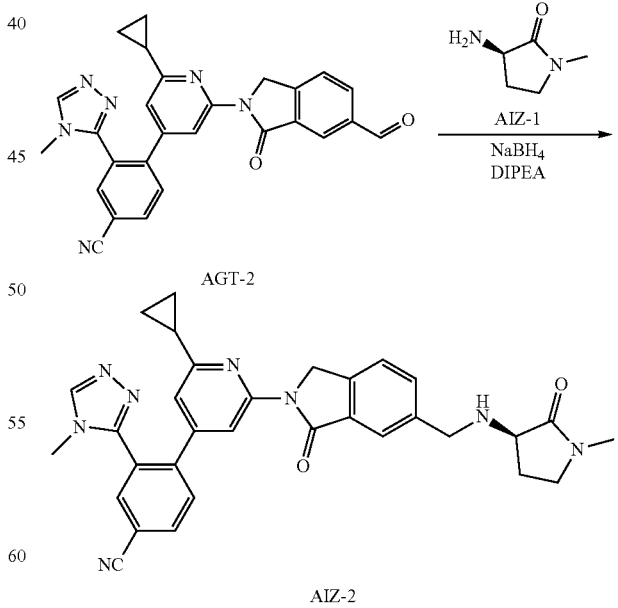

To a stirred solution of intermediate (AGT-2) (30 mg, 1 Eq, 65 µmol) and (3R)-3-amino-1-methylpyrrolidin-2-one (AIZ-1) (10 mg, 1.2 Eq, 78 µmol) in MeOH (8 mL) was added DIPEA (34 mg, 4 Eq, 0.26 mmol) at rt. The resulting mixture was stirred for 2 h at 60° C. The mixture was allowed to cool down to rt. To the above mixture was added NaBH₄ (12 mg, 5 Eq, 0.33 mmol) at 0° C. The resulting mixture was stirred for 1 h at rt. The reaction was then quenched by the addition of MeOH (2 mL) at 0° C. The mixture was concentrated in vacuo. The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 34% B to 53% B in 8 min; Wave Length: 254/220 nm; RT: 7.89) to afford the title compound (AIZ-2) (10.7 mg, 19 μmol, 29%, 99.8% Purity) as a white solid. m/z 559.3 (M+H)⁺ (ES+). ¹H NMR (400 MHz, DMSO-d6) δ 8.55 (s, 1H), 8.24-8.19 (m, 2H), 7.97 (d, J=1.4 Hz, 1H), 7.89-7.75 (m, 2H), 7.64 (d, J=2.2 Hz, 2H), 6.90 (d, J=1.4 Hz, 1H), 5.00 (s, 2H), 3.91 (s, 2H), 3.49 (s, 3H), 3.29-3.18 (m, 3H), 2.73 (s, 3H), 2.22-2.13 (m, 1H), 2.08-2.00 (m, 1H), 1.72-1.62 (m, 1H), 1.00-0.94 (m, 4H).

Example 283: Synthesis of (S)-4-(2-Cyclopropyl-6-(6-(((2-hydroxybutyl)amino)methyl)-1-oxoisoindolin-2-yl)pyridin-4-yl)-3-(4-methyl-4H-1,2,4-triazol-3-yl)benzonitrile (AJA-2)

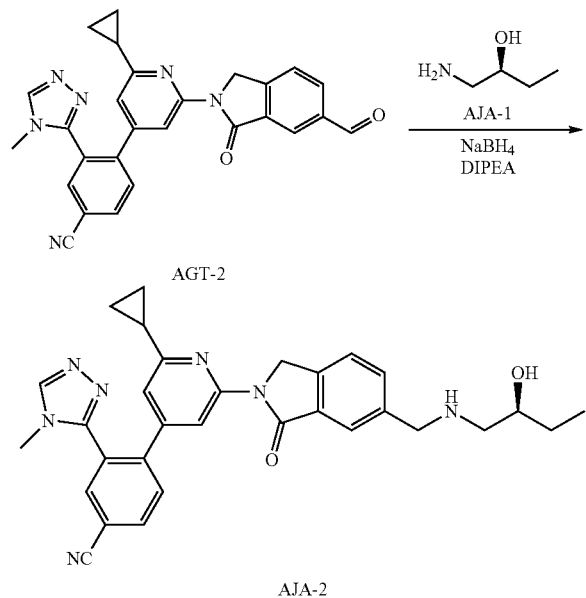

To a stirred solution of intermediate (AGT-2) (30 mg, 1 Eq, 65 μmol) and (2S)-1-aminobutan-2-ol (AJA-1) (7 mg, 1.2 Eq, 78 μmol) in MeOH (8 mL) was added DIPEA (25 mg, 3 Eq, 0.20 mmol) at rt. The resulting mixture was stirred for 2 h at 60° C. The mixture was allowed to cool down to rt. To the above mixture was added NaBH₄ (12 mg, 5 Eq, 0.33 mmol) at 0° C. The resulting mixture was stirred for 1 h at rt. The reaction was then quenched by the addition of MeOH (2 mL) at 0° C. The mixture was concentrated in vacuo. The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 35% B to 45% B in 9 min; Wave Length: 254/220 nm; RT: 8.2) to afford the title compound (AJA-2) (6.7 mg, 13 μmol, 19%, 98.6% Purity) as a white solid. m/z 534.3 (M+H)⁺ (ES+). ¹H NMR (400 MHz, Methanol-d4) δ 8.55-8.47 (m, 1H), 8.15-8.10 (m, 1H), 8.10-8.03 (m, 2H), 7.94-7.90 (m, 1H), 7.83 (d, J=1.8 Hz, 1H), 7.72-7.62 (m, 2H), 6.92 (d, J=1.5 Hz, 1H), 5.03 (d, J=2.8 Hz, 2H), 4.04-3.94 (m, 2H), 3.70-3.62 (m, 1H), 3.49 (d, J=1.7 Hz, 3H), 2.78-2.71 (m, 1H), 2.64-2.56 (m, 1H), 2.06-1.99 (m, 1H), 1.54-1.38 (m, 2H), 1.06-0.92 (m, 7H).

Example 284: Synthesis of N-(2-(((2-(4-(4-Cyano-2-(4-methyl-4H-1,2,4-triazol-3-yl)phenyl)-6-cyclopropylpyridin-2-yl)-3-oxoisoindolin-5-yl)methyl)amino)ethyl)acetamide (AJB-2)

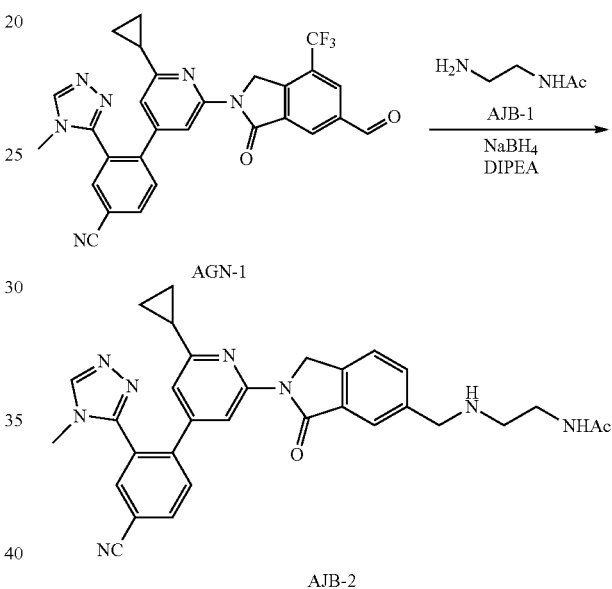

A solution of intermediate (AGN-1) (40 mg, 1 Eq, 76 μmol), DIPEA (39 mg, 4 Eq, 0.30 mmol) and N-(2-aminoethyl)acetamide (AJB-1) (9 mg, 1.2 Eq, 91 μmol) in MeOH (8 mL) was stirred overnight at rt. To the above mixture was added NaBH₄ (14 mg, 5 Eq, 0.38 mmol) at 0° C. The resulting mixture was stirred for 1 h at rt. The reaction was then quenched by the addition of MeOH (2 mL) at 0° C. The mixture was concentrated in vacuo. The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 35% B to 45% B in 9 min; Wave Length: 254/220 nm; RT: 8.47) to afford the title compound (AJB-2) (10.4 mg, 17 μmol, 22%, 99.6% Purity) as a white solid. m/z 615.2 (M+H)⁺ (ES+). ¹H NMR (400 MHz, DMSO-d6) δ 8.56-8.51 (m, 1H), 8.25-8.18 (m, 2H), 8.07-7.97 (m, 3H), 7.91-7.84 (m, 1H), 7.80 (s, 1H), 6.90 (d, J=2.0 Hz, 1H), 5.16 (s, 2H), 3.88 (s, 2H), 3.50-3.45 (m, 3H), 3.14 (d, J=6.3 Hz, 3H), 2.55 (d, J=5.6 Hz, 1H), 2.11-2.03 (m, 1H), 1.82-1.77 (m, 3H), 1.02-0.90 (m, 4H).

Example 285: Synthesis of 2-(6-Ethoxy-4-(4-fluoro-2-(4-methyl-4H-1,2,4-triazol-3-yl)phenyl)pyridin-2-yl)-6-(hydroxymethyl)-4-methoxyisoindolin-1-one (AJC-1)

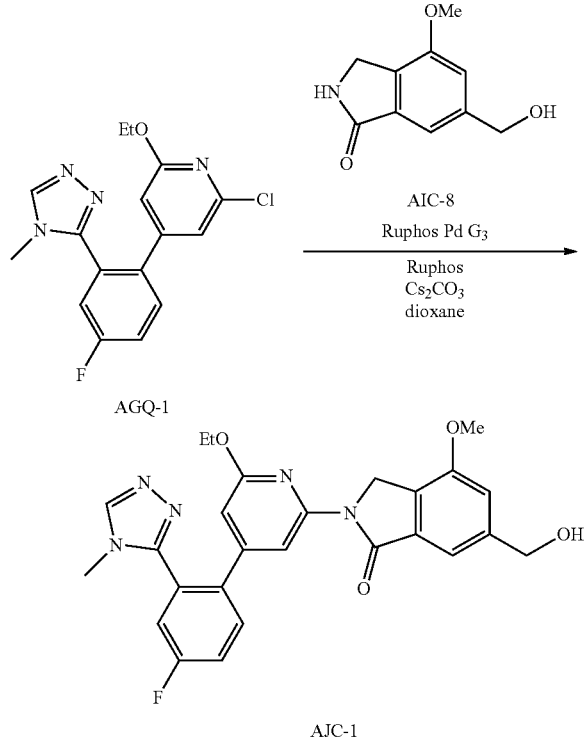

To a stirred solution of intermediate (AGQ-1) (50 mg, 1 Eq, 0.15 mmol) and intermediate (AIC-8) (44 mg, 1.5 Eq, 0.23 mmol) in dioxane (5 mL) was added $Cs_2CO_3$ (98 mg, 2 Eq, 0.30 mmol) at rt under nitrogen atmosphere. To the above mixture was added RuPhos (28 mg, 0.4 Eq, 0.06 mmol) and RuPhos Palladacycle Gen.3 (25 mg, 0.2 Eq, 0.03 mmol) at rt under nitrogen atmosphere. The resulting mixture was stirred for additional 2 h at 100° C. under nitrogen atmosphere. The mixture was allowed to cool down to rt. The resulting mixture was concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: water (0.1% $NH_4HCO_3$+0.1% $NH_3·H_2O$), Mobile Phase B: MeCN; Flow rate: 60 mL/min; Gradient: 36% B to 46% B in 9 min; Wave Length: 254/220 nm; RT: 8.18) to afford the title compound (AJC-1) (17.5 mg, 36 μmol, 24%, 99.5% Purity) as a white solid. m/z 490.0 $(M+H)^+$ (ES+). $^1H$ NMR (400 MHz, DMSO-d6) δ 8.51 (s, 1H), 7.81 (d, J=1.3 Hz, 1H), 7.73-7.66 (m, 1H), 7.64-7.54 (m, 2H), 7.33 (d, J=1.1 Hz, 1H), 7.24 (d, J=1.2 Hz, 1H), 6.27 (d, J=1.2 Hz, 1H), 5.40 (t, J=5.8 Hz, 1H), 4.94 (s, 2H), 4.61 (d, J=5.8 Hz, 2H), 4.37-4.27 (m, 2H), 3.92 (s, 3H), 3.43 (s, 3H), 1.34 (t, J=7.1 Hz, 3H).

Example 286: Synthesis of 3'-(6-(Hydroxymethyl)-1-oxoisoindolin-2-yl)-2-(4-methyl-4H-1,2,4-triazol-3-yl)-[1,1'-biphenyl]-4-carbonitrile (AJD-2)

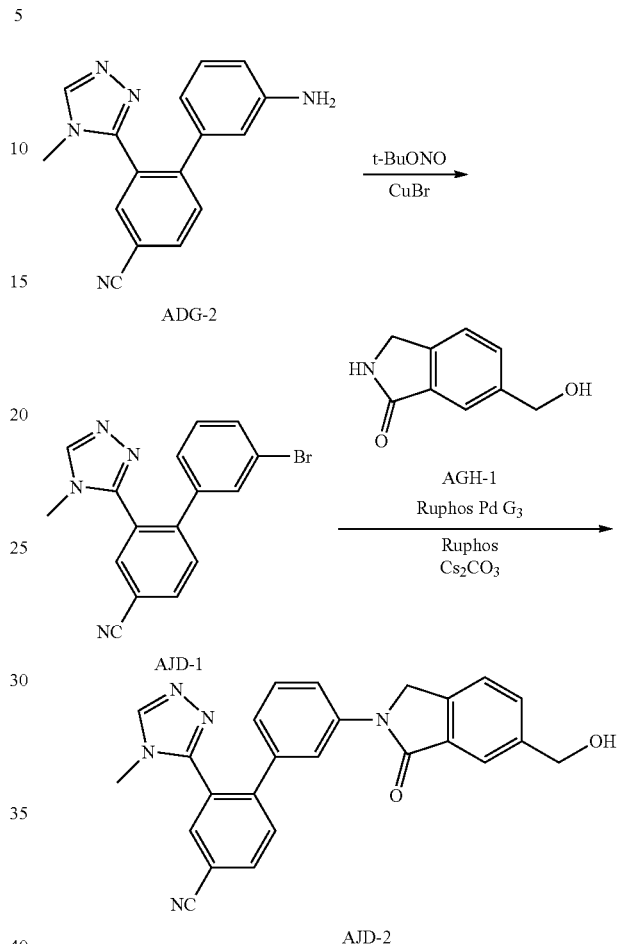

Step 1: 3'-bromo-2-(4-methyl-4H-1,2,4-triazol-3-yl)-[1,1'-biphenyl]-4-carbonitrile (AJD-1)

To a stirred mixture of t-$BuNO_2$ (607 mg, 6 Eq, 5.89 mmol) in ACN (10 mL) was added CuBr (211 mg, 1.5 Eq, 1.47 mmol) at 0° C. The resulting mixture was stirred for 1 h at 0° C. To the above mixture was added 3'-amino-2-(4-methyl-1,2,4-triazol-3-yl)-[1,1'-biphenyl]-4-carbonitrile (ADG-2) (270 mg, 1 Eq, 0.98 mmol) at 0° C. The resulting mixture was stirred for additional 1 h at 50° C. The mixture was cooled to rt and concentrated in vacuo. The residue was applied on a silica gel column chromatography with DCM/methyl (12/1) to afford the sub-title compound (AJE-1) (140 mg, 0.41 mmol, 42%, 95% Purity) as a yellow solid. m/z 339.0/341.0 $(M+H)^+$ (ES+)

Step 2: 3'-(6-(Hydroxymethyl)-1-oxoisoindolin-2-yl)-2-(4-methyl-4H-1,2,4-triazol-3-yl)-[1,1'-biphenyl]-4-carbonitrile (AJD-2)

To a stirred mixture of the product from step 1 above (AJD-1) (140 mg, 1 Eq, 0.41 mmol), intermediate (AGH-1) (81 mg, 1.2 Eq, 0.50 mmol) and $Cs_2CO_3$ (403 mg, 3 Eq, 1.24 mmol) in dioxane (10 mL) were added RuPhos Palladacycle Gen.3 (69 mg, 0.2 Eq, 83 μmol) and RuPhos (77 mg, 0.4 Eq, 0.17 mmol) at rt under nitrogen atmosphere. The resulting mixture was stirred for 2 h at 100° C. under nitrogen atmosphere. The mixture was allowed to cool down to rt. The resulting mixture was diluted with water and extracted with EtOAc (3×50 mL). The combined organic layers were washed with brine (2×50 mL), dried (Na$_2$SO$_4$). After filtration, the filtrate was concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 20% B to 40% B in 8 min; Wave Length: 254/220 nm; RT: 7.53) to afford the title compound (AJD-2) (1.9 mg, 4.5 μmol, 1.1%, 99.6% Purity) as a white solid. m/z 422.0 (M+H)$^+$ (ES+). $^1$H NMR (400 MHz, DMSO-d6) δ 8.47 (d, J=1.9 Hz, 1H), 8.19 (d, J=8.1, 1.8 Hz, 1H), 8.12 (d, J=1.9 Hz, 1H), 8.01 (d, J=8.3 Hz, 1H), 7.88 (d, J=8.0, 1.8 Hz, 1H), 7.75-7.69 (m, 2H), 7.62 (s, 2H), 7.41 (t, J=8.0 Hz, 1H), 6.91 (d, J=7.7 Hz, 1H), 5.37 (d, J=6.6, 4.8 Hz, 1H), 4.90 (s, 2H), 4.62 (d, J=5.7 Hz, 2H), 3.16 (d, J=1.8 Hz, 3H).

Example 287: Synthesis of 3'-(6-(((Cyclopropylmethyl)amino)methyl)-1-oxoisoindolin-2-yl)-2-(4-methyl-4H-1,2,4-triazol-3-yl)-[1,1'-biphenyl]-4-carbonitrile (AJE-2)

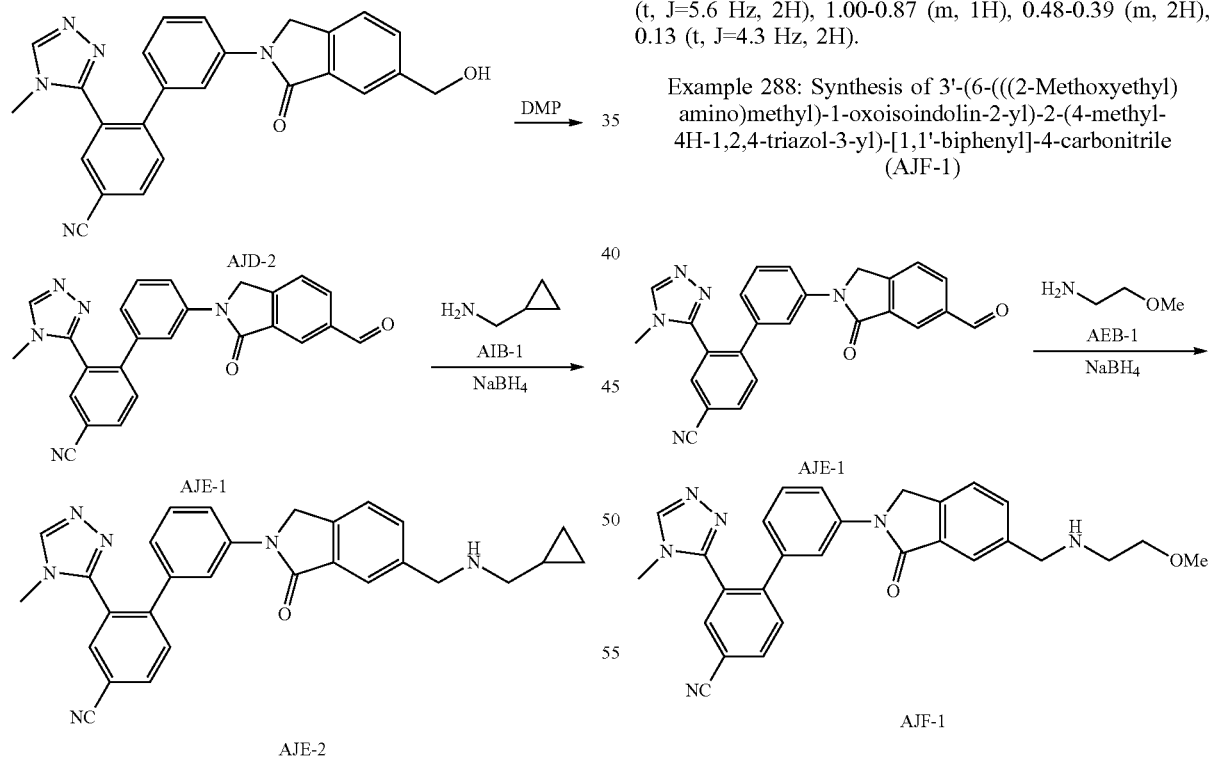

Step 1: 3'-(6-Formyl-1-oxo-3H-isoindol-2-yl)-2-(4-methyl-1,2,4-triazol-3-yl)-[1,1'-biphenyl]-4-carbonitrile (AJE-1)

To a stirred mixture of compound (AJD-2) (30 mg, 1 Eq, 71 μmol) in DCM (10 mL) was added DMP (36 mg, 1.2 Eq, 85 μmol) at rt. The resulting mixture was stirred for 1 h at rt. The resulting mixture was filtered; the filter cake was washed with DCM (3×3 mL). The filtrate was concentrated in vacuo. The crude resulting mixture was used in the next step directly without further purification. m/z 420.1 (M+H)$^+$ (ES+)

Step 2: 3'-(6-((((Cyclopropylmethyl)amino)methyl)-1-oxoisoindolin-2-yl)-2-(4-methyl-4H-1,2,4-triazol-3-yl)-[1,1'-biphenyl]-4-carbonitrile (AJE-2)

A mixture of the product from step 1 above (AJE-1) (30 mg, 1 Eq, 72 μmol) and 1-cyclopropylmethanamine (AIB-1) (8 mg, 1.5 Eq, 0.11 mmol) in MeOH (10 mL) was stirred for 12 h at rt. To the above mixture was added NaBH$_4$ (5 mg, 2 Eq, 0.14 mmol) at 0° C. The resulting mixture was stirred for 1 h at rt. The reaction was then quenched by the addition of MeOH (2 mL) at 0° C. The mixture was concentrated in vacuo. The crude product was purified by Prep-HPLC with the following conditions (Column: Sunfire prep C18 column, 30*150 mm, 5 μm; Mobile Phase A: water (0.1% FA), Mobile Phase B: MeCN; Flow rate: 60 mL/min; Gradient: 2% B to 27% B in 10 min; Wave Length: 254 nm; RT: 9.47) to afford the title compound (AJE-2) (6.0 mg, 13 μmol, 18%, 99.2% Purity) as a yellow solid. m/z 475.2 (M+H)$^+$ (ES+). $^1$H NMR (400 MHz, DMSO-d6) δ 8.46 (s, 1H), 8.25 (s, 1H), 8.19 (d, J=8.1, 1.8 Hz, 1H), 8.12 (d, J=1.8 Hz, 1H), 8.01 (d, J=8.3, 2.3 Hz, 1H), 7.87 (d, J=8.1 Hz, 1H), 7.78 (s, 1H), 7.72-7.58 (m, 3H), 7.41 (t, J=8.0 Hz, 1H), 6.92 (d, J=7.7 Hz, 1H), 4.89 (s, 2H), 3.90 (d, J=4.6 Hz, 2H), 3.16 (s, 3H), 2.45 (t, J=5.6 Hz, 2H), 1.00-0.87 (m, 1H), 0.48-0.39 (m, 2H), 0.13 (t, J=4.3 Hz, 2H).

Example 288: Synthesis of 3'-(6-(((2-Methoxyethyl)amino)methyl)-1-oxoisoindolin-2-yl)-2-(4-methyl-4H-1,2,4-triazol-3-yl)-[1,1'-biphenyl]-4-carbonitrile (AJF-1)

A mixture of intermediate (AJE-1) (30 mg, 1 Eq, 72 μmol) and 2-methoxyethan-1-amine (AEB-1) (6.5 mg, 1.2 Eq, 86 μmol) in MeOH (10 mL) was stirred for 12 h at rt. To the above mixture was added NaBH$_4$ (5.4 mg, 2 Eq, 0.14 mmol) at 0° C. The resulting mixture was stirred for 1 h at rt. The reaction was then quenched by the addition of MeOH (2 mL) at 0° C. The mixture was concentrated in vacuo. The crude product was purified by Prep-HPLC with the following conditions (Column: Sunfire prep C18 column, 30*150 mm, 5 μm; Mobile Phase A: water (0.1% FA), Mobile Phase B: MeCN; Flow rate: 60 mL/min; Gradient: 2% B to 27% B in 10 min; Wave Length: 254 nm; RT: 9) to afford the title compound (AJF-1) (4.3 mg, 9.0 μmol, 12%, 95.9% Purity) as a white solid. m/z 479.1 (M+H)⁺ (ES+). ¹H NMR (400 MHz, DMSO-d6) δ 8.46 (s, 1H), 8.19 (d, J=8.1, 1.8 Hz, 1H), 8.12 (d, J=1.8 Hz, 1H), 8.01 (d, J=8.3, 2.3 Hz, 1H), 7.87 (d, J=8.1 Hz, 1H), 7.76-7.67 (m, 2H), 7.66-7.55 (m, 2H), 7.41 (t, J=8.0 Hz, 1H), 6.92 (d, J=7.6 Hz, 1H), 4.88 (s, 2H), 3.82 (s, 2H), 3.40 (t, J=5.7 Hz, 2H), 3.24 (m, 3H), 3.15 (m, 3H), 2.64 (t, J=5.7 Hz, 2H).

Example 289: Synthesis of 4-(2-cyclopropyl-6-(6-(((1-(methoxymethyl)cyclobutyl)amino)methyl)-1-oxoisoindolin-2-yl)pyridin-4-yl)-3-(4-methyl-4H-1,2,4-triazol-3-yl)benzonitrile (AJG-2)

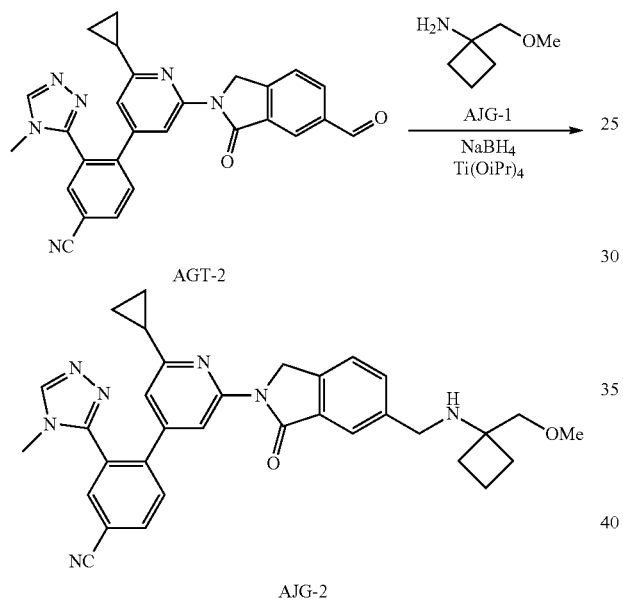

A solution of intermediate (AGT-2) (30 mg, 1 Eq, 65 μmol), 1-(methoxymethyl)cyclobutan-1-amine (AJG-1) (9 mg, 1.2 Eq, 78 μmol) and Ti(Oi-Pr)₄ (74 mg, 4 Eq, 0.26 mmol) in THF (8 mL) was stirred overnight at 60° C. The mixture was allowed to cool down to rt. To the above mixture was added NaBH₄ (12 mg, 5 Eq, 0.33 mmol) at 0° C. The resulting mixture was stirred for additional 1 h at rt. The reaction was then quenched by the addition of MeOH (2 mL) at 0° C. The mixture was concentrated in vacuo. The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 46% B to 63% B in 8 min; Wave Length: 254/220 nm; RT: 7.8) to afford the title compound (AJG-2) (3.2 mg, 5.7 μmol, 8.8%, 99.8% Purity) as a white solid. m/z 560.3 (M+H)⁺ (ES+). ¹H NMR (400 MHz, Methanol-d4) δ 8.50 (s, 1H), 8.14-8.10 (m, 1H), 8.10-8.04 (m, 2H), 7.93 (d, J=8.1 Hz, 1H), 7.83 (s, 1H), 7.70-7.66 (m, 1H), 7.61 (d, J=7.8 Hz, 1H), 6.92 (d, J=1.4 Hz, 1H), 5.03 (s, 2H), 3.82 (s, 2H), 3.55 (s, 2H), 3.50 (s, 3H), 3.42 (s, 3H), 2.13-1.95 (m, 5H), 1.89-1.77 (m, 2H), 1.07-1.01 m, 2H), 1.01-0.96 (m, 2H).

Example 290: Synthesis of 4-(2-(6-Acetyl-1-oxoisoindolin-2-yl)-6-cyclopropylpyridin-4-yl)-3-(4-methyl-4H-1,2,4-triazol-3-yl)benzonitrile (AJH-3)

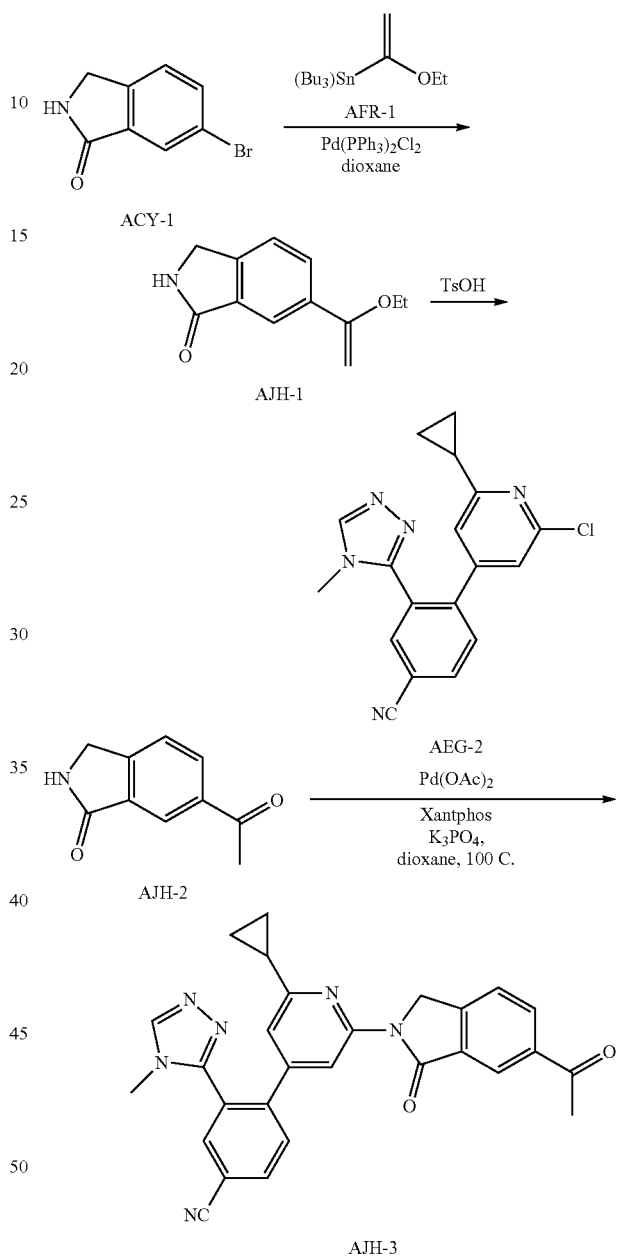

Step 1: 6-(1-Ethoxyethenyl)-2,3-dihydroisoindol-1-one (AJH-1)

To a stirred solution of intermediate (ACY-1) (2.00 g, 1 Eq, 9.43 mmol) and dibutyl(1-ethoxyethenyl)propylstannane (AFR-1) (3.93 g, 1.2 Eq, 11.3 mmol) in dioxane (15 mL) was added Pd(PPh₃)₂Cl₂ (662 mg, 0.1 Eq, 0.94 mmol) at rt under nitrogen atmosphere. The resulting mixture was stirred overnight at 80° C. under nitrogen atmosphere. The mixture was allowed to cool down to rt. The resulting mixture was concentrated in vacuo. The residue was purified by Prep-TLC with DCM/MeOH (10/1) to afford the sub-title compound (AJH-1) (1.7 g, 8.33 mmol, 89%, 92% Purity) as a yellow solid. m/z 204.1 (M+H)$^+$ (ES+)

Step 2: 6-Acetyl-2,3-dihydroisoindol-1-one (AJH-2)

To a stirred solution of the product from step 1 above (AJH-1) (1.7 g, 1 Eq, 8.33 mmol) in DCM (20 mL) at rt was added TsOH (2.88 g, 2 Eq, 16.7 mmol). The resulting mixture was stirred for 1 h at rt. The mixture was concentrated in vacuo. The residue was purified by Prep-TLC with DCM/MeOH (10/1) to afford the sub-title compound (AJH-2) (1.2 g, 6.85 mmol, 82%, 93% Purity) as a yellow solid. m/z 176.1 (M+H)$^+$ (ES+)

Step 3: 4-(2-(6-Acetyl-1-oxoisoindolin-2-yl)-6-cyclopropylpyridin-4-yl)-3-(4-methyl-4H-1,2,4-triazol-3-yl)benzonitrile (AJH-3)

To a stirred solution of the product from step 2 above (AJH-2) (25 mg, 1.2 Eq, 0.14 mmol), intermediate (AEG-2) (40 mg, 1 Eq, 0.12 mmol) and Cs$_2$CO$_3$ (77 mg, 2 Eq, 0.24 mmol) in dioxane (8 mL) were added RuPhos (22 mg, 0.4 Eq, 48 μmol) and RuPhos Palladacycle Gen.3 (20 mg, 0.2 Eq, 24 μmol) at rt under nitrogen atmosphere. The resulting mixture was stirred for 2 h at 100° C. under nitrogen atmosphere. The mixture was cooled to rt and concentrated in vacuo. The residue was purified by Prep-TLC with DCM/MeOH (10/1). The product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 40% B to 50% B in 8 min; Wave Length: 254/220 nm; RT: 7.67) to afford the title compound (AJH-3) (3.2 mg, 6.7 μmol, 5.7%, 99.7% Purity) as a white solid. m/z 475.1 (M+H)$^+$ (ES+). $^1$H NMR (400 MHz, DMSO-d6) δ 8.54 (s, 1H), 8.29-8.24 (m, 2H), 8.24-8.20 (m, 2H), 7.98 (d, J=1.5 Hz, 1H), 7.90-7.84 (m, 2H), 6.93 (d, J=1.4 Hz, 1H), 5.12 (s, 2H), 3.49 (s, 3H), 2.68 (s, 3H), 2.09-2.03 (m, 1H), 1.02-0.95 (m, 4H).

Example 291: Synthesis of 4-(2-Cyclopropyl-6-(6-(1-((cyclopropylmethyl)amino)ethyl)-1-oxoisoindolin-2-yl)pyridin-4-yl)-3-(4-methyl-4H-1,2,4-triazol-3-yl)benzonitrile (AJI-1)

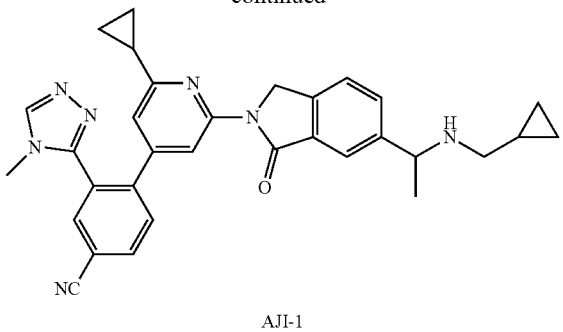

AJI-1

To a stirred solution of intermediate (AJH-3) (100 mg, 1 Eq, 0.21 mmol) and 1-cyclopropylmethanamine (AIB-1) (18 mg, 1.2 Eq, 0.25 mmol) in DCM (10 mL) was added Ti(Oi-Pr)$_4$ (180 mg, 3 Eq, 0.63 mmol) at rt. The resulting mixture was stirred overnight at 60° C. The mixture was allowed to cool down to rt. To the above mixture was added NaBH$_4$ (40 mg, 5 Eq, 1.06 mmol) at 0° C. The resulting mixture was stirred for additional 2 h at rt. The reaction was then quenched by the addition of MeOH (2 mL) at 0° C. The mixture was concentrated in vacuo. The resulting mixture was diluted with water and extracted with DCM/MeOH (10/1) (3×20 mL). The combined organic layers were washed with brine (2×20 mL), dried (Na$_2$SO$_4$). After filtration, the filtrate was concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 45% B to 58% B in 8 min; Wave Length: 254/220 nm) to afford the title compound (AJ-1) (53 mg, 0.10 mml, 47%, 98.3% Purity) as a white solid. m/z 530.2 (M+H)$^+$ (ES+). $^1$H NMR (400 MHz, Methanol-d4) δ 8.50 (s, 1H), 8.16-8.03 (m, 3H), 7.92 (d, J=8.1 Hz, 1H), 7.86-7.77 (m, 1H), 7.70-7.59 (m, 2H), 6.93 (d, J=1.4 Hz, 1H), 5.03 (s, 2H), 4.03-3.93 (m, 1H), 3.50 (s, 3H), 2.43-2.32 (m, 1H), 2.27-2.15 (m, 1H), 2.08-1.97 (m, 1H), 1.43 (d, J=6.7 Hz, 3H), 1.08-0.86 (m, 5H), 0.54-0.41 (m, 2H), 0.13-0.03 (m, 2H).

Example 292: Synthesis of (R)-4-(2-Cyclopropyl-6-(6-(1-((cyclopropylmethyl)amino)ethyl)-1-oxoisoindolin-2-yl)pyridin-4-yl)-3-(4-methyl-4H-1,2,4-triazol-3-yl)benzonitrile (AJJ-1)

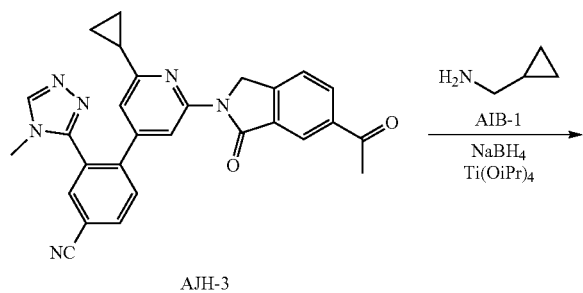

AJH-3

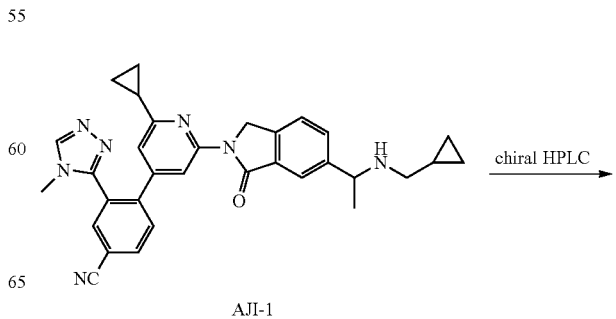

AJI-1

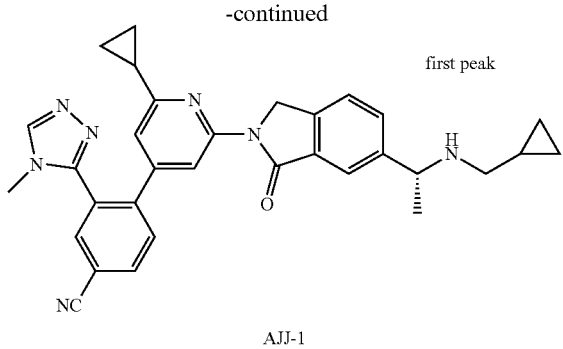

first peak

AJJ-1

The crude product (AJI-1) (50 mg, 1 Eq, 94 μmol) was purified by Prep-CHIRAL-HPLC with the following conditions (Column: CHIRAL ART Amylose-SA, 2*25 cm, 5 μm; Mobile Phase A: MtBE (0.5% 2M NH$_3$-MeOH)-HPLC, Mobile Phase B: EtOH-HPLC; Flow rate: 20 mL/min; Gradient: 50% B to 50% B in 25 min; Wave Length: 220/254 nm, RT1(min): 14.486) to afford the title compound (AJJ-1) (19.6 mg, 37 μmol, 39%, 99.6% Purity) as a white solid. m/z 530.2 (M+H)$^+$ (ES+). $^1$H NMR (400 MHz, Methanol-d4) δ 8.50 (s, 1H), 8.15-8.10 (m, 1H), 8.10-8.07 (m, 1H), 8.06 (d, J=1.4 Hz, 1H), 7.95-7.91 (m, 1H), 7.82-7.77 (m, 1H), 7.70-7.64 (m, 1H), 7.62 (d, J=7.9 Hz, 1H), 6.92 (d, J=1.4 Hz, 1H), 5.03 (s, 2H), 4.02-3.93 (m, 1H), 3.50 (s, 3H), 2.42-2.32 (m, 1H), 2.25-2.15 (m, 1H), 2.09-1.98 (m, 1H), 1.43 (d, J=6.7 Hz, 3H), 1.07-1.02 (m, 2H), 1.01-0.95 (m, 2H), 0.95-0.87 (m, 1H), 0.52-0.44 (m, 2H), 0.13-0.03 (m, 2H). Column: CHIRALPAK IA-3, 4.6*50 mm, 3 μm; Mobile Phase A: MtBE (0.1% DEA):EtOH=50:50; Flow rate: 1 mL/min; RT: 2.408.

Example 293: Synthesis of (S)-4-(2-Cyclopropyl-6-(6-(1-((cyclopropylmethyl)amino)ethyl)-1-oxoisoindolin-2-yl)pyridin-4-yl)-3-(4-methyl-4H-1,2,4-triazol-3-yl)benzonitrile (AJK-1)

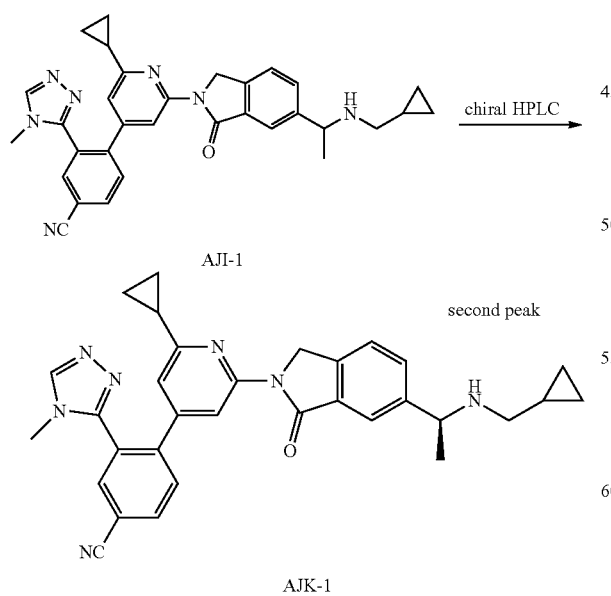

AJK-1

The crude product (AJI-1) (50 mg, 1 Eq, 94 μmol) was purified by Prep-CHIRAL-HPLC with the following conditions (Column: CHIRAL ART Amylose-SA, 2*25 cm, 5 μm; Mobile Phase A: MtBE (0.5% 2M NH$_3$-MeOH)-HPLC, Mobile Phase B: EtOH-HPLC; Flow rate: 20 mL/min; Gradient: 50% B to 50% B in 25 min; Wave Length: 220/254 nm, RT2(min): 22.279) to afford the title compound (AJK-1) (17 mg, 32 μmol, 33%, 98.5% Purity) as a white solid. m/z 530.2 (M+H)$^+$ (ES+). $^1$H NMR (400 MHz, Methanol-d4) δ 8.50 (s, 1H), 8.15-8.10 (m, 1H), 8.10-8.07 (m, 1H), 8.06 (d, J=1.4 Hz, 1H), 7.95-7.91 (m, 1H), 7.82-7.77 (m, 1H), 7.70-7.64 (m, 1H), 7.62 (d, J=7.9 Hz, 1H), 6.92 (d, J=1.4 Hz, 1H), 5.03 (s, 2H), 4.02-3.93 (m, 1H), 3.50 (s, 3H), 2.42-2.32 (m, 1H), 2.25-2.15 (m, 1H), 2.09-1.98 (m, 1H), 1.43 (d, J=6.7 Hz, 3H), 1.07-1.02 (m, 2H), 1.01-0.95 (m, 2H), 0.95-0.87 (m, 1H), 0.52-0.44 (m, 2H), 0.13-0.03 (m, 2H). Column: CHIRALPAK IA-3, 4.6*50 mm, 3 um; Mobile Phase A: MtBE(0.1% DEA):EtOH=50:50; Flow rate: 1 mL/min; RT: 3.250.

Example 294: Synthesis of 4-(2-cyclopropyl-6-(6-hydroxy-1-oxoisoindolin-2-yl)pyridin-4-yl)-3-(4-methyl-4H-1,2,4-triazol-3-yl)benzonitrile (AJL-2)

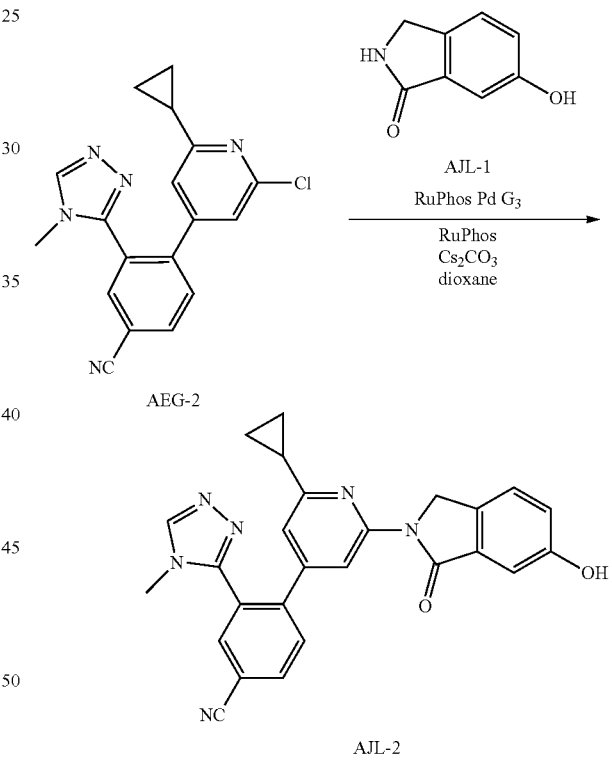

To a stirred solution of intermediate (AEG-2) (150 mg, 1 Eq, 0.45 mmol), 6-hydroxy-2,3-dihydroisoindol-1-one (AJL-1) (74 mg, 1.1 Eq, 0.49 mmol) and Cs$_2$CO$_3$ (291 mg, 2 Eq, 0.89 mmol) in dioxane (10 mL) were added RuPhos (84 mg, 0.4 Eq, 0.18 mmol) and RuPhos Palladacycle Gen.3 (75 mg, 0.2 Eq, 89 μmol) at rt under nitrogen atmosphere. The resulting mixture was stirred for 2 h at 100° C. under nitrogen atmosphere. The mixture was allowed to cool down to rt. The resulting mixture was diluted with water and extracted with EtOAc (3×50 mL). The combined organic layers were washed with brine (2×50 mL), dried (Na$_2$SO$_4$). After filtration, the filtrate was concentrated in vacuo. The residue was purified by Prep-TLC with DCM/MeOH (12/1).

The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 38% B to 55% B in 8 min; Wave Length: 254/220 nm) to afford the title compound (AJL-2) (9.7 mg, 22 μmol, 4.8%, 99.8% Purity) as a white solid. m/z 449.1 (M+H)⁺ (ES+). ¹H NMR (400 MHz, DMSO-d6) δ 9.88 (s, 1H), 8.54 (s, 1H), 8.23-8.16 (m, 2H), 7.98 (d, J=1.4 Hz, 1H), 7.86 (d, J=8.6 Hz, 1H), 7.50 (d, J=8.1 Hz, 1H), 7.12-7.04 (m, 2H), 6.85 (d, J=1.4 Hz, 1H), 4.90 (s, 2H), 3.45 (s, 3H), 2.07-1.99 (m, 1H), 1.01-0.89 (m, 4H).

Example 295: Synthesis of (S)-4-(2-Cyclopropyl-6-(6-(2,3-dihydroxypropoxy)-1-oxoisoindolin-2-yl)pyridin-4-yl)-3-(4-methyl-4H-1,2,4-triazol-3-yl)benzonitrile (AJM-3)

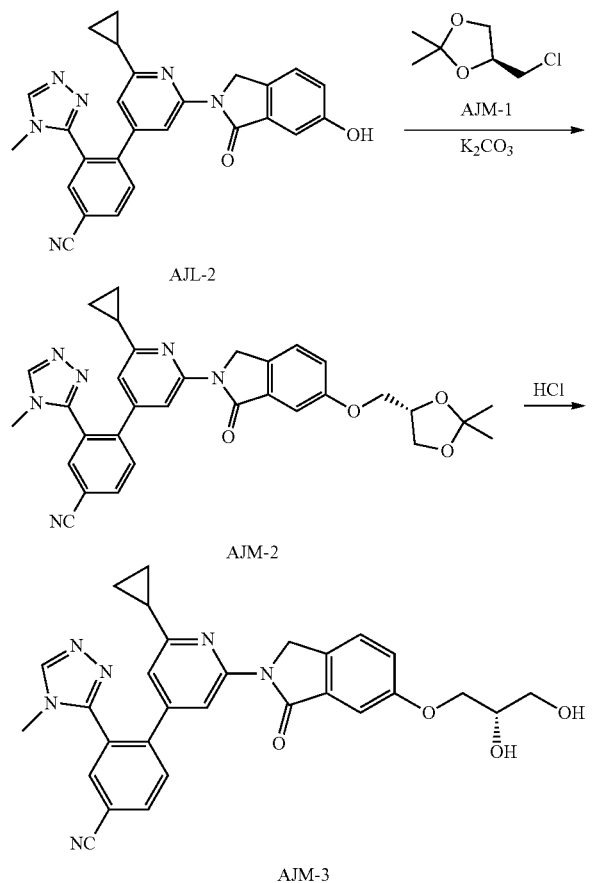

Step 1: 4-[2-Cyclopropyl-6-(6-{[(4S)-2,2-dimethyl-1,3-dioxolan-4-yl]methoxy}-1-oxo-3H-isoindol-2-yl)pyridin-4-yl]-3-(4-methyl-1,2,4-triazol-3-yl)benzonitrile (AJM-2)

To a stirred solution of compound (AJL-2) (40 mg, 1 Eq, 89 μmol) and (4S)-4-(chloromethyl)-2,2-dimethyl-1,3-dioxolane (AJM-1) (20 mg, 1.5 Eq, 0.13 mmol) in DMSO (5 mL) was added K₂CO₃ (37 mg, 3 Eq, 0.27 mmol) at rt. The resulting mixture was stirred for 2 h at 120° C. The mixture was allowed to cool down to rt. The resulting mixture was diluted with water and extracted with EtOAc (3×10 mL). The combined organic layers were washed with brine (2×10 mL), dried (Na₂SO₄). After filtration, the filtrate was concentrated in vacuo. The residue was purified by Prep-TLC with DCM/MeOH (12/1) to afford the sub-title compound (AJM-2) (28 mg, 50 μmol, 56%, 95% Purity) as a colorless oil. m/z 563.2 (M+H)⁺ (ES+).

Step 2: (S)-4-(2-Cyclopropyl-6-(6-(2,3-dihydroxypropoxy)-1-oxoisoindolin-2-yl)pyridin-4-yl)-3-(4-methyl-4H-1,2,4-triazol-3-yl)benzonitrile (AJM-3)

To a stirred solution of the product from step 1 above (AJM-2) (25 mg, 1 Eq, 44 μmol) in MeOH (4 mL) was added aq. HCl (4 mL, 2 M) dropwise at rt. The resulting mixture was stirred for 1 h at rt. The resulting mixture was concentrated in vacuo. The crude product was purified by Prep-HPLC with the following conditions (Column: Xselect CSH C18 OBD Column 30*150 mm, 5 μm, n; Mobile Phase A: water (0.1% FA), Mobile Phase B: MeCN; Flow rate: 60 mL/min; Gradient: 13% B to 43% B in 10 min; Wave Length: 254 nm) to afford the title compound (AJM-3) (6.7 mg, 13 μmol, 29%, 99.8% Purity) as a white solid. m/z 523.2 (M+H)⁺ (ES+). ¹H NMR (400 MHz, DMSO-d6) δ 8.53 (s, 1H), 8.25-8.18 (m, 2H), 7.97 (d, J=1.4 Hz, 1H), 7.87 (d, J=8.5 Hz, 1H), 7.60 (d, J=8.4 Hz, 1H), 7.30-7.21 (m, 2H), 6.88 (d, J=1.5 Hz, 1H), 4.96 (d, J=13.3 Hz, 3H), 4.67 (d, J=6.1 Hz, 1H), 4.14-4.07 (m, 1H), 4.00-3.92 (m, 1H), 3.87-3.78 (m, 1H), 3.47 (s, 5H), 2.11-2.00 (m, 1H), 0.97 (d, J=6.4 Hz, 4H).

Example 296: Synthesis of (R)-4-(2-Cyclopropyl-6-(6-(2,3-dihydroxypropoxy)-1-oxoisoindolin-2-yl)pyridin-4-yl)-3-(4-methyl-4H-1,2,4-triazol-3-yl)benzonitrile (AJN-3)

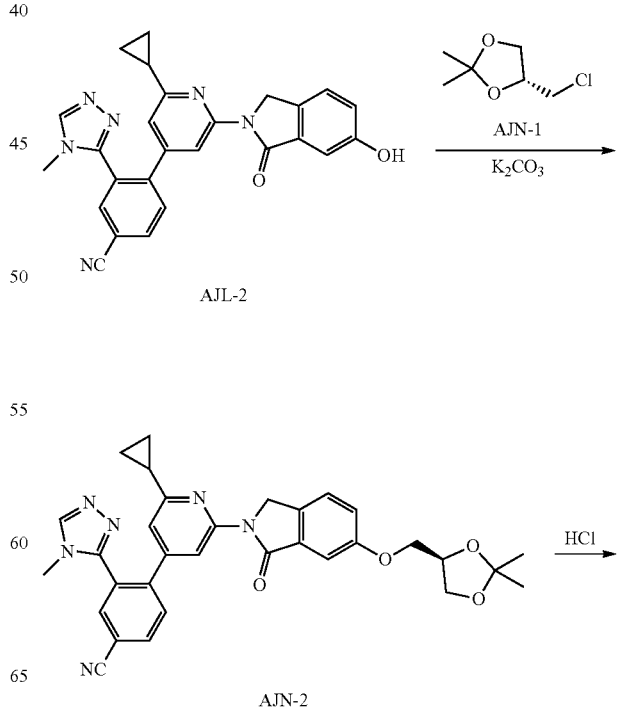

-continued

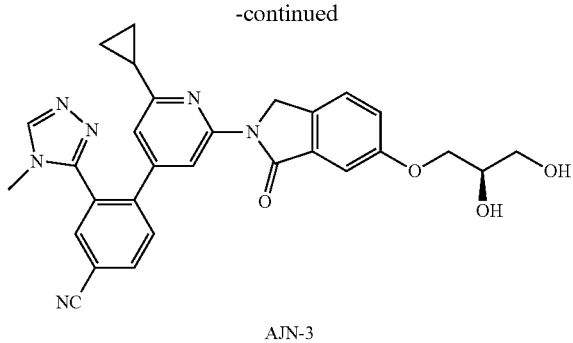

AJN-3

Step 1: 4-[2-Cyclopropyl-6-(6-{[(4R)-2,2-dimethyl-1,3-dioxolan-4-yl]methoxy}-1-oxo-3H-isoindol-2-yl)pyridin-4-yl]-3-(4-methyl-1,2,4-triazol-3-yl)benzonitrile (AJN-2)

To a stirred solution of compound (AJL-2) (40 mg, 1 Eq, 89 µmol) and (4R)-4-(chloromethyl)-2,2-dimethyl-1,3-dioxolane (AJN-1) (21 mg, 1.5 Eq, 0.13 mmol) in DMSO (5 mL) was added $K_2CO_3$ (25 mg, 2 Eq, 0.18 mmol) at rt. The resulting mixture was stirred for 2 h at 120° C. The mixture was allowed to cool down to rt. The resulting mixture was diluted with water and extracted with EtOAc (3×10 mL). The combined organic layers were washed with brine (2×20 mL), dried ($Na_2SO_4$). After filtration, the filtrate was concentrated in vacuo. The residue was purified by Prep-TLC with DCM/MeOH (12/1) to afford the sub-title compound (AJN-2) (32 mg, 57 µmol, 64%, 95% Purity) as a yellow solid. m/z 563.2 $(M+H)^+$ (ES+).

Step 2: (R)-4-(2-Cyclopropyl-6-(6-(2,3-dihydroxypropoxy)-1-oxoisoindolin-2-yl)pyridin-4-yl)-3-(4-methyl-4H-1,2,4-triazol-3-yl)benzonitrile (AJN-3)

To a stirred solution of the product from step 1 above (AJN-2) (27 mg, 1 Eq, 48 µmol) in MeOH (4 mL) was added aq. HCl (4 mL, 2 M) dropwise at rt. The resulting mixture was stirred for 1 h at rt. The resulting mixture was concentrated in vacuo. The crude product was purified by Prep-HPLC with the following conditions (Column: Sunfire prep C18 column, 30*150 mm, 5 µm; Mobile Phase A: water (0.1% FA), Mobile Phase B: MeCN; Flow rate: 60 mL/min; Gradient: 13% B to 43% B in 10 min; Wave Length: 254 nm) to afford the title compound (AJN-3) (8.2 mg, 16 µmol, 33%, 99.8% Purity) as a white solid. m/z 523.2 $(M+H)^+$ (ES+). $^1$H NMR (400 MHz, DMSO-d6) δ 8.54 (d, J=2.8 Hz, 1H), 8.26-8.11 (m, 2H), 7.98 (d, J=2.5 Hz, 1H), 7.91-7.82 (m, 1H), 7.64-7.56 (m, 1H), 7.30-7.14 (m, 2H), 6.89 (d, J=2.6 Hz, 1H), 5.01-4.84 (m, 3H), 4.73-4.63 (m, 1H), 4.17-4.06 (m, 1H), 3.99-3.91 (m, 1H), 3.82 (d, J=7.1 Hz, 1H), 3.47 (d, J=3.0 Hz, 5H), 2.11-2.00 (m, 1H), 1.01-0.84 (m, 4H).

Example 297: Synthesis of 2-(6-Ethoxy-4-(4-fluoro-2-(4-methyl-4H-1,2,4-triazol-3-yl)phenyl)pyridin-2-yl)-6-((((1-hydroxycyclobutyl)methyl)(methyl)amino)methyl)-4-methoxyisoindolin-1-one (AJO-2)

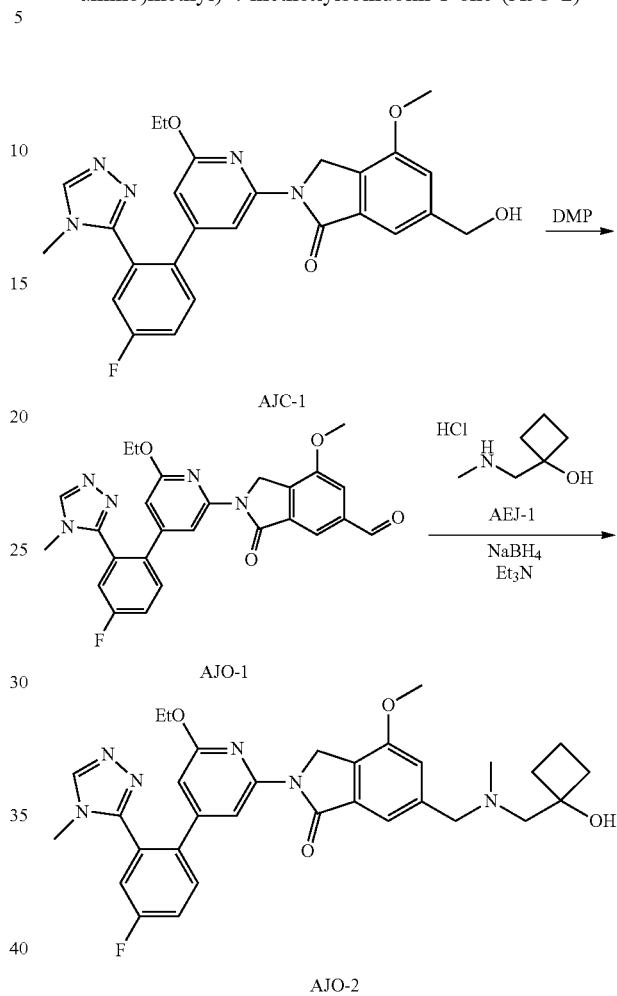

Step 1: 2-(6-Ethoxy-4-(4-fluoro-2-(4-methyl-4H-1,2,4-triazol-3-yl)phenyl)pyridin-2-yl)-7-methoxy-3-oxoisoindoline-5-carbaldehyde (AJO-1)

To a stirred solution of compound (AJC-1) (50 mg, 1 Eq, 0.10 mmol) in DCM (5 mL) was added DMP (65 mg, 1.5 Eq, 0.15 mmol) at rt. The resulting mixture was stirred for 1 h at rt. The resulting mixture was filtered; the filter cake was washed with DCM (2×3 mL). The filtrate was concentrated in vacuo. The residue was purified by Prep-TLC with DCM/MeOH (20/1) to afford the sub-title compound (AJO-1) (50 mg, 0.10 mmol, 95%, 98% Purity) as an off-white solid. m/z 488.2 $(M+H)^+$ (ES+)

Step 2: 2-(6-Ethoxy-4-(4-fluoro-2-(4-methyl-4H-1,2,4-triazol-3-yl)phenyl)pyridin-2-yl)-6-((((1-hydroxycyclobutyl)methyl)(methyl)amino)methyl)-4-methoxyisoindolin-1-one (AJO-2)

To a stirred solution of the product from step 1 above (AJO-1) (40 mg, 1 Eq, 82 µmol) and 1-[(methylamino)methyl]cyclobutan-1-ol, HCl (AEJ-1) (15 mg, 1.2 Eq, 98 µmol) in DCM (5 mL) was added $Et_3N$ (25 mg, 3 Eq, 0.25 mmol) at rt under nitrogen atmosphere. The resulting mixture was stirred overnight at rt under nitrogen atmosphere. To the above mixture was added NaBH$_4$ (16 mg, 5 Eq, 0.41 mmol) at 0° C. The resulting mixture was stirred for additional 2 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 48% B to 60% B in 8 min; Wave Length: 254/220 nm; RT: 7.7) to afford the title compound (AJO-2) (3.2 mg, 5.5 μmol, 6.6%, 99.7% Purity) as a white solid. m/z 587.2 (M+H)$^+$ (ES+). $^1$H NMR (400 MHz, DMSO-d6) δ 8.51 (s, 1H), 7.78 (d, J=1.2 Hz, 1H), 7.73-7.64 (m, 1H), 7.59 (t, J=8.4 Hz, 2H), 7.37-7.24 (m, 2H), 6.28 (d, J=1.2 Hz, 1H), 4.92 (d, J=17.0 Hz, 3H), 4.38-4.28 (m, 2H), 3.91 (s, 3H), 3.68 (s, 2H), 3.43 (s, 3H), 2.46 (s, 2H), 2.26 (s, 3H), 2.08-2.00 (m, 2H), 1.96-1.85 (m, 2H), 1.68-1.54 (m, 2H), 1.34 (t, J=7.1 Hz, 3H).

Example 298: Synthesis of 3'-Cyclopropyl-5'-(6-(hydroxymethyl)-1-oxoisoindolin-2-yl)-2-(4-methyl-4H-1,2,4-triazol-3-yl)-[1,1'-biphenyl]-4-carbonitrile (AJP-7)

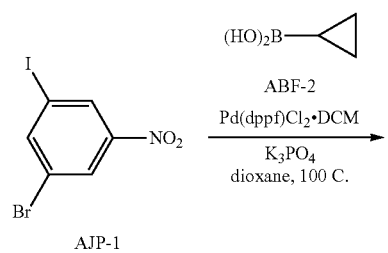

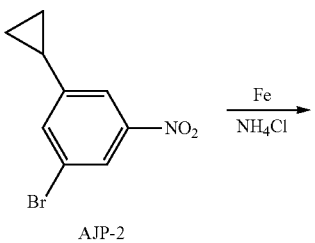

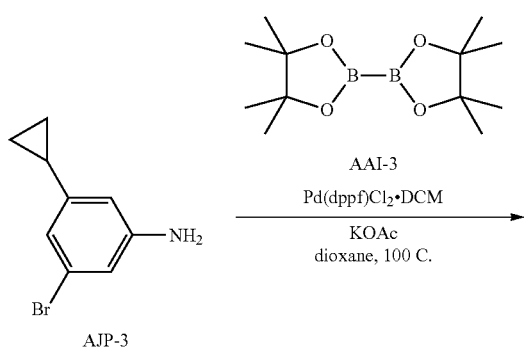

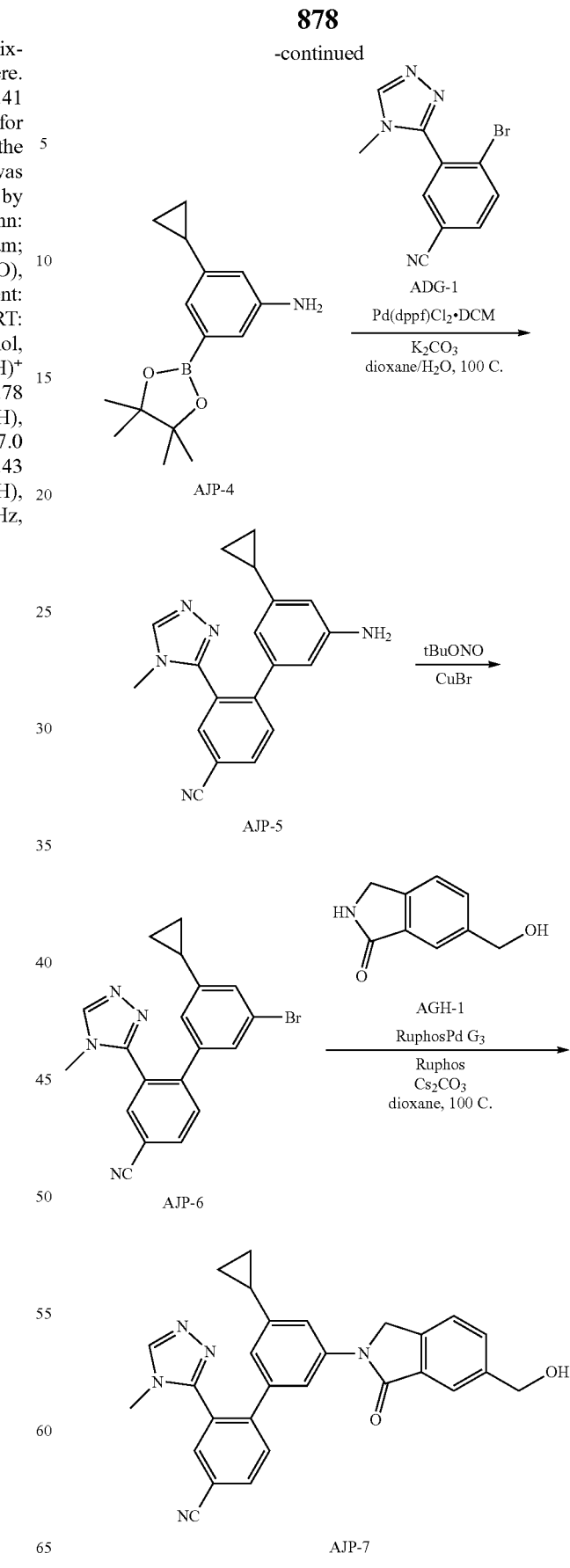

Step 1: 1-Bromo-3-cyclopropyl-5-nitrobenzene (AJP-2)

To a stirred solution of 1-bromo-3-iodo-5-nitrobenzene (AJP-1) (500 mg, 1 Eq, 1.53 mmol) and cyclopropylboronic acid (ABF-2) (196 mg, 1.5 Eq, 2.29 mmol) in dioxane (30 mL) was added $K_3PO_4$ (647 mg, 2 Eq, 3.05 mmol) at rt under nitrogen atmosphere. To the above mixture was added Pd(dppf)$Cl_2$.DCM (124 mg, 0.1 Eq, 0.15 mmol) at rt under nitrogen atmosphere. The resulting mixture was stirred for 2 h at 100° C. under nitrogen atmosphere. The mixture was allowed to cool down to rt. The resulting mixture was diluted with water and extracted with EtOAc (3×80 mL). The combined organic layers were washed with brine (2×80 mL), dried ($Na_2SO_4$). After filtration, the filtrate was concentrated in vacuo. The residue was purified by Prep-TLC with EtOAc/petroleum ether (1/10) to afford the sub-title compound (AJP-2) (400 mg, 1.66 mmol, 94%, 90% Purity) as a white solid. m/z 242.0/244.0 (M+H)$^+$ (ES+)

Step 2: 3-Bromo-5-cyclopropylaniline (AJP-3)

To a stirred solution of the product from step 1 above (AJP-2) (900 mg, 1 Eq, 3.72 mmol) and $NH_4Cl$ (795 mg, 4 Eq, 14.9 mmol) in EtOH (40 mL) was added iron powder (1.25 g, 6 Eq, 22.3 mmol) at rt under nitrogen atmosphere. The resulting mixture was stirred for 3 h at 80° C. under nitrogen atmosphere. The mixture was allowed to cool down to rt. The resulting mixture was concentrated in vacuo. The resulting mixture was diluted with water and extracted with EtOAc (3×80 mL). The combined organic layers were washed with brine (2×80 mL), dried ($Na_2SO_4$). After filtration, the filtrate was concentrated in vacuo. The residue was purified by Prep-TLC with EtOAc/petroleum ether (1/8) to afford the sub-title compound (AJP-3) (500 mg, 2.37 mmol, 54%, 92% Purity) as an off-white solid. m/z 212.0/214.0 (M+H)$^+$ (ES+)

Step 3: 3-Cyclopropyl-5-(4,4,5,5-tetramethyl-1,3,2-dioxaborolan-2-yl)aniline (AJP-4)

To a stirred solution of the product from step 2 above (AJP-3) (500 mg, 1 Eq, 2.36 mmol) and bis(pinacolato)diboron (AAI-3) (898 mg, 1.5 Eq, 3.54 mmol) in dioxane (25 mL) was added KOAc (694 mg, 3 Eq, 7.07 mmol) at rt under nitrogen atmosphere. To the above mixture was added Pd(dppf)$Cl_2$.DCM (192 mg, 0.1 Eq, 0.24 mmol) at rt under nitrogen atmosphere. The resulting mixture was stirred for 2 h at 100° C. under nitrogen atmosphere. The mixture was allowed to cool down to rt. The resulting mixture was concentrated in vacuo. The residue was purified by Prep-TLC with EtOAc/petroleum ether (1/3) to afford the sub-title compound (AJP-4) (480 mg, 1.85 mmol, 72%, 92% Purity) as an off-white solid. m/z 260.2 (M+H)$^+$ (ES+)

Step 4: 3'-Amino-5'-cyclopropyl-2-(4-methyl-1,2,4-triazol-3-yl)-[1,1'-biphenyl]-4-carbonitrile (AJP-5)

To a stirred solution of 4-bromo-3-(4-methyl-1,2,4-triazol-3-yl)benzonitrile (ADG-1) (360 mg, 1 Eq, 1.37 mmol) and the product from step 3 above (AJQ-4) (390 mg, 1.1 Eq, 1.51 mmol) in dioxane (15 mL) was added $K_2CO_3$ (567 mg, 3 Eq, 4.10 mmol) at rt under nitrogen atmosphere. To the above mixture was added Pd(dppf)$Cl_2$.DCM (111 mg, 0.1 Eq, 0.14 mmol) at rt under nitrogen atmosphere. The resulting mixture was stirred for 3 h at 100° C. under nitrogen atmosphere. The mixture was allowed to cool down to rt. The resulting mixture was concentrated in vacuo. The residue was purified by Prep-TLC with DCM/MeOH (20/1) to afford the sub-title compound (AJQ-5) (220 mg, 0.70 mmol, 46%, 91% Purity) as a light brown solid. m/z 316.1 (M+H)$^+$ (ES+)

Step 5: 3'-Bromo-5'-cyclopropyl-2-(4-methyl-1,2,4-triazol-3-yl)-[1,1'-biphenyl]-4-carbonitrile (AJP-6)

A solution of CuBr (150 mg, 1.5 Eq, 1.05 mmol) and t-BuONO (432 mg, 6 Eq, 4.19 mmol) in MeCN (12 mL) at 0° C. under nitrogen atmosphere was stirred for 1. To the above mixture was added the product from step 4 above (AJP-5) (220 mg, 1 Eq, 0.70 mmol) in MeCN at 0° C. under nitrogen atmosphere. The resulting mixture was stirred for 1 h at 50° C. under nitrogen atmosphere. The resulting mixture was filtered; the filter cake was washed with MeOH (3×5 mL). The filtrate was concentrated in vacuo. The residue was applied on a silica gel column chromatography with DCM/MeOH (5/1) to afford the sub-title compound (AJP-6) (165 mg, 0.44 mmol, 53%, 94% Purity) as a brown-yellow solid. m/z 379.0/381.0 (M+H)$^+$ (ES+)

Step 6: 3'-Cyclopropyl-5'-(6-(hydroxymethyl)-1-oxoisoindolin-2-yl)-2-(4-methyl-4H-1,2,4-triazol-3-yl)-[1,1'-biphenyl]-4-carbonitrile (AJP-7)

To a stirred solution of the product from step 5 above (AJP-6) (40 mg, 1 Eq, 0.11 mmol) and intermediate (AGH-1) (21 mg, 1.2 Eq, 0.13 mmol) in dioxane (5 mL) was added $Cs_2CO_3$ (69 mg, 2 Eq, 0.21 mmol) at rt under nitrogen atmosphere. To the above mixture was added RuPhos (20 mg, 0.4 Eq, 42 μmol) and RuPhos Palladacycle Gen.3 (18 mg, 0.2 Eq, 21 μmol) at rt under nitrogen atmosphere. The resulting mixture was stirred for additional 2 h at 100° C. under nitrogen atmosphere. The mixture was allowed to cool down to rt. The resulting mixture was concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: water (0.1% $NH_4HCO_3$+0.1% $NH_3 \cdot H_2O$), Mobile Phase B: MeCN; Flow rate: 60 mL/min; Gradient: 30% B to 40% B in 8 min; Wave Length: 254/220 nm; RT: 7.67) to afford the title compound (AJP-7) (4.1 mg, 8.9 μmol, 8.4%, 99.8% Purity) as a white solid. m/z 462.1 (M+H)$^+$ (ES+). $^1$H NMR (400 MHz, DMSO-d6) δ 8.48 (s, 1H), 8.20-8.15 (m, 1H), 8.10 (d, J=1.7 Hz, 1H), 7.87 (d, J=8.1 Hz, 1H), 7.77-7.70 (m, 2H), 7.63-7.56 (m, 3H), 6.44 (t, J=1.6 Hz, 1H), 5.39 (t, J=5.8 Hz, 1H), 4.92 (s, 2H), 4.62 (d, J=5.7 Hz, 2H), 3.12 (s, 3H), 1.92-1.83 (m, 1H), 0.97-0.84 (m, 2H), 0.56-0.46 (m, 2H).

Example 299: Synthesis of 3'-Cyclopropyl-5'-(6-(((2-methoxyethyl)amino)methyl)-1-oxoisoindolin-2-yl)-2-(4-methyl-4H-1,2,4-triazol-3-yl)-[1,1'-biphenyl]-4-carbonitrile (AJQ-2)

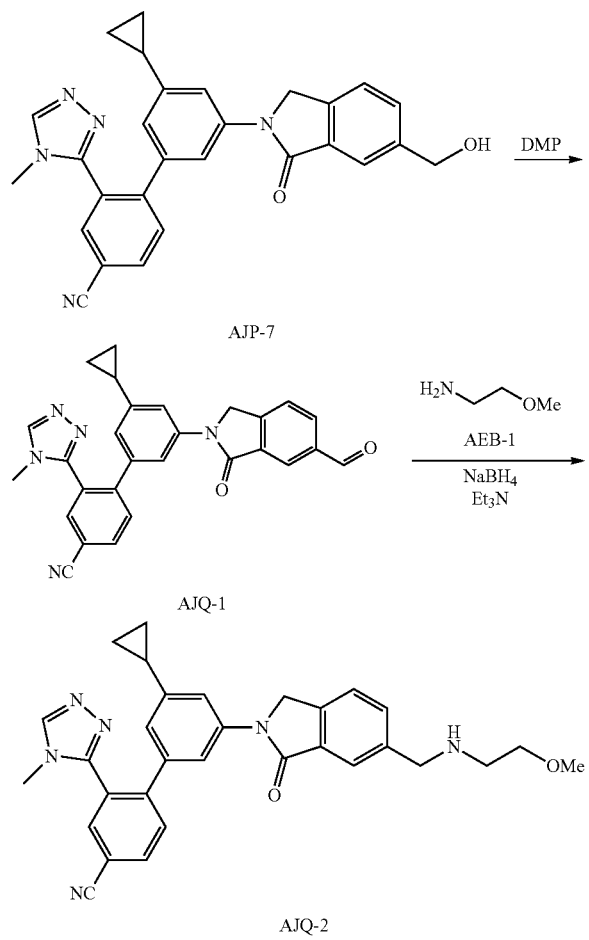

Step 1: 3'-Cyclopropyl-5'-(6-formyl-1-oxo-3H-isoindol-2-yl)-2-(4-methyl-1,2,4-triazol-3-yl)-[1,1'-biphenyl]-4-carbonitrile (AJQ-1)

To a stirred solution of compound (AJP-7) (30 mg, 1 Eq, 65 µmol) in DCM (5 mL) was added DMP (41 mg, 1.5 Eq, 98 µmol) at rt under nitrogen atmosphere. The resulting mixture was stirred for 1 h at rt under nitrogen atmosphere. The resulting mixture was concentrated in vacuo. The resulting mixture was filtered; the filter cake was washed with MeOH (3×2 mL). The filtrate was concentrated in vacuo. The residue was purified by Prep-TLC with DCM/MeOH (10/1) to afford the sub-title compound (AJQ-1) (28 mg, 61 µmol, 89%, 95% Purity) as a light yellow solid. m/z 460.2 (M+H)+ (ES+)

Step 2: 3'-Cyclopropyl-5'-(6-(((2-methoxyethyl)amino)methyl)-1-oxoisoindolin-2-yl)-2-(4-methyl-4H-1,2,4-triazol-3-yl)-[1,1'-biphenyl]-4-carbonitrile (AJQ-2)

To a stirred solution of the product from step 1 above (AJQ-1) (30 mg, 1 Eq, 65 µmol) and 2-methoxyethan-1-amine (AEB-1) (7 mg, 1.5 Eq, 98 µmol) in DCM (4 mL) was added Et$_3$N (20 mg, 3 Eq, 0.20 mmol) at rt under nitrogen atmosphere. The resulting mixture was stirred overnight at rt under nitrogen atmosphere. To the above mixture was added NaBH$_4$ (12 mg, 5 Eq, 0.33 mmol) at rt. The resulting mixture was stirred for additional 2 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 µm; Mobile Phase A: water (0.1% NH$_4$HCO$_3$+0.1% NH$_3$·H$_2$O), Mobile Phase B: MeCN; Flow rate: 60 mL/min; Gradient: 25% B to 45% B in 9 min; Wave Length: 254/220 nm; RT: 8.33) to afford the title compound (AJQ-2) (12.0 mg, 23 µmol, 35%, 99.1% Purity) as a white solid. m/z 519.2 (M+H)+ (ES+). $^1$H NMR (400 MHz, DMSO-d6) δ 8.48 (s, 1H), 8.19-8.14 (m, 1H), 8.10 (d, J=1.8 Hz, 1H), 7.87 (d, J=8.1 Hz, 1H), 7.77-7.67 (m, 2H), 7.65-7.60 (m, 1H), 7.60-7.54 (m, 2H), 6.45 (d, J=1.6 Hz, 1H), 4.91 (s, 2H), 3.82 (s, 2H), 3.41 (t, J=5.7 Hz, 2H), 3.20 (s, 3H), 3.12 (s, 3H), 2.64 (t, J=5.7 Hz, 2H), 1.93-1.82 (m, 1H), 0.98-0.87 (m, 2H), 0.58-0.47 (m, 2H).

Example 300: Synthesis of 3'-Cyclopropyl-5'-(6-{[(cyclopropylmethyl)amino]methyl}-1-oxo-3H-isoindol-2-yl)-2-(4-methyl-1,2,4-triazol-3-yl)-[1,1'-biphenyl]-4-carbonitrile (AJR-1)

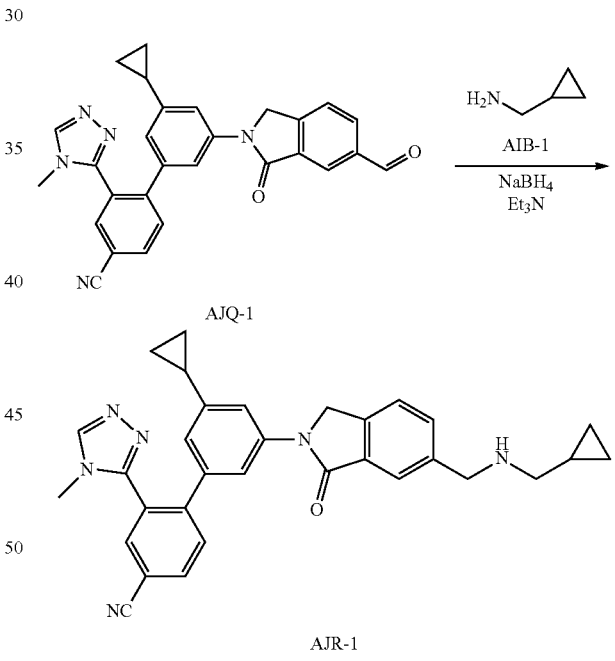

To a stirred solution of intermediate (AJQ-1) (30 mg, 1 Eq, 65 µmol) and 1-cyclopropylmethanamine (AIB-1) (7 mg, 1.5 Eq, 98 µmol) in DCM (4 mL) was added Et$_3$N (20 mg, 3 Eq, 0.20 mmol) at rt under nitrogen atmosphere. The resulting mixture was stirred overnight at rt under nitrogen atmosphere. To the above mixture was added NaBH$_4$ (12 mg, 5 Eq, 0.33 mmol) at 0° C. The resulting mixture was stirred for additional 2 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 33% B to 48% B in 8 min; Wave Length: 254/220 nm; RT: 7.77) to afford the title compound (AJR-1) (11.4 mg, 22 μmol, 34%, 98.9% Purity) as a white solid. m/z 515.2 (M+H)⁺ (ES+). ¹H NMR (400 MHz, DMSO-d6) δ 8.48 (s, 1H), 8.20-8.15 (m, 1H), 8.10 (d, J=1.8 Hz, 1H), 7.87 (d, J=8.1 Hz, 1H), 7.77-7.73 (m, 2H), 7.66-7.62 (m, 1H), 7.62-7.47 (m, 2H), 6.45 (t, J=1.6 Hz, 1H), 4.91 (s, 2H), 3.85 (s, 2H), 3.12 (s, 3H), 2.39 (d, J=6.7 Hz, 2H), 1.93-1.82 (m, 1H), 1.06-0.79 (m, 3H), 0.57-0.46 (m, 2H), 0.46-0.32 (m, 2H), 0.11-0.02 (m, 2H).

Example 301: Synthesis of 2-(6-Cyclopropyl-4-(4-fluoro-2-(4-methyl-4H-1,2,4-triazol-3-yl)phenyl)pyridin-2-yl)-6-((((1-hydroxycyclobutyl)methyl)(methyl)amino)methyl)isoindolin-1-one (AJS-1)

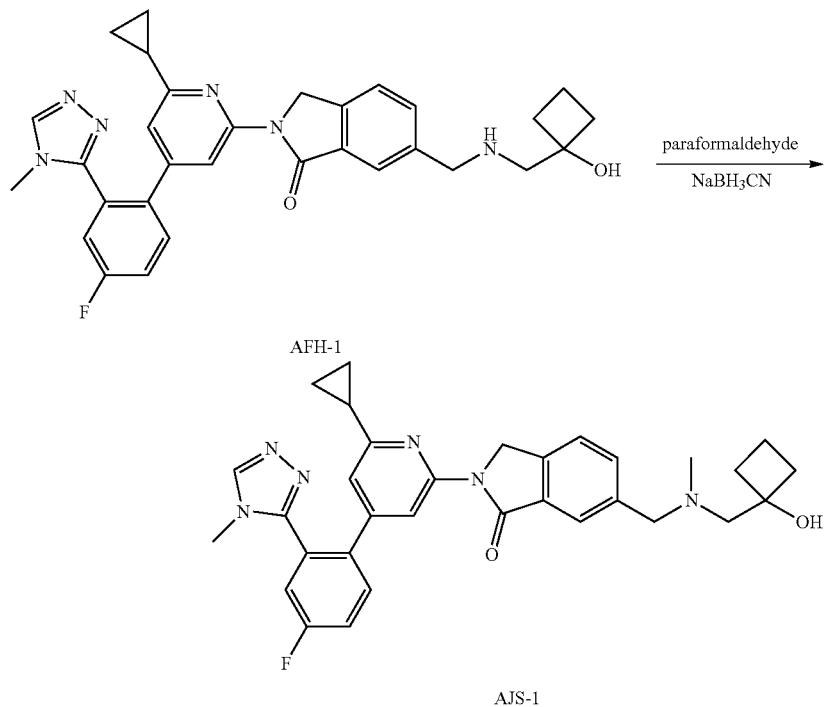

A solution of compound (AFH-1) (20 mg, 1 Eq, 37 μmol) and paraformaldehyde (10 mg, 3 Eq, 0.11 mmol) in MeOH (2 mL) was stirred at 50° C. then cooled and NaBH₃CN (7 mg, 3 Eq, 0.11 mmol) added at rt. The resulting mixture was stirred at rt for 1 h. The resulting mixture was diluted with water and extracted with EtOAc (3×10 mL). The combined organic layers were washed with brine (2×10 mL), dried (Na₂SO₄). After filtration, the filtrate was concentrated in vacuo. The crude product was purified by Prep-HPLC with the following conditions (Column: Xselect CSH C18 OBD Column 30*150 mm, 5 μm, n; Mobile Phase A: water (0.1% FA), Mobile Phase B: MeCN; Flow rate: 60 mL/min; Gradient: 8% B to 38% B in 10 min; Wave Length: 254 nm; RT: 8.38) to afford the title compound (AJS-1) (6.2 mg, 11 μmol, 28%, 95.7% Purity) as a white solid. m/z 553.3 (M+H)⁺ (ES+). ¹H NMR (300 MHz, DMSO-d6) δ 8.50 (s, 1H), 8.13 (s, 0.324H), 7.97 (d, J=1.4 Hz, 1H), 7.81-7.44 (m, 6H), 6.81 (d, J=1.4 Hz, 1H), 5.02 (s, 2H), 3.77 (s, 2H), 3.43 (s, 3H), 2.49 (s, 2H), 2.28 (s, 3H), 2.08-1.96 (m, 3H), 1.92 (d, J=9.8 Hz, 2H), 1.62 (d, J=10.4 Hz, 1H), 1.43-1.26 (m, 1H), 0.95 (d, J=6.4 Hz, 4H).

Example 302: Synthesis of 2-{6-Ethoxy-4-[4-fluoro-2-(4-methyl-1,2,4-triazol-3-yl)phenyl]pyridin-2-yl}-6-({[(1-hydroxycyclobutyl)methyl] (methyl)amino}methyl)-3H-isoindol-1-one (AJT-1)

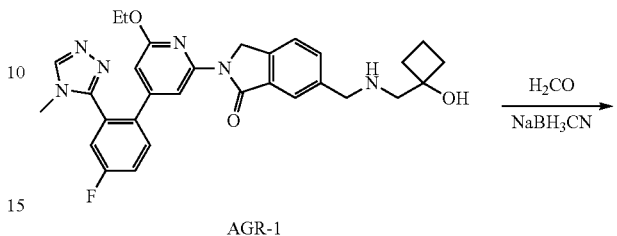

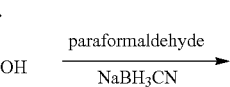

-continued

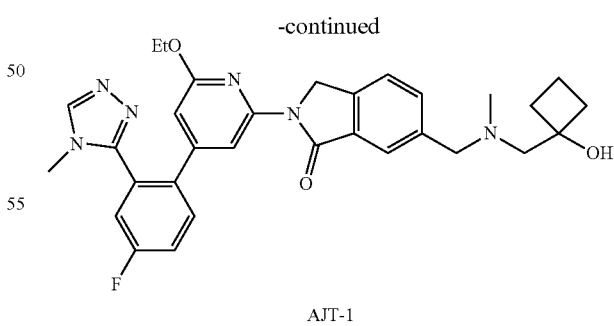

To a stirred mixture of compound (AGR-1) (30 mg, 1 Eq, 55 μmol) and formaldehyde (5 mg, 3 Eq, 0.17 mmol) in MeOH (10 mL) was added NaBH₃CN (7 mg, 2 Eq, 0.11 mmol) at rt. The resulting mixture was stirred for 2 h at rt. The resulting mixture was concentrated in vacuo. The residue was purified by Prep-TLC with DCM/MeOH (8/1). The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 50% B to 70% B in 8 min; Wave Length: 254/220 nm; RT: 6.25) to afford the title compound (AJT-1) (3.9 mg, 7.0 μmol, 13%, 99.5% Purity) as a white solid. m/z 557.2 (M+H)⁺ (ES+). ¹H NMR (400 MHz, DMSO-d6) δ 8.51 (s, 1H), 7.80 (d, J=1.2 Hz, 1H), 7.76-7.67 (m, 2H), 7.65 (d, J=1.7 Hz, 2H), 7.61-7.53 (m, 2H), 6.28 (d, J=1.2 Hz, 1H), 5.06 (s, 2H), 4.86 (s, 1H), 4.37-4.28 (m, 2H), 3.69 (s, 2H), 3.43 (s, 3H), 2.47 (s, 2H), 2.22 (s, 3H), 2.03 (d, J=12.1, 8.8, 3.2 Hz, 2H), 1.90 (d, J=12.0, 9.3 Hz, 2H), 1.61 (m, 1H), 1.34 (t, J=7.1 Hz, 4H).

Example 303: Synthesis of 4-(2-Cyclopropyl-6-{6-[(2S)-2-hydroxy-3-(methylamino) propoxy]-1-oxo-3H-isoindol-2-yl}pyridin-4-yl)-3-(4-methyl-1,2,4-triazol-3-yl) benzonitrile (AJU-3)

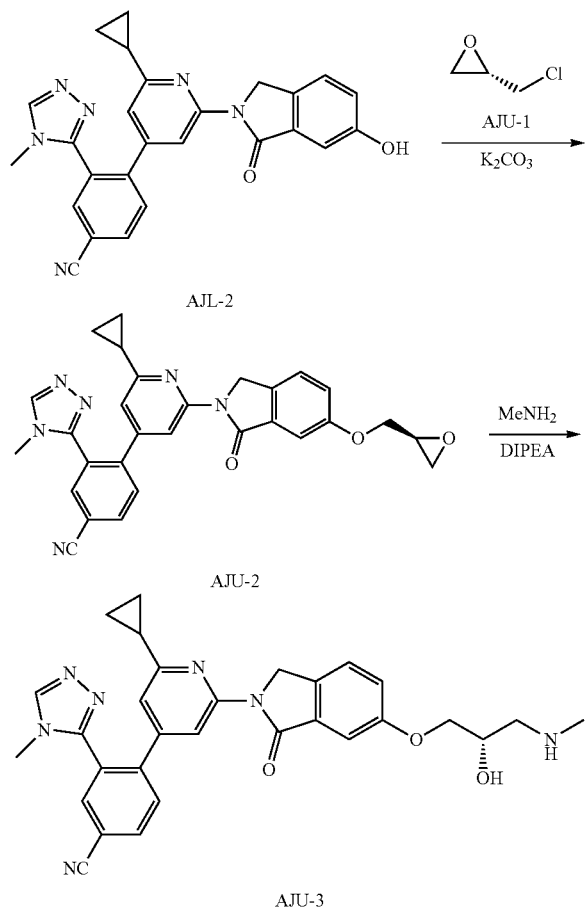

Step 1: 4-(2-Cyclopropyl-6-{6-[(2S)-oxiran-2-yl-methoxy]-1-oxo-3H-isoindol-2-yl}pyridin-4-yl)-3-(4-methyl-1,2,4-triazol-3-yl)benzonitrile (AJU-2)

To a stirred solution of intermediate (AJL-2) (60 mg, 1 Eq, 0.13 mmol) and (S)-epichlorohydrin (AJU-1) (19 mg, 1.5 Eq, 0.20 mmol) in DMSO (5 mL) was added K₂CO₃ (37 mg, 2 Eq, 0.27 mmol) at rt. The resulting mixture was stirred for 2 h at 60° C. The mixture was allowed to cool down to rt. The resulting mixture was diluted with water and extracted with EtOAc (3×20 mL). The combined organic layers were washed with brine (2×20 mL), dried (Na₂SO₄). After filtration, the filtrate was concentrated in vacuo. The residue was purified by Prep-TLC with DCM/MeOH (12/1) to afford the sub-title compound (AJU-2) (45 mg, 89 μmol, 67%, 95% Purity) as a yellow solid. m/z 505.2 (M+H)⁺ (ES+).

Step 2: 4-(2-Cyclopropyl-6-{6-[(2S)-2-hydroxy-3-(methylamino)propoxy]-1-oxo-3H-isoindol-2-yl}pyridin-4-yl)-3-(4-methyl-1,2,4-triazol-3-yl)benzonitrile (AJU-3)

To a stirred solution of the product from step 1 above (AJU-2) (42 mg, 1 Eq, 83 μmol) and methylamine (4 mg, 1.5 Eq, 0.12 mmol) in MeOH (5 mL) was added DIPEA (32 mg, 3 Eq, 0.25 mmol) at rt. The resulting mixture was stirred for 12 h at 60° C. The mixture was allowed to cool down to rt and then concentrated in vacuo. The crude product was purified by Prep-HPLC with the following conditions (Column: Xselect CSH C18 OBD Column 30*150 mm, 5 μm, n; Mobile Phase A: water (0.1% FA), Mobile Phase B: MeCN; Flow rate: 60 mL/min; Gradient: 2% B to 30% B in 10 min; Wave Length: 254 nm; RT: 10.6) to afford the title compound (AJU-3) (18.9 mg, 35 μmol, 42%, 9.6% Purity) as a white solid. m/z 536.3 (M+H)⁺ (ES+). ¹H NMR (400 MHz, DMSO-d6) δ 8.53 (s, 1H), 8.39 (s, 0.506H), 8.20 (d, J=8.2 Hz, 2H), 7.96 (d, J=1.5 Hz, 1H), 7.87 (d, J=7.9 Hz, 1H), 7.62 (d, J=8.1 Hz, 1H), 7.28 (d, J=8.7 Hz, 2H), 6.90 (d, J=1.5 Hz, 1H), 4.95 (s, 2H), 4.13-3.98 (m, 3H), 3.46 (s, 3H), 2.97-2.90 (m, 1H), 2.86-2.79 (m, 1H), 2.47 (s, 3H), 2.11-1.09 (m, 1H), 0.97 (d, J=5.3 Hz, 4H).

Example 304: Synthesis of 4-(2-Cyclopropyl-6-{6-[(2R)-2-hydroxy-3-(methylamino) propoxy]-1-oxo-3H-isoindol-2-yl}pyridin-4-yl)-3-(4-methyl-1,2,4-triazol-3-yl)benzonitrile (AJV-3)

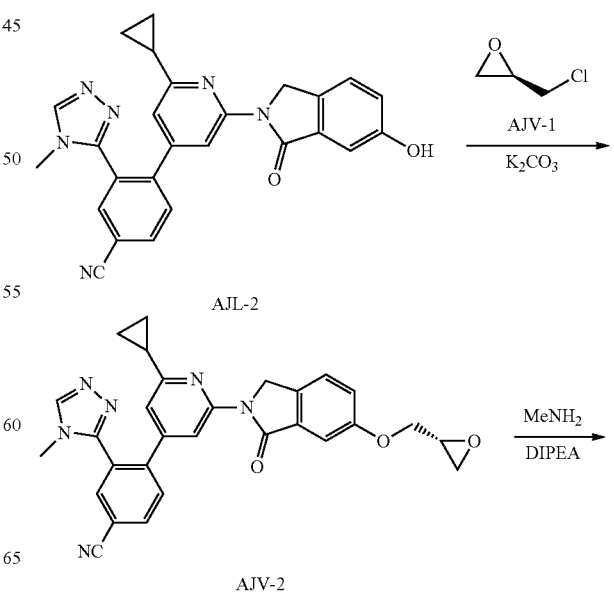

-continued

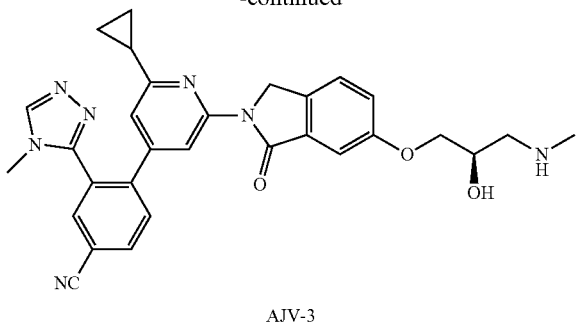

AJV-3

Step 1: 4-(2-Cyclopropyl-6-{6-[(2R)-oxiran-2-yl-methoxy]-1-oxo-3H-isoindol-2-yl}pyridin-4-yl)-3-(4-methyl-1,2,4-triazol-3-yl)benzonitrile (AJV-2)

To a stirred solution of intermediate (AJL-2) (100 mg, 1 Eq, 0.22 mmol) and (R)-epichlorohydrin (AJV-1) (31 mg, 1.5 Eq, 0.34 mmol) in DMSO (5 mL) was added $K_2CO_3$ (62 mg, 2 Eq, 0.45 mmol) at rt. The resulting mixture was stirred for 1 h at 60° C. The mixture was allowed to cool down to rt. The resulting mixture was diluted with water and extracted with EtOAc (3×50 mL). The combined organic layers were washed with brine (2×50 mL), dried ($Na_2SO_4$). After filtration, the filtrate was concentrated in vacuo. The residue was purified by Prep-TLC with DCM/MeOH (12/1) to afford the sub-title compound (AJV-2) (63 mg, 0.12 mmol, 56%, 92% Purity) as a yellow solid. m/z 505.2 (M+H)+ (ES+).

Step 2: 4-(2-Cyclopropyl-6-{6-[(2R)-2-hydroxy-3-(methylamino)propoxy]-1-oxo-3H-isoindol-2-yl}pyridin-4-yl)-3-(4-methyl-1,2,4-triazol-3-yl)benzonitrile (AJV-3)

To a stirred solution of the product from step 1 above (AJV-2) (39 mg, 1 Eq, 77 μmol) and methylamine (3.6 mg, 1.5 Eq, 0.12 mmol) in MeOH (5 mL) was added DIPEA (30 mg, 3 Eq, 0.23 mmol) at rt. The resulting mixture was stirred for 12 h at 60° C. The mixture was allowed to cool down to rt and then concentrated in vacuo. The crude product was purified by Prep-HPLC with the following conditions (Column: Xselect CSH C18 OBD Column 30*150 mm, 5 μm, n; Mobile Phase A: water (0.1% FA), Mobile Phase B: MeCN; Flow rate: 60 mL/min; Gradient: 2% B to 32% B in 10 min; Wave Length: 254 nm) to afford the title compound (AJV-3) (20.1 mg, 37 μmol, 48%, 99.6% Purity) as a white solid. m/z 536.3 (M+H)+ (ES+). $^1$H NMR (400 MHz, DMSO-d6) δ 8.53 (s, 1H), 8.39 (s, 0.549H), 8.20 (d, J=7.7 Hz, 2H), 7.96-7.87 (m, 2H), 7.62 (d, J=8.1 Hz, 1H), 7.31-7.24 (m, 2H), 6.89 (d, J=1.4 Hz, 1H), 4.95 (s, 2H), 4.11-3.98 (m, 3H), 3.46 (s, 3H), 2.97-2.90 (m, 1H), 2.84-2.80 (m, 1H), 2.47 (s, 3H), 2.10-2.00 (m, 1H), 1.01-0.90 (m, 4H).

Example 305: Synthesis of 2-{6-Cyclopropyl-4-[2-methyl-4-(4-methyl-1,2,4-triazol-3-yl)pyrazol-3-yl]pyridin-2-yl}-6-({[(1-hydroxycyclobutyl)methyl](methyl)amino}methyl)-4-(trifluoromethyl)-3H-isoindol-1-one (AJW-1)

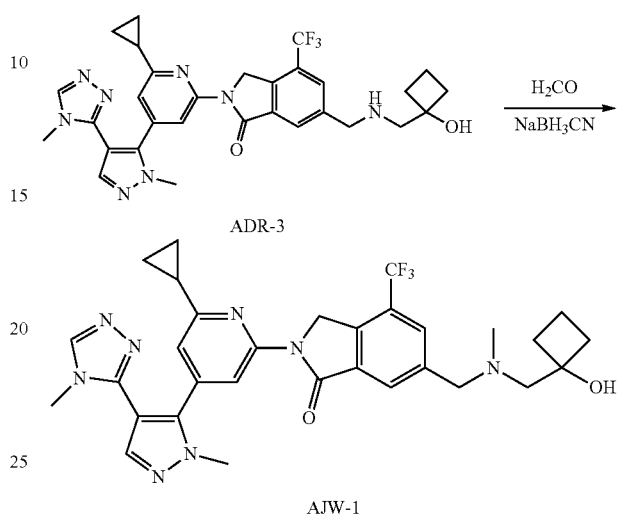

To a stirred mixture of compound (ADR-3) (30 mg, 1 Eq, 51 μmol) and formaldehyde (5 mg, 3 Eq, 0.15 mmol) in MeOH (10 mL) was added $NaBH_3CN$ (6.4 mg, 2 Eq, 0.10 mmol) at rt. The resulting mixture was stirred for 2 h at rt. The resulting mixture was concentrated in vacuo. The residue was purified by Prep-TLC with DCM/MeOH (8/1). The crude product was purified by Prep-HPLC with the following conditions (Column: XBridge Prep OBD C18 Column, 30*150 mm, 5 μm; Mobile Phase A: water (0.1% $NH_4HCO_3$+0.1% $NH_3·H_2O$), Mobile Phase B: MeCN; Flow rate: 60 mL/min; Gradient: 45% B to 52% B in 10 min; Wave Length: 254/220 nm; RT: 9.12) to afford the title compound (AJW-1) (3.1 mg, 5.1 μmol, 10%, 99.4% Purity) as a white solid. m/z 607.2 (M+H)+ (ES+). $^1$H NMR (400 MHz, DMSO-d6) δ 8.48 (s, 1H), 8.18 (d, J=1.3 Hz, 1H), 8.02 (d, J=10.0 Hz, 2H), 7.96 (s, 1H), 7.22 (d, J=1.3 Hz, 1H), 5.20 (s, 2H), 4.94 (s, 1H), 3.91 (s, 3H), 3.80 (s, 2H), 3.54 (s, 3H), 2.49 (s, 2H), 2.25 (s, 3H), 2.19-2.08 (m, 1H), 2.02 (t, J=8.9, 3.2 Hz, 2H), 1.90 (d, J=12.2, 9.3 Hz, 2H), 1.61 (m, 1H), 1.33 (d, J=10.8, 8.6 Hz, 1H), 1.03 (d, J=6.4 Hz, 4H).

Example 306: Synthesis of 4-{2-Cyclopropyl-6-[6-({[(1-fluorocyclobutyl)methyl] amino}methyl)-1-oxo-3H-isoindol-2-yl]pyridin-4-yl}-3-(4-methyl-1,2,4-triazol-3-yl)benzonitrile (AJX-1)

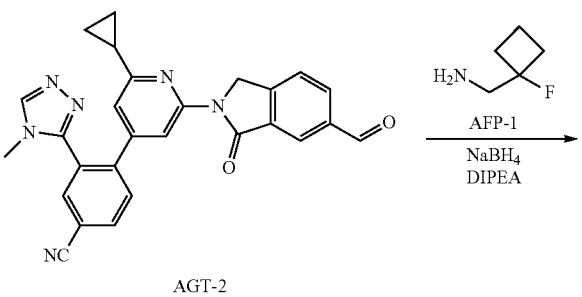

889
-continued

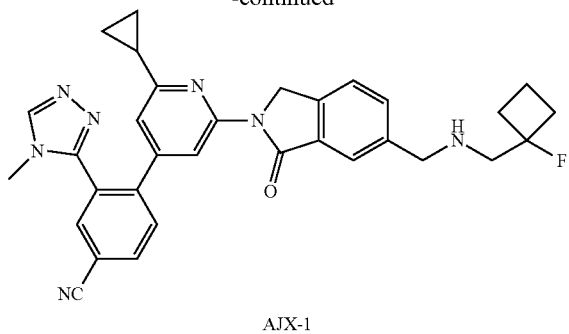

AJX-1

890
-continued

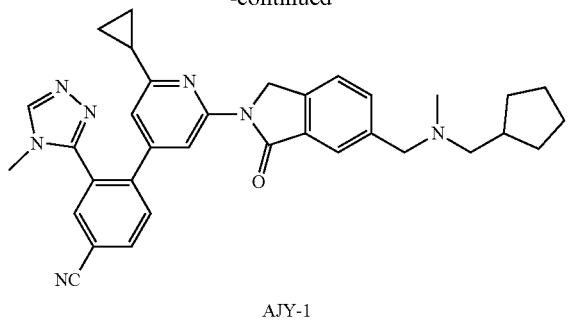

AJY-1

To a stirred solution of intermediate (AGT-2) (30 mg, 1 Eq, 65 μmol) and 1-(1-fluorocyclobutyl)methanamine (AFP-1) (8 mg, 1.2 Eq, 78 μmol) in MeOH (8 mL) was added DIPEA (25 mg, 3 Eq, 0.20 mmol) at rt. The resulting mixture was stirred overnight at 60° C. The mixture was allowed to cool down to rt. To the above mixture was added NaBH$_4$ (12 mg, 5 Eq, 0.33 mmol) at 0° C. The resulting mixture was stirred for additional 1 h at rt. The reaction was then quenched by the addition of MeOH (2 mL) at 0° C. The mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 46% B to 60% B in 8 min; Wave Length: 254/220 nm; RT: 7.73) to afford the title compound (AJX-1) (4.3 mg, 7.8 μmol, 12%, 99.3% Purity) as a white solid. m/z 548.2 (M+H)$^+$ (ES+). $^1$H NMR (400 MHz, DMSO-d6) δ 8.55 (s, 1H), δ 8.16-8.03 (m, 3H), 7.89-7.86 (m, 1H), 7.77 (s, 1H), 7.64 (d, J=2.2 Hz, 2H), 6.90 (d, J=1.4 Hz, 1H), 5.00 (s, 2H), 3.91 (s, 2H), 3.49 (s, 3H), 3.28-3.24 (m, 1H), 3.23-3.18 (m, 1H), 2.73 (s, 4H), 2.21-2.13 (m, 1H), 2.08-2.00 (m, 1H), 1.72-1.63 (m, 1H), 1.01-0.94 (m, 4H).

Example 307: Synthesis of 4-[2-(6-{1[(Cyclopentylmethyl)(methyl)amino]methyl}-1-oxo-3H-isoindol-2-yl]-6-cyclopropylpyridin-4-yl]-3-(4-methyl-1,2,4-triazol-3-yl)benzonitrile (AJY-1)

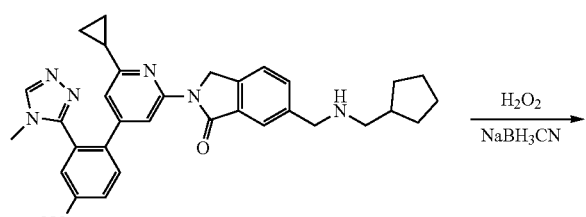

AIG-1

To a stirred mixture of compound (AIG-2) (30 mg, 1 Eq, 55 μmol) and formaldehyde (2.5 mg, 1.5 Eq, 83 μmol) in MeOH (10 mL) was added NaBH$_3$CN (7 mg, 2 Eq, 0.11 mmol) at rt. The resulting mixture was stirred for 2 h at rt. The mixture was concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 70% B to 82% B in 8 min; Wave Length: 254/220 nm; RT: 7.15) to afford the title compound (AJY-1) (5.3 mg, 9.5 μmol, 17%, 99.8% Purity) as a white solid. m/z 558.2 (M+H)$^+$ (ES+). $^1$H NMR (400 MHz, DMSO-d6) δ 8.54 (s, 1H), 8.21 (d, J=3.5, 1.7 Hz, 2H), 7.99 (d, J=1.3 Hz, 1H), 7.87 (d, J=8.5 Hz, 1H), 7.70-7.58 (m, 3H), 6.87 (d, J=1.3 Hz, 1H), 5.01 (s, 2H), 3.51 (d, J=33.7 Hz, 5H), 2.27-2.00 (m, 7H), 1.76-1.65 (m, 2H), 1.49 (q, J=8.1, 6.5 Hz, 4H), 1.18 (d, J=13.7, 4.1 Hz, 2H), 0.97 (d, J=6.4 Hz, 4H).

Example 308: Synthesis of 4-(2-(6-(1-(((Cyclobutylmethyl)amino)ethyl)-1-oxoisoindolin-2-yl)-6-cyclopropylpyridin-4-yl)-3-(4-methyl-4H-1,2,4-triazol-3-yl)benzonitrile (AJZ-1)

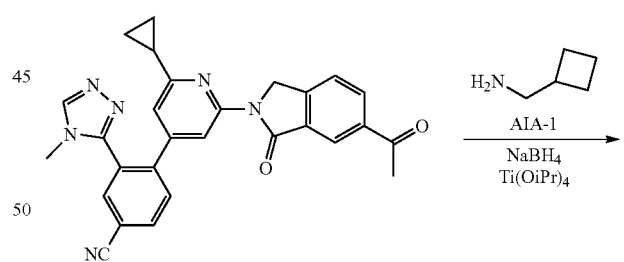

AJH-3

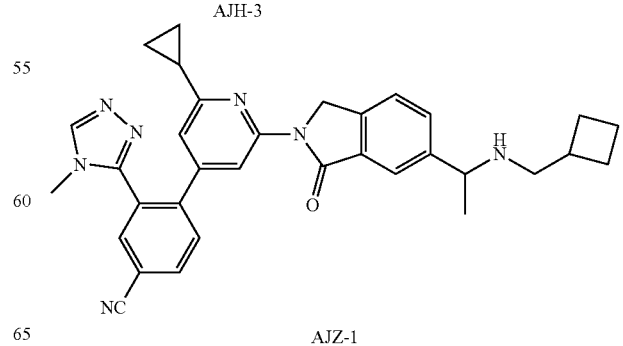

AJZ-1

A solution of intermediate (AJH-3) (90 mg, 1 Eq, 0.19 mmol), cyclobutylmethanamine, HCl (AIA-1) (19 mg, 1.2 Eq 0.23 mmol) and Ti(Oi-Pr)$_4$ (216 mg, 4 Eq, 0.76 mmol) in THF (12 mL) was stirred overnight at 60° C. The mixture was allowed to cool down to rt. To the above mixture was added NaBH$_4$ (36 mg, 5 Eq, 0.95 mmol) at 0° C. The resulting mixture was stirred for additional 1 h at rt. The reaction was then quenched by the addition of MeOH (2 mL) at 0° C. The mixture was concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 46% B to 60% B in 8 min; Wave Length: 254/220 nm; RT: 7.73) to afford the title compound (AJZ-1) (2.0 mg, 3.7 μmol, 1.9%, 99.8% Purity) as a white solid. m/z 544.3 (M+H)$^+$ (ES+). $^1$H NMR (400 MHz, Methanol-d4) δ 8.50 (s, 1H), 8.14-8.04 (m, 3H), 7.92 (d, J=8.0 Hz, 1H), 7.79 (d, J=1.6 Hz, 1H), 7.68-7.59 (m, 2H), 6.92 (d, J=1.5 Hz, 1H), 5.03 (s, 2H), 3.93-3.84 (m, 1H), 3.50 (s, 3H), 2.54-2.34 (m, 3H), 2.11-1.99 (m, 3H), 1.94-1.74 (m, 2H), 1.68-1.54 (m, 2H), 1.40 (d, J=6.6 Hz, 3H), 1.28 (s, 1H), 1.05-0.99 (m, 3H).

Example 309: Synthesis of (R)-4-(2-(6-(1-((Cyclobutylmethyl)amino)ethyl)-1-oxoisoindolin-2-yl)-6-cyclopropylpyridin-4-yl)-3-(4-methyl-4H-1,2,4-triazol-3-yl)benzonitrile (AKA-1)

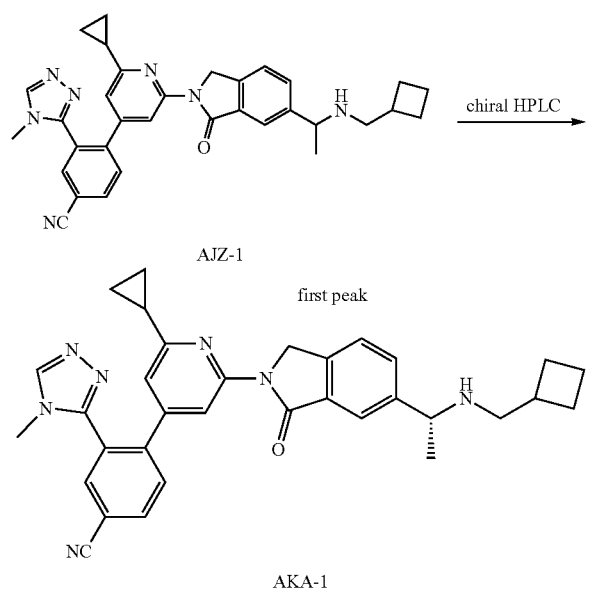

AKA-1

The crude product (AJZ-1) (30 mg, 1 Eq, 55 μmol) was purified by Prep-HPLC with the following conditions (Column: CHIRAL ART Amylose-SA, 2*25 cm, 5 μm; Mobile Phase A: MtBE (0.5% 2M NH$_3$-MeOH)-HPLC, Mobile Phase B: EtOH-HPLC; Flow rate: 20 mL/min; Gradient: 50% B to 50% B in 25 min; Wave Length: 220/254 nm; RT1(min): 15.086 Sample Solvent: EtOH-HPLC; Injection Volume: 1.5 mL) to afford the title compound (AKA-1) (9.5 mg, 17 μmol, 32%, 99.6% Purity) as a white solid. m/z 544.2 (M+H)$^+$ (ES+). $^1$H NMR (400 MHz, Methanol-d4) δ 8.50 (s, 1H), 8.15-8.05 (m, 3H), 7.92 (d, J=8.0 Hz, 1H), 7.80-7.76 (m, 1H), 7.68-7.60 (m, 2H), 6.92 (d, J=1.4 Hz, 1H), 5.03 (s, 2H), 3.91-3.84 (m, 1H), 3.50 (s, 3H), 2.52-2.33 (m, 3H), 2.10-1.99 (m, 3H), 1.95-1.84 (m, 1H), 1.84-1.72 (m, 1H), 1.68-1.54 (m, 2H), 1.40 (d, J=6.6 Hz, 3H), 1.07-1.01 (m, 2H), 1.01-0.96 (m, 2H). Column: CHIRALPAK IA-3, 4.6*50 mm, 3 μm; Mobile Phase A: MtBE(0.1% DEA):EtOH=50:50; Flow rate: 1 mL/min; RT: 2.565.

Example 310: Synthesis of (S)-4-(2-(6-(1-((Cyclobutylmethyl)amino)ethyl)-1-oxoisoindolin-2-yl)-6-cyclopropylpyridin-4-yl)-3-(4-methyl-4H-1,2,4-triazol-3-yl)benzonitrile (AKB-1)

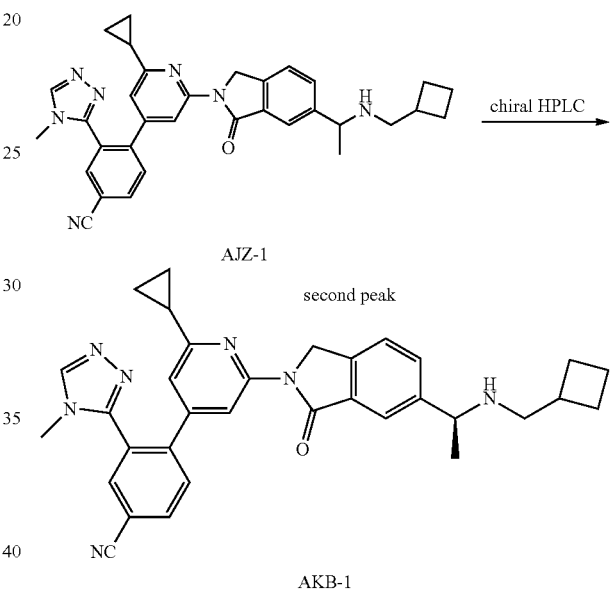

AKB-1

The crude product (AJZ-1) (30 mg, 1 Eq, 55 μmol) was purified by Prep-HPLC with the following conditions (Column: CHIRAL ART Amylose-SA, 2*25 cm, 5 μm; Mobile Phase A: MtBE (0.5% 2M NH$_3$-MeOH)-HPLC, Mobile Phase B: EtOH-HPLC; Flow rate: 20 mL/min; Gradient: 50% B to 50% B in 25 min; Wave Length: 220/254 nm; RT2(min): 24.157; Sample Solvent: EtOH-HPLC; Injection Volume: 1.5 mL) to afford he title compound (AKB-1) (9.8 mg, 18 μmol, 33%, 98.5% Purity) as a white solid. m/z 544.2 (M+H)$^+$ (ES+). $^1$H NMR (400 MHz, Methanol-d4) δ 8.50 (s, 1H), 8.15-8.04 (m, 3H), 7.93 (d, J=8.0 Hz, 1H), 7.81 (d, J=1.3 Hz, 1H), 7.70-7.62 (m, 2H), 6.93 (d, J=1.5 Hz, 1H), 5.04 (s, 2H), 3.97 (d, J=6.8 Hz, 1H), 3.50 (s, 3H), 2.61-2.54 (m, 1H), 2.53-2.40 (m, 2H), 2.11-2.00 (m, 3H), 1.95-1.86 (m, 1H), 1.85-1.75 (m, 1H), 1.70-1.58 (m, 2H), 1.45 (d, J=6.7 Hz, 3H), 1.29 (s, 1H), 1.07-1.02 (m, 2H), 1.02-0.96 (m, 2H). Column: CHIRALPAK IA-3, 4.6*50 mm, 3 μm; Mobile Phase A: MtBE(0.1% DEA):EtOH=50:50; Flow rate: 1 mL/min; RT: 3.845.

Example 311: Synthesis of 4-{2-Cyclopropyl-6-[6-({[(3,3-difluorocyclobutyl)methyl]amino}methyl)-1-oxo-3H-isoindol-2-yl]pyridin-4-yl}-3-(4-methyl-1,2,4-triazol-3-yl)benzonitrile (AKC-2)

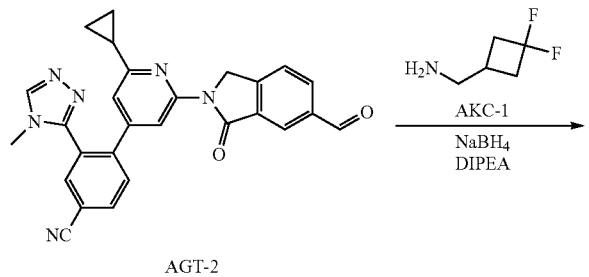

AGT-2

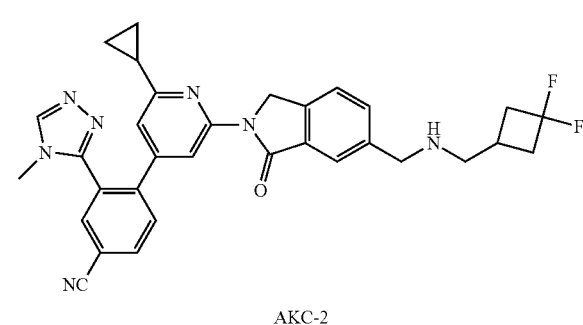

AKC-2

A solution of 1-(3,3-difluorocyclobutyl)methanamine (AKC-1) (11.8 mg, 1.5 Eq, 98 μmol) and DIPEA (10 mg, 1.2 Eq, 78 μmol) in MeOH (3 mL) was stirred for 10 min at rt. To the above mixture was added intermediate (AGT-2) (30 mg, 1 Eq, 65 μmol) at rt. The resulting mixture was stirred for additional 1 h at 60° C. The mixture was allowed to cool down to rt. To the above mixture was added NaBH$_4$ (5 mg, 2 Eq, 0.13 mmol) at 0° C. The reaction was then quenched by the addition of MeOH (2 mL) at 0° C. The mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 45% B to 55% B in 8 min; Wave Length: 254/220 nm) to afford the title compound (AKC-2) (7.4 mg, 13 μmol, 20%, 99.5% Purity) as a white solid. m/z 566.3 (M+H)$^+$ (ES+). $^1$H NMR (400 MHz, DMSO-d6) δ 8.53 (s, 1H), 8.22-8.19 (m, 2H), 7.99 (d, J=1.4 Hz, 1H), 7.87 (d, J=8.5 Hz, 1H), 7.74-7.64 (m, 3H), 6.88 (d, J=1.5 Hz, 1H), 5.00 (s, 2H), 3.80 (s, 2H), 3.47 (s, 3H), 2.65-2.57 (m, 4H), 2.31-2.20 (m, 3H), 2.07-2.01 (m, 1H), 0.99-0.94 (m, 4H).

Example 312: Synthesis of 4-(2-{6-[({Bicyclo[1.1.1]pentan-1-ylmethyl}amino) methyl]-1-oxo-3H-isoindol-2-yl}-6-cyclopropylpyridin-4-yl)-3-(4-methyl-1,2,4-triazol-3-yl)benzonitrile (AKD-2)

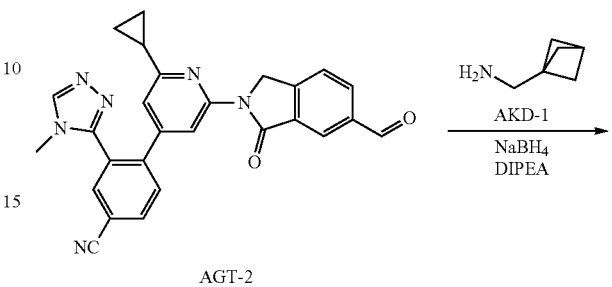

AGT-2

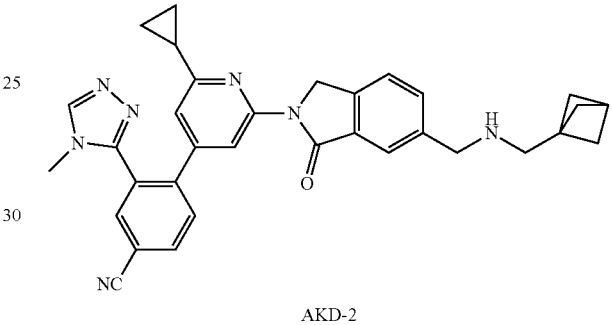

AKD-2

To a stirred solution of intermediate (AGT-2) (30 mg, 1 Eq, 65 μmol) and 1-{bicycle [1.1.1]pentan-1-yl}methanamine (AKD-1) (13 mg, 2 Eq, 0.13 mmol) in MeOH (2 mL) was added DIPEA (51 mg, 6 Eq, 0.39 mmol) at rt. The resulting mixture was stirred overnight at rt under nitrogen atmosphere. To the above mixture was added NaBH$_4$ (7 mg, 3 Eq, 0.20 mmol) at 0° C. The resulting mixture was stirred for additional 1 h at rt. The reaction was then quenched by the addition of MeOH (2 mL) at 0° C. The mixture was concentrated in vacuo. The crude product was purified by Prep-HPLC with the following conditions (Column: Xselect CSH C18 OBD Column 30*150 mm, 5 μm; Mobile Phase A: water (0.1% FA), Mobile Phase B: MeCN; Flow rate: 60 mL/min; Gradient: 2% B to 30% B in 10 min; Wave Length: 254 nm; RT: 11.28) to afford the title compound (AKD-2) (2.3 mg, 4.2 μmol, 6.0%, 99.7% Purity) as a white solid. m/z 542.1 (M+H)$^+$ (ES+). $^1$H NMR (400 MHz, DMSO-d6) δ 8.54 (s, 1H), 8.43 (s, 0.909H), 8.25-8.18 (m, 2H), 7.99 (d, J=1.4 Hz, 1H), 7.87 (d, J=8.5 Hz, 1H), 7.73 (s, 1H), 7.62 (d, J=1.2 Hz, 2H), 6.88 (d, J=1.4 Hz, 1H), 5.00 (s, 2H), 3.79 (s, 2H), 3.48 (s, 3H), 2.47 (d, J=3.3 Hz, 3H), 2.09-2.00 (m, 1H), 1.68 (s, 6H), 1.00-0.93 (m, 4H).

Example 313: Synthesis of 4-{2-Cyclopropyl-6-[6-({[(1-methoxycyclopentyl) methyl]amino}methyl)-1-oxo-3H-isoindol-2-yl]pyridin-4-yl}-3-(4-methyl-1,2,4-triazol-3-yl)benzonitrile (AKE-2)

Example 314: Synthesis of 4-{2-[6-({[(1-Cyanocyclobutyl)methyl]amino}methyl)-1-oxo-3H-isoindol-2-yl]-6-cyclopropylpyridin-4-yl}-3-(4-methyl-1,2,4-triazol-3-yl)benzonitrile (AKF-2)

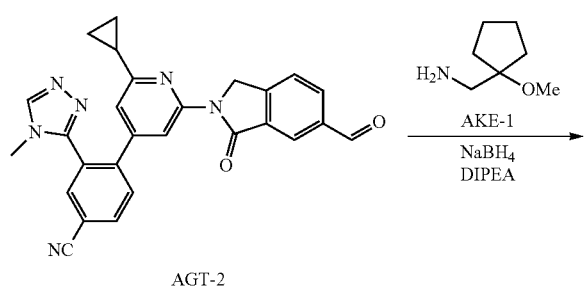

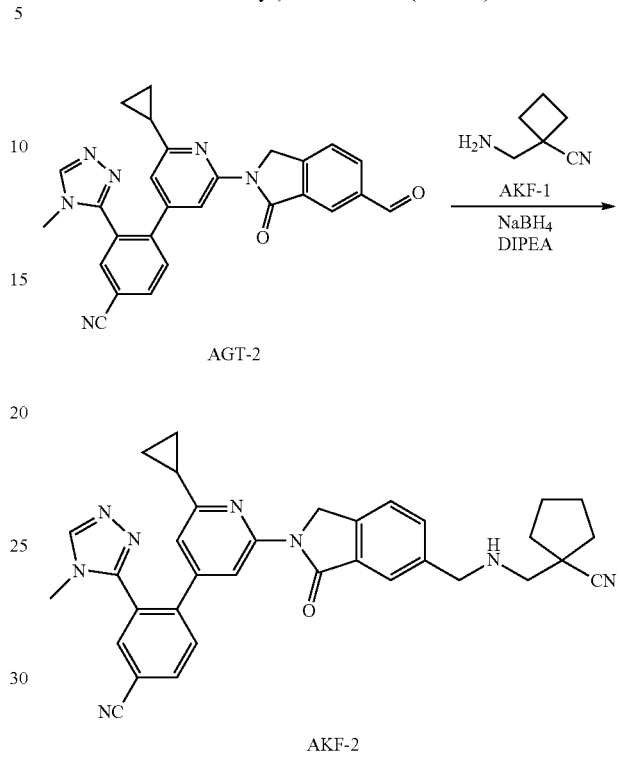

To a stirred solution of intermediate (AGT-2) (30 mg, 1 Eq, 65 μmol) and 1-(1-methoxycyclopentyl)methanamine (AKE-1) (13 mg, 1.5 Eq, 98 μmol) in MeOH (6 mL) were added DIPEA (34 mg, 4 Eq, 0.26 mmol) at rt. The resulting mixture was stirred overnight at rt under nitrogen atmosphere. To the above mixture was added NaBH₄ (12 mg, 5 Eq, 0.33 mmol) at 0° C. The reaction was then quenched by the addition of MeOH (2 mL) at 0° C. The resulting mixture was concentrated in vacuo. The crude product was purified by Prep-HPLC with the following conditions (Column: Xselect CSH C18 OBD Column 30*150 mm, 5 μm; Mobile Phase A: water (0.1% FA), Mobile Phase B: MeCN; Flow rate: 60 mL/min; Gradient: 2% B to 30% B in 10 min; Wave Length: 254 nm; RT: 9.8) to afford the title compound (AKE-2) (11.6 mg, 20 μmol, 31%, 99.7% Purity) as a white solid. m/z 574.2 (M+H)⁺ (ES+). $^1$H NMR (400 MHz, Methanol-d4) δ 8.49 (s, 1H), 8.16-8.10 (m, 2H), 8.09-8.03 (m, 1H), 7.98-7.92 (m, 1H), 7.90-7.85 (m, 1H), 7.77-7.70 (m, 1H), 7.68-7.64 (m, 1H), 6.94 (d, J=1.4 Hz, 1H), 5.05 (s, 2H), 4.06 (s, 2H), 3.49 (s, 3H), 3.08 (s, 3H), 2.81 (s, 2H), 2.09-2.00 (m, 1H), 1.90-1.80 (m, 2H), 1.74-1.64 (m, 2H), 1.66-1.56 (m, 2H), 1.55-1.44 (m, 2H), 1.09-0.94 (m, 4H).

Into a 25 mL round-bottom flask were added intermediate (AGT-2) (60 mg, 1 Eq, 0.13 mmol), 1-(aminomethyl)cyclobutane-1-carbonitrile (AKF-1) (22 mg, 1.5 Eq, 0.20 mmol) in MeOH (5 mL) at rt. To the above mixture was added DIPEA (51 mg, 3 Eq, 0.39 mmol) at rt. The resulting mixture was stirred for additional overnight at 60° C. To the above mixture was added NaBH₄ (25 mg, 5 Eq, 0.65 mmol) at 0° C. The resulting mixture was stirred for additional 1 h at rt. The reaction was then quenched by the addition of MeOH (2 mL) at 0° C. The mixture was concentrated in vacuo. The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 48% B to 52% B in 9 min; Wave Length: 254 nm) to afford the title compound (AKF-2) (4.1 mg, 7.3 μmol, 5.8%, 99.6% Purity) as a white solid. m/z 555.2 (M+H)⁺ (ES+). $^1$H NMR (400 MHz, Methanol-d4) δ 8.50 (s, 1H), 8.14-8.08 (m, 2H), 8.05 (d, J=1.4 Hz, 1H), 7.95-7.91 (m, 1H), 7.84 (s, 1H), 7.74-7.69 (m, 1H), 7.62 (s, 1H), 6.93 (d, J=1.5 Hz, 1H), 5.03 (s, 2H), 3.96 (s, 2H), 3.51 (s, 3H), 2.88 (s, 2H), 2.47-2.41 (m, 2H), 2.23-2.15 (m, 3H), 2.06-2.01 (m, 2H), 1.06-0.97 (m, 4H).

Example 315: Synthesis of 4-{2-Cyclopropyl-6-[4-fluoro-6-({[(2S)-1-methoxy propan-2-yl]amino}methyl)-1-oxo-3H-isoindol-2-yl]pyridin-4-yl}-3-(4-methyl-1,2,4-triazol-3-yl)benzonitrile (AKG-1)

Example 316: Synthesis of 4-{2-Cyclopropyl-6-[4-fluoro-6-({[(2R)-1-methoxy propan-2-yl]amino}methyl)-1-oxo-3H-isoindol-2-yl]pyridin-4-yl}-3-(4-methyl-1,2,4-triazol-3-yl)benzonitrile (AKH-1)

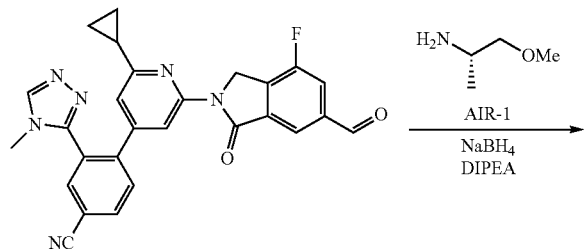

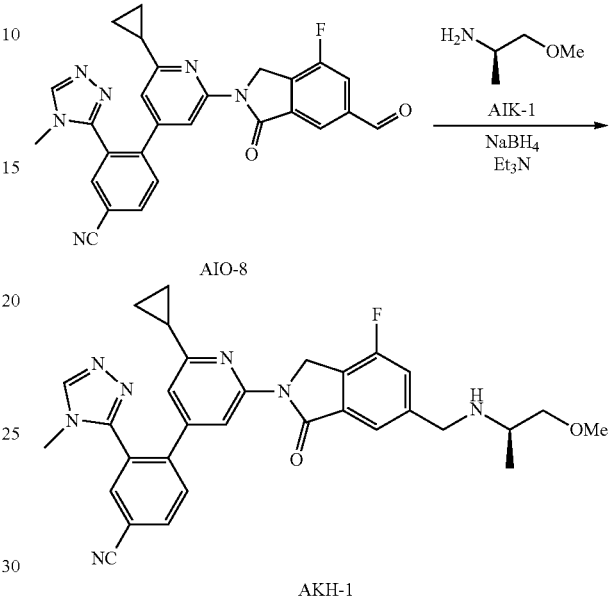

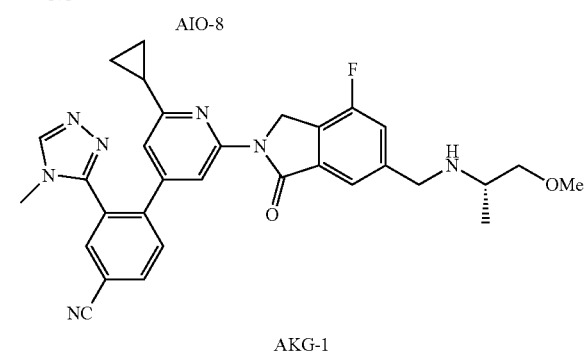

To a stirred solution of intermediate (AIO-8) (30 mg, 1 Eq, 63 μmol) and (2S)-1-methoxypropan-2-amine (AIR-1) (7 mg, 1.2 Eq, 76 μmol) in MeOH (8 mL) was added DIPEA (24 mg, 3 Eq, 0.19 mmol) at rt. The resulting mixture was stirred for 2 h at 60° C. The mixture was allowed to cool down to rt. To the above mixture was added NaBH$_4$ (12 mg, 5 Eq, 0.32 mmol) at 0° C. The resulting mixture was stirred for additional 1 h at rt. The reaction was then quenched by the addition of MeOH (2 mL) at 0° C. The mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 42% B to 52% B in 8 min; Wave Length: 254/220 nm; RT: 7.94) to afford the title compound (AKG-1) (1.6 mg, 2.9 μmol, 4.5%, 97.8% Purity) as a white solid. m/z 552.1 (M+H)$^+$ (ES+). $^1$H NMR (400 MHz, Methanol-d4) δ 8.50 (s, 1H), 8.15-8.08 (m, 2H), 8.03 (d, J=1.4 Hz, 1H), 7.92 (d, J=8.0 Hz, 1H), 7.66 (s, 1H), 7.47-7.43 (m, 1H), 6.95 (d, J=1.5 Hz, 1H), 5.06 (s, 2H), 3.96 (d, J=13.8 Hz, 1H), 3.86 (d, J=13.8 Hz, 1H), 3.50 (s, 3H), 3.36-3.33 (m, 5H), 2.91-2.85 (m, 1H), 2.08-2.01 (m, 1H), 1.08-1.03 (m, 5H), 1.02-0.97 (m, 2H).

Into a 25 mL round-bottom flask were added intermediate (AIO-8) (40 mg, 1 Eq, 84 μmol), (2R)-1-methoxypropan-2-amine (AIK-1) (11 mg, 1.5 Eq, 0.13 mmol) in MeOH (5 mL) at rt. To the above mixture was added Et$_3$N (25 mg, 3 Eq, 0.25 mmol) at rt. The resulting mixture was stirred for additional over night at 60° C. To the above mixture was added NaBH$_4$ (16 mg, 5 Eq, 0.42 mmol) at 0° C. The resulting mixture was stirred for additional 1 h at rt. The reaction was then quenched by the addition of MeOH (2 mL) at 0° C. The mixture was concentrated in vacuo. The crude product was purified by Prep-HPLC with the following conditions (Column: XBridge Prep OBD C18 Column, 19*250 mm, 5 μm; Mobile Phase A: water (0.1% NH$_4$HCO$_3$+0.1% NH$_3$·H$_2$O), Mobile Phase B: MeCN; Flow rate: 25 mL/min; Gradient: 45% B to 55% B in 8 min; Wave Length: 254 nm) to afford the title compound (AKH-1) (10.7 mg, 19 μmol, 23%, 99.9% Purity) as a white solid. m/z 552.1 (M+H)$^+$ (ES+). $^1$H NMR (400 MHz, Methanol-d4) δ 8.50 (s, 1H), 8.15-8.08 (m, 2H), 8.02 (d, J=1.4 Hz, 1H), 7.92 (d, J=8.1 Hz, 1H), 7.66 (d, J=1.2 Hz, 1H), 7.49-7.44 (m, 1H), 6.95 (d, J=1.4 Hz, 1H), 5.07 (s, 2H), 3.99 (d, J=13.8 Hz, 1H), 3.90 (d, J=13.8 Hz, 1H), 3.49 (s, 3H), 3.40-3.32 (m, 5H), 2.96-2.87 (m, 1H), 2.10-2.01 (m, 1H), 1.10 (d, J=6.5 Hz, 3H), 1.06-0.98 (m, 4H).

Example 317: Synthesis of 2-{6-Cyclopropyl-4-[2-methyl-4-(4-methyl-1,2,4-triazol-3-yl)pyrazol-3-yl]pyridin-2-yl}-6-(hydroxymethyl)-4-(trifluoromethyl)-3H-isoindol-1-one (AKI-1)

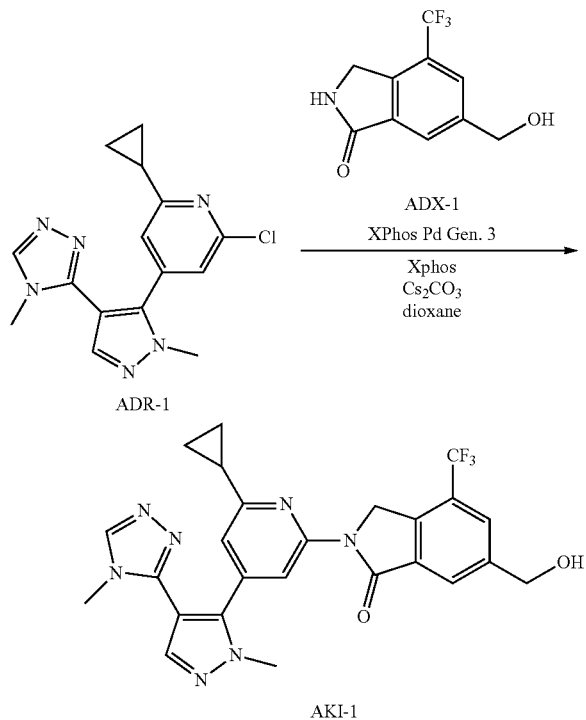

To a stirred mixture of intermediate (ADR-1) (100 mg, 1 Eq, 0.32 mmol), intermediate (ADX-1) (88 mg, 1.2 Eq, 0.38 mmol) and Cs$_2$CO$_3$ (311 mg, 3 Eq, 0.95 mmol) in dioxane (15 mL) were added XPhos Pd G3 (54 mg, 0.2 Eq, 64 µmol) and XPhos (61 mg, 0.4 Eq, 0.13 mmol) at rt under nitrogen atmosphere. The resulting mixture was stirred for 2 h at 100° C. under nitrogen atmosphere. The mixture was allowed to cool down to rt. The resulting mixture was diluted with water and extracted with EtOAc (3×20 mL). The combined organic layers were washed with brine (2×20 mL), dried (Na$_2$SO$_4$). After filtration, the filtrate was concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 µm; Mobile Phase A: water (0.1% NH$_4$HCO$_3$+0.1% NH$_3$·H$_2$O), Mobile Phase B: MeCN; Flow rate: 60 mL/min; Gradient: 33% B to 43% B in 9 min; Wave Length: 254/220 nm; RT: 8.47) to afford the title compound (AKI-1) (6.7 mg, 13 µmol, 4.1%, 99.6% Purity) as a white solid. m/z 510.1 (M+H)$^+$ (ES+). $^1$H NMR (400 MHz, DMSO-d6) δ 8.48 (s, 1H), 8.19 (d, J=1.3 Hz, 1H), 8.04-7.93 (m, 3H), 7.23 (d, J=1.4 Hz, 1H), 5.58 (t, J=5.8 Hz, 1H), 5.20 (s, 2H), 4.70 (d, J=5.6 Hz, 2H), 3.90 (s, 3H), 3.55 (s, 3H), 2.14 (p, J=6.5 Hz, 1H), 1.03 (d, J=5.6 Hz, 4H).

Example 318: Synthesis of 4-{2-Ethoxy-6-[6-({[(1-fluorocyclobutyl)methyl]amino}methyl)-1-oxo-3H-isoindol-2-yl]pyridin-4-yl}-3-(4-methyl-1,2,4-triazol-3-yl)benzonitrile (AKJ-1)

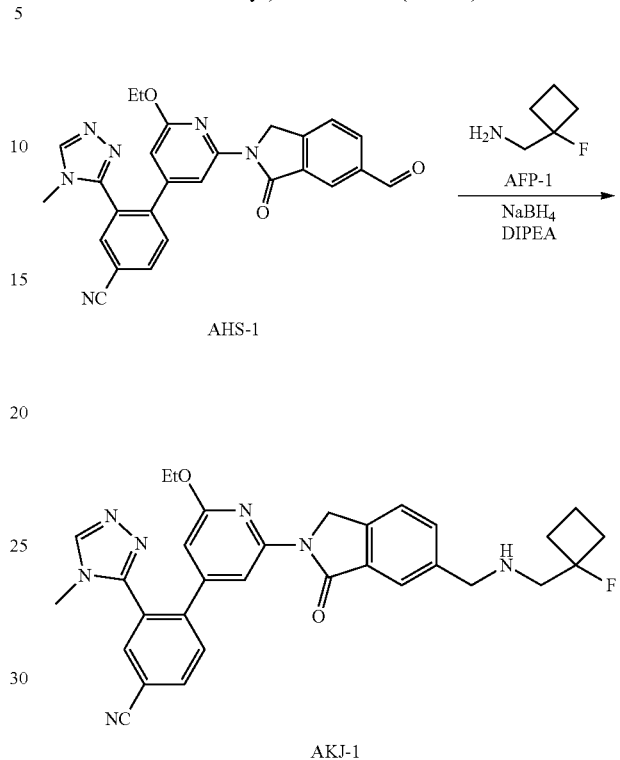

A solution of 1-(1-fluorocyclobutyl)methanamine (AFP-1) (11 mg, 1.2 Eq, 0.10 mmol) and DIPEA (45 mg, 4 Eq, 0.34 mmol) in MeOH (8 mL) was stirred for 5 min at rt. To the above mixture was added intermediate (AHS-1) (40 mg, 1 Eq, 86 µmol) at rt. The resulting mixture was stirred overnight at 60° C. To the above mixture was added NaBH$_4$ (16 mg, 5 Eq, 0.43 mmol) at 0° C. The resulting mixture was stirred for additional 1 h at rt. The reaction was then quenched by the addition of MeOH (2 mL) at 0° C. The mixture was concentrated in vacuo. The crude product was purified by Prep-HPLC with the following conditions (Column: XBridge Prep OBD C18 Column, 30*150 mm, 5 µm; Mobile Phase A: water (0.1% NH$_4$HCO$_3$+0.1% NH$_3$·H$_2$O), Mobile Phase B: MeCN; Flow rate: 60 mL/min; Gradient: 45% B to 54% B in 9 min; Wave Length: 254/220 nm; RT: 8.13) to afford the title compound (AKJ-1) (6.0 mg, 11 µmol, 12%, 98.7% Purity) as a white solid. m/z 552.2 (M+H)$^+$ (ES+). $^1$H NMR (400 MHz, Methanol-d4) δ 8.49 (s, 1H), 8.14-8.05 (m, 2H), 7.92-7.80 (m, 3H), 7.71-7.66 (m, 1H), 7.61 (d, J=7.8 Hz, 1H), 6.42 (d, J=1.3 Hz, 1H), 5.06 (s, 2H), 4.44-4.34 (m, 2H), 3.93 (s, 2H), 3.53 (s, 3H), 2.85 (s, 1H), 2.79 (s, 1H), 2.35-2.12 (m, 4H), 1.88-1.74 (m, 1H), 1.55-1.41 (m, 1H), 1.39 (t, J=7.1 Hz, 3H).

Example 319: Synthesis of 4-{2-Cyclopropyl-6-[4-fluoro-6-({[(1-fluorocyclobutyl)methyl]amino}methyl)-1-oxo-3H-isoindol-2-yl]pyridin-4-yl}-3-(4-methyl-1,2,4-triazol-3-yl)benzonitrile (AKK-1)

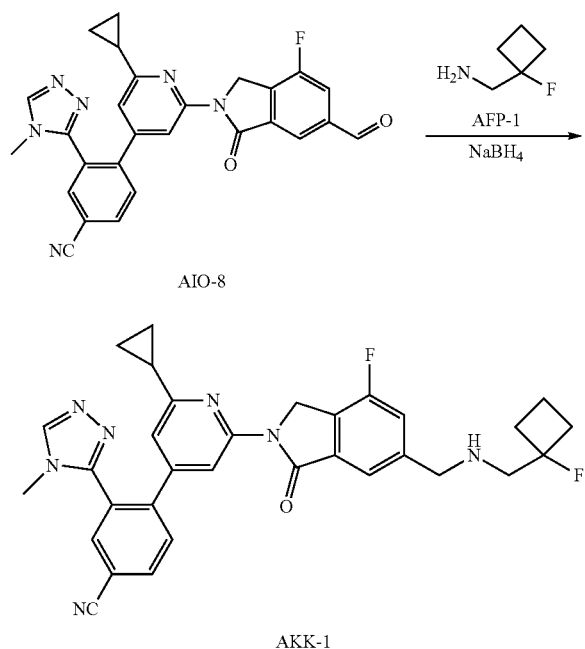

To a stirred solution of intermediate (AIO-8) (30 mg, 1 Eq, 63 μmol) and 1-(1-fluorocyclobutyl)methanamine (AFP-1) (10 mg, 1.5 Eq, 95 μmol) in MeOH (6 mL) were added DIPEA (49 mg, 6 Eq, 0.38 mmol) at rt. The resulting mixture was stirred overnight at 60° C. The mixture was cooled to rt. To the above mixture was added NaBH$_4$ (12 mg, 5 Eq, 0.32 mmol) at 0° C. The resulting mixture was stirred for 2 h at rt. The reaction was then quenched by the addition of MeOH (2 mL) at 0° C. The resulting mixture was concentrated in vacuo. The crude product was purified by Prep-HPLC with the following conditions (Column: Xselect CSH C18 OBD Column 30*150 mm, 5 μm; Mobile Phase A: water (0.1% FA), Mobile Phase B: MeCN; Flow rate: 60 mL/min; Gradient: 15% B to 35% B in 10 min; Wave Length: 254 nm; RT: 9.43) to afford the title compound (AKK-1) (9.0 mg, 16 μmol, 25%, 99.9% Purity) as a white solid. m/z 566.1 (M+H)$^+$ (ES+). $^1$H NMR (400 MHz, DMSO-d6) δ 8.54 (s, 1H), 8.25-8.18 (m, 2H), 7.95 (d, J=1.4 Hz, 1H), 7.91-7.84 (m, 1H), 7.64 (s, 1H), 7.53 (d, J=10.0 Hz, 1H), 6.92 (d, J=1.4 Hz, 1H), 5.07 (s, 2H), 3.87 (s, 2H), 3.51-3.47 (m, 3H), 2.74-2.68 (m, 2H), 2.20-2.10 (m, 4H), 2.01 (s, 1H), 1.74 (s, 1H), 1.51-1.32 (m, 1H), 0.98 (d, J=8.2 Hz, 4H).

Example 320: Synthesis of 4-{2-Cyclopropyl-6-[6-(hydroxymethyl)-5-methoxy-1-oxo-3H-isoindol-2-yl]pyridin-4-yl}-3-(4-methyl-1,2,4-triazol-3-yl)benzonitrile (AKL-2)

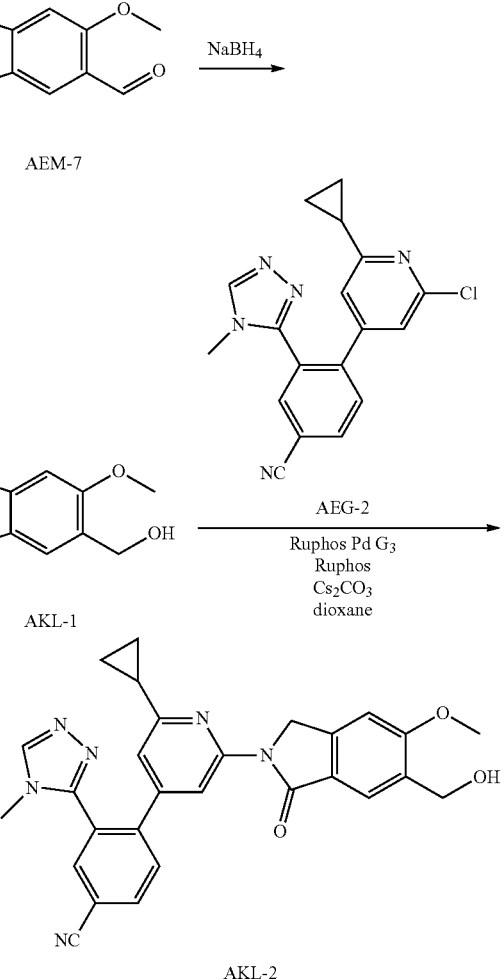

Step 1: 6-(Hydroxymethyl)-5-methoxy-2,3-dihydroisoindol-1-one (AKL-1)

A solution of intermediate (AEM-7) (40 mg, 1 Eq, 0.21 mmol) and NaBH$_4$ (16 mg, 2 Eq, 0.42 mmol) in MeOH (10 mL) was stirred for 1 h at rt. The reaction was then quenched by the addition of MeOH (2 mL) at 0° C. The mixture was concentrated in vacuo. The residue was purified by Prep-TLC with DCM/MeOH (8/1) to afford the sub-title compound (AKL-1) (20 mg, 0.10 mmol, 49%, 96% Purity) as a white solid. m/z 194.1 (M+H)$^+$ (ES+)

Step 2: 4-{2-Cyclopropyl-6-[6-(hydroxymethyl)-5-methoxy-1-oxo-3H-isoindol-2-yl]pyridin-4-yl}-3-(4-methyl-1,2,4-triazol-3-yl)benzonitrile (AKL-2)

To a solution of intermediate (AEG-2) (20 mg, 1 Eq, 60 μmol), the product from step 1 above (AKL-1) (12.7 mg, 1.1 Eq, 66 μmol) and Cs$_2$CO$_3$ (58 mg, 3 Eq, 0.18 mmol) in 1,4-dioxane (4 mL) were added RuPhos (11 mg, 0.4 Eq, 24

μmol) and RuPhos Palladacycle Gen.3 (10 mg, 0.2 Eq, 12 μmol) at rt under nitrogen atmosphere. The resulting mixture was stirred for 2 h at 100° C. under nitrogen atmosphere. The mixture was cooled to rt and concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: water (0.1% $NH_4HCO_3$+0.1% $NH_3 \cdot H_2O$), Mobile Phase B: MeCN; Flow rate: 60 mL/min; Gradient: 38% B to 48% B in 8 min; Wave Length: 254/220 nm) to afford the title compound (AKL-2) (9.2 mg, 18 μmol, 31%, 99.8% Purity) as a white solid. m/z 493.1 (M+H)$^+$ (ES+). $^1$H NMR (400 MHz, DMSO-d6) δ 8.54 (s, 1H), 8.22-8.19 (m, 2H), 7.99 (d, J=1.4 Hz, 1H), 7.87 (d, J=8.5 Hz, 1H), 7.68 (d, J=8.4 Hz, 1H), 7.17 (d, J=8.5 Hz, 1H), 6.80 (d, J=1.4 Hz, 1H), 5.14-5.09 (m, 3H), 4.67 (d, J=5.5 Hz, 2H), 3.89 (s, 3H), 3.45 (s, 3H), 2.07-2.01 (m, 1H), 0.99-0.90 (m, 4H).

Example 321: Synthesis of 4-[2-(6-{[(Cyclobutylmethyl)amino]methyl}-5-methoxy-1-oxo-3H-isoindol-2-yl)-6-cyclopropylpyridin-4-yl]-3-(4-methyl-1,2,4-triazol-3-yl)benzonitrile (AKM-2)

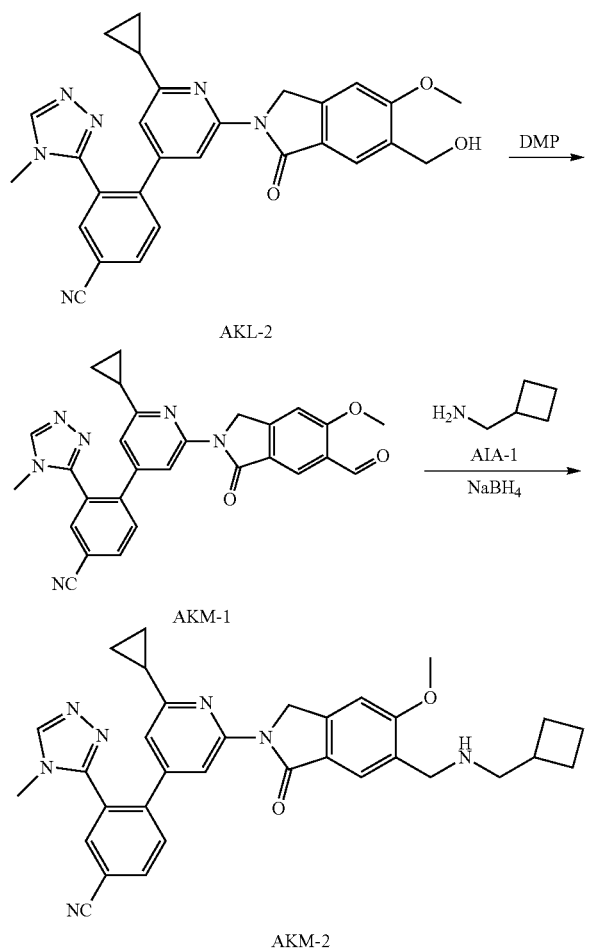

Step 1: 4-[2-Cyclopropyl-6-(6-formyl-5-methoxy-1-oxo-3H-isoindol-2-yl)pyridin-4-yl]-3-(4-methyl-1,2,4-triazol-3-yl)benzonitrile (AKM-1)

A solution of compound (AKL-2) (40 mg, 1 Eq, 81 μmol) and DMP (69 mg, 2 Eq, 0.16 mmol) in DCM (6 mL) was stirred for 1 h at rt. The resulting mixture was filtered the filter cake was washed with DCM (3×5 mL). The filtrate was concentrated in vacuo. The crude product was used in the next step directly without further purification. m/z 491.2 (M+H)$^+$ (ES+)

Step 2: 4-[2-(6-{[(Cyclobutylmethyl)amino]methyl}-5-methoxy-1-oxo-3H-isoindol-2-yl)-6-cyclopropylpyridin-4-yl]-3-(4-methyl-1,2,4-triazol-3-yl)benzonitrile (AKM-2)

A solution of 1-cyclobutylmethanamine, HCl (AIA-1) (12 mg, 1.2 Eq, 98 μmol) and DIPEA (16 mg, 1.5 Eq, 0.12 mmol) in MeOH (9 mL) was stirred for 10 min at rt. To the above mixture was added the product from step 1 above (AKM-1) (40 mg, 1 Eq, 82 μmol) at rt. The resulting mixture was stirred overnight at 60° C. The mixture was allowed to cool down to rt. To the above mixture was added $NaBH_4$ (6 mg, 2 Eq, 0.16 mmol) at 0° C. The resulting mixture was stirred for additional 1 h at rt. The reaction was then quenched by the addition of MeOH (2 mL) at 0° C. The mixture was concentrated in vacuo. The crude product was purified by Prep-HPLC with the following conditions (Column: XBridge Prep OBD C18 Column, 30*150 mm, 5 μm; Mobile Phase A: water (0.1% $NH_4HCO_3$+0.1% $NH_3 \cdot H_2O$), Mobile Phase B: MeCN; Flow rate: 60 mL/min; Gradient: 45% B to 55% B in 8 min; Wave Length: 254/220 nm) to afford the title compound (AKM-2) (14.9 mg, 27 μmol, 32%, 98.9% Purity) as a white solid. m/z 560.1 (M+H)$^+$ (ES+). $^1$H NMR (400 MHz, DMSO-d6) δ 8.54 (t, J=6.6 Hz, 1H), 8.22-8.18 (m, 2H), 7.97 (d, J=1.4 Hz, 1H), 7.86 (d, J=8.6 Hz, 1H), 7.65 (d, J=8.4 Hz, 1H), 7.17 (d, J=8.4 Hz, 1H), 6.84 (d, J=1.4 Hz, 1H), 5.06 (s, 2H), 3.89 (s, 3H), 3.79 (s, 2H), 3.45 (s, 3H), 2.54 (d, J=7.0 Hz, 2H), 2.47-2.40 (m, 1H), 2.06-1.97 (m, 3H), 1.88-1.77 (m, 2H), 1.70-1.61 (m, 2H), 1.04-0.89 (m, 4H).

Example 322: Synthesis of 4-[2-(5-Chloro-6-formyl-1-oxo-3H-isoindol-2-yl)-6-cyclopropylpyridin-4-yl]-3-(4-methyl-1,2,4-triazol-3-yl)benzonitrile (AKN-12)

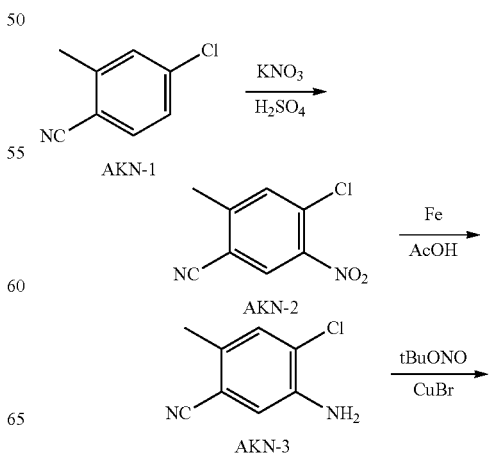

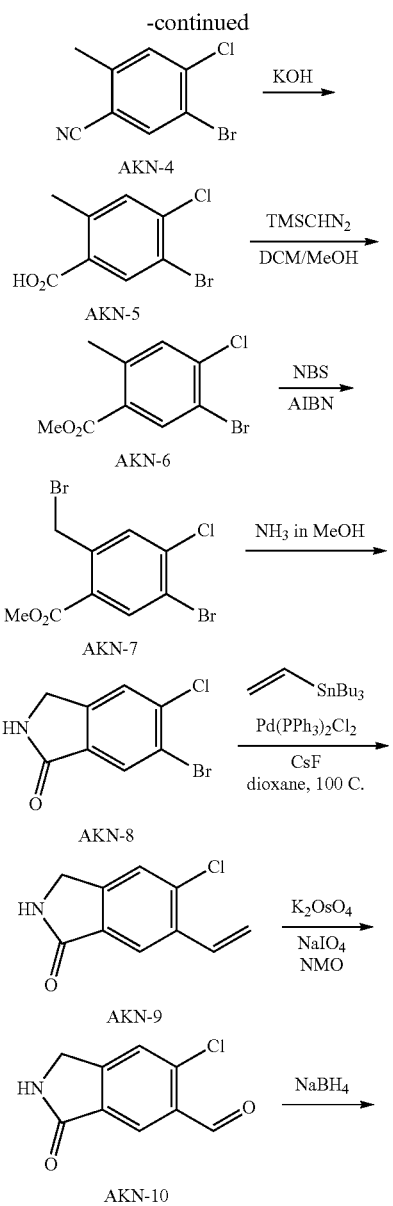

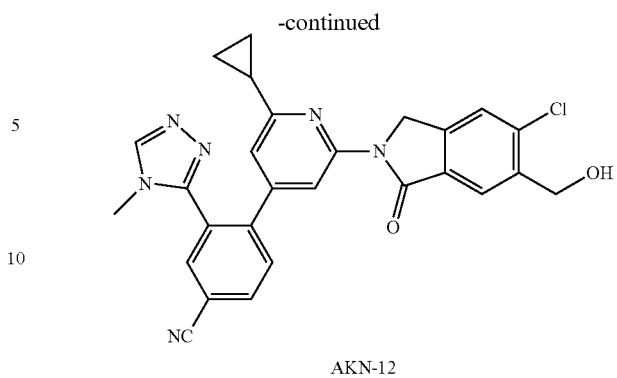

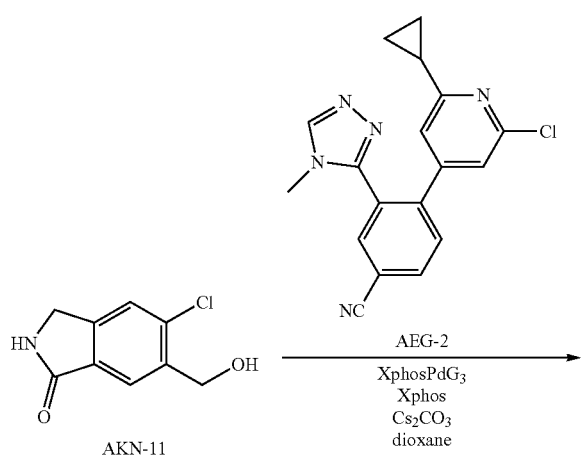

Step 1: 4-Chloro-2-methyl-5-nitrobenzonitrile (AKN-2)

A mixture of 4-chloro-2-methylbenzonitrile (AKN-1) (20.0 g, 1 Eq, 132 mmol) and KNO₃ (13.3 g, 1 Eq, 132 mmol) in conc. H₂SO₄ (140 mL) was stirred for 2 h at 0° C. The resulting mixture was diluted with water and extracted with EtOAc (3×200 mL). The combined organic layers were washed with brine (2×200 mL), dried (Na₂SO₄). After filtration, the filtrate was concentrated in vacuo. The residue was applied on a silica gel column chromatography with petroleum ether/EtOAc (10/1) to afford the crude product which was recrystallized to afford the sub-title compound (AKN-2) (20.0 g, 102 mmol, 77%, 90% Purity) as a white solid. m/z 197.0/199.0 (M+H)⁺ (ES+)

Step 2: 5-Amino-4-chloro-2-methylbenzonitrile (AKN-3)

A mixture of the product from step 1 above (AKN-2) (20.0 g, 1 Eq, 102 mmol) and Fe (28.4 g, 5 Eq, 509 mmol) in AcOH (48 mL, 8.17 Eq, 831 mmol), EtOH (200 mL) and water (100 mL) was stirred at rt for 3 h. The resulting mixture was diluted with water and extracted with EtOAc (3×200 mL). The combined organic layers were washed with brine (2×200 mL), dried (Na₂SO₄). After filtration, the filtrate was concentrated in vacuo to afford the sub-title compound (AKN-3) (8.0 g, 48.2 mmol, 47%, 92% Purity) as a yellow solid. m/z 167.0/169.0 (M+H)⁺ (ES+)

Step 3: 5-Bromo-4-chloro-2-methylbenzonitrile (AKN-4)

A mixture of the product from step 2 above (AKN-3) (8.0 g, 1 Eq, 48.0 mmol), CuBr₂ (16.1 g, 1.5 Eq, 72.0 mmol) and tBu-nitrite (9.90 g, 2 Eq, 96.0 mmol) in MeCN (133 mL) was stirred at rt for 3 h. The resulting mixture was diluted with water and extracted with EtOAc (3×100 mL). The combined organic layers were washed with brine (2×100 mL), dried (Na₂SO₄). After filtration, the filtrate was concentrated in vacuo. The residue was applied on a silica gel column chromatography with petroleum ether/EtOAc (10/1) to afford the sub-title compound (AKN-4) (6.0 g, 26.2 mmol, 54%, 90% Purity) as a white solid. m/z 229.9/231.9 (M+H)⁺ (ES+).

Step 4: 5-Bromo-4-chloro-2-methylbenzoic acid (AKN-5)

A mixture of the product from step 3 above (AKN-4) (6.0 g, 1 Eq, 26.0 mmol), aq. KOH (280 mL, 2 M) was stirred at 110° C. overnight. The mixture was cooled to rt. The resulting mixture was diluted with water and extracted with EtOAc (3×100 mL). The combined organic layers were washed with brine (2×200 mL), dried ($Na_2SO_4$). After filtration, the filtrate was concentrated in vacuo. This resulted in the sub-title compound (AKN-5) (5.0 g, 20.2 mmol, 77%, 85% Purity) as a white solid. m/z 248.9/250.9 $(M+H)^+$ (ES+)

Step 5: Methyl 5-bromo-4-chloro-2-methylbenzoate (AKN-6)

A solution of the product from step 4 above (AKN-5) (5.0 g, 1 Eq, 20.0 mmol) in DCM (50 mL) and MeOH (50 mL) was treated with $TMSCHN_2$ (11.5 mL, 10 Eq, 200.4 mmol) at rt for 1 h. The resulting mixture was concentrated in vacuo. The residue was applied on a silica gel column chromatography with petroleum ether/EtOAc (10/1) to afford the sub-title compound (AKN-6) (5.0 g, 19.1 mmol, 95%, 90% Purity) as a white solid. m/z 262.9/264.9 $(M+H)^+$ (ES+).

Step 6: Methyl 5-bromo-2-(bromomethyl)-4-chlorobenzoate (AKN-7)

A solution of the product from step 5 above (AKN-6) (5.0 g, 1 Eq, 190 mmol) in DCE (100 mL) was treated with AIBN (1.25 g, 0.4 Eq, 7.61 mmol) and NBS (5.07 g, 1.5 Eq, 28.5 mmol) at rt under nitrogen atmosphere. The resulting mixture was stirred at 80° C. under nitrogen atmosphere overnight. The mixture was cooled to rt and concentrated in vacuo. The resulting mixture was used in the next step directly without further purification. m/z 342.8/344.8 $(M+H)^+$ (ES+)

Step 7: 6-Bromo-5-chloro-2,3-dihydroisoindol-1-one (AKN-8)

A solution of the product from step 6 above (AKN-7) (5.0 g, 1 Eq, 14.6 mmol) in $NH_3$ in MeOH (120 mL, 7 M) was stirred at rt for 16 h. The precipitated solids were collected by filtration and washed with EtOAc (3×30 mL). The resulting mixture was concentrated in vacuo. This resulted in the sub-title compound (AKN-8) (3.0 g, 12.2 mmol, 83%, 92% Purity) as a white solid. m/z 245.9/247.9 $(M+H)^+$ (ES+).

Step 8: 5-Chloro-6-ethenyl-2,3-dihydroisoindol-1-one (AKN-9)

To a stirred mixture of the product from step 7 above (AKN-8) (500 mg, 1 Eq, 2.03 mmol), tributyl(ethenyl)stannane (643 mg, 1 Eq, 2.03 mmol) and CsF (616 mg, 2 Eq, 4.06 mmol) in dioxane (12 mL) was added $Pd(PPh_3)_2Cl_2$ (285 mg, 0.2 Eq, 0.41 mmol) at rt under nitrogen atmosphere. The resulting mixture was stirred for 2 h at 120° C. under nitrogen atmosphere. The mixture was cooled to rt and concentrated in vacuo. The crude product was purified by reverse flash column chromatography with the following conditions: Column, C18; mobile phase, water (0.1% $NH_4HCO_3$) and MeCN (20% ACN up to 80% in 15 min); Detector, UV 254/220 nm. This resulted in the sub-title compound (AKN-9) (120 mg, 0.62 mmol, 31%, 90% Purity) as a white solid. m/z 194.0/196.0 $(M+H)^+$ (ES+).

Step 9: 6-Chloro-3-oxo-1,2-dihydroisoindole-5-carbaldehyde (AKN-10)

To a solution of the compound the product from step 8 above (AKN-9) (312 mg, 1 Eq, 1.61 mmol), NMO (378 mg, 2 Eq, 3.22 mmol) and CA (619 mg, 2 Eq, 3.22 mmol) in t-BuOH (10 mL) and $H_2O$ (10 mL) was added $K_2OsO_4.2H_2O$ (59 mg, 0.1 Eq, 0.16 mmol) was stirred at rt 2 h. To the above mixture was added $NaIO_4$ (66 mg, 2 Eq, 0.31 mmol) at rt. The resulting mixture was stirred 1 h at rt. The resulting mixture was diluted with water and extracted with EtOAc (3×50 mL). The combined organic layers were washed with brine (2×50 mL), dried ($Na_2SO_4$). After filtration, the filtrate was concentrated in vacuo. The resulting mixture was used in the next step directly without further purification. m/z 196.0/198.0 $(M+H)^+$ (ES+)

Step 10: 5-Chloro-6-(hydroxymethyl)-2,3-dihydroisoindol-1-one (AKN-11)

To a stirred mixture of the product from step 9 above (AKN-10) (250 mg, 1 Eq, 1.28 mmol) in THF (20 mL) was added $NaBH_4$ (97 mg, 2 Eq, 2.56 mmol) at 0° C. The resulting mixture was stirred at rt for 1 h. The reaction was quenched by the addition of sat. $NH_4Cl$ (aq.) (10 mL) at 0° C. The resulting mixture was diluted with water and extracted with EtOAc (3×50 mL). The combined organic layers were washed with brine (2×50 mL), dried ($Na_2SO_4$). After filtration, the filtrate was concentrated in vacuo. The crude product was purified by reverse flash column chromatography with the following conditions: Column, C18; mobile phase, water (0.1% $NH_4HCO_3$) and MeCN (10% MeCN up to 50% in 20 min); Detector, UV 254/220 nm. This resulted in the sub-title compound (AKN-11) (160 mg, 0.81 mmol, 63%, 95% Purity) as a white solid. m/z 198.0/200.0 $(M+H)^+$ (ES+).

Step 11: 4-{2-[5-Chloro-6-(hydroxymethyl)-1-oxo-3H-isoindol-2-yl]-6-cyclopropylpyridin-4-yl}-3-(4-methyl-1,2,4-triazol-3-yl)benzonitrile (AKN-12)

To a stirred mixture of intermediate (AEG-2) (20 mg, 1 Eq, 60 µmol), the product from step 10 above (AKN-11) (13 mg, 1.1 Eq, 66 µmol) and $Cs_2CO_3$ (58 mg, 3 Eq, 0.18 mmol) in dioxane (3 mL) were added XPhos Pd G3 (10 mg, 0.2 Eq, 12 µmol) and Xphos (6 mg, 0.2 Eq, 12 µmol) at rt under nitrogen atmosphere. The resulting mixture was stirred for 1 h at 100° C. under nitrogen atmosphere. The mixture was cooled to rt and concentrated in vacuo. The residue was purified by Prep-TLC with DCM/MeOH (10/1). The crude product was purified by Prep-HPLC with the following conditions (Column: Xselect CSH C18 OBD Column 30*150 mm, 5 µm, n; Mobile Phase A: water (0.1% FA), Mobile Phase B: MeCN; Flow rate: 60 mL/min; Gradient: 30% B to 60% B in 10 min; Wave Length: 254 nm; RT: 8.73) to afford the title compound (AKN-12) (1.0 mg, 2.0 µmol, 3.4%, 99.0% Purity) as a white solid. m/z 497.3/499.3 $(M+H)^+$ (ES+). $^1H$ NMR (300 MHz, Methanol-d4) δ 8.51 (s, 1H), 8.17-8.00 (m, 4H), 7.92 (d, J=8.0 Hz, 1H), 7.69 (s, 1H), 6.94 (d, J=1.4 Hz, 1H), 5.03 (s, 2H), 4.77 (s, 2H), 3.51 (s, 3H), 2.10-1.96 (m, 1H), 1.09-0.90 (m, 4H).

Example 323: Synthesis of 4-(2-(5-Chloro-6-(((cyclopentylmethyl)amino)methyl)-1-oxoisoindolin-2-yl)-6-cyclopropylpyridin-4-yl)-3-(4-methyl-4H-1,2,4-triazol-3-yl)benzonitrile (AKO-2)

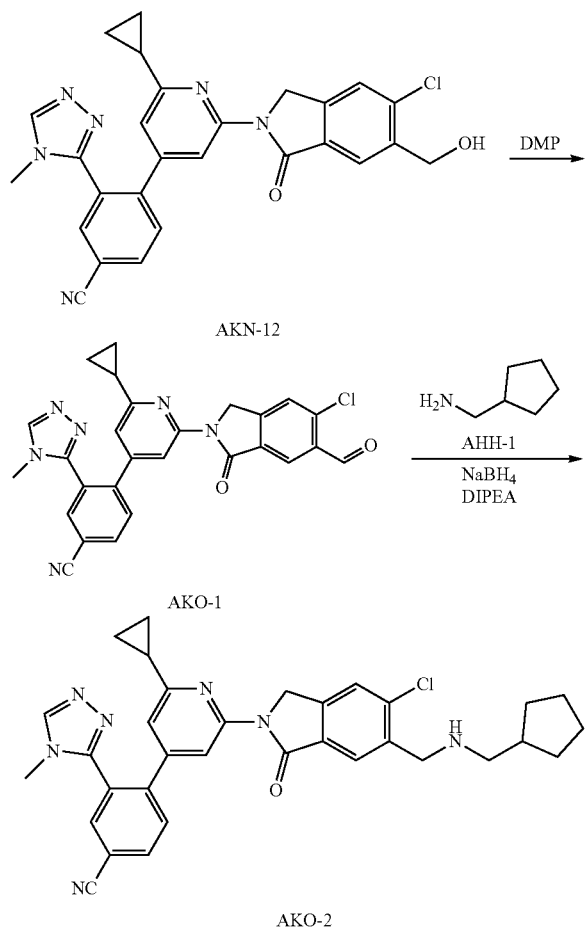

Step 1: 4-[2-(5-Chloro-6-formyl-1-oxo-3H-isoindol-2-yl)-6-cyclopropylpyridin-4-yl]-3-(4-methyl-1,2,4-triazol-3-yl)benzonitrile (AKO-1)

A solution of compound (AKN-12) (20 mg, 1 Eq, 40 μmol) in DCM (1 mL) was treated with DMP (26 mg, 1.5 Eq, 60 μmol) at rt for 1 h. The resulting mixture was filtered the filter cake was washed with DCM (3×3 mL). The filtrate was concentrated in vacuo. The crude product was used in the next step directly without further purification. m/z 495.1/497.1 (M+H)+ (ES+).

Step 2: 4-(2-(5-Chloro-6-(((cyclopentylmethyl)amino)methyl)-1-oxoisoindolin-2-yl)-6-cyclopropylpyridin-4-yl)-3-(4-methyl-4H-1,2,4-triazol-3-yl)benzonitrile (AKO-2)

A mixture of the product from step 1 above (AKO-1) (10 mg, 1 Eq, 20 μmol) and 1-cyclopentylmethanamine (AHH-1) (2.2 mg, 1.1 Eq, 22 μmol) in MeOH (2 mL) was stirred for 1 h at 60° C. Then was added NaBH$_4$ (2.5 mg, 2 Eq, 40 μmol) at rt for 1 h. The reaction was then quenched by the addition of MeOH (2 mL) at 0° C. The mixture was concentrated in vacuo. The crude product was purified by Prep-HPLC with the following conditions (Column: Xselect CSH C18 OBD Column 30*150 mm, 5 μm, n; Mobile Phase A: water (0.1% FA), Mobile Phase B: MeCN; Flow rate: 60 mL/min; Gradient: 6% B to 36% B in 10 min; Wave Length: 254 nm; RT: 10.63) to afford the title compound (AKO-2) (3.0 mg, 5.2 μmol, 24%, 93.4% Purity) as a white solid. m/z 578.3/580.3 (M+H)+ (ES+). $^1$H NMR (300 MHz, Methanol-d4) δ 8.47 (s, 1H), 8.18-8.07 (m, 2H), 8.05-7.99 (m, 2H), 7.94-7.82 (m, 2H), 6.97 (d, J=1.4 Hz, 1H), 5.08 (s, 2H), 4.37 (s, 2H), 3.47 (s, 3H), 3.01 (d, J=7.4 Hz, 2H), 2.29-2.17 (m, 1H), 2.10-1.99 (m, 1H), 2.00-1.87 (m, 2H), 1.75-1.60 (m, 4H), 1.34-1.24 (m, 2H), 1.07-0.97 (m, 4H).

Example 324: Synthesis of 4-{2-Cyclopropyl-6-[6-({[(1-hydroxycyclobutyl)methyl](methyl)amino}methyl)-1-oxo-3H-isoindol-2-yl]pyridin-4-yl}-3-(4-methyl-1,2,4-triazol-3-yl)benzonitrile (AKP-1)

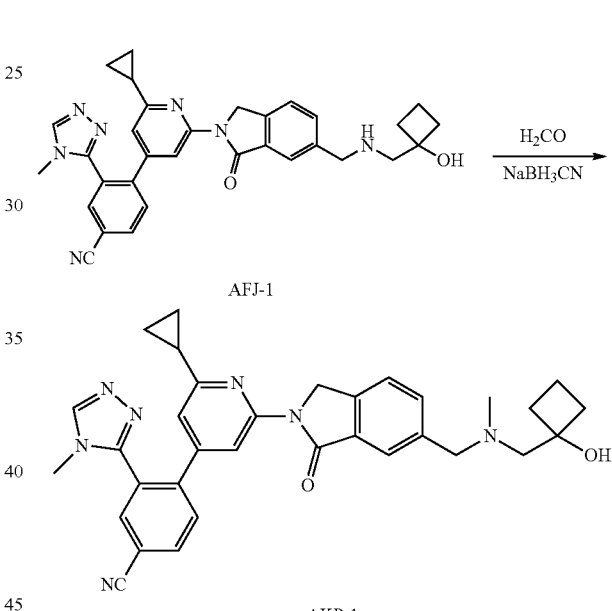

A solution of compound (AFJ-1) (40 mg, 1 Eq, 73 μmol) and formaldehyde (1 mL) in MeOH (8 mL) was stirred overnight at rt. To the above mixture was added NaBH$_3$CN (23 mg, 0.37 mmol, 5 Eq). The resulting mixture was stirred for additional 2 days at rt. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 46% B to 60% B in 8 min; Wave Length: 254/220 nm; RT: 7.95) to afford the title compound (AKP-1) (2.6 mg, 4.6 μmol, 6.3%, 99.6% Purity) as a white solid. m/z 560.2 (M+H)+ (ES+). $^1$H NMR (400 MHz, Methanol-d4) δ 8.50 (s, 1H), 8.14-8.04 (m, 3H), 7.92 (d, J=8.0 Hz, 1H), 7.81 (s, 1H), 7.72-7.65 (m, 1H), 7.60 (d, J=7.8 Hz, 1H), 6.92 (d, J=1.4 Hz, 1H), 5.03 (s, 2H), 3.72 (s, 2H), 3.51 (s, 3H), 2.58 (s, 2H), 2.30 (s, 3H), 2.15-1.96 (m, 5H), 1.82-1.67 (m, 1H), 1.52-1.35 (m, 1H), 1.09-0.94 (m, 4H).

Example 325: Synthesis of 4-[2-(6-{3-Azabicyclo[3.1.0]hexan-3-ylmethyl}-4-fluoro-1-oxo-3H-isoindol-2-yl)-6-cyclopropylpyridin-4-yl]-3-(4-methyl-1,2,4-triazol-3-yl)benzonitrile (AKQ-2)

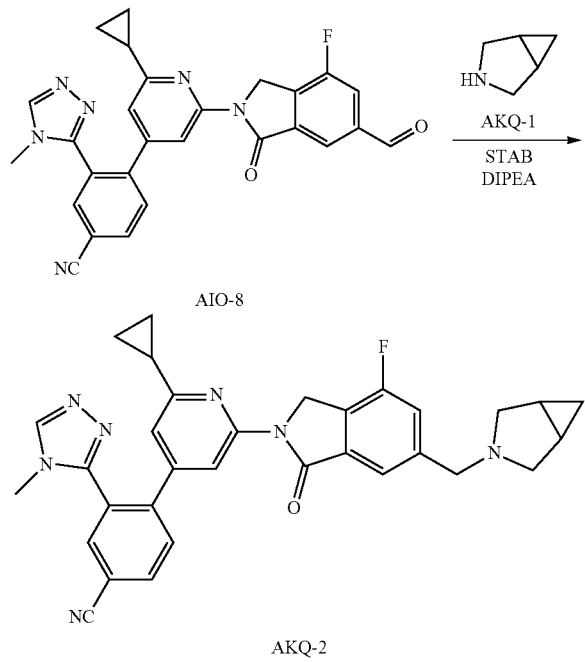

To a stirred mixture of intermediate (AIO-8) (40 mg, 1 Eq, 84 μmol) and 3-azabicyclo[3.1.0]hexane (AKQ-1) (10 mg, 1.5 Eq, 0.13 mmol) in DCM (5 mL) was added DIPEA (13 mg, 1.2 Eq, 0.10 mmol) at rt under nitrogen atmosphere. The resulting mixture was stirred overnight at rt. To the above mixture was added NaBH(OAc)$_3$ (35 mg, 2 Eq, 0.17 mmol) at 0° C. The resulting mixture was stirred for additional 2 h at rt. The resulting mixture was diluted with water and extracted with DCM (3×10 mL). The combined organic layers were washed with brine (2×10 mL), dried (Na$_2$SO$_4$). After filtration, the filtrate was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 44% B to 56% B in 8 min; Wave Length: 254/220 nm; RT: 6.32) to afford the title compound (AKQ-2) (2.6 mg, 4.8 μmol, 5.7%, 99.7% Purity) as a white solid. m/z 546.3 (M+H)$^+$ (ES+). $^1$H NMR (400 MHz, Methanol-d4) δ 8.51 (s, 1H), 8.16-8.07 (m, 2H), 8.01 (d, J=1.4 Hz, 1H), 7.95-7.89 (m, 1H), 7.59 (s, 1H), 7.35 (d, J=9.6 Hz, 1H), 6.97 (d, J=1.4 Hz, 1H), 5.06 (s, 2H), 3.70 (s, 2H), 3.51 (s, 3H), 2.94 (d, J=8.6 Hz, 2H), 2.42 (d, J=8.5 Hz, 2H), 2.10-2.00 (m, 1H), 1.51-1.26 (m, 2H), 1.22-0.82 (m, 4H), 0.81-0.74 (m, 1H), 0.39 (td, J=7.7, 4.2 Hz, 1H).

Example 326: Synthesis of 4-(2-Cyclopropyl-6-{4-fluoro-6-[(1S,4S)-2-oxa-5-azabicyclo[2.2.1]heptan-5-ylmethyl]-1-oxo-3H-isoindol-2-yl}pyridin-4-yl)-3-(4-methyl-1,2,4-triazol-3-yl)benzonitrile (AKR-3)

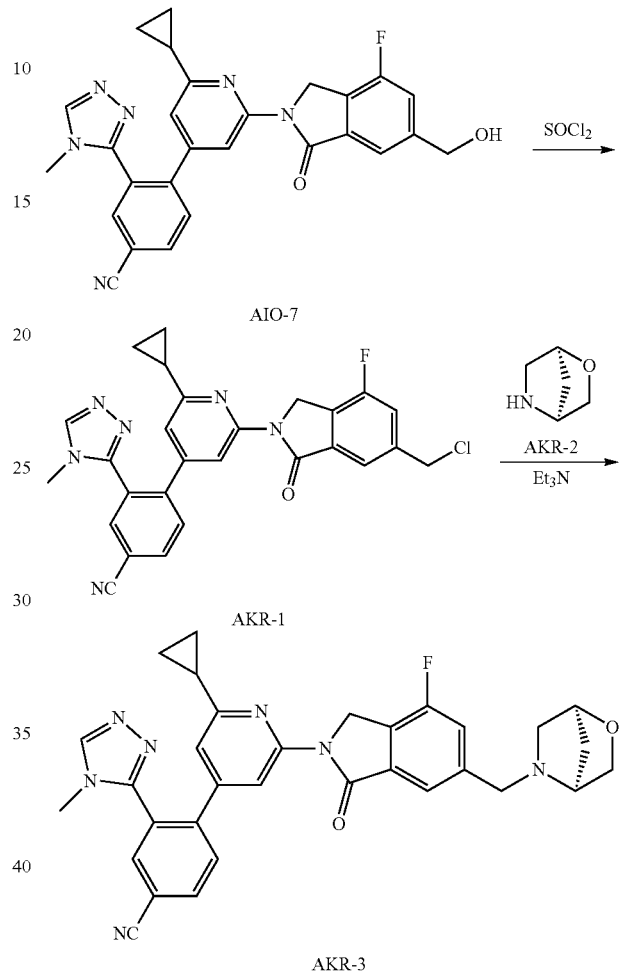

Step 1: 4-{2-[6-(Chloromethyl)-4-fluoro-1-oxo-3H-isoindol-2-yl]-6-cyclopropylpyridin-4-yl}-3-(4-methyl-1,2,4-triazol-3-yl)benzonitrile (AKR-1)

To a stirred mixture of intermediate (AIO-7) (60 mg, 1 Eq, 0.13 mmol) in DCM (10 mL) was added SOCl$_2$ (0.6 mL) at 0° C. The resulting mixture was stirred for 30 min at rt. The reaction was then quenched by the addition of MeOH (2 mL) at 0° C. The resulting mixture was concentrated in vacuo. The residue was purified by Prep-TLC with DCM/MeOH (9/1) to afford the sub-title compound (AKR-1) (58 mg, 0.12 mmol, 93%, 93% Purity) as a white solid. m/z 499.1/501.1 (M+H)$^+$ (ES+)

Step 2: 4-(2-Cyclopropyl-6-{4-fluoro-6-[(1S,4S)-2-oxa-5-azabicyclo[2.2.1]heptan-5-ylmethyl]-1-oxo-3H-isoindol-2-yl}pyridin-4-yl)-3-(4-methyl-1,2,4-triazol-3-yl) (AKR-3)

To a stirred mixture of the product from step 1 above (AKR-1) (58 mg, 1 Eq, 0.12 mmol) and (1S,4S)-2-oxa-5- azabicyclo[2.2.1]heptane (AKR-2) (17 mg, 1.5 Eq, 0.17 mmol) in DCM (10 mL) was added Et₃N (35 mg, 3 Eq, 0.35 mmol) at rt. The resulting mixture was stirred for 12 h at 60° C. The mixture was cooled to rt and concentrated in vacuo. The residue was purified by Prep-TLC with DCM/MeOH (8/1). The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 38% B to 48% B in 9 min; Wave Length: 254/210 nm; RT: 8.35) to afford the title compound (AKR-3) (13.6 mg, 24 μmol, 21%, 99.9% Purity) as a white solid. m/z 562.1 (M+H)⁺ (ES+). ¹H NMR (400 MHz, DMSO-d6) δ 8.54 (s, 1H), 8.21 (h, J=1.7 Hz, 2H), 7.95 (d, J=1.4 Hz, 1H), 7.87 (d, J=8.5 Hz, 1H), 7.70 (d, J=8.5 Hz, 1H), 7.50 (d, J=9.9 Hz, 1H), 6.92 (d, J=1.4 Hz, 1H), 5.07 (s, 2H), 4.36 (s, 1H), 3.93 (d, J=7.5 Hz, 1H), 3.88-3.78 (m, 2H), 3.54 (d, J=7.5, 1.9 Hz, 1H), 3.47 (s, 4H), 2.75 (d, J=9.9, 1.8 Hz, 1H), 2.43 (d, J=9.9 Hz, 1H), 2.09-2.01 (m, 1H), 1.87-1.79 (m, 1H), 1.61 (d, J=10.0 Hz, 1H), 1.04-0.91 (m, 4H).

Example 327: Synthesis of 4-[2-(6-{1[(Cyclobutylmethyl)amino]methyl}-4-fluoro-1-oxo-3H-isoindol-2-yl)-6-cyclopropylpyridin-4-yl]-3-(4-methyl-1,2,4-triazol-3-yl)benzonitrile (AKS-1)

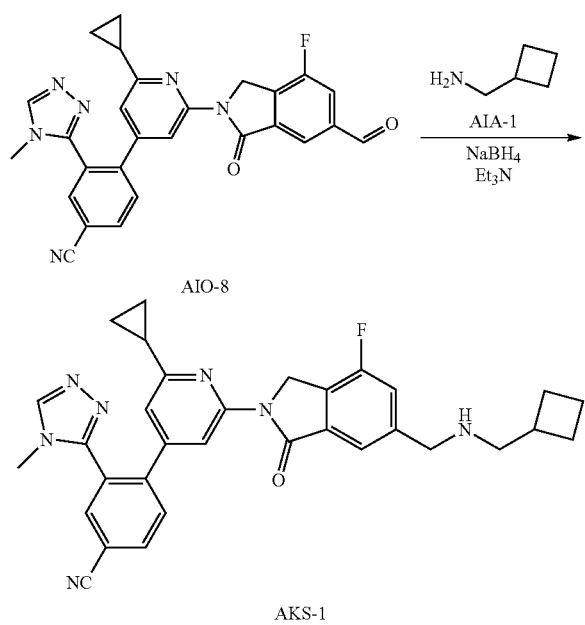

To a stirred solution of intermediate (AIO-8) (30 mg, 1 Eq, 63 μmol) and 1-cyclobutylmethanamine (AIA-1) (5. mg, 1 Eq, 63 μmol) in MeOH (5 mL) was added Et₃N (32 mg, 5 Eq, 0.32 mmol) for 2 h at 60° C. under nitrogen atmosphere. To the above mixture was added NaBH₄ (24 mg, 10 Eq, 0.63 mmol) at 0° C. The resulting mixture was stirred for 2 h at rt. The reaction was then quenched by the addition of MeOH (2 mL) at 0° C. The resulting mixture was concentrated in vacuo. The crude product was purified by Prep-HPLC with the following conditions: Column: XBridge Prep OBD C18 Column, 19×250 mm, 5 μm; Mobile Phase A: water (0.1% NH₄HCO₃) Mobile Phase B: MeCN; Flow rate: 25 mL/min; Gradient: 56 B to 62 B in 8 min; Detector, UV 254/210 nm; RT: 7.03. The product-containing fractions were combined and evaporated partially in vacuo and lyophilized overnight to afford the title compound (AKS-1) (12.7 mg, 23 μmol, 37%, 99.5% Purity) as a white solid. m/z 548.3 (M+H)⁺ (ES+). ¹H NMR (400 MHz, DMSO-d6) δ 8.54 (s, 1H), 8.24-8.20 (m, 2H), 7.95 (d, J=1.4 Hz, 1H), 7.87 (d, J=8.5 Hz, 1H), 7.61 (s, 1H), 7.50 (d, J=10.0 Hz, 1H), 6.92 (d, J=1.4 Hz, 1H), 5.07 (s, 2H), 3.78 (s, 2H), 3.48 (s, 3H), 2.48 (s, 2H), 2.42-2.38 (m, 1H), 1.87-1.75 (m, 3H), 1.71-1.55 (m, 4H), 1.23 (s, 1H), 1.01-0.96 (m, 4H).

Example 328: Synthesis of 4-[2-(6-{[(Cyclobutylmethyl)(methyl)amino]methyl}-4-fluoro-1-oxo-3H-isoindol-2-yl)-6-cyclopropylpyridin-4-yl]-3-(4-methyl-1,2,4-triazol-3-yl)benzonitrile (AKT-1)

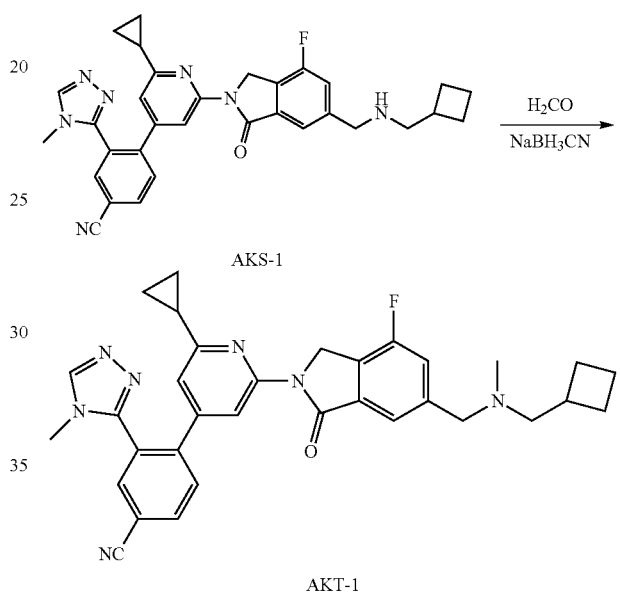

To a stirred solution of compound (AKS-1) (30 mg, 1 Eq, 55 μmol) and formaldehyde (5 mg, 0.165 mmol, 3 Eq) in MeOH (5 mL) was added NaBH₃CN (7 mg, 2 Eq, 0.11 mmol) at rt. The resulting mixture was stirred for 2 h at rt. The reaction was then quenched by the addition of MeOH (2 mL) at 0° C. The resulting mixture was diluted with water and extracted with DCM (3×20 mL). The combined organic layers were washed with brine (2×20 mL), dried (Na₂SO₄). After filtration, the filtrate was concentrated in vacuo. The crude product was purified by Prep-HPLC with the following conditions: Column: XBridge Prep OBD C18 Column, 19×250 mm, 5 μm; Mobile Phase A: water (0.1% NH₄HCO₃+0.1% NH₃·H₂O) Mobile Phase B: MeCN; Flow rate: 60 mL/min; Gradient: 65 B to 76 B in 8 min; Detector, UV 254/210 nm; RT: 7.85. The product-containing fractions were combined and evaporated partially in vacuo and lyophilized overnight to afford the title compound (AKT-1) (2.7 mg, 4.8 μmol, 8.8%, 99.8% Purity) as a white solid. m/z 562.1 (M+H)⁺ (ES+). ¹H NMR (400 MHz, DMSO-d6) δ 8.54 (s, 1H), 8.25-8.18 (m, 2H), 7.95 (d, J=1.4 Hz, 1H), 7.87 (d, J=8.4 Hz, 1H), 7.57 (s, 1H), 7.45 (d, J=9.9 Hz, 1H), 6.92 (d, J=1.4 Hz, 1H), 5.08 (s, 2H), 3.55 (s, 2H), 3.47 (s, 3H), 3.17 (d, J=5.2 Hz, 1H), 2.39 (s, 2H), 2.11 (s, 3H), 2.03 (t, J=10.6 Hz, 3H), 1.84 (t, J=9.0 Hz, 1H), 1.76 (d, J=9.6 Hz, 1H), 1.63 (d, J=9.2 Hz, 2H), 0.98 (d, J=6.1 Hz, 4H).

Example 329: Synthesis of 4-[2-Cyclopropyl-6-(6-{1[(1-ethylcyclopropyl)amino] methyl}-1-oxo-4-(trifluoromethyl)-3H-isoindol-2-yl)pyridin-4-yl]-3-(4-methyl-1,2,4-triazol-3-yl)benzonitrile (AKU-2)

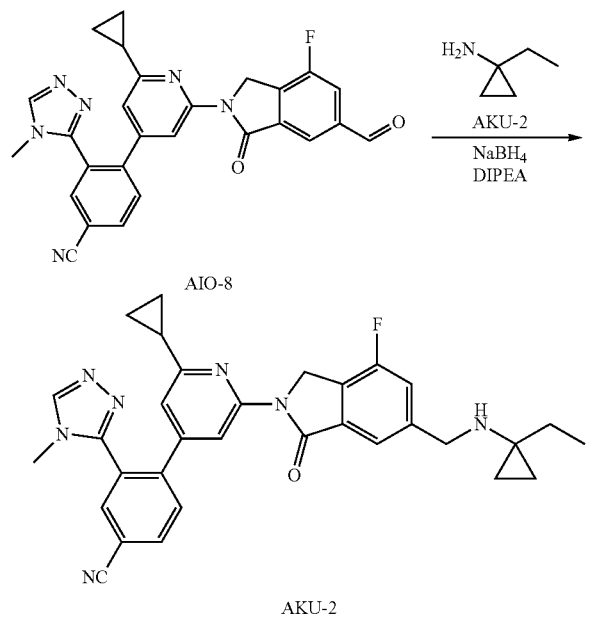

To a stirred mixture of 1-ethylcyclopropan-1-amine (AKU-1) (92 mg, 10 Eq, 0.76 mmol) in MeOH (3 ml) was added DIPEA (49 mg, 0.38 mmol, 5 Eq) at rt. The resulting mixture was stirred for 5 min at rt. To the above mixture was added intermediate (AIO-8) (40 mg, 1 Eq, 76 μmol) at rt. The resulting mixture was stirred for additional 1 h at 60° C. The mixture was cooled to rt. To the above mixture was added NaBH₄ (10 mg, 3.5 Eq, 0.26 mmol) at 0° C. The resulting mixture was stirred for additional 1 h at rt. The reaction was then quenched by the addition of MeOH (2 mL) at 0° C. The resulting mixture was concentrated in vacuo. The residue was purified by Prep-TLC with DCM/MeOH (15/1). The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 62% B to 82% B in 8 min; Wave Length: 254/220 nm) to afford the title compound (AKU-2) (8.1 mg, 14 μmol, 18%, 99.6% Purity) as a white solid. m/z 598.1 (M+H)⁺ (ES+). ¹H NMR (400 MHz, DMSO-d6) δ 8.54 (d, J=2.0 Hz, 1H), 8.23-8.16 (m, 2H), 8.04-7.92 (m, 3H), 7.90-7.85 (m, 1H), 6.90 (d, J=1.5 Hz, 1H), 5.14 (s, 2H), 3.88 (s, 2H), 3.47 (s, 3H), 2.11-2.02 (m, 1H), 1.47-1.39 (m, 2H), 1.00-0.86 (m, 7H), 0.52-0.46 (m, 2H), 0.32 (t, J=2.9 Hz, 2H).

Example 330: Synthesis of 4-{2-Cyclopropyl-6-[4-fluoro-6-({[(2R)-2-methoxypropyl]amino}methyl)-1-oxo-3H-isoindol-2-yl]pyridin-4-yl}-3-(4-methyl-1,2,4-triazol-3-yl)benzonitrile (AKV-1)

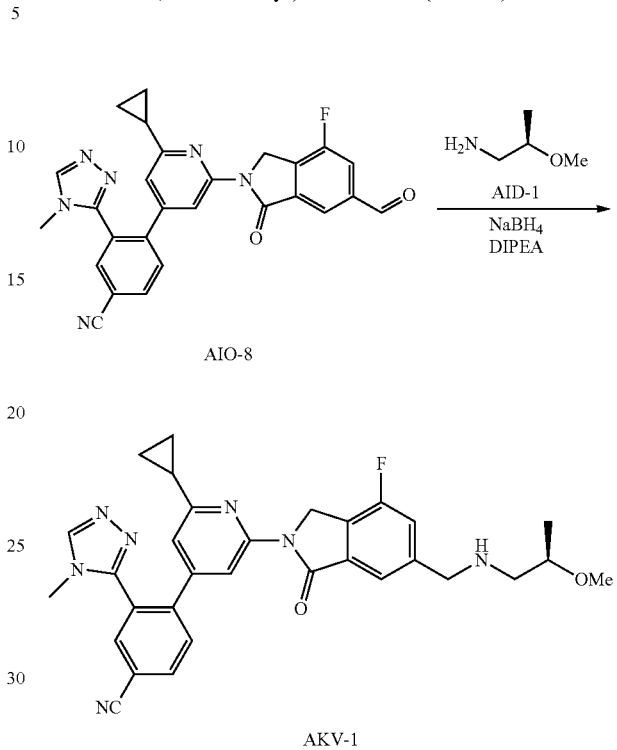

To a stirred mixture of intermediate (AIO-8) (40 mg, 1 Eq, 84 μmol) in MeOH (6 mL) was added (2R)-2-methoxypropan-1-amine (AID-1) (80 mg, 11 Eq, 0.90 mmol) at rt. The resulting mixture was stirred for 1 h at rt. The resulting mixture was stirred for additional 1 h at 60° C. To the above mixture was added NaBH₄ (25 mg, 7.9 Eq, 0.66 mmol) at 0° C. The resulting mixture was stirred for additional 1 h at rt. The reaction was then quenched by the addition of MeOH (2 mL) at 0° C. The resulting mixture was concentrated in vacuo. The residue was purified by Prep-TLC with DCM/MeOH (15/1). The crude product was purified by Prep-HPLC with the following conditions (Column: Xselect CSH C18 OBD Column 30*150 mm, 5 μm; Mobile Phase A: water (0.1% FA), Mobile Phase B: MeCN; Flow rate: 60 mL/min; Gradient: 2% B to 32% B in 10 min; Wave Length: 254 nm) to afford the title compound (AKV-1) (14.2 mg, 26 μmol, 31%, 99.2% Purity) as a white solid. m/z 552.1 (M+H)⁺ (ES+). ¹H NMR (400 MHz, DMSO-d6) δ 8.54 (s, 1H), 8.26-8.15 (m, 2H), 7.95 (d, J=1.4 Hz, 1H), 7.91-7.80 (m, 1H), 7.62 (s, 1H), 7.51 (d, J=9.9 Hz, 1H), 6.95-6.85 (m, 1H), 5.07 (s, 2H), 3.82 (s, 2H), 3.48 (s, 3H), 3.40-3.36 (m, 1H), 3.23 (s, 3H), 2.49-2.39 (m, 2H), 2.13-1.98 (m, 1H), 1.07 (d, J=6.1 Hz, 3H), 1.00-0.86 (m, 4H).

Example 331: Synthesis of 4-{2-Cyclopropyl-6-[4-fluoro-6-({[(2S)-2-methoxypropyl]amino}methyl)-1-oxo-3H-isoindol-2-yl]pyridin-4-yl}-3-(4-methyl-1,2,4-triazol-3-yl)benzonitrile (AKW-1)

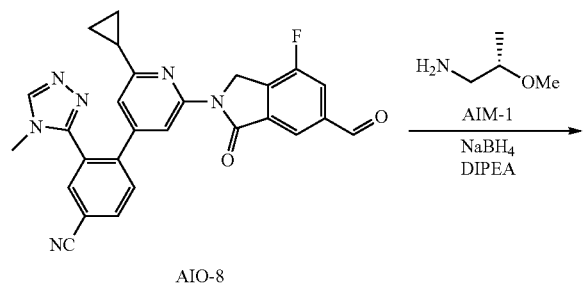

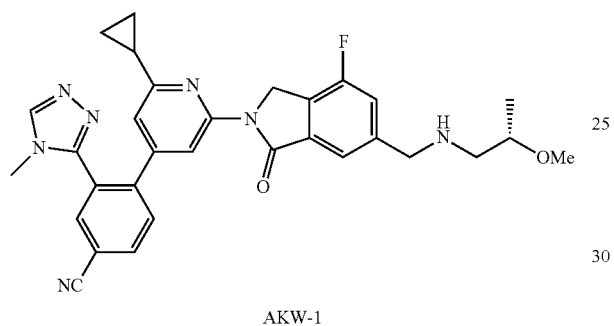

To a stirred solution of intermediate (AIO-8) (30 mg, 1 Eq, 63 μmol) and (2S)-2-methoxypropan-1-amine (AIM-1) (7 mg, 1.2 Eq, 76 μmol) in MeOH (8 mL) was added DIPEA (24 mg, 3 Eq, 0.19 mmol) at rt. The resulting mixture was stirred overnight at 60° C. The mixture was allowed to cool down to rt. To the above mixture was added NaBH₄ (12 mg, 5 Eq, 0.32 mmol) at 0° C. The resulting mixture was stirred for additional 1 h at rt. The reaction was then quenched by the addition of MeOH (2 mL) at 0° C. The resulting mixture was concentrated in vacuo. The crude product was purified by Prep-HPLC with the following conditions (Column: XSelect CSH Prep C18 OBD Column, 19*250 mm, 5 μm; Mobile Phase A: water (0.1% FA), Mobile Phase B: MeCN; Flow rate: 25 mL/min; Gradient: 17% B to 47% B in 8 min; Wave Length: 254/220 nm; RT: 7.18) to afford the title compound (AKW-1) (3.4 mg, 6.2 μmol, 9.6%, 97.8% Purity) as a white solid. m/z 552.1 (M+H)⁺ (ES+). ¹H NMR (400 MHz, Methanol-d4) δ 8.50 (s, 1H), 8.14-8.08 (m, 2H), 8.02 (d, J=1.4 Hz, 1H), 7.92 (d, J=8.0 Hz, 1H), 7.67 (s, 1H), 7.46 (d, J=9.6 Hz, 1H), 6.96 (d, J=1.4 Hz, 1H), 5.07 (s, 2H), 3.95 (s, 2H), 3.57-3.51 (m, 1H), 3.49 (s, 3H), 3.35 (s, 3H), 2.66-2.62 (m, 2H), 2.08-2.00 (m, 1H), 1.13 (d, J=6.1 Hz, 3H), 1.07-0.97 (m, 4H).

Example 332: Synthesis of 4-{2-Ethoxy-6-[6-(hydroxymethyl)-1-oxo-3H-isoindol-2-yl]pyridin-4-yl}-3-(4-methyl-1,2,4-triazol-3-yl)benzonitrile (AKX-1)

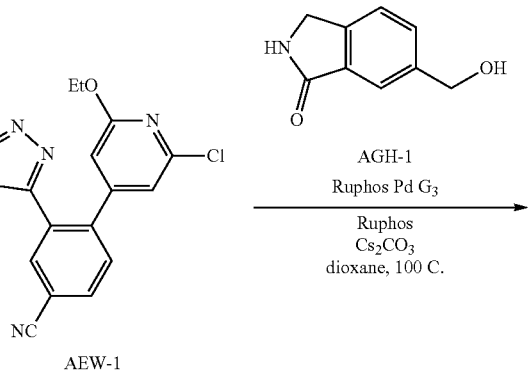

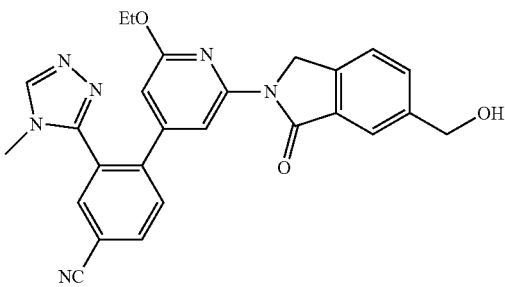

To a solution of intermediate (AEW-1) (20 mg, 1 Eq, 59 μmol), intermediate (AGH-1) (12 mg, 1.3 Eq, 77 μmol) and Cs₂CO₃ (38 mg, 2 Eq, 0.12 mmol) in 1,4-dioxane (8 mL) were added RuPhos (11 mg, 0.4 Eq, 24 μmol) and RuPhos Palladacycle Gen.3 (10 mg, 0.2 Eq, 12 μmol) at rt under nitrogen atmosphere. The resulting mixture was stirred for 2 h at 100° C. The mixture was cooled to rt and concentrated in vacuo. The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 30% B to 44% B in 9 min; Wave Length: 254/220 nm; RT: 8.02) to afford the title compound (AKX-1) (3.0 mg, 6.4 μmol, 11%, 99.5% Purity) as a white solid. m/z 467.1 (M+H)⁺ (ES+). ¹H NMR (400 MHz, Methanol-d4) δ 8.50 (s, 1H), 8.14-8.05 (m, 2H), 7.90 (d, J=8.0 Hz, 1H), 7.86-7.80 (m, 2H), 7.69-7.58 (m, 2H), 6.42 (d, J=1.3 Hz, 1H), 5.06 (s, 2H), 4.71 (s, 2H), 4.44-4.34 (m, 2H), 3.53 (s, 3H), 1.39 (t, J=7.0 Hz, 3H).

Example 333: Synthesis of 4-[2-Cyclopropyl-6-(4-fluoro-6-{[(3S)-3-methylpiperidin-1-yl]methyl}-1-oxo-3H-isoindol-2-yl)pyridin-4-yl]-3-(4-methyl-1,2,4-triazol-3-yl)benzonitrile (AKY-1)

Example 334: Synthesis of 4-{2-Cyclopropyl-6-[4-fluoro-6-({[(1-fluorocyclopropyl) methyl] amino}methyl)-1-oxo-3H-isoindol-2-yl]pyridin-4-yl}-3-(4-methyl-1,2,4-triazol-3-yl)benzonitrile (AKZ-2)

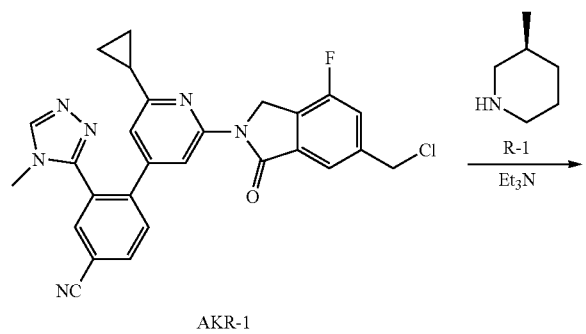

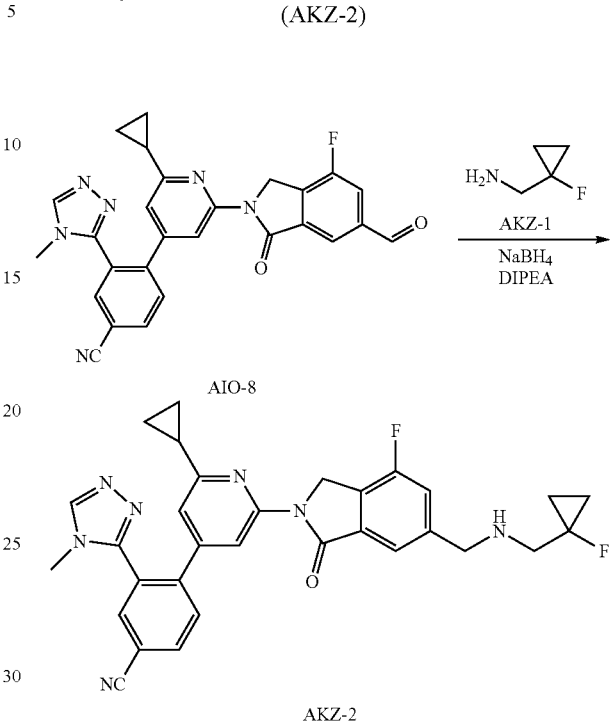

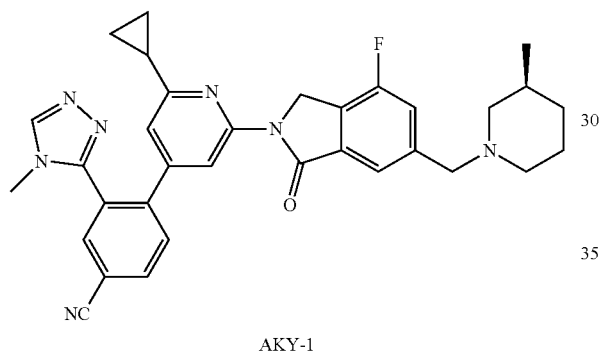

AKY-1

To a stirred solution of intermediate (AKR-1) (30 mg, 1 Eq, 60 µmol) and (3S)-3-methylpiperidine (R-1) (9 mg, 1.5 Eq, 90 µmol) in DCM (8 mL) was added Et3N (30 mg, 5 Eq, 0.30 mmol) at rt. The resulting mixture was stirred overnight at rt under nitrogen atmosphere. The resulting mixture was concentrated in vacuo. The crude product was purified by Prep-HPLC with the following conditions (Column: Xselect CSH C18 OBD Column 30*150 mm, 5 µm; Mobile Phase A: water (0.1% FA), Mobile Phase B: MeCN; Flow rate: 60 mL/min; Gradient: 2% B to 32% B in 10 min; Wave Length: 254 nm; RT: 11.48) to afford the title compound (AKY-1) (8.6 mg, 15 µmol, 25%, 99.5% Purity) as a white solid. m/z 562.1 (M+H)$^+$ (ES+). $^1$H NMR (400 MHz, DMSO-d6) δ 8.54 (s, 1H), 8.25-8.18 (m, 2H), 7.94 (d, J=1.3 Hz, 1H), 7.87 (d, J=8.5 Hz, 1H), 7.55 (s, 1H), 7.46 (d, J=9.9 Hz, 1H), 6.93 (d, J=1.4 Hz, 1H), 5.07 (s, 2H), 3.67-3.58 (m, 2H), 3.57-3.50 (m, 3H), 2.71 (s, 2H), 2.09-2.00 (m, 1H), 1.94-1.84 (m, 1H), 1.60 (s, 4H), 1.54-1.43 (m, 1H), 0.98 (d, J=7.4 Hz, 4H), 0.83-0.79 (m, 4H).

A solution of 1-(1-fluorocyclopropyl)methanamine (AKZ-1) (6.7 mg, 1.2 Eq, 76 µmol) in MeOH (8 mL) was treated with DIPEA (24 mg, 3 Eq, 0.19 mmol) for 5 min at rt followed by the addition of intermediate (AIO-8) (30 mg, 1 Eq, 63 µmol) at rt. The resulting mixture was stirred overnight at 60° C. The mixture was allowed to cool down to rt. To the above mixture was added NaBH$_4$ (12 mg, 5 Eq, 0.32 mmol) at 0° C. The resulting mixture was stirred for additional 1 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 µm; Mobile Phase A: water (0.1% NH$_4$HCO$_3$+0.1% NH$_3$·H$_2$O), Mobile Phase B: MeCN; Flow rate: 25 mL/min; Gradient: 50% B to 66% B in 8 min; Wave Length: 254/220 nm; RT: 7.62) to afford the title compound (AKZ-2) (11 mg, 20 µmol, 32%, 99.6% Purity) as a white solid. m/z 552.1 (M+H)$^+$ (ES+). $^1$H NMR (400 MHz, Methanol-d4) δ 8.49 (s, 1H), 8.14-8.07 (m, 2H), 8.02 (d, J=1.4 Hz, 1H), 7.92 (d, J=8.0 Hz, 1H), 7.66 (d, J=1.2 Hz, 1H), 7.48-7.43 (m, 1H), 6.95 (d, J=1.4 Hz, 1H), 5.06 (s, 2H), 3.97 (s, 2H), 3.49 (s, 3H), 2.92 (d, J=21.5 Hz, 2H), 2.09-2.01 (m, 1H), 1.07-0.96 (m, 6H), 0.70-0.62 (m, 2H).

Example 335: Synthesis of 4-{2-[4-Bromo-6-(hydroxymethyl)-1-oxo-3H-isoindol-2-yl]-6-cyclopropylpyridin-4-yl}-3-(4-methyl-1,2,4-triazol-3-yl)benzonitrile (ALA-5)

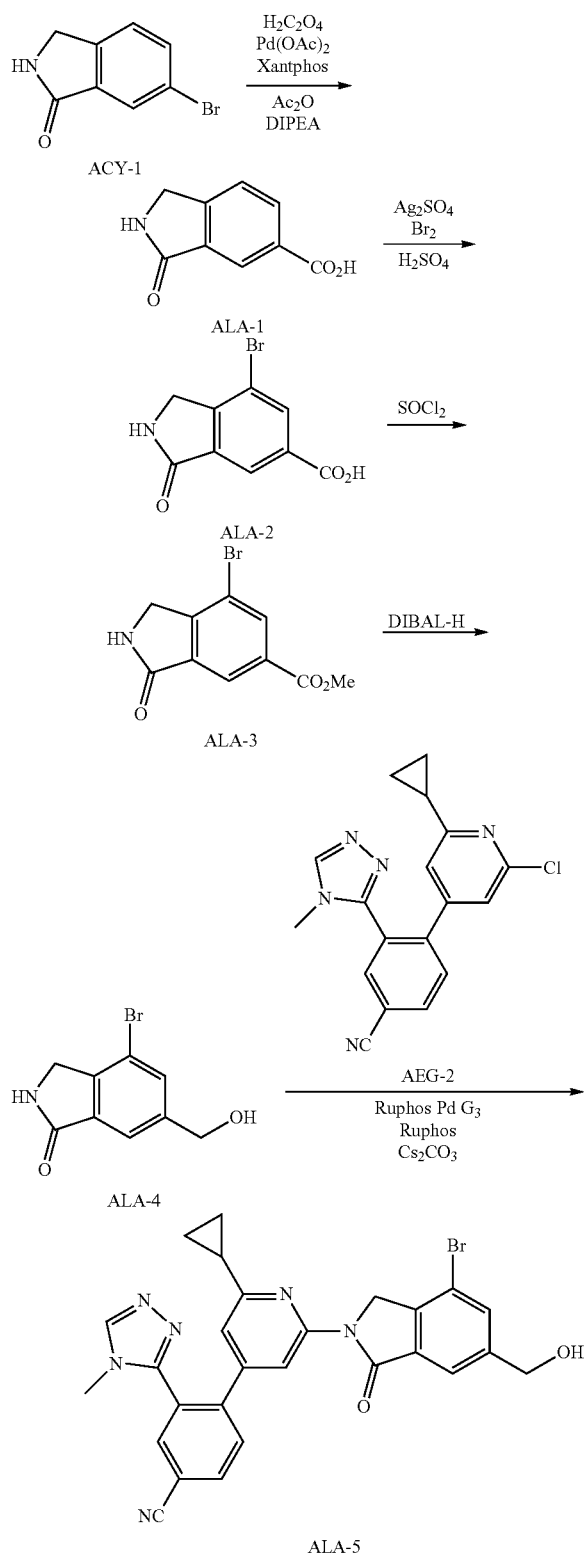

Step 1: 3-Oxo-1,2-dihydroisoindole-5-carboxylic acid (ALA-1)

To a stirred solution of 6-bromo-2,3-dihydroisoindol-1-one (ACY-1) (500 mg, 1 Eq, 2.36 mmol) and oxalic acid (357 mg, 1.2 Eq, 2.83 mmol) in DMF (10 mL) were added $Ac_2O$ (361 mg, 1.5 Eq, 3.54 mmol) and DIPEA (4.57 g, 1.5 Eq, 3.54 mmol) at rt under nitrogen atmosphere. To the above mixture were added Xantphos (273 mg, 0.2 Eq, 0.47 mmol) and $Pd(OAc)_2$ (53 mg, 0.1 Eq, 0.24 mmol) at rt under nitrogen atmosphere. The resulting mixture was stirred for 2 h at 100° C. under nitrogen atmosphere. The mixture was allowed to cool down to rt. The crude product was purified by reverse flash column chromatography with the following conditions: Column, C18; mobile phase, water (0.1% $NH_4HCO_3$) and MeCN (10% MeCN up to 20% in 20 min); Detector, UV 254/220 nm. This resulted in the sub-title compound (ALB-1) (226 mg, 1.28 mmol, 54%, 95% Purity) as a white solid. m/z 178.0 $(M+H)^+$ (ES+).

Step 2: 7-Bromo-3-oxo-1,2-dihydroisoindole-5-carboxylic acid (ALA-2)

To a stirred solution of the product from step 1 above (ALA-1) (226 mg, 1 Eq, 1.27 mmol) in conc. $H_2SO_4$ (5 mL) were added $Ag_2SO_4$ (398 mg, 1 Eq, 1.28 mmol) and $Br_2$ (245 mg, 1.2 Eq, 1.53 mmol) at rt. The resulting mixture was stirred for 12 h at 80° C. The mixture was allowed to cool down to rt. The reaction was then quenched by the addition of 10 mL of ice water at 0° C. The crude product was purified by reverse flash column chromatography with the following conditions: Column, C18; mobile phase, water (0.1% $NH_4HCO_3$) and MeCN (20% MeCN up to 30% in 10 min); Detector, UV 254/220 nm. This resulted in the sub-title compound (ALA-2) (150 mg, 0.59 mmol, 46%, 92% Purity) as a yellow solid. m/z 256.0/258.0 $(M+H)^+$ (ES+).

Step 3: Methyl 7-bromo-3-oxo-1,2-dihydroisoindole-5-carboxylate (ALA-3)

To a stirred solution of the product from step 2 above (ALA-2) (150 mg, 1 Eq, 0.59 mmol) in MeOH (10 mL) were added $SOCl_2$ (209 mg, 3 Eq, 1.76 mmol) in portions at 0° C. under nitrogen atmosphere. The resulting mixture was stirred for 2 hours at 80° C. under nitrogen atmosphere. The mixture was allowed to cool down to rt and then concentrated in vacuo. The residue was purified by TLC with DCM/MeOH (12/1) to afford the sub-title compound (ALA-3) (150 mg, 0.56 mmol, 95%, 92% Purity) as a yellow solid. m/z 270.0/272.0 $(M+H)^+$ (ES+)

Step 4: 4-Bromo-6-(hydroxymethyl)-2,3-dihydroisoindol-1-one (ALA-4)

To a stirred solution of the product from step 3 above (ALA-3) (150 mg, 1 Eq, 0.56 mmol) in THF (10 mL) was added DIBAL-H (g) in THF (5.6 mL, 1.0 M, 10 Eq, 5.60 mmol) in portions at 0° C. under nitrogen atmosphere. The resulting mixture was stirred for 15 min at 0° C. under nitrogen atmosphere. The reaction was then quenched by the addition of 3 mL of ice water at 0° C. and then concentrated in vacuo. The residue was purified by TLC with DCM/MeOH (10/1) to afford the sub-title compound (ALA-4) (90 mg, 0.37 mmol, 67%, 90% Purity) as a white solid. m/z 242.0/244.0 $(M+H)^+$ (ES+)

Step 5: 4-{2-[4-Bromo-6-(hydroxymethyl)-1-oxo-3H-isoindol-2-yl]-6-cyclopropylpyridin-4-yl}-3-(4-methyl-1,2,4-triazol-3-yl)benzonitrile (ALA-5)

To a stirred solution of the product from step 4 above (ALA-4) (90 mg, 1 Eq, 0.37 mmol), intermediate (AEG-2) (250 mg, 2 Eq, 0.74 mmol) and Cs$_2$CO$_3$ (243 mg, 2 Eq, 0.74 mmol) in dioxane (10 mL) were added Ruphos (69 mg, 0.4 Eq, 0.15 mmol) and RuPhos Palladacycle Gen.3 (62 mg, 0.2 Eq, 74 µmol) at rt under nitrogen atmosphere. The resulting mixture was stirred for 2 h at 60° C. under nitrogen atmosphere. The mixture was cooled to rt, diluted with water and extracted with EtOAc (3×20 mL). The combined organic layers were washed with brine (2×20 mL), dried (Na$_2$SO$_4$). After filtration, the filtrate was concentrated in vacuo. The residue was purified by TLC with DCM/MeOH (12/1). The crude product was purified by Prep-HPLC with the following conditions (Column: Xselect CSH C18 OBD Column 30*150 mm, 5 µm; Mobile Phase A: water (0.1% FA), Mobile Phase B: MeCN; Flow rate: 60 mL/min; Gradient: 25% B to 55% B in 10 min; Wave Length: 254 nm) to afford the title compound (ALA-5) (6.1 mg, 11 µmol, 30%, 98.3% Purity) as a white solid. m/z 541.1/543.1 (M+H)$^+$ (ES+). $^1$H NMR (400 MHz, DMSO-d6) δ 8.54 (s, 1H), 8.25-8.18 (m, 2H), 7.97 (d, J=1.4 Hz, 1H), 7.90-7.82 (m, 2H), 7.74 (s, 1H), 6.88 (d, J=1.5 Hz, 1H), 5.50 (t, J=5.8 Hz, 1H), 4.91 (s, 2H), 4.62 (d, J=5.8 Hz, 2H), 3.47 (s, 3H), 2.13-2.04 (m, 1H), 1.07-0.92 (m, 4H).

Example 336: Synthesis of 4-[2-(4-Bromo-6-{[(2-methoxyethyl)amino]methyl}-1-oxo-3H-isoindol-2-yl)-6-cyclopropylpyridin-4-yl]-3-(4-methyl-1,2,4-triazol-3-yl)benzonitrile (ALB-2)

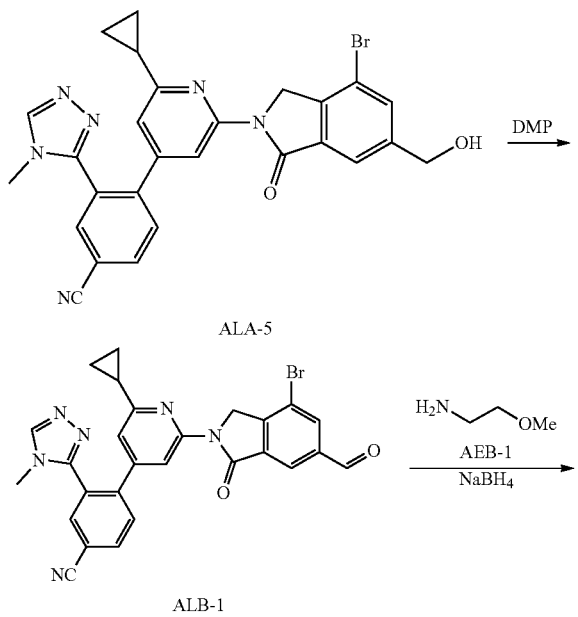

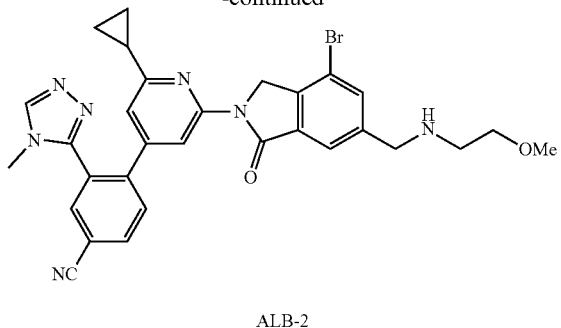

Step 1: 4-[2-(4-Bromo-6-formyl-1-oxo-3H-isoindol-2-yl)-6-cyclopropylpyridin-4-yl]-3-(4-methyl-1,2,4-triazol-3-yl)benzonitrile (ALB-1)

A solution of compound (ALA-5) (60 mg, 1 Eq, 0.11 mmol) and DMP (62 mg, 1.3 Eq, 0.14 mmol) in DCM (5 mL) was stirred for 1 h at rt. The resulting mixture was filtered; the filter cake was washed with DCM (3×3 mL). The filtrate was concentrated in vacuo. The crude product was used in the next step directly without further purification. m/z 539.1/541.1 (M+H)$^+$ (ES+).

Step 2: 4-[2-(4-Bromo-6-{[(2-methoxyethyl)amino]methyl}-1-oxo-3H-isoindol-2-yl)-6-cyclopropylpyridin-4-yl]-3-(4-methyl-1,2,4-triazol-3-yl)benzonitrile (ALB-2)

A solution of the product from step 1 above (ALB-1) (60 mg, 1 Eq, 0.11 mmol) and 2-methoxyethan-1-amine (AEB-1) (13 mg, 1.5 Eq, 0.17 mmol) in MeOH (5 mL) was stirred for 1 h at 60° C. To the above mixture was added NaBH$_4$ (8 mg, 2 Eq, 0.22 mmol) in portions at 0° C. The resulting mixture was stirred for 1 h at rt. The reaction was then quenched by the addition of MeOH (2 mL) at 0° C. and then concentrated in vacuo. The residue was purified by TLC with DCM/MeOH (10/1). The crude product was purified by Prep-HPLC with the following conditions (Column: Xselect CSH C18 OBD Column 30*150 mm, 5 µm, n; Mobile Phase A: Water (0.1% FA), Mobile Phase B: MeCN; Flow rate: 60 mL/min; Gradient: 2% B to 32% B in 10 min; Wave Length: 254 nm) to afford the title compound (ALB-2) (9.7 mg, 16 µmol, 15%, 99.5% Purity) as a white solid. m/z 598.0/600.0 (M+H)$^+$ (ES+). $^1$H NMR (400 MHz, DMSO-d6) δ 8.54 (s, 1H), 8.25-8.16 (m, 2H), 7.96 (d, J=1.3 Hz, 1H), 7.90-7.85 (m, 2H), 7.76 (s, 1H), 6.89 (d, J=1.4 Hz, 1H), 4.90 (s, 2H), 3.84 (s, 2H), 3.48 (s, 3H), 3.40 (t, J=5.6 Hz, 2H), 3.24 (s, 3H), 2.64 (t, J=5.6 Hz, 2H), 2.11-2.04 (m, 1H), 1.02-0.94 (m, 4H).

Example 337: Synthesis of 4-{2-Cyclopropyl-6-[4-fluoro-6-({[(2R,3R)-3-methoxybutan-2-yl]amino}methyl)-1-oxo-3H-isoindol-2-yl]pyridin-4-yl}-3-(4-methyl-1,2,4-triazol-3-yl)benzonitrile (ALC-2)

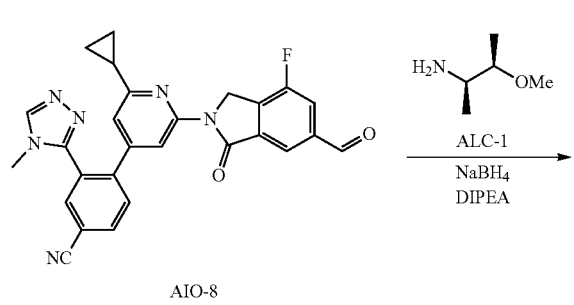

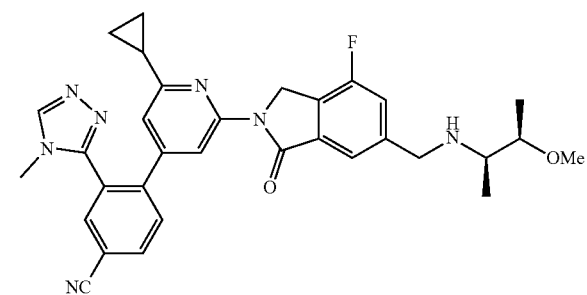

A solution of intermediate (AIO-8) (30 mg, 1 Eq, 63 µmol), DIPEA (32 mg, 4 Eq, 0.25 mmol) and (2R,3R)-3-methoxybutan-2-amine (ALC-1) (8.4 mg, 1.3 Eq, 82 µmol) in MeOH (8 mL) was stirred overnight at 60° C. To the above mixture was added NaBH₄ (12 mg, 5 Eq, 0.32 mmol) at 0° C. The resulting mixture was stirred for additional 1 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 µm; Mobile Phase A: water (0.1% $NH_4HCO_3$+0.1% $NH_3·H_2O$), Mobile Phase B: MeCN; Flow rate: 60 mL/min; Gradient: 43% B to 53% B in 9 min; Wave Length: 254/220 nm; RT: 8.45) to afford the title compound (ALC-2) (8.0 mg, 14 µmol, 23%, 99.8% Purity) as a white solid. m/z 566.2 (M+H)⁺ (ES+). ¹H NMR (400 MHz, Methanol-d4) δ 8.49 (s, 1H), 8.16-8.06 (m, 2H), 8.03 (d, J=1.4 Hz, 1H), 7.92 (d, J=8.1 Hz, 1H), 7.65 (d, J=1.2 Hz, 1H), 7.47-7.41 (m, 1H), 6.95 (d, J=1.4 Hz, 1H), 5.06 (s, 2H), 3.98 (d, J=13.8 Hz, 1H), 3.81 (d, J=13.8 Hz, 1H), 3.50 (s, 3H), 3.34 (s, 3H), 3.21-3.10 (m, 1H), 2.63-2.51 (m, 1H), 2.09-1.98 (m, 1H), 1.11 (d, J=6.1 Hz, 3H), 1.07-0.97 (m, 7H).

Example 338: Synthesis of 4-[2-Cyclopropyl-6-(6-{[(2-fluoro-2-methylpropyl)amino]methyl}-1-oxo-3H-isoindol-2-yl)pyridin-4-yl]-3-(4-methyl-1,2,4-triazol-3-yl)benzonitrile (ALD-2)

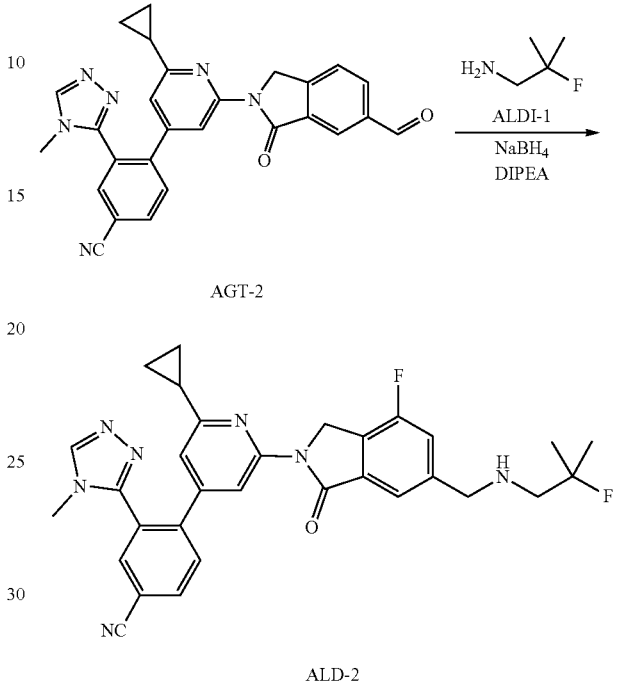

A solution of 2-fluoro-2-methylpropan-1-amine (ALD-1) (7 mg, 1.2 Eq, 78 µmol) in MeOH (20 mL) was treated with DIPEA (34 mg, 4 Eq, 0.26 mmol) for 5 min at rt followed by the addition of intermediate (AGT-2) (30 mg, 1 Eq, 65 µmol) at rt. The resulting mixture was stirred overnight at 60° C. The mixture was allowed to cool down to rt. To the above mixture was added NaBH₄ (12 mg, 5 Eq, 0.33 mmol) at 0° C. The resulting mixture was stirred for additional 1 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 µm; Mobile Phase A: water (0.1% $NH_4HCO_3$+0.1% $NH_3·H_2O$), Mobile Phase B: MeCN; Flow rate: 60 mL/min; Gradient: 45% B to 52% B in 9 min; Wave Length: 254/220 nm; RT: 8.83) to afford the title compound (ALD-2) (6.1 mg, 11 µmol, 17%, 99.8% Purity) as a white solid. m/z 536.1 (M+H)⁺ (ES+). ¹H NMR (400 MHz, Methanol-d4) δ 8.50 (s, 1H), 8.14-8.07 (m, 2H), 8.05 (d, J=1.4 Hz, 1H), 7.92 (d, J=8.0 Hz, 1H), 7.81 (d, J=1.5 Hz, 1H), 7.69-7.66 (m, 1H), 7.60 (d, J=7.8 Hz, 1H), 6.92 (d, J=1.4 Hz, 1H), 5.02 (s, 2H), 3.91 (s, 2H), 3.50 (s, 3H), 2.68 (d, J=19.6 Hz, 2H), 2.07-1.99 (m, 1H), 1.39 (s, 3H), 1.33 (s, 3H), 1.06-0.95 (m, 4H).

Example 339: Synthesis of 4-{2-Cyclopropyl-6-[6-(hydroxymethyl)-1-oxo-3H-pyrrolo[3,4-c]pyridin-2-yl] pyridin-4-yl}-3-(4-methyl-1,2,4-triazol-3-yl)benzonitrile (ALE-7)

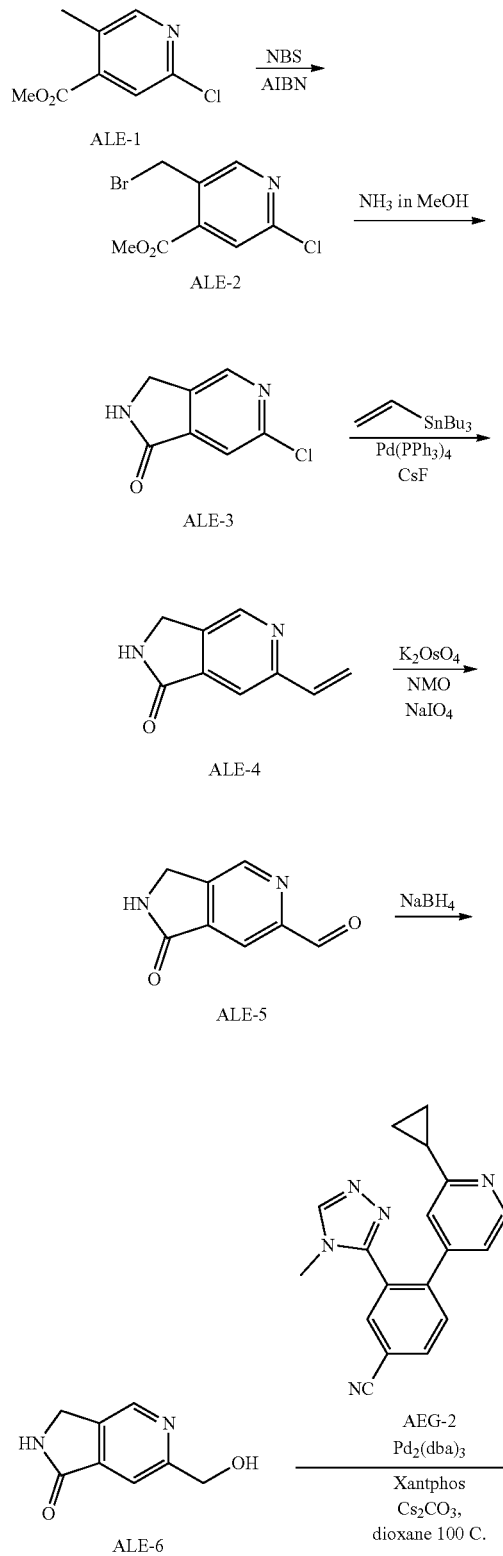

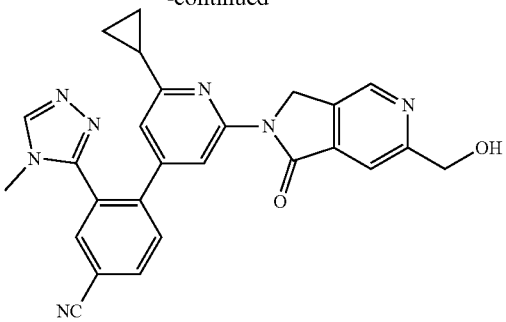

ALE-7

Step 1: Methyl 5-(bromomethyl)-2-chloropyridine-4-carboxylate (ALE-2)

To a stirred solution of methyl 2-chloro-5-methylpyridine-4-carboxylate (ALE-1) (900 mg, 1 Eq, 4.85 mmol) and NBS (949 mg, 1.1 Eq, 5.33 mmol) in (trifluoromethyl)benzene (25 mL) was added AIBN (239 mg, 0.3 Eq, 1.45 mmol) at rt under nitrogen atmosphere. The resulting mixture was stirred overnight at 80° C. under nitrogen atmosphere. The mixture was cooled to rt and concentrated in vacuo. The residue was purified by Prep-TLC with EtOAc/petroleum ether (1/5) to afford the sub-title compound (ALE-2) (920 g, 3.5 mmol, 40%, 95% Purity) as a light yellow oil. m/z 263.9/265.9 (M+H)$^+$ (ES+).

Step 2: 6-Chloro-2H,3H-pyrrolo[3,4-c] pyridin-1-one (ALE-3)

A solution of the product from step 1 above (ALE-2) (920 mg, 1 Eq, 3.48 mmol) in NH$_3$/MeOH (10 mL, 7 M) was stirred for 2 h at rt under nitrogen atmosphere. The resulting mixture was concentrated in vacuo. The crude product was purified by reverse flash column chromatography with the following conditions: Column, C18; mobile phase, water (0.1% NH$_4$HCO$_3$) and MeCN (0% MeCN up to 20% in 20 min); Detector, UV 254/220 nm. The product-containing fractions were combined and concentrated in vacuo. This resulted in the sub-title compound (ALE-3) (400 mg, 2.38 mmol, 58%, 90% Purity) as an off-white solid. m/z 169.0/171.0 (M+H)$^+$ (ES+).

Step 3: 6-Ethenyl-2H,3H-pyrrolo[3,4-c] pyridin-1-one (ALE-4)

To a stirred solution of the product from step 2 above (ALE-3) (240 mg, 1 Eq, 1.42 mmol) and tributyl(ethenyl)stannane (542 mg, 1.2 Eq, 1.71 mmol) in dioxane (12 mL) was added CsF (433 mg, 2 Eq, 2.85 mmol) at rt under nitrogen atmosphere. To the above mixture was added Pd(PPh$_3$)$_4$ (329 mg, 0.2 Eq, 0.29 mmol) at rt under nitrogen atmosphere. The resulting mixture was stirred for additional overnight at 100° C. under nitrogen atmosphere. The mixture was allowed to cool down to rt. The resulting mixture was concentrated in vacuo. The crude product was purified by reverse flash column chromatography with the following conditions: Column, C18; mobile phase, water (0.1% FA) and MeCN (0% MeCN up to 20% in 30 min); Detector, UV 254/220 nm. The product-containing fractions were combined and concentrated in vacuo. This resulted in the subtitle compound (ALE-4) (180 mg, 1.12 mmol, 73%, 92% Purity) as a white solid. m/z 161.1 (M+H)+ (ES+).

Step 4: 1-Oxo-2H,3H-pyrrolo[3,4-c]pyridine-6-carbaldehyde (ALF-5)

To a stirred solution of the product from step 3 above (ALE-4) (180 mg, 1 Eq, 1.12 mmol) and 2-hydroxypropane-1,2,3-tricarboxylic acid (281 mg, 1.3 Eq, 1.46 mmol) in t-BuOH (5 mL) and H$_2$O (5 mL) were added NMO (171 mg, 1.3 Eq, 1.46 mmol) and K$_2$OsO$_4$ (41 mg, 0.1 Eq, 0.11 mmol) at rt under nitrogen atmosphere. The resulting mixture was stirred for 2 h at rt under nitrogen atmosphere. To the above mixture was added NaIO$_4$ (481 mg, 2 Eq, 2.25 mmol) at 0° C. The resulting mixture was stirred for 1 h at rt under nitrogen atmosphere. The mixture was concentrated in vacuo. The residue was purified by Prep-TLC with DCM/MeOH (5/1) to afford the sub-title compound (ALE-5) (80 mg, 0.49 mmol, 42%, 90% Purity) as a white solid. m/z 163.0 (M+H)+ (ES+).

Step 5: 6-(Hydroxymethyl)-2H,3H-pyrrolo[3,4-c]pyridin-1-one (ALE-6)

To a stirred solution of the product from step 4 above (ALE-5) (80 mg, 1 Eq, 0.49 mmol) in MeOH (8 mL) was added NaBH$_4$ (93 mg, 5 Eq, 2.47 mmol) at 0° C. under nitrogen atmosphere. The resulting mixture was stirred for 2 h at rt under nitrogen atmosphere. The reaction was then quenched by the addition of MeOH (2 mL) at 0° C. The mixture was concentrated in vacuo. The residue was purified by Prep-TLC with DCM/MeOH (15/1) to afford the sub-title compound (ALE-6) (40 mg, 0.24 mmol, 44%, 93% Purity) as an off-white solid. m/z 165.1 (M+H)+ (ES+).

Step 6: 4-{2-Cyclopropyl-6-[6-(hydroxymethyl)-1-oxo-3H-pyrrolo[3,4-c]pyridin-2-yl]pyridin-4-yl}-3-(4-methyl-1,2,4-triazol-3-yl)benzonitrile (ALE-7)

To a stirred solution of intermediate (AEG-2) (30 mg, 1 Eq, 89 μmol) and the product from step 5 above (ALE-6) (16 mg, 1.1 Eq, 98 μmol) in dioxane (5 mL) was added Cs$_2$CO$_3$ (58 mg, 2 Eq, 0.18 mmol) at rt under nitrogen atmosphere. To the above mixture was added RuPhos (17 mg, 0.4 Eq, 36 μmol) and RuPhos Palladacycle Gen.3 (15 mg, 0.2 Eq, 18 μmol) at rt under nitrogen atmosphere. The resulting mixture was stirred for additional 1 h at 100° C. under nitrogen atmosphere. The mixture was allowed to cool down to rt. The resulting mixture was concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 24% B to 34% B in 9 min; Wave Length: 254/220 nm; RT: 8.92) to afford the title compound (ALE-7) (3.5 mg, 7.6 μmol, 8.4%, 99.8% Purity) as a white solid. m/z 464.0 (M+H)+ (ES+). $^1$H NMR (400 MHz, DMSO-d6) δ 8.92 (d, J=1.2 Hz, 1H), 8.55 (s, 1H), 8.22 (d, J=7.2 Hz, 2H), 7.98 (d, J=1.4 Hz, 1H), 7.95-7.86 (m, 1H), 7.77 (d, J=1.2 Hz, 1H), 6.95 (d, J=1.4 Hz, 1H), 5.62 (t, J=5.9 Hz, 1H), 5.12 (s, 2H), 4.68 (d, J=5.9 Hz, 2H), 3.49 (s, 3H), 2.10-1.97 (m, 1H), 1.02-0.90 (m, 4H).

Example 340: Synthesis of 4-[2-(6-{[(Cyclobutylmethyl)amino]methyl}-1-oxo-3H-pyrrolo[3,4-c]pyridin-2-yl)-6-cyclopropylpyridin-4-yl]-3-(4-methyl-1,2,4-triazol-3-yl)benzonitrile (ALF-2)

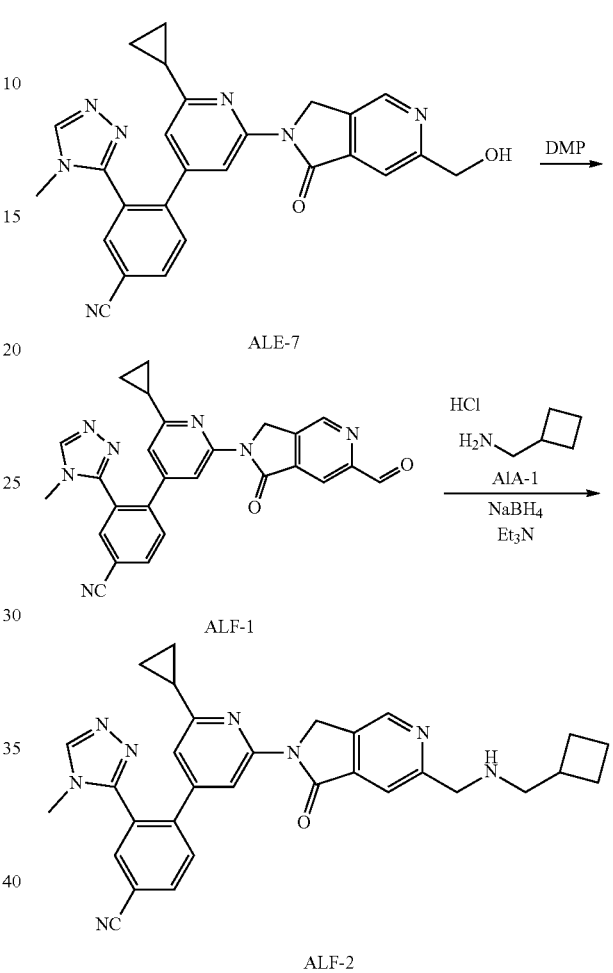

Step 1: 4-(2-Ethyl-6-{6-formyl-1-oxo-3H-pyrrolo[3,4-c]pyridin-2-yl}pyridin-4-yl)-3-(4-methyl-1,2,4-triazol-3-yl)benzonitrile (ALF-1)

To a stirred solution of compound (ALE-7) (50 mg, 1 Eq, 0.11 mmol) in DCM (5 mL) was added DMP (23 mg, 0.5 Eq, 54 μmol) at rt under nitrogen atmosphere. The resulting mixture was stirred for 1 h at rt under nitrogen atmosphere. The resulting mixture was concentrated in vacuo. The residue was purified by Prep-TLC with DCM/MeOH (10/1) to afford the sub-title compound (ALF-1) (50 mg, 0.11 mmol, 98%, 94% Purity) as an off-white solid. m/z 462.2 (M+H)+ (ES+).

Step 2: 4-[2-(6-{1[(Cyclobutylmethyl)amino]methyl}-1-oxo-3H-pyrrolo[3,4-c]pyridin-2-yl)-6-cyclopropylpyridin-4-yl]-3-(4-methyl-1,2,4-triazol-3-yl)benzonitrile (ALF-2)

To a stirred solution of the product from step 1 above (ALF-1) (30 mg, 1 Eq, 65 μmol) and DIPEA (25 mg, 3 Eq, 0.20 mmol) in MeOH (5 mL) was added 1-cyclobutylmethanamine, HCl (AIA-1) (12 mg, 1.5 Eq, 98 µmol) at rt under nitrogen atmosphere. The resulting mixture was stirred overnight at rt under nitrogen atmosphere. To the above mixture was added NaBH₄ (12 mg, 5 Eq, 0.33 mmol) at 0° C. The resulting mixture was stirred for additional 2 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 µm; Mobile Phase A: water (0.1% NH₄HCO₃+0.1% NH₃·H₂O), Mobile Phase B: MeCN; Flow rate: 60 mL/min; Gradient: 40% B to 60% B in 8 min; Wave Length: 254/220 nm; RT: 7.4) to afford the title compound (ALF-2) (7.5 mg, 14 µmol, 21%, 97.1%) as a white solid. m/z 531.1 (M+H)⁺ (ES+). ¹H NMR (400 MHz, DMSO-d6) δ 8.92 (d, J=1.1 Hz, 1H), 8.55 (s, 1H), 8.22 (d, J=7.1 Hz, 2H), 7.97 (d, J=1.4 Hz, 1H), 7.92-7.82 (m, 1H), 7.78 (d, J=1.1 Hz, 1H), 6.95 (d, J=1.4 Hz, 1H), 5.11 (s, 2H), 3.89 (s, 2H), 3.49 (s, 3H), 2.55 (d, J=7.2 Hz, 2H), 2.47-2.37 (m, 1H), 2.10-1.95 (m, 3H), 1.90-1.74 (m, 2H), 1.70-1.58 (m, 2H), 1.07-0.89 (m, 4H).

Example 341: Synthesis of 3'-cyclopropyl-5'-[4-fluoro-6-({[(2R)-1-methoxypropan-2-yl]amino}methyl)-1-oxo-3H-isoindol-2-yl]-2-(4-methyl-1,2,4-triazol-3-yl)-[1,1'-biphenyl]-4-carbonitrile (ALG-3)

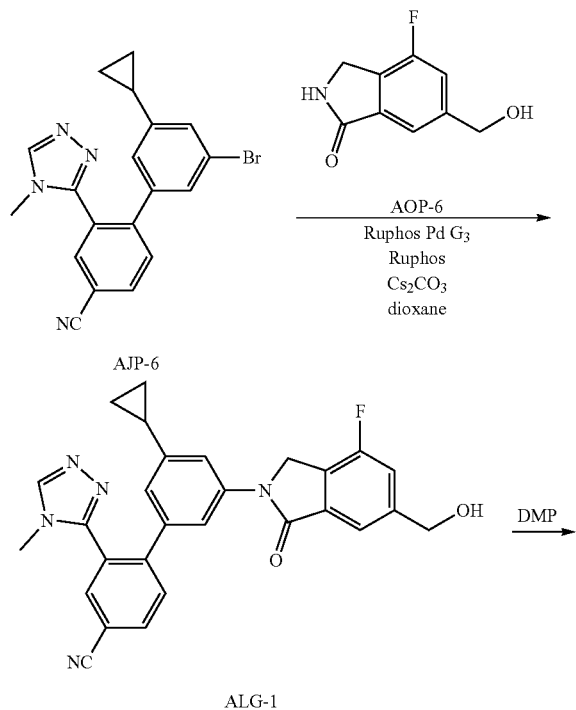

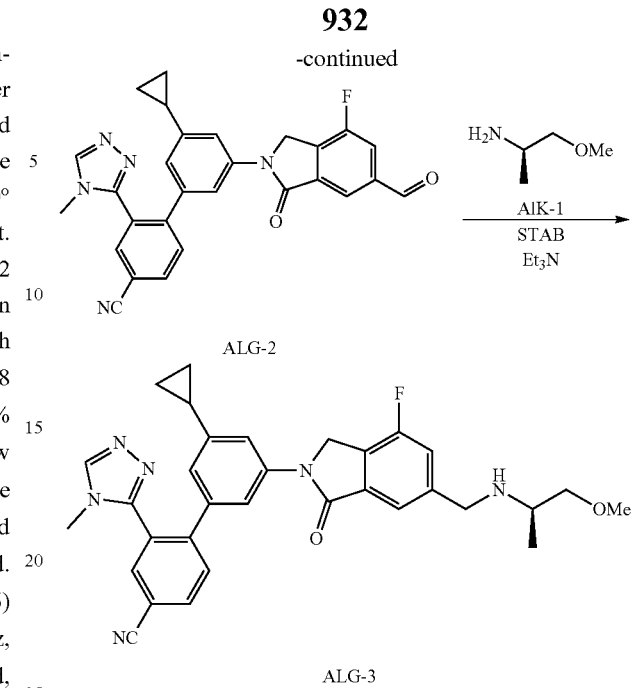

Step 1: 3'-Cyclopropyl-5'-[4-fluoro-6-(hydroxymethyl)-1-oxo-3H-isoindol-2-yl]-2-(4-methyl-1,2,4-triazol-3-yl)-[1,1'-biphenyl]-4-carbonitrile (ALG-1)

To a stirred mixture of intermediate (AJP-6) (160 mg, 1 Eq, 0.42 mmol), intermediate (AIO-6) (92 mg, 1.2 Eq, 0.51 mmol) and Cs₂CO₃ (412 mg, 3 Eq, 1.27 mmol) in dioxane (10 mL) were added RuPhos (79 mg, 0.4 Eq, 0.17 mmol) and RuPhos Palladacycle Gen.3 (71 mg, 0.2 Eq, 0.08 mmol) at rt under nitrogen atmosphere. The resulting mixture was stirred for 2 h at 100° C. under nitrogen atmosphere. The mixture was cooled to rt and concentrated in vacuo. The residue was purified by Prep-TLC with DCM/MeOH (10/1) to afford the sub-title compound (ALG-1) (100 mg, 0.21 mmol, 49%, 95% Purity) as a yellow solid. m/z 480.2 (M+H)⁺ (ES+)

Step 2: 3'-Cyclopropyl-5'-(4-fluoro-6-formyl-1-oxo-3H-isoindol-2-yl)-2-(4-methyl-1,2,4-triazol-3-yl)-[1,1'-biphenyl]-4-carbonitrile (ALG-2)

To a stirred mixture of the product from step 1 above (ALG-1) (40 mg, 1 Eq, 83 µmol) in DCM (10 mL) was added DMP (42 mg, 1.2 Eq, 0.10 mmol) at rt. The resulting mixture was stirred for 1 h at rt. The resulting mixture was filtered; the filter cake was washed with DCM (3×3 mL). The filtrate was concentrated in vacuo. The crude product was used in the next step directly without further purification. m/z 478.2 (M+H)⁺ (ES+)

Step 3: 3'-Cyclopropyl-5'-[4-fluoro-6-({[(2R)-1-methoxypropan-2-yl]amino}methyl)-1-oxo-3H-isoindol-2-yl]-2-(4-methyl-1,2,4-triazol-3-yl)-[1,1'-biphenyl]-4-carbonitrile (ALG-3)

A solution of the product from step 2 above (ALG-2) (35 mg, 1 Eq, 73 µmol) in MeOH (12 mL) was treated with (2R)-1-methoxypropan-2-amine (AIK-1) (9.8 mg, 1.5 Eq, 0.11 mmol) for 2 h at 60° C. under nitrogen atmosphere. The mixture was allowed to cool down to rt. To the above mixture was added NaBH₄ (6 mg, 2 Eq, 0.15 mmol) in portions at 0° C. The resulting mixture was stirred for 1 h at rt under air atmosphere. The reaction was then quenched by the addition of MeOH (2 mL) at 0° C. The resulting mixture was concentrated in vacuo. The residue was purified by Prep-TLC with DCM/MeOH (8/1). The crude product was purified by Prep-HPLC with the following conditions (Column: XBridge Prep OBD C18 Column, 30*150 mm, 5 µm; Mobile Phase A: water (0.1% NH₄HCO₃+0.1% NH₃·H₂O), Mobile Phase B: MeCN; Flow rate: 60 mL/min; Gradient: 38% B to 48% B in 8 min; Wave Length: 254/220 nm; RT: 7.67) to afford the title compound (ALG-3) (9.6 mg, 13 µmol, 24%, 99.6% Purity) as a white solid. m/z 551.1 (M+H)⁺ (ES+). ¹H NMR (400 MHz, DMSO-d6) δ 8.48 (s, 1H), 8.17 (d, J=8.1, 1.8 Hz, 1H), 8.09 (d, J=1.8 Hz, 1H), 7.87 (d, J=8.1 Hz, 1H), 7.73 (d, J=1.8 Hz, 1H), 7.62 (s, 2H), 7.51 (d, J=10.0 Hz, 1H), 6.45 (s, 1H), 5.01 (s, 2H), 3.96-3.75 (m, 2H), 3.27 (d, J=9.3, 6.3 Hz, 4H), 3.18 (d, J=9.3, 5.5 Hz, 1H), 3.11 (s, 3H), 2.74 (p, J=6.2 Hz, 1H), 1.88 (t, J=8.6, 5.0 Hz, 1H), 1.03-0.87 (m, 5H), 0.58-0.46 (m, 2H).

Example 342: Synthesis of 3'-Cyclopropyl-5'-[4-fluoro-6-({[(2S)-1-methoxypropan-2-yl]amino}methyl)-1-oxo-3H-isoindol-2-yl]-2-(4-methyl-1,2,4-triazol-3-yl)-[1,1'-biphenyl]-4-carbonitrile (ALH-1)

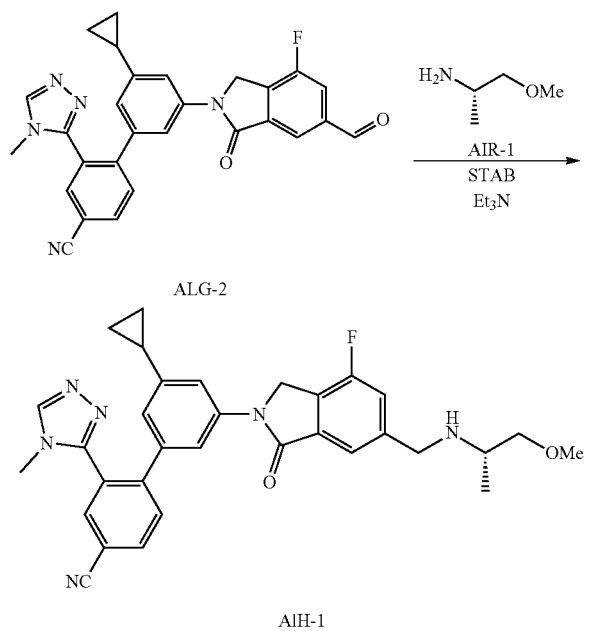

A solution of intermediate (ALG-2) (35 mg, 1 Eq, 73 µmol) in MeOH (12 mL) was treated with (2S)-1-methoxypropan-2-amine (AIR-1) (10 mg, 1.5 Eq, 0.11 mmol) for 2 h at 60° C. under nitrogen atmosphere. The mixture was allowed to cool down to rt. To the above mixture was added NaBH₄ (6 mg, 2 Eq, 0.15 mmol) in portions at 0° C. The resulting mixture was stirred for 1 h at rt under air atmosphere. The reaction was then quenched by the addition of MeOH (2 mL) at 0° C. The resulting mixture was concentrated in vacuo. The residue was purified by Prep-TLC with DCM/MeOH (8/1). The crude product was purified by Prep-HPLC with the following conditions (Column: XBridge Prep OBD C18 Column, 30*150 mm, 5 µm; Mobile Phase A: water (0.1% NH₄HCO₃+0.1% NH₃·H₂O), Mobile Phase B: MeCN; Flow rate: 60 mL/min; Gradient: 38% B to 48% B in 8 min; Wave Length: 254/220 nm; RT: 7.67) to afford 3 the title compound (ALH-1) (8.8 mg, 16 µmol, 22%, 99.8% Purity) as a white solid. m/z 551.1 (M+H)⁺ (ES+). ¹H NMR (400 MHz, DMSO-d6) δ 8.48 (d, J=2.5 Hz, 1H), 8.18 (d, J=8.1, 1.9 Hz, 1H), 8.10 (d, J=1.9 Hz, 1H), 7.87 (d, J=8.1 Hz, 1H), 7.77-7.71 (m, 1H), 7.62 (t, J=1.8 Hz, 2H), 7.51 (d, J=10.0 Hz, 1H), 6.45 (t, J=1.6 Hz, 1H), 5.02 (s, 2H), 3.92-3.81 (m, 2H), 3.30-3.26 (m, 1H), 3.24 (d, J=2.3 Hz, 3H), 3.18 (d, J=9.4, 5.5 Hz, 1H), 3.12 (d, J=2.5 Hz, 3H), 2.76-2.71 (m, 1H), 1.87 (d, J=8.3, 4.8 Hz, 1H), 1.01-0.88 (m, 5H), 0.56-0.48 (m, 2H).

Example 343: Synthesis of 4-{2-Cyclopropyl-6-[4-fluoro-6-({[(3R,4R)-4-hydroxyoxolan-3-yl]amino}methyl)-1-oxo-3H-isoindol-2-yl]pyridin-4-yl}-3-(4-methyl-1,2,4-triazol-3-yl)benzonitrile (ALI-2)

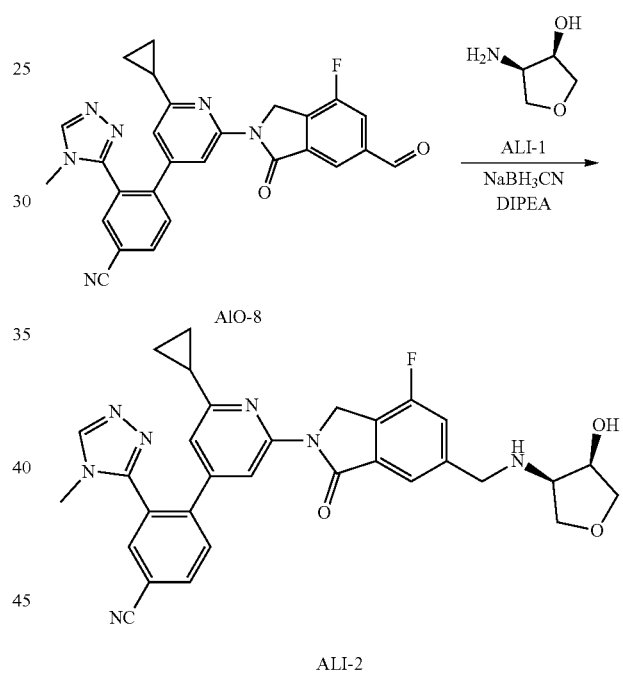

A solution of intermediate (AIO-8) (30 mg, 63 µmol, 1 Eq), DIPEA (32 mg, 4 Eq, 0.25 mmol) and (3R,4R)-4-aminooxolan-3-ol (ALI-1) (8 mg, 1.3 Eq 82 µmol) in MeOH (8 mL) was stirred overnight at 60° C. The mixture was allowed to cool down to rt. To the above mixture was added NaBH₃CN (79 mg, 20 Eq, 1.26 mmol) at rt. The resulting mixture was stirred for additional 2 days at 60° C. The mixture was cooled to rt and concentrated in vacuo. The crude product was purified by Prep-HPLC with the following conditions (Column: Xselect CSH C18 OBD Column 30*150 mm 5 µm; Mobile Phase A: water (0.1% FA), Mobile Phase B: MeCN; Flow rate: 60 mL/min; Gradient: 19% B to 26% B in 10 min; Wave Length: 254 nm; RT: 9.5) to afford the title compound (ALI-2) (4.2 mg, 7.4 µmol, 12%, 98.1% Purity) as a white solid. m/z 566.0 (M+H)⁺ (ES+). ¹H NMR (400 MHz, Methanol-d4) δ 8.49 (s, 1H), 8.16-8.06 (m, 2H), 8.02 (d, J=1.4 Hz, 1H), 7.92 (d, J=8.0 Hz, 1H), 7.69 (s, 1H), 7.48 (d, J=9.7 Hz, 1H), 6.95 (d, J=1.4 Hz, 1H), 5.07 (s, 2H), 4.31-4.24 (m, 1H), 4.01 (d, J=13.6 Hz, 1H), 3.97-3.85 (m, 3H), 3.82-3.76 (m, 1H), 3.50 (d, J=9.7 Hz, 4H), 3.38-3.32 (m, 1H), 2.09-1.99 (m, 1H), 1.09-0.95 (m, 4H).

Example 344: Synthesis of 4-(2-Cyclopropyl-6-{6-[(3-fluoroazetidin-1-yl)methyl]-1-oxo-3H-isoindol-2-yl}pyridin-4-yl)-3-(4-methyl-1,2,4-triazol-3-yl)benzonitrile (ALJ-1)

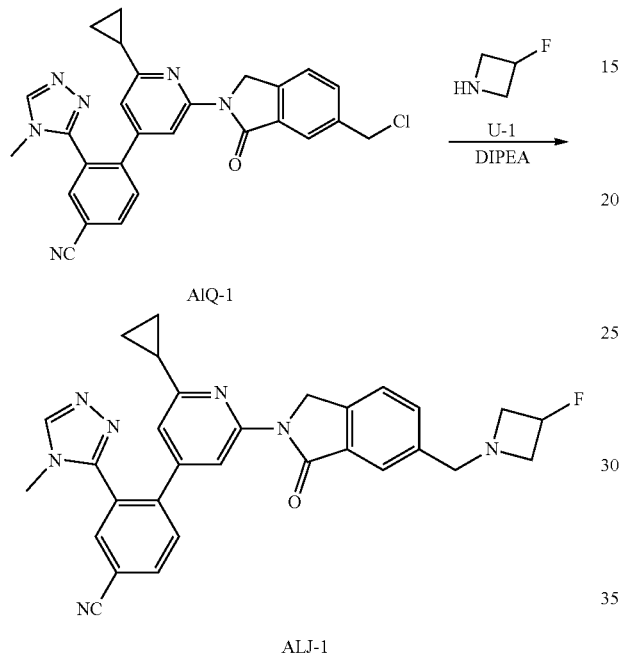

A solution of 3-fluoroazetidine (U-1) (8 mg, 1.2 Eq, 0.11 mmol) in DCM (12 mL) was treated with DIPEA (48 mg, 4 Eq, 0.38 mmol) for 5 min at rt followed by the addition of intermediate (AIQ-1) (45 mg, 1 Eq, 94 μmol) at rt. The resulting mixture was stirred overnight at 60° C. The mixture was allowed to cool down to rt. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% $NH_4HCO_3$+0.1% $NH_3 \cdot H_2O$), Mobile Phase B: MeCN; Flow rate: 60 mL/min; Gradient: 45% B to 50% B in 8 min; Wave Length: 254/220 nm; RT: 7.43) to afford the title compound (ALJ-1) (26.7 mg, 51 μmol, 55%, 99.6% Purity) as a white solid. m/z 520.1 $(M+H)^+$ (ES+). $^1$H NMR (400 MHz, Methanol-d4) δ 8.50 (s, 1H), 8.14-8.08 (m, 2H), 8.04 (d, J=1.4 Hz, 1H), 7.92 (d, J=8.0 Hz, 1H), 7.75 (s, 1H), 7.61 (d, J=1.2 Hz, 2H), 6.92 (d, J=1.4 Hz, 1H), 5.25-5.18 (m, 1H), 5.01 (s, 2H), 3.79 (s, 2H), 3.68-3.59 (m, 2H), 3.50 (s, 3H), 3.36-3.33 (m, 1H), 3.29-3.25 (m, 1H), 2.06-1.99 m, 1H), 1.05-0.95 (m, 4H).

Example 345: Synthesis of 4-{2-[6-(2-Aminopropan-2-yl)-1-oxo-3H-isoindol-2-yl]-6-cyclopropylpyridin-4-yl}-3-(4-methyl-1,2,4-triazol-3-yl)benzonitrile (ALK-9)

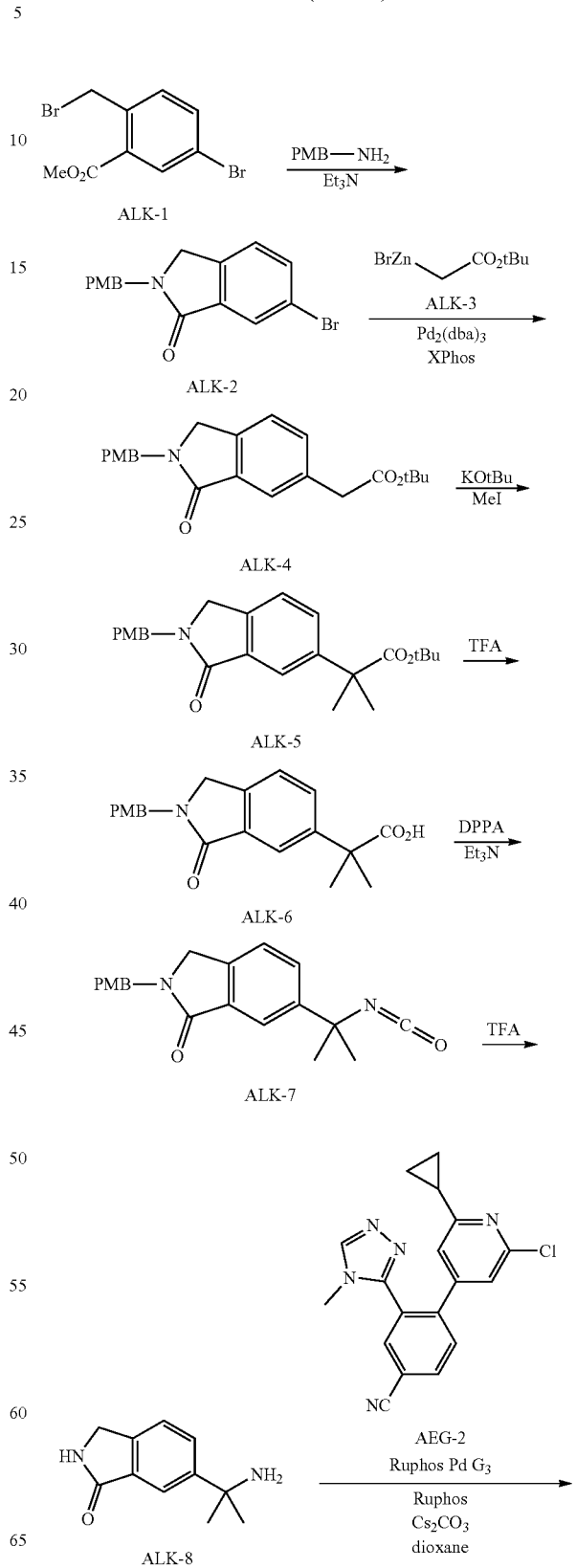

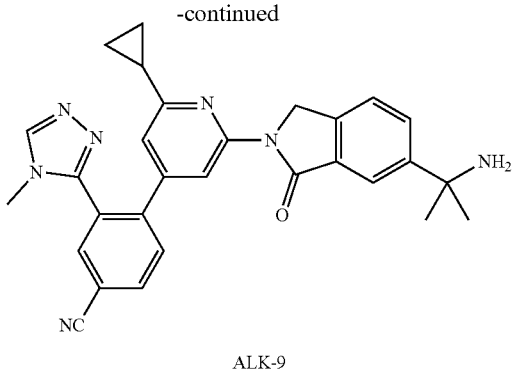

ALK-9

Step 1: 6-Bromo-2-[(4-methoxyphenyl) methyl]-3H-isoindol-1-one (ALK-2)

A solution of methyl 5-bromo-2-(bromomethyl) benzoate (ALK-1) (3.00 g, 1 Eq, 9.74 mmol) and Et₃N (1.97 g, 2 Eq, 19.5 mmol) and PMB-NH₂ (2.00 g, 1.5 Eq, 14.6 mmol) in MeOH (50 mL) was stirred overnight at 80° C. The mixture was cooled to rt and concentrated in vacuo. The residue was applied on a silica gel column chromatography with petroleum ether/EtOAc (3/1) to afford the sub-title compound (ALK-2) (2.5 g, 7.55 mmol, 77%, 90% Purity) as a Brown yellow solid. m/z 332.0/334.0 (M+H)⁺ (ES+)

Step 2: tert-Butyl 2-{2-[(4-methoxyphenyl)methyl]-3-oxo-1H-isoindol-5-yl}acetate (ALK-4)

A solution of the product from step 1 above (ALK-2) (500 mg, 1 Eq, 1.51 mmol) and Pd₂(dba)₃ (69 mg, 0.05 Eq, 75 μmol) and XPhos (72 mg, 0.1 Eq, 0.15 mmol) in THF (15 mL) was stirred for 30 min at rt under nitrogen atmosphere. To the above mixture was added tert-butyl 2-(zinciolambda2-bromanyl)acetate (ALK-3) (1.96 g, 5 Eq, 7.53 mmol) at rt under nitrogen atmosphere. The resulting mixture was stirred for additional overnight at 80° C. under nitrogen atmosphere. The mixture was cooled to rt and concentrated in vacuo. The residue was purified by Prep-TLC with EtOAc/petroleum ether (1/2) to afford the sub-title compound (ALK-4) (400 mg, 1.09 mmol, 72%, 94% Purity) as an off-white solid. m/z 368.2 (M+H)⁺ (ES+)

Step 3: tert-Butyl 2-{2-[(4-methoxyphenyl)methyl]-3-oxo-1H-isoindol-5-yl}-2-methylpropanoate (ALK-5)

To a stirred solution of the product from step 2 above (ALK-4) (400 mg, 1 Eq, 1.09 mmol) and t-BuOK (366 mg, 3 Eq, 3.27 mmol) in THF (10 mL) were added CH₃I (773 mg, 5 Eq, 5.45 mmol) at 0° C. The resulting mixture was stirred for 1 h at 0° C. The reaction was then quenched by the addition of 5 mL of MeOH at 0° C. The resulting mixture was concentrated in vacuo. The residue was purified by Prep-TLC with EtOAc/petroleum ether (1/3) to afford the sub-title compound (ALK-5) (230 mg, 0.58 mmol, 53%, 92% Purity) as a yellow oil. m/z 396.2 (M+H)⁺ (ES+)

Step 4: 2-{2-[(4-Methoxyphenyl)methyl]-3-oxo-1H-isoindol-5-yl}-2-methylpropanoic acid (ALK-6)

A solution of the product from step 3 above (ALK-5) (230 mg, 1 Eq, 0.58 mmol) and TFA (2 mL) in DCM (6 mL) was stirred for 2 h at rt. The resulting mixture was diluted with water and extracted with DCM (3×80 mL). The combined organic layers were washed with brine (2×80 mL), dried (Na₂SO₄). After filtration, the filtrate was concentrated in vacuo. This resulted in the sub-title compound (ALK-6) (140 mg, 0.32 mmol, 71%, 94% Purity) as a brown-yellow oil. m/z 340.2 (M+H)⁺ (ES+)

Step 5: 6-(2-Isocyanatopropan-2-yl)-2-[(4-methoxyphenyl)methyl]-3H-isoindol-1-one (ALK-7)

To a stirred solution of the product from step 5 above (ALK-6) (130 mg, 1 Eq, 0.38 mmol) and DPPA (264 mg, 2.5 Eq, 0.96 mmol) in DCM (6 mL) were added Et₃N (97 mg, 2.5 Eq, 0.96 mmol) at rt. The resulting mixture was stirred for 2 h at rt. The residue was purified by Prep-TLC with EtOAc/petroleum ether (1/3) to afford the sub-title compound (ALK-7) (80 mg, 0.24 mmol, 62%, 90% Purity) as a brown-yellow solid. m/z 337.2 (M+H)⁺ (ES+)

Step 6: 6-(2-Aminopropan-2-yl)-2,3-dihydroisoindol-1-one (ALK-8)

A solution of the product from step 5 above (ALK-7) (80 mg, 1 Eq, 0.24 mmol) in TFA (10 mL) was stirred overnight at 100° C. The mixture was allowed to cool down to rt. The crude product was purified by reverse flash column chromatography with the following conditions: Column, C18; mobile phase, water (0.1% NH₄HCO₃) and MeCN (0% MeCN up to 70% in 20 min); Detector, UV 254/220 nm. This resulted in the sub-title compound (ALK-8) (30 mg, 0.16 mmol, 66%, 92% Purity) as a yellow solid. m/z 191.1 (M+H)⁺ (ES+)

Step 7: 4-{2-[6-(2-Aminopropan-2-yl)-1-oxo-3H-isoindol-2-yl]-6-cyclopropylpyridin-4-yl}-3-(4-methyl-1,2,4-triazol-3-yl)benzonitrile (ALK-9)

To a stirred solution of the product from step 6 above (ALK-8) (30 mg, 1 Eq, 0.16 mmol), intermediate (AEG-2) (58 mg, 1.1 Eq, 0.17 mmol) and Cs₂CO₃ (103 mg, 2 Eq, 0.32 mmol) in dioxane (5 mL) were added RuPhos Palladacycle Gen.3 (26 mg, 0.2 Eq, 32 μmol) and RuPhos (29 mg, 0.4 Eq, 63 μmol) at rt under nitrogen atmosphere. The resulting mixture was stirred for 2 h at 100° C. under nitrogen atmosphere. The mixture was cooled to rt and concentrated in vacuo. The crude product was purified by Prep-HPLC with the following conditions (Column: XSelect CSH Prep C18 OBD Column, 19*250 mm, 5 μm; Mobile Phase A: water (0.1% NH₄HCO₃+0.1% NH₃·H₂O), Mobile Phase B: MeCN; Flow rate: 60 mL/min; Gradient: 38% B to 48% B in 8 min; Wave Length: 254/220 nm) to afford the title compound (ALK-9) (5.3 mg, 11 μmol, 6.8%, 99.5% Purity) as a white solid. m/z 490.1 (M+H)⁺ (ES+). ¹H NMR (400 MHz, DMSO-d6) δ 8.54 (s, 1H), 8.21 (d, J=6.8 Hz, 2H), 7.97-7.84 (m, 4H), 7.63 (d, J=8.0 Hz, 1H), 6.92 (d, J=1.4 Hz, 1H), 4.99 (s, 2H), 3.50 (s, 3H), 2.10-2.02 (m, 1H), 1.44 (s, 6H), 1.04-0.94 (m, 4H).

Example 346: Synthesis of 4-[2-Cyclopropyl-6-(6-{2-[(cyclopropylmethyl)amino] propan-2-yl}-1-oxo-3H-isoindol-2-yl)pyridin-4-yl]-3-(4-methyl-1,2,4-triazol-3-yl)benzonitrile (ALL-2)

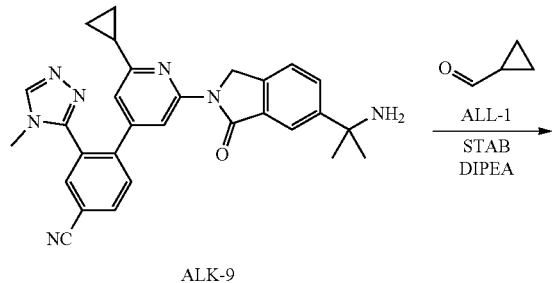

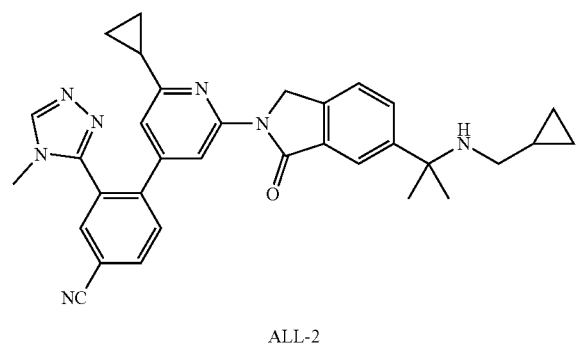

To a stirred solution of compound (ALK-9) (30 mg, 1 Eq, 61 μmol) and cyclopropanecarbaldehyde (ALL-1) (13 mg, 3 Eq, 0.18 mmol) in MeOH (5 mL) was added DIPEA (48 mg, 6 Eq, 0.37 mmol) at rt. The resulting mixture was stirred for 4 h at 60° C. The mixture was allowed to cool down to rt. To the above mixture was added NaBH(OAc)$_3$ (65 mg, 5 Eq, 0.31 mmol) at rt. The resulting mixture was stirred for additional overnight at rt. The resulting mixture was concentrated in vacuo. The crude product was purified by Prep-HPLC with the following conditions (Column: Xselect CSH C18 OBD Column 30*150 mm, 5 μm, n; Mobile Phase A: water (0.1% NH$_4$HCO$_3$+0.1% NH$_3$·H$_2$O), Mobile Phase B: MeCN; Flow rate: 60 mL/min; Gradient: 31% B to 61% B in 10 min; Wave Length: 254 nm) to afford the title compound (ALL-2) (6.6 mg, 12 μmol, 20%, 98.8% Purity) as a white solid. m/z 544.1 (M+H)$^+$ (ES+). $^1$H NMR (400 MHz, Methanol-d4) δ 8.50 (s, 1H), 8.15-8.08 (m, 2H), 8.05 (d, J=1.4 Hz, 1H), 7.96-7.91 (m, 1H), 7.90-7.88 (m, 1H), 7.84-7.80 (m, 1H), 7.62 (d, J=8.1 Hz, 1H), 6.93 (d, J=1.5 Hz, 1H), 5.02 (s, 2H), 3.51 (s, 3H), 2.13-1.99 (m, 3H), 1.53 (s, 6H), 1.08-0.94 (m, 4H), 0.92-0.81 (m, 1H), 0.48-0.40 (m, 2H), 0.05-0.02 (m, 2H).

Example 347: Synthesis of 4-{2-[4-Fluoro-6-(hydroxymethyl)-1-oxo-3H-isoindol-2-yl]-6-(trifluoromethyl)pyridin-4-yl}-3-(4-methyl-1,2,4-triazol-3-yl)benzonitrile (ALM-3)

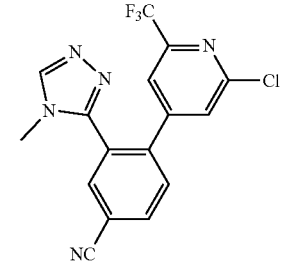

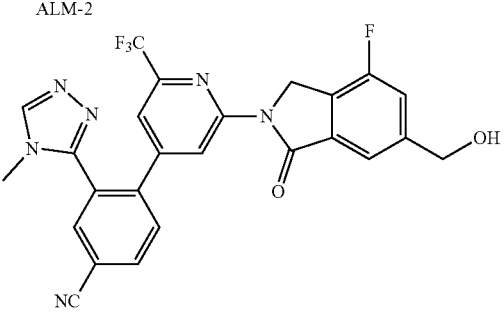

Step 1: 4-[2-Chloro-6-(trifluoromethyl)pyridin-4-yl]-3-(4-methyl-1,2,4-triazol-3-yl)benzonitrile (ALM-2)

To a stirred solution of intermediate (ADG-1) (100 mg, 1 Eq, 0.38 mmol) and 2-chloro-6-(trifluoromethyl)pyridin-4-ylboronic acid (ALM-1) (94 mg, 1.1 Eq, 0.42 mmol) in THF (10 mL) and H$_2$O (1 mL) was added Na$_2$CO$_3$ (121 mg, 3 Eq, 1.14 mmol) at rt under nitrogen atmosphere. To the above mixture was added Pd(PPh$_3$)$_4$ (44 mg, 0.1 Eq, 38 μmol) at rt under nitrogen atmosphere. The resulting mixture was stirred for additional 2 h at 80° C. under nitrogen atmosphere. The mixture was allowed to cool down to rt. The resulting mixture was concentrated in vacuo. The residue was purified by Prep-TLC with DCM/MeOH (15/1) to afford the sub-title compound (ALM-2) (68 mg, 0.19 mmol, 47%, 95% Purity) as an off-white solid. m/z 364.0/366.0 (M+H)$^+$ (ES+)

Step 2: 4-{2-[4-Fluoro-6-(hydroxymethyl)-1-oxo-3H-isoindol-2-yl]-6-(trifluoromethyl)pyridin-4-yl}-3-(4-methyl-1,2,4-triazol-3-yl)benzonitrile (ALM-3)

To a stirred solution of the product from step 1 above (ALM-2) (30 mg, 1 Eq, 0.08 mmol) and intermediate (AIO-6) (22 mg, 1.5 Eq, 0.12 mmol) in dioxane (5 mL) was added $Cs_2CO_3$ (54 mg, 2 Eq, 0.16 mmol) at rt under nitrogen atmosphere. To the above mixture was added RuPhos (16 mg, 0.4 Eq, 33 μmol) and RuPhos Palladacycle Gen.3 (14 mg, 0.2 Eq, 16 μmol) at rt under nitrogen atmosphere. The resulting mixture was stirred for additional 1 h at 100° C. under nitrogen atmosphere. The mixture was allowed to cool down to rt. The resulting mixture was concentrated in vacuo. The residue was purified by Prep-TLC with DCM/MeOH (15/1). The crude product was purified by Prep-HPLC with the following conditions (Column: XBridge Prep OBD C18 Column, 30*150 mm, 5 μm; Mobile Phase A: water (0.1% $NH_4HCO_3$+0.1% $NH_3 \cdot H_2O$), Mobile Phase B: MeCN; Flow rate: 60 mL/min; Gradient: 38% B to 48% B in 9 min; Wave Length: 254/220 nm; RT: 8.3) to afford the title compound (ALM-3) (3.9 mg, 7.7 μmol, 9.3%, 99.8% Purity) as a white solid. m/z 509.0 $(M+H)^+$ (ES+). $^1$H NMR (400 MHz, DMSO-d6) δ 8.58 (s, 1H), 8.49 (s, 1H), 8.37-8.24 (m, 2H), 7.99 (d, J=8.1 Hz, 1H), 7.65 (s, 1H), 7.50 (d, J=10.3 Hz, 2H), 5.53 (t, J=5.8 Hz, 1H), 5.14 (s, 2H), 4.63 (d, J=5.7 Hz, 2H), 3.59 (s, 3H).

Example 348: Synthesis of 4-[2-(4-Fluoro-6-{[(2-methoxyethyl)amino]methyl}-1-oxo-3H-isoindol-2-yl)-6-(trifluoromethyl)pyridin-4-yl]-3-(4-methyl-1,2,4-triazol-3-yl)benzonitrile (ALN-2)

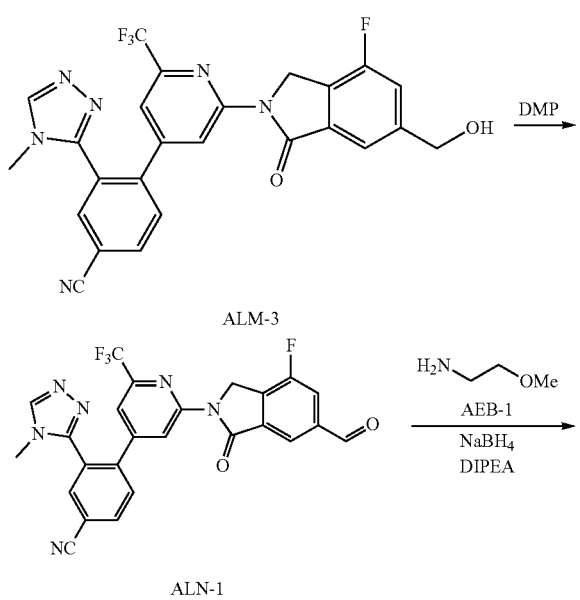

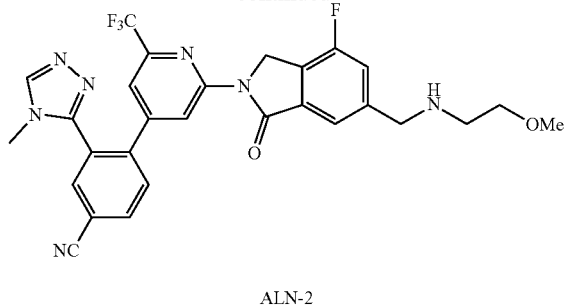

ALN-2

Step 1: 4-[2-(4-Fluoro-6-formyl-1-oxo-3H-isoindol-2-yl)-6-(trifluoromethyl) pyridin-4-yl]-3-(4-methyl-1,2,4-triazol-3-yl) benzonitrile (ALN-1)

To a stirred solution of compound (ALM-3) (55 mg, 1 Eq, 0.11 mmol) in DCM (5 mL) was added DMP (69 mg, 1.5 Eq, 0.16 mmol) at rt under nitrogen atmosphere. The resulting mixture was stirred for 1 h at rt under nitrogen atmosphere. The resulting mixture was filtered; the filter cake was washed with DCM (3×2 mL). The filtrate was concentrated in vacuo. This resulted in the sub-title compound (ALN-1) (50 mg, 99 μmol, 86%, 96% Purity) as an off-white solid. m/z 507.1 $(M+H)^+$ (ES+).

Step 2: 4-[2-(4-Fluoro-6-{[(2-methoxyethyl)amino]methyl}-1-oxo-3H-isoindol-2-yl)-6-(trifluoromethyl)pyridin-4-yl]-3-(4-methyl-1,2,4-triazol-3-yl)benzonitrile (ALN-2)

To a stirred solution of the product from step 1 above (ALN-1) (35 mg, 1 Eq, 0.07 mmol) and 2-methoxyethan-1-amine (AEB-1) (8 mg, 1.5 Eq, 0.10 mmol) in MeOH (5 mL) was added DIPEA (27 mg, 3 Eq, 0.21 mmol) at rt under nitrogen atmosphere. The resulting mixture was stirred overnight at rt under nitrogen atmosphere. To the above mixture was added $NaBH_4$ (13 mg, 5 Eq, 0.35 mmol) at 0° C. The resulting mixture was stirred for additional 2 h at rt. The reaction was then quenched by the addition of MeOH (2 mL) at 0° C. The resulting mixture was concentrated in vacuo. The crude product was purified by Prep-HPLC with the following conditions (Column: Xselect CSH C18 OBD Column 30*150 mm, 5 μm, n; Mobile Phase A: water (0.1% FA), Mobile Phase B: MeCN; Flow rate: 60 mL/min; Gradient: 2% B to 30% B in 10 min; Wave Length: 254 nm; RT: 7.7) to afford the title compound (ALN-2) (13.1 mg, 23 μmol, 33%, 99.8% Purity) as a white solid. m/z 566.1 $(M+H)^+$ (ES+). $^1$H NMR (400 MHz, DMSO-d6) δ 8.58 (s, 1H), 8.47 (d, J=1.3 Hz, 1H), 8.32 (d, J=1.7 Hz, 1H), 8.28-8.22 (m, 1H), 7.99 (d, J=8.1 Hz, 1H), 7.67 (s, 1H), 7.55 (d, J=9.9 Hz, 1H), 7.50 (d, J=1.3 Hz, 1H), 5.12 (s, 2H), 3.84 (s, 2H), 3.59 (s, 3H), 3.40 (t, J=5.7 Hz, 2H), 3.24 (s, 3H), 2.63 (t, J=5.7 Hz, 2H).

Example 349: Synthesis of 4-{2-Cyclopropyl-6-[4-fluoro-6-({[(1-methylcyclobutyl)methyl]amino}methyl)-1-oxo-3H-isoindol-2-yl]pyridin-4-yl}-3-(4-methyl-1,2,4-triazol-3-yl)benzonitrile (ALO-2)

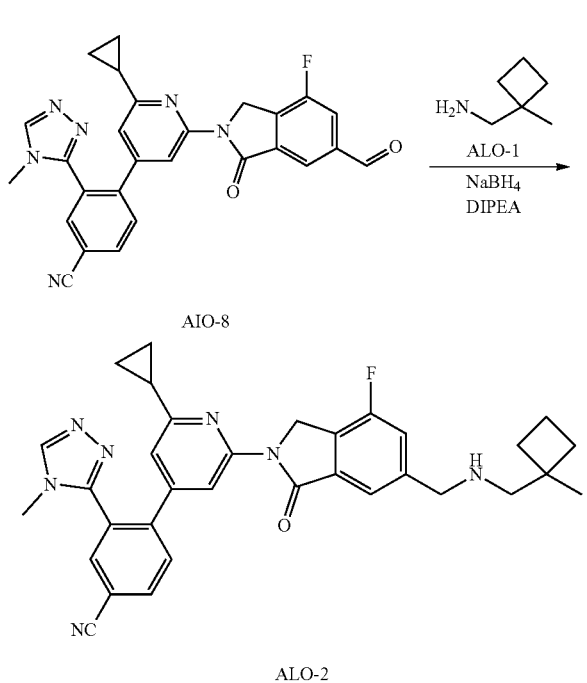

A solution of 1-(1-methylcyclobutyl)methanamine (ALO-1) (13 mg, 1.3 Eq, 0.14 mmol) and DIPEA (54 mg, 4 Eq, 0.42 mmol) in MeOH (8 mL) was stirred for 5 min at rt. To the above mixture was added intermediate (AIO-8) (50 mg, 1 Eq, 0.10 mmol) at rt. The resulting mixture was stirred for additional overnight at 60° C. The mixture was allowed to cool down to rt. To the above mixture was added NaBH$_4$ (20 mg, 5 Eq, 0.52 mmol) at 0° C. The resulting mixture was stirred for additional 1 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 60% B to 73% B in 8 min; Wave Length: 254/220 nm; RT: 7.57) to afford the title compound (ALO-2) (7.2 mg, 13 μmol, 12%, 99.5% Purity) as a white solid. m/z 562.1 (M+H)$^+$ (ES+). $^1$H NMR (400 MHz, Methanol-d4) δ 8.49 (s, 1H), 8.16-8.06 (m, 2H), 8.03 (d, J=1.4 Hz, 1H), 7.92 (d, J=8.0 Hz, 1H), 7.66 (s, 1H), 7.46 (d, J=9.8 Hz, 1H), 6.94 (d, J=1.5 Hz, 1H), 5.06 (s, 2H), 3.89 (s, 2H), 3.49 (s, 3H), 2.52 (s, 2H), 2.10-1.99 (m, 1H), 1.98-1.75 (m, 4H), 1.74-1.60 (m, 2H), 1.17 (s, 3H), 1.07-0.92 (m, 4H).

Example 350: Synthesis of 4-{2-Cyclopropyl-6-[6-({[(1-methylcyclobutyl)methyl]amino}methyl)-1-oxo-3H-isoindol-2-yl]pyridin-4-yl}-3-(4-methyl-1,2,4-triazol-3-yl)benzonitrile (ALP-1)

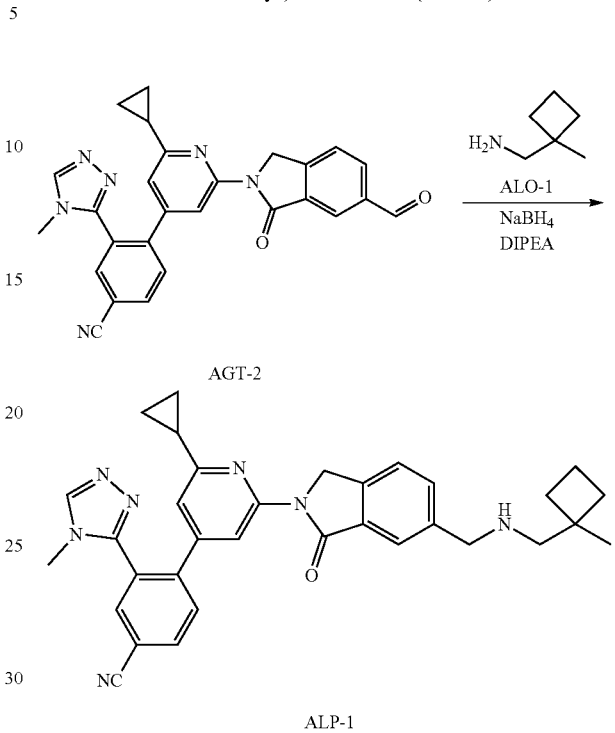

A solution of 1-(1-methylcyclobutyl)methanamine (ALO-1) (8.0 mg, 1.2 Eq, 78 μmol) in MeOH (12 mL) was treated with DIPEA (34 mg, 4 Eq, 0.26 mmol) for 5 min at rt. To the above mixture was added intermediate (AGT-2) (30 mg, 1 Eq, 65 μmol) at rt. The resulting mixture was stirred overnight at 60° C. The mixture was allowed to cool down to rt. To the above mixture was added NaBH$_4$ (12 mg, 5 Eq, 0.33 mmol) at 0° C. The resulting mixture was stirred for additional 1 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 50% B to 65% B in 9 min; Wave Length: 254/220 nm; RT: 8.9) to afford the title compound (ALP-1) (8.5 mg, 16 μmol, 24%, 99.6% Purity) as a white solid. m/z 544.1 (M+H)$^+$ (ES+). $^1$H NMR (400 MHz, Methanol-d4) δ 8.49 (s, 1H), 8.14-8.05 (m, 3H), 7.92 (d, J=8.1 Hz, 1H), 7.81 (s, 1H), 7.71-7.59 (m, 2H), 6.91 (d, J=1.5 Hz, 1H), 5.02 (s, 2H), 3.88 (s, 2H), 3.50 (s, 3H), 2.52 (s, 2H), 2.07-1.98 (m, 1H), 1.94-1.75 (m, 4H), 1.72-1.62 (m, 2H), 1.16 (s, 3H), 1.06-0.93 (m, 4H).

Example 351: Synthesis of 4-(2-Cyclopropyl-6-{6-[(cyclopropylamino)methyl]-1-oxo-3H-isoindol-2-yl}pyridin-4-yl)-3-(4-methyl-1,2,4-triazol-3-yl)benzonitrile (ALQ-2)

Example 352: Synthesis of 4-(2-Cyclopropyl-6-{6-[(cyclopropylamino)methyl]-4-fluoro-1-oxo-3H-isoindol-2-yl}pyridin-4-yl)-3-(4-methyl-1,2,4-triazol-3-yl)benzonitrile (ALR-1)

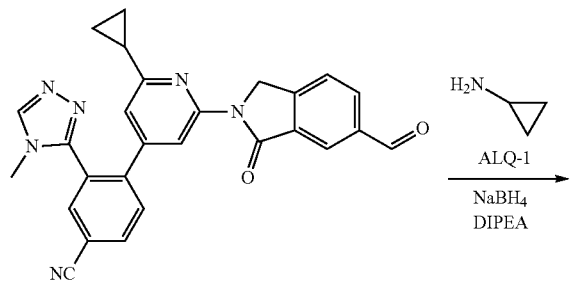

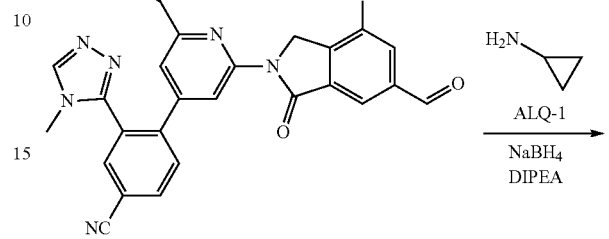

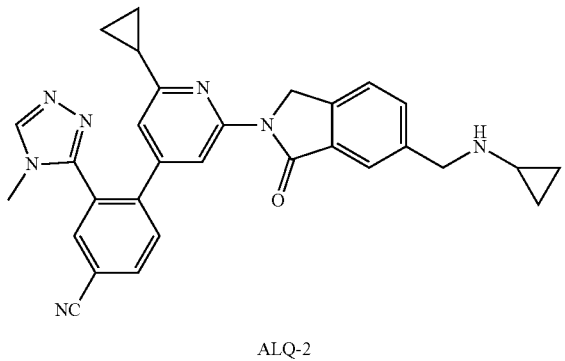

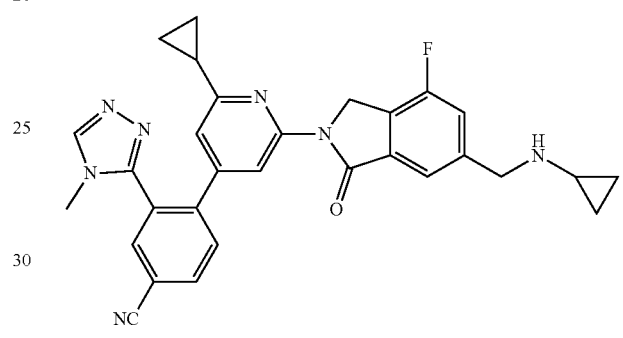

To a stirred solution of intermediate (AGT-2) (25 mg, 1 Eq, 54 µmol) and aminocyclopropane (ALQ-1) (4 mg, 1.2 Eq, 65 µmol) in MeOH (8 mL) was added DIPEA (28 mg, 4 Eq, 0.22 mmol) at rt. The resulting mixture was stirred overnight at 60° C. The mixture was allowed to cool down to rt. To the above mixture was added NaBH$_4$ (10 mg, 5 Eq, 0.27 mmol) at 0° C. The resulting mixture was stirred for additional 1 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 µm; Mobile Phase A: water (0.1% NH$_4$HCO$_3$+0.1% NH$_3$·H$_2$O), Mobile Phase B: MeCN; Flow rate: 60 mL/min; Gradient: 41% B to 51% B in 8 min; Wave Length: 254/220 nm; RT: 7.82) to afford the title compound (ALQ-2) (5.3 mg, 11 µmol, 18%, 92.9% Purity) as a white solid. m/z 502.1 (M+H)$^+$ (ES+). $^1$H NMR (400 MHz, Methanol-d4) δ 8.49 (s, 1H), 8.14-8.04 (m, 3H), 7.92 (d, J=8.0 Hz, 1H), 7.80 (s, 1H), 7.68-7.65 (m, 1H), 7.61 (d, J=7.7 Hz, 1H), 6.91 (d, J=1.4 Hz, 1H), 5.02 (s, 2H), 3.90 (s, 2H), 3.50 (s, 3H), 2.15-1.99 (m, 2H), 1.04-0.96 (m, 4H), 0.50-0.44 (m, 2H), 0.42-0.37 (m, 2H).

A solution of intermediate (AIO-8) (35 mg, 1 Eq, 73 µmol), DIPEA (38 mg, 4 Eq, 0.29 mmol) and aminocyclopropane (ALQ-1) (6.3 mg, 1.5 Eq, 0.11 mmol) in MeOH (8 mL) was stirred overnight at 60° C. The mixture was allowed to cool down to rt. To the above mixture was added NaBH$_4$ (14 mg, 5 Eq, 0.37 mmol) at 0° C. The resulting mixture was stirred for additional 1 day at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 µm; Mobile Phase A: water (0.1% NH$_4$HCO$_3$+0.1% NH$_3$·H$_2$O), Mobile Phase B: MeCN; Flow rate: 60 mL/min; Gradient: 46% B to 55% B in 8 min; Wave Length: 254/220 nm; RT: 7.55) to afford the title compound (ALR-1) (2.7 mg, 5.2 µmol, 6.6%, 92.3% Purity) as a white solid. m/z 520.1 (M+H)$^+$ (ES+). $^1$H NMR (400 MHz, Methanol-d4) δ 8.49 (s, 1H), 8.16-8.06 (m, 2H), 8.03 (d, J=1.4 Hz, 1H), 7.92 (d, J=8.1 Hz, 1H), 7.65 (s, 1H), 7.43 (d, J=9.8 Hz, 1H), 6.94 (d, J=1.5 Hz, 1H), 5.06 (s, 2H), 3.91 (s, 2H), 3.49 (s, 3H), 2.15-2.09 (m, 1H), 2.08-2.00 (m, 1H), 1.09-0.95 (m, 4H), 0.52-0.43 (m, 2H), 0.41-0.34 (m, 2H).

Example 353: Synthesis of 4-[2-Cyclopropyl-6-(6-{[(3S)-3-methylpiperidin-1-yl]methyl}-1-oxo-3H-isoindol-2-yl)pyridin-4-yl]-3-(4-methyl-1,2,4-triazol-3-yl)benzonitrile (ALS-1)

Example 354: Synthesis of 4-{2-Cyclopropyl-6-[6-({[1-(methoxymethyl)cyclopropyl]amino}methyl)-1-oxo-3H-isoindol-2-yl]pyridin-4-yl}-3-(4-methyl-1,2,4-triazol-3-yl)benzonitrile (ALT-2)

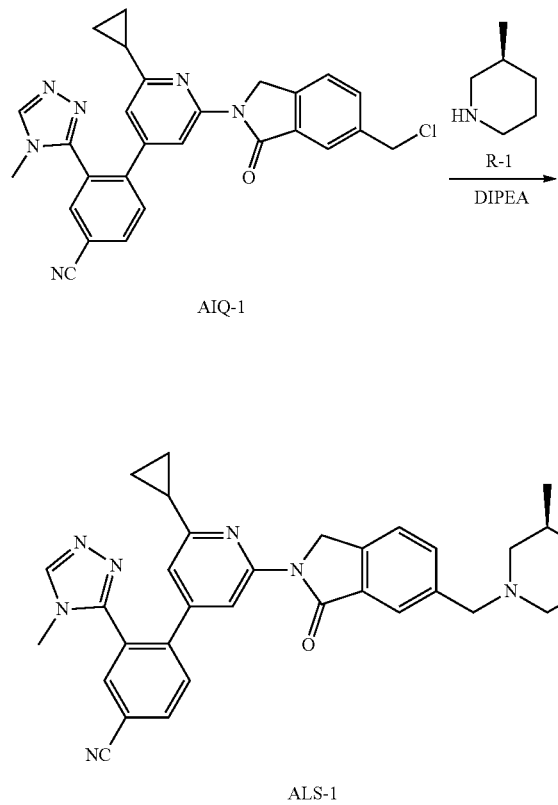

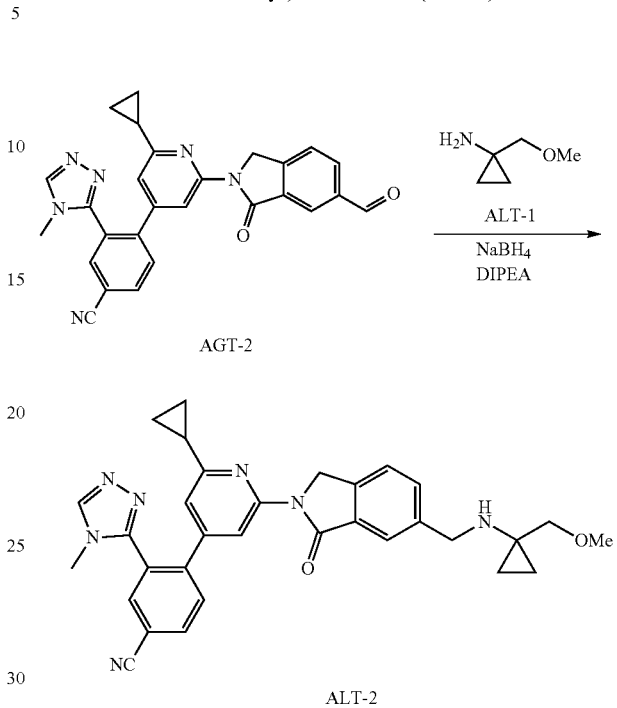

A solution of (3S)-3-methylpiperidine (R-1) (9 mg, 93 μmol, 1.5 Eq) and DIPEA (32 mg, 4 Eq, 0.25 mmol) in DCM (8 mL) was stirred for 5 min at rt. To the above mixture was added intermediate (AIQ-1) (30 mg, 1 Eq, 62 μmol) at rt. The resulting mixture was stirred for additional overnight at 60° C. The mixture was cooled to rt and concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 55% B to 65% B in 9 min; Wave Length: 254/220 nm; RT: 8.18) to afford the title compound (ALS-1) (9.5 mg, 17 μmol, 28%, 99.1% Purity) as a white solid. m/z 544.1 (M+H)$^+$ (ES+). $^1$H NMR (400 MHz, Methanol-d4) δ 8.50 (s, 1H), 8.16-8.07 (m, 2H), 8.05 (d, J=1.3 Hz, 1H), 7.92 (d, J=8.0 Hz, 1H), 7.78 (s, 1H), 7.68-7.58 (m, 2H), 6.93 (d, J=1.4 Hz, 1H), 5.03 (s, 2H), 3.61 (s, 2H), 3.51 (s, 3H), 2.88-2.77 (m, 2H), 2.07-1.91 (m, 2H), 1.76-1.52 (m, 5H), 1.06-0.93 (m, 4H), 0.85 (d, J=5.6 Hz, 4H).

A solution of 1-(methoxymethyl)cyclopropan-1-amine (ALT-1) (8.0 mg, 1.2 Eq, 78 μmol) in MeOH (8 mL) was treated with DIPEA (34 mg, 4 Eq, 0.26 mmol) for 5 min at rt followed by the addition of intermediate (AGT-2) (30 mg, 1 Eq, 65 μmol) at rt. The resulting mixture was stirred overnight at 60° C. The mixture was allowed to cool down to rt. To the above mixture was added NaBH$_4$ (12 mg, 5 Eq, 0.33 mmol) at 0° C. The resulting mixture was stirred for additional 1 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 43% B to 53% B in 8 min, 53% B; Wave Length: 254/220 nm; RT: 7.83) to afford the title compound (ALT-2) (9.6 mg, 18 μmol, 27%, 99.6% Purity) as a white solid. m/z 546.1 (M+H)$^+$ (ES+). $^1$H NMR (400 MHz, Methanol-d4) δ 8.50 (s, 1H), 8.14-8.03 (m, 3H), 7.93-7.90 (m, 1H), 7.80-7.78 (m, 1H), 7.67-7.55 (m, 2H), 6.91 (d, J=1.5 Hz, 1H), 5.00 (s, 2H), 3.93 (s, 2H), 3.50 (s, 3H), 3.41 (d, J=13.5 Hz, 5H), 2.06-1.96 (m, 1H), 1.06-0.95 (m, 4H), 0.71-0.65 (m, 2H), 0.57-0.51 (m, 2H).

Example 355: Synthesis of 4-(2-Cyclopropyl-6-{6-[(4,4-difluoropiperidin-1-yl)methyl]-1-oxo-3H-isoindol-2-yl}pyridin-4-yl)-3-(4-methyl-1,2,4-triazol-3-yl)benzonitrile (ALU-2)

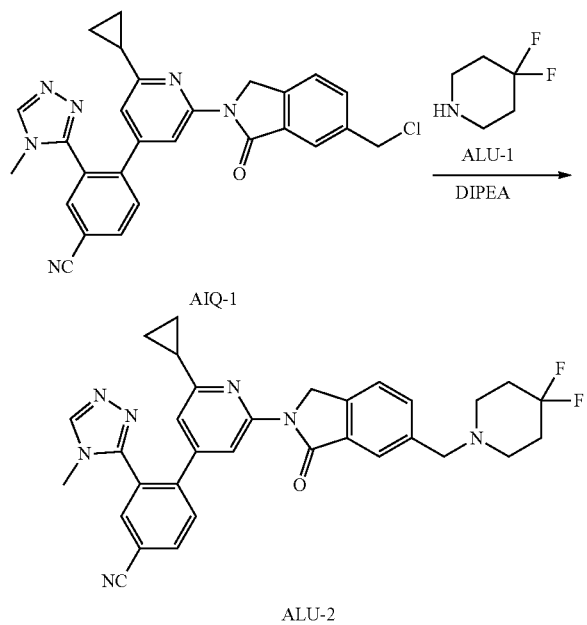

A solution of 4,4-difluoropiperidine (ALU-1) (15 mg, 1.5 Eq, 0.12 mmol) and DIPEA (43 mg, 4 Eq, 0.33 mmol) in DCM (8 mL) was stirred for 5 min at rt. To the above mixture was added intermediate (AIQ-1) (40 mg, 1 Eq, 83 μmol) at rt. The resulting mixture was stirred for additional 4 days at 60° C. The mixture was cooled to rt and concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 47% B to 57% B in 10 min; Wave Length: 254/220 nm; RT: 9.58) to afford the title compound (AIU-2) (9.0 mg, 16 μmol, 19%, 99.4% Purity) as a white solid. m/z 566.0 (M+H)$^+$ (ES+). $^1$H NMR (400 MHz, Methanol-d4) δ 8.50 (s, 1H), 8.15-8.02 (m, 3H), 7.92 (d, J=8.0 Hz, 1H), 7.81 (s, 1H), 7.69-7.58 (m, 2H), 6.93 (d, J=1.4 Hz, 1H), 5.02 (s, 2H), 3.69 (s, 2H), 3.51 (s, 3H), 2.59 (t, J=5.6 Hz, 4H), 2.09-1.92 (m, 5H), 1.08-0.94 (m, 4H).

Example 356: Synthesis of 4-[2-Cyclopropyl-6-(6-{[(2,2-difluoro-2-methoxyethyl)amino]methyl}-4-fluoro-1-oxo-3H-isoindol-2-yl)pyridin-4-yl]-3-(4-methyl-1,2,4-triazol-3-yl)benzonitrile (ALV-4)

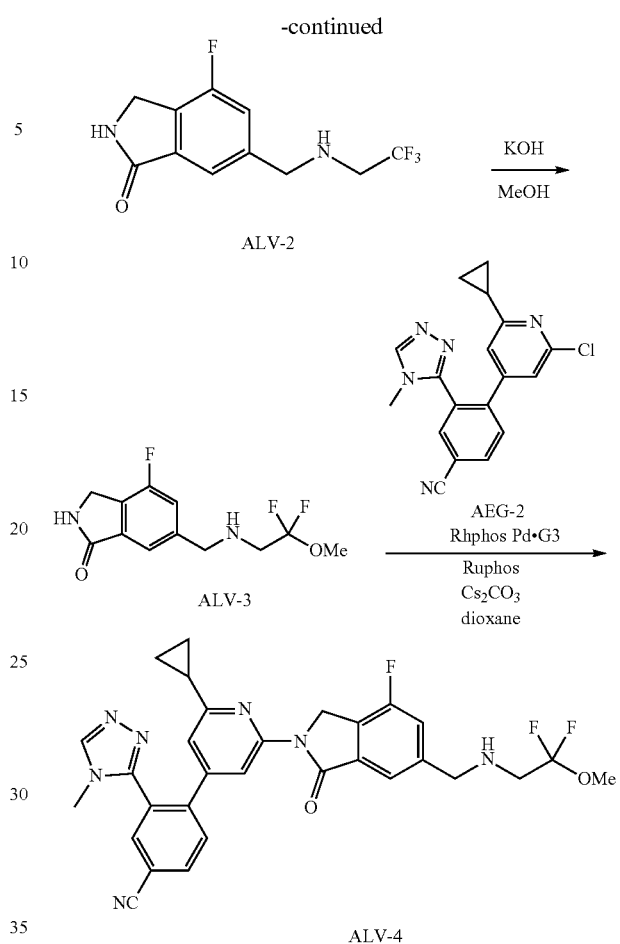

Step 1: 4-Fluoro-6-{[(2,2,2-trifluoroethyl)amino]methyl}-2,3-dihydroisoindol-1-one (ALV-2)

To a stirred solution of intermediate (AIO-5) (300 mg, 1 Eq, 1.68 mmol) and 2,2,2-trifluoroethylamine (ALV-1) (332 mg, 2 Eq, 3.35 mmol) in MeOH (20 mL) was added AcOH (6 mL) at rt under nitrogen atmosphere. To the above mixture was added NaBH$_3$CN (316 mg, 3 Eq, 5.03 mmol) at rt under nitrogen atmosphere. The resulting mixture was stirred for additional overnight at rt under nitrogen atmosphere. To the above mixture was added NaBH$_4$ (317 mg, 5 Eq, 8.38 mmol) at 0° C. The resulting mixture was stirred for additional 2 h at rt. The reaction was then quenched by the addition of MeOH (2 mL) at 0° C. The resulting mixture was concentrated in vacuo. The residue was purified by Prep-TLC with DCM/MeOH (10/1) to afford the sub-title compound (ALV-2) (260 mg, 0.99 mmol, 54%, 93% Purity) as an off-white solid. m/z 263.1 (M+H)$^+$ (ES+)

Step 2: 6-{[(2,2-Difluoro-2-methoxyethyl)amino]methyl}-4-fluoro-2,3-dihydroisoindol-1-one (ALV-3)

To a stirred solution of the product from step 1 above (ALV-2) (100 mg, 1 Eq, 0.38 mmol) in THF (5 mL) and MeOH (5 mL) was added KOH (2.14 g, 100 Eq, 38.1 mmol) at rt under nitrogen atmosphere. The resulting mixture was stirred overnight at 100° C. under nitrogen atmosphere. The mixture was cooled to rt and concentrated in vacuo. The residue was purified by Prep-TLC with DCM/MeOH (10/1) to afford the sub-title compound (ALV-3) (53 mg, 0.19 mmol, 48%, 96% Purity) as a white solid. m/z 275.1 (M+H)+ (ES+)

Step 3: 4-[2-Cyclopropyl-6-(6-{[(2,2-difluoro-2-methoxyethyl)amino]methyl}-4-fluoro-1-oxo-3H-isoindol-2-yl)pyridin-4-yl]-3-(4-methyl-1,2,4-triazol-3-yl)benzonitrile (ALV-4)

To a stirred solution of intermediate (AEG-2) (30 mg, 1 Eq, 0.09 mmol) and the product from step 2 above (ALV-3) (27 mg, 1.1 Eq, 0.10 mmol) in dioxane (5 mL) was added Cs₂CO₃ (58 mg, 2 Eq, 0.18 mmol) at rt under nitrogen atmosphere. To the above mixture were added RuPhos (17 mg, 0.4 Eq, 0.04 mmol) and RuPhos Palladacycle Gen.3 (15 mg, 0.2 Eq, 0.02 mmol) at rt under nitrogen atmosphere. The resulting mixture was stirred for additional 1 h at 100° C. under nitrogen atmosphere. The mixture was allowed to cool down to rt. The resulting mixture was filtered; the filter cake was washed with MeOH (2×3 mL). The filtrate was concentrated in vacuo. The residue was purified by Prep-TLC with DCM/MeOH (20/1). The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 47% B to 55% B in 9 min; Wave Length: 254/220 nm; RT: 8.6) to afford the title compound (ALV-4) (18.1 mg, 32 μmol, 34%, 96.6% Purity) as an off-white solid. m/z 574.0 (M+H)+ (ES+). ¹H NMR (400 MHz, DMSO-d6) δ 8.54 (s, 1H), 8.21 (d, J=6.8 Hz, 2H), 7.96 (d, J=1.3 Hz, 1H), 7.91-7.80 (m, 1H), 7.35 (d, J=1.1 Hz, 1H), 7.28 (d, J=1.2 Hz, 1H), 6.90 (d, J=1.4 Hz, 1H), 4.88 (s, 2H), 3.90 (d, J=17.4 Hz, 5H), 3.49 (s, 3H), 3.25-3.04 (m, 3H), 2.04 (d, J=6.4 Hz, 1H), 1.00-0.86 (m, 4H).

Example 357: Synthesis of -[2-Cyclopropyl-6-(4-fluoro-1-oxo-6-{[(2,2,2-trifluoroethyl)amino]methyl}-3H-isoindol-2-yl)pyridin-4-yl]-3-(4-methyl-1,2,4-triazol-3-yl)benzonitrile (ALW-1)

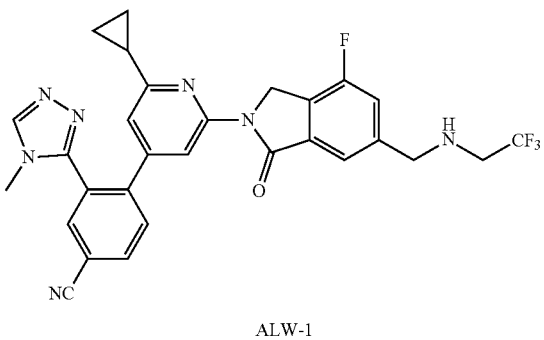

ALW-1

To a stirred solution of intermediate (AEG-2) (30 mg, 1 Eq, 0.09 mmol) and intermediate (ALV-2) (27 mg, 1.1 Eq, 0.10 mmol) in dioxane (5 mL) was added Cs₂CO₃ (58 mg, 2 Eq, 0.18 mmol) were added RuPhos (17 mg, 0.4 Eq, 0.04 mmol) and RuPhos Palladacycle Gen.3 (15 mg, 0.2 Eq, 0.02 mmol) at rt under nitrogen atmosphere. The resulting mixture was stirred for additional 1 h at 100° C. under nitrogen atmosphere. The mixture was allowed to cool down to rt. The resulting mixture was filtered; the filter cake was washed with MeOH (2×3 mL). The filtrate was concentrated in vacuo. The residue was purified by Prep-TLC with DCM/MeOH (20/1). The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 47% B to 55% B in 9 min; Wave Length: 254/220 nm; RT: 8.6) to afford the title compound (ALW-1) (17.3 mg, 31 μmol, 34%, 97.8% Purity) as a white solid. m/z 562.0 (M+H)+ (ES+). ¹H NMR (400 MHz, DMSO-d6) δ 8.54 (s, 1H), 8.26-8.14 (m, 2H), 7.95 (d, J=1.4 Hz, 1H), 7.91-7.82 (m, 1H), 7.64 (d, J=1.2 Hz, 1H), 7.54-7.48 (m, 1H), 6.93 (d, J=1.4 Hz, 1H), 5.08 (s, 2H), 3.91 (d, J=4.9 Hz, 2H), 3.48 (s, 3H), 3.26-3.13 (m, 2H), 2.12-1.98 (m, 1H), 1.02-0.93 (m, 4H).

Example 358: Synthesis of 4-{2-Cyclopropyl-6-[4,5-difluoro-6-(hydroxymethyl)-1-oxo-3H-isoindol-2-yl]pyridin-4-yl}-3-(4-methyl-1,2,4-triazol-3-yl)benzonitrile (ALX-9)

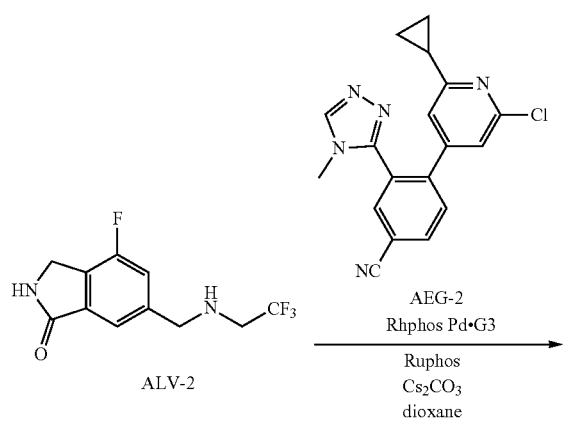

AEG-2
Rhphos Pd·G3
Ruphos
Cs₂CO₃
dioxane

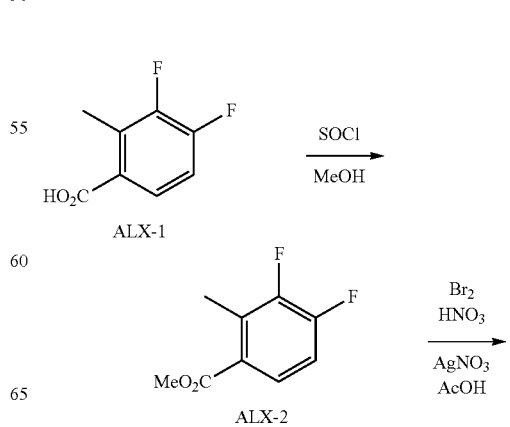

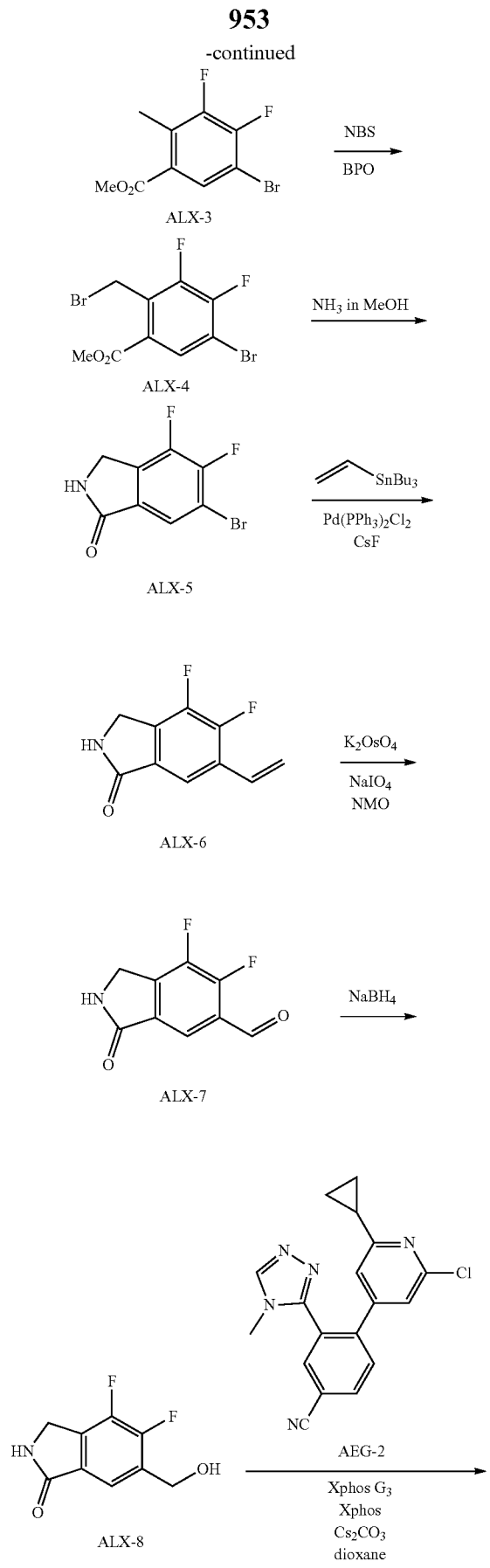

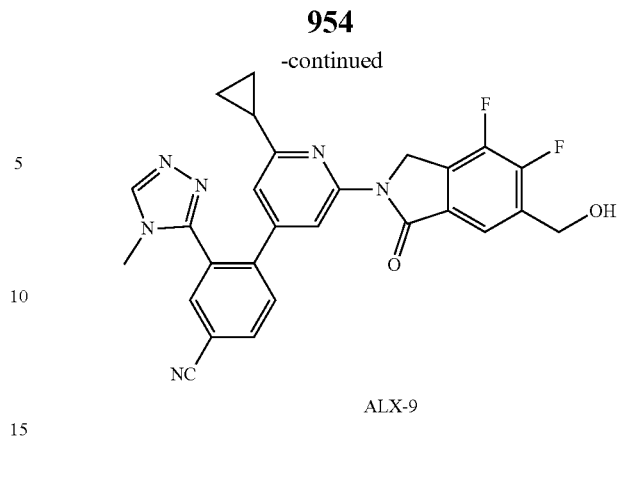

ALX-9

Step 1: Methyl 3,4-difluoro-2-methylbenzoate (ALX-2)

A mixture of 3,4-difluoro-2-methylbenzoic acid (ALX-1) (5.0 g, 1 Eq, 29.1 mmol) and $SOCl_2$ (10.4 g, 3 Eq, 87.2 mmol) in MeOH (100 mL) was stirred for 2 h at 80° C. under nitrogen atmosphere. The mixture was cooled to rt and concentrated in vacuo. The residue was applied on a silica gel column chromatography with petroleum ether/EtOAc (3/1). This resulted in the sub-title compound (ALX-2) (5.0 g, 26.9 mmol, 92%, 92% Purity) as a yellow solid. m/z 187.1 $(M+H)^+$ (ES+)

Step 2: Methyl 5-bromo-3,4-difluoro-2-methylbenzoate (ALX-3)

To a stirred mixture of the product from step 1 above (ALX-2) (2.00 g, 1 Eq, 10.7 mmol), $Br_2$ (6.87 g, 4 Eq, 43.0 mmol) and conc. $HNO_3$ (6.77 g, 10 Eq, 107 mmol) in AcOH (40 mL) was added $AgNO_3$ (2.37 g, 1.3 Eq, 14.0 mmol) at 0° C. The resulting mixture was stirred overnight at rt under nitrogen atmosphere. The mixture was cooled to rt, diluted with water and extracted with EtOAc (3×100 mL). The combined organic layers were washed with brine (2×100 mL), dried ($Na_2SO_4$). After filtration, the filtrate was concentrated in vacuo. The residue was applied on a silica gel column chromatography with petroleum ether/EtOAc (5/1) to afford the sub-title compound (ALX-3) (2.0 g, 7.58 mmol, 70%, 90% Purity) as a yellow oil. m/z 265.0/267.0 $(M+H)^+$ (ES+)

Step 3: Methyl 5-bromo-2-(bromomethyl)-3,4-difluorobenzoate (ALX-4)

To a stirred mixture of the product from step 2 above (ALX-3) (1.9 g, 1 Eq, 7.17 mmol) and NBS (1.91 g, 1.5 Eq, 10.8 mmol) in $CHCl_3$ (40 mL) was added BPO (920 mg, 0.5 Eq, 3.58 mmol) at rt under nitrogen atmosphere. The resulting mixture was stirred overnight at 80° C. under nitrogen atmosphere. The resulting mixture was diluted with water and extracted with EtOAc (3×100 mL). The combined organic layers were washed with brine (2×100 mL), dried ($Na_2SO_4$). After filtration, the filtrate was concentrated in vacuo. The crude product used directly in next step without any further purification. m/z 344.9/346.9 $(M+H)^+$ (ES+)

Step 4: 6-Bromo-4,5-difluoro-2,3-dihydroisoindol-1-one (ALX-5)

A mixture of the product from step 3 above (ALX-4) (3 g, 8.722 mmol, 1 Eq) and $NH_3$ in MeOH (20 mL) was stirred for 2 h at rt under air atmosphere. The residue was purified by silica gel column chromatography, eluted with PE/EA (1:1) to afford the sub-title compound (ALX-5) (900 mg, 3.65 mmol, 42%, 92% Purity) as a yellow solid. m/z 247.9/249.9 (M+H)+ (ES+).

Step 5: 6-Ethenyl-4,5-difluoro-2,3-dihydroisoindol-1-one (ALX-6)

To a stirred mixture of the product from step 4 above (ALZ-5) (700 mg, 1 Eq, 2.82 mmol), tributyl(ethenyl)stannane (1.04 g, 1.2 Eq, 3.29 mmol) and CsF (857 mg, 2 Eq, 5.64 mmol) indioxane (20 mL) was added Pd(PPh$_3$)$_2$Cl$_2$ (198 mg, 0.1 Eq, 0.28 mmol) at rt under nitrogen atmosphere. The resulting mixture was stirred for 2 h at 100° C. under nitrogen atmosphere. The mixture was cooled to rt and concentrated in vacuo. The residue was purified by Prep-TLC with DCM/MeOH (20/1) to afford the sub-title compound (ALX-6) (550 mg, 2.82 mmol, 99%, 80% Purity) as a yellow solid. m/z 196.1 (M+H)+ (ES+).

Step 6: 6,7-Difluoro-3-oxo-1,2-dihydroisoindole-5-carbaldehyde (ALX-7)

To a stirred mixture of the product from step 5 above (ALX-6) (500 mg, 1 Eq, 2.56 mmol) and K$_2$OSO$_4$·2H$_2$O (94 mg, 0.1 Eq, 0.26 mmol) in t-BuOH (20 mL) and H$_2$O (20 mL) was added NMO (390 mg, 1.3 Eq, 3.33 mmol) at rt under nitrogen atmosphere. The resulting mixture was stirred for 2 h at rt under nitrogen atmosphere. To the above mixture was added NaIO$_4$ (1.10 g, 2 Eq, 5.12 mmol) at 0° C. The resulting mixture was stirred for additional 1 h at rt. The crude product was purified by reverse flash column chromatography with the following conditions: Column, C18; mobile phase, water (0.1% NH$_4$HCO$_3$) and MeCN (20% MeCN up to 48% in 15 min); Detector, UV 254/220 nm. The product-containing fractions were combined and concentrated in vacuo. This resulted in the sub-title compound (ALX-7) (200 mg, 1.01 mmol, 40%, 95% Purity) as a yellow solid. m/z 198.0 (M+H)+ (ES+).

Step 7: 4,5-Difluoro-6-(hydroxymethyl)-2,3-dihydroisoindol-1-one (ALX-8)

A solution of the product from step 6 above (ALX-7) (170 mg, 1 Eq, 0.86 mmol) in MeOH (10 mL) was treated with NaBH$_4$ (65 mg, 2 Eq, 1.72 mmol) at 0° C. The resulting mixture was stirred for 2 h at rt under nitrogen atmosphere. The reaction was then quenched by the addition of MeOH (2 mL) at 0° C. The resulting mixture was concentrated in vacuo. The crude product was purified by reverse flash column chromatography with the following conditions: Column, C18; mobile phase, water (0.1% NH$_4$HCO$_3$) and MeCN (20% MeCN up to 45% in 10 min); Detector, UV 254/220 nm. The product-containing fractions were combined and concentrated in vacuo. This resulted in the sub-title compound (ALX-8) (70 mg, 0.35 mmol, 41%, 91% Purity) as a yellow solid. m/z 200.0 (M+H)+ (ES+).

Step 8: 4-{2-Cyclopropyl-6-[4,5-difluoro-6-(hydroxymethyl)-1-oxo-3H-isoindol-2-yl]pyridin-4-yl}-3-(4-methyl-1,2,4-triazol-3-yl)benzonitrile (ALX-9)

To a stirred mixture of the product from step 7 above (ALX-8) (30 mg, 1 Eq, 0.15 mmol), intermediate (AEG-2) (40 mg, 0.8 Eq, 0.12 mmol) and Cs$_2$CO$_3$ (98 mg, 2 Eq, 0.30 mmol) in dioxane (5 mL) were added XPhos (29 mg, 0.4 Eq, 0.06 mmol) and XPhos Pd G3 (26 mg, 0.2 Eq, 0.03 mmol) at rt under nitrogen atmosphere. The resulting mixture was stirred for 2 h at 100° C. under nitrogen atmosphere. The mixture was cooled to rt and concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 µm; Mobile Phase A: water (0.1% NH$_4$HCO$_3$+0.1% NH$_3$·H$_2$O), Mobile Phase B: MeCN; Flow rate: 60 mL/min; Gradient: 36% B to 46% B in 9 min; Wave Length: 254/220 nm; RT: 8.87) to afford the title compound (ALX-9) (7.2 mg, 14 µmol, 9.6%, 99.6% Purity) as a white solid. m/z 499.1 (M+H)+ (ES+). $^1$H NMR (400 MHz, DMSO-d6) δ 8.54 (s, 1H), 8.25-8.18 (m, 2H), 7.96-7.83 (m, 2H), 7.71 (d, J=5.2 Hz, 1H), 6.92 (d, J=1.4 Hz, 1H), 5.59 (t, J=5.9 Hz, 1H), 5.13 (s, 2H), 4.66 (d, J=5.8 Hz, 2H), 3.48 (s, 3H), 2.11-2.00 (m, 1H), 1.01-0.94 (m, 4H).

Example 359: Synthesis of 4-{2-Cyclopropyl-6-[4,5-difluoro-1-oxo-6-({[2-(trifluoromethoxy)ethyl]amino}methyl)-3H-isoindol-2-yl]pyridin-4-yl}-3-(4-methyl-1,2,4-triazol-3-yl)benzonitrile (ALY-2)

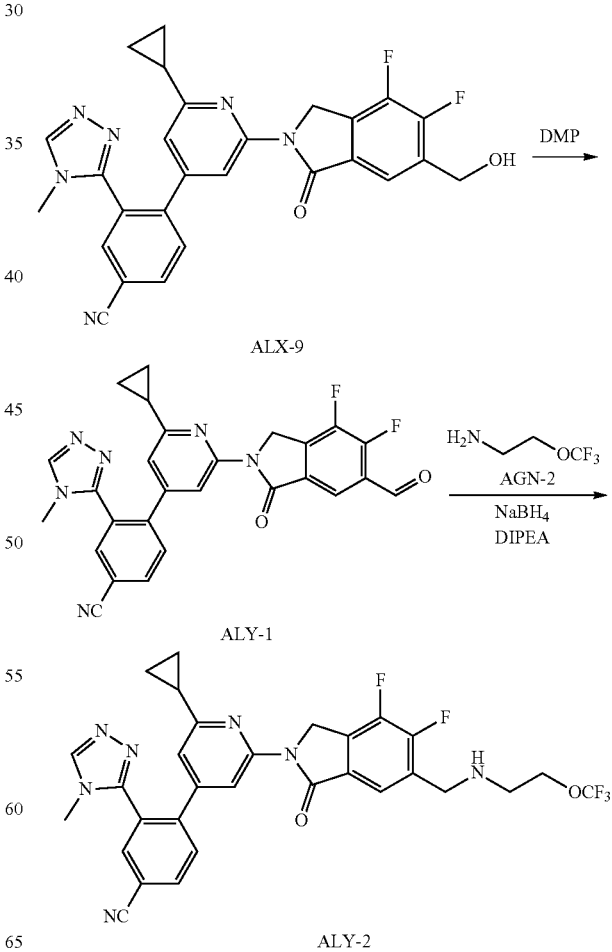

Step 1: 4-[2-Cyclopropyl-6-(4,5-difluoro-6-formyl-1-oxo-3H-isoindol-2-yl)pyridin-4-yl]-3-(4-methyl-1,2,4-triazol-3-yl)benzonitrile (ALY-1)

A solution of compound (ALX-9) (30 mg, 1 Eq, 0.06 mmol) in DCM (3 mL) was treated with DMP (33 mg, 1.3 Eq, 78 µmol) at rt. The resulting mixture was stirred for 3 h at rt under nitrogen atmosphere. The resulting mixture was filtered, the filter cake was washed with DCM (3×3 mL). The crude product used directly in next step without any further purification. m/z 497.1 (M+H)$^+$ (ES+)

Step 2: 4-{2-Cyclopropyl-6-[4,5-difluoro-1-oxo-6-({[2-(trifluoromethoxy)ethyl]amino} methyl)-3H-isoindol-2-yl]pyridin-4-yl}-3-(4-methyl-1,2,4-triazol-3-yl)benzonitrile (ALY-2)

To a stirred mixture of the product from step 1 above (ALY-1) (20 mg, 1 Eq, 0.04 mmol) and 2-(trifluoromethoxy)ethanamine (AGN-2) (8 mg, 1.5 Eq, 0.06 mmol) in MeOH (2 mL) was added DIPEA (10 mg, 2 Eq, 0.08 mmol) at rt under nitrogen atmosphere. The resulting mixture was stirred overnight at rt. To the above mixture was added NaBH$_4$ (3 mg, 2 Eq, 0.08 mmol) at 0° C. The resulting mixture was stirred for additional 2 h at rt. The reaction was then quenched by the addition of MeOH (2 mL) at 0° C. The resulting mixture was concentrated in vacuo. The residue was purified by Prep-HPLC with the following conditions (Column: XBridge Prep OBD C18 Column, 30*150 mm, 5 µm; Mobile Phase A: water (0.1% NH$_4$HCO$_3$+0.1% NH$_3$·H$_2$O), Mobile Phase B: MeCN; Flow rate: 60 mL/min; Gradient: 36% B to 46% B in 9 min; Wave Length: 254/220 nm; RT: 8.87) to afford the title compound (ALY-2) (3.6 mg, 5.9 µmol, 14%, 94.4% Purity) as a white solid. m/z 610.1 (M+H)$^+$ (ES+). $^1$H NMR (400 MHz, DMSO-d6) δ 8.54 (d, J=5.4 Hz, 1H), 8.22 (d, J=6.9 Hz, 2H), 7.94-7.84 (m, 2H), 7.77 (d, J=5.2 Hz, 1H), 7.00-6.92 (m, 1H), 5.14 (d, J=8.4 Hz, 2H), 4.12 (t, J=5.4 Hz, 2H), 3.89 (s, 2H), 3.49 (d, J=5.0 Hz, 3H), 2.82 (t, J=5.3 Hz, 2H), 2.09-2.04 (m, 1H), 0.98 (d, J=8.0 Hz, 4H).

Example 360: Synthesis of 4-{2-Cyclopropyl-6-[6-({[2-(methylamino)ethyl]amino}methyl)-1-oxo-3H-isoindol-2-yl]pyridin-4-yl}-3-(4-methyl-1,2,4-triazol-3-yl)benzonitrile (ALZ-3)

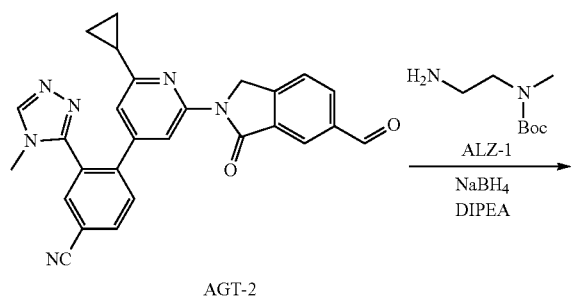

AGT-2

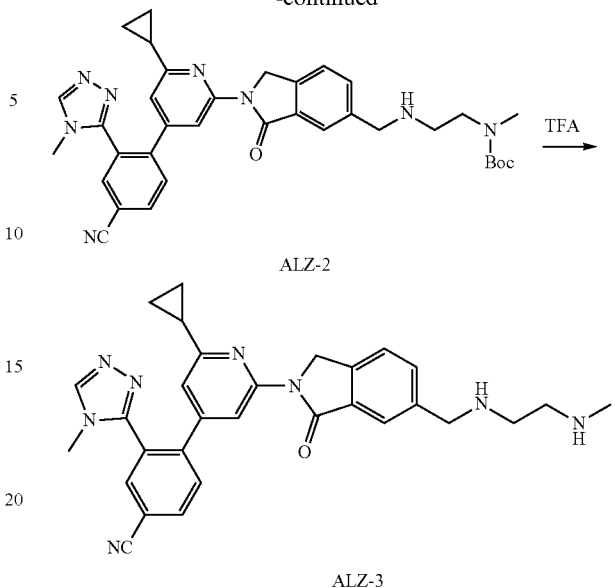

Step 1: tert-Butyl N-(2-{[(2-{4-[4-cyano-2-(4-methyl-1,2,4-triazol-3-yl)phenyl]-6-cyclopropylpyridin-2-yl}-3-oxo-7-(trifluoromethyl)-1H-isoindol-5-yl)methyl]amino}ethyl)-N-methylcarbamate (ALZ-2)

To a stirred mixture of intermediate (AGT-2) (60 mg, 1 Eq, 0.11 mmol) and tert-butyl N-(2-aminoethyl)-N-methylcarbamate (ALZ-1) (24 mg, 1.2 Eq, 0.14 mmol) in MeOH (5 mL) was added DIPEA (44 mg, 3 Eq, 0.34 mmol) at rt. The resulting mixture was stirred overnight at 60° C. The mixture was cooled to rt. To the above mixture was added NaBH$_4$ (13 mg, 3 Eq, 0.34 mmol) at rt. The resulting mixture was stirred for additional 1 h at rt. The reaction was then quenched by the addition of MeOH (2 mL) at 0° C. The resulting mixture was concentrated in vacuo. The residue was purified by Prep-TLC with DCM/MeOH (10/1) to afford the sub-title compound (ALZ-2) (40 mg, 64 µmol, 51%, 95% Purity) as a yellow solid. m/z 619.3 (M+H)$^+$ (ES+)

Step 2: 4-{2-Cyclopropyl-6-[6-({[2-(methylamino)ethyl]amino}methyl)-1-oxo-3H-isoindol-2-yl]pyridin-4-yl}-3-(4-methyl-1,2,4-triazol-3-yl)benzonitrile (ALZ-3)

A solution of the product from step 1 above (ALZ-2) (60 mg, 1 Eq, 87 µmol) and TFA (2 mL) in DCM (10 mL) was stirred for 1 h at rt. The resulting mixture was concentrated in vacuo. The crude product was purified by Prep-HPLC with the following conditions (Column: Xselect CSH C18 OBD Column 30*150 mm, 5 µm, n; Mobile Phase A: water (0.1% FA), Mobile Phase B: MeCN; Flow rate: 60 mL/min; Gradient: 2% B to 25% B in 10 min; Wave Length: 254 nm; RT: 11.02) to afford the title compound (ALZ-3) (15.5 mg, 30 µmol, 27%, 95.0% Purity) as a white solid. m/z 519.3 (M+H)$^+$ (ES+). $^1$H NMR (400 MHz, DMSO-d6) δ 8.52 (d, J=2.5 Hz, 1H), 8.36 (s, 0.761H), 8.28-8.14 (m, 2H), 7.96 (d, J=3.8 Hz, 1H), 7.91-7.84 (m, 1H), 7.80 (s, 1H), 7.66 (d, J=1.4 Hz, 2H), 6.91 (d, J=1.5 Hz, 1H), 5.01 (s, 2H), 3.82 (s, 2H), 3.62 (s, 3H), 2.94 (s, 2H), 2.71 (t, J=6.4 Hz, 2H), 2.54 (s, 3H), 2.10-2.01 (m, 1H), 1.05-0.91 (m, 4H).

Example 361: Synthesis of 4-(2-Cyclopropyl-6-{6-[({[1-(hydroxymethyl)cyclobutyl]methyl}amino)methyl]-1-oxo-3H-isoindol-2-yl}pyridin-4-yl)-3-(4-methyl-1,2,4-triazol-3-yl)benzonitrile (AMA-2)

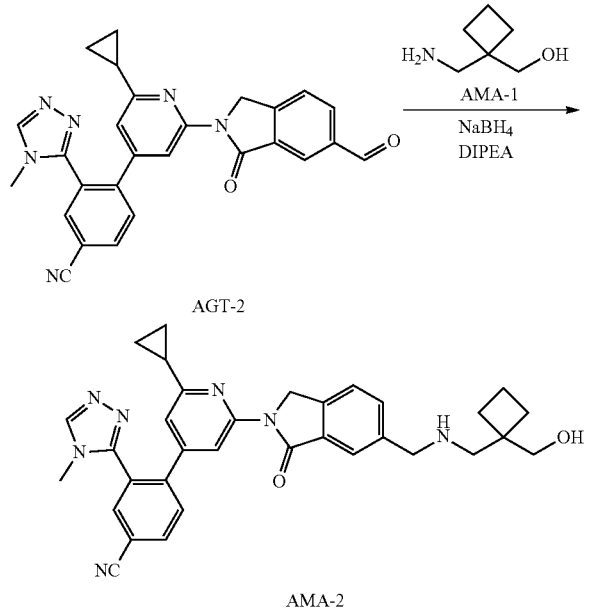

To a stirred mixture of intermediate (AGT-2) (30 mg, 1 Eq, 65 µmol) and [1-(aminomethyl)cyclobutyl]methanol (AMA-1) (8 mg, 1 Eq, 65 µmol) in MeOH (10 mL) was added DIPEA (25 mg, 3 Eq, 0.20 mmol) at rt. The resulting mixture was stirred overnight at 60° C. The mixture was cooled to rt. To the above mixture was added NaBH$_4$ (7 mg, 3 Eq, 0.20 mmol) at rt. The resulting mixture was stirred for additional 1 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 µm; Mobile Phase A: water (0.1% NH$_4$HCO$_3$+0.1% NH$_3$·H$_2$O), Mobile Phase B: MeCN; Flow rate: 60 mL/min; Gradient: 40% B to 50% B in 8 min; Wave Length: 254/220 nm; RT: 7.83) to afford the title compound (AMA-2) (2.3 mg, 4.1 µmol, 5.7%, 90.0% Purity) as a white solid. m/z 561.2 (M+H)$^+$ (ES+). $^1$H NMR (400 MHz, Methanol-d4) δ 8.49 (s, 1H), 8.16-8.03 (m, 3H), 7.92 (d, J=8.1 Hz, 1H), 7.81 (s, 1H), 7.70-7.60 (m, 2H), 6.92 (d, J=1.3 Hz, 1H), 5.03 (s, 2H), 3.92 (s, 2H), 3.63 (s, 2H), 3.50 (s, 3H), 2.77 (s, 2H), 2.07-1.99 (m, 1H), 1.98-1.75 (m, 6H), 1.10-0.92 (m, 4H).

Example 362: Synthesis of N-(2-{[(2-{4-[4-Cyano-2-(4-methyl-1,2,4-triazol-3-yl)phenyl]-6-cyclopropylpyridin-2-yl}-3-oxo-1H-isoindol-5-yl)methyl]amino}ethyl)acetamide (AMB-1)

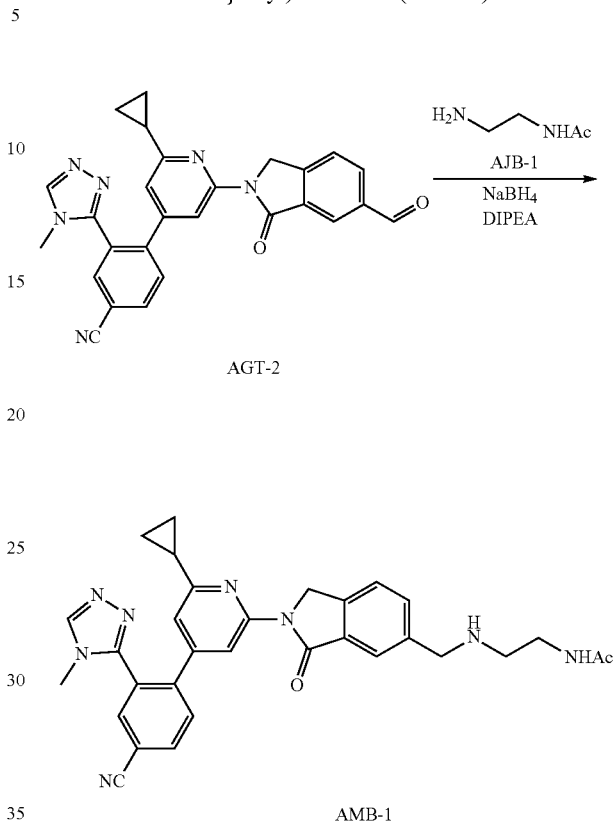

A solution of intermediate (AGT-2) (30 mg, 1 Eq, 65 µmol), N-(2-aminoethyl)acetamide (AJB-1) (8 mg, 1.2 Eq, 78 µmol) and DIPEA (34 mg, 4 Eq, 0.26 mmol) in MeOH (8 mL) was stirred overnight at rt. To the above mixture was added NaBH$_4$ (12 mg, 5 Eq, 0.33 mmol) at 0° C. The resulting mixture was stirred for additional 1 h at rt. The reaction was then quenched by the addition of MeOH (2 mL) at 0° C. The mixture was acidified to pH 5 with FA at 0° C. The mixture was concentrated in vacuo. The crude product was purified by Prep-HPLC with the following conditions (Column: XBridge Shield RP18 OBD Column, 30*150 mm, 5 µm; Mobile Phase A: water (0.1% NH$_4$HCO$_3$), Mobile Phase B: MeCN; Flow rate: 60 mL/min; Gradient: 20% B to 35% B in 10 min; Wave Length: 254/220 nm; RT: 10.7) to afford the title compound (AMB-1) (8.6 mg, 16 µmol, 23%, 96.1% Purity) as a white solid. m/z 547.3 (M+H)$^+$ (ES+). $^1$H NMR (400 MHz, Methanol-d4) δ 8.48 (s, 1H), 8.15-8.09 (m, 1H), 8.09-8.04 (m, 2H), 7.92 (d, J=8.1 Hz, 1H), 7.83-7.78 (m, 1H), 7.68-7.59 (m, 2H), 6.90 (d, J=1.4 Hz, 1H), 5.02 (s, 2H), 3.87 (s, 2H), 3.49 (s, 3H), 3.32 (s, 2H), 2.71 (t, J=6.4 Hz, 2H), 2.08-1.97 (m, 1H), 1.94 (s, 3H), 1.06-0.93 (m, 4H).

Example 363: Synthesis of 4-[2-Cyclopropyl-6-(6-{[(cyclopropylmethyl)amino]methyl}-4-fluoro-1-oxo-3H-isoindol-2-yl)pyridin-4-yl]-3-(4-methyl-1,2,4-triazol-3-yl)benzonitrile (AMC-2)

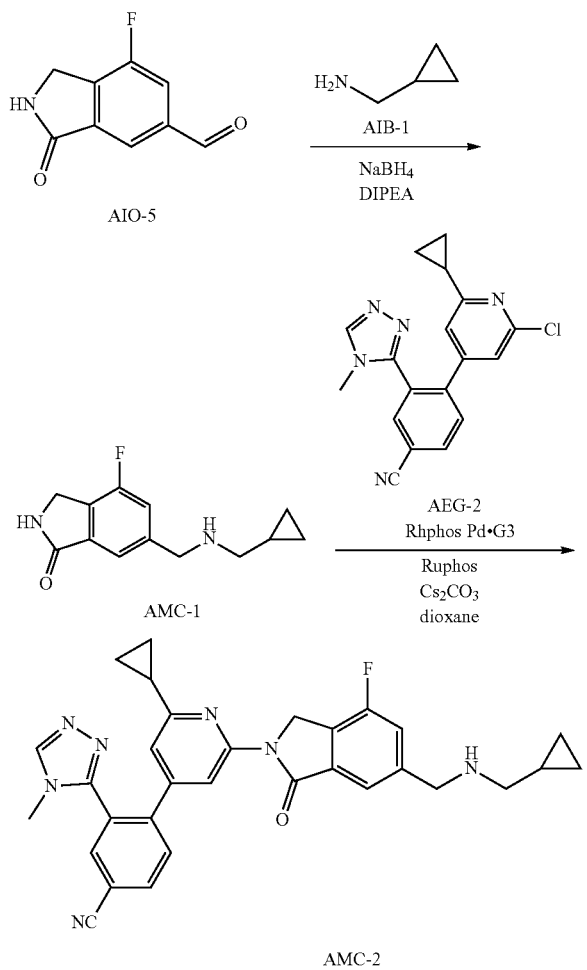

Step 1: 6-{[(Cyclopropylmethyl)amino]methyl}-4-fluoro-2,3-dihydroisoindol-1-one (AMC-1)

To a stirred mixture of intermediate (AIO-5) (150 mg, 1 Eq, 0.84 mmol) and 1-cyclopropylmethanamine (AIB-1) (71 mg, 1.2 Eq, 1.00 mmol) in MeOH (20 mL) was added DIPEA (325 mg, 3 Eq, 2.51 mmol) at rt. The resulting mixture was stirred overnight at 60° C. The mixture was cooled to rt. To the above mixture was added NaBH$_4$ (95 mg, 3 Eq, 2.51 mmol) at 0° C. The resulting mixture was stirred for additional 1 h at rt. The reaction was then quenched by the addition of 5 mL of MeOH at 0° C. The resulting mixture was concentrated in vacuo. The residue was purified by Prep-TLC with DCM/MeOH (10/1) to afford the sub-title compound (AMC-1) (130 mg, 0.56 mmol, 66%, 94% Purity) as a yellow solid. m/z 235.1 (M+H)$^+$ (ES+)

Step 2: 4-[2-Cyclopropyl-6-(6-{[(cyclopropylmethyl)amino]methyl}-4-fluoro-1-oxo-3H-isoindol-2-yl)pyridin-4-yl]-3-(4-methyl-1,2,4-triazol-3-yl)benzonitrile (AMC-2)

To a stirred mixture of the product from step 1 above (AMC-1) (130 mg, 1 Eq, 0.56 mmol), intermediate (AEG-2) (186 mg, 1 Eq, 0.56 mmol) and Cs$_2$CO$_3$ (362 mg, 2 Eq, 1.11 mmol) in dioxane (20 mL) were added RuPhos (104 mg, 0.4 Eq, 0.22 mmol) and RuPhos Palladacycle Gen.3 (93 mg, 0.2 Eq, 0.11 mmol) at rt under nitrogen atmosphere. The resulting mixture was stirred for 2 h at 60° C. under nitrogen atmosphere. The mixture was cooled to rt and concentrated in vacuo. The crude product was purified by reverse flash column chromatography with the following conditions: Column, C18; mobile phase, water (0.1% NH$_4$HCO$_3$) and MeCN (20% MeCN up to 60% in 20 min); Detector, UV 254/220 nm. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 39% B to 59% B in 9 min; Wave Length: 254/220 nm; RT: 8.05) to afford the title compound (AMC-2) (29.4 mg, 55 Purity, 9.9%, 99.2% Purity) as a white solid. m/z 534.1 (M+H)$^+$ (ES+). $^1$H NMR (400 MHz, DMSO-d6) δ 8.54 (s, 1H), 8.31-8.06 (m, 2H), 7.95 (d, J=1.4 Hz, 1H), 7.92-7.83 (m, 1H), 7.62 (s, 1H), 7.51 (d, J=10.0 Hz, 1H), 6.92 (d, J=1.4 Hz, 1H), 5.06 (s, 2H), 3.83 (s, 2H), 3.48 (s, 3H), 2.36 (d, J=6.6 Hz, 2H), 2.12-1.98 (m, 1H), 1.11-0.94 (m, 4H), 0.93-0.78 (m, 1H), 0.44-0.32 (m, 2H), 0.14-0.04 (m, 2H).

Example 364: Synthesis of 4-{2-Cyclopropyl-6-[4-fluoro-6-({[(2S,3S)-3-methoxybutan-2-yl]amino}methyl)-1-oxo-3H-isoindol-2-yl]pyridin-4-yl}-3-(4-methyl-1,2,4-triazol-3-yl)benzonitrile (AMD-2)

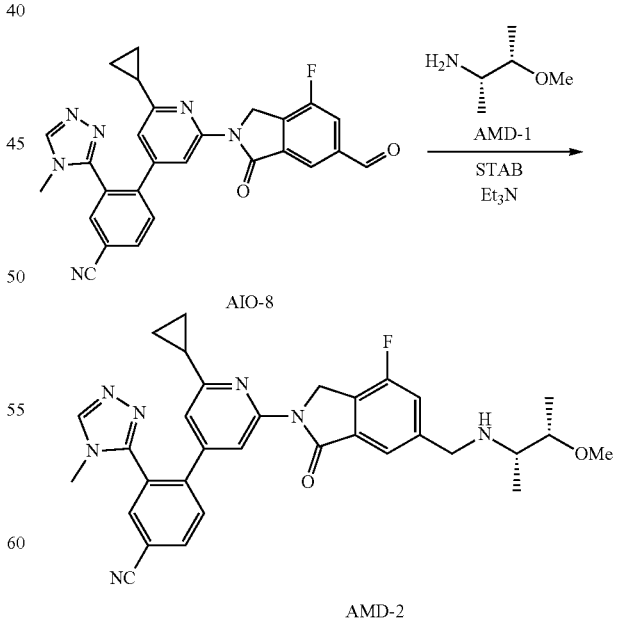

To a stirred mixture of intermediate (AIO-8) (30 mg, 1 Eq, 63 μmol) and (2S,3S)-3-methoxybutan-2-amine (AMD-1) (6 mg, 1 Eq, 63 μmol) in DCM (2 mL) was added Et$_3$N (24 mg, 3 Eq, 0.19 mmol) at rt. The resulting mixture was stirred overnight at 60° C. The mixture was cooled to rt. To the above mixture was added NaBH(OAc)₃ (7 mg, 3 Eq, 0.19 mmol) at rt. The resulting mixture was stirred for additional 1 h at rt. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 50% B to 67% B in 8 min; Wave Length: 254/220 nm; RT: 6.65) to afford the title compound (AMD-2) (15.5 mg, 27 μmol, 44%, 99.6% Purity) as a white solid. m/z 566.1 (M+H)⁺ (ES+). ¹H NMR (400 MHz, DMSO-d6) δ 8.54 (s, 1H), 8.25-8.18 (m, 2H), 7.95 (d, J=1.4 Hz, 1H), 7.90-7.84 (m, 1H), 7.65 (s, 1H), 7.53 (d, J=10.0 Hz, 1H), 6.93 (d, J=1.4 Hz, 1H), 5.08 (s, 2H), 3.86 (d, J=26.5 Hz, 2H), 3.48 (s, 3H), 3.31 (s, 1H), 3.23 (s, 4H), 2.10-2.02 (m, 1H), 1.11-0.87 (m, 10H).

Example 365: Synthesis of 4-[2-Cyclopropyl-6-(6-{[(3,3-difluoropropyl)amino]methyl}-4-fluoro-1-oxo-3H-isoindol-2-yl)pyridin-4-yl]-3-(4-methyl-1,2,4-triazol-3-yl)benzonitrile (AME-2)

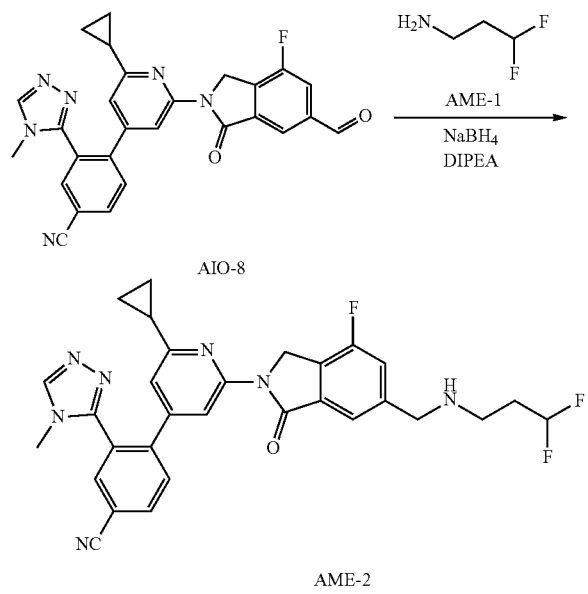

To a stirred mixture of intermediate (AIO-8) (30 mg, 1 Eq, 63 μmol) and 3,3-difluoropropan-1-amine (AME-1) (6 mg, 1 Eq, 63 μmol) in MeOH (5 mL) was added DIPEA (24 mg, 3 Eq, 0.19 mmol) at rt. The resulting mixture was stirred overnight at 60° C. The mixture was cooled to rt. To the above mixture was added NaBH₄ (7 mg, 3 Eq, 0.19 mmol) at rt. The resulting mixture was stirred for additional 1 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 42% B to 52% B in 10 min; Wave Length: 254/220 nm; RT: 8.92) to afford the title compound (AME-2) (4.8 mg, 8.6 μmol, 14%, 98.4% Purity) as a white solid. m/z 558.0 (M+H)⁺ (ES+). ¹H NMR (400 MHz, DMSO-d6) δ 8.54 (s, 1H), 8.38-8.08 (m, 2H), 7.95 (d, J=1.4 Hz, 1H), 7.91-7.79 (m, 1H), 7.63 (s, 1H), 7.56-7.47 (m, 1H), 6.93 (d, J=1.4 Hz, 1H), 6.32-5.99 (m, 1H), 5.07 (s, 2H), 3.81 (s, 2H), 3.48 (s, 3H), 2.59 (t, J=7.0 Hz, 2H), 2.17-1.80 (m, 3H), 1.22-0.74 (m, 4H).

Example 366: Synthesis of 4-[2-(6-{[(cyclobutylmethyl)(methyl)amino]methyl}-1-oxo-3H-isoindol-2-yl)-6-cyclopropylpyridin-4-yl]-3-(4-methyl-1,2,4-triazol-3-yl)benzonitrile (AMF-1)

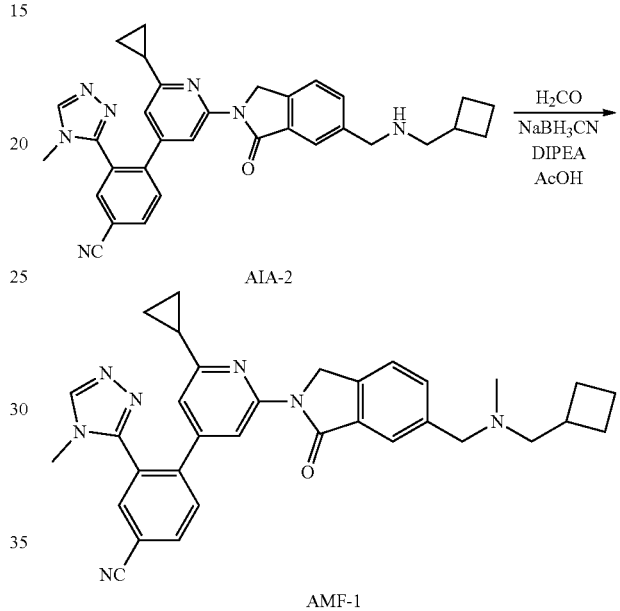

To a stirred mixture of compound (AIA-2) (30 mg, 1 Eq, 57 μmol) and HCHO (1.7 mg, 1 Eq, 57 μmol) in MeOH (5 mL) was added DIPEA (22 mg, 3 Eq, 0.17 mmol) at rt. The resulting mixture was stirred overnight at 60° C. under air atmosphere. The mixture was cooled to rt. To the above mixture was added AcOH (0.50 m) and NaBH₃CN (11 mg, 3 Eq, 0.17 mmol) at rt. The resulting mixture was stirred for additional 1 h at rt. The resulting mixture was concentrated in vacuo. The crude product was purified by Prep-HPLC with the following conditions (Column: Xselect CSH C18 OBD Column 30*150 mm, 5 μm, n; Mobile Phase A: water (0.1% FA), Mobile Phase B: MeCN; Flow rate: 60 mL/min; Gradient: 15% B to 45% B in 10 min; Wave Length: 254 nm; RT: 7.87) to afford the title compound (AMF-1) (7.4 mg, 14 μmol, 24%, 98.9% Purity) as a white solid. m/z 544.2 (M+H)⁺ (ES+). ¹H NMR (400 MHz, Methanol-d4) δ 8.50 (s, 1H), 8.16-8.00 (m, 3H), 7.92 (d, J=8.1 Hz, 1H), 7.78 (s, 1H), 7.68-7.58 (m, 2H), 6.93 (d, J=1.5 Hz, 1H), 5.03 (s, 2H), 3.65 (s, 2H), 3.50 (s, 3H), 2.70-2.58 (m, 1H), 2.50 (s, 2H), 2.22 (d, J=3.7 Hz, 3H), 2.15-1.98 (m, 3H), 1.98-1.86 (m, 1H), 1.85-1.64 (m, 3H), 1.08-0.94 (m, 4H).

Example 367: Synthesis of 2-(4-(4-Chloro-2-(4-methyl-4H-1,2,4-triazol-3-yl)phenyl)-6-cyclopropylpyridin-2-yl)-6-((((1-hydroxycyclobutyl)methyl)(methyl)amino)methyl)isoindolin-1-one (AMI-1)

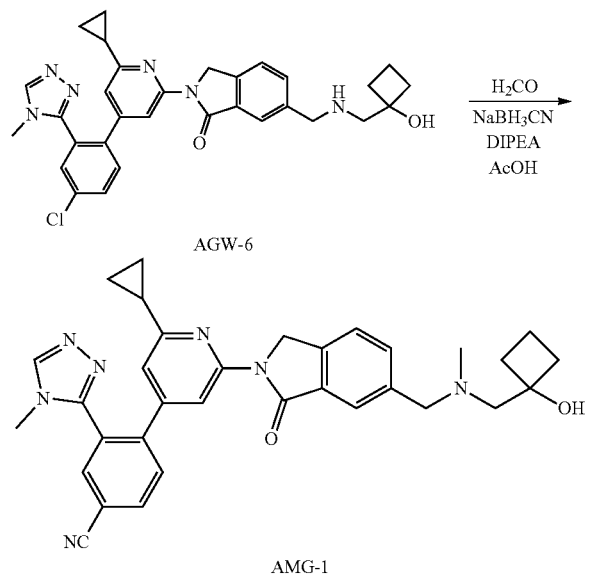

Into a 25 mL round-bottom flask were added compound (AGW-6) (60 mg, 1 Eq, 0.11 mmol), HCHO (1 mL) in MeOH (5 ml) at rt. To the above stirred solution was added NaBH₃CN (34 mg, 5 Eq, 0.54 mmol) at rt. The resulting mixture was stirred for additional 2 h at 60° C. The mixture was cooled to rt and concentrated in vacuo. The crude product was purified by Prep-HPLC with the following conditions (Column: Xselect CSH C18 OBD Column 30*150 mm, 5 µm, n; Mobile Phase A: water (0.05% TFA), Mobile Phase B: MeCN; Flow rate: 60 mL/min; Gradient: 2% B to 32% B in 10 min; Wave Length: 254 nm) to afford the title compound (AMG-1) (7.2 mg, 13 µmol, 12%, 99.8% Purity) as a white solid. m/z 569.2/571.2 (M+H)⁺ (ES+). ¹H NMR (400 MHz, DMSO-d6) δ 8.50 (s, 1H), 8.00 (s, 1H), 7.84-7.79 (m, 1H), 7.79-7.74 (m, 2H), 7.69 (d, J=8.3 Hz, 1H), 7.64 (s, 2H), 6.80 (s, 1H), 5.00 (s, 2H), 4.89 (s, 1H), 3.86 (s, 2H), 3.41 (s, 3H) 2.53 (s, 3H), 2.09-1.83 (m, 7H), 1.61 (d, J=10.7 Hz, 1H), 1.44-1.35 (m, 1H), 0.95 (d, J=6.4 Hz, 4H).

Example 368: Synthesis of 4-[2-Cyclopropyl-6-(6-{[(2-hydroxy-2-methylpropyl)(methyl)amino]methyl}-1-oxo-3H-isoindol-2-yl)pyridin-4-yl]-3-(4-methyl-1,2,4-triazol-3-yl)benzonitrile (AMH-1)

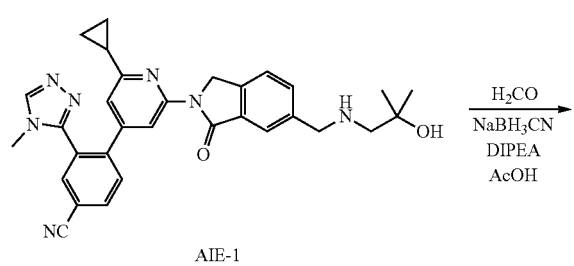

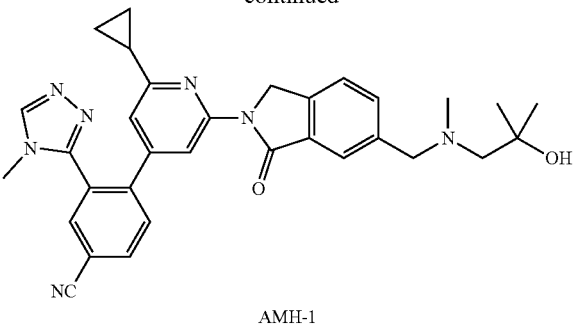

To a stirred mixture of compound (AIE-1) (60 mg, 1 Eq, 0.11 mmol) and HCHO (17 mg, 5 Eq, 0.56 mmol) in MeOH (5 mL) was added DIPEA (44 mg, 3 Eq, 0.34 mmol) at rt. The resulting mixture was stirred overnight at 60° C. The mixture was cooled to rt. To the above mixture was added NaBH₃CN (21 mg, 3 Eq, 0.34 mmol) and AcOH (0.2 mL) at rt. The resulting mixture was stirred for additional 1 h at rt. The resulting mixture was concentrated in vacuo. The crude product was purified by Prep-HPLC with the following conditions (Column: Xselect CSH C18 OBD Column 30*150 mm, 5 µm, n; Mobile Phase A: water (0.1% FA), Mobile Phase B: MeCN; Flow rate: 60 mL/min; Gradient: 6% B to 36% B in 10 min; Wave Length: 254 nm; RT: 9.4) to afford the title compound (AMH-1) (3.6 mg, 6.6 µmol, 5.8%, 99.5% Purity) as a white solid. m/z 548.1 (M+H)⁺ (ES+). ¹H NMR (400 MHz, Methanol-d4) δ 8.51 (s, 1H), 8.16-8.07 (m, 2H), 8.04 (d, J=1.4 Hz, 1H), 7.96-7.89 (m, 1H), 7.83 (t, J=1.1 Hz, 1H), 7.73-7.66 (m, 1H), 7.59 (d, J=7.8 Hz, 1H), 6.93 (d, J=1.4 Hz, 1H), 5.02 (s, 2H), 3.73 (s, 2H), 3.51 (s, 3H), 2.45 (s, 2H), 2.30 (s, 3H), 2.09-1.98 (m, 1H), 1.21 (s, 6H), 1.08-0.95 (m, 4H).

Example 369: Synthesis of 2-{6-Cyclopropyl-4-[4-fluoro-2-(4-methyl-1,2,4-triazol-3-yl)phenyl]pyridin-2-yl}-4-fluoro-6-(hydroxymethyl)-3H-isoindol-1-one (AMI-1)

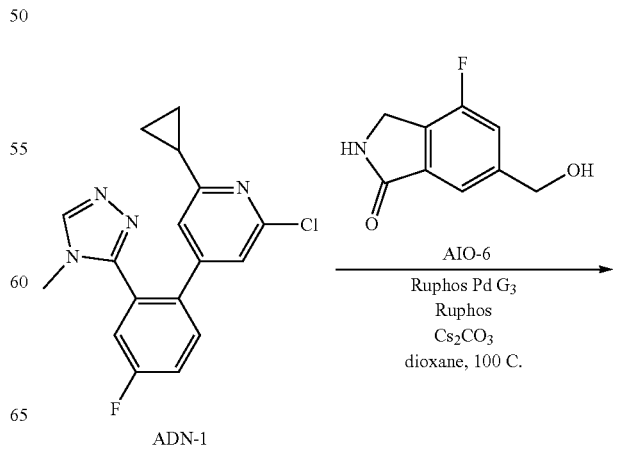

967

-continued

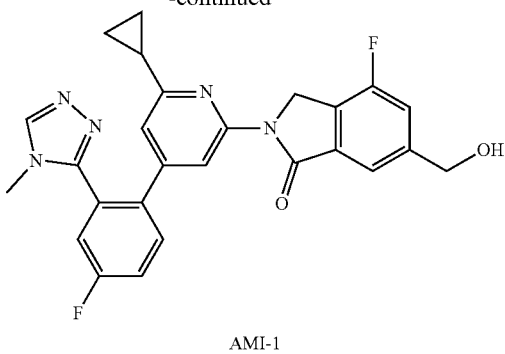

AMI-1

Into a 25 mL round-bottom flask were added intermediate (ADN-1) (60 mg, 1 Eq, 0.18 mmol), intermediate (AIO-6) (40 mg, 1.2 Eq, 0.22 mmol) and $Cs_2CO_3$ (178 mg, 3 Eq, 0.55 mmol) in 1,4-dioxane (5 mL) at rt under nitrogen atmosphere. To the above stirred solution were added RuPhos (34 mg, 0.4 Eq, 73 μmol) and RuPhos Palladacycle Gen.3 (31 mg, 0.2 Eq, 36 μmol) at rt under nitrogen atmosphere. The resulting mixture was stirred for 2 h at 100° C. under nitrogen atmosphere. The mixture was cooled to rt, diluted with water and extracted with EtOAc (3×20 mL). The combined organic layers were washed with brine (2×20 mL), dried ($Na_2SO_4$). After filtration, the filtrate was concentrated in vacuo. The crude product was purified by Prep-HPLC with the following conditions (Column: XBridge Prep OBD C18 Column, 30*150 mm, 5 μm; Mobile Phase A: water (0.1% $NH_4HCO_3$+0.1% $NH_3 \cdot H_2O$), Mobile Phase B: MeCN; Flow rate: 60 mL/min; Gradient: 50% B to 65% B in 8 min; Wave Length: 254 nm) to afford the title compound (AMI-1) (7.8 mg, 16 μmol, 9.0%, 99.8% Purity) as a white solid. m/z 474.1 $(M+H)^+$ (ES+). $^1$H NMR (400 MHz, DMSO-d6) δ 8.51 (s, 1H), 7.96 (d, J=1.4 Hz, 1H), 7.75-7.69 (m, 1H), 7.64-7.57 (m, 3H), 7.45 (d, J=9.9 Hz, 1H), 6.83 (d, J=1.4 Hz, 1H), 5.53-5.47 (m, 1H), 5.07 (s, 2H), 4.62 (d, J=5.7 Hz, 2H), 3.43 (s, 3H), 2.06-1.98 (m, 1H), 0.99-0.93 (m, 4H).

Example 370: Synthesis of 2-{6-Cyclopropyl-4-[4-fluoro-2-(4-methyl-1,2,4-triazol-3-yl)phenyl]pyridin-2-yl}-4-fluoro-6-({[(1-hydroxycyclobutyl)methyl]amino}methyl)-3H-isoindol-1-one (AMJ-1)

968

-continued

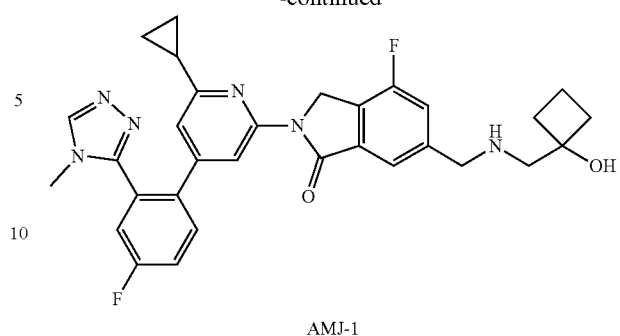

AMJ-1

Into a 25 mL round-bottom flask were added compound (AMI-1) (60 mg, 1 Eq, 0.13 mmol), DMP (70 mg, 1.3 Eq, 0.17 mmol) and DCM (5 ml) at rt. The resulting mixture was stirred for 2 h at rt. To the above stirred solution was added DIPEA (49 mg, 3 Eq, 0.38 mmol) and 1-(aminomethyl)cyclobutan-1-ol (AW-1) (17 mg, 1.3 Eq, 0.17 mmol) at rt. The resulting mixture was stirred for additional over night at 60° C. The mixture was cooled to rt. To the above stirred solution was added $NaBH_4$ (60 mg, 5 Eq, 1.59 mmol) at 0° C. The resulting mixture was stirred for additional 1 h at rt. The mixture was concentrated in vacuo. The crude product was purified by Prep-HPLC with the following conditions (Column: XBridge Prep OBD C18 Column, 30*150 mm, 5 μm; Mobile Phase A: water (0.1% $NH_4HCO_3$+0.1% $NH_3 \cdot H_2O$), Mobile Phase B: MeCN; Flow rate: 60 mL/min; Gradient: 50% B to 65% B in 8 min; Wave Length: 254/220 nm; RT: 7.38). This resulted in the title compound (AMJ-1) (4.7 mg, 8.5 μmol, 6.6%, 99.4% Purity) as a white solid. m/z 557.2 $(M+H)^+$ (ES+). $^1$H NMR (400 MHz, Methanol-d4) δ 8.47 (s, 1H), 8.01 (d, J=1.4 Hz, 1H), 7.80-7.74 (m, 1H), 7.67 (s, 1H), 7.56-7.45 (m, 3H), 6.89 (d, J=1.4 Hz, 1H), 5.07 (s, 2H), 3.95 (s, 2H), 3.47 (s, 3H), 2.71 (s, 2H), 2.13-1.98 (m, 5H), 1.78-1.70 (m, 1H), 1.56-1.46 (m, 1H), 1.06-0.95 (m, 4H).

Example 371: Synthesis of 4-{2-Cyclopropyl-6-[6-({[2-(methylamino)ethyl]amino}methyl)-1-oxo-4-(trifluoromethyl)-3H-isoindol-2-yl]pyridin-4-yl}-3-(4-methyl-1,2,4-triazol-3-yl)benzonitrile (AMK-3)

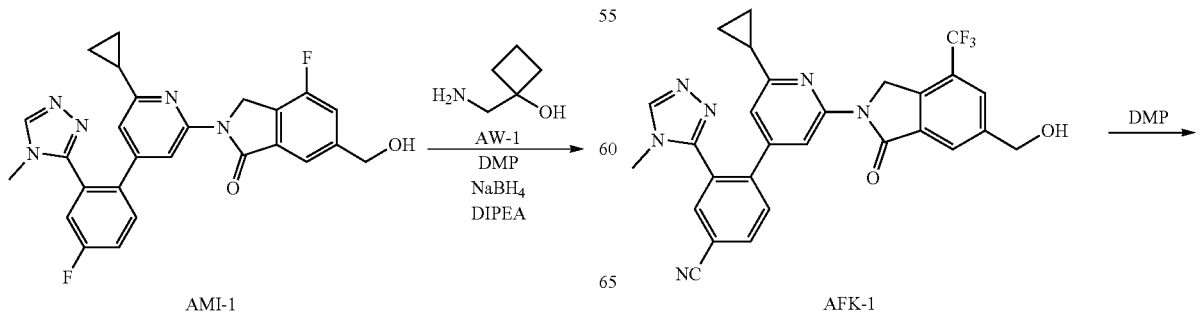

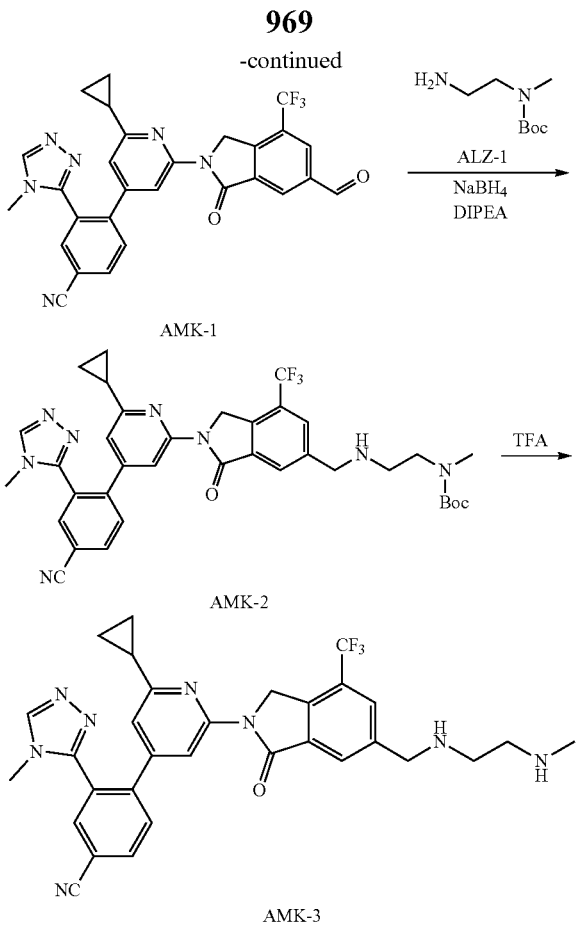

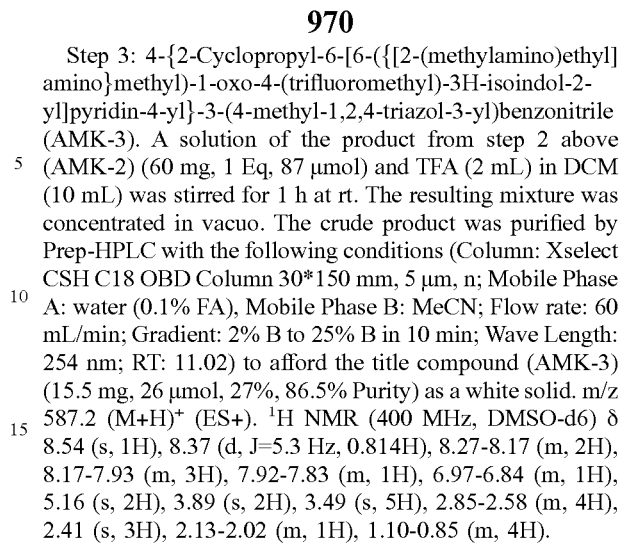

Step 1: 4-{2-Cyclopropyl-6-[6-formyl-1-oxo-4-(trifluoromethyl)-3H-isoindol-2-yl]pyridin-4-yl}-3-(4-methyl-1,2,4-triazol-3-yl)benzonitrile (AMK-1)

A solution of compound (AFK-1) (30 mg, 1 Eq, 57 µmol) and DMP (31 mg, 1.3 Eq, 74 µmol) in DCM (5 mL) was stirred for 1 h at rt under air atmosphere. The resulting mixture was filtered; the filter cake was washed with MeOH (2×3 mL). The filtrate was concentrated in vacuo. The crude product mixture was used in the next step directly without further purification. m/z 529.2 (M+H)+ (ES+)

Step 2: tert-Butyl N-(2-{[(2-{4-[4-cyano-2-(4-methyl-1,2,4-triazol-3-yl)phenyl]-6-cyclopropylpyridin-2-yl}-3-oxo-7-(trifluoromethyl)-1H-isoindol-5-yl)methyl]amino}ethyl)-N-methylcarbamate (AMK-2)

To a stirred mixture of the product from step 1 above (AMK-1) (60 mg, 1 Eq, 0.11 mmol) and tert-butyl N-(2-aminoethyl)-N-methylcarbamate (ALZ-1) (24 mg, 1.2 Eq, 0.14 mmol) in MeOH (5 mL) was added DIPEA (44 mg, 3 Eq, 0.34 mmol) at rt. The resulting mixture was stirred overnight at 60° C. To the above mixture was added NaBH₄ (13 mg, 3 Eq, 0.34 mmol) at rt. The resulting mixture was stirred for additional 1 h at rt. The reaction was then quenched by the addition of MeOH (2 mL) at 0° C. The resulting mixture was concentrated in vacuo. The residue was purified by Prep-TLC with DCM/MeOH (10/1) to afford the sub-title compound (AMK-2) (40 mg, 58 µmol, 51%, 95% Purity) as a yellow solid. m/z 687.2 (M+H)+ (ES+)

Step 3: 4-{2-Cyclopropyl-6-[6-({[2-(methylamino)ethyl]amino}methyl)-1-oxo-4-(trifluoromethyl)-3H-isoindol-2-yl]pyridin-4-yl}-3-(4-methyl-1,2,4-triazol-3-yl)benzonitrile (AMK-3). A solution of the product from step 2 above (AMK-2) (60 mg, 1 Eq, 87 µmol) and TFA (2 mL) in DCM (10 mL) was stirred for 1 h at rt. The resulting mixture was concentrated in vacuo. The crude product was purified by Prep-HPLC with the following conditions (Column: Xselect CSH C18 OBD Column 30*150 mm, 5 µm, n; Mobile Phase A: water (0.1% FA), Mobile Phase B: MeCN; Flow rate: 60 mL/min; Gradient: 2% B to 25% B in 10 min; Wave Length: 254 nm; RT: 11.02) to afford the title compound (AMK-3) (15.5 mg, 26 µmol, 27%, 86.5% Purity) as a white solid. m/z 587.2 (M+H)+ (ES+). ¹H NMR (400 MHz, DMSO-d6) δ 8.54 (s, 1H), 8.37 (d, J=5.3 Hz, 0.814H), 8.27-8.17 (m, 2H), 8.17-7.93 (m, 3H), 7.92-7.83 (m, 1H), 6.97-6.84 (m, 1H), 5.16 (s, 2H), 3.89 (s, 2H), 3.49 (s, 5H), 2.85-2.58 (m, 4H), 2.41 (s, 3H), 2.13-2.02 (m, 1H), 1.10-0.85 (m, 4H).

Example 372: Synthesis of 2-{6-Cyclopropyl-4-[4-fluoro-2-(4-methyl-1,2,4-triazol-3-yl)phenyl]pyridin-2-yl}-4-fluoro-6-({[(1-hydroxycyclobutyl)methyl](methyl)amino}methyl)-3H-isoindol-1-one (AML-1)

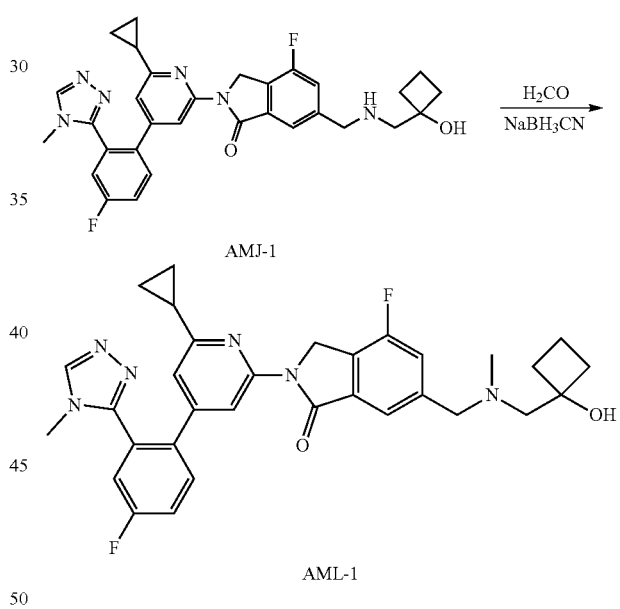

Into a 100 mL round-bottom flask were added compound (AMJ-1) (50 mg, 1 Eq, 0.09 mmol) and MeOH (5 mL) at rt. To the above stirred solution was added formaldehyde (1 mL) and NaBH₃CN (17 mg, 3 Eq, 0.27 mmol) at rt. The resulting mixture was stirred for additional 2 h at 60° C. The mixture was cooled to rt and concentrated in vacuo. The crude product was purified by Prep-HPLC with the following conditions (Column: XBridge Prep OBD C18 Column, 30*150 mm, 5 µm; Mobile Phase A: water (0.1% NH₄HCO₃+0.1% NH₃·H₂O), Mobile Phase B: MeCN; Flow rate: 60 mL/min; Gradient: 50% B to 65% B in 8 min; Wave Length: 254 nm) to afford the title compound (AML-1) (4.4 mg, 8.53%) as a white solid. m/z 571.1 (M+H)+ (ES+). ¹H NMR (400 MHz, Methanol-d4) δ 8.47 (s, 1H), 8.00 (d, J=1.4 Hz, 1H), 7.81-7.76 (m, 1H), 7.67-7.64 (m, 1H), 7.56-7.50 (m, 1H), 7.49-7.45 (m, 2H), 6.89 (d, J=1.4 Hz, 1H), 5.06 (s, 2H), 3.73 (s, 2H), 3.47 (s, 3H), 2.59 (s, 2H), 2.31 (s, 3H), 2.14-1.98 (m, 5H), 1.83-1.74 (m, 1H), 1.51-1.43 (m, 1H), 1.06-0.96 (m, 4H).

Example 373: Synthesis of 2-{6-Cyclopropyl-4-[4-fluoro-2-(4-methyl-1,2,4-triazol-3-yl)phenyl]pyridin-2-yl}-6-{[(2-hydroxy-2-methylpropyl)(methyl)amino]methyl}-3H-isoindol-1-one (AMM-1)

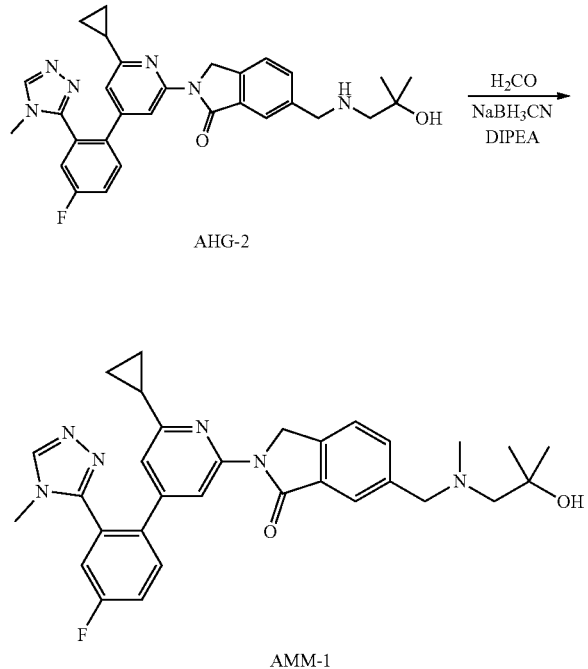

To a stirred solution of compound (AHG-2) (50 mg, 1 Eq, 95 μmol) and HCHO (29 mg, 10 Eq, 0.95 mmol) in MeOH (10 mL) were added DIPEA (49 mg, 4 Eq, 0.38 mmol) and NaBH$_3$CN (24 mg, 4 Eq, 0.38 mmol) at rt. The resulting mixture was stirred overnight at 60° C. The mixture was cooled to rt and concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 50% B to 65% B in 8 min; Wave Length: 254/220 nm; RT: 7.52) to afford the title compound (AMM-1) (5.3 mg, 9.8 μmol, 10%, 98.5% Purity) as a white solid. m/z 541.2 (M+H)$^+$ (ES+). $^1$H NMR (400 MHz, Methanol-d4) δ 8.48 (s, 1H), 8.02 (d, J=1.4 Hz, 1H), 7.83 (t, J=1.0 Hz, 1H), 7.80-7.75 (m, 1H), 7.71-7.67 (m, 1H), 7.61-7.57 (m, 1H), 7.56-7.51 (m, 1H), 7.49-7.45 (m, 1H), 6.86 (d, J=1.4 Hz, 1H), 5.02 (s, 2H), 3.73 (s, 2H), 3.48 (s, 3H), 2.45 (s, 2H), 2.30 (s, 3H), 2.05-1.95 (m, 1H), 1.21 (s, 6H), 1.05-0.99 (m, 2H), 0.99-0.94 (m, 2H).

Example 374: Synthesis of 4-(2-Cyclopropyl-6-{6-[(1S,4S)-2-oxa-5-azabicyclo[2.2.1] heptan-5-ylmethyl]-1-oxo-3H-isoindol-2-yl}pyridin-4-yl)-3-(4-methyl-1,2,4-triazol-3-yl)benzonitrile (AMN-1)

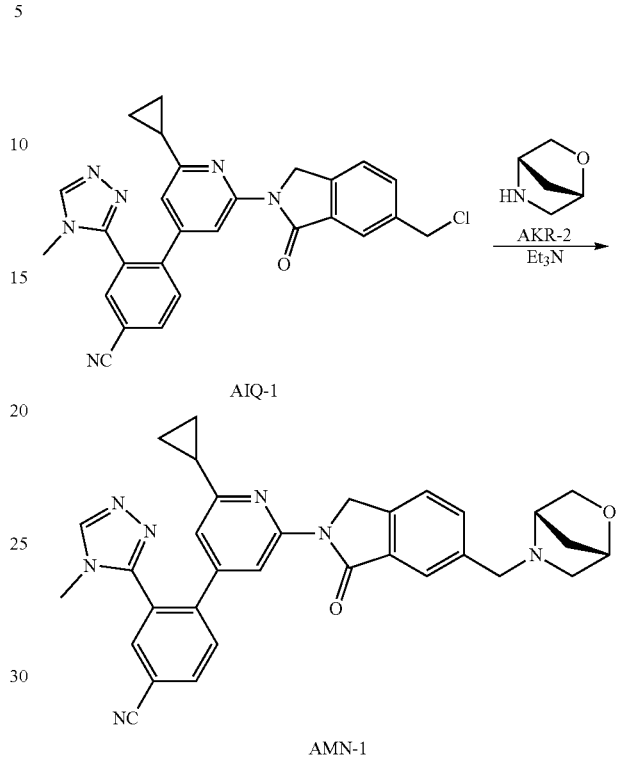

To a stirred solution of intermediate (AIQ-1) (40 mg, 1 Eq, 83 μmol) and (1S,4S)-2-oxa-5-azabicyclo[2.2.1]heptane (AKR-2) (12 mg, 1.5 Eq, 0.12 mmol) in DCM (5 mL) was added Et$_3$N (2 mg, 5 Eq, 0.42 mmol) at rt. The resulting mixture was stirred overnight at 60° C. The mixture was cooled to rt and concentrated in vacuo. The resulting mixture was diluted with water and extracted with DCM (3×20 mL). The combined organic layers were washed with brine (2×20 mL), dried (Na$_2$SO$_4$). After filtration, the filtrate was concentrated in vacuo. The crude product was purified by Prep-HPLC with the following conditions: Column: XBridge Prep OBD C18 Column, 30×150 mm, 5 μm; Mobile Phase A: water (0.1% NH$_4$HCO$_3$+0.1% NH$_3$·H$_2$O) Mobile Phase B: MeCN; Flow rate: 60 mL/min; Gradient: 35 B to 45 B in 9 min; Detector, UV 254/210 nm; RT: 8.05. The product-containing fractions were combined and evaporated partially in vacuo and lyophilized overnight to afford the title compound (AMN-1) (10.2 mg, 19 μmol, 23%, 99.8% Purity) as a white solid. m/z 544.2 (M+H)$^+$ (ES+). $^1$H NMR (400 MHz, DMSO-d6) δ 8.54 (s, 1H), 8.25-8.15 (m, 2H), 7.98 (d, J=1.4 Hz, 1H), 7.87 (d, J=8.6 Hz, 1H), 7.72 (s, 1H), 7.68-7.61 (m, 2H), 6.89 (d, J=1.4 Hz, 1H), 5.00 (s, 2H), 4.36 (d, J=2.2 Hz, 1H), 3.94 (d, J=7.5 Hz, 1H), 3.90-3.76 (m, 2H), 3.57-3.42 (m, 5H), 2.76-2.70 (m, 1H), 2.42 (d, J=10.0 Hz, 1H), 2.09-2.00 (m, 1H), 1.87-1.79 (m, 1H), 1.63-1.54 (m, 1H), 0.97 (d, J=6.3 Hz, 4H).

Example 378: Synthesis of 4-(2-Cyclopropyl-6-{6-[(oxan-4-ylamino)methyl]-1-oxo-3H-isoindol-2-yl}pyridin-4-yl)-3-(4-methyl-1,2,4-triazol-3-yl)benzonitrile (AMO-2)

Example 379: Synthesis of 4-[2-Cyclopropyl-6-(4,5-difluoro-6-{[(2-methoxyethyl)amino]methyl}-1-oxo-3H-isoindol-2-yl)pyridin-4-yl]-3-(4-methyl-1,2,4-triazol-3-yl)benzonitrile (AMP-1)

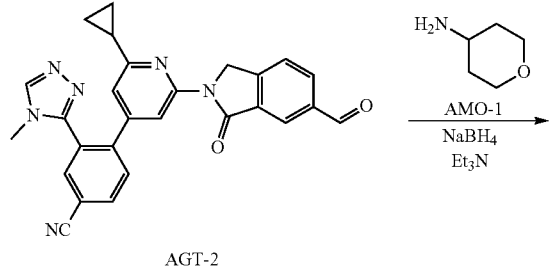
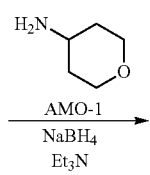
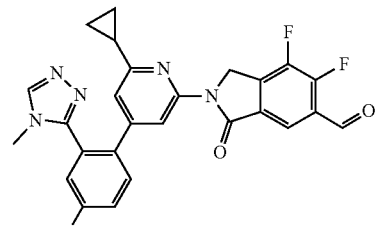
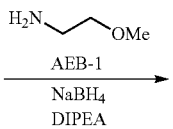

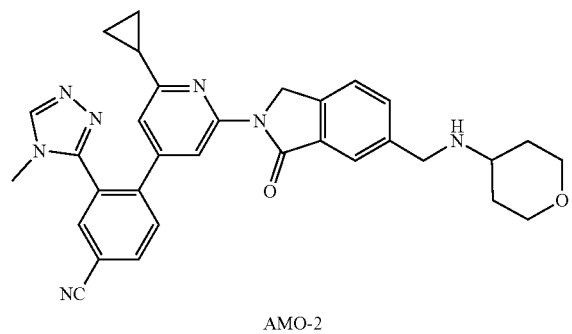
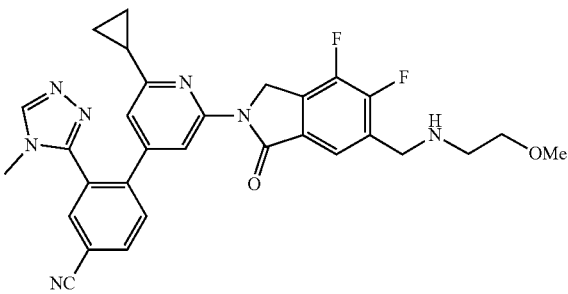

To a stirred solution of intermediate (AGT-2) (40 mg, 1 Eq, 87 µmol) and tetrahydro-2H-pyran-4-amine (AMO-1) (18 mg, 2 Eq, 0.17 mmol) in MeOH (5 mL) was added Et₃N (44 mg, 5 Eq, 0.44 mmol) for 2 h at 60° C. The mixture was cooled to rt. To the above mixture was added NaBH₄ (33 mg, 10 Eq, 0.87 mmol) at 0° C. The resulting mixture was stirred for 2 h at rt. The reaction was then quenched by the addition of MeOH (2 mL) at 0° C. The resulting mixture was concentrated in vacuo. The crude product was purified by Prep-HPLC with the following conditions: Column: XBridge Prep OBD C18 Column, 30×150 mm, 5 µm; Mobile Phase A: water (0.1% NH₄HCO₃+0.1% NH₃·H₂O) Mobile Phase B: MeCN; Flow rate: 60 mL/min; Gradient: 38 B to 48 B in 8 min; Detector, UV 254/210 nm; RT: 7.52. The product-containing fractions were combined and evaporated partially in vacuo and lyophilized overnight to afford the title compound (AMO-2) (11.9 mg, 22 µmol, 25%, 99.2% Purity) as a white solid. m/z 546.2 (M+H)⁺ (ES+). ¹H NMR (300 MHz, DMSO-d6) δ 8.54 (s, 1H), 8.27-8.13 (m, 2H), 7.98 (d, J=1.4 Hz, 1H), 7.87 (d, J=8.5 Hz, 1H), 7.78 (s, 1H), 7.70-7.60 (m, 2H), 6.89 (d, J=1.4 Hz, 1H), 5.01 (s, 2H), 3.83 (d, J=15.3 Hz, 4H), 3.48 (s, 3H), 3.31-3.20 (m, 3H), 2.07-2.02 (m, 1H), 1.81-1.77 (m, 2H), 1.31-1.24 (m, 2H), 0.98-0.96 (m, 4H).

Into a 25 mL round-bottom flask were added intermediate (ALY-1) (50 mg, 1 Eq, 0.10 mmol) in MeOH (5 mL) at rt. To the above mixture was added DIPEA (39 mg, 3 Eq, 0.30 mmol) and 2-methoxyethan-1-amine (AEB-1) (9 mg, 1.2 Eq, 0.12 mmol) at rt. The resulting mixture was stirred for additional 12 h at 60° C. The mixture was cooled to rt. To the above mixture was added NaBH₄ (15 mg, 4 Eq, 0.40 mmol) at 0° C. The resulting mixture was stirred for additional 1 h at rt. The mixture was concentrated in vacuo. The crude product was purified by Prep-HPLC with the following conditions (Column: XBridge Prep OBD C18 Column, 30*150 mm, 5 µm; Mobile Phase A: water (0.1% NH₄HCO₃+0.1% NH₃·H₂O), Mobile Phase B: MeCN; Flow rate: 60 mL/min; Gradient: 40% B to 50% B in 9 min; Wave Length: 254 nm) to afford the title compound (AMP-1) (1.5 mg, 2.7 µmol, 2.5%, 93.3% Purity) as a white solid. m/z 556.0 (M+H)⁺ (ES+). ¹H NMR (400 MHz, Methanol-d4) δ 8.49 (s, 1H), 8.15-8.08 (m, 2H), 8.00 (d, J=1.4 Hz, 1H), 7.92 (d, J=8.0 Hz, 1H), 7.74 (d, J=5.4 Hz, 1H), 6.95 (d, J=1.5 Hz, 1H), 5.11 (s, 2H), 3.96 (s, 2H), 3.53 (d, J=5.2 Hz, 2H), 3.49 (s, 3H), 3.35 (s, 3H), 2.82-2.77 (m, 2H), 2.07-2.02 (m, 1H), 1.08-1.04 (m, 2H), 1.02-0.99 (m, 2H).

Example 380: Synthesis of 4-[2-Cyclopropyl-6-(6-{[cyclopropyl(methyl)amino] methyl}-4-fluoro-1-oxo-3H-isoindol-2-yl)pyridin-4-yl]-3-(4-methyl-1,2,4-triazol-3-yl)benzonitrile (AMQ-2)

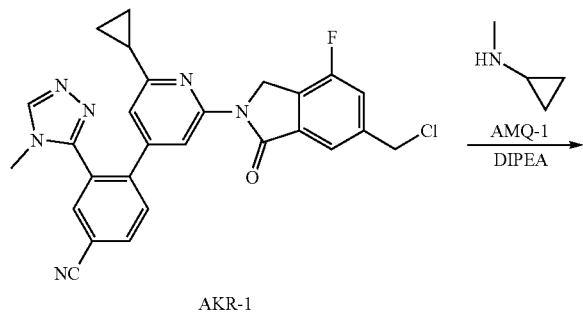

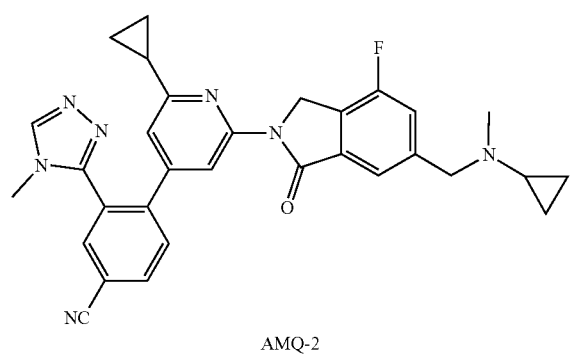

To a stirred mixture of intermediate (AKR-1) (30 mg, 1 Eq, 0.06 mmol) and N-methylcyclopropanamine (AMQ-1) (6.4 mg, 1.5 Eq, 0.09 mmol) in DCM (5 mL) was added DIPEA (23 mg, 3 Eq, 0.18 mmol) at 60° C. The mixture was cooled to rt and concentrated in vacuo. The crude product was purified by Prep-HPLC with the following conditions (Column: Xselect CSH C18 OBD Column 30*150 mm, 5 µm; Mobile Phase A: water (0.1% FA), Mobile Phase B: MeCN; Flow rate: 60 mL/min; Gradient: 3% B to 33% B in 10 min; Wave Length: 254 nm; RT: 10.72) to afford the title compound (AMQ-2) (5.8 mg, 11 µmol, 18%, 99.3% Purity) as a white solid. m/z 534.1 (M+H)$^+$ (ES+). $^1$H NMR (400 MHz, Methanol-d4) δ 8.50 (s, 1H), 8.16-8.07 (m, 2H), 8.01 (d, J=1.4 Hz, 1H), 7.92 (d, J=8.0 Hz, 1H), 7.63 (s, 1H), 7.39 (d, J=9.6 Hz, 1H), 6.97 (d, J=1.4 Hz, 1H), 5.07 (s, 2H), 3.89 (s, 2H), 3.50 (s, 3H), 2.37 (s, 3H), 2.11-2.00 (m, 1H), 1.92 (s, 1H), 1.09-0.95 (m, 4H), 0.62-0.43 (m, 4H).

Example 381: Synthesis of 4-[2-Cyclopropyl-6-(4-fluoro-6-{[(3S)-3-hydroxy-3-methylpiperidin-1-yl]methyl}-1-oxo-3H-isoindol-2-yl)pyridin-4-yl]-3-(4-methyl-1,2,4-triazol-3-yl)benzonitrile (AMR-2)

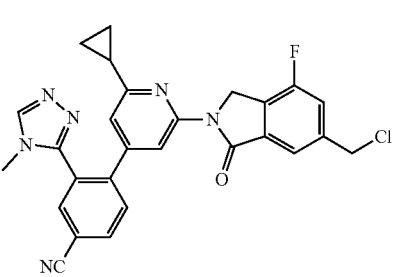

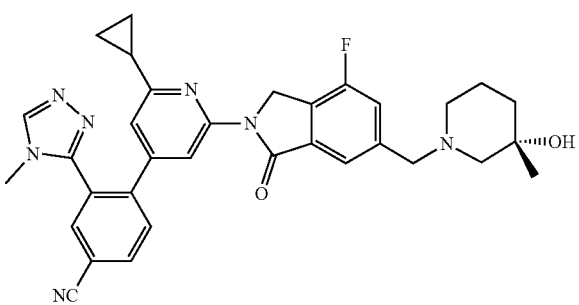

To a stirred solution of intermediate (AKR-1) (30 mg, 1 Eq, 0.06 mmol) and (3S)-3-methylpiperidin-3-ol (AMR-1) (8.3 mg, 1.2 Eq, 72 µmol) in DCM (8 mL) was added DIPEA (31 mg, 4 Eq, 0.24 mmol) at rt. The resulting mixture was stirred overnight at 60° C. The mixture was cooled to rt and concentrated in vacuo. The crude product was purified by Prep-HPLC with the following conditions (Column: XBridge Prep OBD C18 Column, 30*150 mm, 5 µm; Mobile Phase A: water (0.1%% NH$_4$HCO$_3$+0.1% NH$_3$·H$_2$O), Mobile Phase B: MeCN; Flow rate: 60 mL/min; Gradient: 52% B to 62% B in 9 min; Wave Length: 254/220 nm; RT: 7.32) to afford the title compound (AMR-2) (8.6 mg, 15 µmol, 25%, 99.3% Purity) as a white solid. m/z 578.0 (M+H)$^+$ (ES+). $^1$H NMR (400 MHz, Methanol-d4) δ 8.50 (s, 1H), 8.15-8.07 (m, 2H), 8.02 (d, J=1.4 Hz, 1H), 7.92 (d, J=8.0 Hz, 1H), 7.66-7.63 (m, 1H), 7.49 (d, J=9.8 Hz, 1H), 6.96 (d, J=1.5 Hz, 1H), 5.06 (s, 2H), 3.61 (s, 2H), 3.50 (s, 3H), 2.52 (s, 1H), 2.39-2.25 (m, 2H), 2.18 (d, J=10.9 Hz, 1H), 2.09-2.01 (m, 1H), 1.85-1.76 (m, 1H), 1.58-1.43 (m, 3H), 1.19 (s, 3H), 1.07-0.97 (m, 4H).

Example 382: Synthesis of 4-[2-Cyclopropyl-6-(4-fluoro-6-{2-oxa-6-azaspiro [3.3]heptan-6-ylmethyl}-1-oxo-3H-isoindol-2-yl)pyridin-4-yl]-3-(4-methyl-1,2,4-triazol-3-yl)benzonitrile (AMS-2)

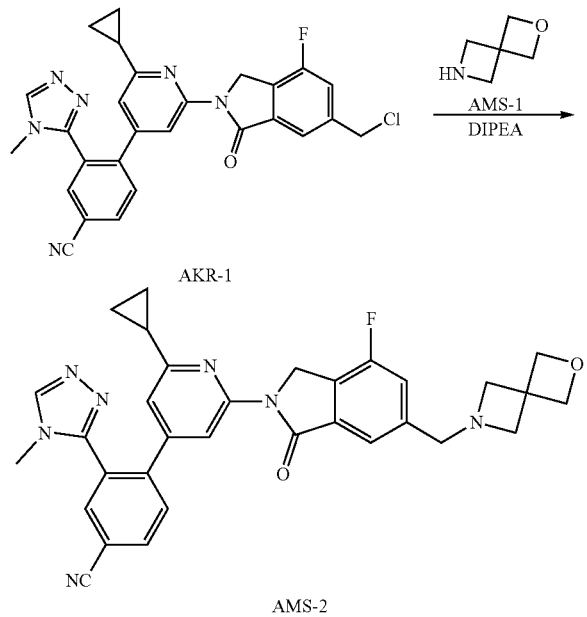

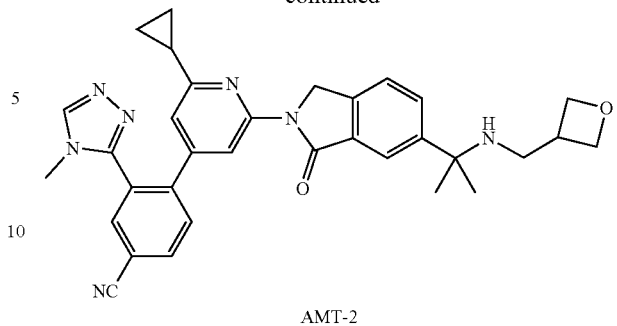

To a stirred solution of intermediate (AKR-1) (30 mg, 1 Eq, 0.06 mmol) and 2-oxa-6-azaspiro[3.3]heptane (AMS-1) (8.9 mg, 1.5 Eq, 0.09 mmol) in DCM (8 mL) was added DIPEA (31 mg, 4 Eq, 0.24 mmol) at rt. The resulting mixture was stirred for 1 d at 60° C. The mixture was cooled to rt and concentrated in vacuo. The crude product was purified by Prep-HPLC with the following conditions (Column: Xselect CSH C18 OBD Column 30*150 mm, 5 μm; Mobile Phase A: water (0.1% FA), Mobile Phase B: MeCN; Flow rate: 60 mL/min; Gradient: 9% B to 39% B in 10 min; Wave Length: 254 nm; RT: 8.45) to afford the title compound (AMS-2) (7.6 mg, 14 μmol, 22%, 99.3% Purity) as a white solid. m/z 562.0 (M+H)+ (ES+). $^1$H NMR (400 MHz, DMSO-d6) δ 8.54 (s, 1H), 8.29-8.18 (m, 2H), 7.95 (d, J=1.4 Hz, 1H), 7.87 (d, J=8.5 Hz, 1H), 7.50 (s, 1H), 7.41 (d, J=9.8 Hz, 1H), 6.92 (d, J=1.4 Hz, 1H), 5.07 (s, 2H), 4.61 (s, 4H), 3.61 (s, 2H), 3.49 (s, 3H), 3.47 (s, 4H), 2.11-2.00 (m, 1H), 1.01-0.94 (m, 4H).

Example 383: Synthesis of 4-[2-Cyclopropyl-6-(6-{2-[(oxetan-3-ylmethyl)amino]propan-2-yl}-1-oxo-3H-isoindol-2-yl) pyridin-4-yl]-3-(4-methyl-1,2,4-triazol-3-yl) benzonitrile (AMT-2)

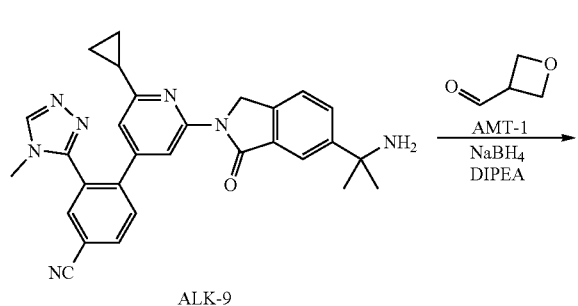

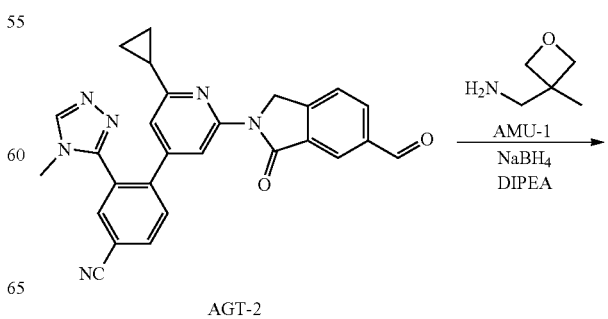

To a stirred solution of intermediate (ALK-9) (30 mg, 1 Eq, 61 μmol) and oxetane-3-carbaldehyde (AMT-1) (16 mg, 3 Eq, 0.18 mmol) in MeOH (3 mL) was added DIPEA (40 mg, 5 Eq, 0.31 mmol) at rt. The resulting mixture was stirred for 2 h at 60° C. The mixture was cooled to rt. To the above mixture was added NaBH$_4$ (12 mg, 5 Eq, 0.31 mmol) at rt. The resulting mixture was stirred for additional 2 h at rt. The resulting mixture was concentrated in vacuo. The residue was purified by Prep-TLC with DCM/MeOH (5/1). The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 35% B to 48% B in 9 min; Wave Length: 254/220 nm) to afford the title compound (AMT-2) (4.0 mg, 7.2 μmol, 11%, 98.1% Purity) as a white solid. m/z 560.1 (M+H)+ (ES+). $^1$H NMR (400 MHz, Methanol-d4) δ 8.51 (s, 1H), 8.17-8.09 (m, 2H), 8.05 (d, J=1.4 Hz, 1H), 7.97-7.90 (m, 2H), 7.87-7.81 (m, 1H), 7.63 (d, J=8.1 Hz, 1H), 6.94 (d, J=1.5 Hz, 1H), 5.03 (s, 2H), 4.78-4.72 (m, 2H), 4.26 (t, J=6.0 Hz, 2H), 3.51 (s, 3H), 3.06-2.96 (m, 1H), 2.57 (d, J=7.5 Hz, 2H), 2.09-1.98 (m, 1H), 1.53 (s, 6H), 1.08-0.96 (m, 4H).

Example 384: Synthesis of 4-{2-Cyclopropyl-6-[6-({[(3-methyloxetan-3-yl)methyl]amino}methyl)-1-oxo-3H-isoindol-2-yl]pyridin-4-yl}-3-(4-methyl-1,2,4-triazol-3-yl)benzonitrile (AMU-2)

979
-continued

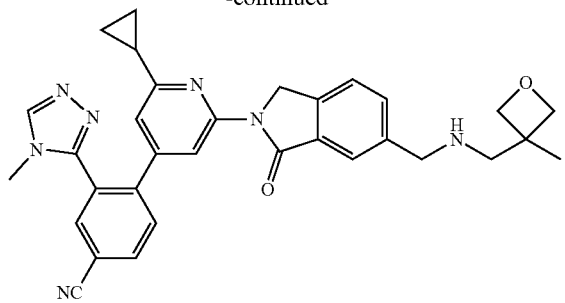

AMU-2

980
-continued

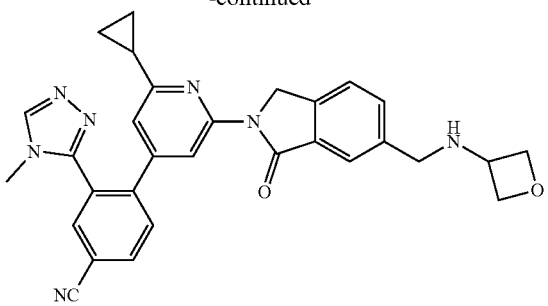

AMV-2

To a stirred mixture of intermediate (AGT-2) (30 mg, 1 Eq, 64 μmol), 1-(3-methyloxetan-3-yl)methanamine (AMU-1) (12 mg, 1.8 Eq, 0.12 mmol) and DIPEA (33.11 mg, 0.256 mmol, 4 Eq) in MeOH (8 mL) at rt. The resulting mixture was stirred for 2 h at 60° C. The mixture was cooled to rt. To the above mixture was added NaBH$_4$ (10 mg, 4 Eq, 0.26 mmol) at 0° C. The resulting mixture was stirred overnight at 60° C. The mixture was cooled to rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 50% B to 63% B in 9 min; Wave Length: 254/220 nm; RT: 8.98) to afford the title compound (AMU-2) (6.0 mg, 11 μmol, 17%, 98.9% Purity) as a white solid. m/z 546.1 (M+H)$^+$ (ES+). $^1$H NMR (400 MHz, Methanol-d4) δ 8.50 (s, 1H), 8.17-8.04 (m, 3H), 7.96-7.84 (m, 2H), 7.74-7.70 (m, 1H), 7.65 (d, J=7.9 Hz, 1H), 6.93 (d, J=1.4 Hz, 1H), 5.04 (s, 2H), 4.46 (d, J=5.9 Hz, 2H), 4.35 (d, J=5.9 Hz, 2H), 4.01 (s, 2H), 3.49 (s, 3H), 2.89 (s, 2H), 2.07-1.97 (m, 1H), 1.34 (s, 3H), 1.09-0.92 (m, 4H).

Example 385: Synthesis of 4-(2-Cyclopropyl-6-{6-[(oxetan-3-ylamino)methyl]-1-oxo-3H-isoindol-2-yl}pyridin-4-yl)-3-(4-methyl-1,2,4-triazol-3-yl)benzonitrile (AMV-2)

To a stirred solution of intermediate (AGT-2) (30 mg, 1 Eq, 65 μmol) and oxetan-3-amine (AMV-1) (5.7 mg, 1.2 Eq, 78 μmol) in MeOH (12 mL) was added DIPEA (25 mg, 3 Eq, 0.20 mmol) at rt. The resulting mixture was stirred overnight at 60° C. The mixture was allowed to cool down to rt. To the above mixture was added NaBH$_4$ (12 mg, 5 Eq, 0.33 mmol) at 0° C. The resulting mixture was stirred for additional 1 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 35% B to 45% B in 8 min; Wave Length: 254/220 nm; RT: 7.22) to afford the title compound (AMV-2) (11.5 mg, 22 μmol, 34%, 99.3% Purity) as a white solid. m/z 518.0 (M+H)$^+$ (ES+). $^1$H NMR (400 MHz, Methanol-d4) δ 8.50 (s, 1H), 8.14-8.04 (m, 3H), 7.92 (d, J=8.1 Hz, 1H), 7.79 (d, J=1.6 Hz, 1H), 7.67-7.59 (m, 2H), 6.92 (d, J=1.5 Hz, 1H), 5.02 (s, 2H), 4.71 (t, J=6.8 Hz, 2H), 4.44 (t, J=6.4 Hz, 2H), 4.05-3.98 (m, 1H), 3.80 (s, 2H), 3.49 (s, 3H), 2.06-1.99 (m, 1H), 1.06-0.95 (m, 4H).

Example 386: Synthesis of 4-{2-Cyclopropyl-6-[4-fluoro-6-({[(1-hydroxycyclobutyl)methyl](methyl)amino}methyl)-1-oxo-3H-isoindol-2-yl]pyridin-4-yl}-3-(4-methyl-1,2,4-triazol-3-yl)benzonitrile (AMW-2)

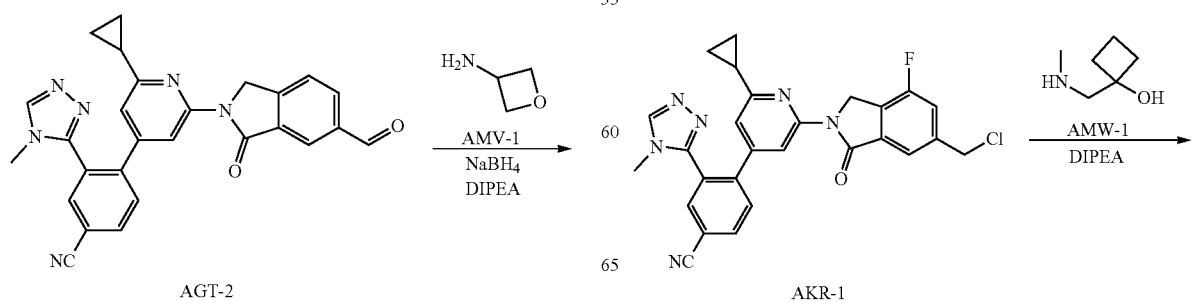

981

-continued

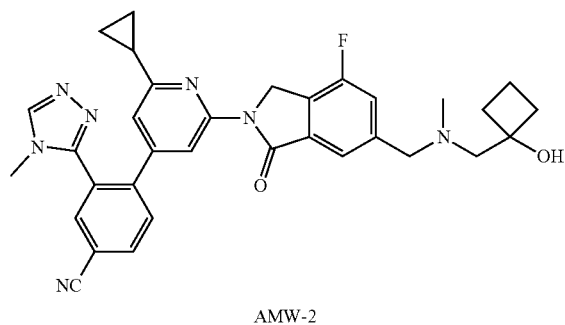

AMW-2

To a stirred solution of intermediate (AKR-1) (30 mg, 1 Eq, 0.06 mmol) and 1-[(methylamino) methyl] cyclobutan-1-ol (AMW-1) (14 mg, 2 Eq, 0.12 mmol) in DCM (5 mL) was added DIPEA (23 mg, 3 Eq, 0.18 mmol) at rt. The resulting mixture was stirred for 4 days at 60° C. The mixture was allowed to cool down to rt. The resulting mixture was concentrated in vacuo. The crude product was purified by Prep-HPLC with the following conditions (Column: Xselect CSH C18 OBD Column 30*150 mm, 5 μm; Mobile Phase A: water (0.1% FA), Mobile Phase B: MeCN; Flow rate: 60 mL/min; Gradient: 4% B to 34% B in 10 min; Wave Length: 254 nm) to afford the title compound (AMW-2) (7.4 mg, 13 μmol, 21%, 98.1% Purity) as a white solid. m/z 578.0 (M+H)+ (ES+). $^1$H NMR (400 MHz, DMSO-d6) δ 8.55 (s, 1H), 8.25-8.20 (m, 2H), 7.94 (d, J=1.4 Hz, 1H), 7.89-7.84 (m, 1H), 7.61 (s, 1H), 7.52 (d, J=10.1 Hz, 1H), 6.93 (d, J=1.4 Hz, 1H), 5.08 (s, 2H), 4.93 (s, 1H), 3.72 (s, 2H), 3.48 (s, 3H), 2.48 (s, 2H), 2.23 (s, 3H), 2.10-1.98 (m, 3H), 1.95-1.84 (m, 2H), 1.67-1.57 (m, 1H), 1.42-1.32 (m, 1H), 1.03-0.93 (m, 4H).

Example 387: Synthesis of 4-(2-{6-[(1R,5S)-2-Azabicyclo[3.1.0]hexan-2-ylmethyl]-4-fluoro-1-oxo-3H-isoindol-2-yl}-6-cyclopropylpyridin-4-yl)-3-(4-methyl-1,2,4-triazol-3-yl)benzonitrile (AMX-3)

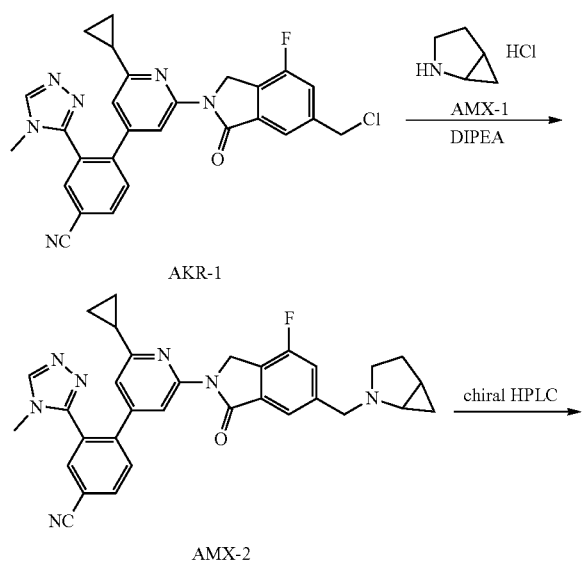

982

-continued
first peak

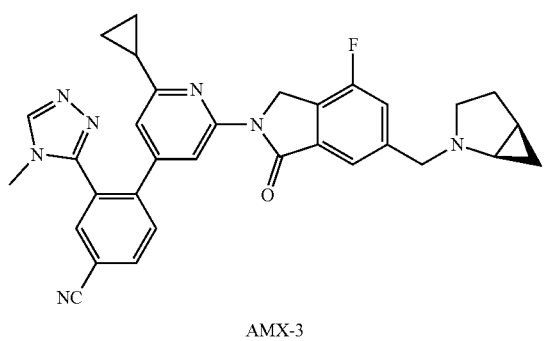

AMX-3

Step 1: 4-[2-(6-{2-Azabicyclo[3.1.0]hexan-2-ylmethyl}-4-fluoro-1-oxo-3H-isoindol-2-yl)-6-cyclopropylpyridin-4-yl]-3-(4-methyl-1,2,4-triazol-3-yl)benzonitrile (AMX-2)

To a stirred solution of intermediate (AKR-1) (100 mg, 1 Eq, 0.20 mmol) and DIPEA (78 mg, 3 Eq, 0.60 mmol) in DCM (15 mL) was added 2-azabicyclo [3.1.0] hexane, HCl (AMX-1) (29 mg, 1.2 Eq, 0.24 mmol) at rt under nitrogen atmosphere. The resulting mixture was stirred overnight at 60° C. under nitrogen atmosphere. The mixture was allowed to cool down to rt. The resulting mixture was concentrated in vacuo. The residue was purified by Prep-TLC with DCM/MeOH (10/1). The crude product was purified by Prep-HPLC with the following conditions (Column: Xselect CSH C18 OBD Column 30*150 mm, 5 μm; Mobile Phase A: water (0.1% FA), Mobile Phase B: MeCN; Flow rate: 60 mL/min; Gradient: 18% B to 24% B in 15 min; Wave Length: 254 nm; RT: 14.03) to afford the sub-title compound (AMX-2) (43 mg, 79 μmol, 39%, 99% Purity) as a white solid. m/z 546.1 (M+H)+ (ES+).

Step 2: 4-(2-{6-[(1R,5S)-2-Azabicyclo[3.1.0]hexan-2-ylmethyl]-4-fluoro-1-oxo-3H-isoindol-2-yl}-6-cyclopropylpyridin-4-yl)-3-(4-methyl-1,2,4-triazol-3-yl)benzonitrile (AMX-3)

The product of the product from step 1 above (AMX-2) (40 mg, 1 Eq, 73 μmol) was purified by Chiral Prep-HPLC with the following conditions (Column: CHIRALPAK IF, 2*25 cm, 5 μm; Mobile Phase A: MtBE (0.5% 2M NH$_3$-MeOH)-HPLC, Mobile Phase B: MeOH:DCM=1:1-HPLC; Flow rate: 17 mL/min; Gradient: 20% B to 20% B in 55 min; Wave Length: 220/254 nm; RT1(min): 44.016 Sample Solvent: EtOH-HPLC; Injection Volume: 1 mL) to afford the title compound (AMX-3) (10.5 mg, 19 μmol, 26%, 99.1% Purity) as a white solid. m/z 546.1 (M+H)+ (ES+). $^1$H NMR (300 MHz, Methanol-d4) δ 8.49 (s, 1H), 8.16-8.07 (m, 2H), 8.02 (d, J=1.4 Hz, 1H), 7.92 (d, J=8.0 Hz, 1H), 7.69 (d, J=1.2 Hz, 1H), 7.51-7.44 (m, 1H), 6.95 (d, J=1.4 Hz, 1H), 5.07 (s, 2H), 3.84 (s, 2H), 3.50 (s, 3H), 2.98-2.85 (m, 1H), 2.74-2.65 (m, 1H), 2.22-2.10 (m, 1H), 2.11-1.87 (m, 3H), 1.56-1.46 (m, 1H), 1.09-0.94 (m, 4H), 0.91-0.82 (m, 1H), 0.32-0.21 (m, 1H). ChiralHPLC-PH-NIMB-0898-0: Column: CHIRALPAK IF-3, 4.6*50 mm, 3 μm; Mobile Phase A: MtBE (0.1% DEA):(MeOH:DCM=1:1)=80:20; Flow rate: 1 mL/min; RT: 5.437.

Example 388: Synthesis of 4-(2-{6-[(1S,5R)-2-Azabicyclo[3.1.0]hexan-2-ylmethyl]-4-fluoro-1-oxo-3H-isoindol-2-yl}-6-cyclopropylpyridin-4-yl)-3-(4-methyl-1,2,4-triazol-3-yl)benzonitrile (AMY-1)

Example 389: Synthesis of 4-[2-Cyclopropyl-6-(4,5-difluoro-6-{[(2-methoxyethyl)(methyl)amino]methyl}-1-oxo-3H-isoindol-2-yl)pyridin-4-yl]-3-(4-methyl-1,2,4-triazol-3-yl)benzonitrile (AMZ-3)

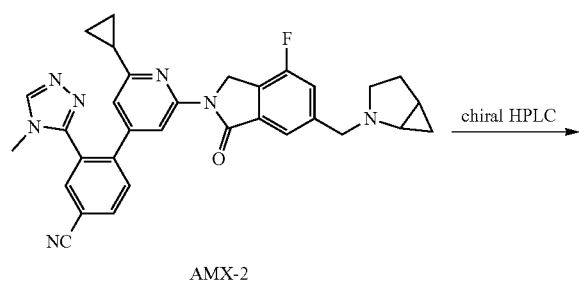

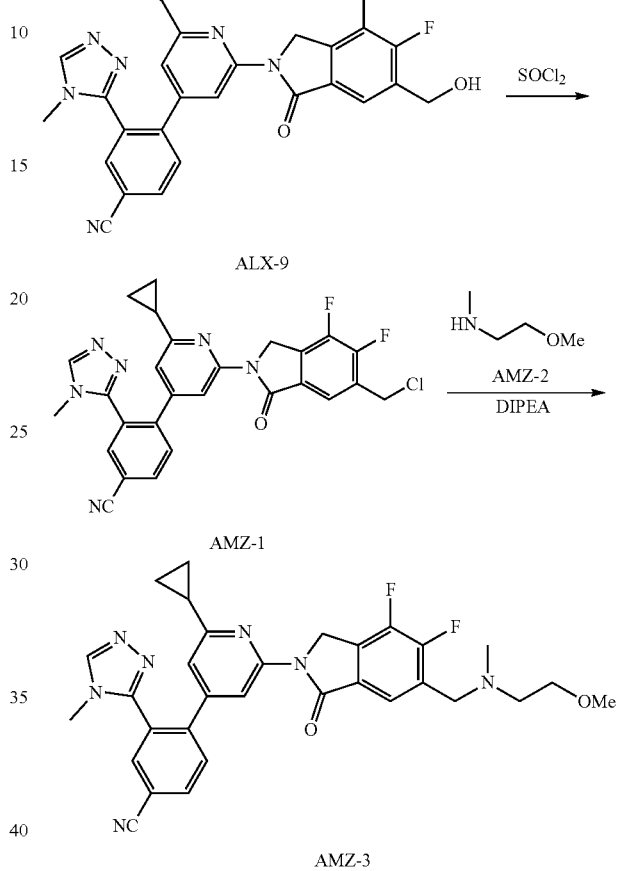

Compound (AMX-2) (40 mg, 1 Eq, 73 µmol) was purified by Chiral Prep-HPLC with the following conditions (Column: CHIRALPAK IF, 2*25 cm, 5 µm; Mobile Phase A: MtBE (0.5% 2M NH$_3$-MeOH)-HPLC, Mobile Phase B: MeOH:DCM=1:1-HPLC; Flow rate: 17 mL/min; Gradient: 20% B to 20% B in 55 min; Wave Length: 220/254 nm; RT2(min): 19.329; Sample Solvent: EtOH-HPLC; Injection Volume: 1 mL) to afford the title compound (AMY-1) (7.5 mg, 14 µmol, 19%, 99.1% Purity) as a white solid. m/z 546.1 (M+H)$^+$ (ES+). $^1$H NMR (300 MHz, Methanol-d4) δ 8.49 (s, 1H), 8.16-8.07 (m, 2H), 8.02 (d, J=1.4 Hz, 1H), 7.92 (d, J=8.0 Hz, 1H), 7.69 (d, J=1.2 Hz, 1H), 7.51-7.44 (m, 1H), 6.95 (d, J=1.4 Hz, 1H), 5.07 (s, 2H), 3.84 (s, 2H), 3.50 (s, 3H), 2.98-2.85 (m, 1H), 2.74-2.65 (m, 1H), 2.22-2.10 (m, 1H), 2.11-1.87 (m, 3H), 1.56-1.46 (m, 1H), 1.09-0.94 (m, 4H), 0.91-0.82 (m, 1H), 0.32-0.21 (m, 1H). ChiralHPLC-PH-NIMB-0898-0: Column: CHIRALPAK IF-3, 4.6*50 mm, 3 µm; Mobile Phase A: MtBE(0.1% DEA):(MeOH:DCM=1:1)=80:20; Flow rate: 1 mL/min; RT: 5.995.

Step 1: 4-{2-[6-(Chloromethyl)-4,5-difluoro-1-oxo-3H-isoindol-2-yl]-6-cyclopropylpyridin-4-yl}-3-(4-methyl-1,2,4-triazol-3-yl)benzonitrile (AMZ-1)

Into a 50 mL round-bottom flask was added intermediate (ALX-9) (100 mg, 1 Eq, 0.20 mmol) in DCM (10 mL) at rt. To the above stirred solution was added SOCl$_2$ (72 mg, 3 Eq, 0.60 mmol) at 0° C. The resulting mixture was stirred for additional 2 h at rt. The reaction was then quenched by the addition of 5 mL of MeOH at 0° C. The resulting mixture was diluted with water and extracted with DCM (3×10 mL). The combined organic layers were washed with brine (2×10 mL), dried (Na$_2$SO$_4$). After filtration, the filtrate was concentrated in vacuo. This resulted in the sub-title compound (AMZ-1) (74 mg, 0.14 mmol, 62%, 92% Purity) as a white solid. m/z 517.1/519.1 (M+H)$^+$ (ES+)

Step 2: 4-[2-Cyclopropyl-6-(4,5-difluoro-6-{[(2-methoxyethyl)(methyl)amino]methyl}-1-oxo-3H-isoindol-2-yl)pyridin-4-yl]-3-(4-methyl-1,2,4-triazol-3-yl)benzonitrile (AMZ-3)

Into a 25 mL round-bottom flask were added the product from step 1 above (AMZ-1) (30 mg, 1 Eq, 58 µmol) and 2-methoxy-N-methylethan-1-amine (AMZ-2) (11 mg, 2 Eq, 0.12 mmol) in MeOH (5 mL) at rt. To the above mixture was added DIPEA (23 mg, 3 Eq, 0.17 mmol) at rt. The resulting mixture was stirred for additional 2 h at 60° C. The mixture was cooled to rt and concentrated in vacuo. The residue was purified by Prep-TLC with EtOAc/petroleum ether (1/1). The crude product was purified by Prep-HPLC with the following conditions (Column: Xselect CSH C18 OBD Column 30*150 mm, 5 μm; Mobile Phase A: water (0.1% FA), Mobile Phase B: MeCN; Flow rate: 60 mL/min; Gradient: 4% B to 34% B in 10 min; Wave Length: 254 nm) to afford the title compound (AMZ-3) (18.0 mg, 54%, 99.5% Purity) as a white solid. m/z 570.1 (M+H)$^+$ (ES+). $^1$H NMR (400 MHz, Methanol-d4) δ 8.50 (s, 1H), 8.14-8.08 (m, 2H), 7.98 (d, J=1.4 Hz, 1H), 7.92 (d, J=8.1 Hz, 1H), 7.75 (d, J=5.2 Hz, 1H), 6.96 (d, J=1.4 Hz, 1H), 5.10 (s, 2H), 3.79-3.75 (m, 2H), 3.60-3.55 (m, 2H), 3.51 (s, 3H), 3.35 (s, 3H), 2.71-2.65 (m, 2H), 2.29 (s, 3H), 2.09-2.01 (m, 1H), 1.08-0.97 (m, 4H).

Example 390: Synthesis of 4-[2-(6-{3-Azabicyclo[3.1.0]hexan-3-ylmethyl}-1-oxo-3H-isoindol-2-yl)-6-cyclopropylpyridin-4-yl]-3-(4-methyl-1,2,4-triazol-3-yl)benzonitrile (ANA-1)

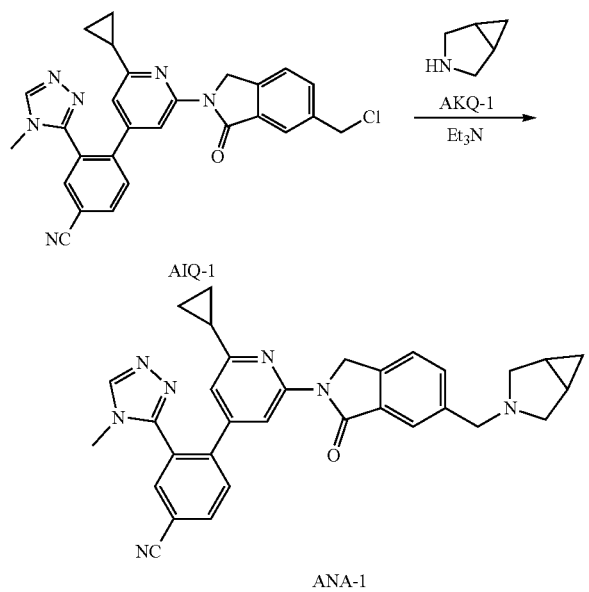

To a stirred mixture of intermediate (AIQ-1) (20 mg, 1 Eq, 42 μmol) and 3-azabicyclo[3.1.0]hexane (AKQ-1) (3.8 mg, 1.1 Eq, 46 μmol) in DCM (2 mL) was added Et$_3$N (25 mg, 6 Eq, 0.25 mmol) at rt. The resulting mixture was stirred overnight at 60° C. The mixture was allowed to cool down to rt. The resulting mixture was concentrated in vacuo. The crude product was purified by reverse flash column chromatography with the following conditions: Column, C18; mobile phase, water (0.1% NH$_4$HCO$_3$) and MeCN (20% MeCN up to 80% in 20 min); Detector, UV 254/220 nm. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 50% B to 63% B in 9 min; Wave Length: 254/220 nm; RT: 8.98) to afford the title compound (ANA-1) (3.2 mg, 6.0 μmol, 15%, 99.9% Purity) as a white solid. m/z 528.2 (M+H)$^+$ (ES+). $^1$H NMR (400 MHz, Methanol-d4) δ 8.51 (s, 1H), 8.16-8.07 (m, 2H), 8.03 (d, J=1.5 Hz, 1H), 7.92 (d, J=8.0 Hz, 1H), 7.74 (s, 1H), 7.64-7.54 (m, 2H), 6.93 (d, J=1.5 Hz, 1H), 5.01 (s, 2H), 3.69 (s, 2H), 3.51 (s, 3H), 2.92 (d, J=8.7 Hz, 2H), 2.42 (d, J=8.8 Hz, 2H), 2.09-1.98 (m, 1H), 1.43-1.35 (m, 2H), 1.08-0.94 (m, 4H), 0.81-0.73 (m, 1H), 0.42-0.32 (m, 1H).

Example 391: Synthesis of 4-[2-Cyclopropyl-6-(4-fluoro-6-{[(oxetan-3-ylmethyl)amino]methyl}-1-oxo-3H-isoindol-2-yl)pyridin-4-yl]-3-(4-methyl-1,2,4-triazol-3-yl)benzonitrile (ANB-1)

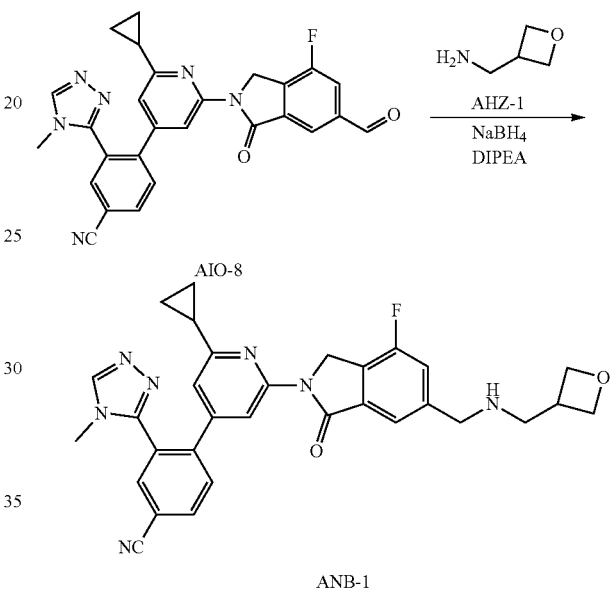

To a stirred solution of intermediate (AIO-8) (30 mg, 1 Eq, 63 μmol) and 1-(oxetan-3-yl)methanamine (AHZ-1) (7 mg, 1.2 Eq, 76 μmol) in MeOH (8 mL) was added DIPEA (24 mg, 3 Eq, 0.19 mmol) at rt. The resulting mixture was stirred overnight at 60° C. The mixture was allowed to cool down to rt. To the above mixture was added NaBH$_4$ (12 mg, 5 Eq, 0.32 mmol) at 0° C. The resulting mixture was stirred for additional 1 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 34% B to 44% B in 9 min; Wave Length: 254/220 nm; RT: 8.48) to afford the title compound (ANB-1) (7.9 mg, 14 μmol, 23%, 99.8% Purity) as a white solid. m/z 550.0 (M+H)$^+$ (ES+). $^1$H NMR (400 MHz, Methanol-d4) δ 8.49 (s, 1H), 8.15-8.07 (m, 2H), 8.03 (d, J=1.4 Hz, 1H), 7.92 (d, J=8.0 Hz, 1H), 7.65 (d, J=1.1 Hz, 1H), 7.46-7.41 (m, 1H), 6.95 (d, J=1.4 Hz, 1H), 5.06 (s, 2H), 4.82-4.78 (m, 2H), 4.40 (t, J=6.1 Hz, 2H), 3.87 (s, 2H), 3.49 (s, 3H), 3.20-3.11 (m, 1H), 2.90 (d, J=7.4 Hz, 2H), 2.08-2.00 (m, 1H), 1.08-0.95 (m, 4H).

987

Example 392: Synthesis of 4-[2-Cyclopropyl-6-(4-fluoro-6-{[(2R,3S)-3-hydroxy-2-methylpyrrolidin-1-yl]methyl}-1-oxo-3H-isoindol-2-yl)pyridin-4-yl]-3-(4-methyl-1,2,4-triazol-3-yl)benzonitrile (ANC-2)

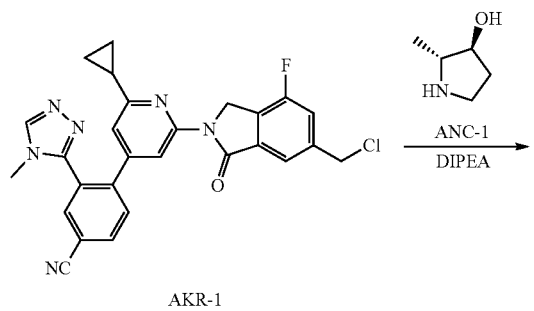

AKR-1

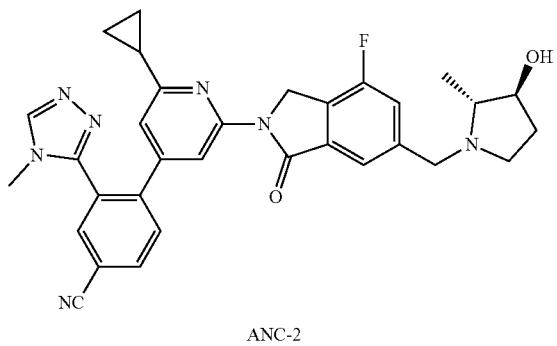

ANC-2

To a stirred mixture of intermediate (AKR-1) (30 mg, 1 Eq, 0.06 mmol) and (2R,3S)-2-methylpyrrolidin-3-ol (ANC-1) (9 mg, 1.5 Eq, 0.09 mmol) in DCM (5 mL) was added DIPEA (23 mg, 3 Eq, 0.18 mmol) at 60° C. The mixture was cooled to rt and concentrated in vacuo. The crude product was purified by Prep-HPLC with the following conditions (Column: Xselect CSH C18 OBD Column 30*150 mm 5 μm; Mobile Phase A: water (0.1% FA), Mobile Phase B: MeCN; Flow rate: 60 mL/min; Gradient: 7% B to 37% B in 10 min; Wave Length: 254 nm; RT: 9.03) to afford the title compound (ANC-2) (6.1 mg, 11 μmol, 18%, 99.8% Purity) as a white solid. m/z 564.1 (M+H)$^+$ (ES+). $^1$H NMR (400 MHz, DMSO-d6) δ 8.54 (s, 1H), 8.25-8.18 (m, 2H), 7.92 (d, J=1.4 Hz, 1H), 7.87 (d, J=8.5 Hz, 1H), 7.55 (s, 1H), 7.44 (d, J=9.8 Hz, 1H), 6.94 (d, J=1.4 Hz, 1H), 5.07 (s, 2H), 4.01 (d, J=13.7 Hz, 1H), 3.70-3.61 (m, 1H), 3.48 (s, 3H), 3.35 (d, J=13.8 Hz, 1H), 2.74-2.67 (m, 1H), 2.31-2.21 (m, 2H), 2.11-2.03 (m, 1H), 1.98-1.87 (m, 1H), 1.51-1.41 (m, 1H), 1.12 (d, J=6.2 Hz, 3H), 1.03-0.92 (m, 4H).

988

Example 393: Synthesis of 4-[2-(6-{5-Azaspiro[2.4]heptan-5-ylmethyl}-1-oxo-3H-isoindol-2-yl)-6-cyclopropylpyridin-4-yl]-3-(4-methyl-1,2,4-triazol-3-yl)benzonitrile (AND-1)

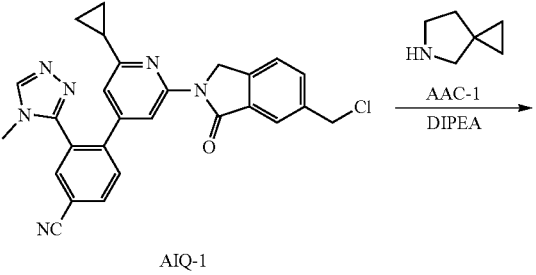

AIQ-1

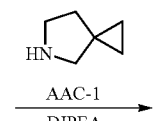

AND-1

A solution of intermediate (AIQ-1) (15 mg, 1 Eq, 31 μmol), DIPEA (16 mg, 4 Eq, 0.12 mmol) and 5-azaspiro[2.4]heptane (AAC-1) (4 mg, 1.3 Eq, 0.04 mmol) in DCM (3 mL) was stirred for 3 days at 60° C. The mixture was cooled to rt and concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 51% B to 61% B in 8 min; Wave Length: 254/220 nm; RT: 7.35) to afford the title compound (AND-1) (6.7 mg, 12 μmol, 39%, 99.0% Purity) as a white solid. m/z 542.1 (M+H)$^+$ (ES+). $^1$H NMR (400 MHz, Methanol-d4) δ 8.50 (s, 1H), 8.13-8.07 (m, 2H), 8.05 (d, J=1.4 Hz, 1H), 7.92 (d, J=8.1 Hz, 1H), 7.80 (s, 1H), 7.70-7.66 (m, 1H), 7.61 (d, J=7.8 Hz, 1H), 6.92 (d, J=1.5 Hz, 1H), 5.02 (s, 2H), 3.75 (s, 2H), 3.51 (s, 3H), 2.79 (t, J=7.0 Hz, 2H), 2.53 (s, 2H), 2.07-1.99 (m, 1H), 1.85 (t, J=6.9 Hz, 2H), 1.06-0.96 (m, 4H), 0.56 (d, J=2.2 Hz, 4H).

Example 394: Synthesis of 4-[2-Cyclopropyl-6-(4,5-difluoro-6-{[(oxetan-3-ylmethyl)amino]methyl}-1-oxo-3H-isoindol-2-yl)pyridin-4-yl]-3-(4-methyl-1,2,4-triazol-3-yl)benzonitrile (ANE-1)

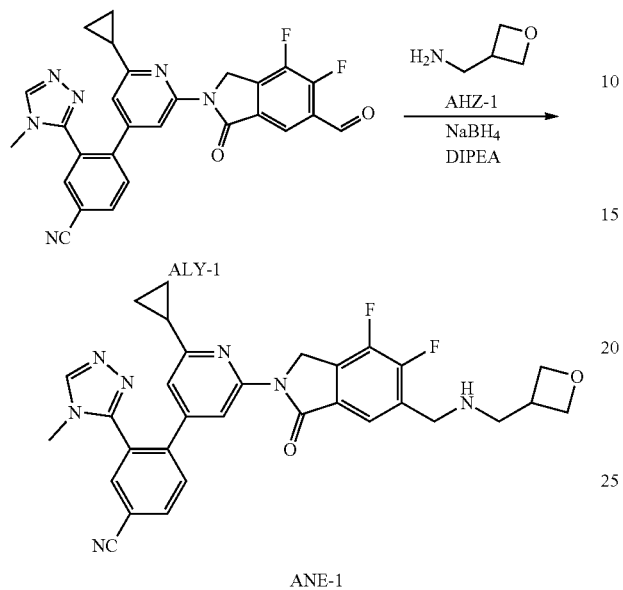

Into a 25 mL round-bottom flask were added intermediate (ALY-1) (30 mg, 1 Eq, 61 μmol) in MeOH (5 mL) at rt. To the above mixture was added DIPEA (24 mg, 3 Eq, 0.18 mmol) and 1-(oxetan-3-yl) methanamine (AHZ-1) (6 mg, 1.2 Eq, 73 μmol) at rt. The resulting mixture was stirred for additional 12 h at 60° C. The mixture was cooled to rt. To the above mixture was added NaBH$_4$ (12 mg, 5 Eq, 0.31 mmol) at 0° C. The resulting mixture was stirred for additional 1 h at rt. The mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 38% B to 48% B in 8 min; Wave Length: 254 nm) to afford the title compound (ANE-1) (10.9 mg, 19 μmol, 31%, 97.4% Purity) as a white solid. m/z 568.0 (M+H)$^+$ (ES+). $^1$H NMR (400 MHz, Methanol-d4) δ 8.49 (s, 1H), 8.14-8.08 (m, 2H), 8.00 (d, J=1.4 Hz, 1H), 7.92 (d, J=8.0 Hz, 1H), 7.74 (d, J=5.3 Hz, 1H), 6.96 (d, J=1.4 Hz, 1H), 5.11 (s, 2H), 4.85-4.79 (m, 2H), 4.44-4.38 (m, 2H), 3.93 (s, 2H), 3.49 (s, 3H), 3.20-3.13 (m, 1H), 2.94 (d, J=7.4 Hz, 2H), 2.08-2.02 (m, 1H), 1.07-0.98 (m, 4H).

Example 395: Synthesis of 4-[2-Cyclopropyl-6-(4-fluoro-6-{hexahydrofuro[3,2-b]pyrrol-4-ylmethyl}-1-oxo-3H-isoindol-2-yl) pyridin-4-yl]-3-(4-methyl-1,2,4-triazol-3-yl) benzonitrile (ANF-11)

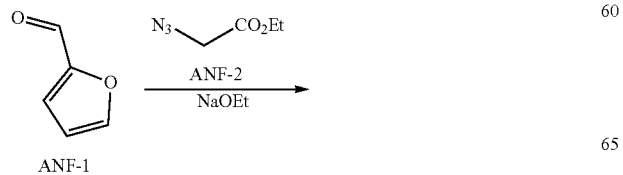

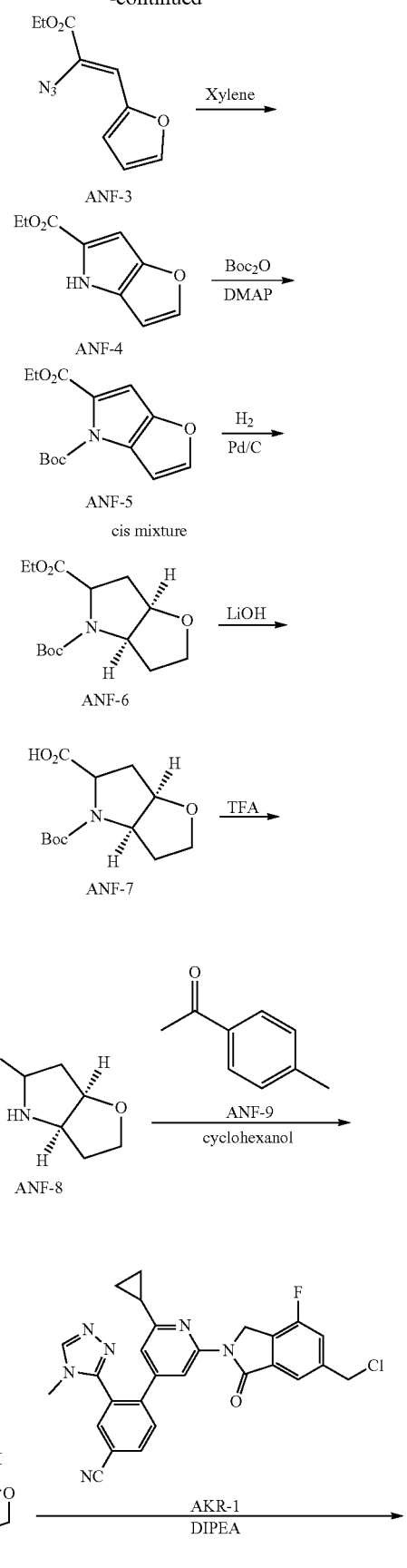

-continued
cis mixture

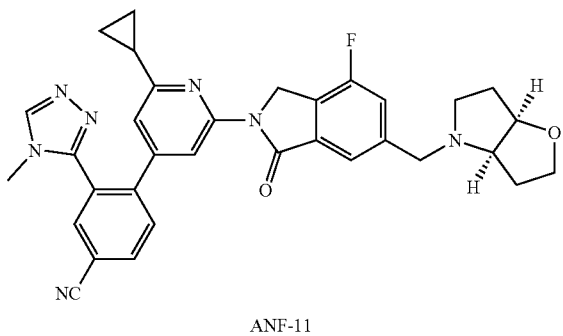

ANF-11

Step 1: Ethyl (2Z)-2-azido-3-(furan-2-yl)prop-2-enoate (ANF-3)

To a stirred solution of EtONa (4.25 g, 1.5 Eq, 62.4 mmol) in EtOH (50 mL) were added furan-2-carbaldehyde (ANF-1) (4.00 g, 1 Eq, 41.6 mmol) and ethyl 2-azidoacetate (ANF-2) (16.1 g, 3 Eq, 125 mmol) dropwise at 0° C. under nitrogen atmosphere. The resulting mixture was stirred for 2 h at 0° C. under nitrogen atmosphere. The resulting mixture was extracted with EtOAc (3×20 mL). The resulting mixture was diluted with water and extracted with EtOAc (3×100 mL). The combined organic layers were washed with brine (2×100 mL), dried (Na$_2$SO$_4$). After filtration, the filtrate was concentrated in vacuo. The residue was applied on a silica gel column chromatography with petroleum ether/EtOAc (10/1) to afford the sub-title compound (ANF-3) (2.8 g, 13.5 mmol, 32%, 90% Purity) as a yellow oil. m/z 208.1 (M+H)$^+$ (ES+)

Step 2: Ethyl 4H-furo[3,2-b]pyrrole-5-carboxylate (ANF-4)

A solution of the product from step 1 above (ANF-3) (2.8 g, 1 Eq, 13.5 mmol) in xylene (40 mL) was stirred for 2 h at 110° C. The mixture was allowed to cool down to rt. The resulting mixture was concentrated in vacuo. The residue was applied on a silica gel column chromatography with petroleum ether/EtOAc (3/1) to afford the sub-title compound (ANF-4) (2.0 g, 11.1 mmol, 83%, 92% Purity) as a brown oil. m/z 180.1 (M+H)$^+$ (ES+)

Step 3: 4-tert-Butyl 5-ethyl furo[3,2-b]pyrrole-4,5-dicarboxylate (ANF-5)

To a stirred solution of the product from step 2 above (ANF-4) (2.00 g, 1 Eq, 11.2 mmol) and DMAP (68 mg, 0.05 Eq, 0.56 mmol) in MeCN (30 mL) was added Boc$_2$O (2.92 g, 1.2 Eq, 13.4 mmol) at rt. The resulting mixture was stirred for 1 h at rt. The resulting mixture was concentrated in vacuo. The residue was applied on a silica gel column chromatography with petroleum ether/EtOAc (6/1) to afford the sub-title compound (ANF-5) (2.5 g, 8.96 mmol, 80%, 91% Purity) as a brown oil. m/z 280.1 (M+H)$^+$ (ES+)

Step 4: 4-tert-Butyl 5-ethyl hexahydrofuro[3,2-b]pyrrole-4,5-dicarboxylate (ANF-6)

To a stirred solution of the product from step 3 above (ANF-5) (2.5 g, 1 Eq, 8.95 mmol) in EtOH (50 mL) was added Pd/C 39 (495 mg, 10% Wt, 0.52 Eq, 4.66 mmol) at rt under nitrogen atmosphere. The resulting mixture was stirred overnight at 60° C. under hydrogen atmosphere. The mixture was allowed to cool down to rt. The resulting mixture was filtered; the filter cake was washed with EtOH (3×10 mL). The filtrate was concentrated in vacuo. The crude product was used in the next step directly without further purification. m/z 286.2 (M+H)$^+$ (ES+)

Step 5: 4-(tert-Butoxycarbonyl)-hexahydrofuro[3,2-b]pyrrole-5-carboxylic acid (ANF-7)

To a stirred solution of the product from step 4 above (ANF-6) (2.4 g, 1 Eq, 8.41 mmol) and LiOH (1.01 g, 5 Eq, 42.1 mmol) in THF (30 mL) and water (10 mL) at rt. The resulting mixture was stirred overnight at 60° C. The mixture was allowed to cool down to rt. The mixture was acidified to pH3 with aq. HCl (1 M). The resulting mixture was diluted with water and extracted with EtOAc (3×100 mL). The combined organic layers were washed with brine (2×100 mL), dried (Na$_2$SO$_4$). After filtration, the filtrate was concentrated in vacuo. The crude product was used in the next step directly without further purification. m/z 258.1 (M+H)$^+$ (ES+)

Step 6: Hexahydro-2H-furo[3,2-b]pyrrole-5-carboxylic acid (ANF-8)

A solution of the product from step 5 above (ANF-7) (2.00 g, 1 Eq, 7.77 mmol) in TFA (10 mL) and DCM (30 mL) was stirred for 2 h at rt. The resulting mixture was concentrated in vacuo. The crude product was used in the next step directly without further purification. m/z 158.1 (M+H)$^+$ (ES+)

Step 7: Hexahydro-2H-furo[3,2-b] pyrrole (ANF-10)

To a stirred solution of the product from step 6 above (ANF-8) (1.00 g, 1 Eq, 6.36 mmol) and p-methylacetophenone (ANF-9) (85.4 mg, 0.1 Eq, 0.64 mmol) in cyclohexanol (30 mL) was stirred for 4 h at 160° C. The mixture was allowed to cool down to rt. The resulting mixture was diluted with water and extracted with EtOAc (3×80 mL). The combined organic layers were washed with aq. HCl (10%) (2×200 mL), dried (Na$_2$SO$_4$). After filtration, the filtrate was concentrated in vacuo. The crude product was used in the next step directly without further purification. m/z 114.1 (M+H)$^+$ (ES+)

Step 8: 4-[2-Cyclopropyl-6-(4-fluoro-6-{hexahydrofuro[3,2-b]pyrrol-4-ylmethyl}-1-oxo-3H-isoindol-2-yl)pyridin-4-yl]-3-(4-methyl-1,2,4-triazol-3-yl)benzonitrile (ANF-11)

To a stirred solution of intermediate (AKR-1) (100 mg, 1 Eq, 0.2 mmol) and the product from step 7 above (ANF-10) (45 mg, 2 Eq, 0.40 mmol) in DCM (10 mL) was added DIPEA (104 mg, 4 Eq, 0.8 mmol) at rt. The resulting mixture was stirred for 4 days at 60° C. The mixture was allowed to cool down to rt. The resulting mixture was concentrated in vacuo. The crude product was purified by Prep-HPLC with the following conditions (Column: Xselect CSH C18 OBD Column 30*150 mm, 5 μm, n; Mobile Phase A: water (0.1% FA), Mobile Phase B: MeCN; Flow rate: 60 mL/min; Gradient: 4% B to 34% B in 10 min; Wave Length: 254 nm) to afford the title compound (ANF-11) (28 mg, 49 μmol, 24%, 99.3% Purity) as a white solid. m/z 576.0 (M+H)$^+$ (ES+). ¹H NMR (400 MHz, Methanol-d4) δ 8.50 (s, 1H), 8.14-8.07 (m, 2H), 8.03-7.90 (m, 2H), 7.65 (s, 1H), 7.45-7.40 (m, 1H), 6.96 (d, J=1.4 Hz, 1H), 5.08 (s, 2H), 4.62-4.52 (m, 1H), 4.04-3.87 (m, 2H), 4.84-3.76 (m, 1H), 3.61-3.49 (m, 4H), 3.28-3.23 (m, 1H), 2.94-2.84 (m, 1H), 2.32-2.23 (m, 1H), 2.15-2.01 (m, 2H), 1.87-1.65 (m, 3H), 1.12-0.98 (m, 4H).

Example 396: Synthesis of rel-4-(2-Cyclopropyl-6-(4-fluoro-6-(((3aR,6aR)-hexahydro-4H-furo[3,2-b]pyrrol-4-yl)methyl)-1-oxoisoindolin-2-yl)pyridin-4-yl)-3-(4-methyl-4H-1,2,4-triazol-3-yl)benzonitrile (ANG-1)

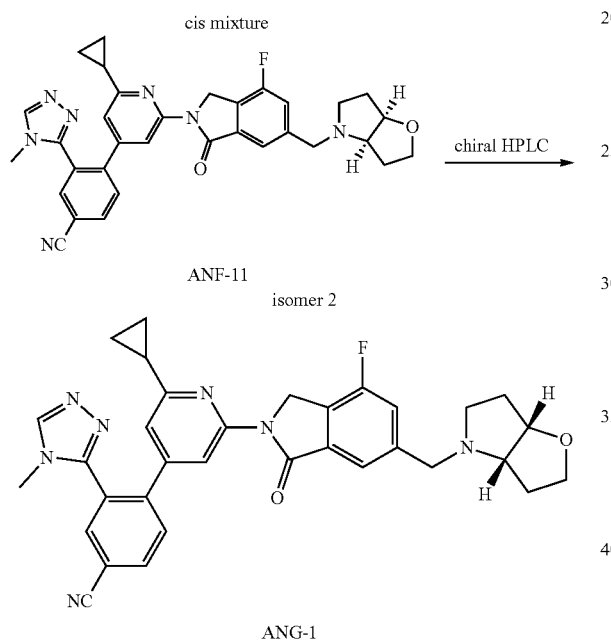

The crude product (ANF-11) (28 mg, 1 Eq, 49 μmol) was purified by Prep-CHIRAL-HPLC with the following conditions (Column: CHIRALPAK ID, 2*25 cm, 5 μm; Mobile Phase A: MtBE (0.5% 2M NH₃-MeOH)-HPLC, Mobile Phase B: MeOH:DCM=1:1-HPLC; Flow rate: 20 mL/min; Gradient: 25% B to 25% B in 33 min; Wave Length: 220/254 nm) to afford the title compound (ANG-1) (11.4 mg, 20 μmol, 41%, 99.7% Purity) as a white solid. m/z 576.0 (M+H)⁺ (ES+). ¹H NMR (400 MHz, Methanol-d4) δ 8.50 (s, 1H), 8.16-8.06 (m, 2H), 8.01 (d, J=1.4 Hz, 1H), 7.92 (d, J=8.0 Hz, 1H), 7.65 (s, 1H), 7.42 (d, J=9.8 Hz, 1H), 6.97 (d, J=1.4 Hz, 1H), 5.06 (s, 2H), 4.60-4.53 (m, 1H), 4.04-3.96 (m, 1H), 3.96-3.88 (m, 1H), 3.84-3.76 (m, 1H), 3.54 (d, J=26.8 Hz, 4H), 3.28-3.22 (m, 1H), 2.92-2.84 (m, 1H), 2.31-2.23 (m, 1H), 2.15-2.00 (m, 2H), 1.89-1.64 (m, 3H), 1.09-0.95 (m, 4H). Column: CHIRALPAK ID-3, 4.6*50 mm 3 um; Mobile Phase A: MtBE(0.1% DEA):(MeOH:DCM=1:1)=75:25; Flow rate: 1 mL/min; RT: 6.869.

Example 397: Synthesis of rel-4-(2-Cyclopropyl-6-(4-fluoro-6-(((3aR,6aR)-hexahydro-4H-furo[3,2-b]pyrrol-4-yl)methyl)-1-oxoisoindolin-2-yl) pyridin-4-yl)-3-(4-methyl-4H-1,2,4-triazol-3-yl)benzonitrile (ANH-1)

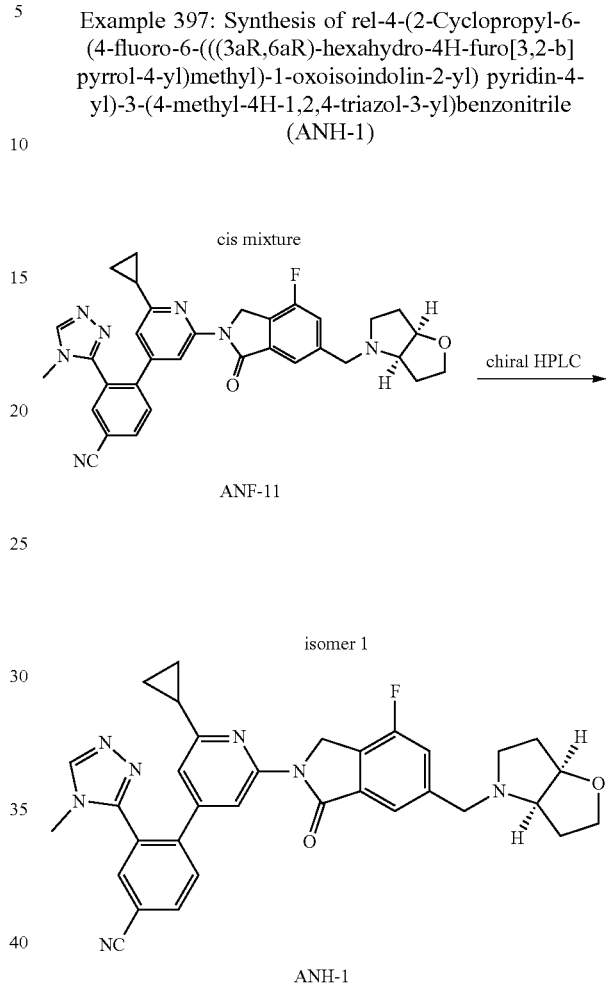

The crude product (ANF-11) (28 mg, 1 Eq, 49 μmol) was purified by Prep-CHIRAL-HPLC with the following conditions (Column: CHIRALPAK ID, 2*25 cm, 5 μm; Mobile Phase A: MtBE (0.5% 2M NH₃-MeOH)-HPLC, Mobile Phase B: MeOH:DCM=1:1-HPLC; Flow rate: 20 mL/min; Gradient: 25% B to 25% B in 33 min; Wave Length: 220/254 nm) to afford the title compound (ANH-1) (11.4 mg, 20 μmol, 41%, 99.9% Purity) as a white solid. m/z 576.0 (M+H)⁺ (ES+). ¹H NMR (400 MHz, Methanol-d4) δ 8.50 (s, 1H), 8.15-8.00 (m, 3H), 7.92 (d, J=8.0 Hz, 1H), 7.65 (s, 1H), 7.42 (d, J=9.8 Hz, 1H), 6.97 (d, J=1.4 Hz, 1H), 5.06 (s, 2H), 4.62-4.53 (m, 1H), 4.03-3.89 (m, 2H), 3.85-3.77 (m, 1H), 3.61-3.47 (m, 4H), 3.28-3.21 (m, 1H), 2.94-2.85 (m, 1H), 2.34-2.23 (m, 1H), 2.16-2.01 (m, 2H), 1.83-1.67 (m, 3H), 1.12-0.95 (m, 4H). Column: CHIRALPAK ID-3, 4.6*50 mm 3 um; Mobile Phase A: MtBE(0.1% DEA):(MeOH:DCM=1:1)=75:25; Flow rate: 1 mL/min; RT: 5.844.

Example 398: Synthesis of 4-(2-{6-[(Cyclobutylamino)methyl]-1-oxo-3H-isoindol-2-yl}-6-cyclopropylpyridin-4-yl)-3-(4-methyl-1,2,4-triazol-3-yl)benzonitrile (ANI-2)

Example 399: Synthesis of (R)-4-(2-Cyclopropyl-6-(6-(((1-(oxetan-3-yl)ethyl)amino)methyl)-1-oxoisoindolin-2-yl)pyridin-4-yl)-3-(4-methyl-4H-1,2,4-triazol-3-yl)benzonitrile (ANJ-2)

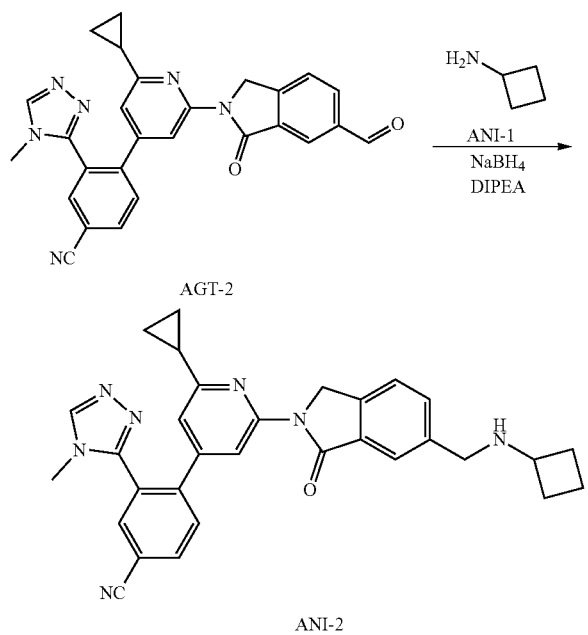

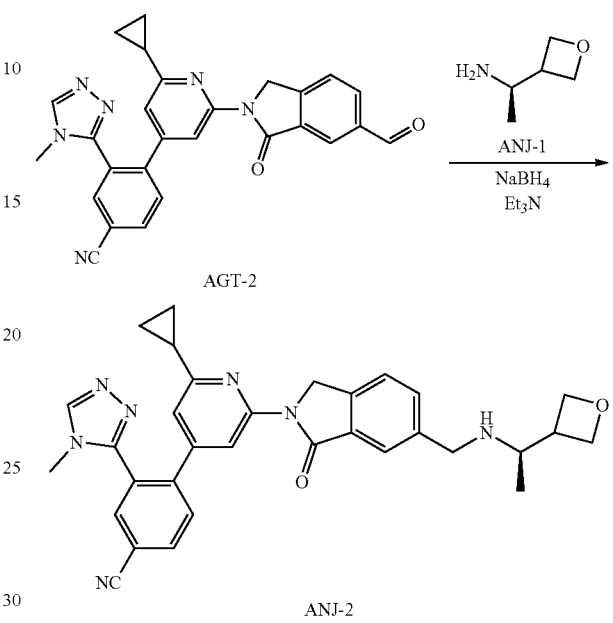

Into a 25 mL round-bottom flask were added intermediate (AGT-2) (30 mg, 1 Eq, 65 μmol) and MeOH (3 mL) at rt. To the above mixture was added DIPEA (25 mg, 3 Eq, 0.20 mmol) and cyclobutylamine (ANI-1) (5.6 mg, 1.2 Eq, 78 μmol) at rt. The resulting mixture was stirred for additional 12 h at 60° C. The mixture was allowed to cool down to rt. To the above mixture was added NaBH$_4$ (12 mg, 5 Eq, 0.33 mmol) at 0° C. The resulting mixture was stirred for additional 1 h at rt. The reaction was then quenched by the addition of MeOH (2 mL) at 0° C. The mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 41% B to 51% B in 9 min; Wave Length: 254 nm) to afford the title compound (ANI-2) (5.1 mg, 10 μmol, 15%, 99.7% Purity) as a white solid. m/z 516.1 (M+H)$^+$ (ES+). $^1$H NMR (400 MHz, Methanol-d4) δ 8.49 (s, 1H), 8.14-8.04 (m, 3H), 7.92 (d, J=8.0 Hz, 1H), 7.79 (s, 1H), 7.68-7.59 (m, 2H), 6.91 (d, J=1.3 Hz, 1H), 5.05-4.99 (m, 2H), 3.78 (d, J=2.6 Hz, 2H), 3.49 (s, 3H), 3.27 (s, 1H), 2.23-2.14 (m, 2H), 2.05-1.99 (m, 1H), 1.88-1.79 (m, 2H), 1.75-1.65 (m, 2H), 1.06-0.96 (m, 4H).

To a stirred solution of intermediate (AGT-2) (30 mg, 1 Eq, 65 μmol), (1R)-1-(oxetan-3-yl)ethanamine (ANJ-1) (6.6 mg, 1 Eq, 65 μmol) in MeOH (3 mL) was added Et$_3$N (33 mg, 5 Eq, 0.325 mmol) for 2 h at 60° C. The mixture was allowed to cool down to rt. To the above mixture was added NaBH$_4$ (25 mg, 10 Eq, 0.65 mmol) at 0° C. The resulting mixture was stirred for 2 h at rt. The reaction was then quenched by the addition of MeOH (2 mL) at 0° C. The resulting mixture was diluted with water and extracted with DCM (3×10 mL). The combined organic layers were washed with brine (2×10 mL), dried (Na$_2$SO$_4$). After filtration, the filtrate was concentrated in vacuo. The crude product was purified by Prep-HPLC with the following conditions: Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 40% B to 50% B in 8 min; Wave Length: 254/220 nm; RT: 7.82. The product-containing fractions were combined and evaporated partially in vacuo and lyophilized overnight to afford the title compound (ANJ-2) (6.4 mg, 12 μmol, 18%, 99.9% Purity) as a white solid. m/z 546.7 (M+H)$^+$ (ES+). $^1$H NMR (400 MHz, DMSO-d6) δ 8.54 (s, 1H), 8.38-8.11 (m, 2H), 7.99 (d, J=1.4 Hz, 1H), 7.95-7.83 (m, 1H), 7.76 (s, 1H), 7.72-7.38 (m, 2H), 6.89 (d, J=1.4 Hz, 1H), 5.00 (s, 2H), 4.71-4.43 (m, 2H), 4.42-4.16 (m, 2H), 3.86 (d, J=14.0 Hz, 1H), 3.73 (d, J=13.9 Hz, 1H), 3.48 (s, 3H), 2.84 (s, 2H), 2.09-1.94 (m, 1H), 1.41-0.54 (m, 7H).

Example 400: Synthesis of (S)-4-(2-Cyclopropyl-6-(6-(((1-(oxetan-3-yl)ethyl)amino)methyl)-1-oxoisoindolin-2-yl)pyridin-4-yl)-3-(4-methyl-4H-1,2,4-triazol-3-yl)benzonitrile (ANK-2)

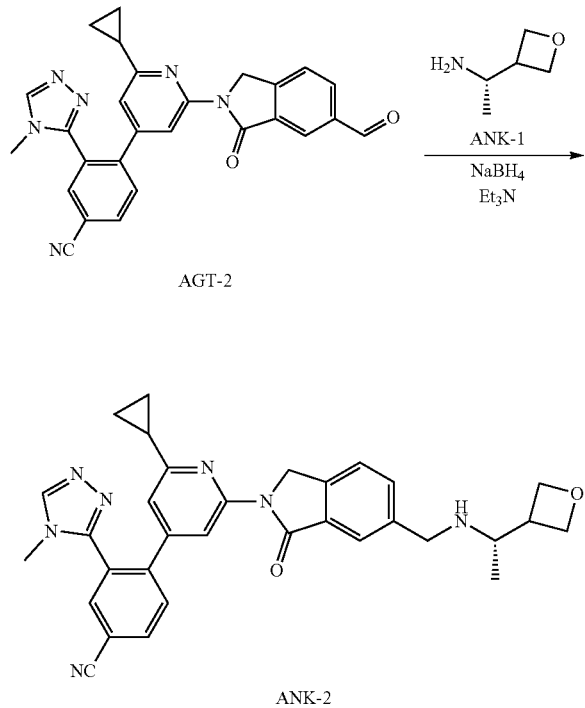

To a stirred mixture of intermediate (AGT-2) (30 mg, 1 Eq, 65 μmol) and (1S)-1-(oxetan-3-yl)ethanamine (ANK-1) (6.6 mg, 1 Eq, 65 μmol) in MeOH (10 mL) was added DIPEA (25 mg, 3 Eq, 0.20 mmol) at rt. The resulting mixture was stirred overnight at 60° C. The mixture was allowed to cool down to rt. To the above mixture was added NaBH$_4$ (7.4 mg, 3 Eq, 0.40 mmol) at rt. The resulting mixture was stirred for additional 1 h at rt. The reaction was then quenched by the addition of MeOH (2 mL) at 0° C. The resulting mixture was concentrated in vacuo. The crude product was purified by Prep-HPLC with the following conditions (Column: Xselect CSH C18 OBD Column 30*150 mm, 5 μm; Mobile Phase A: water (0.1% FA), Mobile Phase B: MeCN; Flow rate: 60 mL/min; Gradient: 6% B to 36% B in 10 min; Wave Length: 254 nm; RT: 8.8) to afford the title compound (ANK-2) (16.6 mg, 30 μmol, 45%, 99.2% Purity) as a white solid. m/z 546.2 (M+H)$^+$ (ES+). $^1$H NMR (400 MHz, DMSO-d6) δ 8.54 (s, 1H), 8.25-8.18 (m, 2H), 8.01-7.92 (m, 1H), 7.91-7.84 (m, 1H), 7.76 (s, 1H), 7.69-7.60 (m, 2H), 6.89 (d, J=1.5 Hz, 1H), 5.00 (s, 2H), 4.61-4.50 (m, 2H), 4.38-4.22 (m, 2H), 3.90-3.68 (m, 2H), 3.48 (s, 3H), 2.91-2.76 (m, 2H), 2.10-1.99 (m, 1H), 1.02-0.87 (m, 7H).

Example 401: Synthesis of 4-{2-Cyclopropyl-6-[6-({[(3-fluorooxetan-3-yl)methyl]amino}methyl)-1-oxo-3H-isoindol-2-yl]pyridin-4-yl}-3-(4-methyl-1,2,4-triazol-3-yl)benzonitrile (ANL-2)

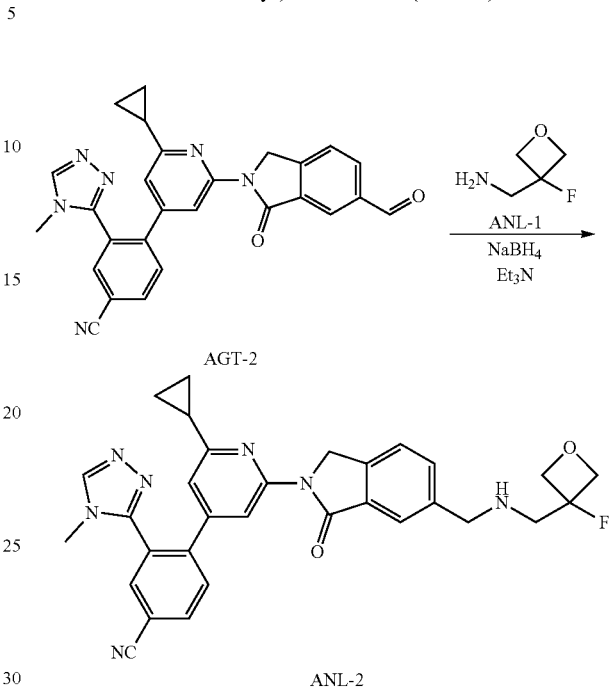

To a stirred mixture of intermediate (AGT-2) (30 mg, 1 Eq, 65 μmol) and 1-(3-fluorooxetan-3-yl)methanamine (ANL-1) (10 mg, 1.5 Eq, 98 μmol) in MeOH (1 mL) was added DIPEA (17 mg, 2 Eq, 0.13 mmol) at rt under nitrogen atmosphere. The resulting mixture was stirred for h at 60° C. under nitrogen atmosphere. The mixture was allowed to cool down to rt. To the above mixture was added NaBH$_4$ (4.9 mg, 2 Eq, 0.13 mmol). The resulting mixture was stirred for additional 2 h at rt. The reaction was then quenched by the addition of MeOH (2 mL) at 0° C. The resulting mixture was concentrated in vacuo. The residue was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 38% B to 48% B in 8 min; Wave Length: 254/220 nm; RT: 7.28) to afford the title compound (ANL-2) (2.1 mg, 38 μmol, 5.8%, 98.1% Purity) as a white solid. m/z 550.2 (M+H)$^+$ (ES+). $^1$H NMR (400 MHz, Methanol-d4) δ 8.49 (s, 1H), 8.25-7.99 (m, 3H), 7.92 (d, J=8.0 Hz, 1H), 7.83 (s, 1H), 7.68 (d, J=7.8 Hz, 1H), 7.62 (d, J=7.8 Hz, 1H), 6.92 (d, J=1.4 Hz, 1H), 5.03 (s, 2H), 4.72 (d, J=7.8 Hz, 1H), 4.68 (d, J=7.8 Hz, 1H), 4.62 (d, J=7.7 Hz, 1H), 4.57 (d, J=7.7 Hz, 1H), 3.93 (s, 2H), 3.50 (s, 3H), 3.07 (s, 1H), 3.02 (s, 1H), 2.07-1.97 (m, 1H), 1.08-0.88 (m, 4H).

Example 402: Synthesis of 4-{2-Cyclopropyl-6-[6-({[2-(oxetan-3-yl)propan-2-yl]amino}methyl)-1-oxo-3H-isoindol-2-yl]pyridin-4-yl}-3-(4-methyl-1,2,4-triazol-3-yl)benzonitrile (ANM-2)

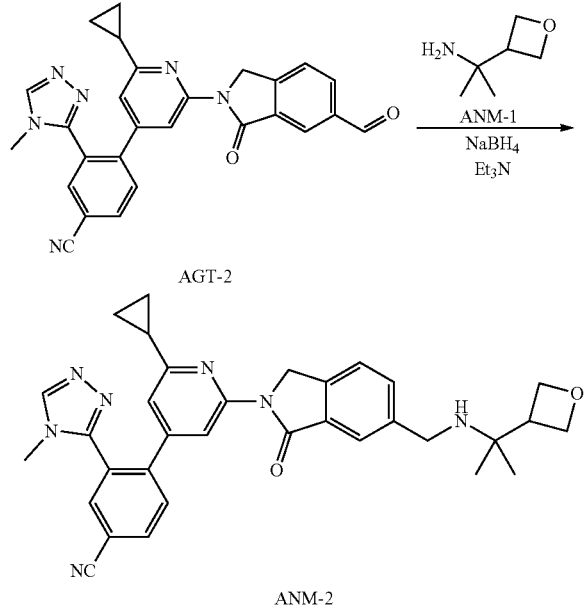

To a stirred solution of intermediate (AGT-2) (25 mg, 1 Eq, 54 μmol) and 2-(oxetan-3-yl)propan-2-amine (ANM-1) (6 mg, 1 Eq, 54 μmol) in MeOH (1.5 mL) was added Et₃N (27 mg, 5 Eq, 0.27 mmol) at rt under nitrogen atmosphere. The resulting mixture was stirred for h at 60° C. under nitrogen atmosphere. The mixture was allowed to cool down to rt. To the above mixture was added NaBH₄ (21 mg, 10 Eq, 0.54 mmol) at 0° C. The resulting mixture was stirred for 2 h at rt. The reaction was then quenched by the addition of MeOH (2 mL) at 0° C. The resulting mixture was concentrated in vacuo. The crude product was purified by Prep-HPLC with the following conditions: Column: XBridge Prep OBD C18 Column, 30×150 mm, 5 μm; Mobile Phase A: water (0.1% NH₄HCO₃) Mobile Phase B: MeCN; Flow rate: 60 mL/min; Gradient: 44 B to 56 B in 8 min; Detector, UV 254/220 nm; RT: 5.7. The product-containing fractions were combined and evaporated partially in vacuo and lyophilized overnight to afford the title compound (ANM-2) (11.1 mg, 20 μmol, 36%, 96.4% Purity) as a white solid. m/z 560.3 (M+H)⁺ (ES+). ¹H NMR (400 MHz, Methanol-d4) δ 8.50 (s, 1H), 8.15-8.07 (m, 2H), 8.05 (d, J=1.4 Hz, 1H), 7.93 (d, J=8.2 Hz, 1H), 7.82 (s, 1H), 7.67-7.63 (m, 1H), 7.59 (d, J=7.9 Hz, 1H), 6.92 (d, J=1.4 Hz, 1H), 5.02 (s, 2H), 4.74-4.65 (m, 2H), 4.63 (d, J=6.5 Hz, 2H), 3.76 (s, 2H), 3.50 (s, 3H), 3.14-3.10 (m, 1H), 2.07-1.98 (m, 1H), 1.23 (s, 6H), 1.07-0.92 (m, 4H).

Example 403: Synthesis of (R)-4-(2-Cyclopropyl-6-(6-(1-((oxetan-3-ylmethyl)amino)ethyl)-1-oxoisoindolin-2-yl)pyridin-4-yl)-3-(4-methyl-4H-1,2,4-triazol-3-yl)benzonitrile (ANN-2)

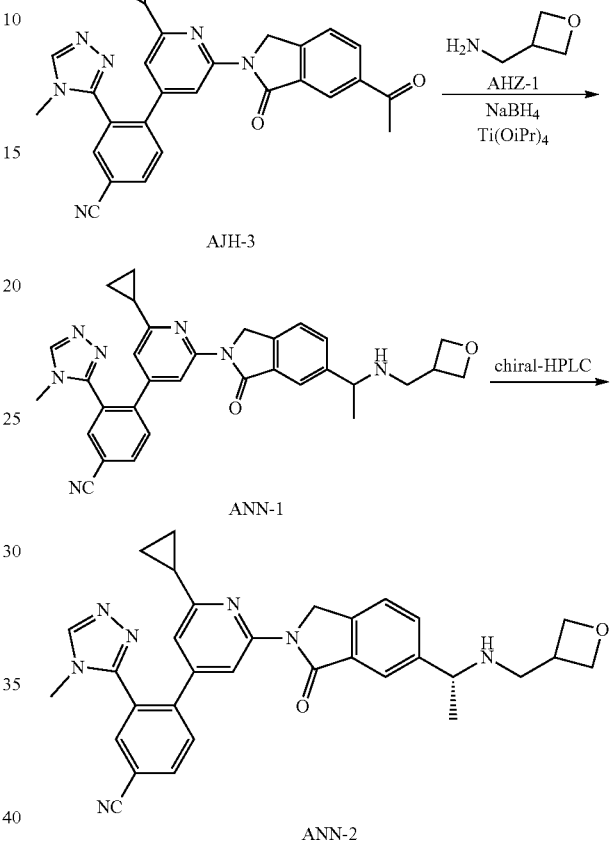

Step 1: 4-(2-Cyclopropyl-6-(6-(1-((oxetan-3-ylmethyl)amino)ethyl)-1-oxoisoindolin-2-yl)pyridin-4-yl)-3-(4-methyl-4H-1,2,4-triazol-3-yl)benzonitrile (ANN-1)

To a stirred mixture of intermediate (AJH-3) (50 mg, 1 Eq, 0.11 mmol) and 1-(oxetan-3-yl)methanamine (AHZ-1) (11 mg, 1.2 Eq, 0.13 mmol) in THF (5 mL) was added Ti(Oi-Pr)₄ (60 mg, 2 Eq, 0.21 mmol) at rt under nitrogen atmosphere. The resulting mixture was stirred for 2 h at rt under nitrogen atmosphere. To the above mixture was added NaBH₄ (13 mg, 5 Eq, 0.55 mmol) at 0° C. The reaction was then quenched by the addition of MeOH (2 mL) at 0° C. The resulting mixture was concentrated in vacuo. The residue was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 33% B to 43% B in 8 min; Wave Length: 254/220 nm; RT: 7.85) to afford the sub-title compound (ANN-1) (25 mg, 46 μmol, 43%, 98% Purity) as a white solid. m/z 546.3 (M+H)⁺ (ES+)

Step 2: (R)-4-(2-Cyclopropyl-6-(6-(1-((oxetan-3-ylmethyl)amino)ethyl)-1-oxoisoindolin-2-yl)pyridin-4-yl)-3-(4-methyl-4H-1,2,4-triazol-3-yl)benzonitrile (ANN-2)

The crude product of the product from step 1 above (ANN-1) (25 mg, 1 Eq, 46 µmol) was purified by Prep-CHIRAL-HPLC with the following conditions: (Column: CHIRAL ART Cellulose-SA, 2*25 cm, 5 µm; Mobile Phase A: MtBE (0.5% 2M NH₃-MeOH)-HPLC, Mobile Phase B: MeOH:DCM=1:1-HPLC; Flow rate: 20 mL/min; Gradient: 35% B to 35% B in 25 min; Wave Length: 220/254 nm; RT1(min): 16.877, Sample Solvent: EtOH-HPLC; Injection Volume: 0.5 mL) to afford the title compound (ANN-2) (8.2 mg, 15 µmol, 33%, 99.3% Purity) as a white solid. m/z 546.3 $(M+H)^+$ (ES+). $^1$H NMR (400 MHz, DMSO-d6) δ 8.54 (s, 1H), 8.25-8.18 (m, 2H), 7.98 (d, J=1.4 Hz, 1H), 7.91-7.84 (m, 1H), 7.76 (s, 1H), 7.66 (s, 2H), 6.90 (d, J=1.4 Hz, 1H), 5.00 (s, 2H), 4.62-4.54 (m, 2H), 4.20-4.15 (m, 2H), 3.82 (s, 1H), 3.48 (s, 3H), 2.97 (s, 1H), 2.70-2.61 (m, 1H), 2.40-2.27 (m, 1H), 2.10-2.00 (m, 1H), 1.25 (d, J=14.0 Hz, 3H), 0.97 (d, J=6.4 Hz, 4H). Column: CHIRALPAK IA-3, 4.6*50 mm, 3 µm; Mobile Phase A: MtBE(0.1% DEA):(MeOH:DCM=1:1)=65:35; Flow rate: 1 mL/min; RT: 3.801

Example 404: Synthesis of (S)-4-(2-Cyclopropyl-6-(6-(1-((oxetan-3-ylmethyl) amino)ethyl)-1-oxoisoindolin-2-yl)pyridin-4-yl)-3-(4-methyl-4H-1,2,4-triazol-3-yl)benzonitrile (ANO-1)

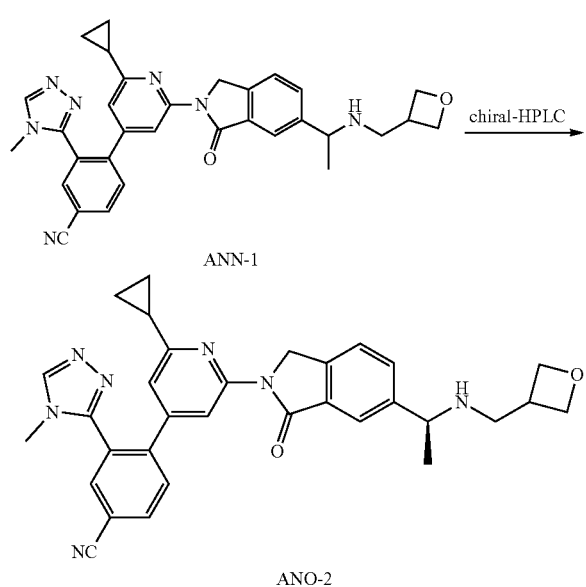

The crude product (ANN-1) (25 mg, 1 Eq, 46 µmol) was purified by Prep-CHIRAL-HPLC with the following conditions: (Column: CHIRAL ART Cellulose-SA, 2*25 cm, 5 µm; Mobile Phase A: MtBE (0.5% 2M NH₃-MeOH)-HPLC, Mobile Phase B: MeOH:DCM=1:1-HPLC; Flow rate: 20 mL/min; Gradient: 35% B to 35% B in 25 min; Wave Length: 220/254 nm; RT2(min): 21.967; Sample Solvent: EtOH-HPLC; Injection Volume: 0.5 ml) to afford the title compound (ANO-1) (7.7 mg, 14 µmol, 31%, 99.8% Purity) as a white solid. m/z 546.3 $(M+H)^+$ (ES+). $^1$H NMR (400 MHz, DMSO-d6) δ 8.54 (s, 1H), 8.25-8.18 (m, 2H), 7.98 (d, J=1.4 Hz, 1H), 7.87 (d, J=8.6 Hz, 1H), 7.77 (s, 1H), 7.67 (s, 2H), 6.90 (d, J=1.4 Hz, 1H), 5.01 (s, 2H), 4.62-4.54 (m, 2H), 4.21-4.13 (m, 2H), 3.82 (s, 1H), 3.48 (s, 3H), 2.98 (s, 1H), 2.80-2.58 (m, 2H), 2.11-2.00 (m, 1H), 1.28 (s, 3H), 0.97 (d, J=6.4 Hz, 4H). Column: CHIRALPAK IA-3, 4.6*50 mm, 3 µm; Mobile Phase A: MtBE(0.1% DEA):(MeOH:DCM=1:1)=65:35; Flow rate: 1 mL/min; RT: 3.023.

Example 405: Synthesis of 4-[2-Cyclopropyl-6-(1-oxo-6-{[(3S)-oxolan-3-ylamino]methyl}-3H-isoindol-2-yl)pyridin-4-yl]-3-(4-methyl-1,2,4-triazol-3-yl)benzonitrile (ANP-2)

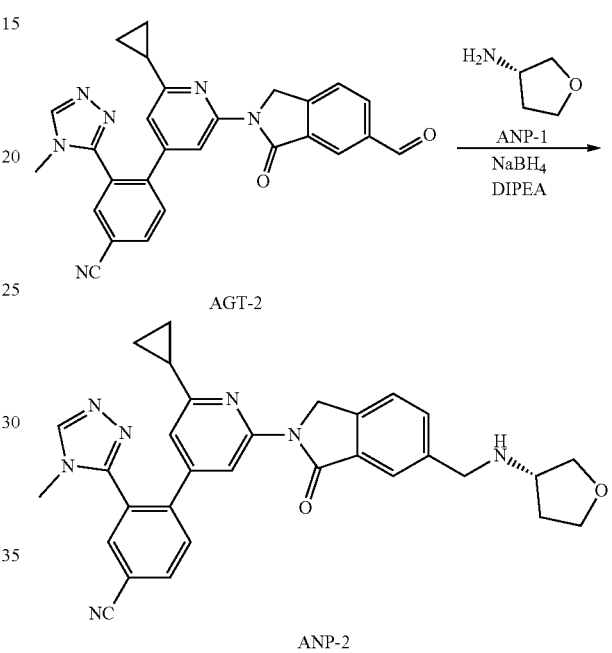

To a stirred solution of intermediate (AGT-2) (30 mg, 1 Eq, 65 µmol) and (3R)-oxolan-3-amine (ANP-1) (7 mg, 1.2 Eq, 78 µmol) in MeOH (8 mL) was added DIPEA (25 mg, 3 Eq, 0.20 mmol) at rt. The resulting mixture was stirred overnight at 60° C. The mixture was allowed to cool down to rt. To the above mixture was added NaBH₄ (12 mg, 5 Eq, 0.33 mmol) at 0° C. The resulting mixture was stirred for additional 1 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 µm; Mobile Phase A: water (0.1% NH₄HCO₃+0.1% NH₃·H₂O), Mobile Phase B: MeCN; Flow rate: 60 mL/min; Gradient: 30% B to 40% B in 10 min; Wave Length: 254/220 nm; RT: 9.5) to afford the title compound (ANP-2) (11.3 mg, 21 µmol, 32%, 99.0% Purity) as a white solid. m/z 532.0 $(M+H)^+$ (ES+). $^1$H NMR (400 MHz, Methanol-d4) δ 8.50 (s, 1H), 8.15-8.04 (m, 3H), 7.92 (d, J=8.0 Hz, 1H), 7.81 (d, J=1.6 Hz, 1H), 7.69-7.65 (m, 1H), 7.61 (d, J=7.8 Hz, 1H), 6.92 (d, J=1.4 Hz, 1H), 5.02 (s, 2H), 3.97-3.88 (m, 1H), 3.88-3.79 (m, 3H), 3.79-3.72 (m, 1H), 3.62-3.58 (m, 1H), 3.50 (s, 3H), 3.43-3.37 (m, 1H), 2.18-1.99 (m, 2H), 1.86-1.77 (m, 1H), 1.06-0.95 (m, 4H).

Example 406: Synthesis of 4-[2-Cyclopropyl-6-(1-oxo-6-{[(3S)-oxolan-3-ylamino]methyl}-3H-isoindol-2-yl)pyridin-4-yl]-3-(4-methyl-1,2,4-triazol-3-yl)benzonitrile (ANQ-2)

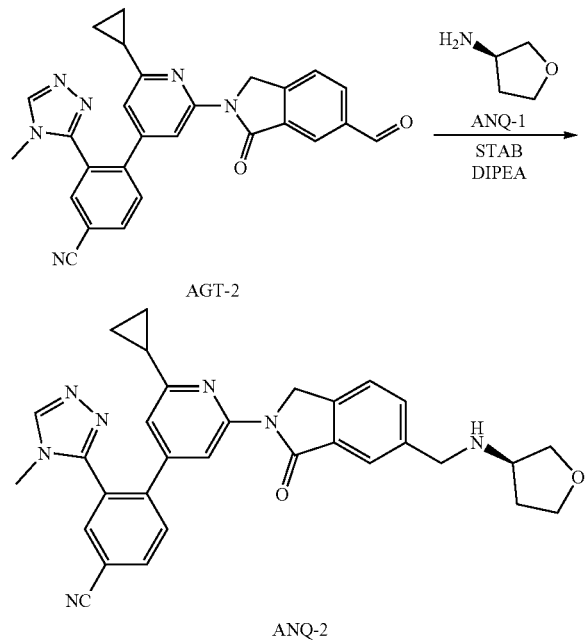

Example 407: Synthesis of 5-Chloro-2-{6-cyclopropyl-4-[4-fluoro-2-(4-methyl-1,2,4-triazol-3-yl)phenyl]pyridin-2-yl}-6-({[(1R,2S)-2-hydroxycyclopentyl]amino}methyl)-3H-isoindol-1-one (ANR-2)

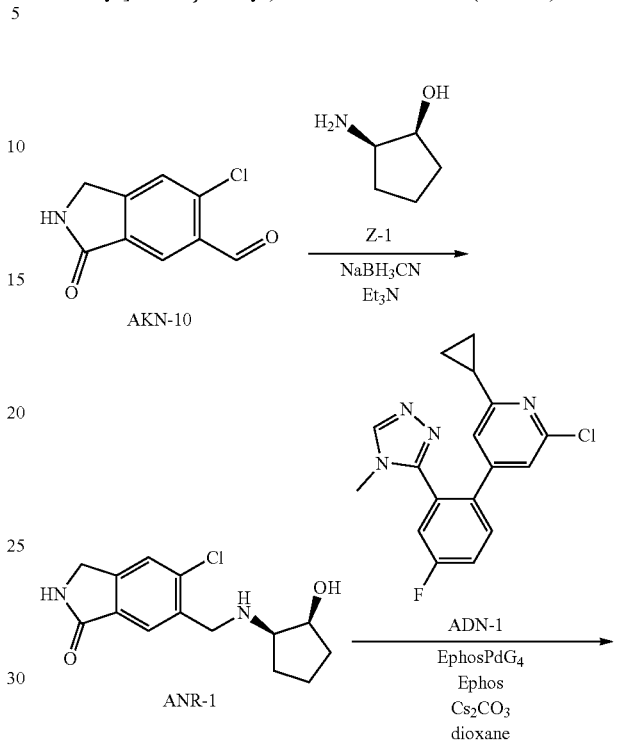

To a stirred mixture of intermediate (AGT-2) (30 mg, 1 Eq, 65 μmol) and (3S)-oxolan-3-amine (ANQ-1) (8.5 mg, 1.5 Eq, 98 μmol) in MeOH (2 mL) were added DIPEA (17 mg, 2 Eq, 0.13 mmol) at rt under nitrogen atmosphere. The resulting mixture was stirred for 2 h at 60° C. under nitrogen atmosphere. The mixture was allowed to cool down to rt. To the above mixture was added NaBH(OAc)$_3$ (28 mg, 2 Eq, 0.13 mmol) at rt under nitrogen atmosphere. The resulting mixture was stirred for additional overnight at rt. The resulting mixture was filtered; the filter cake was washed with MeOH (2×3 mL). The filtrate was concentrated in vacuo. The crude product was purified by Prep-HPLC with the following conditions (Column: Xselect CSH C18 OBD Column 30*150 mm, 5 μm, n; Mobile Phase A: water (0.1% FA), Mobile Phase B: MeCN; Flow rate: 60 mL/min; Gradient: 6% B to 36% B in 10 min; Wave Length: 254 nm; RT: 8.7) to afford the title compound (ANQ-2) (11.4 mg, 21 μmol, 33%, 99.6% Purity) as a white solid. m/z 532.3 (M+H)$^+$ (ES+). $^1$H NMR (400 MHz, DMSO-d6) δ 8.55 (s, 1H), 8.22 (d, J=1.7 Hz, 1H), 8.22-8.18 (m, 1H), 7.97 (d, J=1.4 Hz, 1H), 7.91-7.84 (m, 1H), 7.76 (s, 1H), 7.64 (d, J=1.3 Hz, 2H), 6.90 (d, J=1.4 Hz, 1H), 5.00 (s, 2H), 3.85-3.73 (m, 3H), 3.72-3.60 (m, 2H), 3.49 (s, 3H), 3.48-3.42 (m, 1H), 3.31-3.21 (m, 1H), 2.12-1.99 (m, 1H), 1.99-1.86 (m, 1H), 1.76-1.64 (m, 1H), 1.00-0.93 (m, 4H).

Step 1: 5-Chloro-6-({[(1R,2S)-2-hydroxycyclopentyl]amino}methyl)-2,3-dihydroisoindol-1-one (ANR-1)

To a solution of intermediate (AKN-10) (200 mg, 1 Eq, 1.02 mmol) and (1S,2R)-2-aminocyclopentan-1-ol (Z-1) (114 mg, 1.1 Eq, 1.12 mmol) in DCM (20 mL) was added Et$_3$N (310 mg, 3 Eq, 3.07 mmol) at rt. The resulting mixture was stirred at rt for 1 h. Then was added NaBH$_3$CN (129 mg, 2 Eq, 2.04 mmol) at rt. The resulting mixture was stirred at rt for 1 h. The resulting mixture was concentrated in vacuo. The residue was purified by Prep-TLC with DCM/MeOH (12/1) to afford the sub-title compound (ANR-1) (200 mg, 0.71 mmol, 70%, 95% Purity) as a yellow oil. m/z 281.1/283.1 (M+H)$^+$ (ES+)

Step 2: 5-Chloro-2-{6-cyclopropyl-4-[4-fluoro-2-(4-methyl-1,2,4-triazol-3-yl) phenyl]pyridin-2-yl}-6-({[(1R,2S)-2-hydroxycyclopentyl]amino}methyl)-3H-isoindol-1-one (ANR-2)

To a stirred mixture of the product from step 1 above (ANR-1) (40 mg, 1 Eq, 0.14 mmol), intermediate (ADN-1) (47 mg, 1 Eq, 0.14 mmol) and Cs$_2$CO$_3$ (139 mg, 3 Eq, 0.43 mmol) in dioxane (10 mL) were added EPhos (30 mg, 0.4 Eq, 57 μmol) and EPhos Pd G4 (26 mg, 0.2 Eq, 28 mmol) at rt under nitrogen atmosphere. The resulting mixture was stirred for 2 h at 90° C. under nitrogen atmosphere. The mixture was cooled to rt and concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$), Mobile Phase B: ACN; Flow rate: 60 mL/min; Gradient: 50% B to 72% B in 8 min; Wave Length: 254/220 nm; RT: 7.12) to afford the title compound (ANR-2) (1.0 mg, 1.7 μmol, 1.2%, 98.1% Purity) as a white solid. m/z 573.1/575.1 (M+H)$^+$ (ES+). $^1$H NMR (400 MHz, DMSO-d6) δ 8.50 (s, 1H), 7.96 (d, J=10.5 Hz, 2H), 7.82 (s, 1H), 7.75-7.69 (m, 1H), 7.60 (t, J=8.9 Hz, 2H), 6.83 (s, 1H), 5.02 (s, 2H), 4.46 (s, 1H), 3.96 (d, J=39.3 Hz, 2H), 3.44 (s, 3H), 2.90 (s, 1H), 2.02 (d, J=6.0 Hz, 1H), 1.64 (d, J=39.2 Hz, 7H), 1.00-0.90 (m, 4H).

Example 408: Synthesis of 2-{6-Ethoxy-4-[4-fluoro-2-(4-methyl-1,2,4-triazol-3-yl)phenyl]pyridin-2-yl}-6-({[(1-hydroxycyclobutyl)methyl](methyl)amino}methyl)-3H-isoindol-1-one (ANS-1)

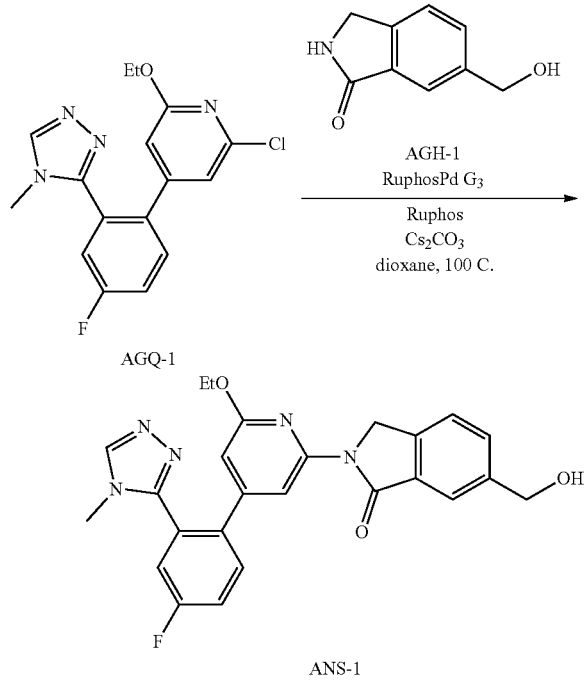

Into a 20 mL sealed tube were added intermediate (AGQ-1) (36 mg, 1 Eq, 0.11 mmol), intermediate (AGH-1) (26 mg, 1.5 Eq, 0.16 mmol) and Cs$_2$CO$_3$ (70 mg, 2 Eq, 0.22 mmol) in 1,4-dioxane (5 mL) at rt under nitrogen atmosphere. To the above mixture were added RuPhos Palladacycle Gen.3 (18 mg, 0.2 Eq, 22 μmol) and RuPhos (20 mg, 0.4 Eq, 43 μmol) at rt under nitrogen atmosphere. The resulting mixture was stirred for additional 3 h at 100° C. under nitrogen atmosphere. The mixture was cooled to rt and concentrated in vacuo. The crude product was purified by reverse flash column chromatography with the following conditions: Column, C18; mobile phase, water (0.1% FA) and MeCN (10% MeCN up to 50% in 10 min); Detector, UV 254/220 nm. The crude product was purified by Prep-HPLC with the following conditions (Column: Xselect CSH C18 OBD Column 30*150 mm, 5 μm; Mobile Phase A: water (0.1% FA), Mobile Phase B: MeCN; Flow rate: 60 mL/min; Gradient: 17% B to 47% B in 10 min; Wave Length: 254 nm; RT: 11.03) to afford the title compound (ANS-1) (1.5 mg, 3.3 μmol, 3.0%, 99.0% Purity). m/z 460.0 (M+H)$^+$ (ES+). $^1$H NMR (400 MHz, Methanol-d4) δ 8.47 (s, 1H), 7.83 (t, J=1.6 Hz, 2H), 7.78-7.73 (m, 1H), 7.71-7.59 (m, 2H), 7.55-7.49 (m, 1H), 7.47-7.43 (m, 1H), 6.37 (d, J=1.2 Hz, 1H), 5.07 (s, 2H), 4.72 (s, 2H), 4.37 (t, J=7.1 Hz, 2H), 3.51 (s, 3H), 1.38 (t, J=7.1 Hz, 3H).

Example 409: Synthesis of 4-[2-Cyclopropyl-6-(4-fluoro-6-{[(2-methoxyethyl)(methyl)amino]methyl}-1-oxo-3H-isoindol-2-yl)pyridin-4-yl]-3-(4-methyl-1,2,4-triazol-3-yl)benzonitrile (ANT-1)

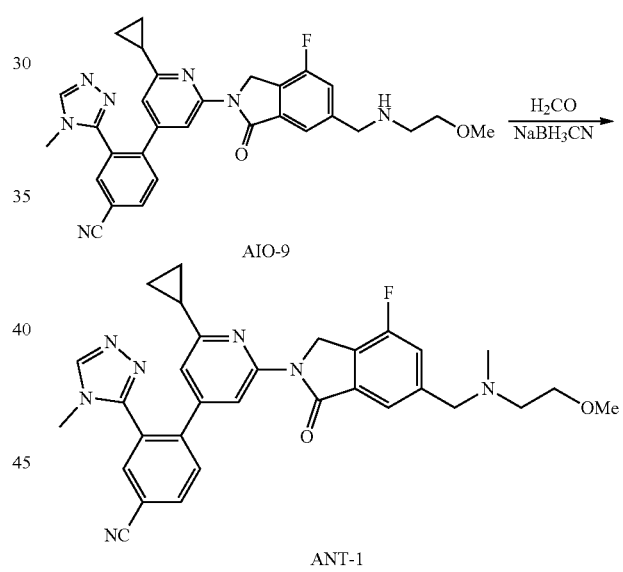

To a stirred mixture of compound (AIO-9) (38 mg, 1 Eq, 71 μmol) and HCHO (6.37 mg, 3 Eq, 0.21 mmol) in MeOH (10 mL) was added NaBH$_3$CN (9 mg, 2 Eq, 0.14 mmol) at rt. The resulting mixture was stirred for 2 h at rt. The resulting mixture was concentrated in vacuo. The residue was purified by Prep-TLC with DCM/MeOH (10/1). The crude product was purified by Prep-HPLC with the following conditions (Column: XBridge Prep OBD C18 Column, 19*250 mm, 5 μm; Mobile Phase A: water (0.1% NH$_4$HCO$_3$+0.1% NH$_3$·H$_2$O), Mobile Phase B: MeCN; Flow rate: 25 mL/min; Gradient: 50% B to 68% B in 8 min; Wave Length: 254/220 nm; RT: 7.55) to afford the title compound (ANT-1) (7.4 mg, 13 μmol, 19%, 99.3% Purity) as a white solid. m/z 552.1 (M+H)$^+$ (ES+). $^1$H NMR (400 MHz, DMSO-d6) δ 8.54 (s, 1H), 8.27-8.17 (m, 2H), 7.96-7.85 (m, 2H), 7.58 (s, 1H), 7.47 (d, J=10.1 Hz, 1H), 6.93 (d, J=1.4 Hz, 1H), 5.08 (s, 2H), 3.63 (s, 2H), 3.47 (d, J=4.7 Hz, 5H), 3.24

(s, 3H), 2.55 (d, J=5.9 Hz, 2H), 2.19 (s, 3H), 2.06 (d, J=7.9, 4.8 Hz, 1H), 1.02-0.93 (m, 4H).

Example 410: Synthesis of 4-(2-cyclopropyl-6-(4-fluoro-6-(((1S,4S)-1-methyl-2-oxa-5-azabicyclo[2.2.1]heptan-5-yl)methyl)-1-oxoisoindolin-2-yl)pyridin-4-yl)-3-(4-methyl-4H-1,2,4-triazol-3-yl)benzonitrile (ANU-3)

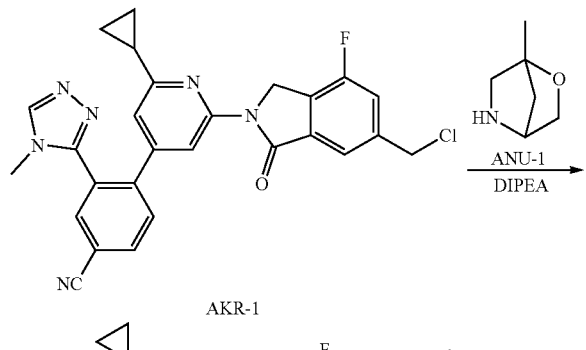

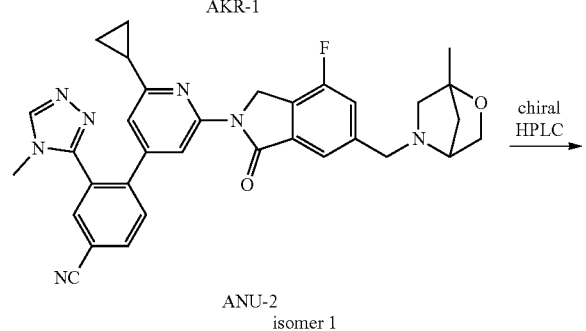

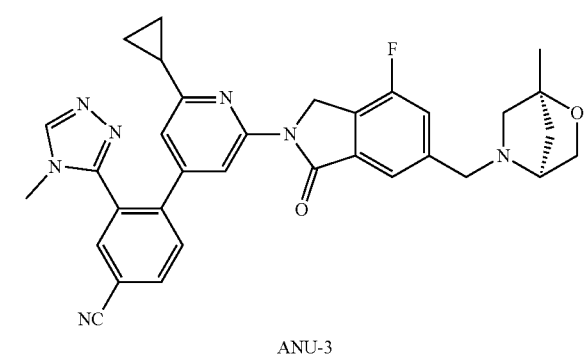

Step 1: 4-(2-Cyclopropyl-6-(4-fluoro-6-((1-methyl-2-oxa-5-azabicyclo[2.2.1]heptan-5-yl)methyl)-1-oxoisoindolin-2-yl)pyridin-4-yl)-3-(4-methyl-4H-1,2,4-triazol-3-yl)benzonitrile (ANU-2)

To a stirred mixture of intermediate (AKR-1) (60 mg, 1 Eq, 0.12 mmol) and 1-methyl-2-oxa-5-azabicyclo[2.2.1]heptane (ANU-1) (14 mg, 1 Eq, 0.12 mmol) in DCM (10 mL) was added DIPEA (47 mg, 3 Eq, 0.36 mmol) at rt. The resulting mixture was stirred overnight at 60° C. The resulting mixture was concentrated in vacuo. The mixture was cooled to rt and concentrated in vacuo. The crude product was purified by Prep-HPLC with the following conditions (Column: Xselect CSH C18 OBD Column 30*150 mm, 5 μm, n; Mobile Phase A: water (0.1% FA), Mobile Phase B: MeCN; Flow rate: 60 mL/min; Gradient: 5% B to 35% B in 10 min; Wave Length: 254 nm; RT: 9.6) to afford the title compound (ANU-2) (40 mg, 69 μmol, 58%, 99% Purity) as a white solid. m/z 576.1 (M+H)$^+$ (ES+)

Step 2: 4-(2-Cyclopropyl-6-(4-fluoro-6-(((1S,4S)-1-methyl-2-oxa-5-azabicyclo[2.2.1]heptan-5-yl)methyl)-1-oxoisoindolin-2-yl)pyridin-4-yl)-3-(4-methyl-4H-1,2,4-triazol-3-yl)benzonitrile (ANU-3)

The crude product of the product from step 1 above (ANU-2) (40 mg, 69 μmol, 1 Eq) was purified by Prep-CHIRAL-HPLC with the following conditions (Column: CHIRALPAK ID, 2*25 cm, 5 μm; Mobile Phase A: Hex:DCM=1:1 (0.5% 2M NH$_3$-MeOH)-HPLC, Mobile Phase B: EtOH-HPLC; Flow rate: 20 mL/min; Gradient: 50% B to 50% B in 19 min; Wave Length: 220/254 nm; RT1 (min): 10.824) to afford the title compound (ANU-3) (10.2 mg, 18 μmol, 15%, 99.0% Purity) as a white solid. m/z 576.1 (M+H)$^+$ (ES+). $^1$H NMR (400 MHz, Methanol-d4) δ 8.50 (s, 1H), 8.16-8.06 (m, 2H), 8.01 (t, J=1.3 Hz, 1H), 7.92 (d, J=8.0 Hz, 1H), 7.67 (s, 1H), 7.45 (d, J=9.8 Hz, 1H), 6.95 (t, J=1.3 Hz, 1H), 5.05 (s, 2H), 4.15 (d, J=7.8 Hz, 1H), 3.90 (d, J=2.6 Hz, 2H), 3.78-3.71 (m, 1H), 3.50 (d, J=1.1 Hz, 4H), 2.82 (d, J=9.9 Hz, 1H), 2.56-2.48 (m, 1H), 2.10-2.00 (m, 1H), 2.00-1.92 (m, 1H), 1.64 (d, J=9.9 Hz, 1H), 1.39 (s, 3H), 1.08-0.96 (m, 4H). Column: CHIRALPAK ID-3, 4.6*50 mm 3 um; Mobile Phase A: (Hex:DCM=1:1)(0.1% DEA):EtOH=50:50; Flow rate: 1 mL/min; RT: 2.676.

Example 411: Synthesis of 4-(2-Cyclopropyl-6-(4-fluoro-6-(((1R,4R)-1-methyl-2-oxa-5-azabicyclo[2.2.1]heptan-5-yl)methyl)-1-oxoisoindolin-2-yl)pyridin-4-yl)-3-(4-methyl-4H-1,2,4-triazol-3-yl)benzonitrile (ANV-1)

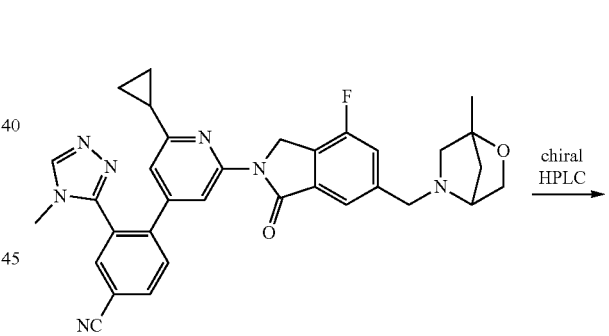

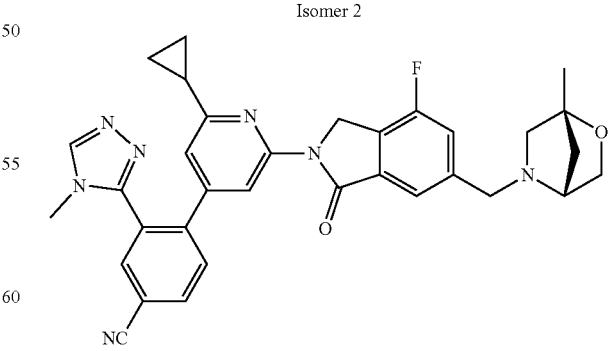

The crude product (ANU-2) (40 mg, 69 μmol, 1 Eq) was purified by Prep-CHIRAL-HPLC with the following conditions (Column: CHIRALPAK ID, 2*25 cm, 5 μm; Mobile Phase A: Hex:DCM=1:1 (0.5% 2M NH3-MeOH)-HPLC, Mobile Phase B: EtOH-HPLC; Flow rate: 20 mL/min; Gradient: 50% B to 50% B in 19 min; Wave Length: 220/254 nm; RT2(min): 17.038) to afford the title compound (ANX-1) (4.3 mg, 7.4 µmol, 6.2%, 99.4% Purity) as a white solid. m/z 576.1 (M+H)$^+$ (ES+). $^1$H NMR (400 MHz, Methanol-d4) δ 8.50 (s, 1H), 8.18-8.05 (m, 2H), 8.02 (d, J=1.3 Hz, 1H), 7.92 (d, J=8.0 Hz, 1H), 7.68 (s, 1H), 7.45 (d, J=9.8 Hz, 1H), 6.96 (d, J=1.4 Hz, 1H), 5.06 (s, 2H), 4.15 (d, J=7.8 Hz, 1H), 3.90 (d, J=3.0 Hz, 2H), 3.78-3.70 (m, 1H), 3.51 (s, 4H), 2.83 (d, J=9.9 Hz, 1H), 2.52 (d, J=9.9 Hz, 1H), 2.08-1.95 (m, 2H), 1.64 (d, J=9.9 Hz, 1H), 1.39 (s, 3H), 1.09-0.95 (m, 4H). Column: CHIRALPAK ID-3, 4.6*50 mm, 3 µm; Mobile Phase A: (Hex:DCM=1:1)(0.1% DEA):EtOH=50:50; Flow rate: 1 mL/min; RT: 4.676.

Example 412: Synthesis of 4-[2-Cyclopropyl-6-(4-fluoro-1-oxo-6-{[(1,1,1-trifluoro-3-methoxypropan-2-yl)amino]methyl}-3H-isoindol-2-yl)pyridin-4-yl]-3-(4-methyl-1,2,4-triazol-3-yl)benzonitrile (ANW-3)

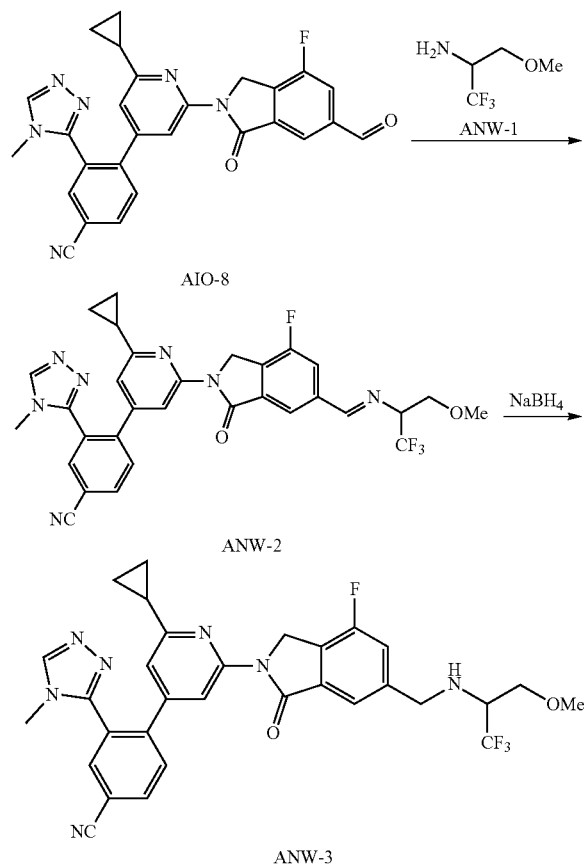

Step 1: 4-[2-Cyclopropyl-6-(4-fluoro-1-oxo-6-{[(1,1,1-trifluoro-3-methoxypropan-2-yl)amino]methyl}-3H-isoindol-2-yl)pyridin-4-yl]-3-(4-methyl-1,2,4-triazol-3-yl)benzonitrile (ANW-2)

A solution of intermediate (AIO-8) (50 mg, 1 Eq, 0.10 mmol) and 1,1,1-trifluoro-3-methoxypropan-2-amine (ANW-1) (22.43 mg, 1.5 Eq, 0.16 mmol) in DMF (2 mL) was stirred for 2 h at 60° C. The mixture was cooled to rt and concentrated in vacuo. The crude product was purified by Prep-HPLC with the following conditions (Column: XBridge Prep OBD C18 Column, 30*150 mm, 5 µm; Mobile Phase A: water (0.1% NH$_4$HCO$_3$+0.1% NH$_3$·H$_2$O), Mobile Phase B: MeCN; Flow rate: 60 mL/min; Gradient: 52% B to 62% B in 9 min; Wave Length: 254/220 nm; RT: 8.83) to afford the sub-title compound (ANW-2) (16 mg, 26 µmol, 24%, 98% Purity) as a white solid. m/z 604.0 (M+H)$^+$ (ES+)

Step 2: 4-[2-Cyclopropyl-6-(4-fluoro-1-oxo-6-{[(1,1,1-trifluoro-3-methoxypropan-2-yl)amino]methyl}-3H-isoindol-2-yl)pyridin-4-yl]-3-(4-methyl-1,2,4-triazol-3-yl)benzonitrile (ANW-3)

A solution of the product from step 1 above (ANW-2) (15 mg, 1 Eq, 31 µmol) and NaBH$_4$ (142 mg, 120 Eq, 3.72 mmol) in MeOH (8 mL) was stirred for 3 days at rt. The resulting mixture was concentrated in vacuo. The crude product was purified by Prep-HPLC with the following conditions (Column: XBridge Prep OBD C18 Column, 30*150 mm, 5 µm; Mobile Phase A: water (0.1% NH$_4$HCO$_3$+0.1% NH$_3$·H$_2$O), Mobile Phase B: MeCN; Flow rate: 60 mL/min; Gradient: 52% B to 62% B in 9 min, 62% B; Wave Length: 254/220 nm; RT: 8.3) to afford the title compound (ANW-3) (2.0 mg, 3.3 µmol, 11%, 99.7% Purity) as a white solid. m/z 606.0 (M+H)$^+$ (ES+). $^1$H NMR (400 MHz, Methanol-d4) δ 8.50 (s, 1H), 8.16-8.07 (m, 2H), 8.02 (d, J=1.5 Hz, 1H), 7.92 (d, J=8.0 Hz, 1H), 7.68 (s, 1H), 7.47 (d, J=9.9 Hz, 1H), 6.96 (d, J=1.5 Hz, 1H), 5.06 (s, 2H), 4.04 (s, 2H), 3.66-3.53 (m, 1H), 3.44 (d, J=57.4 Hz, 5H), 3.31 (s, 3H), 2.09-1.97 (m, 1H), 1.08-0.83 (m, 4H).

Example 413: Synthesis of 4-[2-Cyclopropyl-6-(6-{[methyl(oxetan-3-ylmethyl)amino] methyl}-1-oxo-3H-isoindol-2-yl) pyridin-4-yl]-3-(4-methyl-1,2,4-triazol-3-yl)benzonitrile (ANX-2)

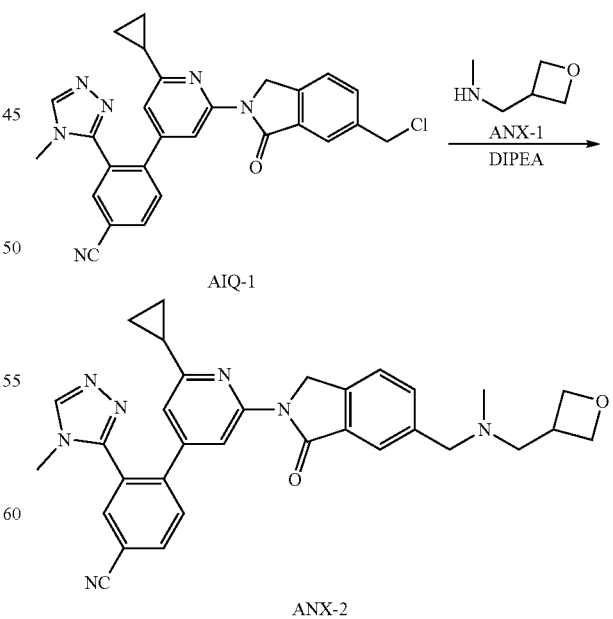

To a stirred solution of intermediate (AIQ-1) (30 mg, 1 Eq, 62 µmol) and methyl(oxetan-3-ylmethyl)amine (ANX- 1) (11 mg, 1.8 Eq, 0.11 mmol) in DCM (10 mL) was added DIPEA (40 mg, 5 Eq, 0.31 mmol) at rt. The resulting mixture was stirred for 7 days at 60° C. The mixture was cooled to rt and concentrated in vacuo. The crude product was purified by Prep-HPLC with the following conditions (Column: Xselect CSH C18 OBD Column 30*150 mm, 5 μm, n; Mobile Phase A: water (0.1% NH$_4$HCO$_3$+0.1% NH$_3$·H$_2$O), Mobile Phase B: MeCN; Flow rate: 60 mL/min; Gradient: 2% B to 32% B in 10 min; Wave Length: 254 nm; RT: 9.88) to afford the title compound (ANX-2) (13.2 mg, 24 μmol, 39%, 99.7% Purity) as a white solid. m/z 546.0 (M+H)$^+$ (ES+). $^1$H NMR (400 MHz, DMSO-d6) δ 8.54 (s, 1H), 8.21 (t, 2H), 7.98 (d, J=1.4 Hz, 1H), 7.87 (d, J=8.5 Hz, 1H), 7.69-7.63 (m, 2H), 7.60 (d, J=7.8, 1.5 Hz, 1H), 6.88 (d, J=1.4 Hz, 1H), 5.01 (s, 2H), 4.63 (d, J=7.8, 5.8 Hz, 2H), 4.21 (t, J=6.0 Hz, 2H), 3.55-3.47 (m, 5H), 3.22-3.18 (m, 1H), 2.66 (d, J=7.5 Hz, 2H), 2.08-2.03 (m, 4H), 0.97 (d, J=6.4 Hz, 4H).

Example 414: Synthesis of 4-{2-Cyclopropyl-6-[1-oxo-6-({[(3S)-oxolan-3-ylmethyl]amino}methyl)-3H-isoindol-2-yl]pyridin-4-yl}-3-(4-methyl-1,2,4-triazol-3-yl)benzonitrile (ANY-2)

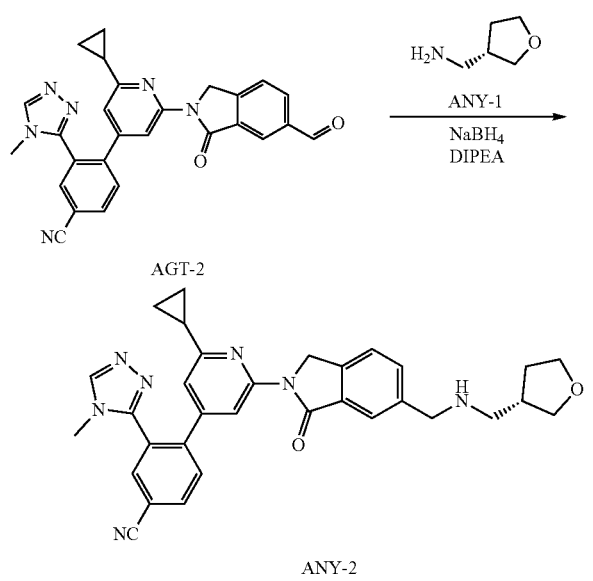

A solution of intermediate (AGT-2) (30 mg, 1 Eq, 65 μmol), DIPEA (34 mg, 4 Eq, 0.26 mmol) and 1-[(3S)-oxolan-3-yl]methanamine (ANY-1) (9 mg, 1.3 Eq, 85 μmol) in MeOH (8 mL) was stirred overnight at 60° C. The mixture was cooled to rt. To the above mixture was added NaBH$_4$ (12 mg, 5 Eq, 0.33 mmol) at 0° C. The resulting mixture was stirred for additional 1 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 35% B to 45% B in 9 min; Wave Length: 254/220 nm; RT: 8.3) to afford the title compound (ANY-2) (12 mg, 22 μmol, 34%, 99.6% Purity) as a white solid. m/z 546.1 (M+H)$^+$ (ES+). $^1$H NMR (400 MHz, Methanol-d4) δ 8.49 (s, 1H), 8.16-8.02 (m, 3H), 7.92 (d, J=8.1 Hz, 1H), 7.81 (s, 1H), 7.70-7.55 (m, 2H), 6.91 (d, J=1.4 Hz, 1H), 5.02 (s, 2H), 3.93-3.77 (m, 4H), 3.75-3.66 (m, 1H), 3.52-3.41 (m, 4H), 2.64-2.50 (m, 2H), 2.48-2.38 (m, 1H), 2.12-1.98 (m, 2H), 1.64-1.54 (m, 1H), 1.06-0.90 (m, 4H).

Example 415: Synthesis of 4-{2-Cyclopropyl-6-[1-oxo-6-({[(3R)-oxolan-3-ylmethyl]amino}methyl)-3H-isoindol-2-yl]pyridin-4-yl}-3-(4-methyl-1,2,4-triazol-3-yl)benzonitrile (ANZ-2)

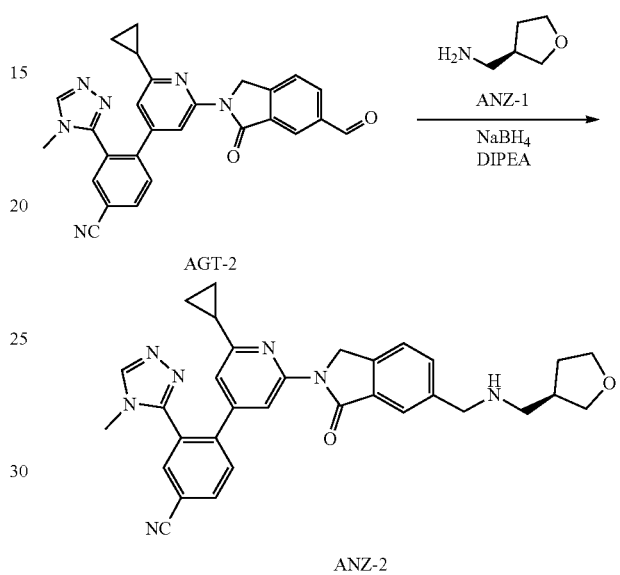

To a stirred solution of intermediate (AGT-2) (30 mg, 1 Eq, 65 μmol) and 1-[(3R)-oxolan-3-yl]methanamine (ANZ-1) (8 mg, 1.2 Eq, 78 μmol) in MeOH (8 mL) was added DIPEA (25 mg, 3 Eq, 0.20 mmol) at rt. The resulting mixture was stirred overnight at 60° C. The mixture was allowed to cool down to rt. To the above mixture was added NaBH$_4$ (12 mg, 5 Eq, 0.33 mmol) at 0° C. The resulting mixture was stirred for additional 1 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 35% B to 45% B in 9 min; Wave Length: 254/220 nm; RT: 8.33) to afford the title compound (ANZ-2) (11.7 mg, 21 μmol, 33%, 99.8% Purity) as a white solid. m/z 546.0 (M+H)$^+$ (ES+). $^1$H NMR (400 MHz, Methanol-d4) δ 8.50 (s, 1H), 8.15-8.03 (m, 3H), 7.92 (d, J=8.0 Hz, 1H), 7.80 (t, J=1.1 Hz, 1H), 7.69-7.59 (m, 2H), 6.92 (d, J=1.5 Hz, 1H), 5.02 (s, 2H), 3.91-3.77 (m, 4H), 3.75-3.68 (m, 1H), 3.52-3.43 (m, 4H), 2.65-2.53 (m, 2H), 2.47-2.39 (m, 1H), 2.12-1.99 (m, 2H), 1.64-1.54 (m, 1H), 1.07-0.94 (m, 4H).

Example 416: Synthesis of 4-[2-(6-{[Cyclobutyl(methyl)amino]methyl}-1-oxo-3H-isoindol-2-yl)-6-cyclopropylpyridin-4-yl]-3-(4-methyl-1,2,4-triazol-3-yl)benzonitrile (AOA-2)

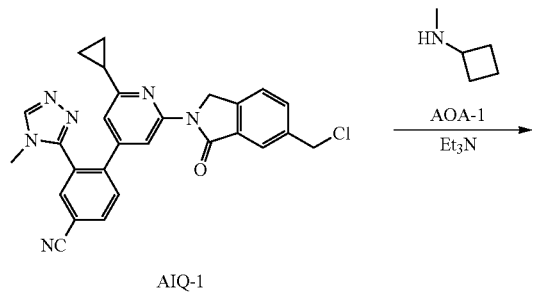

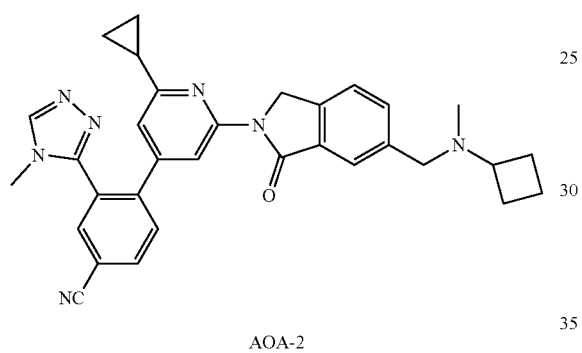

To a stirred mixture of intermediate (AIQ-1) (39 mg, 1 Eq, 81 μmol) and N-methylcyclobutanamine (AOA-1) (14 mg, 2 Eq, 0.16 mmol) in EtOH (4 mL) was added Et$_3$N (24 mg, 3 Eq, 0.24 mmol) at rt under nitrogen atmosphere. The resulting mixture was stirred for 6 h at 60° C. under nitrogen atmosphere. The mixture was cooled to rt and concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 10% B to 80% B in 10 min; Wave Length: 254 nm; RT: 7.5) to afford the title compound (AOA-2) (14.2 mg, 27 μmol, 33%, 99.7% Purity) as a white solid. m/z 530.2 (M+H)$^+$ (ES+). $^1$H NMR (400 MHz, Methanol-d4) δ 8.50 (s, 1H), 8.16-8.03 (m, 3H), 7.92 (d, J=8.0 Hz, 1H), 7.77 (s, 1H), 7.67-7.55 (m, 2H), 6.93 (d, J=1.5 Hz, 1H), 5.03 (s, 2H), 3.52 (d, J=8.7 Hz, 5H), 2.99-2.89 (m, 1H), 2.15-2.06 (m, 2H), 2.04 (s, 4H), 2.00-1.90 (m, 2H), 1.78-1.66 (m, 2H), 1.28 (s, 1H), 1.07-0.94 (m, 4H).

Example 417: Synthesis of (S)-4-(2-Cyclopropyl-6-(6-(1-(oxetan-3-ylamino)ethyl)-1-oxoisoindolin-2-yl)pyridin-4-yl)-3-(4-methyl-4H-1,2,4-triazol-3-yl)benzonitrile (AOB-2)

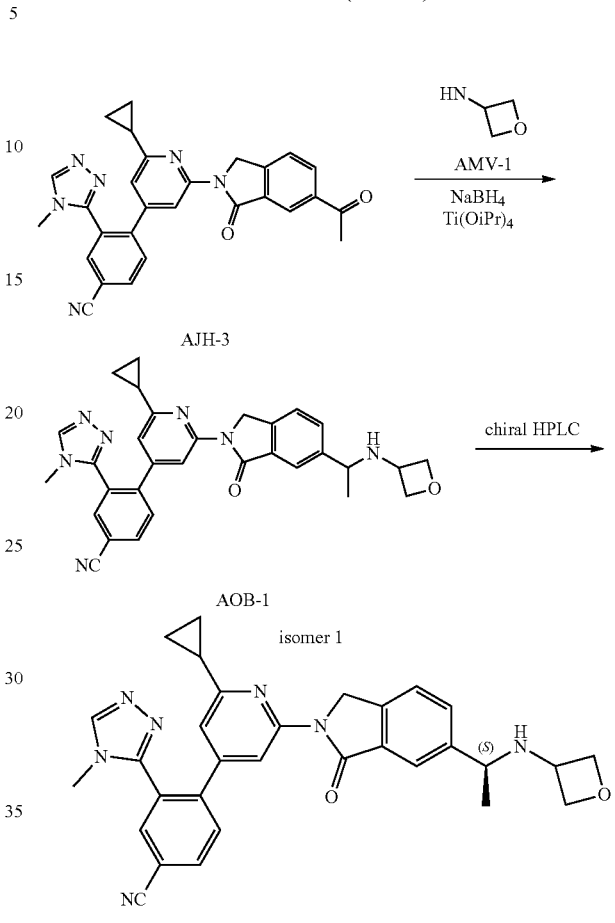

Step 1: 4-(2-Cyclopropyl-6-(6-(1-(oxetan-3-ylamino)ethyl)-1-oxoisoindolin-2-yl)pyridin-4-yl)-3-(4-methyl-4H-1,2,4-triazol-3-yl)benzonitrile (AOB-1)

Into a 25 mL round-bottom flask were added intermediate (AJH-3) (100 mg, 1 Eq, 0.21 mmol) in THF (5 mL) at rt. To the above stirred solution was added oxetan-3-amine (AMV-1) (23 mg, 1.5 Eq, 0.32 mmol) and Ti(Oi-Pr)$_4$ (299 mg, 5 Eq, 1.06 mmol) at rt. The resulting mixture was stirred for additional 16 h at 60° C. under nitrogen atmosphere. The mixture was cooled to rt. To the above mixture was added NaBH$_4$ (40 mg, 5 Eq, 1.06 mmol) at 0° C. The resulting mixture was stirred for additional 1 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 45% B to 55% B in 8 min; Wave Length: 254/220 nm; RT: 7.8) to afford the sub-title compound (AOB-1) (24 mg, 45 μmol, 22% 98% Purity) as a white solid. m/z 532.2 (M+H)$^+$ (ES+)

Step 2: (S)-4-(2-Cyclopropyl-6-(6-(1-(oxetan-3-ylamino)ethyl)-1-oxoisoindolin-2-yl)pyridin-4-yl)-3-(4-methyl-4H-1,2,4-triazol-3-yl)benzonitrile (AOB-2)

The crude product from step 1 above (AOB-1) (24 mg 0.045 mmol, 1 Eq) was separated by Chiral-Prep-HPLC with the following conditions: Column: CHIRALPAK ID, 2*25 cm, 5 μm; Mobile Phase A: Hex:DCM=1:1 (0.5% 2M NH3-MeOH)-HPLC, Mobile Phase B: EtOH-HPLC; Flow rate: 20 mL/min; Gradient: 20% B to 20% B in 26 min; Wave Length: 220/254 nm; RT1(min): 15.85. This resulted in the title compound (AOB-2) (5.8 mg, 11 μmol, 10%, 99.8% Purity) as a white solid. m/z 532.2 (M+H)+ (ES+). $^1$H NMR (400 MHz, Methanol-d4) δ 8.50 (s, 1H), 8.15-8.07 (m, 2H), 8.06 (d, J=1.4 Hz, 1H), 7.92 (d, J=8.1 Hz, 1H), 7.79 (s, 1H), 7.67-7.58 (m, 2H), 6.92 (d, J=1.4 Hz, 1H), 5.03 (s, 2H), 4.71 (t, J=6.7 Hz, 1H), 4.53 (t, J=6.4 Hz, 1H), 4.39 (t, J=6.7 Hz, 1H), 4.23 (t, J=6.4 Hz, 1H), 3.92-3.82 (m, 2H), 3.50 (s, 3H), 2.07-1.98 (m, 1H), 1.41 (d, J=6.6 Hz, 3H), 1.07-1.95 (m, 4H). Column: CHIRALPAK ID-3, 4.6*50 mm 3 μm; Mobile Phase A: Hex:DCM=1:1) (0.1% DEA):EtOH=80:20; Flow rate: 1 mL/min; RT: 2.505.

Example 418: Synthesis of (R)-4-(2-Cyclopropyl-6-(6-(1-(oxetan-3-ylamino)ethyl)-1-oxoisoindolin-2-yl)pyridin-4-yl)-3-(4-methyl-4H-1,2,4-triazol-3-yl)benzonitrile (AOC-1)

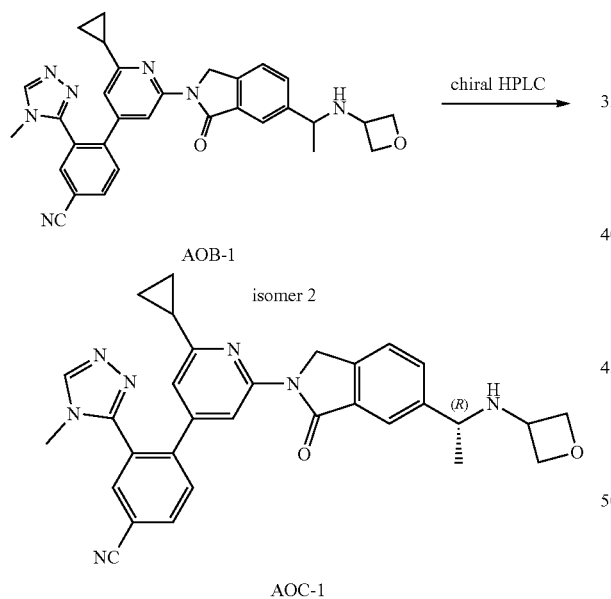

AOC-1

The crude product (AOB-1) (24 mg 0.045 mmol, 1 Eq) was separated by Chiral-Prep-HPLC with the following conditions: Column: CHIRALPAK ID, 2*25 cm, 5 μm; Mobile Phase A: Hex:DCM=1:1 (0.5% 2M NH3-MeOH)-HPLC, Mobile Phase B: EtOH-HPLC; Flow rate: 20 mL/min; Gradient: 20% B to 20% B in 26 min; Wave Length: 220/254 nm; RT2(min): 22.09. This resulted in the title compound (AOC-1) (7.2 mg, 14 μmol, 14%, 99.7% Purity) as a white solid. m/z 532.2 (M+H)+ (ES+). $^1$H NMR (400 MHz, Methanol-d4) δ 8.50 (s, 1H), 8.15-8.01 (m, 3H), 7.92 (d, J=8.0 Hz, 1H), 7.79 (d, J=1.6 Hz, 1H), 7.68-7.58 (m, 2H), 6.92 (d, J=1.4 Hz, 1H), 5.03 (s, 2H), 4.71 (t, J=6.7 Hz, 1H), 4.53 (t, J=6.4 Hz, 1H), 4.39 (t, J=6.8 Hz, 1H), 4.23 (t, J=6.4 Hz, 1H), 3.93-3.18 (m, 2H), 3.50 (s, 3H), 2.07-1.98 (m, 1H), 1.41 (d, J=6.7 Hz, 3H), 1.09-0.94 (m, 4H). Column: CHIRALPAK ID-3, 4.6*50 mm, 3 um; Mobile Phase A: Hex:DCM=1:1)(0.1% DEA):EtOH=80:20; Flow rate: 1 mL/min; RT: 3.255.

Example 419: Synthesis of 4-(2-Cyclopropyl-6-{6-[(1S)-1-{2-oxa-6-azaspiro[3.3]heptan-6-yl}ethyl]-1-oxo-3H-isoindol-2-yl}pyridin-4-yl)-3-(4-methyl-1,2,4-triazol-3-yl)benzonitrile (AOD-2)

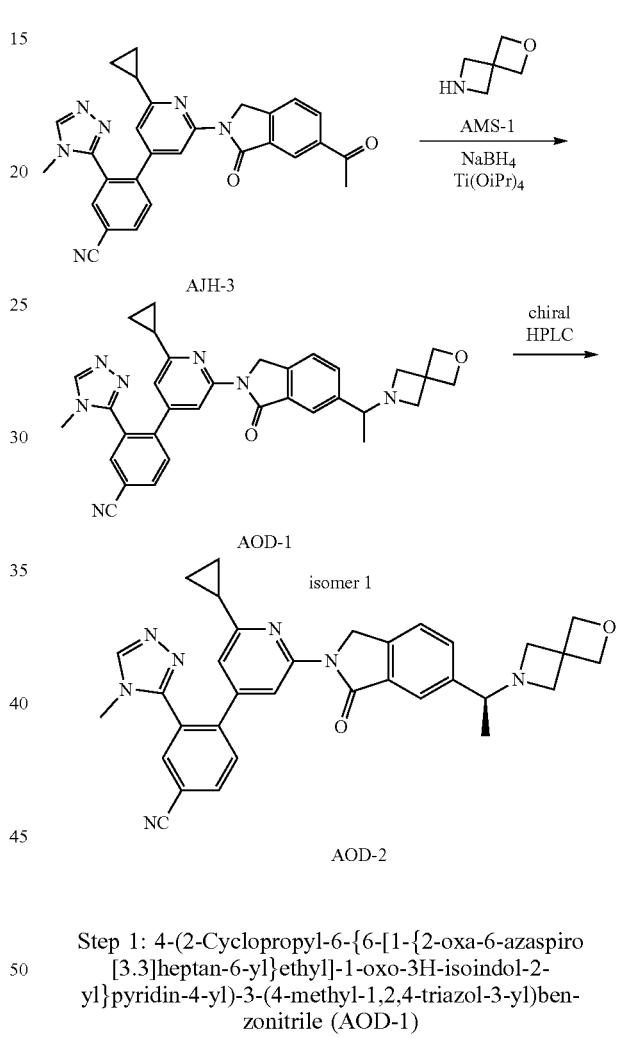

Step 1: 4-(2-Cyclopropyl-6-{6-[1-{2-oxa-6-azaspiro[3.3]heptan-6-yl}ethyl]-1-oxo-3H-isoindol-2-yl}pyridin-4-yl)-3-(4-methyl-1,2,4-triazol-3-yl)benzonitrile (AOD-1)

To a stirred mixture of intermediate (AJH-3) (20 mg, 1 Eq, 42 μmol), 2-oxa-6-azaspiro[3.3]heptane (AMS-1) (5 mg, 1.2 Eq, 50 μmol) and Ti(Oi-Pr)4 (24 mg, 2 Eq, 84 μmol) in THF (1 mL) was added NaBH4 (3 mg, 2 Eq, 84 μmol) at rt under nitrogen atmosphere. The resulting mixture was stirred overnight at rt under nitrogen atmosphere. The reaction was then quenched by the addition of MeOH (2 mL) at 0° C. The resulting mixture was concentrated in vacuo. The residue was purified by Prep-TLC with DCM/MeOH (10/1). The crude product was purified by Prep-HPLC with the following conditions (Column: XBridge Prep OBD C18 Column, 30*150 mm, 5 μm; Mobile Phase A: water (0.1% NH4HCO3+0.1% NH3·H2O), Mobile Phase B: MeCN; Flow rate: 60 mL/min; Gradient: 38% B to 48% B in 8 min; Wave Length: 254/220 nm; RT: 7.44) to afford the sub-title compound (AOD-1) (15 mg, 27 µmol, 63%, 98% Purity) as a white solid. m/z 558.2 (M+H)⁺ (ES+)

Step 2: 4-(2-Cyclopropyl-6-{6-[(1S)-1-{2-oxa-6-azaspiro[3.3]heptan-6-yl}ethyl]-1-oxo-3H-isoindol-2-yl}pyridin-4-yl)-3-(4-methyl-1,2,4-triazol-3-yl)benzonitrile (AOD-2)

The crude product of the product from step 1 above (AOD-1) (15 mg, 1 Eq, 27 µmol) was purified by Prep-CHIRAL-HPLC with the following conditions: (Column: CHIRALPAK IF, 2*25 cm, 5 µm; Mobile Phase A: MtBE (0.5% 2M NH3-MeOH)-HPLC, Mobile Phase B: MeOH:DCM=1:1-HPLC; Flow rate: 20 mL/min; Gradient: 50% B to 50% B in 15 min; Wave Length: 220/254 nm; RT1 (min): 9.004) to afford the title compound (AOD-2) (3.2 mg, 5.7 µmol, 21%, 98.3% Purity) as a white solid. m/z 558.2 (M+H)⁺ (ES+). ¹H NMR (300 MHz, Methanol-d4) δ 8.50 (s, 1H), 8.17-8.02 (m, 3H), 7.92 (d, J=8.0 Hz, 1H), 7.76 (s, 1H), 7.61 (d, J=1.4 Hz, 2H), 6.92 (d, J=1.5 Hz, 1H), 5.02 (s, 2H), 4.72 (s, 4H), 3.50 (s, 3H), 3.48-3.38 (m, 3H), 3.28 (s, 2H), 2.06-1.97 (m, 1H), 1.25 (d, J=6.4 Hz, 3H), 1.06-0.95 (m, 4H). Column: CHIRALPAK IF-3, 4.6*50 mm, 3 µm; Mobile Phase A: MtBE(0.1% DEA):(MeOH:DCM=1:1) =50:50; Flow rate: 1 mL/min; RT: 1.654.

Example 420: Synthesis of 4-(2-Cyclopropyl-6-{6-[(1R)-1-{2-oxa-6-azaspiro[3.3]heptan-6-yl}ethyl]-1-oxo-3H-isoindol-2-yl}pyridin-4-yl)-3-(4-methyl-1,2,4-triazol-3-yl)benzonitrile (AOE-1)

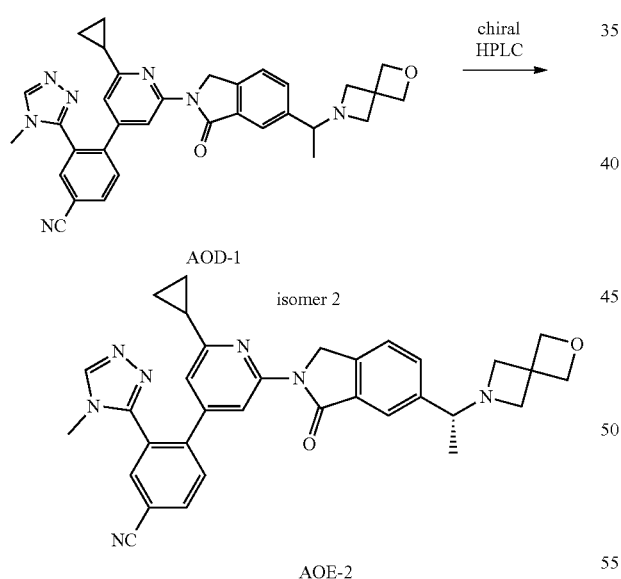

The crude product (AOD-1) (15 mg, 1 Eq, 27 µmol) was purified by Prep-CHIRAL-HPLC with the following conditions: (Column: CHIRALPAK IF, 2*25 cm, 5 µm; Mobile Phase A: MtBE(0.5% 2M NH3-MeOH)-HPLC, Mobile Phase B: MeOH:DCM=1:1-HPLC; Flow rate: 20 mL/min; Gradient: 50% B to 50% B in 15 min; Wave Length: 220/254 nm; RT2(min): 13.774) to afford the title compound (AOE-1) (3.3 mg, 5.9 µmol, 22%, 98.8% Purity) as a white solid. m/z 558.2 (M+H)⁺ (ES+). ¹H NMR (300 MHz, Methanol-d4) δ 8.50 (s, 1H), 8.17-8.01 (m, 3H), 7.92 (d, J=8.0 Hz, 1H), 7.76 (s, 1H), 7.61 (s, 2H), 6.92 (d, J=1.8 Hz, 1H), 5.01 (d, J=2.1 Hz, 2H), 4.72 (s, 4H), 3.50 (s, 3H), 3.51-3.38 (m, 3H), 3.28 (d, J=7.0 Hz, 2H), 2.15-1.95 (m, 1H), 1.25 (d, J=6.4 Hz, 3H), 1.08-0.94 (m, 4H). Column: CHIRALPAK IF-3, 4.6*50 mm, 3 µm; Mobile Phase A: MtBE(0.1% DEA):(MeOH:DCM=1:1)=50:50; Flow rate: 1 mL/min; RT: 3.796.

Example 421: Synthesis of 4-[2-Cyclopropyl-6-(4-fluoro-6-{1[(4-hydroxy-3-methyl oxolan-3-yl)amino]methyl}-1-oxo-3H-isoindol-2-yl)pyridin-4-yl]-3-(4-methyl-1,2,4-triazol-3-yl)benzonitrile (AOF-9)

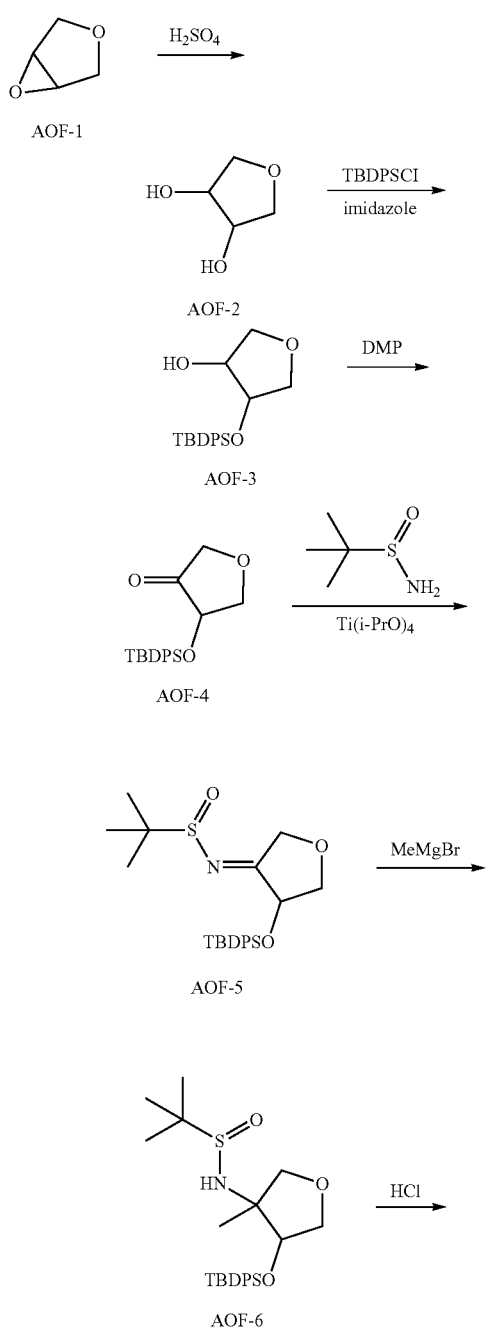

-continued

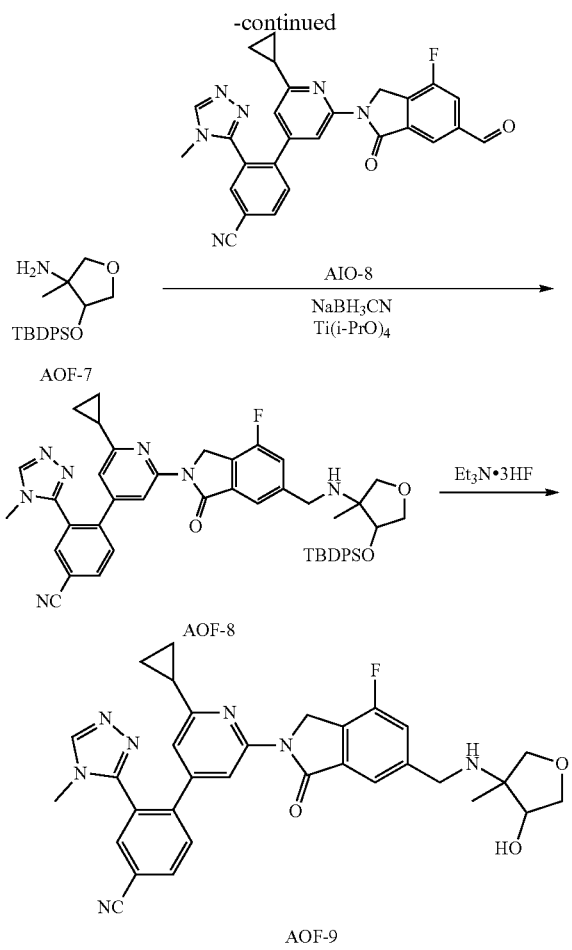

Step 1: Oxolane-3,4-diol (AOF-2)

To a stirred solution of 3,6-dioxabicyclo[3.1.0]hexane (AOF-1) (20.0 g, 1 Eq, 232 mmol) in water (40 mL) was added conc. $H_2SO_4$ (6 mL) at 0° C. The resulting mixture was stirred overnight at rt. The mixture was cooled to rt. The mixture was basified to pH 8 with sat. aq. of $Na_2CO_3$. The resulting mixture was filtered; the filter cake was washed with THF (3×20 mL). The resulting mixture was concentrated in vacuo to afford the sub-title compound (AOF-1) (31 g, 298 mmol, crude) as a colorless crude oil. m/z 105.0 $(M+H)^+$ (ES+)

Step 2: 4-[(tert-Butyldiphenylsilyl)oxy]oxolan-3-ol (AOF-3)

To a stirred solution of the product from step 1 above (AOF-2) (30.0 g, 1 Eq, 288 mmol) and imidazole (19.6 g, 1 Eq, 288 mmol) in MeCN (50 mL) were added TBDPS-Cl (63.4 g, 0.8 Eq, 231 mmol) at rt under nitrogen atmosphere. The resulting mixture was stirred for 4 h at 80° C. under nitrogen atmosphere. The mixture was cooled to rt and concentrated in vacuo. The residue was applied on a silica gel column chromatography with petroleum ether/EtOAc (7/1) to afford the sub-title compound (AOF-3) (28 g, 81.9 mmol, 28%, 85% Purity) as a white solid. m/z 343.2 $(M+H)^+$ (ES+)

Step 3: 4-[(tert-Butyldiphenylsilyl)oxy]oxolan-3-one (AOF-4)

To a stirred solution of the product from step 2 above (AOF-3) (600 mg, 1 Eq, 1.75 mmol) in DCM (8 mL) were added DMP (2.23 g, 3 Eq, 5.26 mmol) at rt. The resulting mixture was stirred overnight at rt. The resulting mixture was filtered; the filter cake was washed with petroleum ether (3×5 mL). The filtrate was concentrated in vacuo. The resulting mixture was diluted with water and extracted with EtOAc (3×80 mL). The combined organic layers were washed with brine (2×80 mL), dried ($Na_2SO_4$). After filtration, the filtrate was concentrated in vacuo. The residue was purified by Prep-TLC with EtOAc/petroleum ether (1/20) to afford the sub-title compound (AOF-4) (480 mg, 1.41 mmol, 80%, 92% Purity) as a yellow oil. m/z 341.1 $(M+H)^+$ (ES+)

Step 4: N-[(3E)-4-[(tert-Butyldiphenylsilyl)oxy]oxolan-3-ylidene]-2-methylpropane-2-sulfinamide (AOF-5)

To a stirred solution of the product from step 3 above (AOF-4) (1.00 g, 1 Eq, 2.94 mmol) and tert-butanesulfinamide (712 mg, 2 Eq, 5.87 mmol) in DCM (20 mL) was added Ti(i-PrO)$_4$ (2.50 g, 3 Eq, 8.81 mmol) at rt under nitrogen atmosphere. The resulting mixture was stirred overnight at 60° C. under nitrogen atmosphere. The mixture was cooled to rt and concentrated in vacuo. The residue was purified by Prep-TLC with EtOAc/petroleum ether (1/4) to afford the sub-title compound (AOF-5) (1.00 g, 77%, 90% Purity) as a white solid. m/z 444.2 $(M+H)^+$ (ES+)

Step 5: N-{4-[(tert-Butyldiphenylsilyl)oxy]-3-methyloxolan-3-yl}-2-methylpropane-2-sulfinamide (AOF-6)

To a stirred solution of the product from step 4 above (AOF-5) (1.40 g, 1 Eq, 3.16 mmol) in THF (50 mL) was added MeMgBr (753 mg, 2 Eq, 6.31 mmol) dropwise at −78° C. under nitrogen atmosphere. The resulting mixture was stirred for additional 1 h at −78° C. under nitrogen atmosphere. The reaction was then quenched by the addition of 10 mL of ice water at 0° C. The resulting mixture was concentrated in vacuo. The crude product was purified by reverse flash column chromatography with the following conditions: Column, C18; mobile phase, water (0.1% $NH_4HCO_3$) and MeCN (10% ACN up to 80% in 30 min); Detector, UV 254/220 nm. This resulted in the sub-title compound (AOF-6) (195 mg, 0.42 mmol, 13%, 95% Purity) as a white solid. m/z 460.2 $(M+H)^+$ (ES+).

Step 6: 4-[(tert-Butyldiphenylsilyl)oxy]-3-methyloxolan-3-amine (AOF-7)

To a stirred mixture of the product from step 5 above (AOF-6) (195 mg, 1 Eq, 0.42 mmol) in MeOH (3 mL) was added HCl (g) in 1,4-dioxane (1 mL, 4 M) in portions at 0° C. under nitrogen atmosphere. The resulting mixture was stirred for additional 30 min at rt under nitrogen atmosphere. The resulting mixture was concentrated in vacuo. The residue was purified by Prep-TLC with DCM/MeOH (8/1) to afford the sub-title compound (AOF-7) (130 mg, 0.37 mmol, 86%, 92% Purity) as a white solid. m/z 356.2 $(M+H)^+$ (ES+)

Step 7: 4-(2-{6-[({4-[(tert-Butyldiphenylsilyl)oxy]-3-methyloxolan-3-yl}amino)methyl]-4-fluoro-1-oxo-3H-isoindol-2-yl}-6-cyclopropylpyridin-4-yl)-3-(4-methyl-1,2,4-triazol-3-yl)benzonitrile (AOF-8)

To a stirred solution of the product from step 6 above (AOF-7) (130 mg, 1 Eq, 0.37 mmol) and intermediate (AIO-8) (210 mg, 1.2 Eq, 0.44 mmol) in DCM (10 mL) was added Ti(i-PrO)₄ (312 mg, 3 Eq, 1.10 mmol) at rt under nitrogen atmosphere. The resulting mixture was stirred overnight at 60° C. under nitrogen atmosphere. The mixture was cooled to rt. To the above mixture was added NaBH₃CN (69 mg, 1.10 mmol, 3 Eq) at rt. The resulting mixture was stirred for additional 2 h at rt. The resulting mixture was concentrated in vacuo. The residue was purified by Prep-TLC with DCM/MeOH (12/1) to afford the sub-title compound (AOF-8) (237 mg, 0.29 mmol, 79%, 95% Purity) as a white solid. m/z 818.4 (M+H)⁺ (ES+)

Step 8: 4-[2-Cyclopropyl-6-(4-fluoro-6-{[(4-hydroxy-3-methyloxolan-3-yl)amino]methyl}-1-oxo-3H-isoindol-2-yl)pyridin-4-yl]-3-(4-methyl-1,2,4-triazol-3-yl)benzonitrile (AOF-9)

To a stirred mixture of the product from step 7 above (AOF-8) (170 mg, 1 Eq, 0.21 mmol) in THF (5 mL) was added Et₃N·3HF (0.5 mL) dropwise at rt under nitrogen atmosphere. The resulting mixture was stirred overnight at rt. The resulting mixture was concentrated in vacuo. The residue was purified by Prep-TLC with DCM/MeOH (12/1). The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 30% B to 46% B in 10 min; Wave Length: 254 nm; RT: 9.07) to afford the title compound (AOF-9) (20 mg, 34 μmol, 17%, 99.6% Purity) as a white solid. m/z 580.0 (M+H)⁺ (ES+). ¹H NMR (400 MHz, DMSO-d6) δ 8.53 (s, 1H), 8.22-8.20 (m, 2H), 7.94 (d, J=1.4 Hz, 1H), 7.88-7.86 (d, J=8.5 Hz, 1H), 7.65 (s, 1H), 7.53-7.51 (d, J=10.0 Hz, 1H), 6.93 (d, J=1.4 Hz, 1H), 5.20-5.19 (d, J=4.4 Hz, 1H), 5.07 (s, 2H), 4.01-3.97 (m, 1H), 3.84-3.80 (m, 3H), 3.63-3.60 (m, 1H), 3.48 (d, J=3.8 Hz, 4H), 3.42-3.40 (d, J=7.8 Hz, 1H), 2.07-2.04 (m, 1H), 1.13 (s, 3H), 0.98 (m, 4H).

Example 422: Synthesis of 4-[2-Cyclopropyl-6-(4-fluoro-6-{[(4-hydroxy-3-methyloxolan-3-yl)amino]methyl}-1-oxo-3H-isoindol-2-yl)pyridin-4-yl]-3-(4-methyl-1,2,4-triazol-3-yl)benzonitrile (AOG-1)

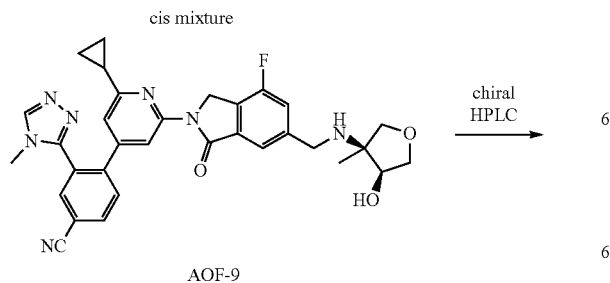

AOF-9

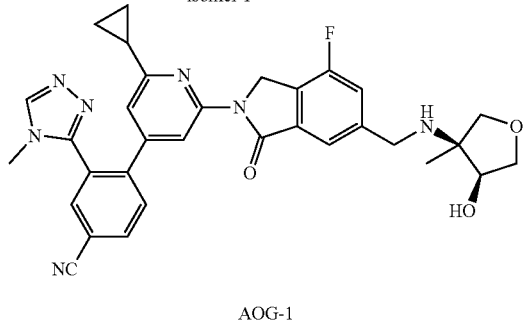

AOG-1

The crude product (AOF-9) (20 mg, 1 Eq, 34 μmol) was purified by Prep-CHIRAL-HPLC with the following conditions (Column: CHIRALPAK IE, 2×25 cm, 5 μm; Mobile Phase A: MtBE (0.5% 2M NH₃-MeOH)-HPLC, Mobile Phase B: EtOH-HPLC; Flow rate: 20 mL/min; Gradient: 50% B to 50% B in 29 min; Wave Length: 220/254 nm; RT1(min): 18.63) to afford the title compound (AOG-1) (8.4 mg, 15 μmol, 42%, 99.5% Purity) as a white solid. m/z 580.0 (M+H)⁺ (ES+). ¹H NMR (400 MHz, DMSO-d6) δ 8.53 (s, 1H), 8.21-8.20 (m, 2H), 7.94 (m, 1H), 7.88-7.86 (d, J=8.5 Hz, 1H), 7.65 (s, 1H), 7.53-7.51 (d, J=10.0 Hz, 1H), 6.93 (m, 1H), 5.20 (s, 1H), 5.06 (s, 2H), 4.01-3.97 (m, 1H), 3.87-3.76 (m, 3H), 3.63-3.60 (m, 1H), 3.48 (d, J=3.5 Hz, 4H), 3.42-3.41 (d, J=7.8 Hz, 1H), 2.09-2.02 (m, 1H), 1.14 (s, 3H), 1.02-0.95 (m, 4H). Column: CHIRALPAK IE-3, 4.6*50 mm, 3 μm; Mobile Phase A: MtBE(0.1% DEA):EtOH=50:50; Flow rate: 1 mL/min; RT: 3.209.

Example 423: Synthesis of rel-4-{2-Cyclopropyl-6-[4-fluoro-6-({[(3R,4R)-4-hydroxy-3-methyloxolan-3-yl]amino}methyl)-1-oxo-3H-isoindol-2-yl]pyridin-4-yl}-3-(4-methyl-1,2,4-triazol-3-yl)benzonitrile (AOH-1)

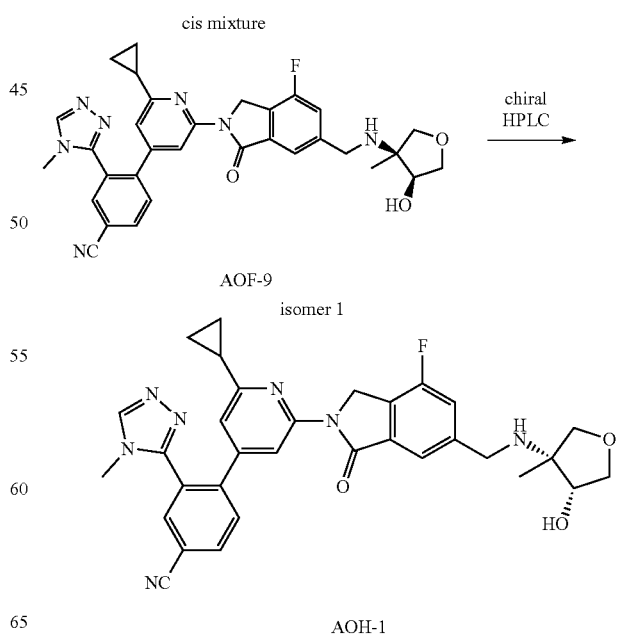

AOF-9

AOH-1

The crude product (AOF-9) (20 mg, 1 Eq, 34 µmol) was purified by Prep-CHIRAL-HPLC with the following conditions (Column: CHIRALPAK IE, 2×25 cm, 5 µm; Mobile Phase A: MtBE (0.5% 2M NH$_3$-MeOH)-HPLC, Mobile Phase B: EtOH-HPLC; Flow rate: 20 mL/min; Gradient: 50% B to 50% B in 29 min; Wave Length: 220/254 nm; RT2(min): 26.30) to afford the title compound (AOH-1) (8.6 mg, 15 µmol, 43%, 99.8% Purity) as a white solid. m/z 580.0 (M+H)$^+$ (ES+). $^1$H NMR (400 MHz, DMSO-d6) δ 8.53 (s, 1H), 8.21-8.20 (m, 2H), 7.94 (s, 1H), 7.88-7.86 (m, 1H), 7.65 (s, 1H), 7.53-7.51 (d, J=10.0 Hz, 1H), 6.93 (s, 1H), 5.20 (s, 1H), 5.07 (s, 2H), 4.01-3.97 (m, 1H), 3.87-3.76 (m, 3H), 3.63-3.60 (m, 1H), 3.48 (d, J=3.1 Hz, 4H), 3.42-3.41 (d, J=7.8 Hz, 1H), 2.09-2.02 (m, 1H), 1.23 (s, 3H), 1.13 (m, 4H). Column: CHIRALPAK IE-3, 4.6*50 mm, 3 µm; Mobile Phase A: MtBE(0.1% DEA):EtOH=50:50; Flow rate: 1 mL/min; RT: 4.632.

Example 424: Synthesis of 4-(2-{6-[2-(Cyclobutylamino)propan-2-yl]-1-oxo-3H-isoindol-2-yl}-6-cyclopropylpyridin-4-yl)-3-(4-methyl-1,2,4-triazol-3-yl)benzonitrile (AOI-1)

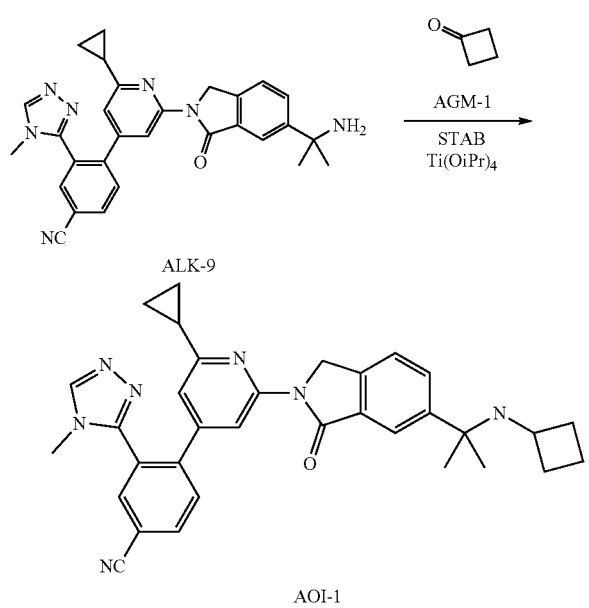

To a stirred solution of compound (ALK-9) (30 mg, 1 Eq, 61 µmol) and cyclobutanone (AGM-1) (13 mg, 3 Eq, 0.18 mmol) in DCM (5 mL) was added Ti(Oi-Pr)$_4$ (26 mg, 1.5 Eq, 91 µmol) at rt. The resulting mixture was stirred overnight at 60° C. The mixture was allowed to cool down to rt. To the above mixture was added NaBH(OAc)$_3$ (65 mg, 5 Eq, 0.31 mmol) at rt. The resulting mixture was stirred for additional 5 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 µm; Mobile Phase A: water (0.1% NH$_4$HCO$_3$+0.1% NH$_3$·H$_2$O), Mobile Phase B: MeCN; Flow rate: 60 mL/min; Gradient: 51% B to 61% B in 8 min; Wave Length: 254/220 nm) to afford the title compound (AOI-1) (4.1 mg, 7.5 µmol, 12%, 97.2% Purity) as a white solid. m/z 544.1 (M+H)$^+$ (ES+). $^1$H NMR (400 MHz, Methanol-d4) δ 8.51 (s, 1H), 8.15-8.09 (m, 2H), 8.05 (d, J=1.4 Hz, 1H), 7.96-7.90 (m, 2H), 7.86-7.81 (m, 1H), 7.61 (d, J=8.1 Hz, 1H), 6.94 (d, J=1.4 Hz, 1H), 5.02 (s, 2H), 3.51 (s, 3H), 3.09-2.99 (m, 1H), 2.07-2.01 (m, 1H), 1.93-1.84 (m, 2H), 1.79-1.65 (m, 2H), 1.61-1.53 (m, 1H), 1.50 (s, 6H), 1.49-1.38 (m, 1H), 1.06-0.96 (m, 4H).

Example 425: Synthesis of 4-{2-[6-({[(1R)-1-Cyclobutylethyl]amino}methyl)-1-oxo-3H-isoindol-2-yl]-6-cyclopropylpyridin-4-yl}-3-(4-methyl-1,2,4-triazol-3-yl)benzonitrile (AOJ-2)

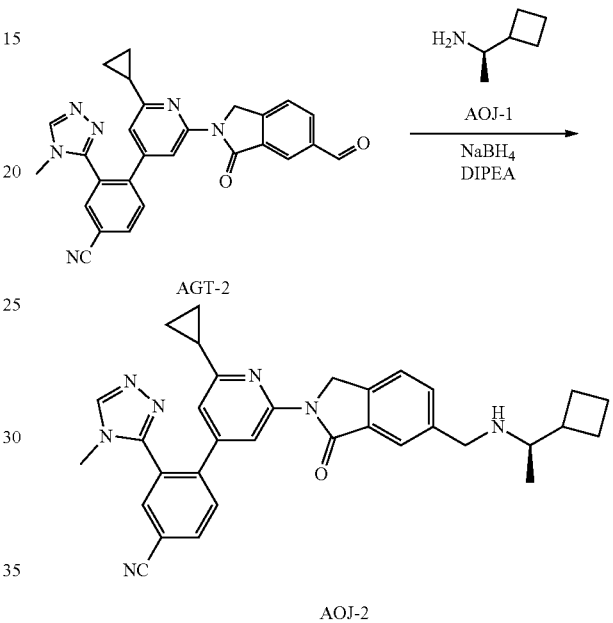

A solution of (1R)-1-cyclobutylethanamine (AOJ-1) (13 mg, 2 Eq, 0.13 mmol) and DIPEA (34 mg, 4 Eq, 0.26 mmol) in MeOH (8 mL) was stirred for 5 min at rt. To the above mixture was added intermediate (AGT-2) (30 mg, 1 Eq, 65 µmol) at rt. The resulting mixture was stirred overnight at 60° C. The mixture was cooled to rt. To the above mixture was added NaBH$_4$ (12 mg, 5 Eq, 0.33 mmol) at 0° C. The resulting mixture was stirred for additional 1 h at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 µm; Mobile Phase A: water (0.1% NH$_4$HCO$_3$+0.1% NH$_3$·H$_2$O), Mobile Phase B: MeCN; Flow rate: 60 mL/min; Gradient: 46% B to 58% B in 8 min; Wave Length: 254/220 nm; RT: 7.8) to afford the title compound (AOJ-2) (15.3 mg, 28 µmol, 43%, 99.3% Purity) as a white solid. m/z 544.1 (M+H)$^+$ (ES+). $^1$H NMR (400 MHz, Methanol-d4) δ 8.49 (s, 1H), 8.14-8.03 (m, 3H), 7.92 (d, J=8.1 Hz, 1H), 7.79 (d, J=1.5 Hz, 1H), 7.68-7.58 (m, 2H), 6.91 (d, J=1.5 Hz, 1H), 5.02 (s, 2H), 3.92 (d, J=13.5 Hz, 1H), 3.80 (d, J=13.5 Hz, 1H), 3.49 (s, 3H), 2.61-1.51 (m, 1H), 2.33-2.22 (m, 1H), 2.12-1.92 (m, 3H), 1.91-1.80 (m, 1H), 1.78-1.62 (m, 3H), 1.08-0.93 (m, 7H).

Example 426: Synthesis of 4-{2-[6-({[(1S)-1-Cyclobutylethyl]amino}methyl)-1-oxo-3H-isoindol-2-yl]-6-cyclopropylpyridin-4-yl}-3-(4-methyl-1,2,4-triazol-3-yl)benzonitrile (AOK-2)

Example 427: Synthesis of 4-[2-Cyclopropyl-6-(6-{2-oxa-6-azaspiro[3.3]heptan-6-ylmethyl}-1-oxo-3H-isoindol-2-yl)pyridin-4-yl]-3-(4-methyl-1,2,4-triazol-3-yl)benzonitrile (AOL-1)

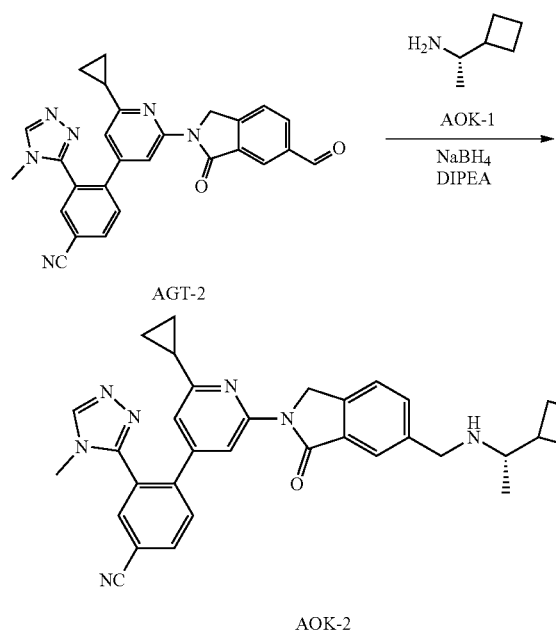

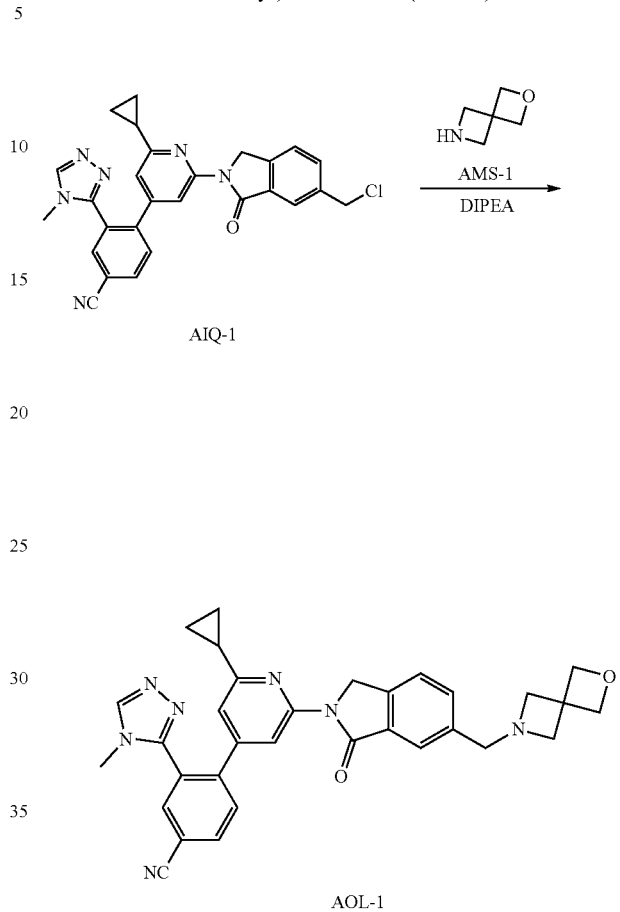

To a stirred mixture intermediate (AGT-2) (30 mg, 1 Eq, 65 μmol) and (1S)-1-cyclobutylethanamine (AOK-1) (12 mg, 1.8 Eq, 0.12 mmol) in MeOH (8 mL) was added DIPEA (25 mg, 3 Eq, 0.20 mmol) at rt. The resulting mixture was stirred for additional overnight at 60° C. The mixture was cooled to rt. To the above mixture was added NaBH₄ (7 mg, 3 Eq, 0.20 mmol) at 0° C. The resulting mixture was stirred overnight at rt. The reaction was then quenched by the addition of MeOH (2 mL) at 0° C. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 50% B to 61% B in 8 min; Wave Length: 254/220 nm; RT: 7.5) to afford the title compound (AOK-2) (15.0 mg, 28 μmol, 42%, 99.4% Purity) as a white solid. m/z 544.1 (M+H)⁺ (ES+). ¹H NMR (400 MHz, Methanol-d4) δ 8.50 (s, 1H), 8.15-8.02 (m, 3H), 7.92 (d, J=8.1 Hz, 1H), 7.79 (d, J=1.6 Hz, 1H), 7.70-7.57 (m, 2H), 6.92 (d, J=1.4 Hz, 1H), 5.02 (s, 2H), 3.91 (d, J=13.5 Hz, 1H), 3.80 (d, J=13.5 Hz, 1H), 3.50 (s, 3H), 2.58-2.46 (m, 1H), 2.33-2.21 (m, 1H), 2.15-1.93 (m, 3H), 1.93-1.82 (m, 1H), 1.78-1.59 (m, 3H), 1.06-0.90 (m, 7H).

To a stirred solution of intermediate (AIQ-1) (30 mg, 1 Eq, 62 μmol) and 2-oxa-6-azaspiro[3.3]heptane (AMS-1) (11 mg, 1.8 Eq, 0.11 mmol) in DCM (8 mL) was added DIPEA (40 mg, 5 Eq, 0.31 mmol) at rt. The resulting mixture was stirred for 2 days at 60° C. under air atmosphere. The mixture was cooled to rt and concentrated in vacuo. The crude product was purified by Prep-HPLC with the following conditions Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 30% B to 40% B in 9 min; Wave Length: 254/220 nm; RT: 8.9) to afford the title compound (AOL-1) (11 mg, 20 μmol, 32%, 99.9% Purity) as a white solid. m/z 544.1 (M+H)⁺ (ES+). ¹H NMR (400 MHz, DMSO-d6) δ 8.55 (s, 1H), 8.26-8.18 (m, 2H), 7.98 (d, J=1.4 Hz, 1H), 7.91-7.81 (m, 1H), 7.65-7.59 (m, 2H), 7.57-7.53 (m, 1H), 6.89 (d, J=1.4 Hz, 1H), 5.00 (s, 2H), 4.61 (s, 4H), 3.59 (s, 2H), 3.48 (s, 3H), 3.30 (s, 4H), 2.08-2.00 (m, 1H), 0.97 (d, J=6.4 Hz, 4H).

Example 428: Synthesis of 4-[2-(6-{[(2-Cyclobutyl-propan-2-yl)amino]methyl}-1-oxo-3H-isoindol-2-yl)-6-cyclopropylpyridin-4-yl]-3-(4-methyl-1,2,4-triazol-3-yl)benzonitrile (AOM-2)

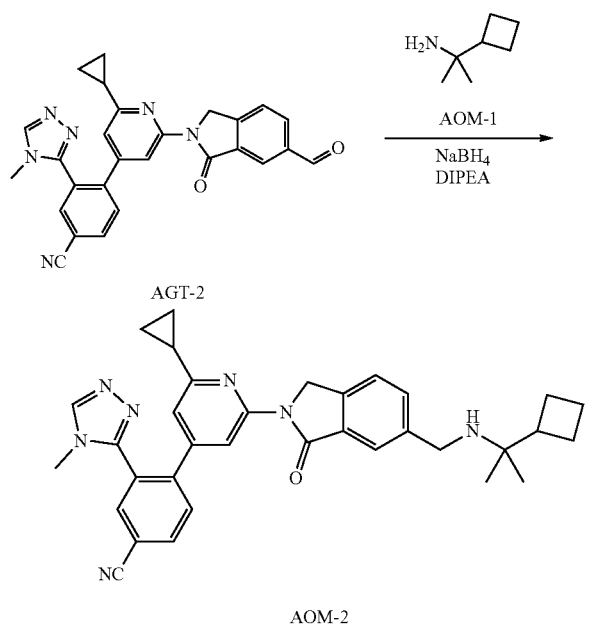

A solution of 2-cyclobutylpropan-2-amine (AOM-1) (9 mg, 1.2 Eq, 78 μmol) in MeOH (8 mL) was treated with DIPEA (34 mg, 4 Eq, 0.26 μmol) for 5 min at rt followed by the addition of intermediate (AGT-2) (30 mg, 1 Eq, 65 μmol) at rt. The resulting mixture was stirred overnight at 60° C. The mixture was allowed to cool down to rt. To the above mixture was added NaBH₄ (12 mg, 5 Eq, 0.33 mmol) at 0° C. The resulting mixture was stirred for additional 1 h at rt. The reaction was then quenched by the addition of MeOH (2 mL) at 0° C. The resulting mixture was concentrated in vacuo. The crude product was purified by Prep-HPLC with the following conditions (Column: Xselect CSH C18 OBD Column 30*150 mm, 5 μm; Mobile Phase A: water (0.1% NHHCO+0.1% NH·HO), Mobile Phase B: MeCN; Flow rate: 60 mL/min; Gradient: 38% B to 68% B in 10 min; Wave Length: 254 nm; RT: 7.87) to afford the title compound (AOM-2) (14.3 mg, 26 μmol, 39%, 99.7% Purity) as a white solid. m/z 558.1 (M+H)⁺ (ES+). ¹H NMR (400 MHz, Methanol-d4) δ 8.50 (s, 1H), 8.14-8.07 (m, 2H), 8.03 (d, J=1.4 Hz, 1H), 7.92 (d, J=8.0 Hz, 1H), 7.79 (d, J=1.5 Hz, 1H), 7.66-7.63 (m, 1H), 7.58 (d, J=7.9 Hz, 1H), 6.91 (d, J=1.4 Hz, 1H), 4.99 (s, 2H), 3.77 (s, 2H), 3.50 (s, 3H), 2.67-2.57 (m, 1H), 2.05-1.98 (m, 1H), 1.97-1.85 (m, 5H), 1.75-1.66 (m, 1H), 1.11 (s, 6H), 1.05-0.94 (m, 4H).

Example 429: Synthesis of 2-{[(2-{4-[4-Cyano-2-(4-methyl-1,2,4-triazol-3-yl)phenyl]-6-cyclopropylpyridin-2-yl}-3-oxo-1H-isoindol-5-yl)methyl](oxetan-3-ylmethyl)amino}-N,N-dimethylacetamide (AON-2)

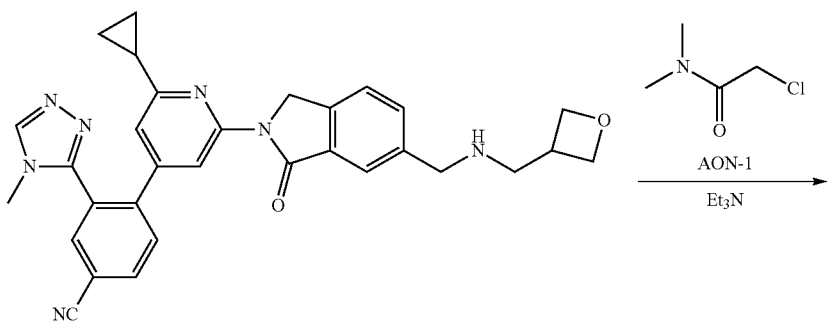

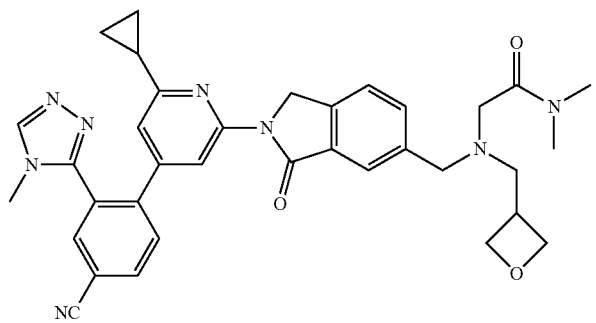

To a stirred solution of compound (AHZ-2) (30 mg, 1 Eq, 56 μmol) and DIPEA (36 mg, 5 Eq, 0.28 mmol) in EtOH (5 mL) was added 2-chloro-N, N-dimethylacetamide (AON-1) (34 mg, 5 Eq, 0.28 mmol) at rt under nitrogen atmosphere. The resulting mixture was stirred overnight at 60° C. under nitrogen atmosphere. The mixture was cooled to rt and concentrated in vacuo. The crude product was purified by Prep-HPLC with the following conditions (Column: Xselect CSH C18 OBD Column 30*150 mm, 5 μm; Mobile Phase A: water (0.1% FA), Mobile Phase B: MeCN; Flow rate: 60 mL/min; Gradient: 6% B to 36% B in 10 min; Wave Length: 254 nm; RT: 9.67) to afford the title compound (AON-2) (9.7 mg, 16 μmol, 28%, 99.6% Purity) as a white solid. m/z 617.1 (M+H)$^+$ (ES+). $^1$H NMR (400 MHz, Methanol-d4) δ 8.50 (s, 1H), 8.16-8.07 (m, 2H), 8.04 (d, J=1.4 Hz, 1H), 7.92 (d, J=8.0 Hz, 1H), 7.77 (s, 1H), 7.68-7.57 (m, 2H), 6.92 (d, J=1.4 Hz, 1H), 5.02 (s, 2H), 4.77-4.69 (m, 2H), 4.29 (t, J=6.0 Hz, 2H), 3.77 (s, 2H), 3.50 (s, 3H), 3.35 (s, 2H), 3.28-3.20 (m, 1H), 2.99 (s, 3H), 2.92 (d, J=7.7 Hz, 2H), 2.88 (s, 3H), 2.08-1.97 (m, 1H), 1.08-0.94 (m, 4H).

Example 430: Synthesis of 4-[2-Cyclopropyl-6-(6-{2,5-dioxa-8-azaspiro[3.5]nonan-8-ylmethyl}-1-oxo-3H-isoindol-2-yl) pyridin-4-yl]-3-(4-methyl-1,2,4-triazol-3-yl)benzonitrile (AOO-2)

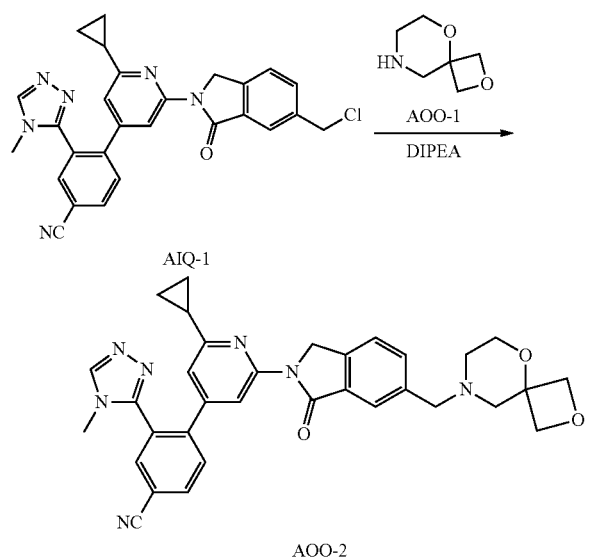

To a stirred solution of intermediate (AIQ-1) (30 mg, 1 Eq, 62 μmol) and DIPEA (40 mg, 5 Eq, 0.31 mmol) in DCM (5 mL) was added 2,5-dioxa-8-azaspiro[3.5]nonane, HCl (AOO-1) (52 mg, 5 Eq, 0.31 mmol) at rt under nitrogen atmosphere. The resulting mixture was stirred for 5 days at 60° C. under nitrogen atmosphere. The mixture was allowed to cool down to rt. The resulting mixture was concentrated in vacuo. The crude product was purified by Prep-HPLC with the following conditions (Column: Xselect CSH C18 OBD Column 30*150 mm, 5 μm; Mobile Phase A: water (0.1% FA), Mobile Phase B: MeCN; Flow rate: 60 mL/min; Gradient: 5% B to 35% B in 10 min; Wave Length: 254 nm; RT: 10.92) to afford the title compound (AOO-2) (17.7 mg, 31 μmol, 49%, 99.6% Purity) as a white solid. m/z 574.0 (M+H)$^+$ (ES+). $^1$H NMR (400 MHz, Methanol-d4) δ 8.51 (s, 1H), 8.16-8.07 (m, 2H), 8.04 (d, J=1.4 Hz, 1H), 7.92 (d, J=8.0 Hz, 1H), 7.81 (s, 1H), 7.71-7.64 (m, 1H), 7.62 (d, J=7.9 Hz, 1H), 6.94 (d, J=1.4 Hz, 1H), 5.03 (s, 2H), 4.54 (d, J=6.7 Hz, 2H), 4.41 (d, J=6.7 Hz, 2H), 3.70-3.63 (m, 4H), 3.51 (s, 3H), 2.66 (s, 2H), 2.49-2.39 (m, 2H), 2.09-1.98 (m, 1H), 1.09-0.94 (m, 4H).

Example 431: Synthesis of rac-4-(2-{6-[(3R,5S)-5-Cyclobutylmorpholin-3-yl]-1-oxo-3H-isoindol-2-yl}-6-cyclopropylpyridin-4-yl)-3-(4-methyl-1,2,4-triazol-3-yl)benzonitrile (AOP-4)

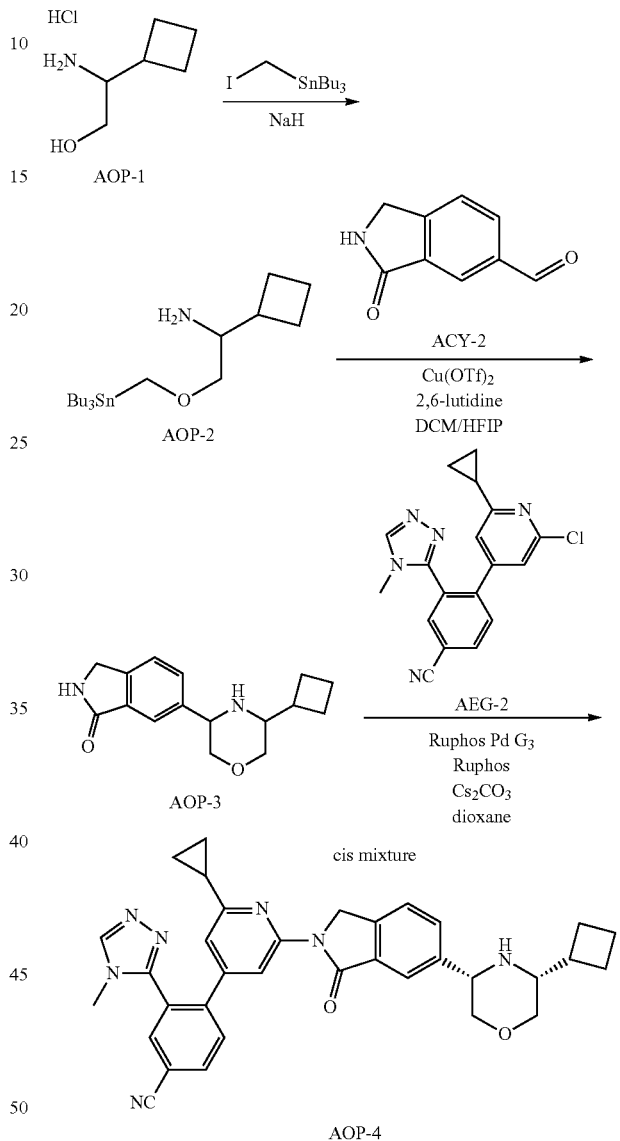

Step 1: [(2-Amino-2-cyclobutylethoxy)methyl]tributylstannane (AOP-2)

To a stirred solution of 2-amino-2-cyclobutylethanol, HCl (AOP-1) (500 mg, 1 Eq, 3.30 mmol) in DMF (25 mL) was added NaH (396 mg, 5 Eq, 16.5 mmol) at 0° C. under nitrogen atmosphere. The resulting mixture was stirred for 1 h at 0° C. under nitrogen atmosphere. To the above mixture was added tributyl(iodomethyl)stannane (2.13 g, 1.5 Eq, 4.95 mmol) at 0° C. under nitrogen atmosphere. The resulting mixture was stirred for additional 3 h at rt. The resulting mixture was concentrated in vacuo. The crude product was purified by Prep-HPLC with the following conditions (Column: XBridge Prep OBD C18 Column, 30*150 mm, 5 μm;

Mobile Phase A: water (0.1% NH₄HCO₃+0.1% NH₃·H₂O), Mobile Phase B: MeCN; Flow rate: 60 mL/min; Gradient: 41% B to 51% B in 9 min; Wave Length: 254/220 nm; RT: 8.3) to afford the sub-title compound (AOP-2) (350 mg, 0.84 mmol, 24%, 97% Purity) as a brown yellow oil. m/z 419.2 (M+H)⁺ (ES+)

Step 2: 6-(5-Cyclobutylmorpholin-3-yl)-2,3-dihydroisoindol-1-one (AOP-3)

A solution of the product from step 1 above (AOP-2) (280 mg, 1 Eq, 0.67 mmol) and intermediate (ACY-2) (129 mg, 1.2 Eq, 0.80 mmol) in DCM (8 mL) was stirred overnight at rt under nitrogen atmosphere. To the above mixture were added Cu(OTf)₂ (242 mg, 1 Eq, 0.67 mmol) and 2,6-lutidine (72 mg, 1 Eq, 0.67 mmol) in HFIP (4 mL) over 1 h at rt. The resulting mixture was stirred for additional 2 days at 60° C. under nitrogen atmosphere. The mixture was allowed to cool down to rt. The resulting mixture was concentrated in vacuo. The crude product was purified by Prep-HPLC with the following conditions: (Column: XBridge Prep OBD C18 Column, 30*150 mm, 5 μm; Mobile Phase A: water (0.1% NH₄HCO₃+0.1% NH₃·H₂O), Mobile Phase B: MeCN; Flow rate: 60 mL/min; Gradient: 20% B to 35% B in 8 min; Wave Length: 254/220 nm; RT: 7.57) to afford the sub-title compound (AOP-3) (70 mg, 0.26 mmol, 35%, 98% Purity) as an off-white solid. m/z 273.2 (M+H)⁺ (ES+)

Step 3: rac-4-(2-{6-[(3R,5S)-5-Cyclobutylmorpholin-3-yl]-1-oxo-3H-isoindol-2-yl}-6-cyclopropylpyridin-4-yl)-3-(4-methyl-1,2,4-triazol-3-yl)benzonitrile (AOP-4)

To a stirred solution of intermediate (AEG-2) (20 mg, 1 Eq, 0.06 mmol) and the product from step 2 above (AOP-3) (18 mg, 1.1 Eq, 0.07 mmol) in dioxane (5 mL) was added Cs₂CO₃ (39 mg, 2 Eq, 0.12 mmol) at rt under nitrogen atmosphere. To the above mixture were added RuPhos (11 mg, 0.4 Eq, 24 μmol) and RuPhos Palladacycle Gen.3 (10 mg, 0.2 Eq, 12 μmol) at rt under nitrogen atmosphere. The resulting mixture was stirred for 1 h at 100° C. under nitrogen atmosphere. The mixture was allowed to cool down to rt. The resulting mixture was concentrated in vacuo. The residue was purified by Prep-TLC with DCM/MeOH (20/1). The crude product was purified by Prep-HPLC with the following conditions (Column: Xselect CSH C18 OBD Column 30*150 mm, 5 μm, n; Mobile Phase A: water (0.1% FA), Mobile Phase B: MeCN; Flow rate: 60 mL/min; Gradient: 8% B to 38% B in 10 min; Wave Length: 254 nm; RT: 9.08) to afford the title compound (AOP-4) (3.5 mg, 6.1 μmol, 10%, 99.7% Purity) as a white solid. m/z 572.1 (M+H)⁺ (ES+). ¹H NMR (400 MHz, Methanol-d4) δ 8.50 (s, 1H), 8.15-8.04 (m, 3H), 7.95-7.89 (m, 2H), 7.73-7.69 (m, 1H), 7.63-7.57 (m, 1H), 6.92 (d, J=1.4 Hz, 1H), 5.01 (s, 2H), 4.05-3.99 (m, 1H), 3.82-3.76 (m, 2H), 3.51 (s, 3H), 3.25 (d, J=10.7 Hz, 1H), 3.11 (t, J=10.7 Hz, 1H), 2.97-2.89 (m, 1H), 2.36-2.25 (m, 1H), 2.10-1.80 (m, 7H), 1.05-0.94 (m, 4H).

Example 432: Synthesis of rel-4-(2-{6-[(3R,5S)-5-Cyclobutylmorpholin-3-yl]-1-oxo-3H-isoindol-2-yl}-6-cyclopropylpyridin-4-yl)-3-(4-methyl-1,2,4-triazol-3-yl)benzonitrile (AOQ-1)

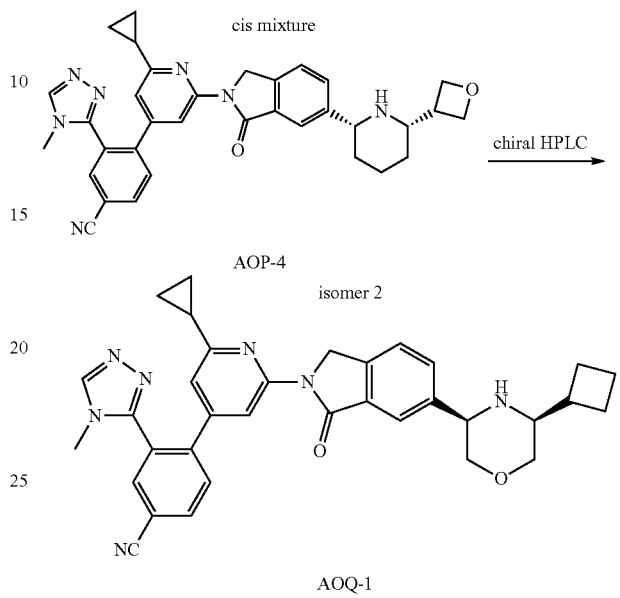

The crude product (AOP-4) (20 mg, 1 Eq, 35 μmol) was purified by Prep-Chiral HPLC with the following conditions (Column: CHIRALPAK ID, 2*25 cm, 5 μm; Mobile Phase A: EtOH-HPLC, Mobile Phase B: Hex:DCM=1:1 (0.5% 2M NH₃-MeOH)-HPLC; Flow rate: 16 mL/min; Gradient: 50% B to 50% B in 35 min; Wave Length: 220/254 nm; RT2 (min): 25.34) to afford the title compound (AOQ-1) (10.4 mg, 18 μmol, 52%, 99.8% Purity) as an off-white solid. m/z 572.1 (M+H)⁺ (ES+). ¹H NMR (400 MHz, Methanol-d4) δ 8.50 (s, 1H), 8.15-8.07 (m, 2H), 8.04 (d, J=1.4 Hz, 1H), 7.95-7.89 (m, 2H), 7.73-7.69 (m, 1H), 7.63-7.57 (m, 1H), 6.92 (d, J=1.4 Hz, 1H), 5.01 (s, 2H), 4.05-3.99 (m, 1H), 3.82-3.76 (m, 2H), 3.51 (s, 3H), 3.25 (d, J=10.7 Hz, 1H), 3.11 (t, J=10.7 Hz, 1H), 2.97-2.89 (m, 1H), 2.36-2.25 (m, 1H), 2.10-1.80 (m, 7H), 1.05-0.94 (m, 4H). Column: CHIRALPAK ID-3, 4.6*50 mm, 3 μm; Mobile Phase A: Hex:DCM=1:1)(0.1% DEA):EtOH=50:50; Flow rate: 1 mL/min; RT: 3.932.

Example 433: Synthesis of rel-4-(2-{6-[(3R,5S)-5-Cyclobutylmorpholin-3-yl]-1-oxo-3H-isoindol-2-yl}-6-cyclopropylpyridin-4-yl)-3-(4-methyl-1,2,4-triazol-3-yl)benzonitrile (AOR-1)

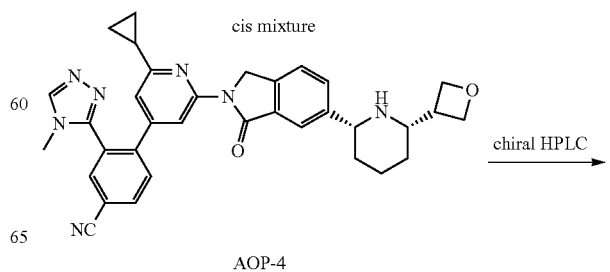

isomer 1

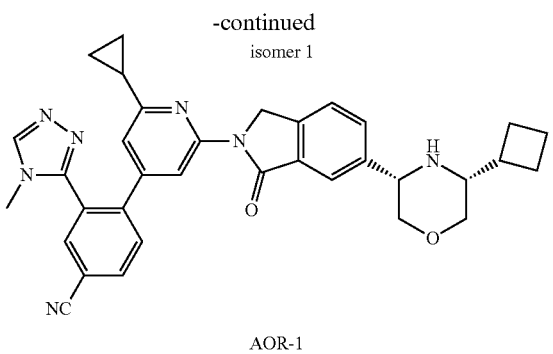

AOR-1

The crude product (AOP-4) (20 mg, 1 Eq, 35 µmol) was purified by Prep-Chiral HPLC with the following conditions (Column: CHIRALPAK ID, 2*25 cm, 5 µm; Mobile Phase A: EtOH-HPLC, Mobile Phase B: Hex:DCM=1:1 (0.5% 2M NH₃-MeOH)-HPLC; Flow rate: 16 mL/min; Gradient: 50% B to 50% B in 35 min; Wave Length: 220/254 nm; RT1 (min): 12.75) to afford the title compound (AOR-1) (5.1 mg, 8.9 µmol, 25%, 99.9% Purity) as a white solid. m/z 572.1 (M+H)⁺ (ES+). ¹H NMR (400 MHz, Methanol-d4) δ 8.50 (s, 1H), 8.15-8.07 (m, 2H), 8.04 (d, J=1.4 Hz, 1H), 7.95-7.89 (m, 2H), 7.73-7.69 (m, 1H), 7.63-7.57 (m, 1H), 6.92 (d, J=1.4 Hz, 1H), 5.01 (s, 2H), 4.05-3.99 (m, 1H), 3.82-3.76 (m, 2H), 3.51 (s, 3H), 3.25 (d, J=10.7 Hz, 1H), 3.11 (t, J=10.7 Hz, 1H), 2.97-2.89 (m, 1H), 2.36-2.25 (m, 1H), 2.10-1.80 (m, 7H), 1.05-0.94 (m, 4H). Column: CHIRALPAK ID-3, 4.6*50 mm, 3 µm; Mobile Phase A: Hex:DCM=1:1)(0.1% DEA):EtOH=50:50; Flow rate: 1 mL/min; RT: 2.171.

Example 434: Synthesis of 4-[2-(6-{2-[(Cyclobutylmethyl)amino]propan-2-yl}-1-oxo-3H-isoindol-2-yl)-6-cyclopropylpyridin-4-yl]-3-(4-methyl-1,2,4-triazol-3-yl)benzonitrile (AOS-2)

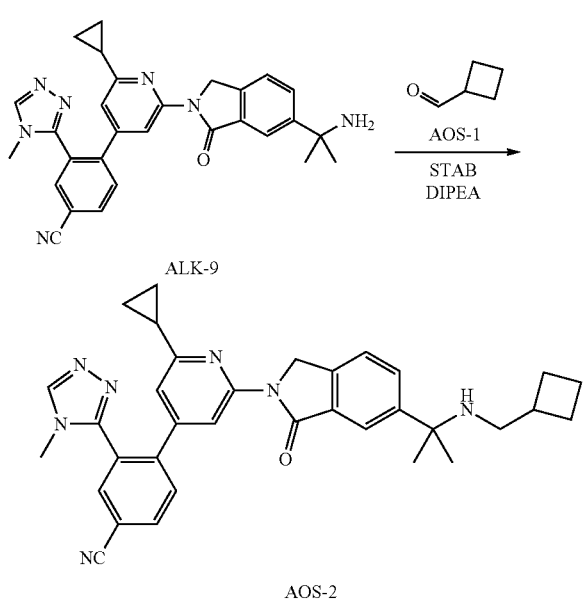

AOS-2

To a stirred mixture of compound (ALK-9) (40 mg, 1 Eq, 82 µmol) and cyclobutyral (AOS-1) (69 mg, 10 Eq, 0.82 mmol) in MeOH (2.5 mL) was added DIPEA (32 mg, 3 Eq, 0.25 mmol) at rt. To the above mixture was added NaBH(OAc)₃ (52 mg, 3 Eq, 0.25 mmol) at rt. The resulting mixture was stirred for additional 4 days at 60° C. The mixture was allowed to cool down to rt. The resulting mixture was concentrated in vacuo. The crude product was purified by Prep-HPLC with the following conditions (Column: XBridge Prep OBD C18 Column, 30*150 mm, 5 µm; Mobile Phase A: water (0.1% NH₄HCO₃+0.1% NH₃·H₂O), Mobile Phase B: MeCN; Flow rate: 60 mL/min; Gradient: 45% B to 60% B in 8 min; Wave Length: 254/220 nm; RT: 7.72) to afford the title compound (AOS-2) (4.5 mg, 8.1 µmol, 9.9%, 99.8% Purity) as a white solid. m/z 558.1 (M+H)⁺ (ES+). ¹H NMR (400 MHz, Methanol-d4) δ 8.48 (s, 1H), 8.16-8.07 (m, 2H), 8.07-7.97 (m, 2H), 7.93 (d, J=8.0 Hz, 1H), 7.88-7.75 (m, 2H), 6.98 (d, J=1.5 Hz, 1H), 5.09 (s, 2H), 3.48 (s, 3H), 2.68 (d, J=7.4 Hz, 2H), 2.54-2.45 (m, 1H), 2.16-2.02 (m, 3H), 1.99-1.76 (m, 8H), 1.71-1.60 (m, 2H), 1.10-0.96 (m, 4H).

Example 435: Synthesis of 4-(2-Cyclopropyl-6-(4-fluoro-6-((hexahydro-1H-furo[3,4-b]pyrrol-1-yl)methyl)-1-oxoisoindolin-2-yl)pyridin-4-yl)-3-(4-methyl-4H-1,2,4-triazol-3-yl)benzonitrile (AOT-2)

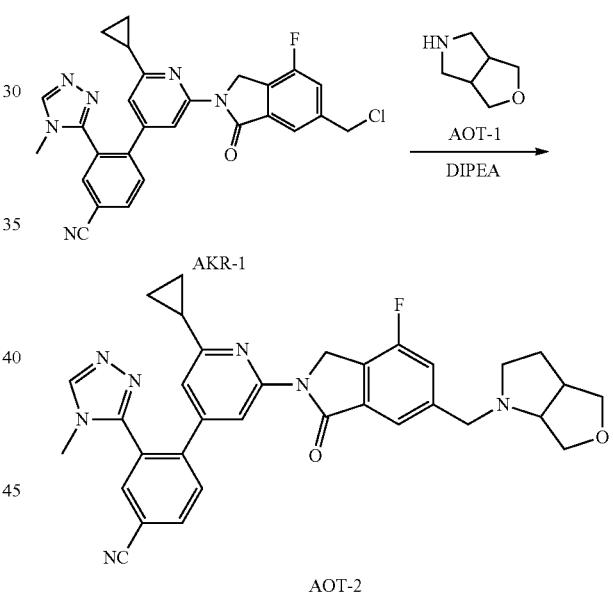

AOT-2

To a stirred mixture of intermediate (AKR-1) (60 mg, 1 Eq, 0.12 mmol) and hexahydro-1H-cyclopenta[c]furan (AOT-1) (15 mg, 1.1 Eq, 0.13 mmol) in DCM (5 mL) was added DIPEA (47 mg, 3 Eq, 0.36 mmol) at rt. The resulting mixture was stirred for overnight at 60° C. The mixture was allowed to cool down to rt. The resulting mixture was concentrated in vacuo. The crude product was purified by Prep-HPLC with the following conditions (Column: Xselect Peptide CSH C18 19*150 mm, 5 µm; Mobile Phase A: water (0.1% FA), Mobile Phase B: MeCN; Flow rate: 60 mL/min; Gradient: 4% B to 34% B in 10 min; Wave Length: 254 nm; RT: 9.93) to afford the title compound (AOT-2) (5.0 mg, 8.7 µmol, 7.2%, 99.4% Purity) as a white solid. m/z 576.1 (M+H)⁺ (ES+). ¹H NMR (400 MHz, Methanol-d4) δ 8.50 (s, 1H), 8.16-8.07 (m, 2H), 8.02 (d, J=1.4 Hz, 1H), 7.92 (d, J=8.0 Hz, 1H), 7.65 (d, J=1.1 Hz, 1H), 7.46-7.39 (m, 1H), 6.95 (d, J=1.4 Hz, 1H), 5.07 (s, 2H), 3.90 (d, J=12.9 Hz, 1H), 3.86-3.71 (m, 2H), 3.66 (d, J=12.9 Hz, 1H), 3.49 (s, 3H), 3.48-3.39 (m, 1H), 3.24 (t, J=6.1 Hz, 1H), 3.19-3.08 (m, 1H), 3.04-2.98 (m, 1H), 2.98-2.87 (m, 1H), 2.71-2.55 (m, 1H), 2.10-1.99 (m, 1H), 1.96-1.85 (m, 1H), 1.85-1.71 (m, 1H), 1.09-0.95 (m, 4H).

Example 436: Synthesis of 4-(2-Cyclopropyl-6-(4-fluoro-6-(((3aS,6aS)-hexahydro-1H-furo[3,4-b]pyrrol-1-yl)methyl)-1-oxoisoindolin-2-yl)pyridin-4-yl)-3-(4-methyl-4H-1,2,4-triazol-3-yl)benzonitrile (AOU-1)

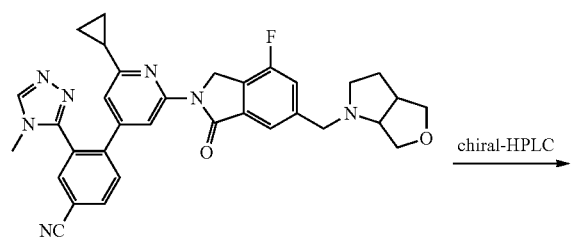

The crude product (AOT-2) (20 mg, 1 Eq, 35 µmol) was purified by Prep-Chiral HPLC with the following conditions (Column: CHIRALPAK IG, 2*25 cm, 5 µm; Mobile Phase A: Hex:DCM=1:1 (0.5% 2M $NH_3$-MeOH)-HPLC, Mobile Phase B: IPA-HPLC; Flow rate: 20 mL/min; Gradient: 50% B to 50% B in 16 min; Wave Length: 220/254 nm; RT1 (min): 9.534) to afford the title compound (AOU-1) (9.8 mg, 17 µmol, 49%, 99.8% Purity) as a white solid. m/z 576.1 $(M+H)^+$ (ES+). $^1$H NMR (400 MHz, Methanol-d4) δ 8.50 (s, 1H), 8.16-8.06 (m, 2H), 8.01 (d, J=1.4 Hz, 1H), 7.92 (d, J=8.1 Hz, 1H), 7.64 (s, 1H), 7.45-7.38 (m, 1H), 6.95 (d, J=1.4 Hz, 1H), 5.05 (s, 2H), 3.89 (d, J=12.9 Hz, 1H), 3.85-3.71 (m, 2H), 3.65 (d, J=12.9 Hz, 1H), 3.51-3.39 (m, 4H), 3.24 (t, J=6.1 Hz, 1H), 3.18-3.07 (m, 1H), 3.04-2.87 (m, 2H), 2.71-2.55 (m, 1H), 2.09-1.98 (m, 1H), 1.96-1.71 (m, 2H), 1.08-0.95 (m, 4H). Column: CHIRALPAK IG-3, 4.6*50 mm, 3 µm; Mobile Phase A: Hex:DCM=1:1) (0.1% DEA):IPA=50:50; Flow rate: 1 mL/min; RT: 2.236.

Example 437: Synthesis of 4-(2-Cyclopropyl-6-(4-fluoro-6-(((3aR,6aR)-hexahydro-1H-furo[3,4-b]pyrrol-1-yl)methyl)-1-oxoisoindolin-2-yl)pyridin-4-yl)-3-(4-methyl-4H-1,2,4-triazol-3-yl)benzonitrile (AOV-1)

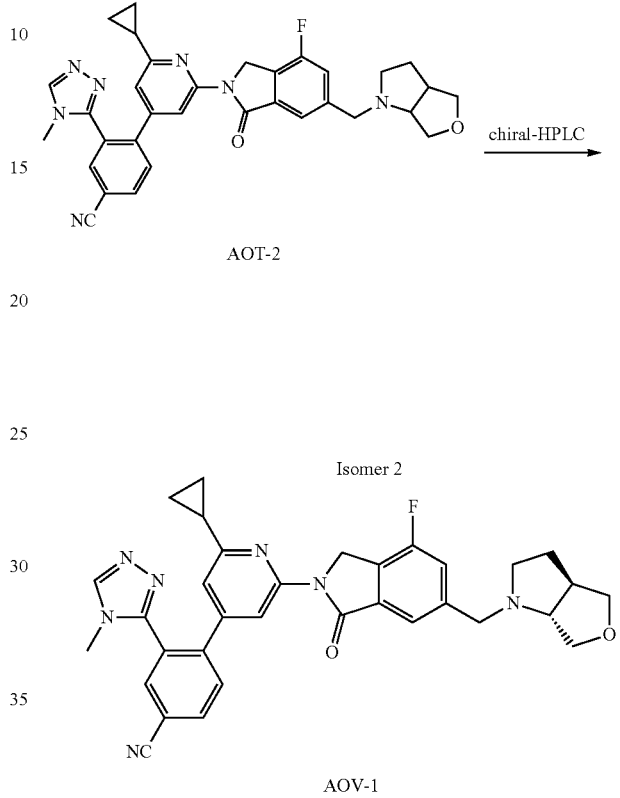

The crude product (AOT-2) (20 mg, 1 Eq, 35 µmol) was purified by Prep-Chiral HPLC with the following conditions (Column: CHIRALPAK IG, 2*25 cm, 5 µm; Mobile Phase A: Hex:DCM=1:1 (0.5% 2M $NH_3$-MeOH)-HPLC, Mobile Phase B: IPA-HPLC; Flow rate: 20 mL/min; Gradient: 50% B to 50% B in 16 min; Wave Length: 220/254 nm; RT2 (min): 13.427) to afford the title compound (AOV-1) (10.0 mg, 17 µmol, 50%, 99.8% Purity) as a white solid. m/z 576.1 $(M+H)^+$ (ES+). $^1$H NMR (400 MHz, Methanol-d4) δ 8.50 (s, 1H), 8.16-8.06 (m, 2H), 8.01 (d, J=1.4 Hz, 1H), 7.92 (d, J=8.0 Hz, 1H), 7.64 (d, J=1.2 Hz, 1H), 7.45-7.38 (m, 1H), 6.95 (d, J=1.4 Hz, 1H), 5.06 (s, 2H), 3.89 (d, J=12.9 Hz, 1H), 3.85-3.70 (m, 2H), 3.65 (d, J=12.9 Hz, 1H), 3.52-3.38 (m, 4H), 3.24 (t, J=6.2 Hz, 1H), 3.17-3.07 (m, 1H), 3.04-2.96 (m, 1H), 2.96-2.85 (m, 1H), 2.71-2.54 (m, 1H), 2.09-1.99 (m, 1H), 1.96-1.71 (m, 2H), 1.09-0.95 (m, 4H). Column: CHIRALPAK IG-3, 4.6*50 mm 3 um; Mobile Phase A: Hex:DCM=1:1)(0.1% DEA):IPA=50:50; Flow rate: 1 mL/min; RT: 3.345.

Example 438: Synthesis of 4-[2-Cyclopropyl-6-(4-fluoro-6-{[(2R)-2-(methoxymethyl)azetidin-1-yl]methyl}-1-oxo-3H-isoindol-2-yl)pyridin-4-yl]-3-(4-methyl-1,2,4-triazol-3-yl)benzonitrile (AOW-2)

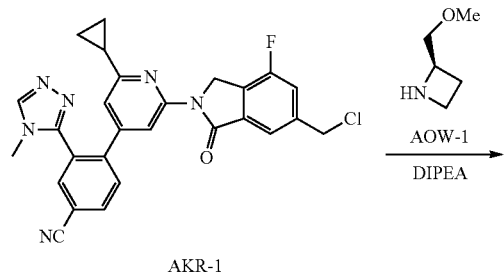

To a stirred solution of intermediate (AKR-1) (30 mg, 1 Eq, 60 μmol) and (R)-2-(methoxymethyl)azetidine (AOW-1) (7 mg, 1.2 Eq, 72 μmol) in DCM (6 mL) was added DIPEA (31 mg, 4 Eq, 0.24 mmol) at rt. The resulting mixture was stirred for overnight at 60° C. The mixture was cooled to rt and concentrated in vacuo. The crude product was purified by Prep-HPLC with the following conditions (Column: Xselect CSH C18 OBD Column 30*150 mm, 5 μm, n; Mobile Phase A: water (0.1% $NH_4HCO_3$+0.1% $NH_3·H_2O$), Mobile Phase B: MeCN; Flow rate: 60 mL/min; Gradient: 38% B to 68% B in 10 min; Wave Length: 254 nm; RT: 7.87) to afford the title compound (AOW-2) (10.5 mg, 19 μmol, 31%, 99.3% Purity) as a white solid. m/z 564.0 $(M+H)^+$ (ES+). $^1H$ NMR (400 MHz, Methanol-d4) δ 8.50 (s, 1H), 8.15-8.07 (m, 2H), 8.02 (d, J=1.5 Hz, 1H), 7.94-7.90 (m, 1H), 7.61 (d, J=1.2 Hz, 1H), 7.41-7.37 (m, 1H), 6.95 (d, J=1.4 Hz, 1H), 5.06 (s, 2H), 3.91 (d, J=13.2 Hz, 1H), 3.65 (d, J=13.3 Hz, 1H), 3.50 (s, 3H), 3.41-3.36 (m, 2H), 3.33 (s, 1H), 3.31 (s, 3H), 3.29-3.26 (m, 1H), 3.02-2.93 (m, 1H), 2.10-1.96 (m, 3H), 1.08-0.96 (m, 4H).

Example 439: Synthesis of 4-{2-Cyclopropyl-6-[4,5-difluoro-6-({[(1-hydroxycyclobutyl)methyl]amino}methyl)-1-oxo-3H-isoindol-2-yl]pyridin-4-yl}-3-(4-methyl-1,2,4-triazol-3-yl)benzonitrile (AOX-1)

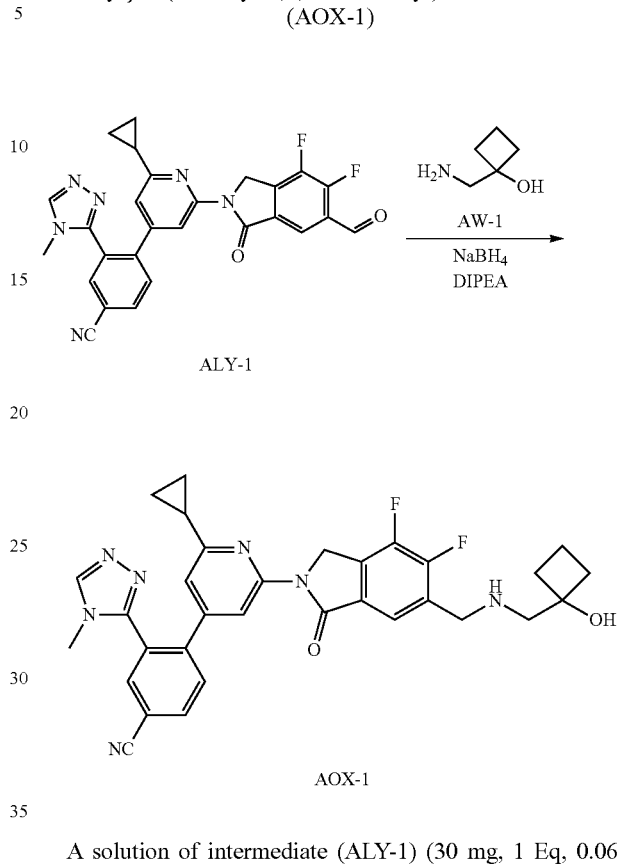

A solution of intermediate (ALY-1) (30 mg, 1 Eq, 0.06 mmol), DIPEA (31 mg, 4 Eq, 0.24 mmol) and 1-(aminomethyl)cyclobutan-1-ol (AW-1) (12 mg, 2 Eq, 0.12 mmol) in MeOH (8 mL) was stirred for overnight at 40° C. The mixture was allowed to cool down to rt. To the above mixture was added $NaBH_4$ (11 mg, 5 Eq, 0.30 mmol) at 0° C. The resulting mixture was stirred for additional 1 h at rt. The reaction was then quenched by the addition of 2 mL of MeOH at 0° C. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% $NH_4HCO_3$+0.1% $NH_3·H_2O$), Mobile Phase B: MeCN; Flow rate: 60 mL/min; Gradient: 44% B to 54% B in 8 min; Wave Length: 254/220 nm; RT: 7.12) to afford the title compound (AOX-1) (8.6 mg, 15 μmol, 24%, 98.8% Purity) as a white solid. m/z 582.1 $(M+H)^+$ (ES+). $^1H$ NMR (400 MHz, Methanol-d4) δ 8.48 (s, 1H), 8.15-8.06 (m, 2H), 8.00 (d, J=1.4 Hz, 1H), 7.91 (d, J=8.0 Hz, 1H), 7.77 (d, J=5.2 Hz, 1H), 6.95 (d, J=1.5 Hz, 1H), 5.10 (s, 2H), 3.99 (s, 2H), 3.49 (s, 3H), 2.72 (s, 2H), 2.16-1.97 (m, 5H), 1.81-1.68 (m, 1H), 1.61-1.48 (m, 1H), 1.09-0.95 (m, 4H).

Example 440: Synthesis of (S)-4-(2-Cyclopropyl-6-(4-fluoro-6-((2-(methoxymethyl)pyrrolidin-1-yl)methyl)-1-oxoisoindolin-2-yl)pyridin-4-yl)-3-(4-methyl-4H-1,2,4-triazol-3-yl)benzonitrile (AOY-2)

Example 441: Synthesis of 4-[2-Cyclopropyl-6-(4-fluoro-6-{[(2R)-2-(fluoromethyl)pyrrolidin-1-yl]methyl}-1-oxo-3H-isoindol-2-yl)pyridin-4-yl]-3-(4H-1,2,4-triazol-3-yl)benzonitrile (AOZ-2)

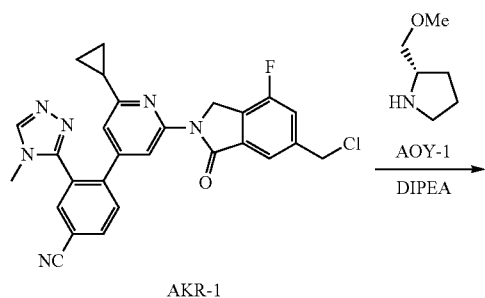

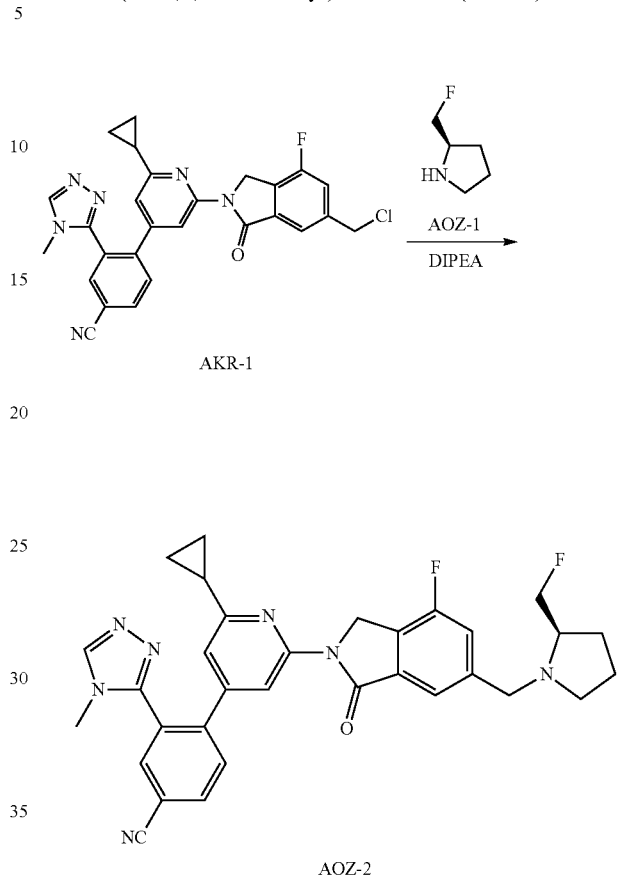

To a stirred mixture of intermediate (AKR-1) (30 mg, 1 Eq, 0.06 mmol) and (2S)-2-(methoxymethyl)pyrrolidine (AOY-1) (14 mg, 2 Eq, 0.12 mmol) in DCM (5 mL) was added DIPEA (23 mg, 3 Eq, 0.18 mmol) at rt. The resulting mixture was stirred for overnight at 60° C. The mixture was cooled to rt and concentrated in vacuo. The crude product was purified by Prep-HPLC with the following conditions (Column: XBridge Prep OBD C18 Column, 30*150 mm, 5 μm; Mobile Phase A: water (0.1% $NH_4HCO_3$+0.1% $NH_3·H_2O$), Mobile Phase B: MeCN; Flow rate: 60 mL/min; Gradient: 50% B to 60% B in 9 min; Wave Length: 254/220 nm; RT: 8.08) to afford the title compound (AOY-2) (4.5 mg, 7.8 μmol, 11%, 99.9% Purity) as a white solid. m/z 578.0 $(M+H)^+$ (ES+). $^1$H NMR (400 MHz, Methanol-d4) δ 8.51 (s, 1H), 8.16-8.07 (m, 2H), 8.01 (d, J=1.4 Hz, 1H), 7.96-7.89 (m, 1H), 7.65 (s, 1H), 7.46-7.39 (m, 1H), 6.96 (d, J=1.4 Hz, 1H), 5.06 (s, 2H), 4.25 (d, J=13.5 Hz, 1H), 3.51 (s, 4H), 3.50-3.44 (m, 1H), 3.42-3.37 (m, 1H), 3.35 (s, 3H), 2.94-2.85 (m, 1H), 2.85-2.74 (m, 1H), 2.33-2.22 (m, 1H), 2.08-1.91 (m, 2H), 1.79-1.68 (m, 2H), 1.66-1.55 (m, 1H), 1.09-0.95 (m, 4H).

To a stirred mixture of intermediate (AKR-1) (30 mg, 1 Eq, 0.06 mmol) and (2R)-2-(fluoromethyl)pyrrolidine (AOZ-1) (12 mg, 2 Eq, 0.12 mmol) in DCM (5 mL) was added DIPEA (23 mg, 3 Eq, 0.18 mmol) at rt. The resulting mixture was stirred for overnight at 60° C. The mixture was cooled to rt and concentrated in vacuo. The crude product was purified by Prep-HPLC with the following conditions (Column: XBridge Prep OBD C18 Column, 30*150 mm, 5 μm; Mobile Phase A: water (0.1% $NH_4HCO_3$+0.1% $NH_3·H_2O$), Mobile Phase B: MeCN; Flow rate: 60 mL/min; Gradient: 50% B to 60% B in 9 min; Wave Length: 254/220 nm; RT: 8.98) to afford the title compound (AOZ-2) (4.1 mg, 7.3 μmol, 12%, 93.1% Purity) as a white solid. m/z 566.3 $(M+H)^+$ (ES+). $^1$H NMR (400 MHz, Methanol-d4) δ 8.50 (s, 1H), 8.16-8.07 (m, 2H), 8.00 (d, J=1.4 Hz, 1H), 7.95-7.89 (m, 1H), 7.65 (d, J=1.1 Hz, 1H), 7.46-7.38 (m, 1H), 6.96 (d, J=1.4 Hz, 1H), 5.06 (s, 2H), 4.44 (d, J=5.2 Hz, 1H), 4.32 (d, J=5.2 Hz, 1H), 4.19 (d, J=13.6 Hz, 1H), 3.59 (d, J=13.6 Hz, 1H), 3.51 (s, 3H), 3.02-2.87 (m, 2H), 2.39-2.28 (m, 1H), 2.08-1.92 (m, 2H), 1.80-1.59 (m, 3H), 1.09-0.95 (m, 4H).

Example 442: Synthesis of 4-[2-Cyclopropyl-6-(4-fluoro-6-{[(2S)-2-(fluoromethyl)pyrrolidin-1-yl]methyl}-1-oxo-3H-isoindol-2-yl)pyridin-4-yl]-3-(4-methyl-1,2,4-triazol-3-yl)benzonitrile (APA-2)

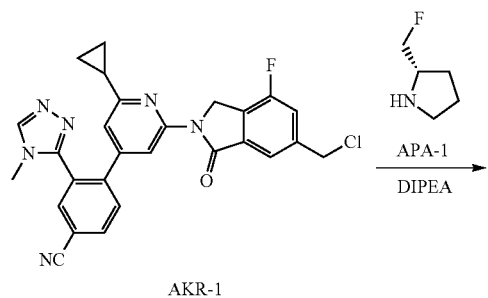

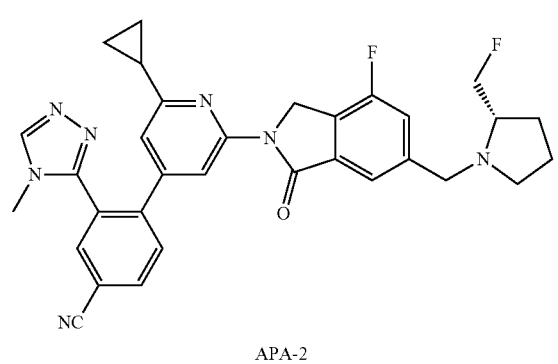

Example 443: Synthesis of 4-[2-Cyclopropyl-6-(4-fluoro-6-{[(2R)-2-(methoxymethyl)pyrrolidin-1-yl]methyl}-1-oxo-3H-isoindol-2-yl)pyridin-4-yl]-3-(4-methyl-1,2,4-triazol-3-yl)benzonitrile (APB-2)

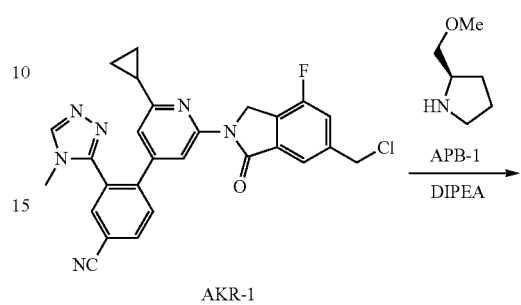

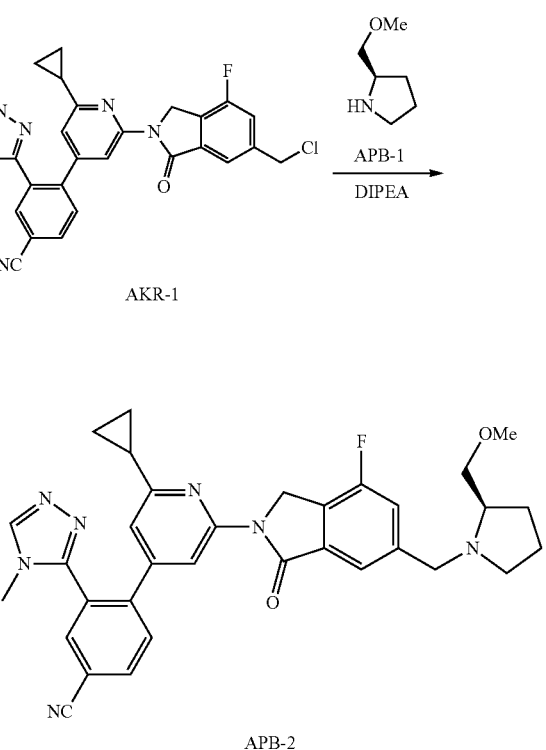

To a stirred mixture of intermediate (AKR-1) (30 mg, 1 Eq, 0.06 mmol) and (2S)-2-(fluoromethyl)pyrrolidine, HCl (APA-1) (11 mg, 1.8 Eq, 0.11 mmol) in DCM (8 mL) was added DIPEA (31 mg, 4 Eq, 0.24 mmol) at rt. The resulting mixture was stirred for overnight at 60° C. The mixture was cooled to rt and concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 50% B to 60% B in 9 min; Wave Length: 254/220 nm; RT: 8.83) to afford the title compound (APA-2) (10.1 mg, 18 μmol, 29%, 97.5% Purity) as a white solid. m/z 566.9 (M+H)$^+$ (ES+). $^1$H NMR (400 MHz, DMSO-d6) δ 8.55 (s, 1H), 8.25-8.18 (m, 2H), 7.92-7.84 (m, 2H), 7.61-7.56 (m, 1H), 7.51-7.44 (m, 1H), 6.95 (d, J=1.4 Hz, 1H), 5.07 (s, 2H), 4.43-4.31 (m, 2H), 4.12 (d, J=13.8 Hz, 1H), 3.58 (d, J=13.8 Hz, 1H), 3.49 (s, 3H), 2.98-2.83 (m, 1H), 2.83-2.76 (m, 1H), 2.29-2.23 (m, 1H), 2.09-2.01 (m, 1H), 1.94-1.87 (m, 1H), 1.73-1.52 (m, 3H), 1.02-0.94 (m, 4H).

To a stirred mixture of intermediate (AKS-1) (30 mg, 1 Eq, 0.06 mmol) and (2R)-2-(methoxymethyl)pyrrolidine (APB-1) (12 mg, 1.8 Eq, 0.11 mmol) in MeOH (8 mL) was added DIPEA (39 mg, 5 Eq, 0.30 mmol) at rt. The resulting mixture was stirred for overnight at rt. The resulting mixture was concentrated in vacuo. The crude product was purified by Prep-HPLC with the following conditions (Column: XBridge Prep OBD C18 Column, 30*150 mm, 5 μm; Mobile Phase A: water (0.1% NH$_4$HCO$_3$+0.1% NH$_3$·H$_2$O), Mobile Phase B: MeCN; Flow rate: 60 mL/min; Gradient: 50% B to 60% B in 8 min; Wave Length: 254/220 nm; RT: 7.9) to afford the title compound (APB-2) (17.4 mg, 30 μmol, 50%, 99.8% Purity) as a white solid. m/z 578.0 (M+H)$^+$ (ES+). $^1$H NMR (400 MHz, DMSO-d6) δ 8.55 (s, 1H), 8.25-8.18 (m, 2H), 7.93 (d, J=1.3 Hz, 1H), 7.90-7.84 (m, 1H), 7.57 (s, 1H), 7.46 (d, J=9.9 Hz, 1H), 6.95 (d, J=1.4 Hz, 1H), 5.07 (s, 2H), 4.17 (d, J=13.9 Hz, 1H), 3.49 (s, 4H), 3.42 (d, J=9.5, 5.4 Hz, 1H), 3.30-3.20 (m, 4H), 2.83-2.68 (m, 2H), 2.23-2.12 (m, 1H), 2.08-2.01 (m, 1H), 1.90-1.84 (m, 1H), 1.70-1.58 (m, 2H), 1.58-1.45 (m, 1H), 1.01-0.94 (m, 4H).

Example 444: Synthesis of 4-(2-cyclopropyl-6-(6-(2-(((3-methyloxetan-3-yl)methyl)amino)propan-2-yl)-1-oxoisoindolin-2-yl)pyridin-4-yl)-3-(4-methyl-4H-1,2,4-triazol-3-yl)benzonitrile (Compound #433), 4-(2-cyclopropyl-6-(6-((ethyl(oxetan-3-ylmethyl)amino)methyl)-1-oxoisoindolin-2-yl)pyridin-4-yl)-3-(4-methyl-4H-1,2,4-triazol-3-yl)benzonitrile (Compound #434), 4-(2-cyclopropyl-6-(5-fluoro-6-(hydroxymethyl)-1-oxoisoindolin-2-yl)pyridin-4-yl)-3-(4-methyl-4H-1,2,4-triazol-3-yl)benzonitrile (Compound #435), and 4-(2-cyclopropyl-6-(5-fluoro-6-((((1-hydroxycyclobutyl)methyl)amino)methyl)-1-oxoisoindolin-2-yl)pyridin-4-yl)-3-(4-methyl-4H-1,2,4-triazol-3-yl)benzonitrile (Compound #436)

The compounds in Table 3 were prepared according to similar methods described in the above Examples.

TABLE 3

Characterization Data of Further Compounds

| Compound # | | LCMS Data | 1H NMR Data |
|---|---|---|---|
| 433 | NDI-213375 | m/z 574.3 (M + H) + (ES+) | (400 MHz, Methanol-d4) δ 8.54-8.49 (m, 1H), 8.18-8.01 (m, 3H), 7.97-7.82 (m, 3H), 7.62 (d, J = 8.0 Hz, 1H), 6.94 (t, J = 3.9 Hz, 1H), 5.03 (t, J = 4.1 Hz, 2H), 4.45-4.16 (m, 4H), 3.55-3.44 (m, 3H), 2.49-2.36 (m, 2H), 2.04 (s, 1H), 1.59-1.48 (m, 6H), 1.33-1.22 (m, 3H), 1.10-0.86 (m, 4H). |
| 434 | NDI-213376 | m/z 560.3 (M + H) + (ES+) | (400 MHz, Methanol-d4) δ 8.53 (s, 1H), 8.18-8.10 (m, 2H), 8.07 (d, J = 1.4 Hz, 1H), 7.95 (d, J = 8.0 Hz, 1H), 7.80 (s, 1H), 7.68-7.59 (m, 2H), 6.96 (d, J = 1.5 Hz, 1H), 5.05 (s, 2H), 4.79-4.71 m, 2H), 4.34 (t, J = 6.1 Hz, 2H), 3.68 (s, 2H), 3.54 (s, 3H), 3.23 (d, J = 7.1 Hz, 1H), 2.82 (d, J = 7.6 Hz, 2H), 2.58-2.48 (m, 2H), 2.10-2.01 (m, 1H), 1.15-0.97 (m, 7H). |
| 435 | NDI-213455 | m/z 481.2 (M + H) + (ES+) | (400 MHz, DMSO-d6) δ 8.56 (d, J = 2.6 Hz, 1H), 8.27-8.17 (m, 2H), 7.98 (d, J = 3.0 Hz, 1H), 7.91-7.80 (m, 2H), 7.56 (d, J = 9.5 Hz, 1H), 6.90 (d, J = 3.1 Hz, 1H), 5.51-5.43 (m, 1H), 5.03 (s, 2H), 4.64 (d, J = 5.7 Hz, 2H), 3.50 (d, J = 2.8 Hz, 3H), 2.11-2.01 (m, 1H), 0.98 (d, J = 6.4 Hz, 4H). |
| 436 | NDI-213452 | m/z 564.7 (M + H) + (ES+) | (400 MHz, Methanol-d4) δ 8.53 (d, J = 2.4 Hz, 1H), 8.18-8.08 (m, 2H), 8.05 (s, 1H), 7.94 (d, J = 7.3 Hz, 2H), 7.44 (d, J = 9.4 Hz, 1H), 6.96 (s, 1H), 5.05 (s, 2H), 3.98 (s, 2H), 3.53 (d, J = 2.2 Hz, 3H), 2.75 (s, 2H), 2.17-1.99 (m, 5H), 1.77 (d, J = 10.9 Hz, 1H), 1.62-1.50 (m, 1H), 1.10-0.94 (m, 4H). |

Example 445: Cbl-b Biochemical Assay (TR-FRET)

Recombinant human Cbl-b (aa 36-427) was expressed in *E. coli*, purified and biotinylated in vitro. The protein was diluted to 12 nM in freshly prepared assay buffer consisting of 50 mM HEPES, pH 7.0, 100 mM NaCl, 5 mM MgCl2, 0.01% Triton-X 100, 0.01% BSA and 1 mM DTT.

Recombinant human Src (aa 254-536)-GSSGSS-Zap-70 (aa 281-297) fusion protein was expressed in *E. coli* and purified. Protein was diluted in assay buffer to 2-5 nM and supplemented with ATP to 1 mM.

Fluorescein-BODIPY labeled UBED2D(C85K)-Ub was prepared by conjugating ubiquitin (Ub) labeled at its N-terminus with Fluorescein-BODIPY maleimide (ThermoFisher Catalog no B10250) to *E. coli* expressed and purified UBED2D(C85K) [see Dou et al Nature Structural and Molecular Biology 8: 982-987, 2013]. Recombinant human UBE2D2(C85K) was expressed in *E. coli*, purified and ubiquitinated and Bodipy labelled in vitro. Protein was diluted to 200 nM in assay buffer without $MgCl_2$ (or Cisbio PPI buffer). Streptavidin-Terbium was added to 2 nM and EDTA to 10 mM, to provide a binding assay mix.

Compounds were dissolved in DMSO and diluted to prepare a ten-point dilution series. 100 nl of each compound concentration was dispensed in duplicate in a 384 well black assay plate using acoustic dispensing. Wells for maximum signal controls received 100 nl of DMSO only and wells for minimum signal controls received 100 nl of a reference inhibitor compound at a final assay concentration of 100 mM to produce 100% inhibition.

5 μl of diluted Cbl-b enzyme was added to all wells of the assay plate and incubated at RT for 30-60 min. The enzyme assay was initiated by addition of 5 μl of Src-Zap/ATP mix to all wells, and the plate incubated at RT for 60 min. The enzyme reaction was terminated and the binding reaction was initiated by adding 10 μl of binding assay mix to all wells and incubating the plate at RT for 60 min prior to assay read.

Final assay conditions consisted of 6 nM Cbl-b, 1-2.5 nM Src-Zap70, 0.5 mM ATP, 1% (v/v) DMSO (enzyme reaction) and 100 nM UBE2D2(C85K)-Ub-FL-BODIPY, 5 mM EDTA, 1 nM Streptavidin-Tb (binding reaction).

The HTRF assay signal was measured at 520 nm on an Envision plate reader, with reference signal at 485 or 620 nm. Data was normalized using maximum and minimum assay controls: % Inhibition=100−(100*((maximum control)−unknown)/(maximum control−minimum control)). A 4-parameter dose-response equation was used to fit the normalized dose-response data and derive an IC50 for test compounds.

Table 4 shows the activity of selected compounds of this invention in the TR-FRET biochemical assay. Compounds having an activity designated as "A" provided an $IC_{50} \leq 0.2$ μM; compounds having an activity designated as "B" provided an $IC_{50} > 0.20$ μM. but ≤1 μM; compounds designated as "C" provided an $IC_{50} > 1$ μM but ≤10 μM; compounds designated as "D" provided an $IC_{50} > 10$ μM but <50 μM.

TABLE 4

Cbl-b Biochemical Assay (TR-FRET) Results

| Compound ID | TR-FRET hCbl-b IC$_{50}$ (µM) |
| --- | --- |
| ABI-1 | A |
| AAZ-7 | C |
| M-2 | C |
| ABX-6 | A |
| AG-1 | A |
| AE-2 | A |
| AM-2 | A |
| AN-1 | A |
| AAU-1 | A |
| ACM-8 | A |
| ABR-1 | A |
| AQ-1 | A |
| AP-1 | A |
| ACT-2 | A |
| ACG-3 | A |
| ABP-3 | A |
| ACE-1 | A |
| ACA-1 | A |
| ACI-1 | A |
| ACW-1 | A |
| ACQ-7 | A |
| CAN-5 | A |
| AD-3 | A |
| ABV-1 | D |
| ABF-8 | A |
| ABW-3 | B |
| ABU-2 | B |
| AAI-7 | B |
| AD-4 | B |
| AAL-8 | D |
| AAG-8 | D |
| ACD-1 | C |
| K-3 | C |
| J-4 | D |
| ABS-1 | A |
| AC-3 | C |
| L-5 | D |
| ABM-1 | C |
| ABK-7 | B |
| U-2 | A |
| Y-2 | B |
| Z-1 | A |
| T-2 | A |
| P-2 | B |
| AAY-6 | C |
| ABG-3 | D |
| AAW-2 | C |
| AAO-1 | D |
| AAE-6 | D |
| ACK-3 | A |
| AAA-8 | D |
| O-3 | D |
| H-5 | D |
| F-9 | C |
| X-2 | A |
| AB-2 | A |
| ADR-3 | A |
| AFO-2 | A |
| ADZ-2 | A |
| AFT-2 | A |
| AFU-1 | A |
| AEY-1 | A |
| AGW-6 | A |
| AGR-1 | A |
| AGP-1 | A |
| AFH-1 | A |
| AFN-3 | A |
| AHG-2 | A |
| ADF-2 | A |
| AGQ-2 | A |
| AHH-3 | A |
| AFK-1 | A |
| AEF-1 | A |
| AGO-2 | A |
| AEN-1 | A |

TABLE 4-continued

Cbl-b Biochemical Assay (TR-FRET) Results

| Compound ID | TR-FRET hCbl-b IC$_{50}$ (µM) |
| --- | --- |
| ADJ-1 | A |
| ADQ-2 | A |
| AEL-2 | A |
| AEC-2 | A |
| AEH-1 | A |
| ADT-2 | A |
| AGG-2 | A |
| AGZ-1 | A |
| AES-1 | A |
| AGE-3 | A |
| AET-6 | A |
| AEB-2 | A |
| AFW-3 | A |
| AFQ-3 | A |
| AFV-3 | A |
| AEJ-3 | A |
| ADO-2 | A |
| ADV-1 | A |
| AEI-5 | A |
| AHF-4 | A |
| BE-3 | A |
| AEZ-1 | A |
| AGS-2 | A |
| AGT-3 | A |
| AFF-2 | A |
| AHI-4 | A |
| AGD-2 | A |
| AEO-2 | A |
| AFL-2 | A |
| ADU-3 | A |
| AFJ-1 | A |
| AEQ-3 | A |
| AGA-1 | A |
| AEW-2 | A |
| AW-2 | A |
| ACY-4 | A |
| AFG-1 | A |
| AHC-1 | A |
| AFX-1 | A |
| AGC-5 | A |
| AZ-2 | A |
| AFM-2 | A |
| AFZ-1 | A |
| AGU-10 | A |
| ADX-2 | A |
| ADP-8 | A |
| AFI-1 | A |
| AAV-6 | C |
| AAF-9 | D |
| ABY-1 | A |
| ABQ-1 | D |
| AI-2 | A |
| AF-1 | A |
| AL-1 | A |
| AH-2 | A |
| ACR-7 | A |
| AK-2 | A |
| AJ-1 | A |
| AO-1 | A |
| AR-1 | A |
| ACS-4 | A |
| ABN-2 | A |
| ABC-7 | A |
| ACF-1 | A |
| ACB-1 | A |
| ACH-1 | A |
| ACP-3 | A |
| ACV-2 | A |
| ACO-1 | A |
| AS-2 | A |
| ABL-4 | D |
| ABZ-7 | A |
| ABJ-4 | B |
| AAR-5 | B |
| ABH-2 | B |

TABLE 4-continued

Cbl-b Biochemical Assay (TR-FRET) Results

| Compound ID | TR-FRET hCbl-b IC$_{50}$ (µM) |
|---|---|
| AAS-6 | D |
| AAJ-0 | C |
| ACC-8 | A |
| ABO-5 | A |
| I-1 | D |
| ACL-1 | A |
| ACU-2 | A |
| AAT-1 | B |
| N-5 | C |
| AAP-1 | C |
| ABT-2 | B |
| AAQ-1 | A |
| V-2 | A |
| W-2 | A |
| AA-2 | A |
| AAK-2 | B |
| AAN-7 | C |
| ABD-1 | B |
| ABE-1 | C |
| AAD-1 | A |
| AAM-3 | C |
| ABB-5 | C |
| AAX-2 | D |
| ACJ-6 | D |
| G-4 | D |
| S-2 | B |
| R-2 | A |
| ABA-4 | D |
| AED-2 | A |
| AGV-1 | A |
| AGN-3 | A |
| AFR-7 | A |
| AGL-1 | A |
| AGI-3 | A |
| AGM-5 | A |
| AFE-1 | A |
| AEU-8 | A |
| ADH-1 | A |
| AHB-1 | A |
| AFA-2 | A |
| AGH-2 | A |
| AEV-3 | A |
| AHA-2 | A |
| AGK-1 | A |
| AGJ-2 | A |
| AGB-1 | A |
| AEM-9 | A |
| ADB-1 | A |
| AND-2 | A |
| AT-1 | A |
| AEE-2 | A |
| AU-2 | A |
| AEK-3 | A |
| ADC-2 | A |
| ADI-1 | A |
| AGF-3 | A |
| AFS-1 | A |
| ADY-2 | A |
| AEG-3 | A |
| AFB-8 | A |
| AGY-3 | A |
| AFP-2 | A |
| AHE-4 | A |
| AEA-2 | A |
| ADA-2 | A |
| ADE-2 | A |
| AHM-12 | B |
| BA-4 | A |
| BD-3 | A |
| ADL-4 | A |
| ADS-6 | A |
| AV-3 | B |
| BC-4 | B |
| AEX-2 | A |
| ADD-2 | D |
| AER-1 | A |
| ADM-6 | B |
| ADG-3 | A |
| ACZ-5 | A |
| AY-1 | B |
| ACX-2 | D |
| ADK-1 | C |
| AX-3 | D |
| ADW-5 | C |
| BB-1 | B |
| AEP-2 | B |
| AFD-1 | A |
| AFC-1 | C |
| AFY-1 | C |
| AGX-8 | D |
| AHD-9 | D |
| AHK-1 | B |
| AHJ-11 | C |
| AHL-8 | D |
| AJI-1 | A |
| AMJ-1 | A |
| AIJ-2 | A |
| ALB-2 | A |
| AMD-2 | A |
| ANI-2 | A |
| AKW-1 | A |
| ALP-1 | A |
| AIA-2 | A |
| AJJ-1 | A |
| AMC-2 | A |
| AIV-2 | A |
| AIG-1 | A |
| ANR-2 | A |
| AII-9 | A |
| AMP-1 | A |
| AKS-1 | A |
| ALO-2 | A |
| AHT-2 | A |
| AIR-2 | A |
| AKG-1 | A |
| AIB-2 | A |
| AIO-9 | A |
| AKB-1 | A |
| ANB-1 | A |
| AJZ-1 | A |
| ALH-1 | A |
| AJW-1 | A |
| AIM-2 | A |
| AKZ-2 | A |
| AIF-1 | A |
| ALD-2 | A |
| AKY-1 | A |
| AJK-1 | A |
| AKC-2 | A |
| AJO-2 | A |
| AMO-2 | A |
| ALS-1 | A |
| AJS-1 | A |
| AMG-1 | A |
| ALQ-2 | A |
| AMF-1 | A |
| ALC-2 | A |
| AJX-1 | A |
| AND-1 | A |
| ANK-2 | A |
| AIP-2 | A |
| AIN-2 | A |
| AKT-1 | A |
| AID-2 | A |
| AKK-1 | A |
| ALA-5 | A |
| AKV-1 | A |
| AHP-1 | A |
| AIE-1 | A |
| AHZ-2 | A |

TABLE 4-continued

Cbl-b Biochemical Assay (TR-FRET) Results

| Compound ID | TR-FRET hCbl-b IC$_{50}$ (μM) |
|---|---|
| AKP-1 | A |
| AKD-2 | A |
| ALT-2 | A |
| AHS-2 | A |
| AKH-1 | A |
| AIK-2 | A |
| AMA-2 | A |
| AIH-2 | A |
| AKO-2 | A |
| AJA-2 | A |
| AKJ-1 | A |
| AIW-2 | A |
| AIL-3 | A |
| AHX-2 | A |
| AMM-1 | A |
| AJT-1 | A |
| ALV-4 | A |
| AKE-2 | A |
| AIC-11 | A |
| ALW-1 | A |
| ALF-2 | A |
| ALX-9 | A |
| AKF-2 | A |
| ANJ-2 | A |
| AKQ-2 | A |
| AJR-1 | A |
| AHQ-4 | A |
| AHR-4 | A |
| AIX-2 | A |
| AJQ-2 | A |
| ANG-1 | A |
| AHO-4 | A |
| AKR-3 | A |
| ALY-2 | A |
| ANT-1 | A |
| AHW-1 | A |
| AKU-2 | A |
| AJY-1 | A |
| AJC-1 | A |
| AKI-1 | A |
| AKL-2 | A |
| AJB-2 | A |
| AMK-3 | A |
| AJE-2 | A |
| AHV-1 | A |
| AIT-1 | A |
| AJL-2 | A |
| ANS-1 | A |
| AJN-3 | A |
| AJM-3 | A |
| AIS-2 | A |
| AJD-2 | C |
| AHN-9 | D |
| AHY-5 | D |
| AHU-12 | A |
| AIQ-2 | A |
| ALZ-3 | A |
| AMB-1 | A |
| AIY-2 | A |
| AIZ-2 | A |
| AJF-1 | A |
| AJG-2 | A |
| AJH-3 | A |
| AJU-3 | A |
| AJV-3 | A |
| AJP-7 | B |
| AKA-1 | A |
| AKM-2 | C |
| AKN-12 | A |
| AKX-1 | A |
| ALG-3 | A |
| ALI-2 | A |
| AME-2 | A |
| ALJ-1 | A |
| ALE-7 | B |
| ALL-2 | A |
| ALN-2 | A |
| ALM-3 | A |
| ALK-9 | A |
| ALR-1 | A |
| AIU-1 | A |
| ALU-2 | A |
| AMH-1 | A |
| AMI-1 | A |
| AML-1 | A |
| AMN-1 | A |
| AMQ-2 | A |
| AMR-2 | A |
| AMS-2 | A |
| AMT-2 | A |
| AMU-2 | A |
| AMV-2 | A |
| AMW-2 | A |
| AMZ-3 | A |
| AMX-3 | A |
| AMY-1 | A |
| ANA-1 | A |
| ANC-2 | A |
| ANE-1 | A |
| ANF-11 | A |
| ANH-1 | A |
| ANL-2 | A |
| ANM-2 | A |
| ANN-2 | A |
| ANO-1 | A |
| ANP-2 | A |
| ANQ-2 | A |
| ANU-3 | A |
| ANV-1 | A |
| ANW-3 | A |
| ANX-2 | A |
| ANY-2 | A |
| ANZ-2 | A |
| AOA-1 | A |
| AOB-2 | A |
| AOC-2 | A |
| AOF-9 | A |
| AOO-2 | A |
| AOD-2 | A |
| AOE-1 | A |
| AOG-1 | A |
| AOH-1 | A |
| AOI-1 | A |
| AOL-1 | A |
| AOM-2 | A |
| AOJ-2 | A |
| AOK-2 | A |
| AON-2 | A |
| AOR-1 | A |
| AOQ-1 | A |
| AOS-2 | A |
| AOT-2 | A |
| AOU-1 | A |
| AOV-1 | A |
| AOP-4 | A |
| AOZ-2 | A |
| APA-2 | A |
| AOW-2 | A |
| APB-2 | A |
| AOY-2 | A |
| AOX-1 | A |

Example 446: c-Cbl Biochemical Assay (TR-FRET)

Recombinant human c-Cbl (aa 47-435) was expressed in *E. coli*, purified and biotinylated in vitro. The protein was diluted to 12 nM in freshly prepared assay buffer consisting of 50 mM HEPES, pH 7.0, 100 mM NaCl, 5 mM MgCl$_2$, 0.01% Triton-X 100, 0.01% BSA and 1 mM DTT. Recombinant human Src (aa 254-536)-GSSGSS-Zap-70 (aa 281-297) fusion protein was expressed in *E. coli* and purified. Protein was diluted in assay buffer to 5-20 nM and ATP was added to 1 mM.

Recombinant human UBE2D2(C85K) was expressed in *E. coli*, purified and ubiquitinated and Bodipy labelled in vitro. Protein was diluted to 200 nM in assay buffer without MgCl$_2$ (or Cisbio PPI buffer). Streptavidin-Terbium was added to 2 nM and EDTA to 10 mM, to provide a binding assay mix.

Compounds were dissolved in DMSO and diluted to prepare a ten-point half log dilution series. 100 nl of each compound concentration was dispensed in duplicate in a 384 well black assay plate using acoustic dispensing. Wells for maximum signal controls received 100 nl of DMSO only and wells for minimum controls received 100 nl of a reference inhibitor compound at a final assay concentration of 100 mM to produce 100% inhibition.

5 µl of diluted c-cbl enzyme was added to all wells of the assay plate and incubated at RT for 30 min. The enzyme assay was initiated by addition of 5 µl of Src-Zap/ATP mix to all wells, and the plate incubated at RT for 60-90 min. The enzyme reaction was terminated and the binding reaction was initiated by adding 10 µl of binding assay mix to all wells and incubating the plate at RT for 60 min prior to assay read.

Final assay conditions consisted of 6 nM c-cbl, 2.5-10 nM Src-Zap70, 0.5 mM ATP, 1% (v/v) DMSO (enzyme reaction) and 100 nM UBE2D2(C85K)-Ub-FL-BODIPY, 5 mM EDTA, 1 nM Streptavidin-Tb (binding reaction).

The HTRF assay signal was measured at 520 nm on an Envision plate reader, with reference signal at 485 or 620 nm. Data was normalized using maximum and minimum assay controls: % Inhibition=100−(100*((maximum control)−unknown)/(maximum control−minimum control)). A 4-parameter dose-response equation was used to fit the normalized dose-response data and derive an IC$_{50}$ for test compounds.

Table 5 lists the compounds of this invention tested in the TR-FRET c-Cbl biochemical assay. All compounds tested have an IC$_{50}$≤1 µM.

TABLE 5 c-Cbl Biochemical Assay (TR-FRET) Results
Compound ID

ABI-1
AG-1
AF-1
AN-1
ACR-7
ABR-1
AO-1
ACT-2
ABN-2
ACE-1
ACB-1
ACW-1
CAN-5
AS-2
ACC-8
ABS-1
Z-1
AA-2
X-2
ABY-1
AI-2
AM-2

TABLE 5-continued c-Cbl Biochemical Assay (TR-FRET) Results
Compound ID

AH-2
ACM-8
AJ-1
AP-1
ACS-4
ABP-3
ACF-1
ACI-1
ACP-3
ACO-1
ABF-8
ABO-5
ACU-2
W-2
ABD-1
R-2
ABX-6
AE-2
AL-1
AAU-1
AK-2
AQ-1
AR-1
ACG-3
ABC-7
ACA-1
ACH-1
ACV-2
AD-3
AD-4
ACL-1
AAQ-1
T-2
ACK-3
AB-2

Table 5A shows the activity of selected compounds of this invention in the TR-FRET c-Cbl biochemical assay. Compounds having an activity designated as "A" provided an IC$_{50}$≤0.2 µM; compounds having an activity designated as "B" provided an IC$_{50}$>0.20 µM. but ≤1 µM; compounds designated as "C" provided an IC$_{50}$>1 µM but ≤10 µM; compounds designated as "D" provided an IC$_{50}$>10 µM but <50 µM.

TABLE 5A

Cbl-b Biochemical Assay (TR-FRET) Results

| Compound ID | c-Cbl Biochemical Assay IC$_{50}$ µM |
|---|---|
| AJI-1 | A |
| AMJ-1 | A |
| AIJ-2 | A |
| ALB-2 | A |
| AMD-2 | A |
| ANI-2 | A |
| AKW-1 | A |
| ALP-1 | A |
| AIA-2 | A |
| AJJ-1 | A |
| AMC-2 | A |
| AIV-2 | A |
| AIG-1 | A |
| ANR-2 | A |
| AII-9 | A |
| AMP-1 | A |
| AKS-1 | A |
| ALO-2 | A |
| AHT-2 | A |
| AIR-2 | A |
| AKG-1 | A |
| AIB-2 | A |

TABLE 5A-continued

Cbl-b Biochemical Assay (TR-FRET) Results

| Compound ID | c-Cbl Biochemical Assay IC$_{50}$ μM |
|---|---|
| AIO-9 | A |
| AKB-1 | A |
| ANB-1 | A |
| AJZ-1 | A |
| ALH-1 | A |
| AJW-1 | A |
| AIM-2 | A |
| AKZ-2 | A |
| AIF-1 | A |
| ALD-2 | A |
| AKY-1 | A |
| AJK-1 | A |
| AKC-2 | A |
| AJO-2 | A |
| AMO-2 | A |
| ALS-1 | A |
| AJS-1 | A |
| AMG-1 | A |
| ALQ-2 | A |
| AMF-1 | A |
| ALC-2 | A |
| AJX-1 | A |
| AND-1 | A |
| ANK-2 | A |
| AIP-2 | A |
| AIN-2 | A |
| AKT-1 | A |
| AID-2 | A |
| AKK-1 | A |
| ALA-5 | A |
| AKV-1 | A |
| AHP-1 | A |
| AIE-1 | A |
| AHZ-2 | A |
| AKP-1 | A |
| AKD-2 | A |
| ALT-2 | A |
| AHS-2 | A |
| AKH-1 | A |
| AIK-2 | A |
| AMA-2 | A |
| AIH-2 | A |
| AKO-2 | A |
| AJA-2 | A |
| AKJ-1 | A |
| AIW-2 | A |
| AIL-3 | A |
| AHX-2 | A |
| AMM-1 | A |
| AJT-1 | A |
| ALV-4 | A |
| AKE-2 | A |
| AIC-11 | A |
| ALW-1 | A |
| ALF-2 | A |
| ALX-9 | A |
| AKF-2 | A |
| ANJ-2 | A |
| AKQ-2 | A |
| AJR-1 | A |
| AHQ-4 | A |
| AHR-4 | A |
| AIX-2 | A |
| AJQ-2 | A |
| ANG-1 | A |
| AHO-4 | A |
| AKR-3 | A |
| ALY-2 | A |
| ANT-1 | A |
| AHW-1 | A |
| AKU-2 | A |
| AJY-1 | A |
| AJC-1 | A |
| AKI-1 | A |
| AKL-2 | A |
| AJB-2 | A |
| AMK-3 | A |
| AJE-2 | A |
| AHV-1 | A |
| AIT-1 | A |
| AJL-2 | A |
| ANS-1 | B |
| AJN-3 | A |
| AJM-3 | A |
| AIS-2 | A |
| AJD-2 | C |
| AHN-9 | D |
| AHY-5 | D |
| AHU-12 | B |
| AIQ-2 | A |
| ALZ-3 | A |
| AMB-1 | A |
| AIY-2 | A |
| AIZ-2 | A |
| AJF-1 | A |
| AJG-2 | A |
| AJH-3 | A |
| AJU-3 | A |
| AJV-3 | A |
| AJP-7 | C |
| AKA-1 | A |
| AKM-2 | C |
| AKN-12 | A |
| AKX-1 | B |
| ALG-3 | A |
| ALI-2 | A |
| AME-2 | A |
| ALJ-1 | A |
| ALE-7 | A |
| ALL-2 | A |
| ALN-2 | A |
| ALM-3 | B |
| ALK-9 | A |
| ALR-1 | A |
| AIU-1 | A |
| ALU-2 | A |
| AMH-1 | A |
| AMI-1 | A |
| AML-1 | A |
| AMN-1 | A |
| AMQ-2 | A |
| AMR-2 | A |
| AMS-2 | A |
| AMT-2 | A |
| AMU-2 | A |
| AMV-2 | A |
| AMW-2 | A |
| AMZ-3 | A |
| AMX-3 | A |
| AMY-1 | A |
| ANA-1 | A |
| ANC-2 | A |
| ANE-1 | A |
| ANF-11 | A |
| ANH-1 | A |
| ANL-2 | A |
| ANM-2 | A |
| ANN-2 | A |
| ANO-1 | A |
| ANP-2 | A |
| ANQ-2 | A |
| ANU-3 | A |
| ANV-1 | A |
| ANW-3 | A |
| ANX-2 | A |
| ANY-2 | A |
| ANZ-2 | A |
| AOA-1 | A |
| AOB-2 | A |
| AOC-2 | A |

TABLE 5A-continued

Cbl-b Biochemical Assay (TR-FRET) Results

| Compound ID | c-Cbl Biochemical Assay IC$_{50}$ μM |
|---|---|
| AOF-9 | A |
| AOO-2 | A |
| AOD-2 | A |
| AOE-1 | A |
| AOG-1 | A |
| AOH-1 | A |
| AOI-1 | A |
| AOL-1 | A |
| AOM-2 | A |
| AOJ-2 | A |
| AOK-2 | A |
| AON-2 | A |
| AOR-1 | A |
| AOQ-1 | A |
| AOS-2 | A |
| AOT-2 | A |
| AOU-1 | A |
| AOV-1 | A |
| AOP-4 | A |
| AOZ-2 | A |
| APA-2 | A |
| AOW-2 | A |
| APB-2 | A |
| AOY-2 | A |
| AOX-1 | A |

Example 447: Jurkat Reporter Assay (NFAT Luciferase)

A commercial NFAT luciferase construct was purchased, and transfected into Jurkat cells to generate the stable cell line. Jurkat (clone E6-1) cells were engineered for stable expression of an NFAT luciferase reporter. Cells were maintained in RPMI 1640 medium with 10% FBS, 200 μg/ml Hygromycin B and 1% Penicillin/Streptomycin, and assayed in the same medium omitting Hygromycin B.

Test compounds were dissolved in DMSO (typically at 20 mM) and a ten-point half log dilution series prepared using acoustic dispensing. 125 nl of each compound concentration was dispensed in duplicate into wells of a 384 well white assay plate, typically providing a top final assay compound concentration of 100 mM. Assay low control wells received DMSO only and high controls received a standard compound (NDI-996179) providing a final assay concentration of 100 mM.

Jurkat cells were harvested and resuspended in assay medium at 4.445×10$^5$ cells/ml. 22.5 μl (10,000 cells) was added to the wells of a white 384 well assay plate and incubated for 15 min at 37° C. in 5% CO$_2$. Anti-CD3 antibody (Thermofisher #16-0037-85) was diluted in assay medium to 10 μg/ml. 2.5 μl was added to wells of the assay plate and incubated for 6 hr at 37° C. in 5% CO$_2$. Additional control wells were included which received assay medium in place of anti-CD3.

Assay plates were equilibrated to RT and 25 μl of Steady-Glo® reagent (Promega #E2520) added to all wells. The plate was centrifuged at 100×g for 1 min and incubated for 10 min. Luminescence was read on an Envision plate reader.

Data was normalised using high and low assay controls: % activation=100−(100*((high control)−unknown)/(high control−low control)) Normalised data was fitted to a non-linear regression equation (log inhibitor vs response-variable slope 4-parameters) to derive compound EC50 values. Fold activation over baseline was expressed as mean luminescence values from high control wells/mean luminescence values from low control wells (anti CD3 only). Maximum activation of compounds was also expressed as a normalised value referenced to the standard compound (maximum % activation of test compound/100)

Table 6 shows selected compounds of this invention tested in the Jurkat reporter assay. All compounds tested have an EC$_{50}$≤1 μM.

TABLE 6

Jurkat reporter assay (NFAT Luciferase) Results
Compound ID

ABI-1
AE-2
AL-1
ACR-7
ABR-1
AO-1
ACG-3
ABC-7
ACA-1
CAN-5
ABF-8
AAQ-1
T-2
R-2
AG-1
AF-1
AN-1
ACM-8
AJ-1
AP-1
ABN-2
ACE-1
ACB-1
ACO-1
ACL-1
Z-1
AA-2
AI-2
AM-2
AH-2
AK-2
AQ-1
AR-1
ABP-3
ACF-1
ACI-1
AD-3
ABS-1
W-2
ACK-3
AJI-1
AMJ-1
AIJ-2
ALB-2
AMD-2
ANI-2
AKW-1
ALP-1
AIA-2
AJJ-1
AMC-2
AIV-2
AIG-1
ANR-2
AII-9
AMP-1
AKS-1
ALO-2
AHT-2
AIR-2
AKG-1
AIB-2
AIO-9
AKB-1
ANB-1
AJZ-1

TABLE 6-continued

Jurkat reporter assay (NFAT Luciferase) Results
Compound ID

| |
|---|
| ALH-1 |
| AJW-1 |
| AIM-2 |
| AKZ-2 |
| AIF-1 |
| ALD-2 |
| AKY-1 |
| AJK-1 |
| AKC-2 |
| AJO-2 |
| AMO-2 |
| ALS-1 |
| AJS-1 |
| AMG-1 |
| ALQ-2 |
| AMF-1 |
| ALC-2 |
| AJX-1 |
| AND-1 |
| ANK-2 |
| AIP-2 |
| AIN-2 |
| AKT-1 |
| AID-2 |
| AKK-1 |
| ALA-5 |
| AKV-1 |
| AHP-1 |
| AIE-1 |
| AHZ-2 |
| AKP-1 |
| AKD-2 |
| ALT-2 |
| AHS-2 |
| AKH-1 |
| AIK-2 |
| AMA-2 |
| AIH-2 |
| AKO-2 |
| AJA-2 |
| AKJ-1 |
| AIW-2 |
| AIL-3 |
| AHX-2 |
| AMM-1 |
| AJT-1 |
| ALV-4 |
| AKE-2 |
| AIC-11 |
| ALW-1 |
| ALF-2 |
| ALX-9 |
| AKF-2 |
| ANJ-2 |
| AKQ-2 |
| AJR-1 |
| AHQ-4 |
| AHR-4 |
| AIX-2 |
| AJQ-2 |
| ANG-1 |
| AHO-4 |
| AKR-3 |
| ALY-2 |
| ANT-1 |
| AHW-1 |
| AKU-2 |
| AJY-1 |
| AJC-1 |
| AKI-1 |
| AKL-2 |
| AJB-2 |
| AMK-3 |
| AJE-2 |
| AHV-1 |
| AIT-1 |
| AJL-2 |

TABLE 6-continued

Jurkat reporter assay (NFAT Luciferase) Results
Compound ID

| |
|---|
| ANS-1 |
| AJN-3 |
| AJM-3 |
| AIS-2 |
| AIQ-2 |
| ALZ-3 |
| AMB-1 |
| AIY-2 |
| AIZ-2 |
| AJF-1 |
| AJG-2 |
| AJH-3 |
| AJU-3 |
| AJV-3 |
| AKA-1 |
| AKN-12 |
| ALG-3 |
| ALI-2 |
| AME-2 |
| ALJ-1 |
| ALE-7 |
| ALL-2 |
| ALN-2 |
| ALK-9 |
| ALR-1 |
| AIU-1 |
| ALU-2 |
| AMH-1 |
| AMI-1 |
| AML-1 |
| AMN-1 |
| AMQ-2 |
| AMR-2 |
| AMS-2 |
| AMT-2 |
| AMU-2 |
| AMV-2 |
| AMW-2 |
| AMZ-3 |
| AMX-3 |
| AMY-1 |
| ANA-1 |
| ANC-2 |
| ANE-1 |
| ANF-11 |
| ANH-1 |
| ANL-2 |
| ANM-2 |
| ANN-2 |
| ANO-1 |
| ANP-2 |
| ANQ-2 |
| ANU-3 |
| ANV-1 |
| ANW-3 |
| ANX-2 |
| ANY-2 |
| ANZ-2 |
| AOA-1 |
| AOB-2 |
| AOC-2 |
| AOF-9 |
| AOO-2 |
| AOD-2 |
| AOE-1 |
| AOG-1 |
| AOH-1 |
| AOI-1 |
| AOL-1 |
| AOM-2 |
| AOJ-2 |
| AOK-2 |
| AON-2 |
| AOR-1 |
| AOQ-1 |
| AOS-2 |
| AOT-2 |

TABLE 6-continued

Jurkat reporter assay (NFAT Luciferase) Results
Compound ID

AOU-1
AOV-1
AOP-4
AOZ-2
APA-2
AOW-2
APB-2
AOY-2
AOX-1

Table 6A shows selected compounds of this invention tested in the Jurkat reporter assay. Compounds having an activity designated as "A" provided an $EC_{50} \leq 0.2$ µM; compounds having an activity designated as "B" provided an $EC_{50} > 0.20$ µM. but $\leq 1$ µM; compounds designated as "C" provided an $EC_{50} > 1$ µM but $\leq 10$ µM; compounds designated as "D" provided an $EC_{50} > 10$ µM but $<50$ µM.

TABLE 6A

Jurkat reporter assay (NFAT Luciferase) Results

| Compound ID | Jurkat NFAT EC50 (µM) |
|---|---|
| ADR-3 | A |
| AFO-2 | A |
| ADZ-2 | A |
| AFT-2 | A |
| AFU-1 | A |
| AEY-1 | A |
| AGW-6 | A |
| AGR-1 | A |
| AGP-1 | A |
| AFH-1 | A |
| AFN-3 | A |
| AED-2 | A |
| AGV-1 | A |
| AGN-3 | A |
| AFR-7 | A |
| AGL-1 | A |
| AGI-3 | A |
| AGM-5 | A |
| AFE-1 | A |
| AEU-8 | A |
| ADH-1 | A |
| AHB-1 | A |
| AHG-2 | A |
| ADF-2 | A |
| AGQ-2 | A |
| AHH-3 | A |
| AFK-1 | A |
| AEF-1 | A |
| AGO-2 | A |
| AEN-1 | A |
| ADJ-1 | A |
| ADQ-2 | A |
| AEL-2 | A |
| AEC-2 | A |
| AEH-1 | A |
| ADT-2 | A |
| AGG-2 | A |
| AGZ-1 | A |
| AES-1 | A |
| AGE-3 | A |
| AET-6 | A |
| AEB-2 | A |
| AFW-3 | A |
| AFQ-3 | A |
| AFV-3 | A |
| AEJ-3 | A |
| ADO-2 | A |
| ADV-1 | A |
| AEI-5 | A |

TABLE 6A-continued

Jurkat reporter assay (NFAT Luciferase) Results

| Compound ID | Jurkat NFAT EC50 (µM) |
|---|---|
| AHF-4 | A |
| BE-3 | A |
| AEZ-1 | A |
| AGS-2 | A |
| AGT-3 | A |
| AFF-2 | A |
| AHI-4 | A |
| AGD-2 | A |
| AFA-2 | A |
| AGH-2 | A |
| AEV-3 | A |
| AHA-2 | A |
| AGK-1 | A |
| AGJ-2 | A |
| AGB-1 | A |
| AEM-9 | A |
| ADB-1 | B |
| AND-2 | B |
| AT-1 | B |
| AEE-2 | B |
| AU-2 | B |
| AEK-3 | B |
| ADC-2 | B |
| ADI-1 | B |
| AGF-3 | B |
| AFS-1 | B |
| ADY-2 | B |
| AEG-3 | B |
| AFB-8 | B |
| AGY-3 | B |
| AFP-2 | B |
| AHE-4 | C |
| AEA-2 | C |
| ADA-2 | C |
| ADE-2 | C |
| AHM-12 | C |
| BA-4 | C |
| BD-3 | C |
| ADL-4 | C |
| ADS-6 | C |
| AV-3 | C |
| BC-4 | C |
| AEX-2 | C |
| AEO-2 | A |
| AFL-2 | A |
| ADU-3 | A |
| AFJ-1 | A |
| AEQ-3 | A |
| AGA-1 | A |
| AEW-2 | A |
| AW-2 | A |
| ACY-4 | A |
| AFG-1 | A |
| AHC-1 | A |
| AFX-1 | A |
| AGC-5 | A |
| AZ-2 | A |
| AFM-2 | A |
| AFZ-1 | A |
| AGU-10 | A |
| ADX-2 | A |
| ADP-8 | A |
| AFI-1 | A |
| ADD-2 | D |
| AER-1 | D |
| ADM-6 | D |
| ADG-3 | D |
| ACZ-5 | D |
| AY-1 | D |
| ACX-2 | D |
| ADK-1 | D |
| AX-3 | D |
| ADW-5 | D |
| BB-1 | D |
| AEP-2 | D |

TABLE 6A-continued

Jurkat reporter assay (NFAT Luciferase) Results

| Compound ID | Jurkat NFAT EC50 (μM) |
|---|---|
| AFD-1 | D |
| AFC-1 | D |
| AFY-1 | D |
| AGX-8 | D |
| AHD-9 | D |
| AHK-1 | D |
| AHJ-11 | D |
| AHL-8 | D |

Example 448: T-Cell AlphaLISA Assay

Test compounds were dissolved in DMSO (typically at 20 mM) and a ten-point half log dilution series prepared using acoustic dispensing. 300 nl of each compound concentration was dispensed in duplicate into wells of a 384 well white assay plate, typically providing a top final assay compound concentration of 50 mM. Assay low control wells received DMSO only and high controls received a standard compound (NDI-996238) providing a final assay concentration of 50 mM.

Cryopreserved human T-cells were thawed and incubated for 24 hrs prior to use in RPMI 1640 medium containing HI FBS 10% and 100 Penicillin-Streptomycin. Cells were harvested and resuspended in assay medium at a concentration of $1.25 \times 10^6$ cells per ml. 40 μl (50,000 cells) were added to the wells of a white 384 well assay plate and 5 μl (0.5 ag/ml) anti-CD28 antibody (Life Technologies #16-0289-85) and 5 μL (0.75 μg/ml) anti-CD-3 antibody (Thermofisher #16-0037-85) is added to the appropriate wells. The plates were then incubated for 48 hours at 37° C. in 5% $CO_2$.

At the end of the incubation period, the assay plate was centrifuges at 300×g for 5 mins and 50 μL of the supernatant was transferred to a plate for IL-2 analysis. IL2 levels were measured following the manufacturers protocol (Perkin Elmer #AL221C). Briefly, human IL2 (0.3 μg) was dissolved in 100 μL 1× AlphaLISA Immunoassay buffer. A half log IL2 standard curve was generated with a top concentration of 30 μg/mL in varying amounts of assay medium, as per manufacturers protocol. 2 μL of sample or IL-2 standard is added to 384-well Proxiplate alongside 8 μL of a 2.5× MIX of AlphaLISA Anti-Analyte Acceptor beads (10 μg/mL final) and Biotinylated Antibody Anti-Analyte (1 nM final). The plate is incubated for 60 minutes at 25° C. in the dark prior to the addition of 10 μL of 2× SA-Donor beads (40 μg/mL final) and further incubated for 30 minutes at 25° C. in the dark. Absorbance was read at 570 nm using Envision (PerkinElmer)

Data was normalised using high and low assay controls: % activation=100−(100*((high control)−unknown)/(high control−low control)). Normalised data was fitted to a non-linear regression equation (log inhibitor vs response-variable slope 4-parameters) to derive compound EC50 values. Fold activation over baseline was expressed as mean luminescence values from high control wells/mean luminescence values from low control wells (anti CD3/anti-CD28 alone). Maximum activation of compounds was also expressed as a normalised value referenced to the standard compound (maximum % activation of test compound/100).

Table 7 shows the selected compounds of this invention tested in the T-cell assay. All compounds tested have an $EC_{50} \leq 1$ μM.

TABLE 7

T- cell AlphaLISA Assay Results
Compound ID

AG-1
AF-1
ACM-8
AQ-1
AR-1
ACE-1
ACO-1
Z-1
R-2
AI-2
AH-2
AK-2
AO-1
ABN-2
ACF-1
ABF-8
W-2
AE-2
ACR-7
ABR-1
AP-1
ABC-7
ACA-1
ACL-1
ACK-3
AJI-1
AMJ-1
AIJ-2
ALB-2
AMD-2
ANI-2
AIA-2
AJJ-1
AMC-2
AIV-2
AIG-1
ANR-2
AII-9
AMP-1
AKS-1
AHT-2
AIR-2
AIB-2
AIO-9
AKB-1
ANB-1
AJW-1
AIM-2
AJK-1
AMO-2
ALS-1
AJS-1
AIP-2
AIN-2
AKT-1
AKV-1
AKO-2
AIW-2
AHR-4
AHO-4
AHW-1
AKA-1
AML-1
AMT-2
AMW-2

Table 7A shows the selected compounds of this invention tested in the T-cell assay. All compounds tested have an $EC_{50} \leq 0.2$ μM.

TABLE 7A

T-cell AlphaLISA Assay Results
Compound ID

ADR-3
AFO-2
ADZ-2
AFT-2
AFU-1
AEY-1
AGW-6
AGR-1
AGP-1
AFH-1
AFN-3
AHG-2
ADF-2
AGQ-2
AHH-3
AFK-1
AEF-1
AGO-2
AEN-1
ADJ-1
ADQ-2
AEL-2
AEC-2
AEH-1
ADT-2
AGG-2
AHI-4
AGV-1

Example 449: Table 8. hCbl-b Displacement Assay Results

Table 7 shows select compounds of this invention tested in the hCbl-b Displacement Assay. All compounds tested have an $EC_{50} \leq 10$ μM.

TABLE 8 hCbl-b Displacement Assay Results
Compound ID

ADR-3
AFO-2
ADZ-2
AFT-2
AFU-1
AEY-1
AGW-6
AGR-1
AGP-1
AFH-1
AFN-3
AFK-1
AEF-1
AEN-1
ADJ-1
ADQ-2
AEH-1
ADT-2
AGG-2
AGZ-1
AES-1
AFW-3
ADV-1
AEI-5
BE-3
AGS-2
AHI-4
AEO-2
AFL-2
AFJ-1
AEQ-3
AGA-1

TABLE 8-continued hCbl-b Displacement Assay Results
Compound ID

AW-2
AFM-2
AGU-10
ADX-2
AFI-1
AED-2
AGV-1
ADH-1
AEM-9
ADB-1
AND-2
AT-1
AHG-2
ADF-2
AGQ-2
AHH-3
AFQ-3
AFV-3
AEJ-3
ADO-2
ACY-4
AFG-1
AHC-1
AZ-2
AEE-2
ADI-1
AGY-3
AEA-2

Table 8A shows select compounds of this invention tested in the hCbl-b Displacement Assay. All compounds tested have an $EC_{50} < 50$ nM.

TABLE 8A hCbl-b Displacement Assay Results
Compound ID

AMJ-1
AIJ-2
ALB-2
AMD-2
AIA-2
ANR-2
AII-9
AKS-1
ALO-2
AIR-2
AKG-1
AIB-2
AKB-1
AJW-1
AKZ-2
AKY-1
AKC-2
ALS-1
AMG-1
ALQ-2
AKK-1
ALA-5
AHR-4
AHO-4
AHW-1
AKA-1
ALI-2
AMI-1

Example 450: Jurkat pZAP70 HTRF Assay

Jurkat wild-type (clone E6-1) cells were maintained and assayed in RPMI 1640 medium with 10% FBS, 1% L-glutamine and 1% Penicillin/Streptomycin. Test compounds were dissolved in DMSO (typically at 20 mM) and a ten-point half log dilution series prepared using acoustic dispensing. 62.5 nl of each compound concentration was dispensed in duplicate into wells of a 384 well white assay plate, typically providing a top final assay compound concentration of 10 mM. Assay low control wells received DMSO only and high controls received a standard compound (NDI-205422/NDI-206096) providing a final assay concentration of 10 mM. Jurkat cells were harvested and resuspended in assay medium at $1\times10^7$ cells/ml. 10 µl (100,000 cells) was added to the wells of a white 384 well assay plate containing acoustically dispensed compounds and incubated for 15 min at 37° C. in 5% $CO_2$. Anti-CD3 antibody (Thermofisher #16-0037-85) was diluted in assay medium to 30 µg/ml and 2 µl was added to wells of the assay plate for a final concentration of 5 µg/ml. The assay plate was incubated for 3 hr at 37° C. in 5% $CO_2$. Phospho-Zap70 (Y-319) was quantified using the Cisbio HTRF system (cat #64ZAPPEH). Cells were lysed by addition of 4 µl of lysis buffer for 30 min at RT. 4 µl of diluted donor and acceptor antibody mix was added and the plate sealed and incubated overnight at RT. The assay was read on an Envision plate reader using HTRF read mode with laser excitation and emission read at 665 nm.

Data was normalised using high and low assay controls:

% activation=100−(100*((high control)−unknown)/ (high control−low control))

Normalised data was fitted to a non-linear regression equation (log inhibitor vs response-variable slope 4-parameters) to derive compound EC50 values. Maximum activation of compounds was also expressed as a normalised value referenced to the standard compound (maximum % activation of test compound/100).

Table 9 shows select compounds of this invention tested in the Jurkat pZAP70 HTRF Assay. Compounds having an activity designated as "A" provided an $EC_{50} \leq 0.2$ µM; compounds having an activity designated as "B" provided an $EC_{50} > 0.20$ µM. but $\leq 1$ µM; compounds designated as "C" provided an $EC_{50} > 1$ µM but $\leq 10$ µM; compounds designated as "D" provided an $EC_{50} > 10$ µM but $< 50$ µM.

TABLE 9

ZAP70 Jurkat Assay Results

| Compound ID | ZAP70 Jurkat $EC_{50}$ (µM) |
|---|---|
| ADR-3 | A |
| AFO-2 | A |
| ADZ-2 | A |
| AFT-2 | A |
| AFU-1 | A |
| AEY-1 | A |
| AGW-6 | A |
| AGR-1 | A |
| AGP-1 | B |
| AFH-1 | A |
| AFN-3 | A |
| AHG-2 | A |
| ADF-2 | A |
| AGQ-2 | B |
| AHH-3 | A |
| AFK-1 | A |
| AEF-1 | A |
| AGO-2 | A |
| AEN-1 | A |
| ADJ-1 | A |
| ADQ-2 | A |
| AEL-2 | A |
| AEO-2 | A |
| AFL-2 | A |
| ADU-3 | B |
| AFJ-1 | A |
| AEQ-3 | A |
| AGA-1 | B |
| AEW-2 | B |
| AW-2 | A |
| ACY-4 | A |
| AFG-1 | B |
| AHC-1 | A |
| AFX-1 | A |
| AGC-5 | B |
| AZ-2 | A |
| AFM-2 | B |
| AFZ-1 | B |
| AGU-10 | A |
| ADX-2 | B |
| ADP-8 | C |
| AFI-1 | A |
| AED-2 | B |
| AGV-1 | A |
| AEC-2 | A |
| AEH-1 | A |
| ADT-2 | A |
| AGG-2 | A |
| AGZ-1 | A |
| AES-1 | B |
| AGE-3 | A |
| AET-6 | A |
| AEB-2 | A |
| AFW-3 | A |
| AFQ-3 | A |
| AFV-3 | B |
| AEJ-3 | A |
| ADO-2 | A |
| ADV-1 | A |
| AEI-5 | A |
| AEZ-1 | B |
| AGS-2 | A |
| AGT-3 | A |
| AFF-2 | A |
| AHI-4 | B |
| AGD-2 | A |
| AGN-3 | B |
| AFR-7 | A |
| AGL-1 | B |
| AGI-3 | A |
| AGM-5 | B |
| AFE-1 | B |
| AEU-8 | B |
| ADH-1 | B |
| AHB-1 | A |
| AFA-2 | B |
| AGH-2 | C |
| AEV-3 | C |
| AHA-2 | B |
| AGK-1 | B |
| AGJ-2 | C |
| AGB-1 | C |
| AEM-9 | A |
| ADB-1 | C |
| AND-2 | C |
| AGF-3 | C |
| AFS-1 | D |

Table 9A shows select compounds of this invention tested in the Jurkat pZAP70 HTRF Assay. All compounds tested have an $EC_{50} < 1$ µM.

TABLE 9A

ZAP70 Jurkat Assay Results
Compound ID

AJI-1
AMJ-1
AIJ-2
ALB-2
AMD-2
ANI-2
AKW-1
ALP-1
AIA-2
AJJ-1
AMC-2
AIV-2
AIG-1
ANR-2
AII-9
AMP-1
AKS-1
ALO-2
AHT-2
AIR-2
AKG-1
AIB-2
AIO-9
AKB-1
ANB-1
AJZ-1
ALH-1
AJW-1
AIM-2
AKZ-2
AIF-1
ALD-2
AKY-1
AJK-1
AKC-2
AJO-2
AMO-2
ALS-1
AJS-1
AMG-1
ALQ-2
AMF-1
ALC-2
AJX-1
AND-1
ANK-2
AIP-2
AIN-2
AKT-1
AID-2
AKK-1
ALA-5
AKV-1
AHP-1
AIE-1
AHZ-2
AKP-1
AKD-2
ALT-2
AHS-2
AKH-1
AIK-2
AMA-2
AIH-2
AKO-2
AJA-2
AKJ-1
AIW-2
AIL-3
AHX-2
AMM-1
AJT-1
ALV-4
AKE-2
AIC-11
ALW-1
ALF-2

TABLE 9A-continued

ZAP70 Jurkat Assay Results
Compound ID

ALX-9
AKF-2
ANJ-2
AKQ-2
AJR-1
AHQ-4
AHR-4
AIX-2
AJQ-2
ANG-1
AHO-4
AKR-3
ALY-2
ANT-1
AHW-1
AKU-2
AJY-1
AJC-1
AKI-1
AKL-2
AJB-2
AMK-3
AJE-2
AHV-1
AIT-1

While we have described a number of embodiments of this invention, it is apparent that our examples may be altered to provide other embodiments that utilize the compounds and methods of this invention. Therefore, it will be appreciated that the scope of this invention is to be defined by the appended claims rather than by the specific embodiments that have been represented by way of example.

The invention claimed is:

1. A compound of formula I:

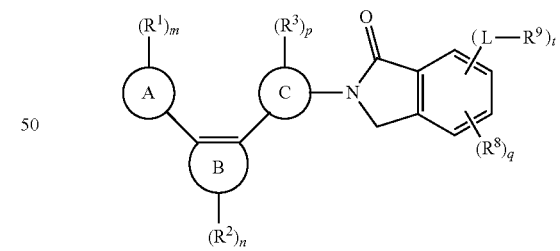

or a pharmaceutically acceptable salt thereof, wherein:

Ring A together with its $R^1$ substituents is

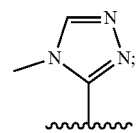

1069
Ring B together with its R² substituents is
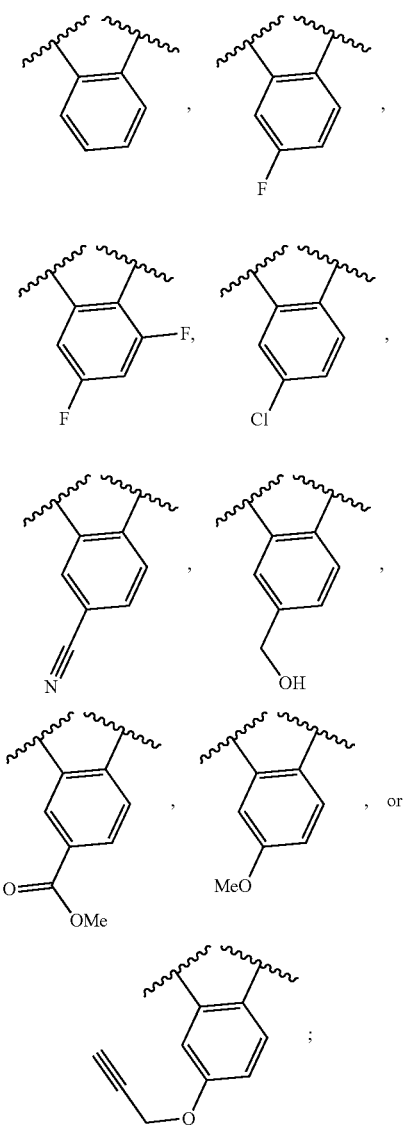
Ring C together with its R³ substituents is
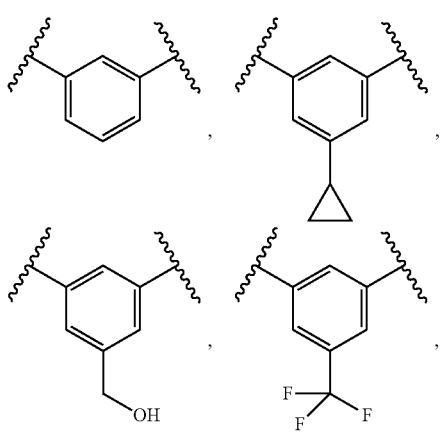
-continued
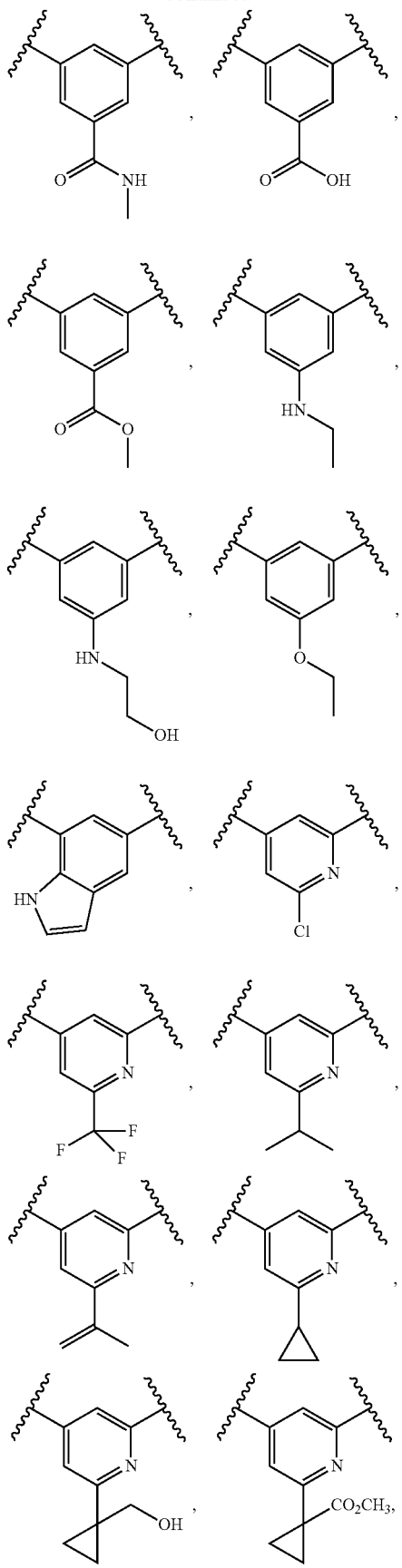

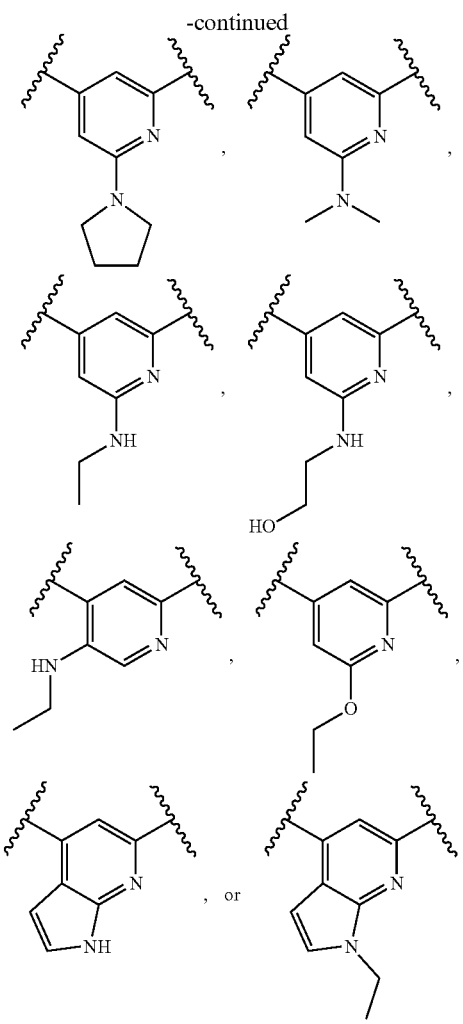
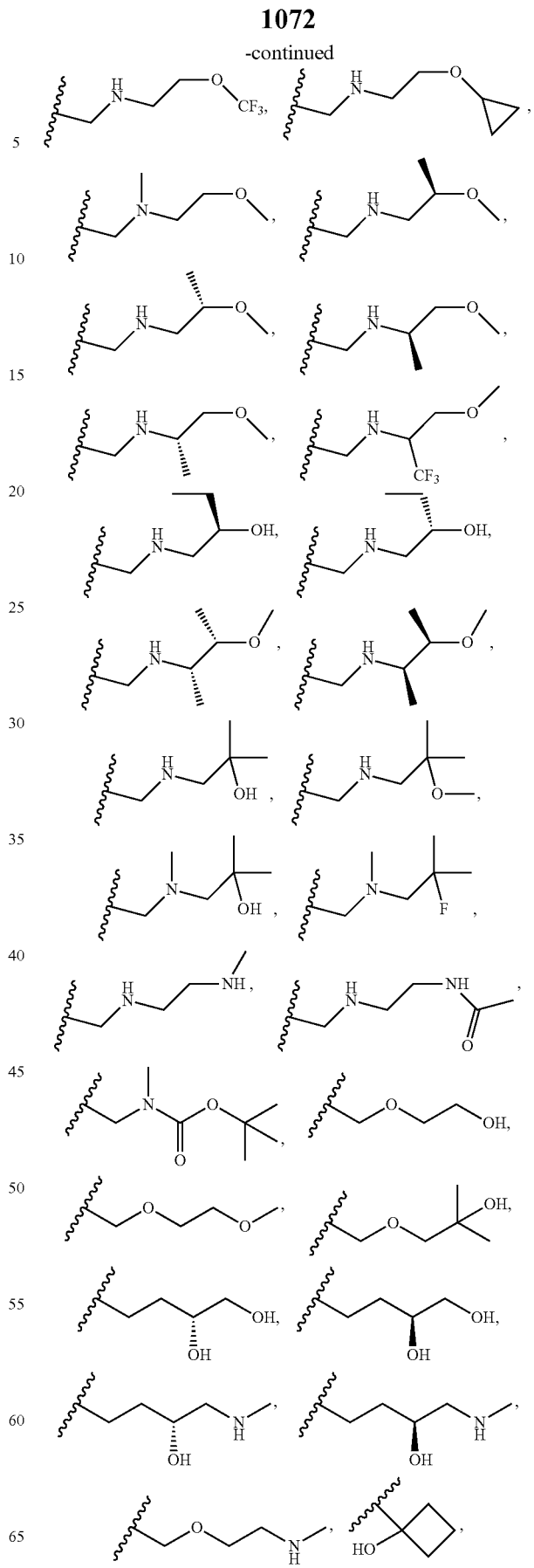
each R[8] is independently hydrogen, fluoro, chloro, bromo, methyl, —CF$_3$, —OH, or —OMe;
-L-R[9] is —COMe,
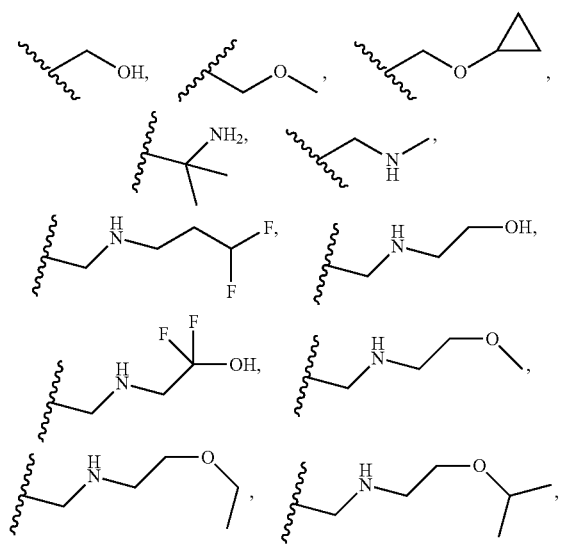

1073
-continued
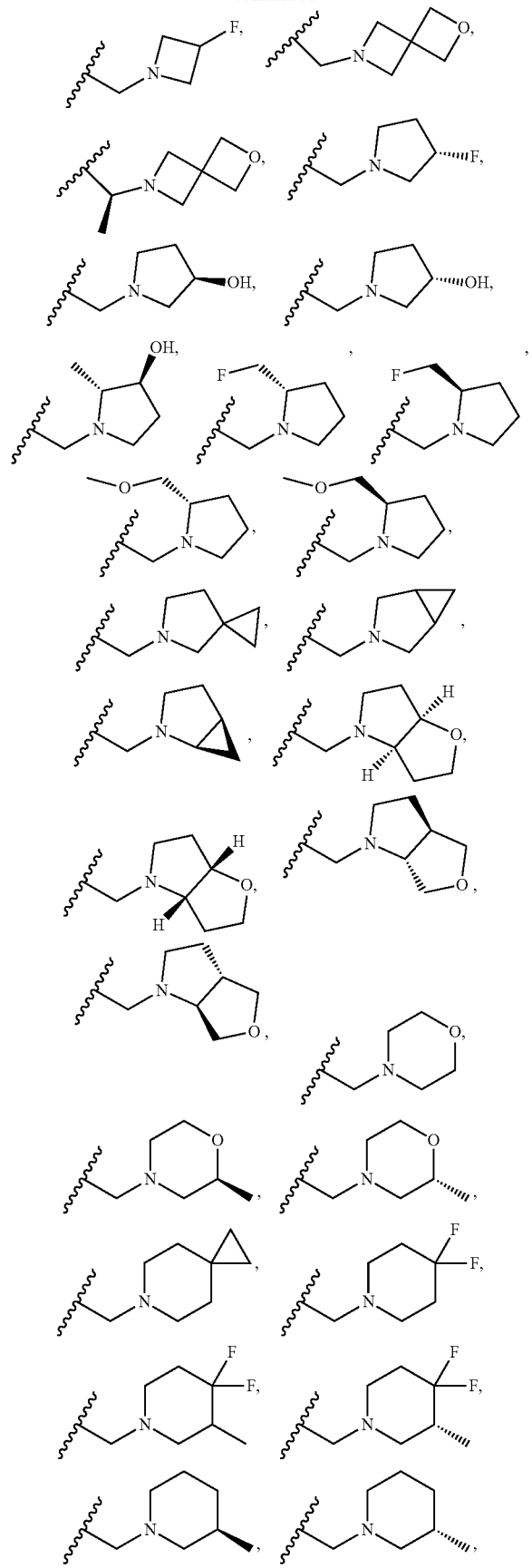
1074
-continued
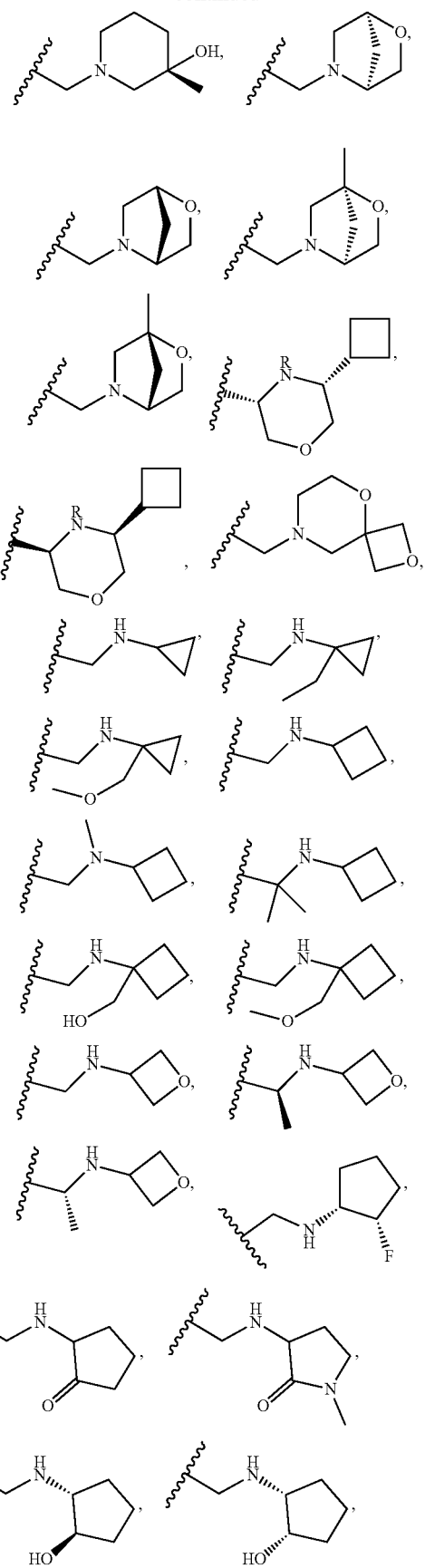

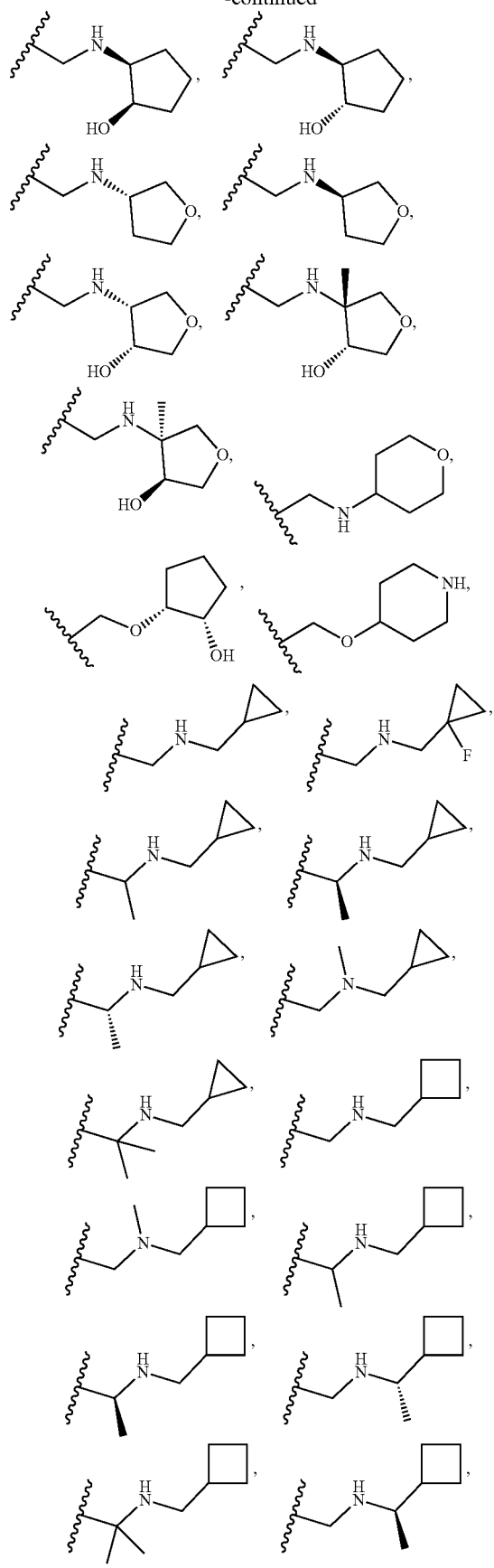
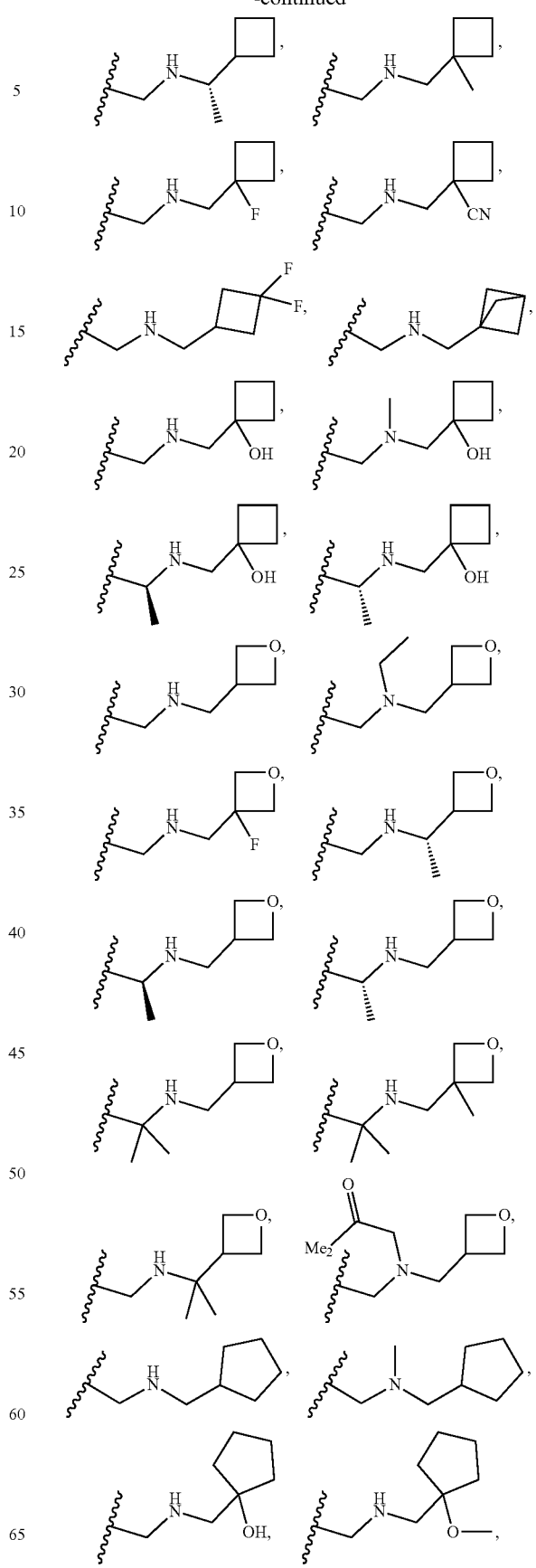

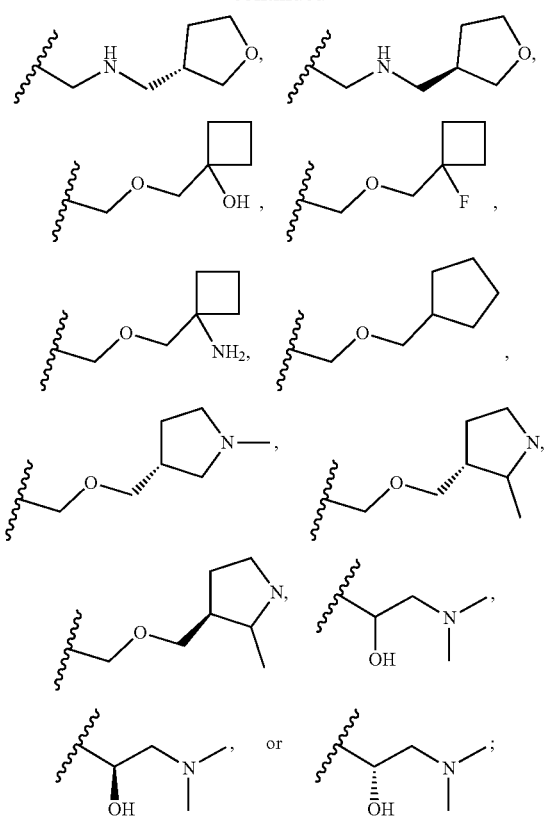

q is 0, 1, or 2; and
t is 0 or 1.

2. The compound of claim 1, wherein Ring B together with its R² substituents is

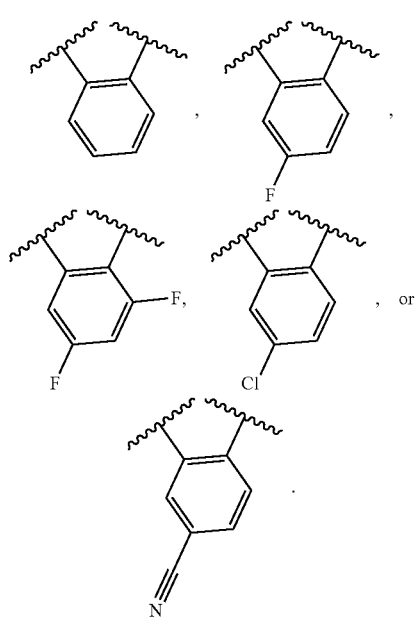

3. The compound of claim 1, wherein Ring B together with its R² substituents is

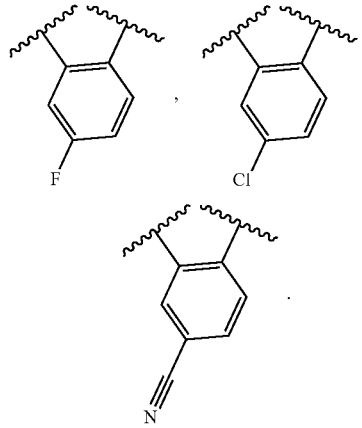

4. The compound of claim 1, wherein the compound is either of the following formulae:

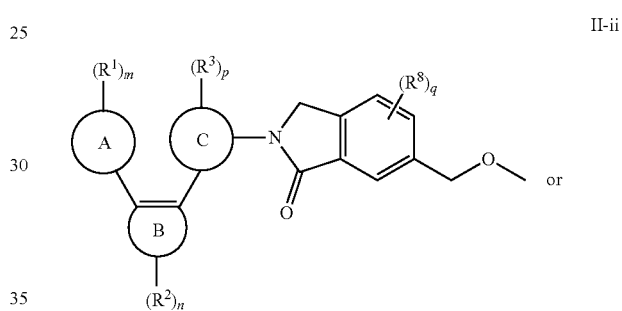

II-ii

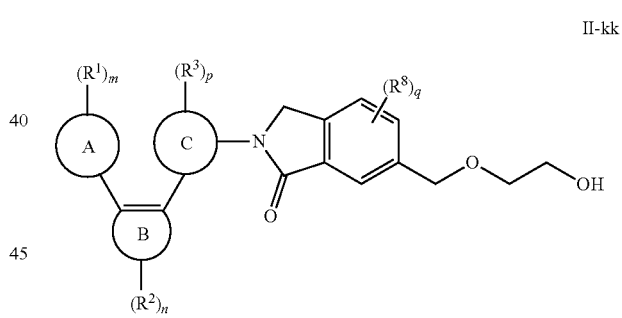

II-kk or a pharmaceutically acceptable salt thereof.

5. The compound of claim 1, wherein the compound is any one of the following formulae:

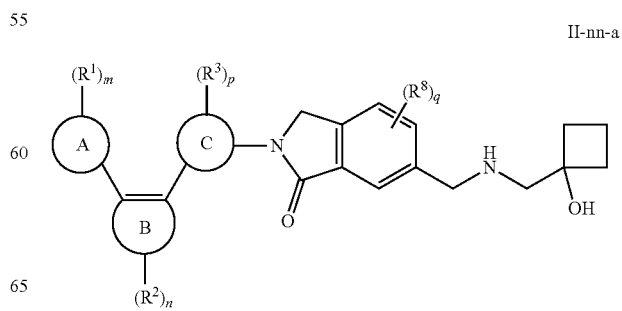

II-nn-a

II-qq-a
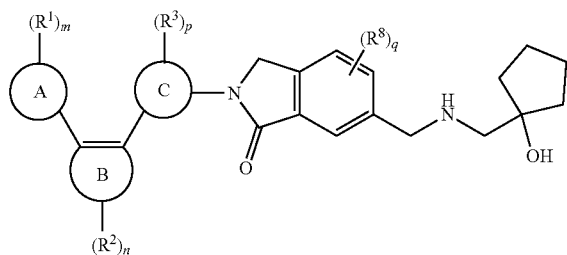
II-bbb-a
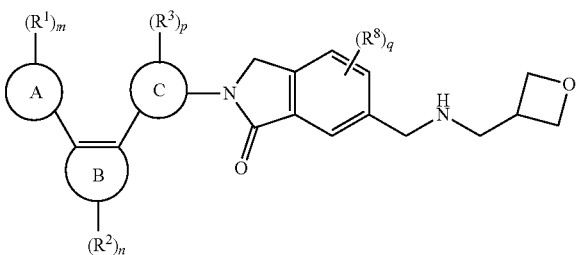
II-rr-a
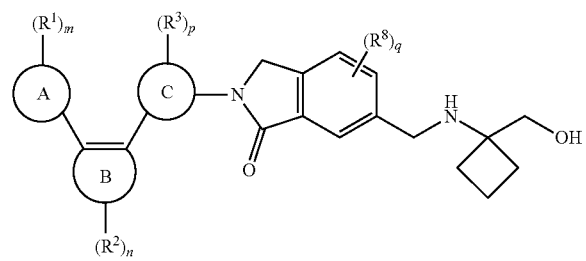
II-ccc-a
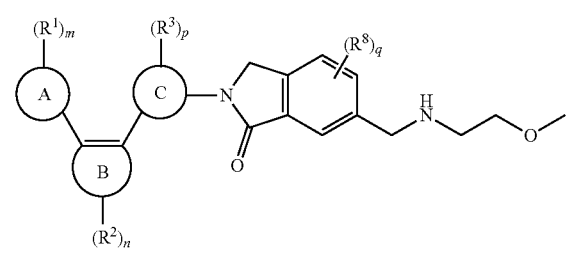
II-yy-a
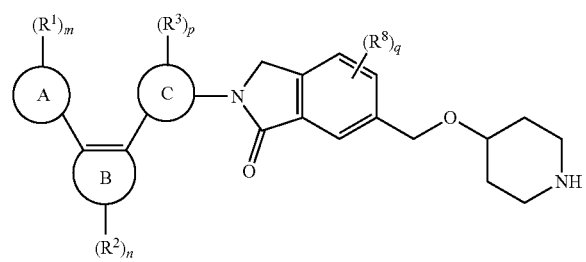
II-ddd-a
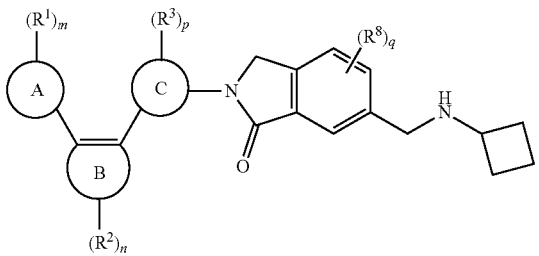
II-zz-a
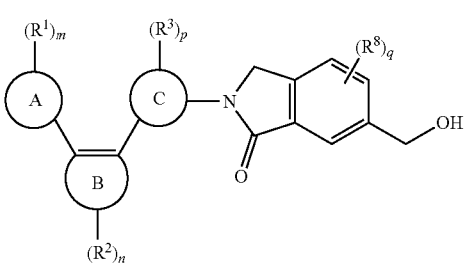
II-eee-a
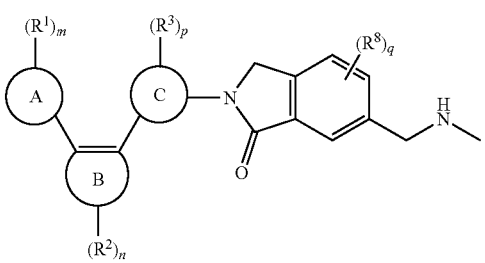
or a pharmaceutically acceptable salt thereof.
6. The compound of claim 1, wherein the compound is any one of the following formulae:
II-aaa-a
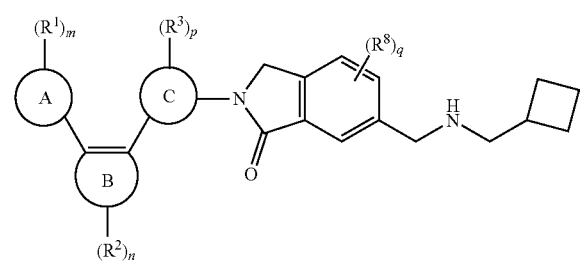
II'-ii
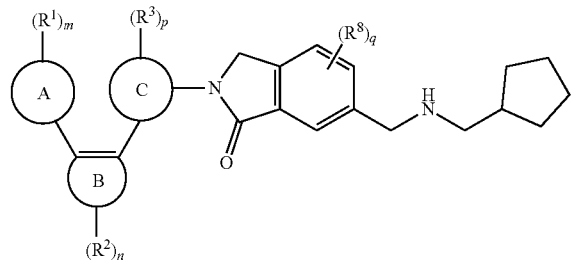

II'-kk
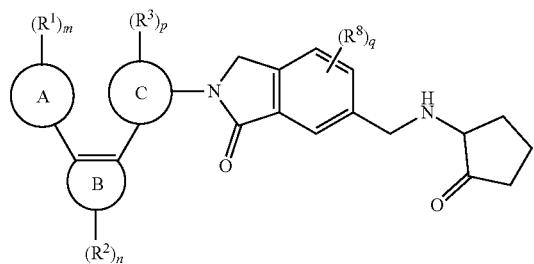
II'-qq
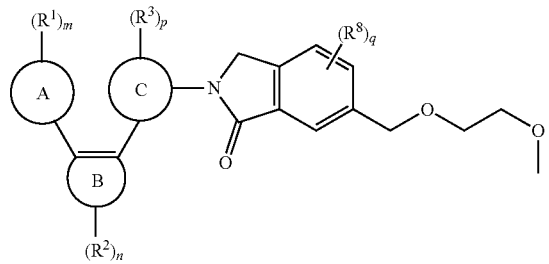
II'-ll
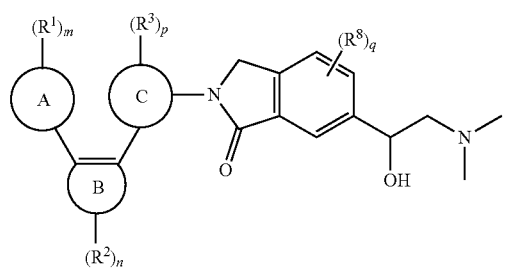
II'-rr
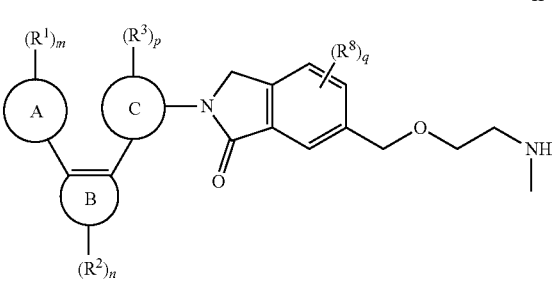
II'-mm
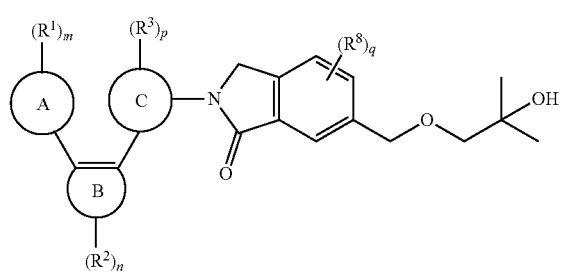
II'-ss
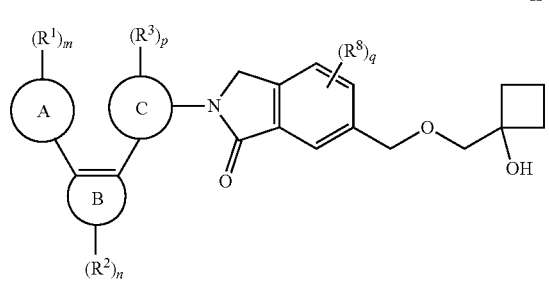
II'-oo
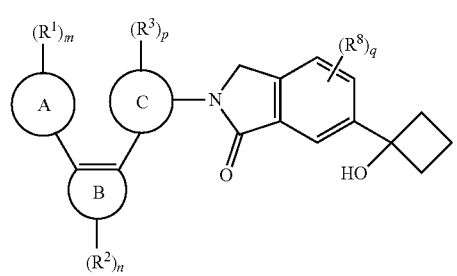
II'-tt
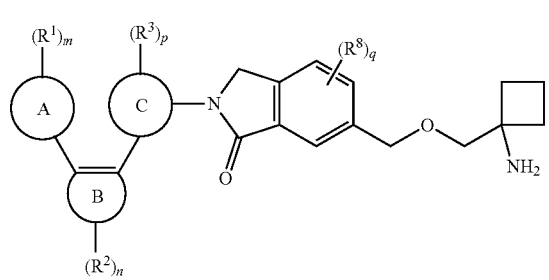
II'-pp
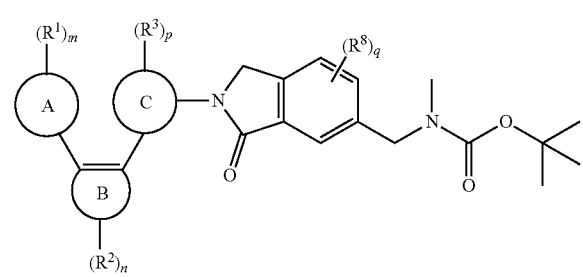
II'-uu
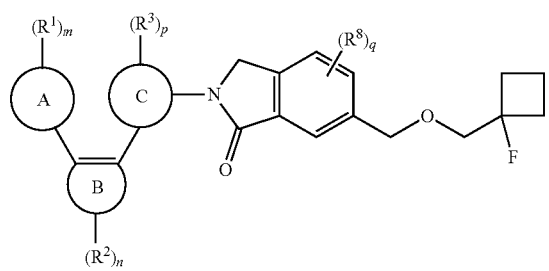
or a pharmaceutically acceptable salt thereof.

7. A compound selected from:
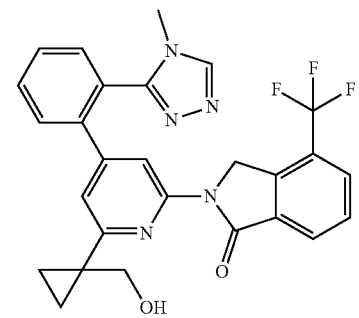
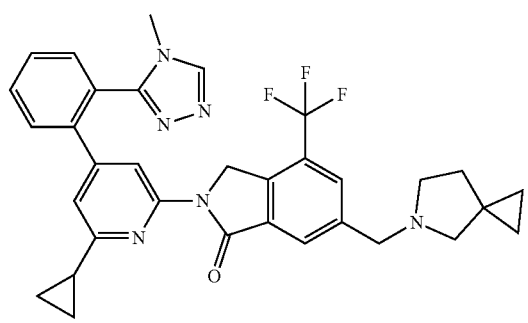
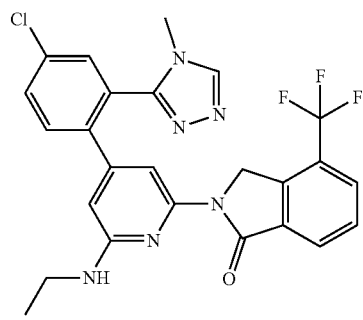
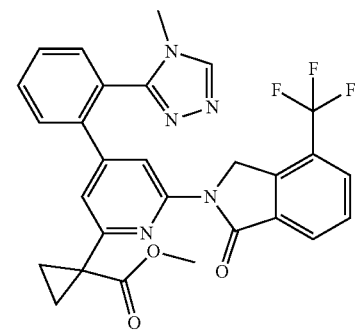
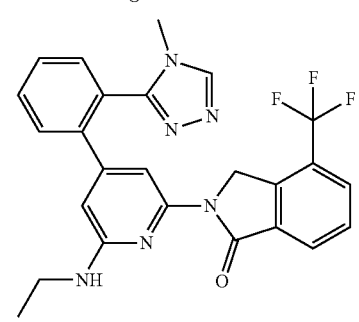
-continued
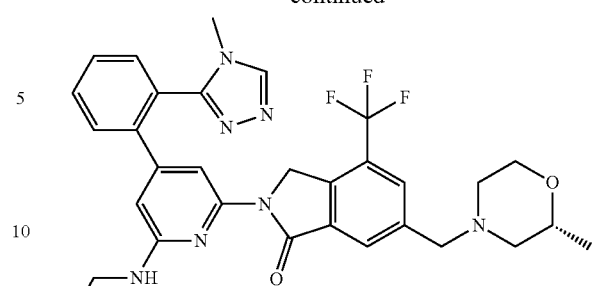
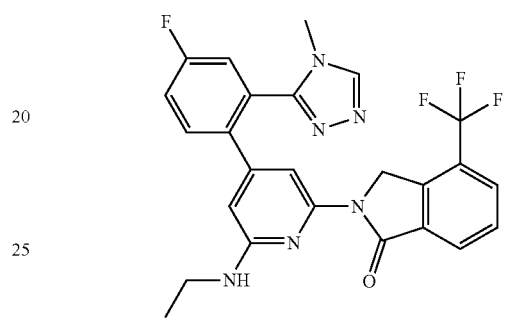
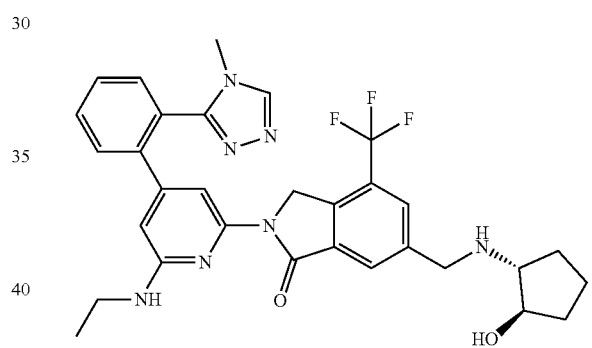
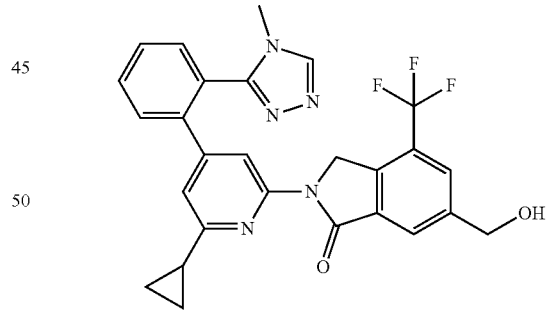
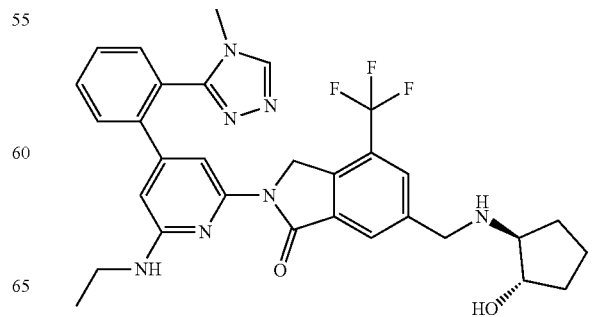

1085                                    1086
-continued                              -continued
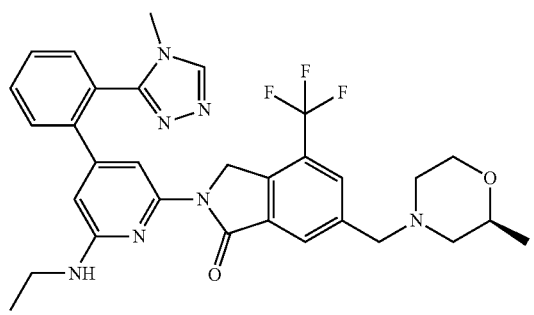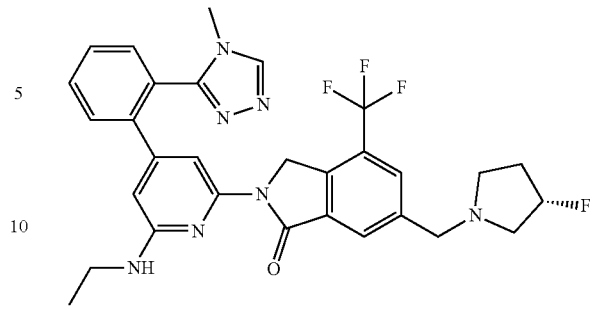
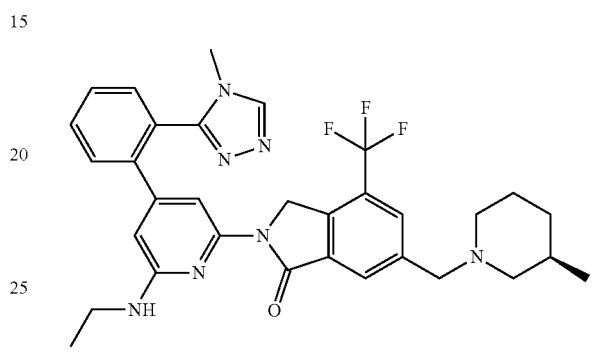
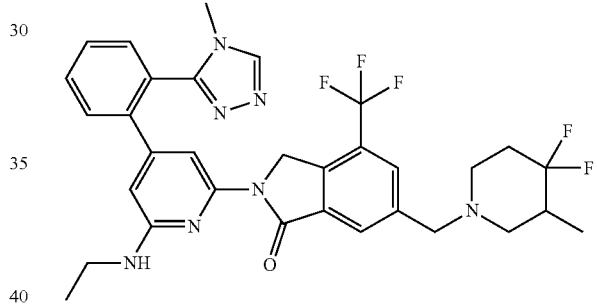
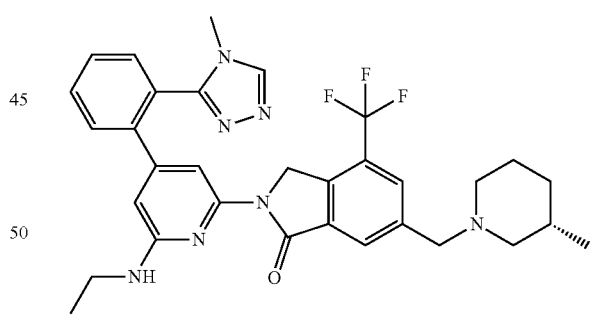
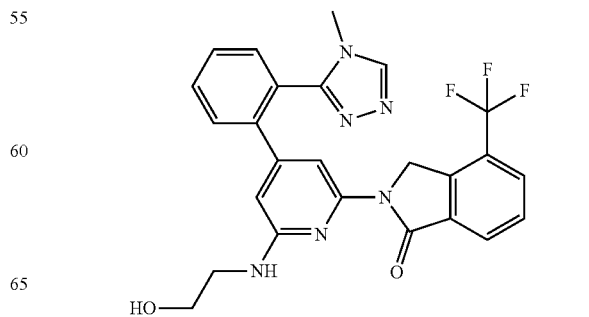

1087
-continued
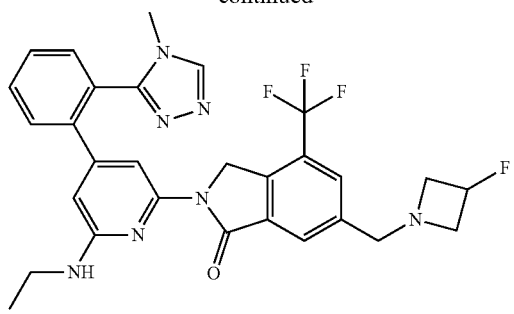
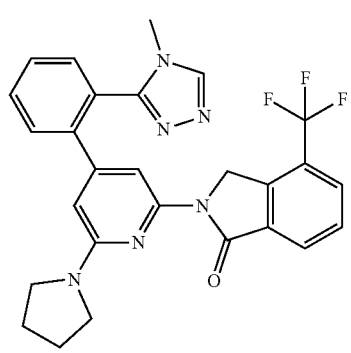
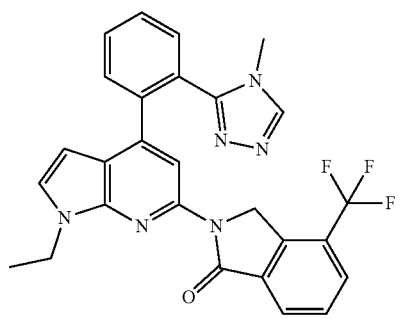
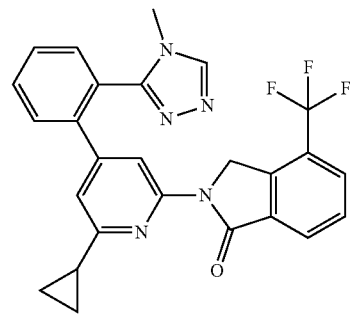
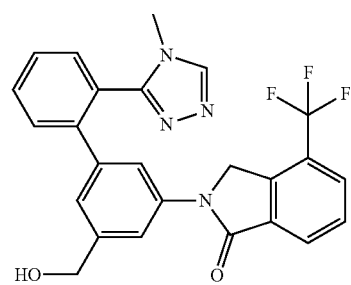
1088
-continued
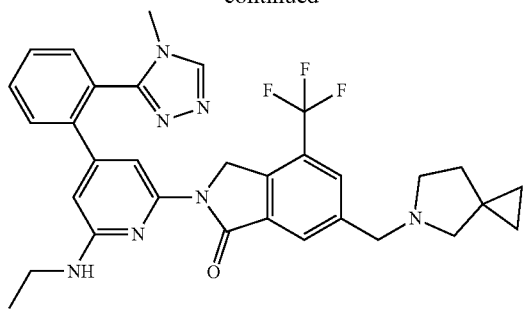
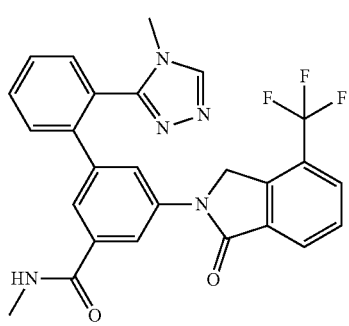
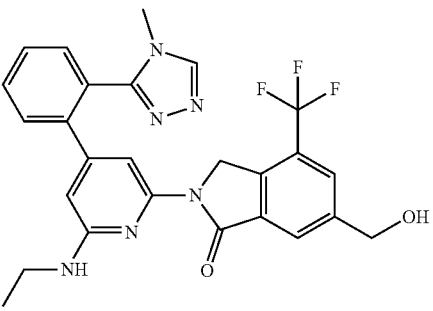
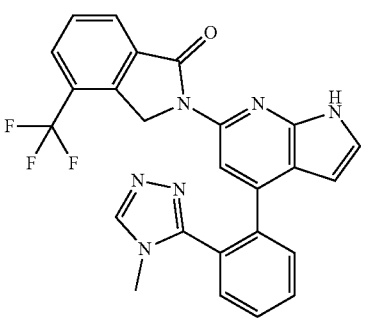
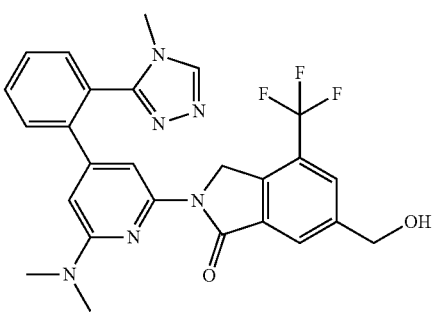

1089
-continued
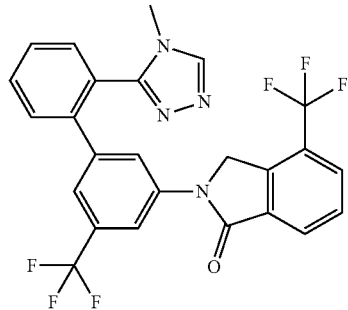
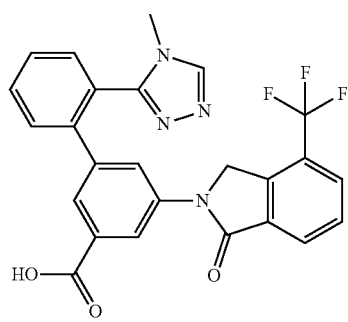
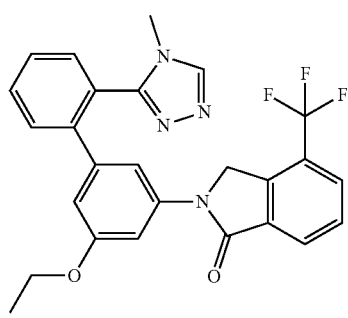
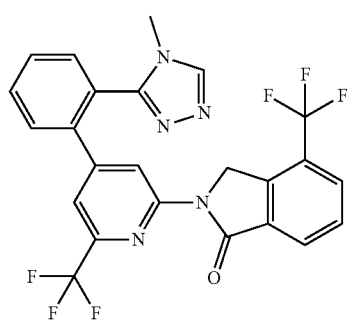
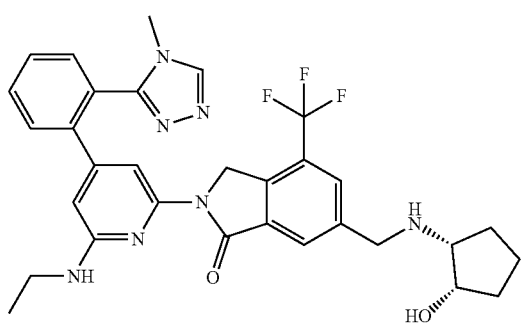
1090
-continued
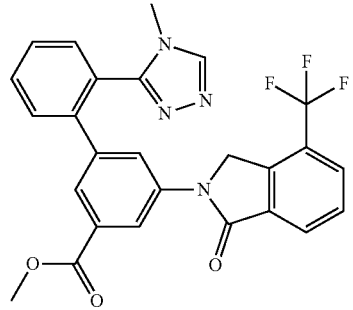
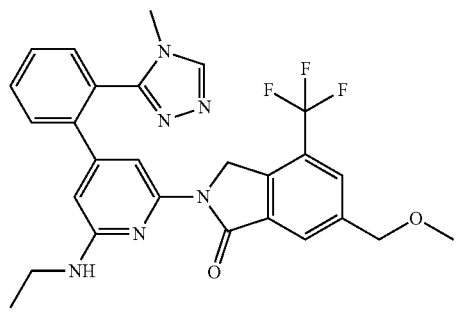
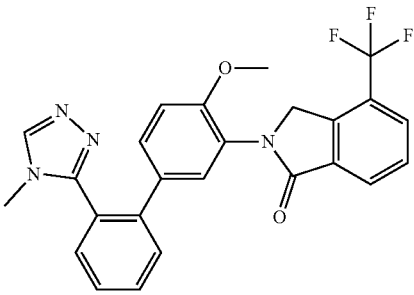
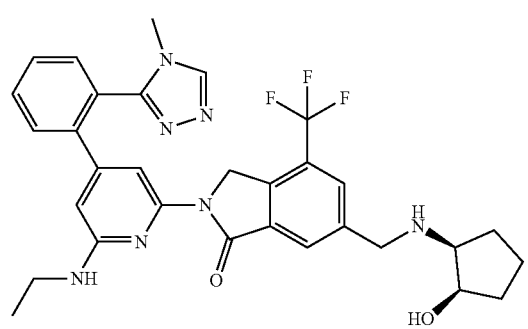
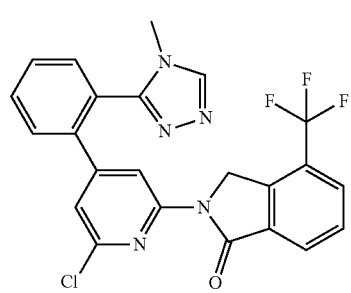

1091
-continued
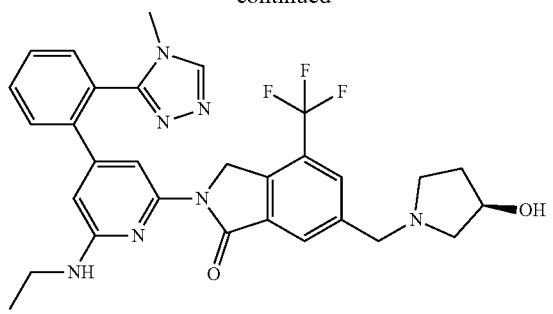
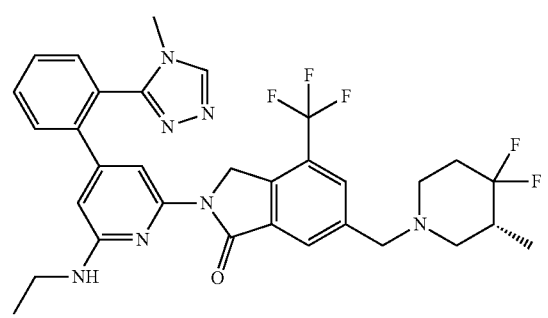
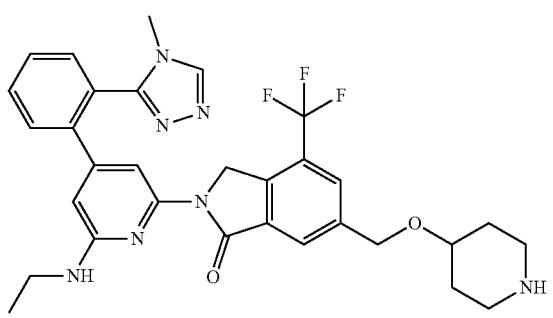
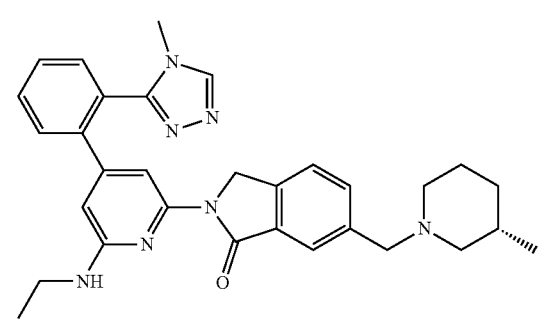
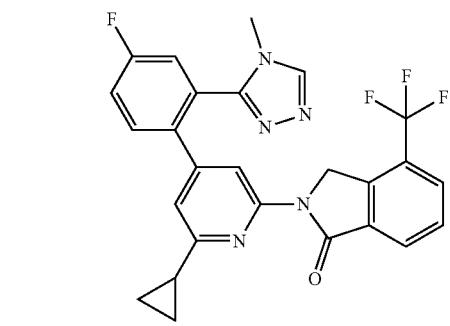
1092
-continued
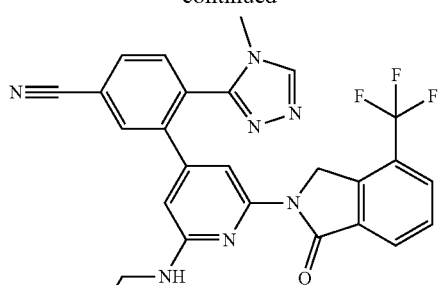
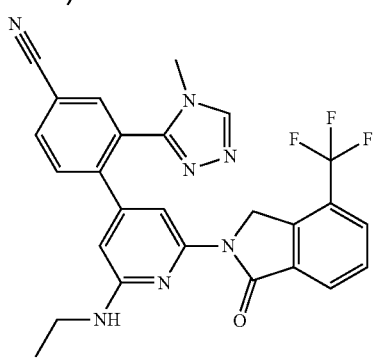
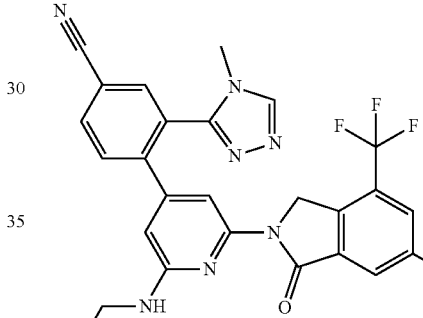
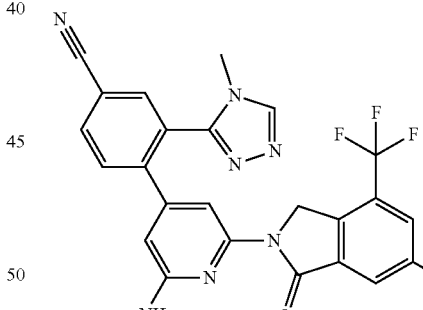
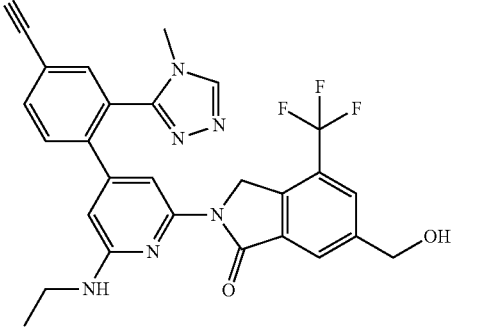

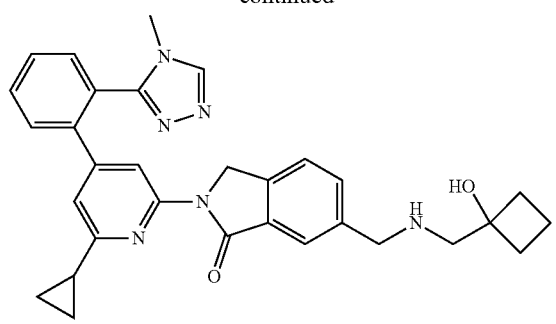
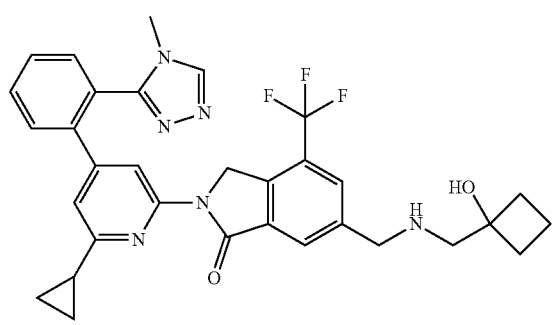
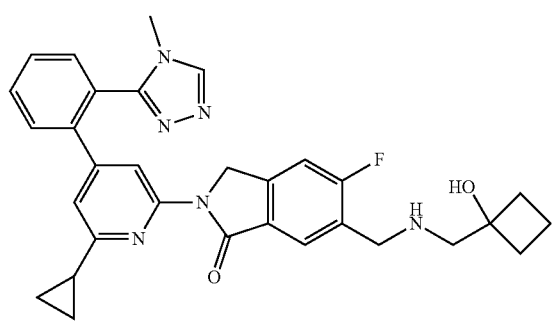
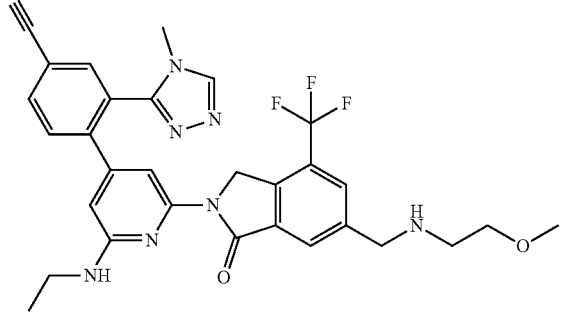
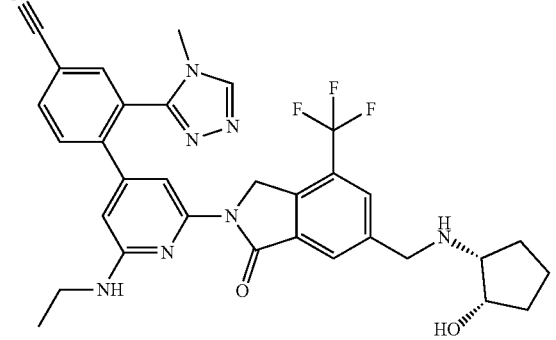
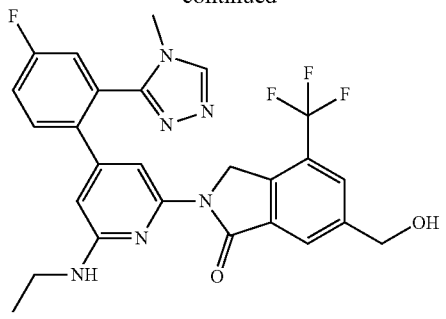
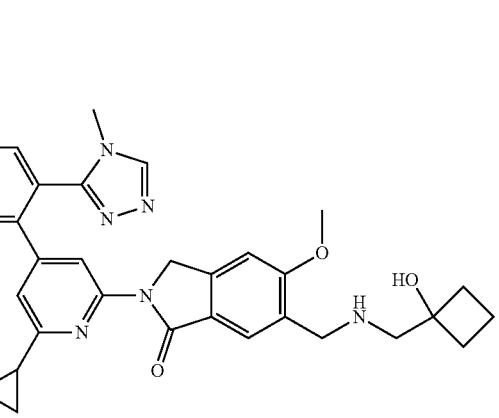
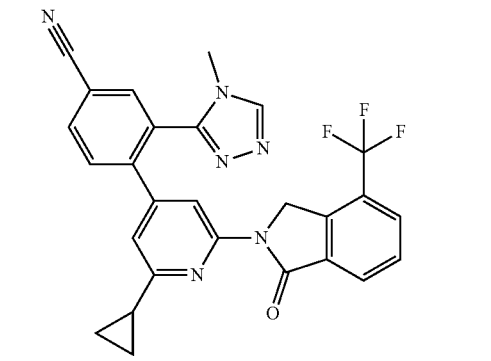

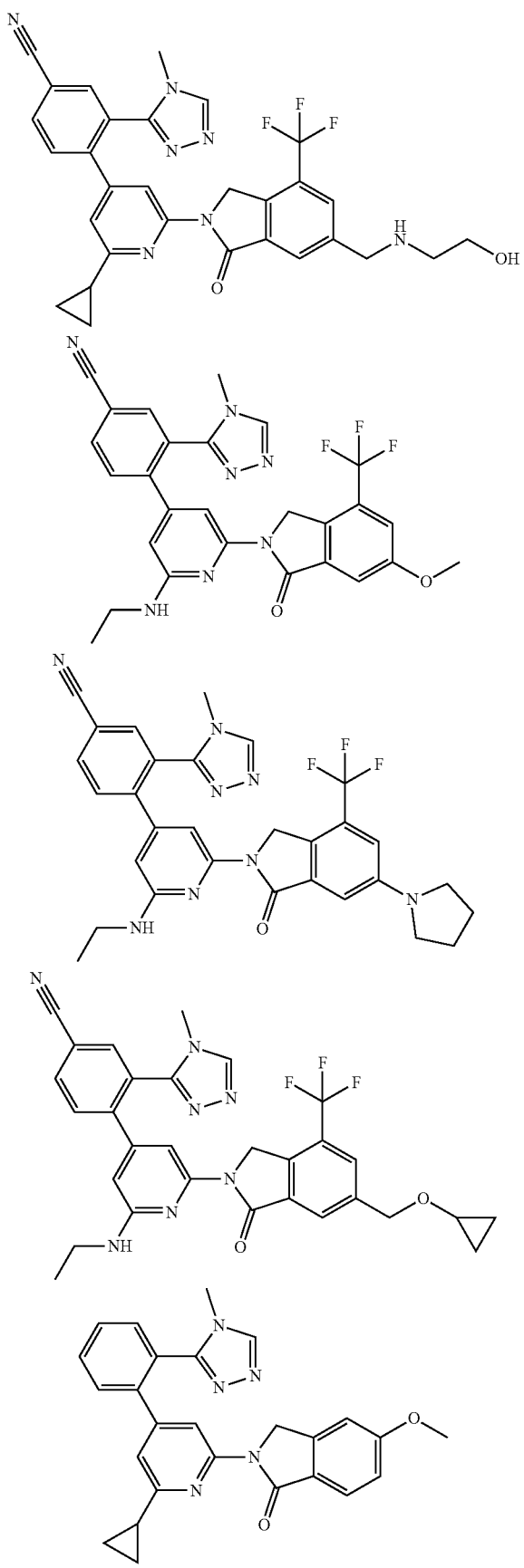
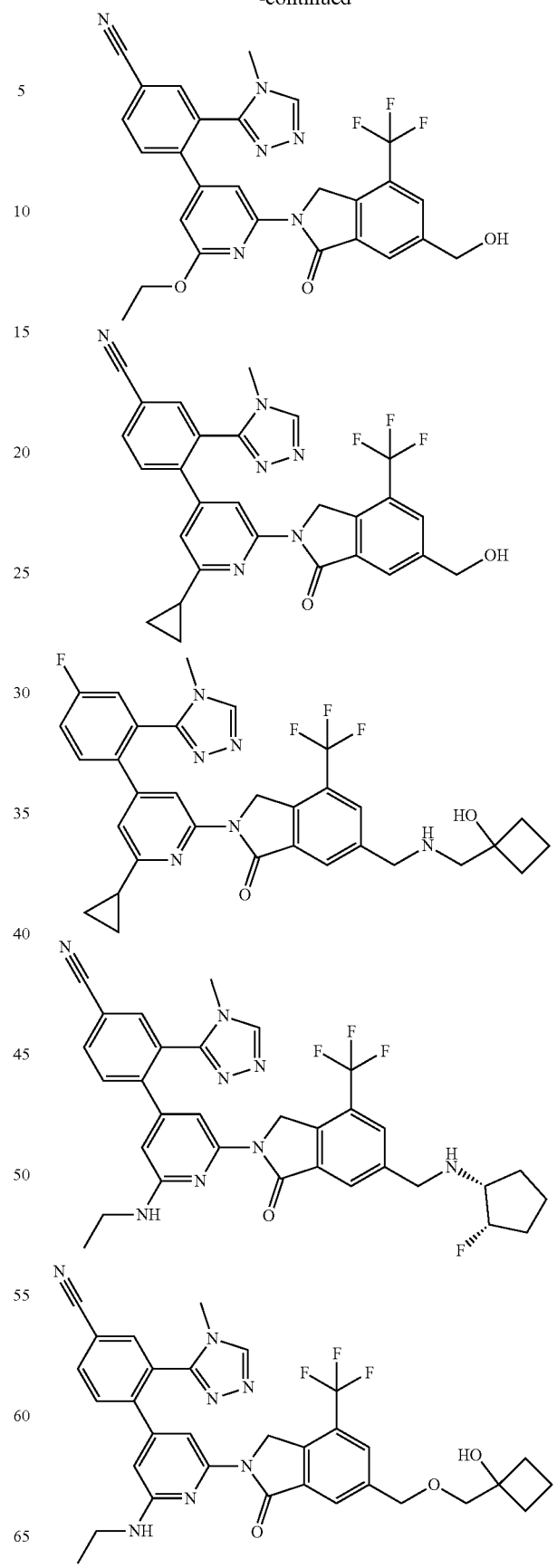

1097
-continued
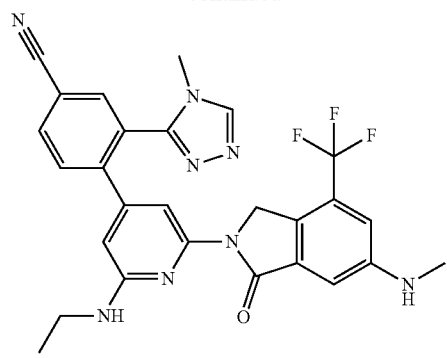
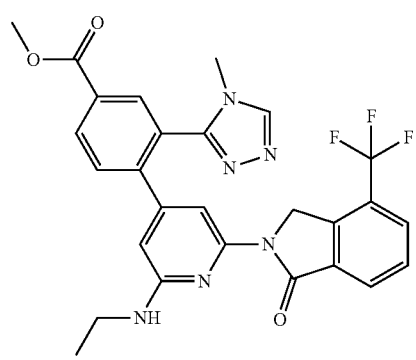
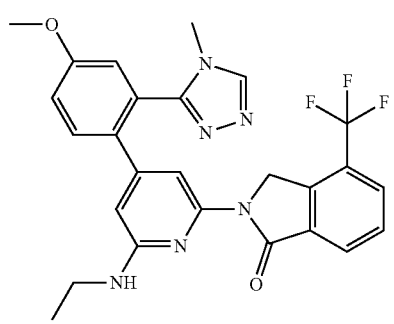
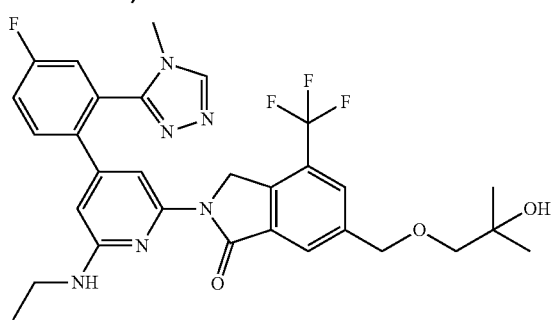
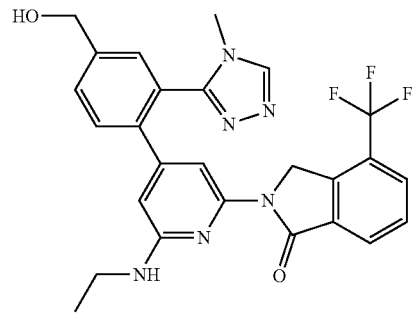
1098
-continued
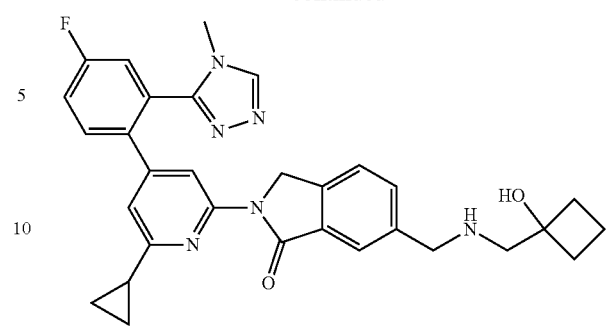
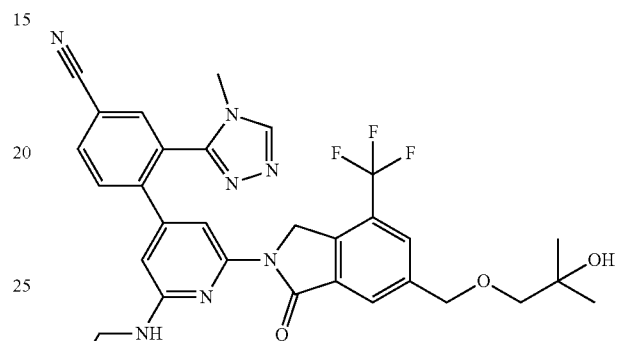
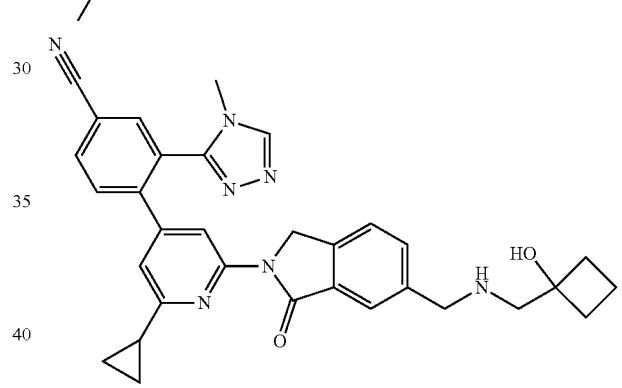
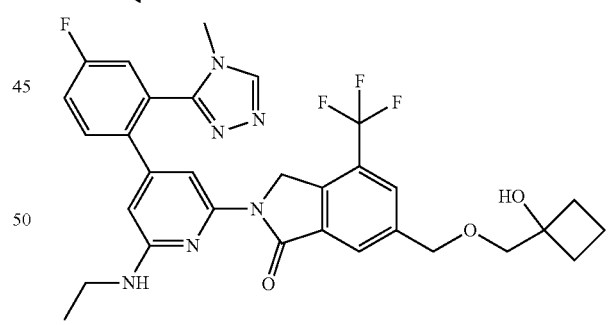
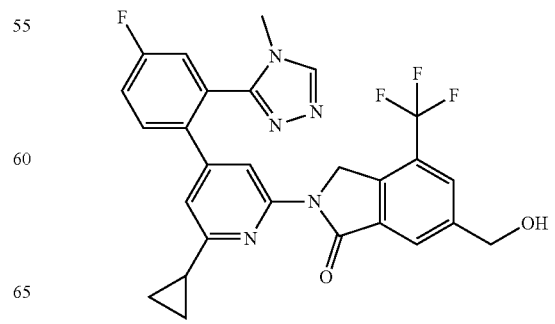

1099
-continued
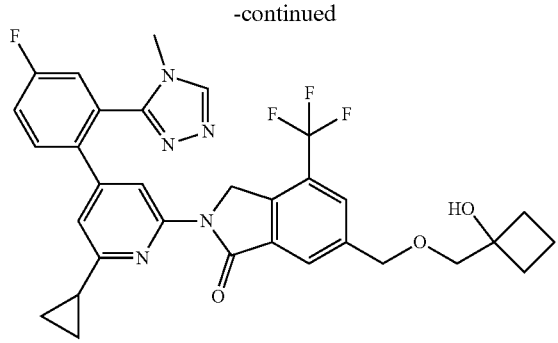
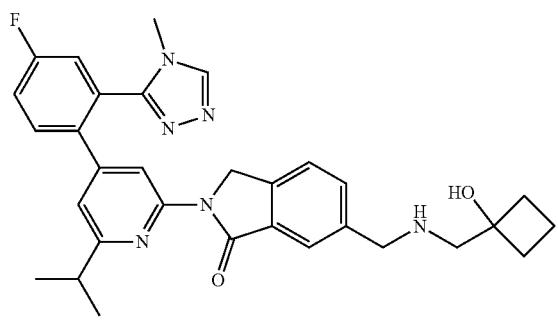
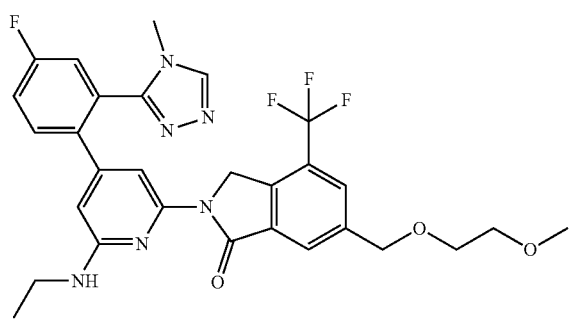
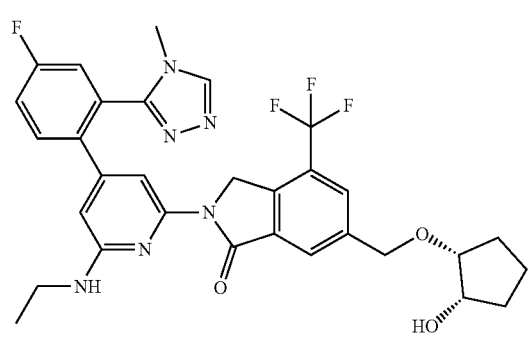
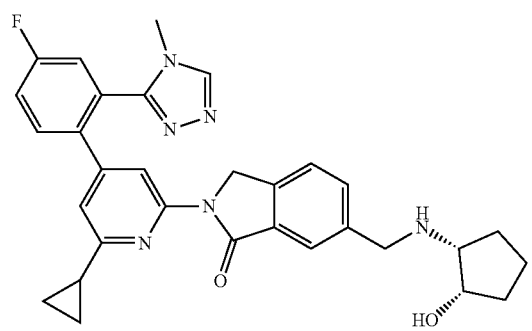
1100
-continued
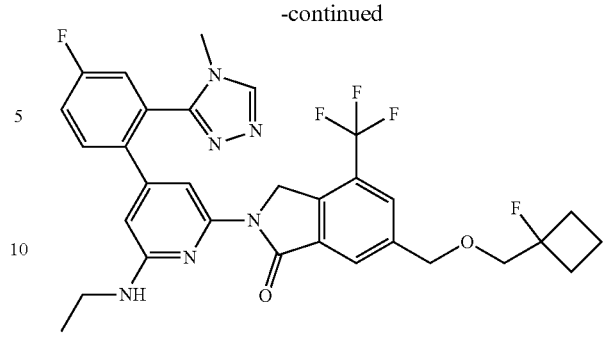
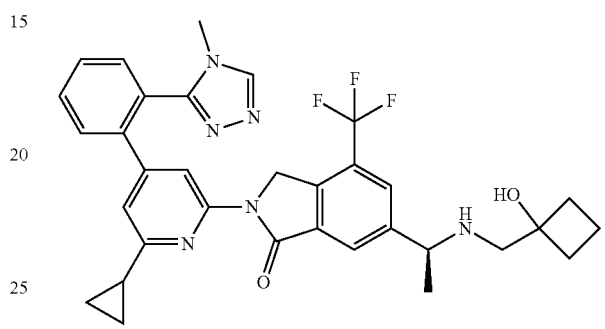
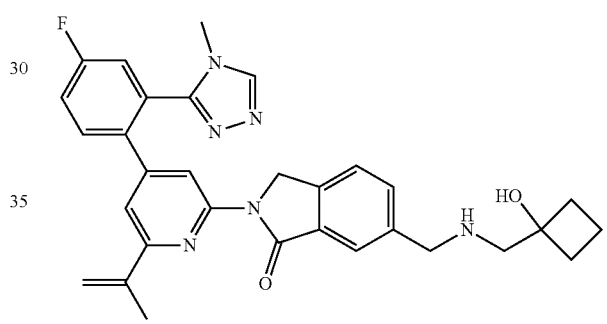
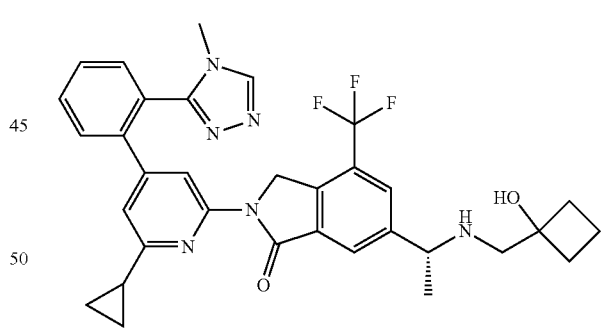
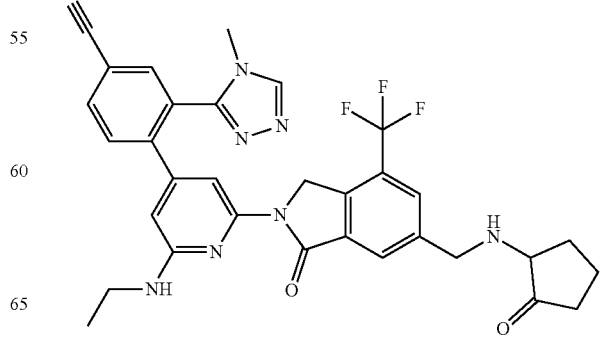

1101
-continued
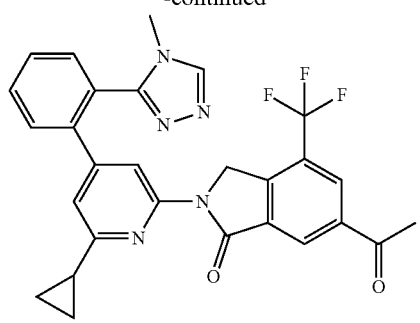
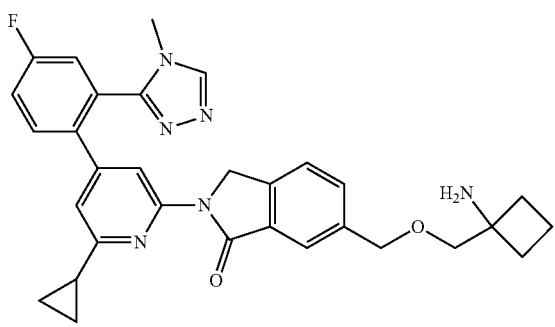
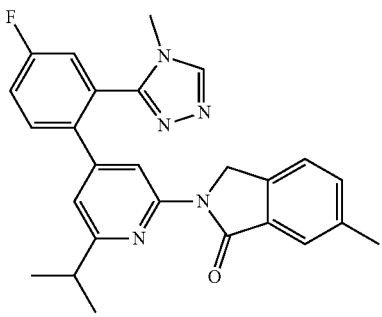
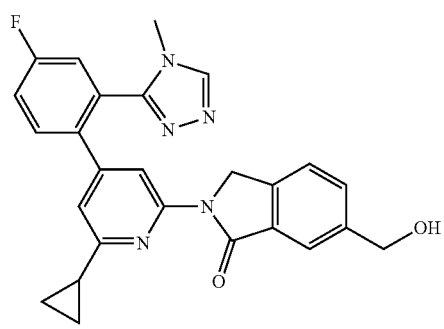
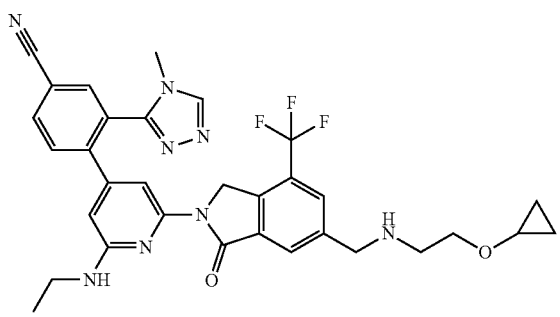
1102
-continued
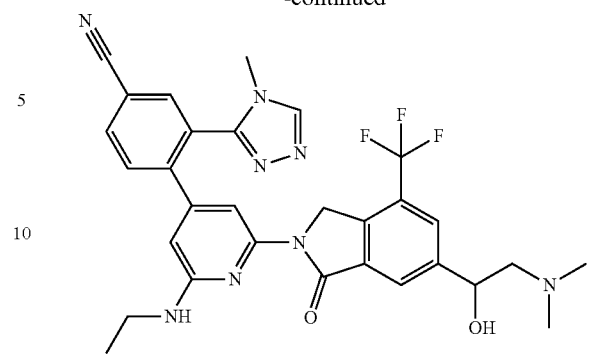
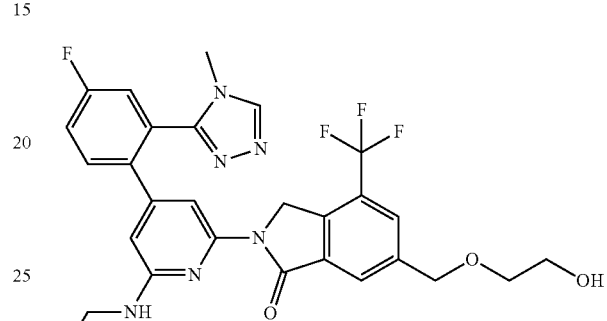
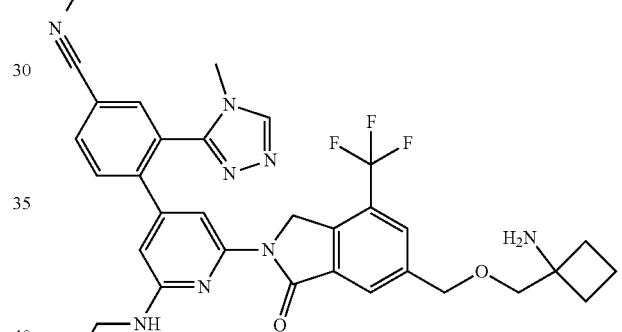
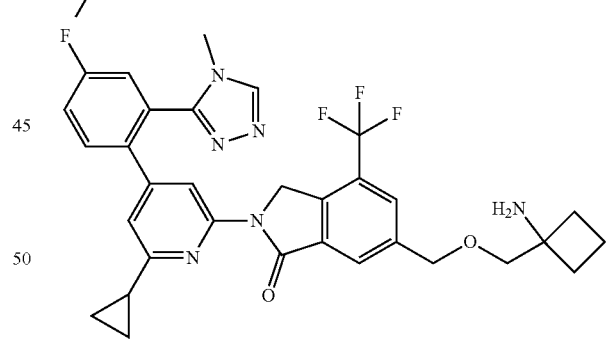
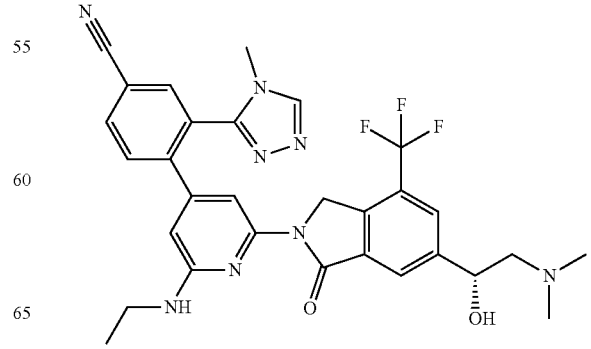

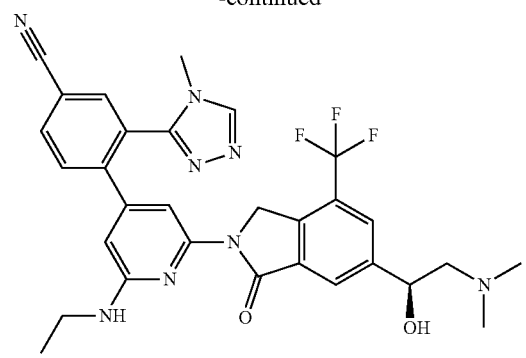
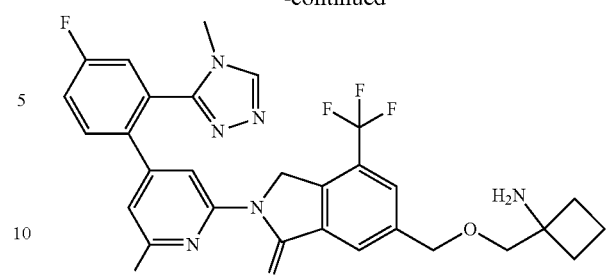
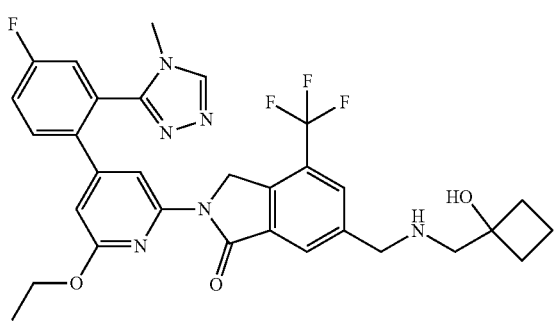
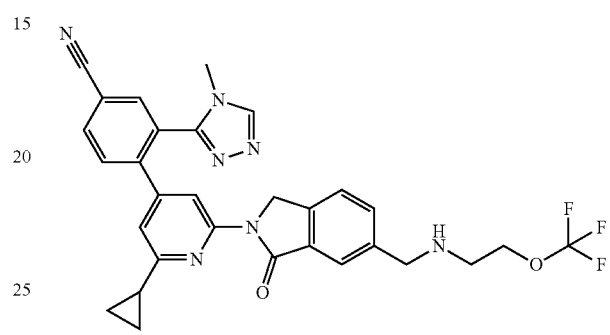
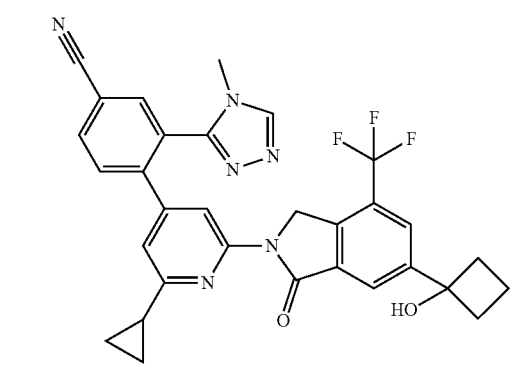
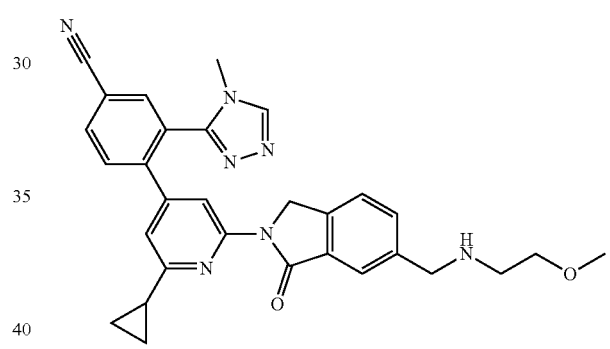
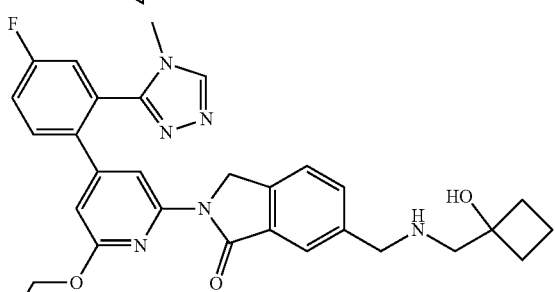
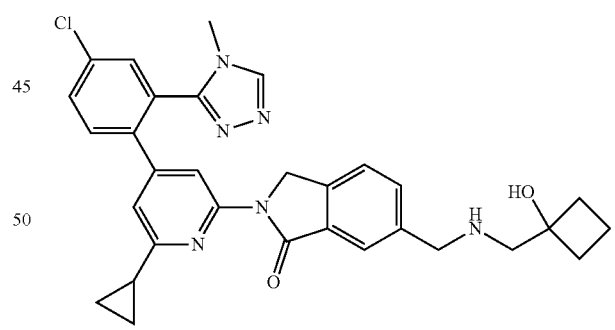
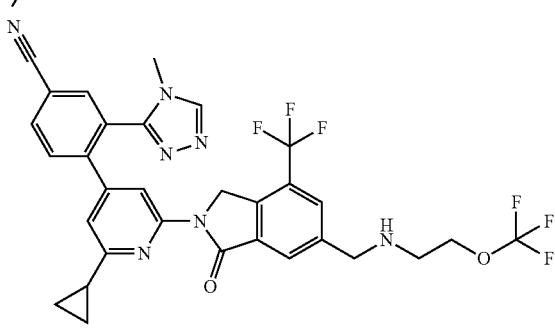
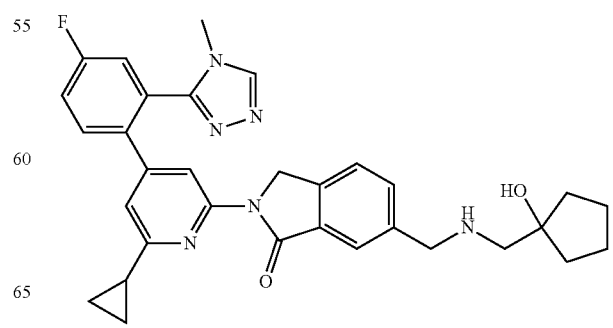

1105 -continued
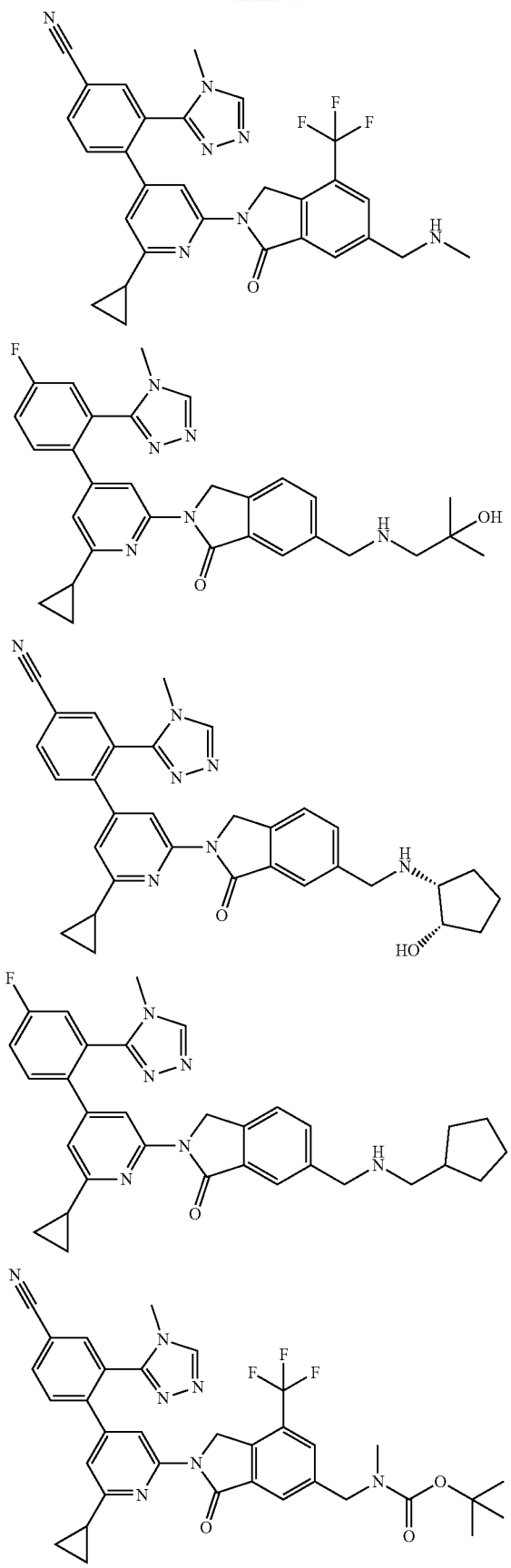
1106 -continued
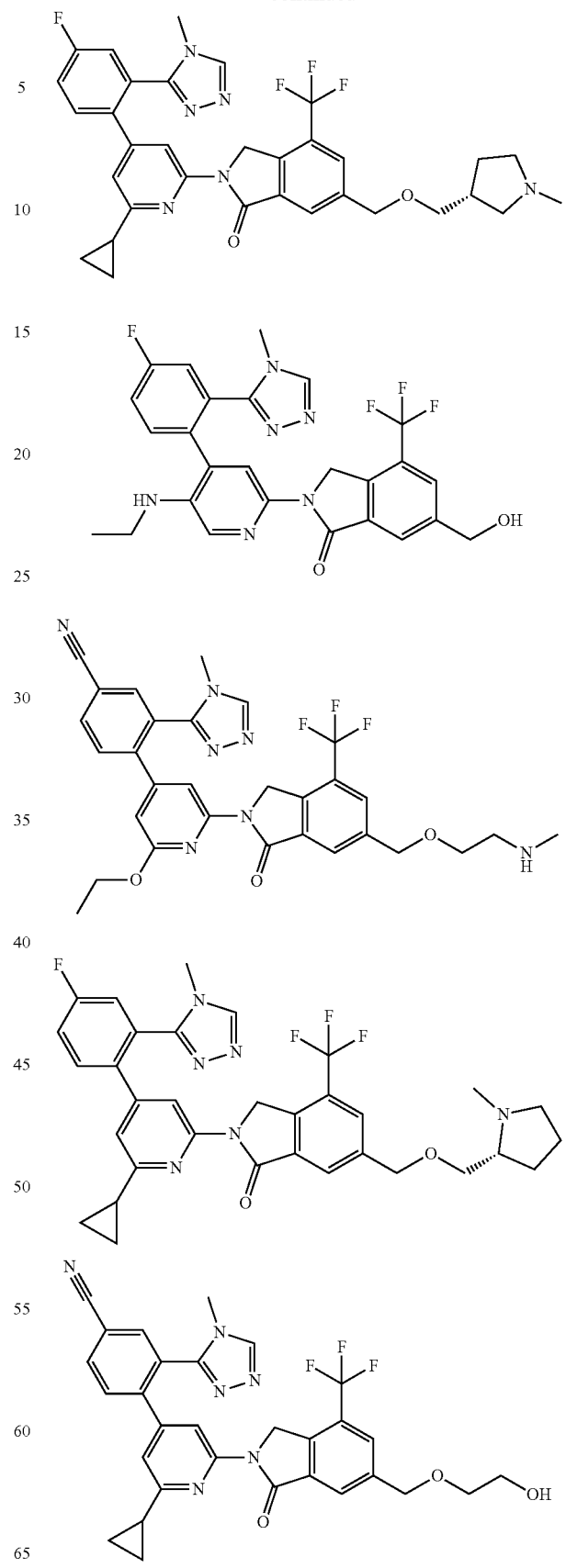

1107
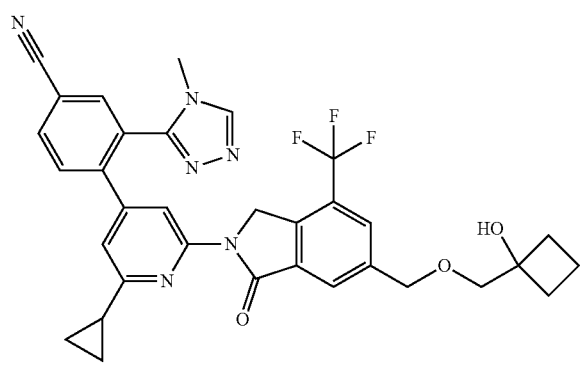
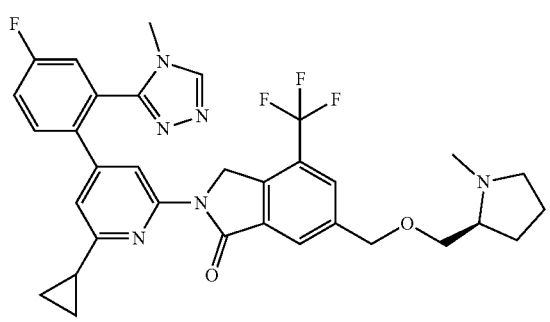
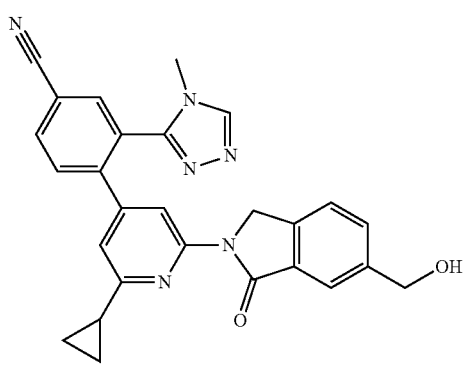
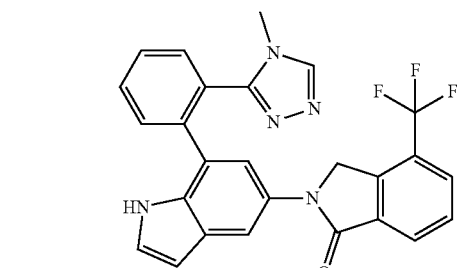
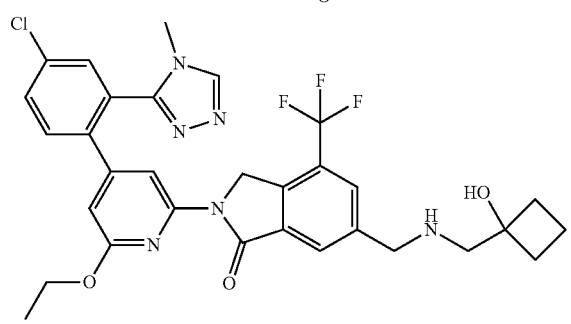
1108
-continued
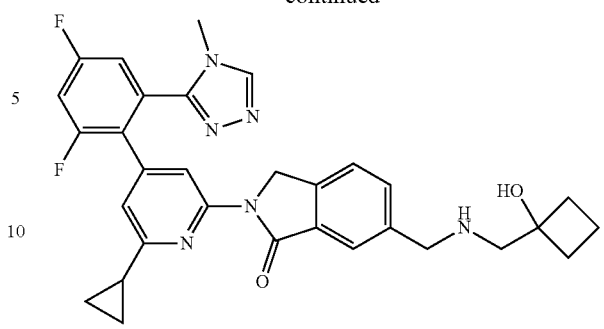
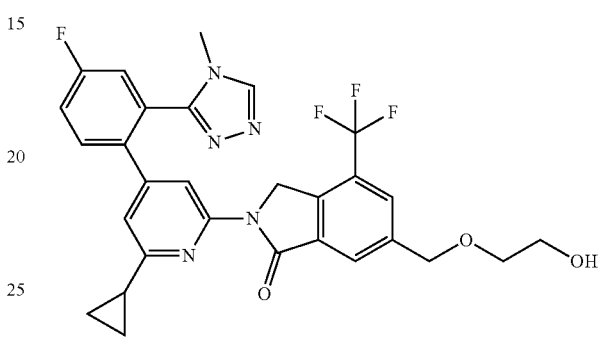
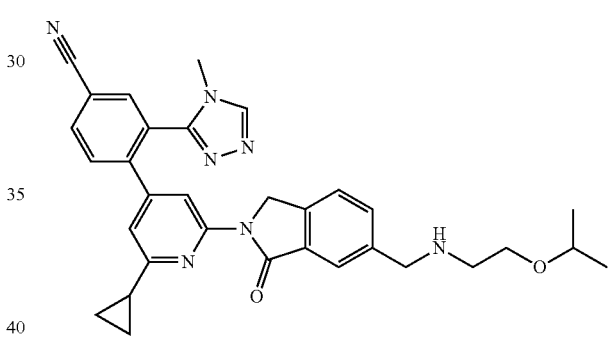
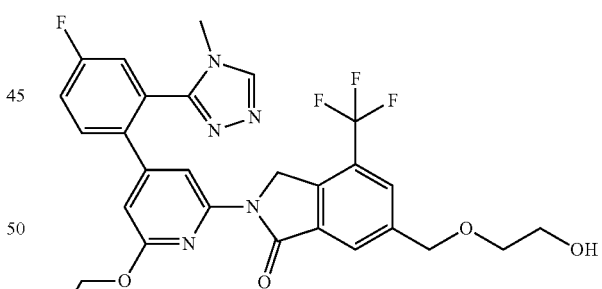
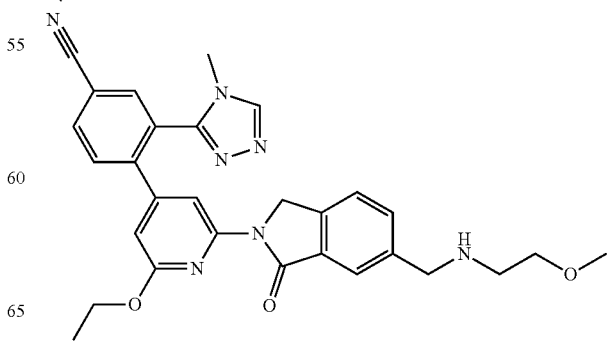

1109
-continued
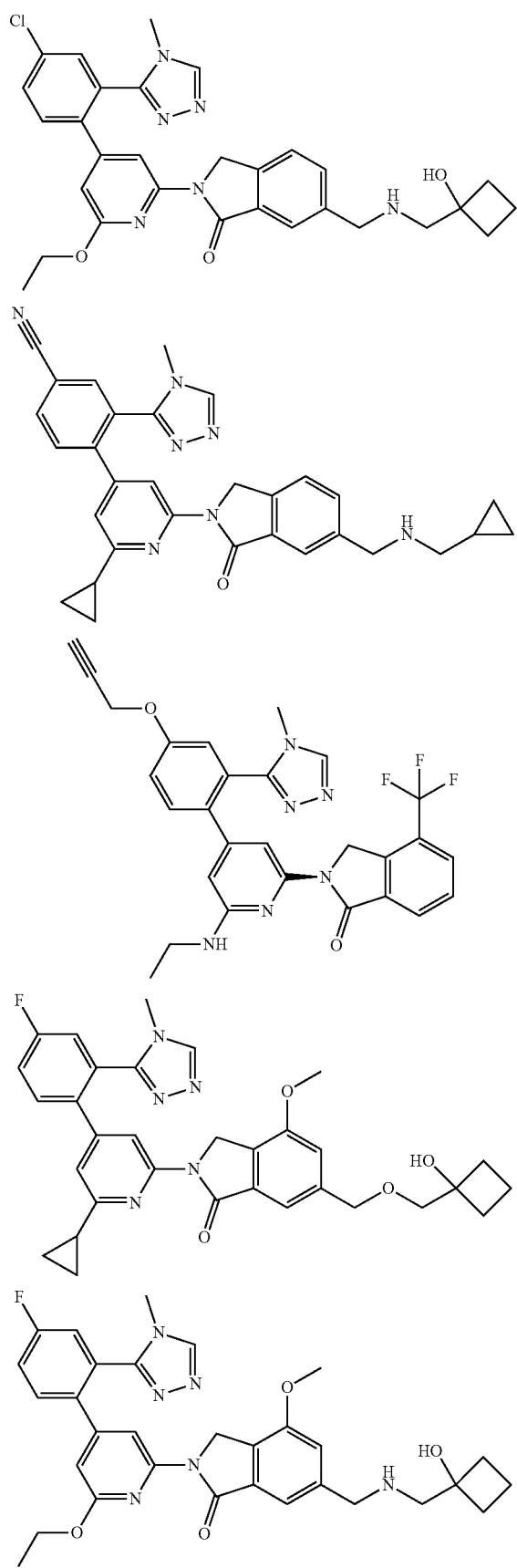
1110
-continued
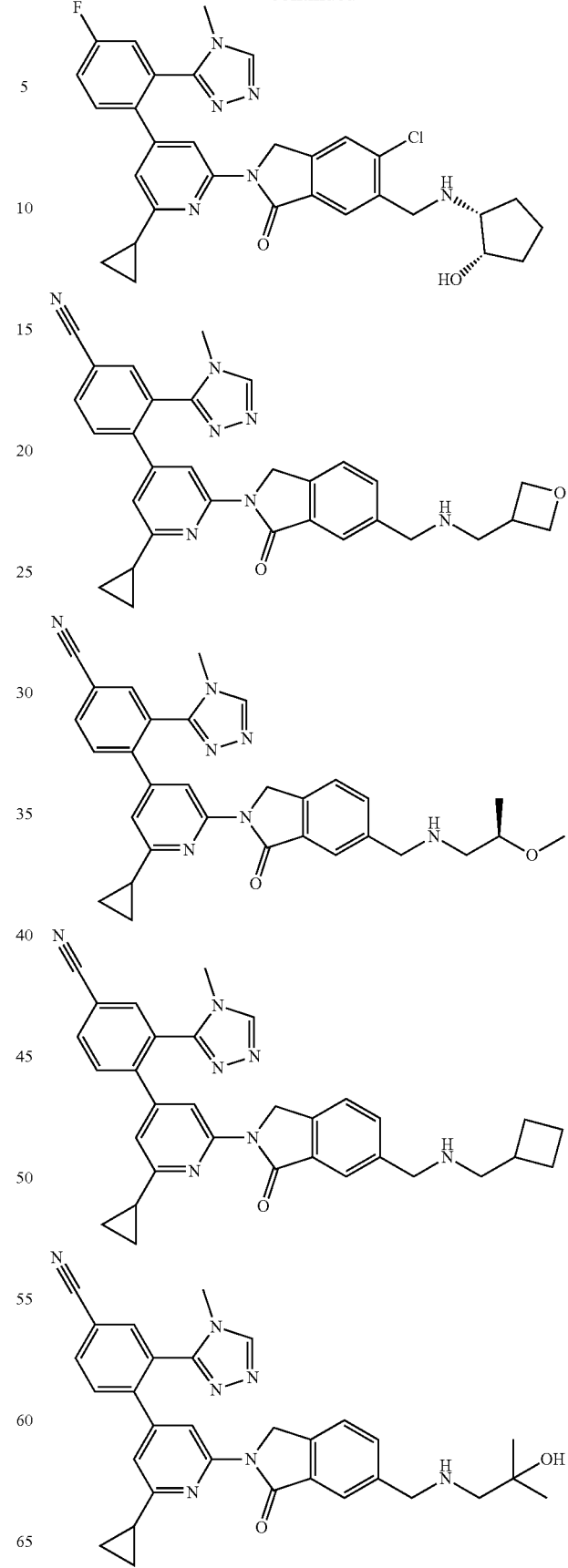

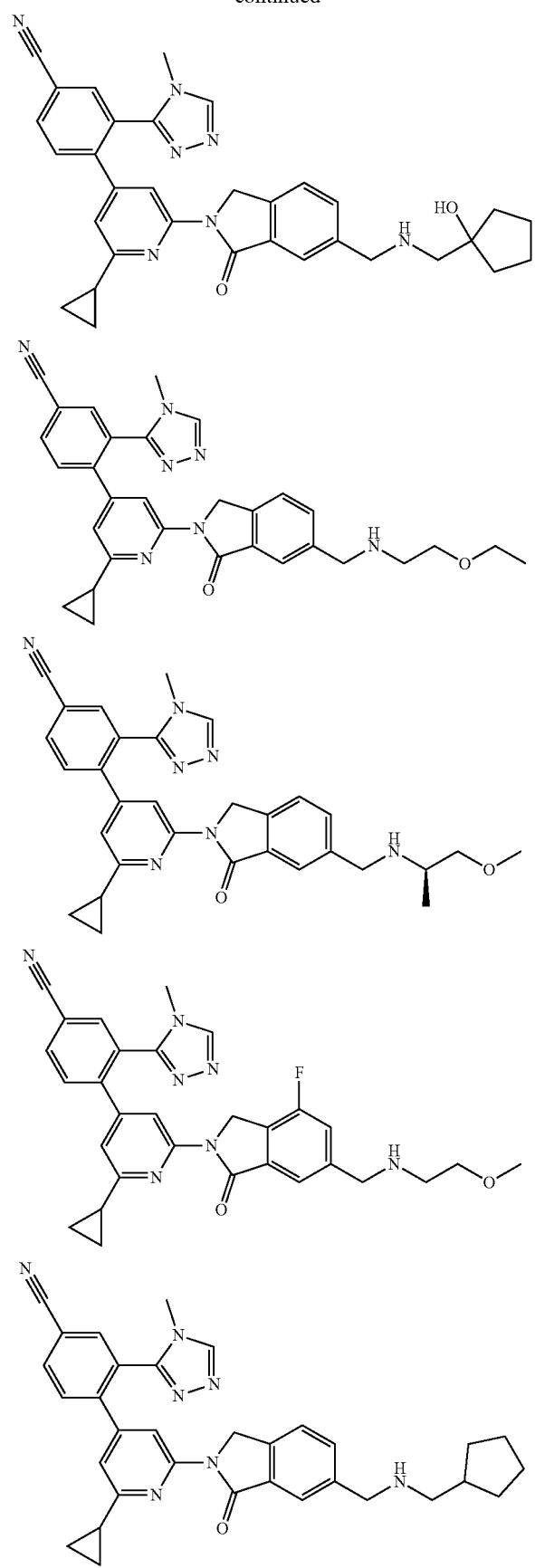
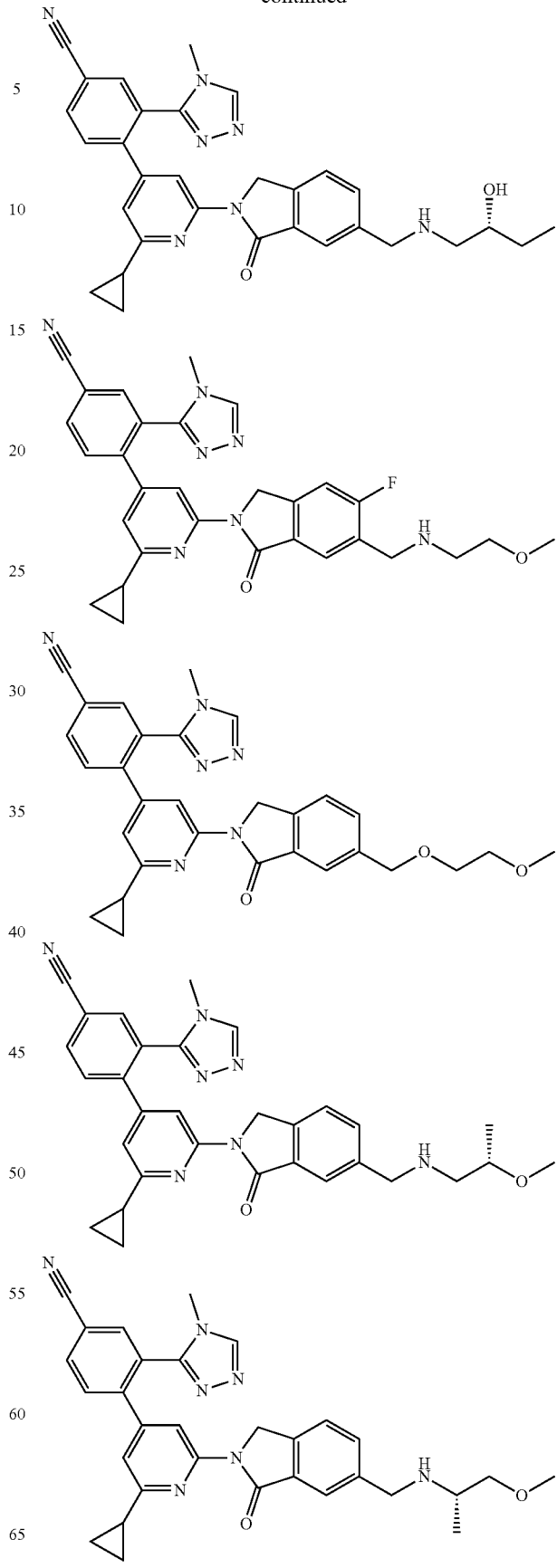

1113
-continued
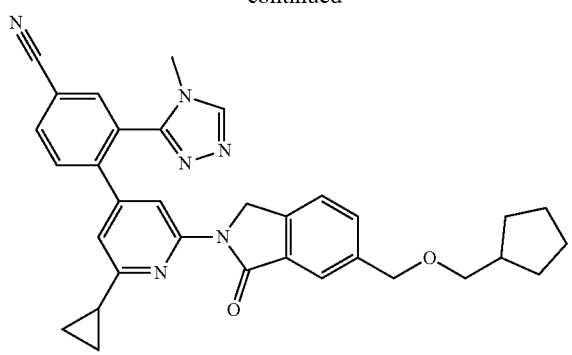
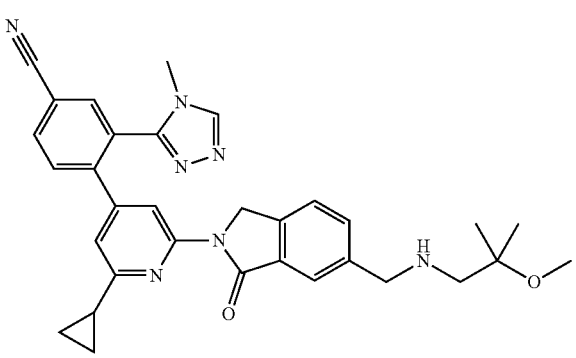
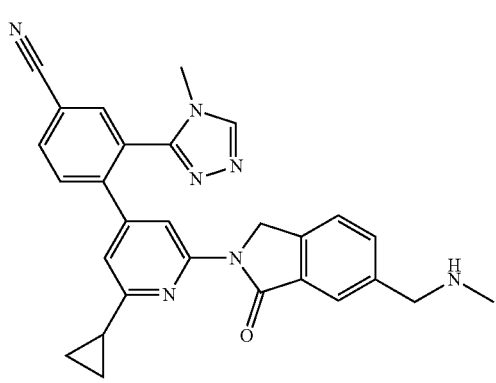
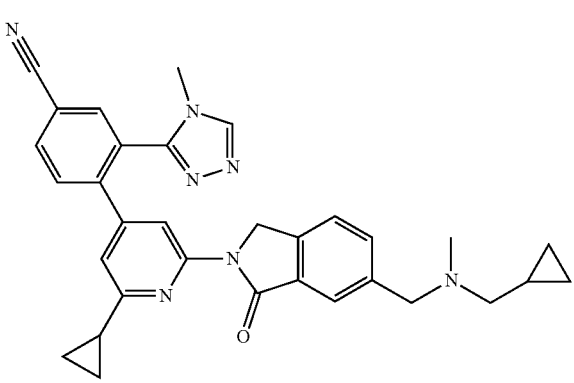
1114
-continued
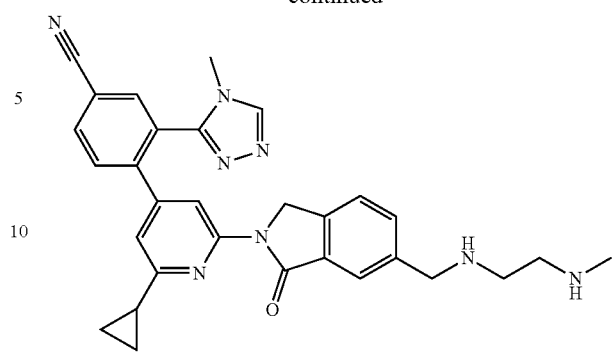
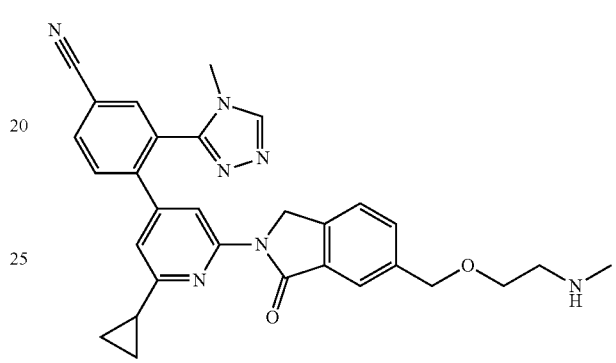
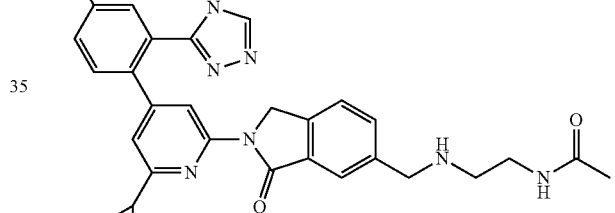
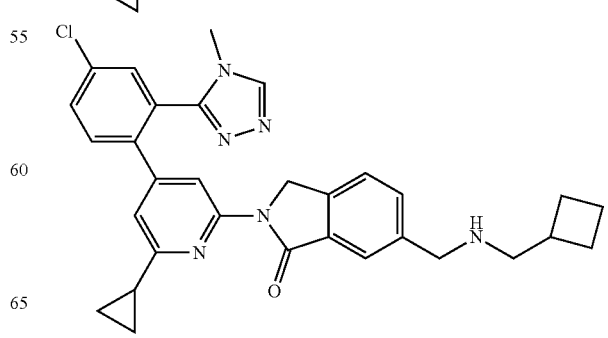

1115
-continued
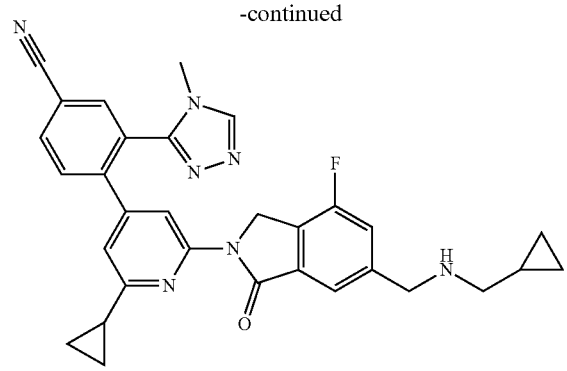
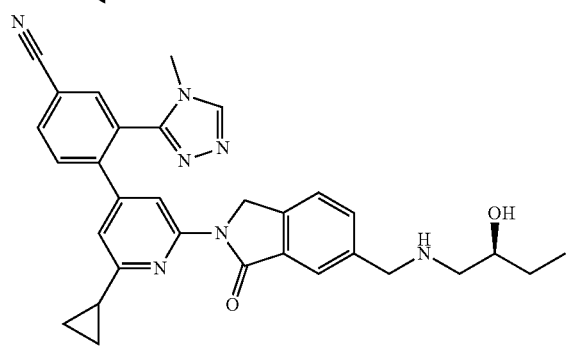
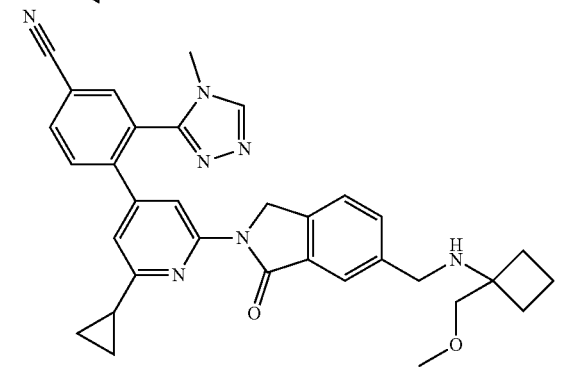
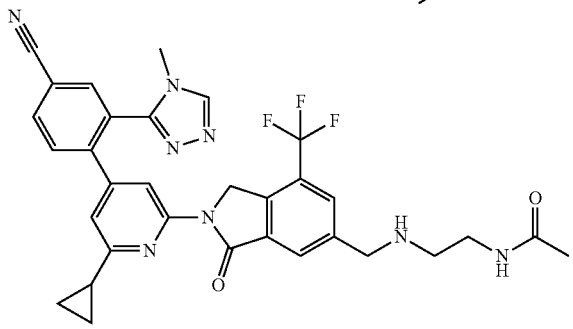
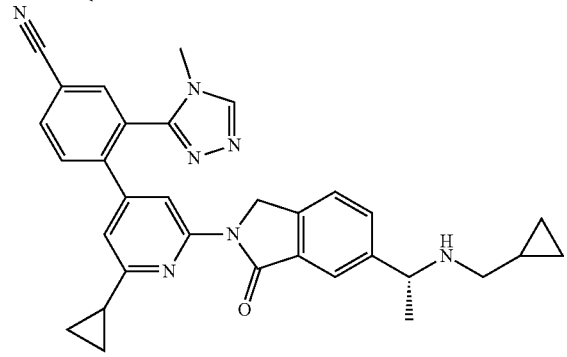
1116
-continued
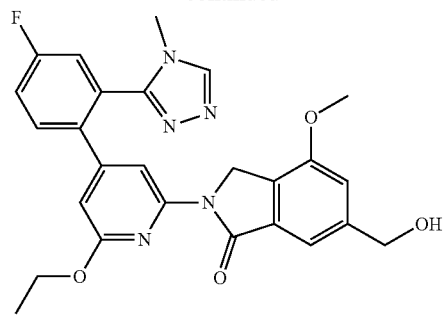
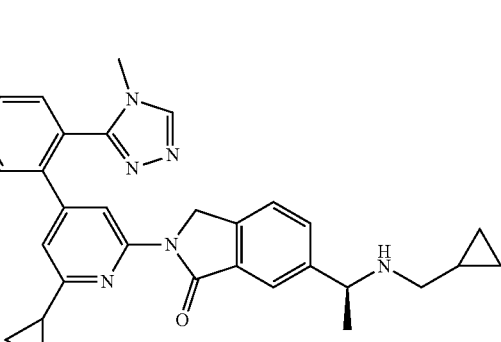
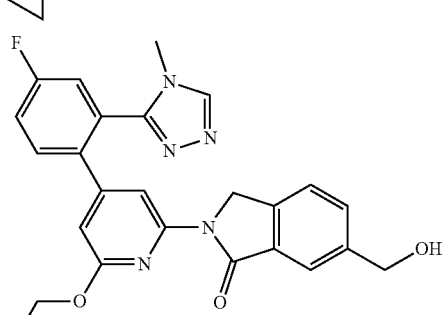
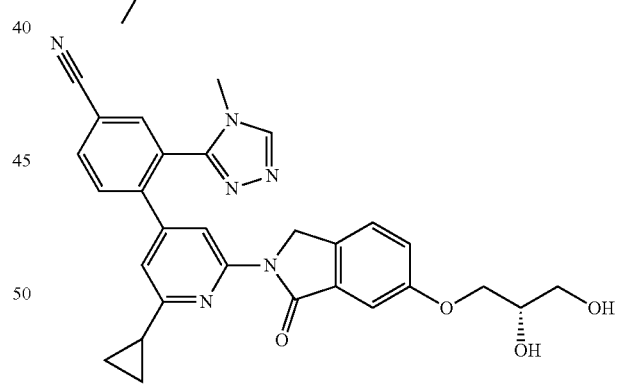
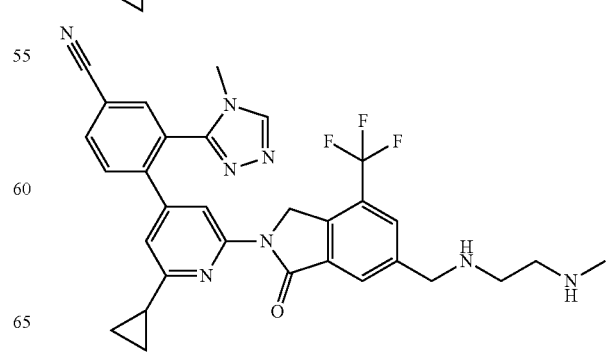

1117
-continued
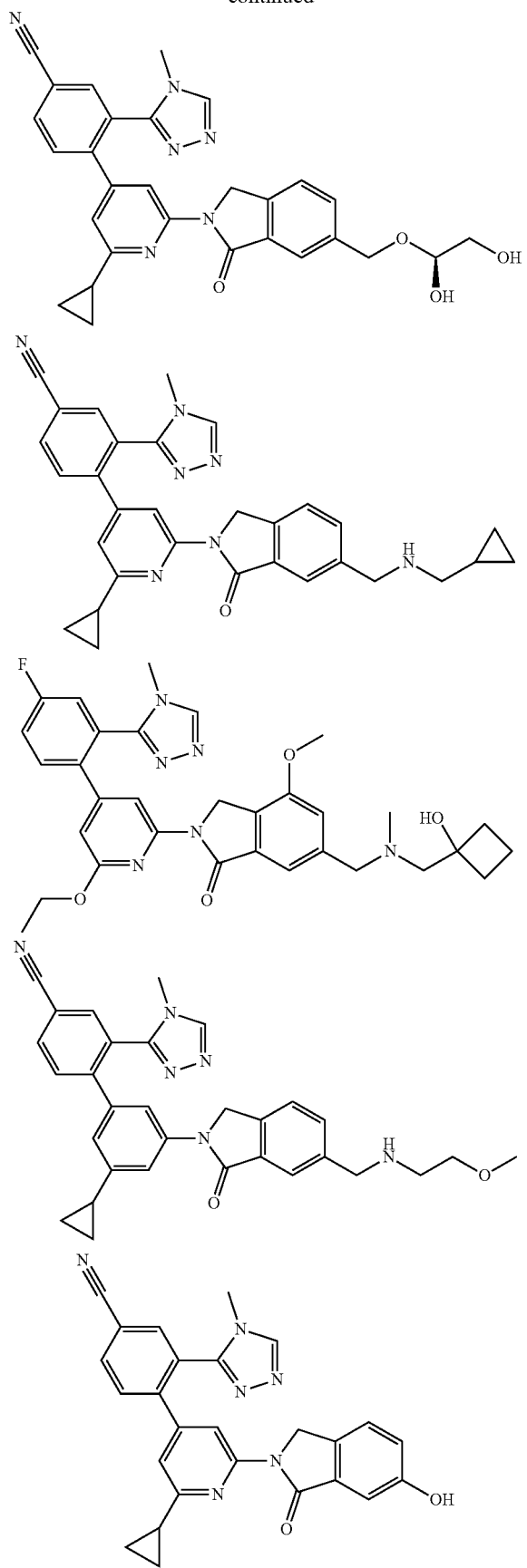
1118
-continued
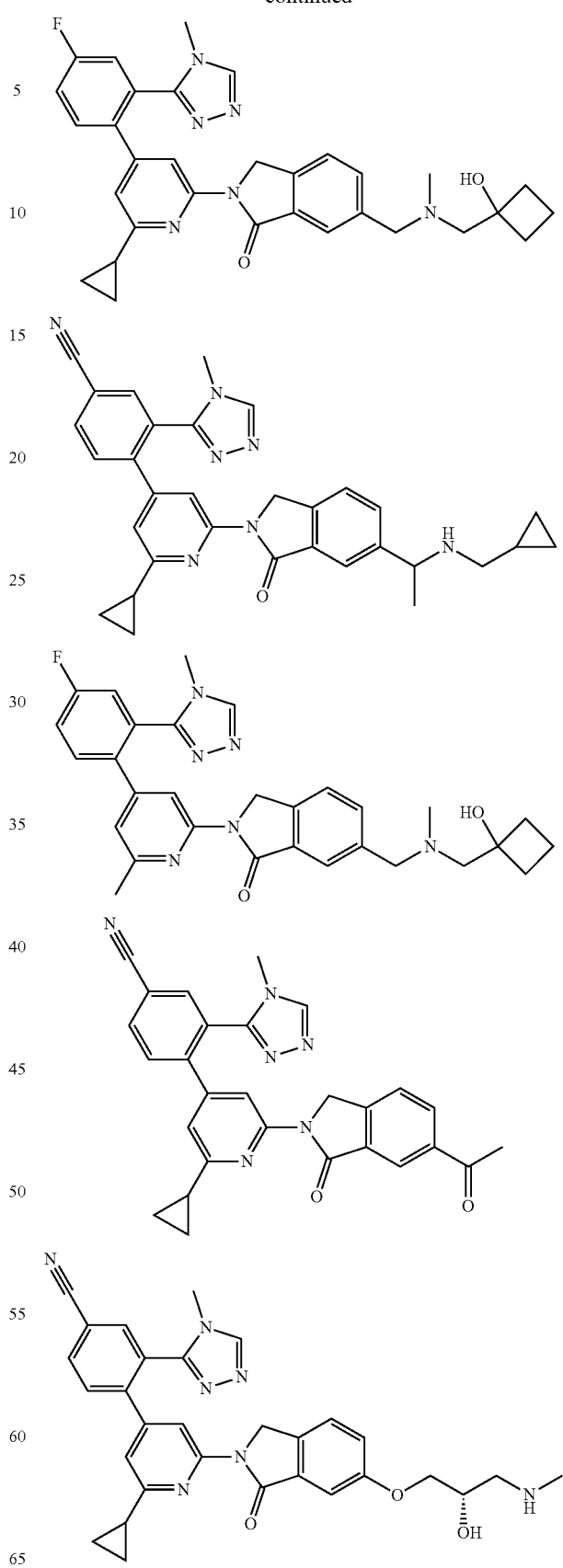

1119
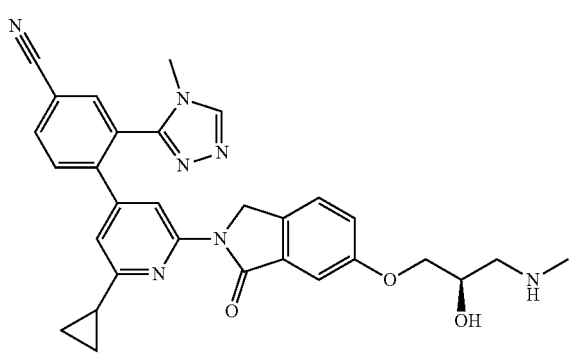
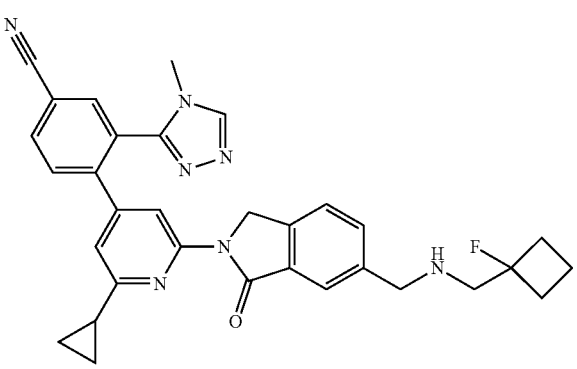
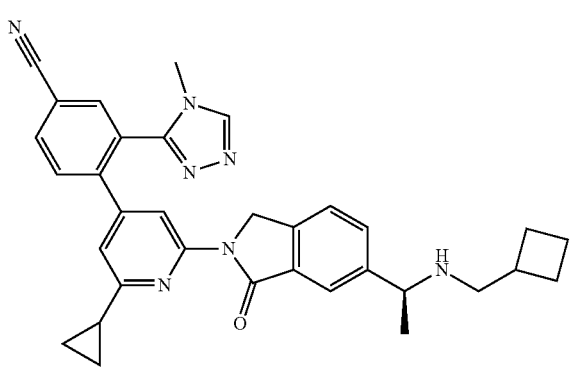
1120
-continued
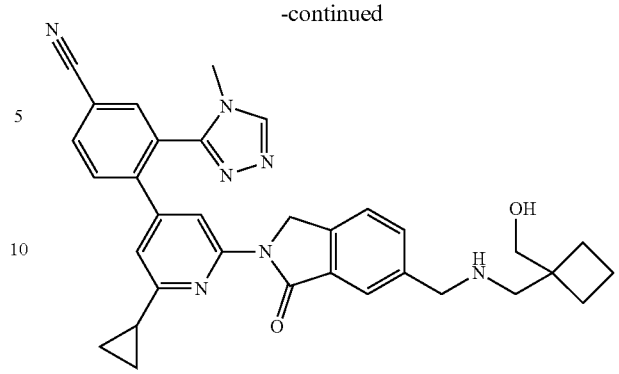
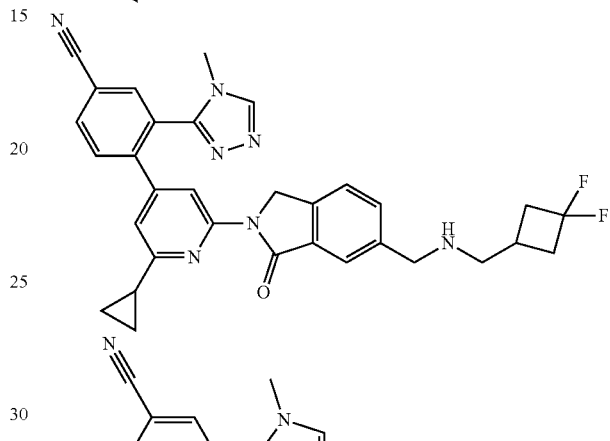
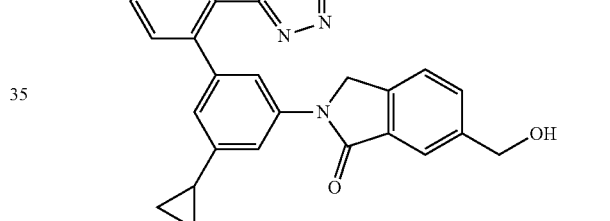
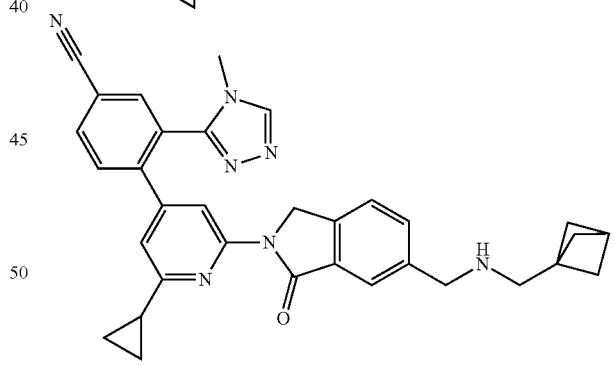
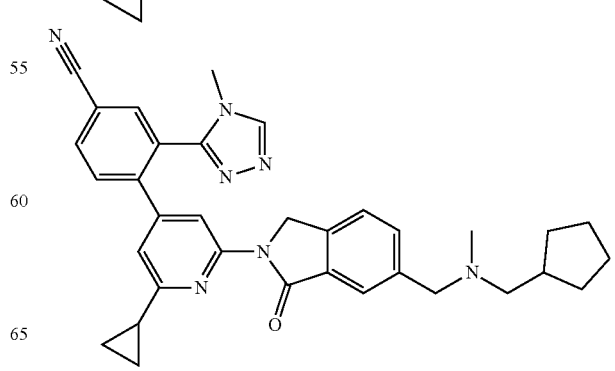

1121
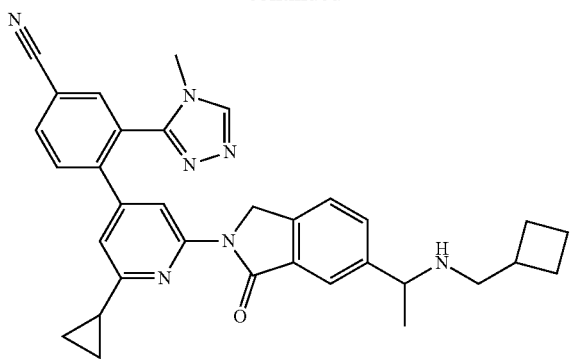
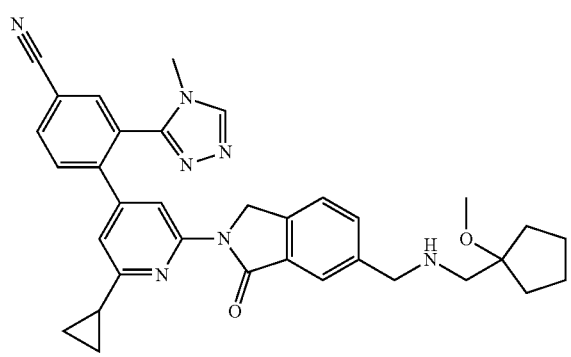
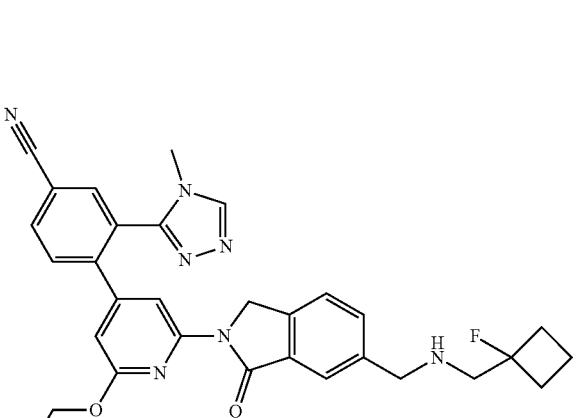
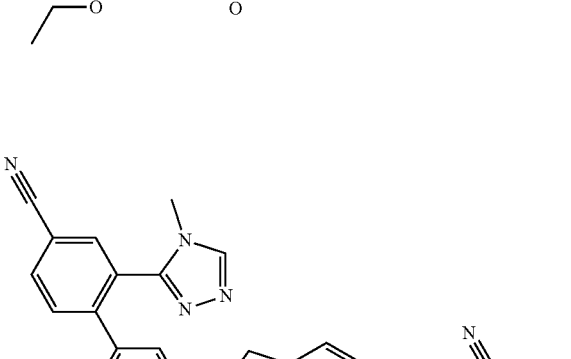
1122
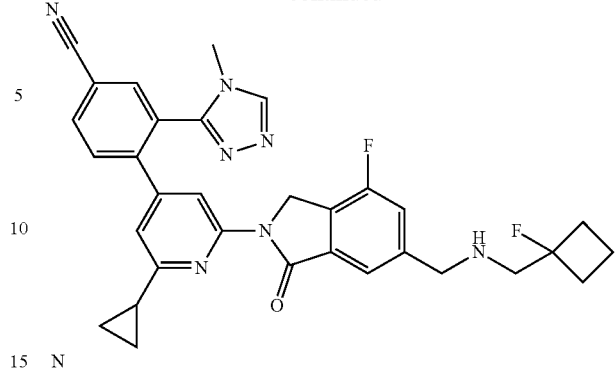
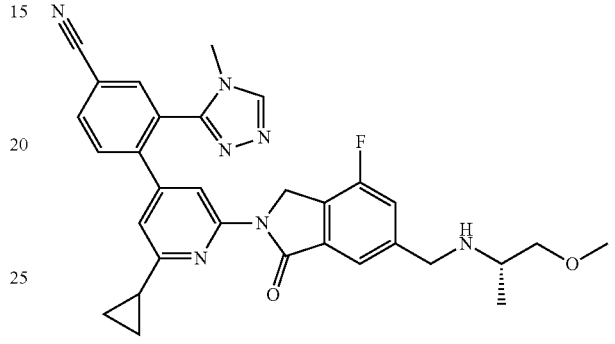
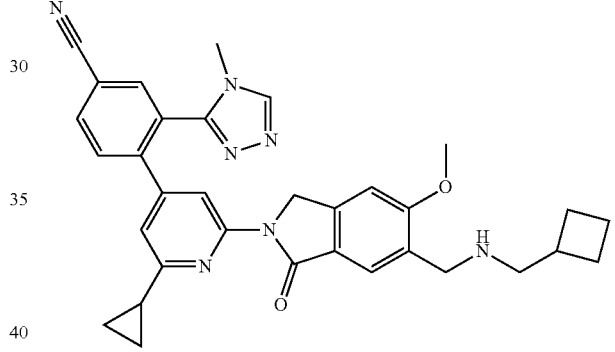
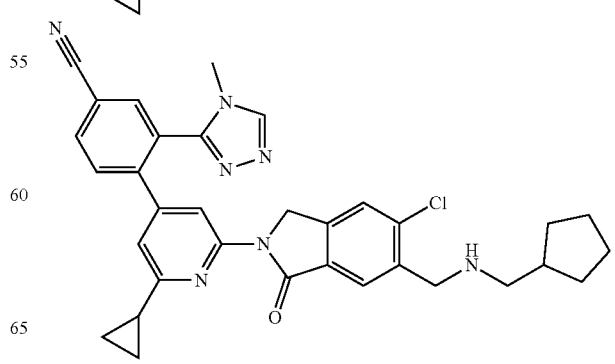

1123
-continued
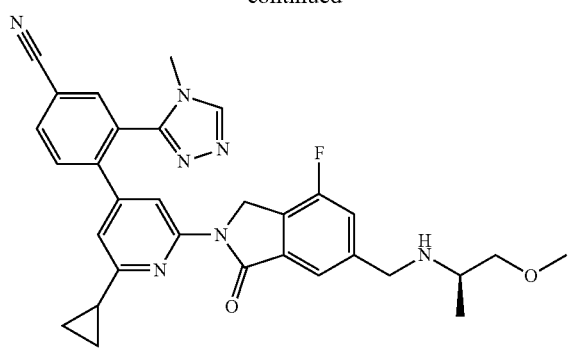
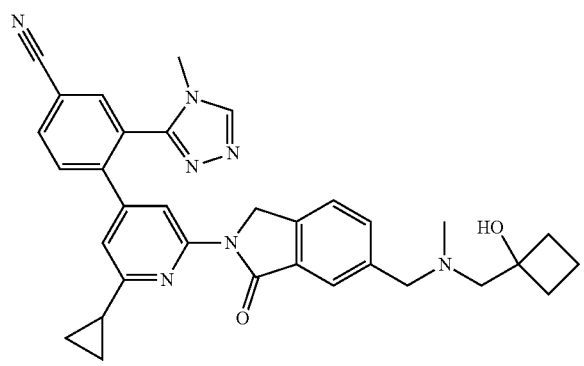
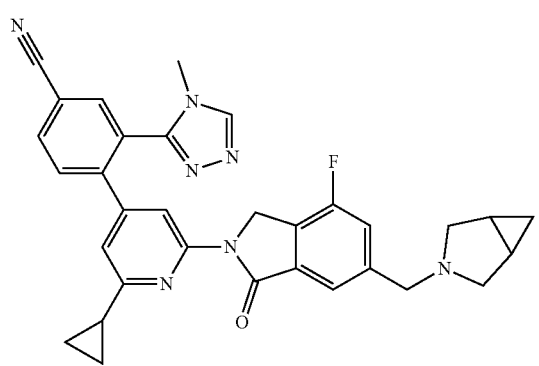
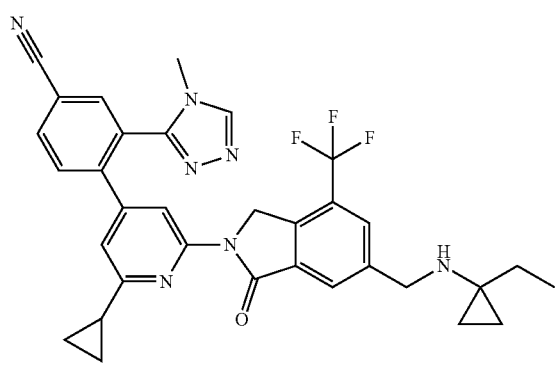
1124
-continued
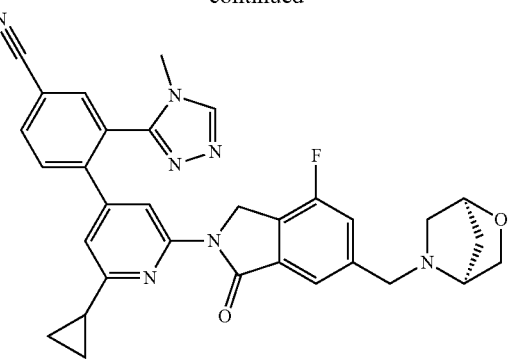
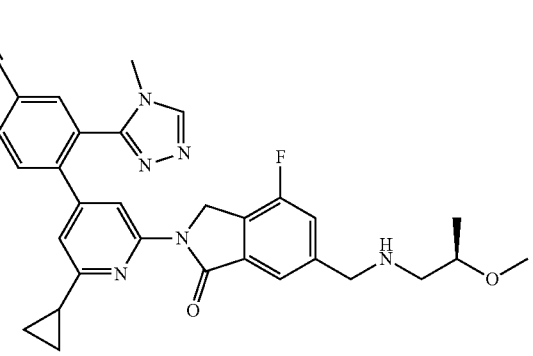
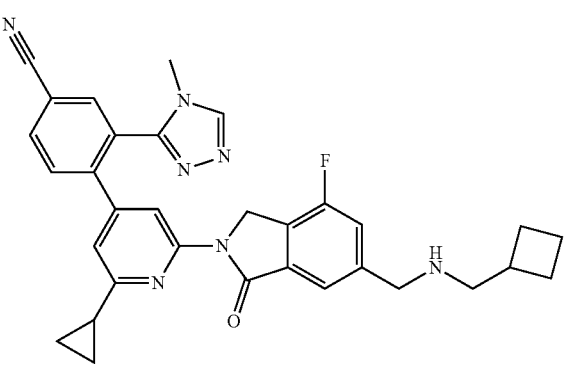
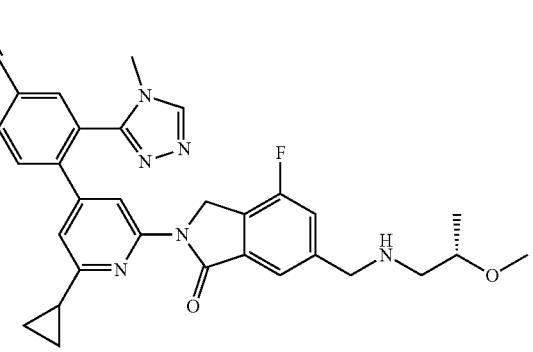

1125
-continued
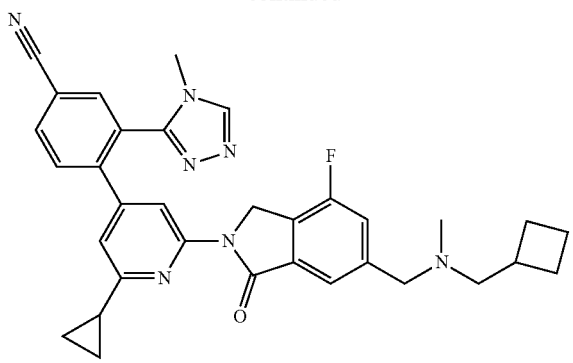
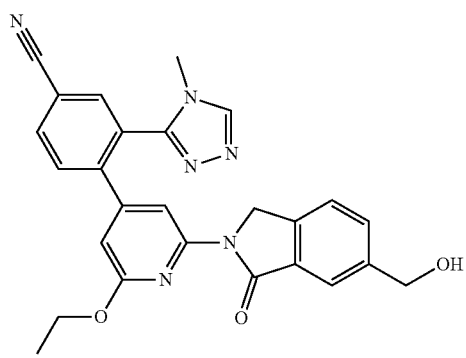
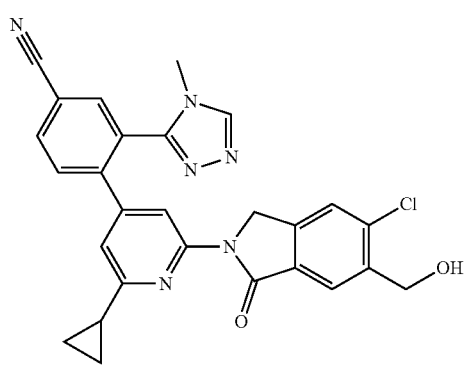
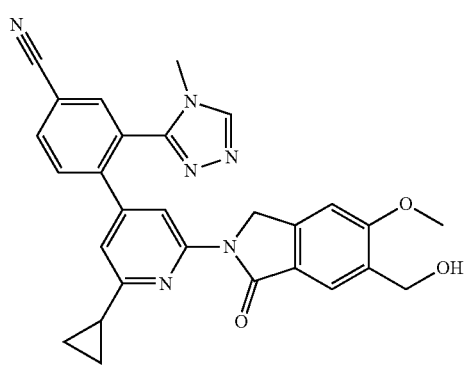
1126
-continued
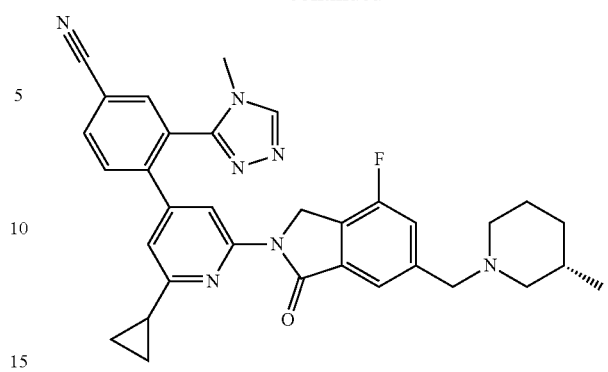
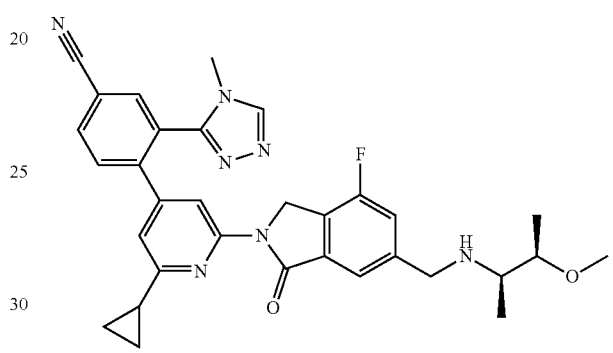
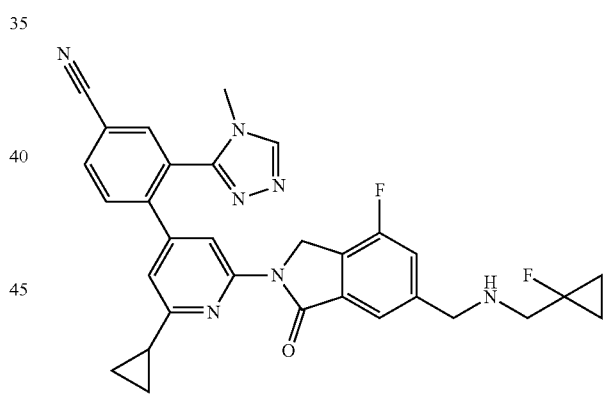
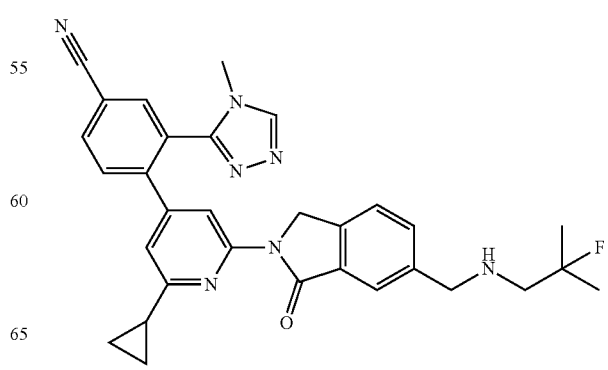

1127
-continued
1128
-continued
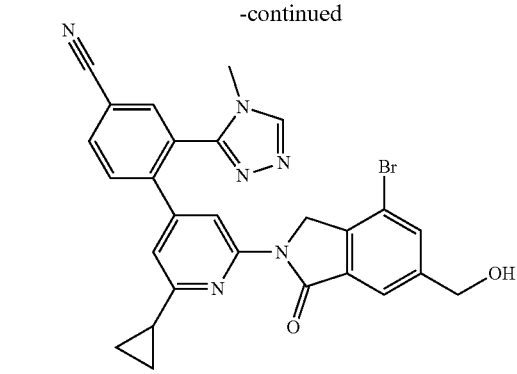
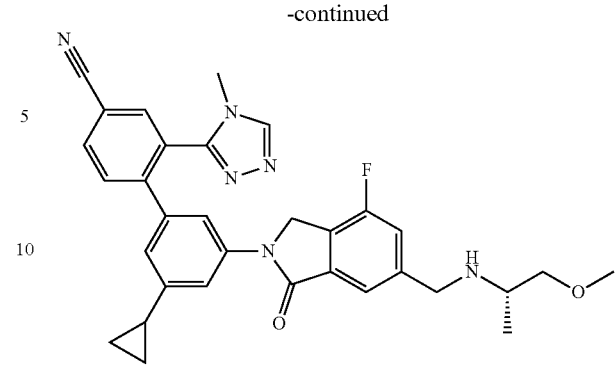
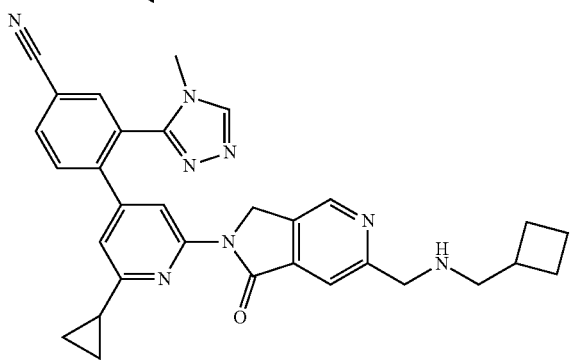
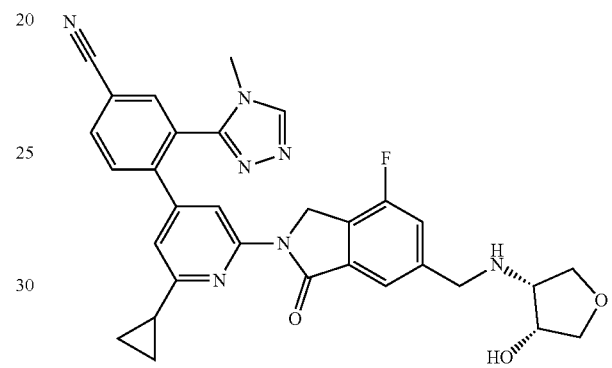
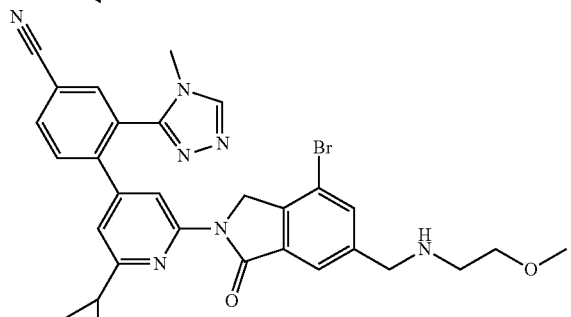
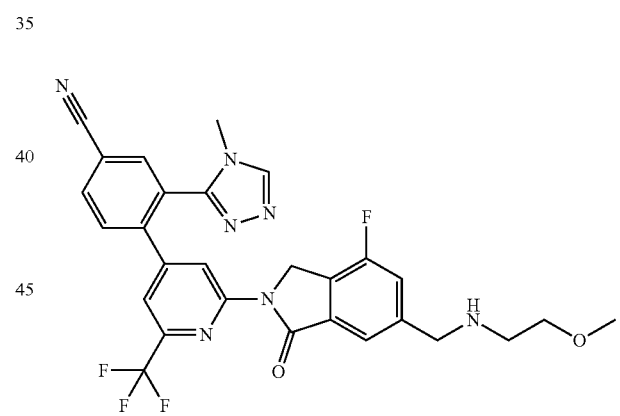
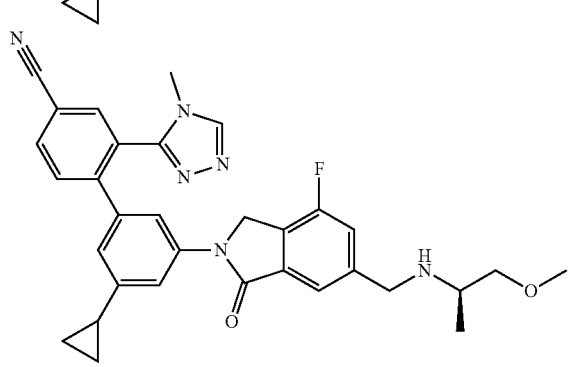
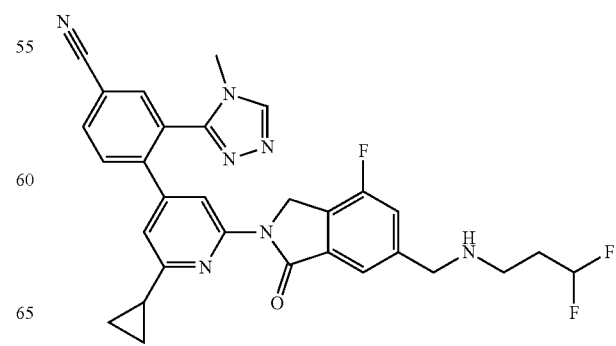

1129
-continued
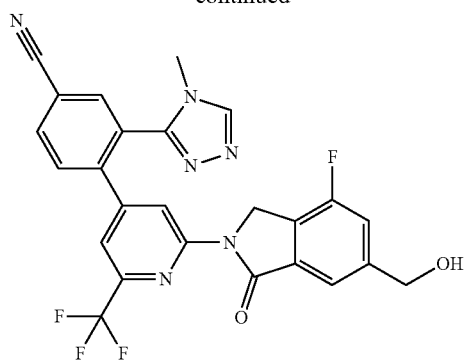
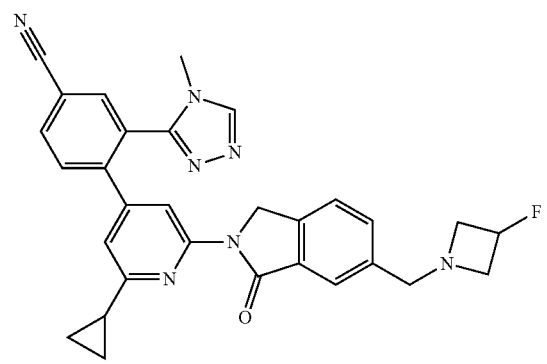
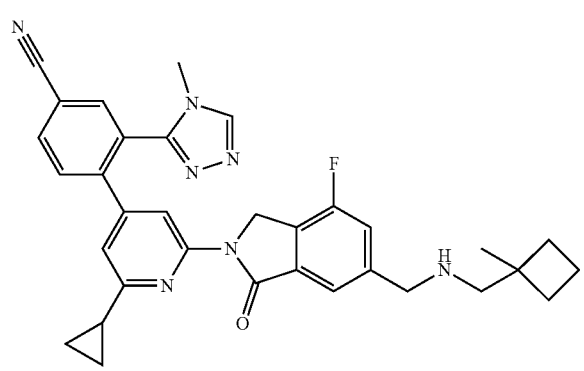
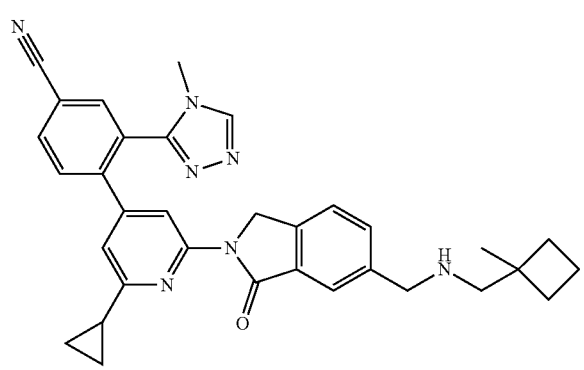
1130
-continued
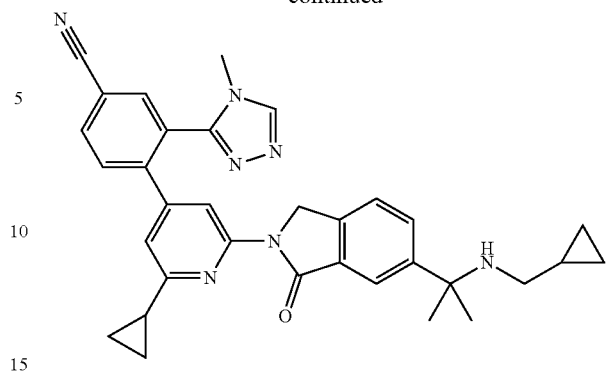
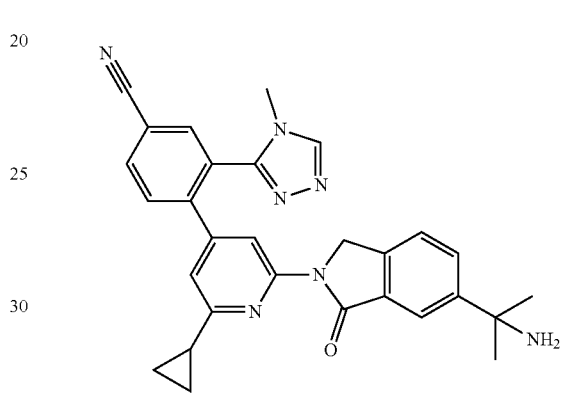
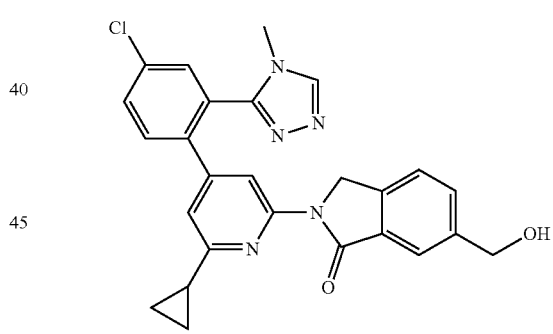
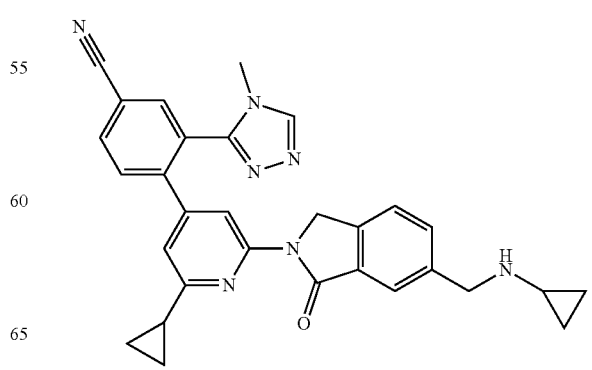

1131
-continued
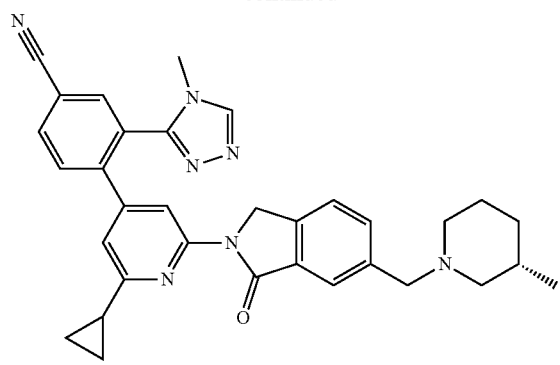
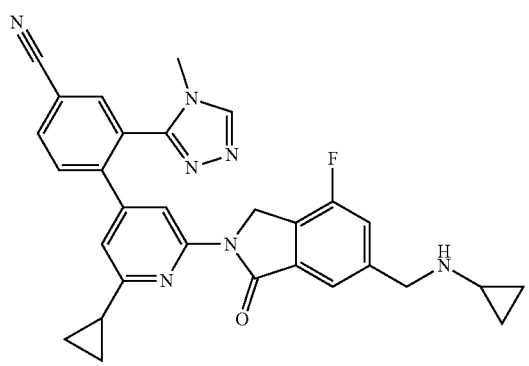
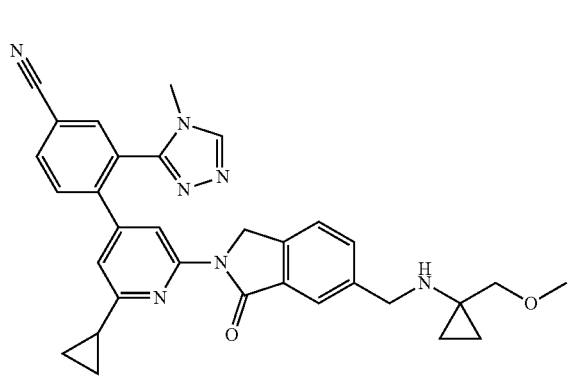
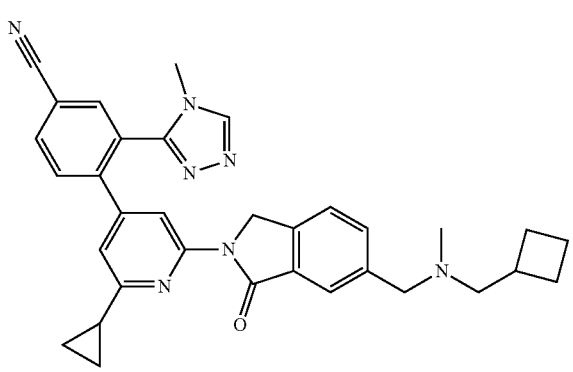
1132
-continued
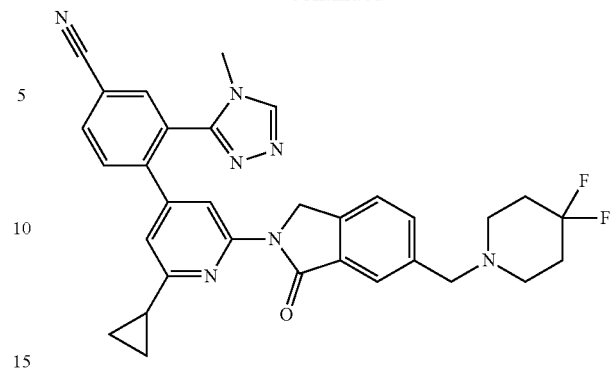
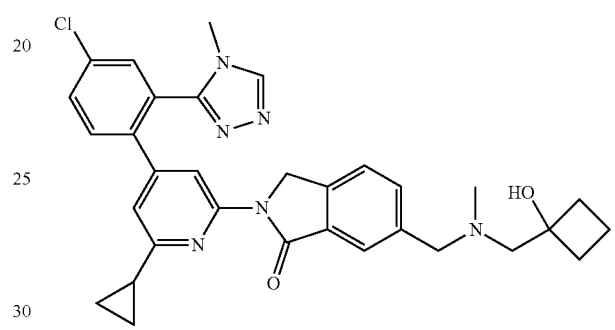
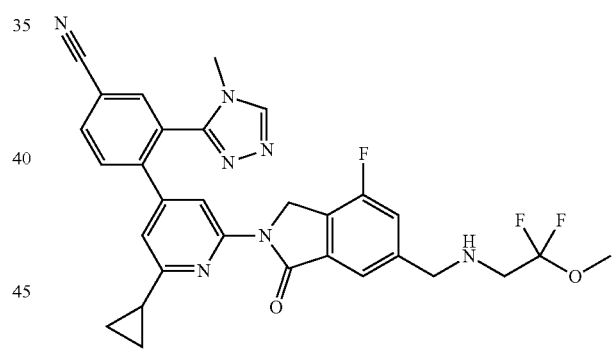
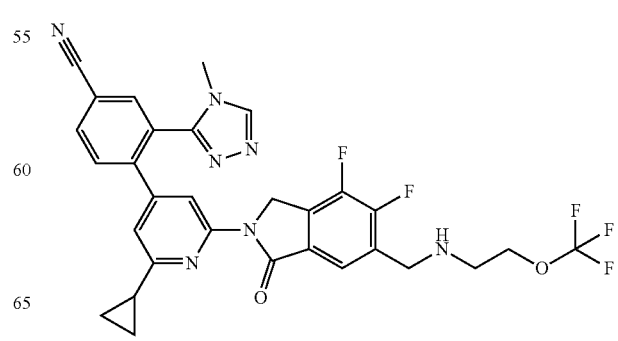

1133
-continued
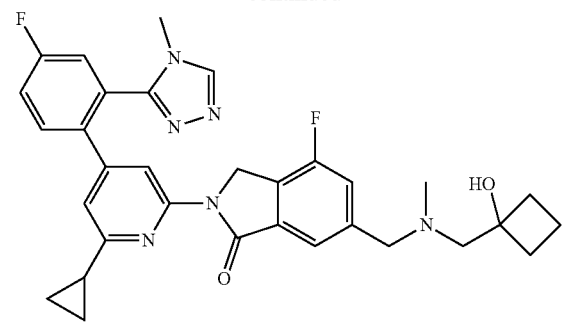
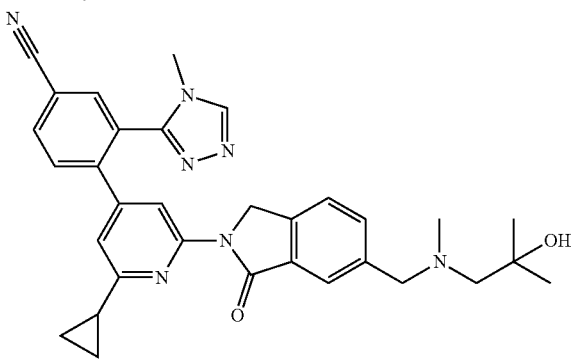
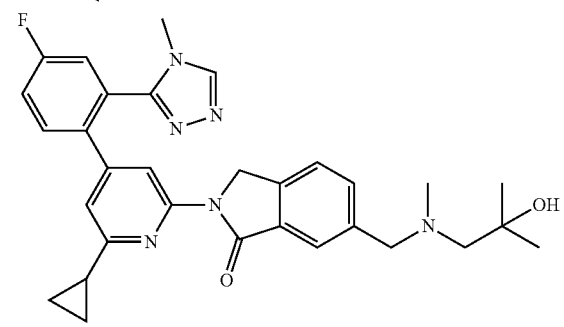
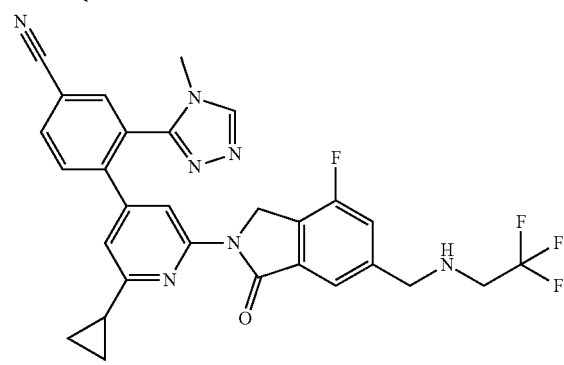
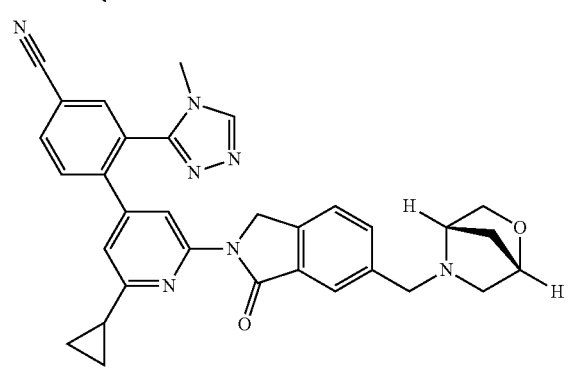
1134
-continued
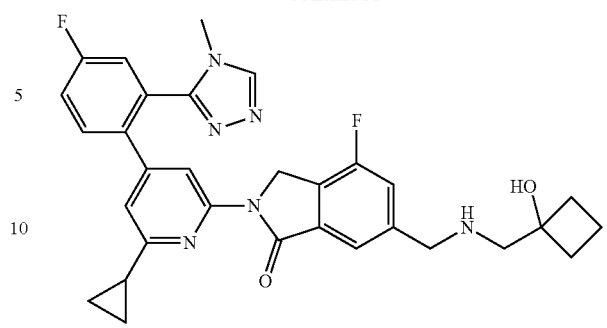
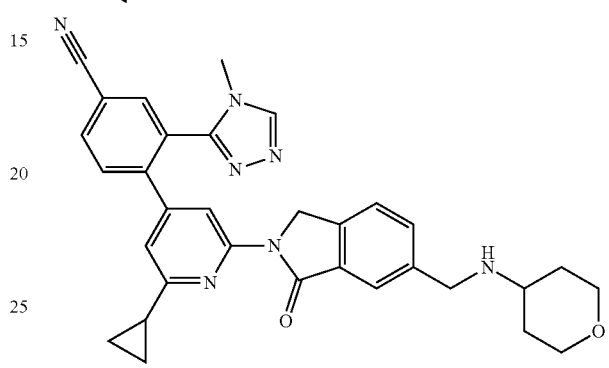
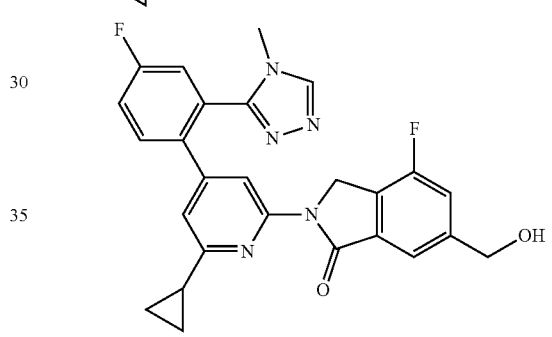
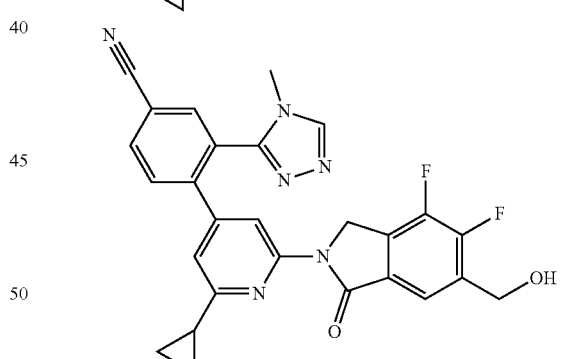
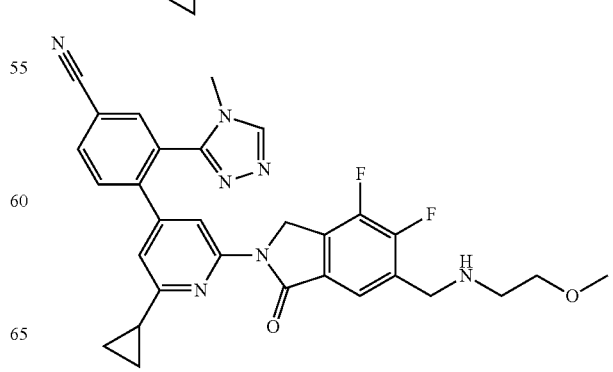

1135
-continued
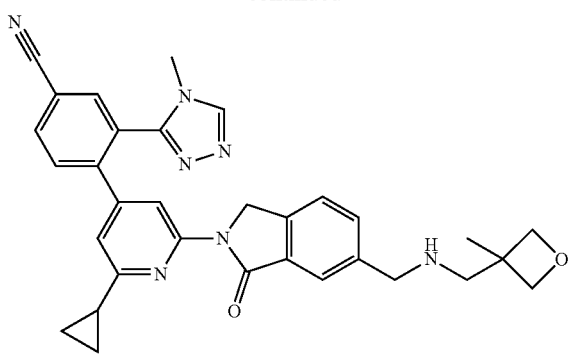
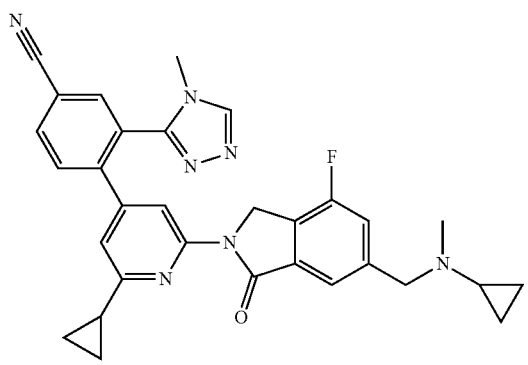
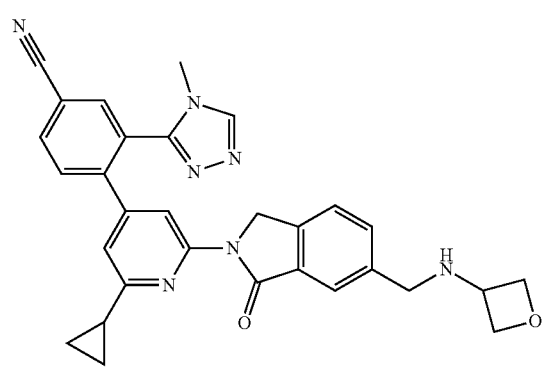
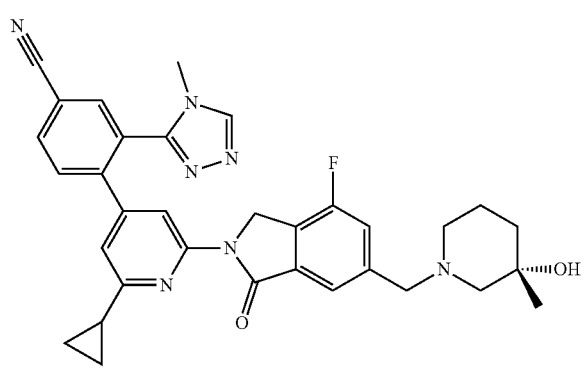
1136
-continued
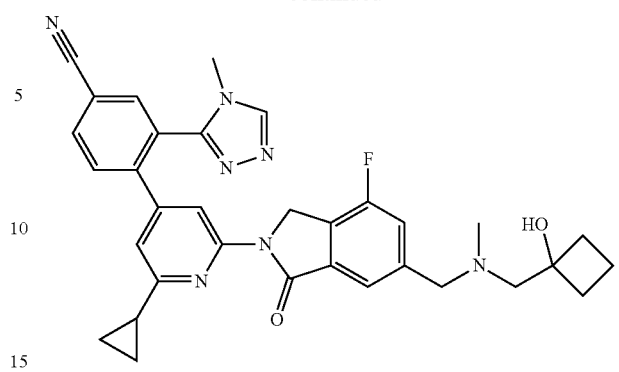
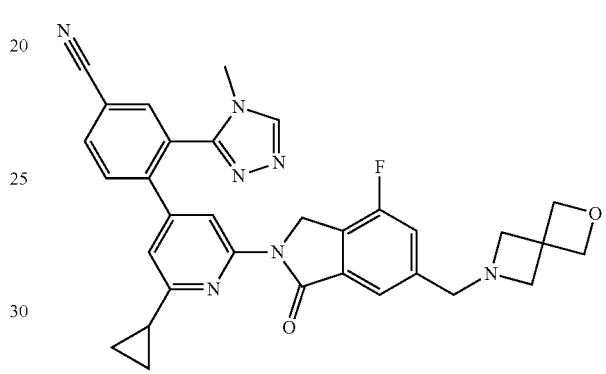
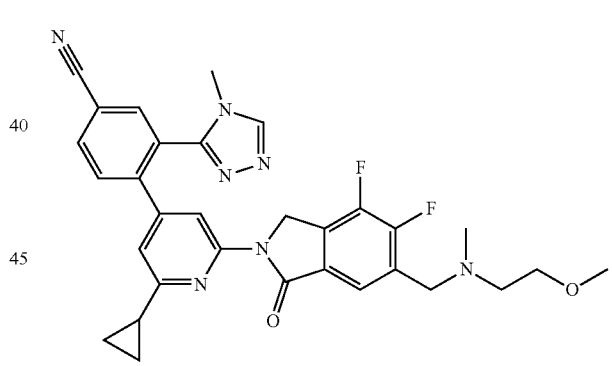
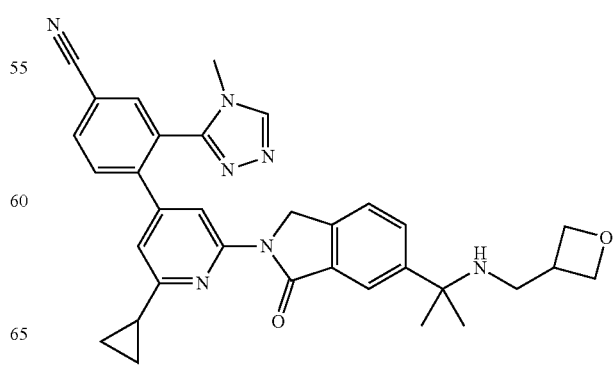

1137
-continued
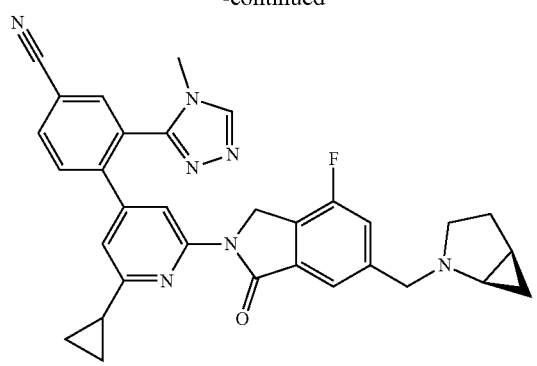
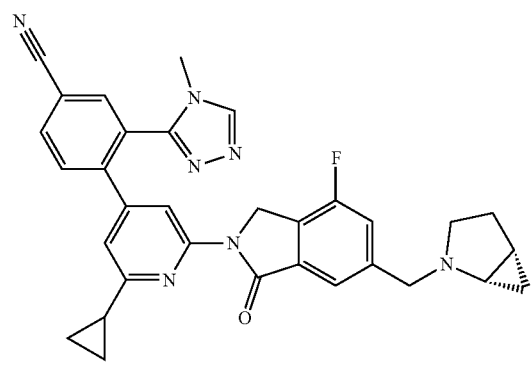
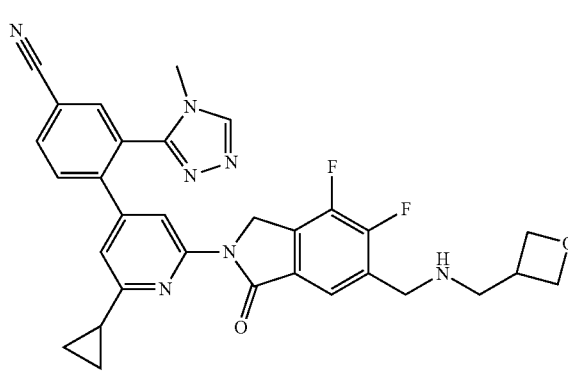
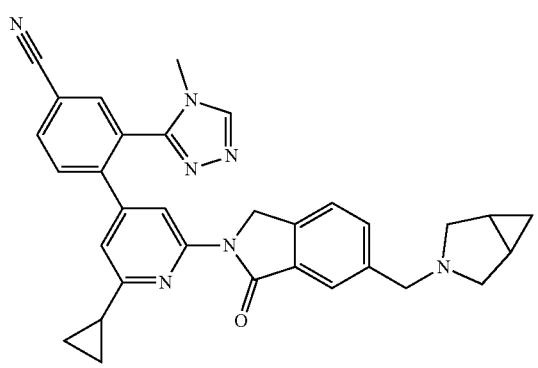
1138
-continued
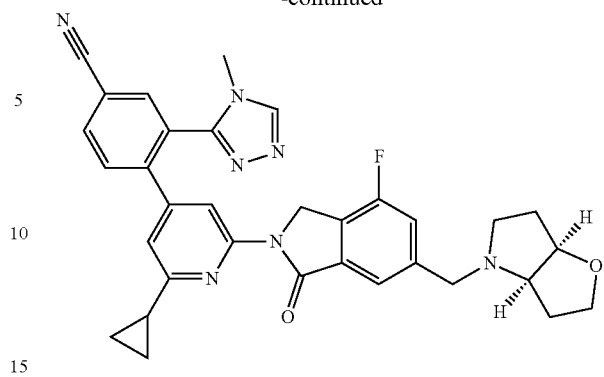
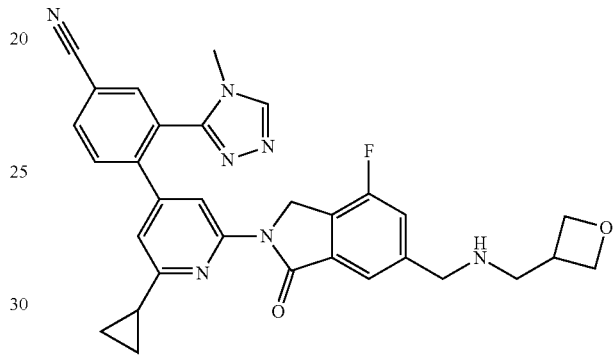
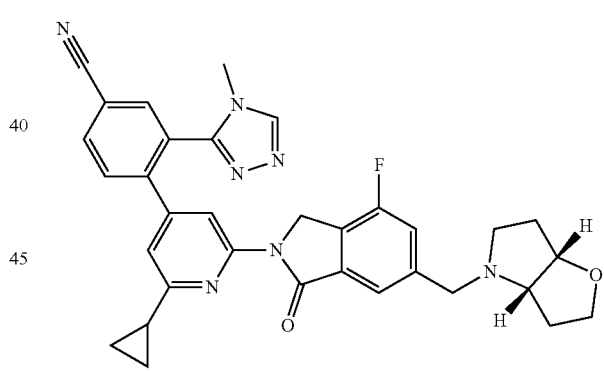
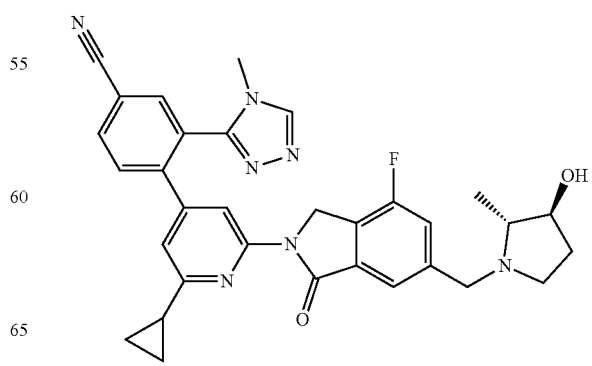

1139
-continued
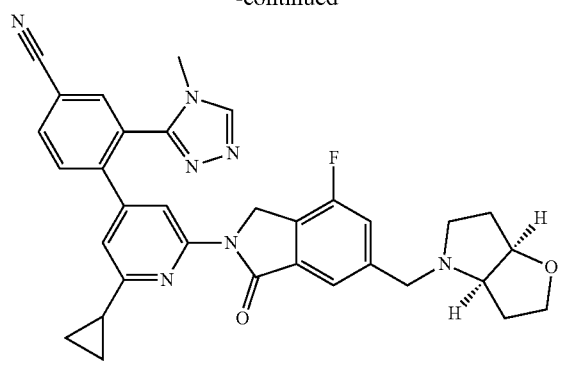
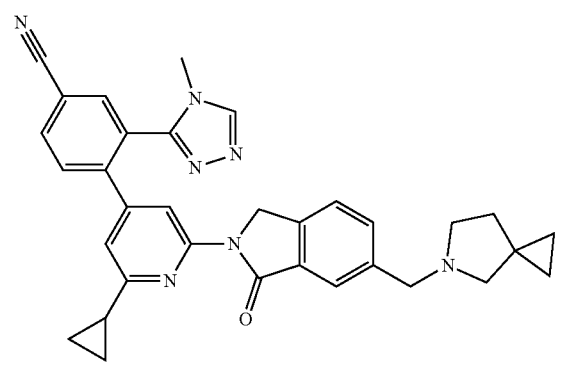
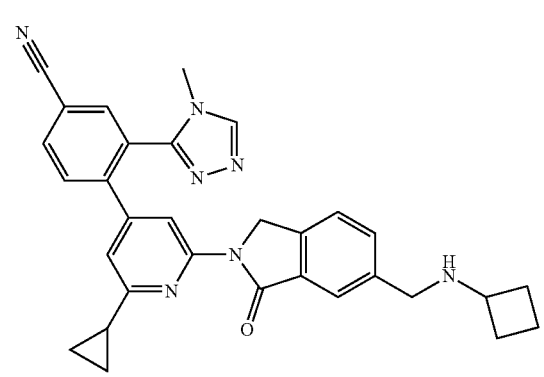
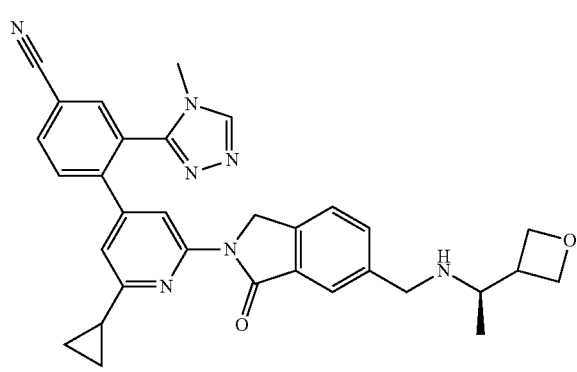
1140
-continued
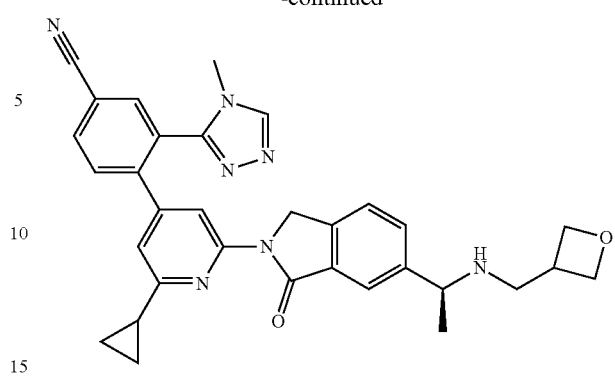
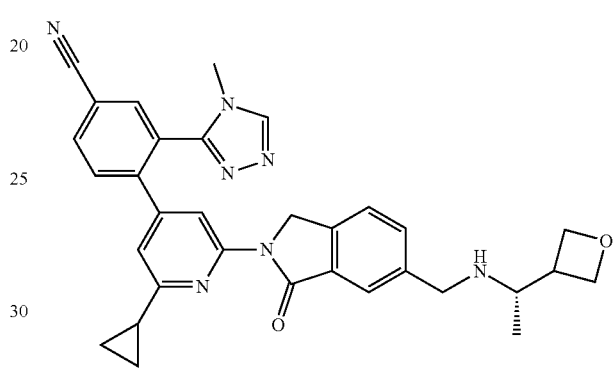
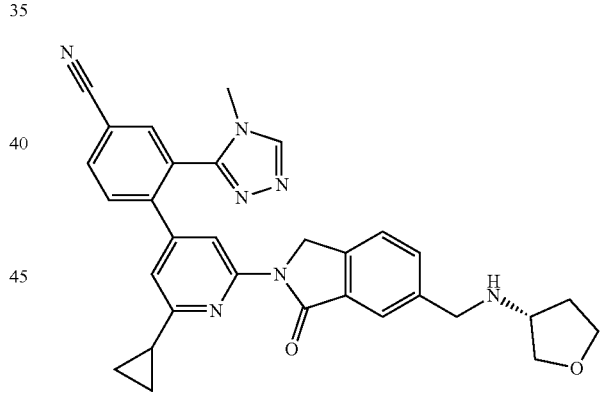
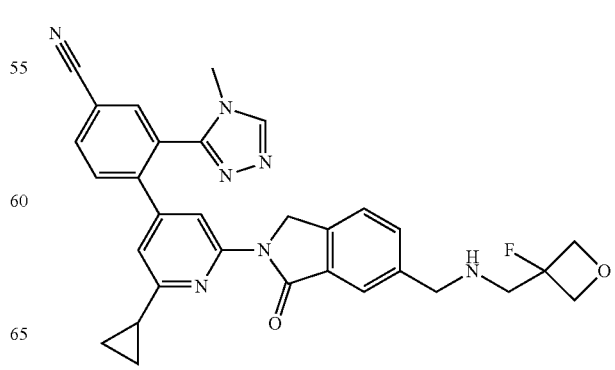

1141
-continued
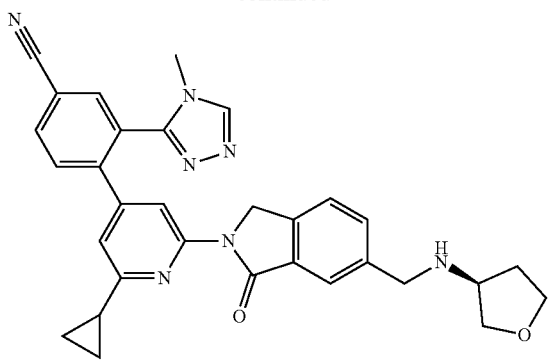
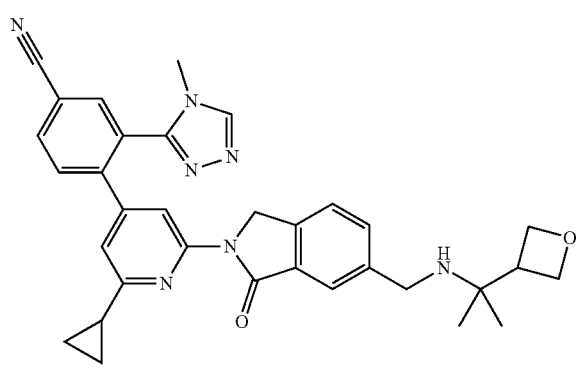
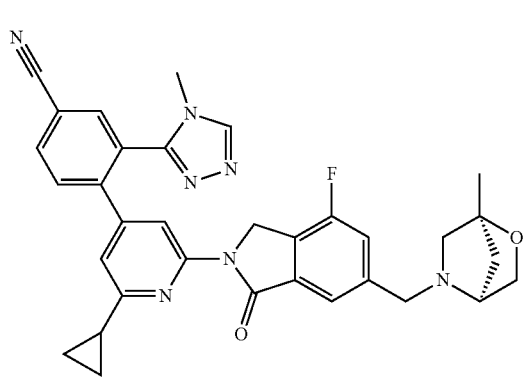
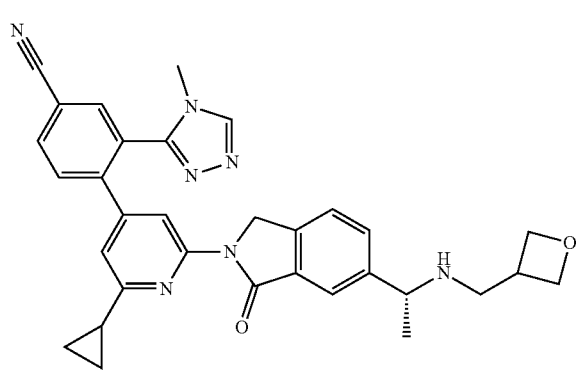
1142
-continued
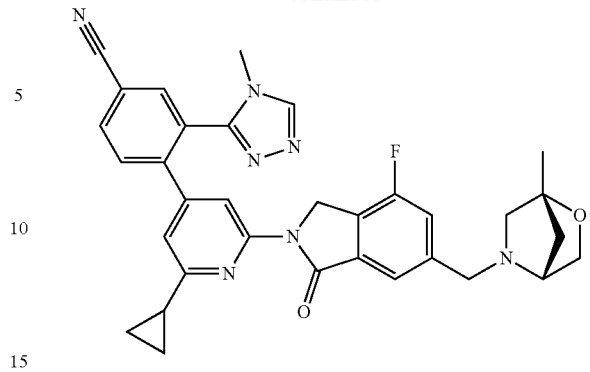
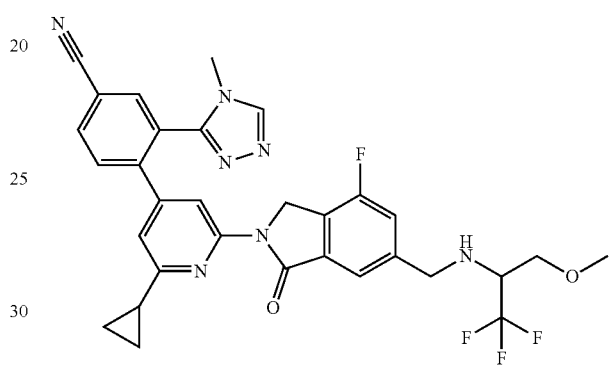
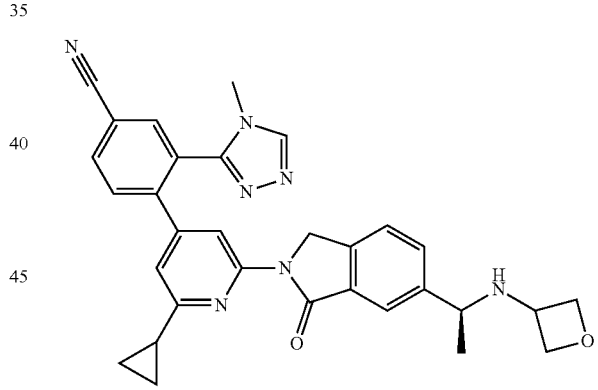
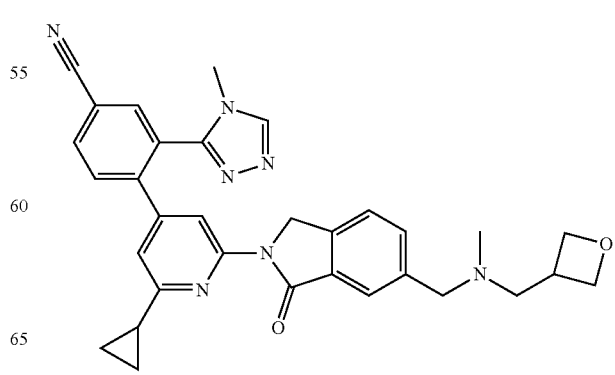

1143
-continued
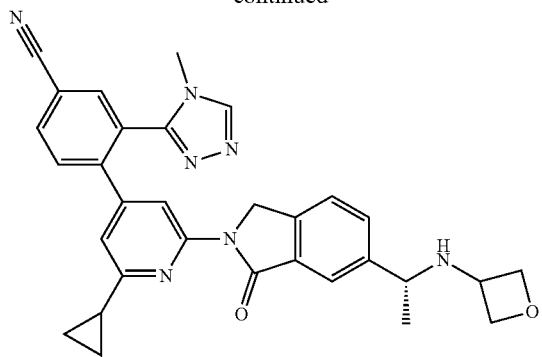
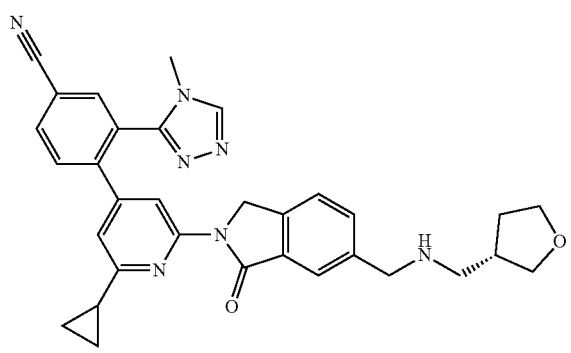
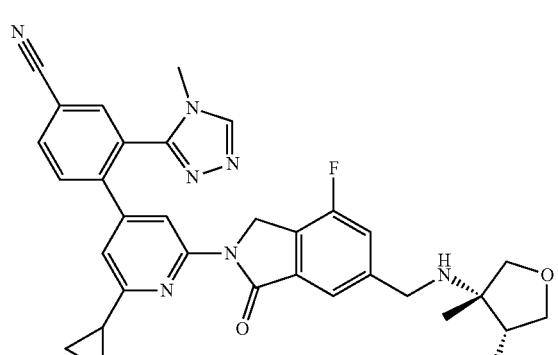
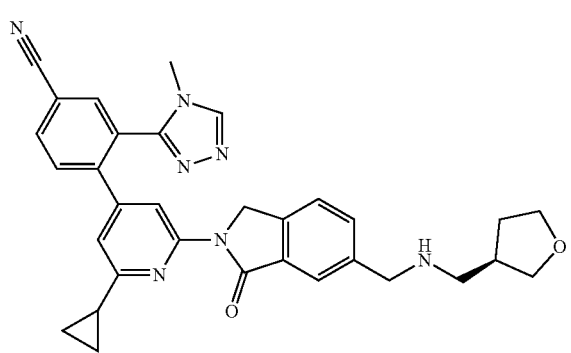
1144
-continued
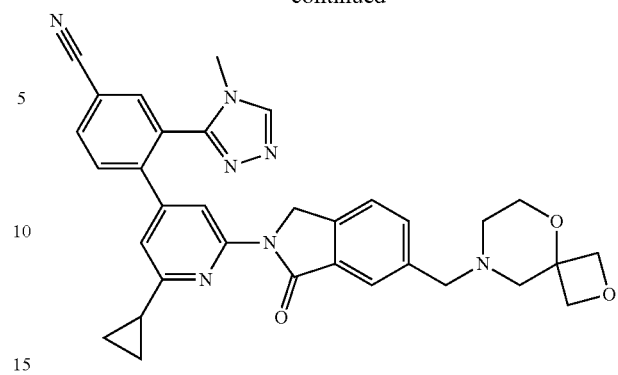
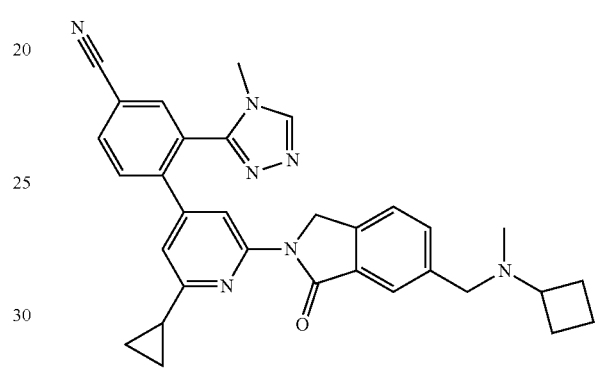
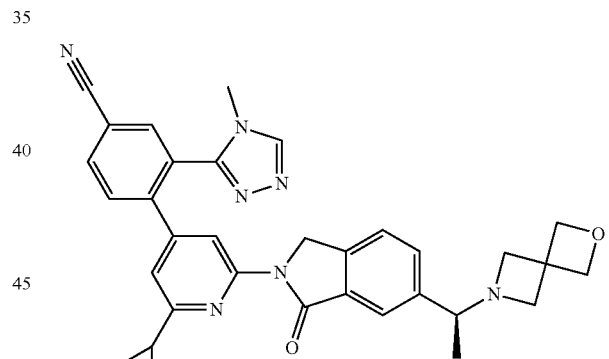
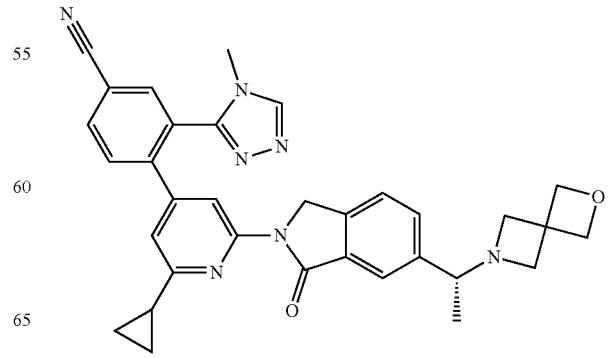

1145
-continued
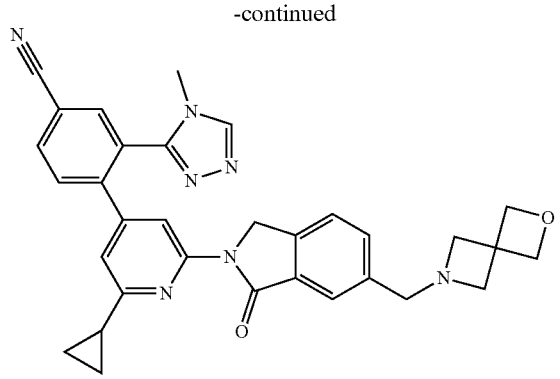
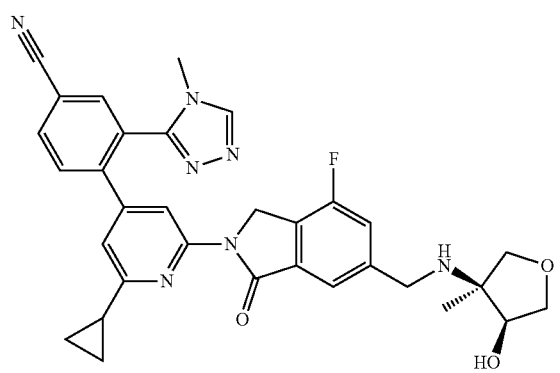
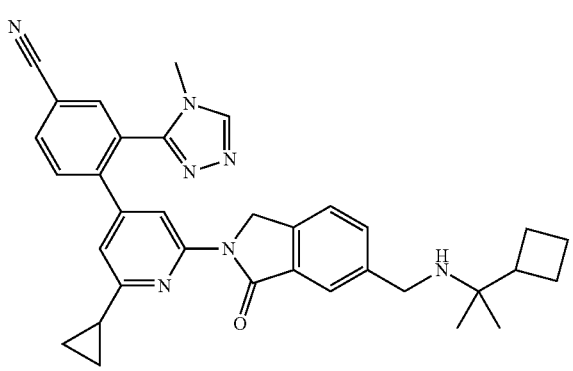
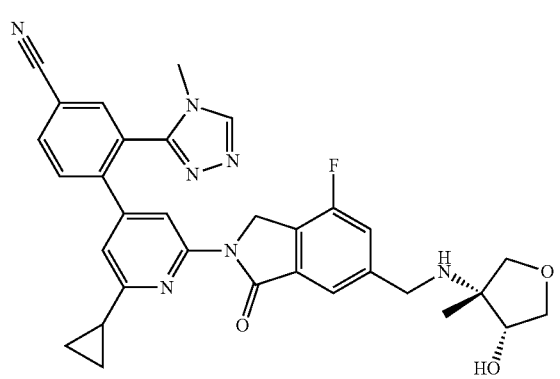
1146
-continued
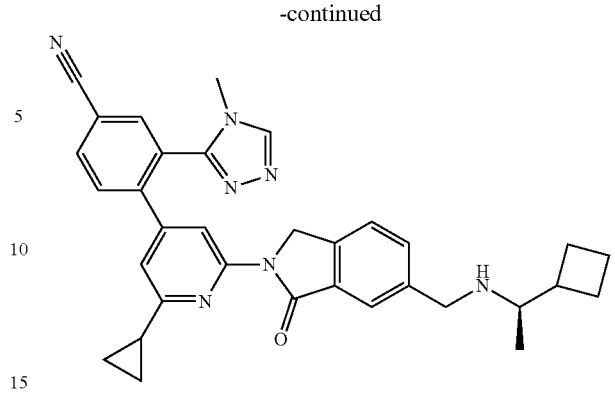
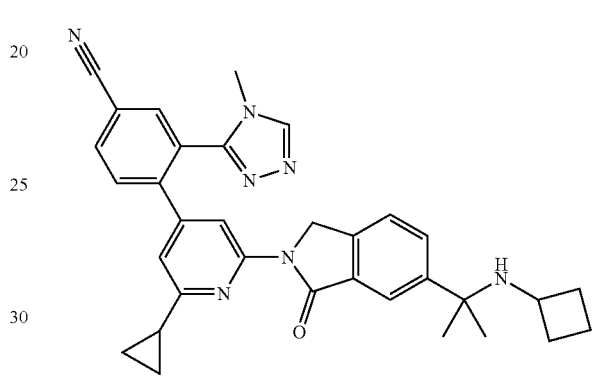
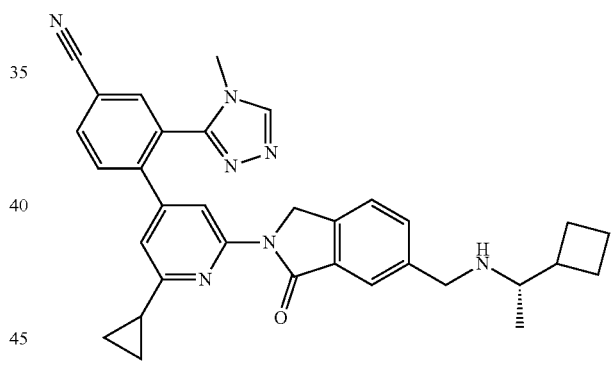
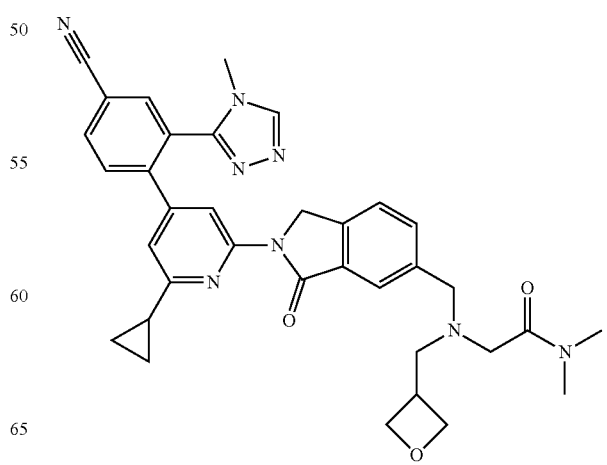

1147
-continued
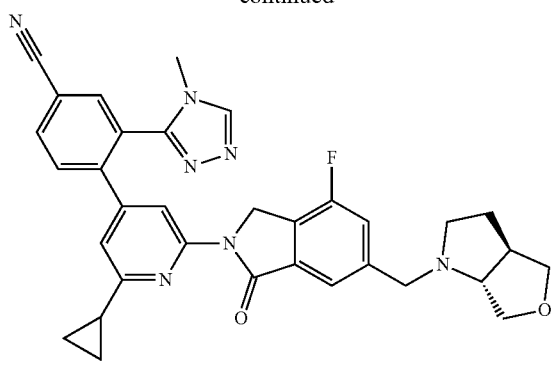
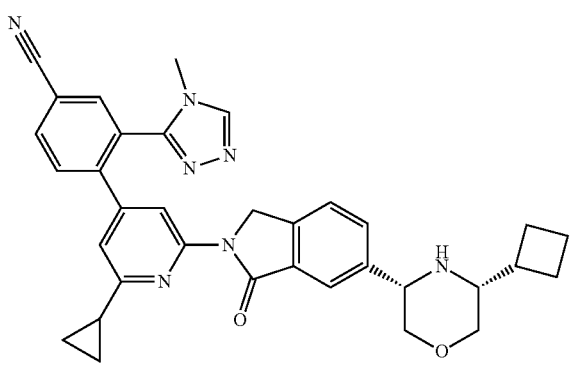
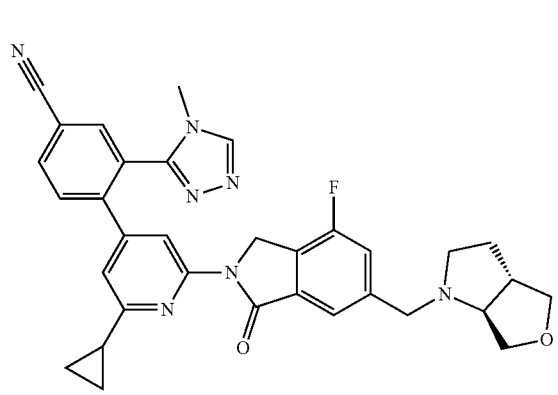
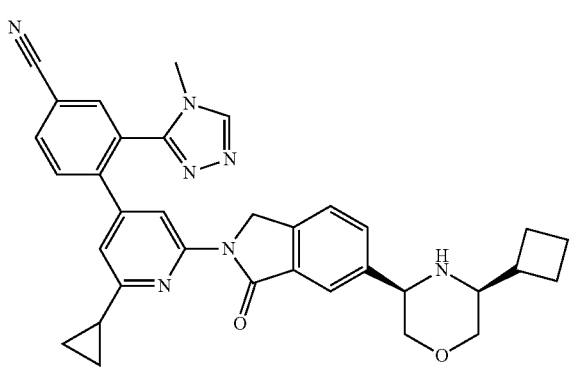
1148
-continued
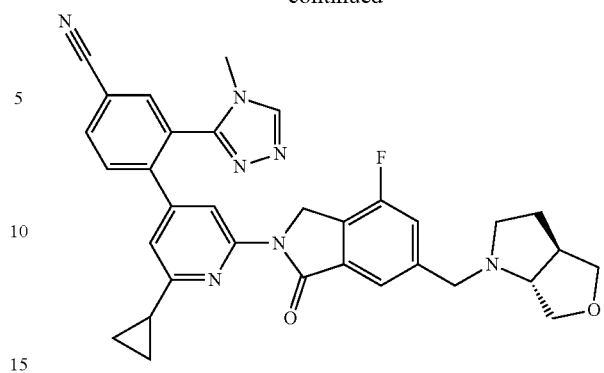
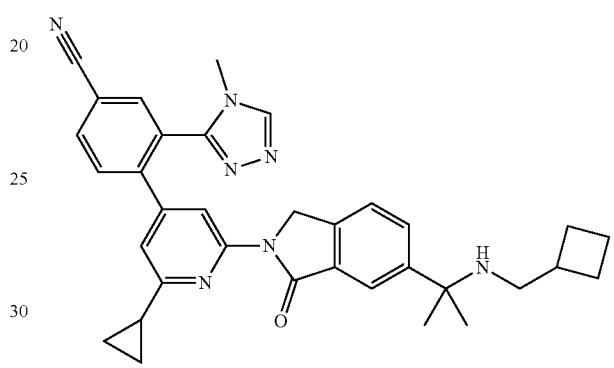
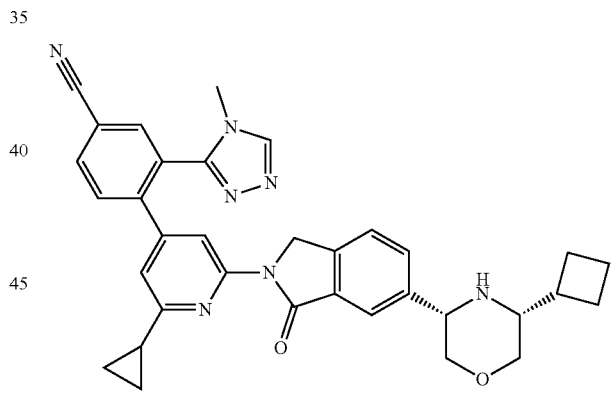
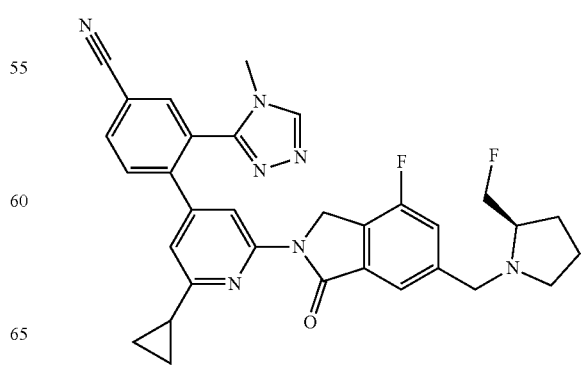

1149
-continued
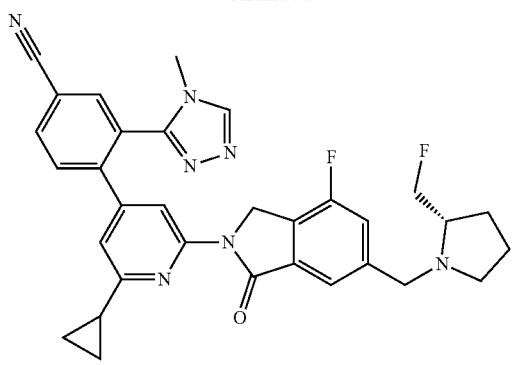
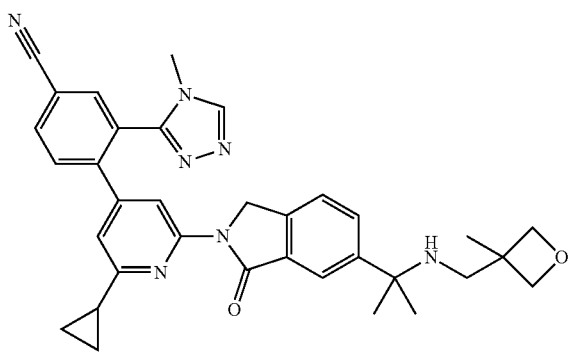
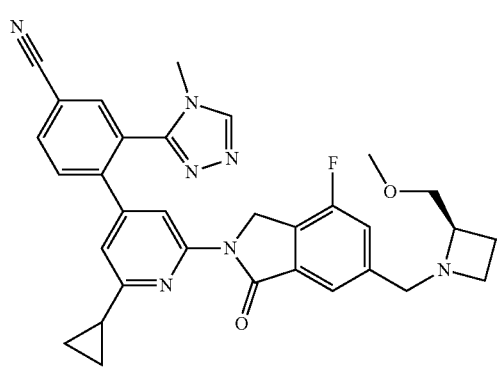
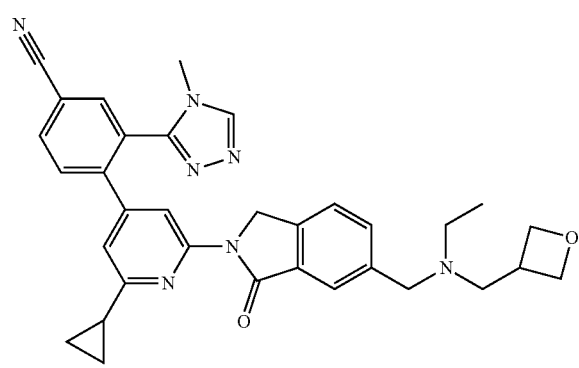
1150
-continued
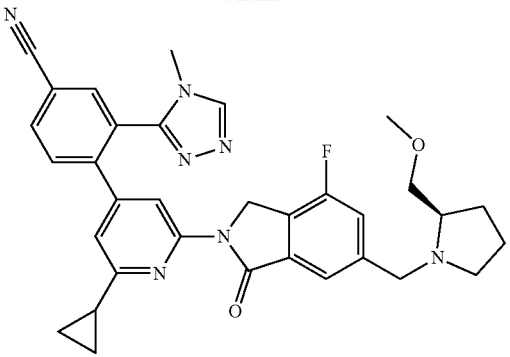
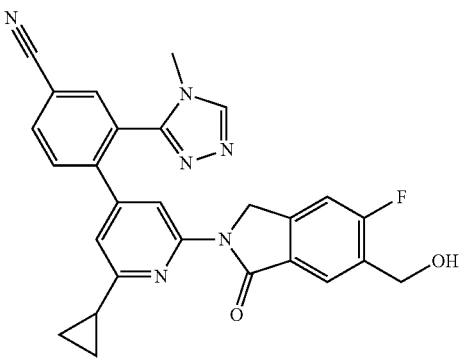
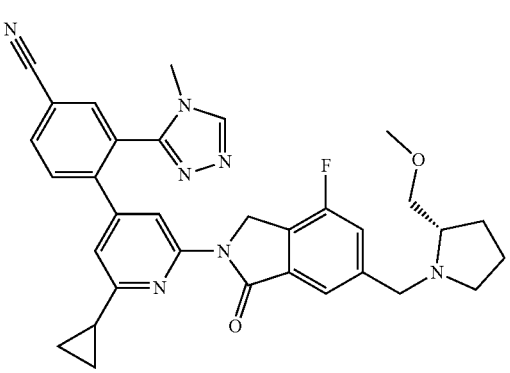
and
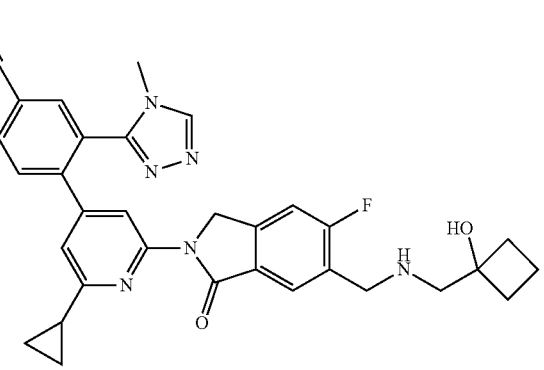

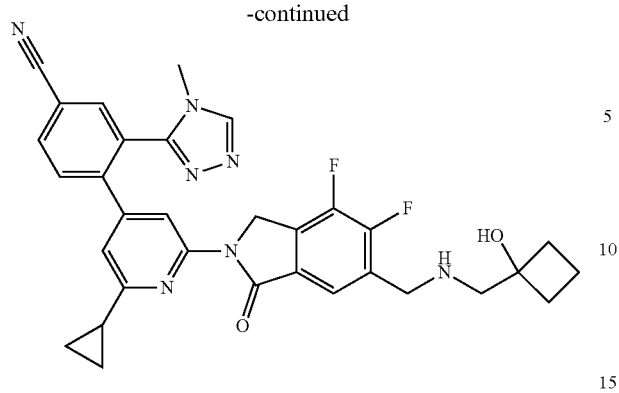
or a pharmaceutically acceptable salt thereof.
8. A pharmaceutical composition comprising a compound according to claim 1, or a pharmaceutically acceptable salt thereof, and a pharmaceutically acceptable carrier, adjuvant, or vehicle.
* * * * *